United States Patent
Lu et al.

(10) Patent No.: US 10,954,214 B2
(45) Date of Patent: Mar. 23, 2021

(54) PYRAZOLE DERIVATIVES AS MALT1 INHIBITORS

(71) Applicant: Janssen Pharmaceutica NV, Beerse (BE)

(72) Inventors: Tianbao Lu, Churchville, PA (US); Brett Douglas Allison, San Diego, CA (US); Joseph Kent Barbay, Flourtown, PA (US); Peter J. Connolly, New Providence, NJ (US); Maxwell David Cummings, Ambler, PA (US); Gaston Diels, Beerse (BE); James Patrick Edwards, Ambler, PA (US); Kevin D. Kreutter, Plainsboro, NJ (US); Ulrike Philippar, Antwerp (BE); Fang Shen, Fort Washington, NJ (US); Johannes Wilhelmus John Fitzgerald Thuring, Antwerp (BE); Tongfei Wu, Hever (BE); Didier Jean-Claude Berthelot, La Neuville Chant d'Oisel (FR)

(73) Assignee: Janssen Pharmaceutica NV, Beerse (BE)

( * ) Notice: Subject to any disclaimer, the term of this patent is extended or adjusted under 35 U.S.C. 154(b) by 0 days.

(21) Appl. No.: 15/847,999

(22) Filed: Dec. 20, 2017

(65) Prior Publication Data
US 2018/0170909 A1 Jun. 21, 2018

Related U.S. Application Data

(60) Provisional application No. 62/437,384, filed on Dec. 21, 2016.

(51) Int. Cl.
| C07D 401/14 | (2006.01) |
| C07D 401/12 | (2006.01) |
| A61P 35/00 | (2006.01) |
| A61P 37/00 | (2006.01) |
| A61P 19/02 | (2006.01) |
| C07D 487/04 | (2006.01) |
| C07D 405/14 | (2006.01) |
| C07D 491/04 | (2006.01) |
| C07D 495/04 | (2006.01) |
| C07D 413/14 | (2006.01) |
| C07D 471/04 | (2006.01) |
| C07D 417/14 | (2006.01) |

(52) U.S. Cl.
CPC ............ *C07D 401/14* (2013.01); *A61P 19/02* (2018.01); *A61P 35/00* (2018.01); *A61P 37/00* (2018.01); *C07D 401/12* (2013.01); *C07D 405/14* (2013.01); *C07D 413/14* (2013.01); *C07D 417/14* (2013.01); *C07D 471/04* (2013.01); *C07D 487/04* (2013.01); *C07D 491/04* (2013.01); *C07D 495/04* (2013.01)

(58) Field of Classification Search
CPC .................................................... C07D 401/14
USPC ........................................... 546/141; 514/307
See application file for complete search history.

(56) References Cited

U.S. PATENT DOCUMENTS

| 6,339,099 B1 | 1/2002 | Lam et al. |
| 7,151,113 B2 | 12/2006 | Dyckman et al. |
| 7,223,782 B2 | 5/2007 | Atkinson et al. |
| 7,253,170 B2 | 8/2007 | Dyckman et al. |
| 7,390,810 B2 | 6/2008 | Dyckman et al. |
| 7,396,935 B2 | 7/2008 | Dyckman et al. |
| 7,414,056 B2 | 8/2008 | Dyckman et al. |
| 7,592,338 B2 | 9/2009 | Dyckman et al. |
| 7,605,273 B2 | 10/2009 | Dyckman et al. |
| 9,375,008 B2 | 6/2016 | Gross et al. |

FOREIGN PATENT DOCUMENTS

| WO | WO 2001002385 A1 | 1/2001 |
| WO | WO 2003/037274 A2 | 5/2003 |
| WO | WO 2003/037274 A3 | 5/2003 |
| WO | WO 2004/098518 A2 | 11/2004 |
| WO | WO 2004/098518 A3 | 11/2004 |
| WO | WO 2008/008286 A2 | 1/2008 |
| WO | WO 2008/008286 A3 | 1/2008 |
| WO | WO 2015/181747 A1 | 12/2015 |

(Continued)

OTHER PUBLICATIONS

Yu et al., "Physical characterization of, etc.," PSTT, vl. 1(3), 118-127). (Year: 1998).*
Braga et al., "Making crystals from . . . " J. Royal Soc. Chem. Commun. p. 3635-3645. (Year: 2005).*
Bernstein, "Polymorphism in . . . " p. 115-118, 272. (Year: 2002).*
Davidovich et al., "Detection of polymorphism . . . " Am. Pharm. Rev. v.&(1) p. 10, 12, 14, 16, 100). (Year: 2004).*
Dean "Analytical Chem . . . " p. 10.24-10.26. (Year: 1995).*

(Continued)

*Primary Examiner* — Patricia L Morris

(57) ABSTRACT

Disclosed are compounds, compositions and methods for treating of diseases, syndromes, conditions, and disorders that are affected by the modulation of MALT1. Such compounds are represented by Formula (I) as follows:

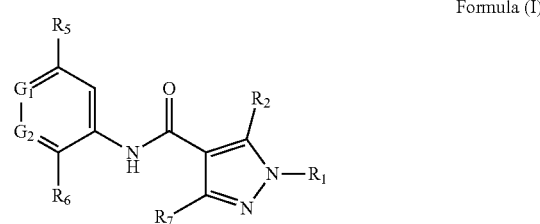

Formula (I)

wherein $R_1$, $R_2$, $R_3$, $R_4$, $R_5$, $R_6$, $R_5$, $G_1$, and $G_2$ are defined herein.

37 Claims, No Drawings

(56) References Cited

FOREIGN PATENT DOCUMENTS

| WO | WO 2018/114501 A1 | 6/2018 |
|---|---|---|
| WO | WO 2018/114503 A1 | 6/2018 |
| WO | WO 2018/115880 A1 | 6/2018 |
| WO | WO 2018/116201 A1 | 6/2018 |
| WO | WO 2018/116259 A1 | 6/2018 |
| WO | WO 2018/119036 A1 | 6/2018 |

OTHER PUBLICATIONS

Ivanisevic et al. "Use of X-ray . . . " Pharm. Sci. Encycl. p. 1-42. (Year: 2010).*
Seddon "Pseudopolynnorph . . . " Crystal Growth & design v.4(6) p. 108 (2 pages from internet) (Year: 2004).*
Jain et al., "Polymorphism in Pharmacy", Indian Drugs 23(6) 315-329. (Year: 1986).*
Jordan "Tamoxifen . . . " Nature Rev. v.2, p. 205-213. (Year: 2003).*
Kirk-Othmer Encyclopedia of Chemical Technology, 8, pp. 95-147. (Year: 2002).*
Vippagunta et al., "Crystalline Solids", Advanced Drug Delivery Reviews 48 3-26. (Year: 2001).*
Guillory (in Brittain ed.), "Polymorphism in Pharmaceutical Solids.," NY: Marcel Dekker, Inc., 1-2, 125-181, 183-226. (Year: 1999).*
Bornancin et al., "Deficiency of MALT1 Paracaspase Activity Results in Unbalanced Regulatory and Effector T and B Cell Responses Leading to Multiorgan Inflammation.", J. Immunology, Apr. 15, 2015, vol. 194(8), pp. 3723-3734.
Demeyer et al., "Targeting MALT1 Proteolytic Activity in Immunity, Inflammation and Disease: Good or Bad?", Trends Mol Med, 2016, vol. 22(2), pp. 135-150.
Fontan et al., "MALT1 Small Molecule Inhibitors Specifically Suppress ABC-DLBCL In Vitro and In Vivo.", Cancer Cell, Dec. 11, 2012, vol. 22(6), pp. 812-824.
Gewies et al., "Uncoupling Malt1 Threshold Function from Paracaspase Activity Results in Destructive Autoimmune Inflammation.", Cell Reports, Nov. 20, 2014, 9, pp. 1292-1305.
Jabara et al., "A homozygous mucosa-associated lymphoid tissue 1 (MALT1) mutation in a family with combined immunodeficiency.", J. Allergy Clin. Immunol., Jul. 2013, vol. 132, pp. 151-158.
Jaworski et al., "Malt1 protease inactivation efficiently dampens immune responses but causes spontaneous autoimmunity.", The EMBO Journall , 2014, vol. 33(23), pp. 2765-2781.
Jaworski et al., "The paracaspase MALT1: biological function and potential for therapeutic inhibition.", Cell Mol Life Science, 2016, vol. 73, pp. 459-473.
McGuire et al., "Pharmacological inhibition of MALT1 protease activity protects mice in a mouse model of multiple sclerosis.", J. Neuroinflammation, 2014, vol. 11, p. 124.
McKinnon et al., "Combined immunodeficiency associated with homozygous MALT1 mutations.", J. Allergy Clin. Immunol. 2014, vol. 133, pp. 1458-1462.
Nagel et al., "Pharmacologic Inhibition of MALT1 Protease by Phenothiazines as a Therapeutic Approach for the Treatment of Aggressive ABC-DLBCL.", Cancer Cell, Dec. 11, 2012, vol. 22, pp. 825-837.
Punwani et al., "Combined Immunodeficiency Due to MALT1 Mutations, Treated by Hematopoietic Cell Transplantation.", J. Clin. Immunol., 2015, vol. 35, pp. 135-146.
Rosebeck et al., "Cleavage of NIK by the API2-MALT1 Fusion Oncoprotein Leads to Noncanonical NK-kB Activation.", Science, Jan. 28, 2011, vol. 331, pp. 468-472.
Rosebeck et al., "API2-MALT1 oncoprotein promotes lymphomagenesis via unique program of substrate ubiquitination and proteolysis.", World J Biol Chem, Feb. 26, 2016, vol. 7(1), pp. 128-137.
Yu et al., "MALT1 Protease Activity Is Required for Innate and Adaptive Immune Responses.", PLOS One, May 12, 2015, pp. 1-20.
Lim, K., et al., "Pathogentic importance and therapeutica implications of NK-Kβ in lymphoid malignancies", Immunological Reviews, (2012), vol. 246, pp. 359-378.
Bundgaard, H., "Design of Prodrugs", (1985), Table of Contents.
McOmie, J., "Protective Groups in Organic Chemistry", (1973), Title Page and Table of Contents.
T.W. Greene & P.G.M. Wutz (eds.), Protective Groups in Organic Synthesis, $2^{nd}$ edition, John Wiley & Sons, Inc., (1991), Table of Contents.
T.W. Greene & P.G.M. Wutz (eds.), Protective Groups in Organic Synthesis, $3^{rd}$ edition, John Wiley & Sons, Inc., (1999), Table of Contents.

* cited by examiner

PYRAZOLE DERIVATIVES AS MALT1 INHIBITORS

CROSS-REFERENCE TO RELATED APPLICATIONS

This Application claims priority to U.S. Provisional Patent Application No. 62/437,384, filed Dec. 21, 2016, which is hereby incorporated by reference in its entirety.

FIELD OF THE INVENTION

The present invention relates to novel compounds that are MALT1 (mucosa-associated lymphoid tissue lymphoma translocation protein 1) inhibitors. These compounds may be useful for the treatment of a disease, syndrome, condition, or disorder, particularly a MALT1-related disease, syndrome, condition, or disorder, including but not limited to, cancer and immunological diseases. The invention also relates to pharmaceutical compositions comprising one or more of such compounds, to processes to prepare such compounds and compositions, and to the use of such compounds or pharmaceutical compositions for the treatment of cancer and autoimmunological diseases, syndromes, disorders, or conditions associated with MALT1 inhibitors.

BACKGROUND OF THE INVENTION

MALT1 (mucosa-associated lymphoid tissue lymphoma translocation 1) is a key mediator of the classical $NF_\kappa B$ signaling pathway. MALT1 is the only human paracaspase and transduces signals from the B cell receptor (BCR) and T cell receptor (TCR). MALT1 is the active subunit of the CBM complex which is formed upon receptor activation. The CBM complex consists of multiple subunits of three proteins: CARD11 (caspase recruitment domain family member 11), BCL10 (B-cell CLL/Lymphoma 10) and MALT1. MALT1 affects $NF_\kappa B$ signaling by two mechanisms: firstly, MALT1 functions as a scaffolding protein and recruits $NF_\kappa B$ signaling proteins such as TRAF6, TAB-TAK1 or NEMO-IKKα/β; and secondly, MALT1, as a cysteine protease, cleaves and thereby deactivates negative regulators of $NF_\kappa B$ signaling, such as RelB, A20 or CYLD. The ultimate endpoint of MALT1 activity is the nuclear translocation of the $NF_\kappa B$ transcription factor complex and activation of $NF_\kappa B$ signaling (Jaworski et al., Cell Mol Life Science 2016. 73, 459-473).

Constitutive activation of $NF_\kappa B$ signaling is the hallmark of ABC-DLBCL (Diffuse Large B cell Lymphoma of the Activated B Cell-like subtype), the more aggressive form of DLBCL. DLBCL is the most common form of non-Hodgkin's lymphoma (NHL), accounting for approximately 25% of lymphoma cases while ABC-DLBCL comprises approximately 40% of DLBCL. $NF_\kappa B$ pathway activation is driven by mutations of signaling components, such as CD79A/B, CARD11, MYD88 or A20, in ABC-DLBCL patients (Staudt, Cold Spring Harb Perspect Biol 2010, 2; Lim et al, Immunol Rev 2012, 246, 359-378).

The use of BTK inhibitors, for example Ibrutinib, provides clinical proof-of-concept that inhibiting $NF_\kappa B$ signaling in ABC-DLBCL is efficacious. MALT1 is downstream of BTK in the $NF_\kappa B$ signaling pathway and a MALT1 inhibitor could target ABC-DLBCL patients not responding to Ibrutinib, mainly patients with CARD11 mutations, as well as treat patients that acquired resistance to Ibrutinib.

Small molecule tool compound inhibitors of MALT1 protease have demonstrated efficacy in preclinical models of ABC-DLBCL (Fontan et al., Cancer Cell 2012, 22, 812-824; Nagel et al., Cancer Cell 2012, 22, 825-837). Interestingly, covalent catalytic site and allosteric inhibitors of MALT1 protease function have been described, suggesting that inhibitors of this protease may be useful as pharmaceutical agents (Demeyer et al., Trends Mol Med 2016, 22, 135-150).

The chromosomal translocation creating the API2-MALT1 fusion oncoprotein is the most common mutation identified in MALT (mucosa-associated lymphoid tissue) lymphoma. API2-MALT1 is a potent activator of the $NF_\kappa B$ pathway (Rosebeck et al., World J Biol Chem 2016, 7, 128-137). API2-MALT1 mimics ligand-bound TNF receptor, promotes TRAF2-dependent ubiquitination of RIP1 which acts as a scaffold for activating canonical $NF_\kappa B$ signaling. Furthermore, API2-MALT1 has been shown to cleave and generate a stable, constitutively active fragment of $NF_\kappa B$-inducing kinase (NIK) thereby activating the non-canonical $NF_\kappa B$ pathway (Rosebeck et al., Science, 2011, 331, 468-472).

In addition to lymphomas, MALT1 has been shown to play a critical role in innate and adaptive immunity (Jaworski M, et al., Cell Mol Life Sci. 2016). MALT1 protease inhibitor can attenuate disease onset and progression of mouse experimental allergic encephalomyelitis, a mouse model of multiple sclerosis (Mc Guire et al., J. Neuroinflammation 2014, 11, 124). Mice expressing catalytically inactive MALT1 mutant showed loss of marginal zone B cells and B1 B cells and general immune deficiency characterized as decreased T and B cell activation and proliferation. However, those mice also developed spontaneous multi-organ autoimmune inflammation at the age of 9 to 10 weeks. It is still poorly understood why MALT1 protease dead knock-in mice show a break of tolerance while conventional MALT1 KO mice do not. One hypothesis suggests the unbalanced immune homeostasis in MALT1 protease dead knock-in mice may be caused by incomplete deficiency in T and B cell but severe deficiency of immunoregulatory cells (Jaworski et al., EMBO J. 2014; Gewies et al., Cell Reports 2014; Bornancin et al., J. Immunology 2015; Yu et al., PLOS One 2015). Similarly, MALT deficiency in humans has been associated with combined immunodeficiency disorder (McKinnon et al., J. Allergy Clin. Immunol. 2014, 133, 1458-1462; Jabara et al., J. Allergy Clin. Immunol. 2013, 132, 151-158; Punwani et al., J. Clin. Immunol. 2015, 35, 135-146). Given the difference between genetic mutation and pharmacological inhibition, a phenotype of MALT1 protease dead knock-in mice might not resemble that of patients treated with MALT1 protease inhibitors. A reduction of immunosuppressive T cells by MALT1 protease inhibition may be beneficial to cancer patients by potentially increasing antitumor immunity.

Thus, MALT1 inhibitors of the present invention may provide a therapeutic benefit to patients suffering from cancer and/or immunological diseases.

SUMMARY OF THE INVENTION

The present invention is directed to compounds of Formula (I)

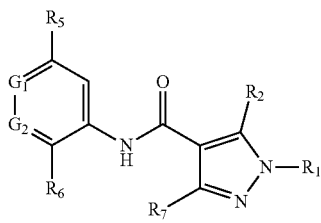

Formula (I)

wherein

R₁ is selected from the group consisting of
i) naphthalen-1-yl, optionally substituted with a fluoro or amino substituent;
and
ii) a heteroaryl of nine to ten members containing one to four heteroatoms selected from the group consisting of O, N, and S; such that no more than one heteroatom is O or S; wherein said heteroaryl of ii) is optionally independently substituted with one or two substituents selected from deuterium, methyl, ethyl, propyl, isopropyl, trifluoromethyl, cyclopropyl, methoxymethyl, difluoromethyl, 1,1-difluoroethyl, hydroxymethyl, 1-hydroxyethyl, 1-ethoxyethyl, hydroxy, methoxy, ethoxy, fluoro, chloro, bromo, methylthio, cyano, amino, methylamino, dimethylamino, 4-oxotetrahydrofuran-2-yl, 5-oxopyrrolidin-2-yl, 1,4-dioxanyl, aminocarbonyl, methylcarbonyl, methylaminocarbonyl, oxo, 1-(t-butoxycarbonyl)azetidin-2-yl, N-(methyl)formamidomethyl, tetrahydrofuran-2-yl, 3-hydroxy-pyrrolidin-1-yl, pyrrolidin-2-yl, 3-hydroxyazetidinyl, azetidin-3-yl, or azetidin-2-yl;

R₂ is selected from the group consisting of $C_{1-4}$alkyl, 1-methoxy-ethyl, difluoromethyl, fluoro, chloro, bromo, cyano, and trifluoromethyl;

G₁ is N or C(R₄);
G₂ is N or C(R₃); such that only one of G₁ and G₂ are N in any instance;

R₃ is independently selected from the group consisting of trifluoromethyl, cyano, $C_{1-4}$alkyl, fluoro, chloro, bromo, methylcarbonyl, methylthio, methylsulfinyl, and methanesulfonyl; or, when G₁ is N, R₃ is further selected from $C_{1-4}$alkoxycarbonyl;

R₄ is selected from the group consisting of
i) hydrogen, when G₂ is N;
ii) $C_{1-4}$alkoxy;
iii) cyano;
iv) cyclopropyloxy;
v) a heteroaryl selected from the group consisting of triazolyl, oxazolyl, isoxazolyl, pyrazolyl, pyrrolyl, thiazolyl, tetrazolyl, oxadiazolyl, imidazolyl, 2-amino-pyrimidin-4-yl, 2H-[1,2,3]triazolo[4,5-c]pyridin-2-yl, 2H-[1,2,3]triazolo[4,5-b]pyridin-2-yl, 3H-[1,2,3]triazolo[4,5-b]pyridin-3-yl, 1H-[1,2,3]triazolo[4,5-c]pyridin-1-yl, wherein the heteroaryl is optionally substituted with one or two substituents independently selected from oxo, $C_{1-4}$alkyl, carboxy, methoxycarbonyl, aminocarbonyl, hydroxymethyl, aminomethyl, (dimethylamino)methyl, amino, methoxymethyl, trifluoromethyl, amino($C_{2-4}$alkyl)amino, or cyano;

vi) 1-methyl-piperidin-4-yloxy;
vii) 4-methyl-piperazin-1-ylcarbonyl;
viii) (4-aminobutyl)aminocarbonyl;
ix) (4-amino)butoxy;
x) 4-(4-aminobutyl)-piperazin-1-ylcarbonyl;
xi) methoxycarbonyl;
xii) 5-chloro-6-(methoxycarbonyl)pyridin-3-ylaminocarbonyl;
xiii) 1,1-dioxo-isothiazolidin-2-yl;
xiv) 3-methyl-2-oxo-2,3-dihydro-1H-imidazol-1-yl;
xv) 2-oxopyrrolidin-1-yl;
xvi) (F)-(4-aminobut-1-en-1-yl-aminocarbonyl;
xvii) difluoromethoxy;
and
xviii) morpholin-4-ylcarbonyl;

R₅ is independently selected from the group consisting of hydrogen, chloro, fluoro, bromo, methoxy, methylsulfonyl, cyano, $C_{1-4}$alkyl, ethynyl, morpholin-4-yl, trifluoromethyl, hydroxyethyl, methylcarbonyl, methylsulfinyl, 3-hydroxy-pyrrolidin-1-yl, pyrrolidin-2-yl, 3-hydroxyazetidinyl, azetidin-3-yl, azetidin-2-yl, methylthio, and 1,1-difluoroethyl;

or R₄ and R₅ may be taken together to form 8-chloro-4-methyl-3-oxo-3,4-dihydro-2H-benzo[b][1,4]oxazin-6-yl, 8-chloro-3-oxo-3,4-dihydro-2H-benzo[b][1,4]oxazin-6-yl, 2-methyl-1-oxo-1,2,3,4-tetrahydroisoquinolin-7-yl, 4-methyl-3-oxo-3,4-dihydro-2H-benzo[b][1,4]oxazin-6-yl, 3-oxo-3,4-dihydro-2H-benzo[b][1,4]oxazin-6-yl, 1-methyl-1H-pyrazolo[3,4-b]pyridin-5-yl, 1H-pyrazolo[3,4-b]pyridin-5-yl, 2,3-dihydro-[1,4]dioxino[2,3-b]pyridin-5-yl, 1,3-dioxolo[4,5]pyridine-5-yl, 1-oxo-1,3-dihydroisobenzofuran-5-yl, 2,2-dimethylbenzo[d][1,3]dioxol-5-yl, 2,3-dihydrobenzo[b][1,4]dioxin-6-yl, 1-oxoisoindolin-5-yl, or 2-methyl-1-oxoisoindolin-5-yl, 1H-indazol-5-yl;

R₆ is hydrogen, $C_{1-4}$alkyl, fluoro, 2-methoxy-ethoxy, chloro, cyano, or trifluoromethyl;

R₇ is hydrogen or fluoro;

provided that a compound of Formula (I) is other than
a compound wherein R₁ is isoquinolin-8-yl, R₂ is trifluoromethyl, G₁ is C(R₄) wherein R₄ is 2H-1,2,3-triazol-2-yl, G₂ is N, and R₅ is hydrogen;
a compound wherein R₁ is isoquinolin-8-yl, R₂ is trifluoromethyl, G₁ is C(R₄) wherein R₄ is 1H-imidazol-1-yl, G₂ is N, and R₅ is chloro;
a compound wherein R₁ is isoquinolin-8-yl, R₂ is trifluoromethyl, G₁ is C(R₄) wherein R₄ is 1H-1,2,3-triazol-1-yl, G₂ is N, and R₅ is hydrogen;
a compound wherein R₁ is isoquinolin-8-yl, R₂ is trifluoromethyl, G₁ is C(R₄) wherein R₄ is hydrogen, G₂ is N, and R₅ is fluoro;
a compound wherein R₁ quinolin-4-yl, R₂ is hydrogen, G₁ is C(R₄) wherein R₄ is (2H)-1,2,3-triazol-2-yl, G₂ is N, and R₅ is chloro;
or an enantiomer, diastereomer, or pharmaceutically acceptable salt form thereof.

The present invention also provides a pharmaceutical composition comprising, consisting of and/or consisting essentially of a pharmaceutically acceptable carrier, a pharmaceutically acceptable excipient, and/or a pharmaceutically acceptable diluent and a compound of Formula (I), or a pharmaceutically acceptable salt form thereof.

Also provided are processes for making a pharmaceutical composition comprising, consisting of, and/or consisting essentially of admixing a compound of Formula (I), and a pharmaceutically acceptable carrier, a pharmaceutically acceptable excipient, and/or a pharmaceutically acceptable diluent.

The present invention further provides methods for treating or ameliorating a disease, syndrome, condition, or disorder in a subject, including a mammal and/or human in which the disease, syndrome, or condition is affected by the inhibition of MALT1, including but not limited to, cancer and/or immunological diseases, using a compound of Formula (I).

The present invention also is directed to the use of any of the compounds described herein in the preparation of a medicament wherein the medicament is prepared for treating a disease, syndrome, condition, or disorder that is affected by the inhibition of MALT1, such as cancer and/or immunological diseases.

The present invention is also directed to the preparation of substituted pyrazole derivatives that act as an inhibitor of MALT1.

Exemplifying the invention are methods of treating a disease, syndrome, condition, or disorder mediated by MALT1, selected from the group consisting of lymphomas, leukemias, carcinomas, and sarcomas, e.g. non-Hodgkin's lymphoma, diffuse large B-cell lymphoma (DLBCL), mantle cell lymphoma (MCL), follicular lymphoma (FL), mucosa-associated lymphoid tissue (MALT) lymphoma, marginal zone lymphoma, T-cell lymphoma, Hodgkin's lymphoma, Burkitt's lymphoma, multiple myeloma, chonic lymphocytic leukemia (CLL), lymphoblastic T cell leukemia, chonic myelogenous leukemia (CML), hairy-cell leukemia, acute lymphoblastic T cell leukemia, plasmacytoma, immunoblastic large cell leukemia, megakaryoblastic leukemia, acute megakaryocytic leukemia, promyelocytic leukemia, erytholeukemia, brain (gliomas), glioblastomas, breast cancer, colorectal/colon cancer, prostate cancer, lung cancer including non-small-cell, gastric cancer, endometrial cancer, melanoma, pancreatic cancer, liver cancer, kidney cancer, squamous cell carcinoma, ovarian cancer, sarcoma, osteosarcoma, thyroid cancer, bladder cancer, head and neck cancer, testicular cancer, Ewing's sarcoma, rhabdomyosarcoma, medulloblastoma, neuroblastoma, cervical cancer, renal cancer, urothelial cancer, vulval cancer, esophageal cancer, salivary gland cancer, nasopharangeal cancer, buccal cancer, cancer of the mouth, and GIST (gastrointestinal stromal tumor), comprising, consisting of, and/or consisting essentially of, administering to a subject in need thereof a therapeutically effective amount of any of the compounds or pharmaceutical compositions described in the present invention.

In another embodiment, the present invention is directed to a compound of Formula (I) for use in the treatment of a disease, syndrome, condition, or disorder affected by the inhibition of MALT1, selected from the group consisting of lymphomas, leukemias, carcinomas, and sarcomas, e.g. non-Hodgkin's lymphoma, diffuse large B-cell lymphoma (DLBCL), mantle cell lymphoma (MCL), follicular lymphoma (FL), mucosa-associated lymphoid tissue (MALT) lymphoma, marginal zone lymphoma, T-cell lymphoma, Hodgkin's lymphoma, Burkitt's lymphoma, multiple myeloma, chonic lymphocytic leukemia (CLL), lymphoblastic T cell leukemia, chonic myelogenous leukemia (CML), hairy-cell leukemia, acute lymphoblastic T cell leukemia, plasmacytoma, immunoblastic large cell leukemia, megakaryoblastic leukemia, acute megakaryocytic leukemia, promyelocytic leukemia, erytholeukemia, brain (gliomas), glioblastomas, breast cancer, colorectal/colon cancer, prostate cancer, lung cancer including non-small-cell, gastric cancer, endometrial cancer, melanoma, pancreatic cancer, liver cancer, kidney cancer, squamous cell carcinoma, ovarian cancer, sarcoma, osteosarcoma, thyroid cancer, bladder cancer, head and neck cancer, testicular cancer, Ewing's sarcoma, rhabdomyosarcoma, medulloblastoma, neuroblastoma, cervical cancer, renal cancer, urothelial cancer, vulval cancer, esophageal cancer, salivary gland cancer, nasopharangeal cancer, buccal cancer, cancer of the mouth, and GIST (gastrointestinal stromal tumor).

In another embodiment, the present invention is directed to a composition comprising a compound of Formula (I) for the treatment of a disease, syndrome, condition, or disorder affected by inhibition of MALT1, selected from the group consisting of lymphomas, leukemias, carcinomas, and sarcomas, e.g. non-Hodgkin's lymphoma, diffuse large B-cell lymphoma (DLBCL), mantle cell lymphoma (MCL), follicular lymphoma (FL), mucosa-associated lymphoid tissue (MALT) lymphoma, marginal zone lymphoma, T-cell lymphoma, Hodgkin's lymphoma, Burkitt's lymphoma, multiple myeloma, chonic lymphocytic leukemia (CLL), lymphoblastic T cell leukemia, chonic myelogenous leukemia (CML), hairy-cell leukemia, acute lymphoblastic T cell leukemia, plasmacytoma, immunoblastic large cell leukemia, megakaryoblastic leukemia, acute megakaryocytic leukemia, promyelocytic leukemia, erytholeukemia, brain (gliomas), glioblastomas, breast cancer, colorectal/colon cancer, prostate cancer, lung cancer including non-small-cell, gastric cancer, endometrial cancer, melanoma, pancreatic cancer, liver cancer, kidney cancer, squamous cell carcinoma, ovarian cancer, sarcoma, osteosarcoma, thyroid cancer, bladder cancer, head and neck cancer, testicular cancer, Ewing's sarcoma, rhabdomyosarcoma, medulloblastoma, neuroblastoma, cervical cancer, renal cancer, urothelial cancer, vulval cancer, esophageal cancer, salivary gland cancer, nasopharangeal cancer, buccal cancer, cancer of the mouth, and GIST (gastrointestinal stromal tumor).

In another embodiment, the present invention is directed to a composition comprising a compound of Formula (I) for the treatment of a disease, syndrome, condition, or disorder affected by inhibition of MALT1, selected from the group consisting of diffuse large B-cell lymphoma (DLBCL), mantle cell lymphoma (MCL), follicular lymphoma (FL), and mucosa-associated lymphoid tissue (MALT) lymphoma.

An embodiment of the present invention is directed to a composition comprising a compound of Formula (I) for the treatment of immunological diseases that are affected by the inhibition of MALT1, including but not limited to, autoimmune and inflammatory disorders, e.g. arthritis, inflammatory bowel disease, gastritis, ankylosing spondylitis, ulcerative colitis, pancreatits, Crohn's disease, celiac disease, multiple sclerosis, systemic lupus erythematosus, lupus nephritis, rheumatic fever, gout, organ or transplact rejection, chronic allograft rejection, acute or chronic graft-versus-host disease, dermatitis including atopic, dermatomyositis, psoriasis, Behcet's diseases, uveitis, myasthenia gravis, Grave's disease, Hashimoto thyroiditis, Sjoergen's syndrome, blistering disorders, antibody-mediated vasculitis syndromes, immune-complex vasculitides, allergic disorders, asthma, bronchitis, chronic obstructive pulmonary disease (COPD), cystic fibrosis, pneumonia, pulmonary diseases including oedema, embolism, fibrosis, sarcoidosis, hypertension and emphysema, silicosis, respiratory failure, acute respiratory distress syndrome, BENTA disease, berylliosis, and polymyositis.

In another embodiment, the present invention is directed to a composition comprising a compound of Formula (I) for the treatment of a disease, syndrome, condition, or disorder affected by inhibition of MALT1, selected from the group consisting of rheumatoid arthritis (RA), psoritic arthritis (PsA), psorisis (Pso), ulcerative colitis (UC), Crohn's disease, systemic lupus erythematosus (SLE), asthma, and chronic obstructive pulmonary disease (COPD).

Another embodiment of the present invention is directed to a pharmaceutical composition comprising a compound of Formula (I).

DETAILED DESCRIPTION OF THE INVENTION

With reference to substituents, the term "independently" refers to the situation where when more than one substituent is possible, the substituents may be the same or different from each other.

The term "alkyl" whether used alone or as part of a substituent group, refers to straight and branched carbon chains having 1 to 8 carbon atoms. Therefore, designated numbers of carbon atoms (e.g., $C_{1-8}$) refer independently to the number of carbon atoms in an alkyl moiety or to the alkyl portion of a larger alkyl-containing substituent. In substituent groups with multiple alkyl groups such as, $(C_{1-6}alkyl)_2amino-$, the $C_{1-6}alkyl$ groups of the dialkylamino may be the same or different.

The term "alkoxy" refers to an —O-alkyl group, wherein the term "alkyl" is as defined above.

The terms "alkenyl" and "alkynyl" refer to straight and branched carbon chains having 2 to 8 carbon atoms, wherein an alkenyl chain contains at least one double bond and an alkynyl chain contains at least one triple bond.

The term "cycloalkyl" refers to saturated or partially saturated, monocyclic or polycyclic hydrocarbon rings of 3 to 14 carbon atoms. Examples of such rings include cyclopropyl, cyclobutyl, cyclopentyl, cyclohexyl, cycloheptyl, and adamantyl.

The term "heterocyclyl" refers to a nonaromatic monocyclic or bicyclic ring system having 3 to 10 ring members that include at least 1 carbon atom and from 1 to 4 heteroatoms independently selected from N, O, and S. Included within the term heterocyclyl is a nonaromatic cyclic ring of 5 to 7 members in which 1 to 2 members are N, or a nonaromatic cyclic ring of 5 to 7 members in which 0, 1 or 2 members are N and up to 2 members are O or S and at least one member must be either N, O, or S; wherein, optionally, the ring contains 0 to 1 unsaturated bonds, and, optionally, when the ring is of 6 or 7 members, it contains up to 2 unsaturated bonds. The carbon atom ring members that form a heterocycle ring may be fully saturated or partially saturated. The term "heterocyclyl" also includes two 5 membered monocyclic heterocycloalkyl groups bridged to form a bicyclic ring. Such groups are not considered to be fully aromatic and are not referred to as heteroaryl groups. When a heterocycle is bicyclic, both rings of the heterocycle are non-aromatic and at least one of the rings contains a heteroatom ring member. Examples of heterocycle groups include, and are not limited to, pyrrolinyl (including 2H-pyrrole, 2-pyrrolinyl or 3-pyrrolinyl), pyrrolidinyl, imidazolinyl, imidazolidinyl, pyrazolinyl, pyrazolidinyl, piperidinyl, morpholinyl, thiomorpholinyl, and piperazinyl. Unless otherwise noted, the heterocycle is attached to its pendant group at any heteroatom or carbon atom that results in a stable structure.

The term "aryl" refers to an unsaturated, aromatic monocyclic or bicyclic ring of 6 to 10 carbon members. Examples of aryl rings include phenyl and naphthalenyl.

The term "heteroaryl" refers to an aromatic monocyclic or bicyclic aromatic ring system having 5 to 10 ring members and which contains carbon atoms and from 1 to 4 heteroatoms independently selected from the group consisting of N, O, and S. Included within the term heteroaryl are aromatic rings of 5 or 6 members wherein the ring consists of carbon atoms and has at least one heteroatom member. Suitable heteroatoms include nitrogen, oxygen, and sulfur. In the case of 5 membered rings, the heteroaryl ring preferably contains one member of nitrogen, oxygen or sulfur and, in addition, up to 3 additional nitrogens. In the case of 6 membered rings, the heteroaryl ring preferably contains from 1 to 3 nitrogen atoms. For the case wherein the 6 membered ring has 3 nitrogens, at most 2 nitrogen atoms are adjacent. Examples of heteroaryl groups include furyl, thienyl, pyrrolyl, oxazolyl, thiazolyl, imidazolyl, pyrazolyl, oxazolyl, thiazolyl, oxadiazolyl, triazolyl, thiadiazolyl, pyridinyl, pyridazinyl, pyrimidinyl, pyrazinyl, indolyl, isoindolyl, benzofuryl, benzothienyl, indazolyl, benzimidazolyl, benzothiazolyl, benzoxazolyl, benzisoxazolyl, benzothiadiazolyl, benzotriazolyl, quinolinyl, isoquinolinyl and quinazolinyl. Unless otherwise noted, the heteroaryl is attached to its pendant group at any heteroatom or carbon atom that results in a stable structure.

The term "halogen" or "halo" refers to fluorine, chlorine, bromine and iodine atoms.

The term "carboxy" refers to the group —C(=O)OH.
The term "formyl" refers to the group —C(=O)H.
The term "oxo" or "oxido" refers to the group (=O).

Whenever the term "alkyl" or "aryl" or either of their prefix roots appear in a name of a substituent (e.g., arylalkyl, alkylamino) the name is to be interpreted as including those limitations given above for "alkyl" and "aryl." Designated numbers of carbon atoms (e.g., $C_1$-$C_6$) refer independently to the number of carbon atoms in an alkyl moiety, an aryl moiety, or in the alkyl portion of a larger substituent in which alkyl appears as its prefix root. For alkyl and alkoxy substituents, the designated number of carbon atoms includes all of the independent members included within a given range specified. For example $C_{1-6}$ alkyl would include methyl, ethyl, propyl, butyl, pentyl and hexyl individually as well as sub-combinations thereof (e.g., $C_{1-2}$, $C_{1-3}$, $C_{1-4}$, $C_{1-5}$, $C_{2-6}$, $C_{3-6}$, $C_{4-6}$, $C_{5-6}$, $C_{2-5}$, etc.).

In general, under standard nomenclature rules used throughout this disclosure, the terminal portion of the designated side chain is described first followed by the adjacent functionality toward the point of attachment. Thus, for example, a "$C_1$-$C_6$ alkylcarbonyl" substituent refers to a group of the formula:

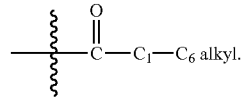

The label "R" at a stereocenter designates that the stereocenter is purely of the R-configuration as defined in the art; likewise, the label "S" means that the stereocenter is purely of the S-configuration. As used herein, the labels "*R" or "*S" at a stereocenter are used to designate that the stereocenter is of pure but unknown absolute configuration.

As used herein, the label "RS" refers to a stereocenter that exists as a mixture of the R- and S-configurations.

A compound containing one stereocenter drawn without a stereo bond designation is a mixture of two enantiomers. A compound containing two stereocenters both drawn without stereo bond designations is a mixture of four diastereomers. A compound with two stereocenters both labeled "RS" and drawn with stereo bond designations is a mixture of two enantiomers with relative stereochemistry as drawn. A compound with two stereocenters both labeled "*RS" and drawn with stereo bond designations is a mixture of two enantiomers with a single, but unknown, relative stereochemistry.

Unlabeled stereocenters drawn without stereo bond designations are mixtures of the R- and S-configurations. For unlabeled stereocenters drawn with stereo bond designations, the relative and absolute stereochemistry is as depicted.

Unless otherwise noted, it is intended that the definition of any substituent or variable at a particular location in a molecule be independent of its definitions elsewhere in that molecule. It is understood that substituents and substitution patterns on the compounds of the present invention can be selected by one of ordinary skill in the art to provide compounds that are chemically stable and that can be readily synthesized by techniques known in the art as well as those methods set forth herein.

The term "subject" refers to an animal, preferably a mammal, most preferably a human, who has been the object of treatment, observation or experiment.

The term "therapeutically effective amount" refers to an amount of an active compound or pharmaceutical agent, including a compound of the present invention, which elicits the biological or medicinal response in a tissue system, animal or human that is being sought by a researcher, veterinarian, medical doctor or other clinician, including reduction or inhibition of an enzyme or a protein activity, or ameliorating symptoms, alleviating conditions, slowing or delaying disease progression, or preventing a disease.

In one embodiment, the term "therapeutically effective amount" refers to the amount of a compound of the present invention that, when administered to a subject, is effective to (1) at least partially alleviate, inhibit, prevent, and/or ameliorate a condition, or a disorder or a disease (i) mediated by MALT1; or (ii) associated with MALT1 activity; or (iii) characterized by activity (normal or abnormal) of MALT1; or (2) reduce or inhibit the activity of MALT1; or (3) reduce or inhibit the expression of MALT1; or (4) modify the protein levels of MALT1.

The term "composition" refers to a product that includes the specified ingredients in therapeutically effective amounts, as well as any product that results, directly, or indirectly, from combinations of the specified ingredients in the specified amounts.

The term "MALT1-mediated" refers to any disease, syndrome, condition, or disorder that might occur in the absence of MALT1 but can occur in the presence of MALT1. Suitable examples of a disease, syndrome, condition, or disorder mediated by MALT1 include, but are not limited to, lymphomas, leukemias, carcinomas, and sarcomas, e.g. non-Hodgkin's lymphoma, diffuse large B-cell lymphoma (DLBCL), mantle cell lymphoma (MCL), follicular lymphoma (FL), mucosa-associated lymphoid tissue (MALT) lymphoma, marginal zone lymphoma, T-cell lymphoma, Hodgkin's lymphoma, Burkitt's lymphoma, multiple myeloma, chonic lymphocytic leukemia (CLL), lymphoblastic T cell leukemia, chonic myelogenous leukemia (CML), hairy-cell leukemia, acute lymphoblastic T cell leukemia, plasmacytoma, immunoblastic large cell leukemia, megakaryoblastic leukemia, acute megakaryocytic leukemia, promyelocytic leukemia, erytholeukemia, brain (gliomas), glioblastomas, breast cancer, colorectal/colon cancer, prostate cancer, lung cancer including non-small-cell, gastric cancer, endometrial cancer, melanoma, pancreatic cancer, liver cancer, kidney cancer, squamous cell carcinoma, ovarian cancer, sarcoma, osteosarcoma, thyroid cancer, bladder cancer, head and neck cancer, testicular cancer, Ewing's sarcoma, rhabdomyosarcoma, medulloblastoma, neuroblastoma, cervical cancer, renal cancer, urothelial cancer, vulval cancer, esophageal cancer, salivary gland cancer, nasopharangeal cancer, buccal cancer, cancer of the mouth, and GIST (gastrointestinal stromal tumor).

As used herein, the term "MALT1 inhibitor" refers to an agent that inhibits or reduces at least one condition, symptom, disorder, and/or disease of MALT1.

As used herein, unless otherwise noted, the term "affect" or "affected" (when referring to a disease, syndrome, condition or disorder that is affected by the inhibition of MALT1) includes a reduction in the frequency and/or severity of one or more symptoms or manifestations of said disease, syndrome, condition or disorder; and/or includes the prevention of the development of one or more symptoms or manifestations of said disease, syndrome, condition or disorder or the development of the disease, condition, syndrome or disorder.

As used herein, the term "treat", "treating", or "treatment" of any disease, condition, syndrome or disorder refers, in one embodiment, to ameliorating the disease, condition, syndrome or disorder (i.e. slowing or arresting or reducing the development of the disease or at least one of the clinical symptoms thereof). In another embodiment, "treat", "treating", or "treatment" refers to alleviating or ameliorating at lease one physical parameter including those which may not be discernible by the patient. In a further embodiment, "treat", "treating", or "treatment" refers to modulating the disease, condition, syndrome or disorder either physically (e.g. stabilization of a discernible symptom), physiologically, (e.g. stabilization of a physical parameter), or both. In yet another embodiment, "treat", "treating", or "treatment" refers to preventing or delaying the onset or development or progression of the disease, condition, syndrome or disorder.

The compounds of the instant invention are useful in methods for treating or ameliorating a disease, a syndrome, a condition or a disorder that is affected by the inhibition of MALT1. Such methods comprise, consist of and/or consist essentially of administering to a subject, including an animal, a mammal, and a human in need of such treatment, amelioration and/or prevention, a therapeutically effective amount of a compound of Formula (I), or an enantiomer, diastereomer, solvate or pharmaceutically acceptable salt thereof.

One embodiment of the present invention is directed to a method of treating a MALT1-dependent or MALT1-mediated disease or condition in a subject in need thereof, including an animal, a mammal, and a human in need of such treatment, comprising administering to the subject a therapeutically effective amount of a compound of Formula (I).

In another embodiment, the MALT1-dependent or MALT1-mediated disease or condition is selected from cancers of hematopoietic origin or solid tumors such as chonic myelogenous leukemia, myeloid leukemia, non-Hodgkin lymphoma, and other B cell lymphomas.

In particular, the compounds of Formula (I), or an enantiomer, diastereomer, solvate or pharmaceutically acceptable salt form thereof are useful for treating or ameliorating diseases, syndromes, conditions, or disorders such as diffuse large B-cell lymphoma (DLBCL), mantle cell lymphoma (MCL), follicular lymphoma (FL), and mucosa-associated lymphoid tissue (MALT) lymphoma.

More particularly, the compounds of Formula (I), or an enantiomer, diastereomer, solvate or pharmaceutically acceptable salt form thereof, are useful for treating or ameliorating diffuse large B-cell lymphoma (DLBCL), mantle cell lymphoma (MCL), follicular lymphoma (FL), and mucosa-associated lymphoid tissue (MALT) lymphoma, comprising administering to a subject in need thereof a therapeutically effective amount of a compound of Formula (I), or an enantiomer, diastereomer, solvate or pharmaceutically acceptable salt form thereof as herein defined.

Further, the compounds of Formula (I), or an enantiomer, diastereomer, solvate or pharmaceutically acceptable salt form thereof, are useful for treating or ameliorating an immunological disease, syndrome, disorder, or condition selected from the group consisting of rheumatoid arthritis (RA), psoritic arthritis (PsA), psorisis (Pso), ulcerative colitis (UC), Crohn's disease, systemic lupus erythematosus (SLE), asthma, and chronic obstructive pulmonary disease (COPD).

Embodiments of the present invention include a compound of Formula (I)

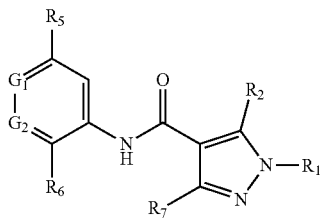

Formula (I)

wherein
AA) $R_1$ is
  i) naphthalen-1-yl, optionally substituted with a fluoro or amino substituent; or
  ii) a heteroaryl of nine to ten members containing one to four heteroatoms selected from the group consisting of O, N, and S; such that no more than one heteroatom is O or S; wherein said heteroaryl of ii) is optionally independently substituted with one or two substituents selected from deuterium, methyl, ethyl, propyl, isopropyl, trifluoromethyl, methoxymethyl, difluoromethyl, 1,1-difluoroethyl, hydroxymethyl, 1-hydroxyethyl, hydroxy, methoxy, fluoro, chloro, bromo, cyano, amino, methylamino, 4-oxotetrahydrofuran-2-yl, 5-oxopyrrolidin-2-yl, 1,4-dioxanyl, aminocarbonyl, methylaminocarbonyl, oxo, N-(methyl)formamidomethyl, tetrahydrofuran-2-yl, 3-hydroxy-pyrrolidin-1-yl, pyrrolidin-2-yl, 3-hydroxyazetidinyl, azetidin-3-yl, or azetidin-2-yl;
BB) $R_1$ is
  i) naphthalen-1-yl, optionally substituted with a fluoro or amino substituent; or
  ii) a heteroaryl of nine to ten members containing one to four heteroatoms selected from the group consisting of O, N, and S; such that no more than one heteroatom is O or S; wherein said heteroaryl of ii) is optionally independently substituted with one or two substituents selected from deuterium, methyl, difluoromethyl, hydroxymethyl, 1-hydroxyethyl, hydroxy, fluoro, cyano, amino, aminocarbonyl, methylaminocarbonyl, oxo, tetrahydrofuran-2-yl, 3-hydroxy-pyrrolidin-1-yl, pyrrolidin-2-yl, 3-hydroxyazetidinyl, azetidin-3-yl, or azetidin-2-yl;
CC) $R_1$ is
  i) naphthalen-1-yl, optionally substituted with an amino or fluoro substituent; or
  ii) a heteroaryl of nine to ten members containing one to four heteroatoms selected from the group consisting of O, N, and S; such that no more than one heteroatom is O or S; wherein said heteroaryl of ii) is optionally independently substituted with one or two substituents selected from hydroxymethyl, 1-hydroxyethyl, hydroxy, fluoro, cyano, amino, 3-hydroxyazetidinyl, or oxo;
DD) $R_1$ is
  i) naphthalen-1-yl, 4-amino-naphthalen-1-yl, 4-fluoronaphthalen-1-yl, or 5-fluoronaphthalen-1-yl; or
  ii) a heteroaryl selected from the group consisting of isoquinolin-1-yl, isoquinolin-4-yl, isoquinolin-5-yl, isoquinolin-8-yl, quinolin-7-yl, cinnolin-4-yl, imidazo[1,2-a]pyrazin-8-yl, phthalazin-1-yl, naphthyridin-5-yl, thieno[3,2-c]pyridin-4-yl, furo[3,2-c]pyridin-4-yl, furo[2,3-c]pyridin-7-yl, quinoxalin-5-yl, 1H-indazolylfuro[3,2-b]pyridin-7-yl, pyrazolo[1,5-a]pyrazin-4-yl, quinolin-4-yl, quinolin-5-yl, 1-aminoisoquinolin-4-yl, 1-oxo-1,2-dihydroisoquinolin-5-yl, benzo[d]thiazol-7-yl, 1-hydroxyisoquinolin-5-yl, benzo[d][1,2,3]thiadiazol-7-yl, thieno[2,3-c]pyridin-4-yl, pyrazolo[1,5-a]pyridin-4-yl, thieno[3,2-b]pyridin-7-yl, 2-oxo-1,2-dihydroquinolin-4-yl, 1-amino-8-fluoroisoquinolin-4-yl, 8-fluoroisoquinolin-4-yl, 1-cyanoisoquinolin-5-yl, pyrrolo[2,1-f][1,2,4]triazin-4-yl, 7-(1-hydroxyethyl)thieno[2,3-c]pyridin-4-yl, thieno[2,3-d]pyrimidin-4-yl, thieno[2,3-c]pyridin-7-yl, 1,7-naphthyridin-5-yl, pyrrolo[1,2-a]pyrazin-1-yl, imidazo[1,2-a]pyridin-5-yl, 1-aminocarbonyl-isoquinolin-4-yl, benzo[d]thiazol-4-yl, 8-fluoro-1-hydroxyisoquinolin-4-yl, thieno[3,2-d]pyrimidin-4-yl, 8-fluoroimidazo[1,2-a]pyridin-5-yl, 3-methylimidazo[1,2-a]pyridin-5-yl, 1-oxo-quinolin-4-yl, 8-aminoquinolin-5-yl, benzo[d]oxazol-4-yl, 3-methylthieno[3,2-b]pyridin-7-yl, 1-(hydroxymethyl)isoquinolin-4-yl, (3R-hydroxypyrrolidin-1-yl)isoquinolin-4-yl, (1-hydroxyethyl)isoquinolin-4-yl, 8-fluoroisoquinolin-4-yl, 2-(difluoromethyl)quinolin-4-yl, 8-fluoroquinolin-5-yl, 1-hydroxyisoquinolin-4-yl, 1-(tetrahydrofuran-2-yl)isoquinolin-4-yl, 7-(difluoromethyl)thieno[2,3-c]pyridin-4-yl, 1-(1-hydroxyethyl)isoquinolin-4-yl, 1-cyanoisoquinolin-4-yl, 1-(1R)-hydroxyethyl)isoquinolin-4-yl, quinazolin-4-yl, 2-methylimidazo[1,2-a]pyridin-3-yl, thiazolo[5,4-d]pyrimidin-7-yl, 6-N-oxido-1H-pyrazol-1-yl)thieno[2,3-c]pyridin-4-yl, imidazo[1,2-a]pyridin-3-yl, furo[2,3-d]pyrimidin-4-yl, 2-fluoroquinolin-5-yl, isoquinolin-5-yl, benzo[d]isothiazol-3-yl, 7-methylpyrazolo[1,5-a]pyridin-4-yl, 1-(hydroxyethyl)quinolin-4-yl, 1-(methoxymethyl)isoquinolin-4-yl, 1-fluoroisoquinolin-4-yl, 1-(difluoromethyl)isoquinolin-4-yl, 8-fluoroquinolin-4-yl, 8-fluoroquinolin-5-yl, 1-(tetrahydrofuran-2(R)-yl)isoquinolin-4-yl, 2-amino-[1,2,4]triazolo[1,5-a]pyridin-5-yl, 1-(4-oxotetrahydrofuran-2-yl)isoquinolin-4-yl, 2-(aminocarbonyl)quinolin-4-yl, 1H-indazol-7-yl, 1-(1,4-dioxan-2-yl)isoquinolin-4-yl, 2-methylimidazo[1,2-a]pyridin-5-yl, 1-chloroisoquinolin-4-yl, 2-cyanoquinolin-4-yl, 8-fluoro-1-(methylamino)isoquinolin-4-yl, benzo[d]isoxazol-3-yl, 2-aminobenzo[d]thiazol-7-yl, 2-fluoroquinolin-5-yl, 1,7-naphthyridin-4-yl, imidazo[1,2-a]pyrazin-5-yl, (N-(methyl)formamido)methyl)isoquinolin-4-yl, [1,2,4]triazolo[1,5-a]pyridin-5-yl, 2-methylbenzo[d]oxazol-7-yl, 1,5-naphthyridin-4-yl, 5-oxopyrrolidin-2-ylisoquinolin-4-yl, 1-methyl-1H-indazol-3-yl, 8-fluoroimidazo[1,2-a]pyridin-5-yl, 1-(tetrahydrofuran-2-yl)isoquinolin-4-yl, 1-(4-oxotetrahydrofuran- 2-yl)isoquinolin-4-yl, 1-(1,1-difluoroethyl)isoquinolin-4-yl, 1-(1(*S)-hydroxyethyl)isoquinolin-4-yl, 1-(methylamino)isoquinolin-4-yl, 4-fluoroisoquinolin-1-yl, 1H-pyrazolo[4,3-b]pyridin-7-yl, 5-fluoroquinolin-8-yl, 6-fluoroimidazo[1,2-a]pyridin-5-yl, 2-methylfuro[3,2-b]pyridin-7-yl, 8-(difluoromethyl)quinolin-5-yl, 1-(4-oxotetrahydrofuran-2R-yl)isoquinolin-4-yl, 1-(dimethylamino)isoquinolin-4-yl, 1-methyl-1H-pyrazolo[3,4-c]pyridin-7-yl, 2-methyl-[1,2,4]triazolo[1,5-a]pyridin-5-yl, 2-methoxyquinolin-4-yl, imidazo[1,2-a]pyrimidin-5-yl, 2-(difluoromethyl)thieno[2,3-c]pyridin-4-yl, quinolin-5-yl, 1-(1-ethoxyethyl)isoquinolin-4-yl, 2-(azetidin-2-yl)quinolin-4-yl, 2-methylbenzo[d]thiazol-7-yl, 2-acetylquinolin-4-yl, 1-(methylthio)isoquinolin-4-yl, 2-aminoquinolin-5-yl, 1-methoxyisoquinolin-5-yl, imidazo[1,2-b]pyridazin-6-yl, 1-(pyrrolidin-2-yl)isoquinolin-4-yl, 4-(difluoromethyl)quinolin-5-yl, 1-acetylisoquinolin-5-yl, 2-aminoquinolin-5-yl, 1-(azetidin-2-yl)isoquinolin-4-yl, 1-ethoxyisoquinolin-4-yl, 1-methyl-1H-pyrazolo[3,4-b]pyridin-4-yl, 1-aminoisoquinolin-5-yl, 1-methyl-1H-indazol-4-yl, 2-aminoquinolin-4-yl, 2-oxo-1,2-dihydroquinolin-5-yl, 1-(azetidin-3-yl)isoquinolin-4-yl, 2-methylthieno[3,2-b]pyridin-7-yl, benzo[d][1,2,3]thiadiazol-4-yl, 1-(1(S)-hydroxyethyl)isoquinolin-5-yl, imidazo[1,2-a]pyridin-8-yl, 2-methyl-1-oxo-1,2-dihydroisoquinolin-5-yl, 2-(tetrahydrofuran-2-yl)quinolin-5-yl, 1-(1(R)-hydroxyethyl)isoquinolin-5-yl, 1,6-naphthyridin-4-yl, 1H-pyrazolo[3,4-d]pyrimidin-4-yl, 2-aminocarbonyl-quinolin-5-yl, 2-chloroquinolin-5-yl, 2-chloroquinolin-4-yl, 2-cyanoquinolin-5-yl, 1-aminoisoquinolin-5-yl, 2-methoxyquinolin-5-yl, 2-methylbenzo[d]oxazol-4-yl, 2-(difluoromethyl)quinolin-5-yl, 2-(azetidin-2-yl)quinolin-5-yl, 1-(azetidin-2-yl)isoquinolin-5-yl, 1,5-bis(tetrahydrofuran-2-yl)isoquinolin-4-yl, 1-oxo-1,2-dihydroisoquinolin-4-yl, 2-methyl-1-oxo-1,2-dihydroisoquinolin-4-yl, 1-(3-hydroxyazetidin-1-yl)isoquinolin-4-yl, 8-fluoro-1-(3-hydroxyazetidin-1-yl)isoquinolin-4-yl, (R)-8-fluoro-1-(3-hydroxypyrrolidin-1-yl)isoquinolin-4-yl, (S)-8-fluoro-1-(3-hydroxypyrrolidin-1-yl)isoquinolin-4-yl, 3-hydroxyazetidin-1-yl)thieno[2,3-c]pyridin-4-yl, 8-(3-hydroxyazetidin-1-yl)imidazo[1,2-a]pyridin-5-yl, 7-(3-hydroxyazetidin-1-yl)pyrazolo[1,5-a]pyridin-4-yl, 1-(3-hydroxyazetidin-1-yl)isoquinolin-5-yl, and 1-(1-t-butoxycarbonylazetidin-2-yl)isoquinolin-5-yl;

EE) $R_1$ is
  i) napthalen-1-yl or 4-fluoronaphthalen-1-yl, 4-aminonaphthalen-1-yl or 5-fluoronaphthalen-1-yl; or
  ii) a heteroaryl selected from the group consisting of thieno[3,2-c]pyridin-4-yl, isoquinolin-4-yl, 8-fluoroquinolin-4-yl, furo[3,2-c]pyridin-4-yl, quinolin-5-yl, furo[2,3-c]pyridin-7-yl, benzofuran-4-yl 1,7-naphthyridin-5-yl, pyrrolo[1,2-a]pyrazin-1-yl, imidazo[1,2-a]pyridin-5-yl, 1-aminocarbonyl-isoquinolin-4-yl, pyrrolo[1,2-a]pyrazin-1-yl, benzo[d]thiazol-4-yl, 8-fluoro-1-hydroxyisoquinolin-4-yl, thieno[3,2-d]pyrimidin-4-yl, 8-fluoroimidazo[1,2-a]pyridin-5-yl, 3-methylimidazo[1,2-a]pyridin-5-yl, 1-aminoisoquinolin-4-yl, 1-oxo-quinolin-4-yl, 8-aminoquinolin-5-yl, benzo[d]oxazol-4-yl, 3-methylthieno[3,2-b]pyridin-7-yl, 1-(hydroxymethyl)isoquinolin-4-yl, (3R-hydroxypyrrolidin-1-yl)isoquinolin-4-yl, (1-hydroxyethyl)isoquinolin-4-yl, 8-fluoroisoquinolin-4-yl, 2-(difluoromethyl)quinolin-5-yl, 8-fluoroquinolin-5-yl, 1-hydroxyisoquinolin-4-yl, benzo[d]thiazol-4-yl, 1-aminoisoquinolin-4-yl, 1-(tetrahydrofuran-2-yl)isoquinolin-4-yl, 7-(difluoromethyl)thieno[2,3-c]pyridin-4-yl, 1-(1-hydroxyethyl)isoquinolin-4-yl, 1-cyanoisoquinolin-4-yl, 1-(1(R)-hydroxyethyl)isoquinolin-4-yl, quinazolin-4-yl, 2-methylimidazo[1,2-a]pyridin-3-yl, thiazolo[5,4-d]pyrimidin-7-yl, imidazo[1,2-a]pyridin-5-yl, benzo[d][1,2,3]thiadiazol-7-yl, 6-N-oxido-1H-pyrazol-1-yl)thieno[2,3-c]pyridin-4-yl, imidazo[1,2-a]pyridin-3-yl, furo[2,3-d]pyrimidin-4-yl, 2-fluoroquinolin-5-yl, isoquinolin-5-yl, benzo[d]isothiazol-3-yl, 7-methylpyrazolo[1,5-a]pyridin-4-yl, 1-oxo-1,2-dihydroisoquinolin-4-yl, 2-methyl-1-oxo-1,2-dihydroisoquinolin-4-yl, 1-(3-hydroxyazetidin-1-yl)isoquinolin-4-yl, 8-fluoro-1-(3-hydroxyazetidin-1-yl)isoquinolin-4-yl, (R)-8-fluoro-1-(3-hydroxypyrrolidin-1-yl)isoquinolin-4-yl, (S)-8-fluoro-1-(3-hydroxypyrrolidin-1-yl)isoquinolin-4-yl, 3-hydroxyazetidin-1-yl)thieno[2,3-c]pyridin-4-yl, 8-(3-hydroxyazetidin-1-yl)imidazo[1,2-a]pyridin-5-yl, 7-(3-hydroxyazetidin-1-yl)pyrazolo[1,5-a]pyridin-4-yl, 1-(3-hydroxyazetidin-1-yl)isoquinolin-5-yl, and 1-(hydroxyethyl)quinolin-4-yl;

FF) $R_2$ is independently selected from the group consisting of methyl, isopropyl, cyano, bromo, chloro, and trifluoromethyl;

GG) $R_2$ is independently selected from the group consisting of methyl, isopropyl, cyano, and trifluoromethyl;

HH) $R_2$ is trifluoromethyl;

II) $R_3$ is independently selected from the group consisting of trifluoromethyl, cyano, methylcarbonyl, methylthio, methylsulfinyl, methanesulfonyl, and chloro; or, when $G_1$ is N, $R_3$ is further selected from $C_{1-4}$alkoxycarbonyl;

JJ) $R_3$ is independently selected from the group consisting of trifluoromethyl, cyano, and chloro;

KK) $G_2$ is N or $C(R_3)$, wherein $R_3$ is chloro;

LL) $G_2$ is N;

MM) $R_4$ is selected from the group consisting of
  i) hydrogen, when $G_2$ is N;
  ii) $C_{1-4}$alkoxy;
  iii) cyano;
  iv) cyclopropyloxy;
  v) carboxy;
  vi) a heteroaryl selected from the group consisting of triazolyl, oxazolyl, pyrazolyl, thiazolyl, oxadiazolyl, imidazolyl, and pyrimidin-4-yl, wherein the heteroaryl is optionally substituted with one or two substituents independently selected from the group consisting of $C_{1-4}$alkyl, carboxy, methoxycarbonyl, hydroxymethyl, aminocarbonyl, (dimethylamino)methyl, amino, methoxymethyl, trifluoromethyl, amino($C_{2-4}$alkyl) amino, and cyano;
  vii) 1-methyl-piperidin-4-yloxy;
  viii) 4-methyl-piperazin-1-ylcarbonyl;
  ix) (4-aminobutyl)aminocarbonyl;
  x) (4-amino)butoxy;
  xi) methoxycarbonyl;
  xii) 5-chloro-6-(methoxycarbonyl)pyridin-3-ylaminocarbonyl;
  xiii) 1,1-dioxo-isothiazolidin-2-yl; and
  xiv) morpholin-4-ylcarbonyl;

NN) $R_4$ is selected from the group consisting of
  i) hydrogen;
  ii) $C_{1-4}$alkoxy;
  iii) cyano;
  iv) cyclopropyloxy;
  v) a heteroaryl selected from the group consisting of triazolyl, oxazolyl, pyrazolyl, thiazolyl, oxadiazolyl, and imidazolyl, wherein the heteroaryl is optionally substituted with one or two substituents independently selected from the group consisting of methyl, carboxy, methoxycarbonyl, hydroxymethyl, aminocarbonyl, (dimethylamino)methyl, and amino, methoxymethyl;
vi) (4-amino)butoxy;
vii) methoxycarbonyl;
viii) 5-chloro-6-(methoxycarbonyl)pyridin-3-ylaminocarbonyl; and
ix) 1,1-dioxo-isothiazolidin-2-yl;
OO) $R_4$ is selected from the group consisting of
i) methoxy;
ii) a heteroaryl independently selected from the group consisting of 2H-1,2,3-triazol-2-yl, 4-carboxy-2H-1,2,3-triazol-2-yl, 4-(hydroxymethyl)-2H-1,2,3-triazol-2-yl, 4-methyl-2H-1,2,3-triazol-2-yl, oxazol-2-yl, 4-amino-2H-1,2,3-triazol-2-yl, 4-(hydroxymethyl)-1H-pyrazol-1-yl, 4-(hydroxymethyl)-2H-1,2,3-triazol-2-yl, 4-((dimethylamino)methyl)-2H-1,2,3-triazol-2-yl, 4-methoxycarbonyl-2H-1,2,3-triazol-2-yl, 4-aminocarbonyl-2H-1,2,3-triazol-2-yl, 1-methyl-1H-pyrazol-3-yl, 1,3,4-oxadiazol-2-yl, 2-methyl-2H-tetrazol-5-yl, 5-amino-1-methyl-1H-pyrazol-3-yl, 4-(hydroxyethyl)-1H-pyrazol-1-yl, 4-cyano-2H-1,2,3-triazol-2-yl, 5-amino-1H-1,2,3-triazol-1-yl, 2H-1,2,3-triazol-4-yl, 2H-tetrazol-5-yl, 4-(aminomethyl)-1H-pyrazol-1-yl, 4-(methoxymethyl)-2H-1,2,3-triazol-2-yl, 2-methyl-2H-tetrazol-5-yl, and 4-methyl-1H-1,2,3-triazol-1-yl; and
iii) methoxycarbonyl;
PP) $R_4$ is independently selected from the group consisting of 2H-1,2,3-triazol-2-yl, 4-carboxy-2H-1,2,3-triazol-2-yl, 4-(hydroxymethyl)-2H-1,2,3-triazol-2-yl, 4-methyl-2H-1,2,3-triazol-2-yl, oxazol-2-yl, 1H-imidazol-2-yl, 4-amino-2H-1,2,3-triazol-2-yl, 4-(hydroxymethyl)-1H-pyrazol-1-yl, 4-(hydroxymethyl)-2H-1,2,3-triazol-2-yl, 4-((dimethylamino)methyl)-2H-1,2,3-triazol-2-yl, 4-methoxycarbonyl-2H-1,2,3-triazol-2-yl, 4-aminocarbonyl-2H-1,2,3-triazol-2-yl, 1-methyl-1H-pyrazol-3-yl, and 1,3,4-oxadiazol-2-yl;
QQ) $R_5$ is hydrogen, chloro, fluoro, bromo, cyano, methyl, ethyl, or trifluoromethyl; or, $R_4$ and $R_5$ may be taken together to form 8-chloro-4-methyl-3-oxo-3,4-dihydro-2H-benzo[b][1,4]oxazin-6-yl or 8-chloro-3-oxo-3,4-dihydro-2H-benzo[b][1,4]oxazin-6-yl;
RR) $R_5$ is hydrogen, chloro, bromo, cyano, or trifluoromethyl; or, $R_4$ and $R_5$ may be taken together to form 8-chloro-4-methyl-3-oxo-3,4-dihydro-2H-benzo[b][1,4]oxazin-6-yl or 8-chloro-3-oxo-3,4-dihydro-2H-benzo[b][1,4]oxazin-6-yl;
SS) $R_5$ is hydrogen, chloro, bromo, or cyano;
TT) $R_5$ is hydrogen, chloro, or cyano;
UU) $R_6$ is hydrogen or methyl;
VV) $R_7$ is hydrogen;
and any combination of embodiments AA) though VV) above, provided it is understood that combinations in which different embodiments of the same substituent would be combined are excluded; such that only one of $G_1$ and $G_2$ are N in any instance;

and provided that a compound of Formula (I) is other than a compound wherein $R_1$ is isoquinolin-8-yl, $R_2$ is trifluoromethyl, $G_1$ is $C(R_4)$ wherein $R_4$ is 2H-1,2,3-triazol-2-yl, $G_2$ is N, and $R_5$ is hydrogen;
a compound wherein $R_1$ is isoquinolin-8-yl, $R_2$ is trifluoromethyl, $G_1$ is $C(R_4)$ wherein $R_4$ is 1H-imidazol-1-yl, $G_2$ is N, and $R_5$ is chloro;
a compound wherein $R_1$ is isoquinolin-8-yl, $R_2$ is trifluoromethyl, $G_1$ is $C(R_4)$ wherein $R_4$ is 1H-1,2,3-triazol-1-yl, $G_2$ is N, and $R_5$ is hydrogen;
a compound wherein $R_1$ is isoquinolin-8-yl, $R_2$ is trifluoromethyl, $G_1$ is $C(R_4)$ wherein $R_4$ is hydrogen, $G_2$ is N, and $R_5$ is fluoro;
a compound wherein $R_1$ quinolin-4-yl, $R_2$ is hydrogen, $G_1$ is $C(R_4)$ wherein $R_4$ is (2H)-1,2,3-triazol-2-yl, $G_2$ is N, and $R_5$ is chloro;
or an enantiomer, diastereomer, or pharmaceutically acceptable salt form thereof.

Embodiments of the present invention include a compound of Formula (I)

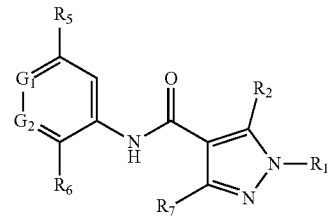

Formula (I)

wherein
$R_1$ is selected from the group consisting of
i) naphthalen-1-yl, 4-amino-naphthalen-1-yl, or 4-fluoronaphthalen-1-yl, 5-fluoronaphthalen-1-yl; and
ii) a heteroaryl of nine to ten members containing one to four heteroatoms selected from the group consisting of O, N, and S; such that no more than one heteroatom is O or S; wherein said heteroaryl of ii) is optionally independently substituted with one or two substituents selected from deuterium, methyl, ethyl, propyl, isopropyl, trifluoromethyl, methoxymethyl, difluoromethyl, 1,1-difluoroethyl, hydroxymethyl, 1-hydroxyethyl, hydroxy, methoxy, fluoro, chloro, bromo, cyano, amino, methylamino, 4-oxotetrahydrofuran-2-yl, 5-oxopyrrolidin-2-yl, 1,4-dioxanyl, aminocarbonyl, methylaminocarbonyl, oxo, N-(methyl)formamidomethyl, tetrahydrofuran-2-yl, 3-hydroxy-pyrrolidin-1-yl, pyrrolidin-2-yl, 3-hydroxyazetidinyl, azetidin-3-yl, or azetidin-2-yl;
$R_2$ is independently selected from the group consisting of methyl, isopropyl, cyano, bromo, chloro, and trifluoromethyl;
$G_1$ is N or $C(R_4)$;
$G_2$ is N or $C(R_3)$; such that only one of $G_1$ and $G_2$ is N in any instance;
$R_3$ is independently selected from the group consisting of trifluoromethyl, cyano, methylcarbonyl, methylthio, methylsulfinyl, methanesulfonyl, and chloro; or, when $G_1$ is N, $R_3$ is further selected from $C_{1-4}$alkoxycarbonyl;
$R_4$ is independently selected from the group consisting of
i) hydrogen, when $G_2$ is N;
ii) $C_{1-4}$alkoxy;
iii) cyano;
iv) cyclopropyloxy;
v) carboxy;
vi) a heteroaryl selected from the group consisting of triazolyl, oxazolyl, pyrazolyl, thiazolyl, oxadiazolyl, imidazolyl, and pyrimidin-4-yl, wherein the heteroaryl is optionally substituted with one or two substituents independently selected from the group consisting of $C_{1-4}$alkyl, carboxy, methoxycarbonyl, hydroxymethyl, aminocarbonyl, (dimethylamino)methyl, amino, methoxymethyl, trifluoromethyl, amino($C_{2-4}$alkyl)amino, and cyano;

vii) 1-methyl-piperidin-4-yloxy;
viii) 4-methyl-piperazin-1-ylcarbonyl;
ix) (4-aminobutyl)aminocarbonyl;
x) (4-amino)butoxy;
xi) methoxycarbonyl;
xii) 5-chloro-6-(methoxycarbonyl)pyridin-3-ylaminocarbonyl;
xiii) 1,1-dioxo-isothiazolidin-2-yl;
and
xiv) morpholin-4-ylcarbonyl;

$R_5$ is hydrogen, chloro, fluoro, bromo, cyano, methyl, ethyl, or trifluoromethyl; or, $R_4$ and $R_5$ may be taken together to form 8-chloro-4-methyl-3-oxo-3,4-dihydro-2H-benzo[b][1,4]oxazin-6-yl or 8-chloro-3-oxo-3,4-dihydro-2H-benzo[b][1,4]oxazin-6-yl;

$R_6$ is hydrogen or methyl;
$R_7$ is hydrogen;

and provided that a compound of Formula (I) is other than
a compound wherein $R_1$ is isoquinolin-8-yl, $R_2$ is trifluoromethyl, $G_1$ is $C(R_4)$ wherein $R_4$ is 2H-1,2,3-triazol-2-yl, $G_2$ is N, and $R_5$ is hydrogen;
a compound wherein $R_1$ is isoquinolin-8-yl, $R_2$ is trifluoromethyl, $G_1$ is $C(R_4)$ wherein $R_4$ is 1H-imidazol-1-yl, $G_2$ is N, and $R_5$ is chloro;
a compound wherein $R_1$ is isoquinolin-8-yl, $R_2$ is trifluoromethyl, $G_1$ is $C(R_4)$ wherein $R_4$ is 1H-1,2,3-triazol-1-yl, $G_2$ is N, and $R_5$ is hydrogen;
a compound wherein $R_1$ is isoquinolin-8-yl, $R_2$ is trifluoromethyl, $G_1$ is $C(R_4)$ wherein $R_4$ is hydrogen, $G_2$ is N, and $R_5$ is fluoro;
a compound wherein $R_1$ quinolin-4-yl, $R_2$ is hydrogen, $G_1$ is $C(R_4)$ wherein $R_4$ is (2H)-1,2,3-triazol-2-yl, $G_2$ is N, and $R_5$ is chloro;
or an enantiomer, diastereomer, or pharmaceutically acceptable salt form thereof.

Embodiments of the present invention include a compound of Formula (I)

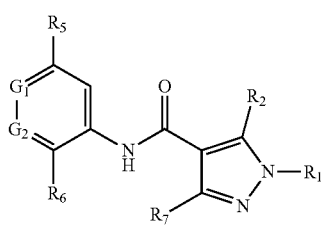

Formula (I)

wherein
$R_1$ is selected from the group consisting of
i) naphthalen-1-yl, optionally substituted with a fluoro or amino substituent;
or
ii) a heteroaryl of nine to ten members containing one to four heteroatoms selected from the group consisting of O, N, and S; such that no more than one heteroatom is O or S; wherein said heteroaryl of ii) is optionally independently substituted with one or two substituents selected from deuterium, methyl, difluoromethyl, hydroxymethyl, 1-hydroxyethyl, hydroxy, fluoro, cyano, amino, aminocarbonyl, methylaminocarbonyl, oxo, tetrahydrofuran-2-yl, 3-hydroxy-pyrrolidin-1-yl, pyrrolidin-2-yl, 3-hydroxyazetidinyl, azetidin-3-yl, or azetidin-2-yl;

$R_2$ is selected from the group consisting of methyl, isopropyl, cyano, and trifluoromethyl;

$G_1$ is N or $C(R_4)$;
$G_2$ is N or $C(R_3)$; such that only one of $G_1$ and $G_2$ is N in any instance;

$R_3$ is independently selected from the group consisting of trifluoromethyl, cyano, and chloro;

$R_4$ is independently selected from the group consisting of
i) hydrogen;
ii) $C_{1-4}$alkoxy;
iii) cyano;
iv) cyclopropyloxy;
v) a heteroaryl selected from the group consisting of triazolyl, oxazolyl, pyrazolyl, thiazolyl, oxadiazolyl, and imidazolyl, wherein the heteroaryl is optionally substituted with one or two substituents independently selected from the group consisting of methyl, carboxy, methoxycarbonyl, hydroxymethyl, aminocarbonyl, (dimethylamino)methyl, and amino, methoxymethyl;
vi) (4-amino)butoxy;
vii) methoxycarbonyl;
viii) 5-chloro-6-(methoxycarbonyl)pyridin-3-ylaminocarbonyl;
and
ix) 1,1-dioxo-isothiazolidin-2-yl;

$R_5$ is hydrogen, chloro, bromo, or cyano;
$R_6$ is hydrogen or methyl;
$R_7$ is hydrogen;

provided that a compound of Formula (I) is other than
a compound wherein $R_1$ is isoquinolin-8-yl, $R_2$ is trifluoromethyl, $G_1$ is $C(R_4)$ wherein $R_4$ is 2H-1,2,3-triazol-2-yl, $G_2$ is N, and $R_5$ is hydrogen;
a compound wherein $R_1$ is isoquinolin-8-yl, $R_2$ is trifluoromethyl, $G_1$ is $C(R_4)$ wherein $R_4$ is 1H-imidazol-1-yl, $G_2$ is N, and $R_5$ is chloro;
a compound wherein $R_1$ is isoquinolin-8-yl, $R_2$ is trifluoromethyl, $G_1$ is $C(R_4)$ wherein $R_4$ is 1H-1,2,3-triazol-1-yl, $G_2$ is N, and $R_5$ is hydrogen;
a compound wherein $R_1$ is isoquinolin-8-yl, $R_2$ is trifluoromethyl, $G_1$ is $C(R_4)$ wherein $R_4$ is hydrogen, $G_2$ is N, and $R_5$ is fluoro;
a compound wherein $R_1$ quinolin-4-yl, $R_2$ is hydrogen, $G_1$ is $C(R_4)$ wherein $R_4$ is (2H)-1,2,3-triazol-2-yl, $G_2$ is N, and $R_5$ is chloro;
or an enantiomer, diastereomer, or pharmaceutically acceptable salt form thereof.

Embodiments of the present invention include a compound of Formula (I)

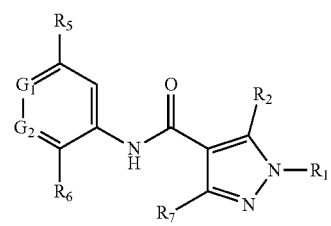

Formula (I)

wherein
R₁ is selected from the group consisting of
i) naphthalen-1-yl, optionally substituted with a fluoro or amino substituent; and
ii) a heteroaryl of nine to ten members containing one to four heteroatoms selected from the group consisting of O, N, and S; such that no more than one heteroatom is O or S; wherein said heteroaryl of ii) is optionally independently substituted with one or two substituents selected from hydroxymethyl, 1-hydroxyethyl, hydroxy, fluoro, cyano, amino, oxo, 3-hydroxy-pyrrolidin-1-yl, pyrrolidin-2-yl, 3-hydroxyazetidinyl, azetidin-3-yl, or azetidin-2-yl;

R₂ is selected from the group consisting of methyl, isopropyl, cyano, and trifluoromethyl;

G₁ is N or C(R₄);

G₂ is N or C(R₃); such that only one of G₁ and G₂ is N in any instance;

R₃ is independently selected from the group consisting of trifluoromethyl, cyano, and chloro;

R₄ is selected from the group consisting of
i) methoxy;
ii) a heteroaryl selected from the group consisting of 2H-1,2,3-triazol-2-yl, 4-carboxy-2H-1,2,3-triazol-2-yl, 4-(hydroxymethyl)-2H-1,2,3-triazol-2-yl, 4-methyl-2H-1,2,3-triazol-2-yl, oxazol-2-yl, 4-amino-2H-1,2,3-triazol-2-yl, 4-(hydroxymethyl)-1H-pyrazol-1-yl, 4-(hydroxymethyl)-2H-1,2,3-triazol-2-yl, 4-((dimethylamino)methyl)-2H-1,2,3-triazol-2-yl, 4-methoxycarbonyl-2H-1,2,3-triazol-2-yl, 4-aminocarbonyl-2H-1,2,3-triazol-2-yl, 1-methyl-1H-pyrazol-3-yl, 1,3,4-oxadiazol-2-yl, 2-methyl-2H-tetrazol-5-yl, 5-amino-1-methyl-1H-pyrazol-3-yl, 4-(hydroxymethyl)-1H-pyrazol-1-yl, 4-cyano-2H-1,2,3-triazol-2-yl, 5-amino-1H-1,2,3-triazol-1-yl, 2H-1,2,3-triazol-4-yl, 2H-tetrazol-5-yl, 4-(aminomethyl)-1H-pyrazol-1-yl, 4-(methoxymethyl)-2H-1,2,3-triazol-2-yl, 2-methyl-2H-tetrazol-5-yl, and 4-methyl-1H-1,2,3-triazol-1-yl; and
iii) methoxycarbonyl;

R₅ is hydrogen, chloro, or cyano;
R₆ is hydrogen or methyl;
R₇ is hydrogen;

or an enantiomer, diastereomer, or pharmaceutically acceptable salt form thereof.

Embodiments of the present invention include a compound of Formula (I)

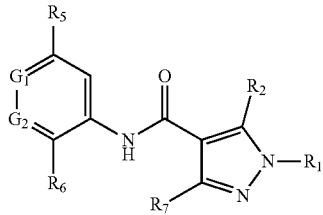

Formula (I)

wherein
R₁ is independently selected from the group consisting of
i) naphthalen-1-yl, 4-amino-naphthalen-1-yl, 4-fluoronaphthalen-1-yl, or 5-fluoronaphthalen-1-yl; and
ii) a heteroaryl selected from the group consisting of isoquinolin-1-yl, isoquinolin-4-yl, isoquinolin-5-yl, isoquinolin-8-yl, quinolin-7-yl, cinnolin-4-yl, imidazo[1,2-a]pyrazin-8-yl, phthalazin-1-yl, naphthyridin-5-yl, thieno[3,2-c]pyridin-4-yl, furo[3,2-c]pyridin-4-yl, furo[2,3-c]pyridin-7-yl, quinoxalin-5-yl, 1H-indazolylfuro[3,2-b]pyridin-7-yl, pyrazolo[1,5-a]pyrazin-4-yl, quinolin-4-yl, quinolin-5-yl, 1-aminoisoquinolin-4-yl, 1-oxo-1,2-dihydroisoquinolin-5-yl, benzo[d]thiazol-7-yl, 1-hydroxyisoquinolin-5-yl, benzo[d][1,2,3]thiadiazol-7-yl, thieno[2,3-c]pyridin-4-yl, pyrazolo[1,5-a]pyridin-4-yl, thieno[3,2-b]pyridin-7-yl, 2-oxo-1,2-dihydroquinolin-4-yl, 1-amino-8-fluoroisoquinolin-4-yl, 8-fluoroisoquinolin-4-yl, 1-cyanoisoquinolin-5-yl, pyrrolo[2,1-f][1,2,4]triazin-4-yl, 7-(1-hydroxyethyl)thieno[2,3-c]pyridin-4-yl, thieno[2,3-d]pyrimidin-4-yl, thieno[2,3-c]pyridin-7-yl, 1,7-naphthyridin-5-yl, pyrrolo[1,2-a]pyrazin-1-yl, imidazo[1,2-a]pyridin-5-yl, 1-aminocarbonyl-isoquinolin-4-yl, benzo[d]thiazol-4-yl, 8-fluoro-1-hydroxyisoquinolin-4-yl, thieno[3,2-d]pyrimidin-4-yl, 8-fluoroimidazo[1,2-a]pyridin-5-yl, 3-methylimidazo[1,2-a]pyridin-5-yl, 1-oxo-quinolin-4-yl, 8-aminoquinolin-5-yl, benzo[d]oxazol-4-yl, 3-methylthieno[3,2-b]pyridin-7-yl, 1-(hydroxymethyl)isoquinolin-4-yl, (3R-hydroxypyrrolidin-1-yl)isoquinolin-4-yl, (1-hydroxyethyl)isoquinolin-4-yl, 8-fluoroisoquinolin-4-yl, 2-(difluoromethyl)quinolin-4-yl, 8-fluoroquinolin-5-yl, 1-hydroxyisoquinolin-4-yl, 1-(tetrahydrofuran-2-yl)isoquinolin-4-yl, 7-(difluoromethyl)thieno[2,3-c]pyridin-4-yl, 1-(1-hydroxyethyl)isoquinolin-4-yl, 1-cyanoisoquinolin-4-yl, 1-(1(R)-hydroxyethyl)isoquinolin-4-yl, quinazolin-4-yl, 2-methylimidazo[1,2-a]pyridin-3-yl, thiazolo[5,4-d]pyrimidin-7-yl, 6-N-oxido-1H-pyrazol-1-yl)thieno[2,3-c]pyridin-4-yl, imidazo[1,2-a]pyridin-3-yl, furo[2,3-d]pyrimidin-4-yl, 2-fluoroquinolin-5-yl, isoquinolin-5-yl, benzo[d]isothiazol-3-yl, 7-methylpyrazolo[1,5-a]pyridin-4-yl, 1-(hydroxyethyl)quinolin-4-yl, 1-(methoxymethyl)isoquinolin-4-yl, 1-fluoroisoquinolin-4-yl, 1-(difluoromethyl)isoquinolin-4-yl, 8-fluoroquinolin-4-yl, 8-fluoroquinolin-5-yl, 1-(tetrahydrofuran-2(R)-yl)isoquinolin-4-yl, 2-amino-[1,2,4]triazolo[1,5-a]pyridin-5-yl, 1-(4-oxotetrahydrofuran-2-yl)isoquinolin-4-yl, 2-(aminocarbonyl)quinolin-4-yl, 1H-indazol-7-yl, 1-(1,4-dioxan-2-yl)isoquinolin-4-yl, 2-methylimidazo[1,2-a]pyridin-5-yl, 1-chloroisoquinolin-4-yl, 2-cyanoquinolin-4-yl, 8-fluoro-1-(methylamino)isoquinolin-4-yl, benzo[d]isoxazol-3-yl, 2-aminobenzo[d]thiazol-7-yl, 2-fluoroquinolin-5-yl, 1,7-naphthyridin-4-yl, imidazo[1,2-a]pyrazin-5-yl, (N-(methyl)formamido)methyl)isoquinolin-4-yl, [1,2,4]triazolo[1,5-a]pyridin-5-yl, 2-methylbenzo[d]oxazol-7-yl, 1,5-naphthyridin-4-yl, 5-oxopyrrolidin-2-ylisoquinolin-4-yl, 1-methyl-1H-indazol-3-yl, 8-fluoroimidazo[1,2-a]pyridin-5-yl, 1-(tetrahydrofuran-2-yl)isoquinolin-4-yl, 1-(4-oxotetrahydrofuran-2-yl)isoquinolin-4-yl, 1-(1,1-difluoroethyl)isoquinolin-4-yl, 1-(1(ˣS)-hydroxyethyl)isoquinolin-4-yl, 1-(methylamino)isoquinolin-4-yl, 4-fluoroisoquinolin-1-yl, 1H-pyrazolo[4,3-b]pyridin-7-yl, 5-fluoroquinolin-8-yl, 6-fluoroimidazo[1,2-a]pyridin-5-yl, 2-methylfuro[3,2-b]pyridin-7-yl, 8-(difluoromethyl)quinolin-5-yl, 1-(4-oxotetrahydrofuran-2R-yl)isoquinolin-4-yl, 1-(dimethylamino)isoquinolin-4-yl, 1-methyl-1H-pyrazolo[3,4-c]pyridin-7-yl, 2-methyl-[1,2,4]triazolo[1,5-a]pyridin-5-yl, 2-methoxyquinolin-4-yl, imidazo[1,2-a]pyrimidin-5-yl, 2-(difluoromethyl)thieno[2,3-c]pyridin-4-yl, quinolin-5-yl, 1-(1-ethoxyethyl)isoquinolin-4-yl, 2-(azetidin-2-yl)quinolin-4-yl, 2-methylbenzo[d]thiazol-7-yl, 2-acetylquinolin-4-yl, 1-(methylthio)isoquinolin-4-yl, 2-aminoquinolin-5-yl, 1-methoxyisoquinolin-5-yl, imidazo[1,2-b]pyridazin-6-yl, 1-(pyrrolidin-2-yl)isoquinolin-4-yl, 4-(difluoromethyl)quinolin-5-yl, 1-acetylisoquinolin-5-yl, 2-aminoquinolin-5-yl, 1-(azetidin-2-yl)isoquinolin-4-yl, 1-ethoxyisoquinolin-4-yl, 1-methyl-1H-pyrazolo[3,4-b]pyridin-4-yl, 1-aminoisoquinolin-5-yl, 1-methyl-1H-indazol-4-yl, 2-aminoquinolin-4-yl, 2-oxo-1,2-dihydroquinolin-5-yl, 1-(azetidin-3-yl)isoquinolin-4-yl, 2-methylthieno[3,2-b]pyridin-7-yl, benzo[d][1,2,3]thiadiazol-4-yl, 1-(1(S)-hydroxyethyl)isoquinolin-5-yl, imidazo[1,2-a]pyridin-8-yl, 2-methyl-1-oxo-1,2-dihydroisoquinolin-5-yl, 2-(tetrahydrofuran-2-yl)quinolin-5-yl, 1-(1(R)-hydroxyethyl)isoquinolin-5-yl, 1,6-naphthyridin-4-yl, 1H-pyrazolo[3,4-d]pyrimidin-4-yl, 2-aminocarbonylquinolin-5-yl, 2-chloroquinolin-5-yl, 2-chloroquinolin-4-yl, 2-cyanoquinolin-5-yl, 1-aminoisoquinolin-5-yl, 2-methoxyquinolin-5-yl, 2-methylbenzo[d]oxazol-4-yl, 2-(difluoromethyl)quinolin-5-yl, 2-(azetidin-2-yl)quinolin-5-yl, 1-(azetidin-2-yl)isoquinolin-5-yl, 1,5-bis(tetrahydrofuran-2-yl)isoquinolin-4-yl, 1-oxo-1,2-dihydroisoquinolin-4-yl, 2-methyl-1-oxo-1,2-dihydroisoquinolin-4-yl, 1-(3-hydroxyazetidin-1-yl)isoquinolin-4-yl, 8-fluoro-1-(3-hydroxyazetidin-1-yl)isoquinolin-4-yl, (R)-8-fluoro-1-(3-hydroxypyrrolidin-1-yl)isoquinolin-4-yl, (S)-8-fluoro-1-(3-hydroxypyrrolidin-1-yl)isoquinolin-4-yl, 3-hydroxyazetidin-1-yl)thieno[2,3-c]pyridin-4-yl, 8-(3-hydroxyazetidin-1-yl)imidazo[1,2-a]pyridin-5-yl, 7-(3-hydroxyazetidin-1-yl)pyrazolo[1,5-a]pyridin-4-yl, 1-(3-hydroxyazetidin-1-yl)isoquinolin-5-yl, and 1-(1-t-butoxycarbonylazetidin-2-yl)isoquinolin-5-yl;

$R_2$ is trifluoromethyl;

$G_1$ is N or $C(R_4)$;

$G_2$ is N or $C(R_3)$; such that only one of $G_1$ and $G_2$ is N in any instance;

$R_3$ is independently selected from the group consisting of trifluoromethyl, cyano, and chloro;

$R_4$ is independently selected from the group consisting of 2H-1,2,3-triazol-2-yl, 4-carboxy-2H-1,2,3-triazol-2-yl, 4-(hydroxymethyl)-2H-1,2,3-triazol-2-yl, 4-methyl-2H-1,2,3-triazol-2-yl, oxazol-2-yl, 1H-imidazol-2-yl, 4-amino-2H-1,2,3-triazol-2-yl, 4-(hydroxymethyl)-1H-pyrazol-1-yl, 4-(hydroxymethyl)-2H-1,2,3-triazol-2-yl, 4-((dimethylamino)methyl)-2H-1,2,3-triazol-2-yl, 4-methoxycarbonyl-2H-1,2,3-triazol-2-yl, 4-aminocarbonyl-2H-1,2,3-triazol-2-yl, 1-methyl-1H-pyrazol-3-yl, and 1,3,4-oxadiazol-2-yl;

$R_5$ is hydrogen, chloro, bromo, or cyano;

$R_6$ is hydrogen or methyl;

$R_7$ is hydrogen;

or an enantiomer, diastereomer, or pharmaceutically acceptable salt form thereof.

Embodiments of the present invention include a compound of Formula (I)

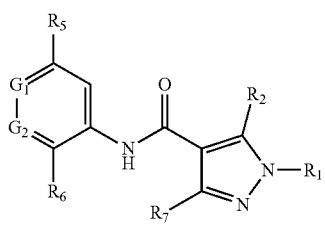

Formula (I)

wherein $R_1$ is independently selected from the group consisting of
i) napthalen-1-yl, 4-amino-naphthalen-1-yl, 4-fluoronaphthalen-1-yl, or 5-fluoronaphthalen-1-yl;
and
ii) a heteroaryl selected from the group consisting of thieno[3,2-c]pyridin-4-yl, isoquinolin-4-yl, 8-fluoroquinolin-4-yl, furo[3,2-c]pyridin-4-yl, quinolin-5-yl, furo[2,3-c]pyridin-7-yl, benzofuran-4-yl 1,7-naphthyridin-5-yl, pyrrolo[1,2-a]pyrazin-1-yl, imidazo[1,2-a]pyridin-5-yl, 1-aminocarbonyl-isoquinolin-4-yl, pyrrolo[1,2-a]pyrazin-1-yl, benzo[d]thiazol-4-yl, 8-fluoro-1-hydroxyisoquinolin-4-yl, thieno[3,2-d]pyrimidin-4-yl, 8-fluoroimidazo[1,2-a]pyridin-5-yl, 3-methylimidazo[1,2-a]pyridin-5-yl, 1-aminoisoquinolin-4-yl, 1-oxo-quinolin-4-yl, 8-aminoquinolin-5-yl, benzo[d]oxazol-4-yl, 3-methylthieno[3,2-b]pyridin-7-yl, 1-(hydroxymethyl)isoquinolin-4-yl, (3R-hydroxypyrrolidin-1-yl)isoquinolin-4-yl, (1-hydroxyethyl)isoquinolin-4-yl, 8-fluoroisoquinolin-4-yl, 2-(difluoromethyl)quinolin-4-yl, 8-fluoroquinolin-5-yl, 1-hydroxyisoquinolin-4-yl, benzo[d]thiazol-4-yl, 1-aminoisoquinolin-4-yl, 1-(tetrahydrofuran-2-yl)isoquinolin-4-yl, 7-(difluoromethyl)thieno[2,3-c]pyridin-4-yl, 1-(1-hydroxyethyl)isoquinolin-4-yl, 1-cyanoisoquinolin-4-yl, 1-(1(R)-hydroxyethyl)isoquinolin-4-yl, quinazolin-4-yl, 2-methylimidazo[1,2-a]pyridin-3-yl, thiazolo[5,4-d]pyrimidin-7-yl, imidazo[1,2-a]pyridin-5-yl, benzo[d][1,2,3]thiadiazol-7-yl, 6-N-oxido-1H-pyrazol-1-yl)thieno[2,3-c]pyridin-4-yl, imidazo[1,2-a]pyridin-3-yl, furo[2,3-d]pyrimidin-4-yl, 2-fluoroquinolin-5-yl, isoquinolin-5-yl, benzo[d]isothiazol-3-yl, 7-methylpyrazolo[1,5-a]pyridin-4-yl, 1-oxo-1,2-dihydroisoquinolin-4-yl, 2-methyl-1-oxo-1,2-dihydroisoquinolin-4-yl, 1-(3-hydroxyazetidin-1-yl)isoquinolin-4-yl, 8-fluoro-1-(3-hydroxyazetidin-1-yl)isoquinolin-4-yl, (R)-8-fluoro-1-(3-hydroxypyrrolidin-1-yl)isoquinolin-4-yl, (S)-8-fluoro-1-(3-hydroxypyrrolidin-1-yl)isoquinolin-4-yl, 3-hydroxyazetidin-1-yl)thieno[2,3-c]pyridin-4-yl, 8-(3-hydroxyazetidin-1-yl)imidazo[1,2-a]pyridin-5-yl, 7-(3-hydroxyazetidin-1-yl)pyrazolo[1,5-a]pyridin-4-yl, 1-(3-hydroxyazetidin-1-yl)isoquinolin-5-yl and 1-(hydroxyethyl)quinolin-4-yl;

$R_2$ is trifluoromethyl;

$G_1$ is N or $C(R_4)$;

$G_2$ is N or $C(R_3)$; such that only one of $G_1$ and $G_2$ is N in any instance;

$R_3$ is independently selected from the group consisting of trifluoromethyl, cyano, and chloro;

$R_4$ is independently selected from the group consisting of 2H-1,2,3-triazol-2-yl, 4-carboxy-2H-1,2,3-triazol-2-yl, 4-(hydroxymethyl)-2H-1,2,3-triazol-2-yl, 4-methyl-2H-1,2,3-triazol-2-yl, oxazol-2-yl, 1H-imidazol-2-yl, 4-amino-2H-1,2,3-triazol-2-yl, 4-(hydroxymethyl)-1H-pyrazol-1-yl, 4-(hydroxymethyl)-2H-1,2,3-triazol-2-yl, 4-((dimethylamino)methyl)-2H-1,2,3-triazol-2-yl, 4-methoxycarbonyl-2H-1,2,3-triazol-2-yl, 4-aminocarbonyl-2H-1,2,3-triazol-2-yl, 1-methyl-1H-pyrazol-3-yl, and 1,3,4-oxadiazol-2-yl;

$R_5$ is hydrogen, chloro, or cyano;

$R_6$ is hydrogen or methyl;

$R_7$ is hydrogen;

or an enantiomer, diastereomer, or pharmaceutically acceptable salt form thereof.

Additional embodiments of the present invention include compounds of Formula (I) as herein defined, or an enantiomer, diastereomer, solvate, or a pharmaceutically acceptable salt form thereof, as exemplified in the listing in Table 1, below.

TABLE 1

| Structure | Cpd No. | Cpd Name |
|---|---|---|
| 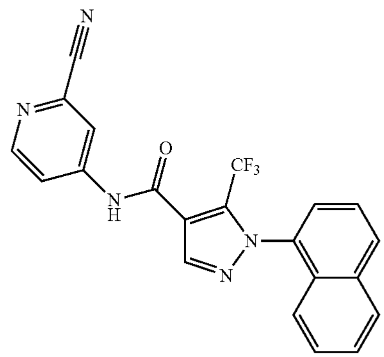 [SMILES: N#Cc1cc(NC(=O)c2cnn(-c3cccc4ccccc34)c2C(F)(F)F)ccn1] | 1 | N-(2-cyanopyridin-4-yl)-1-(naphthalen-1-yl)-5-(trifluoromethyl)-1H-pyrazole-4-carboxamide |
| 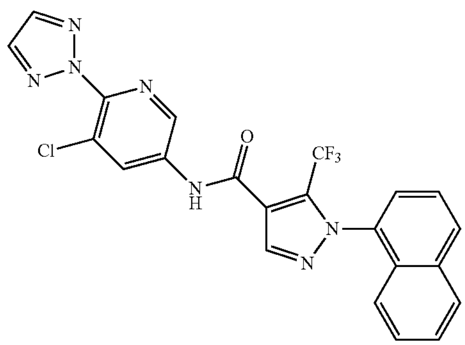 [SMILES: O=C(Nc1cnc(-n2nccn2)c(Cl)c1)c1cnn(-c2cccc3ccccc23)c1C(F)(F)F] | 2 | N-(5-chloro-6-(2H-1,2,3-triazol-2-yl)pyridin-3-yl)-1-(naphthalen-1-yl)-5-(trifluoromethyl)-1H-pyrazole-4-carboxamide |
| 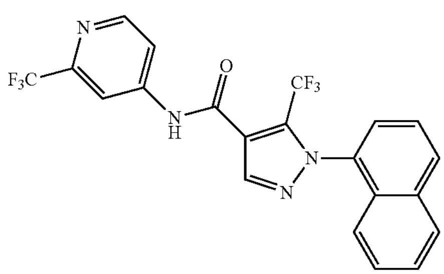 [SMILES: O=C(Nc1ccnc(C(F)(F)F)c1)c1cnn(-c2cccc3ccccc23)c1C(F)(F)F] | 3 | 1-(naphthalen-1-yl)-5-(trifluoromethyl)-N-(2-(trifluoromethyl)pyridin-4-yl)-1H-pyrazole-4-carboxamide |
| 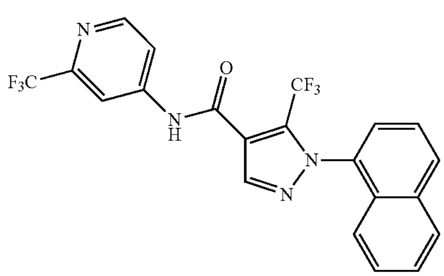 [SMILES: O=C(Nc1ccnc(C(F)(F)F)c1)c1cnn(-c2cccc3ccccc23)c1C(F)(F)F] | 4 | 1-(naphthalen-1-yl)-5-(trifluoromethyl)-N-(5-(trifluoromethyl)pyridin-3-yl)-1H-pyrazole-4-carboxamide |
| 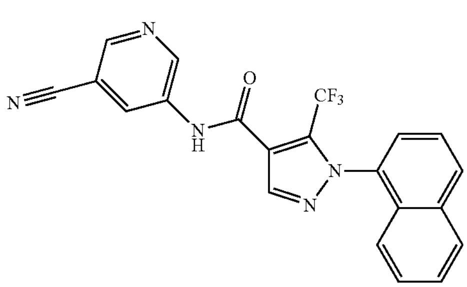 [SMILES: N#Cc1cncc(NC(=O)c2cnn(-c3cccc4ccccc34)c2C(F)(F)F)c1] | 5 | N-(5-cyanopyridin-3-yl)-1-(naphthalen-1-yl)-5-(trifluoromethyl)-1H-pyrazole-4-carboxamide |

TABLE 1-continued

| Structure | Cpd No. | Cpd Name |
|---|---|---|
| 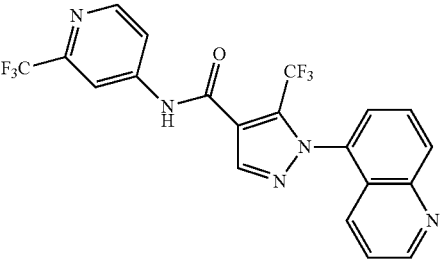 [SMILES: O=C(Nc1ccnc(C(F)(F)F)c1)c1cnn(-c2cccc3ncccc23)c1C(F)(F)F] | 6 | 1-(quinolin-5-yl)-5-(trifluoromethyl)-N-(2-(trifluoromethyl)pyridin-4-yl)-1H-pyrazole-4-carboxamide |
| 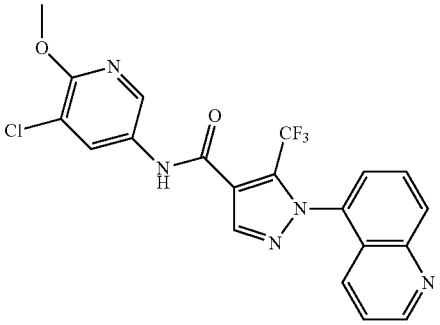 [SMILES: COc1ncc(NC(=O)c2cnn(-c3cccc4ncccc34)c2C(F)(F)F)cc1Cl] | 7 | N-(5-chloro-6-methoxypyridin-3-yl)-1-(quinolin-5-yl)-5-(trifluoromethyl)-1H-pyrazole-4-carboxamide |
| 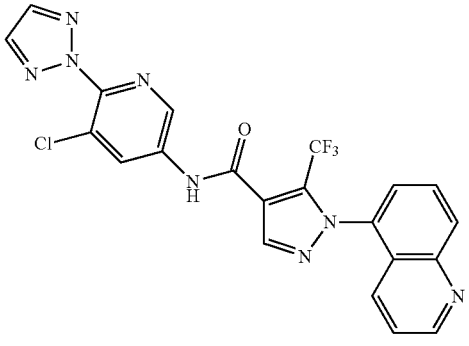 [SMILES: O=C(Nc1cnc(-n2nccn2)c(Cl)c1)c1cnn(-c2cccc3ncccc23)c1C(F)(F)F] | 8 | N-(5-chloro-6-(2H-1,2,3-triazol-2-yl)pyridin-3-yl)-1-(quinolin-5-yl)-5-(trifluoromethyl)-1H-pyrazole-4-carboxamide |
| 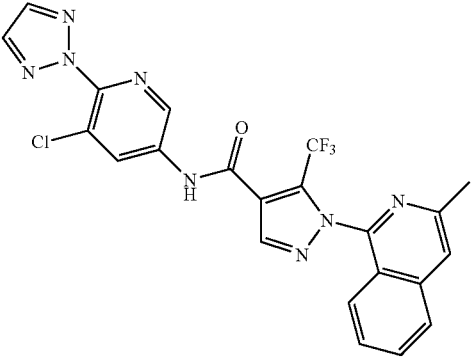 [SMILES: Cc1cc2ccccc2c(-n2ncc(C(=O)Nc3cnc(-n4nccn4)c(Cl)c3)c2C(F)(F)F)n1] | 9 | N-(5-chloro-6-(2H-1,2,3-triazol-2-yl)pyridin-3-yl)-1-(3-methylisoquinolin-1-yl)-5-(trifluoromethyl)-1H-pyrazole-4-carboxamide |

TABLE 1-continued

| Structure | Cpd No. | Cpd Name |
|---|---|---|
| 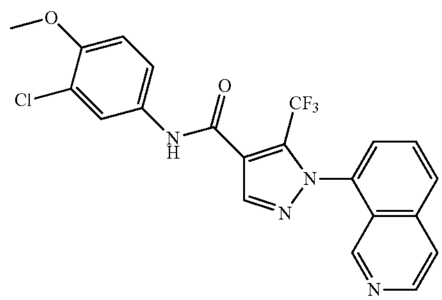 [SMILES: COc1ccc(NC(=O)c2cnn(-c3cccc4ccncc34)c2C(F)(F)F)cc1Cl] | 10 | N-(3-chloro-4-methoxyphenyl)-1-(isoquinolin-8-yl)-5-(trifluoromethyl)-1H-pyrazole-4-carboxamide |
| 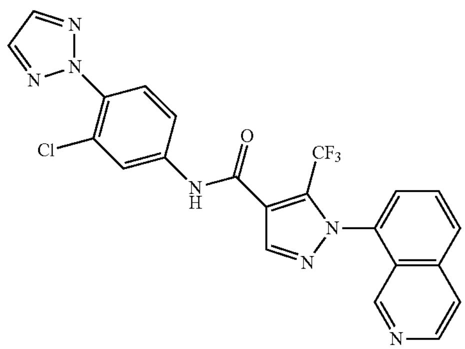 [SMILES: O=C(Nc1ccc(-n2nccn2)c(Cl)c1)c1cnn(-c2cccc3ccncc23)c1C(F)(F)F] | 11 | N-(3-chloro-4-(2H-1,2,3-triazol-2-yl)phenyl)-1-(isoquinolin-8-yl)-5-(trifluoromethyl)-1H-pyrazole-4-carboxamide |
| 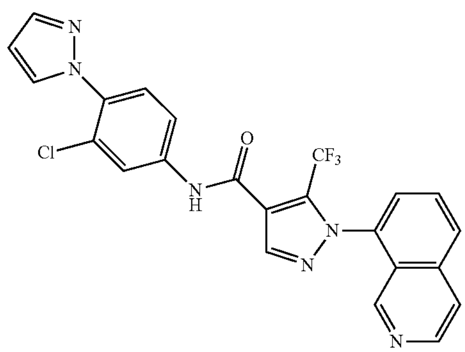 [SMILES: O=C(Nc1ccc(-n2cccn2)c(Cl)c1)c1cnn(-c2cccc3ccncc23)c1C(F)(F)F] | 12 | N-(3-chloro-4-(1H-pyrazol-1-yl)phenyl)-1-(isoquinolin-8-yl)-5-(trifluoromethyl)-1H-pyrazole-4-carboxamide |
| 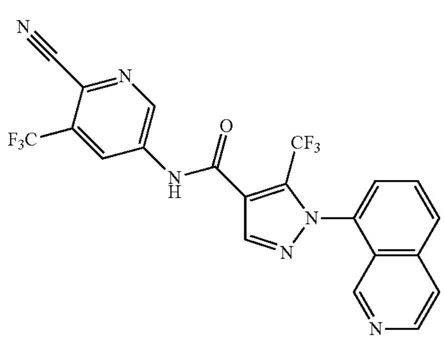 [SMILES: N#Cc1ncc(NC(=O)c2cnn(-c3cccc4ccncc34)c2C(F)(F)F)cc1C(F)(F)F] | 13 | N-(6-cyano-5-(trifluoromethyl)pyridin-3-yl)-1-(isoquinolin-8-yl)-5-(trifluoromethyl)-1H-pyrazole-4-carboxamide |

TABLE 1-continued

| Structure | Cpd No. | Cpd Name |
|---|---|---|
| 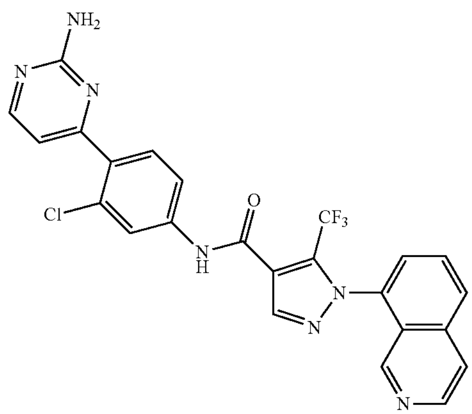 [SMILES: Nc1nccc(-c2ccc(NC(=O)c3cnn(-c4cccc5ccncc45)c3C(F)(F)F)cc2Cl)n1] | 14 | N-(4-(2-aminopyrimidin-4-yl)-3-chlorophenyl)-1-(isoquinolin-8-yl)-5-(trifluoromethyl)-1H-pyrazole-4-carboxamide |
| 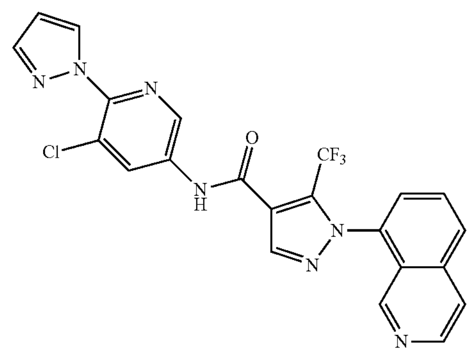 [SMILES: O=C(Nc1cnc(-n2cccn2)c(Cl)c1)c1cnn(-c2cccc3ccncc23)c1C(F)(F)F] | 15 | N-(5-chloro-6-(1H-pyrazol-1-yl)pyridin-3-yl)-1-(isoquinolin-8-yl)-5-(trifluoromethyl)-1H-pyrazole-4-carboxamide |
| 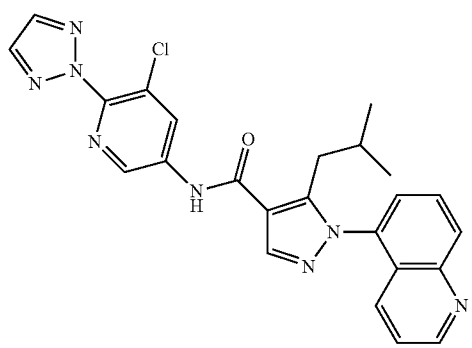 [SMILES: CC(C)Cc1c(C(=O)Nc2cnc(-n3nccn3)c(Cl)c2)cnn1-c1cccc2ncccc12] | 16 | N-(5-chloro-6-(2H-1,2,3-triazol-2-yl)pyridin-3-yl)-5-isobutyl-1-(quinolin-5-yl)-1H-pyrazole-4-carboxamide |
| 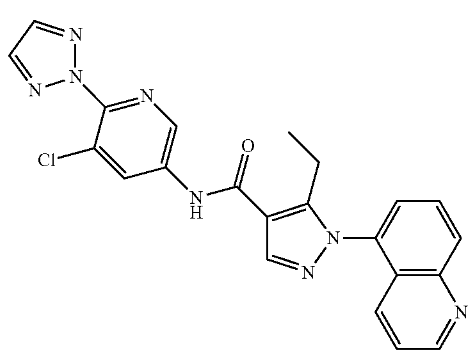 [SMILES: CCc1c(C(=O)Nc2cnc(-n3nccn3)c(Cl)c2)cnn1-c1cccc2ncccc12] | 17 | N-(5-chloro-6-(2H-1,2,3-triazol-2-yl)pyridin-3-yl)-5-ethyl-1-(quinolin-5-yl)-1H-pyrazole-4-carboxamide |

TABLE 1-continued

| Structure | Cpd No. | Cpd Name |
|---|---|---|
| 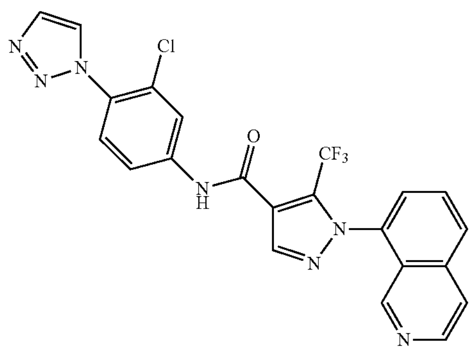 [SMILES: O=C(Nc1ccc(-n2ccnn2)c(Cl)c1)c1cnn(-c2cccc3ccncc23)c1C(F)(F)F] | 18 | N-(3-chloro-4-(1H-1,2,3-triazol-1-yl)phenyl)-1-(isoquinolin-8-yl)-5-(trifluoromethyl)-1H-pyrazole-4-carboxamide |
| 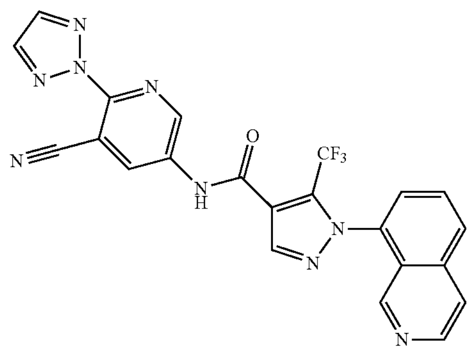 [SMILES: N#Cc1cc(NC(=O)c2cnn(-c3cccc4ccncc34)c2C(F)(F)F)cnc1-n1nccn1] | 19 | N-(5-cyano-6-(2H-1,2,3-triazol-2-yl)pyridin-3-yl)-1-(isoquinolin-8-yl)-5-(trifluoromethyl)-1H-pyrazole-4-carboxamide |
| 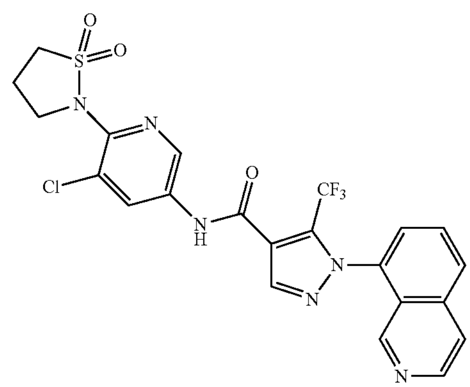 [SMILES: O=C(Nc1cnc(N2CCCS2(=O)=O)c(Cl)c1)c1cnn(-c2cccc3ccncc23)c1C(F)(F)F] | 20 | N-(5-chloro-6-(1,1-dioxidoisothiazolidin-2-yl)pyridin-3-yl)-1-(isoquinolin-8-yl)-5-(trifluoromethyl)-1H-pyrazole-4-carboxamide |
| 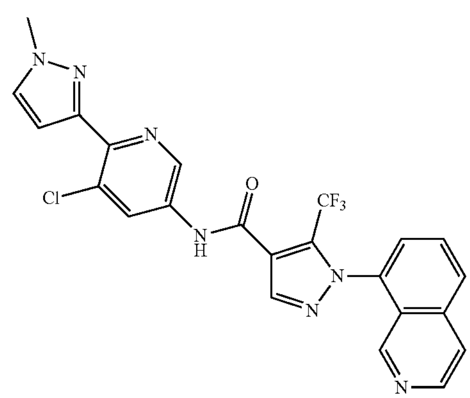 [SMILES: Cn1ccc(-c2ncc(NC(=O)c3cnn(-c4cccc5ccncc45)c3C(F)(F)F)cc2Cl)n1] | 21 | N-(5-chloro-6-(1-methyl-1H-pyrazol-3-yl)pyridin-3-yl)-1-(isoquinolin-8-yl)-5-(trifluoromethyl)-1H-pyrazole-4-carboxamide |

TABLE 1-continued

| Structure | Cpd No. | Cpd Name |
|---|---|---|
| 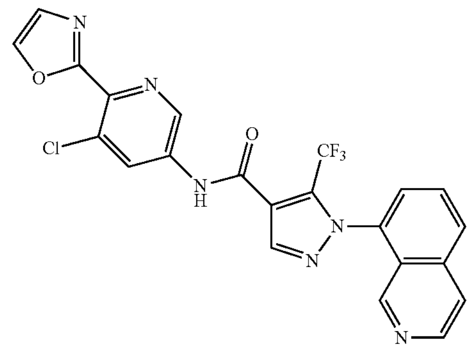 [SMILES: O=C(Nc1cnc(-c2ncco2)c(Cl)c1)c1cnn(-c2cccc3ccncc23)c1C(F)(F)F] | 22 | N-(5-chloro-6-(oxazol-2-yl)pyridin-3-yl)-1-(isoquinolin-8-yl)-5-(trifluoromethyl)-1H-pyrazole-4-carboxamide |
| 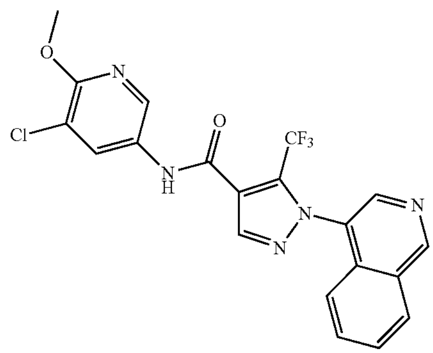 [SMILES: COc1ncc(NC(=O)c2cnn(-c3cncc4ccccc34)c2C(F)(F)F)cc1Cl] | 23 | N-(5-chloro-6-methoxypyridin-3-yl)-1-(isoquinolin-4-yl)-5-(trifluoromethyl)-1H-pyrazole-4-carboxamide |
| 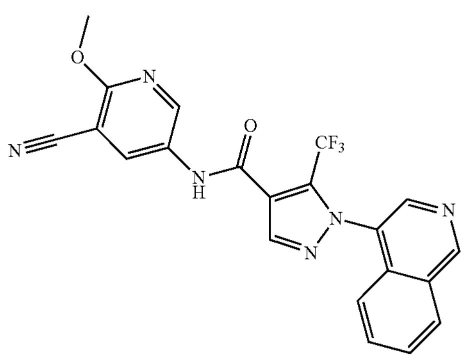 [SMILES: COc1ncc(NC(=O)c2cnn(-c3cncc4ccccc34)c2C(F)(F)F)cc1C#N] | 24 | N-(5-cyano-6-methoxypyridin-3-yl)-1-(isoquinolin-4-yl)-5-(trifluoromethyl)-1H-pyrazole-4-carboxamide |
| 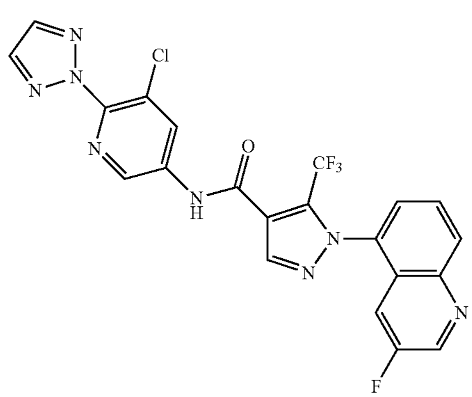 [SMILES: O=C(Nc1cnc(-n2nccn2)c(Cl)c1)c1cnn(-c2cccc3ncc(F)cc23)c1C(F)(F)F] | 25 | N-(5-chloro-6-(2H-1,2,3-triazol-2-yl)pyridin-3-yl)-1-(3-fluoroquinolin-5-yl)-5-(trifluoromethyl)-1H-pyrazole-4-carboxamide |

TABLE 1-continued

| Structure | Cpd No. | Cpd Name |
|---|---|---|
| 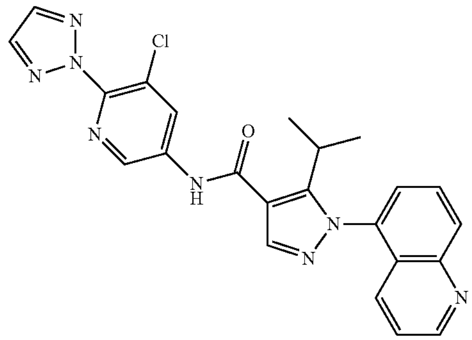 [SMILES: CC(C)c1c(C(=O)Nc2cnc(-n3nccn3)c(Cl)c2)cnn1-c1cccc2ncccc12] | 26 | N-(5-chloro-6-(2H-1,2,3-triazol-2-yl)pyridin-3-yl)-5-isopropyl-1-(quinolin-5-yl)-1H-pyrazole-4-carboxamide |
| 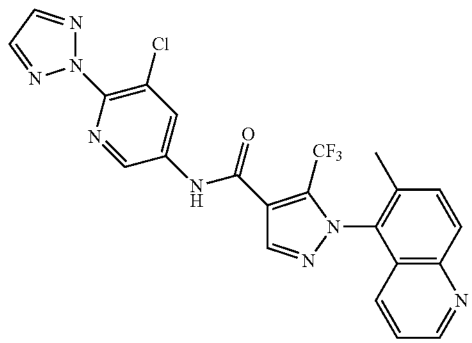 [SMILES: Cc1ccc2ncccc2c1-n1ncc(C(=O)Nc2cnc(-n3nccn3)c(Cl)c2)c1C(F)(F)F] | 27 | N-(5-chloro-6-(2H-1,2,3-triazol-2-yl)pyridin-3-yl)-1-(6-methylquinolin-5-yl)-5-(trifluoromethyl)-1H-pyrazole-4-carboxamide |
| 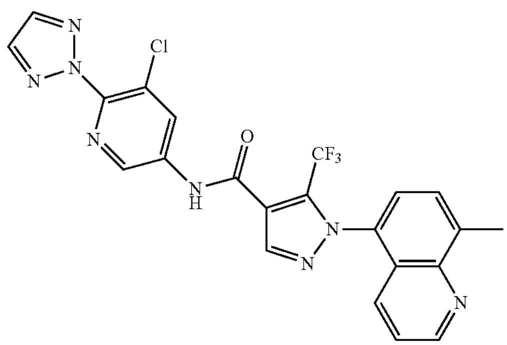 [SMILES: Cc1ccc(-n2ncc(C(=O)Nc3cnc(-n4nccn4)c(Cl)c3)c2C(F)(F)F)c2cccnc12] | 28 | N-(5-chloro-6-(2H-1,2,3-triazol-2-yl)pyridin-3-yl)-1-(8-methylquinolin-5-yl)-5-(trifluoromethyl)-1H-pyrazole-4-carboxamide |
| 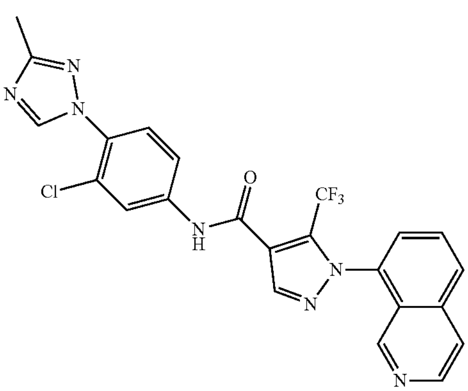 [SMILES: Cc1ncn(-c2ccc(NC(=O)c3cnn(-c4cccc5ccncc45)c3C(F)(F)F)cc2Cl)n1] | 29 | N-(3-chloro-4-(3-methyl-1H-1,2,4-triazol-1-yl)phenyl)-1-(isoquinolin-8-yl)-5-(trifluoromethyl)-1H-pyrazole-4-carboxamide |

TABLE 1-continued

| Structure | Cpd No. | Cpd Name |
|---|---|---|
| 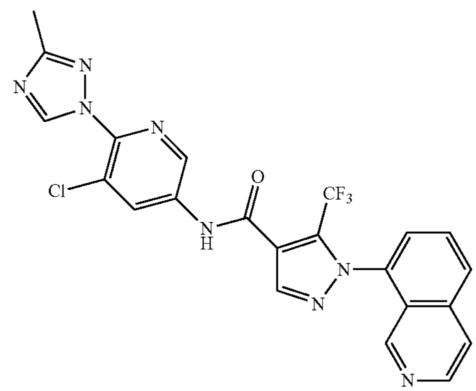 [SMILES: Cc1ncn(-c2ncc(NC(=O)c3cnn(-c4cccc5ccncc45)c3C(F)(F)F)cc2Cl)n1] | 30 | N-(5-chloro-6-(3-methyl-1H-1,2,4-triazol-1-yl)pyridin-3-yl)-1-(isoquinolin-8-yl)-5-(trifluoromethyl)-1H-pyrazole-4-carboxamide |
| 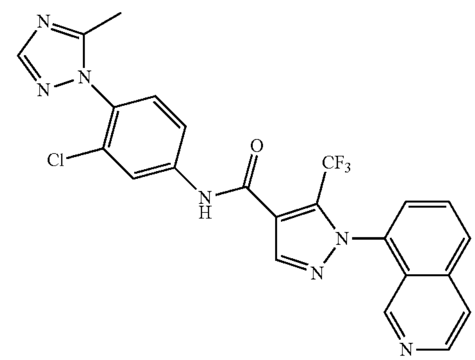 [SMILES: Cc1ncnn1-c1ccc(NC(=O)c2cnn(-c3cccc4ccncc34)c2C(F)(F)F)cc1Cl] | 31 | N-(3-chloro-4-(5-methyl-1H-1,2,4-triazol-1-yl)phenyl)-1-(isoquinolin-8-yl)-5-(trifluoromethyl)-1H-pyrazole-4-carboxamide |
| 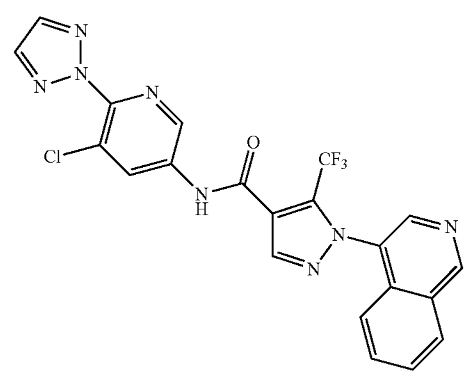 [SMILES: O=C(Nc1cnc(-n2nccn2)c(Cl)c1)c1cnn(-c2cncc3ccccc23)c1C(F)(F)F] | 32 | N-(5-chloro-6-(2H-1,2,3-triazol-2-yl)pyridin-3-yl)-1-(isoquinolin-4-yl)-5-(trifluoromethyl)-1H-pyrazole-4-carboxamide |
| 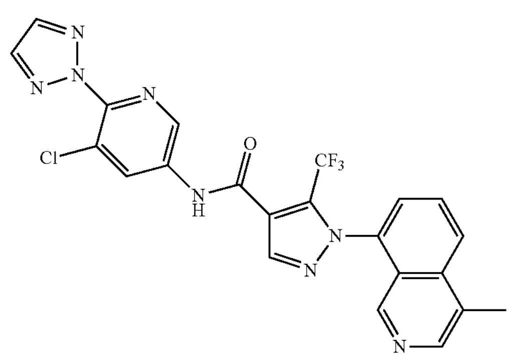 [SMILES: Cc1cncc2c(-n3ncc(C(=O)Nc4cnc(-n5nccn5)c(Cl)c4)c3C(F)(F)F)cccc12] | 33 | N-(5-chloro-6-(2H-1,2,3-triazol-2-yl)pyridin-3-yl)-1-(4-methylisoquinolin-8-yl)-5-(trifluoromethyl)-1H-pyrazole-4-carboxamide |

TABLE 1-continued

| Structure | Cpd No. | Cpd Name |
|---|---|---|
| 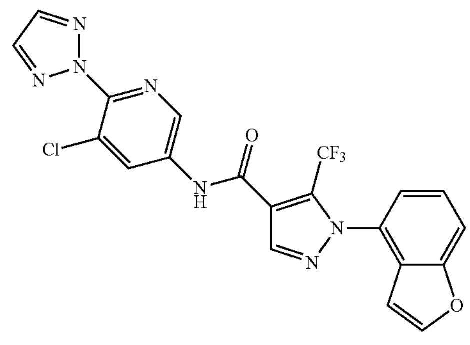 [SMILES: O=C(Nc1cnc(-n2nccn2)c(Cl)c1)c1cnn(-c2cccc3occc23)c1C(F)(F)F] | 34 | 1-(benzofuran-4-yl)-N-(5-chloro-6-(2H-1,2,3-triazol-2-yl)pyridin-3-yl)-5-(trifluoromethyl)-1H-pyrazole-4-carboxamide |
| 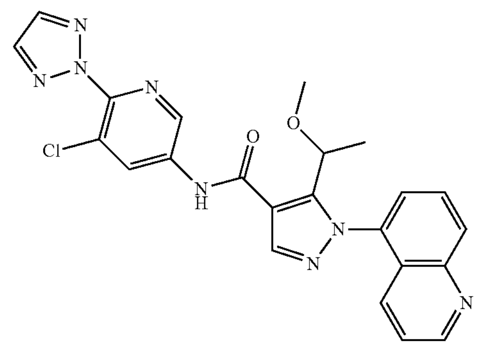 [SMILES: COC(C)c1c(C(=O)Nc2cnc(-n3nccn3)c(Cl)c2)cnn1-c1cccc2ncccc12] | 35 | N-(5-chloro-6-(2H-1,2,3-triazol-2-yl)pyridin-3-yl)-5-(1-methoxyethyl)-1-(quinolin-5-yl)-1H-pyrazole-4-carboxamide |
| 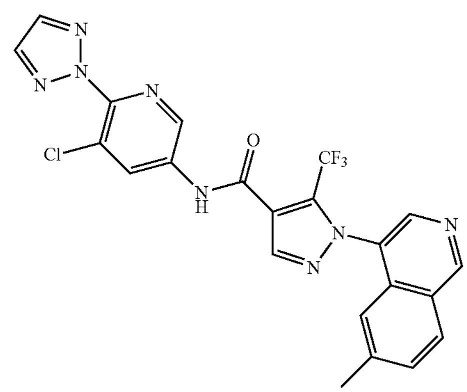 [SMILES: Cc1ccc2cncc(-n3ncc(C(=O)Nc4cnc(-n5nccn5)c(Cl)c4)c3C(F)(F)F)c2c1] | 36 | N-(5-chloro-6-(2H-1,2,3-triazol-2-yl)pyridin-3-yl)-1-(6-methylisoquinolin-4-yl)-5-(trifluoromethyl)-1H-pyrazole-4-carboxamide |
| 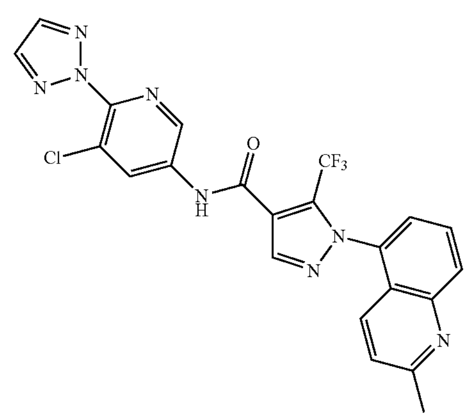 [SMILES: Cc1ccc2c(-n3ncc(C(=O)Nc4cnc(-n5nccn5)c(Cl)c4)c3C(F)(F)F)cccc2n1] | 37 | N-(5-chloro-6-(2H-1,2,3-triazol-2-yl)pyridin-3-yl)-1-(2-methylquinolin-5-yl)-5-(trifluoromethyl)-1H-pyrazole-4-carboxamide |

TABLE 1-continued

| Structure | Cpd No. | Cpd Name |
|---|---|---|
| 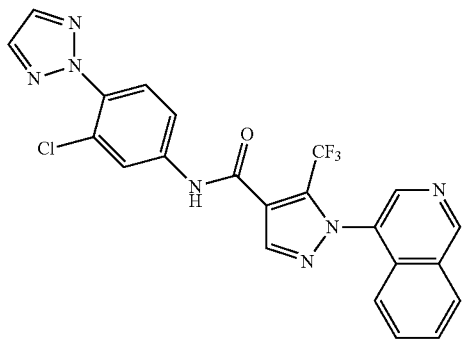 [SMILES: O=C(Nc1ccc(-n2nccn2)c(Cl)c1)c1cnn(-c2cncc3ccccc23)c1C(F)(F)F] | 38 | N-(3-chloro-4-(2H-1,2,3-triazol-2-yl)phenyl)-1-(isoquinolin-4-yl)-5-(trifluoromethyl)-1H-pyrazole-4-carboxamide |
| 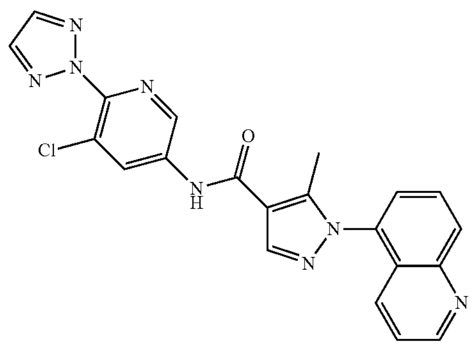 [SMILES: Cc1c(C(=O)Nc2cnc(-n3nccn3)c(Cl)c2)cnn1-c1cccc2ncccc12] | 39 | N-(5-chloro-6-(2H-1,2,3-triazol-2-yl)pyridin-3-yl)-5-methyl-1-(quinolin-5-yl)-1H-pyrazole-4-carboxamide |
| 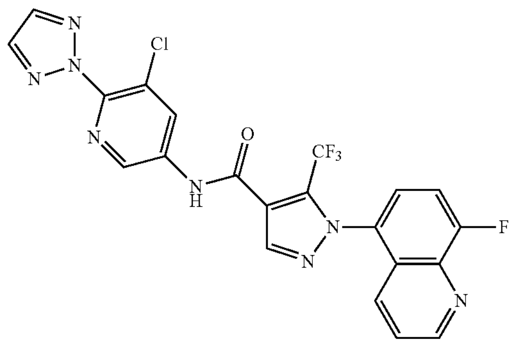 [SMILES: O=C(Nc1cnc(-n2nccn2)c(Cl)c1)c1cnn(-c2ccc(F)c3ncccc23)c1C(F)(F)F] | 40 | N-(5-chloro-6-(2H-1,2,3-triazol-2-yl)pyridin-3-yl)-1-(8-fluoroquinolin-5-yl)-5-(trifluoromethyl)-1H-pyrazole-4-carboxamide |
| 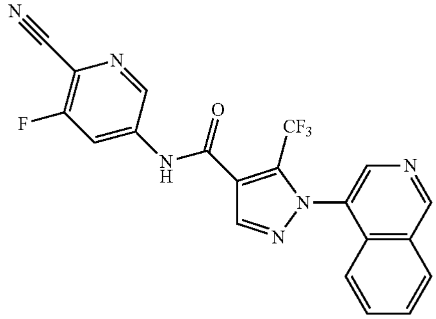 [SMILES: N#Cc1ncc(NC(=O)c2cnn(-c3cncc4ccccc34)c2C(F)(F)F)cc1F] | 41 | N-(6-cyano-5-fluoropyridin-3-yl)-1-(isoquinolin-4-yl)-5-(trifluoromethyl)-1H-pyrazole-4-carboxamide |

TABLE 1-continued

| Structure | Cpd No. | Cpd Name |
|---|---|---|
| 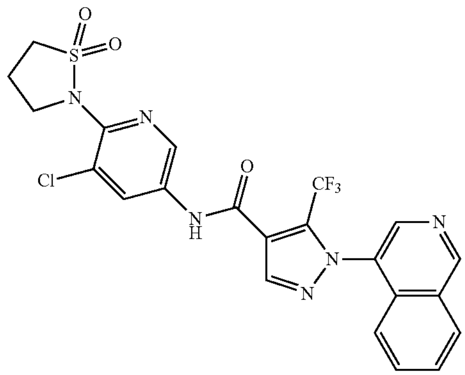 [SMILES: O=C(Nc1cnc(N2CCCS2(=O)=O)c(Cl)c1)c1cnn(-c2cncc3ccccc23)c1C(F)(F)F] | 42 | N-(5-chloro-6-(1,1-dioxidoisothiazolidin-2-yl)pyridin-3-yl)-1-(isoquinolin-4-yl)-5-(trifluoromethyl)-1H-pyrazole-4-carboxamide |
| 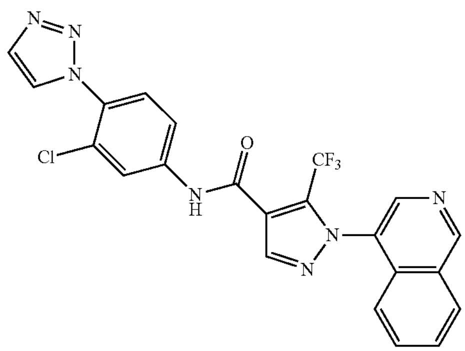 [SMILES: O=C(Nc1ccc(-n2ccnn2)c(Cl)c1)c1cnn(-c2cncc3ccccc23)c1C(F)(F)F] | 43 | N-(3-chloro-4-(1H-1,2,3-triazol-1-yl)phenyl)-1-(isoquinolin-4-yl)-5-(trifluoromethyl)-1H-pyrazole-4-carboxamide |
| 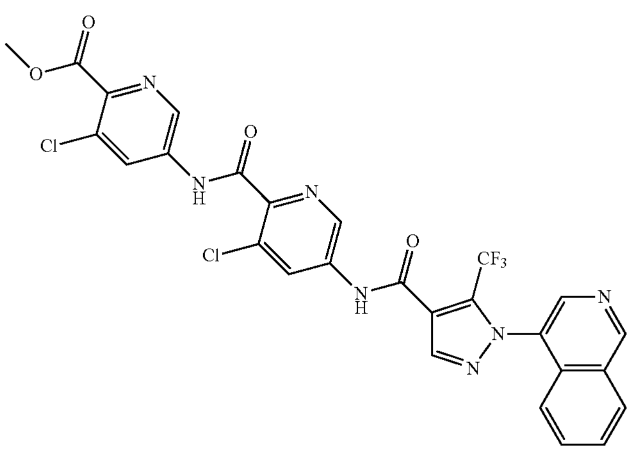 [SMILES: COC(=O)c1ncc(NC(=O)c2ncc(NC(=O)c3cnn(-c4cncc5ccccc45)c3C(F)(F)F)cc2Cl)cc1Cl] | 44 | methyl 3-chloro-5-(3-chloro-5-(1-(isoquinolin-4-yl)-5-(trifluoromethyl)-1H-pyrazole-4-carboxamido)picolinamido)picolinate |
| 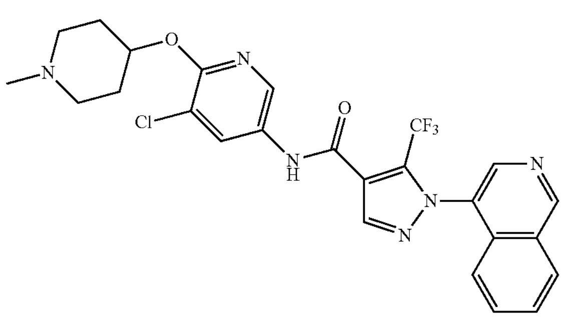 [SMILES: CN1CCC(Oc2ncc(NC(=O)c3cnn(-c4cncc5ccccc45)c3C(F)(F)F)cc2Cl)CC1] | 45 | N-(5-chloro-6-((1-methylpiperidin-4-yl)oxy)pyridin-3-yl)-1-(isoquinolin-4-yl)-5-(trifluoromethyl)-1H-pyrazole-4-carboxamide |

TABLE 1-continued

| Structure | Cpd No. | Cpd Name |
|---|---|---|
| 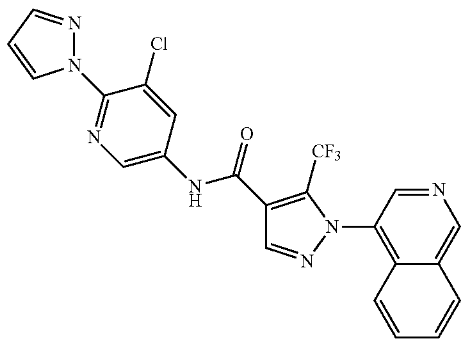 [SMILES: O=C(Nc1cnc(-n2cccn2)c(Cl)c1)c1cnn(-c2cncc3ccccc23)c1C(F)(F)F] | 46 | N-(5-chloro-6-(1H-pyrazol-1-yl)pyridin-3-yl)-1-(isoquinolin-4-yl)-5-(trifluoromethyl)-1H-pyrazole-4-carboxamide |
| 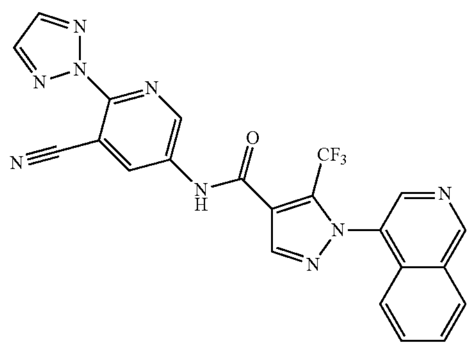 [SMILES: N#Cc1cc(NC(=O)c2cnn(-c3cncc4ccccc34)c2C(F)(F)F)cnc1-n1nccn1] | 47 | N-(5-cyano-6-(2H-1,2,3-triazol-2-yl)pyridin-3-yl)-1-(isoquinolin-4-yl)-5-(trifluoromethyl)-1H-pyrazole-4-carboxamide |
| 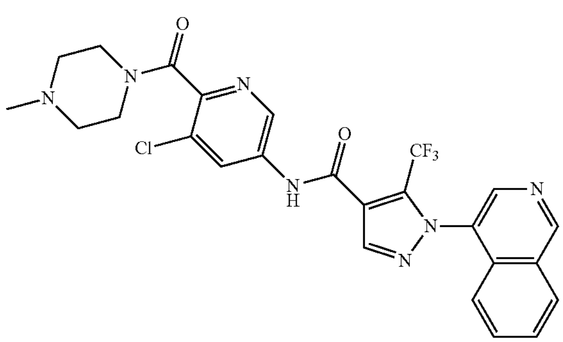 [SMILES: CN1CCN(C(=O)c2ncc(NC(=O)c3cnn(-c4cncc5ccccc45)c3C(F)(F)F)cc2Cl)CC1] | 48 | N-(5-chloro-6-(4-methylpiperazine-1-carbonyl)pyridin-3-yl)-1-(isoquinolin-4-yl)-5-(trifluoromethyl)-1H-pyrazole-4-carboxamide |
| 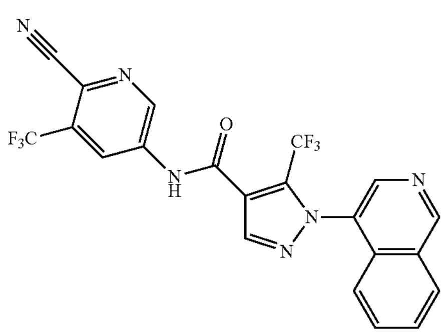 [SMILES: N#Cc1ncc(NC(=O)c2cnn(-c3cncc4ccccc34)c2C(F)(F)F)cc1C(F)(F)F] | 49 | N-(6-cyano-5-(trifluoromethyl)pyridin-3-yl)-1-(isoquinolin-4-yl)-5-(trifluoromethyl)-1H-pyrazole-4-carboxamide |

TABLE 1-continued

| Structure | Cpd No. | Cpd Name |
|---|---|---|
| 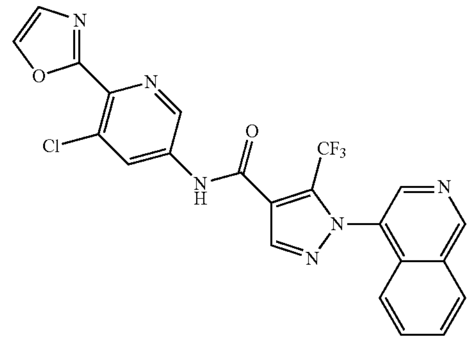 [SMILES: O=C(Nc1cnc(-c2ncco2)c(Cl)c1)c1cnn(-c2cncc3ccccc23)c1C(F)(F)F] | 50 | N-(5-chloro-6-(oxazol-2-yl)pyridin-3-yl)-1-(isoquinolin-4-yl)-5-(trifluoromethyl)-1H-pyrazole-4-carboxamide |
| 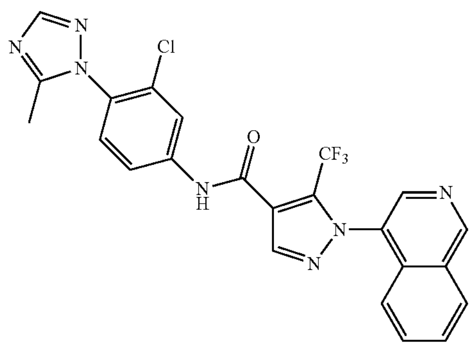 [SMILES: Cc1ncnn1-c1ccc(NC(=O)c2cnn(-c3cncc4ccccc34)c2C(F)(F)F)cc1Cl] | 51 | N-(3-chloro-4-(5-methyl-1H-1,2,4-triazol-1-yl)phenyl)-1-(isoquinolin-4-yl)-5-(trifluoromethyl)-1H-pyrazole-4-carboxamide |
| 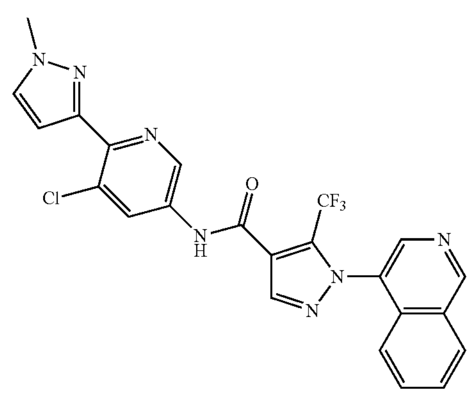 | 52 | N-(5-chloro-6-(1-methyl-1H-pyrazol-3-yl)pyridin-3-yl)-1-(isoquinolin-4-yl)-5-(trifluoromethyl)-1H-pyrazole-4-carboxamide |
| 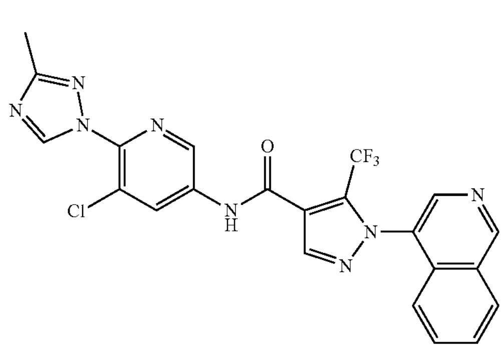 [SMILES: Cc1ncn(-c2ncc(NC(=O)c3cnn(-c4cncc5ccccc45)c3C(F)(F)F)cc2Cl)n1] | 53 | N-(5-chloro-6-(3-methyl-1H-1,2,4-triazol-1-yl)pyridin-3-yl)-1-(isoquinolin-4-yl)-5-(trifluoromethyl)-1H-pyrazole-4-carboxamide |

TABLE 1-continued

| Structure | Cpd No. | Cpd Name |
|---|---|---|
| 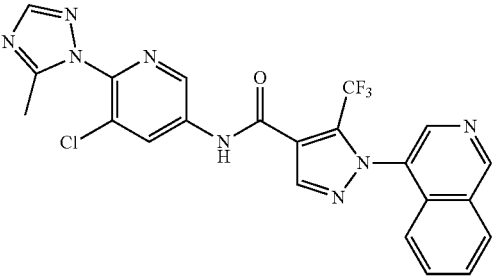 [SMILES: Cc1ncnn1-c1ncc(NC(=O)c2cnn(-c3cncc4ccccc34)c2C(F)(F)F)cc1Cl] | 54 | N-(5-chloro-6-(5-methyl-1H-1,2,4-triazol-1-yl)pyridin-3-yl)-1-(isoquinolin-4-yl)-5-(trifluoromethyl)-1H-pyrazole-4-carboxamide |
| 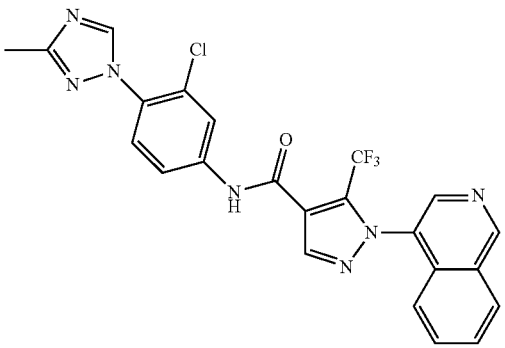 [SMILES: Cc1ncn(-c2ccc(NC(=O)c3cnn(-c4cncc5ccccc45)c3C(F)(F)F)cc2Cl)n1] | 55 | N-(3-chloro-4-(3-methyl-1H-1,2,4-triazol-1-yl)phenyl)-1-(isoquinolin-4-yl)-5-(trifluoromethyl)-1H-pyrazole-4-carboxamide |
| 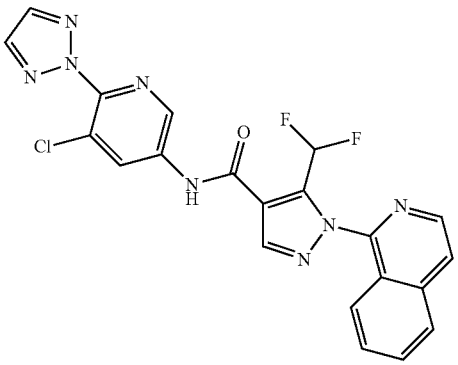 [SMILES: O=C(Nc1cnc(-n2nccn2)c(Cl)c1)c1cnn(-c2nccc3ccccc23)c1C(F)F] | 56 | N-(5-chloro-6-(2H-1,2,3-triazol-2-yl)pyridin-3-yl)-5-(difluoromethyl)-1-(isoquinolin-1-yl)-1H-pyrazole-4-carboxamide |
| 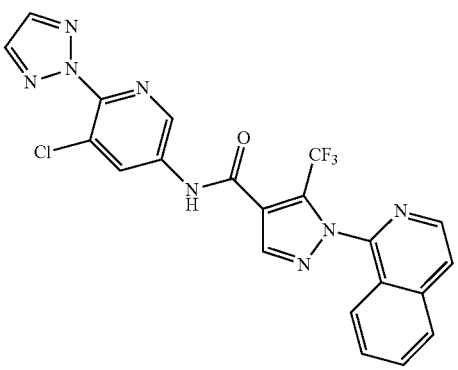 [SMILES: O=C(Nc1cnc(-n2nccn2)c(Cl)c1)c1cnn(-c2nccc3ccccc23)c1C(F)(F)F] | 57 | N-(5-chloro-6-(2H-1,2,3-triazol-2-yl)pyridin-3-yl)-1-(isoquinolin-1-yl)-5-(trifluoromethyl)-1H-pyrazole-4-carboxamide |

TABLE 1-continued

| Structure | Cpd No. | Cpd Name |
|---|---|---|
| 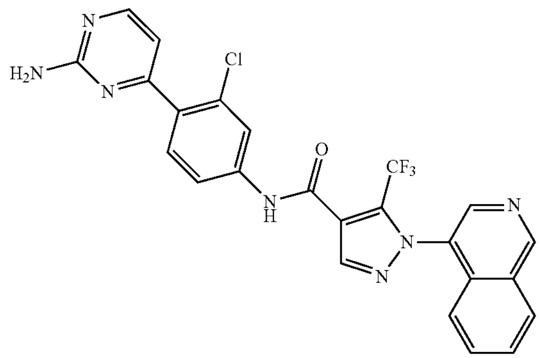 [SMILES: Nc1nccc(-c2ccc(NC(=O)c3cnn(-c4cncc5ccccc45)c3C(F)(F)F)cc2Cl)n1] | 58 | N-(4-(2-aminopyrimidin-4-yl)-3-chlorophenyl)-1-(isoquinolin-4-yl)-5-(trifluoromethyl)-1H-pyrazole-4-carboxamide |
| 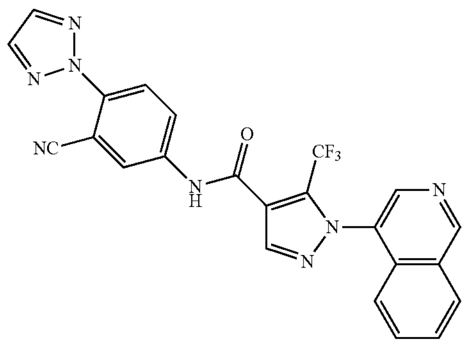 | 59 | N-(3-cyano-4-(2H-1,2,3-triazol-2-yl)phenyl)-1-(isoquinolin-4-yl)-5-(trifluoromethyl)-1H-pyrazole-4-carboxamide |
| 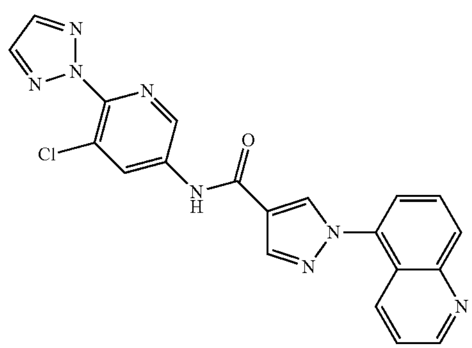 [SMILES: O=C(Nc1cnc(-n2nccn2)c(Cl)c1)c1cnn(-c2cccc3ncccc23)c1] | 60 | N-(5-chloro-6-(2H-1,2,3-triazol-2-yl)pyridin-3-yl)-1-(quinolin-5-yl)-1H-pyrazole-4-carboxamide |
| 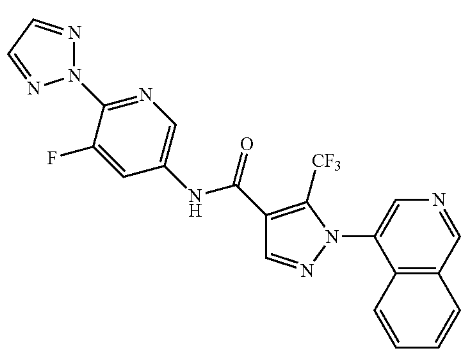 [SMILES: O=C(Nc1cnc(-n2nccn2)c(F)c1)c1cnn(-c2cncc3ccccc23)c1C(F)(F)F] | 61 | N-(5-fluoro-6-(2H-1,2,3-triazol-2-yl)pyridin-3-yl)-1-(isoquinolin-4-yl)-5-(trifluoromethyl)-1H-pyrazole-4-carboxamide |

TABLE 1-continued

| Structure | Cpd No. | Cpd Name |
|---|---|---|
| 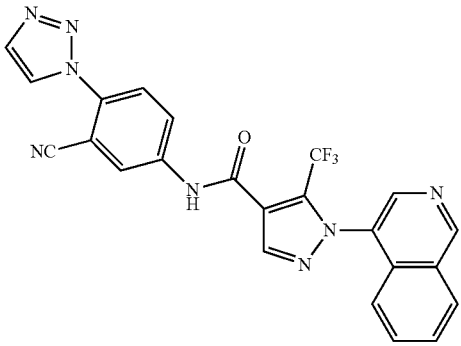 | 62 | N-(3-cyano-4-(1H-1,2,3-triazol-1-yl)phenyl)-1-(isoquinolin-4-yl)-5-(trifluoromethyl)-1H-pyrazole-4-carboxamide |
| 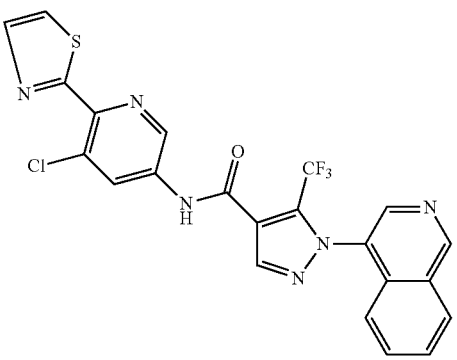 [SMILES: O=C(Nc1cnc(-c2nccs2)c(Cl)c1)c1cnn(-c2cncc3ccccc23)c1C(F)(F)F] | 63 | N-(5-chloro-6-(thiazol-2-yl)pyridin-3-yl)-1-(isoquinolin-4-yl)-5-(trifluoromethyl)-1H-pyrazole-4-carboxamide |
| 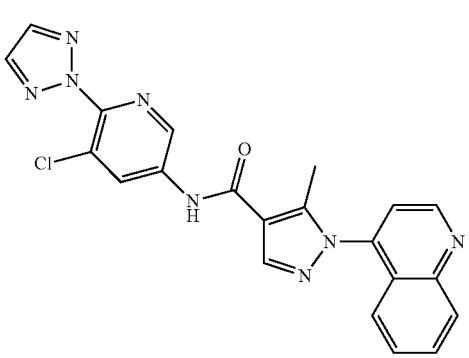 | 64 | N-(5-chloro-6-(2H-1,2,3-triazol-2-yl)pyridin-3-yl)-5-methyl-1-(quinolin-4-yl)-1H-pyrazole-4-carboxamide |
| 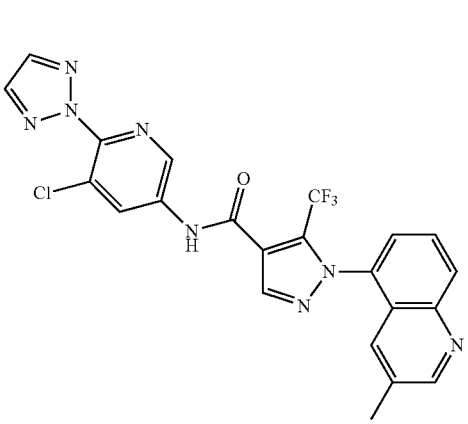 [SMILES: Cc1cnc2cccc(-n3ncc(C(=O)Nc4cnc(-n5nccn5)c(Cl)c4)c3C(F)(F)F)c2c1] | 65 | N-(5-chloro-6-(2H-1,2,3-triazol-2-yl)pyridin-3-yl)-1-(3-methylquinolin-5-yl)-5-(trifluoromethyl)-1H-pyrazole-4-carboxamide |

TABLE 1-continued

| Structure | Cpd No. | Cpd Name |
|---|---|---|
| 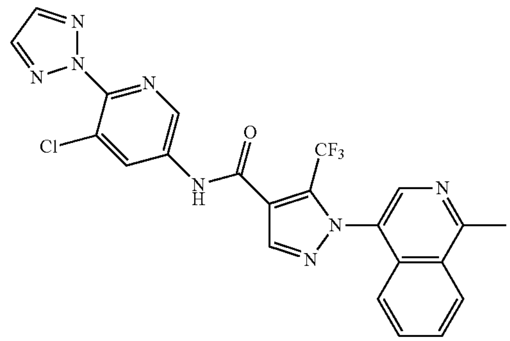 [SMILES: Cc1ncc(-n2ncc(C(=O)Nc3cnc(-n4nccn4)c(Cl)c3)c2C(F)(F)F)c2ccccc12] | 66 | N-(5-chloro-6-(2H-1,2,3-triazol-2-yl)pyridin-3-yl)-1-(1-methylisoquinolin-4-yl)-5-(trifluoromethyl)-1H-pyrazole-4-carboxamide |
| 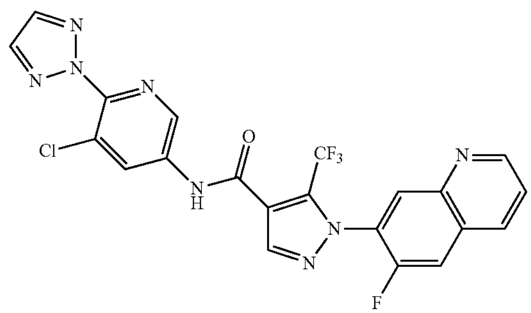 [SMILES: O=C(Nc1cnc(-n2nccn2)c(Cl)c1)c1cnn(-c2cc3ncccc3cc2F)c1C(F)(F)F] | 67 | N-(5-chloro-6-(2H-1,2,3-triazol-2-yl)pyridin-3-yl)-1-(6-fluoroquinolin-7-yl)-5-(trifluoromethyl)-1H-pyrazole-4-carboxamide |
| 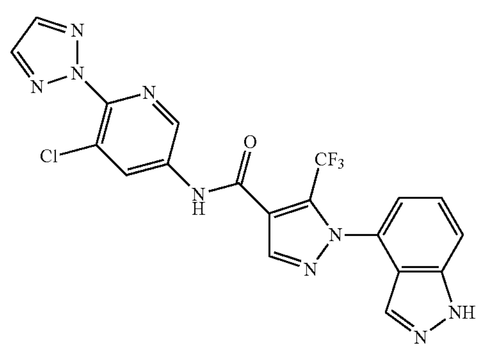 [SMILES: O=C(Nc1cnc(-n2nccn2)c(Cl)c1)c1cnn(-c2cccc3[nH]ncc23)c1C(F)(F)F] | 68 | N-(5-chloro-6-(2H-1,2,3-triazol-2-yl)pyridin-3-yl)-1-(1H-indazol-4-yl)-5-(trifluoromethyl)-1H-pyrazole-4-carboxamide |
| 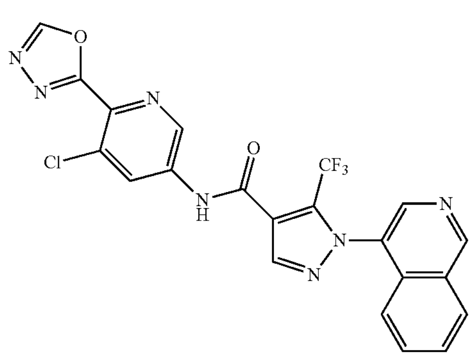 [SMILES: O=C(Nc1cnc(-c2nnco2)c(Cl)c1)c1cnn(-c2cncc3ccccc23)c1C(F)(F)F] | 69 | N-(5-chloro-6-(1,3,4-oxadiazol-2-yl)pyridin-3-yl)-1-(isoquinolin-4-yl)-5-(trifluoromethyl)-1H-pyrazole-4-carboxamide |

TABLE 1-continued

| Structure | Cpd No. | Cpd Name |
|---|---|---|
| 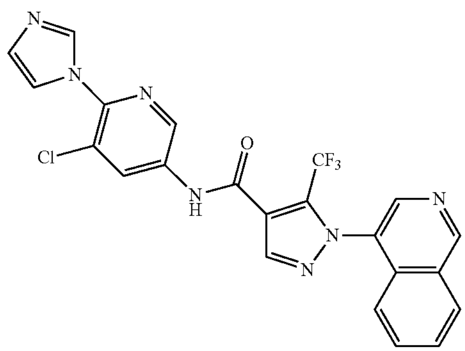 [SMILES: O=C(Nc1cnc(-n2ccnc2)c(Cl)c1)c1cnn(-c2cncc3ccccc23)c1C(F)(F)F] | 70 | N-(5-chloro-6-(1H-imidazol-1-yl)pyridin-3-yl)-1-(isoquinolin-4-yl)-5-(trifluoromethyl)-1H-pyrazole-4-carboxamide |
| 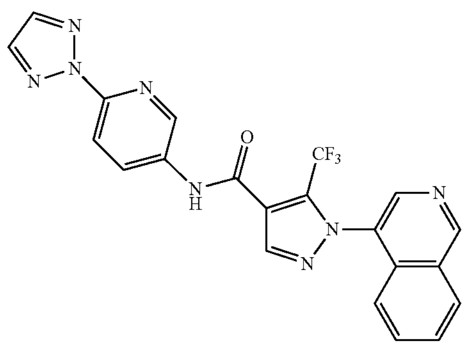 [SMILES: O=C(Nc1ccc(-n2nccn2)nc1)c1cnn(-c2cncc3ccccc23)c1C(F)(F)F] | 71 | N-(6-(2H-1,2,3-triazol-2-yl)pyridin-3-yl)-1-(isoquinolin-4-yl)-5-(trifluoromethyl)-1H-pyrazole-4-carboxamide |
| 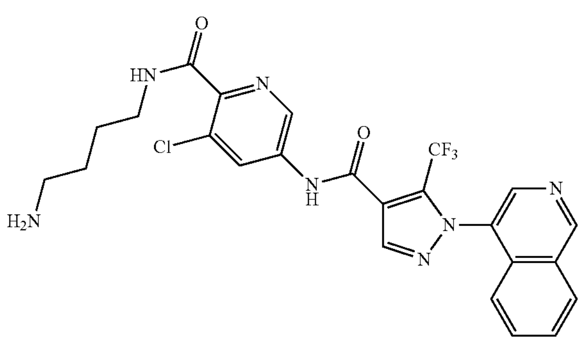 [SMILES: NCCCCNC(=O)c1ncc(NC(=O)c2cnn(-c3cncc4ccccc34)c2C(F)(F)F)cc1Cl] | 72 | N-(4-aminobutyl)-3-chloro-5-(1-(isoquinolin-4-yl)-5-(trifluoromethyl)-1H-pyrazole-4-carboxamido)picolinamide |
| 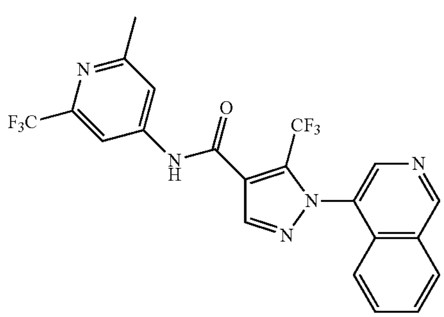 [SMILES: Cc1cc(NC(=O)c2cnn(-c3cncc4ccccc34)c2C(F)(F)F)cc(C(F)(F)F)n1] | 73 | 1-(isoquinolin-4-yl)-N-(2-methyl-6-(trifluoromethyl)pyridin-4-yl)-5-(trifluoromethyl)-1H-pyrazole-4-carboxamide |

TABLE 1-continued

| Structure | Cpd No. | Cpd Name |
|---|---|---|
| 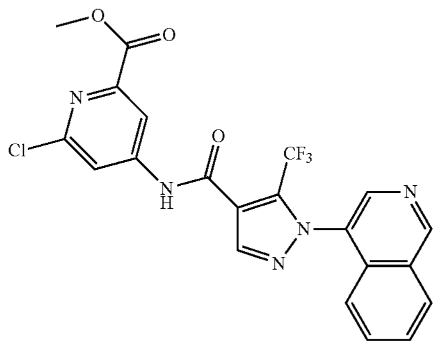 [SMILES: COC(=O)c1cc(NC(=O)c2cnn(-c3cncc4ccccc34)c2C(F)(F)F)cc(Cl)n1] | 74 | methyl 6-chloro-4-(1-(isoquinolin-4-yl)-5-(trifluoromethyl)-1H-pyrazole-4-carboxamido)picolinate |
| 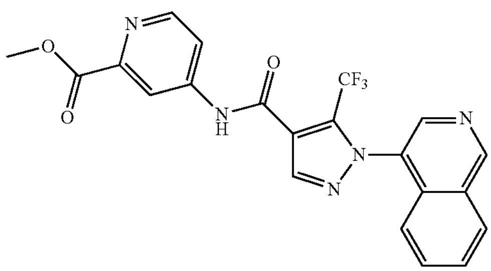 [SMILES: COC(=O)c1cc(NC(=O)c2cnn(-c3cncc4ccccc34)c2C(F)(F)F)ccn1] | 75 | methyl 4-(1-(isoquinolin-4-yl)-5-(trifluoromethyl)-1H-pyrazole-4-carboxamido)picolinate |
| 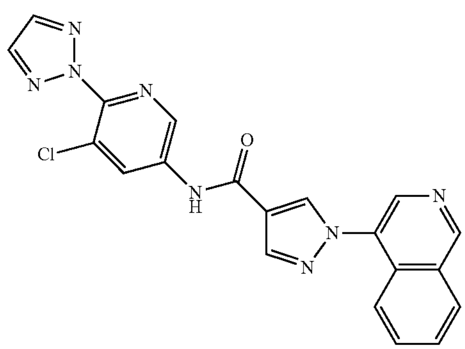 [SMILES: O=C(Nc1cnc(-n2nccn2)c(Cl)c1)c1cnn(-c2cncc3ccccc23)c1] | 76 | N-(5-chloro-6-(2H-1,2,3-triazol-2-yl)pyridin-3-yl)-1-(isoquinolin-4-yl)-1H-pyrazole-4-carboxamide |
| 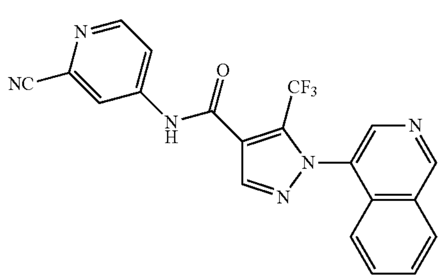 [SMILES: N#Cc1cc(NC(=O)c2cnn(-c3cncc4ccccc34)c2C(F)(F)F)ccn1] | 77 | N-(2-cyanopyridin-4-yl)-1-(isoquinolin-4-yl)-5-(trifluoromethyl)-1H-pyrazole-4-carboxamide |

TABLE 1-continued

| Structure | Cpd No. | Cpd Name |
|---|---|---|
| 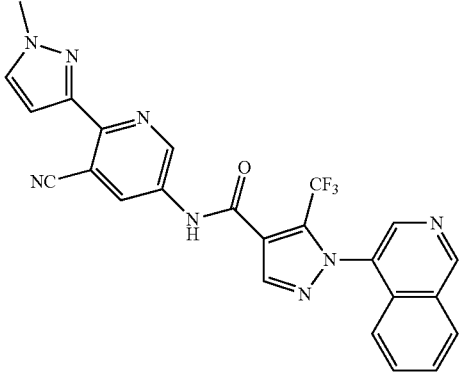 [SMILES: Cn1ccc(-c2ncc(NC(=O)c3cnn(-c4cncc5ccccc45)c3C(F)(F)F)cc2C#N)n1] | 78 | N-(5-cyano-6-(1-methyl-1H-pyrazol-3-yl)pyridin-3-yl)-1-(isoquinolin-4-yl)-5-(trifluoromethyl)-1H-pyrazole-4-carboxamide |
| 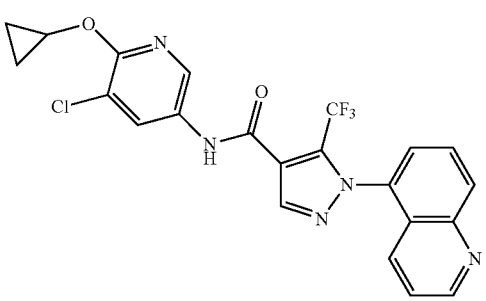 [SMILES: O=C(Nc1cnc(OC2CC2)c(Cl)c1)c1cnn(-c2cccc3ncccc23)c1C(F)(F)F] | 79 | N-(5-chloro-6-cyclopropoxypyridin-3-yl)-1-(quinolin-5-yl)-5-(trifluoromethyl)-1H-pyrazole-4-carboxamide |
| 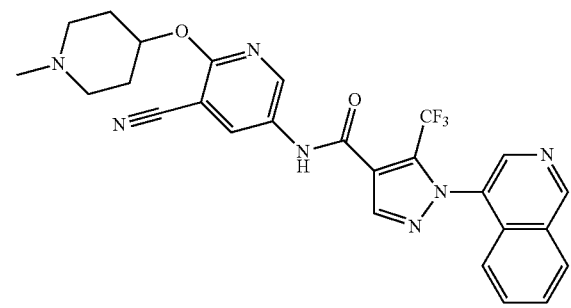 [SMILES: CN1CCC(Oc2ncc(NC(=O)c3cnn(-c4cncc5ccccc45)c3C(F)(F)F)cc2C#N)CC1] | 80 | N-(5-cyano-6-((1-methylpiperidin-4-yl)oxy)pyridin-3-yl)-1-(isoquinolin-4-yl)-5-(trifluoromethyl)-1H-pyrazole-4-carboxamide |
| 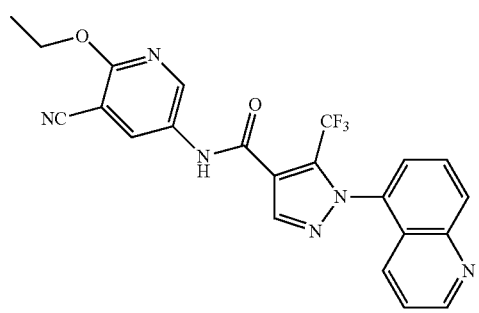 [SMILES: CCOc1ncc(NC(=O)c2cnn(-c3cccc4ncccc34)c2C(F)(F)F)cc1C#N] | 81 | N-(5-cyano-6-ethoxypyridin-3-yl)-1-(quinolin-5-yl)-5-(trifluoromethyl)-1H-pyrazole-4-carboxamide |
| 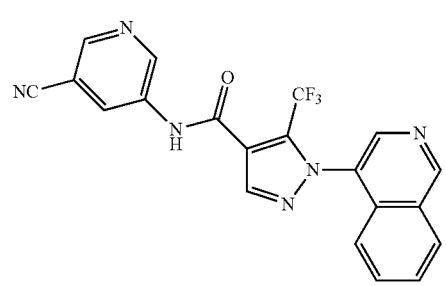 [SMILES: N#Cc1cncc(NC(=O)c2cnn(-c3cncc4ccccc34)c2C(F)(F)F)c1] | 82 | N-(5-cyanopyridin-3-yl)-1-(isoquinolin-4-yl)-5-(trifluoromethyl)-1H-pyrazole-4-carboxamide |

TABLE 1-continued

| Structure | Cpd No. | Cpd Name |
|---|---|---|
| 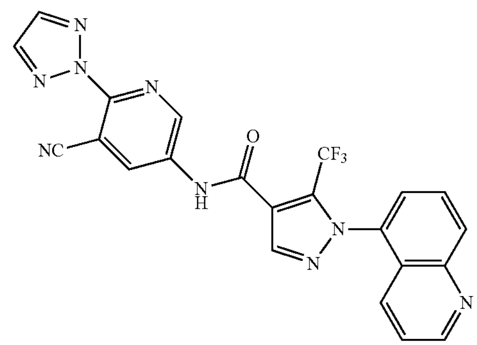 [SMILES: N#Cc1cc(NC(=O)c2cnn(-c3cccc4ncccc34)c2C(F)(F)F)cnc1-n1nccn1] | 83 | N-(5-cyano-6-(2H-1,2,3-triazol-2-yl)pyridin-3-yl)-1-(quinolin-5-yl)-5-(trifluoromethyl)-1H-pyrazole-4-carboxamide |
| 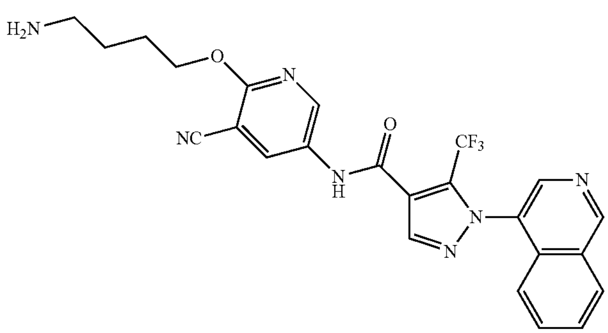 [SMILES: N#Cc1cc(NC(=O)c2cnn(-c3cncc4ccccc34)c2C(F)(F)F)cnc1OCCCCN] | 84 | N-(6-(4-aminobutoxy)-5-cyanopyridin-3-yl)-1-(isoquinolin-4-yl)-5-(trifluoromethyl)-1H-pyrazole-4-carboxamide |
| 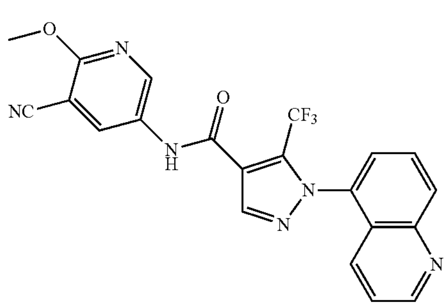 [SMILES: COc1ncc(NC(=O)c2cnn(-c3cccc4ncccc34)c2C(F)(F)F)cc1C#N] | 85 | N-(5-cyano-6-methoxypyridin-3-yl)-1-(quinolin-5-yl)-5-(trifluoromethyl)-1H-pyrazole-4-carboxamide |
| 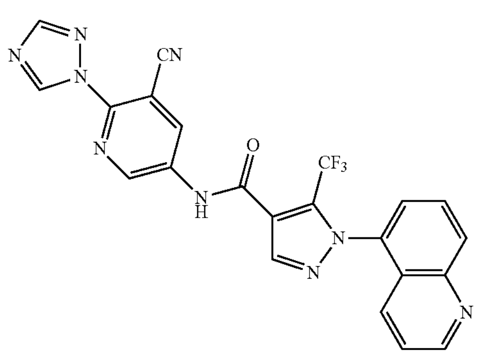 [SMILES: N#Cc1cc(NC(=O)c2cnn(-c3cccc4ncccc34)c2C(F)(F)F)cnc1-n1cncn1] | 86 | N-(5-cyano-6-(1H-1,2,4-triazol-1-yl)pyridin-3-yl)-1-(quinolin-5-yl)-5-(trifluoromethyl)-1H-pyrazole-4-carboxamide |

TABLE 1-continued

| Structure | Cpd No. | Cpd Name |
|---|---|---|
| 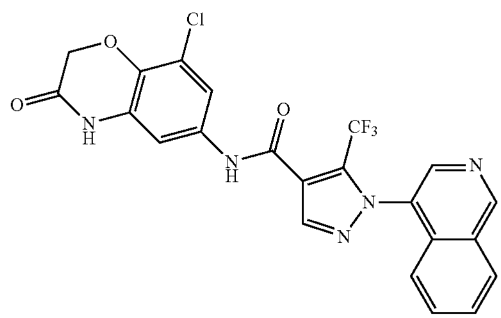 [SMILES: O=C1COc2c(Cl)cc(NC(=O)c3cnn(-c4cncc5ccccc45)c3C(F)(F)F)cc2N1] | 87 | N-(8-chloro-3-oxo-3,4-dihydro-2H-benzo[b][1,4]oxazin-6-yl)-1-(isoquinolin-4-yl)-5-(trifluoromethyl)-1H-pyrazole-4-carboxamide |
| 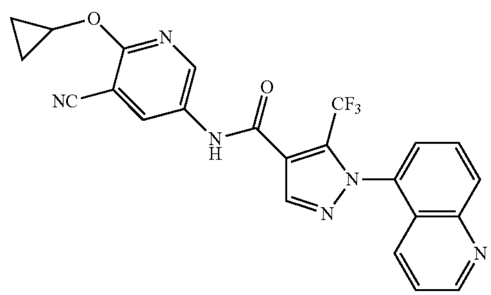 [SMILES: N#Cc1cc(NC(=O)c2cnn(-c3cccc4ncccc34)c2C(F)(F)F)cnc1OC1CC1] | 88 | N-(5-cyano-6-cyclopropoxypyridin-3-yl)-1-(quinolin-5-yl)-5-(trifluoromethyl)-1H-pyrazole-4-carboxamide |
| 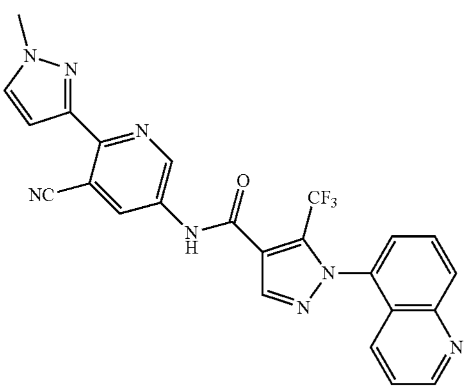 [SMILES: Cn1ccc(-c2ncc(NC(=O)c3cnn(-c4cccc5ncccc45)c3C(F)(F)F)cc2C#N)n1] | 89 | N-(5-cyano-6-(1-methyl-1H-pyrazol-3-yl)pyridin-3-yl)-1-(quinolin-5-yl)-5-(trifluoromethyl)-1H-pyrazole-4-carboxamide |
| 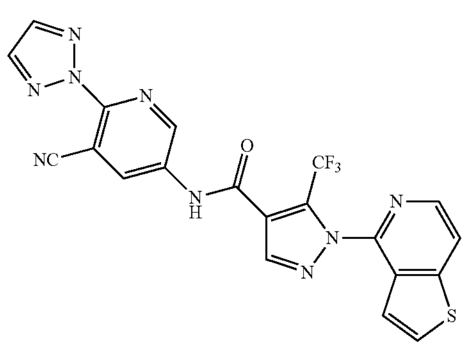 [SMILES: N#Cc1cc(NC(=O)c2cnn(-c3nccc4sccc34)c2C(F)(F)F)cnc1-n1nccn1] | 90 | N-(5-cyano-6-(2H-1,2,3-triazol-2-yl)pyridin-3-yl)-1-(thieno[3,2-c]pyridin-4-yl)-5-(trifluoromethyl)-1H-pyrazole-4-carboxamide |

TABLE 1-continued

| Structure | Cpd No. | Cpd Name |
|---|---|---|
| 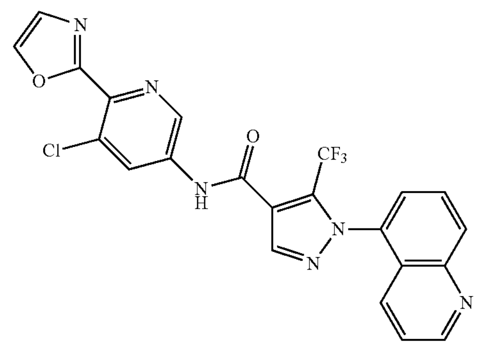 [SMILES: O=C(Nc1cnc(-c2ncco2)c(Cl)c1)c1cnn(-c2cccc3ncccc23)c1C(F)(F)F] | 91 | N-(5-chloro-6-(oxazol-2-yl)pyridin-3-yl)-1-(quinolin-5-yl)-5-(trifluoromethyl)-1H-pyrazole-4-carboxamide |
| 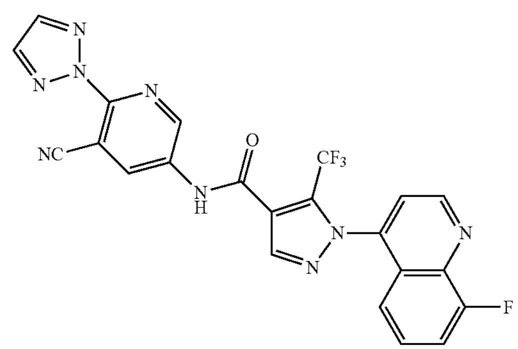 [SMILES: N#Cc1cc(NC(=O)c2cnn(-c3ccnc4c(F)cccc34)c2C(F)(F)F)cnc1-n1nccn1] | 92 | N-(5-cyano-6-(2H-1,2,3-triazol-2-yl)pyridin-3-yl)-1-(8-fluoroquinolin-4-yl)-5-(trifluoromethyl)-1H-pyrazole-4-carboxamide |
| 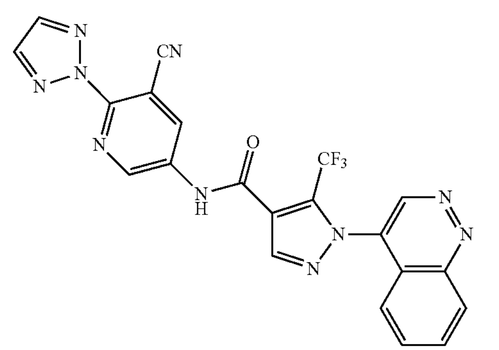 [SMILES: N#Cc1cc(NC(=O)c2cnn(-c3cnnc4ccccc34)c2C(F)(F)F)cnc1-n1nccn1] | 93 | 1-(cinnolin-4-yl)-N-(5-cyano-6-(2H-1,2,3-triazol-2-yl)pyridin-3-yl)-5-(trifluoromethyl)-1H-pyrazole-4-carboxamide |
| 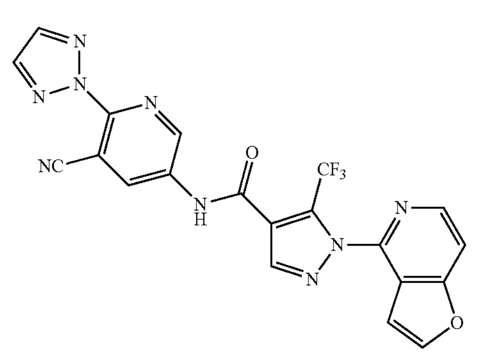 [SMILES: N#Cc1cc(NC(=O)c2cnn(-c3nccc4occc34)c2C(F)(F)F)cnc1-n1nccn1] | 94 | N-(5-cyano-6-(2H-1,2,3-triazol-2-yl)pyridin-3-yl)-1-(furo[3,2-c]pyridin-4-yl)-5-(trifluoromethyl)-1H-pyrazole-4-carboxamide |

TABLE 1-continued

| Structure | Cpd No. | Cpd Name |
|---|---|---|
| 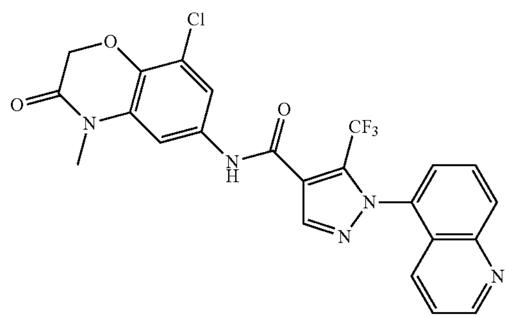 [SMILES: CN1C(=O)COc2c(Cl)cc(NC(=O)c3cnn(-c4cccc5ncccc45)c3C(F)(F)F)cc21] | 95 | N-(8-chloro-4-methyl-3-oxo-3,4-dihydro-2H-benzo[b][1,4]oxazin-6-yl)-1-(quinolin-5-yl)-5-(trifluoromethyl)-1H-pyrazole-4-carboxamide |
| 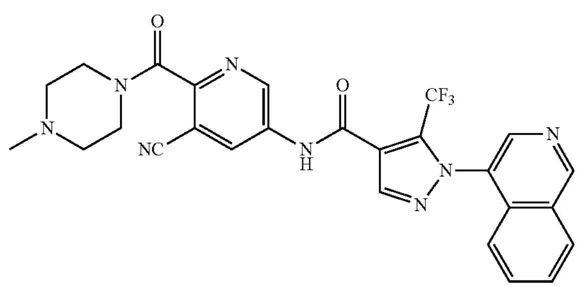 [SMILES: CN1CCN(C(=O)c2ncc(NC(=O)c3cnn(-c4cncc5ccccc45)c3C(F)(F)F)cc2C#N)CC1] | 96 | N-(5-cyano-6-(4-methylpiperazine-1-carbonyl)pyridin-3-yl)-1-(isoquinolin-4-yl)-5-(trifluoromethyl)-1H-pyrazole-4-carboxamide |
| 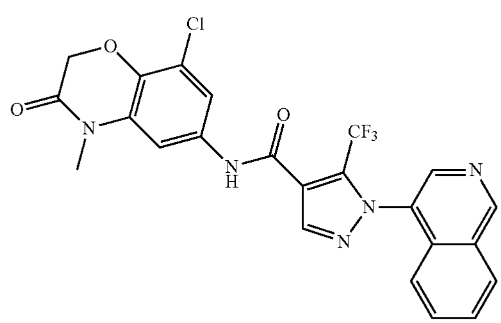 [SMILES: CN1C(=O)COc2c(Cl)cc(NC(=O)c3cnn(-c4cncc5ccccc45)c3C(F)(F)F)cc21] | 97 | N-(8-chloro-4-methyl-3-oxo-3,4-dihydro-2H-benzo[b][1,4]oxazin-6-yl)-1-(isoquinolin-4-yl)-5-(trifluoromethyl)-1H-pyrazole-4-carboxamide |
| 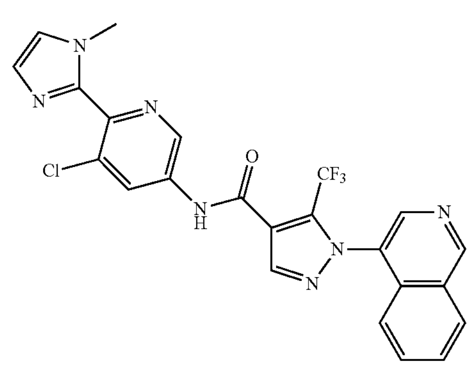 [SMILES: Cn1ccnc1-c1ncc(NC(=O)c2cnn(-c3cncc4ccccc34)c2C(F)(F)F)cc1Cl] | 98 | N-(5-chloro-6-(1-methyl-1H-imidazol-2-yl)pyridin-3-yl)-1-(isoquinolin-4-yl)-5-(trifluoromethyl)-1H-pyrazole-4-carboxamide |

TABLE 1-continued

| Structure | Cpd No. | Cpd Name |
|---|---|---|
| 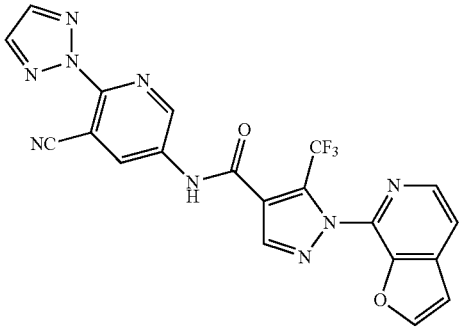 [SMILES: N#Cc1cc(NC(=O)c2cnn(-c3nccc4ccoc34)c2C(F)(F)F)cnc1-n1nccn1] | 99 | N-(5-cyano-6-(2H-1,2,3-triazol-2-yl)pyridin-3-yl)-1-(furo[2,3-c]pyridin-7-yl)-5-(trifluoromethyl)-1H-pyrazole-4-carboxamide |
| 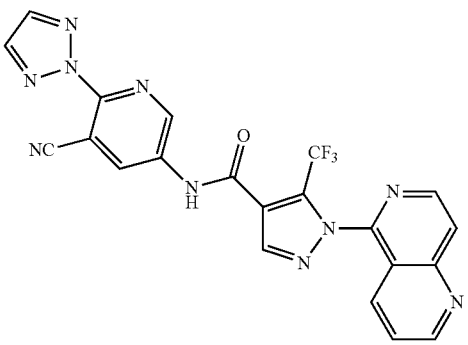 [SMILES: N#Cc1cc(NC(=O)c2cnn(-c3nccc4ncccc34)c2C(F)(F)F)cnc1-n1nccn1] | 100 | N-(5-cyano-6-(2H-1,2,3-triazol-2-yl)pyridin-3-yl)-1-(1,6-naphthyridin-5-yl)-5-(trifluoromethyl)-1H-pyrazole-4-carboxamide |
| 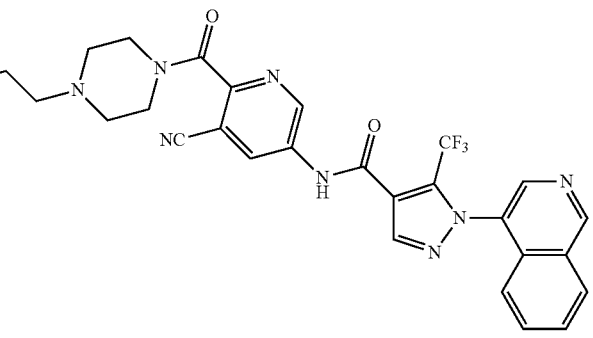 | 101 | N-(6-(4-(4-aminobutyl)piperazine-1-carbonyl)-5-cyanopyridin-3-yl)-1-(isoquinolin-4-yl)-5-(trifluoromethyl)-1H-pyrazole-4-carboxamide |
| 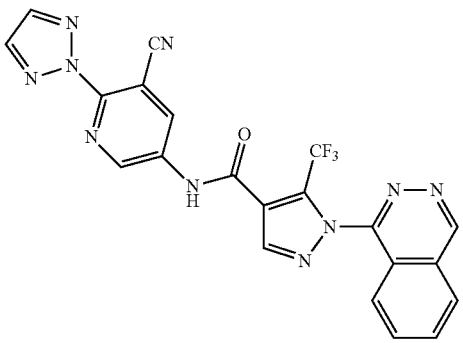 [SMILES: N#Cc1cc(NC(=O)c2cnn(-c3nncc4ccccc34)c2C(F)(F)F)cnc1-n1nccn1] | 102 | N-(5-cyano-6-(2H-1,2,3-triazol-2-yl)pyridin-3-yl)-1-(phthalazin-1-yl)-5-(trifluoromethyl)-1H-pyrazole-4-carboxamide |

TABLE 1-continued

| Structure | Cpd No. | Cpd Name |
|---|---|---|
| 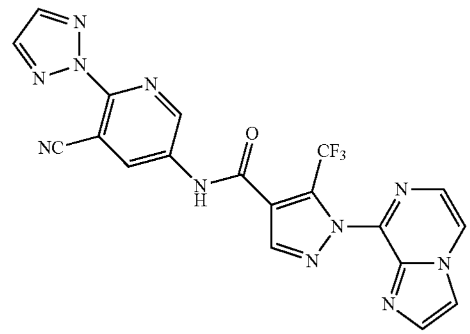 [SMILES: N#Cc1cc(NC(=O)c2cnn(-c3nccn4ccnc34)c2C(F)(F)F)cnc1-n1nccn1] | 103 | N-(5-cyano-6-(2H-1,2,3-triazol-2-yl)pyridin-3-yl)-1-(imidazo[1,2-a]pyrazin-8-yl)-5-(trifluoromethyl)-1H-pyrazole-4-carboxamide |
| 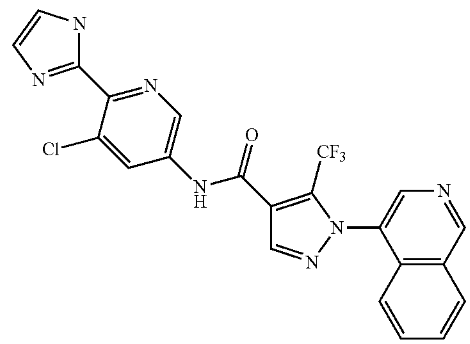 [SMILES: O=C(Nc1cnc(-c2ncc[nH]2)c(Cl)c1)c1cnn(-c2cncc3ccccc23)c1C(F)(F)F] | 104 | N-(5-chloro-6-(1H-imidazol-2-yl)pyridin-3-yl)-1-(isoquinolin-4-yl)-5-(trifluoromethyl)-1H-pyrazole-4-carboxamide |
| 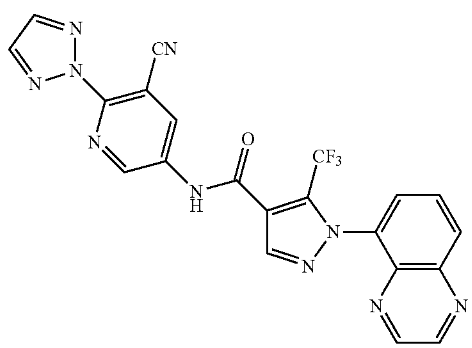 [SMILES: N#Cc1cc(NC(=O)c2cnn(-c3cccc4nccnc34)c2C(F)(F)F)cnc1-n1nccn1] | 105 | N-(5-cyano-6-(2H-1,2,3-triazol-2-yl)pyridin-3-yl)-1-(quinoxalin-5-yl)-5-(trifluoromethyl)-1H-pyrazole-4-carboxamide |
| 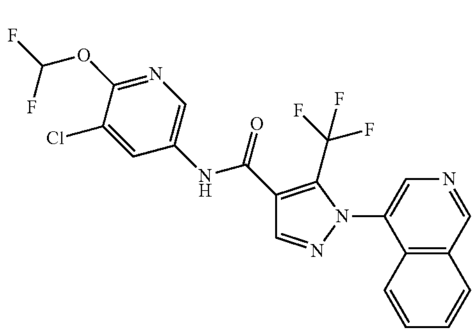 [SMILES: O=C(Nc1cnc(OC(F)F)c(Cl)c1)c1cnn(-c2cncc3ccccc23)c1C(F)(F)F] | 106 | N-(5-chloro-6-(difluoromethoxy)pyridin-3-yl)-1-(isoquinolin-4-yl)-5-(trifluoromethyl)-1H-pyrazole-4-carboxamide |

TABLE 1-continued

| Structure | Cpd No. | Cpd Name |
|---|---|---|
| 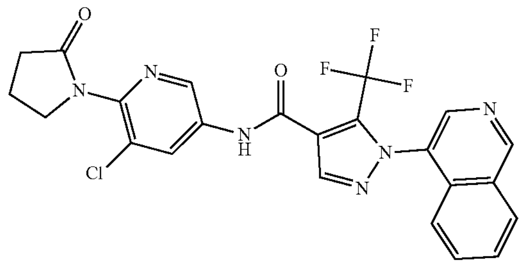 [SMILES: O=C(Nc1cnc(N2CCCC2=O)c(Cl)c1)c1cnn(-c2cncc3ccccc23)c1C(F)(F)F] | 107 | N-(5-chloro-6-(2-oxopyrrolidin-1-yl)pyridin-3-yl)-1-(isoquinolin-4-yl)-5-(trifluoromethyl)-1H-pyrazole-4-carboxamide |
| 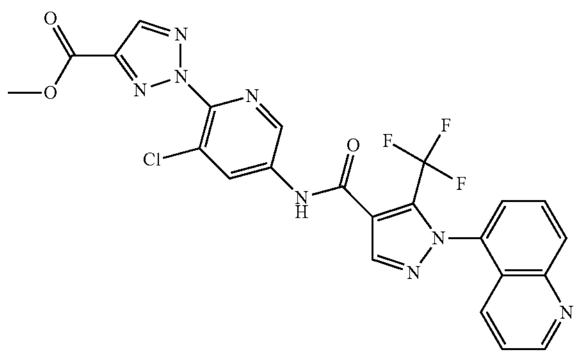 [SMILES: COC(=O)c1cnn(-c2ncc(NC(=O)c3cnn(-c4cccc5ncccc45)c3C(F)(F)F)cc2Cl)n1] | 108 | methyl2-(3-chloro-5-(1-(quinolin-5-yl)-5-(trifluoromethyl)-1H-pyrazole-4-carboxamido)pyridin-2-yl)-2H-1,2,3-triazole-4-carboxylate |
| 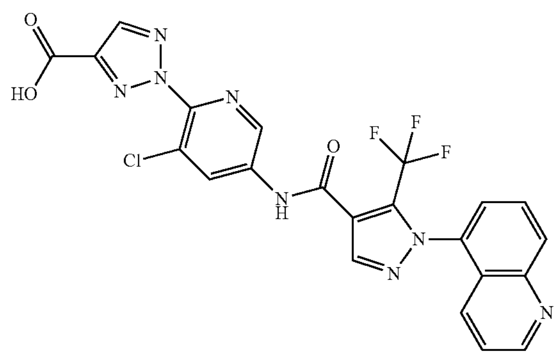 [SMILES: O=C(O)c1cnn(-c2ncc(NC(=O)c3cnn(-c4cccc5ncccc45)c3C(F)(F)F)cc2Cl)n1] | 109 | 2-(3-chloro-5-(1-(quinolin-5-yl)-5-(trifluoromethyl)-1H-pyrazole-4-carboxamido)pyridin-2-yl)-2H-1,2,3-triazole-4-carboxylic acid |
| 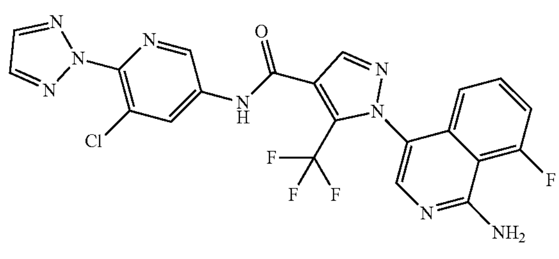 [SMILES: Nc1ncc(-n2ncc(C(=O)Nc3cnc(-n4nccn4)c(Cl)c3)c2C(F)(F)F)c2cccc(F)c12] | 110 | 1-(1-amino-8-fluoroisoquinolin-4-yl)-N-(5-chloro-6-(2H-1,2,3-triazol-2-yl)pyridin-3-yl)-5-(trifluoromethyl)-1H-pyrazole-4-carboxamide |
| 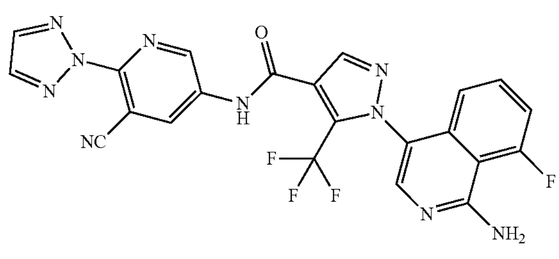 [SMILES: N#Cc1cc(NC(=O)c2cnn(-c3cnc(N)c4c(F)cccc34)c2C(F)(F)F)cnc1-n1nccn1] | 111 | 1-(1-amino-8-fluoroisoquinolin-4-yl)-N-(5-cyano-6-(2H-1,2,3-triazol-2-yl)pyridin-3-yl)-5-(trifluoromethyl)-1H-pyrazole-4-carboxamide |

TABLE 1-continued

| Structure | Cpd No. | Cpd Name |
|---|---|---|
| 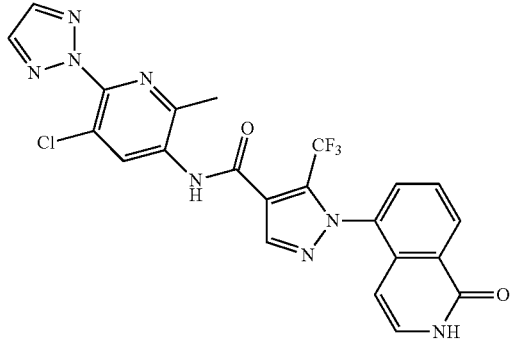 [SMILES: Cc1nc(-n2nccn2)c(Cl)cc1NC(=O)c1cnn(-c2cccc3c(=O)[nH]ccc23)c1C(F)(F)F] | 112 | N-(5-chloro-2-methyl-6-(2H-1,2,3-triazol-2-yl)pyridin-3-yl)-1-(1-oxo-1,2-dihydroisoquinolin-5-yl)-5-(trifluoromethyl)-1H-pyrazole-4-carboxamide |
| 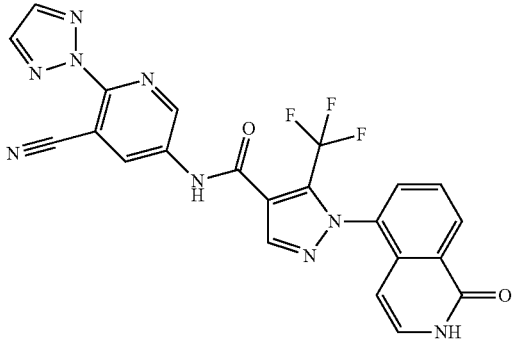 [SMILES: N#Cc1cc(NC(=O)c2cnn(-c3cccc4c(=O)[nH]ccc34)c2C(F)(F)F)cnc1-n1nccn1] | 113 | N-(5-cyano-6-(2H-1,2,3-triazol-2-yl)pyridin-3-yl)-1-(1-oxo-1,2-dihydroisoquinolin-5-yl)-5-(trifluoromethyl)-1H-pyrazole-4-carboxamide |
| 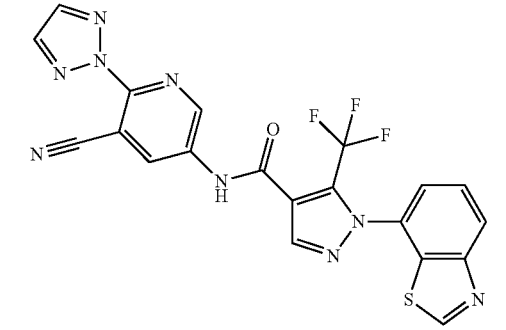 [SMILES: N#Cc1cc(NC(=O)c2cnn(-c3cccc4ncsc34)c2C(F)(F)F)cnc1-n1nccn1] | 114 | 1-(benzo[d]thiazol-7-yl)-N-(5-cyano-6-(2H-1,2,3-triazol-2-yl)pyridin-3-yl)-5-(trifluoromethyl)-1H-pyrazole-4-carboxamide |
| 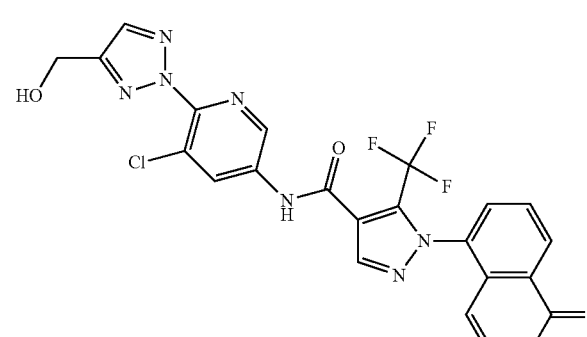 | 115 | N-(5-chloro-6-(4-(hydroxymethyl)-2H-1,2,3-triazol-2-yl)pyridin-3-yl)-1-(1-oxo-1,2-dihydroisoquinolin-5-yl)-5-(trifluoromethyl)-1H-pyrazole-4-carboxamide |

TABLE 1-continued

| Structure | Cpd No. | Cpd Name |
|---|---|---|
| 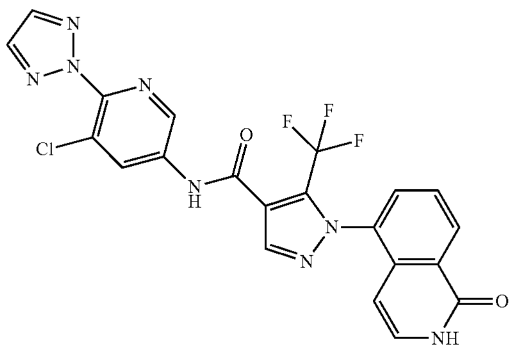 [SMILES: O=C(Nc1cnc(-n2nccn2)c(Cl)c1)c1cnn(-c2cccc3c(=O)[nH]ccc23)c1C(F)(F)F] | 116 | N-(5-chloro-6-(2H-1,2,3-triazol-2-yl)pyridin-3-yl)-1-(1-hydroxyisoquinolin-5-yl)-5-(trifluoromethyl)-1H-pyrazole-4-carboxamide |
| 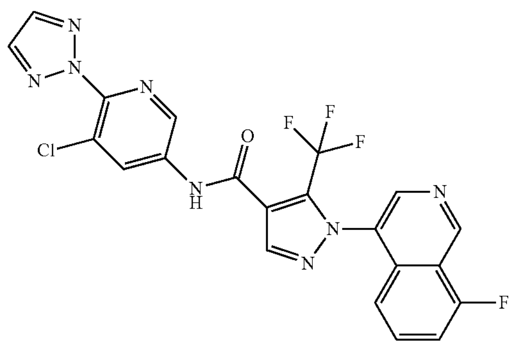 [SMILES: O=C(Nc1cnc(-n2nccn2)c(Cl)c1)c1cnn(-c2cncc3c(F)cccc23)c1C(F)(F)F] | 117 | N-(5-chloro-6-(2H-1,2,3-triazol-2-yl)pyridin-3-yl)-1-(8-fluoroisoquinolin-4-yl)-5-(trifluoromethyl)-1H-pyrazole-4-carboxamide |
| 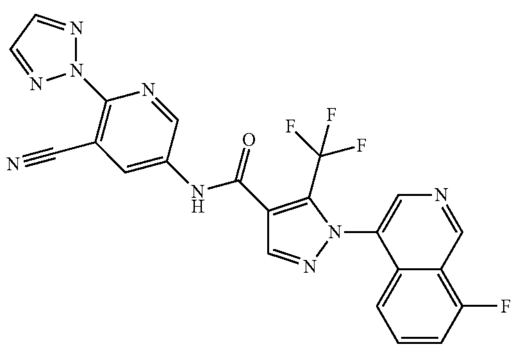 [SMILES: N#Cc1cc(NC(=O)c2cnn(-c3cncc4c(F)cccc34)c2C(F)(F)F)cnc1-n1nccn1] | 118 | N-(5-cyano-6-(2H-1,2,3-triazol-2-yl)pyridin-3-yl)-1-(8-fluoroisoquinolin-4-yl)-5-(trifluoromethyl)-1H-pyrazole-4-carboxamide |
| 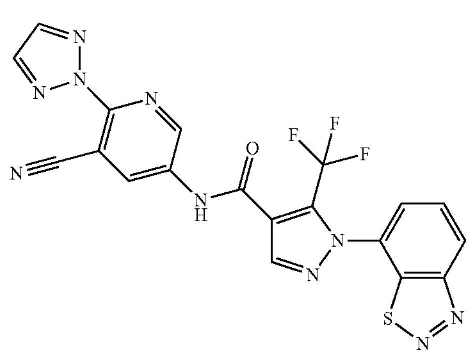 [SMILES: N#Cc1cc(NC(=O)c2cnn(-c3cccc4nnsc34)c2C(F)(F)F)cnc1-n1nccn1] | 119 | 1-(benzo[d][1,2,3]thiadiazol-7-yl)-N-(5-cyano-6-(2H-1,2,3-triazol-2-yl)pyridin-3-yl)-5-(trifluoromethyl)-1H-pyrazole-4-carboxamide |

TABLE 1-continued

| Structure | Cpd No. | Cpd Name |
|---|---|---|
| 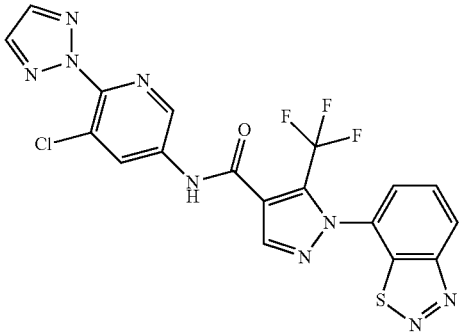 [SMILES: O=C(Nc1cnc(-n2nccn2)c(Cl)c1)c1cnn(-c2cccc3nnsc23)c1C(F)(F)F] | 120 | 1-(benzo[d][1,2,3]thiadiazol-7-yl)-N-(5-chloro-6-(2H-1,2,3-triazol-2-yl)pyridin-3-yl)-5-(trifluoromethyl)-1H-pyrazole-4-carboxamide |
| 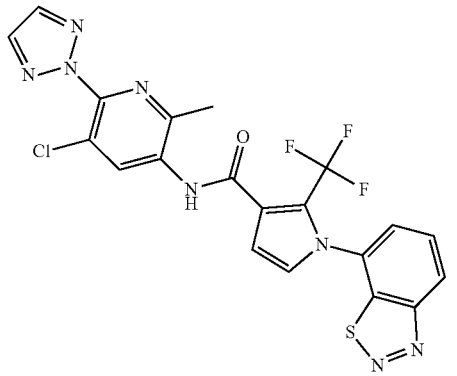 [SMILES: Cc1nc(-n2nccn2)c(Cl)cc1NC(=O)c1ccn(-c2cccc3nnsc23)c1C(F)(F)F] | 121 | 1-(benzo[d][1,2,3]thiadiazol-7-yl)-N-(5-chloro-2-methyl-6-(2H-1,2,3-triazol-2-yl)pyridin-3-yl)-5-(trifluoromethyl)-1H-pyrazole-4-carboxamide |
| 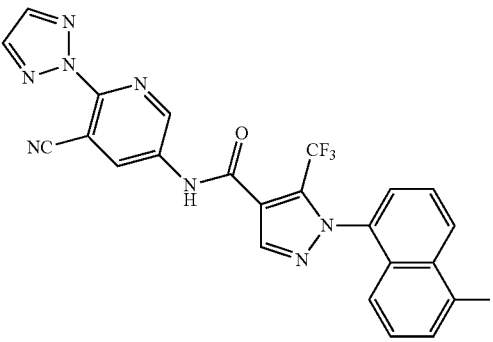 | 122 | N-(5-cyano-6-(2H-1,2,3-triazol-2-yl)pyridin-3-yl)-1-(5-fluoronaphthalen-1-yl)-5-(trifluoromethyl)-1H-pyrazole-4-carboxamide |
| 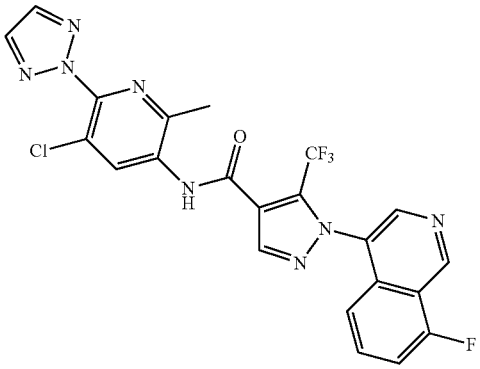 [SMILES: Cc1nc(-n2nccn2)c(Cl)cc1NC(=O)c1cnn(-c2cncc3c(F)cccc23)c1C(F)(F)F] | 123 | N-(5-chloro-2-methyl-6-(2H-1,2,3-triazol-2-yl)pyridin-3-yl)-1-(8-fluoroisoquinolin-4-yl)-5-(trifluoromethyl)-1H-pyrazole-4-carboxamide |

TABLE 1-continued

| Structure | Cpd No. | Cpd Name |
|---|---|---|
| 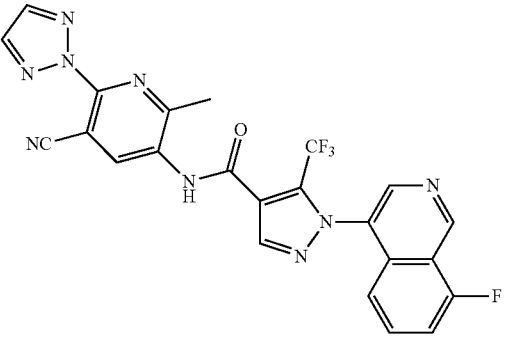 [SMILES: Cc1nc(-n2nccn2)c(C#N)cc1NC(=O)c1cnn(-c2cncc3c(F)cccc23)c1C(F)(F)F] | 124 | N-(5-cyano-2-methyl-6-(2H-1,2,3-triazol-2-yl)pyridin-3-yl)-1-(8-fluoroisoquinolin-4-yl)-5-(trifluoromethyl)-1H-pyrazole-4-carboxamide |
| 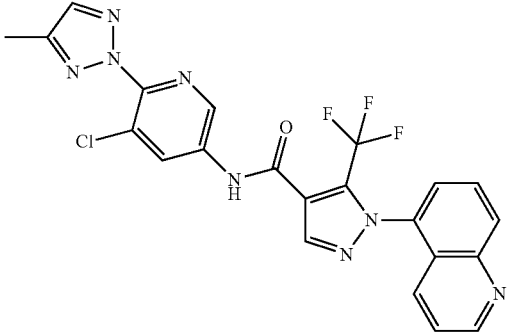 [SMILES: Cc1cnn(-c2ncc(NC(=O)c3cnn(-c4cccc5ncccc45)c3C(F)(F)F)cc2Cl)n1] | 125 | N-(5-chloro-6-(4-methyl-2H-1,2,3-triazol-2-yl)pyridin-3-yl)-1-(quinolin-5-yl)-5-(trifluoromethyl)-1H-pyrazole-4-carboxamide |
| 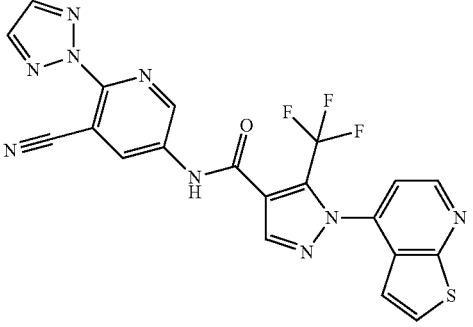 [SMILES: N#Cc1cc(NC(=O)c2cnn(-c3ccnc4sccc34)c2C(F)(F)F)cnc1-n1nccn1] | 126 | N-(5-cyano-6-(2H-1,2,3-triazol-2-yl)pyridin-3-yl)-1-(thieno[2,3-b]pyridin-4-yl)-5-(trifluoromethyl)-1H-pyrazole-4-carboxamide |
| 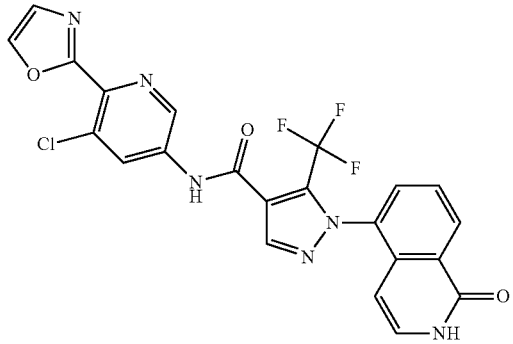 [SMILES: O=C(Nc1cnc(-c2ncco2)c(Cl)c1)c1cnn(-c2cccc3c(=O)[nH]ccc23)c1C(F)(F)F] | 127 | N-(5-chloro-6-(oxazol-2-yl)pyridin-3-yl)-1-(1-oxo-1,2-dihydroisoquinolin-5-yl)-5-(trifluoromethyl)-1H-pyrazole-4-carboxamide |

TABLE 1-continued

| Structure | Cpd No. | Cpd Name |
|---|---|---|
| 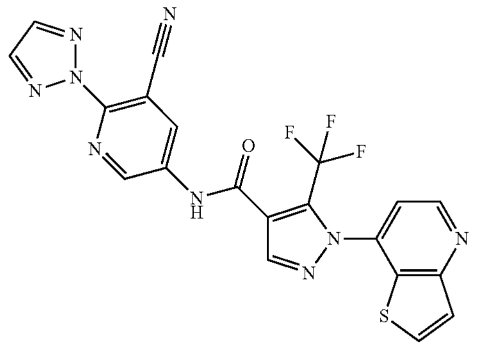 [SMILES: N#Cc1cc(NC(=O)c2cnn(-c3ccnc4ccsc34)c2C(F)(F)F)cnc1-n1nccn1] | 128 | N-(5-cyano-6-(2H-1,2,3-triazol-2-yl)pyridin-3-yl)-1-(thieno[3,2-b]pyridin-7-yl)-5-(trifluoromethyl)-1H-pyrazole-4-carboxamide |
| 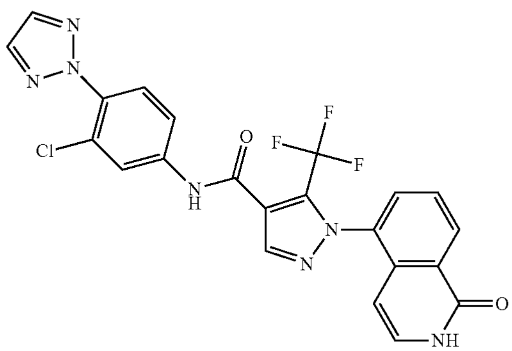 [SMILES: O=C(Nc1ccc(-n2nccn2)c(Cl)c1)c1cnn(-c2cccc3c(=O)[nH]ccc23)c1C(F)(F)F] | 129 | N-(3-chloro-4-(2H-1,2,3-triazol-2-yl)phenyl)-1-(1-oxo-1,2-dihydroisoquinolin-5-yl)-5-(trifluoromethyl)-1H-pyrazole-4-carboxamide |
| 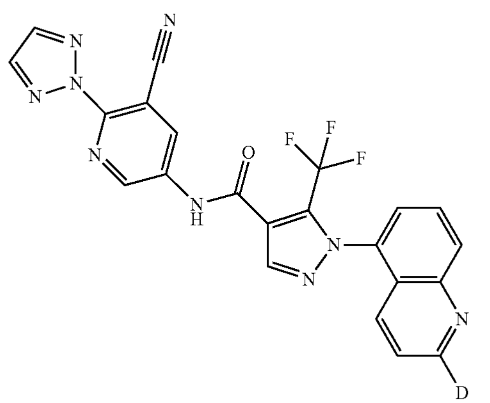 [SMILES: [2H]c1ccc2c(-n3ncc(C(=O)Nc4cnc(-n5nccn5)c(C#N)c4)c3C(F)(F)F)cccc2n1] | 130 | N-(5-cyano-6-(2H-1,2,3-triazol-2-yl)pyridin-3-yl)-1-(2-D-quinolin-5-yl)-5-(trifluoromethyl)-1H-pyrazole-4-carboxamide |
| 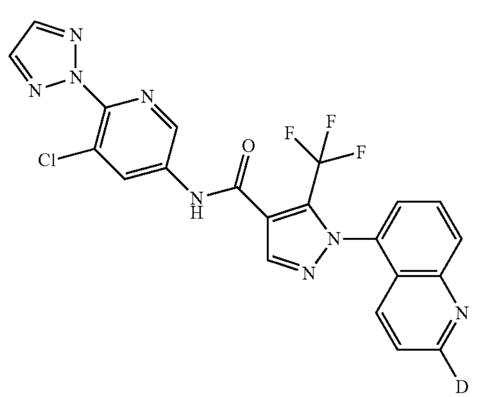 [SMILES: [2H]c1ccc2c(-n3ncc(C(=O)Nc4cnc(-n5nccn5)c(Cl)c4)c3C(F)(F)F)cccc2n1] | 131 | N-(5-chloro-6-(2H-1,2,3-triazol-2-yl)pyridin-3-yl)-1-(2-Dquinolin-5-yl)-5-(trifluoromethyl)-1H-pyrazole-4-carboxamide |

TABLE 1-continued

| Structure | Cpd No. | Cpd Name |
|---|---|---|
| 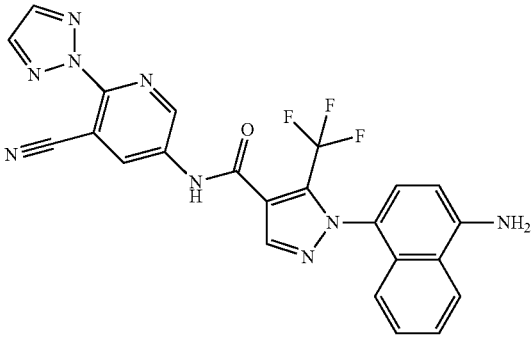 [SMILES: N#Cc1cc(NC(=O)c2cnn(-c3ccc(N)c4ccccc34)c2C(F)(F)F)cnc1-n1nccn1] | 132 | 1-(4-aminonaphthalen-1-yl)-N-(5-cyano-6-(2H-1,2,3-triazol-2-yl)pyridin-3-yl)-5-(trifluoromethyl)-1H-pyrazole-4-carboxamide |
| 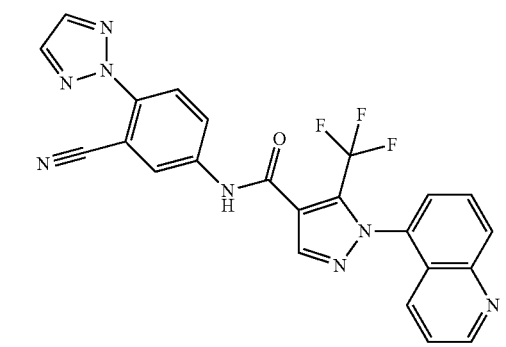 [SMILES: N#Cc1cc(NC(=O)c2cnn(-c3cccc4ncccc34)c2C(F)(F)F)ccc1-n1nccn1] | 133 | N-(3-cyano-4-(2H-1,2,3-triazol-2-yl)phenyl)-1-(quinolin-5-yl)-5-(trifluoromethyl)-1H-pyrazole-4-carboxamide |
| 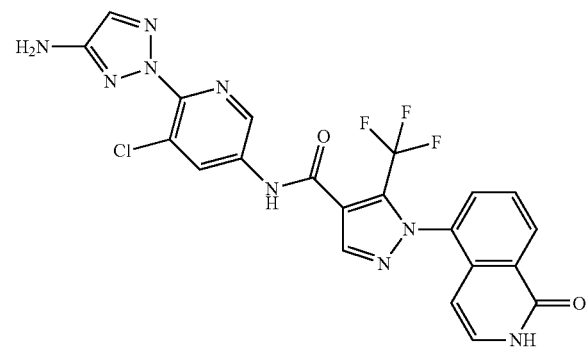 [SMILES: Nc1cnn(-c2ncc(NC(=O)c3cnn(-c4cccc5c(=O)[nH]ccc45)c3C(F)(F)F)cc2Cl)n1] | 134 | N-(6-(4-amino-2H-1,2,3-triazol-2-yl)-5-chloropyridin-3-yl)-1-(1-oxo-1,2-dihydroisoquinolin-5-yl)-5-(trifluoromethyl)-1H-pyrazole-4-carboxamide |
| 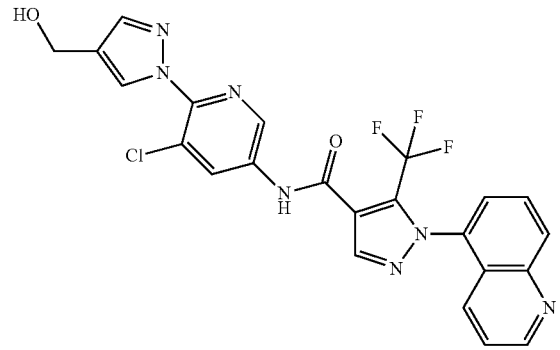 [SMILES: O=C(Nc1cnc(-n2cc(CO)cn2)c(Cl)c1)c1cnn(-c2cccc3ncccc23)c1C(F)(F)F] | 135 | N-(5-chloro-6-(4-(hydroxymethyl)-1H-pyrazol-1-yl)pyridin-3-yl)-1-(quinolin-5-yl)-5-(trifluoromethyl)-1H-pyrazole-4-carboxamide |

TABLE 1-continued

| Structure | Cpd No. | Cpd Name |
|---|---|---|
| 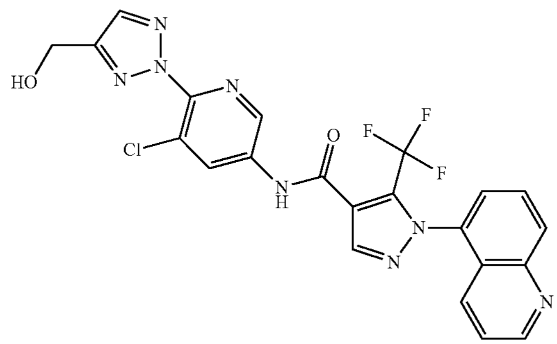 [SMILES: O=C(Nc1cnc(-n2ncc(CO)n2)c(Cl)c1)c1cnn(-c2cccc3ncccc23)c1C(F)(F)F] | 136 | N-(5-chloro-6-(4-(hydroxymethyl)-2H-1,2,3-triazol-2-yl)pyridin-3-yl)-1-(quinolin-5-yl)-5-(trifluoromethyl)-1H-pyrazole-4-carboxamide |
| 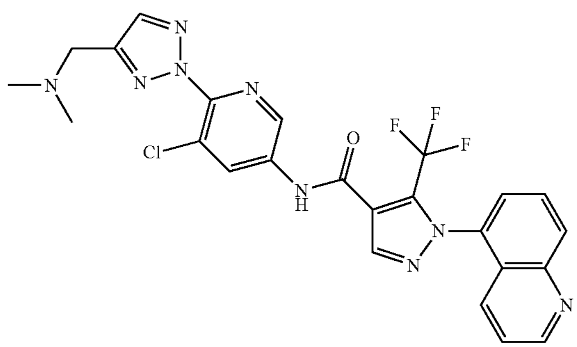 [SMILES: CN(C)Cc1cnn(-c2ncc(NC(=O)c3cnn(-c4cccc5ncccc45)c3C(F)(F)F)cc2Cl)n1] | 137 | N-(5-chloro-6-(4-((dimethylamino)methyl)-2H-1,2,3-triazol-2-yl)pyridin-3-yl)-1-(quinolin-5-yl)-5-(trifluoromethyl)-1H-pyrazole-4-carboxamide |
| 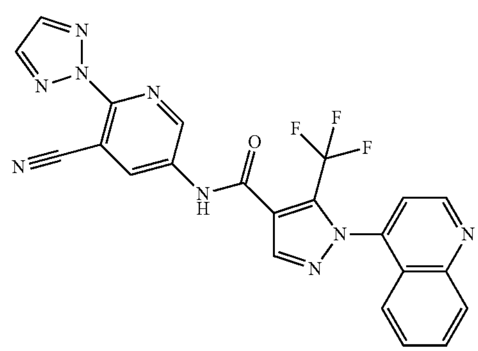 [SMILES: N#Cc1cc(NC(=O)c2cnn(-c3ccnc4ccccc34)c2C(F)(F)F)cnc1-n1nccn1] | 138 | N-(5-cyano-6-(2H-1,2,3-triazol-2-yl)pyridin-3-yl)-1-(quinolin-4-yl)-5-(trifluoromethyl)-1H-pyrazole-4-carboxamide |
| 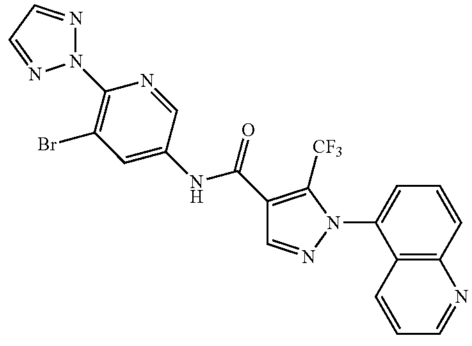 [SMILES: O=C(Nc1cnc(-n2nccn2)c(Br)c1)c1cnn(-c2cccc3ncccc23)c1C(F)(F)F] | 139 | N-(5-bromo-6-(2H-1,2,3-triazol-2-yl)pyridin-3-yl)-1-(quinolin-5-yl)-5-(trifluoromethyl)-1H-pyrazole-4-carboxamide |

TABLE 1-continued

| Structure | Cpd No. | Cpd Name |
|---|---|---|
| 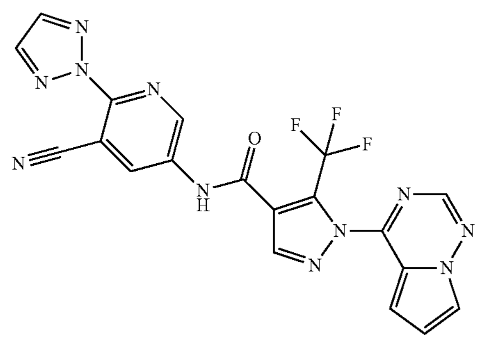 [SMILES: N#Cc1cc(NC(=O)c2cnn(-c3ncnn4cccc34)c2C(F)(F)F)cnc1-n1nccn1] | 140 | N-(5-cyano-6-(2H-1,2,3-triazol-2-yl)pyridin-3-yl)-1-(pyrrolo[2,1-f][1,2,4]triazin-4-yl)-5-(trifluoromethyl)-1H-pyrazole-4-carboxamide |
| 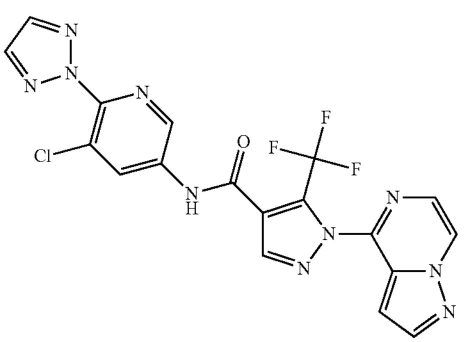 | 141 | N-(5-chloro-6-(2H-1,2,3-triazol-2-yl)pyridin-3-yl)-1-(pyrazolo[1,5-a]pyrazin-4-yl)-5-(trifluoromethyl)-1H-pyrazole-4-carboxamide |
| 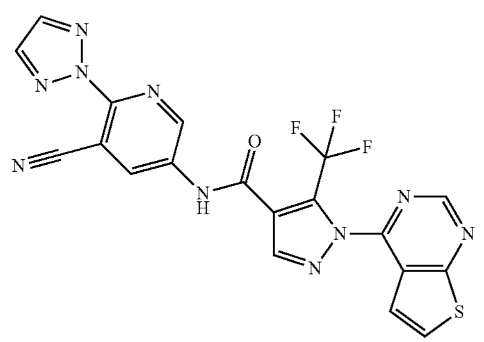 [SMILES: N#Cc1cc(NC(=O)c2cnn(-c3ncnc4sccc34)c2C(F)(F)F)cnc1-n1nccn1] | 142 | N-(5-cyano-6-(2H-1,2,3-triazol-2-yl)pyridin-3-yl)-1-(thieno[2,3-d]pyrimidin-4-yl)-5-(trifluoromethyl)-1H-pyrazole-4-carboxamide |
| 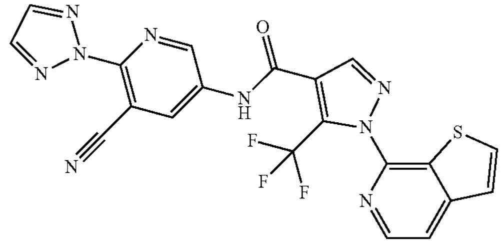 [SMILES: N#Cc1cc(NC(=O)c2cnn(-c3nccc4ccsc34)c2C(F)(F)F)cnc1-n1nccn1] | 143 | N-(5-cyano-6-(2H-1,2,3-triazol-2-yl)pyridin-3-yl)-1-(thieno[2,3-c]pyrimidin-7-yl)-5-(trifluoromethyl)-1H-pyrazole-4-carboxamide |

TABLE 1-continued

| Structure | Cpd No. | Cpd Name |
|---|---|---|
| 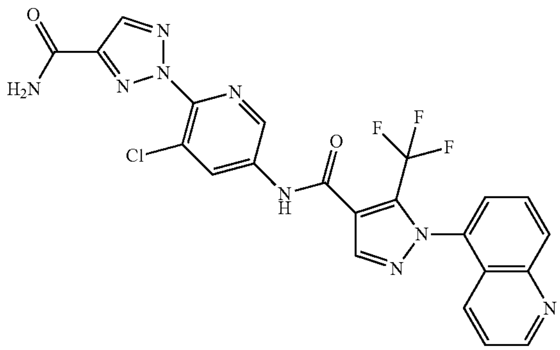 [SMILES: NC(=O)c1cnn(-c2ncc(NC(=O)c3cnn(-c4cccc5ncccc45)c3C(F)(F)F)cc2Cl)n1] | 144 | 2-(3-chloro-5-(1-(quinolin-5-yl)-5-(trifluoromethyl)-1H-pyrazole-4-carboxamido)pyridin-2-yl)-2H-1,2,3-triazole-4-carboxamide |
| 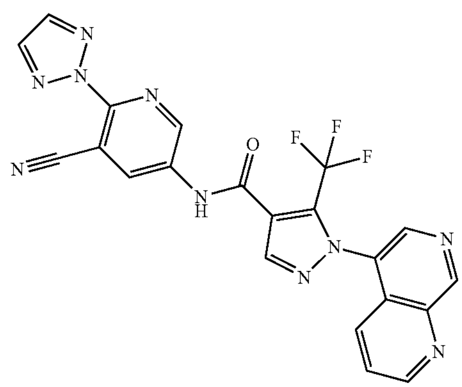 [SMILES: N#Cc1cc(NC(=O)c2cnn(-c3cncc4ncccc34)c2C(F)(F)F)cnc1-n1nccn1] | 145 | N-(5-cyano-6-(2H-1,2,3-triazol-2-yl)pyridin-3-yl)-1-(1,7-naphthyridin-5-yl)-5-(trifluoromethyl)-1H-pyrazole-4-carboxamide |
| 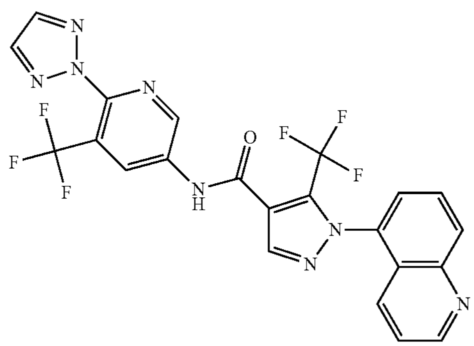 [SMILES: O=C(Nc1cnc(-n2nccn2)c(C(F)(F)F)c1)c1cnn(-c2cccc3ncccc23)c1C(F)(F)F] | 146 | N-(6-(2H-1,2,3-triazol-2-yl)-5-(trifluoromethyl)pyridin-3-yl)-1-(quinolin-5-yl)-5-(trifluoromethyl)-1H-pyrazole-4-carboxamide |
| 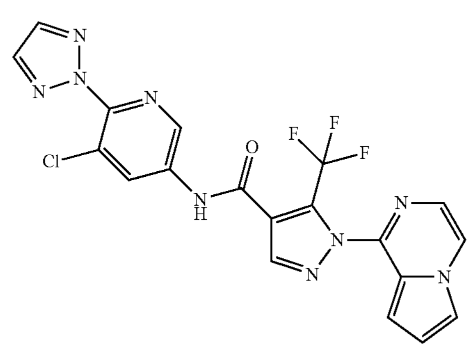 [SMILES: O=C(Nc1cnc(-n2nccn2)c(Cl)c1)c1cnn(-c2nccn3cccc23)c1C(F)(F)F] | 147 | N-(5-chloro-6-(2H-1,2,3-triazol-2-yl)pyridin-3-yl)-1-(pyrrolo[1,2-a]pyrazin-1-yl)-5-(trifluoromethyl)-1H-pyrazole-4-carboxamide |

TABLE 1-continued

| Structure | Cpd No. | Cpd Name |
|---|---|---|
| 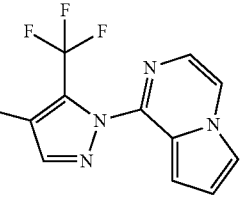 | 148 | N-(5-cyano-6-(2H-1,2,3-triazol-2-yl)pyridin-3-yl)-1-(pyrrolo[1,2-a]pyrazin-1-yl)-5-(trifluoromethyl)-1H-pyrazole-4-carboxamide |
| 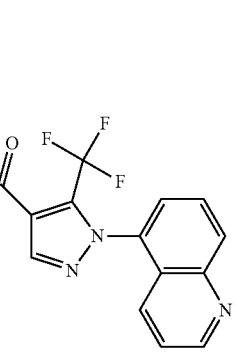 | 149 | N-(5-cyano-6-(2-methyl-2H-tetrazol-5-yl)pyridin-3-yl)-1-(quinolin-5-yl)-5-(trifluoromethyl)-1H-pyrazole-4-carboxamide |
| 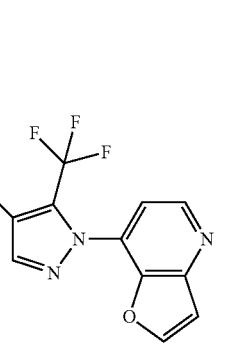 | 150 | N-(5-cyano-6-(2H-1,2,3-triazol-2-yl)pyridin-3-yl)-1-(furo[3,2-b]pyridin-7-yl)-5-(trifluoromethyl)-1H-pyrazole-4-carboxamide |
| 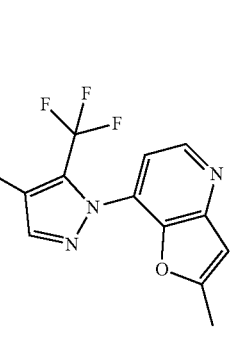 | 151 | N-(5-cyano-6-(2H-1,2,3-triazol-2-yl)pyridin-3-yl)-1-(2-methylfuro[3,2-b]pyridin-7-yl)-5-(trifluoromethyl)-1H-pyrazole-4-carboxamide |
| 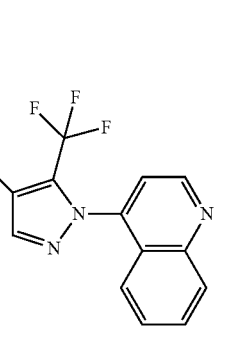 | 152 | N-(5-cyano-6-(2H-1,2,3-triazol-2-yl)pyridin-3-yl)-1-(4-fluoro-2-methoxyphenyl)-5-(trifluoromethyl)-1H-pyrazole-4-carboxamide |

TABLE 1-continued

| Structure | Cpd No. | Cpd Name |
|---|---|---|
| 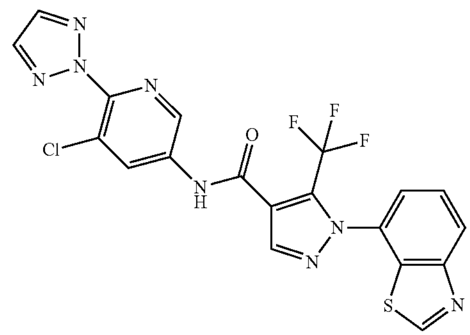 [SMILES: O=C(Nc1cnc(-n2nccn2)c(Cl)c1)c1cnn(-c2cccc3ncsc23)c1C(F)(F)F] | 153 | 1-(benzo[d]thiazol-7-yl)-N-(5-chloro-6-(2H-1,2,3-triazol-2-yl)pyridin-3-yl)-5-(trifluoromethyl)-1H-pyrazole-4-carboxamide |
| 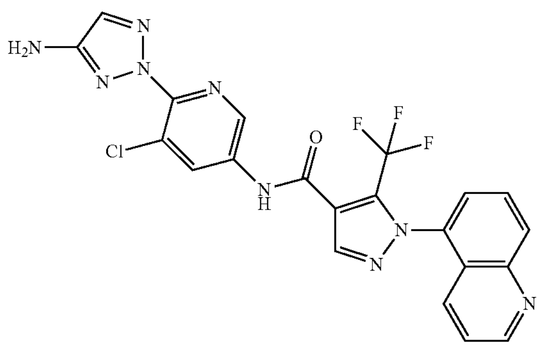 [SMILES: Nc1cnn(-c2ncc(NC(=O)c3cnn(-c4cccc5ncccc45)c3C(F)(F)F)cc2Cl)n1] | 154 | N-(6-(4-amino-2H-1,2,3-triazol-2-yl)-5-chloropyridin-3-yl)-1-(quinolin-5-yl)-5-(trifluoromethyl)-1H-pyrazole-4-carboxamide |
| 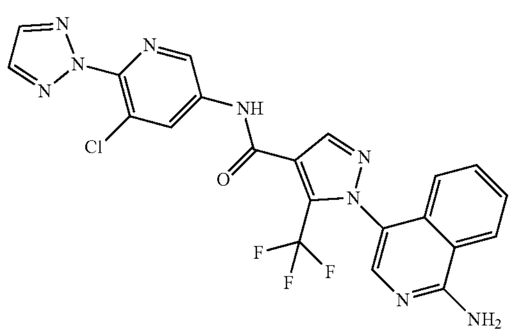 [SMILES: Nc1ncc(-n2ncc(C(=O)Nc3cnc(-n4nccn4)c(Cl)c3)c2C(F)(F)F)c2ccccc12] | 155 | 1-(1-aminoisoquinolin-4-yl)-N-(5-chloro-6-(2H-1,2,3-triazol-2-yl)pyridin-3-yl)-5-(trifluoromethyl)-1H-pyrazole-4-carboxamide |
| 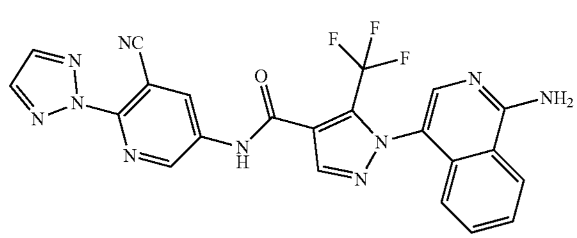 [SMILES: N#Cc1cc(NC(=O)c2cnn(-c3cnc(N)c4ccccc34)c2C(F)(F)F)cnc1-n1nccn1] | 156 | 1-(1-aminoisoquinolin-4-yl)-N-(5-cyano-6-(2H-1,2,3-triazol-2-yl)pyridin-3-yl)-5-(trifluoromethyl)-1H-pyrazole-4-carboxamide |

TABLE 1-continued

| Structure | Cpd No. | Cpd Name |
|---|---|---|
| 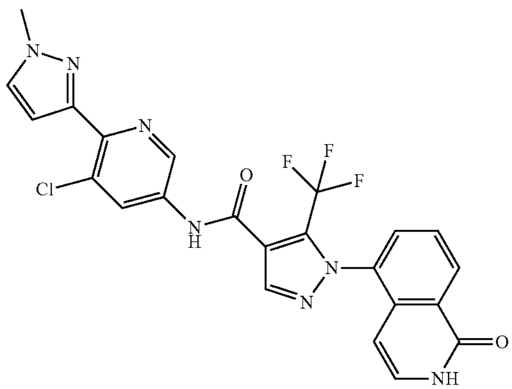 [SMILES: Cn1ccc(-c2ncc(NC(=O)c3cnn(-c4cccc5c(=O)[nH]ccc45)c3C(F)(F)F)cc2Cl)n1] | 157 | N-(5-chloro-6-(1-methyl-1H-pyrazol-3-yl)pyridin-3-yl)-1-(1-oxo-1,2-dihydroisoquinolin-5-yl)-5-(trifluoromethyl)-1H-pyrazole-4-carboxamide |
| 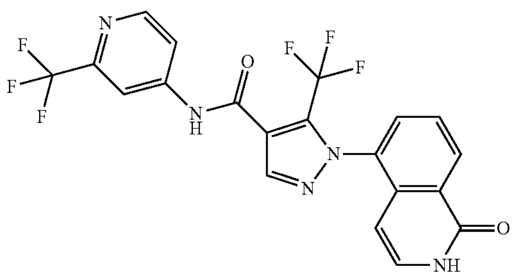 [SMILES: O=C(Nc1ccnc(C(F)(F)F)c1)c1cnn(-c2cccc3c(=O)[nH]ccc23)c1C(F)(F)F] | 158 | 1-(1-oxo-1,2-dihydroisoquinolin-5-yl)-5-(trifluoromethyl)-N-(2-(trifluoromethyl)pyridin-4-yl)-1H-pyrazole-4-carboxamide |
| 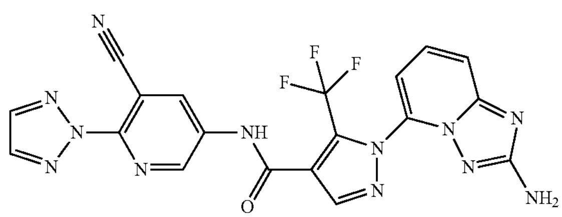 [SMILES: N#Cc1cc(NC(=O)c2cnn(-c3cccc4nc(N)nn34)c2C(F)(F)F)cnc1-n1nccn1] | 159 | 1-(2-amino-[1,2,4]triazolo[1,5-a]pyridin-5-yl)-N-(5-cyano-6-(2H-1,2,3-triazol-2-yl)pyridin-3-yl)-5-(trifluoromethyl)-1H-pyrazole-4-carboxamide |
| 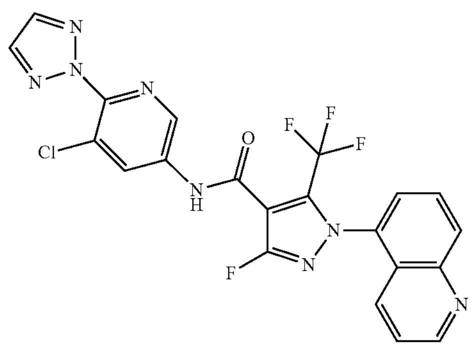 [SMILES: O=C(Nc1cnc(-n2nccn2)c(Cl)c1)c1c(F)nn(-c2cccc3ncccc23)c1C(F)(F)F] | 160 | N-(5-chloro-6-(2H-1,2,3-triazol-2-yl)pyridin-3-yl)-3-fluoro-1-(quinolin-5-yl)-5-(trifluoromethyl)-1H-pyrazole-4-carboxamide |
| 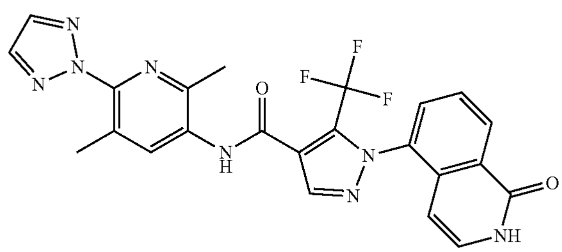 [SMILES: Cc1cc(NC(=O)c2cnn(-c3cccc4c(=O)[nH]ccc34)c2C(F)(F)F)c(C)nc1-n1nccn1] | 161 | N-(2,5-dimethyl-6-(2H-1,2,3-triazol-2-yl)pyridin-3-yl)-1-(1-oxo-1,2-dihydroisoquinolin-5-yl)-5-(trifluoromethyl)-1H-pyrazole-4-carboxamide |

TABLE 1-continued

| Structure | Cpd No. | Cpd Name |
|---|---|---|
| 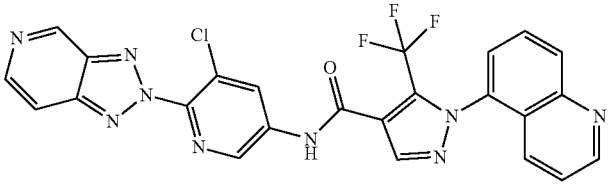 [SMILES: O=C(Nc1cnc(-n2nc3ccncc3n2)c(Cl)c1)c1cnn(-c2cccc3ncccc23)c1C(F)(F)F] | 162 | N-(6-(2H-[1,2,3]triazolo[4,5-c]pyridin-2-yl)-5-chloropyridin-3-yl)-1-(quinolin-5-yl)-5-(trifluoromethyl)-1H-pyrazole-4-carboxamide |
| 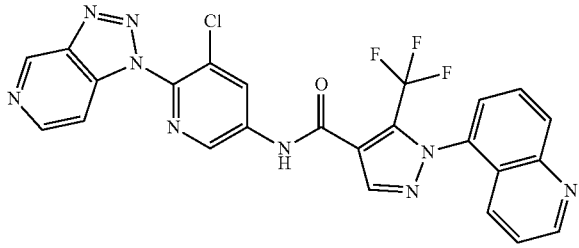 [SMILES: O=C(Nc1cnc(-n2nnc3cnccc32)c(Cl)c1)c1cnn(-c2cccc3ncccc23)c1C(F)(F)F] | 163 | N-(6-(1H-[1,2,3]triazolo[4,5-c]pyridin-1-yl)-5-chloropyridin-3-yl)-1-(quinolin-5-yl)-5-(trifluoromethyl)-1H-pyrazole-4-carboxamide |
| 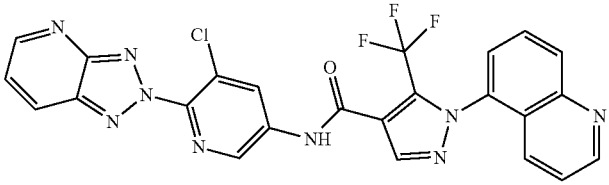 [SMILES: O=C(Nc1cnc(-n2nc3cccnc3n2)c(Cl)c1)c1cnn(-c2cccc3ncccc23)c1C(F)(F)F] | 164 | N-(6-(2H-[1,2,3]triazolo[4,5-b]pyridin-2-yl)-5-chloropyridin-3-yl)-1-(quinolin-5-yl)-5-(trifluoromethyl)-1H-pyrazole-4-carboxamide |
| 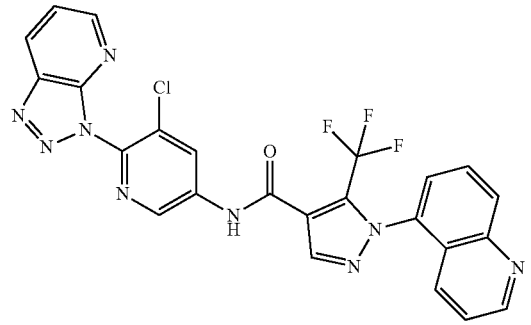 [SMILES: O=C(Nc1cnc(-n2nnc3cccnc32)c(Cl)c1)c1cnn(-c2cccc3ncccc23)c1C(F)(F)F] | 165 | N-(6-(3H-[1,2,3]triazolo[4,5-b]pyridin-3-yl)-5-chloropyridin-3-yl)-1-(quinolin-5-yl)-5-(trifluoromethyl)-1H-pyrazole-4-carboxamide |
| 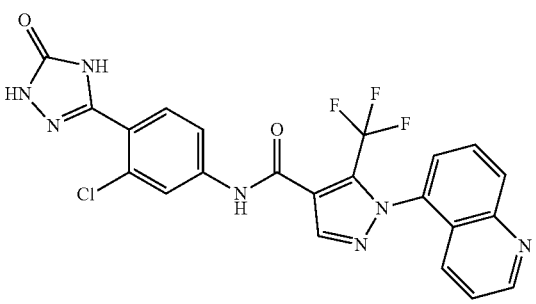 [SMILES: O=C(Nc1ccc(-c2n[nH]c(=O)[nH]2)c(Cl)c1)c1cnn(-c2cccc3ncccc23)c1C(F)(F)F] | 166 | N-(3-chloro-4-(5-oxo-4,5-dihydro-1H-1,2,4-triazol-3-yl)phenyl)-1-(quinolin-5-yl)-5-(trifluoromethyl)-1H-pyrazole-4-carboxamide |
| 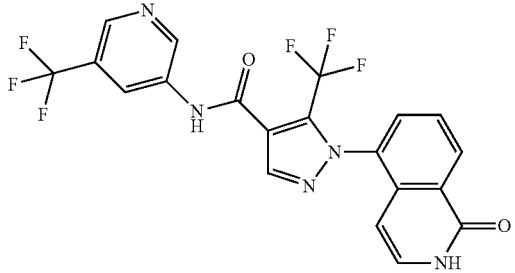 [SMILES: O=C(Nc1cncc(C(F)(F)F)c1)c1cnn(-c2cccc3c(=O)[nH]ccc23)c1C(F)(F)F] | 167 | 1-(1-oxo-1,2-dihydroisoquinolin-5-yl)-5-(trifluoromethyl)-N-(5-(trifluoromethyl)pyridin-3-yl)-1H-pyrazole-4-carboxamide |

TABLE 1-continued

| Structure | Cpd No. | Cpd Name |
|---|---|---|
| 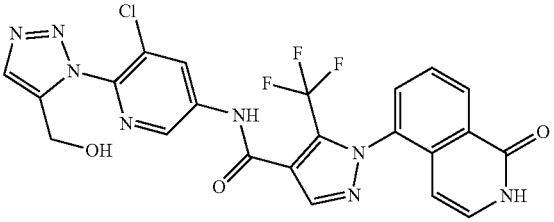 [SMILES: O=C(Nc1cnc(-n2nncc2CO)c(Cl)c1)c1cnn(-c2cccc3c(=O)[nH]ccc23)c1C(F)(F)F] | 168 | N-(5-chloro-6-(5-(hydroxymethyl)-1H-1,2,3-triazol-1-yl)pyridin-3-yl)-1-(1-oxo-1,2-dihydroisoquinolin-5-yl)-5-(trifluoromethyl)-1H-pyrazole-4-carboxamide |
| 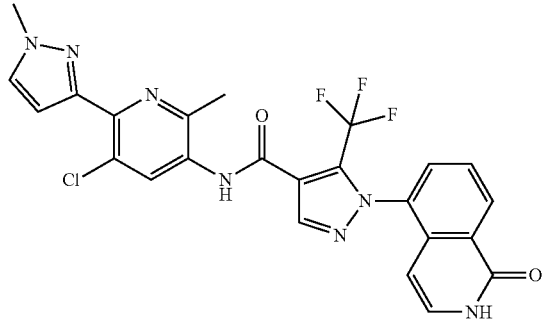 [SMILES: Cc1nc(-c2ccn(C)n2)c(Cl)cc1NC(=O)c1cnn(-c2cccc3c(=O)[nH]ccc23)c1C(F)(F)F] | 169 | N-(5-chloro-2-methyl-6-(1-methyl-1H-pyrazol-3-yl)pyridin-3-yl)-1-(1-oxo-1,2-dihydroisoquinolin-5-yl)-5-(trifluoromethyl)-1H-pyrazole-4-carboxamide |
| 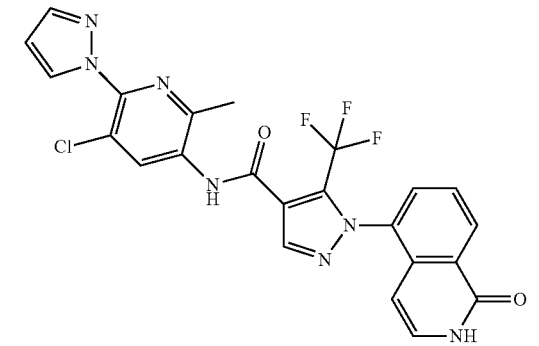 [SMILES: Cc1nc(-n2cccn2)c(Cl)cc1NC(=O)c1cnn(-c2cccc3c(=O)[nH]ccc23)c1C(F)(F)F] | 170 | N-(5-chloro-2-methyl-6-(1H-pyrazol-1-yl)pyridin-3-yl)-1-(1-oxo-1,2-dihydroisoquinolin-5-yl)-5-(trifluoromethyl)-1H-pyrazole-4-carboxamide |
| 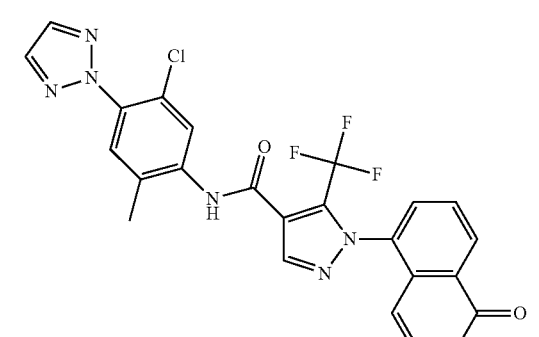 | 171 | N-(5-chloro-2-methyl-4-(2H-1,2,3-triazol-2-yl)phenyl)-1-(1-oxo-1,2-dihydroisoquinolin-5-yl)-5-(trifluoromethyl)-1H-pyrazole-4-carboxamide |

TABLE 1-continued

| Structure | Cpd No. | Cpd Name |
|---|---|---|
| 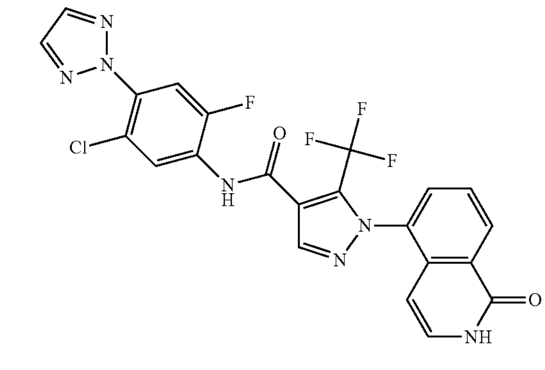 [SMILES: O=C(Nc1cc(Cl)c(-n2nccn2)cc1F)c1cnn(-c2cccc3c(=O)[nH]ccc23)c1C(F)(F)F] | 172 | N-(5-chloro-2-fluoro-4-(2H-1,2,3-triazol-2-yl)phenyl)-1-(1-oxo-1,2-dihydroisoquinolin-5-yl)-5-(trifluoromethyl)-1H-pyrazole-4-carboxamide |
| 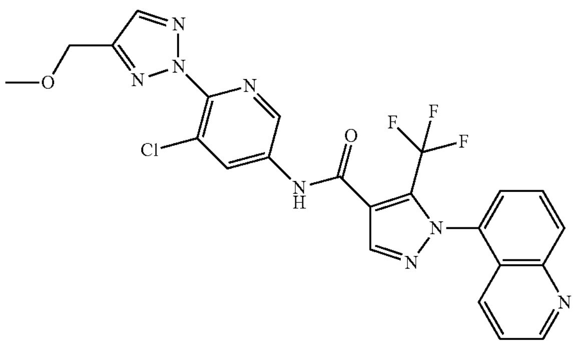 [SMILES: COCc1cnn(-c2ncc(NC(=O)c3cnn(-c4cccc5ncccc45)c3C(F)(F)F)cc2Cl)n1] | 173 | N-(5-chloro-6-(4-(methoxymethyl)-2H-1,2,3-triazol-2-yl)pyridin-3-yl)-1-(quinolin-5-yl)-5-(trifluoromethyl)-1H-pyrazole-4-carboxamide |
| 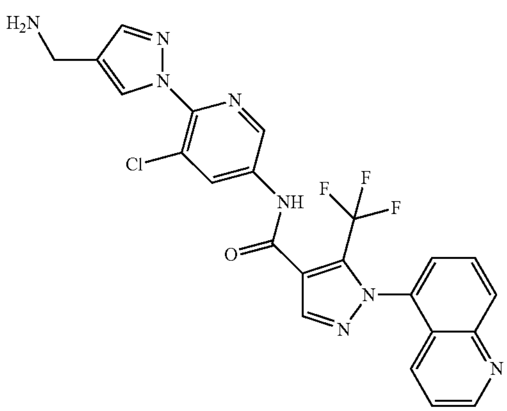 [SMILES: NCc1cnn(-c2ncc(NC(=O)c3cnn(-c4cccc5ncccc45)c3C(F)(F)F)cc2Cl)c1] | 174 | N-(4-(4-(aminomethyl)-1H-pyrazol-1-yl)-3-chlorophenyl)-1-(quinolin-5-yl)-5-(trifluoromethyl)-1H-pyrazole-4-carboxamide |
| 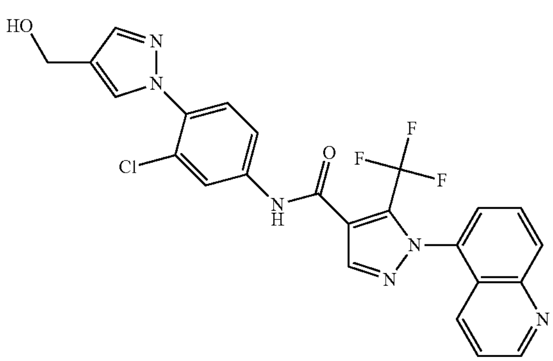 [SMILES: O=C(Nc1ccc(-n2cc(CO)cn2)c(Cl)c1)c1cnn(-c2cccc3ncccc23)c1C(F)(F)F] | 175 | N-(3-chloro-4-(4-(hydroxymethyl)-1H-pyrazol-1-yl)phenyl)-1-(quinolin-5-yl)-5-(trifluoromethyl)-1H-pyrazole-4-carboxamide |

TABLE 1-continued

| Structure | Cpd No. | Cpd Name |
|---|---|---|
| 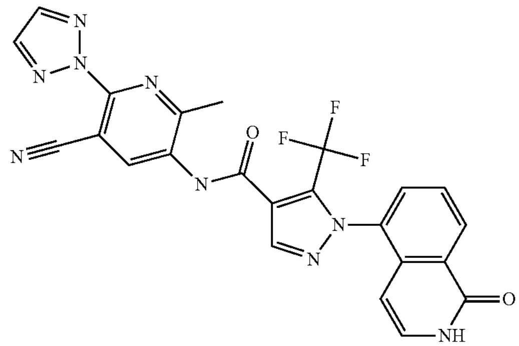 [SMILES: Cc1nc(-n2nccn2)c(C#N)cc1NC(=O)c1cnn(-c2cccc3c(=O)[nH]ccc23)c1C(F)(F)F] | 176 | N-(5-cyano-2-methyl-6-(2H-1,2,3-triazol-2-yl)pyridin-3-yl)-1-(1-oxo-1,2-dihydroisoquinolin-5-yl)-5-(trifluoromethyl)-1H-pyrazole-4-carboxamide |
| 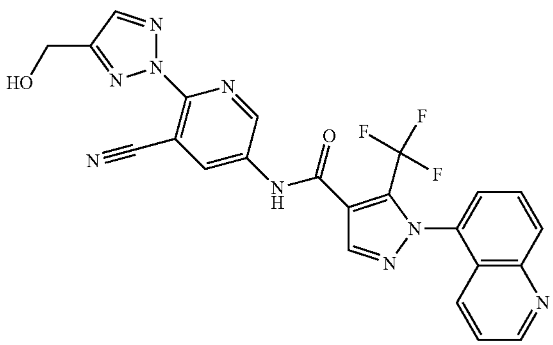 [SMILES: N#Cc1cc(NC(=O)c2cnn(-c3cccc4ncccc34)c2C(F)(F)F)cnc1-n1ncc(CO)n1] | 177 | N-(5-cyano-6-(4-(hydroxymethyl)-2H-1,2,3-triazol-2-yl)pyridin-3-yl)-1-(quinolin-5-yl)-5-(trifluoromethyl)-1H-pyrazole-4-carboxamide |
| 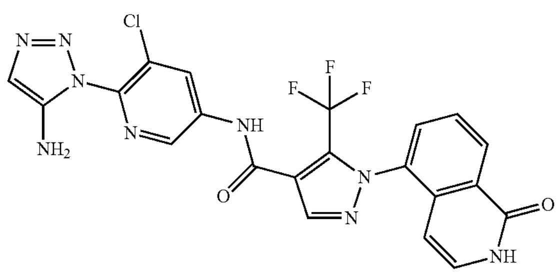 [SMILES: Nc1cnnn1-c1ncc(NC(=O)c2cnn(-c3cccc4c(=O)[nH]ccc34)c2C(F)(F)F)cc1Cl] | 178 | N-(6-(5-amino-1H-1,2,3-triazol-1-yl)-5-chloropyridin-3-yl)-1-(1-oxo-1,2-dihydroisoquinolin-5-yl)-5-(trifluoromethyl)-1H-pyrazole-4-carboxamide |
| 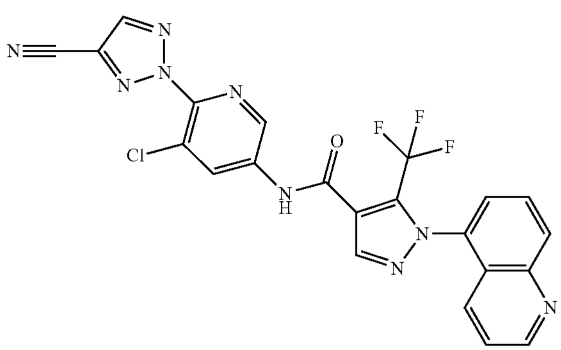 [SMILES: N#Cc1cnn(-c2ncc(NC(=O)c3cnn(-c4cccc5ncccc45)c3C(F)(F)F)cc2Cl)n1] | 179 | N-(5-chloro-6-(4-cyano-2H-1,2,3-triazol-2-yl)pyridin-3-yl)-1-(quinolin-5-yl)-5-(trifluoromethyl)-1H-pyrazole-4-carboxamide |

TABLE 1-continued

| Structure | Cpd No. | Cpd Name |
|---|---|---|
| 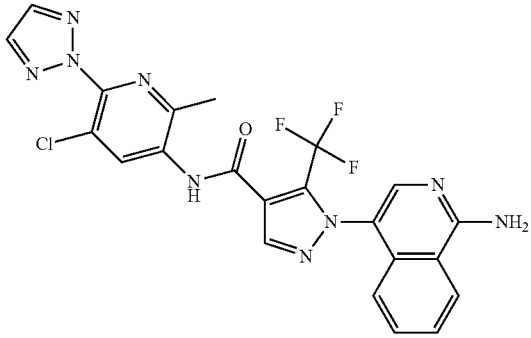 [SMILES: Cc1nc(-n2nccn2)c(Cl)cc1NC(=O)c1cnn(-c2cnc(N)c3ccccc23)c1C(F)(F)F] | 180 | 1-(1-aminoisoquinolin-4-yl)-N-(5-chloro-2-methyl-6-(2H-1,2,3-triazol-2-yl)pyridin-3-yl)-5-(trifluoromethyl)-1H-pyrazole-4-carboxamide |
| 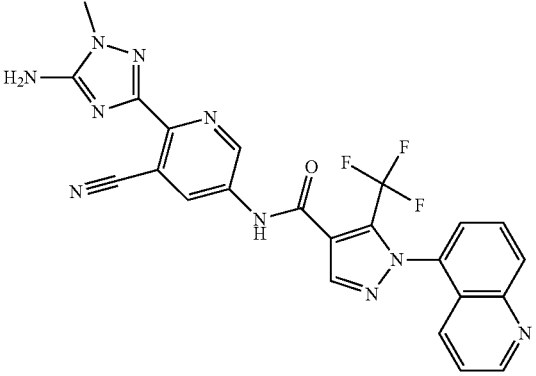 [SMILES: Cn1nc(-c2ncc(NC(=O)c3cnn(-c4cccc5ncccc45)c3C(F)(F)F)cc2C#N)nc1N] | 181 | N-(6-(5-amino-1-methyl-1H-pyrazol-3-yl)-5-cyanopyridin-3-yl)-1-(quinolin-5-yl)-5-(trifluoromethyl)-1H-pyrazole-4-carboxamide |
| 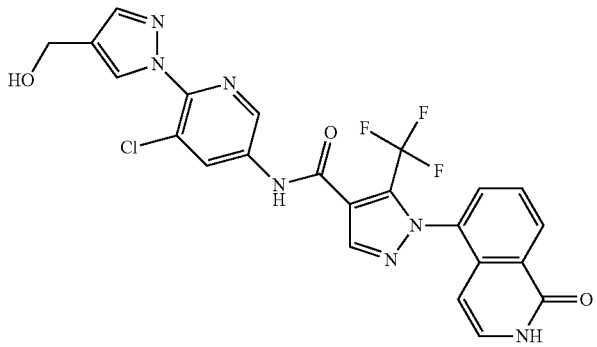 [SMILES: O=C(Nc1cnc(-n2cc(CO)cn2)c(Cl)c1)c1cnn(-c2cccc3c(=O)[nH]ccc23)c1C(F)(F)F] | 182 | N-(5-chloro-6-(4-(hydroxymethyl)-1H-pyrazol-1-yl)pyridin-3-yl)-1-(1-oxo-1,2-dihydroisoquinolin-5-yl)-5-(trifluoromethyl)-1H-pyrazole-4-carboxamide |
| 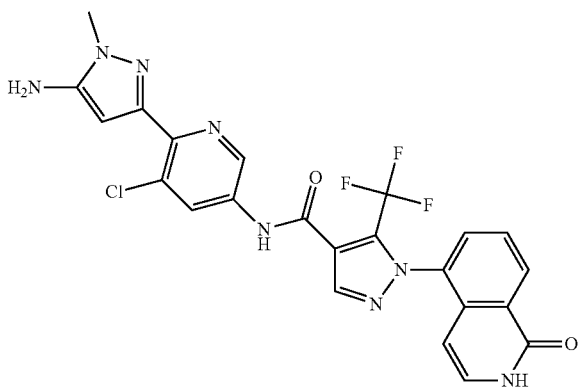 [SMILES: Cn1nc(-c2ncc(NC(=O)c3cnn(-c4cccc5c(=O)[nH]ccc45)c3C(F)(F)F)cc2Cl)cc1N] | 183 | N-(6-(5-amino-1-methyl-1H-pyrazol-3-yl)-5-chloropyridin-3-yl)-1-(1-oxo-1,2-dihydroisoquinolin-5-yl)-5-(trifluoromethyl)-1H-pyrazole-4-carboxamide |

TABLE 1-continued

| Structure | Cpd No. | Cpd Name |
|---|---|---|
| 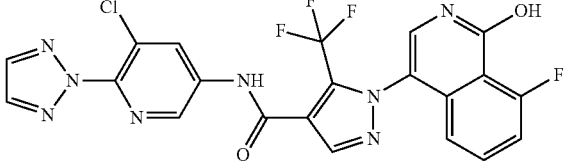 | 184 | N-(5-chloro-6-(2H-1,2,3-triazol-2-yl)pyridin-3-yl)-1-(8-fluoro-1-hydroxyisoquinolin-4-yl)-5-(trifluoromethyl)-1H-pyrazole-4-carboxamide |
| 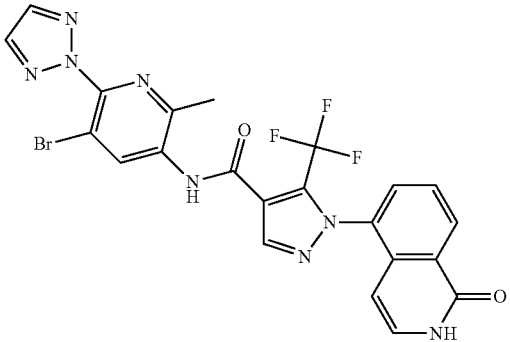 [SMILES: Cc1nc(-n2nccn2)c(Br)cc1NC(=O)c1cnn(-c2cccc3c(=O)[nH]ccc23)c1C(F)(F)F] | 185 | N-(5-bromo-2-methyl-6-(2H-1,2,3-triazol-2-yl)pyridin-3-yl)-1-(1-oxo-1,2-dihydroisoquinolin-5-yl)-5-(trifluoromethyl)-1H-pyrazole-4-carboxamide |
| 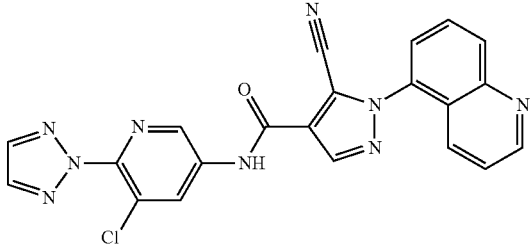 [SMILES: N#Cc1c(C(=O)Nc2cnc(-n3nccn3)c(Cl)c2)cnn1-c1cccc2ncccc12] | 186 | N-(5-chloro-6-(2H-1,2,3-triazol-2-yl)pyridin-3-yl)-5-cyano-1-(quinolin-5-yl)-1H-pyrazole-4-carboxamide |
| 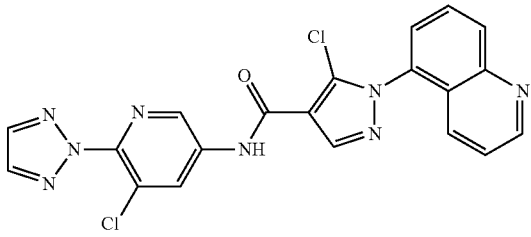 [SMILES: O=C(Nc1cnc(-n2nccn2)c(Cl)c1)c1cnn(-c2cccc3ncccc23)c1Cl] | 187 | 5-chloro-N-(5-chloro-6-(2H-1,2,3-triazol-2-yl)pyridin-3-yl)-1-(quinolin-5-yl)-1H-pyrazole-4-carboxamide |
| 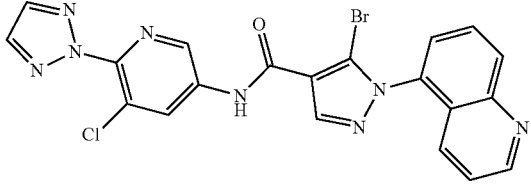 [SMILES: O=C(Nc1cnc(-n2nccn2)c(Cl)c1)c1cnn(-c2cccc3ncccc23)c1Br] | 188 | 5-bromo-N-(5-chloro-6-(2H-1,2,3-triazol-2-yl)pyridin-3-yl)-1-(quinolin-5-yl)-1H-pyrazole-4-carboxamide |
| 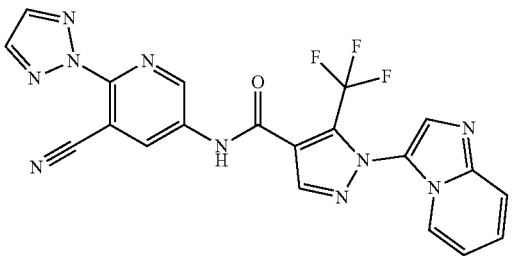 [SMILES: N#Cc1cc(NC(=O)c2cnn(-c3cnc4ccccn34)c2C(F)(F)F)cnc1-n1nccn1] | 189 | N-(5-cyano-6-(2H-1,2,3-triazol-2-yl)pyridin-3-yl)-1-(imidazo[1,2-a]pyridin-3-yl)-5-(trifluoromethyl)-1H-pyrazole-4-carboxamide |

TABLE 1-continued

| Structure | Cpd No. | Cpd Name |
|---|---|---|
| 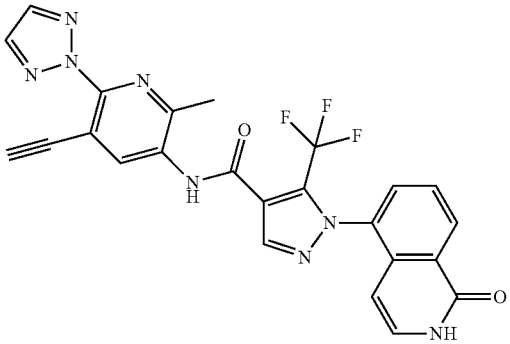 [SMILES: C#Cc1cc(NC(=O)c2cnn(-c3cccc4c(=O)[nH]ccc34)c2C(F)(F)F)c(C)nc1-n1nccn1] | 190 | N-(5-ethynyl-2-methyl-6-(2H-1,2,3-triazol-2-yl)pyridin-3-yl)-1-(1-oxo-1,2-dihydroisoquinolin-5-yl)-5-(trifluoromethyl)-1H-pyrazole-4-carboxamide |
| 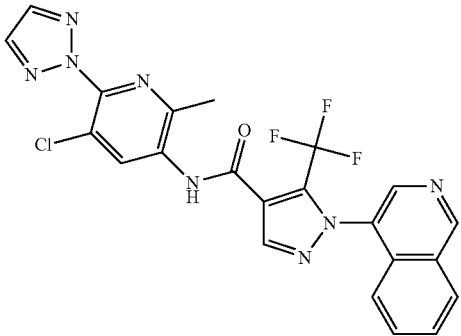 [SMILES: Cc1nc(-n2nccn2)c(Cl)cc1NC(=O)c1cnn(-c2cncc3ccccc23)c1C(F)(F)F] | 191 | N-(5-chloro-2-methyl-6-(2H-1,2,3-triazol-2-yl)pyridin-3-yl)-1-(isoquinolin-4-yl)-5-(trifluoromethyl)-1H-pyrazole-4-carboxamide |
| 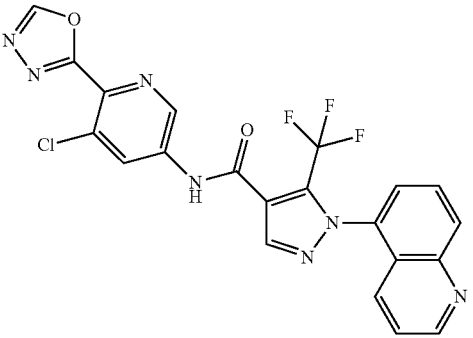 [SMILES: O=C(Nc1cnc(-c2nnco2)c(Cl)c1)c1cnn(-c2cccc3ncccc23)c1C(F)(F)F] | 192 | N-(5-chloro-6-(1,3,4-oxadiazol-2-yl)pyridin-3-yl)-1-(quinolin-5-yl)-5-(trifluoromethyl)-1H-pyrazole-4-carboxamide |
| 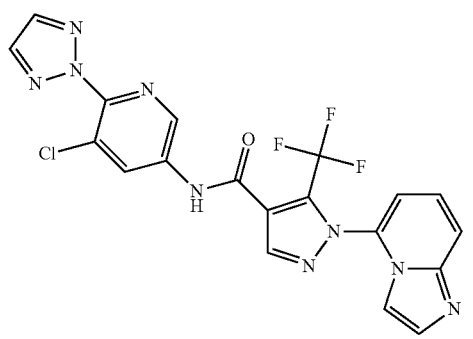 [SMILES: O=C(Nc1cnc(-n2nccn2)c(Cl)c1)c1cnn(-c2cccc3nccn23)c1C(F)(F)F] | 193 | N-(5-chloro-6-(2H-1,2,3-triazol-2-yl)pyridin-3-yl)-1-(imidazo[1,2-a]pyridin-5-yl)-5-(trifluoromethyl)-1H-pyrazole-4-carboxamide |

TABLE 1-continued

| Structure | Cpd No. | Cpd Name |
|---|---|---|
| 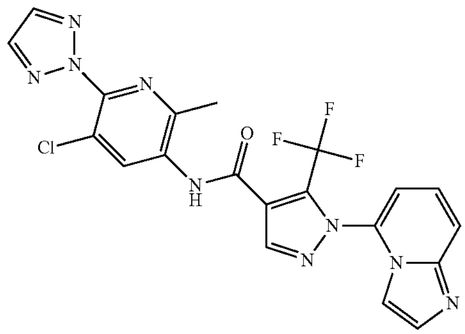 [SMILES: Cc1nc(-n2nccn2)c(Cl)cc1NC(=O)c1cnn(-c2cccc3nccn23)c1C(F)(F)F] | 194 | N-(5-chloro-2-methyl-6-(2H-1,2,3-triazol-2-yl)pyridin-3-yl)-1-(imidazo[1,2-a]pyridin-5-yl)-5-(trifluoromethyl)-1H-pyrazole-4-carboxamide |
| 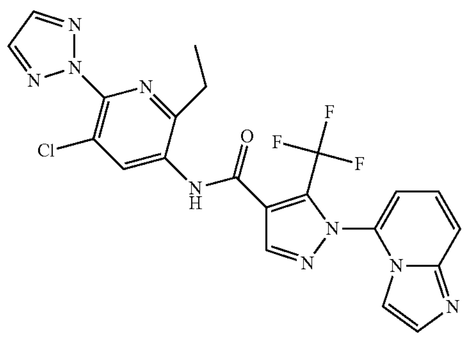 [SMILES: CCc1nc(-n2nccn2)c(Cl)cc1NC(=O)c1cnn(-c2cccc3nccn23)c1C(F)(F)F] | 195 | N-(5-chloro-2-ethyl-6-(2H-1,2,3-triazol-2-yl)pyridin-3-yl)-1-(imidazo[1,2-a]pyridin-5-yl)-5-(trifluoromethyl)-1H-pyrazole-4-carboxamide |
| 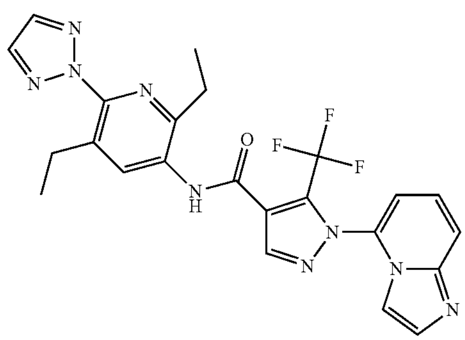 [SMILES: CCc1cc(NC(=O)c2cnn(-c3cccc4nccn34)c2C(F)(F)F)c(CC)nc1-n1nccn1] | 196 | N-(2,5-diethyl-6-(2H-1,2,3-triazol-2-yl)pyridin-3-yl)-1-(imidazo[1,2-a]pyridin-5-yl)-5-(trifluoromethyl)-1H-pyrazole-4-carboxamide |
| 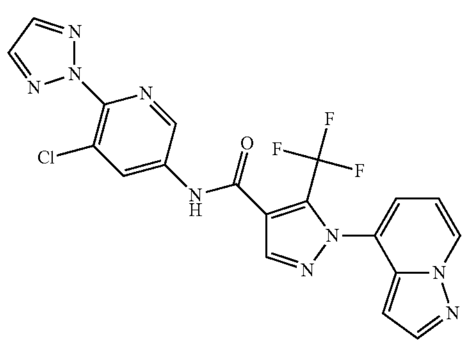 [SMILES: O=C(Nc1cnc(-n2nccn2)c(Cl)c1)c1cnn(-c2cccn3nccc23)c1C(F)(F)F] | 197 | N-(5-chloro-6-(2H-1,2,3-triazol-2-yl)pyridin-3-yl)-1-(pyrazolo[1,5-a]pyridin-4-yl)-5-(trifluoromethyl)-1H-pyrazole-4-carboxamide |

TABLE 1-continued

| Structure | Cpd No. | Cpd Name |
|---|---|---|
| 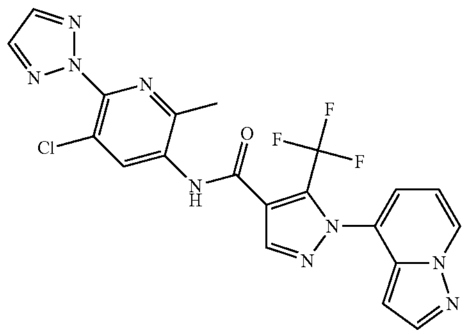 [SMILES: Cc1nc(-n2nccn2)c(Cl)cc1NC(=O)c1cnn(-c2cccn3nccc23)c1C(F)(F)F] | 198 | N-(5-chloro-2-methyl-6-(2H-1,2,3-triazol-2-yl)pyridin-3-yl)-1-(pyrazolo[1,5-a]pyridin-4-yl)-5-(trifluoromethyl)-1H-pyrazole-4-carboxamide |
| 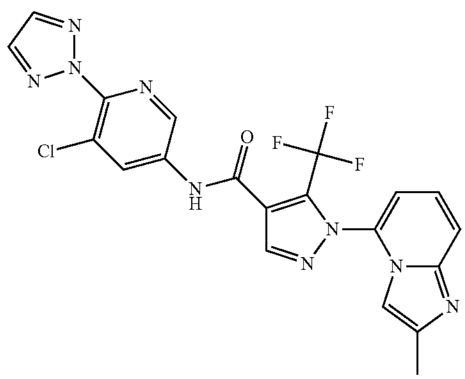 [SMILES: Cc1cn2c(-n3ncc(C(=O)Nc4cnc(-n5nccn5)c(Cl)c4)c3C(F)(F)F)cccc2n1] | 199 | N-(5-chloro-6-(2H-1,2,3-triazol-2-yl)pyridin-3-yl)-1-(2-methylimidazo[1,2-a]pyridin-5-yl)-5-(trifluoromethyl)-1H-pyrazole-4-carboxamide |
| 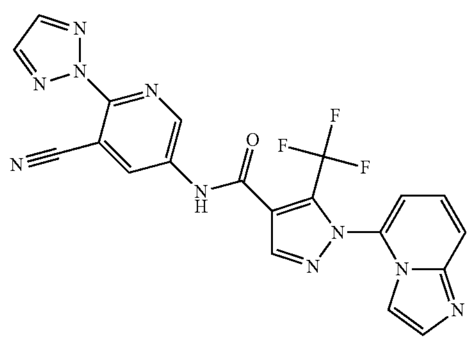 [SMILES: N#Cc1cc(NC(=O)c2cnn(-c3cccc4nccn34)c2C(F)(F)F)cnc1-n1nccn1] | 200 | N-(5-cyano-6-(2H-1,2,3-triazol-2-yl)pyridin-3-yl)-1-(imidazo[1,2-a]pyridin-5-yl)-5-(trifluoromethyl)-1H-pyrazole-4-carboxamide |
| 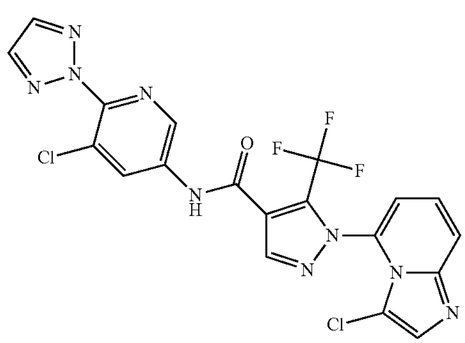 [SMILES: O=C(Nc1cnc(-n2nccn2)c(Cl)c1)c1cnn(-c2cccc3ncc(Cl)n23)c1C(F)(F)F] | 201 | N-(5-chloro-6-(2H-1,2,3-triazol-2-yl)pyridin-3-yl)-1-(3-chloroimidazo[1,2-a]pyridin-5-yl)-5-(trifluoromethyl)-1H-pyrazole-4-carboxamide |

TABLE 1-continued

| Structure | Cpd No. | Cpd Name |
|---|---|---|
| 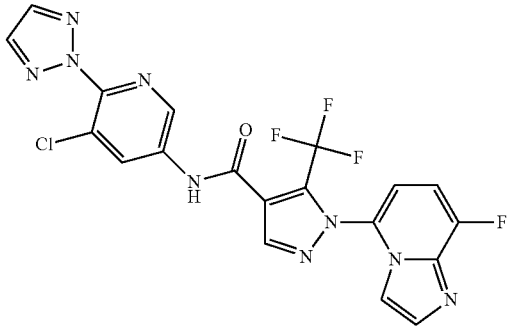 [SMILES: O=C(Nc1cnc(-n2nccn2)c(Cl)c1)c1cnn(-c2ccc(F)c3nccn23)c1C(F)(F)F] | 202 | N-(5-chloro-6-(2H-1,2,3-triazol-2-yl)pyridin-3-yl)-1-(8-fluoroimidazo[1,2-a]pyridin-5-yl)-5-(trifluoromethyl)-1H-pyrazole-4-carboxamide |
| 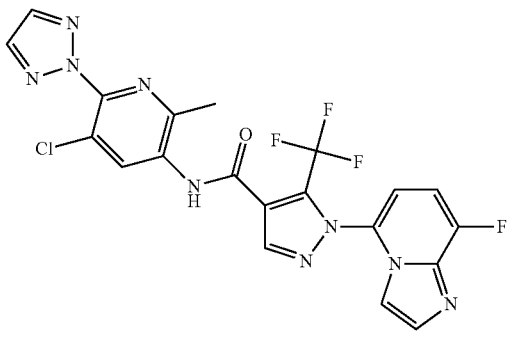 [SMILES: Cc1nc(-n2nccn2)c(Cl)cc1NC(=O)c1cnn(-c2ccc(F)c3nccn23)c1C(F)(F)F] | 203 | N-(5-chloro-2-methyl-6-(2H-1,2,3-triazol-2-yl)pyridin-3-yl)-1-(8-fluoroimidazo[1,2-a]pyridin-5-yl)-5-(trifluoromethyl)-1H-pyrazole-4-carboxamide |
| 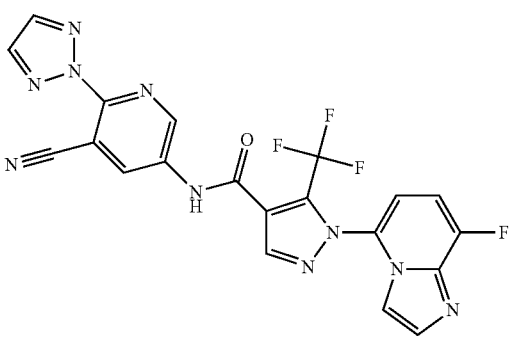 [SMILES: N#Cc1cc(NC(=O)c2cnn(-c3ccc(F)c4nccn34)c2C(F)(F)F)cnc1-n1nccn1] | 204 | N-(5-cyano-6-(2H-1,2,3-triazol-2-yl)pyridin-3-yl)-1-(8-fluoroimidazo[1,2-a]pyridin-5-yl)-5-(trifluoromethyl)-1H-pyrazole-4-carboxamide |
| 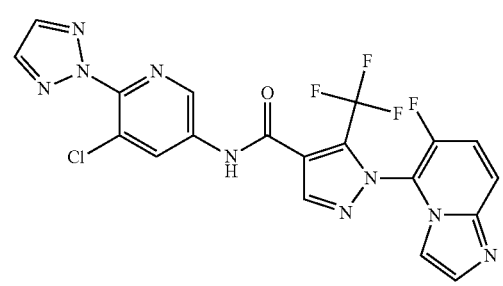 [SMILES: O=C(Nc1cnc(-n2nccn2)c(Cl)c1)c1cnn(-c2c(F)ccc3nccn23)c1C(F)(F)F] | 205 | N-(5-chloro-6-(2H-1,2,3-triazol-2-yl)pyridin-3-yl)-1-(6-fluoroimidazo[1,2-a]pyridin-5-yl)-5-(trifluoromethyl)-1H-pyrazole-4-carboxamide |

TABLE 1-continued

| Structure | Cpd No. | Cpd Name |
|---|---|---|
| 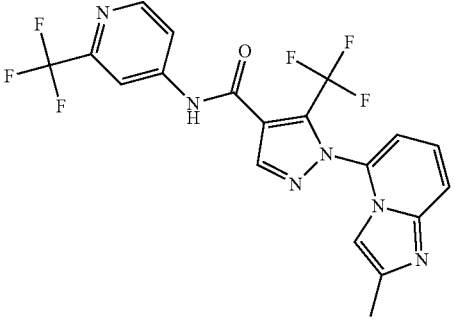 [SMILES: Cc1cn2c(-n3ncc(C(=O)Nc4ccnc(C(F)(F)F)c4)c3C(F)(F)F)cccc2n1] | 206 | 1-(2-methylimidazo[1,2-a]pyridin-5-yl)-5-(trifluoromethyl)-N-(2-(trifluoromethyl)pyridin-4-yl)-1H-pyrazole-4-carboxamide |
| 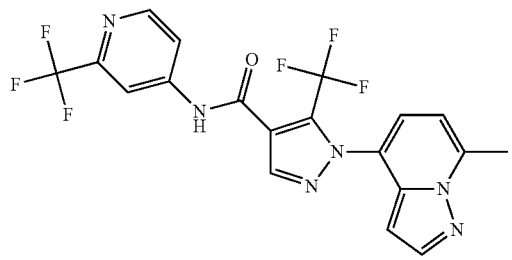 [SMILES: Cc1ccc(-n2ncc(C(=O)Nc3ccnc(C(F)(F)F)c3)c2C(F)(F)F)c2ccnn12] | 207 | 1-(7-methylpyrazolo[1,5-a]pyridin-4-yl)-5-(trifluoromethyl)-N-(2-(trifluoromethyl)pyridin-4-yl)-1H-pyrazole-4-carboxamide |
| 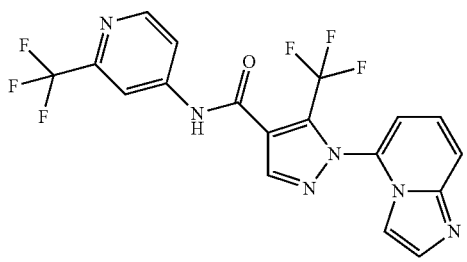 [SMILES: O=C(Nc1ccnc(C(F)(F)F)c1)c1cnn(-c2cccc3nccn23)c1C(F)(F)F] | 208 | 1-(imidazo[1,2-a]pyridin-5-yl)-5-(trifluoromethyl)-N-(2-(trifluoromethyl)pyridin-4-yl)-1H-pyrazole-4-carboxamide |
| 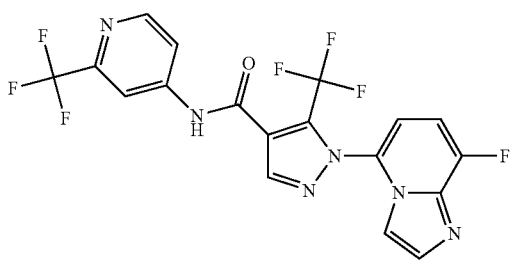 [SMILES: O=C(Nc1ccnc(C(F)(F)F)c1)c1cnn(-c2ccc(F)c3nccn23)c1C(F)(F)F] | 209 | 1-(8-fluoroimidazo[1,2-a]pyridin-5-yl)-5-(trifluoromethyl)-N-(2-(trifluoromethyl)pyridin-4-yl)-1H-pyrazole-4-carboxamide |
| 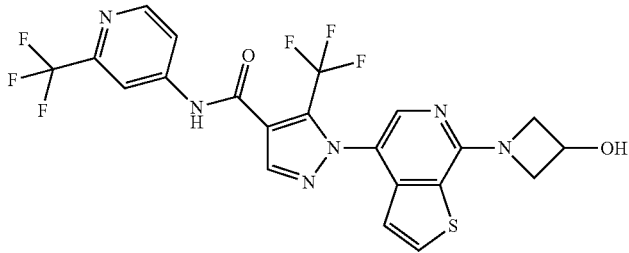 [SMILES: O=C(Nc1ccnc(C(F)(F)F)c1)c1cnn(-c2cnc(N3CC(O)C3)c3sccc23)c1C(F)(F)F] | 210 | 1-(7-(3-hydroxyazetidin-1-yl)thieno[2,3-c]pyridin-4-yl)-5-(trifluoromethyl)-N-(2-(trifluoromethyl)pyridin-4-yl)-1H-pyrazole-4-carboxamide |

TABLE 1-continued

| Structure | Cpd No. | Cpd Name |
|---|---|---|
| 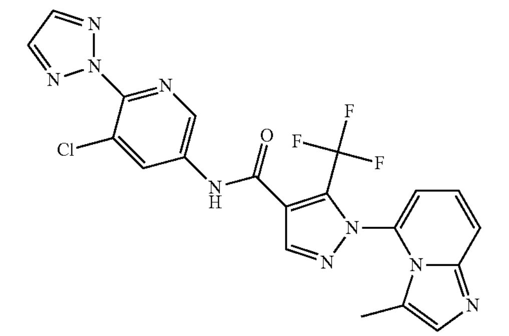 [SMILES: Cc1cnc2cccc(-n3ncc(C(=O)Nc4cnc(-n5nccn5)c(Cl)c4)c3C(F)(F)F)n12] | 211 | N-(5-chloro-6-(2H-1,2,3-triazol-2-yl)pyridin-3-yl)-1-(3-methylimidazo[1,2-a]pyridin-5-yl)-5-(trifluoromethyl)-1H-pyrazole-4-carboxamide |
| 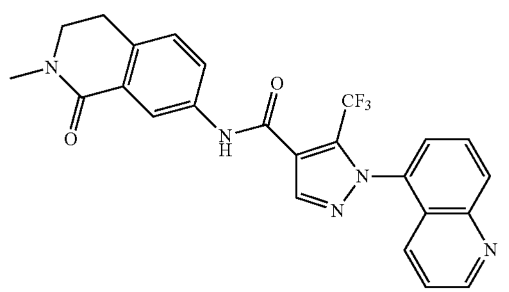 [SMILES: CN1CCc2ccc(NC(=O)c3cnn(-c4cccc5ncccc45)c3C(F)(F)F)cc2C1=O] | 212 | N-(2-methyl-1-oxo-1,2,3,4-tetrahydroisoquinolin-7-yl)-1-(quinolin-5-yl)-5-(trifluoromethyl)-1H-pyrazole-4-carboxamide |
| 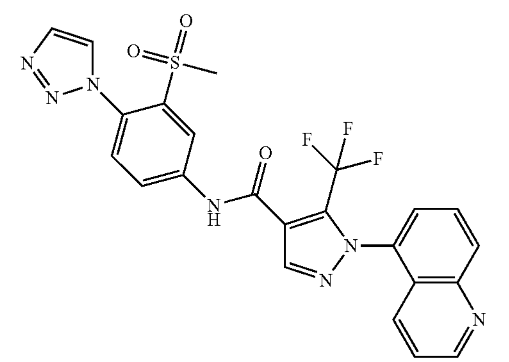 [SMILES: CS(=O)(=O)c1cc(NC(=O)c2cnn(-c3cccc4ncccc34)c2C(F)(F)F)ccc1-n1ccnn1] | 213 | N-(3-(methylsulfonyl)-4-(1H-1,2,3-triazol-1-yl)phenyl)-1-(quinolin-5-yl)-5-(trifluoromethyl)-1H-pyrazole-4-carboxamide |
| 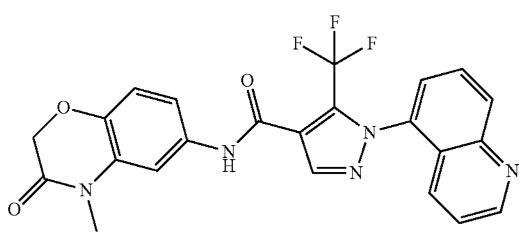 [SMILES: CN1C(=O)COc2ccc(NC(=O)c3cnn(-c4cccc5ncccc45)c3C(F)(F)F)cc21] | 214 | N-(4-methyl-3-oxo-3,4-dihydro-2H-benzo[b][1,4]oxazin-6-yl)-1-(quinolin-5-yl)-5-(trifluoromethyl)-1H-pyrazole-4-carboxamide |
| 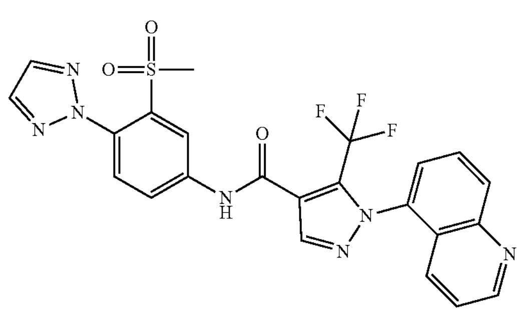 [SMILES: CS(=O)(=O)c1cc(NC(=O)c2cnn(-c3cccc4ncccc34)c2C(F)(F)F)ccc1-n1nccn1] | 215 | N-(3-(methylsulfonyl)-4-(2H-1,2,3-triazol-2-yl)phenyl)-1-(quinolin-5-yl)-5-(trifluoromethyl)-1H-pyrazole-4-carboxamide |

TABLE 1-continued

| Structure | Cpd No. | Cpd Name |
|---|---|---|
| 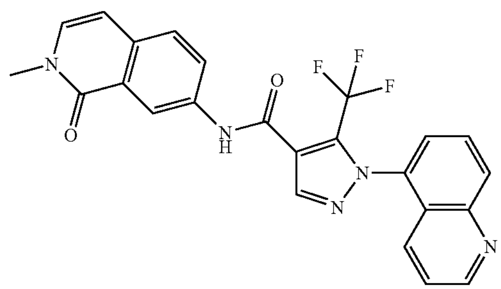 [SMILES: Cn1ccc2ccc(NC(=O)c3cnn(-c4cccc5ncccc45)c3C(F)(F)F)cc2c1=O] | 216 | N-(2-methyl-1-oxo-1,2-dihydroisoquinolin-7-yl)-1-(quinolin-5-yl)-5-(trifluoromethyl)-1H-pyrazole-4-carboxamide |
| 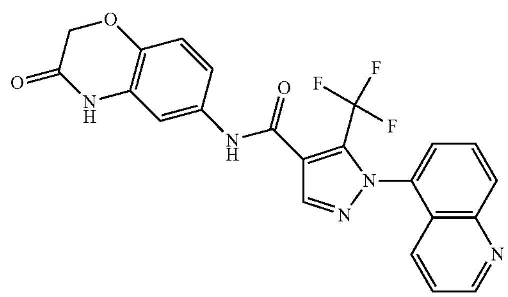 [SMILES: O=C1COc2ccc(NC(=O)c3cnn(-c4cccc5ncccc45)c3C(F)(F)F)cc2N1] | 217 | N-(3-oxo-3,4-dihydro-2H-benzo[b][1,4]oxazin-6-yl)-1-(quinolin-5-yl)-5-(trifluoromethyl)-1H-pyrazole-4-carboxamide |
| 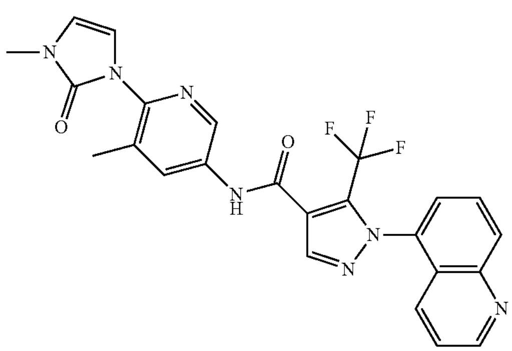 [SMILES: Cc1cc(NC(=O)c2cnn(-c3cccc4ncccc34)c2C(F)(F)F)cnc1-n1ccn(C)c1=O] | 218 | N-(5-methyl-6-(3-methyl-2-oxo-2,3-dihydro-1H-imidazol-1-yl)pyridin-3-yl)-1-(quinolin-5-yl)-5-(trifluoromethyl)-1H-pyrazole-4-carboxamide |
| 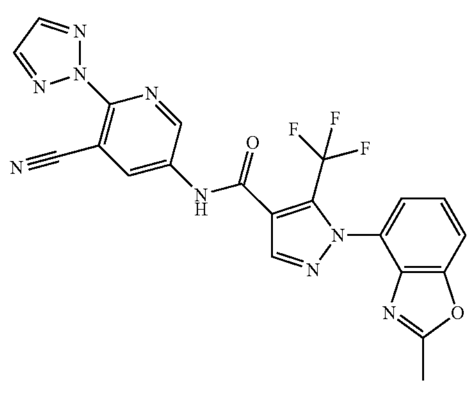 [SMILES: Cc1nc2c(-n3ncc(C(=O)Nc4cnc(-n5nccn5)c(C#N)c4)c3C(F)(F)F)cccc2o1] | 219 | N-(5-cyano-6-(2H-1,2,3-triazol-2-yl)pyridin-3-yl)-1-(2-methylbenzo[d]oxazol-4-yl)-5-(trifluoromethyl)-1H-pyrazole-4-carboxamide |

TABLE 1-continued

| Structure | Cpd No. | Cpd Name |
|---|---|---|
| 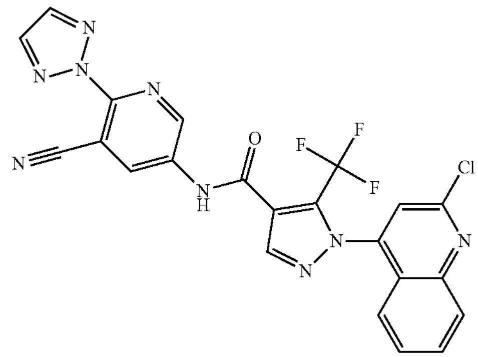 [SMILES: N#Cc1cc(NC(=O)c2cnn(-c3cc(Cl)nc4ccccc34)c2C(F)(F)F)cnc1-n1nccn1] | 220 | 1-(2-chloroquinolin-4-yl)-N-(5-cyano-6-(2H-1,2,3-triazol-2-yl)pyridin-3-yl)-5-(trifluoromethyl)-1H-pyrazole-4-carboxamide |
| 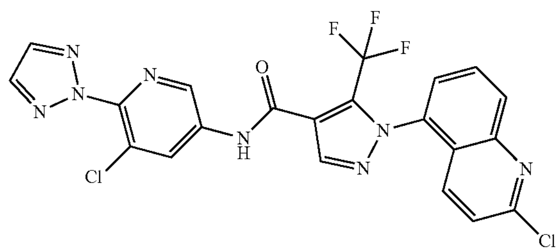 [SMILES: O=C(Nc1cnc(-n2nccn2)c(Cl)c1)c1cnn(-c2cccc3nc(Cl)ccc23)c1C(F)(F)F] | 221 | N-(5-chloro-6-(2H-1,2,3-triazol-2-yl)pyridin-3-yl)-1-(2-chloroquinolin-5-yl)-5-(trifluoromethyl)-1H-pyrazole-4-carboxamide |
| 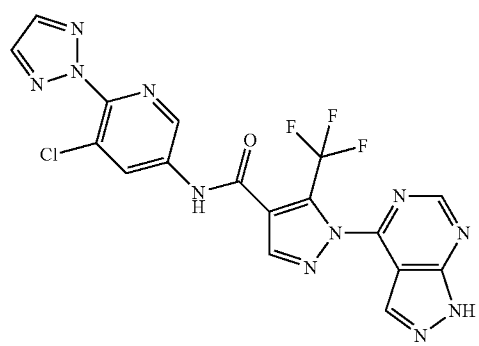 [SMILES: O=C(Nc1cnc(-n2nccn2)c(Cl)c1)c1cnn(-c2ncnc3[nH]ncc23)c1C(F)(F)F] | 222 | N-(5-chloro-6-(2H-1,2,3-triazol-2-yl)pyridin-3-yl)-1-(1H-pyrazolo[3,4-d]pyrimidin-4-yl)-5-(trifluoromethyl)-1H-pyrazole-4-carboxamide |
| 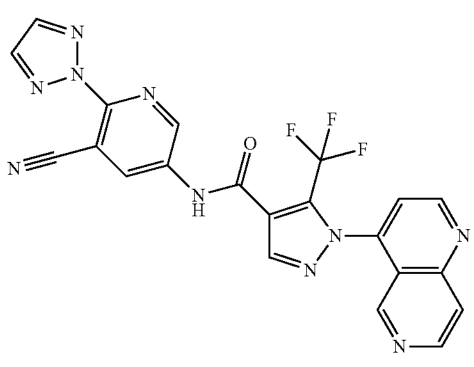 [SMILES: N#Cc1cc(NC(=O)c2cnn(-c3ccnc4ccncc34)c2C(F)(F)F)cnc1-n1nccn1] | 223 | N-(5-cyano-6-(2H-1,2,3-triazol-2-yl)pyridin-3-yl)-1-(1,6-naphthyridin-4-yl)-5-(trifluoromethyl)-1H-pyrazole-4-carboxamide |

TABLE 1-continued

| Structure | Cpd No. | Cpd Name |
|---|---|---|
| 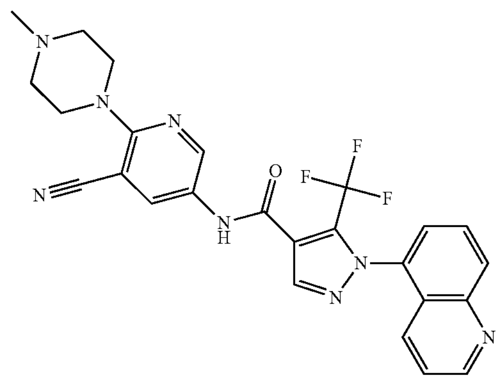 [SMILES: CN1CCN(c2ncc(NC(=O)c3cnn(-c4cccc5ncccc45)c3C(F)(F)F)cc2C#N)CC1] | 224 | N-(5-cyano-6-(4-methylpiperazin-1-yl)pyridin-3-yl)-1-(quinolin-5-yl)-5-(trifluoromethyl)-1H-pyrazole-4-carboxamide |
| 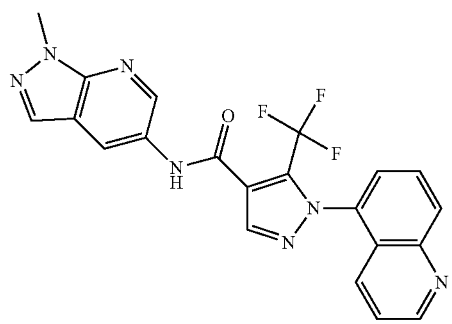 [SMILES: Cn1ncc2cc(NC(=O)c3cnn(-c4cccc5ncccc45)c3C(F)(F)F)cnc21] | 225 | N-(1-methyl-1H-pyrazolo[3,4-b]pyridin-5-yl)-1-(quinolin-5-yl)-5-(trifluoromethyl)-1H-pyrazole-4-carboxamide |
| 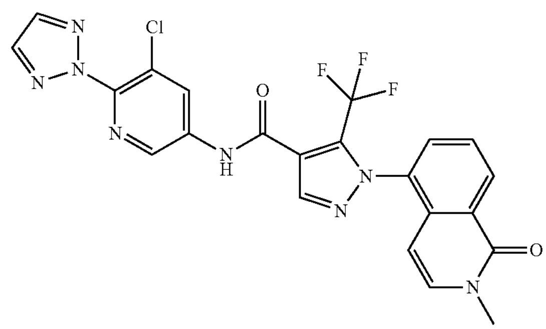 [SMILES: Cn1ccc2c(-n3ncc(C(=O)Nc4cnc(-n5nccn5)c(Cl)c4)c3C(F)(F)F)cccc2c1=O] | 226 | N-(5-chloro-6-(2H-1,2,3-triazol-2-yl)pyridin-3-yl)-1-(2-methyl-1-oxo-1,2-dihydroisoquinolin-5-yl)-5-(trifluoromethyl)-1H-pyrazole-4-carboxamide |
| 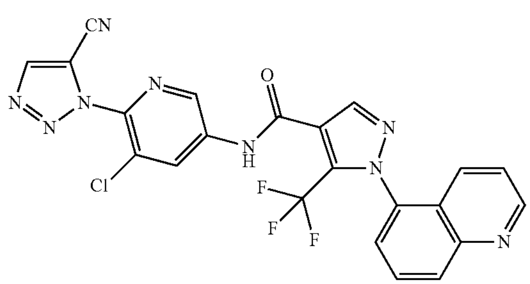 [SMILES: N#Cc1cnnn1-c1ncc(NC(=O)c2cnn(-c3cccc4ncccc34)c2C(F)(F)F)cc1Cl] | 227 | N-(5-chloro-6-(5-cyano-1H-1,2,3-triazol-1-yl)pyridin-3-yl)-1-(quinolin-5-yl)-5-(trifluoromethyl)-1H-pyrazole-4-carboxamide |
| 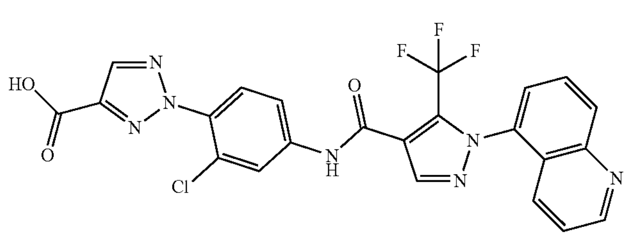 [SMILES: O=C(O)c1cnn(-c2ccc(NC(=O)c3cnn(-c4cccc5ncccc45)c3C(F)(F)F)cc2Cl)n1] | 228 | 2-(2-chloro-4-(1-(quinolin-5-yl)-5-(trifluoromethyl)-1H-pyrazole-4-carboxamido)phenyl)-2H-1,2,3-triazole-4-carboxylic acid |

TABLE 1-continued

| Structure | Cpd No. | Cpd Name |
|---|---|---|
| 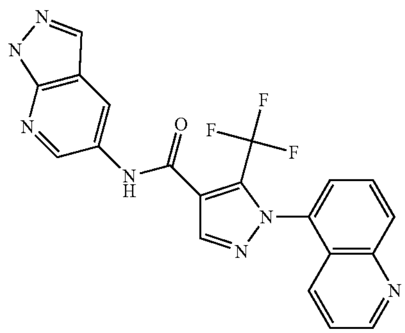 [SMILES: O=C(Nc1cnc2[nH]ncc2c1)c1cnn(-c2cccc3ncccc23)c1C(F)(F)F] | 229 | N-(1H-pyrazolo[3,4-b]pyridin-5-yl)-1-(quinolin-5-yl)-5-(trifluoromethyl)-1H-pyrazole-4-carboxamide |
| 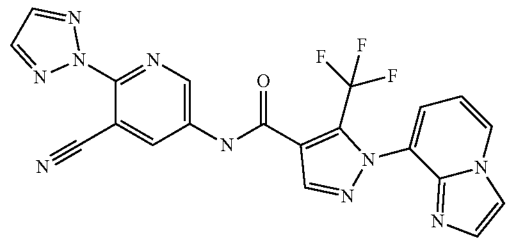 [SMILES: N#Cc1cc(NC(=O)c2cnn(-c3cccn4ccnc34)c2C(F)(F)F)cnc1-n1nccn1] | 230 | N-(5-cyano-6-(2H-1,2,3-triazol-2-yl)pyridin-3-yl)-1-(imidazo[1,2-a]pyridin-8-yl)-5-(trifluoromethyl)-1H-pyrazole-4-carboxamide |
| 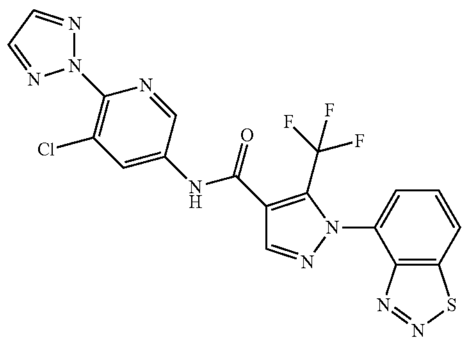 [SMILES: O=C(Nc1cnc(-n2nccn2)c(Cl)c1)c1cnn(-c2cccc3snnc23)c1C(F)(F)F] | 231 | 1-(benzo[d][1,2,3]thiadiazol-4-yl)-N-(5-chloro-6-(2H-1,2,3-triazol-2-yl)pyridin-3-yl)-5-(trifluoromethyl)-1H-pyrazole-4-carboxamide |
| 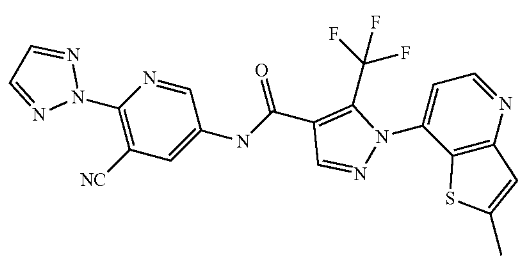 [SMILES: Cc1cc2nccc(-n3ncc(C(=O)Nc4cnc(-n5nccn5)c(C#N)c4)c3C(F)(F)F)c2s1] | 232 | N-(5-cyano-6-(2H-1,2,3-triazol-2-yl)pyridin-3-yl)-1-(2-methylthieno[3,2-b]pyridin-7-yl)-5-(trifluoromethyl)-1H-pyrazole-4-carboxamide |
| 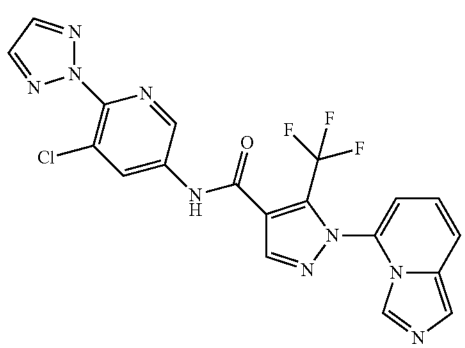 [SMILES: O=C(Nc1cnc(-n2nccn2)c(Cl)c1)c1cnn(-c2cccc3cncn23)c1C(F)(F)F] | 233 | N-(5-chloro-6-(2H-1,2,3-triazol-2-yl)pyridin-3-yl)-1-(imidazo[1,5-a]pyridin-5-yl)-5-(trifluoromethyl)-1H-pyrazole-4-carboxamide |

TABLE 1-continued

| Structure | Cpd No. | Cpd Name |
|---|---|---|
| 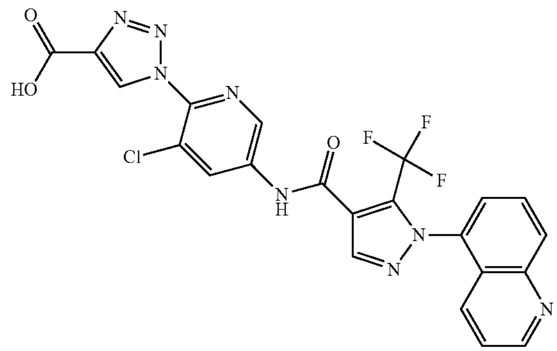 [SMILES: O=C(O)c1cn(-c2ncc(NC(=O)c3cnn(-c4cccc5ncccc45)c3C(F)(F)F)cc2Cl)nn1] | 234 | 1-(3-chloro-5-(1-(quinolin-5-yl)-5-(trifluoromethyl)-1H-pyrazole-4-carboxamido)pyridin-2-yl)-1H-1,2,3-triazole-4-carboxylic acid |
| 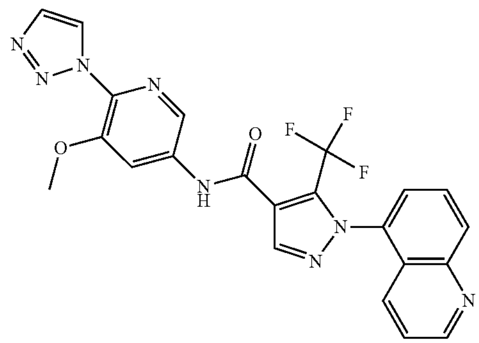 [SMILES: COc1cc(NC(=O)c2cnn(-c3cccc4ncccc34)c2C(F)(F)F)cnc1-n1ccnn1] | 235 | N-(5-methoxy-6-(1H-1,2,3-triazol-1-yl)pyridin-3-yl)-1-(quinolin-5-yl)-5-(trifluoromethyl)-1H-pyrazole-4-carboxamide |
| 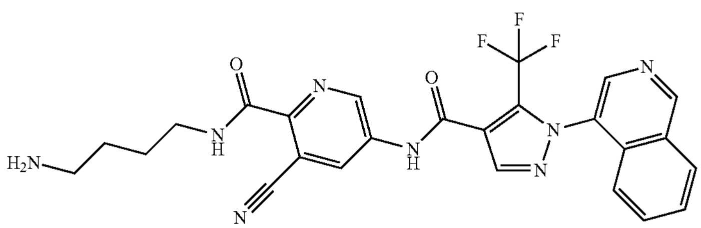 [SMILES: N#Cc1cc(NC(=O)c2cnn(-c3cncc4ccccc34)c2C(F)(F)F)cnc1C(=O)NCCCCN] | 236 | N-(4-aminobutyl)-3-cyano-5-(1-(isoquinolin-4-yl)-5-(trifluoromethyl)-1H-pyrazole-4-carboxamido)picolinamide |
| 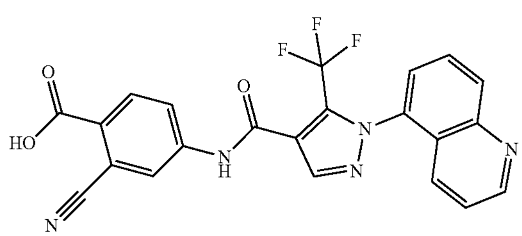 [SMILES: N#Cc1cc(NC(=O)c2cnn(-c3cccc4ncccc34)c2C(F)(F)F)ccc1C(=O)O] | 237 | 2-cyano-4-(1-(quinolin-5-yl)-5-(trifluoromethyl)-1H-pyrazole-4-carboxamido)benzoic acid |
| 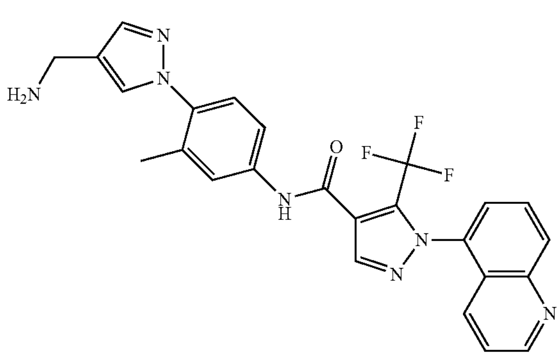 [SMILES: Cc1cc(NC(=O)c2cnn(-c3cccc4ncccc34)c2C(F)(F)F)ccc1-n1cc(CN)cn1] | 238 | N-(4-(4-(aminomethyl)-1H-pyrazol-1-yl)-3-methylphenyl)-1-(quinolin-5-yl)-5-(trifluoromethyl)-1H-pyrazole-4-carboxamide |

TABLE 1-continued

| Structure | Cpd No. | Cpd Name |
|---|---|---|
| 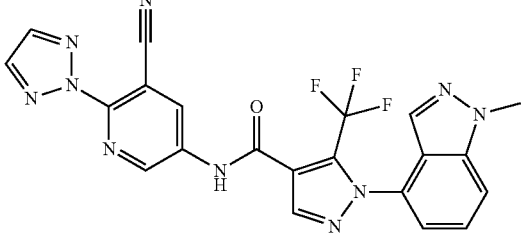 | 239 | N-(5-cyano-6-(2H-1,2,3-triazol-2-yl)pyridin-3-yl)-1-(1-methyl-1H-indazol-4-yl)-5-(trifluoromethyl)-1H-pyrazole-4-carboxamide |
| 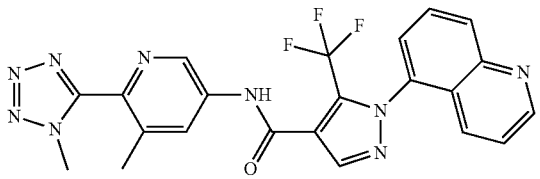 [SMILES: Cc1cc(NC(=O)c2cnn(-c3cccc4ncccc34)c2C(F)(F)F)cnc1-c1nnnn1C] | 240 | N-(5-methyl-6-(1-methyl-1H-tetrazol-5-yl)pyridin-3-yl)-1-(quinolin-5-yl)-5-(trifluoromethyl)-1H-pyrazole-4-carboxamide |
| 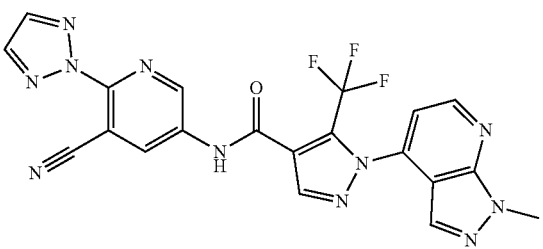 [SMILES: Cn1ncc2c(-n3ncc(C(=O)Nc4cnc(-n5nccn5)c(C#N)c4)c3C(F)(F)F)ccnc21] | 241 | N-(5-cyano-6-(2H-1,2,3-triazol-2-yl)pyridin-3-yl)-1-(1-methyl-1H-pyrazolo[3,4-b]pyridin-4-yl)-5-(trifluoromethyl)-1H-pyrazole-4-carboxamide |
| 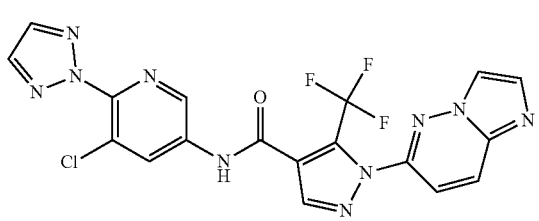 [SMILES: O=C(Nc1cnc(-n2nccn2)c(Cl)c1)c1cnn(-c2ccc3nccn3n2)c1C(F)(F)F] | 242 | N-(5-chloro-6-(2H-1,2,3-triazol-2-yl)pyridin-3-yl)-1-(imidazo[1,2-b]pyridazin-6-yl)-5-(trifluoromethyl)-1H-pyrazole-4-carboxamide |
| 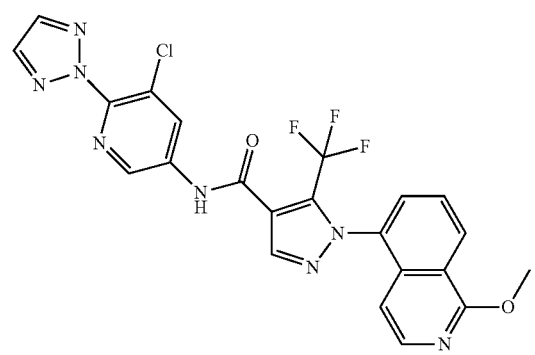 [SMILES: COc1nccc2c(-n3ncc(C(=O)Nc4cnc(-n5nccn5)c(Cl)c4)c3C(F)(F)F)cccc12] | 243 | N-(5-chloro-6-(2H-1,2,3-triazol-2-yl)pyridin-3-yl)-1-(1-methoxyisoquinolin-5-yl)-5-(trifluoromethyl)-1H-pyrazole-4-carboxamide |

TABLE 1-continued

| Structure | Cpd No. | Cpd Name |
|---|---|---|
| 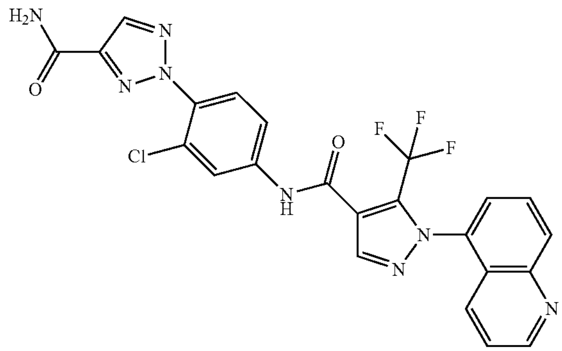 [SMILES: NC(=O)c1cnn(-c2ccc(NC(=O)c3cnn(-c4cccc5ncccc45)c3C(F)(F)F)cc2Cl)n1] | 244 | 2-(2-chloro-4-(1-(quinolin-5-yl)-5-(trifluoromethyl)-1H-pyrazole-4-carboxamido)phenyl)-2H-1,2,3-triazole-4-carboxamide |
| 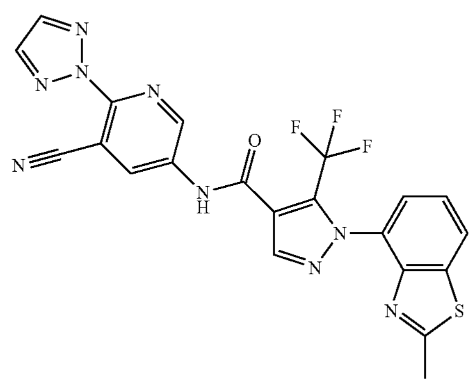 [SMILES: Cc1nc2c(-n3ncc(C(=O)Nc4cnc(-n5nccn5)c(C#N)c4)c3C(F)(F)F)cccc2s1] | 245 | N-(5-cyano-6-(2H-1,2,3-triazol-2-yl)pyridin-3-yl)-1-(2-methylbenzo[d]thiazol-4-yl)-5-(trifluoromethyl)-1H-pyrazole-4-carboxamide |
| 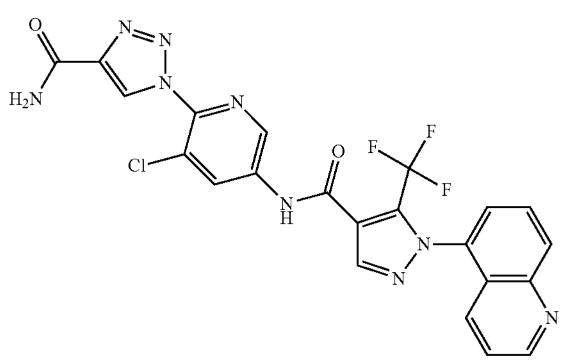 [SMILES: NC(=O)c1cn(-c2ncc(NC(=O)c3cnn(-c4cccc5ncccc45)c3C(F)(F)F)cc2Cl)nn1] | 246 | 1-(3-chloro-5-(1-(quinolin-5-yl)-5-(trifluoromethyl)-1H-pyrazole-4-carboxamido)pyridin-2-yl)-1H-1,2,3-triazole-4-carboxamide |
| 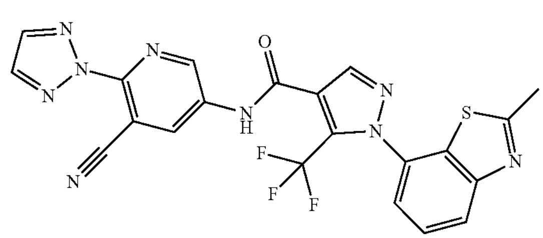 [SMILES: Cc1nc2cccc(-n3ncc(C(=O)Nc4cnc(-n5nccn5)c(C#N)c4)c3C(F)(F)F)c2s1] | 247 | N-(5-cyano-6-(2H-1,2,3-triazol-2-yl)pyridin-3-yl)-1-(2-methylbenzo[d]thiazol-7-yl)-5-(trifluoromethyl)-1H-pyrazole-4-carboxamide |

TABLE 1-continued

| Structure | Cpd No. | Cpd Name |
|---|---|---|
| 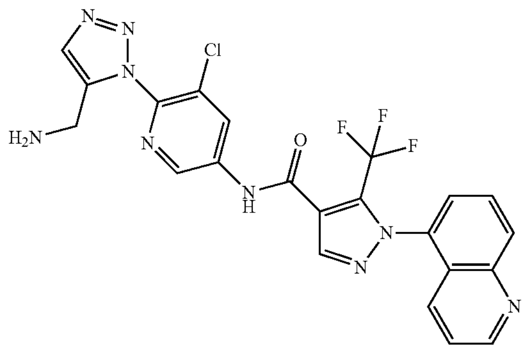 [SMILES: NCc1cnnn1-c1ncc(NC(=O)c2cnn(-c3cccc4ncccc34)c2C(F)(F)F)cc1Cl] | 248 | N-(6-(5-(aminomethyl)-1H-1,2,3-triazol-1-yl)-5-chloropyridin-3-yl)-1-(quinolin-5-yl)-5-(trifluoromethyl)-1H-pyrazole-4-carboxamide |
| 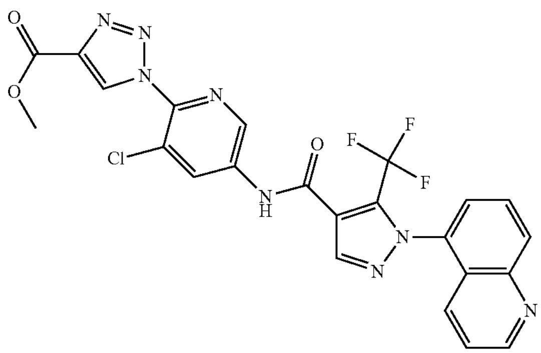 [SMILES: COC(=O)c1cn(-c2ncc(NC(=O)c3cnn(-c4cccc5ncccc45)c3C(F)(F)F)cc2Cl)nn1] | 249 | methyl 1-(3-chloro-5-(1-(quinolin-5-yl)-5-(trifluoromethyl)-1H-pyrazole-4-carboxamido)pyridin-2-yl)-1H-1,2,3-triazole-4-carboxylate |
| 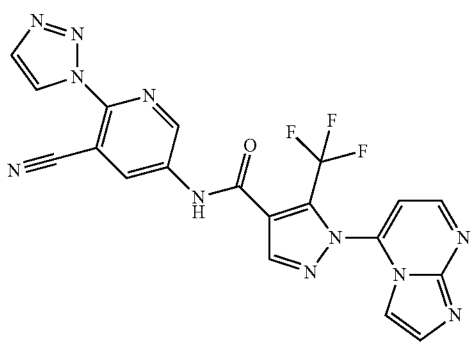 [SMILES: N#Cc1cc(NC(=O)c2cnn(-c3ccnc4nccn34)c2C(F)(F)F)cnc1-n1ccnn1] | 250 | N-(5-cyano-6-(2H-1,2,3-triazol-2-yl)pyridin-3-yl)-1-(imidazo[1,2-a]pyrimidin-5-yl)-5-(trifluoromethyl)-1H-pyrazole-4-carboxamide |
| 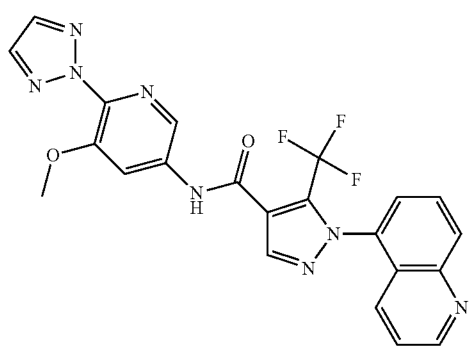 [SMILES: COc1cc(NC(=O)c2cnn(-c3cccc4ncccc34)c2C(F)(F)F)cnc1-n1nccn1] | 251 | N-(5-methoxy-6-(2H-1,2,3-triazol-2-yl)pyridin-3-yl)-1-(quinolin-5-yl)-5-(trifluoromethyl)-1H-pyrazole-4-carboxamide |

TABLE 1-continued

| Structure | Cpd No. | Cpd Name |
|---|---|---|
| 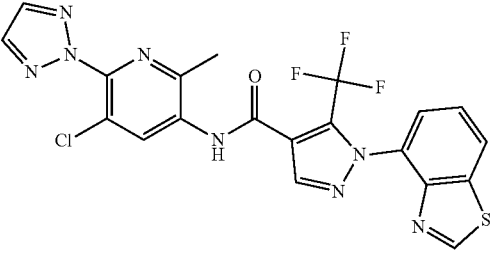 [SMILES: Cc1nc(-n2nccn2)c(Cl)cc1NC(=O)c1cnn(-c2cccc3scnc23)c1C(F)(F)F] | 252 | 1-(benzo[d]thiazol-4-yl)-N-(5-chloro-2-methyl-6-(2H-1,2,3-triazol-2-yl)pyridin-3-yl)-5-(trifluoromethyl)-1H-pyrazole-4-carboxamide |
| 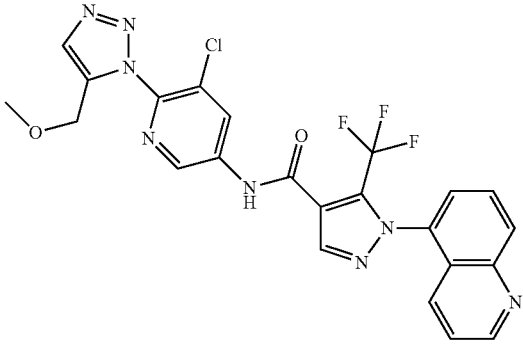 [SMILES: COCc1cnnn1-c1ncc(NC(=O)c2cnn(-c3cccc4ncccc34)c2C(F)(F)F)cc1Cl] | 253 | N-(5-chloro-6-(5-(methoxymethyl)-1H-1,2,3-triazol-1-yl)pyridin-3-yl)-1-(quinolin-5-yl)-5-(trifluoromethyl)-1H-pyrazole-4-carboxamide |
| 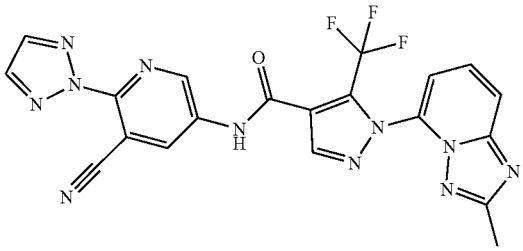 [SMILES: Cc1nc2cccc(-n3ncc(C(=O)Nc4cnc(-n5nccn5)c(C#N)c4)c3C(F)(F)F)n2n1] | 254 | N-(5-cyano-6-(2H-1,2,3-triazol-2-yl)pyridin-3-yl)-1-(2-methyl-[1,2,4]triazolo[1,5-a]pyridin-5-yl)-5-(trifluoromethyl)-1H-pyrazole-4-carboxamide |
| 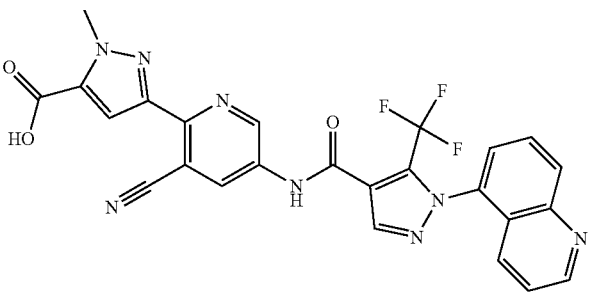 [SMILES: Cn1nc(-c2ncc(NC(=O)c3cnn(-c4cccc5ncccc45)c3C(F)(F)F)cc2C#N)cc1C(=O)O] | 255 | 3-(3-cyano-5-(1-(quinolin-5-yl)-5-(trifluoromethyl)-1H-pyrazole-4-carboxamido)pyridin-2-yl)-1-methyl-1H-pyrazole-5-carboxylic acid |
| 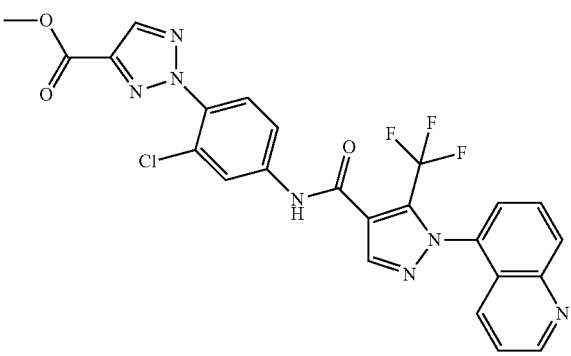 [SMILES: COC(=O)c1cnn(-c2ccc(NC(=O)c3cnn(-c4cccc5ncccc45)c3C(F)(F)F)cc2Cl)n1] | 256 | methyl 2-(2-chloro-4-(1-(quinolin-5-yl)-5-(trifluoromethyl)-1H-pyrazole-4-carboxamido)phenyl)-2H-1,2,3-triazole-4-carboxylate |

TABLE 1-continued

| Structure | Cpd No. | Cpd Name |
|---|---|---|
| 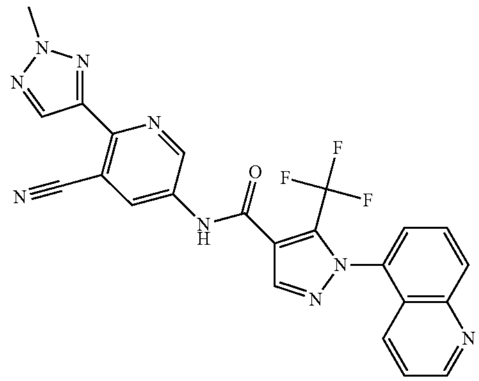 [SMILES: Cn1ncc(-c2ncc(NC(=O)c3cnn(-c4cccc5ncccc45)c3C(F)(F)F)cc2C#N)n1] | 257 | N-(5-cyano-6-(2-methyl-2H-1,2,3-triazol-4-yl)pyridin-3-yl)-1-(quinolin-5-yl)-5-(trifluoromethyl)-1H-pyrazole-4-carboxamide |
| 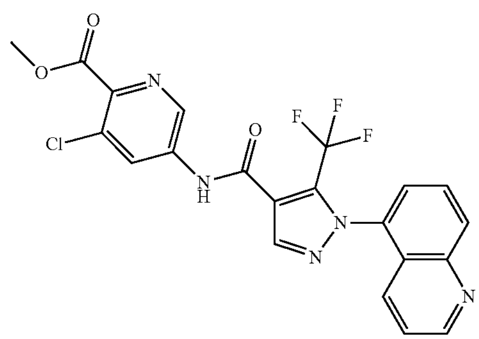 [SMILES: COC(=O)c1ncc(NC(=O)c2cnn(-c3cccc4ncccc34)c2C(F)(F)F)cc1Cl] | 258 | methyl 3-chloro-5-(1-(quinolin-5-yl)-5-(trifluoromethyl)-1H-pyrazole-4-carboxamido)picolinate |
| 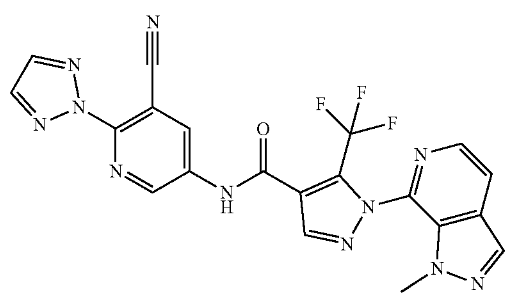 [SMILES: Cn1ncc2ccnc(-n3ncc(C(=O)Nc4cnc(-n5nccn5)c(C#N)c4)c3C(F)(F)F)c21] | 259 | N-(5-cyano-6-(2H-1,2,3-triazol-2-yl)pyridin-3-yl)-1-(1-methyl-1H-pyrazolo[3,4-c]pyridin-7-yl)-5-(trifluoromethyl)-1H-pyrazole-4-carboxamide |
| 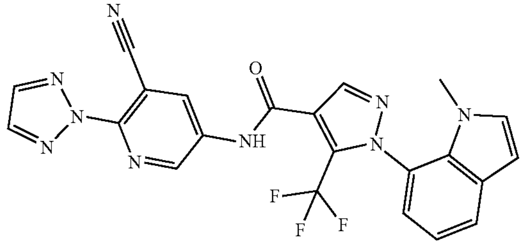 [SMILES: Cn1ccc2cccc(-n3ncc(C(=O)Nc4cnc(-n5nccn5)c(C#N)c4)c3C(F)(F)F)c21] | 260 | N-(5-cyano-6-(2H-1,2,3-triazol-2-yl)pyridin-3-yl)-1-(1-methyl-1H-indazol-7-yl)-5-(trifluoromethyl)-1H-pyrazole-4-carboxamide |

TABLE 1-continued

| Structure | Cpd No. | Cpd Name |
|---|---|---|
| 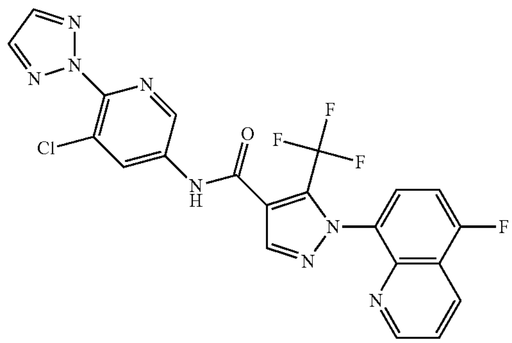 [SMILES: O=C(Nc1cnc(-n2nccn2)c(Cl)c1)c1cnn(-c2ccc(F)c3cccnc23)c1C(F)(F)F] | 261 | N-(5-chloro-6-(2H-1,2,3-triazol-2-yl)pyridin-3-yl)-1-(5-fluoroquinolin-8-yl)-5-(trifluoromethyl)-1H-pyrazole-4-carboxamide |
| 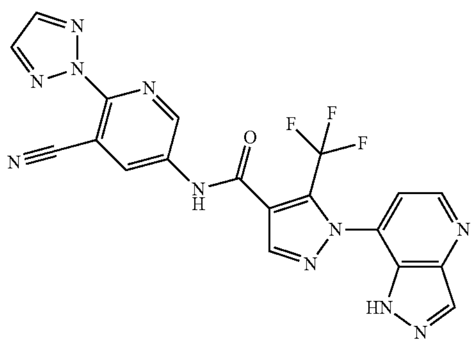 [SMILES: N#Cc1cc(NC(=O)c2cnn(-c3ccnc4cn[nH]c34)c2C(F)(F)F)cnc1-n1nccn1] | 262 | N-(5-cyano-6-(2H-1,2,3-triazol-2-yl)pyridin-3-yl)-1-(1H-pyrazolo[4,3-b]pyridin-7-yl)-5-(trifluoromethyl)-1H-pyrazole-4-carboxamide |
| 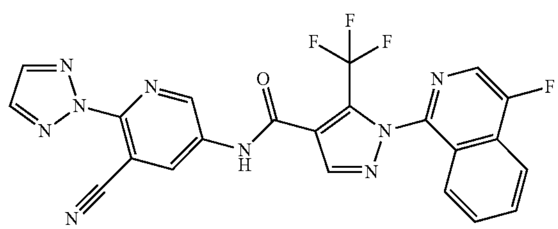 [SMILES: N#Cc1cc(NC(=O)c2cnn(-c3ncc(F)c4ccccc34)c2C(F)(F)F)cnc1-n1nccn1] | 263 | N-(5-cyano-6-(2H-1,2,3-triazol-2-yl)pyridin-3-yl)-1-(4-fluoroisoquinolin-1-yl)-5-(trifluoromethyl)-1H-pyrazole-4-carboxamide |
| 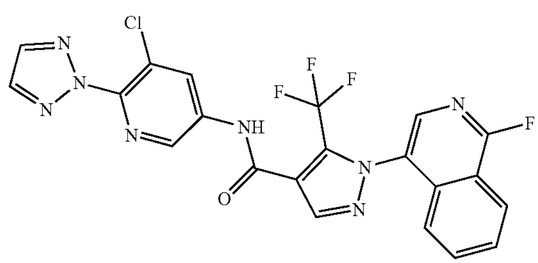 [SMILES: O=C(Nc1cnc(-n2nccn2)c(Cl)c1)c1cnn(-c2cnc(F)c3ccccc23)c1C(F)(F)F] | 264 | N-(5-chloro-6-(2H-1,2,3-triazol-2-yl)pyridin-3-yl)-1-(1-fluoroisoquinolin-4-yl)-5-(trifluoromethyl)-1H-pyrazole-4-carboxamide |
| 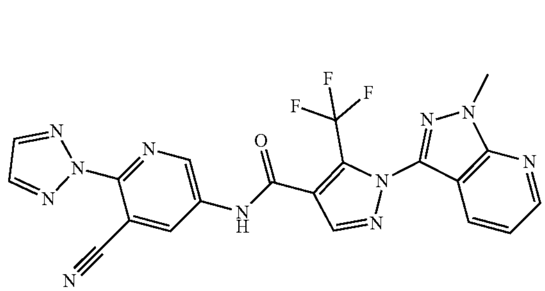 [SMILES: Cn1nc(-n2ncc(C(=O)Nc3cnc(-n4nccn4)c(C#N)c3)c2C(F)(F)F)c2cccnc21] | 265 | N-(5-cyano-6-(2H-1,2,3-triazol-2-yl)pyridin-3-yl)-1-(1-methyl-1H-pyrazolo[3,4-b]pyridin-3-yl)-5-(trifluoromethyl)-1H-pyrazole-4-carboxamide |

TABLE 1-continued

| Structure | Cpd No. | Cpd Name |
|---|---|---|
| 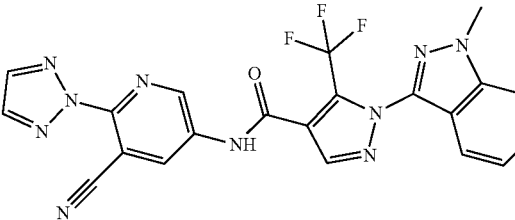 | 266 | N-(5-cyano-6-(2H-1,2,3-triazol-2-yl)pyridin-3-yl)-1-(1-methyl-1H-indazol-3-yl)-5-(trifluoromethyl)-1H-pyrazole-4-carboxamide |
| 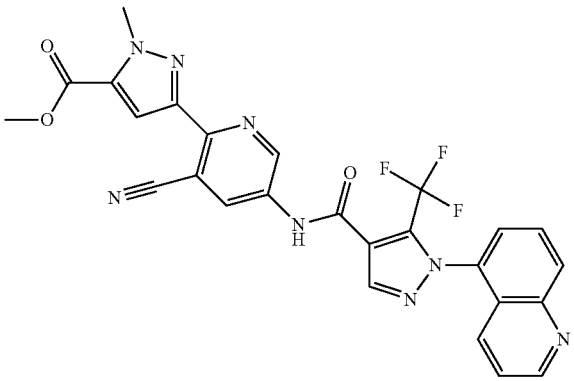 [SMILES: COC(=O)c1cc(-c2ncc(NC(=O)c3cnn(-c4cccc5ncccc45)c3C(F)(F)F)cc2C#N)nn1C] | 267 | methyl 3-(3-cyano-5-(1-(quinolin-5-yl)-5-(trifluoromethyl)-1H-pyrazole-4-carboxamido)pyridin-2-yl)-1-methyl-1H-pyrazole-5-carboxylate |
| 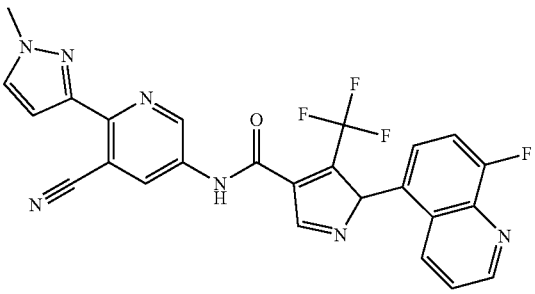 [SMILES: Cn1ccc(-c2ncc(NC(=O)C3=C(C(F)(F)F)C(c4ccc(F)c5ncccc45)N=C3)cc2C#N)n1] | 268 | N-(5-cyano-6-(1-methyl-1H-pyrazol-3-yl)pyridin-3-yl)-1-(8-fluoroquinolin-5-yl)-5-(trifluoromethyl)-1H-pyrazole-4-carboxamide |
| 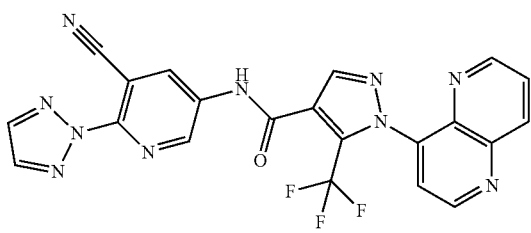 [SMILES: N#Cc1cc(NC(=O)c2cnn(-c3ccnc4cccnc34)c2C(F)(F)F)cnc1-n1nccn1] | 269 | N-(5-cyano-6-(2H-1,2,3-triazol-2-yl)pyridin-3-yl)-1-(1,5-naphthyridin-4-yl)-5-(trifluoromethyl)-1H-pyrazole-4-carboxamide |
| 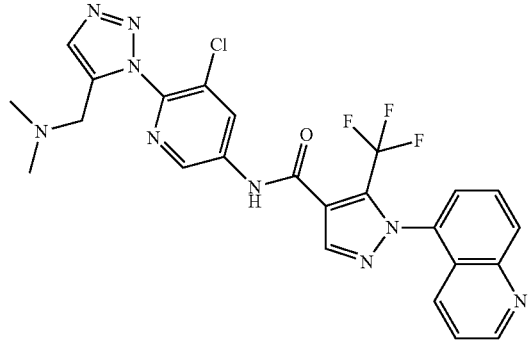 [SMILES: CN(C)Cc1cnnn1-c1ncc(NC(=O)c2cnn(-c3cccc4ncccc34)c2C(F)(F)F)cc1Cl] | 270 | N-(5-chloro-6-(5-((dimethylamino)methyl)-1H-1,2,3-triazol-1-yl)pyridin-3-yl)-1-(quinolin-5-yl)-5-(trifluoromethyl)-1H-pyrazole-4-carboxamide |

TABLE 1-continued

| Structure | Cpd No. | Cpd Name |
|---|---|---|
| 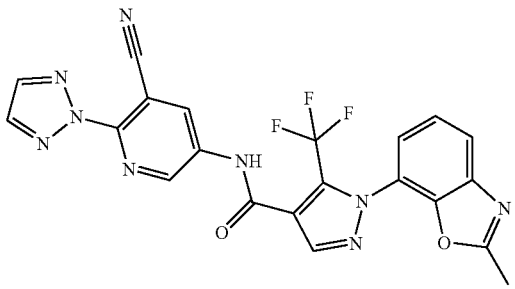 [SMILES: Cc1nc2cccc(-n3ncc(C(=O)Nc4cnc(-n5nccn5)c(C#N)c4)c3C(F)(F)F)c2o1] | 271 | N-(5-cyano-6-(2H-1,2,3-triazol-2-yl)pyridin-3-yl)-1-(2-methylbenzo[d]oxazol-7-yl)-5-(trifluoromethyl)-1H-pyrazole-4-carboxamide |
| 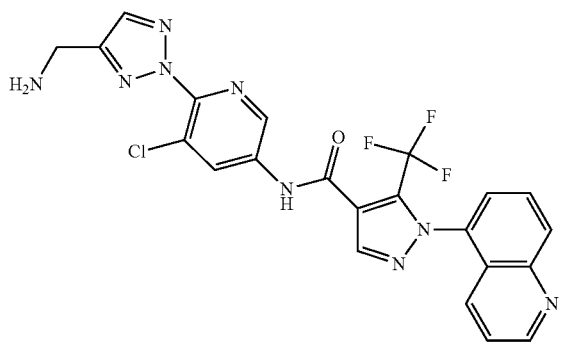 [SMILES: NCc1cnn(-c2ncc(NC(=O)c3cnn(-c4cccc5ncccc45)c3C(F)(F)F)cc2Cl)n1] | 272 | N-(6-(4-(aminomethyl)-2H-1,2,3-triazol-2-yl)-5-chloropyridin-3-yl)-1-(quinolin-5-yl)-5-(trifluoromethyl)-1H-pyrazole-4-carboxamide |
| 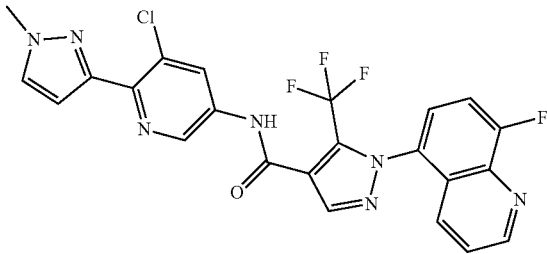 [SMILES: Cn1ccc(-c2ncc(NC(=O)c3cnn(-c4ccc(F)c5ncccc45)c3C(F)(F)F)cc2Cl)n1] | 273 | N-(5-chloro-6-(1-methyl-1H-pyrazol-3-yl)pyridin-3-yl)-1-(8-fluoroquinolin-5-yl)-5-(trifluoromethyl)-1H-pyrazole-4-carboxamide |
| 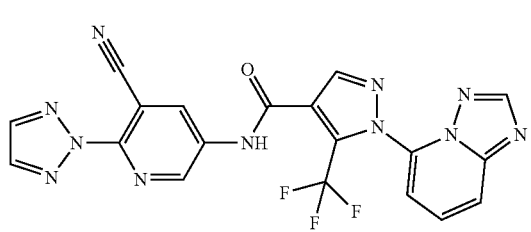 [SMILES: N#Cc1cc(NC(=O)c2cnn(-c3cccc4ncnn34)c2C(F)(F)F)cnc1-n1nccn1] | 274 | 1-([1,2,4]triazolo[1,5-a]pyridin-5-yl)-N-(5-cyano-6-(2H-1,2,3-triazol-2-yl)pyridin-3-yl)-5-(trifluoromethyl)-1H-pyrazole-4-carboxamide |
| 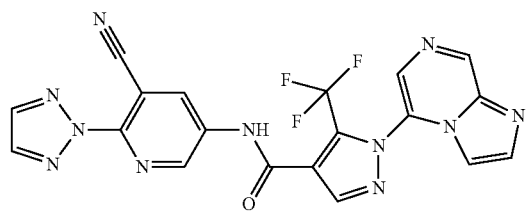 [SMILES: N#Cc1cc(NC(=O)c2cnn(-c3cncc4nccn34)c2C(F)(F)F)cnc1-n1nccn1] | 275 | N-(5-cyano-6-(2H-1,2,3-triazol-2-yl)pyridin-3-yl)-1-(imidazo[1,2-a]pyrazin-5-yl)-5-(trifluoromethyl)-1H-pyrazole-4-carboxamide |

TABLE 1-continued

| Structure | Cpd No. | Cpd Name |
|---|---|---|
| 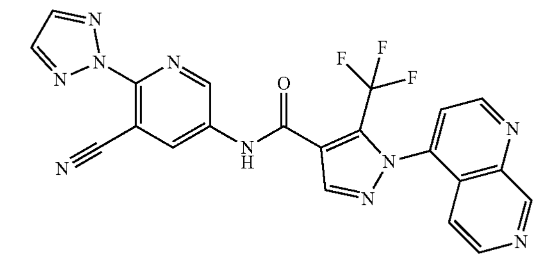 [SMILES: N#Cc1cc(NC(=O)c2cnn(-c3ccnc4cnccc34)c2C(F)(F)F)cnc1-n1nccn1] | 276 | N-(5-cyano-6-(2H-1,2,3-triazol-2-yl)pyridin-3-yl)-1-(1,7-naphthyridin-4-yl)-5-(trifluoromethyl)-1H-pyrazole-4-carboxamide |
| 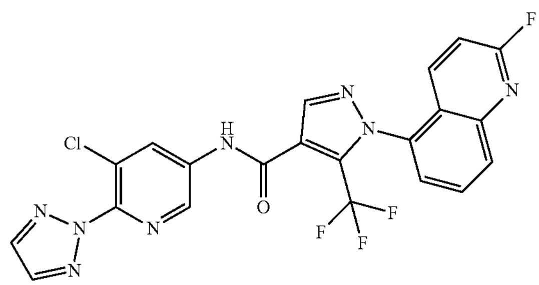 [SMILES: O=C(Nc1cnc(-n2nccn2)c(Cl)c1)c1cnn(-c2cccc3nc(F)ccc23)c1C(F)(F)F] | 277 | N-(5-chloro-6-(2H-1,2,3-triazol-2-yl)pyridin-3-yl)-1-(2-fluoroquinolin-5-yl)-5-(trifluoromethyl)-1H-pyrazole-4-carboxamide |
| 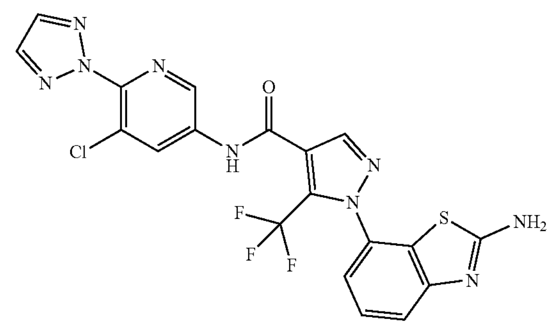 [SMILES: Nc1nc2cccc(-n3ncc(C(=O)Nc4cnc(-n5nccn5)c(Cl)c4)c3C(F)(F)F)c2s1] | 278 | 1-(2-aminobenzo[d]thiazol-7-yl)-N-(5-chloro-6-(2H-1,2,3-triazol-2-yl)pyridin-3-yl)-5-(trifluoromethyl)-1H-pyrazole-4-carboxamide |
| 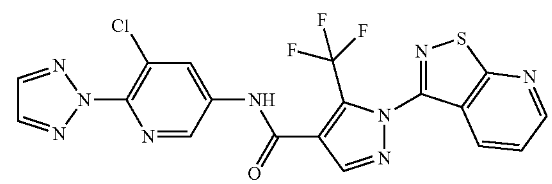 [SMILES: O=C(Nc1cnc(-n2nccn2)c(Cl)c1)c1cnn(-c2nsc3ncccc23)c1C(F)(F)F] | 279 | N-(5-chloro-6-(2H-1,2,3-triazol-2-yl)pyridin-3-yl)-1-(isothiazolo[5,4-b]pyridin-3-yl)-5-(trifluoromethyl)-1H-pyrazole-4-carboxamide |
| 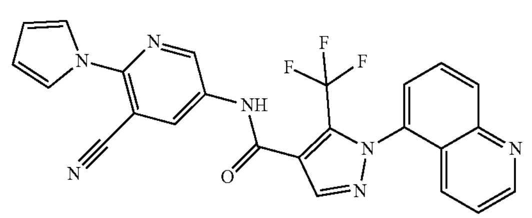 [SMILES: N#Cc1cc(NC(=O)c2cnn(-c3cccc4ncccc34)c2C(F)(F)F)cnc1-n1cccc1] | 280 | N-(5-cyano-6-(1H-pyrrol-1-yl)pyridin-3-yl)-1-(quinolin-5-yl)-5-(trifluoromethyl)-1H-pyrazole-4-carboxamide |
| 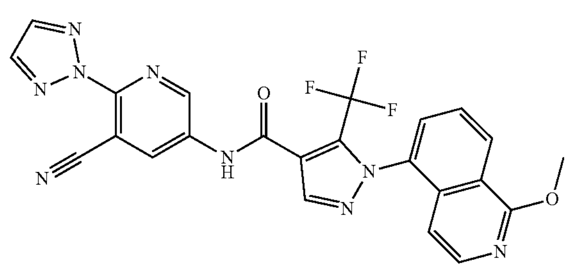 [SMILES: COc1nccc2c(-n3ncc(C(=O)Nc4cnc(-n5nccn5)c(C#N)c4)c3C(F)(F)F)cccc12] | 281 | N-(5-cyano-6-(2H-1,2,3-triazol-2-yl)pyridin-3-yl)-1-(1-methoxyisoquinolin-5-yl)-5-(trifluoromethyl)-1H-pyrazole-4-carboxamide |

TABLE 1-continued

| Structure | Cpd No. | Cpd Name |
|---|---|---|
| 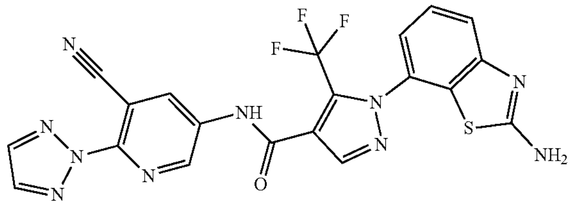 [SMILES: N#Cc1cc(NC(=O)c2cnn(-c3cccc4nc(N)sc34)c2C(F)(F)F)cnc1-n1nccn1] | 282 | 1-(2-aminobenzo[d]thiazol-7-yl)-N-(5-cyano-6-(2H-1,2,3-triazol-2-yl)pyridin-3-yl)-5-(trifluoromethyl)-1H-pyrazole-4-carboxamide |
| 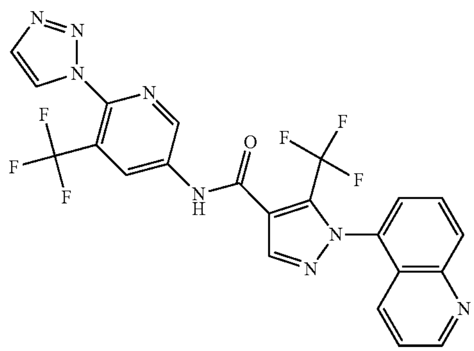 [SMILES: O=C(Nc1cnc(-n2ccnn2)c(C(F)(F)F)c1)c1cnn(-c2cccc3ncccc23)c1C(F)(F)F] | 283 | N-(6-(1H-1,2,3-triazol-1-yl)-5-(trifluoromethyl)pyridin-3-yl)-1-(quinolin-5-yl)-5-(trifluoromethyl)-1H-pyrazole-4-carboxamide |
| 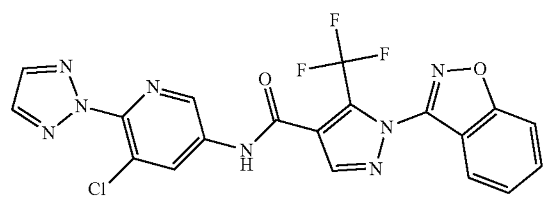 [SMILES: O=C(Nc1cnc(-n2nccn2)c(Cl)c1)c1cnn(-c2noc3ccccc23)c1C(F)(F)F] | 284 | 1-(benzo[d]isoxazol-3-yl)-N-(5-chloro-6-(2H-1,2,3-triazol-2-yl)pyridin-3-yl)-5-(trifluoromethyl)-1H-pyrazole-4-carboxamide |
| 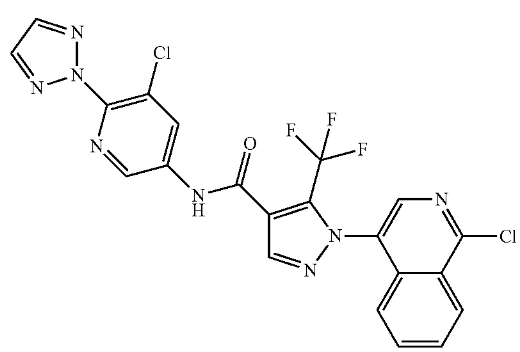 [SMILES: O=C(Nc1cnc(-n2nccn2)c(Cl)c1)c1cnn(-c2cnc(Cl)c3ccccc23)c1C(F)(F)F] | 285 | N-(5-chloro-6-(2H-1,2,3-triazol-2-yl)pyridin-3-yl)-1-(1-chloroisoquinolin-4-yl)-5-(trifluoromethyl)-1H-pyrazole-4-carboxamide |
| 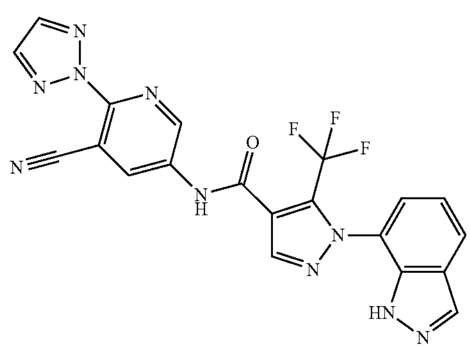 [SMILES: N#Cc1cc(NC(=O)c2cnn(-c3cccc4cn[nH]c34)c2C(F)(F)F)cnc1-n1nccn1] | 286 | N-(5-cyano-6-(2H-1,2,3-triazol-2-yl)pyridin-3-yl)-1-(1H-indazol-7-yl)-5-(trifluoromethyl)-1H-pyrazole-4-carboxamide |

TABLE 1-continued

| Structure | Cpd No. | Cpd Name |
|---|---|---|
| 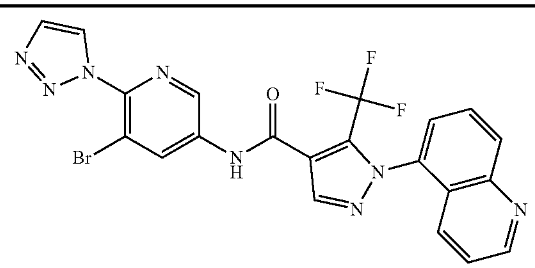 | 287 | N-(5-bromo-6-(1H-1,2,3-triazol-1-yl)pyridin-3-yl)-1-(quinolin-5-yl)-5-(trifluoromethyl)-1H-pyrazole-4-carboxamide |
| 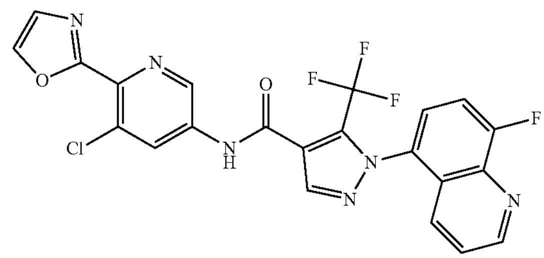 [SMILES: O=C(Nc1cnc(-c2ncco2)c(Cl)c1)c1cnn(-c2ccc(F)c3ncccc23)c1C(F)(F)F] | 288 | N-(5-chloro-6-(oxazol-2-yl)pyridin-3-yl)-1-(8-fluoroquinolin-5-yl)-5-(trifluoromethyl)-1H-pyrazole-4-carboxamide |
| 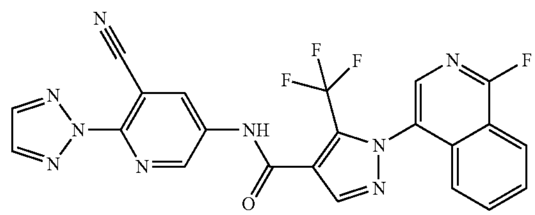 [SMILES: N#Cc1cc(NC(=O)c2cnn(-c3cnc(F)c4ccccc34)c2C(F)(F)F)cnc1-n1nccn1] | 289 | N-(5-cyano-6-(2H-1,2,3-triazol-2-yl)pyridin-3-yl)-1-(1-fluoroisoquinolin-4-yl)-5-(trifluoromethyl)-1H-pyrazole-4-carboxamide |
| 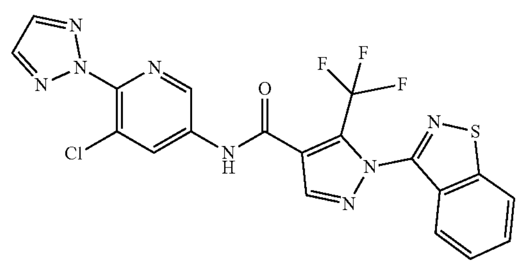 [SMILES: O=C(Nc1cnc(-n2nccn2)c(Cl)c1)c1cnn(-c2nsc3ccccc23)c1C(F)(F)F] | 290 | 1-(benzo[d]isothiazol-3-yl)-N-(5-chloro-6-(2H-1,2,3-triazol-2-yl)pyridin-3-yl)-5-(trifluoromethyl)-1H-pyrazole-4-carboxamide |
| 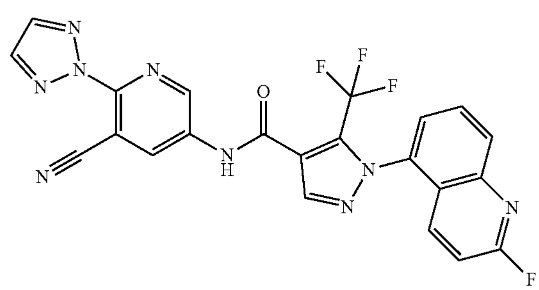 [SMILES: N#Cc1cc(NC(=O)c2cnn(-c3cccc4nc(F)ccc34)c2C(F)(F)F)cnc1-n1nccn1] | 291 | N-(5-cyano-6-(2H-1,2,3-triazol-2-yl)pyridin-3-yl)-1-(2-fluoroquinolin-5-yl)-5-(trifluoromethyl)-1H-pyrazole-4-carboxamide |
| 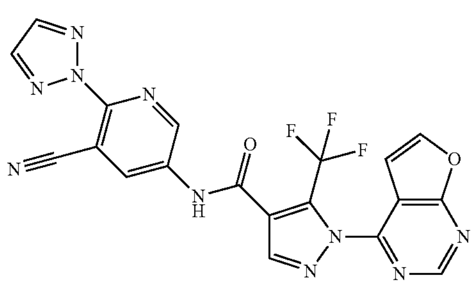 [SMILES: N#Cc1cc(NC(=O)c2cnn(-c3ncnc4occc34)c2C(F)(F)F)cnc1-n1nccn1] | 292 | N-(5-cyano-6-(2H-1,2,3-triazol-2-yl)pyridin-3-yl)-1-(furo[2,3-d]pyrimidin-4-yl)-5-(trifluoromethyl)-1H-pyrazole-4-carboxamide |

TABLE 1-continued

| Structure | Cpd No. | Cpd Name |
|---|---|---|
| 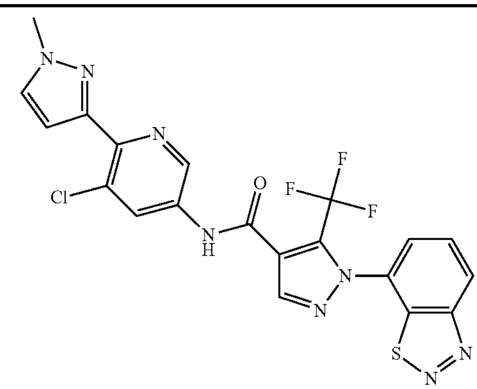 | 293 | 1-(benzo[d][1,2,3]thiadiazol-7-yl)-N-(5-chloro-6-(1-methyl-1H-pyrazol-3-yl)pyridin-3-yl)-5-(trifluoromethyl)-1H-pyrazole-4-carboxamide |
| 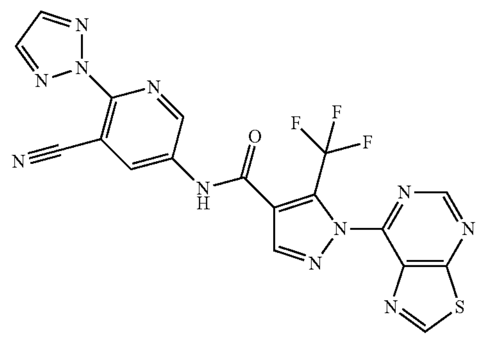 [SMILES: N#Cc1cc(NC(=O)c2cnn(-c3ncnc4scnc34)c2C(F)(F)F)cnc1-n1nccn1] | 294 | N-(5-cyano-6-(2H-1,2,3-triazol-2-yl)pyridin-3-yl)-1-(thiazolo[5,4-d]pyrimidin-7-yl)-5-(trifluoromethyl)-1H-pyrazole-4-carboxamide |
| 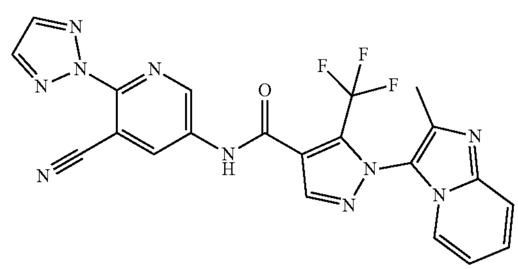 [SMILES: Cc1nc2ccccn2c1-n1ncc(C(=O)Nc2cnc(-n3nccn3)c(C#N)c2)c1C(F)(F)F] | 295 | N-(5-cyano-6-(2H-1,2,3-triazol-2-yl)pyridin-3-yl)-1-(2-methylimidazo[1,2-a]pyridin-3-yl)-5-(trifluoromethyl)-1H-pyrazole-4-carboxamide |
| 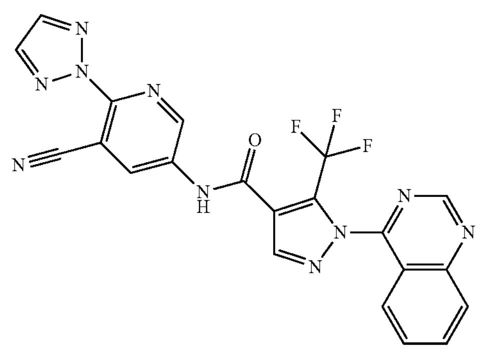 | 296 | N-(5-cyano-6-(2H-1,2,3-triazol-2-yl)pyridin-3-yl)-1-(quinazolin-4-yl)-5-(trifluoromethyl)-1H-pyrazole-4-carboxamide |
| 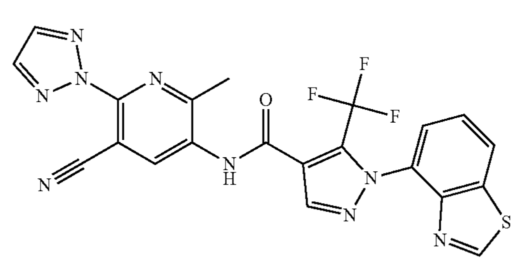 [SMILES: Cc1nc(-n2nccn2)c(C#N)cc1NC(=O)c1cnn(-c2cccc3scnc23)c1C(F)(F)F] | 297 | 1-(benzo[d]thiazol-4-yl)-N-(5-cyano-2-methyl-6-(2H-1,2,3-triazol-2-yl)pyridin-3-yl)-5-(trifluoromethyl)-1H-pyrazole-4-carboxamide |

TABLE 1-continued

| Structure | Cpd No. | Cpd Name |
|---|---|---|
| 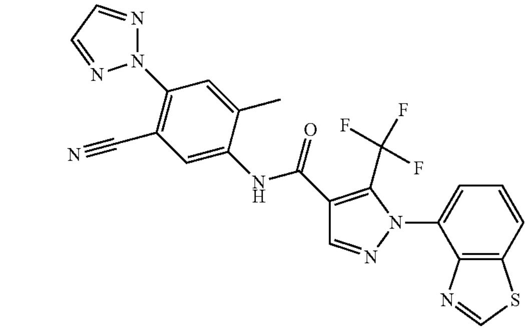 [SMILES: Cc1cc(-n2nccn2)c(C#N)cc1NC(=O)c1cnn(-c2cccc3scnc23)c1C(F)(F)F] | 298 | 1-(benzo[d]thiazol-4-yl)-N-(5-cyano-2-methyl-4-(2H-1,2,3-triazol-2-yl)phenyl)-5-(trifluoromethyl)-1H-pyrazole-4-carboxamide |
| 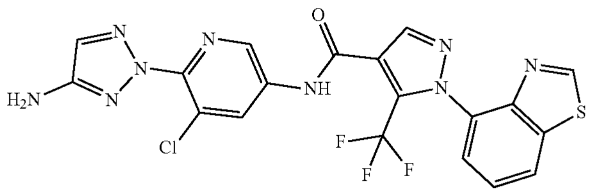 [SMILES: Nc1cnn(-c2ncc(NC(=O)c3cnn(-c4cccc5scnc45)c3C(F)(F)F)cc2Cl)n1] | 299 | N-(6-(4-amino-2H-1,2,3-triazol-2-yl)-5-chloropyridin-3-yl)-1-(benzo[d]thiazol-4-yl)-5-(trifluoromethyl)-1H-pyrazole-4-carboxamide |
| 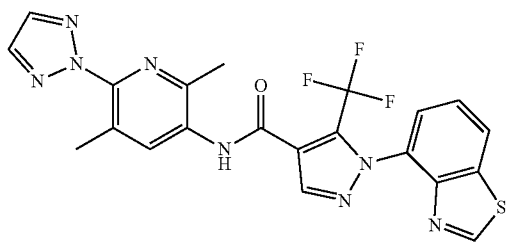 [SMILES: Cc1cc(NC(=O)c2cnn(-c3cccc4scnc34)c2C(F)(F)F)c(C)nc1-n1nccn1] | 300 | 1-(benzo[d]thiazol-4-yl)-N-(2,5-dimethyl-6-(2H-1,2,3-triazol-2-yl)pyridin-3-yl)-5-(trifluoromethyl)-1H-pyrazole-4-carboxamide |
| 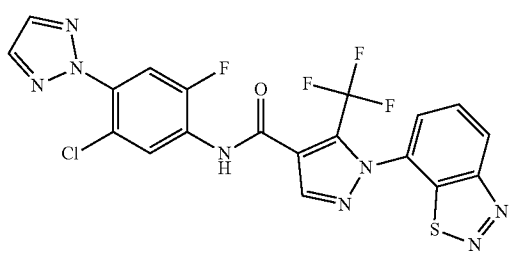 [SMILES: O=C(Nc1cc(Cl)c(-n2nccn2)cc1F)c1cnn(-c2cccc3nnsc23)c1C(F)(F)F] | 301 | 1-(benzo[d][1,2,3]thiadiazol-7-yl)-N-(5-chloro-2-fluoro-4-(2H-1,2,3-triazol-2-yl)phenyl)-5-(trifluoromethyl)-1H-pyrazole-4-carboxamide |
| 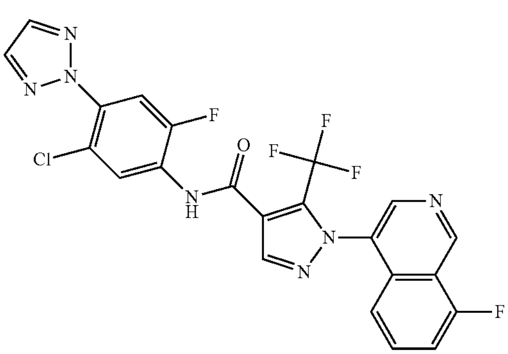 [SMILES: O=C(Nc1cc(Cl)c(-n2nccn2)cc1F)c1cnn(-c2cncc3c(F)cccc23)c1C(F)(F)F] | 302 | N-(5-chloro-2-fluoro-4-(2H-1,2,3-triazol-2-yl)phenyl)-1-(8-fluoroisoquinolin-4-yl)-5-(trifluoromethyl)-1H-pyrazole-4-carboxamide |

TABLE 1-continued

| Structure | Cpd No. | Cpd Name |
|---|---|---|
| 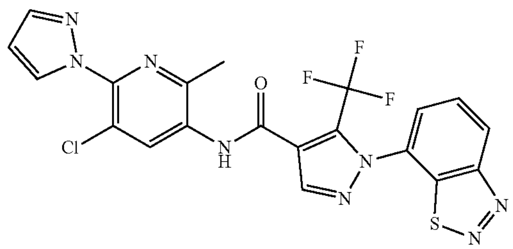 [SMILES: Cc1nc(-n2cccn2)c(Cl)cc1NC(=O)c1cnn(-c2cccc3nnsc23)c1C(F)(F)F] | 303 | 1-(benzo[d][1,2,3]thiadiazol-7-yl)-N-(5-chloro-2-methyl-6-(1H-pyrazol-1-yl)pyridin-3-yl)-5-(trifluoromethyl)-1H-pyrazole-4-carboxamide |
| 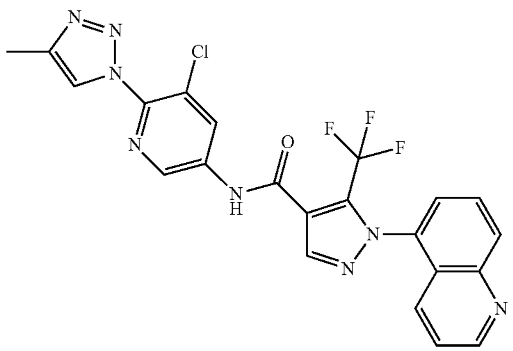 [SMILES: Cc1cn(-c2ncc(NC(=O)c3cnn(-c4cccc5ncccc45)c3C(F)(F)F)cc2Cl)nn1] | 304 | N-(5-chloro-6-(4-methyl-1H-1,2,3-triazol-1-yl)pyridin-3-yl)-1-(quinolin-5-yl)-5-(trifluoromethyl)-1H-pyrazole-4-carboxamide |
| 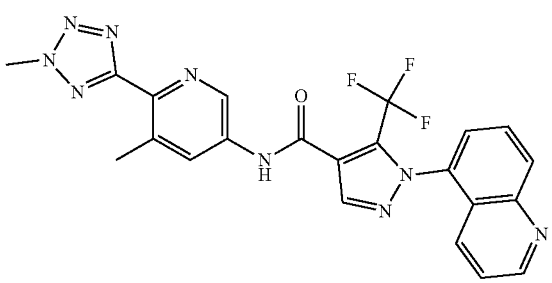 [SMILES: Cc1cc(NC(=O)c2cnn(-c3cccc4ncccc34)c2C(F)(F)F)cnc1-c1nnn(C)n1] | 305 | N-(5-methyl-6-(2-methyl-2H-tetrazol-5-yl)pyridin-3-yl)-1-(quinolin-5-yl)-5-(trifluoromethyl)-1H-pyrazole-4-carboxamide |
| 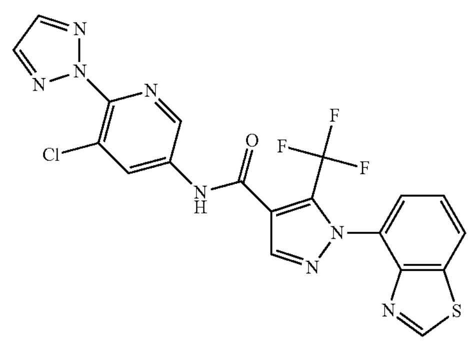 [SMILES: O=C(Nc1cnc(-n2nccn2)c(Cl)c1)c1cnn(-c2cccc3scnc23)c1C(F)(F)F] | 306 | 1-(benzo[d]thiazol-4-yl)-N-(5-chloro-6-(2H-1,2,3-triazol-2-yl)pyridin-3-yl)-5-(trifluoromethyl)-1H-pyrazole-4-carboxamide |
| 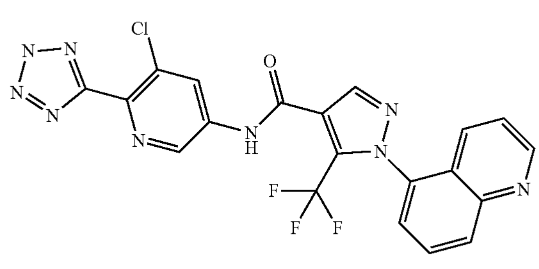 [SMILES: O=C(Nc1cnc(-c2nn[nH]n2)c(Cl)c1)c1cnn(-c2cccc3ncccc23)c1C(F)(F)F] | 307 | N-(5-chloro-6-(2H-tetrazol-5-yl)pyridin-3-yl)-1-(quinolin-5-yl)-5-(trifluoromethyl)-1H-pyrazole-4-carboxamide |

TABLE 1-continued

| Structure | Cpd No. | Cpd Name |
|---|---|---|
| 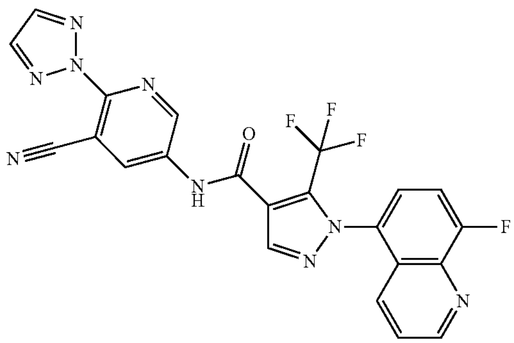 [SMILES: N#Cc1cc(NC(=O)c2cnn(-c3ccc(F)c4ncccc34)c2C(F)(F)F)cnc1-n1nccn1] | 308 | N-(5-cyano-6-(2H-1,2,3-triazol-2-yl)pyridin-3-yl)-1-(8-fluoroquinolin-5-yl)-5-(trifluoromethyl)-1H-pyrazole-4-carboxamide |
| 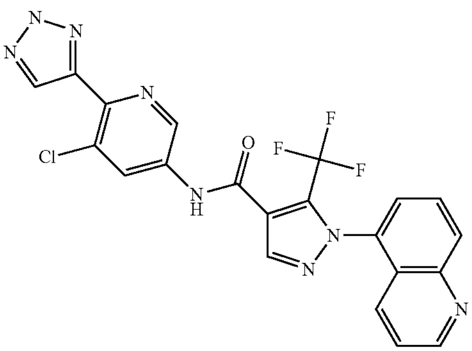 [SMILES: O=C(Nc1cnc(-c2cn[nH]n2)c(Cl)c1)c1cnn(-c2cccc3ncccc23)c1C(F)(F)F] | 309 | N-(5-chloro-6-(2H-1,2,3-triazol-4-yl)pyridin-3-yl)-1-(quinolin-5-yl)-5-(trifluoromethyl)-1H-pyrazole-4-carboxamide |
| 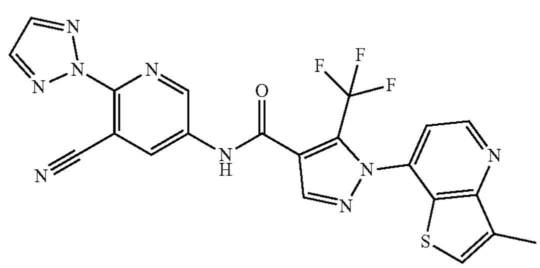 [SMILES: Cc1csc2c(-n3ncc(C(=O)Nc4cnc(-n5nccn5)c(C#N)c4)c3C(F)(F)F)ccnc12] | 310 | N-(5-cyano-6-(2H-1,2,3-triazol-2-yl)pyridin-3-yl)-1-(3-methylthieno[3,2-b]pyridin-7-yl)-5-(trifluoromethyl)-1H-pyrazole-4-carboxamide |
| 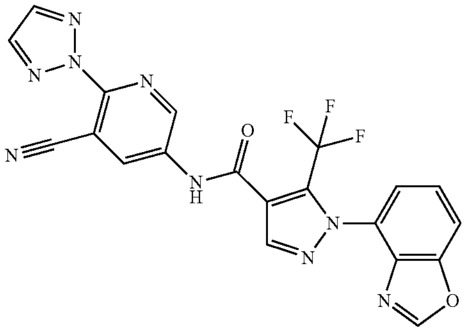 [SMILES: N#Cc1cc(NC(=O)c2cnn(-c3cccc4ocnc34)c2C(F)(F)F)cnc1-n1nccn1] | 311 | 1-(benzo[d]oxazol-4-yl)-N-(5-cyano-6-(2H-1,2,3-triazol-2-yl)pyridin-3-yl)-5-(trifluoromethyl)-1H-pyrazole-4-carboxamide |

TABLE 1-continued

| Structure | Cpd No. | Cpd Name |
|---|---|---|
| 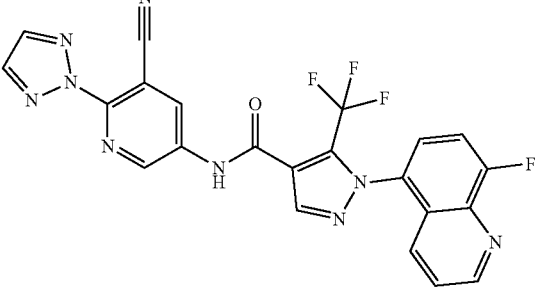 | 312 | N-(5-cyano-6-(2H-1,2,3-triazol-2-yl)pyridin-3-yl)-1-(4-fluoronaphthalen-1-yl)-5-(trifluoromethyl)-1H-pyrazole-4-carboxamide |
| 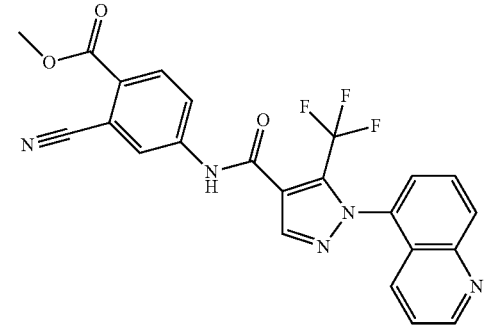 [SMILES: COC(=O)c1ccc(NC(=O)c2cnn(-c3cccc4ncccc34)c2C(F)(F)F)cc1C#N] | 313 | methyl 2-cyano-4-(1-(quinolin-5-yl)-5-(trifluoromethyl)-1H-pyrazole-4-carboxamido)benzoate |
| 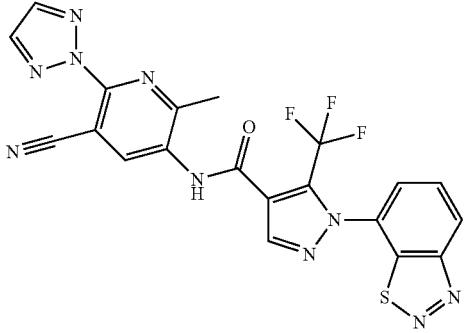 [SMILES: Cc1nc(-n2nccn2)c(C#N)cc1NC(=O)c1cnn(-c2cccc3nnsc23)c1C(F)(F)F] | 314 | 1-(benzo[d][1,2,3]thiadiazol-7-yl)-N-(5-cyano-2-methyl-6-(2H-1,2,3-triazol-2-yl)pyridin-3-yl)-5-(trifluoromethyl)-1H-pyrazole-4-carboxamide |
| 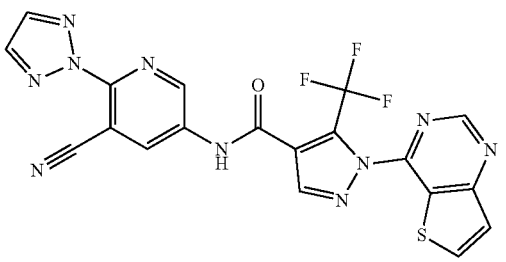 [SMILES: N#Cc1cc(NC(=O)c2cnn(-c3ncnc4ccsc34)c2C(F)(F)F)cnc1-n1nccn1] | 315 | N-(5-cyano-6-(2H-1,2,3-triazol-2-yl)pyridin-3-yl)-1-(thieno[3,2-d]pyrimidin-4-yl)-5-(trifluoromethyl)-1H-pyrazole-4-carboxamide |
| 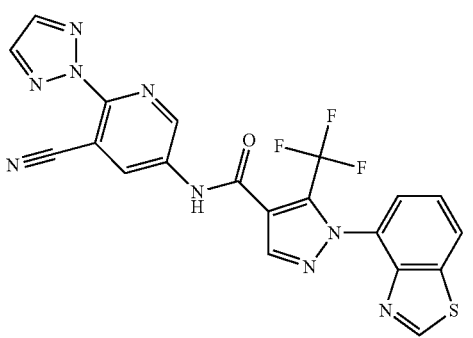 [SMILES: N#Cc1cc(NC(=O)c2cnn(-c3cccc4scnc34)c2C(F)(F)F)cnc1-n1nccn1] | 316 | 1-(benzo[d]thiazol-4-yl)-N-(5-cyano-6-(2H-1,2,3-triazol-2-yl)pyridin-3-yl)-5-(trifluoromethyl)-1H-pyrazole-4-carboxamide |

TABLE 1-continued

| Structure | Cpd No. | Cpd Name |
|---|---|---|
| 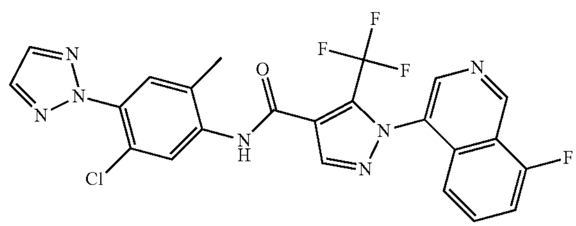 [SMILES: Cc1cc(-n2nccn2)c(Cl)cc1NC(=O)c1cnn(-c2cncc3c(F)cccc23)c1C(F)(F)F] | 317 | N-(5-chloro-2-methyl-4-(2H-1,2,3-triazol-2-yl)phenyl)-1-(8-fluoroisoquinolin-4-yl)-5-(trifluoromethyl)-1H-pyrazole-4-carboxamide |
| 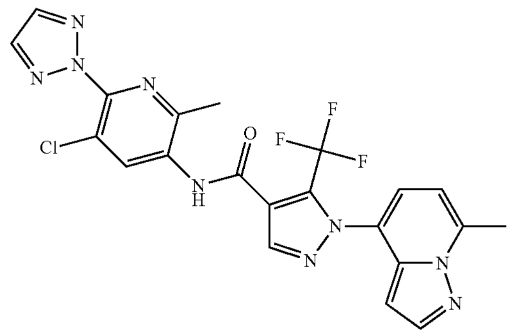 [SMILES: Cc1nc(-n2nccn2)c(Cl)cc1NC(=O)c1cnn(-c2ccc(C)n3nccc23)c1C(F)(F)F] | 318 | N-(5-chloro-2-methyl-6-(2H-1,2,3-triazol-2-yl)pyridin-3-yl)-1-(7-methylpyrazolo[1,5-a]pyridin-4-yl)-5-(trifluoromethyl)-1H-pyrazole-4-carboxamide |
| 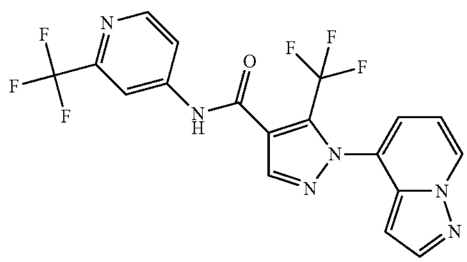 [SMILES: O=C(Nc1ccnc(C(F)(F)F)c1)c1cnn(-c2cccn3nccc23)c1C(F)(F)F] | 319 | 1-(pyrazolo[1,5-a]pyridin-4-yl)-5-(trifluoromethyl)-N-(2-(trifluoromethyl)pyridin-4-yl)-1H-pyrazole-4-carboxamide |
| 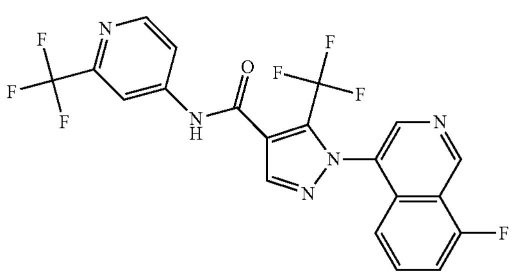 [SMILES: O=C(Nc1ccnc(C(F)(F)F)c1)c1cnn(-c2cncc3c(F)cccc23)c1C(F)(F)F] | 320 | 1-(8-fluoroisoquinolin-4-yl)-5-(trifluoromethyl)-N-(2-(trifluoromethyl)pyridin-4-yl)-1H-pyrazole-4-carboxamide |
| 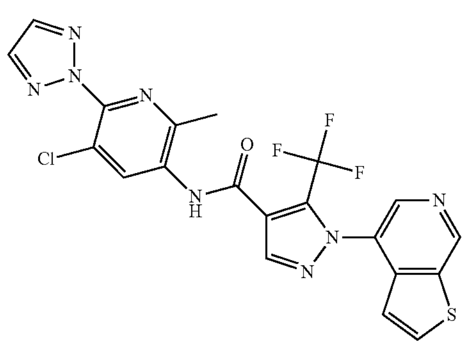 [SMILES: Cc1nc(-n2nccn2)c(Cl)cc1NC(=O)c1cnn(-c2cncc3sccc23)c1C(F)(F)F] | 321 | N-(5-chloro-2-methyl-6-(2H-1,2,3-triazol-2-yl)pyridin-3-yl)-1-(thieno[2,3-c]pyridin-4-yl)-5-(trifluoromethyl)-1H-pyrazole-4-carboxamide |

TABLE 1-continued

| Structure | Cpd No. | Cpd Name |
|---|---|---|
| 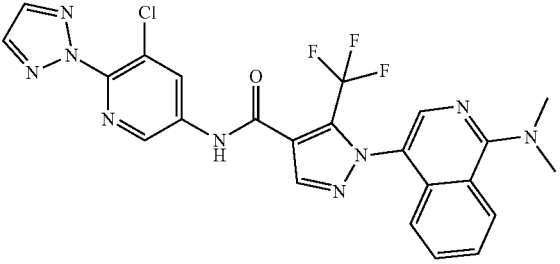 [SMILES: CN(C)c1ncc(-n2ncc(C(=O)Nc3cnc(-n4nccn4)c(Cl)c3)c2C(F)(F)F)c2ccccc12] | 322 | N-(5-chloro-6-(2H-1,2,3-triazol-2-yl)pyridin-3-yl)-1-(1-(dimethylamino)isoquinolin-4-yl)-5-(trifluoromethyl)-1H-pyrazole-4-carboxamide |
| 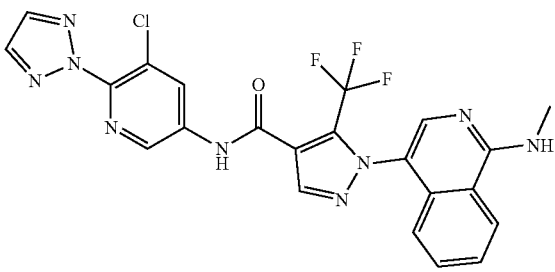 [SMILES: CNc1ncc(-n2ncc(C(=O)Nc3cnc(-n4nccn4)c(Cl)c3)c2C(F)(F)F)c2ccccc12] | 323 | N-(5-chloro-6-(2H-1,2,3-triazol-2-yl)pyridin-3-yl)-1-(1-(methylamino)isoquinolin-4-yl)-5-(trifluoromethyl)-1H-pyrazole-4-carboxamide |
| 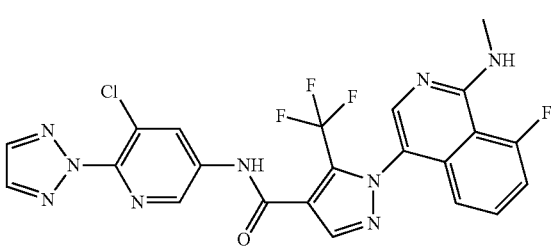 [SMILES: CNc1ncc(-n2ncc(C(=O)Nc3cnc(-n4nccn4)c(Cl)c3)c2C(F)(F)F)c2cccc(F)c12] | 324 | N-(5-chloro-6-(2H-1,2,3-triazol-2-yl)pyridin-3-yl)-1-(8-fluoro-1-(methylamino)isoquinolin-4-yl)-5-(trifluoromethyl)-1H-pyrazole-4-carboxamide |
| 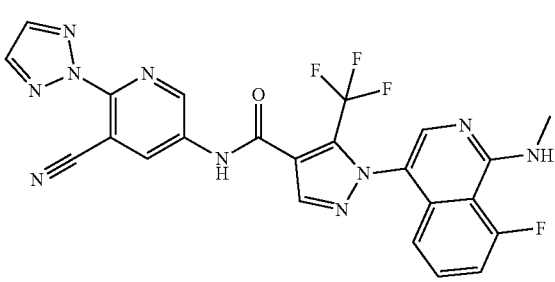 [SMILES: CNc1ncc(-n2ncc(C(=O)Nc3cnc(-n4nccn4)c(C#N)c3)c2C(F)(F)F)c2cccc(F)c12] | 325 | N-(5-cyano-6-(2H-1,2,3-triazol-2-yl)pyridin-3-yl)-1-(8-fluoro-1-(methylamino)isoquinolin-4-yl)-5-(trifluoromethyl)-1H-pyrazole-4-carboxamide |
| 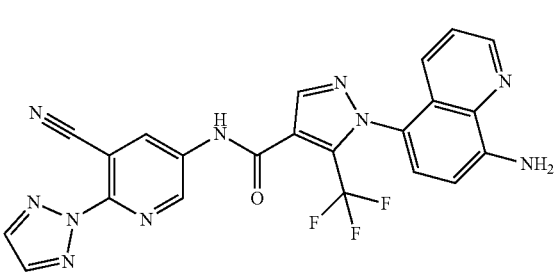 [SMILES: N#Cc1cc(NC(=O)c2cnn(-c3ccc(N)c4ncccc34)c2C(F)(F)F)cnc1-n1nccn1] | 326 | 1-(8-aminoquinolin-5-yl)-N-(5-cyano-6-(2H-1,2,3-triazol-2-yl)pyridin-3-yl)-5-(trifluoromethyl)-1H-pyrazole-4-carboxamide |

TABLE 1-continued

| Structure | Cpd No. | Cpd Name |
|---|---|---|
| 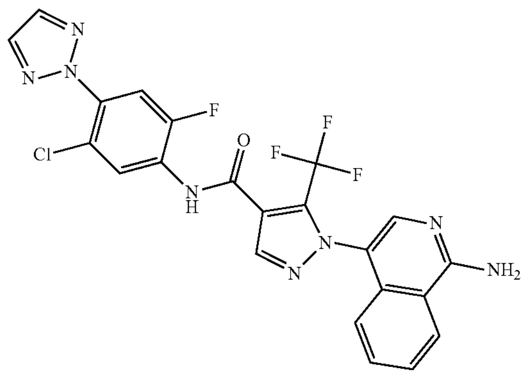 [SMILES: Nc1ncc(-n2ncc(C(=O)Nc3cc(Cl)c(-n4nccn4)cc3F)c2C(F)(F)F)c2ccccc12] | 327 | 1-(1-aminoisoquinolin-4-yl)-N-(5-chloro-2-fluoro-4-(2H-1,2,3-triazol-2-yl)phenyl)-5-(trifluoromethyl)-1H-pyrazole-4-carboxamide |
| 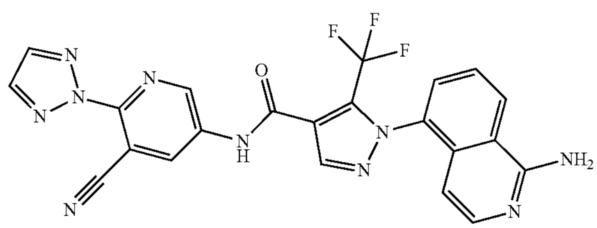 [SMILES: N#Cc1cc(NC(=O)c2cnn(-c3cccc4c(N)nccc34)c2C(F)(F)F)cnc1-n1nccn1] | 328 | 1-(1-aminoisoquinolin-5-yl)-N-(5-cyano-6-(2H-1,2,3-triazol-2-yl)pyridin-3-yl)-5-(trifluoromethyl)-1H-pyrazole-4-carboxamide |
| 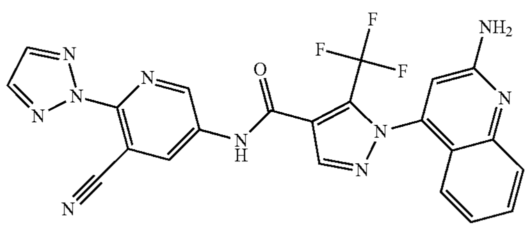 [SMILES: N#Cc1cc(NC(=O)c2cnn(-c3cc(N)nc4ccccc34)c2C(F)(F)F)cnc1-n1nccn1] | 329 | 1-(2-aminoquinolin-4-yl)-N-(5-cyano-6-(2H-1,2,3-triazol-2-yl)pyridin-3-yl)-5-(trifluoromethyl)-1H-pyrazole-4-carboxamide |
| 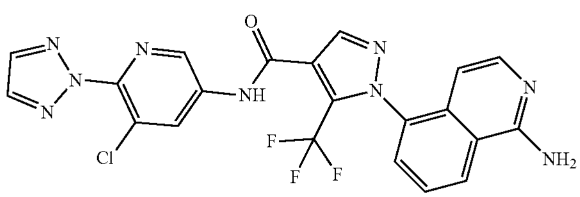 [SMILES: Nc1nccc2c(-n3ncc(C(=O)Nc4cnc(-n5nccn5)c(Cl)c4)c3C(F)(F)F)cccc12] | 330 | 1-(1-aminoisoquinolin-5-yl)-N-(5-chloro-6-(2H-1,2,3-triazol-2-yl)pyridin-3-yl)-5-(trifluoromethyl)-1H-pyrazole-4-carboxamide |
| 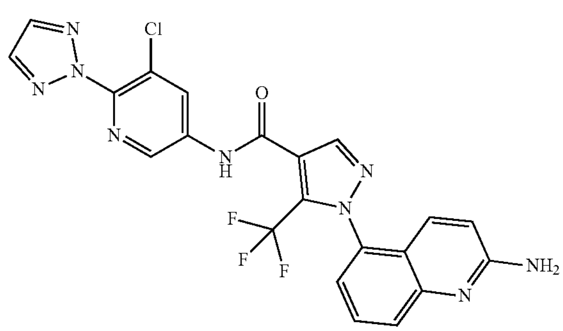 [SMILES: Nc1ccc2c(-n3ncc(C(=O)Nc4cnc(-n5nccn5)c(Cl)c4)c3C(F)(F)F)cccc2n1] | 331 | 1-(2-aminoquinolin-5-yl)-N-(5-chloro-6-(2H-1,2,3-triazol-2-yl)pyridin-3-yl)-5-(trifluoromethyl)-1H-pyrazole-4-carboxamide |

TABLE 1-continued

| Structure | Cpd No. | Cpd Name |
|---|---|---|
| 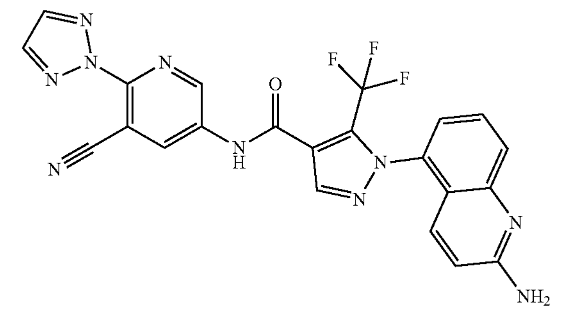 [SMILES: N#Cc1cc(NC(=O)c2cnn(-c3cccc4nc(N)ccc34)c2C(F)(F)F)cnc1-n1nccn1] | 332 | 1-(2-aminoquinolin-5-yl)-N-(5-cyano-6-(2H-1,2,3-triazol-2-yl)pyridin-3-yl)-5-(trifluoromethyl)-1H-pyrazole-4-carboxamide |
| 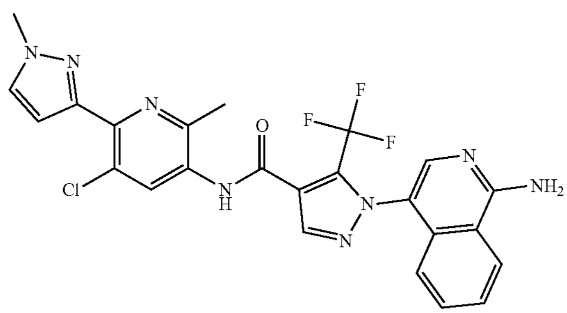 [SMILES: Cc1nc(-c2ccn(C)n2)c(Cl)cc1NC(=O)c1cnn(-c2cnc(N)c3ccccc23)c1C(F)(F)F] | 333 | 1-(1-aminoisoquinolin-4-yl)-N-(5-chloro-2-methyl-6-(1-methyl-1H-pyrazol-3-yl)pyridin-3-yl)-5-(trifluoromethyl)-1H-pyrazole-4-carboxamide |
| 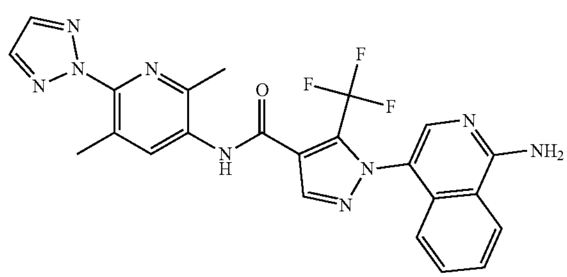 [SMILES: Cc1cc(NC(=O)c2cnn(-c3cnc(N)c4ccccc34)c2C(F)(F)F)c(C)nc1-n1nccn1] | 334 | 1-(1-aminoisoquinolin-4-yl)-N-(2,5-dimethyl-6-(2H-1,2,3-triazol-2-yl)pyridin-3-yl)-5-(trifluoromethyl)-1H-pyrazole-4-carboxamide |
| 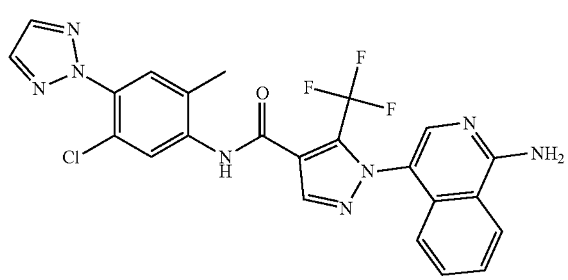 [SMILES: Cc1cc(-n2nccn2)c(Cl)cc1NC(=O)c1cnn(-c2cnc(N)c3ccccc23)c1C(F)(F)F] | 335 | 1-(1-aminoisoquinolin-4-yl)-N-(5-chloro-2-methyl-4-(2H-1,2,3-triazol-2-yl)phenyl)-5-(trifluoromethyl)-1H-pyrazole-4-carboxamide |
| 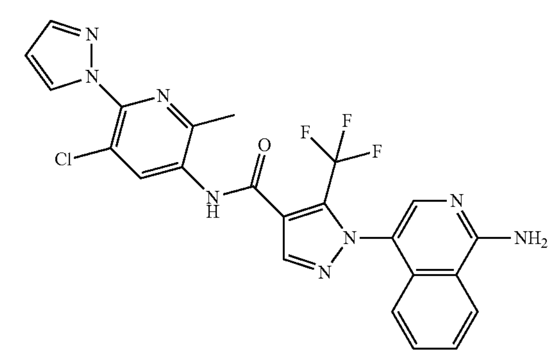 [SMILES: Cc1nc(-n2cccn2)c(Cl)cc1NC(=O)c1cnn(-c2cnc(N)c3ccccc23)c1C(F)(F)F] | 336 | 1-(1-aminoisoquinolin-4-yl)-N-(5-chloro-2-methyl-6-(1H-pyrazol-1-yl)pyridin-3-yl)-5-(trifluoromethyl)-1H-pyrazole-4-carboxamide |

TABLE 1-continued

| Structure | Cpd No. | Cpd Name |
|---|---|---|
| 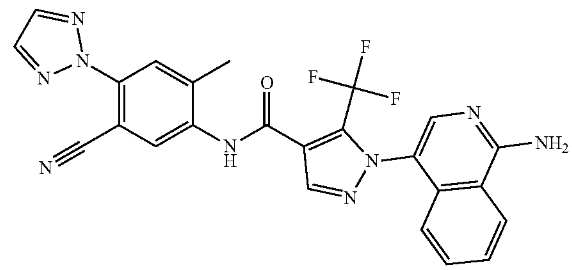 [SMILES: Cc1cc(-n2nccn2)c(C#N)cc1NC(=O)c1cnn(-c2cnc(N)c3ccccc23)c1C(F)(F)F] | 337 | 1-(1-aminoisoquinolin-4-yl)-N-(5-cyano-2-methyl-4-(2H-1,2,3-triazol-2-yl)phenyl)-5-(trifluoromethyl)-1H-pyrazole-4-carboxamide |
| 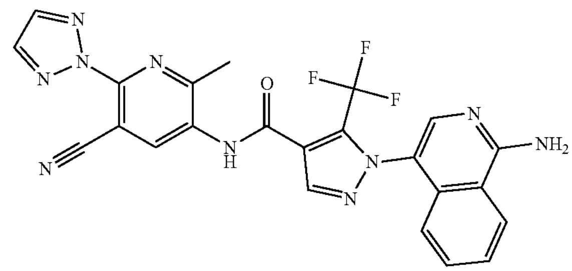 [SMILES: Cc1nc(-n2nccn2)c(C#N)cc1NC(=O)c1cnn(-c2cnc(N)c3ccccc23)c1C(F)(F)F] | 338 | 1-(1-aminoisoquinolin-4-yl)-N-(5-cyano-2-methyl-6-(2H-1,2,3-triazol-2-yl)pyridin-3-yl)-5-(trifluoromethyl)-1H-pyrazole-4-carboxamide |
| 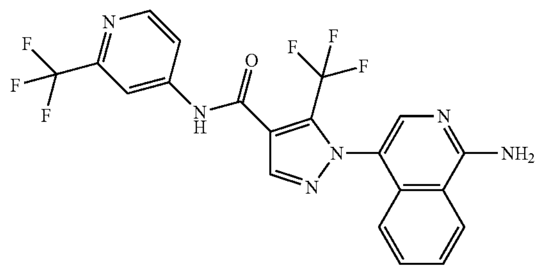 [SMILES: Nc1ncc(-n2ncc(C(=O)Nc3ccnc(C(F)(F)F)c3)c2C(F)(F)F)c2ccccc12] | 339 | 1-(1-aminoisoquinolin-4-yl)-5-(trifluoromethyl)-N-(2-(trifluoromethyl)pyridin-4-yl)-1H-pyrazole-4-carboxamide |
| 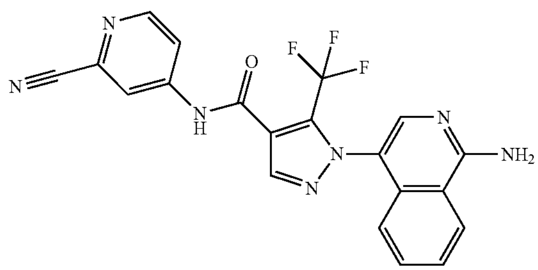 [SMILES: N#Cc1cc(NC(=O)c2cnn(-c3cnc(N)c4ccccc34)c2C(F)(F)F)ccn1] | 340 | 1-(1-aminoisoquinolin-4-yl)-N-(2-cyanopyridin-4-yl)-5-(trifluoromethyl)-1H-pyrazole-4-carboxamide |
| 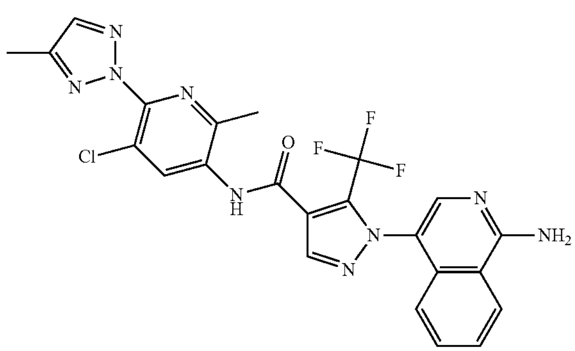 [SMILES: Cc1cnn(-c2nc(C)c(NC(=O)c3cnn(-c4cnc(N)c5ccccc45)c3C(F)(F)F)cc2Cl)n1] | 341 | 1-(1-aminoisoquinolin-4-yl)-N-(5-chloro-2-methyl-6-(4-methyl-2H-1,2,3-triazol-2-yl)pyridin-3-yl)-5-(trifluoromethyl)-1H-pyrazole-4-carboxamide |

TABLE 1-continued

| Structure | Cpd No. | Cpd Name |
|---|---|---|
| 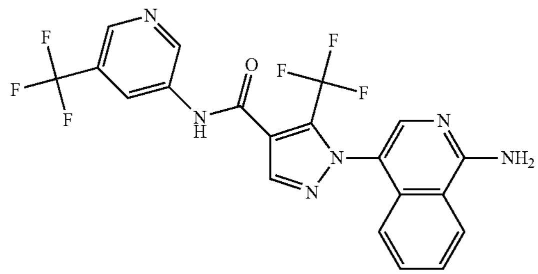 [SMILES: Nc1ncc(-n2ncc(C(=O)Nc3cncc(C(F)(F)F)c3)c2C(F)(F)F)c2ccccc12] | 342 | 1-(1-aminoisoquinolin-4-yl)-5-(trifluoromethyl)-N-(5-(trifluoromethyl)pyridin-3-yl)-1H-pyrazole-4-carboxamide |
| 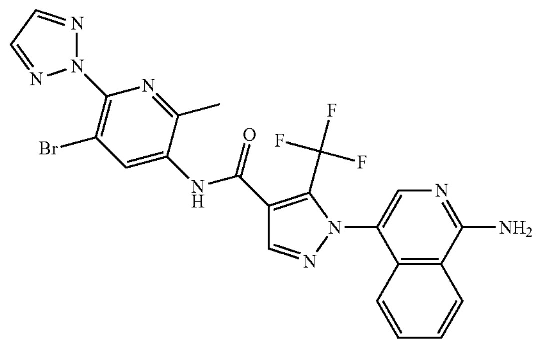 [SMILES: Cc1nc(-n2nccn2)c(Br)cc1NC(=O)c1cnn(-c2cnc(N)c3ccccc23)c1C(F)(F)F] | 343 | 1-(1-aminoisoquinolin-4-yl)-N-(5-bromo-2-methyl-6-(2H-1,2,3-triazol-2-yl)pyridin-3-yl)-5-(trifluoromethyl)-1H-pyrazole-4-carboxamide |
| 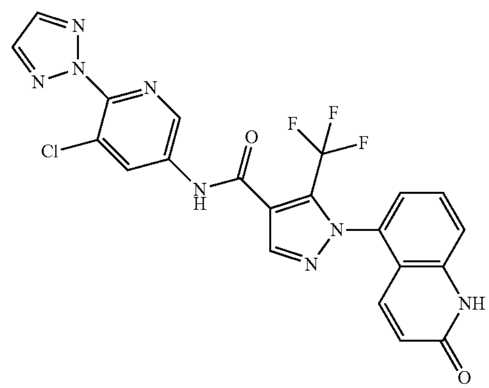 [SMILES: O=C(Nc1cnc(-n2nccn2)c(Cl)c1)c1cnn(-c2cccc3[nH]c(=O)ccc23)c1C(F)(F)F] | 344 | N-(5-chloro-6-(2H-1,2,3-triazol-2-yl)pyridin-3-yl)-1-(2-oxo-1,2-dihydroquinolin-5-yl)-5-(trifluoromethyl)-1H-pyrazole-4-carboxamide |
| 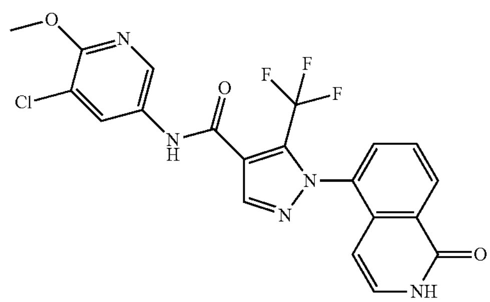 [SMILES: COc1ncc(NC(=O)c2cnn(-c3cccc4c(=O)[nH]ccc34)c2C(F)(F)F)cc1Cl] | 345 | N-(5-chloro-6-methoxypyridin-3-yl)-1-(1-oxo-1,2-dihydroisoquinolin-5-yl)-5-(trifluoromethyl)-1H-pyrazole-4-carboxamide |
| 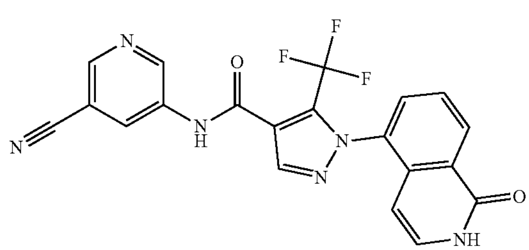 [SMILES: N#Cc1cncc(NC(=O)c2cnn(-c3cccc4c(=O)[nH]ccc34)c2C(F)(F)F)c1] | 346 | N-(5-cyanopyridin-3-yl)-1-(1-oxo-1,2-dihydroisoquinolin-5-yl)-5-(trifluoromethyl)-1H-pyrazole-4-carboxamide |

TABLE 1-continued

| Structure | Cpd No. | Cpd Name |
|---|---|---|
| 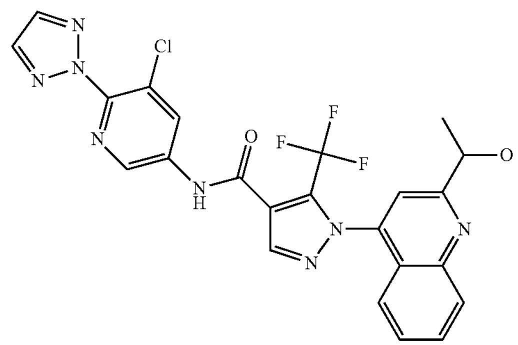 [SMILES: CC(O)c1cc(-n2ncc(C(=O)Nc3cnc(-n4nccn4)c(Cl)c3)c2C(F)(F)F)c2ccccc2n1] | 347 | N-(2-methylpyridin-4-yl)-1-(1-oxo-1,2-dihydroisoquinolin-5-yl)-5-(trifluoromethyl)-1H-pyrazole-4-carboxamide |
| 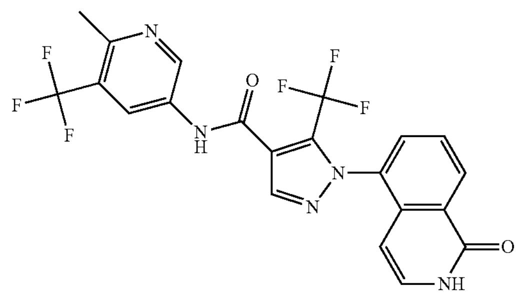 [SMILES: Cc1ncc(NC(=O)c2cnn(-c3cccc4c(=O)[nH]ccc34)c2C(F)(F)F)cc1C(F)(F)F] | 348 | N-(6-methyl-5-(trifluoromethyl)pyridin-3-yl)-1-(1-oxo-1,2-dihydroisoquinolin-5-yl)-5-(trifluoromethyl)-1H-pyrazol-4-carboxamide |
| 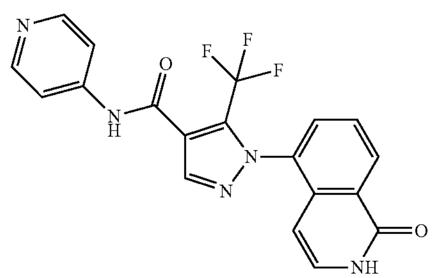 [SMILES: O=C(Nc1ccncc1)c1cnn(-c2cccc3c(=O)[nH]ccc23)c1C(F)(F)F] | 349 | 1-(1-oxo-1,2-dihydroisoquinolin-5-yl)-N-(pyridin-4-yl)-5-(trifluoromethyl)-1H-pyrazole-4-carboxamide |
| 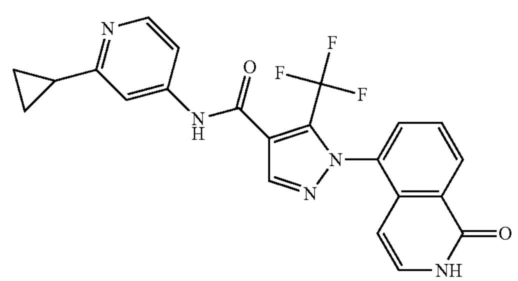 [SMILES: O=C(Nc1ccnc(C2CC2)c1)c1cnn(-c2cccc3c(=O)[nH]ccc23)c1C(F)(F)F] | 350 | N-(2-cyclopropylpyridin-4-yl)-1-(1-oxo-1,2-dihydroisoquinolin-5-yl)-5-(trifluoromethyl)-1H-pyrazole-4-carboxamide |
| 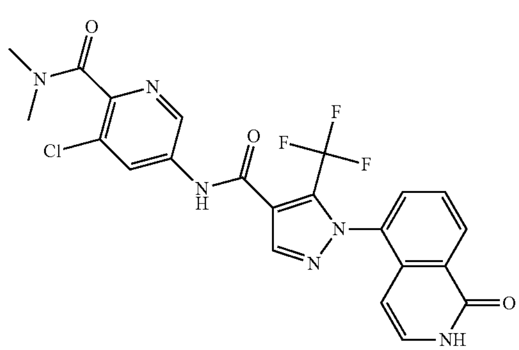 [SMILES: CN(C)C(=O)c1ncc(NC(=O)c2cnn(-c3cccc4c(=O)[nH]ccc34)c2C(F)(F)F)cc1Cl] | 351 | 3-chloro-N,N-dimethyl-5-(1-(1-oxo-1,2-dihydroisoquinolin-5-yl)-5-(trifluoromethyl)-1H-pyrazole-4-carboxamido)picolinamide |

TABLE 1-continued

| Structure | Cpd No. | Cpd Name |
|---|---|---|
| 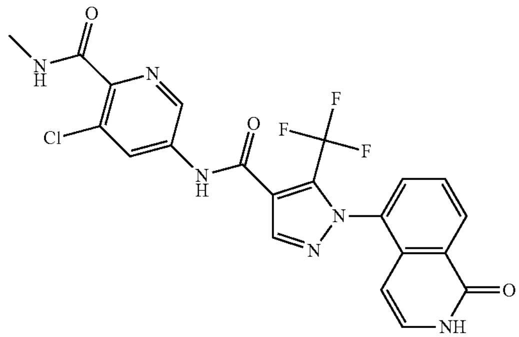 [SMILES: CNC(=O)c1ncc(NC(=O)c2cnn(-c3cccc4c(=O)[nH]ccc34)c2C(F)(F)F)cc1Cl] | 352 | 3-chloro-N-methyl-5-(1-(1-oxo-1,2-dihydroisoquinolin-5-yl)-5-(trifluoromethyl)-1H-pyrazole-4-carboxamido)picolinamide |
| 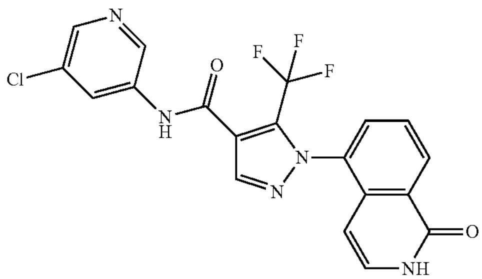 [SMILES: O=C(Nc1cncc(Cl)c1)c1cnn(-c2cccc3c(=O)[nH]ccc23)c1C(F)(F)F] | 353 | N-(5-chloropyridin-3-yl)-1-(1-oxo-1,2-dihydroisoquinolin-5-yl)-5-(trifluoromethyl)-1H-pyrazole-4-carboxamide |
| 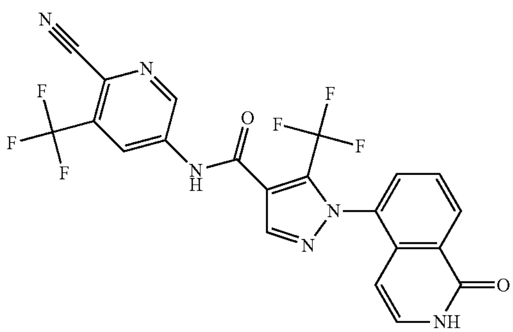 [SMILES: N#Cc1ncc(NC(=O)c2cnn(-c3cccc4c(=O)[nH]ccc34)c2C(F)(F)F)cc1C(F)(F)F] | 354 | N-(6-cyano-5-(trifluoromethyl)pyridin-3-yl)-1-(1-oxo-1,2-dihydroisoquinolin-5-yl)-5-(trifluoromethyl)-1H-pyrazole-4-carboxamide |
| 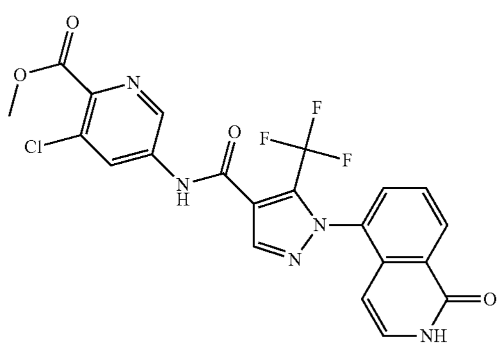 [SMILES: COC(=O)c1ncc(NC(=O)c2cnn(-c3cccc4c(=O)[nH]ccc34)c2C(F)(F)F)cc1Cl] | 355 | methyl 3-chloro-5-(1-(1-oxo-1,2-dihydroisoquinolin-5-yl)-5-(trifluoromethyl)-1H-pyrazole-4-carboxamido)picolinate |
| 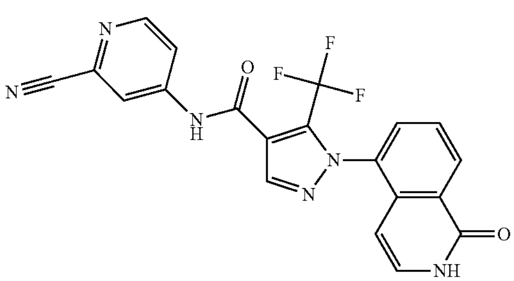 [SMILES: N#Cc1cc(NC(=O)c2cnn(-c3cccc4c(=O)[nH]ccc34)c2C(F)(F)F)ccn1] | 356 | N-(2-cyanopyridin-4-yl)-1-(1-oxo-1,2-dihydroisoquinolin-5-yl)-5-(trifluoromethyl)-1H-pyrazole-4-carboxamide |

TABLE 1-continued

| Structure | Cpd No. | Cpd Name |
|---|---|---|
| 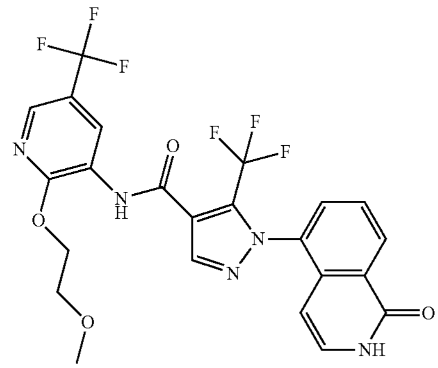 [SMILES: COCCOc1ncc(C(F)(F)F)cc1NC(=O)c1cnn(-c2cccc3c(=O)[nH]ccc23)c1C(F)(F)F] | 357 | N-(2-(2-methoxyethoxy)-5-(trifluoromethyl)pyridin-3-yl)-1-(1-oxo-1,2-dihydroisoquinolin-5-yl)-5-(trifluoromethyl)-1H-pyrazole-4-carboxamide |
| 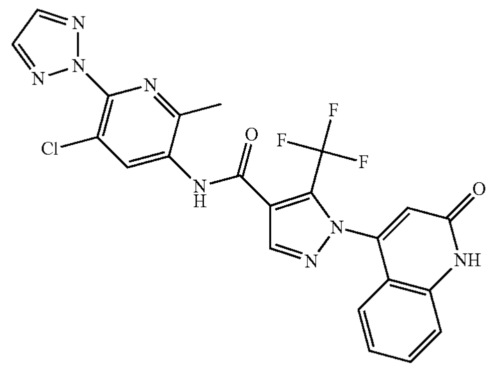 [SMILES: Cc1nc(-n2nccn2)c(Cl)cc1NC(=O)c1cnn(-c2cc(=O)[nH]c3ccccc23)c1C(F)(F)F] | 358 | N-(5-chloro-2-methyl-6-(2H-1,2,3-triazol-2-yl)pyridin-3-yl)-1-(2-oxo-1,2-dihydroquinolin-4-yl)-5-(trifluoromethyl)-1H-pyrazole-4-carboxamide |
| 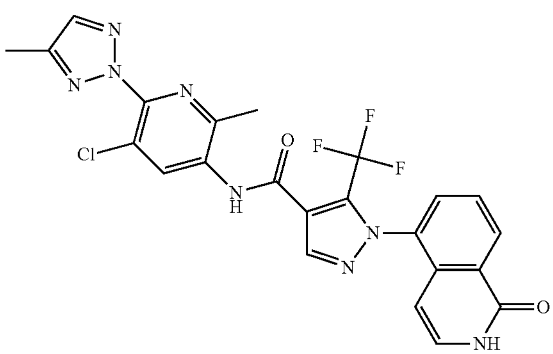 [SMILES: Cc1cnn(-c2nc(C)c(NC(=O)c3cnn(-c4cccc5c(=O)[nH]ccc45)c3C(F)(F)F)cc2Cl)n1] | 359 | N-(5-chloro-2-methyl-6-(4-methyl-2H-1,2,3-triazol-2-yl)pyridin-3-yl)-1-(1-oxo-1,2-dihydroisoquinolin-5-yl)-5-(trifluoromethyl)-1H-pyrazole-4-carboxamide |
| 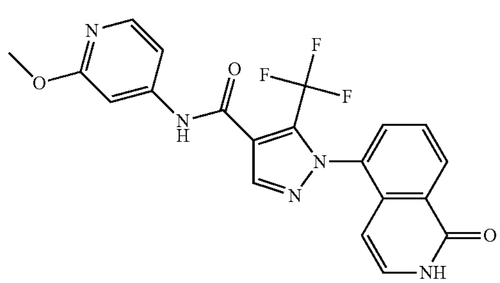 [SMILES: COc1cc(NC(=O)c2cnn(-c3cccc4c(=O)[nH]ccc34)c2C(F)(F)F)ccn1] | 360 | N-(2-methoxypyridin-4-yl)-1-(1-oxo-1,2-dihydroisoquinolin-5-yl)-5-(trifluoromethyl)-1H-pyrazole-4-carboxamide |

TABLE 1-continued

| Structure | Cpd No. | Cpd Name |
|---|---|---|
| 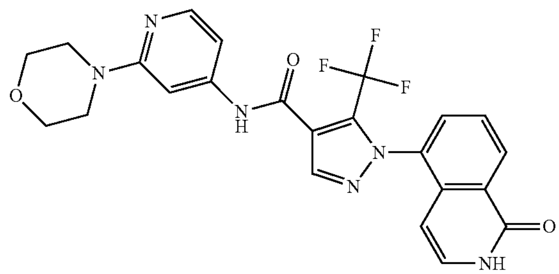 [SMILES: O=C(Nc1ccnc(N2CCOCC2)c1)c1cnn(-c2cccc3c(=O)[nH]ccc23)c1C(F)(F)F] | 361 | N-(2-morpholinopyridin-4-yl)-1-(1-oxo-1,2-dihydroisoquinolin-5-yl)-5-(trifluoromethyl)-1H-pyrazole-4-carboxamide |
| 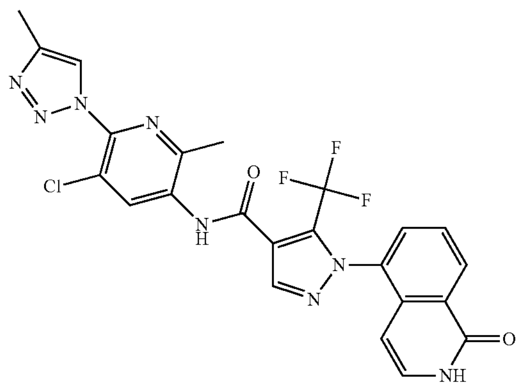 [SMILES: Cc1cn(-c2nc(C)c(NC(=O)c3cnn(-c4cccc5c(=O)[nH]ccc45)c3C(F)(F)F)cc2Cl)nn1] | 362 | N-(5-chloro-2-methyl-6-(4-methyl-1H-1,2,3-triazol-1-yl)pyridin-3-yl)-1-(1-oxo-1,2-dihydroisoquinolin-5-yl)-5-(trifluoromethyl)-1H-pyrazole-4-carboxamide |
| 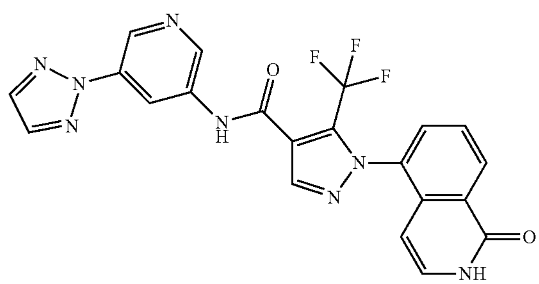 [SMILES: O=C(Nc1cncc(-n2nccn2)c1)c1cnn(-c2cccc3c(=O)[nH]ccc23)c1C(F)(F)F] | 363 | N-(5-(2H-1,2,3-triazol-2-yl)pyridin-3-yl)-1-(1-oxo-1,2-dihydroisoquinolin-5-yl)-5-(trifluoromethyl)-1H-pyrazole-4-carboxamide |
| 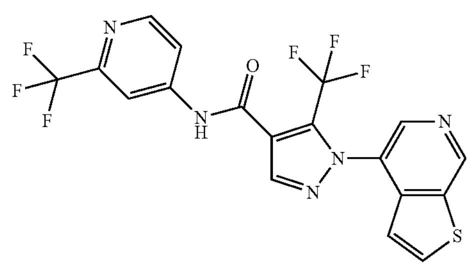 [SMILES: O=C(Nc1ccnc(C(F)(F)F)c1)c1cnn(-c2cncc3sccc23)c1C(F)(F)F] | 364 | 1-(thieno[2,3-c]pyridin-4-yl)-5-(trifluoromethyl)-N-(2-(trifluoromethyl)pyridin-4-yl)-1H-pyrazole-4-carboxamide |
| 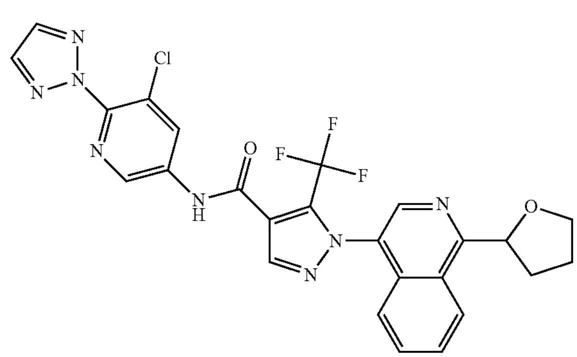 [SMILES: O=C(Nc1cnc(-n2nccn2)c(Cl)c1)c1cnn(-c2cnc(C3CCCO3)c3ccccc23)c1C(F)(F)F] | 365 | N-(5-chloro-6-(2H-1,2,3-triazol-2-yl)pyridin-3-yl)-1-(1-(tetrahydrofuran-2-yl)isoquinolin-4-yl)-5-(trifluoromethyl)-1H-pyrazole-4-carboxamide |

TABLE 1-continued

| Structure | Cpd No. | Cpd Name |
|---|---|---|
| 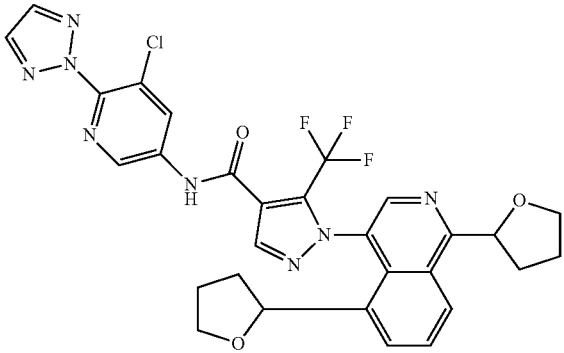 [SMILES: O=C(Nc1cnc(-n2nccn2)c(Cl)c1)c1cnn(-c2cnc(C3CCCO3)c3cccc(C4CCCO4)c23)c1C(F)(F)F] | 366 | 1-(1,5-bis(tetrahydrofuran-2-yl)isoquinolin-4-yl)-N-(5-chloro-6-(2H-1,2,3-triazol-2-yl)pyridin-3-yl)-5-(trifluoromethyl)-1H-pyrazole-4-carboxamide |
| 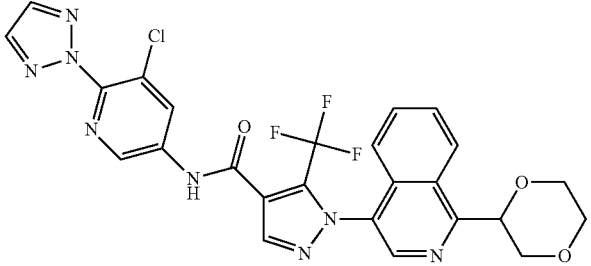 [SMILES: O=C(Nc1cnc(-n2nccn2)c(Cl)c1)c1cnn(-c2cnc(C3COCCO3)c3ccccc23)c1C(F)(F)F] | 367 | 1-(1-(1,4-dioxan-2-yl)isoquinolin-4-yl)-N-(5-chloro-6-(2H-1,2,3-triazol-2-yl)pyridin-3-yl)-5-(trifluoromethyl)-1H-pyrazole-4-carboxamide |
| 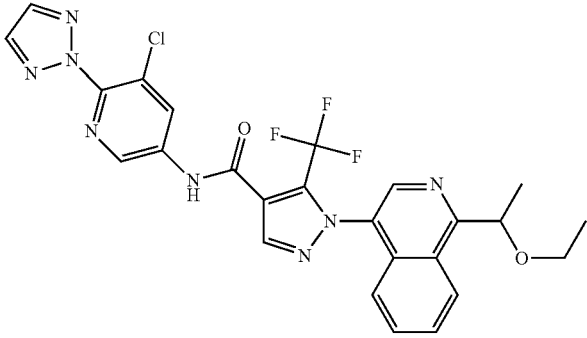 [SMILES: CCOC(C)c1ncc(-n2ncc(C(=O)Nc3cnc(-n4nccn4)c(Cl)c3)c2C(F)(F)F)c2ccccc12] | 368 | N-(5-chloro-6-(2H-1,2,3-triazol-2-yl)pyridin-3-yl)-1-(1-(1-ethoxyethyl)isoquinolin-4-yl)-5-(trifluoromethyl)-1H-pyrazole-4-carboxamide |
| 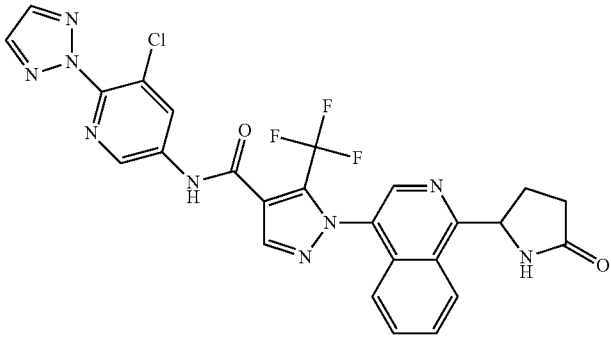 [SMILES: O=C1CCC(c2ncc(-n3ncc(C(=O)Nc4cnc(-n5nccn5)c(Cl)c4)c3C(F)(F)F)c3ccccc23)N1] | 369 | N-(5-chloro-6-(2H-1,2,3-triazol-2-yl)pyridin-3-yl)-1-(1-(5-oxopyrrolidin-2-yl)isoquinolin-4-yl)-5-(trifluoromethyl)-1H-pyrazole-4-carboxamide |

TABLE 1-continued

| Structure | Cpd No. | Cpd Name |
|---|---|---|
| 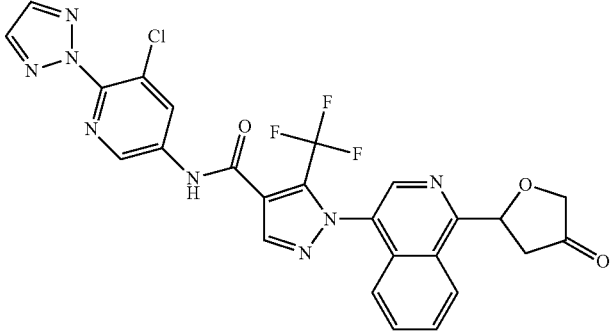 [SMILES: O=C1COC(c2ncc(-n3ncc(C(=O)Nc4cnc(-n5nccn5)c(Cl)c4)c3C(F)(F)F)c3ccccc23)C1] | 370 | N-(5-chloro-6-(2H-1,2,3-triazol-2-yl)pyridin-3-yl)-1-(1-(4-oxotetrahydrofuran-2-yl)isoquinolin-4-yl)-5-(trifluoromethyl)-1H-pyrazole-4-carboxamide |
| 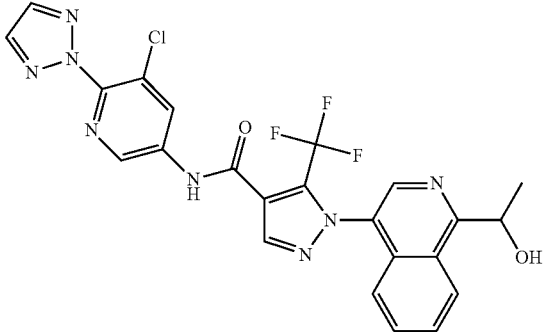 [SMILES: CC(O)c1ncc(-n2ncc(C(=O)Nc3cnc(-n4nccn4)c(Cl)c3)c2C(F)(F)F)c2ccccc12] | 371 | N-(5-chloro-6-(2H-1,2,3-triazol-2-yl)pyridin-3-yl)-1-(1-(1-hydroxyethyl)isoquinolin-4-yl)-5-(trifluoromethyl)-1H-pyrazole-4-carboxamide |
| 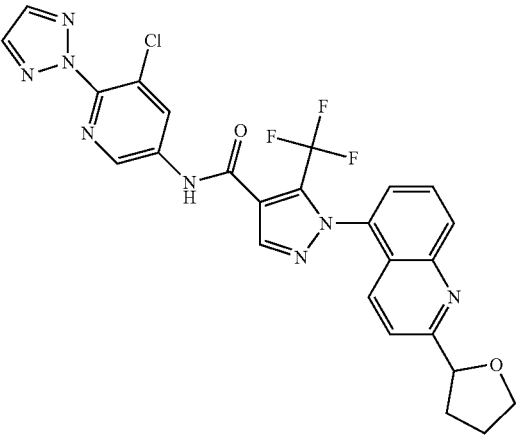 [SMILES: O=C(Nc1cnc(-n2nccn2)c(Cl)c1)c1cnn(-c2cccc3nc(C4CCCO4)ccc23)c1C(F)(F)F] | 372 | N-(5-chloro-6-(2H-1,2,3-triazol-2-yl)pyridin-3-yl)-1-(2-(tetrahydrofuran-2-yl)quinolin-5-yl)-5-(trifluoromethyl)-1H-pyrazole-4-carboxamide |
| 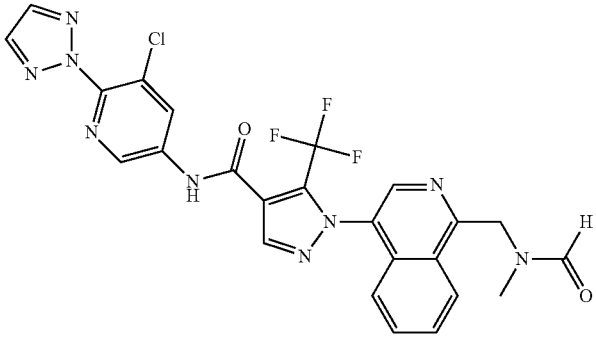 [SMILES: CN(C=O)Cc1ncc(-n2ncc(C(=O)Nc3cnc(-n4nccn4)c(Cl)c3)c2C(F)(F)F)c2ccccc12] | 373 | N-(5-chloro-6-(2H-1,2,3-triazol-2-yl)pyridin-3-yl)-1-(1-((N-methylformamido)methyl)isoquinolin-4-yl)-5-(trifluoromethyl)-1H-pyrazole-4-carboxamide |

TABLE 1-continued

| Structure | Cpd No. | Cpd Name |
|---|---|---|
| 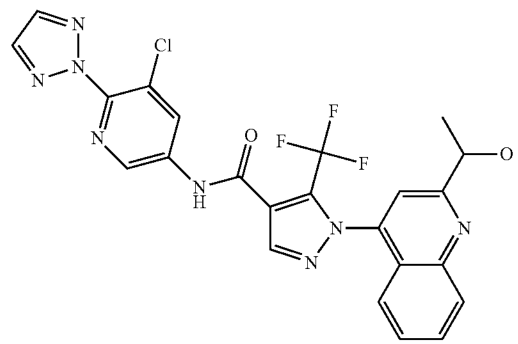 [SMILES: CC(O)c1cc(-n2ncc(C(=O)Nc3cnc(-n4nccn4)c(Cl)c3)c2C(F)(F)F)c2ccccc2n1] | 374 | N-(5-chloro-6-(2H-1,2,3-triazol-2-yl)pyridin-3-yl)-1-(2-(1-hydroxyethyl)quinolin-4-yl)-5-(trifluoromethyl)-1H-pyrazole-4-carboxamide |
| 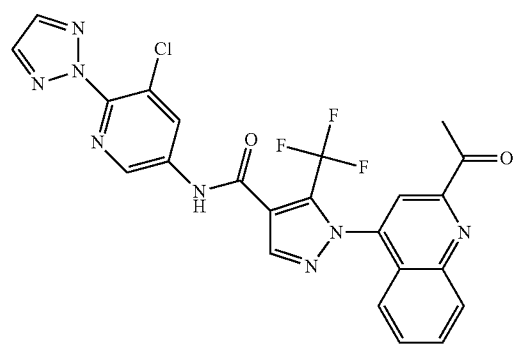 [SMILES: CC(=O)c1cc(-n2ncc(C(=O)Nc3cnc(-n4nccn4)c(Cl)c3)c2C(F)(F)F)c2ccccc2n1] | 375 | 1-(2-acetylquinolin-4-yl)-N-(5-chloro-6-(2H-1,2,3-triazol-2-yl)pyridin-3-yl)-5-(trifluoromethyl)-1H-pyrazole-4-carboxamide |
| 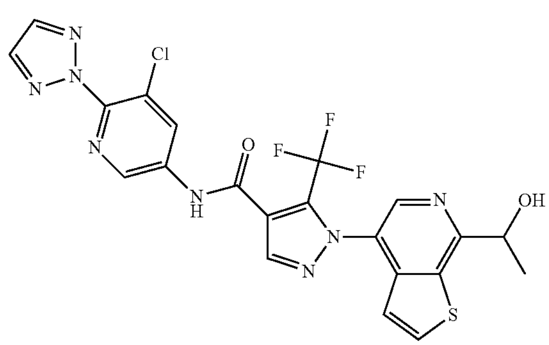 [SMILES: CC(O)c1ncc(-n2ncc(C(=O)Nc3cnc(-n4nccn4)c(Cl)c3)c2C(F)(F)F)c2ccsc12] | 376 | N-(5-chloro-6-(2H-1,2,3-triazol-2-yl)pyridin-3-yl)-1-(7-(1-hydroxyethyl)thieno[2,3-c]pyridin-4-yl)-5-(trifluoromethyl)-1H-pyrazole-4-carboxamide |
| 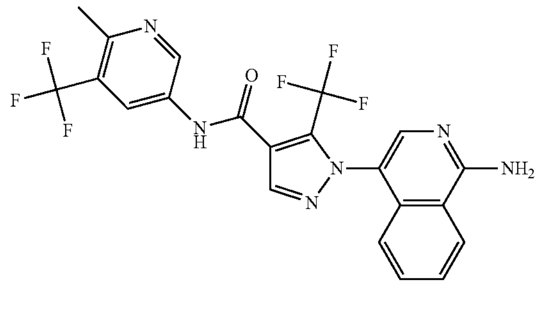 [SMILES: Cc1ncc(NC(=O)c2cnn(-c3cnc(N)c4ccccc34)c2C(F)(F)F)cc1C(F)(F)F] | 377 | 1-(1-aminoisoquinolin-4-yl)-N-(6-methyl-5-(trifluoromethyl)pyridin-3-yl)-5-(trifluoromethyl)-1H-pyrazole-4-carboxamide |

TABLE 1-continued

| Structure | Cpd No. | Cpd Name |
|---|---|---|
| 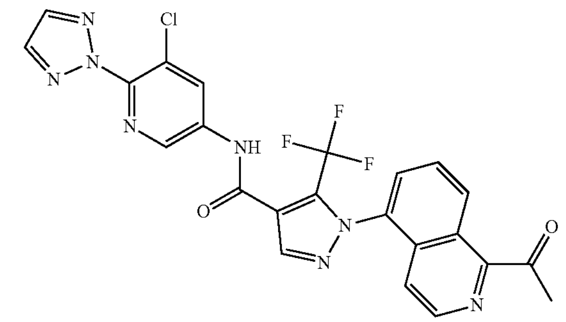 [SMILES: CC(=O)c1nccc2c(-n3ncc(C(=O)Nc4cnc(-n5nccn5)c(Cl)c4)c3C(F)(F)F)cccc12] | 378 | 1-(1-acetylisoquinolin-5-yl)-N-(5-chloro-6-(2H-1,2,3-triazol-2-yl)pyridin-3-yl)-5-(trifluoromethyl)-1H-pyrazole-4-carboxamide |
| 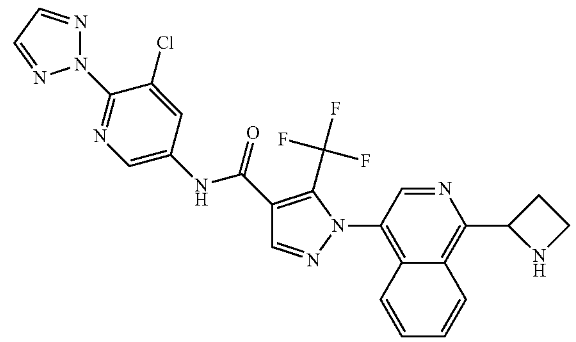 [SMILES: O=C(Nc1cnc(-n2nccn2)c(Cl)c1)c1cnn(-c2cnc(C3CCN3)c3ccccc23)c1C(F)(F)F] | 379 | 1-(1-(azetidin-2-yl)isoquinolin-4-yl)-N-(5-chloro-6-(2H-1,2,3-triazol-2-yl)pyridin-3-yl)-5-(trifluoromethyl)-1H-pyrazole-4-carboxamide |
| 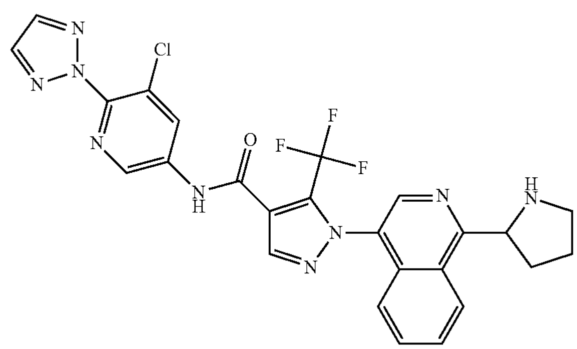 [SMILES: O=C(Nc1cnc(-n2nccn2)c(Cl)c1)c1cnn(-c2cnc(C3CCCN3)c3ccccc23)c1C(F)(F)F] | 380 | N-(5-chloro-6-(2H-1,2,3-triazol-2-yl)pyridin-3-yl)-1-(1-(pyrrolidin-2-yl)isoquinolin-4-yl)-5-(trifluoromethyl)-1H-pyrazole-4-carboxamide |
| 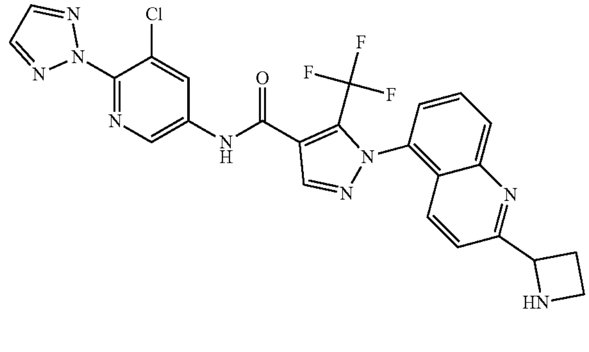 [SMILES: O=C(Nc1cnc(-n2nccn2)c(Cl)c1)c1cnn(-c2cccc3nc(C4CCN4)ccc23)c1C(F)(F)F] | 381 | 1-(2-(azetidin-2-yl)quinolin-5-yl)-N-(5-chloro-6-(2H-1,2,3-triazol-2-yl)pyridin-3-yl)-5-(trifluoromethyl)-1H-pyrazole-4-carboxamide |

TABLE 1-continued

| Structure | Cpd No. | Cpd Name |
|---|---|---|
| 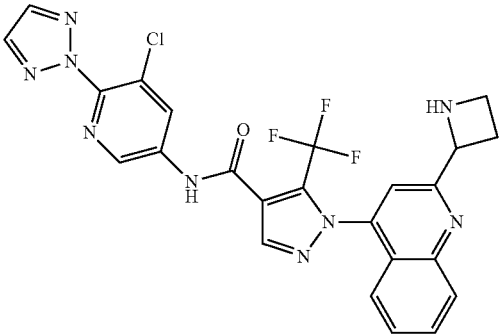 [SMILES: O=C(Nc1cnc(-n2nccn2)c(Cl)c1)c1cnn(-c2cc(C3CCN3)nc3ccccc23)c1C(F)(F)F] | 382 | 1-(2-(azetidin-2-yl)quinolin-4-yl)-N-(5-chloro-6-(2H-1,2,3-triazol-2-yl)pyridin-3-yl)-5-(trifluoromethyl)-1H-pyrazole-4-carboxamide |
| 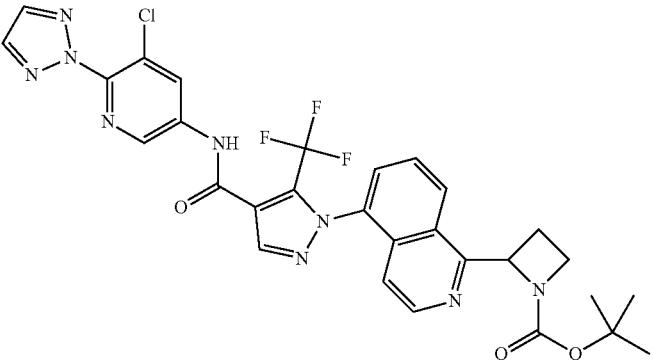 [SMILES: CC(C)(C)OC(=O)N1CCC1c1nccc2c(-n3ncc(C(=O)Nc4cnc(-n5nccn5)c(Cl)c4)c3C(F)(F)F)cccc12] | 383 | tert-butyl 2-(5-(4-((5-chloro-6-(2H-1,2,3-triazol-2-yl)pyridin-3-yl)carbamoyl)-5-(trifluoromethyl)-1H-pyrazol-1-yl)isoquinolin-1-yl)azetidine-1-carboxylate |
| 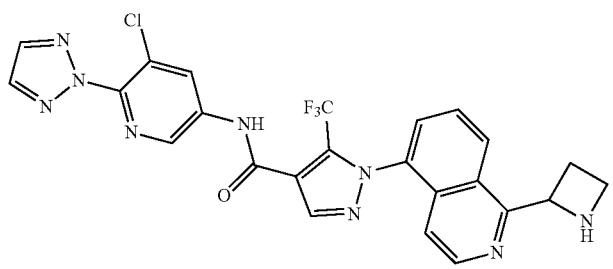 [SMILES: O=C(Nc1cnc(-n2nccn2)c(Cl)c1)c1cnn(-c2cccc3c(C4CCN4)nccc23)c1C(F)(F)F] | 384 | 1-(1-(azetidin-2-yl)isoquinolin-5-yl)-N-(5-chloro-6-(2H-1,2,3-triazol-2-yl)pyridin-3-yl)-5-(trifluoromethyl)-1H-pyrazole-4-carboxamide |
| 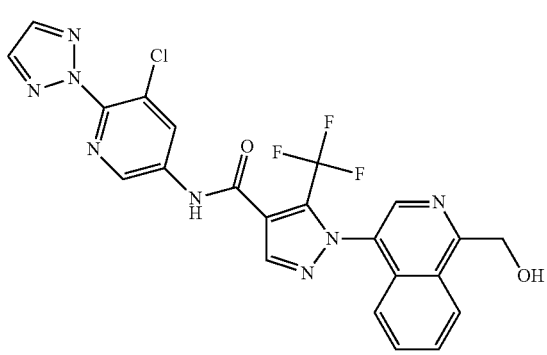 [SMILES: O=C(Nc1cnc(-n2nccn2)c(Cl)c1)c1cnn(-c2cnc(CO)c3ccccc23)c1C(F)(F)F] | 385 | N-(5-chloro-6-(2H-1,2,3-triazol-2-yl)pyridin-3-yl)-1-(1-(hydroxymethyl)isoquinolin-4-yl)-5-(trifluoromethyl)-1H-pyrazole-4-carboxamide |

TABLE 1-continued

| Structure | Cpd No. | Cpd Name |
|---|---|---|
| 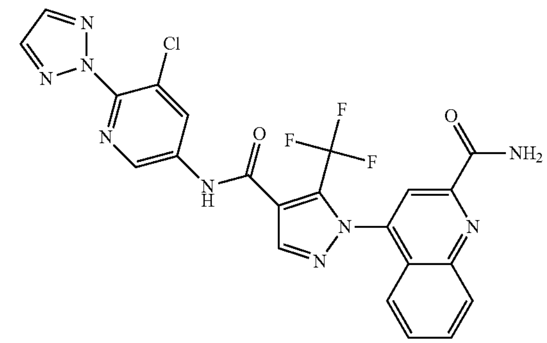 [SMILES: NC(=O)c1cc(-n2ncc(C(=O)Nc3cnc(-n4nccn4)c(Cl)c3)c2C(F)(F)F)c2ccccc2n1] | 386 | 4-(4-((5-chloro-6-(2H-1,2,3-triazol-2-yl)pyridin-3-yl)carbamoyl)-5-(trifluoromethyl)-1H-pyrazol-1-yl)quinoline-2-carboxamide |
| 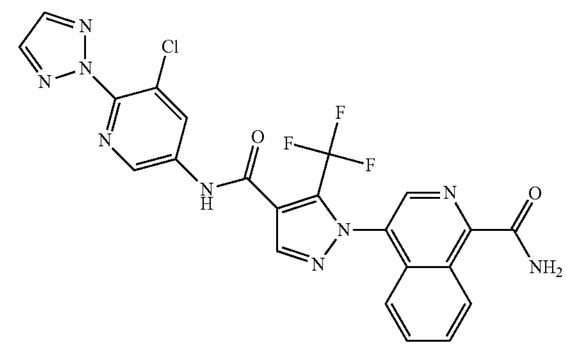 [SMILES: NC(=O)c1ncc(-n2ncc(C(=O)Nc3cnc(-n4nccn4)c(Cl)c3)c2C(F)(F)F)c2ccccc12] | 387 | 4-(4-((5-chloro-6-(2H-1,2,3-triazol-2-yl)pyridin-3-yl)carbamoyl)-5-(trifluoromethyl)-1H-pyrazol-1-yl)isoquinoline-1-carboxamide |
| 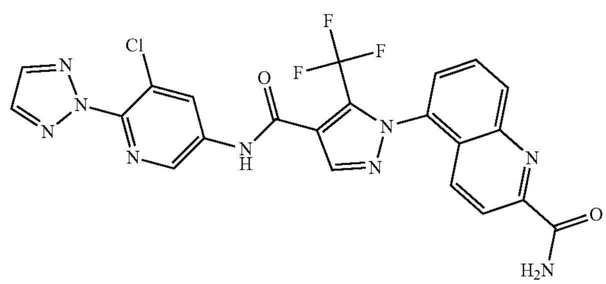 [SMILES: NC(=O)c1ccc2c(-n3ncc(C(=O)Nc4cnc(-n5nccn5)c(Cl)c4)c3C(F)(F)F)cccc2n1] | 388 | 5-(4-((5-chloro-6-(2H-1,2,3-triazol-2-yl)pyridin-3-yl)carbamoyl)-5-(trifluoromethyl)-1H-pyrazol-1-yl)quinoline-2-carboxamide |
| 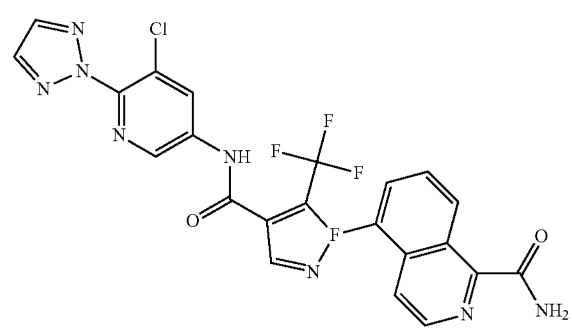 | 389 | 5-(4-((5-chloro-6-(2H-1,2,3-triazol-2-yl)pyridin-3-yl)carbamoyl)-5-(trifluoromethyl)-1H-pyrazol-1-yl)isoquinoline-1-carboxamide |

TABLE 1-continued

| Structure | Cpd No. | Cpd Name |
|---|---|---|
| 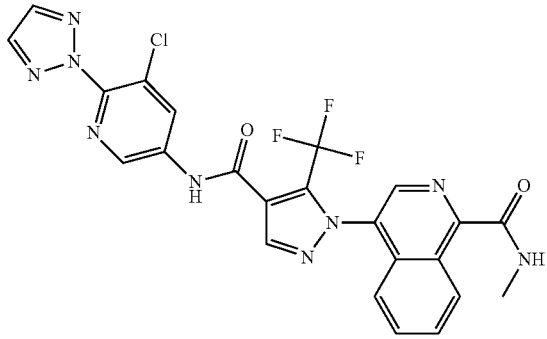 [SMILES: CNC(=O)c1ncc(-n2ncc(C(=O)Nc3cnc(-n4nccn4)c(Cl)c3)c2C(F)(F)F)c2ccccc12] | 390 | 4-(4-((5-chloro-6-(2H-1,2,3-triazol-2-yl)pyridin-3-yl)carbamoyl)-5-(trifluoromethyl)-1H-pyrazol-1-yl)-N-methylisoquinoline-1-carboxamide |
| 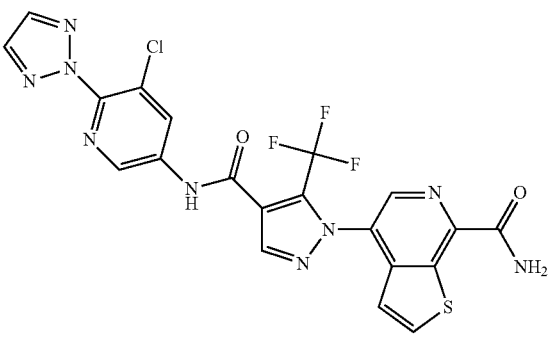 [SMILES: NC(=O)c1ncc(-n2ncc(C(=O)Nc3cnc(-n4nccn4)c(Cl)c3)c2C(F)(F)F)c2ccsc12] | 391 | 4-(4-((5-chloro-6-(2H-1,2,3-triazol-2-yl)pyridin-3-yl)carbamoyl)-5-(trifluoromethyl)-1H-pyrazol-1-yl)thieno[2,3-c]pyridine-7-carboxamide |
| 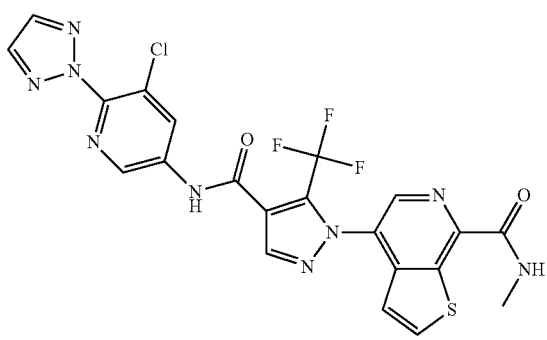 [SMILES: CNC(=O)c1ncc(-n2ncc(C(=O)Nc3cnc(-n4nccn4)c(Cl)c3)c2C(F)(F)F)c2ccsc12] | 392 | 4-(4-((5-chloro-6-(2H-1,2,3-triazol-2-yl)pyridin-3-yl)carbamoyl)-5-(trifluoromethyl)-1H-pyrazol-1-yl)-N-methylthieno[2,3-c]pyridine-7-carboxamide |
| 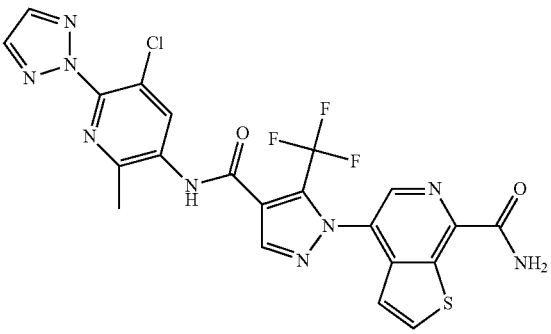 [SMILES: Cc1nc(-n2nccn2)c(Cl)cc1NC(=O)c1cnn(-c2cnc(C(N)=O)c3sccc23)c1C(F)(F)F] | 393 | 4-(4-((5-chloro-2-methyl-6-(2H-1,2,3-triazol-2-yl)pyridin-3-yl)carbamoyl)-5-(trifluoromethyl)-1H-pyrazol-1-yl)thieno[2,3-c]pyridine-7-carboxamide |

TABLE 1-continued

| Structure | Cpd No. | Cpd Name |
|---|---|---|
| 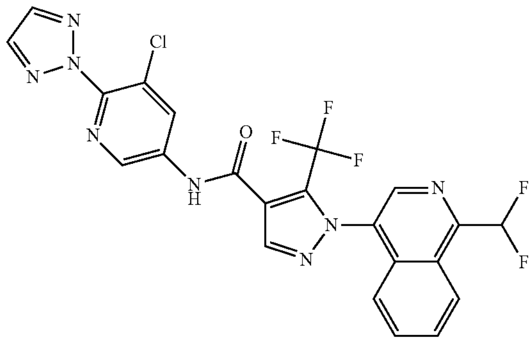 [SMILES: O=C(Nc1cnc(-n2nccn2)c(Cl)c1)c1cnn(-c2cnc(C(F)F)c3ccccc23)c1C(F)(F)F] | 394 | N-(5-chloro-6-(2H-1,2,3-triazol-2-yl)pyridin-3-yl)-1-(1-(difluoromethyl)isoquinolin-4-yl)-5-(trifluoromethyl)-1H-pyrazole-4-carboxamide |
| 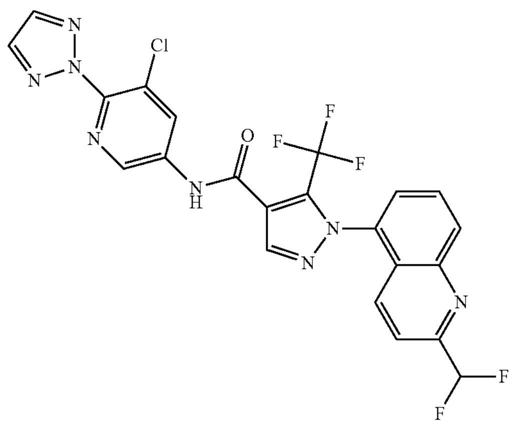 [SMILES: O=C(Nc1cnc(-n2nccn2)c(Cl)c1)c1cnn(-c2cccc3nc(C(F)F)ccc23)c1C(F)(F)F] | 395 | N-(5-chloro-6-(2H-1,2,3-triazol-2-yl)pyridin-3-yl)-1-(2-(difluoromethyl)quinolin-5-yl)-5-(trifluoromethyl)-1H-pyrazole-4-carboxamide |
| 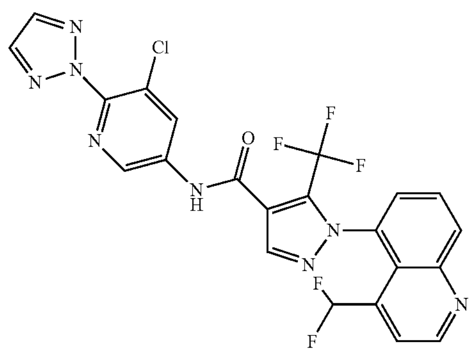 [SMILES: O=C(Nc1cnc(-n2nccn2)c(Cl)c1)c1cnn(-c2cccc3nccc(C(F)F)c23)c1C(F)(F)F] | 396 | N-(5-chloro-6-(2H-1,2,3-triazol-2-yl)pyridin-3-yl)-1-(4-(difluoromethyl)quinolin-5-yl)-5-(trifluoromethyl)-1H-pyrazole-4-carboxamide |
| 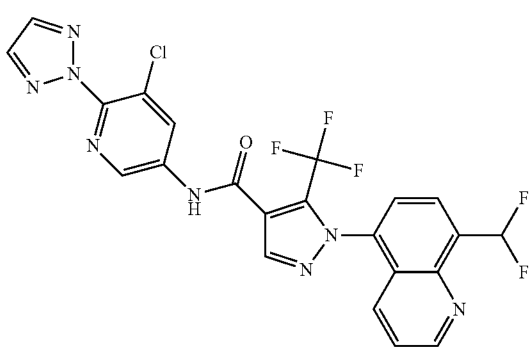 [SMILES: O=C(Nc1cnc(-n2nccn2)c(Cl)c1)c1cnn(-c2ccc(C(F)F)c3ncccc23)c1C(F)(F)F] | 397 | N-(5-chloro-6-(2H-1,2,3-triazol-2-yl)pyridin-3-yl)-1-(8-(difluoromethyl)quinolin-5-yl)-5-(trifluoromethyl)-1H-pyrazole-4-carboxamide |

TABLE 1-continued

| Structure | Cpd No. | Cpd Name |
|---|---|---|
| 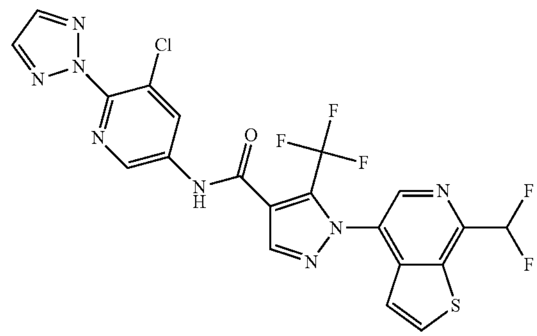 [SMILES: O=C(Nc1cnc(-n2nccn2)c(Cl)c1)c1cnn(-c2cnc(C(F)F)c3sccc23)c1C(F)(F)F] | 398 | N-(5-chloro-6-(2H-1,2,3-triazol-2-yl)pyridin-3-yl)-1-(7-(difluoromethyl)thieno[2,3-c]pyridin-4-yl)-5-(trifluoromethyl)-1H-pyrazole-4-carboxamide |
| 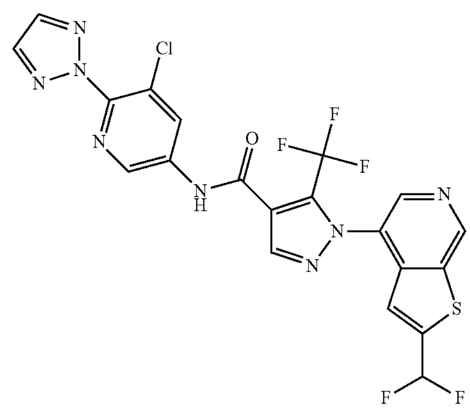 [SMILES: O=C(Nc1cnc(-n2nccn2)c(Cl)c1)c1cnn(-c2cncc3sc(C(F)F)cc23)c1C(F)(F)F] | 399 | N-(5-chloro-6-(2H-1,2,3-triazol-2-yl)pyridin-3-yl)-1-(2-(difluoromethyl)thieno[2,3-c]pyridin-4-yl)-5-(trifluoromethyl)-1H-pyrazole-4-carboxamide |
| 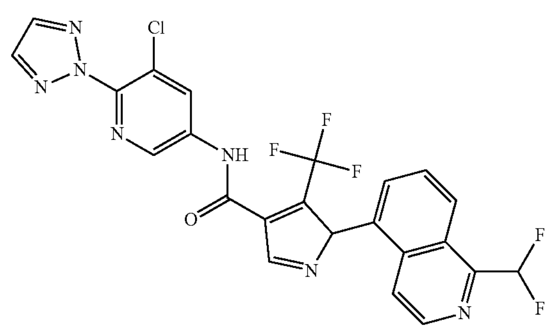 [SMILES: O=C(Nc1cnc(-n2nccn2)c(Cl)c1)C1=C(C(F)(F)F)C(c2cccc3c(C(F)F)nccc23)N=C1] | 400 | N-(5-chloro-6-(2H-1,2,3-triazol-2-yl)pyridin-3-yl)-1-(1-(difluoromethyl)isoquinolin-5-yl)-5-(trifluoromethyl)-1H-pyrazole-4-carboxamid |
| 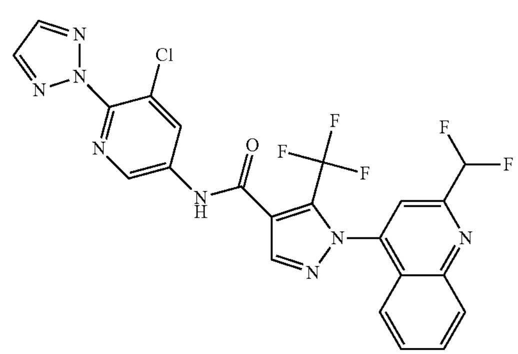 [SMILES: O=C(Nc1cnc(-n2nccn2)c(Cl)c1)c1cnn(-c2cc(C(F)F)nc3ccccc23)c1C(F)(F)F] | 401 | N-(5-chloro-6-(2H-1,2,3-triazol-2-yl)pyridin-3-yl)-1-(2-(difluoromethyl)quinolin-4-yl)-5-(trifluoromethyl)-1H-pyrazole-4-carboxamide |

TABLE 1-continued

| Structure | Cpd No. | Cpd Name |
|---|---|---|
| 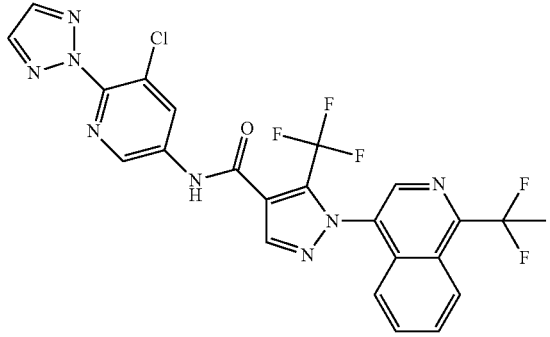 [SMILES: CC(F)(F)c1ncc(-n2ncc(C(=O)Nc3cnc(-n4nccn4)c(Cl)c3)c2C(F)(F)F)c2ccccc12] | 402 | N-(5-chloro-6-(2H-1,2,3-triazol-2-yl)pyridin-3-yl)-1-(1-(1,1-difluoroethyl)isoquinolin-4-yl)-5-(trifluoromethyl)-1H-pyrazole-4-carboxamide |
| 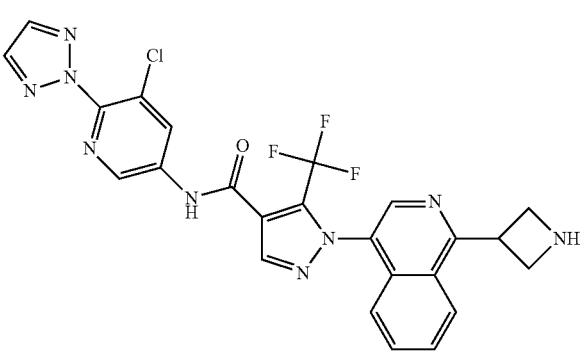 [SMILES: O=C(Nc1cnc(-n2nccn2)c(Cl)c1)c1cnn(-c2cnc(C3CNC3)c3ccccc23)c1C(F)(F)F] | 403 | 1-(1-(azetidin-3-yl)isoquinolin-4-yl)-N-(5-chloro-6-(2H-1,2,3-triazol-2-yl)pyridin-3-yl)-5-(trifluoromethyl)-1H-pyrazole-4-carboxamide |
| 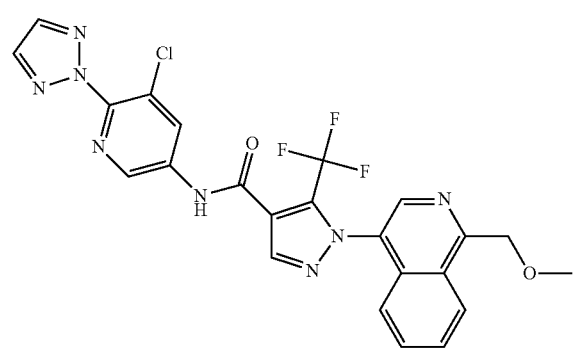 [SMILES: COCc1ncc(-n2ncc(C(=O)Nc3cnc(-n4nccn4)c(Cl)c3)c2C(F)(F)F)c2ccccc12] | 404 | N-(5-chloro-6-(2H-1,2,3-triazol-2-yl)pyridin-3-yl)-1-(1-(methoxymethyl)isoquinolin-4-yl)-5-(trifluoromethyl)-1H-pyrazole-4-carboxamide |
| 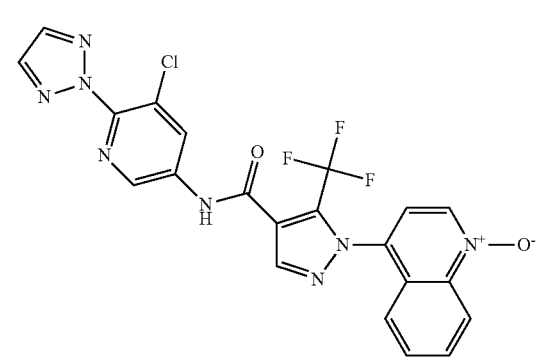 [SMILES: O=C(Nc1cnc(-n2nccn2)c(Cl)c1)c1cnn(-c2cc[n+]([O-])c3ccccc23)c1C(F)(F)F] | 405 | 4-(4-((5-chloro-6-(2H-1,2,3-triazol-2-yl)pyridin-3-yl)carbamoyl)-5-(trifluoromethyl)-1H-pyrazol-1-yl)quinoline 1-oxide |

TABLE 1-continued

| Structure | Cpd No. | Cpd Name |
|---|---|---|
| 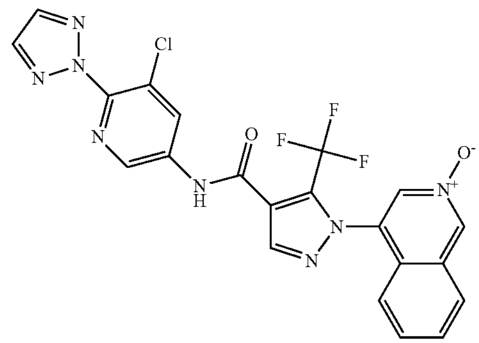 [SMILES: O=C(Nc1cnc(-n2nccn2)c(Cl)c1)c1cnn(-c2c[n+]([O-])cc3ccccc23)c1C(F)(F)F] | 406 | 4-(4-((5-chloro-6-(2H-1,2,3-triazol-2-yl)pyridin-3-yl)carbamoyl)-5-(trifluoromethyl)-1H-pyrazol-1-yl)isoquinoline 2-oxide |
| 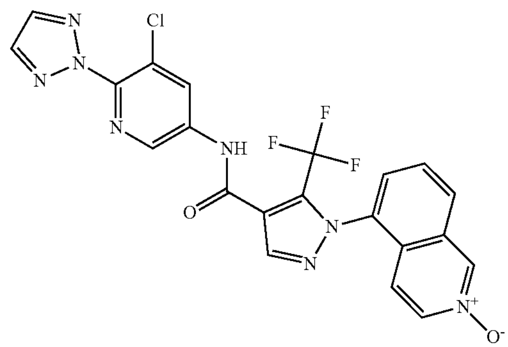 [SMILES: O=C(Nc1cnc(-n2nccn2)c(Cl)c1)c1cnn(-c2cccc3c[n+]([O-])ccc23)c1C(F)(F)F] | 407 | 5-(4-((5-chloro-6-(2H-1,2,3-triazol-2-yl)pyridin-3-yl)carbamoyl)-5-(trifluoromethyl)-1H-pyrazol-1-yl)isoquinoline 2-oxide |
| 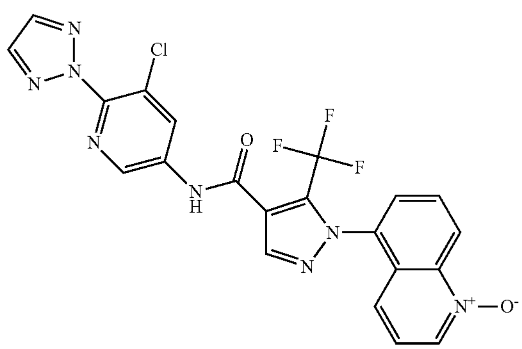 [SMILES: O=C(Nc1cnc(-n2nccn2)c(Cl)c1)c1cnn(-c2cccc3c2ccc[n+]3[O-])c1C(F)(F)F] | 408 | 5-(4-((5-chloro-6-(2H-1,2,3-triazol-2-yl)pyridin-3-yl)carbamoyl)-5-(trifluoromethyl)-1H-pyrazol-1-yl)quinoline 1-oxide |
| 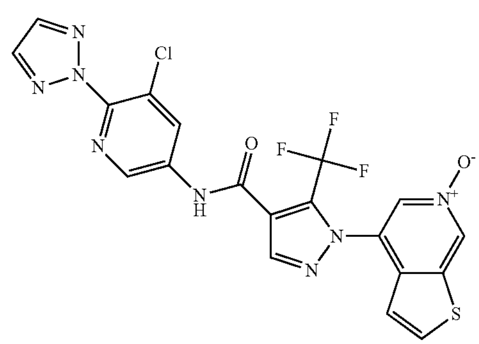 [SMILES: O=C(Nc1cnc(-n2nccn2)c(Cl)c1)c1cnn(-c2c[n+]([O-])cc3sccc23)c1C(F)(F)F] | 409 | 4-(4-((5-chloro-6-(2H-1,2,3-triazol-2-yl)pyridin-3-yl)carbamoyl)-5-(trifluoromethyl)-1H-pyrazol-1-yl)thieno[2,3-c]pyridine 6-oxide |

TABLE 1-continued

| Structure | Cpd No. | Cpd Name |
|---|---|---|
| 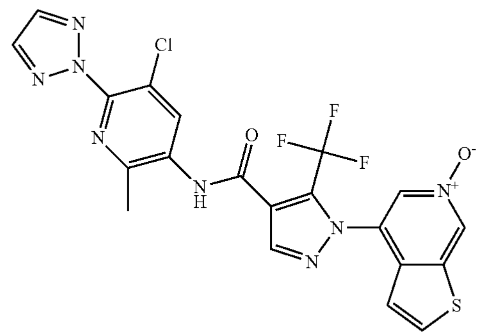 [SMILES: Cc1nc(-n2nccn2)c(Cl)cc1NC(=O)c1cnn(-c2c[n+]([O-])cc3sccc23)c1C(F)(F)F] | 410 | 4-(4-((5-chloro-2-methyl-6-(2H-1,2,3-triazol-2-yl)pyridin-3-yl)carbamoyl)-5-(trifluoromethyl)-1H-pyrazol-1-yl)thieno[2,3-c]pyridine 6-oxide |
| 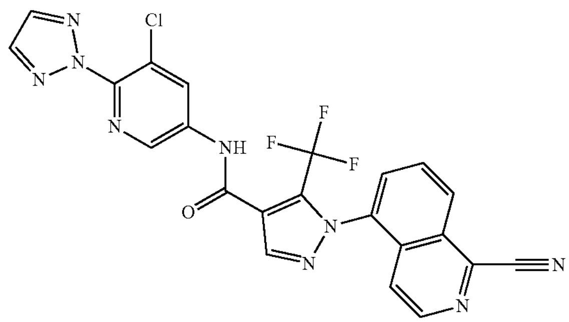 [SMILES: N#Cc1nccc2c(-n3ncc(C(=O)Nc4cnc(-n5nccn5)c(Cl)c4)c3C(F)(F)F)cccc12] | 411 | N-(5-chloro-6-(2H-1,2,3-triazol-2-yl)pyridin-3-yl)-1-(1-cyanoisoquinolin-5-yl)-5-(trifluoromethyl)-1H-pyrazole-4-carboxamide |
| 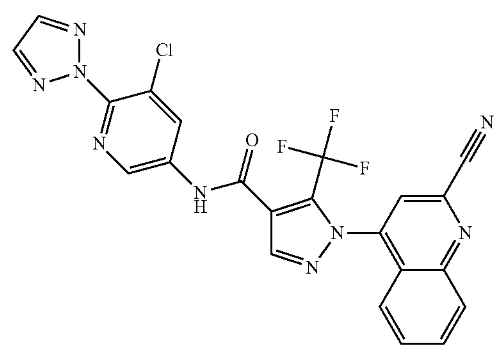 [SMILES: N#Cc1cc(-n2ncc(C(=O)Nc3cnc(-n4nccn4)c(Cl)c3)c2C(F)(F)F)c2ccccc2n1] | 412 | N-(5-chloro-6-(2H-1,2,3-triazol-2-yl)pyridin-3-yl)-1-(2-cyanoquinolin-4-yl)-5-(trifluoromethyl)-1H-pyrazole-4-carboxamide |
| 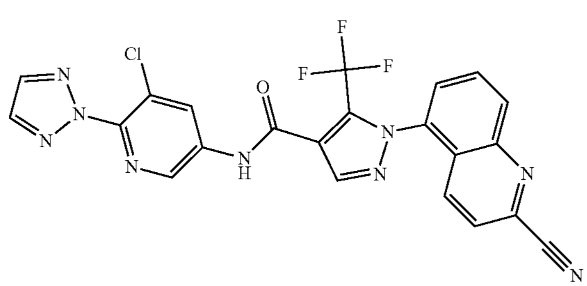 [SMILES: N#Cc1ccc2c(-n3ncc(C(=O)Nc4cnc(-n5nccn5)c(Cl)c4)c3C(F)(F)F)cccc2n1] | 413 | N-(5-chloro-6-(2H-1,2,3-triazol-2-yl)pyridin-3-yl)-1-(2-cyanoquinolin-5-yl)-5-(trifluoromethyl)-1H-pyrazole-4-carboxamide |

TABLE 1-continued

| Structure | Cpd No. | Cpd Name |
|---|---|---|
| 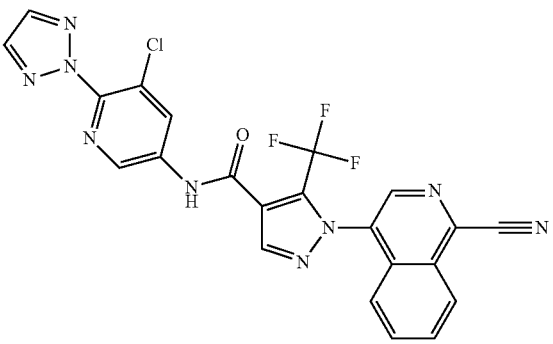 [SMILES: N#Cc1ncc(-n2ncc(C(=O)Nc3cnc(-n4nccn4)c(Cl)c3)c2C(F)(F)F)c2ccccc12] | 414 | N-(5-chloro-6-(2H-1,2,3-triazol-2-yl)pyridin-3-yl)-1-(1-cyanoisoquinolin-4-yl)-5-(trifluoromethyl)-1H-pyrazole-4-carboxamide |
| 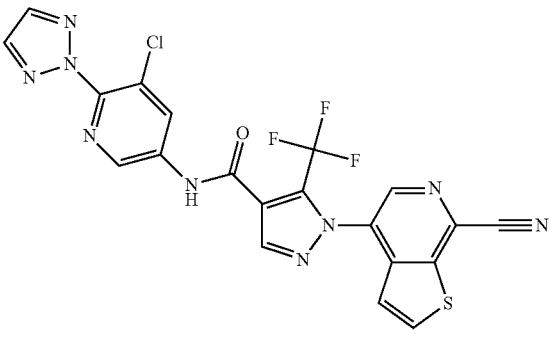 [SMILES: N#Cc1ncc(-n2ncc(C(=O)Nc3cnc(-n4nccn4)c(Cl)c3)c2C(F)(F)F)c2ccsc12] | 415 | N-(5-chloro-6-(2H-1,2,3-triazol-2-yl)pyridin-3-yl)-1-(7-cyanothieno[2,3-c]pyridin-4-yl)-5-(trifluoromethyl)-1H-pyrazole-4-carboxamide |
| 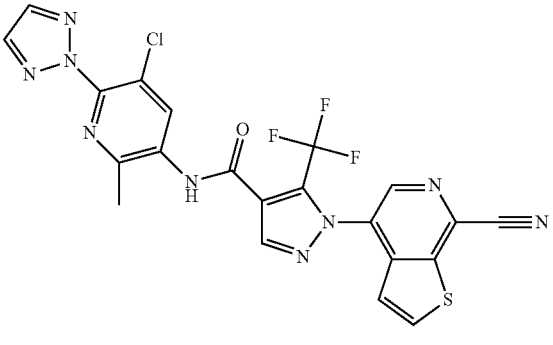 [SMILES: Cc1nc(-n2nccn2)c(Cl)cc1NC(=O)c1cnn(-c2cnc(C#N)c3sccc23)c1C(F)(F)F] | 416 | N-(5-chloro-2-methyl-6-(2H-1,2,3-triazol-2-yl)pyridin-3-yl)-1-(7-cyanothieno[2,3-c]pyridin-4-yl)-5-(trifluoromethyl)-1H-pyrazole-4-carboxamide |
| 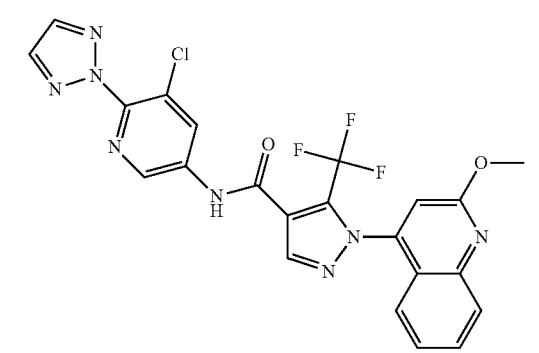 [SMILES: COc1cc(-n2ncc(C(=O)Nc3cnc(-n4nccn4)c(Cl)c3)c2C(F)(F)F)c2ccccc2n1] | 417 | N-(5-chloro-6-(2H-1,2,3-triazol-2-yl)pyridin-3-yl)-1-(2-methoxyquinolin-4-yl)-5-(trifluoromethyl)-1H-pyrazole-4-carboxamide |

TABLE 1-continued

| Structure | Cpd No. | Cpd Name |
|---|---|---|
| 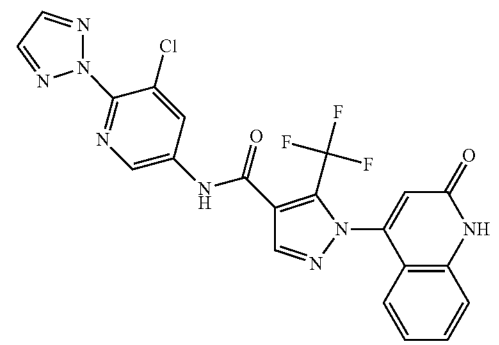 [SMILES: O=C(Nc1cnc(-n2nccn2)c(Cl)c1)c1cnn(-c2cc(=O)[nH]c3ccccc23)c1C(F)(F)F] | 418 | N-(5-chloro-6-(2H-1,2,3-triazol-2-yl)pyridin-3-yl)-1-(2-oxo-1,2-dihydroquinolin-4-yl)-5-(trifluoromethyl)-1H-pyrazole-4-carboxamide |
| 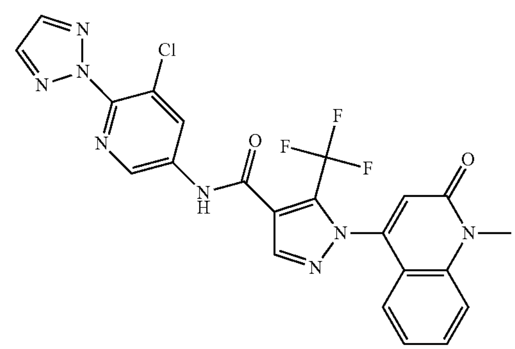 [SMILES: Cn1c(=O)cc(-n2ncc(C(=O)Nc3cnc(-n4nccn4)c(Cl)c3)c2C(F)(F)F)c2ccccc21] | 419 | N-(5-chloro-6-(2H-1,2,3-triazol-2-yl)pyridin-3-yl)-1-(1-methyl-2-oxo-1,2-dihydroquinolin-4-yl)-5-(trifluoromethyl)-1H-pyrazole-4-carboxamide |
| 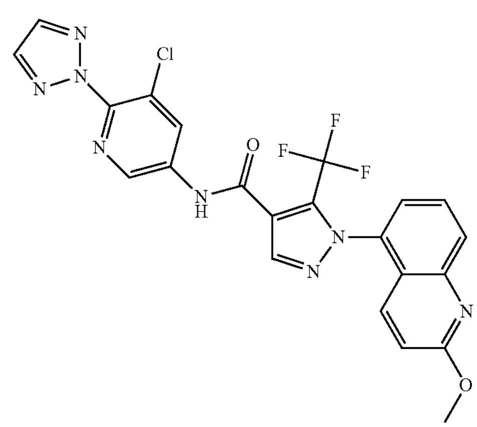 [SMILES: COc1ccc2c(-n3ncc(C(=O)Nc4cnc(-n5nccn5)c(Cl)c4)c3C(F)(F)F)cccc2n1] | 420 | N-(5-chloro-6-(2H-1,2,3-triazol-2-yl)pyridin-3-yl)-1-(2-methoxyquinolin-5-yl)-5-(trifluoromethyl)-1H-pyrazole-4-carboxamide |
| 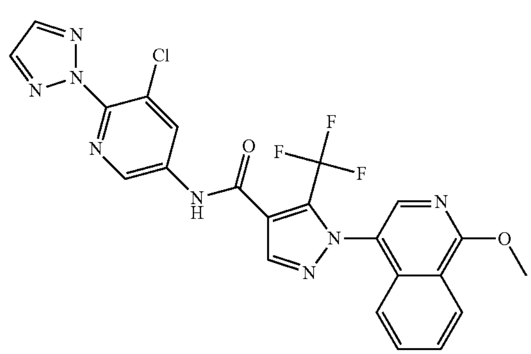 [SMILES: COc1ncc(-n2ncc(C(=O)Nc3cnc(-n4nccn4)c(Cl)c3)c2C(F)(F)F)c2ccccc12] | 421 | N-(5-chloro-6-(2H-1,2,3-triazol-2-yl)pyridin-3-yl)-1-(1-methoxyisoquinolin-4-yl)-5-(trifluoromethyl)-1H-pyrazole-4-carboxamide |

TABLE 1-continued

| Structure | Cpd No. | Cpd Name |
|---|---|---|
| 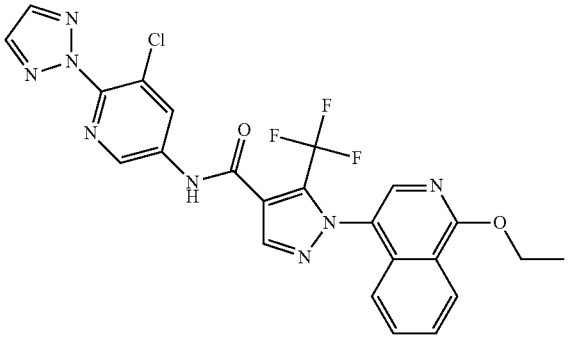 [SMILES: CCOc1ncc(-n2ncc(C(=O)Nc3cnc(-n4nccn4)c(Cl)c3)c2C(F)(F)F)c2ccccc12] | 422 | N-(5-chloro-6-(2H-1,2,3-triazol-2-yl)pyridin-3-yl)-1-(1-ethoxyisoquinolin-4-yl)-5-(trifluoromethyl)-1H-pyrazole-4-carboxamide |
| 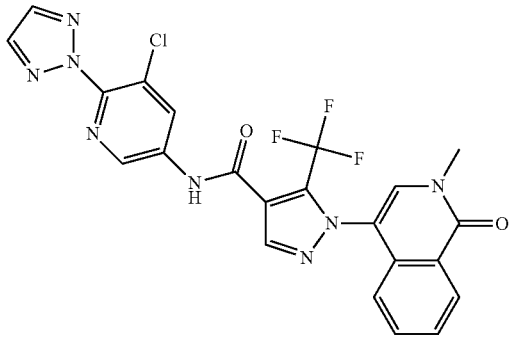 [SMILES: Cn1cc(-n2ncc(C(=O)Nc3cnc(-n4nccn4)c(Cl)c3)c2C(F)(F)F)c2ccccc2c1=O] | 423 | N-(5-chloro-6-(2H-1,2,3-triazol-2-yl)pyridin-3-yl)-1-(2-methyl-1-oxo-1,2-dihydroisoquinolin-4-yl)-5-(trifluoromethyl)-1H-pyrazole-4-carboxamide |
| 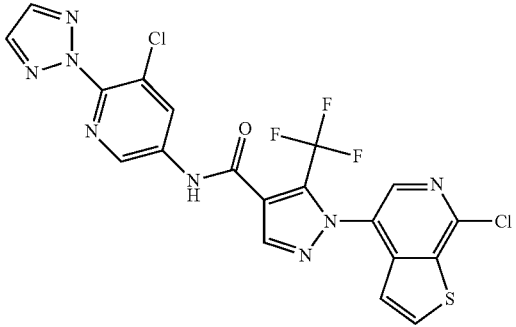 [SMILES: O=C(Nc1cnc(-n2nccn2)c(Cl)c1)c1cnn(-c2cnc(Cl)c3sccc23)c1C(F)(F)F] | 424 | N-(5-chloro-6-(2H-1,2,3-triazol-2-yl)pyridin-3-yl)-1-(7-chlorothieno[2,3-c]pyridin-4-yl)-5-(trifluoromethyl)-1H-pyrazole-4-carboxamide |
| 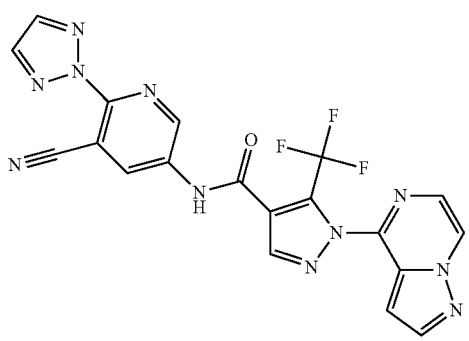 [SMILES: N#Cc1cc(NC(=O)c2cnn(-c3nccn4nccc34)c2C(F)(F)F)cnc1-n1nccn1] | 425 | N-(5-cyano-6-(2H-1,2,3-triazol-2-yl)pyridin-3-yl)-1-(pyrazolo[1,5-a]pyrazin-4-yl)-5-(trifluoromethyl)-1H-pyrazole-4-carboxamide |

TABLE 1-continued

| Structure | Cpd No. | Cpd Name |
|---|---|---|
| 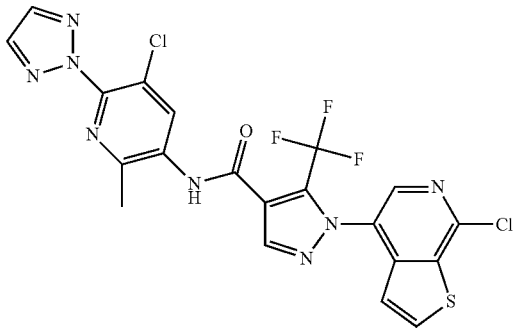 [SMILES: Cc1nc(-n2nccn2)c(Cl)cc1NC(=O)c1cnn(-c2cnc(Cl)c3sccc23)c1C(F)(F)F] | 426 | N-(5-chloro-2-methyl-6-(2H-1,2,3-triazol-2-yl)pyridin-3-yl)-1-(7-chlorothieno[2,3-c]pyridin-4-yl)-5-(trifluoromethyl)-1H-pyrazole-4-carboxamide |
| 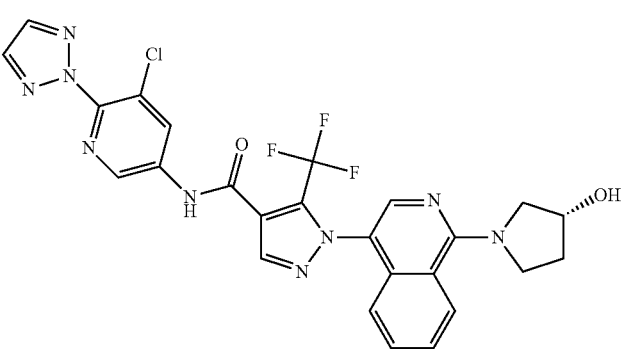 [SMILES: O=C(Nc1cnc(-n2nccn2)c(Cl)c1)c1cnn(-c2cnc(N3CC[C@@H](O)C3)c3ccccc23)c1C(F)(F)F] | 427 | (R)-N-(5-chloro-6-(2H-1,2,3-triazol-2-yl)pyridin-3-yl)-1-(1-(3-hydroxypyrrolidin-1-yl)isoquinolin-4-yl)-5-(trifluoromethyl)-1H-pyrazole-4-carboxamide |
| 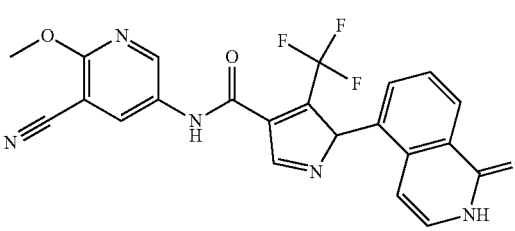 | 428 | N-(5-cyano-6-methoxypyridin-3-yl)-1-(1-oxo-1,2-dihydroisoquinolin-5-yl)-5-(trifluoromethyl)-1H-pyrazole-4-carboxamide |
| 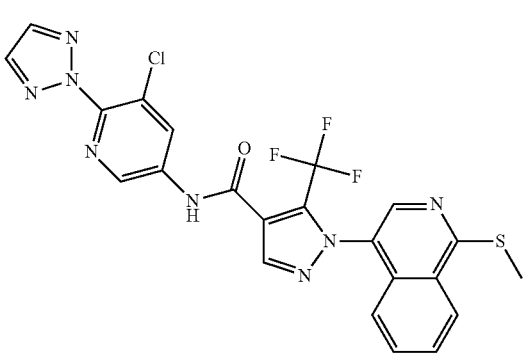 | 429 | N-(5-chloro-6-(2H-1,2,3-triazol-2-yl)pyridin-3-yl)-1-(1-(methylthio)isoquinolin-4-yl)-5-(trifluoromethyl)-1H-pyrazole-4-carboxamide |
| 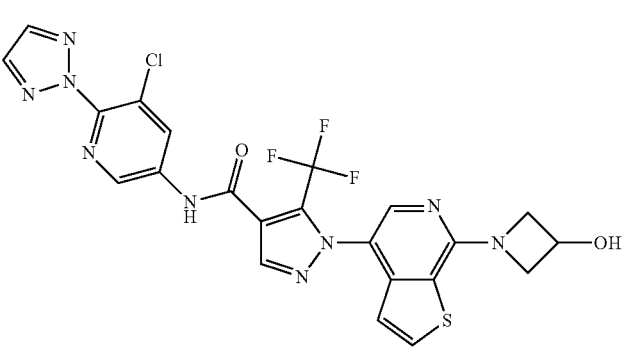 [SMILES: O=C(Nc1cnc(-n2nccn2)c(Cl)c1)c1cnn(-c2cnc(N3CC(O)C3)c3sccc23)c1C(F)(F)F] | 430 | N-(5-chloro-6-(2H-1,2,3-triazol-2-yl)pyridin-3-yl)-1-(7-(3-hydroxyazetidin-1-yl)thieno[2,3-c]pyridin-4-yl)-5-(trifluoromethyl)-1H-pyrazole-4-carboxamide |

TABLE 1-continued

| Structure | Cpd No. | Cpd Name |
|---|---|---|
| 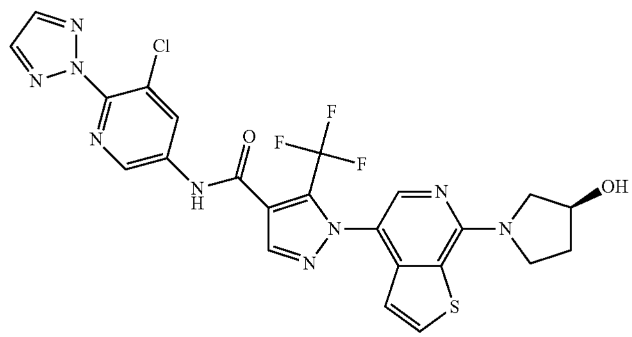 [SMILES: O=C(Nc1cnc(-n2nccn2)c(Cl)c1)c1cnn(-c2cnc(N3CC[C@H](O)C3)c3sccc23)c1C(F)(F)F] | 431 | (S)-N-(5-chloro-6-(2H-1,2,3-triazol-2-yl)pyridin-3-yl)-1-(7-(3-hydroxypyrrolidin-1-yl)thieno[2,3-c]pyridin-4-yl)-5-(trifluoromethyl)-1H-pyrazole-4-carboxamide |
| 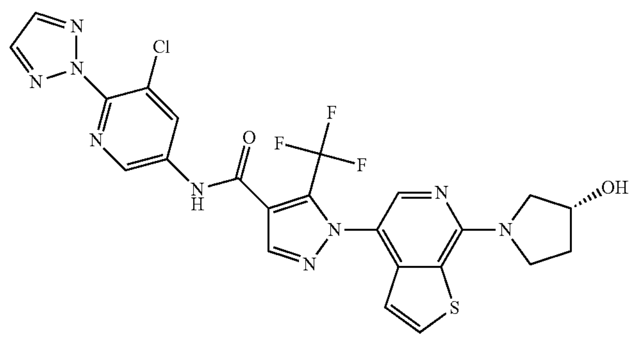 [SMILES: O=C(Nc1cnc(-n2nccn2)c(Cl)c1)c1cnn(-c2cnc(N3CC[C@@H](O)C3)c3sccc23)c1C(F)(F)F] | 432 | (R)-N-(5-chloro-6-(2H-1,2,3-triazol-2-yl)pyridin-3-yl)-1-(7-(3-hydroxypyrrolidin-1-yl)thieno[2,3-c]pyridin-4-yl)-5-(trifluoromethyl)-1H-pyrazole-4-carboxamide |
| 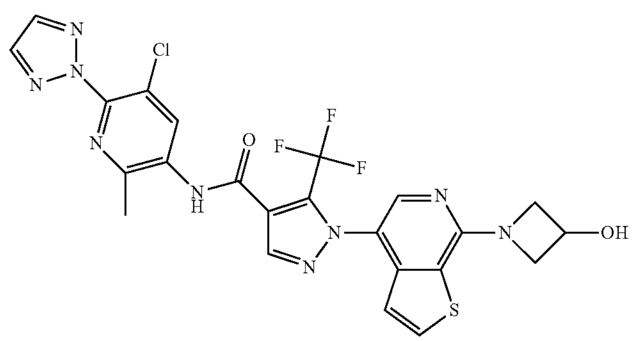 [SMILES: Cc1nc(-n2nccn2)c(Cl)cc1NC(=O)c1cnn(-c2cnc(N3CC(O)C3)c3sccc23)c1C(F)(F)F] | 433 | N-(5-chloro-2-methyl-6-(2H-1,2,3-triazol-2-yl)pyridin-3-yl)-1-(7-(3-hydroxyazetidin-1-yl)thieno[2,3-c]pyridin-4-yl)-5-(trifluoromethyl)-1H-pyrazole-4-carboxamide |
| 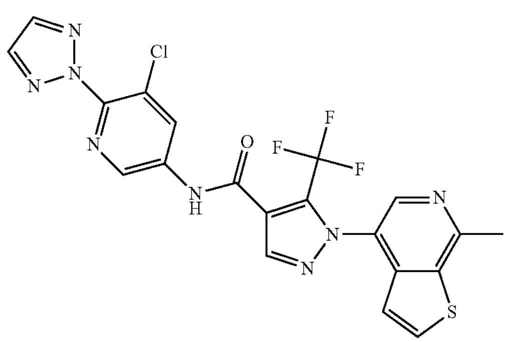 [SMILES: Cc1ncc(-n2ncc(C(=O)Nc3cnc(-n4nccn4)c(Cl)c3)c2C(F)(F)F)c2ccsc12] | 434 | N-(5-chloro-6-(2H-1,2,3-triazol-2-yl)pyridin-3-yl)-1-(7-methylthieno[2,3-c]pyridin-4-yl)-5-(trifluoromethyl)-1H-pyrazole-4-carboxamide |

TABLE 1-continued

| Structure | Cpd No. | Cpd Name |
|---|---|---|
| 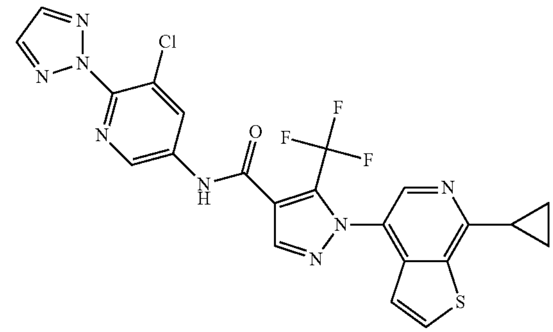 [SMILES: O=C(Nc1cnc(-n2nccn2)c(Cl)c1)c1cnn(-c2cnc(C3CC3)c3sccc23)c1C(F)(F)F] | 435 | N-(5-chloro-6-(2H-1,2,3-triazol-2-yl)pyridin-3-yl)-1-(7-cyclopropylthieno[2,3-c]pyridin-4-yl)-5-(trifluoromethyl)-1H-pyrazole-4-carboxamide |
| 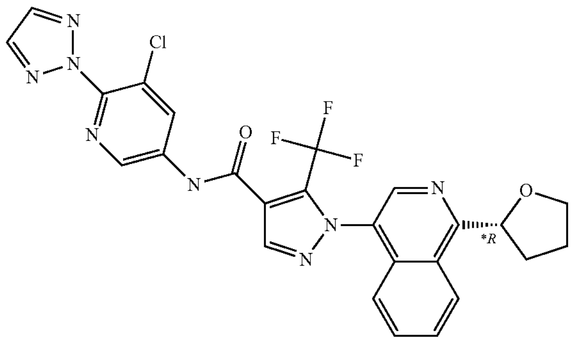 [SMILES: O=C(Nc1cnc(-n2nccn2)c(Cl)c1)c1cnn(-c2cnc([C@H]3CCCO3)c3ccccc23)c1C(F)(F)F] | 436 | (*R)-N-(5-chloro-6-(2H-1,2,3-triazol-2-yl)pyridin-3-yl)-1-(1-(tetrahydrofuran-2-yl)isoquinolin-4-yl)-5-(trifluoromethyl)-1H-pyrazole-4-carboxamide |
| 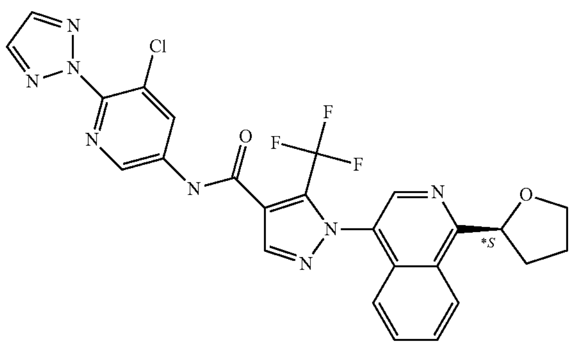 [SMILES: O=C(Nc1cnc(-n2nccn2)c(Cl)c1)c1cnn(-c2cnc([C@@H]3CCCO3)c3ccccc23)c1C(F)(F)F] | 437 | (*S)-N-(5-chloro-6-(2H-1,2,3-triazol-2-yl)pyridin-3-yl)-1-(1-(tetrahydrofuran-2-yl)isoquinolin-4-yl)-5-(trifluoromethyl)-1H-pyrazole-4-carboxamide |
| 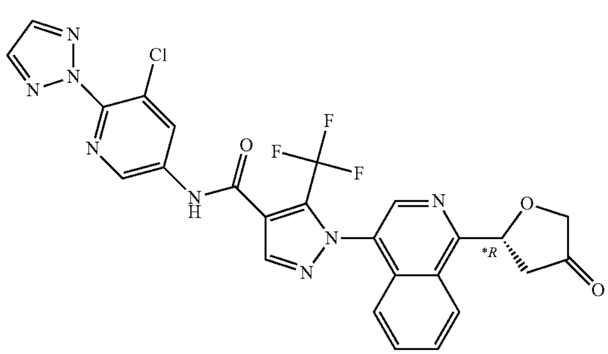 [SMILES: O=C1CO[C@@H](c2ncc(-n3ncc(C(=O)Nc4cnc(-n5nccn5)c(Cl)c4)c3C(F)(F)F)c3ccccc23)C1] | 438 | (*R)-N-(5-chloro-6-(2H-1,2,3-triazol-2-yl)pyridin-3-yl)-1-(1-(4-oxotetrahydrofuran-2-yl)isoquinolin-4-yl)-5-(trifluoromethyl)-1H-pyrazole-4-carboxamide |

TABLE 1-continued

| Structure | Cpd No. | Cpd Name |
|---|---|---|
| 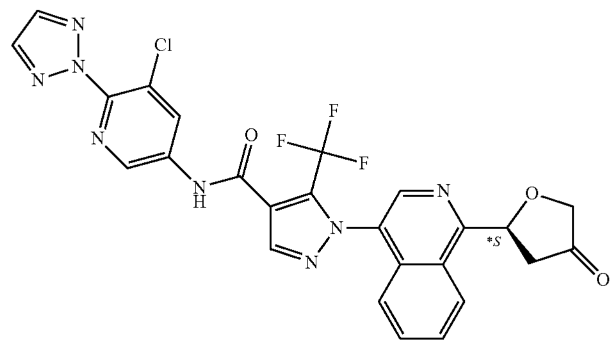 [SMILES: O=C1CO[C@H](c2ncc(-n3ncc(C(=O)Nc4cnc(-n5nccn5)c(Cl)c4)c3C(F)(F)F)c3ccccc23)C1] | 439 | (*S)-N-(5-chloro-6-(2H-1,2,3-triazol-2-yl)pyridin-3-yl)-1-(1-(4-oxotetrahydrofuran-2-yl)isoquinolin-4-yl)-5-(trifluoromethyl)-1H-pyrazole-4-carboxamide |
| 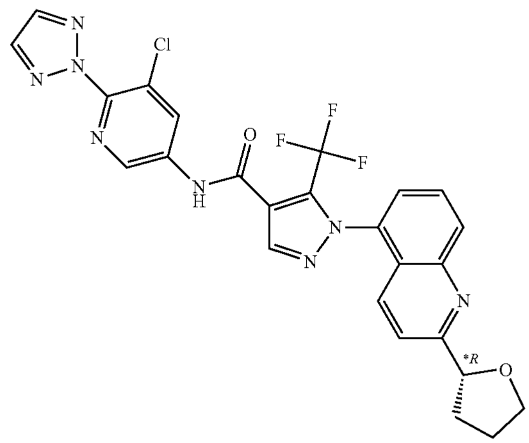 [SMILES: O=C(Nc1cnc(-n2nccn2)c(Cl)c1)c1cnn(-c2cccc3nc([C@H]4CCCO4)ccc23)c1C(F)(F)F] | 440 | (*R)-N-(5-chloro-6-(2H-1,2,3-triazol-2-yl)pyridin-3-yl)-1-(2-(tetrahydrofuran-2-yl)quinolin-5-yl)-5-(trifluoromethyl)-1H-pyrazole-4-carboxamide |
| 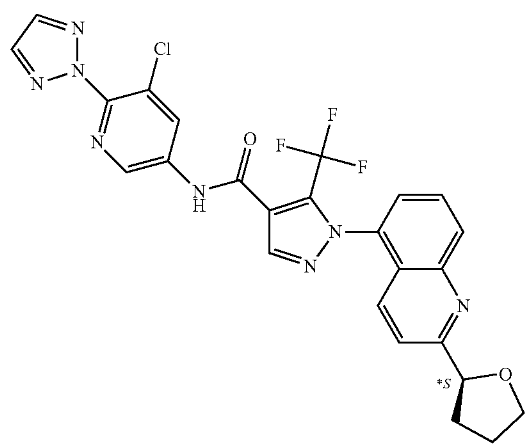 [SMILES: O=C(Nc1cnc(-n2nccn2)c(Cl)c1)c1cnn(-c2cccc3nc([C@@H]4CCCO4)ccc23)c1C(F)(F)F] | 441 | (*S)-N-(5-chloro-6-(2H-1,2,3-triazol-2-yl)pyridin-3-yl)-1-(2-(tetrahydrofuran-2-yl)quinolin-5-yl)-5-(trifluoromethyl)-1H-pyrazole-4-carboxamide |
| 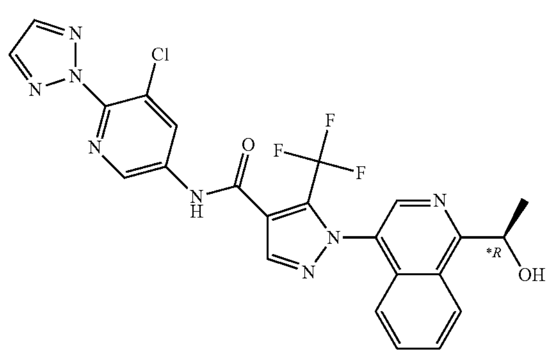 [SMILES: C[C@@H](O)c1ncc(-n2ncc(C(=O)Nc3cnc(-n4nccn4)c(Cl)c3)c2C(F)(F)F)c2ccccc12] | 442 | (*R)-N-(5-chloro-6-(2H-1,2,3-triazol-2-yl)pyridin-3-yl)-1-(1-(1-hydroxyethyl)isoquinolin-4-yl)-5-(trifluoromethyl)-1H-pyrazole-4-carboxamide |

TABLE 1-continued

| Structure | Cpd No. | Cpd Name |
|---|---|---|
| 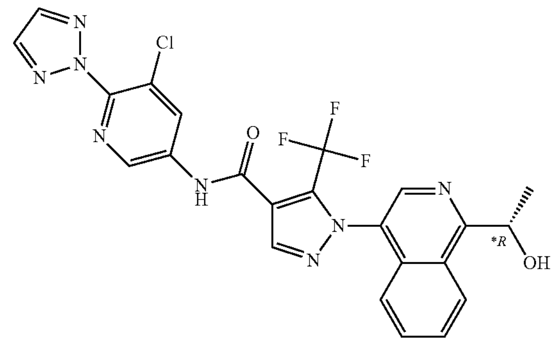 [SMILES: C[C@H](O)c1ncc(-n2ncc(C(=O)Nc3cnc(-n4nccn4)c(Cl)c3)c2C(F)(F)F)c2ccccc12] | 443 | (*S)-N-(5-chloro-6-(2H-1,2,3-triazol-2-yl)pyridin-3-yl)-1-(1-(1-hydroxyethyl)isoquinolin-4-yl)-5-(trifluoromethyl)-1H-pyrazole-4-carboxamide |
| 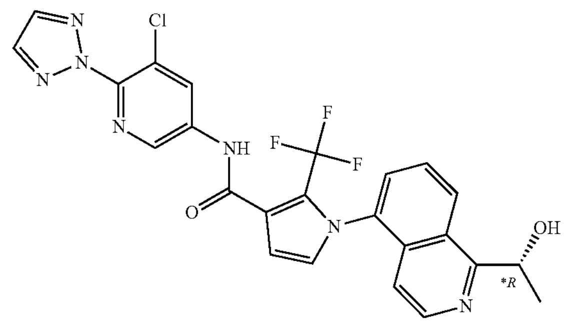 [SMILES: C[C@@H](O)c1nccc2c(-n3ccc(C(=O)Nc4cnc(-n5nccn5)c(Cl)c4)c3C(F)(F)F)cccc12] | 444 | (*R)-N-(5-chloro-6-(2H-1,2,3-triazol-2-yl)pyridin-3-yl)-1-(1-(1-hydroxyethyl)isoquinolin-5-yl)-5-(trifluoromethyl)-1H-pyrazole-4-carboxamide |
| 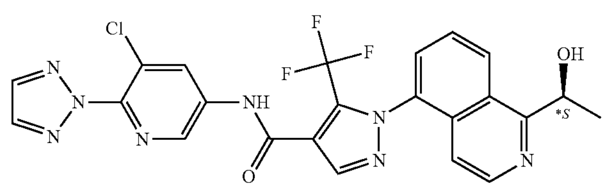 [SMILES: C[C@H](O)c1nccc2c(-n3ncc(C(=O)Nc4cnc(-n5nccn5)c(Cl)c4)c3C(F)(F)F)cccc12] | 445 | (*S)-N-(5-chloro-6-(2H-1,2,3-triazol-2-yl)pyridin-3-yl)-1-(1-(1-hydroxyethyl)isoquinolin-5-yl)-5-(trifluoromethyl)-1H-pyrazole-4-carboxamide |
| 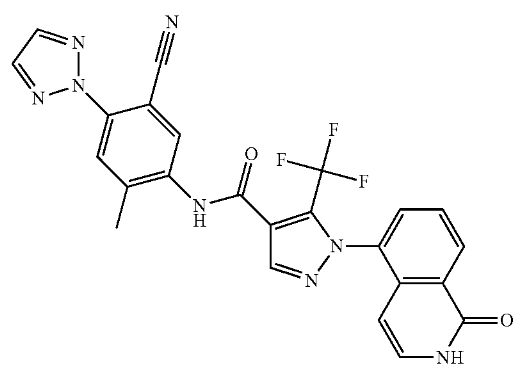 [SMILES: Cc1cc(-n2nccn2)c(C#N)cc1NC(=O)c1cnn(-c2cccc3c(=O)[nH]ccc23)c1C(F)(F)F] | 446 | N-(5-cyano-2-methyl-4-(2H-1,2,3-triazol-2-yl)phenyl)-1-(1-oxo-1,2-dihydroisoquinolin-5-yl)-5-(trifluoromethyl)-1H-pyrazole-4-carboxamide |
| 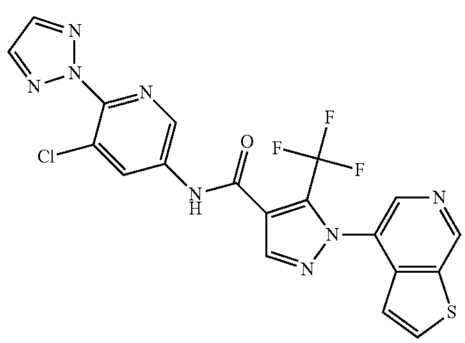 [SMILES: O=C(Nc1cnc(-n2nccn2)c(Cl)c1)c1cnn(-c2cncc3sccc23)c1C(F)(F)F] | 447 | N-(5-chloro-6-(2H-1,2,3-triazol-2-yl)pyridin-3-yl)-1-(thieno[2,3-c]pyridin-4-yl)-5-(trifluoromethyl)-1H-pyrazole-4-carboxamide |

TABLE 1-continued

| Structure | Cpd No. | Cpd Name |
|---|---|---|
| 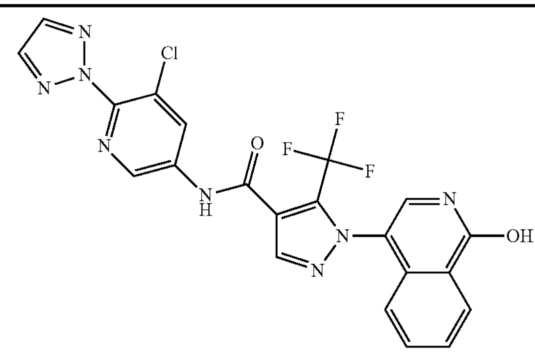 | 448 | N-(5-chloro-6-(2H-1,2,3-triazol-2-yl)pyridin-3-yl)-1-(1-hydroxyisoquinolin-4-yl)-5-(trifluoromethyl)-1H-pyrazole-4-carboxamide |
| 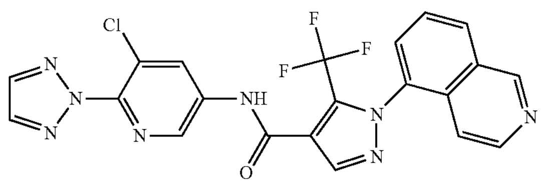 [SMILES: O=C(Nc1cnc(-n2nccn2)c(Cl)c1)c1cnn(-c2cccc3cnccc23)c1C(F)(F)F] | 449 | N-(5-chloro-6-(2H-1,2,3-triazol-2-yl)pyridin-3-yl)-1-(isoquinolin-5-yl)-5-(trifluoromethyl)-1H-pyrazole-4-carboxamide |
| 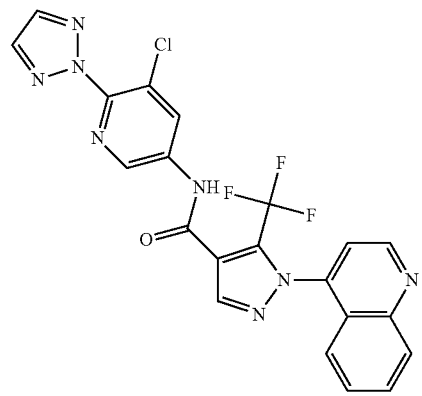 [SMILES: O=C(Nc1cnc(-n2nccn2)c(Cl)c1)c1cnn(-c2ccnc3ccccc23)c1C(F)(F)F] | 450 | N-(5-chloro-6-(2H-1,2,3-triazol-2-yl)pyridin-3-yl)-1-(quinolin-4-yl)-5-(trifluoromethyl)-1H-pyrazole-4-carboxamide |

In a further embodiment, the invention is directed to a compound of Formula (I)

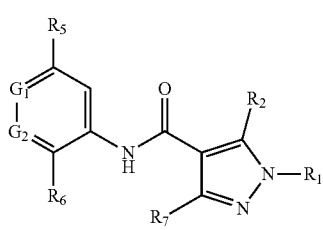

Formula (I)

selected from the group consisting of
N-(2-cyanopyridin-4-yl)-1-(naphthalen-1-yl)-5-(trifluoromethyl)-1H-pyrazole-4-carboxamide;
N-(5-chloro-6-(2H-1,2,3-triazol-2-yl)pyridin-3-yl)-1-(naphthalen-1-yl)-5-(trifluoromethyl)-1H-pyrazole-4-carboxamide;
1-(naphthalen-1-yl)-5-(trifluoromethyl)-N-(2-(trifluoromethyl)pyridin-4-yl)-1H-pyrazole-4-carboxamide;
1-(naphthalen-1-yl)-5-(trifluoromethyl)-N-(5-(trifluoromethyl)pyridin-3-yl)-1H-pyrazole-4-carboxamide;
N-(5-cyanopyridin-3-yl)-1-(naphthalen-1-yl)-5-(trifluoromethyl)-1H-pyrazole-4-carboxamide;
1-(quinolin-5-yl)-5-(trifluoromethyl)-N-(2-(trifluoromethyl)pyridin-4-yl)-1H-pyrazole-4-carboxamide;
N-(5-chloro-6-methoxypyridin-3-yl)-1-(quinolin-5-yl)-5-(trifluoromethyl)-1H-pyrazole-4-carboxamide;
N-(5-chloro-6-(2H-1,2,3-triazol-2-yl)pyridin-3-yl)-1-(quinolin-5-yl)-5-(trifluoromethyl)-1H-pyrazole-4-carboxamide;
N-(5-chloro-6-(2H-1,2,3-triazol-2-yl)pyridin-3-yl)-1-(3-methylisoquinolin-1-yl)-5-(trifluoromethyl)-1H-pyrazole-4-carboxamide;
N-(3-chloro-4-methoxyphenyl)-1-(isoquinolin-8-yl)-5-(trifluoromethyl)-1H-pyrazole-4-carboxamide;
N-(3-chloro-4-(2H-1,2,3-triazol-2-yl)phenyl)-1-(isoquinolin-8-yl)-5-(trifluoromethyl)-1H-pyrazole-4-carboxamide;
N-(3-chloro-4-(1H-pyrazol-1-yl)phenyl)-1-(isoquinolin-8-yl)-5-(trifluoromethyl)-1H-pyrazole-4-carboxamide;
N-(6-cyano-5-(trifluoromethyl)pyridin-3-yl)-1-(isoquinolin-8-yl)-5-(trifluoromethyl)-1H-pyrazole-4-carboxamide;
N-(4-(2-aminopyrimidin-4-yl)-3-chlorophenyl)-1-(isoquinolin-8-yl)-5-(trifluoromethyl)-1H-pyrazole-4-carboxamide;

N-(5-chloro-6-(1H-pyrazol-1-yl)pyridin-3-yl)-1-(isoquinolin-8-yl)-5-(trifluoromethyl)-1H-pyrazole-4-carboxamide;
N-(5-chloro-6-(2H-1,2,3-triazol-2-yl)pyridin-3-yl)-5-isobutyl-1-(quinolin-5-yl)-1H-pyrazole-4-carboxamide;
N-(5-chloro-6-(2H-1,2,3-triazol-2-yl)pyridin-3-yl)-5-ethyl-1-(quinolin-5-yl)-1H-pyrazole-4-carboxamide;
N-(3-chloro-4-(1H-1,2,3-triazol-1-yl)phenyl)-1-(isoquinolin-8-yl)-5-(trifluoromethyl)-1H-pyrazole-4-carboxamide;
N-(5-cyano-6-(2H-1,2,3-triazol-2-yl)pyridin-3-yl)-1-(isoquinolin-8-yl)-5-(trifluoromethyl)-1H-pyrazole-4-carboxamide;
N-(5-chloro-6-(1,1-dioxidoisothiazolidin-2-yl)pyridin-3-yl)-1-(isoquinolin-8-yl)-5-(trifluoromethyl)-1H-pyrazole-4-carboxamide;
N-(5-chloro-6-(1-methyl-1H-pyrazol-3-yl)pyridin-3-yl)-1-(isoquinolin-8-yl)-5-(trifluoromethyl)-1H-pyrazole-4-carboxamide;
N-(5-chloro-6-(oxazol-2-yl)pyridin-3-yl)-1-(isoquinolin-8-yl)-5-(trifluoromethyl)-1H-pyrazole-4-carboxamide;
N-(5-chloro-6-methoxypyridin-3-yl)-1-(isoquinolin-4-yl)-5-(trifluoromethyl)-1H-pyrazole-4-carboxamide;
N-(5-cyano-6-methoxypyridin-3-yl)-1-(isoquinolin-4-yl)-5-(trifluoromethyl)-1H-pyrazole-4-carboxamide;
N-(5-chloro-6-(2H-1,2,3-triazol-2-yl)pyridin-3-yl)-1-(3-fluoroquinolin-5-yl)-5-(trifluoromethyl)-1H-pyrazole-4-carboxamide;
N-(5-chloro-6-(2H-1,2,3-triazol-2-yl)pyridin-3-yl)-5-isopropyl-1-(quinolin-5-yl)-1H-pyrazole-4-carboxamide;
N-(5-chloro-6-(2H-1,2,3-triazol-2-yl)pyridin-3-yl)-1-(6-methylquinolin-5-yl)-5-(trifluoromethyl)-1H-pyrazole-4-carboxamide;
N-(5-chloro-6-(2H-1,2,3-triazol-2-yl)pyridin-3-yl)-1-(8-methylquinolin-5-yl)-5-(trifluoromethyl)-1H-pyrazole-4-carboxamide;
N-(3-chloro-4-(3-methyl-1H-1,2,4-triazol-1-yl)phenyl)-1-(isoquinolin-8-yl)-5-(trifluoromethyl)-1H-pyrazole-4-carboxamide;
N-(5-chloro-6-(3-methyl-1H-1,2,4-triazol-1-yl)pyridin-3-yl)-1-(isoquinolin-8-yl)-5-(trifluoromethyl)-1H-pyrazole-4-carboxamide;
N-(3-chloro-4-(5-methyl-1H-1,2,4-triazol-1-yl)phenyl)-1-(isoquinolin-8-yl)-5-(trifluoromethyl)-1H-pyrazole-4-carboxamide;
N-(5-chloro-6-(2H-1,2,3-triazol-2-yl)pyridin-3-yl)-1-(isoquinolin-4-yl)-5-(trifluoromethyl)-1H-pyrazole-4-carboxamide;
N-(5-chloro-6-(2H-1,2,3-triazol-2-yl)pyridin-3-yl)-1-(4-methylisoquinolin-8-yl)-5-(trifluoromethyl)-1H-pyrazole-4-carboxamide;
1-(benzofuran-4-yl)-N-(5-chloro-6-(2H-1,2,3-triazol-2-yl)pyridin-3-yl)-5-(trifluoromethyl)-1H-pyrazole-4-carboxamide;
N-(5-chloro-6-(2H-1,2,3-triazol-2-yl)pyridin-3-yl)-5-(1-methoxyethyl)-1-(quinolin-5-yl)-1H-pyrazole-4-carboxamide;
N-(5-chloro-6-(2H-1,2,3-triazol-2-yl)pyridin-3-yl)-1-(6-methylisoquinolin-4-yl)-5-(trifluoromethyl)-1H-pyrazole-4-carboxamide;
N-(5-chloro-6-(2H-1,2,3-triazol-2-yl)pyridin-3-yl)-1-(2-methylquinolin-5-yl)-5-(trifluoromethyl)-1H-pyrazole-4-carboxamide;
N-(3-chloro-4-(2H-1,2,3-triazol-2-yl)phenyl)-1-(isoquinolin-4-yl)-5-(trifluoromethyl)-1H-pyrazole-4-carboxamide;
N-(5-chloro-6-(2H-1,2,3-triazol-2-yl)pyridin-3-yl)-5-methyl-1-(quinolin-5-yl)-1H-pyrazole-4-carboxamide;
N-(5-chloro-6-(2H-1,2,3-triazol-2-yl)pyridin-3-yl)-1-(8-fluoroquinolin-5-yl)-5-(trifluoromethyl)-1H-pyrazole-4-carboxamide;
N-(6-cyano-5-fluoropyridin-3-yl)-1-(isoquinolin-4-yl)-5-(trifluoromethyl)-1H-pyrazole-4-carboxamide;
N-(5-chloro-6-(1,1-dioxidoisothiazolidin-2-yl)pyridin-3-yl)-1-(isoquinolin-4-yl)-5-(trifluoromethyl)-1H-pyrazole-4-carboxamide;
N-(3-chloro-4-(1H-1,2,3-triazol-1-yl)phenyl)-1-(isoquinolin-4-yl)-5-(trifluoromethyl)-1H-pyrazole-4-carboxamide;
methyl 3-chloro-5-(3-chloro-5-(1-(isoquinolin-4-yl)-5-(trifluoromethyl)-1H-pyrazole-4-carboxamido)picolinamido)picolinate;
N-(5-chloro-6-((1-methylpiperidin-4-yl)oxy)pyridin-3-yl)-1-(isoquinolin-4-yl)-5-(trifluoromethyl)-1H-pyrazole-4-carboxamide;
N-(5-chloro-6-(1H-pyrazol-1-yl)pyridin-3-yl)-1-(isoquinolin-4-yl)-5-(trifluoromethyl)-1H-pyrazole-4-carboxamide;
N-(5-cyano-6-(2H-1,2,3-triazol-2-yl)pyridin-3-yl)-1-(isoquinolin-4-yl)-5-(trifluoromethyl)-1H-pyrazole-4-carboxamide;
N-(5-chloro-6-(4-methylpiperazine-1-carbonyl)pyridin-3-yl)-1-(isoquinolin-4-yl)-5-(trifluoromethyl)-1H-pyrazole-4-carboxamide;
N-(6-cyano-5-(trifluoromethyl)pyridin-3-yl)-1-(isoquinolin-4-yl)-5-(trifluoromethyl)-1H-pyrazole-4-carboxamide;
N-(5-chloro-6-(oxazol-2-yl)pyridin-3-yl)-1-(isoquinolin-4-yl)-5-(trifluoromethyl)-1H-pyrazole-4-carboxamide;
N-(3-chloro-4-(5-methyl-1H-1,2,4-triazol-1-yl)phenyl)-1-(isoquinolin-4-yl)-5-(trifluoromethyl)-1H-pyrazole-4-carboxamide;
N-(5-chloro-6-(1-methyl-1H-pyrazol-3-yl)pyridin-3-yl)-1-(isoquinolin-4-yl)-5-(trifluoromethyl)-1H-pyrazole-4-carboxamide;
N-(5-chloro-6-(3-methyl-1H-1,2,4-triazol-1-yl)pyridin-3-yl)-1-(isoquinolin-4-yl)-5-(trifluoromethyl)-1H-pyrazole-4-carboxamide;
N-(5-chloro-6-(5-methyl-1H-1,2,4-triazol-1-yl)pyridin-3-yl)-1-(isoquinolin-4-yl)-5-(trifluoromethyl)-1H-pyrazole-4-carboxamide;
N-(3-chloro-4-(3-methyl-1H-1,2,4-triazol-1-yl)phenyl)-1-(isoquinolin-4-yl)-5-(trifluoromethyl)-1H-pyrazole-4-carboxamide;
N-(5-chloro-6-(2H-1,2,3-triazol-2-yl)pyridin-3-yl)-5-(difluoromethyl)-1-(isoquinolin-1-yl)-1H-pyrazole-4-carboxamide;
N-(5-chloro-6-(2H-1,2,3-triazol-2-yl)pyridin-3-yl)-1-(isoquinolin-1-yl)-5-(trifluoromethyl)-1H-pyrazole-4-carboxamide;
N-(4-(2-aminopyrimidin-4-yl)-3-chlorophenyl)-1-(isoquinolin-4-yl)-5-(trifluoromethyl)-1H-pyrazole-4-carboxamide;
N-(3-cyano-4-(2H-1,2,3-triazol-2-yl)phenyl)-1-(isoquinolin-4-yl)-5-(trifluoromethyl)-1H-pyrazole-4-carboxamide;
N-(5-chloro-6-(2H-1,2,3-triazol-2-yl)pyridin-3-yl)-1-(quinolin-5-yl)-1H-pyrazole-4-carboxamide;
N-(5-fluoro-6-(2H-1,2,3-triazol-2-yl)pyridin-3-yl)-1-(isoquinolin-4-yl)-5-(trifluoromethyl)-1H-pyrazole-4-carboxamide;

N-(3-cyano-4-(1H-1,2,3-triazol-1-yl)phenyl)-1-(isoquinolin-4-yl)-5-(trifluoromethyl)-1H-pyrazole-4-carboxamide;

N-(5-chloro-6-(thiazol-2-yl)pyridin-3-yl)-1-(isoquinolin-4-yl)-5-(trifluoromethyl)-1H-pyrazole-4-carboxamide;

N-(5-chloro-6-(2H-1,2,3-triazol-2-yl)pyridin-3-yl)-5-methyl-1-(quinolin-4-yl)-1H-pyrazole-4-carboxamide;

N-(5-chloro-6-(2H-1,2,3-triazol-2-yl)pyridin-3-yl)-1-(3-methylquinolin-5-yl)-5-(trifluoromethyl)-1H-pyrazole-4-carboxamide;

N-(5-chloro-6-(2H-1,2,3-triazol-2-yl)pyridin-3-yl)-1-(1-methylisoquinolin-4-yl)-5-(trifluoromethyl)-1H-pyrazole-4-carboxamide;

N-(5-chloro-6-(2H-1,2,3-triazol-2-yl)pyridin-3-yl)-1-(6-fluoroquinolin-7-yl)-5-(trifluoromethyl)-1H-pyrazole-4-carboxamide;

N-(5-chloro-6-(2H-1,2,3-triazol-2-yl)pyridin-3-yl)-1-(1H-indazol-4-yl)-5-(trifluoromethyl)-1H-pyrazole-4-carboxamide;

N-(5-chloro-6-(1,3,4-oxadiazol-2-yl)pyridin-3-yl)-1-(isoquinolin-4-yl)-5-(trifluoromethyl)-1H-pyrazole-4-carboxamide;

N-(5-chloro-6-(1H-imidazol-1-yl)pyridin-3-yl)-1-(isoquinolin-4-yl)-5-(trifluoromethyl)-1H-pyrazole-4-carboxamide;

N-(6-(2H-1,2,3-triazol-2-yl)pyridin-3-yl)-1-(isoquinolin-4-yl)-5-(trifluoromethyl)-1H-pyrazole-4-carboxamide;

N-(4-aminobutyl)-3-chloro-5-(1-(isoquinolin-4-yl)-5-(trifluoromethyl)-1H-pyrazole-4-carboxamido)picolinamide;

1-(isoquinolin-4-yl)-N-(2-methyl-6-(trifluoromethyl)pyridin-4-yl)-5-(trifluoromethyl)-1H-pyrazole-4-carboxamide;

methyl 6-chloro-4-(1-(isoquinolin-4-yl)-5-(trifluoromethyl)-1H-pyrazole-4-carboxamido)picolinate;

methyl 4-(1-(isoquinolin-4-yl)-5-(trifluoromethyl)-1H-pyrazole-4-carboxamido)picolinate N-(5-chloro-6-(2H-1,2,3-triazol-2-yl)pyridin-3-yl)-1-(isoquinolin-4-yl)-1H-pyrazole-4-carboxamide;

N-(2-cyanopyridin-4-yl)-1-(isoquinolin-4-yl)-5-(trifluoromethyl)-1H-pyrazole-4-carboxamide;

N-(5-cyano-6-(1-methyl-1H-pyrazol-3-yl)pyridin-3-yl)-1-(isoquinolin-4-yl)-5-(trifluoromethyl)-1H-pyrazole-4-carboxamide;

N-(5-chloro-6-cyclopropoxypyridin-3-yl)-1-(quinolin-5-yl)-5-(trifluoromethyl)-1H-pyrazole-4-carboxamide;

N-(5-cyano-6-((1-methylpiperidin-4-yl)oxy)pyridin-3-yl)-1-(isoquinolin-4-yl)-5-(trifluoromethyl)-1H-pyrazole-4-carboxamide;

N-(5-cyano-6-ethoxypyridin-3-yl)-1-(quinolin-5-yl)-5-(trifluoromethyl)-1H-pyrazole-4-carboxamide;

N-(5-cyanopyridin-3-yl)-1-(isoquinolin-4-yl)-5-(trifluoromethyl)-1H-pyrazole-4-carboxamide;

N-(5-cyano-6-(2H-1,2,3-triazol-2-yl)pyridin-3-yl)-1-(quinolin-5-yl)-5-(trifluoromethyl)-1H-pyrazole-4-carboxamide;

N-(6-(4-aminobutoxy)-5-cyanopyridin-3-yl)-1-(isoquinolin-4-yl)-5-(trifluoromethyl)-1H-pyrazole-4-carboxamide;

N-(5-cyano-6-methoxypyridin-3-yl)-1-(quinolin-5-yl)-5-(trifluoromethyl)-1H-pyrazole-4-carboxamide;

N-(5-cyano-6-(1H-1,2,4-triazol-1-yl)pyridin-3-yl)-1-(quinolin-5-yl)-5-(trifluoromethyl)-1H-pyrazole-4-carboxamide;

N-(8-chloro-3-oxo-3,4-dihydro-2H-benzo[b][1,4]oxazin-6-yl)-1-(isoquinolin-4-yl)-5-(trifluoromethyl)-1H-pyrazole-4-carboxamide;

N-(5-cyano-6-cyclopropoxypyridin-3-yl)-1-(quinolin-5-yl)-5-(trifluoromethyl)-1H-pyrazole-4-carboxamide;

N-(5-cyano-6-(1-methyl-1H-pyrazol-3-yl)pyridin-3-yl)-1-(quinolin-5-yl)-5-(trifluoromethyl)-1H-pyrazole-4-carboxamide;

N-(5-cyano-6-(2H-1,2,3-triazol-2-yl)pyridin-3-yl)-1-(thieno[3,2-c]pyridin-4-yl)-5-(trifluoromethyl)-1H-pyrazole-4-carboxamide;

N-(5-chloro-6-(oxazol-2-yl)pyridin-3-yl)-1-(quinolin-5-yl)-5-(trifluoromethyl)-1H-pyrazole-4-carboxamide;

N-(5-cyano-6-(2H-1,2,3-triazol-2-yl)pyridin-3-yl)-1-(8-fluoroquinolin-4-yl)-5-(trifluoromethyl)-1H-pyrazole-4-carboxamide;

1-(cinnolin-4-yl)-N-(5-cyano-6-(2H-1,2,3-triazol-2-yl)pyridin-3-yl)-5-(trifluoromethyl)-1H-pyrazole-4-carboxamide;

N-(5-cyano-6-(2H-1,2,3-triazol-2-yl)pyridin-3-yl)-1-(furo[3,2-c]pyridin-4-yl)-5-(trifluoromethyl)-1H-pyrazole-4-carboxamide;

N-(8-chloro-4-methyl-3-oxo-3,4-dihydro-2H-benzo[b][1,4]oxazin-6-yl)-1-(quinolin-5-yl)-5-(trifluoromethyl)-1H-pyrazole-4-carboxamide;

N-(5-cyano-6-(4-methylpiperazine-1-carbonyl)pyridin-3-yl)-1-(isoquinolin-4-yl)-5-(trifluoromethyl)-1H-pyrazole-4-carboxamide;

N-(8-chloro-4-methyl-3-oxo-3,4-dihydro-2H-benzo[b][1,4]oxazin-6-yl)-1-(isoquinolin-4-yl)-5-(trifluoromethyl)-1H-pyrazole-4-carboxamide;

N-(5-chloro-6-(1-methyl-1H-imidazol-2-yl)pyridin-3-yl)-1-(isoquinolin-4-yl)-5-(trifluoromethyl)-1H-pyrazole-4-carboxamide;

N-(5-cyano-6-(2H-1,2,3-triazol-2-yl)pyridin-3-yl)-1-(furo[2,3-c]pyridin-7-yl)-5-(trifluoromethyl)-1H-pyrazole-4-carboxamide;

N-(5-cyano-6-(2H-1,2,3-triazol-2-yl)pyridin-3-yl)-1-(1,6-naphthyridin-5-yl)-5-(trifluoromethyl)-1H-pyrazole-4-carboxamide;

N-(6-(4-(4-aminobutyl)piperazine-1-carbonyl)-5-cyanopyridin-3-yl)-1-(isoquinolin-4-yl)-5-(trifluoromethyl)-1H-pyrazole-4-carboxamide;

N-(5-cyano-6-(2H-1,2,3-triazol-2-yl)pyridin-3-yl)-1-(phthalazin-1-yl)-5-(trifluoromethyl)-1H-pyrazole-4-carboxamide;

N-(5-cyano-6-(2H-1,2,3-triazol-2-yl)pyridin-3-yl)-1-(imidazo[1,2-a]pyrazin-8-yl)-5-(trifluoromethyl)-1H-pyrazole-4-carboxamide;

N-(5-chloro-6-(1H-imidazol-2-yl)pyridin-3-yl)-1-(isoquinolin-4-yl)-5-(trifluoromethyl)-1H-pyrazole-4-carboxamide;

N-(5-cyano-6-(2H-1,2,3-triazol-2-yl)pyridin-3-yl)-1-(quinoxalin-5-yl)-5-(trifluoromethyl)-1H-pyrazole-4-carboxamide;

N-(2-methyl-1-oxo-1,2,3,4-tetrahydroisoquinolin-7-yl)-1-(quinolin-5-yl)-5-(trifluoromethyl)-1H-pyrazole-4-carboxamide;

tert-butyl 2-(5-(4-((5-chloro-6-(2H-1,2,3-triazol-2-yl)pyridin-3-yl)carbamoyl)-5-(trifluoromethyl)-1H-pyrazol-1-yl)isoquinolin-1-yl)azetidine-1-carboxylate;

N-(3-(methylsulfonyl)-4-(1H-1,2,3-triazol-1-yl)phenyl)-1-(quinolin-5-yl)-5-(trifluoromethyl)-1H-pyrazole-4-carboxamide;

1-(1,5-bis(tetrahydrofuran-2-yl)isoquinolin-4-yl)-N-(5-chloro-6-(2H-1,2,3-triazol-2-yl)pyridin-3-yl)-5-(trifluoromethyl)-1H-pyrazole-4-carboxamide;

N-(4-methyl-3-oxo-3,4-dihydro-2H-benzo[b][1,4]oxazin-6-yl)-1-(quinolin-5-yl)-5-(trifluoromethyl)-1H-pyrazole-4-carboxamide;

1-(1-(azetidin-2-yl)isoquinolin-5-yl)-N-(5-chloro-6-(2H-1,2,3-triazol-2-yl)pyridin-3-yl)-5-(trifluoromethyl)-1H-pyrazole-4-carboxamide;

N-(3-(methylsulfonyl)-4-(2H-1,2,3-triazol-2-yl)phenyl)-1-(quinolin-5-yl)-5-(trifluoromethyl)-1H-pyrazole-4-carboxamide;

N-(2-methyl-1-oxo-1,2-dihydroisoquinolin-7-yl)-1-(quinolin-5-yl)-5-(trifluoromethyl)-1H-pyrazole-4-carboxamide;

1-(2-(azetidin-2-yl)quinolin-5-yl)-N-(5-chloro-6-(2H-1,2,3-triazol-2-yl)pyridin-3-yl)-5-(trifluoromethyl)-1H-pyrazole-4-carboxamide;

N-(3-oxo-3,4-dihydro-2H-benzo[b][1,4]oxazin-6-yl)-1-(quinolin-5-yl)-5-(trifluoromethyl)-1H-pyrazole-4-carboxamide;

1-(benzo[d]thiazol-4-yl)-N-(2,5-dimethyl-6-(2H-1,2,3-triazol-2-yl)pyridin-3-yl)-5-(trifluoromethyl)-1H-pyrazole-4-carboxamide;

N-(5-methyl-6-(3-methyl-2-oxo-2,3-dihydro-1H-imidazol-1-yl)pyridin-3-yl)-1-(quinolin-5-yl)-5-(trifluoromethyl)-1H-pyrazole-4-carboxamide;

N-(2,5-diethyl-6-(2H-1,2,3-triazol-2-yl)pyridin-3-yl)-1-(imidazo[1,2-a]pyridin-5-yl)-5-(trifluoromethyl)-1H-pyrazole-4-carboxamide;

N-(5-chloro-6-(2H-1,2,3-triazol-2-yl)pyridin-3-yl)-1-(2-(difluoromethyl)quinolin-5-yl)-5-(trifluoromethyl)-1H-pyrazole-4-carboxamide;

N-(5-cyano-6-(2H-1,2,3-triazol-2-yl)pyridin-3-yl)-1-(2-methylbenzo[d]oxazol-4-yl)-5-(trifluoromethyl)-1H-pyrazole-4-carboxamide;

N-(5-chloro-6-(2H-1,2,3-triazol-2-yl)pyridin-3-yl)-1-(2-methoxyquinolin-5-yl)-5-(trifluoromethyl)-1H-pyrazole-4-carboxamide;

1-(1-aminoisoquinolin-5-yl)-N-(5-cyano-6-(2H-1,2,3-triazol-2-yl)pyridin-3-yl)-5-(trifluoromethyl)-1H-pyrazole-4-carboxamide;

N-(5-chloro-6-(2H-1,2,3-triazol-2-yl)pyridin-3-yl)-1-(2-cyanoquinolin-5-yl)-5-(trifluoromethyl)-1H-pyrazole-4-carboxamide;

1-(2-methylimidazo[1,2-a]pyridin-5-yl)-5-(trifluoromethyl)-N-(2-(trifluoromethyl)pyridin-4-yl)-1H-pyrazole-4-carboxamide;

1-(2-chloroquinolin-4-yl)-N-(5-cyano-6-(2H-1,2,3-triazol-2-yl)pyridin-3-yl)-5-(trifluoromethyl)-1H-pyrazole-4-carboxamide;

N-(5-chloro-6-(2H-1,2,3-triazol-2-yl)pyridin-3-yl)-1-(2-chloroquinolin-5-yl)-5-(trifluoromethyl)-1H-pyrazole-4-carboxamide;

N-(5-chloro-6-(2H-1,2,3-triazol-2-yl)pyridin-3-yl)-1-(2-(tetrahydrofuran-2-yl)quinolin-5-yl)-5-(trifluoromethyl)-1H-pyrazole-4-carboxamide;

5-(4-((5-chloro-6-(2H-1,2,3-triazol-2-yl)pyridin-3-yl)carbamoyl)-5-(trifluoromethyl)-1H-pyrazol-1-yl)quinoline-2-carboxamide;

N-(5-chloro-6-(2H-1,2,3-triazol-2-yl)pyridin-3-yl)-1-(1H-pyrazolo[3,4-d]pyrimidin-4-yl)-5-(trifluoromethyl)-1H-pyrazole-4-carboxamide;

N-(5-cyano-6-(2H-1,2,3-triazol-2-yl)pyridin-3-yl)-1-(1,6-naphthyridin-4-yl)-5-(trifluoromethyl)-1H-pyrazole-4-carboxamide;

N-(5-cyano-6-(4-methylpiperazin-1-yl)pyridin-3-yl)-1-(quinolin-5-yl)-5-(trifluoromethyl)-1H-pyrazole-4-carboxamide;

(*R)—N-(5-chloro-6-(2H-1,2,3-triazol-2-yl)pyridin-3-yl)-1-(1-(1-hydroxyethyl)isoquinolin-5-yl)-5-(trifluoromethyl)-1H-pyrazole-4-carboxamide;

1-(benzo[d]thiazol-4-yl)-N-(5-cyano-2-methyl-4-(2H-1,2,3-triazol-2-yl)phenyl)-5-(trifluoromethyl)-1H-pyrazole-4-carboxamide;

(*R)—N-(5-chloro-6-(2H-1,2,3-triazol-2-yl)pyridin-3-yl)-1-(2-(tetrahydrofuran-2-yl)quinolin-5-yl)-5-(trifluoromethyl)-1H-pyrazole-4-carboxamide;

N-(5-chloro-6-(2-oxopyrrolidin-1-yl)pyridin-3-yl)-1-(isoquinolin-4-yl)-5-(trifluoromethyl)-1H-pyrazole-4-carboxamide;

N-(1-methyl-1H-pyrazolo[3,4-b]pyridin-5-yl)-1-(quinolin-5-yl)-5-(trifluoromethyl)-1H-pyrazole-4-carboxamide;

N-(5-chloro-6-(2H-1,2,3-triazol-2-yl)pyridin-3-yl)-1-(2-methyl-1-oxo-1,2-dihydroisoquinolin-5-yl)-5-(trifluoromethyl)-1H-pyrazole-4-carboxamide;

N-(5-chloro-6-(5-cyano-1H-1,2,3-triazol-1-yl)pyridin-3-yl)-1-(quinolin-5-yl)-5-(trifluoromethyl)-1H-pyrazole-4-carboxamide;

2-(2-chloro-4-(1-(quinolin-5-yl)-5-(trifluoromethyl)-1H-pyrazole-4-carboxamido)phenyl)-2H-1,2,3-triazole-4-carboxyli c acid;

N-(1H-pyrazolo[3,4-b]pyridin-5-yl)-1-(quinolin-5-yl)-5-(trifluoromethyl)-1H-pyrazole-4-carboxamide;

N-(5-cyano-6-(2H-1,2,3-triazol-2-yl)pyridin-3-yl)-1-(imidazo[1,2-a]pyridin-8-yl)-5-(trifluoromethyl)-1H-pyrazole-4-carboxamide;

(*S)—N-(5-chloro-6-(2H-1,2,3-triazol-2-yl)pyridin-3-yl)-1-(1-(1-hydroxyethyl)isoquinolin-5-yl)-5-(trifluoromethyl)-1H-pyrazole-4-carboxamide;

N-(2-methylpyridin-4-yl)-1-(1-oxo-1,2-dihydroisoquinolin-5-yl)-5-(trifluoromethyl)-1H-pyrazole-4-carboxamide;

1-(benzo[d][1,2,3]thiadiazol-4-yl)-N-(5-chloro-6-(2H-1,2,3-triazol-2-yl)pyridin-3-yl)-5-(trifluoromethyl)-1H-pyrazole-4-carboxamide;

N-(5-cyano-6-(2H-1,2,3-triazol-2-yl)pyridin-3-yl)-1-(2-methylthieno[3,2-b]pyridin-7-yl)-5-(trifluoromethyl)-1H-pyrazole-4-carboxamide;

1-(1-(azetidin-3-yl)isoquinolin-4-yl)-N-(5-chloro-6-(2H-1,2,3-triazol-2-yl)pyridin-3-yl)-5-(trifluoromethyl)-1H-pyrazole-4-carboxamide;

N-(5-chloro-6-(2H-1,2,3-triazol-2-yl)pyridin-3-yl)-1-(imidazo[1,5-a]pyridin-5-yl)-5-(trifluoromethyl)-1H-pyrazole-4-carboxamide;

1-(3-chloro-5-(1-(quinolin-5-yl)-5-(trifluoromethyl)-1H-pyrazole-4-carboxamido)pyridin-2-yl)-1H-1,2,3-triazole-4-carboxylic acid;

N-(5-methoxy-6-(1H-1,2,3-triazol-1-yl)pyridin-3-yl)-1-(quinolin-5-yl)-5-(trifluoromethyl)-1H-pyrazole-4-carboxamide;

N-(5-chloro-6-(2H-1,2,3-triazol-2-yl)pyridin-3-yl)-1-(2-oxo-1,2-dihydroquinolin-5-yl)-5-(trifluoromethyl)-1H-pyrazole-4-carboxamide;

N-(4-aminobutyl)-3-cyano-5-(1-(isoquinolin-4-yl)-5-(trifluoromethyl)-1H-pyrazole-4-carboxamido)picolinamide;

2-cyano-4-(1-(quinolin-5-yl)-5-(trifluoromethyl)-1H-pyrazole-4-carboxamido)benzoic acid N-(4-(4-(aminomethyl)-1H-pyrazol-1-yl)-3-methylphenyl)-1-(quinolin-5-yl)-5-(trifluoromethyl)-1H-pyrazole-4-carboxamide;

1-(2-aminoquinolin-4-yl)-N-(5-cyano-6-(2H-1,2,3-triazol-2-yl)pyridin-3-yl)-5-(trifluoromethyl)-1H-pyrazole-4-carboxamide;

N-(5-cyano-6-(2H-1,2,3-triazol-2-yl)pyridin-3-yl)-1-(1-methyl-1H-indazol-4-yl)-5-(trifluoromethyl)-1H-pyrazole-4-carboxamide;

1-(1-aminoisoquinolin-5-yl)-N-(5-chloro-6-(2H-1,2,3-triazol-2-yl)pyridin-3-yl)-5-(trifluoromethyl)-1H-pyrazole-4-carboxamide;

N-(5-methyl-6-(1-methyl-1H-tetrazol-5-yl)pyridin-3-yl)-1-(quinolin-5-yl)-5-(trifluoromethyl)-1H-pyrazole-4-carboxamide;

N-(5-cyano-6-(2H-1,2,3-triazol-2-yl)pyridin-3-yl)-1-(1-methyl-1H-pyrazolo[3,4-b]pyridin-4-yl)-5-(trifluoromethyl)-1H-pyrazole-4-carboxamide;

N-(5-chloro-6-(2H-1,2,3-triazol-2-yl)pyridin-3-yl)-1-(1-ethoxyisoquinolin-4-yl)-5-(trifluoromethyl)-1H-pyrazole-4-carboxamide;

1-(1-(azetidin-2-yl)isoquinolin-4-yl)-N-(5-chloro-6-(2H-1,2,3-triazol-2-yl)pyridin-3-yl)-5-(trifluoromethyl)-1H-pyrazole-4-carboxamide;

1-(2-aminoquinolin-5-yl)-N-(5-chloro-6-(2H-1,2,3-triazol-2-yl)pyridin-3-yl)-5-(trifluoromethyl)-1H-pyrazole-4-carboxamide;

1-(1-acetylisoquinolin-5-yl)-N-(5-chloro-6-(2H-1,2,3-triazol-2-yl)pyridin-3-yl)-5-(trifluoromethyl)-1H-pyrazole-4-carboxamide;

N-(5-chloro-6-(2H-1,2,3-triazol-2-yl)pyridin-3-yl)-1-(4-(difluoromethyl)quinolin-5-yl)-5-(trifluoromethyl)-1H-pyrazole-4-carboxamide;

N-(5-chloro-6-(2H-1,2,3-triazol-2-yl)pyridin-3-yl)-1-(1-(pyrrolidin-2-yl)isoquinolin-4-yl)-5-(trifluoromethyl)-1H-pyrazole-4-carboxamide;

N-(5-chloro-6-(difluoromethoxy)pyridin-3-yl)-1-(isoquinolin-4-yl)-5-(trifluoromethyl)-1H-pyrazole-4-carboxamide;

N-(5-chloro-6-(2H-1,2,3-triazol-2-yl)pyridin-3-yl)-1-(imidazo[1,2-b]pyridazin-6-yl)-5-(trifluoromethyl)-1H-pyrazole-4-carboxamide;

1-(1-aminoisoquinolin-4-yl)-N-(2,5-dimethyl-6-(2H-1,2,3-triazol-2-yl)pyridin-3-yl)-5-(trifluoromethyl)-1H-pyrazole-4-carboxamide;

N-(5-chloro-6-(2H-1,2,3-triazol-2-yl)pyridin-3-yl)-1-(1-methoxyisoquinolin-5-yl)-5-(trifluoromethyl)-1H-pyrazole-4-carboxamide;

1-(2-aminoquinolin-5-yl)-N-(5-cyano-6-(2H-1,2,3-triazol-2-yl)pyridin-3-yl)-5-(trifluoromethyl)-1H-pyrazole-4-carboxamide;

2-(2-chloro-4-(1-(quinolin-5-yl)-5-(trifluoromethyl)-1H-pyrazole-4-carboxamido)phenyl)-2H-1,2,3-triazole-4-carboxamide;

N-(5-chloro-6-(2H-1,2,3-triazol-2-yl)pyridin-3-yl)-1-(1-(methylthio)isoquinolin-4-yl)-5-(trifluoromethyl)-1H-pyrazole-4-carboxamide;

N-(5-chloro-6-(2H-1,2,3-triazol-2-yl)pyridin-3-yl)-3-fluoro-1-(quinolin-5-yl)-5-(trifluoromethyl)-1H-pyrazole-4-carboxamide;

N-(5-cyano-6-(2H-1,2,3-triazol-2-yl)pyridin-3-yl)-1-(2-methylbenzo[d]thiazol-4-yl)-5-(trifluoromethyl)-1H-pyrazole-4-carboxamide;

1-(3-chloro-5-(1-(quinolin-5-yl)-5-(trifluoromethyl)-1H-pyrazole-4-carboxamido)pyridin-2-yl)-1H-1,2,3-triazole-4-carboxamide;

N-(5-chloro-6-(2H-1,2,3-triazol-2-yl)pyridin-3-yl)-5-cyano-1-(quinolin-5-yl)-1H-pyrazole-4-carboxamide;

1-(7-methylpyrazolo[1,5-a]pyridin-4-yl)-5-(trifluoromethyl)-N-(2-(trifluoromethyl)pyridin-4-yl)-1H-pyrazole-4-carboxamide;

N-(6-(2H-[1,2,3]triazolo[4,5-c]pyridin-2-yl)-5-chloropyridin-3-yl)-1-(quinolin-5-yl)-5-(trifluoromethyl)-1H-pyrazole-4-carboxamide;

1-(2-acetylquinolin-4-yl)-N-(5-chloro-6-(2H-1,2,3-triazol-2-yl)pyridin-3-yl)-5-(trifluoromethyl)-1H-pyrazole-4-carboxamide;

N-(5-cyano-6-(2H-1,2,3-triazol-2-yl)pyridin-3-yl)-1-(2-methylbenzo[d]thiazol-7-yl)-5-(trifluoromethyl)-1H-pyrazole-4-carboxamide;

N-(6-(5-(aminomethyl)-1H-1,2,3-triazol-1-yl)-5-chloropyridin-3-yl)-1-(quinolin-5-yl)-5-(trifluoromethyl)-1H-pyrazole-4-carboxamide;

1-(2-(azetidin-2-yl)quinolin-4-yl)-N-(5-chloro-6-(2H-1,2,3-triazol-2-yl)pyridin-3-yl)-5-(trifluoromethyl)-1H-pyrazole-4-carboxamide;

N-(5-chloro-6-(2H-1,2,3-triazol-2-yl)pyridin-3-yl)-1-(1-(1-ethoxyethyl)isoquinolin-4-yl)-5-(trifluoromethyl)-1H-pyrazole-4-carboxamide;

methyl 1-(3-chloro-5-(1-(quinolin-5-yl)-5-(trifluoromethyl)-1H-pyrazole-4-carboxamido)pyridin-2-yl)-1H-1,2,3-triazole-4-carboxylate 1-(imidazo[1,2-a]pyridin-5-yl)-5-(trifluoromethyl)-N-(2-(trifluoromethyl)pyridin-4-yl)-1H-pyrazole-4-carboxamide;

N-(5-chloro-2-ethyl-6-(2H-1,2,3-triazol-2-yl)pyridin-3-yl)-1-(imidazo[1,2-a]pyridin-5-yl)-5-(trifluoromethyl)-1H-pyrazole-4-carboxamide;

N-(5-chloro-6-(2H-1,2,3-triazol-2-yl)pyridin-3-yl)-1-(2-(difluoromethyl)thieno[2,3-c]pyridin-4-yl)-5-(trifluoromethyl)-1H-pyrazole-4-carboxamide;

N-(5-cyano-6-(2H-1,2,3-triazol-2-yl)pyridin-3-yl)-1-(imidazo[1,2-a]pyrimidin-5-yl)-5-(trifluoromethyl)-1H-pyrazole-4-carboxamide;

N-(5-methoxy-6-(2H-1,2,3-triazol-2-yl)pyridin-3-yl)-1-(quinolin-5-yl)-5-(trifluoromethyl)-1H-pyrazole-4-carboxamide;

N-(5-chloro-6-(2H-1,2,3-triazol-2-yl)pyridin-3-yl)-1-(2-methoxyquinolin-4-yl)-5-(trifluoromethyl)-1H-pyrazole-4-carboxamide;

1-(benzo[d][1,2,3]thiadiazol-7-yl)-N-(5-chloro-2-methyl-6-(1H-pyrazol-1-yl)pyridin-3-yl)-5-(trifluoromethyl)-1H-pyrazole-4-carboxamide;

N-(2,5-dimethyl-6-(2H-1,2,3-triazol-2-yl)pyridin-3-yl)-1-(1-oxo-1,2-dihydroisoquinolin-5-yl)-5-(trifluoromethyl)-1H-pyrazole-4-carboxamide;

1-(benzo[d]thiazol-4-yl)-N-(5-chloro-2-methyl-6-(2H-1,2,3-triazol-2-yl)pyridin-3-yl)-5-(trifluoromethyl)-1H-pyrazole-4-carboxamide;

N-(5-chloro-6-(5-(methoxymethyl)-1H-1,2,3-triazol-1-yl)pyridin-3-yl)-1-(quinolin-5-yl)-5-(trifluoromethyl)-1H-pyrazole-4-carboxamide;

N-(6-(2H-[1,2,3]triazolo[4,5-b]pyridin-2-yl)-5-chloropyridin-3-yl)-1-(quinolin-5-yl)-5-(trifluoromethyl)-1H-pyrazole-4-carboxamide;

N-(5-cyano-6-(2H-1,2,3-triazol-2-yl)pyridin-3-yl)-1-(2-methyl-[1,2,4]triazolo[1,5-a]pyridin-5-yl)-5-(trifluoromethyl)-1H-pyrazole-4-carboxamide;

3-(3-cyano-5-(1-(quinolin-5-yl)-5-(trifluoromethyl)-1H-pyrazole-4-carboxamido)pyridin-2-yl)-1-methyl-1H-pyrazole-5-carboxylic acid;

1-(benzo[d]thiazol-4-yl)-N-(5-cyano-2-methyl-6-(2H-1,2,3-triazol-2-yl)pyridin-3-yl)-5-(trifluoromethyl)-1H-pyrazole-4-carboxamide;

1-(1-aminoisoquinolin-4-yl)-N-(5-chloro-2-methyl-6-(1-methyl-1H-pyrazol-3-yl)pyridin-3-yl)-5-(trifluoromethyl)-1H-pyrazole-4-carboxamide;

N-(6-(3H-[1,2,3]triazolo[4,5-b]pyridin-3-yl)-5-chloropyridin-3-yl)-1-(quinolin-5-yl)-5-(trifluoromethyl)-1H-pyrazole-4-carboxamide;

methyl 2-(2-chloro-4-(1-(quinolin-5-yl)-5-(trifluoromethyl)-1H-pyrazole-4-carboxamido)phenyl)-2H-1,2,3-triazole-4-carboxylate;

N-(5-cyano-6-(2-methyl-2H-1,2,3-triazol-4-yl)pyridin-3-yl)-1-(quinolin-5-yl)-5-(trifluoromethyl)-1H-pyrazole-4-carboxamide;

N-(3-chloro-4-(5-oxo-4,5-dihydro-1H-1,2,4-triazol-3-yl)phenyl)-1-(quinolin-5-yl)-5-(trifluoromethyl)-1H-pyrazole-4-carboxamide;

methyl 3-chloro-5-(1-(quinolin-5-yl)-5-(trifluoromethyl)-1H-pyrazole-4-carboxamido)picolinate;

N-(6-(1H-[1,2,3]triazolo[4,5-c]pyridin-1-yl)-5-chloropyridin-3-yl)-1-(quinolin-5-yl)-5-(trifluoromethyl)-1H-pyrazole-4-carboxamide;

N-(5-cyanopyridin-3-yl)-1-(1-oxo-1,2-dihydroisoquinolin-5-yl)-5-(trifluoromethyl)-1H-pyrazole-4-carboxamide;

N-(5-cyano-6-(2H-1,2,3-triazol-2-yl)pyridin-3-yl)-1-(1-methyl-1H-pyrazolo[3,4-c]pyridin-7-yl)-5-(trifluoromethyl)-1H-pyrazole-4-carboxamide;

1-(1-aminoisoquinolin-4-yl)-N-(5-chloro-2-methyl-6-(1H-pyrazol-1-yl)pyridin-3-yl)-5-(trifluoromethyl)-1H-pyrazole-4-carboxamide;

N-(5-chloro-6-(2H-1,2,3-triazol-2-yl)pyridin-3-yl)-1-(1-(dimethylamino)isoquinolin-4-yl)-5-(trifluoromethyl)-1H-pyrazole-4-carboxamide;

N-(5-chloro-6-(2H-1,2,3-triazol-2-yl)pyridin-3-yl)-1-(8-(difluoromethyl)quinolin-5-yl)-5-(trifluoromethyl)-1H-pyrazole-4-carboxamide;

(*R)—N-(5-chloro-6-(2H-1,2,3-triazol-2-yl)pyridin-3-yl)-1-(1-(4-oxotetrahydrofuran-2-yl)isoquinolin-4-yl)-5-(trifluoromethyl)-1H-pyrazole-4-carboxamide;

N-(5-cyano-6-(2H-1,2,3-triazol-2-yl)pyridin-3-yl)-1-(2-methylfuro[3,2-b]pyridin-7-yl)-5-(trifluoromethyl)-1H-pyrazole-4-carboxamide;

N-(5-chloro-6-(2H-1,2,3-triazol-2-yl)pyridin-3-yl)-1-(1-(difluoromethyl)isoquinolin-5-yl)-5-(trifluoromethyl)-1H-pyrazole-4-carboxamide;

N-(5-cyano-6-(2H-1,2,3-triazol-2-yl)pyridin-3-yl)-1-(1-methyl-1H-indazol-7-yl)-5-(trifluoromethyl)-1H-pyrazole-4-carboxamide;

N-(5-chloro-6-(2H-1,2,3-triazol-2-yl)pyridin-3-yl)-1-(6-fluoroimidazo[1,2-a]pyridin-5-yl)-5-(trifluoromethyl)-1H-pyrazole-4-carboxamide;

N-(5-chloro-6-(2H-1,2,3-triazol-2-yl)pyridin-3-yl)-1-(5-fluoroquinolin-8-yl)-5-(trifluoromethyl)-1H-pyrazole-4-carboxamide;

N-(5-cyano-6-(2H-1,2,3-triazol-2-yl)pyridin-3-yl)-1-(1H-pyrazolo[4,3-b]pyridin-7-yl)-5-(trifluoromethyl)-1H-pyrazole-4-carboxamide;

N-(5-cyano-6-(2H-1,2,3-triazol-2-yl)pyridin-3-yl)-1-(4-fluoroisoquinolin-1-yl)-5-(trifluoromethyl)-1H-pyrazole-4-carboxamide;

5-(4-((5-chloro-6-(2H-1,2,3-triazol-2-yl)pyridin-3-yl)carbamoyl)-5-(trifluoromethyl)-1H-pyrazol-1-yl)isoquinoline-1-carboxamide;

N-(5-chloro-6-(2H-1,2,3-triazol-2-yl)pyridin-3-yl)-1-(1-(methylamino)isoquinolin-4-yl)-5-(trifluoromethyl)-1H-pyrazole-4-carboxamide;

(*S)—N-(5-chloro-6-(2H-1,2,3-triazol-2-yl)pyridin-3-yl)-1-(1-(1-hydroxyethyl)isoquinolin-4-yl)-5-(trifluoromethyl)-1H-pyrazole-4-carboxamide;

N-(5-chloro-6-(2H-1,2,3-triazol-2-yl)pyridin-3-yl)-1-(1-(1,1-difluoroethyl)isoquinolin-4-yl)-5-(trifluoromethyl)-1H-pyrazole-4-carboxamide;

5-chloro-N-(5-chloro-6-(2H-1,2,3-triazol-2-yl)pyridin-3-yl)-1-(quinolin-5-yl)-1H-pyrazole-4-carboxamide;

1-(1-aminoisoquinolin-4-yl)-N-(5-chloro-2-methyl-4-(2H-1,2,3-triazol-2-yl)phenyl)-5-(trifluoromethyl)-1H-pyrazole-4-carboxamide;

N-(5-chloro-6-(2H-1,2,3-triazol-2-yl)pyridin-3-yl)-1-(1-methoxyisoquinolin-4-yl)-5-(trifluoromethyl)-1H-pyrazole-4-carboxamide;

(*S)—N-(5-chloro-6-(2H-1,2,3-triazol-2-yl)pyridin-3-yl)-1-(1-(4-oxotetrahydrofuran-2-yl)isoquinolin-4-yl)-5-(trifluoromethyl)-1H-pyrazole-4-carboxamide;

(*S)—N-(5-chloro-6-(2H-1,2,3-triazol-2-yl)pyridin-3-yl)-1-(1-(tetrahydrofuran-2-yl)isoquinolin-4-yl)-5-(trifluoromethyl)-1H-pyrazole-4-carboxamide;

N-(5-chloro-6-(2H-1,2,3-triazol-2-yl)pyridin-3-yl)-1-(1-fluoroisoquinolin-4-yl)-5-(trifluoromethyl)-1H-pyrazole-4-carboxamide;

N-(5-cyano-6-(2H-1,2,3-triazol-2-yl)pyridin-3-yl)-1-(1-methyl-1H-pyrazolo[3,4-b]pyridin-3-yl)-5-(trifluoromethyl)-1H-pyrazole-4-carboxamide;

N-(5-chloro-2-methyl-6-(2H-1,2,3-triazol-2-yl)pyridin-3-yl)-1-(8-fluoroimidazo[1,2-a]pyridin-5-yl)-5-(trifluoromethyl)-1H-pyrazole-4-carboxamide;

N-(5-cyano-6-(2H-1,2,3-triazol-2-yl)pyridin-3-yl)-1-(1-methyl-1H-indazol-3-yl)-5-(trifluoromethyl)-1H-pyrazole-4-carboxamide;

N-(5-chloro-6-(2H-1,2,3-triazol-2-yl)pyridin-3-yl)-1-(1-(5-oxopyrrolidin-2-yl)isoquinolin-4-yl)-5-(trifluoromethyl)-1H-pyrazole-4-carboxamide;

methyl 3-(3-cyano-5-(1-(quinolin-5-yl)-5-(trifluoromethyl)-1H-pyrazole-4-carboxamido)pyridin-2-yl)-1-methyl-1H-pyrazole-5-carboxylate;

N-(5-cyano-6-(1-methyl-1H-pyrazol-3-yl)pyridin-3-yl)-1-(8-fluoroquinolin-5-yl)-5-(trifluoromethyl)-1H-pyrazole-4-carboxamide;

N-(5-cyano-6-(2H-1,2,3-triazol-2-yl)pyridin-3-yl)-1-(1,5-naphthyridin-4-yl)-5-(trifluoromethyl)-1H-pyrazole-4-carboxamide;

N-(5-chloro-6-(5-((dimethylamino)methyl)-1H-1,2,3-triazol-1-yl)pyridin-3-yl)-1-(quinolin-5-yl)-5-(trifluoromethyl)-1H-pyrazole-4-carboxamide;

N-(5-cyano-6-(2H-1,2,3-triazol-2-yl)pyridin-3-yl)-1-(2-methylbenzo[d]oxazol-7-yl)-5-(trifluoromethyl)-1H-pyrazole-4-carboxamide;

N-(6-(4-(aminomethyl)-2H-1,2,3-triazol-2-yl)-5-chloropyridin-3-yl)-1-(quinolin-5-yl)-5-(trifluoromethyl)-1H-pyrazole-4-carboxamide;

N-(5-chloro-6-(1-methyl-1H-pyrazol-3-yl)pyridin-3-yl)-1-(8-fluoroquinolin-5-yl)-5-(trifluoromethyl)-1H-pyrazole-4-carboxamide;

1-(1-aminoisoquinolin-4-yl)-N-(5-cyano-2-methyl-4-(2H-1,2,3-triazol-2-yl)phenyl)-5-(trifluoromethyl)-1H-pyrazole-4-carboxamide;

1-(benzo[d][1,2,3]thiadiazol-7-yl)-N-(5-chloro-2-fluoro-4-(2H-1,2,3-triazol-2-yl)phenyl)-5-(trifluoromethyl)-1H-pyrazole-4-carboxamide;

1-([1,2,4]triazolo[1,5-a]pyridin-5-yl)-N-(5-cyano-6-(2H-1,2,3-triazol-2-yl)pyridin-3-yl)-5-(trifluoromethyl)-1H-pyrazole-4-carboxamide;

N-(5-chloro-6-(2H-1,2,3-triazol-2-yl)pyridin-3-yl)-1-(1-((N-methylformamido)methyl)isoquinolin-4-yl)-5-(trifluoromethyl)-1H-pyrazole-4-carboxamide;

N-(5-cyano-6-(2H-1,2,3-triazol-2-yl)pyridin-3-yl)-1-(imidazo[1,2-a]pyrazin-5-yl)-5-(trifluoromethyl)-1H-pyrazole-4-carboxamide;

N-(5-cyano-6-(2H-1,2,3-triazol-2-yl)pyridin-3-yl)-1-(1,7-naphthyridin-4-yl)-5-(trifluoromethyl)-1H-pyrazole-4-carboxamide;

N-(5-chloro-2-methyl-6-(1H-pyrazol-1-yl)pyridin-3-yl)-1-(1-oxo-1,2-dihydroisoquinolin-5-yl)-5-(trifluoromethyl)-1H-pyrazole-4-carboxamide;

N-(5-chloro-6-(2H-1,2,3-triazol-2-yl)pyridin-3-yl)-1-(2-fluoroquinolin-5-yl)-5-(trifluoromethyl)-1H-pyrazole-4-carboxamide;

1-(2-aminobenzo[d]thiazol-7-yl)-N-(5-chloro-6-(2H-1,2,3-triazol-2-yl)pyridin-3-yl)-5-(trifluoromethyl)-1H-pyrazole-4-carboxamide;

N-(5-chloro-6-(2H-1,2,3-triazol-2-yl)pyridin-3-yl)-1-(isothiazolo[5,4-b]pyridin-3-yl)-5-(trifluoromethyl)-1H-pyrazole-4-carboxamide;

N-(5-cyano-6-(1H-pyrrol-1-yl)pyridin-3-yl)-1-(quinolin-5-yl)-5-(trifluoromethyl)-1H-pyrazole-4-carboxamide;

N-(5-cyano-6-(2H-1,2,3-triazol-2-yl)pyridin-3-yl)-1-(1-methoxyisoquinolin-5-yl)-5-(trifluoromethyl)-1H-pyrazole-4-carboxamide;

1-(2-aminobenzo[d]thiazol-7-yl)-N-(5-cyano-6-(2H-1,2,3-triazol-2-yl)pyridin-3-yl)-5-(trifluoromethyl)-1H-pyrazole-4-carboxamide;

N-(6-(1H-1,2,3-triazol-1-yl)-5-(trifluoromethyl)pyridin-3-yl)-1-(quinolin-5-yl)-5-(trifluoromethyl)-1H-pyrazole-4-carboxamide;

1-(benzo[d]isoxazol-3-yl)-N-(5-chloro-6-(2H-1,2,3-triazol-2-yl)pyridin-3-yl)-5-(trifluoromethyl)-1H-pyrazole-4-carboxamide;

1-(1-oxo-1,2-dihydroisoquinolin-5-yl)-5-(trifluoromethyl)-N-(2-(trifluoromethyl)pyridin-4-yl)-1H-pyrazole-4-carboxamide;

N-(5-chloro-6-(2H-1,2,3-triazol-2-yl)pyridin-3-yl)-1-(8-fluoro-1-(methylamino)isoquinolin-4-yl)-5-(trifluoromethyl)-1H-pyrazole-4-carboxamide;

5-bromo-N-(5-chloro-6-(2H-1,2,3-triazol-2-yl)pyridin-3-yl)-1-(quinolin-5-yl)-1H-pyrazole-4-carboxamide;

N-(5-chloro-6-(2H-1,2,3-triazol-2-yl)pyridin-3-yl)-1-(2-cyanoquinolin-4-yl)-5-(trifluoromethyl)-1H-pyrazole-4-carboxamide;

N-(5-chloro-6-(2H-1,2,3-triazol-2-yl)pyridin-3-yl)-1-(1-chloroisoquinolin-4-yl)-5-(trifluoromethyl)-1H-pyrazole-4-carboxamide;

1-(pyrazolo[1,5-a]pyridin-4-yl)-5-(trifluoromethyl)-N-(2-(trifluoromethyl)pyridin-4-yl)-1H-pyrazole-4-carboxamide;

N-(5-chloro-6-(2H-1,2,3-triazol-2-yl)pyridin-3-yl)-1-(2-methylimidazo[1,2-a]pyridin-5-yl)-5-(trifluoromethyl)-1H-pyrazole-4-carboxamide;

1-(1-oxo-1,2-dihydroisoquinolin-5-yl)-5-(trifluoromethyl)-N-(5-(trifluoromethyl)pyridin-3-yl)-1H-pyrazole-4-carboxamide;

1-(1-(1,4-dioxan-2-yl)isoquinolin-4-yl)-N-(5-chloro-6-(2H-1,2,3-triazol-2-yl)pyridin-3-yl)-5-(trifluoromethyl)-1H-pyrazole-4-carboxamide;

N-(5-cyano-6-(2H-1,2,3-triazol-2-yl)pyridin-3-yl)-1-(1H-indazol-7-yl)-5-(trifluoromethyl)-1H-pyrazole-4-carboxamide;

4-(4-((5-chloro-6-(2H-1,2,3-triazol-2-yl)pyridin-3-yl)carbamoyl)-5-(trifluoromethyl)-1H-pyrazol-1-yl)quinoline-2-carboxamide;

N-(5-chloro-6-(5-(hydroxymethyl)-1H-1,2,3-triazol-1-yl)pyridin-3-yl)-1-(1-oxo-1,2-dihydroisoquinolin-5-yl)-5-(trifluoromethyl)-1H-pyrazole-4-carboxamide;

N-(5-chloro-6-(2H-1,2,3-triazol-2-yl)pyridin-3-yl)-1-(1-(4-oxotetrahydrofuran-2-yl)isoquinolin-4-yl)-5-(trifluoromethyl)-1H-pyrazole-4-carboxamide;

N-(6-(4-amino-2H-1,2,3-triazol-2-yl)-5-chloropyridin-3-yl)-1-(benzo[d]thiazol-4-yl)-5-(trifluoromethyl)-1H-pyrazole-4-carboxamide;

1-(2-amino-[1,2,4]triazolo[1,5-a]pyridin-5-yl)-N-(5-cyano-6-(2H-1,2,3-triazol-2-yl)pyridin-3-yl)-5-(trifluoromethyl)-1H-pyrazole-4-carboxamide;

(*R)—N-(5-chloro-6-(2H-1,2,3-triazol-2-yl)pyridin-3-yl)-1-(1-(tetrahydrofuran-2-yl)isoquinolin-4-yl)-5-(trifluoromethyl)-1H-pyrazole-4-carboxamide;

N-(5-bromo-6-(1H-1,2,3-triazol-1-yl)pyridin-3-yl)-1-(quinolin-5-yl)-5-(trifluoromethyl)-1H-pyrazole-4-carboxamide;

N-(5-chloro-6-(oxazol-2-yl)pyridin-3-yl)-1-(8-fluoroquinolin-5-yl)-5-(trifluoromethyl)-1H-pyrazole-4-carboxamide;

N-(5-chloro-6-methoxypyridin-3-yl)-1-(1-oxo-1,2-dihydroisoquinolin-5-yl)-5-(trifluoromethyl)-1H-pyrazole-4-carboxamide;

N-(5-chloro-6-(2H-1,2,3-triazol-2-yl)pyridin-3-yl)-1-(1-(difluoromethyl)isoquinolin-4-yl)-5-(trifluoromethyl)-1H-pyrazole-4-carboxamide;

N-(5-cyano-6-(2H-1,2,3-triazol-2-yl)pyridin-3-yl)-1-(1-fluoroisoquinolin-4-yl)-5-(trifluoromethyl)-1H-pyrazole-4-carboxamide;

N-(5-chloro-6-(2H-1,2,3-triazol-2-yl)pyridin-3-yl)-1-(1-(methoxymethyl)isoquinolin-4-yl)-5-(trifluoromethyl)-1H-pyrazole-4-carboxamide;

N-(5-chloro-6-(2H-1,2,3-triazol-2-yl)pyridin-3-yl)-1-(2-(1-hydroxyethyl)quinolin-4-yl)-5-(trifluoromethyl)-1H-pyrazole-4-carboxamide;

N-(5-chloro-2-methyl-6-(2H-1,2,3-triazol-2-yl)pyridin-3-yl)-1-(7-methylpyrazolo[1,5-a]pyridin-4-yl)-5-(trifluoromethyl)-1H-pyrazole-4-carboxamide;

1-(1-aminoisoquinolin-4-yl)-N-(5-chloro-2-fluoro-4-(2H-1,2,3-triazol-2-yl)phenyl)-5-(trifluoromethyl)-1H-pyrazole-4-carboxamide;

1-(benzo[d]isothiazol-3-yl)-N-(5-chloro-6-(2H-1,2,3-triazol-2-yl)pyridin-3-yl)-5-(trifluoromethyl)-1H-pyrazole-4-carboxamide;

N-(5-cyano-6-(2H-1,2,3-triazol-2-yl)pyridin-3-yl)-1-(2-fluoroquinolin-5-yl)-5-(trifluoromethyl)-1H-pyrazole-4-carboxamide;

N-(5-chloro-6-(2H-1,2,3-triazol-2-yl)pyridin-3-yl)-1-(isoquinolin-5-yl)-5-(trifluoromethyl)-1H-pyrazole-4-carboxamide;

N-(5-cyano-6-(2H-1,2,3-triazol-2-yl)pyridin-3-yl)-1-(furo[2,3-d]pyrimidin-4-yl)-5-(trifluoromethyl)-1H-pyrazole-4-carboxamide;

N-(5-cyano-6-(2H-1,2,3-triazol-2-yl)pyridin-3-yl)-1-(imidazo[1,2-a]pyridin-3-yl)-5-(trifluoromethyl)-1H-pyrazole-4-carboxamide;

N-(5-chloro-2-methyl-6-(2H-1,2,3-triazol-2-yl)pyridin-3-yl)-1-(imidazo[1,2-a]pyridin-5-yl)-5-(trifluoromethyl)-1H-pyrazole-4-carboxamide;

4-(4-((5-chloro-6-(2H-1,2,3-triazol-2-yl)pyridin-3-yl)carbamoyl)-5-(trifluoromethyl)-1H-pyrazol-1-yl)thieno[2,3-c]pyridine 6-oxide;

1-(benzo[d][1,2,3]thiadiazol-7-yl)-N-(5-chloro-6-(1-methyl-1H-pyrazol-3-yl)pyridin-3-yl)-5-(trifluoromethyl)-1H-pyrazole-4-carboxamide;

N-(5-cyano-6-(2H-1,2,3-triazol-2-yl)pyridin-3-yl)-1-(thiazolo[5,4-d]pyrimidin-7-yl)-5-(trifluoromethyl)-1H-pyrazole-4-carboxamide;

N-(5-cyano-6-(2H-1,2,3-triazol-2-yl)pyridin-3-yl)-1-(2-methylimidazo[1,2-a]pyridin-3-yl)-5-(trifluoromethyl)-1H-pyrazole-4-carboxamide;

N-(5-cyano-6-methoxypyridin-3-yl)-1-(1-oxo-1,2-dihydroisoquinolin-5-yl)-5-(trifluoromethyl)-1H-pyrazole-4-carboxamide;

N-(5-chloro-2-methyl-6-(1-methyl-1H-pyrazol-3-yl)pyridin-3-yl)-1-(1-oxo-1,2-dihydroisoquinolin-5-yl)-5-(trifluoromethyl)-1H-pyrazole-4-carboxamide;

N-(5-cyano-6-(2H-1,2,3-triazol-2-yl)pyridin-3-yl)-1-(quinazolin-4-yl)-5-(trifluoromethyl)-1H-pyrazole-4-carboxamide;

N-(5-chloro-2-methyl-4-(2H-1,2,3-triazol-2-yl)phenyl)-1-(8-fluoroisoquinolin-4-yl)-5-(trifluoromethyl)-1H-pyrazole-4-carboxamide;

N-(5-chloro-2-methyl-4-(2H-1,2,3-triazol-2-yl)phenyl)-1-(1-oxo-1,2-dihydroisoquinolin-5-yl)-5-(trifluoromethyl)-1H-pyrazole-4-carboxamide;

(*R)—N-(5-chloro-6-(2H-1,2,3-triazol-2-yl)pyridin-3-yl)-1-(1-(1-hydroxyethyl)isoquinolin-4-yl)-5-(trifluoromethyl)-1H-pyrazole-4-carboxamide;

N-(5-chloro-6-(2H-1,2,3-triazol-2-yl)pyridin-3-yl)-1-(1-cyanoisoquinolin-4-yl)-5-(trifluoromethyl)-1H-pyrazole-4-carboxamide;

N-(5-chloro-2-fluoro-4-(2H-1,2,3-triazol-2-yl)phenyl)-1-(1-oxo-1,2-dihydroisoquinolin-5-yl)-5-(trifluoromethyl)-1H-pyrazole-4-carboxamide;

N-(5-chloro-6-(2H-1,2,3-triazol-2-yl)pyridin-3-yl)-1-(1-(1-hydroxyethyl)isoquinolin-4-yl)-5-(trifluoromethyl)-1H-pyrazole-4-carboxamide;

N-(5-cyano-2-methyl-4-(2H-1,2,3-triazol-2-yl)phenyl)-1-(1-oxo-1,2-dihydroisoquinolin-5-yl)-5-(trifluoromethyl)-1H-pyrazole-4-carboxamide;

N-(5-chloro-6-(4-methyl-1H-1,2,3-triazol-1-yl)pyridin-3-yl)-1-(quinolin-5-yl)-5-(trifluoromethyl)-1H-pyrazole-4-carboxamide;

N-(5-methyl-6-(2-methyl-2H-tetrazol-5-yl)pyridin-3-yl)-1-(quinolin-5-yl)-5-(trifluoromethyl)-1H-pyrazole-4-carboxamide;

N-(5-chloro-6-(2H-1,2,3-triazol-2-yl)pyridin-3-yl)-1-(7-(difluoromethyl)thieno[2,3-c]pyridin-4-yl)-5-(trifluoromethyl)-1H-pyrazole-4-carboxamide;

N-(5-chloro-6-(2H-1,2,3-triazol-2-yl)pyridin-3-yl)-1-(1-(tetrahydrofuran-2-yl)isoquinolin-4-yl)-5-(trifluoromethyl)-1H-pyrazole-4-carboxamide;

N-(5-chloro-6-(4-(methoxymethyl)-2H-1,2,3-triazol-2-yl)pyridin-3-yl)-1-(quinolin-5-yl)-5-(trifluoromethyl)-1H-pyrazole-4-carboxamide;

N-(4-(4-(aminomethyl)-1H-pyrazol-1-yl)-3-chlorophenyl)-1-(quinolin-5-yl)-5-(trifluoromethyl)-1H-pyrazole-4-carboxamide;

1-(1-aminoisoquinolin-4-yl)-N-(5-cyano-2-methyl-6-(2H-1,2,3-triazol-2-yl)pyridin-3-yl)-5-(trifluoromethyl)-1H-pyrazole-4-carboxamide;

1-(benzo[d]thiazol-4-yl)-N-(5-chloro-6-(2H-1,2,3-triazol-2-yl)pyridin-3-yl)-5-(trifluoromethyl)-1H-pyrazole-4-carboxamide;

N-(5-chloro-6-(2H-1,2,3-triazol-2-yl)pyridin-3-yl)-1-(1-hydroxyisoquinolin-4-yl)-5-(trifluoromethyl)-1H-pyrazole-4-carboxamide;

N-(5-chloro-6-(2H-tetrazol-5-yl)pyridin-3-yl)-1-(quinolin-5-yl)-5-(trifluoromethyl)-1H-pyrazole-4-carboxamide;

N-(5-cyano-6-(2H-1,2,3-triazol-2-yl)pyridin-3-yl)-1-(8-fluoroquinolin-5-yl)-5-(trifluoromethyl)-1H-pyrazole-4-carboxamide;

N-(5-chloro-6-(2H-1,2,3-triazol-2-yl)pyridin-3-yl)-1-(2-(difluoromethyl)quinolin-4-yl)-5-(trifluoromethyl)-1H-pyrazole-4-carboxamide;

N-(5-cyano-6-(2H-1,2,3-triazol-2-yl)pyridin-3-yl)-1-(8-fluoro-1-(methylamino)isoquinolin-4-yl)-5-(trifluoromethyl)-1H-pyrazole-4-carboxamide;

N-(5-chloro-6-(2H-1,2,3-triazol-4-yl)pyridin-3-yl)-1-(quinolin-5-yl)-5-(trifluoromethyl)-1H-pyrazole-4-carboxamide;

N-(5-chloro-2-fluoro-4-(2H-1,2,3-triazol-2-yl)phenyl)-1-(8-fluoroisoquinolin-4-yl)-5-(trifluoromethyl)-1H-pyrazole-4-carboxamide;

N-(5-chloro-6-(2H-1,2,3-triazol-2-yl)pyridin-3-yl)-1-(1-methyl-2-oxo-1,2-dihydroquinolin-4-yl)-5-(trifluoromethyl)-1H-pyrazole-4-carboxamide;

(*R)—N-(5-chloro-6-(2H-1,2,3-triazol-2-yl)pyridin-3-yl)-1-(1-(3-hydroxypyrrolidin-1-yl)isoquinolin-4-yl)-5-(trifluoromethyl)-1H-pyrazole-4-carboxamide;

N-(5-chloro-6-(2H-1,2,3-triazol-2-yl)pyridin-3-yl)-1-(1-(hydroxymethyl)isoquinolin-4-yl)-5-(trifluoromethyl)-1H-pyrazole-4-carboxamide;

N-(5-cyano-6-(2H-1,2,3-triazol-2-yl)pyridin-3-yl)-1-(3-methylthieno[3,2-b]pyridin-7-yl)-5-(trifluoromethyl)-1H-pyrazole-4-carboxamide;

1-(benzo[d]oxazol-4-yl)-N-(5-cyano-6-(2H-1,2,3-triazol-2-yl)pyridin-3-yl)-5-(trifluoromethyl)-1H-pyrazole-4-carboxamide;

N-(5-cyano-6-(2H-1,2,3-triazol-2-yl)pyridin-3-yl)-1-(4-fluoronaphthalen-1-yl)-5-(trifluoromethyl)-1H-pyrazole-4-carboxamide;

N-(3-chloro-4-(4-(hydroxymethyl)-1H-pyrazol-1-yl)phenyl)-1-(quinolin-5-yl)-5-(trifluoromethyl)-1H-pyrazole-4-carboxamide;

N-(5-cyano-2-methyl-6-(2H-1,2,3-triazol-2-yl)pyridin-3-yl)-1-(1-oxo-1,2-dihydroisoquinolin-5-yl)-5-(trifluoromethyl)-1H-pyrazole-4-carboxamide;

1-(8-aminoquinolin-5-yl)-N-(5-cyano-6-(2H-1,2,3-triazol-2-yl)pyridin-3-yl)-5-(trifluoromethyl)-1H-pyrazole-4-carboxamide;

4-(4-((5-chloro-6-(2H-1,2,3-triazol-2-yl)pyridin-3-yl)carbamoyl)-5-(trifluoromethyl)-1H-pyrazol-1-yl)quinoline 1-oxide;

N-(5-cyano-6-(4-(hydroxymethyl)-2H-1,2,3-triazol-2-yl)pyridin-3-yl)-1-(quinolin-5-yl)-5-(trifluoromethyl)-1H-pyrazole-4-carboxamide;

methyl 2-cyano-4-(1-(quinolin-5-yl)-5-(trifluoromethyl)-1H-pyrazole-4-carboxamido)benzoate;

N-(6-(5-amino-1H-1,2,3-triazol-1-yl)-5-chloropyridin-3-yl)-1-(1-oxo-1,2-dihydroisoquinolin-5-yl)-5-(trifluoromethyl)-1H-pyrazole-4-carboxamide;

N-(5-chloro-6-(4-cyano-2H-1,2,3-triazol-2-yl)pyridin-3-yl)-1-(quinolin-5-yl)-5-(trifluoromethyl)-1H-pyrazole-4-carboxamide;

1-(1-aminoisoquinolin-4-yl)-N-(5-chloro-2-methyl-6-(2H-1,2,3-triazol-2-yl)pyridin-3-yl)-5-(trifluoromethyl)-1H-pyrazole-4-carboxamide;

N-(5-cyano-6-(2H-1,2,3-triazol-2-yl)pyridin-3-yl)-1-(imidazo[1,2-a]pyridin-5-yl)-5-(trifluoromethyl)-1H-pyrazole-4-carboxamide;

1-(benzo[d][1,2,3]thiadiazol-7-yl)-N-(5-cyano-2-methyl-6-(2H-1,2,3-triazol-2-yl)pyridin-3-yl)-5-(trifluoromethyl)-1H-pyrazole-4-carboxamide;

N-(5-chloro-6-(2H-1,2,3-triazol-2-yl)pyridin-3-yl)-1-(8-fluoroimidazo[1,2-a]pyridin-5-yl)-5-(trifluoromethyl)-1H-pyrazole-4-carboxamide;

N-(6-(5-amino-1-methyl-1H-pyrazol-3-yl)-5-cyanopyridin-3-yl)-1-(quinolin-5-yl)-5-(trifluoromethyl)-1H-pyrazole-4-carboxamide;

N-(5-chloro-2-methyl-6-(2H-1,2,3-triazol-2-yl)pyridin-3-yl)-1-(isoquinolin-4-yl)-5-(trifluoromethyl)-1H-pyrazole-4-carboxamide;

N-(5-chloro-6-(4-(hydroxymethyl)-1H-pyrazol-1-yl)pyridin-3-yl)-1-(1-oxo-1,2-dihydroisoquinolin-5-yl)-5-(trifluoromethyl)-1H-pyrazole-4-carboxamide;

N-(5-chloro-6-(2H-1,2,3-triazol-2-yl)pyridin-3-yl)-1-(3-methylimidazo[1,2-a]pyridin-5-yl)-5-(trifluoromethyl)-1H-pyrazole-4-carboxamide;

N-(6-(5-amino-1-methyl-1H-pyrazol-3-yl)-5-chloropyridin-3-yl)-1-(1-oxo-1,2-dihydroisoquinolin-5-yl)-5-(trifluoromethyl)-1H-pyrazole-4-carboxamide;

N-(5-cyano-6-(2H-1,2,3-triazol-2-yl)pyridin-3-yl)-1-(8-fluoroimidazo[1,2-a]pyridin-5-yl)-5-(trifluoromethyl)-1H-pyrazole-4-carboxamide;

N-(5-cyano-6-(2H-1,2,3-triazol-2-yl)pyridin-3-yl)-1-(thieno[3,2-d]pyrimidin-4-yl)-5-(trifluoromethyl)-1H-pyrazole-4-carboxamide;

N-(5-chloro-6-(2H-1,2,3-triazol-2-yl)pyridin-3-yl)-1-(8-fluoro-1-hydroxyisoquinolin-4-yl)-5-(trifluoromethyl)-1H-pyrazole-4-carboxamide;

1-(benzo[d]thiazol-4-yl)-N-(5-cyano-6-(2H-1,2,3-triazol-2-yl)pyridin-3-yl)-5-(trifluoromethyl)-1H-pyrazole-4-carboxamide;

N-(5-chloro-6-(2H-1,2,3-triazol-2-yl)pyridin-3-yl)-1-(quinolin-4-yl)-5-(trifluoromethyl)-1H-pyrazole-4-carboxamide;

N-(5-cyano-6-(2H-1,2,3-triazol-2-yl)pyridin-3-yl)-1-(pyrrolo[1,2-a]pyrazin-1-yl)-5-(trifluoromethyl)-1H-pyrazole-4-carboxamide;

N-(6-(2H-1,2,3-triazol-2-yl)-5-(trifluoromethyl)pyridin-3-yl)-1-(quinolin-5-yl)-5-(trifluoromethyl)-1H-pyrazole-4-carboxamide;

1-(benzo[d][1,2,3]thiadiazol-7-yl)-N-(5-chloro-6-(2H-1,2,3-triazol-2-yl)pyridin-3-yl)-5-(trifluoromethyl)-1H-pyrazole-4-carboxamide;

4-(4-((5-chloro-6-(2H-1,2,3-triazol-2-yl)pyridin-3-yl)carbamoyl)-5-(trifluoromethyl)-1H-pyrazol-1-yl)isoquinoline-1-carboxamide;

N-(5-chloro-6-(2H-1,2,3-triazol-2-yl)pyridin-3-yl)-1-(imidazo[1,2-a]pyridin-5-yl)-5-(trifluoromethyl)-1H-pyrazole-4-carboxamide;

N-(5-chloro-6-(2H-1,2,3-triazol-2-yl)pyridin-3-yl)-1-(pyrrolo[1,2-a]pyrazin-1-yl)-5-(trifluoromethyl)-1H-pyrazole-4-carboxamide;

N-(5-cyano-6-(2-methyl-2H-tetrazol-5-yl)pyridin-3-yl)-1-(quinolin-5-yl)-5-(trifluoromethyl)-1H-pyrazole-4-carboxamide;

N-(5-cyano-6-(2H-1,2,3-triazol-2-yl)pyridin-3-yl)-1-(1,7-naphthyridin-5-yl)-5-(trifluoromethyl)-1H-pyrazole-4-carboxamide;

2-(3-chloro-5-(1-(quinolin-5-yl)-5-(trifluoromethyl)-1H-pyrazole-4-carboxamido)pyridin-2-yl)-2H-1,2,3-triazole-4-carboxamide;

N-(5-chloro-2-methyl-6-(2H-1,2,3-triazol-2-yl)pyridin-3-yl)-1-(pyrazolo[1,5-a]pyridin-4-yl)-5-(trifluoromethyl)-1H-pyrazole-4-carboxamide;

1-(1-aminoisoquinolin-4-yl)-N-(5-cyano-6-(2H-1,2,3-triazol-2-yl)pyridin-3-yl)-5-(trifluoromethyl)-1H-pyrazole-4-carboxamide;

N-(5-cyano-6-(2H-1,2,3-triazol-2-yl)pyridin-3-yl)-1-(thieno[2,3-c]pyridin-7-yl)-5-(trifluoromethyl)-1H-pyrazole-4-carboxamide;

N-(5-cyano-6-(2H-1,2,3-triazol-2-yl)pyridin-3-yl)-1-(thieno[2,3-d]pyrimidin-4-yl)-5-(trifluoromethyl)-1H-pyrazole-4-carboxamide;

N-(5-chloro-6-(1,3,4-oxadiazol-2-yl)pyridin-3-yl)-1-(quinolin-5-yl)-5-(trifluoromethyl)-1H-pyrazole-4-carboxamide;

N-(5-chloro-6-(2H-1,2,3-triazol-2-yl)pyridin-3-yl)-1-(pyrazolo[1,5-a]pyrazin-4-yl)-5-(trifluoromethyl)-1H-pyrazole-4-carboxamide;

N-(5-chloro-6-(2H-1,2,3-triazol-2-yl)pyridin-3-yl)-1-(7-(1-hydroxyethyl)thieno[2,3-c]pyridin-4-yl)-5-(trifluoromethyl)-1H-pyrazole-4-carboxamide;

N-(5-cyano-6-(2H-1,2,3-triazol-2-yl)pyridin-3-yl)-1-(pyrrolo[2,1-f][1,2,4]triazin-4-yl)-5-(trifluoromethyl)-1H-pyrazole-4-carboxamide;

N-(5-chloro-6-(1-methyl-1H-pyrazol-3-yl)pyridin-3-yl)-1-(1-oxo-1,2-dihydroisoquinolin-5-yl)-5-(trifluoromethyl)-1H-pyrazole-4-carboxamide;

methyl2-(3-chloro-5-(1-(quinolin-5-yl)-5-(trifluoromethyl)-1H-pyrazole-4-carboxamido)pyridin-2-yl)-2H-1,2,3-triazole-4-carboxylate;

N-(5-chloro-6-(4-((dimethylamino)methyl)-2H-1,2,3-triazol-2-yl)pyridin-3-yl)-1-(quinolin-5-yl)-5-(trifluoromethyl)-1H-pyrazole-4-carboxamide;

N-(5-bromo-6-(2H-1,2,3-triazol-2-yl)pyridin-3-yl)-1-(quinolin-5-yl)-5-(trifluoromethyl)-1H-pyrazole-4-carboxamide;

N-(5-cyano-6-(2H-1,2,3-triazol-2-yl)pyridin-3-yl)-1-(quinolin-4-yl)-5-(trifluoromethyl)-1H-pyrazole-4-carboxamide;

1-(benzo[d][1,2,3]thiadiazol-7-yl)-N-(5-chloro-2-methyl-6-(2H-1,2,3-triazol-2-yl)pyridin-3-yl)-5-(trifluoromethyl)-1H-pyrazole-4-carboxamide;

N-(5-chloro-6-(2H-1,2,3-triazol-2-yl)pyridin-3-yl)-1-(1-cyanoisoquinolin-5-yl)-5-(trifluoromethyl)-1H-pyrazole-4-carboxamide;

N-(5-chloro-6-(4-(hydroxymethyl)-2H-1,2,3-triazol-2-yl)pyridin-3-yl)-1-(quinolin-5-yl)-5-(trifluoromethyl)-1H-pyrazole-4-carboxamide;

N-(5-chloro-6-(4-(hydroxymethyl)-1H-pyrazol-1-yl)pyridin-3-yl)-1-(quinolin-5-yl)-5-(trifluoromethyl)-1H-pyrazole-4-carboxamide;

N-(5-cyano-6-(2H-1,2,3-triazol-2-yl)pyridin-3-yl)-1-(pyrazolo[1,5-a]pyrazin-4-yl)-5-(trifluoromethyl)-1H-pyrazole-4-carboxamide;

N-(5-cyano-2-methyl-6-(2H-1,2,3-triazol-2-yl)pyridin-3-yl)-1-(8-fluoroisoquinolin-4-yl)-5-(trifluoromethyl)-1H-pyrazole-4-carboxamide;

N-(6-(4-amino-2H-1,2,3-triazol-2-yl)-5-chloropyridin-3-yl)-1-(1-oxo-1,2-dihydroisoquinolin-5-yl)-5-(trifluoromethyl)-1H-pyrazole-4-carboxamide;

N-(6-(4-amino-2H-1,2,3-triazol-2-yl)-5-chloropyridin-3-yl)-1-(quinolin-5-yl)-5-(trifluoromethyl)-1H-pyrazole-4-carboxamide;

1-(1-amino-8-fluoroisoquinolin-4-yl)-N-(5-chloro-6-(2H-1,2,3-triazol-2-yl)pyridin-3-yl)-5-(trifluoromethyl)-1H-pyrazole-4-carboxamide;

1-(1-aminoisoquinolin-4-yl)-N-(5-chloro-6-(2H-1,2,3-triazol-2-yl)pyridin-3-yl)-5-(trifluoromethyl)-1H-pyrazole-4-carboxamide;

N-(3-cyano-4-(2H-1,2,3-triazol-2-yl)phenyl)-1-(quinolin-5-yl)-5-(trifluoromethyl)-1H-pyrazole-4-carboxamide;

N-(5-chloro-6-(2H-1,2,3-triazol-2-yl)pyridin-3-yl)-1-(2-oxo-1,2-dihydroquinolin-4-yl)-5-(trifluoromethyl)-1H-pyrazole-4-carboxamide;

1-(4-aminonaphthalen-1-yl)-N-(5-cyano-6-(2H-1,2,3-triazol-2-yl)pyridin-3-yl)-5-(trifluoromethyl)-1H-pyrazole-4-carboxamide;

1-(1-aminoisoquinolin-4-yl)-N-(5-cyano-6-(2H-1,2,3-triazol-2-yl)pyridin-3-yl)-5-(trifluoromethyl)-1H-pyrazole-4-carboxamide;

N-(5-cyano-6-(2H-1,2,3-triazol-2-yl)pyridin-3-yl)-1-(4-fluoro-2-methoxyphenyl)-5-(trifluoromethyl)-1H-pyrazole-4-carboxamide;

N-(5-chloro-6-(2H-1,2,3-triazol-2-yl)pyridin-3-yl)-1-(2-D-quinolin-5-yl)-5-(trifluoromethyl)-1H-pyrazole-4-carboxamide;

N-(5-cyano-6-(2H-1,2,3-triazol-2-yl)pyridin-3-yl)-1-(2-D-quinolin-5-yl)-5-(trifluoromethyl)-1H-pyrazole-4-carboxamide;

N-(3-chloro-4-(2H-1,2,3-triazol-2-yl)phenyl)-1-(1-oxo-1,2-dihydroisoquinolin-5-yl)-5-(trifluoromethyl)-1H-pyrazole-4-carboxamide;

N-(5-cyano-6-(2H-1,2,3-triazol-2-yl)pyridin-3-yl)-1-(thieno[3,2-b]pyridin-7-yl)-5-(trifluoromethyl)-1H-pyrazole-4-carboxamide;

N-(5-bromo-2-methyl-6-(2H-1,2,3-triazol-2-yl)pyridin-3-yl)-1-(1-oxo-1,2-dihydroisoquinolin-5-yl)-5-(trifluoromethyl)-1H-pyrazole-4-carboxamide;

N-(5-chloro-2-methyl-6-(2H-1,2,3-triazol-2-yl)pyridin-3-yl)-1-(1-oxo-1,2-dihydroisoquinolin-5-yl)-5-(trifluoromethyl)-1H-pyrazole-4-carboxamide;

N-(5-chloro-6-(2H-1,2,3-triazol-2-yl)pyridin-3-yl)-1-(pyrazolo[1,5-a]pyridin-4-yl)-5-(trifluoromethyl)-1H-pyrazole-4-carboxamide;

N-(5-chloro-6-(oxazol-2-yl)pyridin-3-yl)-1-(1-oxo-1,2-dihydroisoquinolin-5-yl)-5-(trifluoromethyl)-1H-pyrazole-4-carboxamide;

N-(5-cyano-6-(2H-1,2,3-triazol-2-yl)pyridin-3-yl)-1-(8-fluoroisoquinolin-4-yl)-5-(trifluoromethyl)-1H-pyrazole-4-carboxamide;

N-(5-cyano-6-(2H-1,2,3-triazol-2-yl)pyridin-3-yl)-1-(thieno[2,3-b]pyridin-4-yl)-5-(trifluoromethyl)-1H-pyrazole-4-carboxamide;

N-(5-chloro-6-(2H-1,2,3-triazol-2-yl)pyridin-3-yl)-1-(thieno[2,3-c]pyridin-4-yl)-5-(trifluoromethyl)-1H-pyrazole-4-carboxamide;

N-(5-chloro-6-(4-methyl-2H-1,2,3-triazol-2-yl)pyridin-3-yl)-1-(quinolin-5-yl)-5-(trifluoromethyl)-1H-pyrazole-4-carboxamide;

N-(5-chloro-2-methyl-6-(2H-1,2,3-triazol-2-yl)pyridin-3-yl)-1-(8-fluoroisoquinolin-4-yl)-5-(trifluoromethyl)-1H-pyrazole-4-carboxamide;

1-(benzo[d][1,2,3]thiadiazol-7-yl)-N-(5-cyano-6-(2H-1,2,3-triazol-2-yl)pyridin-3-yl)-5-(trifluoromethyl)-1H-pyrazole-4-carboxamide;

N-(5-cyano-6-(2H-1,2,3-triazol-2-yl)pyridin-3-yl)-1-(5-fluoronaphthalen-1-yl)-5-(trifluoromethyl)-1H-pyrazole-4-carboxamide;

N-(5-chloro-6-(2H-1,2,3-triazol-2-yl)pyridin-3-yl)-1-(8-fluoroisoquinolin-4-yl)-5-(trifluoromethyl)-1H-pyrazole-4-carboxamide;

N-(5-chloro-6-(2H-1,2,3-triazol-2-yl)pyridin-3-yl)-1-(1-hydroxyisoquinolin-5-yl)-5-(trifluoromethyl)-1H-pyrazole-4-carboxamide;

1-(benzo[d]thiazol-7-yl)-N-(5-chloro-6-(2H-1,2,3-triazol-2-yl)pyridin-3-yl)-5-(trifluoromethyl)-1H-pyrazole-4-carboxamide;

N-(5-chloro-6-(4-(hydroxymethyl)-2H-1,2,3-triazol-2-yl)pyridin-3-yl)-1-(1-oxo-1,2-dihydroisoquinolin-5-yl)-5-(trifluoromethyl)-1H-pyrazole-4-carboxamide;

1-(benzo[d]thiazol-7-yl)-N-(5-cyano-6-(2H-1,2,3-triazol-2-yl)pyridin-3-yl)-5-(trifluoromethyl)-1H-pyrazole-4-carboxamide;

N-(5-cyano-6-(2H-1,2,3-triazol-2-yl)pyridin-3-yl)-1-(1-oxo-1,2-dihydroisoquinolin-5-yl)-5-(trifluoromethyl)-1H-pyrazole-4-carboxamide;

1-(1-amino-8-fluoroisoquinolin-4-yl)-N-(5-cyano-6-(2H-1,2,3-triazol-2-yl)pyridin-3-yl)-5-(trifluoromethyl)-1H-pyrazole-4-carboxamide;

2-(3-chloro-5-(1-(quinolin-5-yl)-5-(trifluoromethyl)-1H-pyrazole-4-carboxamido)pyridin-2-yl)-2H-1,2,3-triazole-4-carboxylic acid;

N-(5-cyano-6-(2H-1,2,3-triazol-2-yl)pyridin-3-yl)-1-(furo[3,2-b]pyridin-7-yl)-5-(trifluoromethyl)-1H-pyrazole-4-carboxamide;

4-(4-((5-chloro-6-(2H-1,2,3-triazol-2-yl)pyridin-3-yl)carbamoyl)-5-(trifluoromethyl)-1H-pyrazol-1-yl)thieno[2,3-c]pyridine-7-carboxamide;

1-(7-(3-hydroxyazetidin-1-yl)thieno[2,3-c]pyridin-4-yl)-5-(trifluoromethyl)-N-(2-(trifluoromethyl)pyridin-4-yl)-1H-pyrazole-4-carboxamide;

N-(5-(2H-1,2,3-triazol-2-yl)pyridin-3-yl)-1-(1-oxo-1,2-dihydroisoquinolin-5-yl)-5-(trifluoromethyl)-1H-pyrazole-4-carboxamide;

1-(1-aminoisoquinolin-4-yl)-N-(5-bromo-2-methyl-6-(2H-1,2,3-triazol-2-yl)pyridin-3-yl)-5-(trifluoromethyl)-1H-pyrazole-4-carboxamide;

N-(5-chloro-2-methyl-6-(4-methyl-1H-1,2,3-triazol-1-yl)pyridin-3-yl)-1-(1-oxo-1,2-dihydroisoquinolin-5-yl)-5-(trifluoromethyl)-1H-pyrazole-4-carboxamide;

N-(2-morpholinopyridin-4-yl)-1-(1-oxo-1,2-dihydroisoquinolin-5-yl)-5-(trifluoromethyl)-1H-pyrazole-4-carboxamide;

N-(2-methoxypyridin-4-yl)-1-(1-oxo-1,2-dihydroisoquinolin-5-yl)-5-(trifluoromethyl)-1H-pyrazole-4-carboxamide;

1-(1-aminoisoquinolin-4-yl)-5-(trifluoromethyl)-N-(5-(trifluoromethyl)pyridin-3-yl)-1H-pyrazole-4-carboxamide;

1-(1-aminoisoquinolin-4-yl)-N-(5-chloro-2-methyl-6-(4-methyl-2H-1,2,3-triazol-2-yl)pyridin-3-yl)-5-(trifluoromethyl)-1H-pyrazole-4-carboxamide;

N-(5-ethynyl-2-methyl-6-(2H-1,2,3-triazol-2-yl)pyridin-3-yl)-1-(1-oxo-1,2-dihydroisoquinolin-5-yl)-5-(trifluoromethyl)-1H-pyrazole-4-carboxamide;

N-(5-chloro-2-methyl-6-(4-methyl-2H-1,2,3-triazol-2-yl)pyridin-3-yl)-1-(1-oxo-1,2-dihydroisoquinolin-5-yl)-5-(trifluoromethyl)-1H-pyrazole-4-carboxamide;

N-(5-chloro-6-(2H-1,2,3-triazol-2-yl)pyridin-3-yl)-1-(2-methyl-1-oxo-1,2-dihydroisoquinolin-4-yl)-5-(trifluoromethyl)-1H-pyrazole-4-carboxamide;

(*R)—N-(5-chloro-6-(2H-1,2,3-triazol-2-yl)pyridin-3-yl)-1-(7-(3-hydroxypyrrolidin-1-yl)thieno[2,3-c]pyridin-4-yl)-5-(trifluoromethyl)-1H-pyrazole-4-carboxamide;

N-(5-chloro-2-methyl-6-(2H-1,2,3-triazol-2-yl)pyridin-3-yl)-1-(7-chlorothieno[2,3-c]pyridin-4-yl)-5-(trifluoromethyl)-1H-pyrazole-4-carboxamide;

(*S)—N-(5-chloro-6-(2H-1,2,3-triazol-2-yl)pyridin-3-yl)-1-(7-(3-hydroxypyrrolidin-1-yl)thieno[2,3-c]pyridin-4-yl)-5-(trifluoromethyl)-1H-pyrazole-4-carboxamide;

N-(5-chloro-2-methyl-6-(2H-1,2,3-triazol-2-yl)pyridin-3-yl)-1-(7-cyanothieno[2,3-c]pyridin-4-yl)-5-(trifluoromethyl)-1H-pyrazole-4-carboxamide;

N-(5-chloro-2-methyl-6-(2H-1,2,3-triazol-2-yl)pyridin-3-yl)-1-(7-(3-hydroxyazetidin-1-yl)thieno[2,3-c]pyridin-4-yl)-5-(trifluoromethyl)-1H-pyrazole-4-carboxamide;

4-(4-((5-chloro-2-methyl-6-(2H-1,2,3-triazol-2-yl)pyridin-3-yl)carbamoyl)-5-(trifluoromethyl)-1H-pyrazol-1-yl)thieno[2,3-c]pyridine-7-carboxamide;

N-(5-chloro-6-(2H-1,2,3-triazol-2-yl)pyridin-3-yl)-1-(7-cyclopropylthieno[2,3-c]pyridin-4-yl)-5-(trifluoromethyl)-1H-pyrazole-4-carboxamide;

N-(5-chloro-6-(2H-1,2,3-triazol-2-yl)pyridin-3-yl)-1-(7-methylthieno[2,3-c]pyridin-4-yl)-5-(trifluoromethyl)-1H-pyrazole-4-carboxamide;

N-(5-chloro-6-(2H-1,2,3-triazol-2-yl)pyridin-3-yl)-1-(7-cyanothieno[2,3-c]pyridin-4-yl)-5-(trifluoromethyl)-1H-pyrazole-4-carboxamide;

4-(4-((5-chloro-6-(2H-1,2,3-triazol-2-yl)pyridin-3-yl)carbamoyl)-5-(trifluoromethyl)-1H-pyrazol-1-yl)-N-methylthieno[2,3-c]pyridine-7-carboxamide;

N-(5-chloro-6-(2H-1,2,3-triazol-2-yl)pyridin-3-yl)-1-(7-(3-hydroxyazetidin-1-yl)thieno[2,3-c]pyridin-4-yl)-5-(trifluoromethyl)-1H-pyrazole-4-carboxamide;

N-(5-chloro-6-(2H-1,2,3-triazol-2-yl)pyridin-3-yl)-1-(7-chlorothieno[2,3-c]pyridin-4-yl)-5-(trifluoromethyl)-1H-pyrazole-4-carboxamide;

1-(1-aminoisoquinolin-4-yl)-5-(trifluoromethyl)-N-(2-(trifluoromethyl)pyridin-4-yl)-1H-pyrazole-4-carboxamide;

N-(6-methyl-5-(trifluoromethyl)pyridin-3-yl)-1-(1-oxo-1,2-dihydroisoquinolin-5-yl)-5-(trifluoromethyl)-1H-pyrazole-4-carboxamide;

1-(1-oxo-1,2-dihydroisoquinolin-5-yl)-N-(pyridin-4-yl)-5-(trifluoromethyl)-1H-pyrazole-4-carboxamide;

N-(2-cyclopropylpyridin-4-yl)-1-(1-oxo-1,2-dihydroisoquinolin-5-yl)-5-(trifluoromethyl)-1H-pyrazole-4-carboxamide;

3-chloro-N,N-dimethyl-5-(1-(1-oxo-1,2-dihydroisoquinolin-5-yl)-5-(trifluoromethyl)-1H-pyrazole-4-carboxamido)picolinamide 1-(1-aminoisoquinolin-4-yl)-N-(2-cyanopyridin-4-yl)-5-(trifluoromethyl)-1H-pyrazole-4-carboxamide;

3-chloro-N-methyl-5-(1-(1-oxo-1,2-dihydroisoquinolin-5-yl)-5-(trifluoromethyl)-1H-pyrazole-4-carboxamido)picolinamide;

1-(1-aminoisoquinolin-4-yl)-N-(6-methyl-5-(trifluoromethyl)pyridin-3-yl)-5-(trifluoromethyl)-1H-pyrazole-4-carboxamide;

N-(5-chloropyridin-3-yl)-1-(1-oxo-1,2-dihydroisoquinolin-5-yl)-5-(trifluoromethyl)-1H-pyrazole-4-carboxamide;

1-(thieno[2,3-c]pyridin-4-yl)-5-(trifluoromethyl)-N-(2-(trifluoromethyl)pyridin-4-yl)-1H-pyrazole-4-carboxamide;

1-(8-fluoroimidazo[1,2-a]pyridin-5-yl)-5-(trifluoromethyl)-N-(2-(trifluoromethyl)pyridin-4-yl)-1H-pyrazole-4-carboxamide;

N-(6-cyano-5-(trifluoromethyl)pyridin-3-yl)-1-(1-oxo-1,2-dihydroisoquinolin-5-yl)-5-(trifluoromethyl)-1H-pyrazole-4-carboxamide;

methyl 3-chloro-5-(1-(1-oxo-1,2-dihydroisoquinolin-5-yl)-5-(trifluoromethyl)-1H-pyrazole-4-carboxamido)picolinate;

1-(8-fluoroisoquinolin-4-yl)-5-(trifluoromethyl)-N-(2-(trifluoromethyl)pyridin-4-yl)-1H-pyrazole-4-carboxamide;

N-(2-cyanopyridin-4-yl)-1-(1-oxo-1,2-dihydroisoquinolin-5-yl)-5-(trifluoromethyl)-1H-pyrazole-4-carboxamide;

N-(2-(2-methoxyethoxy)-5-(trifluoromethyl)pyridin-3-yl)-1-(1-oxo-1,2-dihydroisoquinolin-5-yl)-5-(trifluoromethyl)-1H-pyrazole-4-carboxamide;

N-(5-chloro-2-methyl-6-(2H-1,2,3-triazol-2-yl)pyridin-3-yl)-1-(thieno[2,3-c]pyridin-4-yl)-5-(trifluoromethyl)-1H-pyrazole-4-carboxamide;

N-(5-chloro-2-methyl-6-(2H-1,2,3-triazol-2-yl)pyridin-3-yl)-1-(2-oxo-1,2-dihydroquinolin-4-yl)-5-(trifluoromethyl)-1H-pyrazole-4-carboxamide;

N-(5-chloro-2-methyl-6-(2H-1,2,3-triazol-2-yl)pyridin-3-yl)-1-(1-oxo-1,2-dihydroisoquinolin-5-yl)-5-(trifluoromethyl)-1H-pyrazole-4-carboxamide;

(*S)—N-(5-chloro-6-(2H-1,2,3-triazol-2-yl)pyridin-3-yl)-1-(2-(tetrahydrofuran-2-yl)quinolin-5-yl)-5-(trifluoromethyl)-1H-pyrazole-4-carboxamide;

or a pharmaceutically acceptable salt form thereof.

For use in medicine, salts of compounds of Formula (I) refer to non-toxic "pharmaceutically acceptable salts." Other salts may, however, be useful in the preparation of compounds of Formula (I) or of their pharmaceutically acceptable salt forms thereof. Suitable pharmaceutically acceptable salts of compounds of Formula (I) include acid addition salts that can, for example, be formed by mixing a solution of the compound with a solution of a pharmaceutically acceptable acid such as, hydrochloric acid, sulfuric acid, fumaric acid, maleic acid, succinic acid, acetic acid, benzoic acid, citric acid, tartaric acid, carbonic acid or phosphoric acid. Furthermore, where the compounds of Formula (I) carry an acidic moiety, suitable pharmaceutically acceptable salts thereof may include alkali metal salts such as, sodium or potassium salts; alkaline earth metal salts such as, calcium or magnesium salts; and salts formed with suitable organic ligands such as, quaternary ammonium salts. Thus, representative pharmaceutically acceptable salts include acetate, benzenesulfonate, benzoate, bicarbonate, bisulfate, bitartrate, borate, bromide, calcium edetate, camsylate, carbonate, chloride, clavulanate, citrate, dihydrochloride, edetate, edisylate, estolate, esylate, fumarate, gluceptate, gluconate, glutamate, glycollylarsanilate, hexylresorcinate, hydrabamine, hydrobromide, hydrochloride, hydroxynaphthoate, iodide, isothionate, lactate, lactobionate, laurate, malate, maleate, mandelate, mesylate, methylbromide, methylnitrate, methylsulfate, mucate, napsylate, nitrate, N-methylglucamine ammonium salt, oleate, pamoate (embonate), palmitate, pantothenate, phosphate/diphosphate, polygalacturonate, salicylate, stearate, sulfate, subacetate, succinate, tannate, tartrate, teoclate, tosylate, triethiodide, and valerate.

Representative acids and bases that may be used in the preparation of pharmaceutically acceptable salts include acids including acetic acid, 2,2-dichloroacetic acid, acylated amino acids, adipic acid, alginic acid, ascorbic acid, L-aspartic acid, benzenesulfonic acid, benzoic acid, 4-acetamidobenzoic acid, (+)-camphoric acid, camphorsulfonic acid, (+)-(1S)-camphor-10-sulfonic acid, capric acid, caproic acid, caprylic acid, cinnamic acid, citric acid, cyclamic acid, dodecylsulfuric acid, ethane-1,2-disulfonic acid, ethanesulfonic acid, 2-hydroxy-ethanesulfonic acid, formic acid, fumaric acid, galactaric acid, gentisic acid, glucoheptonic acid, D-gluconic acid, D-glucoronic acid, L-glutamic acid, α-oxo-glutaric acid, glycolic acid, hippuric acid, hydrobromic acid, hydrochloric acid, (+)-L-lactic acid, (±)-DL-lactic acid, lactobionic acid, maleic acid, (−)-L-malic acid, malonic acid, (±)-DL-mandelic acid, methanesulfonic acid, naphthalene-2-sulfonic acid, naphthalene-1,5-disulfonic acid, 1-hydroxy-2-naphthoic acid, nicotinic acid, nitric acid, oleic acid, orotic acid, oxalic acid, palmitic acid, pamoic acid, phosphoric acid, L-pyroglutamic acid, salicylic acid, 4-amino-salicylic acid, sebaic acid, stearic acid, succinic acid, sulfuric acid, tannic acid, (+)-L-tartaric acid, thiocyanic acid, p-toluenesulfonic acid and undecylenic acid; and bases including ammonia, L-arginine, benethamine, benzathine, calcium hydroxide, choline, deanol, diethanolamine, diethylamine, 2-(diethylamino)-ethanol, ethanolamine, ethylenediamine, N-methyl-glucamine, hydrabamine, 1H-imidazole, L-lysine, magnesium hydroxide, 4-(2-hydroxyethyl)-morpholine, piperazine, potassium hydroxide, 1-(2-hydroxyethyl)-pyrrolidine, sodium hydroxide, triethanolamine, tromethamine, and zinc hydroxide.

Embodiments of the present invention include prodrugs of compounds of Formula (I). In general, such prodrugs will be functional derivatives of the compounds that are readily convertible in vivo into the required compound. Thus, in the methods of treating or preventing embodiments of the present invention, the term "administering" encompasses the treatment or prevention of the various diseases, conditions, syndromes and disorders described with the compound specifically disclosed or with a compound that may not be specifically disclosed, but which converts to the specified compound in vivo after administration to a patient. Conventional procedures for the selection and preparation of suitable prodrug derivatives are described, for example, in "Design of Prodrugs", ed. H. Bundgaard, Elsevier, 1985.

Where the compounds according to embodiments of this invention have at least one chiral center, they may accordingly exist as enantiomers. Where the compounds possess two or more chiral centers, they may additionally exist as diastereomers. It is to be understood that all such isomers and mixtures thereof are encompassed within the scope of the present invention. Furthermore, some of the crystalline forms for the compounds may exist as polymorph and as such are intended to be included in the present invention. In addition, some of the compounds may form solvates with water (i.e., hydrates) or common organic solvents, and such solvates are also intended to be encompassed within the scope of this invention. The skilled artisan will understand that the term compound as used herein, is meant to include solvated compounds of Formula (I).

Where the processes for the preparation of the compounds according to certain embodiments of the invention give rise to mixture of stereoisomers, these isomers may be separated by conventional techniques such as, preparative chromatography. The compounds may be prepared in racemic form, or individual enantiomers may be prepared either by enantiospecific synthesis or by resolution. The compounds may, for example, be resolved into their component enantiomers by standard techniques such as, the formation of diastereomeric pairs by salt formation with an optically active acid such as, (−)-di-p-toluoyl-d-tartaric acid and/or (+)-di-p-toluoyl-l-tartaric acid followed by fractional crystallization and regeneration of the free base. The compounds may also be resolved by formation of diastereomeric esters or amides, followed by chomatographic separation and removal of the chiral auxiliary. Alternatively, the compounds may be resolved using a chiral HPLC column.

One embodiment of the present invention is directed to a composition, including a pharmaceutical composition, comprising, consisting of, and/or consisting essentially of the (+)-enantiomer of a compound of Formula (I) wherein said composition is substantially free from the (−)-isomer of said compound. In the present context, substantially free means less than about 25%, preferably less than about 10%, more preferably less than about 5%, even more preferably less than about 2% and even more preferably less than about 1% of the (−)-isomer calculated as $$\%(+) - \text{enantiomer} = \frac{(\text{mass}(+) - \text{enantiomer})}{(\text{mass}(+) - \text{enantiomer}) + (\text{mass}(-) - \text{enantiomer})} \times 100.$$

Another embodiment of the present invention is a composition, including a pharmaceutical composition, comprising, consisting of, and consisting essentially of the (−)-enantiomer of a compound of Formula (I) wherein said composition is substantially free from the (+)-isomer of said compound. In the present context, substantially free from means less than about 25%, preferably less than about 10%, more preferably less than about 5%, even more preferably less than about 2% and even more preferably less than about 1% of the (+)-isomer calculated as $$\%(-) - \text{enantiomer} = \frac{(\text{mass}(-) - \text{enantiomer})}{(\text{mass}(+) - \text{enantiomer}) + (\text{mass}(-) - \text{enantiomer})} \times 100.$$

It is intended that within the scope of the present invention, any one or more element(s), in particular when mentioned in relation to a compound of Formula (I), shall comprise all isotopes and isotopic mixtures of said element(s), either naturally occurring or synthetically produced, either with natural abundance or in an isotopically enriched form. For example, a reference to hydrogen includes within its scope $^1$H, $^2$H (D), and $^3$H (T). Similarly, references to carbon and oxygen include within their scope respectively $^{12}$C, $^{13}$C and $^{14}$C and $^{16}$O and $^{18}$O. The isotopes may be radioactive or non-radioactive. Radiolabelled compounds of formula (I) may comprise one or more radioactive isotope(s) selected from the group of $^3$H, $^{11}$C, $^{18}$F, $^{122}$I, $^{123}$I, $^{125}$I, $^{131}$I, $^{75}$Br, $^{76}$Br, $^{77}$Br and $^{82}$Br. Preferably, the radioactive isotope is selected from the group of $^2$H, $^3$H, and $^{18}$F.

During any of the processes for preparation of the compounds of the various embodiments of the present invention, it may be necessary and/or desirable to protect sensitive or reactive groups on any of the molecules concerned. This may be achieved by means of conventional protecting groups such as those described in *Protective Groups in Organic Chemistry*, Second Edition, J. F. W. McOmie, Plenum Press, 1973; T. W. Greene & P. G. M. Wuts, *Protective Groups in Organic Synthesis*, John Wiley & Sons, 1991; and T. W. Greene & P. G. M. Wuts, *Protective Groups in Organic Synthesis*, Third Edition, John Wiley & Sons, 1999. The protecting groups may be removed at a convenient subsequent stage using methods known from the art.

Even though the compounds of embodiments of the present invention (including their pharmaceutically acceptable salts and pharmaceutically acceptable solvates) can be administered alone, they will generally be administered in admixture with a pharmaceutically acceptable carrier, a pharmaceutically acceptable excipient and/or a pharmaceutically acceptable diluent selected with regard to the intended route of administration and standard pharmaceutical or veterinary practice. Thus, particular embodiments of the present invention are directed to pharmaceutical and veterinary compositions comprising compounds of Formula (I) and at least one pharmaceutically acceptable carrier, pharmaceutically acceptable excipient, and/or pharmaceutically acceptable diluent.

By way of example, in the pharmaceutical compositions of embodiments of the present invention, the compounds of Formula (I) may be admixed with any suitable binder(s), lubricant(s), suspending agent(s), coating agent(s), solubilizing agent(s), and combinations thereof.

Solid oral dosage forms such as, tablets or capsules, containing the compounds of the present invention may be administered in at least one dosage form at a time, as appropriate. It is also possible to administer the compounds in sustained release formulations.

Additional oral forms in which the present inventive compounds may be administered include elixirs, solutions, syrups, and suspensions; each optionally containing flavoring agents and coloring agents.

Alternatively, compounds of Formula (I) can be administered by inhalation (intratracheal or intranasal) or in the form of a suppository or pessary, or they may be applied topically in the form of a lotion, solution, cream, ointment or dusting powder. For example, they can be incorporated into a cream comprising, consisting of, and/or consisting essentially of an aqueous emulsion of polyethylene glycols or liquid paraffin. They can also be incorporated, at a concentration of between about 1% and about 10% by weight of the cream, into an ointment comprising, consisting of, and/or consisting essentially of a wax or soft paraffin base together with any stabilizers and preservatives as may be required. An alternative means of administration includes transdermal administration by using a skin or transdermal patch.

The pharmaceutical compositions of the present invention (as well as the compounds of the present invention alone) can also be injected parenterally, for example, intracavernosally, intravenously, intramuscularly, subcutaneously, intradermally, or intrathecally. In this case, the compositions will also include at least one of a suitable carrier, a suitable excipient, and a suitable diluent.

For parenteral administration, the pharmaceutical compositions of the present invention are best used in the form of a sterile aqueous solution that may contain other substances, for example, enough salts and monosaccharides to make the solution isotonic with blood.

For buccal or sublingual administration, the pharmaceutical compositions of the present invention may be administered in the form of tablets or lozenges, which can be formulated in a conventional manner.

By way of further example, pharmaceutical compositions containing at least one of the compounds of Formula (I) as the active ingredient can be prepared by mixing the compound(s) with a pharmaceutically acceptable carrier, a pharmaceutically acceptable diluent, and/or a pharmaceutically acceptable excipient according to conventional pharmaceutical compounding techniques. The carrier, excipient, and diluent may take a wide variety of forms depending upon the desired route of administration (e.g., oral, parenteral, etc.). Thus, for liquid oral preparations such as, suspensions, syrups, elixirs and solutions, suitable carriers, excipients and diluents include water, glycols, oils, alcohols, flavoring agents, preservatives, stabilizers, coloring agents and the like; for solid oral preparations such as, powders, capsules, and tablets, suitable carriers, excipients and diluents include starches, sugars, diluents, granulating agents, lubricants, binders, disintegrating agents and the like. Solid oral preparations also may be optionally coated with substances such as, sugars, or be enterically coated so as to modulate the major site of absorption and disintegration. For parenteral administration, the carrier, excipient and diluent will usually include sterile water, and other ingredients may be added to increase solubility and preservation of the composition. Injectable suspensions or solutions may also be prepared utilizing aqueous carriers along with appropriate additives such as, solubilizers and preservatives.

A therapeutically effective amount of a compound of Formula (I) or a pharmaceutical composition thereof includes a dose range from about 0.1 mg to about 3000 mg, or any particular amount or range therein, in particular from about 1 mg to about 1000 mg, or any particular amount or range therein, or, more particularly, from about 10 mg to about 500 mg, or any particular amount or range therein, of active ingredient in a regimen of about 1 to about (4×) per day for an average (70 kg) human; although, it is apparent to one skilled in the art that the therapeutically effective amount for a compound of Formula (I) will vary as will the diseases, syndromes, conditions, and disorders being treated.

For oral administration, a pharmaceutical composition is preferably provided in the form of tablets containing about 1.0, about 10, about 50, about 100, about 150, about 200, about 250, and about 500 milligrams of a compound of Formula (I).

An embodiment of the present invention is directed to a pharmaceutical composition for oral administration, comprising a compound of Formula (I) in an amount of from about 25 mg to about 500 mg.

Advantageously, a compound of Formula (I) may be administered in a single daily dose, or the total daily dosage may be administered in divided doses of two, thee and (4×) daily.

Optimal dosages of a compound of Formula (I) to be administered may be readily determined and will vary with the particular compound used, the mode of administration, the strength of the preparation, and the advancement of the disease, syndrome, condition or disorder. In addition, factors associated with the particular subject being treated, including subject gender, age, weight, diet and time of administration, will result in the need to adjust the dose to achieve an appropriate therapeutic level and desired therapeutic effect. The above dosages are thus exemplary of the average case. There can be, of course, individual instances wherein higher or lower dosage ranges are merited, and such are within the scope of this invention.

Compounds of Formula (I) may be administered in any of the foregoing compositions and dosage regimens or by means of those compositions and dosage regimens established in the art whenever use of a compound of Formula (I) is required for a subject in need thereof.

In an embodiment, cancers that may benefit from a treatment with MALT1 inhibitors of the present invention include, but are not limited to, lymphomas, leukemias, carcinomas, and sarcomas, e.g. non-Hodgkin's lymphoma, diffuse large B-cell lymphoma (DLBCL), mantle cell lymphoma (MCL), follicular lymphoma (FL), mucosa-associated lymphoid tissue (MALT) lymphoma, marginal zone lymphoma, T-cell lymphoma, Hodgkin's lymphoma, Burkitt's lymphoma, multiple myeloma, chonic lymphocytic leukemia (CLL), lymphoblastic T cell leukemia, chonic myelogenous leukemia (CML), hairy-cell leukemia, acute lymphoblastic T cell leukemia, plasmacytoma, immunoblastic large cell leukemia, megakaryoblastic leukemia, acute megakaryocytic leukemia, promyelocytic leukemia, erythroleukemia, brain (gliomas), glioblastomas, breast cancer, colorectal/colon cancer, prostate cancer, lung cancer including non-small-cell, gastric cancer, endometrial cancer, melanoma, pancreatic cancer, liver cancer, kidney cancer, squamous cell carcinoma, ovarian cancer, sarcoma, osteosarcoma, thyroid cancer, bladder cancer, head&neck cancer, testicular cancer, Ewing's sarcoma, rhabdomyosarcoma, medulloblastoma, neuroblastoma, cervical cancer, renal cancer, urothelial cancer, vulval cancer, esophageal cancer, salivary gland cancer, nasopharangeal cancer, buccal cancer, cancer of the mouth, and GIST (gastrointestinal stromal tumor).

In another embodiment, MALT1 inhibitors of the present invention may be used for the treatment of immunological diseases including, but not limited to, autoimmune and inflammatory disorders, e.g. arthritis, inflammatory bowel disease, gastritis, ankylosing spondylitis, ulcerative colitis, pancreatits, Crohn's disease, celiac disease, multiple sclerosis, systemic lupus erythematosus, lupus nephitis, rheumatic fever, gout, organ or transplact rejection, chonic allograft rejection, acute or chonic graft-versus-host disease, dermatitis including atopic, dermatomyositis, psoriasis, Behcet's diseases, uveitis, myasthenia gravis, Grave's disease, Hashimoto thyroiditis, Sjoergen's syndrome, blistering disorders, antibody-mediated vasculitis syndromes, immune-complex vasculitides, allergic disorders, asthma, bronchitis, chonic obstructive pulmonary disease (COPD), cystic fibrosis, pneumonia, pulmonary diseases including oedema, embolism, fibrosis, sarcoidosis, hypertension and emphysema, silicosis, respiratory failure, acute respiratory distress syndrome, BENTA disease, berylliosis, and polymyositis.

In another embodiment of the present invention, the compounds of the present invention may be employed in combination with one or more other medicinal agents, more particularly with other anti-cancer agents, e.g. chemotherapeutic, anti-proliferative or immunomodulating agents, or with adjuvants in cancer therapy, e.g. immunosuppressive or anti-inflammatory agents.

Possible combinations of the compounds of the present invention may include, but are not limited to, BTK (Bruton's tyrosine kinase) inhibitors such as ibrutinib, SYK inhibitors, PKC inhibitors, PI3K pathway inhibitors, BCL family inhibitors, JAK inhibitors, PIM kinase inhibitors, rituximab or other B cell antigen-binding antibodies, as well as immune cell redirection agents (e.g. blinatumomab or CAR T-cells) and immunomodulatory agents such as daratumumab, anti-PD1 antibodies, and anti-PD-L1 antibodies.

General Synthetic Methods

Representative compounds of the present invention can be synthesized in accordance with the general synthetic methods described below and illustrated in the schemes and examples that follow. Since the schemes are an illustration, the invention should not be construed as being limited by the chemical reactions and conditions described in the schemes and examples. Compounds analogous to the target compounds of these examples can be made according to similar routes. The disclosed compounds are useful as pharmaceutical agents as described herein. The various starting materials used in the schemes and examples are commercially available or may be prepared by methods well within the skill of persons versed in the art.

Abbreviations used in the instant specification, particularly the schemes and examples, are as follows:
ACN acetonitrile
AcOH acetic acid
BINAP 2,2'-bis(diphenylphosphino)-1,1'-binaphthalene
Boc tert-butyl carbamate
BuLi butyllithium
Cbz benzyl carbamate
DCM dichloromethane
DMA dimethylacetamide
DME ethylene glycol dimethyl ether
DMF dimethylformamide
DMSO dimethyl sulfoxide
EA ethyl acetate
Et ethyl
$Et_2O$ diethyl ether
EtOAc ethyl acetate
EtOH ethyl alcohol
FCC flash column chromatography h hour(s)
HATU O-(7-azabenzotriazol-1-yl)-N,N,N',N'-tetramethyluronium hexafluorophosphate
HCHO formaldehyde
HCl hydrochloric acid
HPLC high performance liquid chromatography
KCN potassium cyanide
LCMS high pressure liquid choatography with mass spectrometer
LDA lithium diisopropylamide
LiOH lithium hydroxyde
Me methyl
MeCN acetonitrile
MeOH methyl alcohol
mg milligram
min minute
NaCN sodium cyanide
NaOH sodium hydroxide
NaOtBu sodium tert-butoxide
$NH_4Cl$ ammonium chloride
Pd/C palladium on charcoal
$Pd_2(dba)_3$ tris(dibenzylideneacetone)dipalladium
$Pd(dppf)Cl_2$ [1,1'-bis(diphenylphosphino)ferrocene]dichloropalladium
$Pd(OAc)_2$ palladium diacetate
$Pd(PPh_3)_4$ tetrakis(triphenylphosphine)palladium
$PPh_3$ triphenyl phosphine
p-TsOH para-toluenesulfonic acid
rt or RT room temperature
TBAF tetrabutyl ammonium fluoride
TMSI iodotrimethylsilane
t-Bu tert-butyl
TFA trifluoroacetic acid
TFAA trifluoroacetic anhydride
THF tetrahydrofuran
TLC thin layer chromatography
Xantphos 4,5-Bis(diphenylphosphino)-9,9-dimethylxanthene
Xphos 2-dicyclohexylphosphino-2',4',6'-triisopropylbiphenyl Compounds of Formula (Ia) wherein $R_7$ is hydrogen, may be prepared according to the process outlined in Scheme 1.

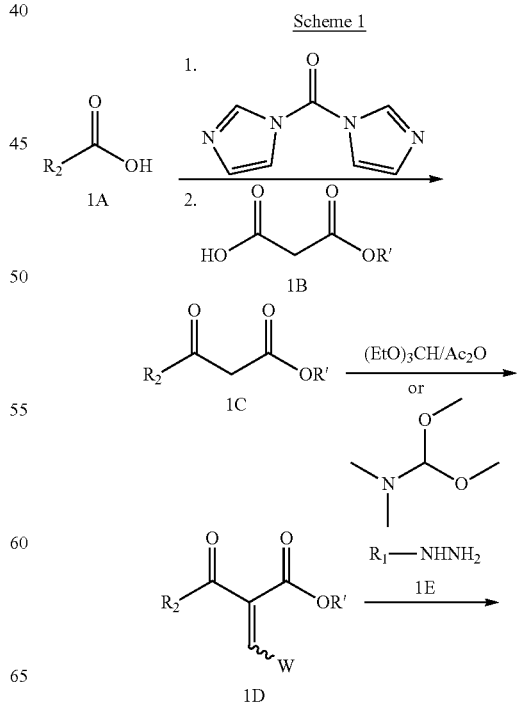

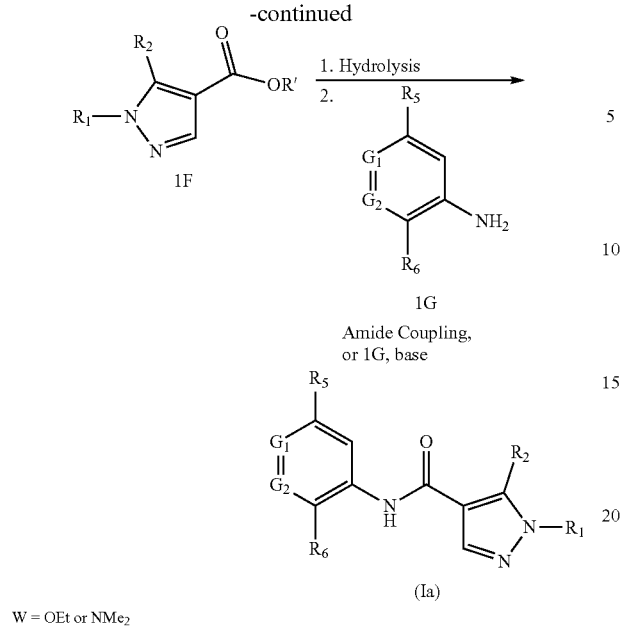

W = OEt or NMe₂

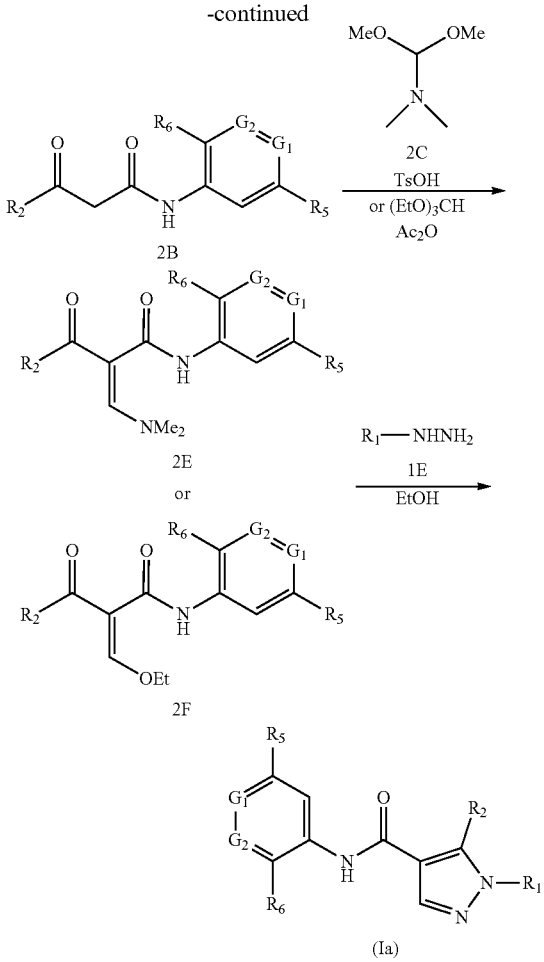

A carboxylic acid of formula (1A) may be treated with carbonyldiimidazole followed by addition of a mono-ester of malonic acid of formula (1B), wherein R' is $C_{1-4}$alkyl, and a base, such as isopropylmagesium chloride, to yield a ketoester of formula (1C). Condensation with triethyl orthoformate in acetic anhydride or with 1,1-dimethoxy-N,N-dimethylmethanamine may yield a 2-ethoxymethylidene-3-oxo ester (or 2-((dimethylamino)methylidene-3-oxo ester) of formula (1D). A compound of formula (1D) may be reacted with a hydrazine of formula (1E) to provide a pyrazole of formula (1F). Hydrolysis of the ester group may be effected via by treatment with aqueous sodium hydroxide in the presence of an alcohol co-solvent, to provide the corresponding carboxylic acid intermediate, which, subsequently, may be converted to a compound of Formula (I) upon amide coupling with a compound of formula (1G). The amide coupling may be carried out, for example, in the presence of phosphorus oxychloride in pyridine to afford the corresponding acid chloride, followed by treatment with a compound of formula (1G), in the presence of a base. In one embodiment, the amide coupling reaction is carried out in the presence of a suitable amide coupling reagent such as HATU, in the presence of a base such as, but not limited to, diisopropylethyl amine.

Alternatively, the pyrazole ester of formula (1F) may be directly converted to a compound of Formula (I) via treatment with a compound of formula (1G) and a base, such as potassium tert-butoxide.

An alternate route to compounds of Formula (Ia) wherein $R_7$ is hydrogen, is illustrated in Scheme 2.

Scheme 2

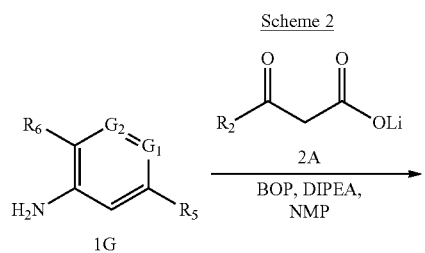

Aniline (1G) may be coupled with a lithium acetoacetate of formula (2A) in the presence of coupling reagent such as BOP, a base such as DIPEA, and a solvent such as NMP, to provide a compound of formula (2B). A compound of formula (2B) may then be reacted with DMF-DMA (2C) in the presence of an acid, such as TsOH, or reacted with triethoxymethane (2D) in AcOH to afford a compound of formula (2E) or (2F), respectively. A compound of formula (2E) or (2F) may then be treated with a hydrazine of formula (1E) to afford a compound of Formula (I).

Scheme 3 illustrates the preparation of certain hydrazine intermediates of formula (1E), useful for the preparation of compounds of Formula (I) of the present invention.

Scheme 3

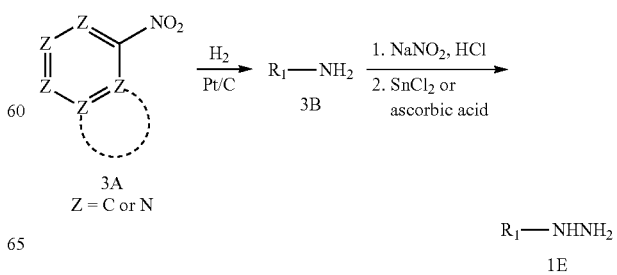

PATH 2

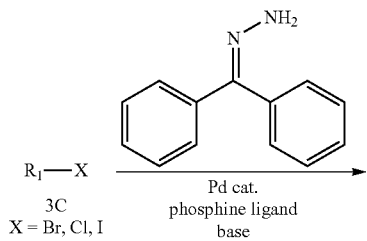

3C
X = Br, Cl, I

Pd cat.
phosphine ligand
base

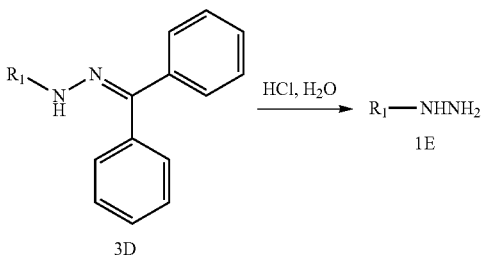

3D

HCl, H₂O → R₁—NHNH₂
1E

PATH 3

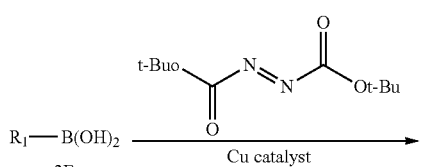

3E

Cu catalyst

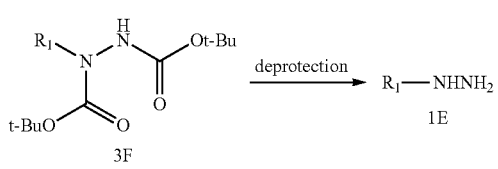

3F deprotection → R₁—NHNH₂
1E

PATH 4

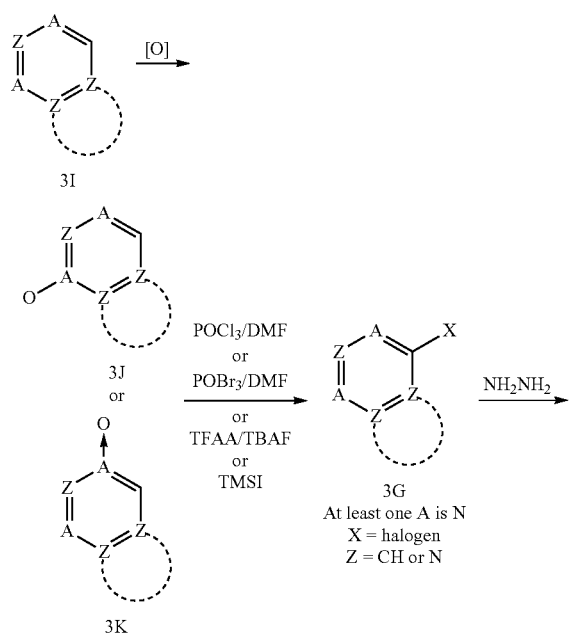

3I 3J or 3K

POCl₃/DMF
or
POBr₃/DMF
or
TFAA/TBAF
or
TMSI

3G
At least one A is N
X = halogen
Z = CH or N

NH₂NH₂ →

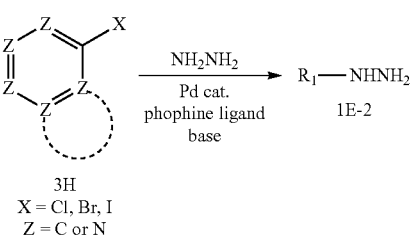

1E-1

PATH 5

3H
X = Cl, Br, I
Z = C or N

NH₂NH₂
Pd cat.
phophine ligand
base

R₁—NHNH₂
1E-2

A heteroaryl amine of formula (3B) may be converted to a heteroaryl diazonium salt via treatment with sodium nitrite under acidic conditions. This intermediate may be reduced, using a reductant such as tin (II) chloride or ascorbic acid, to form the hydrazine of formula (1E). For heteroaryl amines of formula (3B) that are not commercially available, they may be accessed by reduction of the heteronitroarene (3A) using hydrogen and Pt/C or other conventional nitro-reducing conditions (path one).

$R_1$-substituted chlorides, bromides, and iodides may undergo a palladium catalyzed Buchwald Hartwig coupling with benzophenone hydrazine, in the presence of a ligand, such as Xantphos, and a base, such as sodium tert-butoxide, to form a hydrazine of formula (3D). Acidic hydrolysis may afford the hydrazine of formula (1E) (path two).

$R_1$-substituted boronic acids may also serve as a precursor to compounds of formula (1E) by the route shown in path three. A boronic acid of formula (3E) may undergo a $Cu^{2+}$-catalyzed (such as $Cu(OAc)_2$, TEA in $CH_2Cl_2$) addition to di-tert-butylazodicarboxylate to afford an intermediate of formula (3F), which may be deprotected under acidic conditions to yield the compound of formula (1E). Heteroaryl hydrazines of formula (1E-1), having a nitrogen atom in the ortho- or para-position with respect to the hydrazine functionality, may be prepared via direct displacement of a halogen with hydrazine or hydrazine hydrate. (Hetero) haloarenes of formula (3G) that are not commercially available may be prepared from their corresponding (hetero)arenes (3I), with an oxidant such as mCPBA, to form the N-oxide (3J) (or (3K)) that may then be converted to (hetero) haloarene 3G via treatment with POCl₃ and DMF, POBr₃/DMF, TFAA/TBAF, or TMSI (path four). Alternatively, halogenated (hetero)arenes of formula (311) may undergo palladium-catalyzed cross-coupling with hydrazine to directly furnish intermediate (1E-2) (path five).

Scheme 4 illustrates multiple pathways available for the synthesis of intermediate (1G-1), wherein $G_1$ is $C(R_4)$.

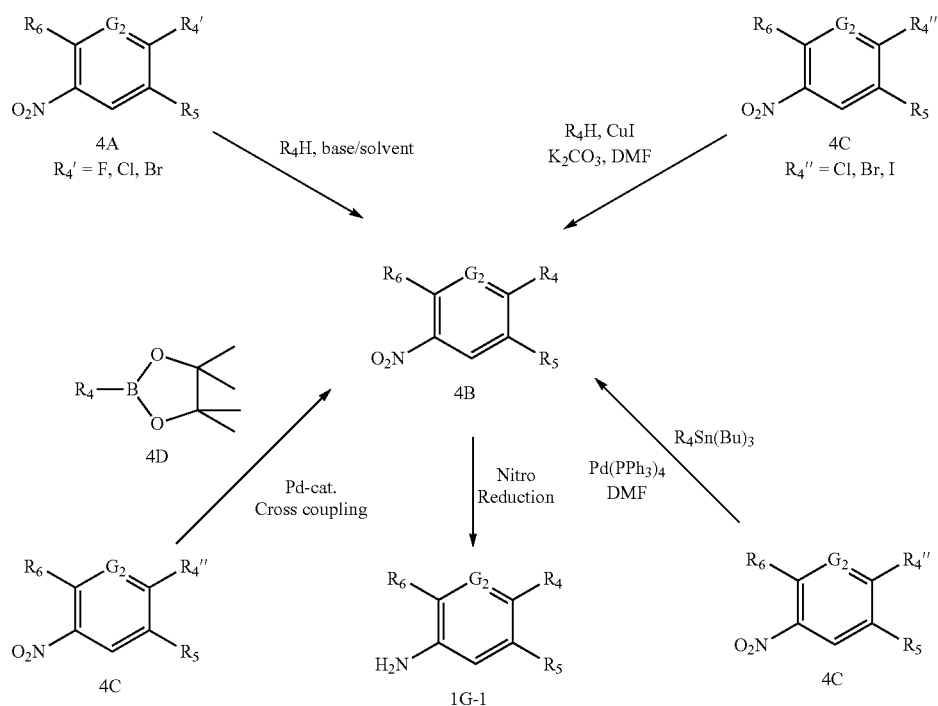

Compound (B-1) may be reacted with a compound of formula R₄H in the presence of a base, such as Cs₂CO₃, in a solvent, such as DMF, to yield a compound of formula (4B). Alternatively, a compound of formula (4C) may be treated with a crossing coupling reagent, such as a boron reagent of formula (4D) or a tin reagent of formula R₄Sn(Bu)₃; in the presence of a palladium catalyst, including but not limited to, Pd(dppf)Cl₂ or Pd(PPh₃)₄; in a suitable solvent or solvent system such as DMF, dioxane/water, or the like; to produce a compound of formula (4B). Another suitable pathway includes the reaction of a compound of formula (4C) with a compound of formula R₄H, in the presence of a coupling reagent such as CuI, with a base such as Cs₂CO₃, and in a solvent such as DMF, to afford a compound of formula (4B). A compound of formula (4B) may be reduced to a compound of formula (1G-1) using a reducing agent such as Zn or Fe in the presence of NH₄Cl, in a solvent such as MeOH.

Scheme 5 illustrates the preparation of certain compounds of Formula (I) wherein R₆ is other than hydrogen.

Scheme 5

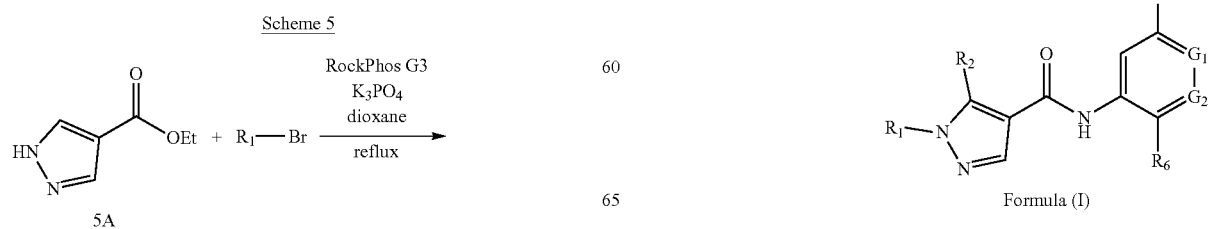

-continued

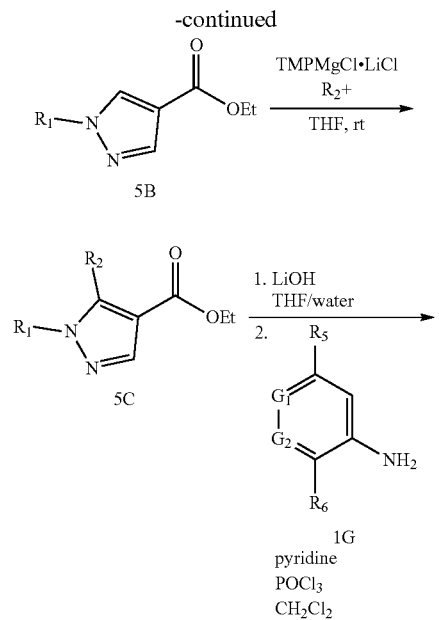

Scheme 6 illustrates the preparation of certain compounds of Formula (I) of the present invention.

Scheme 6

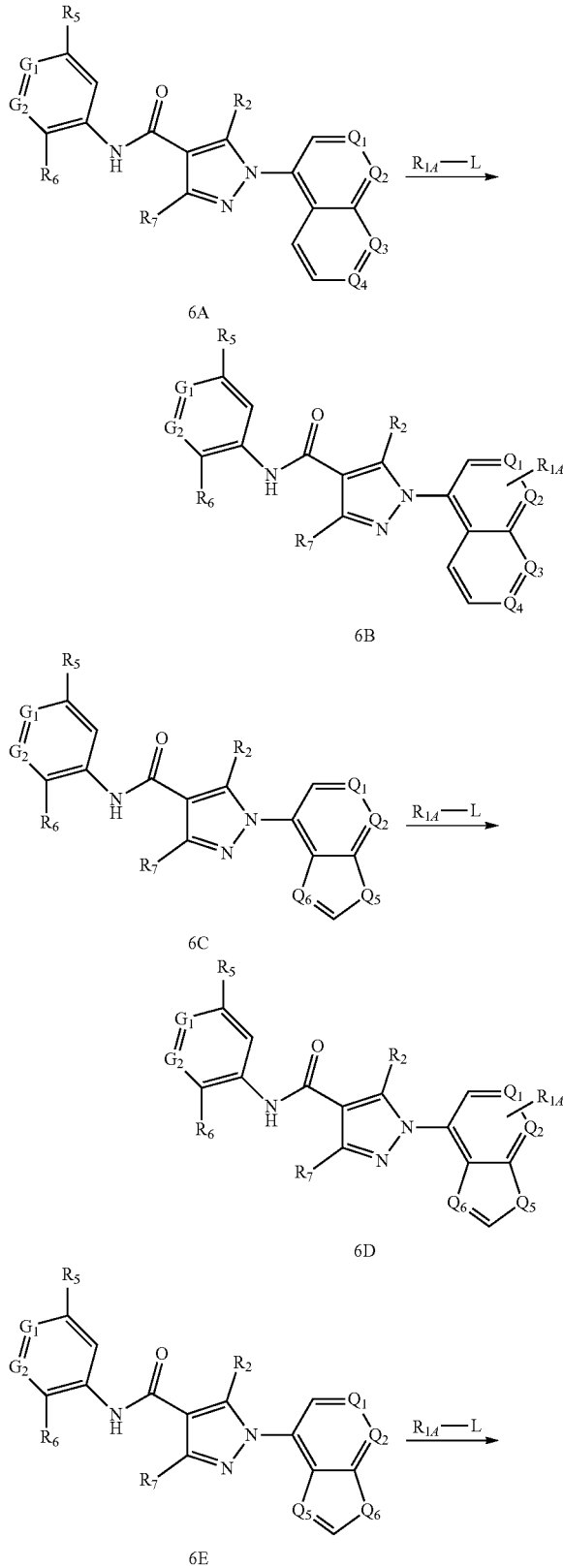

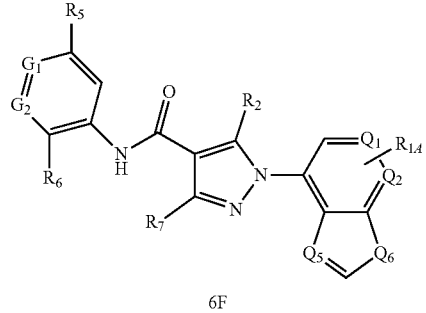

6F

In the instance when L is H, alkylation of compounds of formulae 6A, 6C and 6E may occur via formation of a radical from $R_{1A}$-L, generated by treatment with ammonium persulfate and (IR[DF(CF$_3$)PPY]$_2$(DTBPY))PF$_6$, in a mixture of water and CH$_3$CN or DMSO and TFA, under irradiation with blue LED.

Alternatively, in the instance when L is H, alkylation of compounds of formulae 6A, 6C and 6E may occur via formation of a radical from $R_{1A}$-L, generated by treatment with BPO and (IR[DF(CF$_3$)PPY]$_2$(DTBPY))PF$_6$ in MEOH and TFA, under irradiation with blue LED.

When L is H, alkylation of compounds of formulae 6A, 6C and 6E may occur via formation of a radical from $R_{1A}$-L, generated by treatment with iron(II)sulfate heptahydrate and hydrogen peroxide, in a mixture of water and CH$_3$CN or DMSO and H$_2$SO$_4$.

When L is a zinc sulfonate, alkylation of compounds of formulae 6A, 6C and 6E may occur via formation of a radical from $R_{1A}$-L, generated by treatment with tert-butyl hydroperoxide, in a mixture of water and DCM and TFA.

Likewise, when L is —COOH or a BF$_3$-salt, alkylation of compounds of formulae 6A, 6C and 6E may occur via formation of a radical from $R_{1A}$-L, generated by treatment with ammonium persulfate and silver nitrate, in a mixture of water and DCM or CH$_3$CN or DMSO or dioxane and TFA.

Compounds of formulae 6A, 6C and 6E may also be converted to their corresponding N-oxides via treatment with an oxidizing agent such as m-CPBA in DCM or THF. Said N-oxides by optionally be converted to their corresponding ortho —CN derivatives using trimethylsilyl cyanide and DBU, in a solvent such as THF. Said N-oxides may also be converted to their corresponding alkoxy or cycloalkoxy derivatives by the action of tosylanhydride, Na$_2$CO$_3$ and an appropriately substituted alkyl-OH or cycloalkyl-OH reagent.

Alternatively, the N-oxides of compounds of formulae 6A, 6C and 6E may be converted to their corresponding ortho-chloro derivatives by the action of POCl$_3$, optionally in a solvent such as CHCl$_3$, which may be used as an intermediate for the preparation of C$_{1-6}$alkylthio, C$_{1-6}$cycloalkylthio, and sulfur-linked heterocyclic rings of the present invention. Similarly, the ortho-chloro derivatives may be reacted with appropriately substituted amines to afford C$_{1-6}$alkylamino, C$_{1-6}$cycloalkylamino, or N-linked heterocyclic rings of the present invention. Or, the ortho-chloro derivatives may undergo a Suzuki-type reaction in a subsequent step, with an appropriately substituted corresponding alkyl- or cycloalkyl-boronic acid to form a compound of Formula (I).

SPECIFIC EXAMPLES

In the following Examples, some synthesis products are listed as having been isolated as a residue. It will be understood by one of ordinary skill in the art that the term "residue" does not limit the physical state in which the product was isolated and may include, for example, a solid, an oil, a foam, a gum, a syrup, and the like.

Example 1

1-(Benzofuran-4-yl)-N-(5-chloro-6-(2H-1,2,3-triazol-2-yl)pyridin-3-yl)-5-(trifluoromethyl)-1H-pyrazole-4-carboxamide, Cpd 34

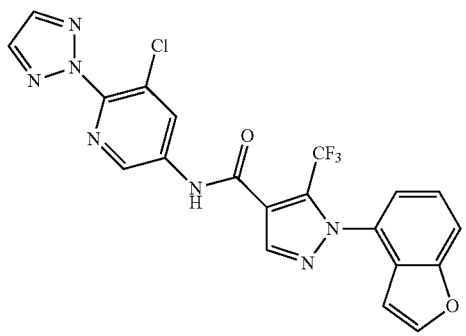 [SMILES: O=C(Nc1cnc(-n2nccn2)c(Cl)c1)c1cnn(-c2cccc3occc23)c1C(F)(F)F]

A. 1-Bromo-3-(2,2-diethoxyethoxy)benzene, 1a

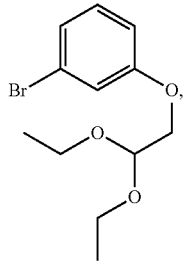

Sodium hydride in mineral oil (7.6 g, 60% purity, 0.19 mol) was added in portions to a 0° C. (ice/water) solution consisting of 3-bromophenol (30 g, 0.17 mmol) and DMF (200 mL), and the resultant mixture was stirred for 10 min at 0° C. 2-Bromo-1,1-diethoxyethane (31 mL, 0.21 mmol) was added to the mixture at 0° C., and the resulting mixture was stirred at 120° C. for 16 h before cooling to room temperature. The resulting solution was poured into water and extracted with ethyl acetate. The organic extracts were dried over anhydrous $Na_2SO_4$, filtered, and concentrated to dryness under reduced pressure to afford the crude product, which was purified by FCC (petroleum ether: ethyl acetate=10:1) to afford compound 1a (50 g, 99%) as a colorless oil. $^1$H NMR (400 MHz, $CDCl_3$) δ ppm 7.18-7.04 (m, 3H), 6.89-6.82 (m, 1H), 4.82 (t, J=5.2 Hz, 1H), 3.99 (d, J=5.2 Hz, 2H), 3.83-3.72 (m, 2H), 3.69-3.58 (m, 2H), 1.26 (t, J=7.2 Hz, 6H).

B. 4-Bromobenzofuran (1b) and 5-Bromobenzofuran (1c)

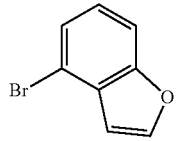

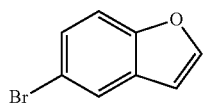

Polyphosphoric acid (PPA) (175 g, 519 mmol) was added to a solution consisting of 1-bromo-3-(2,2-diethoxyethoxy)benzene, 1a (50.0 g, 173 mmol) and toluene (200 mL) at room temperature under an $Ar_{(g)}$ atmosphere. The resulting mixture was stirred at 110° C. for 4 h before cooling to room temperature. The resulting mixture was quenched with cooled water and extracted with ethyl acetate. The organic extracts were dried over $Na_2SO_4$, filtered, and concentrated under reduced pressure to give a crude product, which was purified by FCC (petroleum ether: ethyl acetate=20:1) to give a mixture of compounds 1b and 1c (21 g, 62%) as a colorless oil. $^1$H NMR (400 MHz, $CDCl_3$) δ ppm 7.70 (s, 1H), 7.68 (d, J=2.0 Hz, 1H), 7.61 (d, J=2.0 Hz, 1H), 7.47 (d, J=8.0 Hz, 2H), 7.43-7.34 (m, 2H), 7.18 (t, J=8.0 Hz, 1H), 6.83 (d, J=1.2 Hz, 1H), 6.76 (d, J=1.2 Hz, 1H).

C. 1-(Benzofuran-4-yl)-2-(diphenylmethylene)hydrazine, 1d

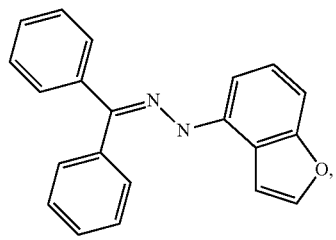

A mixture consisting of compounds 1b and 1c (21 g, 53 mmol), (diphenylmethylene)hydrazine (13 g, 64 mmol), palladium(II) acetate (1.2 g, 5.3 mmol), Xphos (5.1 g, 11 mmol), sodium hydroxide (4.3 g, 0.11 mol), and t-AmOH (150 mL) was stirred at 100° C. for 16 h before cooling to room temperature. The suspension was filtered and the pad was washed with ethyl acetate. The filtrate was concentrated to dryness under reduced pressure to afford a crude product, which was purified by FCC (petroleum ether: ethyl acetate=10:1) to afford compound 1d (5.8 g, 17%) as a brown oil. LCMS (ESI): mass calcd. for $C_{21}H_{16}N_2O$ 312.13, m/z found 313.1 $[M+H]^+$. $^1$H NMR (400 MHz, $CDCl_3$) δ ppm 7.77 (s, 1H), 7.66-7.60 (m, 4H), 7.59-7.52 (m, 2H), 7.43-7.29 (m, 5H), 7.22-7.16 (m, 1H), 7.05 (d, J=8.4 Hz, 1H), 6.98-6.95 (m, 1H), 6.90 (d, J=8.0 Hz, 1H). LCMS (ESI) m/z M+1: 313.0.

D. Benzofuran-4-ylhydrazine dihydrochloride, 1e

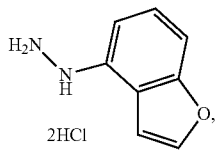

Conc. HCl (50 mL) was added to a solution consisting of 1-(benzofuran-4-yl)-2-(diphenylmethylene)hydrazine, 1d (4.8 g, 15 mmol) and EtOH (5 mL). The resulting mixture was stirred at room temperature for 16 h, concentrated to dryness under reduced pressure to afford a residue, which was added into water (10 mL). The resulting mixture was basified with 2 M NaOH to pH 13, and extracted with ethyl acetate (30 mL×3). The combined organic extracts were dried over anhydrous $Na_2SO_4$, filtered, and the filtrate concentrated to dryness under reduced pressure to afford a crude product 1e (1.1 g, crude), which was used in the following reaction without further purification.

E. Ethyl 2-(ethoxymethylene)-4,4,4-trifluoro-3-oxobutanoate, 1f

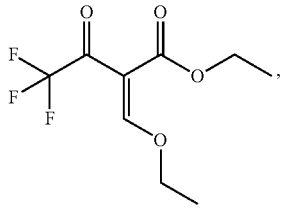

Ethyl 4,4,4-trifluoro-3-oxobutanoate (30 g, 162.9 mmol) was added to a solution of triethoxymethane (72.4 g, 488.8 mmol) in acetic anhydride (50 mL). The mixture was stirred at 135° C. for 18 h. The brown mixture was concentrated to afford ethyl 2-(ethoxymethylene)-4,4,4-trifluoro-3-oxobutanoate, 1f (38 g, 97.1%) as a brown oil, which was used in the following reaction without further purification. $^1$H NMR (400 MHz, CDCl$_3$) δ ppm 1.23-1.33 (m, 3H) 1.40 (dt, J=14.18, 7.19 Hz, 3H) 4.19-4.36 (m, 4H) 7.66-7.87 (m, 1H).

F. Ethyl 1-(benzofuran-4-yl)-5-(trifluoromethyl)-1H-pyrazole-4-carboxylate, 1g

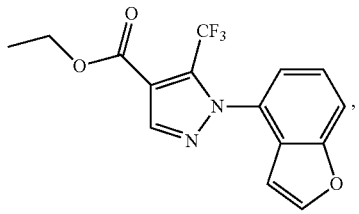

A solution consisting of ethyl 2-(ethoxymethylene)-4,4,4-trifluoro-3-oxobutanoate, 1f (1.43 g, 5.97 mmol), benzofuran-4-ylhydrazine dihydrochloride, 1e (1.10 g, 4.98 mmol), triethylamine (1.39 mL, 9.95 mmol), and ethanol (20 mL) was stirred at 80° C. for 16 h before cooling to room temperature. The resulting solution was concentrated to dryness under reduced pressure, diluted with water (15 mL), and extracted with ethyl acetate (20 mL×3). The combined organic extracts were dried over anhydrous $Na_2SO_4$, filtered, and concentrated to dryness under reduced pressure to afford the crude product, which was purified by FCC (petroleum ether: ethyl acetate=3:1) to afford compound 1g (250 mg, 15%) as a yellow oil. LCMS (ESI): mass calcd. for $C_{15}H_{11}F_3N_2O_3$ 324.07, m/z found 324.9 [M+H]$^+$. $^1$H NMR (400 MHz, CDCl$_3$) δ ppm 8.20 (s, 1H), 7.69 (d, J=2.4 Hz, 1H), 7.68-7.63 (m, 1H), 7.40 (t, J=8.0 Hz, 1H), 7.29 (d, J=8.0 Hz, 1H), 6.61 (dd, J=0.8, 2.4 Hz, 1H), 4.43-4.36 (m, 2H), 1.42-1.38 (m, 3H). LCMS (ESI) m/z M+1: 324.9.

G. 1-(Benzofuran-4-yl)-5-(trifluoromethyl)-1H-pyrazole-4-carboxylic acid, 1h

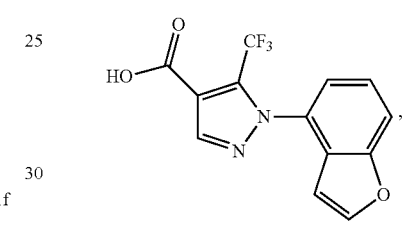

A solution consisting of lithium hydroxide hydrate (97.1 mg, 2.31 mmol) and water (5 mL) was added to a solution consisting of ethyl 1-(benzofuran-4-yl)-5-(trifluoromethyl)-1H-pyrazole-4-carboxylate, 1g (250 mg, 0.771 mmol) and ethanol (10 mL). The mixture was stirred at room temperature for 16 h. The resulting solution was concentrated to dryness under reduced pressure to afford the crude product, which was poured into water (5 mL) and acidified with 3N HCl to about pH 5. The resulting mixture was filtered and the filter cake was washed with water (5 mL), and then dried under reduced pressure to afford compound 1h (200 mg, 88%) as a yellow solid. LCMS (ESI): mass calcd. for $C_{13}H_7F_3N_2O_3$ 296.04, m/z found 337.9 [M+H+CH$_3$CN]$^+$. $^1$H NMR (400 MHz, DMSO-d$_6$) δ ppm 13.40 (br.s., 1H), 8.32 (s, 1H), 8.14 (d, J=2.4 Hz, 1H), 7.87 (d, J=8.4 Hz, 1H), 7.53-7.41 (m, 2H), 6.76 (dd, J=1.2, 2.4 Hz, 1H).

H. 3-Chloro-5-nitro-2-(2H-1,2,3-triazol-2-yl)pyridine, 1i

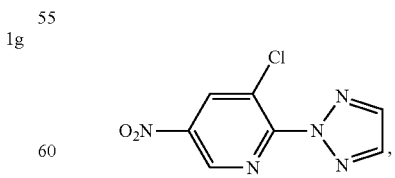

A mixture of 2,3-dichloro-5-nitropyridine (50 g, 259.08 mmol), 1H-1,2,3-triazole (19.683 g, 284.99 mmol), potassium carbonate (46.549 g, 336.81 mmol) and CH$_3$CN (200 mL) was heated to 40° C. and stirred overnight. Ethyl acetate (500 mL) was added. The mixture was washed with water (500 mL×2) and brine (500 mL), dried over anhydrous Na₂SO₄, filtered, and concentrated to dryness under reduced pressure. The residue was triturated with DCM (100 mL), filtered, and the solid was collected to afford compound 1i (40 g, 68%) as an off-white solid. LC-MS: (ES, m/z): [M+1]⁺ 225.9. ¹H NMR (400 MHz, DMSO-d₆) δ ppm 9.40 (d, J=2.0 Hz, 1H), 9.15 (d, J=2.0 Hz, 1H), 8.33 (s, 2H).

I. 5-Chloro-6-(2H-1,2,3-triazol-2-yl)pyridin-3-amine, 1j

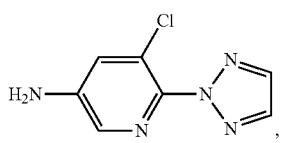

1j

3-Chloro-5-nitro-2-(2H-1,2,3-triazol-2-yl)pyridine, 1i (20 g, 88.656 mmol), MeOH (500 mL) and Pt/C (2 g, 5%, 0.513 mmol) were added to a 1000 mL hydrogenation bottle. The resultant mixture was stirred under a H₂ atmosphere (30 psi) at 25° C. for 20 h. The suspension was filtered though a pad of diatomaceous earth and the filter cake was washed with ethyl acetate (100 mL). The filtrate was concentrated to dryness under reduced pressure to afford a crude product, which was purified by preparative reverse phase HPLC (0% to 50% (v/v) CH₃CN and water with 0.05% NH₃), followed by lyophilization to dryness to afford compound 1j (10.4 g, 60%) as an off-white solid. LC-MS: (ES, m/z): [M+1]⁺ 196.1; ¹H NMR (400 MHz, DMSO-d₆) δ ppm 8.05 (s, 2H), 7.83 (d, J=2.0 Hz, 1H), 7.21 (d, J=2.4 Hz, 1H), 6.19 (s, 2H).

J. 1-(Benzofuran-4-yl)-N-(5-chloro-6-(2H-1,2,3-triazol-2-yl)pyridin-3-yl)-5-(trifluoromethyl)-1H-pyrazole-4-carboxamide, Cpd 34

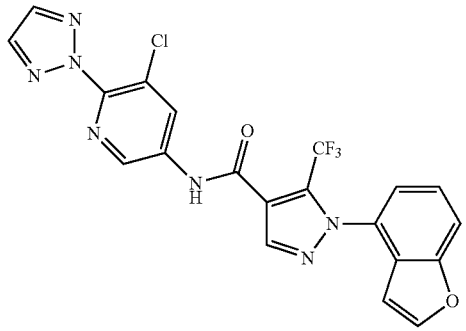 [SMILES: O=C(Nc1cnc(-n2nccn2)c(Cl)c1)c1cnn(-c2cccc3occc23)c1C(F)(F)F]

POCl₃ (112 mg, 0.729 mmol) was added dropwise to solution consisting of 1-(benzofuran-4-yl)-5-(trifluoromethyl)-1H-pyrazole-4-carboxylic acid, 1h (180 mg, 0.608 mmol), 5-chloro-6-(2H-1,2,3-triazol-2-yl)pyridin-3-amine, 1j (131 mg, 0.668 mmol), and pyridine (5 mL) at 0° C. The mixture was stirred at 0° C. for 1 h. The resulting mixture was diluted with sat. aqueous NaHCO₃ (10 mL) and extracted with ethyl acetate (15 mL×3). The organic extracts were dried over anhydrous Na₂SO₄, filtered, and the filtrate concentrated to dryness under reduced pressure to give a crude residue, which was purified by FCC (petroleum ether: ethyl acetate=1:1) to afford crude compound 34 (180 mg).

Further purification by preparative reverse phase HPLC (43% to 73% (v/v) CH₃CN and water with 0.05% NH₃) afforded compound 34, which was then suspended in water (10 mL), frozen using dry ice/acetone, and then lyophilized to dryness to afford compound 34 (166.10 mg, 57%). LCMS (ESI): mass calcd. for $C_{20}H_{11}ClF_3N_7O_2$ 473.06, m/z found 473.9 [M+H]⁺. ¹H NMR (400 MHz, CDCl₃) δ ppm 8.77 (d, J=2.4 Hz, 1H), 8.51 (d, J=2.0 Hz, 1H), 8.26 (s, 1H), 8.16 (s, 1H), 7.95 (s, 2H), 7.76-7.68 (m, 2H), 7.47-7.41 (m, 1H), 7.33 (d, J=7.6 Hz, 1H), 6.63 (d, J=1.6 Hz, 1H).

Example 2

N-(5-Chloro-6-(2H-1,2,3-triazol-2-yl)pyridin-3-yl)-1-(naphthalen-1-yl)-5-(trifluoromethyl)-1H-pyrazole-4-carboxamide, Cpd 2

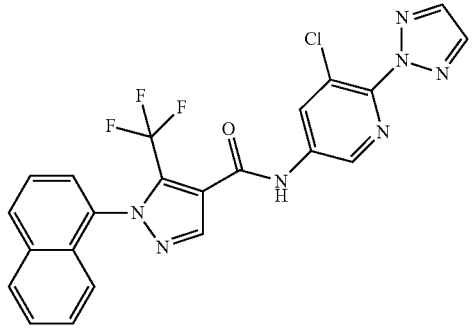 [SMILES: O=C(Nc1cnc(-n2nccn2)c(Cl)c1)c1cnn(-c2cccc3ccccc23)c1C(F)(F)F]

A. Ethyl 1-(naphthalen-1-yl)-5-(trifluoromethyl)-1H-pyrazole-4-carboxylate, 2a

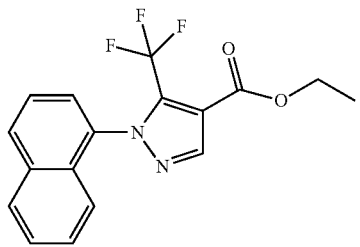

2a

Ethyl 2-(ethoxymethylene)-4,4,4-trifluoro-3-oxobutanoate, 1f (200 mg, 0.833 mmol) was added to a solution consisting of naphthalen-1-ylhydrazine (162 mg, 0.833 mmol), triethylamine (168 mg, 1.67 mmol) and ethanol (5 mL). The mixture was heated to reflux at 80° C. for 16 h. The resulting mixture was concentrated to dryness under reduced pressure to give a crude residue, which was purified by preparative high performance liquid chromatography using Phenomenex Gemini 150×25 mm×10 µm (50% to 80% (v/v) ACN and water with 0.05% NH₃) to afford compound 2a. Compound 2a was suspended in water (10 mL), the mixture frozen using dry ice/acetone, and then lyophilized to dryness to afford compound 2a (129.80 mg, 47%). LCMS (ESI): mass calcd. for $C_{17}H_{13}F_3N_2O_2$ 334.293, m/z found 335.1 [M+H]⁺. ¹H NMR (400 MHz, CDCl₃) δ ppm 8.26 (s, 1H), 8.04 (d, J=8.0 Hz, 1H), 7.95 (d, J=8.0 Hz, 1H), 7.59-7.50 (m, 4H), 7.19 (d, J=8.0 Hz, 1H), 4.42 (q, J=7.2 Hz, 2H), 1.41 (t, J=7.2 Hz, 3H). LCMS (ESI) m/z M+1: 335.0.

B. 1-(Naphthalen-1-yl)-5-(trifluoromethyl)-1H-pyrazole-4-carboxylic acid, 2b

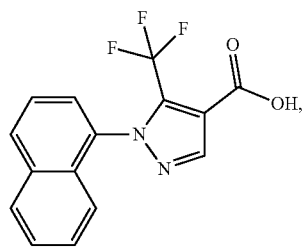

2b

A solution consisting of ethyl 1-(naphthalen-1-yl)-5-(trifluoromethyl)-1H-pyrazole-4-carboxylate, 2a (1.20 g, 3.59 mmol), LiOH (452 mg, 10.8 mmol) and a water: EtOH mixture (12 mL, 1:2) was stirred at room temperature for 16 h. The solution was neutralized to about pH 7 with 4 M HCl, extracted with ethyl acetate (30 mL×3), and dried over anhydrous $Na_2SO_4$. The extracts were concentrated to dryness under reduced pressure to afford compound 2b (1.00 g, 78%), which was used in the following reaction without further purification. LCMS (ESI): mass calcd. For $C_{15}H_9F_3N_2O_2$ 306.239, m/z found 306.9 $[M+H]^+$. $^1$H NMR (400 MHz, DMSO-$d_6$) δ ppm 13.43 (br.s., 1H), 8.38 (s, 1H), 8.21 (d, J=8.0 Hz, 1H), 8.12 (d, J=8.0 Hz, 1H), 7.80-7.74 (m, 1H), 7.72-7.55 (m, 4H), 7.09 (d, J=8.0 Hz, 1H).

C. N-(5-Chloro-6-(2H-1,2,3-triazol-2-yl)pyridin-3-yl)-1-(naphthalen-1-yl)-5-(trifluoromethyl)-1H-pyrazole-4-carboxamide, Cpd 2

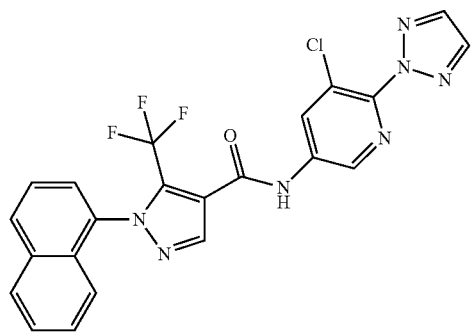 [SMILES: O=C(Nc1cnc(-n2nccn2)c(Cl)c1)c1cnn(-c2cccc3ccccc23)c1C(F)(F)F]

POCl$_3$ (90.1 mg, 0.588 mmol) was added dropwise to a solution consisting of 1-(naphthalen-1-yl)-5-(trifluoromethyl)-1H-pyrazole-4-carboxylic acid, 2b (150 mg, 0.490 mmol), 5-chloro-6-(2H-1,2,3-triazol-2-yl)pyridin-3-amine, 1j (105 mg, 0.539 mmol) and pyridine (2 mL). The mixture was stirred at 0° C. for 1 h. The resulting mixture was concentrated to dryness under reduced pressure to give a crude product, which was purified by preparative reverse phase HPLC (46% to 76% (v/v) ACN and water with 0.05% NH$_3$) to afford compound 2, which was then suspended in water (10 mL), the mixture frozen using dry ice/acetone, and then lyophilized to dryness to afford compound 2 (102.30 mg, 43%). LCMS (ESI): mass calcd. for $C_{22}H_{13}ClF_3N_7O$ 483.833, m/z found 484.1 $[M+H]^+$. $^1$H NMR (400 MHz, DMSO-$d_6$) δ ppm 9.08 (br.s., 1H), 8.86 (d, J=2.0 Hz, 1H), 8.69 (d, J=2.0 Hz, 1H), 8.57 (s, 1H), 8.25 (d, J=8.4 Hz, 1H), 8.20 (s, 2H), 8.15 (d, J=7.2 Hz, 1H), 7.79 (d, J=8.0 Hz, 1H), 7.76-7.62 (m, 3H), 7.13 (d, J=8.0 Hz, 1H). LCMS (ESI) m/z M+1: 483.9.

Example 3

N-(5-Chloro-6-(2H-1,2,3-triazol-2-yl)pyridin-3-yl)-1-(quinolin-5-yl)-5-(trifluoromethyl)-1H-pyrazole-4-carboxamide, Cpd 8

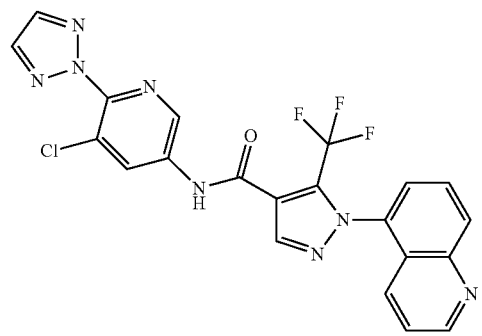 [SMILES: O=C(Nc1cnc(-n2nccn2)c(Cl)c1)c1cnn(-c2cccc3ncccc23)c1C(F)(F)F]

A. Ethyl 1-(quinolin-5-yl)-5-(trifluoromethyl)-1H-pyrazole-4-carboxylate, 3a

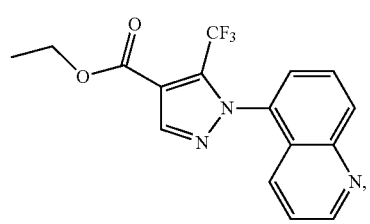

3a

A solution consisting of ethyl 2-(ethoxymethylene)-4,4,4-trifluoro-3-oxobutanoate, 1f (905 mg, 3.77 mmol), 5-hydrazinylquinoline (500 mg, 3.14 mmol), and ethanol (20 mL) was stirred at 80° C. for 16 h before cooling to room temperature. The resulting solution was concentrated to dryness under reduced pressure, and then purified by FCC (petroleum ether: ethyl acetate=1:1) to afford compound 3a (530 mg, 84%) as a brown solid. LC-MS (ESI): mass calcd. for $C_{16}H_{12}F_3N_3O_2$ 335.09, m/z found 335.8 $[M+H]^+$. $^1$H NMR (400 MHz, CDCl$_3$) δ ppm 9.02 (dd, J=1.6, 4.0 Hz, 1H), 8.33 (d, J=8.4 Hz, 1H), 8.27 (s, 1H), 7.86-7.79 (m, 1H), 7.64-7.56 (m, 2H), 7.46 (dd, J=4.4, 8.8 Hz, 1H), 4.43 (q, J=6.8 Hz, 2H), 1.42 (t, J=7.2 Hz, 3H). LCMS (ESI) m/z M+1: 335.8.

B. 1-(Quinolin-5-yl)-5-(trifluoromethyl)-1H-pyrazole-4-carboxylic acid, 3b

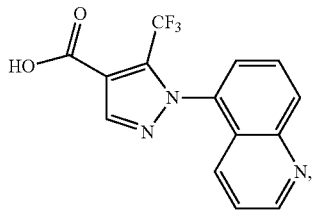

3b

A solution consisting of lithium hydroxide hydrate (375 mg, 8.95 mmol) in water (5 mL) was added to a solution consisting of ethyl 1-(quinolin-5-yl)-5-(trifluoromethyl)-1H-pyrazole-4-carboxylate, 3a (1.00 g, 2.98 mmol) in ethanol (10 mL). The resulting solution was stirred at room temperature for 16 h, concentrated to dryness under reduced pressure, and the resulting mixture was poured into water (2 mL). The aqueous mixture was acidified with 3 N HCl to about pH 5, filtered, and the filter cake was washed with water (10 mL) and dried under reduced pressure to afford compound 3b (910 mg, 99%) as a yellow solid. LC-MS (ESI): mass calcd. for $C_{14}H_8F_3N_3O_2$ 307.06, m/z found 308.0 [M+H]$^+$. $^1$H NMR (400 MHz, DMSO-d$_6$) δ ppm 9.03 (s, 1H), 8.40 (s, 1H), 8.30 (d, J=8.0 Hz, 1H), 8.00-7.82 (m, 2H), 7.69-7.54 (m, 2H). LCMS (ESI) m/z M+1: 308.0.

C. 1-(Quinolin-5-yl)-5-(trifluoromethyl)-1H-pyrazole-4-carbonyl chloride, 3c

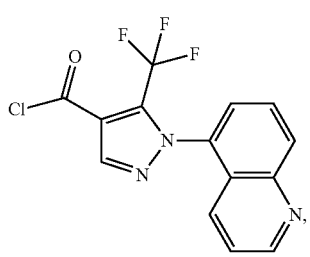

3c

Oxalyl dichloride (0.0830 mL, 0.976 mmol) was added to solution consisting of 1-(quinolin-5-yl)-5-(trifluoromethyl)-1H-pyrazole-4-carboxylic acid, 3b (200 mg, 0.651 mmol), dichloromethane (15 mL), and DMF (catalytic amount). The solution was stirred at room temperature for 1 h. The resulting solution was concentrated to dryness to afford compound 3c (200 mg, crude), which was used in the following reaction without further purification.

D. N-(5-Chloro-6-(2H-1,2,3-triazol-2-yl)pyridin-3-yl)-1-(quinolin-5-yl)-5-(trifluoromethyl)-1H-pyrazole-4-carboxamide, Cpd 8

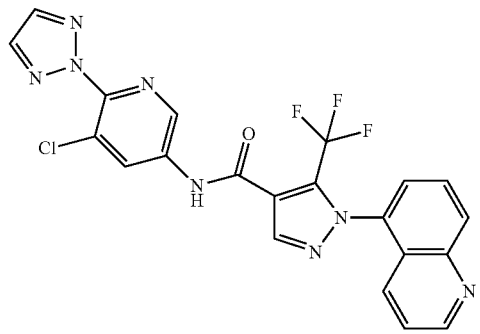 [SMILES: O=C(Nc1cnc(-n2nccn2)c(Cl)c1)c1cnn(-c2cccc3ncccc23)c1C(F)(F)F]

A solution consisting of 1-(quinolin-5-yl)-5-(trifluoromethyl)-1H-pyrazole-4-carbonyl chloride, 3c (200 mg, 0.614 mmol), 5-chloro-6-(2H-1,2,3-triazol-2-yl)pyridin-3-amine, 1j (144 mg, 0.737 mmol), and pyridine (10 mL) was stirred at 90° C. for 1 h before cooling to room temperature. The mixture was concentrated to dryness under reduced pressure, which was then purified by preparative HPLC using a Kromasil 150×25 mm×10 μm column (32% to 62% (v/v) CH$_3$CN and water with 0.05% NH$_3$) to afford compound 8 (149.20 mg, 50%) as a white solid. LCMS (ESI): mass calcd. for $C_{21}H_{12}ClF_3N_8O$ 484.08, m/z found 485.1 [M+H]$^+$. $^1$H NMR (400 MHz, CDCl$_3$) δ ppm 9.05-9.02 (m, 1H), 8.78 (d, J=2.0 Hz, 1H), 8.54 (d, J=2.4 Hz, 1H), 8.39-8.34 (m, 2H), 8.23 (s, 1H), 7.96 (s, 2H), 7.88-7.82 (m, 1H), 7.66-7.57 (m, 2H), 7.48 (dd, J=4.0, 8.0 Hz, 1H). LCMS (ESI) m/z M+1: 485.0.

Example 4

N-(3-chloro-4-(2H-1,2,3-triazol-2-yl)phenyl)-1-(isoquinolin-4-yl)-5-(trifluoromethyl)-1H-pyrazole-4-carboxamide, Cpd 38

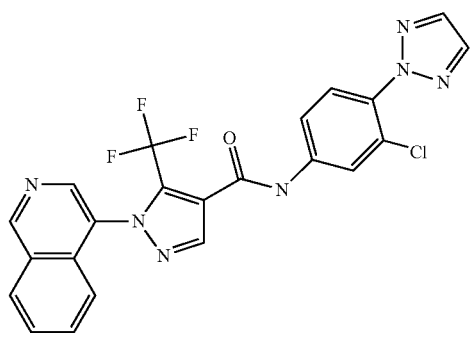 [SMILES: O=C(Nc1ccc(-n2nccn2)c(Cl)c1)c1cnn(-c2cncc3ccccc23)c1C(F)(F)F]

A. 4-Hydrazinylisoquinoline, 4a

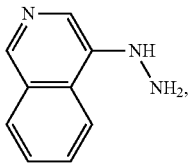

To a stirring solution of isoquinolin-4-amine (5.0 g, 34.68 mmol) in HCl (50 mL, 5N) at 0° C. was added a solution of sodium nitrite (NaNO$_2$, 3.59 g, 52.02 mmol) in water at 0° C. The reaction mixture was stirred at 0° C. for 30 min and a solution of tin (II) chloride dehydrate (SnCl$_2$.2 H$_2$O, 19.56 g, 86.70 mmol) in concentrated hydrochloric acid (5 mL) was added dropwise. The mixture was stirred at room temperature for 2 h. The mixture was adjusted to about pH 12-14 with 20% aqueous sodium hydroxide. At that time, the mixture was extracted with ethyl acetate (200 mL×3). The combined organic extracts were washed with brine (300 mL). The organic portion was dried over Na$_2$SO$_4$, filtered, and the filtrate concentrated under reduced pressure. The resultant crude product was purified by flash chromatography (petroleum ether/ethyl acetate=100:0 to ethyl acetate/methanol=90:10) to afford compound 4a (1.15 g, 20.8%) as a brown solid, which was used in the following reaction without further purification.

B. Ethyl 1-(isoquinolin-4-yl)-5-(trifluoromethyl)-1H-pyrazole-4-carboxylate, 4b

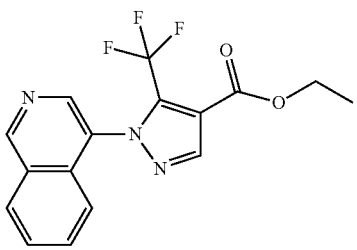

,

A mixture of 4-hydrazinylisoquinoline, 4a (1.15 g, 7.224 mmol) and ethyl (Z)-2-(ethoxymethylene)-4,4,4-trifluoro-3-oxobutanoate, 1f (2.08 g, 8.669 mmol) in EtOH (30 mL) was stirred at 80° C. for 16 h. The resulting solution was cooled to room temperature and concentrated to dryness under reduced pressure to afford a crude product. The crude product was purified by column chromatography over silica gel (petroleum ether/ethyl acetate=100:0 to 70:30) to afford compound 4b (1.77 g, 72.98%) as a yellow solid. LCMS (ESI) m/z M+1: 335.9; $^1$H NMR (400 MHz, CDCl$_3$) δ ppm 1.41 (t, J=7.06 Hz, 3H) 4.42 (q, J=7.06 Hz, 2H) 7.31 (d, J=8.38 Hz, 1H) 7.70-7.80 (m, 1H) 8.12 (dd, J=7.28, 1.10 Hz, 1H) 8.28 (s, 1H) 8.58 (s, 1H) 9.41 (s, 1H).

C. 1-(Isoquinolin-4-yl)-5-(trifluoromethyl)-1H-pyrazole-4-carboxylic acid, 4c

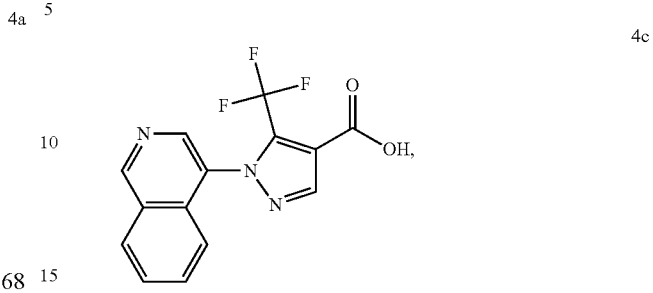

A solution of ethyl 1-(isoquinolin-4-yl)-5-(trifluoromethyl)-1H-pyrazole-4-carboxylate, 4b (500 mg, 1.49 mmol) in concentrated hydrochloric acid (5 mL) was stirred at 130° C. for 3 h. The solvent was concentrated under reduced pressure to afford compound 4c (465.61 mg, 100%) as a yellow solid. LCMS (ESI) m/z M+1: 307.9.

D. 2-(2-Chloro-4-nitrophenyl)-2H-1,2,3-triazole, 4d

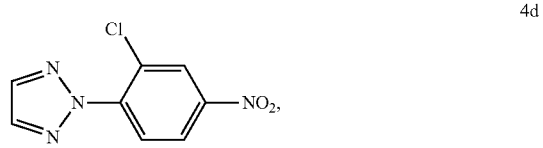 [SMILES: Nc1ccc(-n2nccn2)c(Cl)c1]

To a solution of 3-chloro-4-fluoronitrobenzene (1.2 g, 6.836 mmol) and 2H-1,2,3-triazole (0.567 g, 8.203 mmol) in anhydrous DMA (5 mL) was added K$_2$CO$_3$ (1.89 g, 13.7 mmol). The reaction mixture was stirred at 55° C. overnight. The reaction was concentrated to give a crude oil. The crude product was purified by flash column chromatography over silica gel (petroleum ether/ethyl acetate from 100/0 to 20/80) to give compound 4d (1 g, 65.1%) as a yellow solid. $^1$H NMR (400 MHz, CDCl$_3$) δ ppm 7.88-8.02 (m, 3H), 8.28 (dd, J=8.93, 2.54 Hz, 1H), 8.49 (d, J=2.21 Hz, 1H).

E. 3-Chloro-4-(2H-1,2,3-triazol-2-yl)aniline, 4e

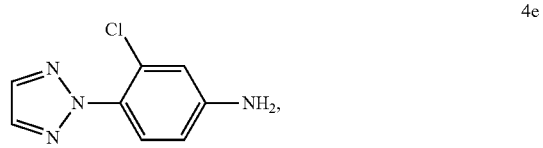

To a solution of 2-(2-chloro-4-nitrophenyl)-2H-1,2,3-triazole, 4d (1 g, 4.45 mmol) in MeOH/THF/water (5 mL/10 mL/5 mL) was added Fe(0) (1.243 g, 22.26 mmol) and ammonium chloride (1.191 g, 22.26 mmol). The reaction mixture was stirred at 60° C. for 2 h. The reaction was filtered and the organic solvent was concentrated under reduced pressure. Water (10 mL) was added and the mixture was extracted with ethyl acetate (15 mL×3). The organic extracts were dried over MgSO$_4$, filtered, and the filtrate was concentrated under reduced pressure to afford a crude product which was purified by flash column chromatography over silica gel (petroleum ether/ethyl acetate from 100/0 to 0/100) to afford 3-chloro-4-(2H-1,2,3-triazol-2-yl)aniline, 4e (0.7 g, 80.8%) as a yellow solid. ¹H NMR (400 MHz, CDCl₃) δ ppm 3.96 (br. s., 2H) 6.63 (d, J=8.41 Hz, 1H), 6.81 (d, J=1.96 Hz, 1H), 7.31 (d, J=8.61 Hz, 1H), 7.84 (s, 2H).

F. N-(3-Chloro-4-(2H-1,2,3-triazol-2-yl)phenyl)-1-(isoquinolin-4-yl)-5-(trifluoromethyl)-1H-pyrazole-4-carboxamide, Cpd 38

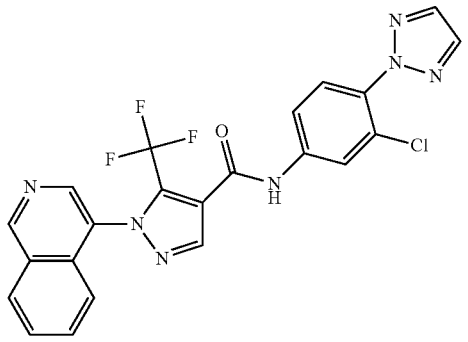 [SMILES: O=C(Nc1ccc(-n2nccn2)c(Cl)c1)c1cnn(-c2cncc3ccccc23)c1C(F)(F)F]

To a solution of 1-(isoquinolin-4-yl)-5-(trifluoromethyl)-1H-pyrazole-4-carboxylic acid, 4c (60 mg, 0.195 mmol), 3-chloro-4-(2H-1,2,3-triazol-2-yl)aniline, 4e (45.6 mg, 0.234 mmol) and pyridine (77.2 mg, 0.98 mmol) in dichloromethane (5 mL) was added POCl₃ (89.8 mg, 0.59 mmol) dropwise. The reaction mixture was stirred at 20° C. for 1 h. Saturated aqueous NaHCO₃ (20 mL) was added and the mixture was extracted with dichloromethane (20 mL×2). The combined organic extracts were washed with brine, dried over Na₂SO₄, filtered, and the filtrates concentrated under reduced pressure to afford a yellow oil. The yellow oil was purified by column chromatography over silica gel (petroleum ether/ethyl acetate=10:1 to petroleum ether/ethyl acetate=0:1) to afford compound 38 (35 mg, 35.8%) as a white solid. ¹H NMR (400 MHz, CDCl₃) δ ppm 7.34 (d, J=8.41 Hz, 1H), 7.58-7.68 (m, 2H), 7.72-7.84 (m, 2H), 7.89 (s, 2H), 7.96-8.06 (m, 2H), 8.15 (d, J=7.43 Hz, 1H), 8.24 (s, 1H), 8.60 (s, 1H), 9.44 (s, 1H); LCMS (ESI) m/z M+1: 483.9.

Example 5

N-(3-Cyano-4-(2H-1,2,3-triazol-2-yl)phenyl)-1-(isoquinolin-4-yl)-5-(trifluoromethyl)-1H-pyrazole-4-carboxamide, Cpd 59

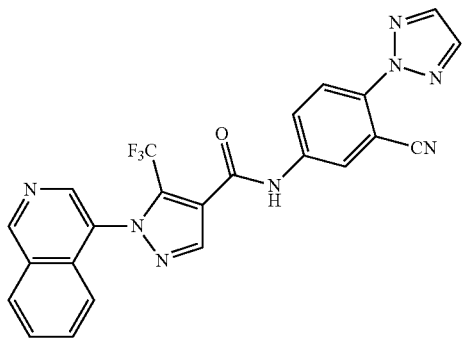 [SMILES: N#Cc1cc(NC(=O)c2cnn(-c3cncc4ccccc34)c2C(F)(F)F)ccc1-n1nccn1]

A. 5-Nitro-2-(2H-1,2,3-triazol-2-yl)benzonitrile, 5a

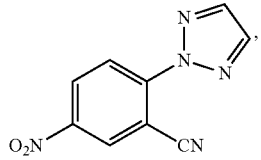

2-Fluoro-5-nitrobenzonitrile (500 mg, 3.01 mmol), 2H-1,2,3-triazole (228.68 mg, 3.311 mmol) and K₂CO₃ (832.02 mg, 6.02 mmol) were added to THF (10 mL) and stirred at 25° C. for 16 h. The reaction mixture was filtered, and the collected solid was washed with ethyl acetate (30 mL×3). The combined organic layers were concentrated under reduced pressure to afford a crude residue as a yellow solid which was purified by flash column chromatography over silica gel (petroleum ether/ethyl acetate, 100:0 to 50:50) to afford 5-nitro-2-(2H-1,2,3-triazol-2-yl)benzonitrile, 5a (140 mg, 21.6%) as a white solid. ¹H NMR (400 MHz, CDCl₃) δ ppm 8.72 (d, J=2.6 Hz, 1H), 8.56 (dd, J=2.5, 9.2 Hz, 1H), 8.42 (d, J=9.0 Hz, 1H), 8.03 (s, 2H).

B. 5-Amino-2-(2H-1,2,3-triazol-2-yl)benzonitrile, 5b

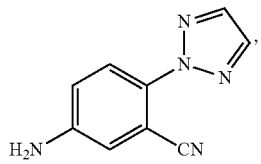

5-Nitro-2-(2H-1,2,3-triazol-2-yl)benzonitrile, 5a (140 mg, 0.651 mmol) was dissolved in THF (8 mL), to which Fe(0) (363.36 mg, 6.507 mmol), NH₄Cl (348.04 mg, 6.507 mmol) and water (8 mL) were added. The reaction mixture was stirred at 80° C. for 4 h. The reaction mixture was filtered though a pad of diatomaceous earth and the pad was washed with ethyl acetate (20 mL×3). Water (50 mL) was added and the organic layer was separated, dried over Na₂SO₄, filtered, and the filtrate concentrated to dryness to give crude compound 5b (140 mg) as yellow solid, which was used in the following reaction without further purification. LCMS (ESI) m/z M+1: 186.1.

277

C. N-(3-Cyano-4-(2H-1,2,3-triazol-2-yl)phenyl)-1-(isoquinolin-4-yl)-5-(trifluoromethyl)-1H-pyrazole-4-carboxamide, Cpd 59

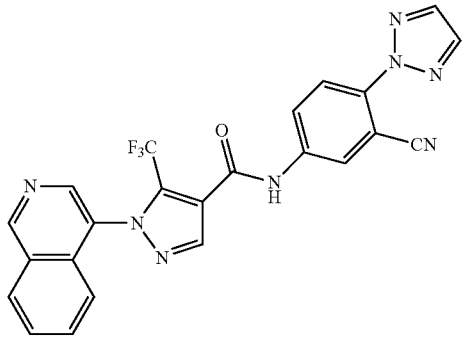 [SMILES: N#Cc1cc(NC(=O)c2cnn(-c3cncc4ccccc34)c2C(F)(F)F)ccc1-n1nccn1]

5-Amino-2-(2H-1,2,3-triazol-2-yl)benzonitrile, 5b (67.03 mg, 0.21 mmol), 1-(isoquinolin-4-yl)-5-(trifluoromethyl)-1H-pyrazole-4-carboxylic acid, 4c (66.95 mg, 0.315 mmol), and pyridine (74.84 mg, 0.946 mmol) were dissolved in dichloromethane (3 mL), and POCl$_3$ (48.36 mg, 0.315 mmol) was added to the mixture. The mixture was stirred at 25° C. for 16 h. Saturated aqueous NH$_4$Cl (20 mL) was added and the mixture was extracted with dichloromethane (20 mL×2). The combined organic extracts were dried over Na$_2$SO$_4$, filtered and the filtrates were concentrated under reduced pressure to afford a yellow oil. The oil was purified by flash column chromatography over silica gel (petroleum ether/ethyl acetate from 100:0 to 40/60) to afford compound 59 (38 mg, 36.3%) as a white solid. $^1$H NMR (400 MHz, DMSO-d$_6$) δ ppm 11.11 (br s, 1H), 9.59 (br s, 1H), 8.77 (br s, 1H), 8.58 (br s, 1H), 8.38 (br s, 2H), 8.29-8.04 (m, 4H), 8.01-7.69 (m, 2H), 7.27 (br d, J=5.5 Hz, 1H). LCMS (ESI) m/z M+1: 475.0.

Example 6

N-(5-Chloro-6-(oxazol-2-yl)pyridin-3-yl)-1-(isoquinolin-4-yl)-5-(trifluoromethyl)-1H-pyrazole-4-carboxamide, Cpd 50

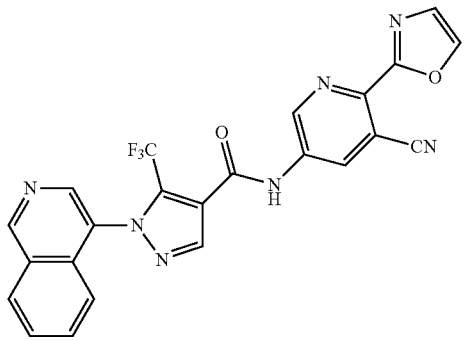 [SMILES: N#Cc1cc(NC(=O)c2cnn(-c3cncc4ccccc34)c2C(F)(F)F)cnc1-c1ncco1]

278

A. 2-(3-Chloro-5-nitropyridin-2-yl)oxazole, 6a

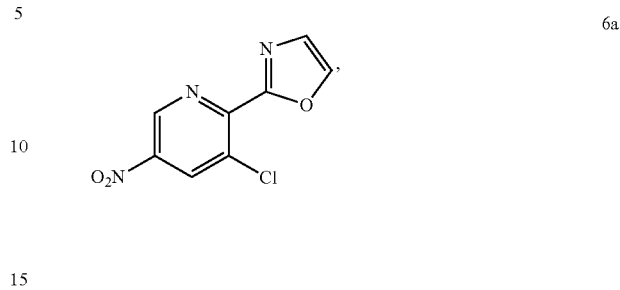

2,3-Dichloro-5-nitropyridine (216 mg, 1.119 mmol) and 2-(tributylstannyl)oxazole (400.1 mg, 1.119 mmol) were dissolved in DMF (3 mL) and purged with N$_2$. Pd(PPh$_3$)$_4$ (129 mg, 0.112 mmol) was added and the reaction was stirred at 110° C. for 16 h. The combined reaction mixture was concentrated under reduced pressure to afford a crude black oil. The oil was purified by flash column chromatography over silica gel (petroleum ether/ethyl acetate from 100/0 to 70/30) to afford 2-(3-chloro-5-nitropyridin-2-yl)oxazole, 6a (150 mg, 59.4%) as a yellow solid. $^1$H NMR (400 MHz, CDCl$_3$) δ ppm 7.49-7.55 (m, 1H) 7.93-7.99 (m, 1H) 8.66-8.72 (m, 1H) 9.40-9.47 (m, 1H); LCMS (ESI) m/z M+1: 225.9.

B. 5-Chloro-6-(oxazol-2-yl)pyridin-3-amine, 6b

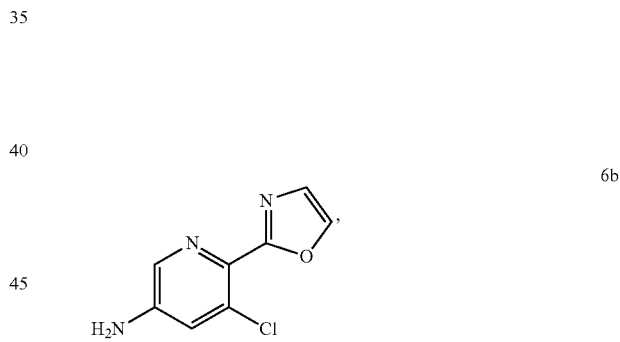

2-(3-Chloro-5-nitropyridin-2-yl)oxazole, 6a (88 mg, 0.39 mmol), Fe(0) (217.8 mg, 3.90 mmol), and NH$_4$Cl (208.6 mg, 3.90 mmol) were added to a mixture of THF (5 mL) and water (1 mL). The reaction mixture was stirred at 80° C. for 3 h. The reaction mixture was filtered though a pad of diatomaceous earth and the pad was washed with ethyl acetate (20 mL×3). The combined filtrates were concentrated to dryness to give a crude yellow oil as product. The crude product was purified by flash column chromatography over silica gel (petroleum ether/ethyl acetate from 50/50 to 0/100) to afford 5-chloro-6-(oxazol-2-yl)pyridin-3-amine, 6b (50 mg, 65.5%) as a yellow oil, which was used in the following reaction without further purification.

C. N-(5-Chloro-6-(oxazol-2-yl)pyridin-3-yl)-1-(isoquinolin-4-yl)-5-(trifluoromethyl)-1H-pyrazole-4-carboxamide, Cpd 50

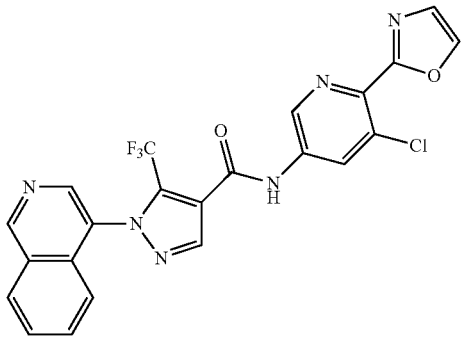 [SMILES: O=C(Nc1cnc(-c2ncco2)c(Cl)c1)c1cnn(-c2cncc3ccccc23)c1C(F)(F)F]

POCl₃ (78.4 mg, 0.511 mmol) was added to a mixture of 5-chloro-6-(oxazol-2-yl)pyridin-3-amine, 6b (50 mg, 0.256 mmol), 1-(isoquinolin-4-yl)-5-(trifluoromethyl)-1H-pyrazole-4-carboxylic acid, 4c (62.8 mg, 0.204 mmol), and pyridine (101 mg, 1.278 mmol) in dichloromethane (5 mL). The reaction mixture was stirred at 20° C. for 16 h. Water (20 mL) was added to the mixture. The mixture was extracted with dichloromethane (30 mL). The organic layer was concentrated under reduced pressure to afford a crude product, which was purified by preparative reverse phase HPLC (water (0.05% HCl):MeCN from 76% to 46%) and lyophilized to give N-(5-chloro-6-(oxazol-2-yl)pyridin-3-yl)-1-(isoquinolin-4-yl)-5-(trifluoromethyl)-1H-pyrazole-4-carboxamide, compound 50 (28 mg, 22.6%) as a white solid. ¹H NMR (400 MHz, METHANOL-d₄) δ ppm 7.50 (s, 1H), 7.65 (d, J=8.38 Hz, 1H), 8.11-8.21 (m, 2H), 8.27 (t, J=7.20 Hz, 1H), 8.53 (s, 1H), 8.60-8.70 (m, 2H), 8.97 (br s, 1H), 9.05 (s, 1H), 9.98 (s, 1H); LCMS (ESI) m/z M+1: 484.9.

Example 7

N-(5-cyano-6-(2H-1,2,3-triazol-2-yl)pyridin-3-yl)-1-(isoquinolin-4-yl)-5-(trifluoromethyl)-1H-pyrazole-4-carboxamide, Cpd 47

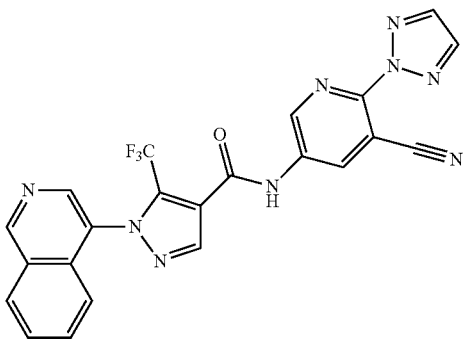 [SMILES: N#Cc1cc(NC(=O)c2cnn(-c3cncc4ccccc34)c2C(F)(F)F)cnc1-n1nccn1]

A. 5-Nitro-2-(2H-1,2,3-triazol-2-yl)nicotinonitrile, 7a

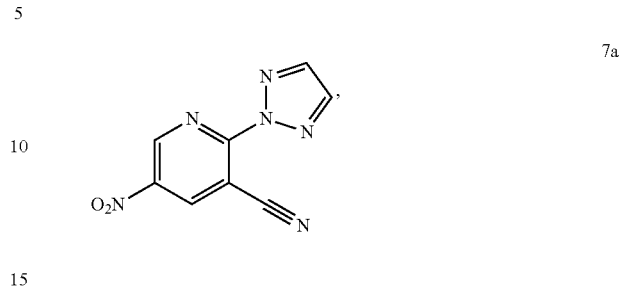

A mixture of 2-chloro-5-nitronicotinonitrile (600 mg, 3.27 mmol), 1,2,3-triazole (270 mg, 3.92 mmol) and K₂CO₃ (1.35 g, 9.8 mmol) in CH₃CN (10 mL) was stirred at 30° C. for 2 h. A yellow solid was collected by filtration and was washed with ethyl acetate (100 mL). The filtrate was concentrated under reduced pressure to give a crude product which was washed with dichloromethane (10 mL). The solid was dried under reduced pressure to give 5-nitro-2-(2H-1,2,3-triazol-2-yl)nicotinonitrile, 7a (0.4 g, 56.6%) as a white solid. ¹H NMR (400 MHz, DMSO-d₆) δ ppm 8.44 (s, 2H), 9.43 (d, J=2.35 Hz, 1H), 9.59 (d, J=2.35 Hz, 1H).

B. 5-Amino-2-(2H-1,2,3-triazol-2-yl)nicotinonitrile, 7b

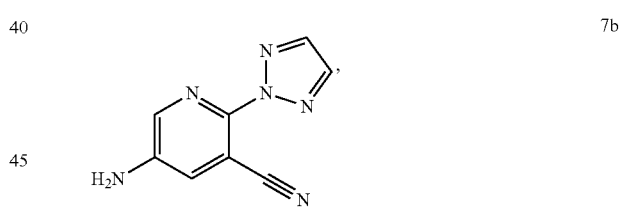

A solution of 5-nitro-2-(2H-1,2,3-triazol-2-yl)nicotinonitrile, 7a (353 mg 1.6 mmol), Fe(0), (456 mg, 8.2 mmol) and NH₄Cl (437 mg, 8.2 mmol) in THF/MeOH/water (4:2:1, 35 mL) was stirred at 60° C. for 1 h. The reaction mixture was filtered, and the filtrate was concentrated under reduced pressure to give a crude product as a yellow oil. Water (20 mL) was added to the yellow oil. The mixture was extracted with ethyl acetate (30×3 mL), dried over MgSO₄, filtered and the filtrate concentrated under reduced pressure to afford 5-amino-2-(2H-1,2,3-triazol-2-yl)nicotinonitrile, 7b (200 mg, 65.7%) as a white solid, which was used in the following reaction without further purification. ¹H NMR (400 MHz, METHANOL-d₄) δ ppm 7.46 (d, J=3.09 Hz, 1H), 8.00 (s, 2H), 8.10 (d, J=3.09 Hz, 1H).

C. N-(5-Cyano-6-(2H-1,2,3-triazol-2-yl)pyridin-3-yl)-1-(isoquinolin-4-yl)-5-(trifluoromethyl)-1H-pyrazole-4-carboxamide, Cpd 47

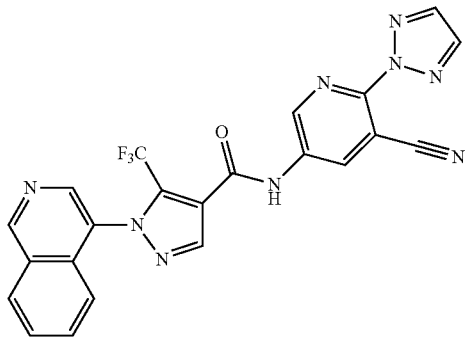 [SMILES: N#Cc1cc(NC(=O)c2cnn(-c3cncc4ccccc34)c2C(F)(F)F)cnc1-n1nccn1]

POCl₃ (82.36 mg, 0.537 mmol) was added to a mixture of 5-amino-2-(2H-1,2,3-triazol-2-yl)nicotinonitrile, 7b (50 mg, 0.269 mmol), 1-(isoquinolin-4-yl)-5-(trifluoromethyl)-1H-pyrazole-4-carboxylic acid, 4c (66 mg, 0.215 mmol), and pyridine (106 mg, 1.343 mmol) in dichloromethane (5 mL), and the mixture was stirred at 20° C. for 2 h. Water (20 mL) was added and the mixture was extracted with dichloromethane (30 mL). The organic layer was concentrated under reduced pressure to afford a crude product. The crude product was purified by preparative high-performance liquid chromatography (water (0.05% HCl):MeCN from 84:16 to 66:44). The pure fractions were collected, the organic solvents concentrated under reduced pressure, and the mixture lyophilized to dryness to afford compound 47 (29 mg, 22.7%) as a yellow solid. ¹H NMR (400 MHz, METHANOL-d₄) δ ppm 7.51 (d, J=8.82 Hz, 1H), 7.97-8.03 (m, 1H), 8.07-8.16 (m, 3H), 8.47-8.51 (m, 2H), 8.85 (s, 1H), 8.91 (d, J=2.43 Hz, 1H), 9.08 (br s, 1H), 9.75 (s, 1H); LCMS (ESI) m/z M+1: 476.0.

Example 8

N-(5-chloro-6-(1-methyl-1H-pyrazol-3-yl)pyridin-3-yl)-1-(isoquinolin-4-yl)-5-(trifluoromethyl)-1H-pyrazole-4-carboxamide, Cpd 52

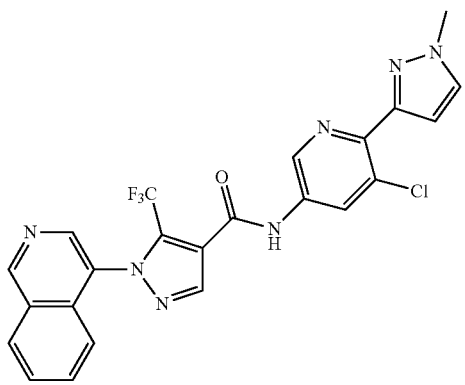 [SMILES: Cn1ccc(-c2ncc(NC(=O)c3cnn(-c4cncc5ccccc45)c3C(F)(F)F)cc2Cl)n1]

A. 5-Chloro-6-(1-methyl-1H-pyrazol-3-yl)pyridin-3-amine, 8a

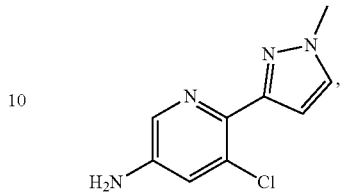

6-Bromo-5-chloropyridin-3-amine (383.87 mg, 1.85 mmol), 1-methyl-3-(4,4,5,5-tetramethyl-1,3,2-dioxaborolan-2-yl)-1H-pyrazole (350 mg, 1.682 mmol) and Na₂CO₃ (356.58 mg, 3.364 mmol) were added to dioxane/water (9:1, 6 mL) and purged with N₂. Pd(dppf)Cl₂ (123.09 mg, 0.168 mmol) was added and the reaction was stirred at 120° C. for 16 h. The reaction mixture was filtered though a pad of diatomaceous earth and the pad was washed with ethyl acetate (20 mL×3). The combined filtrates were concentrated to dryness to give a crude black oil. The black oil was purified by preparative reverse phase HPLC. The pure fractions were collected, the organic solvents concentrated under reduced pressure, and the mixture lyophilized to dryness to afford 5-chloro-6-(1-methyl-1H-pyrazol-3-yl)pyridin-3-amine, 8a (150 mg, 42.7%, yield) as a yellow oil. LCMS (ESI) m/z M+1: 209.1.

B. N-(5-Chloro-6-(1-methyl-1H-pyrazol-3-yl)pyridin-3-yl)-1-(isoquinolin-4-yl)-5-(trifluoromethyl)-1H-pyrazole-4-carboxamide, Cpd 52

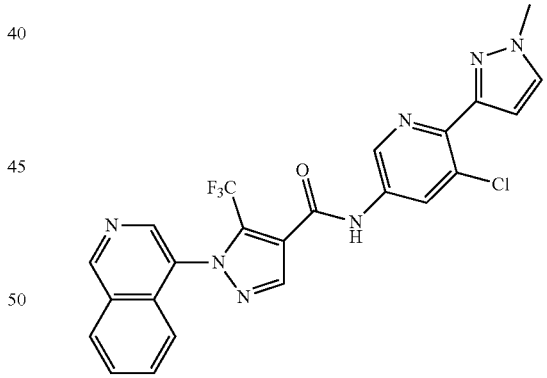

To a solution of ethyl 1-(isoquinolin-4-yl)-5-(trifluoromethyl)-1H-pyrazole-4-carboxylate, 4b (106.95 mg, 0.335 mmol), 5-chloro-6-(1-methyl-1H-pyrazol-3-yl)pyridin-3-amine, 8a (70 mg, 0.335 mmol) and pyridine (132.69 mg, 1.677 mmol) in dichloromethane (5 mL) was added POCl₃ (102.88 mg, 0.671 mmol) dropwise. The reaction mixture was stirred at 20° C. for 1 h. A solution of saturated aqueous NaHCO₃ (20 mL) was added and the mixture was extracted with dichloromethane (20 mL×2). The combined organic phases were washed with brine and dried over Na₂SO₄. The mixture was filtered, and the filtrates concentrated under reduced pressure to afford a crude product as a yellow oil. The crude product was purified by flash column chromatography over silica gel (dichloromethane: MeOH=from 100:0 to 80:20) to afford a residue, which was further purified by preparative reverse phase HPLC. The pure fractions were collected, the organic solvents concentrated under reduced pressure, and the mixture lyophilized to dryness to give N-(5-chloro-6-(1-methyl-1H-pyrazol-3-yl)pyridin-3-yl)-1-(isoquinolin-4-yl)-5-(trifluoromethyl)-1H-pyrazole-4-carboxamide, compound 52 (45 mg, 26.7%) as a yellow solid. $^1$H NMR (400 MHz, DMSO-d$_6$) δ ppm 11.03 (br s, 1H), 9.60 (s, 1H), 8.83 (d, J=2.0 Hz, 1H), 8.77 (s, 1H), 8.58 (s, 1H), 8.42 (d, J=2.0 Hz, 1H), 8.36 (d, J=8.2 Hz, 1H), 7.96-7.89 (m, 1H), 7.88-7.82 (m, 1H), 7.77 (d, J=2.2 Hz, 1H), 7.27 (d, J=8.4 Hz, 1H), 6.75 (d, J=2.0 Hz, 1H), 3.91 (s, 3H). LCMS (ESI) m/z M+1: 497.9.

Example 9

N-(5-chloro-6-(2H-1,2,3-triazol-2-yl)pyridin-3-yl)-1-(isoquinolin-4-yl)-5-(trifluoromethyl)-1H-pyrazole-4-carboxamide, Cpd 32

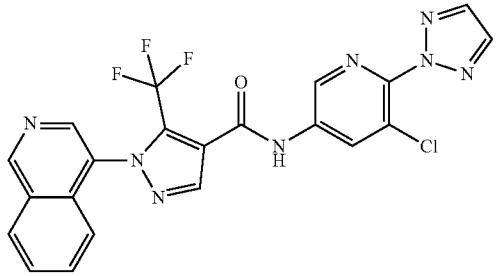

A 20 mL vial equipped with a stirbar was charged with ethyl 1-(isoquinolin-4-yl)-5-(trifluoromethyl)-1H-pyrazole-4-carboxylate, 4b (67 mg, 0.2 mmol), 5-chloro-6-(2H-1,2,3-triazol-2-yl)pyridin-3-amine, 1j (39.9 mg, 0.204 mmol), and THF (0.67 mL, 0.3 M, 0.201 mmol). The resulting solution was treated with 1.01 M KOtBu/THF (0.32 mL, 1.01 M, 0.323 mmol) in one portion at room temperature and then stirred for 25 min. The reaction was then partitioned between 5 M NH$_4$Cl (1 mL) and ethyl acetate (2 mL), and the organic layer was dried over Na$_2$SO$_4$, filtered, and the filtrate concentrated to dryness to provide a beige foam (78 mg). The foam was purified by flash column chromatography on a 12 g Silicycle HP column (10-100% EtOAc in heptane over 25 CVs, then isocratic EtOAc) to provide compound 32 as a foam (27.4 mg, 28%). $^1$H NMR (400 MHz, CDCl$_3$) δ ppm 9.45 (s, 1H), 8.80 (d, J=2.53 Hz, 1H), 8.66 (br s, 1H), 8.49-8.59 (m, 2H), 8.25 (s, 1H), 8.16 (dd, J=1.52, 7.07 Hz, 1H), 7.92-8.00 (m, 2H), 7.71-7.83 (m, 2H); MS m/e 485.0 (M+H).

Example 10

N-(5-chloro-6-(2H-1,2,3-triazol-2-yl)pyridin-3-yl)-1-(isoquinolin-1-yl)-5-(trifluoromethyl)-1H-pyrazole-4-carboxamide, Cpd 57

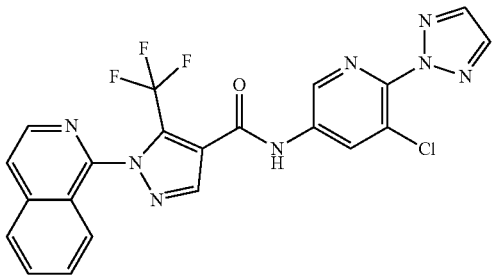 [SMILES: O=C(Nc1cnc(-n2nccn2)c(Cl)c1)c1cnn(-c2nccc3ccccc23)c1C(F)(F)F]

A. 1-Hydrazinylisoquinoline, 10a

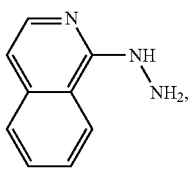

A 2-5 mL Biotage microwave vial equipped with a stirbar was charged with 1-chloroisoquinoline (341.8 mg, 2.089 mmol) and hydrazine (0.66 mL, 1.021 g/mL, 21.028 mmol) at room temperature, and the vial was evacuated/flushed with Argon (4×) and the reaction was stirred at 150° C. for 20 min. The resulting dark yellow homogeneous solution was allowed to cool to room temperature, at which time a precipitate formed. This was taken up in a 3:1 water/CH$_3$CN mixture (2 mL) and the solids were collected by filtration. The yellow filter cake was washed with water (2 mL×3) and then dissolved in DCM (6 mL). The DCM mixture was dried over Na$_2$SO$_4$, filtered, and the filtrate concentrated to provide compound 10a as a yellow solid (189 mg, 57%).

B. N-(5-Chloro-6-(2H-1,2,3-triazol-2-yl)pyridin-3-yl)-1-(isoquinolin-1-yl)-5-(trifluoromethyl)-1H-pyrazole-4-carboxamide, Cpd 57

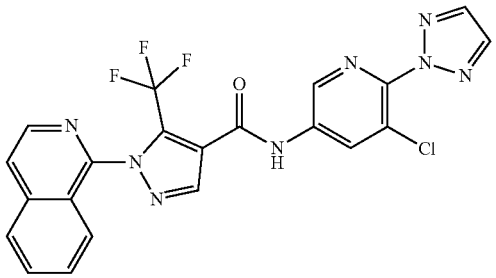 [SMILES: O=C(Nc1cnc(-n2nccn2)c(Cl)c1)c1cnn(-c2nccc3ccccc23)c1C(F)(F)F]

A 4 mL vial equipped with a with stirbar was charged with 1-hydrazinylisoquinoline, 10a (45.5 mg, 0.286 mmol), THF (0.41 mL, 0.7 M, 0.287 mmol), and 0.5 M ethyl 2-(ethoxymethylene)-4,4,4-trifluoro-3-oxobutanoate, 1f/THF (0.57 mL, 0.5 M, 0.285 mmol), and the reaction was stirred at room temperature for 10 min, followed by 90 min of stirring at 70° C. The reaction was then charged with calcium sulfate (183 mg, 1.34 mmol) and stirred at 70° C. for 10 min. The reaction was then cooled to room temperature, treated with 5-chloro-6-(2H-1,2,3-triazol-2-yl)pyridin-3-amine, 1j (56.6 mg, 0.288 mmol) and 1.01 M KOtBu/THF (0.42 mL, 1.01 M, 0.424 mmol) in single portions at room temperature, and the resulting dark reaction was stirred at room temperature for 30 min. The dark reaction was then partitioned between 5 M NH$_4$Cl (1 mL) and ethyl acetate (1 mL), and the organic layer was dried over Na$_2$SO$_4$, filtered, and the filtrate concentrated under reduced pressure. The resultant residue was purified by flash column chromatography (50-100% EtOAc in heptane over 10 CVs) followed by (1:1 acetone/heptane; isocratic) to afford compound 57 (21.3 mg, 15%). $^1$H NMR (400 MHz, CDCl$_3$) δ ppm 8.77 (d, J=2.02 Hz, 1H), 8.50-8.53 (m, 2H), 8.26 (s, 1H), 7.91-8.02 (m, 4H), 7.83 (ddd, J=2.78, 5.56, 8.34 Hz, 1H), 7.67-7.72 (m, 2H); MS m/e 485.1 (M+H).

Example 11

N-(3-cyano-4-(1H-1,2,3-triazol-1-yl)phenyl)-1-(isoquinolin-4-yl)-5-(trifluoromethyl)-1H-pyrazole-4-carboxamide, Cpd 62

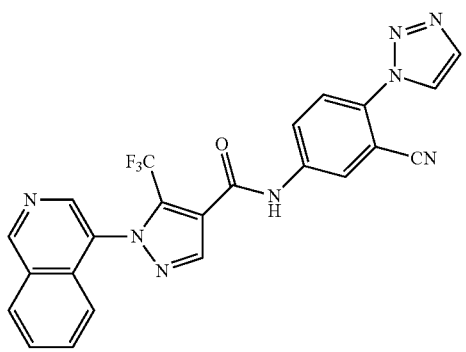 [SMILES: N#Cc1cc(NC(=O)c2cnn(-c3cncc4ccccc34)c2C(F)(F)F)ccc1-n1ccnn1]

A. 5-Nitro-2-(1H-1,2,3-triazol-1-yl)benzonitrile, 11a

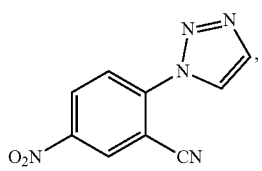

11a

2-Fluoro-5-nitrobenzonitrile (500 mg, 3.01 mmol), triazole (228.7 mg, 3.31 mmol) and K$_2$CO$_3$ (832.0 mg, 6.02 mmol) were added to THF (10 mL) and stirred at 25° C. for 16 h. The reaction mixture was filtered and the residue was washed with ethyl acetate (30 mL×3). The combined organic layers were concentrated under reduced pressure to afford a crude yellow solid. The crude solid was purified by flash column chromatography over silica gel (petroleum ether/ethyl acetate from 100:0 to 50:50) to afford 5-nitro-2-(1H-1,2,3-triazol-1-yl)benzonitrile, 11a (500 mg, 77.2%) as a yellow solid. $^1$H NMR (400 MHz, CDCl$_3$) δ ppm 8.74 (d, J=2.6 Hz, 1H), 8.65 (dd, J=2.4, 9.0 Hz, 1H), 8.48 (d, J=0.9 Hz, 1H), 8.27 (d, J=9.0 Hz, 1H), 7.98 (d, J=0.9 Hz, 1H).

B. 5-Amino-2-(1H-1,2,3-triazol-1-yl)benzonitrile, 11b

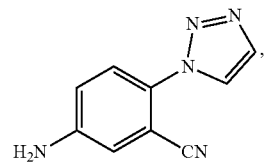

11b

5-Nitro-2-(1H-1,2,3-triazol-1-yl)benzonitrile, 11a (500 mg, 2.32 mmol) was dissolved in THF (10 mL), to which Fe(0) (1297.7 mg, 23.24 mmol), NH$_4$Cl (1243.0 mg, 23.24 mmol) and water (10 mL) were added. The reaction mixture was stirred at 80° C. for 4 h. The reaction mixture was filtered though a pad of diatomaceous earth and the pad was washed with ethyl acetate (20 mL×3). Water (30 mL) was added and the organic layer was separated, dried over Na$_2$SO$_4$, filtered and the filtrate concentrated to dryness to give crude 5-amino-2-(1H-1,2,3-triazol-1-yl)benzonitrile, 11b (460 mg, 104.4%, crude) as a yellow solid. LCMS (ESI) m/z M+1: 185.9.

C. N-(3-cyano-4-(1H-1,2,3-triazol-1-yl)phenyl)-1-(isoquinolin-4-yl)-5-(trifluoromethyl)-1H-pyrazole-4-carboxamide, Cpd 62

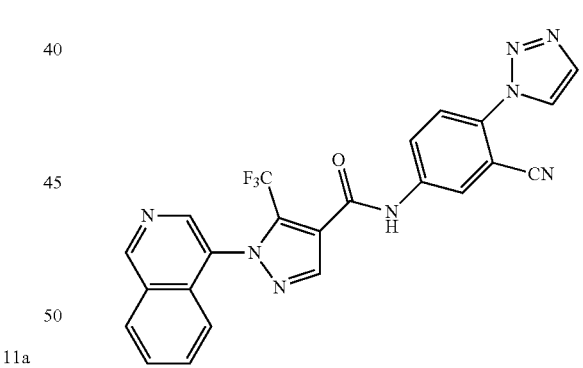

1-(Isoquinolin-4-yl)-5-(trifluoromethyl)-1H-pyrazole-4-carboxylic acid, 4c (75.1 mg, 0.23 mmol), 5-amino-2-(1H-1,2,3-triazol-1-yl)benzonitrile, 11b (66.4 mg, 0.35 mmol), and pyridine (83.1 mg, 1.05 mmol) were dissolved in dichloromethane (3 mL), and POCl$_3$ (53.7 mg, 0.35 mmol) was added. The mixture was stirred at 25° C. for 16 h. Sat. aqueous NH$_4$Cl (20 mL) was added and the mixture was extracted with dichloromethane (20 mL×2). The combined organic layers were dried over Na$_2$SO$_4$, filtered and the filtrates were concentrated under reduced pressure to afford a crude yellow oil. The crude oil was purified by reverse phase HPLC (A: water (0.05% HCl), B: MeCN, then: A (62%) and B (38%) at the end: A: (32%) and B (68%)). The pure fractions were collected, concentrated under reduced pressure, and lyophilized to dryness to afford compound 62 (35 mg, 29%) as a white solid. LCMS (ESI) m/z M+1: 185.9; ¹H NMR (400 MHz, DMSO-d₆) δ ppm 11.48 (s, 1H), 9.69 (s, 1H), 8.86 (s, 1H), 8.77 (br d, J=4.0 Hz, 2H), 8.53 (br d, J=1.3 Hz, 1H), 8.43 (br d, J=8.3 Hz, 1H), 8.31 (br d, J=8.8 Hz, 1H), 8.07 (s, 1H), 8.03-7.96 (m, 1H), 7.96-7.87 (m, 2H), 7.35 (br d, J=8.5 Hz, 1H).

Example 12

N-(5-cyano-6-(1-methyl-1H-pyrazol-3-yl)pyridin-3-yl)-1-(isoquinolin-4-yl)-5-(trifluoromethyl)-1H-pyrazole-4-carboxamide, Cpd 78

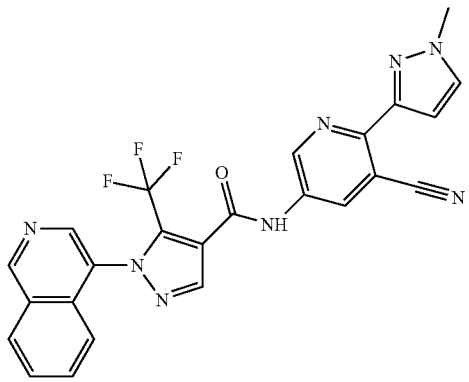 [SMILES: Cn1ccc(-c2ncc(NC(=O)c3cnn(-c4cncc5ccccc45)c3C(F)(F)F)cc2C#N)n1]

A. 5-Amino-2-chloronicotinonitrile, 12a

2-Chloro-5-nitronicotinonitrile (500 mg, 2.72 mmol) was dissolved in THF (10 mL), to which was added Fe (0) (1521.2 mg, 27.24 mmol), NH₄Cl (1457.1 mg, 27.24 mmol) and water (10 mL). The reaction mixture was stirred at 80° C. for 4 h. The reaction mixture was filtered though a pad of diatomaceous earth and the pad was washed with ethyl acetate (20 mL×3). Water (50 mL) was added and the organic layer was separated, dried over Na₂SO₄, filtered and the filtrate was concentrated to dryness to give a crude yellow solid. The crude solid was purified by flash column chromatography over silica gel (petroleum ether/ethyl acetate from 100/0 to 80/20) to afford 5-amino-2-chloronicotinonitrile, 12a (270 mg, 64.5%) as a yellow solid. ¹H NMR (400 MHz, CDCl₃) δ ppm 7.73 (d, J=2.8 Hz, 1H), 7.04 (d, J=2.8 Hz, 1H), 4.96 (br s, 2H).

B. 5-Amino-2-(1-methyl-1H-pyrazol-3-yl)nicotinonitrile, 12b

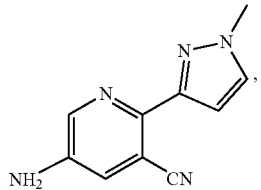

5-Amino-2-chloronicotinonitrile, 12a (100 mg, 0.65 mmol), 1-methyl-3-(4,4,5,5-tetramethyl-1,3,2-dioxaborolan-2-yl)-1H-pyrazole (135.5 mg, 0.65 mmol) and Na₂CO₃ (138.0 mg, 1.30 mmol) were added to a dioxane/water mixture (9:1, 6 mL) and the reaction was purged with N₂. Pd(dppf)Cl₂ (47.6, 0.065 mmol) was added and the reaction was stirred at 100° C. for 16 h. The reaction mixture was concentrated to dryness to give a crude black oil. The crude oil was purified by flash column chromatography over silica gel (dichloromethane/MeOH from 100/0 to 90/10) to afford 5-amino-2-(1-methyl-1H-pyrazol-3-yl)nicotinonitrile, 12b (100 mg, 51.3%) as a black solid. LCMS (ESI) m/z M+1: 200.1.

C. N-(5-cyano-6-(1-methyl-1H-pyrazol-3-yl)pyridin-3-yl)-1-(isoquinolin-4-yl)-5-(trifluoromethyl)-1H-pyrazole-4-carboxamide, Cpd 78

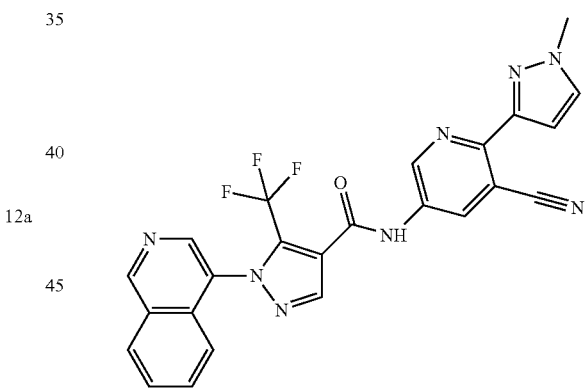

1-(Isoquinolin-4-yl)-5-(trifluoromethyl)-1H-pyrazole-4-carboxylic acid, 4c (70 mg, 0.22 mmol), 5-amino-2-(1-methyl-1H-pyrazol-3-yl)nicotinonitrile, 12b (97.8 mg, 0.33 mmol), and pyridine (74.5 mg, 0.98 mmol) were dissolved in dichloromethane (3 mL), and POCl₃ (50.0 mg, 0.32 mmol) was added. The mixture was stirred at 25° C. for 16 h. Sat. aqueous NaHCO₃ (20 mL) was added and the mixture extracted with dichloromethane (20 mL×2). The combined organic layers were dried over Na₂SO₄, filtered, and the filtrates were concentrated under reduced pressure to afford a crude yellow oil. The oil was purified by reverse phase HPLC (A: water (0.05% HCl), B: MeCN; then: AB (75%/25% to 48%/52%). The pure fractions concentrated under reduced pressure and lyophilized to dryness to give compound 78 (50 mg, 46%) as a yellow solid. LCMS (ESI) m/z M+1: 489.0. ¹H NMR (400 MHz, DMSO-d₆) δ ppm 11.33 (s, 1H), 9.64 (s, 1H), 9.13 (d, J=1.8 Hz, 1H), 8.81 (s, 1H), 8.67 (br s, 2H), 8.39 (br d, J=8.2 Hz, 1H), 7.99-7.91 (m, 1H), 7.90-7.80 (m, 2H), 7.29 (br d, J=8.2 Hz, 1H), 6.85 (d, J=1.8 Hz, 1H), 3.94 (s, 3H).

Example 13

N-(5-cyano-6-(1-methyl-1H-pyrazol-3-yl)pyridin-3-yl)-1-(quinolin-5-yl)-5-(trifluoromethyl)-1H-pyrazole-4-carboxamide, Cpd 89

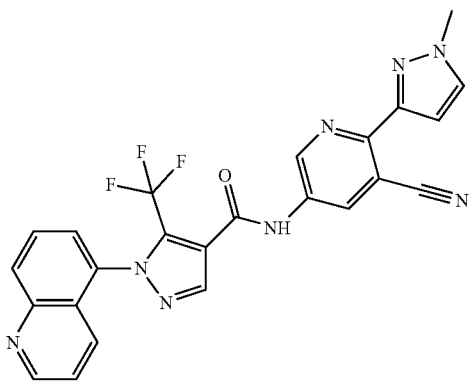 [SMILES: Cn1ccc(-c2ncc(NC(=O)c3cnn(-c4cccc5ncccc45)c3C(F)(F)F)cc2C#N)n1]

A. 5-Hydrazinylquinoline, 13a

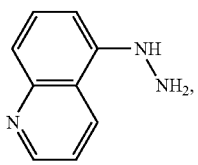

To a stirring solution of isoquinolin-4-amine (3.5 g, 24.28 mmol) in HCl (35 mL, 5 N) at 0° C., was added a solution of sodium nitrite (NaNO$_2$, 2.51 g, 36.42 mmol) in water at 0° C. The reaction mixture was stirred at 0° C. for 30 min and a solution of tin (II) chloride dihydrate (SnCl$_2$.2 H$_2$O, 13.695 g, 60.69 mmol) dissolved in concentrated hydrochloric acid (6.5 mL) was added dropwise. The mixture was stirred at room temperature for 2 h. The mixture was adjusted to pH 12-14 with 20% aqueous sodium hydroxide. The mixture was extracted with ethyl acetate (200 mL×3). The combined organic layers were washed with brine (300 mL). The organic layers were dried over Na$_2$SO$_4$, filtered, and the filtrate concentrated under reduced pressure. The resulting crude product was purified by flash chromatography (petroleum ether/ethyl acetate=100:0 to ethyl acetate/methanol=90:10) to afford compound 13a (1.5 g, 39%) as a brown solid.

B. Ethyl 1-(quinolin-5-yl)-5-(trifluoromethyl)-1H-pyrazole-4-carboxylate, 13b

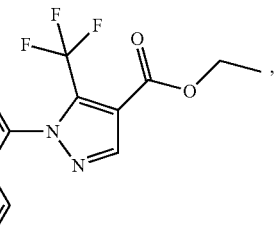

A solution of 5-hydrazinylquinoline, 13a (1.5 g, 9.42 mmol) and ethyl 2-(ethoxymethylene)-4,4,4-trifluoro-3-oxobutanoate, 1f (2.716 g, 11.31 mmol) in EtOH (40 mL) was stirred at 80° C. for 16 h. The resultant solution was cooled to room temperature and concentrated to dryness under reduced pressure to afford a crude product, which was purified by column chromatography over silica gel (petroleum ether/ethyl acetate, 100:0 to 70:30) to afford crude compound 13b (2.56 g, 80.9%) as a yellow solid. LCMS (ESI) m/z M+1: 336.4. $^1$H NMR (400 MHz, CDCl$_3$) δ ppm 1.34-1.47 (m, 3H), 4.36-4.48 (m, 2H), 7.41-7.50 (m, 1H), 7.55-7.67 (m, 2H), 7.77-7.86 (m, 1H), 8.25 (s, 1H), 8.29-8.38 (m, 1H), 8.96-9.06 (m, 1H).

C. N-(5-cyano-6-(1-methyl-1H-pyrazol-3-yl)pyridin-3-yl)-1-(quinolin-5-yl)-5-(trifluoromethyl)-1H-pyrazole-4-carboxamide, Cpd 89

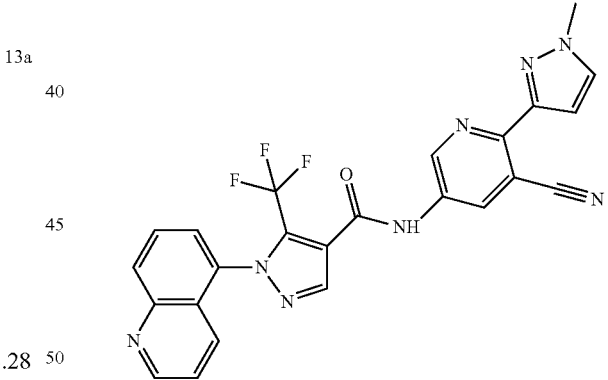

1-(Quinolin-5-yl)-5-(trifluoromethyl)-1H-pyrazole-4-carboxylic acid, 3b (102.2 mg, 0.33 mmol), 5-amino-2-(1-methyl-1H-pyrazol-3-yl)nicotinonitrile, 12b (150 mg, 0.50 mmol), and pyridine (118.47 mg, 1.50 mmol) were dissolved in dichloromethane (3 mL), and POCl$_3$ (76.496 mg, 0.499 mmol) was added. The mixture was stirred at 25° C. for 16 h. Sat. aqueous NaHCO$_3$ (20 mL) was added and the mixture was extracted with dichloromethane (20 mL×2). The combined organic layers were dried over Na$_2$SO$_4$, filtered, and the filtrates were concentrated under reduced pressure to afford a crude yellow oil. The oil was purified by reverse phase HPLC (A: water (0.05% HCl), B: MeCN; then: AB (75%/25% to 45%/55%). The pure fractions were concentrated under reduced pressure and lyophilized to dryness to afford compound 89 (85 mg, 52%) as a yellow solid. LCMS (ESI) m/z M+1: 489.1; ¹H NMR (400 MHz, DMSO-d₆) δ 11.42 (s, 1H), 9.14 (dd, J=2.4, 11.9 Hz, 2H), 8.74-8.61 (m, 2H), 8.39 (d, J=8.6 Hz, 1H), 8.07-7.95 (m, 2H), 7.86-7.73 (m, 3H), 6.84 (d, J=1.8 Hz, 1H), 3.94 (s, 3H).

Example 14

N-(5-Chloro-6-(1H-pyrazol-1-yl)pyridin-3-yl)-1-(isoquinolin-4-yl)-5-(trifluoromethyl)-1H-pyrazole-4-carboxamide, Cpd 46

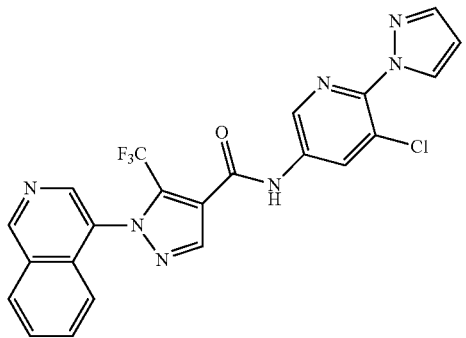 [SMILES: O=C(Nc1cnc(-n2cccn2)c(Cl)c1)c1cnn(-c2cncc3ccccc23)c1C(F)(F)F]

A. 3-Chloro-5-nitro-2-(1H-pyrazol-1-yl)pyridine, 14a

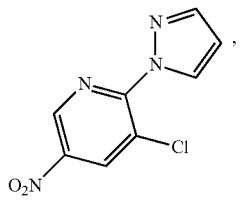

2,3-Dichloro-5-nitropyridine (1 g, 5.18 mmol), pyrazole (529 mg, 7.77 mmol), and Cs₂CO₃ (5.06 g, 15.50 mmol) were added to DMF (15 mL) and stirred at 20° C. for 16 h. The reaction mixture was filtered and the filtrate was concentrated under reduced pressure to give a crude yellow oil. The yellow oil was purified by column chromatography over silica gel (petroleum ether/ethyl acetate=1:0 to petroleum ether/ethyl acetate=10:1) to give compound 14a (511 mg, 43.907%) as a yellow solid. LCMS (ESI) m/z M+1: 224.8; ¹H NMR (400 MHz, CDCl₃) δ ppm 6.57 (d, J=1.76 Hz, 1H), 7.90 (s, 1H), 8.37-8.46 (m, 1H), 8.42 (d, J=2.65 Hz, 1H), 8.71 (d, J=2.21 Hz, 1H), 9.21 (d, J=2.21 Hz, 1H).

B. 5-Chloro-6-(1H-pyrazol-1-yl)pyridin-3-amine, 14b

3-Chloro-5-nitro-2-(1H-pyrazol-1-yl)pyridine, 14a (500 mg, 2.26 mmol) was added to a mixture of Fe (0) (621.6 mg, 11.13 mmol), NH₄Cl (595.4 mg, 11.13 mmol) in MeOH (10 mL), water (5 mL), and THF (20 mL). The reaction was stirred at 60° C. for 1 h. The reaction mixture was filtered, and the filtrate was concentrated under reduced pressure to give a crude yellow oil. The crude oil was purified by column chromatography over silica gel (petroleum ether/ethyl acetate=1:0 to petroleum ether/ethyl acetate=0:1) to give compound 14b (300 mg, 69.2%) as a yellow solid. ¹H NMR (400 MHz, CDCl₃) δ ppm 6.44 (s, 1H), 7.15 (d, J=2.35 Hz, 1H), 7.75 (s, 1H), 7.85-7.91 (m, 2H).

C. N-(5-chloro-6-(1H-pyrazol-1-yl)pyridin-3-yl)-1-(isoquinolin-4-yl)-5-(trifluoromethyl)-1H-pyrazole-4-carboxamide, Cpd 46

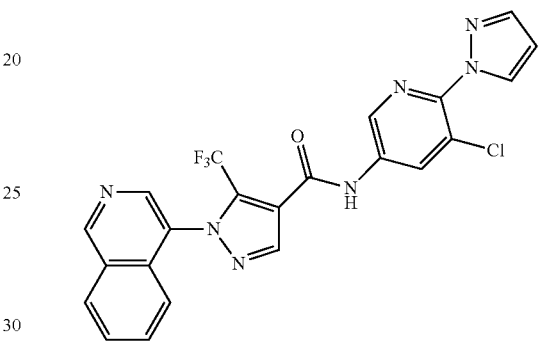

POCl₃ (78.8 mg, 0.514 mmol) was added to a mixture of 5-chloro-6-(1H-pyrazol-1-yl)pyridin-3-amine, 14b (50 mg, 0.26 mmol), 1-(isoquinolin-4-yl)-5-(trifluoromethyl)-1H-pyrazole-4-carboxylic acid, 4c (63.1 mg, 0.21 mmol), and pyridine (101.6 mg, 1.3 mmol) in dichloromethane (5 mL). The reaction mixture was stirred at 20° C. for 16 h. Water (20 mL) was added to the mixture. The mixture was extracted with dichloromethane (30 mL). The organic layer was concentrated under reduced pressure to afford a crude product which was purified by reverse phase HPLC (A: water (0.05% HCl), B: MeCN; then: AB (57%/43% to 27%/73%). The pure fractions were concentrated under reduced pressure and lyophilized to dryness to afford compound 46 (55 mg, 44%) as a pale white solid. LCMS (ESI) m/z M+1: 483.9; ¹H NMR (400 MHz, METHANOL-d₄) δ ppm 6.57 (t, J=2.09 Hz, 1H), 7.38 (d, J=8.60 Hz, 1H), 7.78-7.95 (m, 3H), 8.16 (d, J=2.43 Hz, 1H), 8.33 (d, J=8.16 Hz, 1H), 8.41 (s, 1H), 8.61-8.66 (m, 2H), 8.77 (d, J=2.21 Hz, 1H), 9.51 (s, 1H).

Example 15

N-(3-Chloro-4-(5-methyl-1H-1,2,4-triazol-1-yl)phenyl)-1-(isoquinolin-4-yl)-5-(trifluoromethyl)-1H-pyrazole-4-carboxamide, Cpd 51

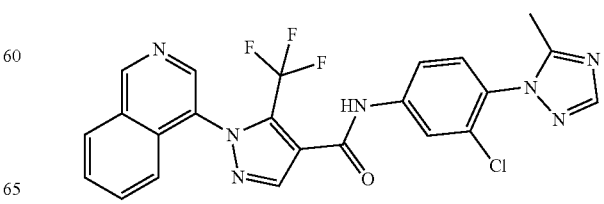

293

A. 1-(2-Chloro-4-nitrophenyl)-5-methyl-1H-1,2,4-triazole, 15a

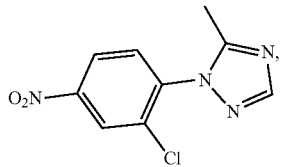

15a

2-Chloro-1-fluoro-4-nitrobenzene (1.6 g, 9.11 mmol), 5-methyl-1H-1,2,4-triazole (1.14 g, 13.7 mmol) and Cs$_2$CO$_3$ (8.9 g, 27.3 mmol) were added to DMF (15 mL). The mixture was stirred at 20° C. for 16 h. The reaction mixture was filtered and the filtrate was concentrated under reduced pressure to give a crude yellow oil. The crude oil was purified by column chromatography over silica gel (petroleum ether/ethyl acetate=7:3 to petroleum ether/ethyl acetate=3:7) to afford compound 15a (1.5 g, 69%) as a yellow solid. $^1$H NMR (400 MHz, CDCl$_3$) δ ppm 2.38-2.56 (m, 1H), 2.39-2.44 (m, 1H), 2.51 (s, 2H), 7.60-7.67 (m, 1H), 7.90 (d, J=8.82 Hz, 1H), 8.02 (s, 1H), 8.23-8.33 (m, 1H), 8.43-8.50 (m, 1H), 8.69 (s, 1H).

B. 3-Chloro-4-(5-methyl-1H-1,2,4-triazol-1-yl)aniline, 15b

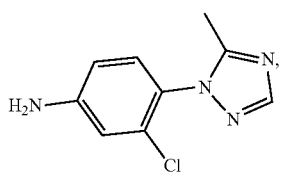

15b 1-(2-Chloro-4-nitrophenyl)-5-methyl-1H-1,2,4-triazole, 15a (1500 mg, 2.26 mmol) was added to the mixture of Fe(0) (877 mg, 15.71 mmol), NH$_4$Cl (840 mg, 15.71 mmol) in MeOH (10 mL), water (5 mL), and THF (20 mL). The reaction was stirred at 60° C. for 1 h. The reaction mixture was filtered and the filtrate was concentrated under reduced pressure to give a crude yellow oil. The crude oil was purified by column chromatography over silica gel (petroleum ether/ethyl acetate=1:1 to petroleum ether/ethyl acetate=0:1) afford compound 15b (1200 mg, 91.5%) as a yellow solid. $^1$H NMR (400 MHz, CDCl$_3$) δ ppm 2.90 (s, 3H), 6.52-6.61 (m, 1H), 6.69-6.77 (m, 1H), 7.06 (d, J=8.61 Hz, 1H), 7.16 (d, J=8.61 Hz, 1H), 7.87 (s, 1H), 7.96 (s, 1H), 8.15 (s, 1H).

294

C. N-(3-chloro-4-(5-methyl-1H-1,2,4-triazol-1-yl)phenyl)-1-(isoquinolin-4-yl)-5-(trifluoromethyl)-1H-pyrazole-4-carboxamide, Cpd 51

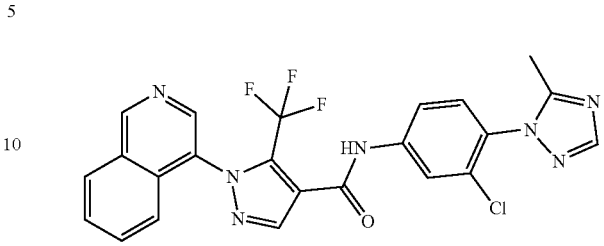

POCl$_3$ (110.23 mg, 0.719 mmol) was added to a mixture of 3-chloro-4-(5-methyl-1H-1,2,4-triazol-1-yl)aniline, 15b (150 mg, 0.36 mmol), 1-(isoquinolin-4-yl)-5-(trifluoromethyl)-1H-pyrazole-4-carboxylic acid, 4c (88.3 mg, 0.29 mmol), and pyridine (142.2 mg, 1.8 mmol) in dichloromethane (10 mL). The reaction mixture was stirred at 20° C. for 16 h. Water (20 mL) was added to the mixture. The mixture was extracted with dichloromethane (30 mL). The organic layer was concentrated under reduced pressure to afford a crude product, which was purified by reverse phase HPLC (A: water (0.05% HCl), B: MeCN; then: AB (62%/38% to 32%/68%). The pure fractions were concentrated under reduced pressure and lyophilized to dryness to afford compound compound 51 (31 mg, 17%) as a pale white solid. LCMS (ESI) m/z M+1: 497.9; $^1$H NMR (400 MHz, METHANOL-d$_4$) δ ppm 2.50 (s, 3H), 7.48 (d, J=8.38 Hz, 1H), 7.64 (d, J=8.82 Hz, 1H), 7.84 (dd, J=8.60, 2.20 Hz, 1H), 7.92-7.98 (m, 1H), 8.00-8.06 (m, 1H), 8.22 (d, J=2.20 Hz, 1H), 8.39-8.48 (m, 2H), 8.67 (br s, 1H), 8.82 (br s, 1H), 9.01 (s, 1H), 9.53-9.91 (m, 1H), 9.72 (br s, 1H).

Example 16

N-(5-cyano-6-(2H-1,2,3-triazol-2-yl)pyridin-3-yl)-1-(quinolin-5-yl)-5-(trifluoromethyl)-1H-pyrazole-4-carboxamide, Cpd 83

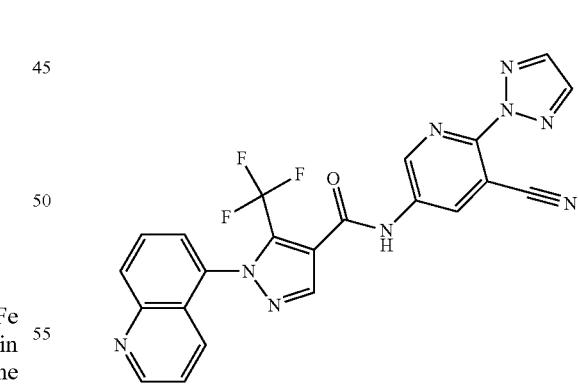

POCl$_3$ (49.4 mg, 0.32 mmol) was added to a mixture of 5-amino-2-(2H-1,2,3-triazol-2-yl)nicotinonitrile, 7b (30 mg, 0.161 mmol), 1-(quinolin-5-yl)-5-(trifluoromethyl)-1H-pyrazole-4-carboxylic acid, 3b (49.5 mg, 0.16 mmol), and pyridine (63.7 mg, 0.81 mmol) in dichloromethane (3 mL). The reaction mixture was stirred at 20° C. for 2 h. Water (20 mL) was added to the mixture. The mixture was extracted with dichloromethane (30 mL). The organic layers were concentrated under reduced pressure to afford a crude product, which was purified by reverse phase HPLC (A: water (0.05% HCl), B: MeCN; then: AB (67%/33% to 37%/63%). The pure fractions were concentrated under reduced pressure and lyophilized to dryness to afford compound 83 (33 mg, 42%) as a white solid. LCMS (ESI) m/z M+1: 475.9. $^1$H NMR (400 MHz, METHANOL-$d_4$) δ ppm 8.07-8.21 (m, 4H), 8.32 (t, J=8.03 Hz, 1H), 8.48-8.57 (m, 3H), 8.94 (d, J=2.26 Hz, 1H), 9.10-9.18 (m, 1H), 9.35 (d, J=4.02 Hz, 1H).

Example 17

N-(5-cyano-6-(1H-1,2,4-triazol-1-yl)pyridin-3-yl)-1-(quinolin-5-yl)-5-(trifluoromethyl)-1H-pyrazole-4-carboxamide, Cpd 86

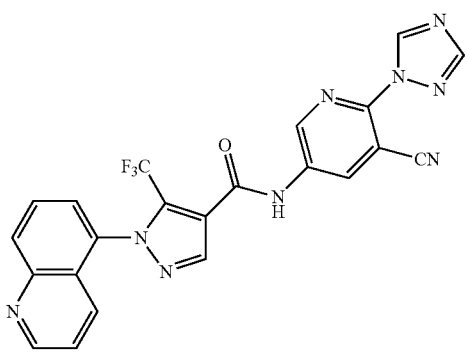 [SMILES: N#Cc1cc(NC(=O)c2cnn(-c3cccc4ncccc34)c2C(F)(F)F)cnc1-n1cncn1]

A. 5-Nitro-2-(1H-1,2,4-triazol-1-yl)nicotinonitrile, 17a

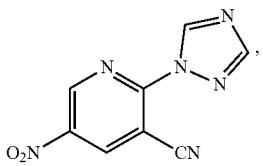

17a

K$_2$CO$_3$ (564.7 mg, 4.09 mmol) was added to a solution of 2-chloro-5-nitronicotinonitrile (250 mg, 1.36 mmol) 1,2,4-triazole (141.1 mg, 2.04 mmol) in MeCN (5 mL). The reaction mixture was filtered and the filtrate was concentrated under reduced pressure to give a crude yellow oil. The crude oil was purified by column chromatography over silica gel (petroleum ether/ethyl acetate=10:1 to petroleum ether/ethyl acetate=1:2) to afford compound 17a (200 mg, 67.9%) as a yellow solid. $^1$H NMR (400 MHz, CDCl$_3$) δ ppm 8.31 (s, 1H), 9.02 (d, J=2.51 Hz, 1H), 9.28 (s, 1H), 9.48 (d, J=2.51 Hz, 1H).

B. 5-Amino-2-(1H-1,2,4-triazol-1-yl)nicotinonitrile, 17b

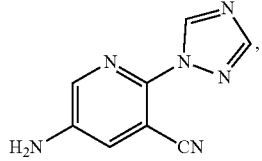

17b

5-Nitro-2-(1H-1,2,4-triazol-1-yl)nicotinonitrile, 17a (100 mg, 0.46 mmol) was added to a mixture of Fe(0) (206.7 mg, 3.7 mmol), NH$_4$Cl (198.0 mg, 3.70 mmol) in THF (4 mL), and water (1 mL). The reaction was stirred at 60° C. for 1 h. The reaction mixture was filtered though a pad of diatomaceous earth and the pad was washed with ethyl acetate (20 mL×3). The combined filtrates were concentrated to dryness to give a crude yellow solid. The crude solid was purified by flash column chromatography over silica gel (petroleum ether/ethyl acetate from 50/50 to 0/100) to afford compound 17b (55 mg, 64%) as a yellow solid. $^1$H NMR (400 MHz, CDCl$_3$) δ ppm 4.08-4.17 (m, 2H), 7.35-7.42 (m, 1H), 7.39 (d, J=2.65 Hz, 1H), 8.17 (s, 1H), 8.93 (s, 1H).

C. N-(5-cyano-6-(1H-1,2,4-triazol-1-yl)pyridin-3-yl)-1-(quinolin-5-yl)-5-(trifluoromethyl)-1H-pyrazole-4-carboxamide, Cpd 86

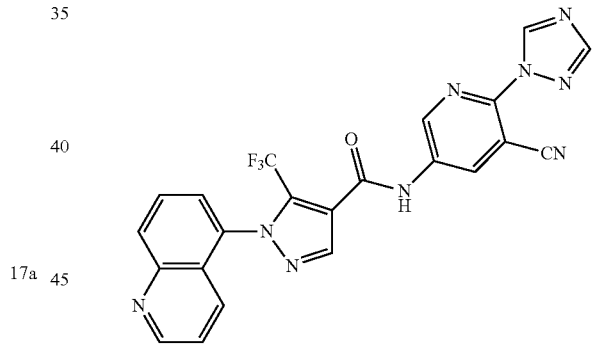

POCl$_3$ (82.4 mg, 0.54 mmol) was added to a mixture of 5-amino-2-(1H-1,2,4-triazol-1-yl)nicotinonitrile, 17b (50 mg, 0.269 mmol), 1-(quinolin-5-yl)-5-(trifluoromethyl)-1H-pyrazole-4-carboxylic acid, 3b (82.5 mg, 0.27 mmol), and pyridine (106.2 mg, 1.34 mmol) in dichloromethane (3 mL). The reaction mixture was stirred at 20° C. for 2 h. Water (20 mL) was added to the mixture. The mixture was extracted with dichloromethane (30 mL). The organic layer was concentrated under reduced pressure to afford a crude product, which was purified by reverse phase HPLC (A: water (0.05% HCl), B: MeCN; then: AB (65%/35% to 35%/65%). The pure fractions were concentrated under reduced pressure and lyophilized to dryness to afford compound 86 (84 mg, 66%) as a white solid. LCMS (ESI) m/z M+1: 475.9; $^1$H NMR (400 MHz, METHANOL-$d_4$) δ ppm 8.16-8.24 (m, 2H), 8.31-8.39 (m, 2H), 8.50 (s, 1H), 8.55 (d, J=8.82 Hz, 1H), 8.64 (d, J=8.60 Hz, 1H), 8.88 (d, J=2.43 Hz, 1H), 9.09 (d, J=2.65 Hz, 1H), 9.35-9.43 (m, 2H).

Example 18

N-(5-Chloro-6-cyclopropoxypyridin-3-yl)-1-(quinolin-5-yl)-5-(trifluoromethyl)-1H-pyrazole-4-carboxamide, Cpd 79

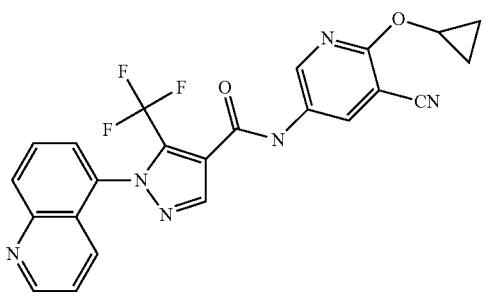 [SMILES: N#Cc1cc(NC(=O)c2cnn(-c3cccc4ncccc34)c2C(F)(F)F)cnc1OC1CC1]

A. 3-Chloro-2-cyclopropoxy-5-nitropyridine, 18a

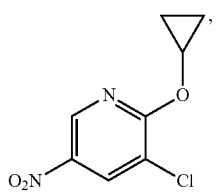

Cyclopropanol (4.304 g, 74.10 mmol) was slowly added to a mixture of NaH (4.042 g, 101.0 mmol) in THF (30 mL) at room temperature. The mixture was stirred at 40° C. for 1 h. 2,3-Dichloro-5-nitropyridine in THF (20 mL) was added to the mixture at 0° C. The mixture was stirred at room temperature for 1 h. The reaction mixture was quenched with water (50 mL). The mixture was extracted with ethyl acetate (200 mL×3). The organic layer was dried over Na$_2$SO$_4$, filtered, and the filtrate concentrated under reduced pressure. The residue was purified by flash column chromatography over silica gel (petroleum ether/ethyl acetate from 100/0 to 90/10) to afford 3-chloro-2-cyclopropoxy-5-nitropyridine, 18a (9 g, 53%) as a yellow solid.

B. 5-Chloro-6-cyclopropoxypyridin-3-amine, 18b

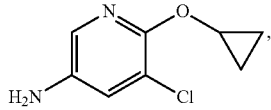

3-Chloro-2-cyclopropoxy-5-nitropyridine, 18a (18 g, 76.79 mmol) was dissolved in a mixture of MeOH/THF/water (2:4:1, 100 mL). Fe(0) (21.47 g, 384 mmol) and NH$_4$Cl (20.54 g, 384 mmol) were added. The reaction mixture was stirred at 60° C. for 2 h. Ethyl acetate (200 mL) was added to the mixture. A precipitate was removed by filtration. The precipitate was washed with ethyl acetate (100 mL), and the filtrate was concentrated under reduced pressure. A 10% NaHCO$_3$ solution (100 mL) was added to the mixture and the mixture was extracted with ethyl acetate (100 mL×2). The organic portion was dried over Na$_2$SO$_4$, filtered, and the filtrate was concentrated under reduced pressure to give a crude yellow oil. The crude product was purified by column chromatography over silica gel (petroleum ether/ethyl acetate=10:1 to petroleum ether/ethyl acetate=1:2) to afford compound 18b (12 g, 78.3%) as a yellow oil. $^1$H NMR (400 MHz, CDCl$_3$) δ ppm 0.78 (d, J=4.52 Hz, 4H), 3.43 (br. s., 2H), 4.22 (quin, J=4.58 Hz, 1H), 7.10 (d, J=2.76 Hz, 1H), 7.62 (d, J=2.51 Hz, 1H).

C. N-(5-chloro-6-cyclopropoxypyridin-3-yl)-1-(quinolin-5-yl)-5-(trifluoromethyl)-1H-pyrazole-4-carboxamide, Cpd 79

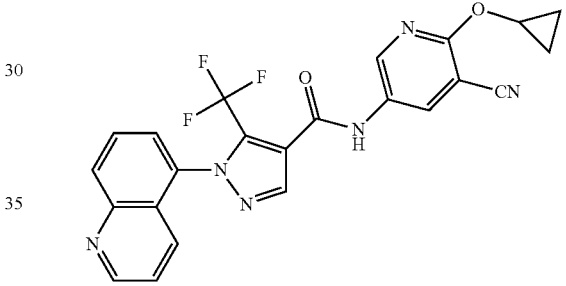

HATU (111.6 mg, 0.294 mmol) was added to a mixture of 5-chloro-6-cyclopropoxypyridin-3-amine, 18b (58.7 mg, 0.29 mmol), 1-(quinolin-5-yl)-5-(trifluoromethyl)-1H-pyrazole-4-carboxylic acid, 3b (75.1 mg, 0.245 mmol) and DIEA (94.85 mg, 0.73 mmol) in DMF (3 mL). The mixture was stirred at room temperature for 2 h. Water (10 mL) was added to the mixture and the mixture was extracted with ethyl acetate (30 mL×2). The organic layer was separated, dried over Na$_2$SO$_4$, filtered and the filtrate concentrated to dryness to give a crude yellow solid. The crude solid was purified by column chromatography over silica gel (petroleum ether/ethyl acetate=10:1 to petroleum ether/ethyl acetate=0:1) to give compound 79 (90 mg, 76%) as a white solid. LCMS (ESI) m/z M+1: 473.9. $^1$H NMR (400 MHz, DMSO-d$_6$) δ ppm 0.73 (br s, 2H), 0.77-0.83 (m, 2H), 4.33 (dt, J=6.21, 3.04 Hz, 1H), 7.56-7.63 (m, 1H), 7.65-7.71 (m, 1H), 7.87-7.93 (m, 1H), 7.95-8.00 (m, 1H), 8.29 (d, J=2.26 Hz, 1H), 8.33 (d, J=8.28 Hz, 1H), 8.45 (d, J=2.51 Hz, 1H), 8.51 (s, 1H), 9.06 (dd, J=4.39, 1.38 Hz, 1H), 10.80 (s, 1H).

Example 19

N-(5-Chloro-6-(1,3,4-oxadiazol-2-yl)pyridin-3-yl)-1-(isoquinolin-4-yl)-5-(trifluoromethyl)-1H-pyrazole-4-carboxamide, Cpd 69

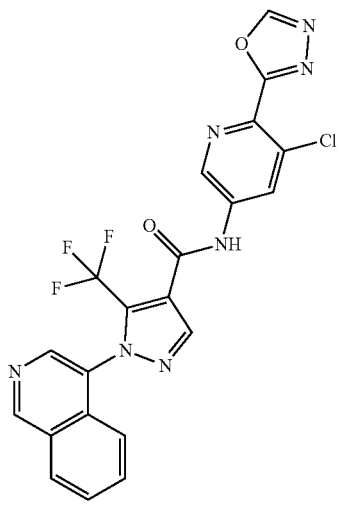 [SMILES: O=C(Nc1cnc(-c2nnco2)c(Cl)c1)c1cnn(-c2cncc3ccccc23)c1C(F)(F)F]

A. Methyl 5-amino-3-chloropicolinate, 19a

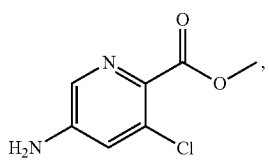

A stirring solution of 5-amino-2-bromo-3-chloropyridine (800 mg, 3.856 mmol), dppf (213.8 mg, 0.386 mmol) and NEt₃ (1.17 g, 11.6 mmol) in MeOH (4 mL) and toluene (20 mL) was carbonylated at 70° C. (35 psi) with Pd(dppf)Cl₂.CH₂Cl₂ (314.9 mg, 0.386 mmol) as a catalyst for 16 h. After uptake of CO (1 equiv), the catalyst was removed by filtration, and the filtrate was concentrated to give a crude product. The crude product was purified by flash column chromatography over silica gel (petroleum ether/ethyl acetate from 100/0 to 70/30) to afford methyl 5-amino-3-chloropicolinate, 19a (400 mg, 56%) as a red solid. $^1$H NMR (400 MHz, CDCl₃) δ ppm 3.95 (s, 3H), 4.20 (br s, 2H), 7.02 (d, J=2.43 Hz, 1H), 8.01 (d, J=2.43 Hz, 1H).

B. Methyl 3-chloro-5-(1-(isoquinolin-4-yl)-5-(trifluoromethyl)-1H-pyrazole-4-carboxamido)picolinate, 19b

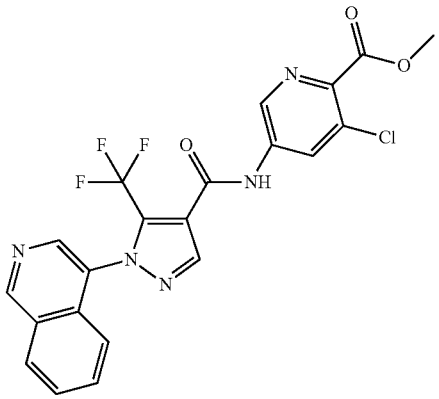 [SMILES: COC(=O)c1ncc(NC(=O)c2cnn(-c3cncc4ccccc34)c2C(F)(F)F)cc1Cl]

To a solution of methyl 5-amino-3-chloropicolinate, 19a (270 mg, 1.45 mmol), 1-(isoquinolin-4-yl)-5-(trifluoromethyl)-1H-pyrazole-4-carboxylic acid, 4c (387.9 mg, 1.206 mmol) and pyridine (388 μL, 4.82 mmol) in dichloromethane (3 mL), POCl₃ (221 μL, 2.41 mmol) was added dropwise. The reaction mixture was stirred at 20° C. for 1 h. Sat. aqueous NaHCO₃ (20 mL) was added and the mixture was extracted with dichloromethane (20 mL×2). The combined organic extracts were washed with brine and dried over Na₂SO₄, filtered, and the filtrate was concentrated under reduced pressure to afford a crude yellow oil. The crude product was purified by column chromatography over silica gel (petroleum ether/ethyl acetate=10:1 to petroleum ether/ethyl acetate=0:1) to give methyl 3-chloro-5-(1-(isoquinolin-4-yl)-5-(trifluoromethyl)-1H-pyrazole-4-carboxamido)picolinate, 19b (190 mg, 33%) as a yellow solid. LCMS (ESI) m/z M+1: 475.9.

C. N-(5-Chloro-6-(hydrazinecarbonyl)pyridin-3-yl)-1-(isoquinolin-4-yl)-5-(trifluoromethyl)-1H-pyrazole-4-carboxamide, 19c

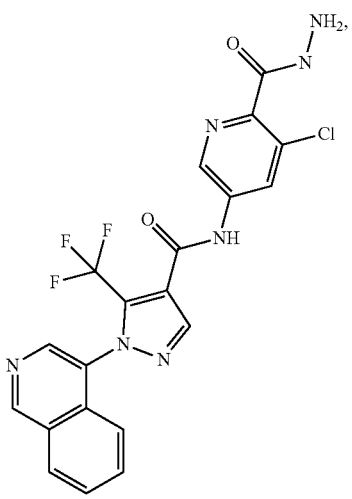

301

To a solution of methyl 3-chloro-5-(1-(isoquinolin-4-yl)-5-(trifluoromethyl)-1H-pyrazole-4-carboxamido)picolinate, 19b (170 mg, 0.36 mmol) in EtOH (5 mL) was added 85% NH₂NH₂.H₂O (2 mL) at room temperature. The mixture was heated to 80° C. and stirred for 4 h. The solvent was concentrated under reduced pressure to give a red solid. The red solid was washed with a mixture of petroleum ether (5 mL) and ethyl acetate (1 mL) to give compound 19c (160 mg, 83%) as a red solid. LCMS (ESI) m/z M+1: 476.0.

D. N-(5-chloro-6-(1,3,4-oxadiazol-2-yl)pyridin-3-yl)-1-(isoquinolin-4-yl)-5-(trifluoromethyl)-1H-pyrazole-4-carboxamide, Cpd 69

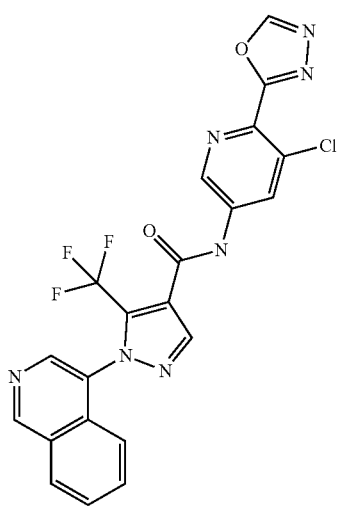 [SMILES: O=C(Nc1cnc(-c2nnco2)c(Cl)c1)c1cnn(-c2cncc3ccccc23)c1C(F)(F)F]

To a solution of N-(5-chloro-6-(hydrazinecarbonyl)pyridin-3-yl)-1-(isoquinolin-4-yl)-5-(trifluoromethyl)-1H-pyrazole-4-carboxamide, 19c (160 mg, 0.296 mmol) and triethyl orthoformate (131.6 mg, 0.888 mmol) in toluene (3 mL) was added HOAc (5.3 mg, 0.09 mmol) at room temperature. The mixture was heated to 100° C. for 2 h. The solvent was concentrated to afford a crude yellow oil. The crude oil was purified by column chromatography over silica gel (petroleum ether/ethyl acetate=10:1 to ethyl acetate/methanol=5:1) to afford compound 69 (26.8 mg, 17%) as a white solid. LCMS (ESI) m/z M+1: 485.9; ¹H NMR (400 MHz, CDCl₃) δ ppm 7.34 (d, J=7.72 Hz, 1H), 7.75-7.83 (m, 2H), 8.16 (d, J=8.16 Hz, 1H), 8.29 (s, 2H) 8.60 (s, 2H), 8.75 (d, J=3.97 Hz, 2H), 9.45 (s, 1H).

302

Example 20

N-(5-Chloro-6-(3-methyl-1H-1,2,4-triazol-1-yl)pyridin-3-yl)-1-(isoquinolin-4-yl)-5-(trifluoromethyl)-1H-pyrazole-4-carboxamide, Cpd 53 and N-(5-Chloro-6-(5-methyl-1H-1,2,4-triazol-1-yl)pyridin-3-yl)-1-(isoquinolin-4-yl)-5-(trifluoromethyl)-1H-pyrazole-4-carboxamide, Cpd 54

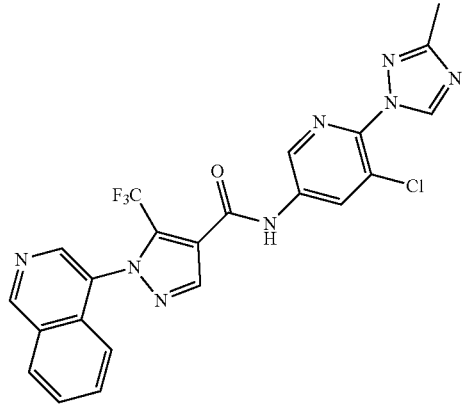
Cpd 53

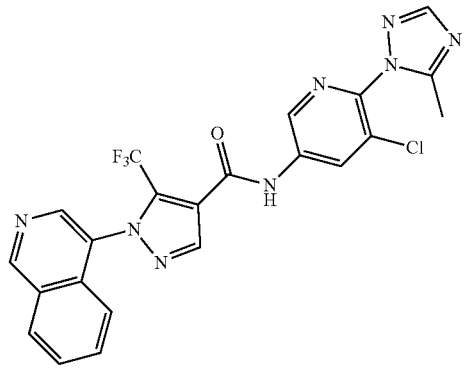
Cpd 54

A. 3-Chloro-2-(3-methyl-1H-1,2,4-triazol-1-yl)-5-nitropyridine (20a) and 3-chloro-2-(5-methyl-1H-1,2,4-triazol-1-yl)-5-nitropyridine (20a-1)

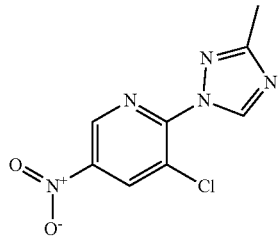
20a

-continued

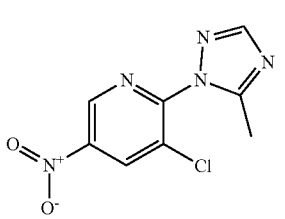
20a-1

2,3-Dichloro-5-nitropyridine (2 g, 10.36 mmol), 3-methyl-1H-1,2,4-triazole (1.722 g, 20.73 mmol) and $Cs_2CO_3$ (6.798 g, 20.73 mmol) were added to DMF (30 mL) and the reaction was stirred at rt for 12 h. The reaction mixture was quenched with water (200 mL). The mixture was extracted with ethyl acetate (100 mL×3). The organic layer was dried over $Na_2SO_4$, filtered, and the filtrate concentrated under reduced pressure. The crude residue was purified by flash column chromatography over silica gel (petroleum ether/ethyl acetate from 100:0 to 50:50) to afford a mixture of compounds 20a and 20a-1 (780 mg, 31%) as a white solid.

B. 5-Chloro-6-(3-methyl-1H-1,2,4-triazol-1-yl)pyridin-3-amine (20b) and 5-chloro-6-(5-methyl-1H-1,2,4-triazol-1-yl)pyridin-3-amine (20b-1)

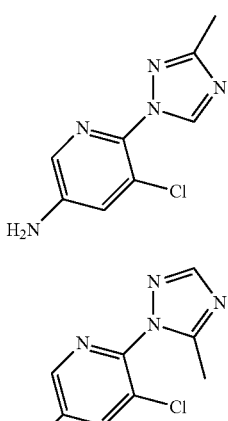

A mixture of 3-chloro-2-(3-methyl-1H-1,2,4-triazol-1-yl)-5-nitropyridine, 20a and 3-chloro-2-(5-methyl-1H-1,2,4-triazol-1-yl)-5-nitropyridine, 20a-1 (780 mg, 1.63 mmol) was dissolved in MeOH (20 mL), and Zn (0) (1.058 g, 16.28 mmol) and aqueous $NH_4Cl$ (20 mL) were added. The reaction mixture was stirred at rt for 16 h. The reaction mixture was filtered though a pad of diatomaceous earth and the pad washed with ethyl acetate (20 mL×3). Water (50 mL) was added and the organic layer was separated, dried over $Na_2SO_4$, filtered and the filtrate was concentrated to dryness to give a crude mixture of compounds 20b and 20b-1 (400 mg, 59%) as a yellow solid. $^1$H NMR (400 MHz, METHANOL-$d_4$) δ ppm 2.43 (s, 3H), 2.85 (d, J=0.66 Hz, 1H), 2.99 (s, 1H), 7.21-7.23 (m, 1H), 7.82 (d, J=2.65 Hz, 1H), 7.86 (dd, J=4.85, 2.43 Hz, 1H), 8.02 (s, 1H), 8.61-8.65 (m, 1H), 8.63 (s, 1H).

C. N-(5-Chloro-6-(3-methyl-1H-1,2,4-triazol-1-yl)pyridin-3-yl)-1-(isoquinolin-4-yl)-5-(trifluoromethyl)-1H-pyrazole-4-carboxamide, Cpd 53 and N-(5-chloro-6-(5-methyl-1H-1,2,4-triazol-1-yl)pyridin-3-yl)-1-(isoquinolin-4-yl)-5-(trifluoromethyl)-1H-pyrazole-4-carboxamide, Cpd 54

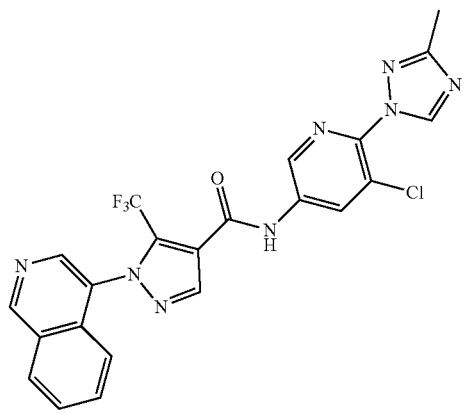
Cpd 53

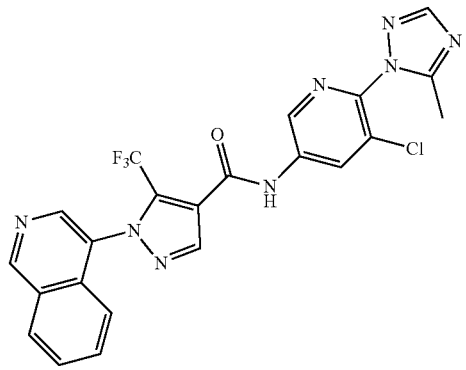
Cpd 54

A mixture of compounds 5-chloro-6-(3-methyl-1H-1,2,4-triazol-1-yl)pyridin-3-amine, 20b and 5-chloro-6-(5-methyl-1H-1,2,4-triazol-1-yl)pyridin-3-amine, 20b-1 (100 mg, 0.31 mmol), 1-(isoquinolin-4-yl)-5-(trifluoromethyl)-1H-pyrazole-4-carboxylic acid, 4c (263.0 mg, 0.63 mmol), and pyridine (62.0 mg, 0.78 mmol) were dissolved in dichloromethane (10 mL), and $POCl_3$ (96.2 mg, 0.63 mmol) was added. The mixture was stirred at rt for 2.5 h. Sat. aqueous $NH_4Cl$ (20 mL) was added and the mixture was extracted with dichloromethane (20 mL×2). The combined organic layers were dried over $Na_2SO_4$, filtered, and the filtrates were concentrated under reduced pressure to afford a crude yellow oil. The crude oil was purified by reverse phase HPLC (A: water (0.05% HCl)-CAN, B: MeCN, A/B: (48%/52%). The pure fractions were concentrated under reduced pressure and lyophilized to dryness to afford a mixture of compounds 53 and 54 (90 mg). The mixture was separated by Supercritical Fluid Chromatography (0.1% $NH_3H_2O$: MEOH. Mobile phase: A: $CO_2$ B: 0.1% $NH_3H_2O$: MEOH; A/B 75/25).

Cpd 53:
N-(5-chloro-6-(3-methyl-1H-1,2,4-triazol-1-yl)pyridin-3-yl)-1-(isoquinolin-4-yl)-5-(trifluoromethyl)-1H-pyrazole-4-carboxamide, (37.8 mg, 24.1%) as a white solid. LCMS (ESI) m/z M+1: 498.9. $^1$H NMR (400 MHz, DMSO-$d_6$) δ ppm 2.34-2.40 (m, 3H), 7.27-7.30 (m, 1H), 7.81-7.90 (m, 1H), 7.90-7.97 (m, 1H), 8.33-8.41 (m, 1H), 8.66-8.72 (m, 1H), 8.74-8.82 (m, 2H), 8.86-8.98 (m, 2H), 9.60 (s, 1H).

Cpd 54:

N-(5-chloro-6-(5-methyl-1H-1,2,4-triazol-1-yl)pyridin-3-yl)-1-(isoquinolin-4-yl)-5-(trifluoromethyl)-1H-pyrazole-4-carboxamide (18.4 mg, 11.7%) as a white solid. LCMS (ESI) m/z M+1: 499.0. $^1$H NMR (400 MHz, DMSO-$d_6$) δ ppm 2.34-2.37 (m, 3H), 7.23-7.32 (m, 1H), 7.82-7.90 (m, 1H), 7.91-7.98 (m, 1H), 8.06-8.12 (m, 1H), 8.33-8.41 (m, 1H), 8.59-8.64 (m, 1H), 8.65-8.70 (m, 1H), 8.75-8.81 (m, 1H), 8.85-8.90 (m, 1H), 9.58-9.64 (m, 1H).

Example 21

N-(3-chloro-4-(1H-1,2,3-triazol-1-yl)phenyl)-1-(isoquinolin-4-yl)-5-(trifluoromethyl)-1H-pyrazole-4-carboxamide, Cpd 18

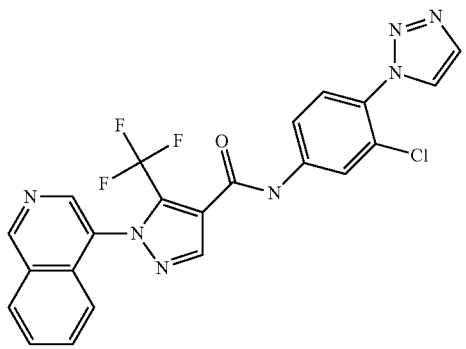 [SMILES: O=C(Nc1ccc(-n2ccnn2)c(Cl)c1)c1cnn(-c2cncc3ccccc23)c1C(F)(F)F]

A. 1-(2-Chloro-4-nitrophenyl)-1H-1,2,3-triazole, 21a

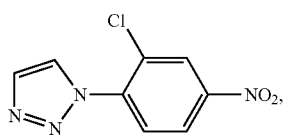

21a

To a solution of 3-chloro-4-fluoronitrobenzene (1.2 g, 6.836 mmol) and 2H-1,2,3-triazole (0.567 g, 8.203 mmol) in anhydrous DMA (5 mL) was added K$_2$CO$_3$ (1.89 g, 13.672 mmol). The reaction mixture was stirred at 55° C. overnight. The reaction was concentrated to give a crude product as an oil. The crude product was purified by flash column chromatography over silica gel (petroleum ether/ethyl acetate from 100/0 to 20/80 to afford 1-(2-chloro-4-nitrophenyl)-1H-1,2,3-triazole, 21a (400 mg, 26.1%) as a yellow solid. $^1$H NMR (400 MHz, CDCl$_3$) δ ppm 7.92-8.00 (m, 2H), 8.20 (s, 1H), 8.35 (dd, J=8.71, 2.32 Hz, 1H), 8.51 (d, J=2.43 Hz, 1H)

B. 3-Chloro-4-(1H-1,2,3-triazol-1-yl)aniline, 21b

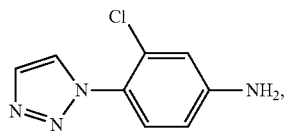

21b

To a solution of 1-(2-chloro-4-nitrophenyl)-1H-1,2,3-triazole, 21a (400 mg, 1.781 mmol) in MeOH/THF/water (5 mL/10 mL/5 mL) was added Fe (0) (497 mg, 8.905 mmol) and ammonium chloride (476 mg, 8.905 mmol). The reaction mixture was stirred at 60° C. for 2 h. The reaction was filtered and the organic solvent was concentrated. Water (10 mL) was added and the mixture was extracted with ethyl acetate (15 mL×3). The separated organic layer was dried over MgSO$_4$, filtered, and the filtrate was concentrated under reduced pressure to give a crude solid. The crude solid was purified by flash column chromatography over silica gel (petroleum ether/ethyl acetate from 100/0 to 0/100 to afford 3-chloro-4-(1H-1,2,3-triazol-1-yl)aniline, 21b (300 mg, 86.6%) as a yellow solid. $^1$H NMR (400 MHz, CDCl$_3$) δ ppm 4.03 (br. s., 2H), 6.66 (dd, J=8.41, 2.15 Hz, 1H), 6.82 (d, J=1.96 Hz, 1H), 7.32 (d, J=8.61 Hz, 1H), 7.85 (d, J=14.09 Hz, 2H)

C. N-(3-Chloro-4-(1H-1,2,3-triazol-1-yl)phenyl)-1-(isoquinolin-4-yl)-5-(trifluoromethyl)-1H-pyrazole-4-carboxamide, Cpd 18

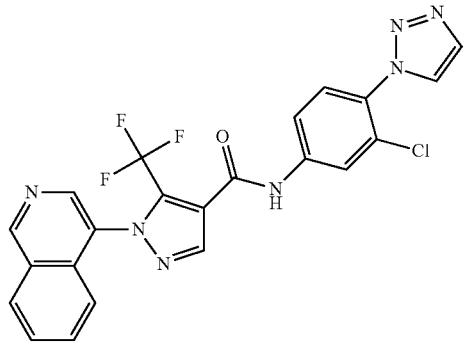 [SMILES: O=C(Nc1ccc(-n2ccnn2)c(Cl)c1)c1cnn(-c2cncc3ccccc23)c1C(F)(F)F]

To a solution of 1-(isoquinolin-4-yl)-5-(trifluoromethyl)-1H-pyrazole-4-carboxylic acid (50 mg, 0.16 mmol), 3-chloro-4-(1H-1,2,3-triazol-1-yl)aniline, 21b (37 mg, 0.19 mmol) and pyridine (63 mg, 0.8 mmol) in dichloromethane (2 mL), was added POCl$_3$ (49.4 mg, 0.32 mmol) dropwise to the mixture. The reaction mixture was stirred at 20° C. for 1 h. Water (5 mL) was added and the reaction mixture was extracted with dichloromethane (5 mL×3). The combined organic extracts were washed with brine and dried over Na$_2$SO$_4$, filtered, and the filtrates were concentrated under reduced pressure to afford a crude yellow oil. The crude oil was purified by reverse phase HPLC (A: water (0.05% ammonia hydroxide v/v), B: MeCN; then: AB (60%/40% to 70%/30%). The pure fractions were concentrated under reduced pressure and lyophilized to dryness to afford compound 18 (30 mg, 39%) as a white solid. LCMS (ESI) m/z M+1: 483.9; $^1$H NMR (400 MHz, CDCl$_3$) δ ppm 7.37 (d, J=8.38 Hz, 1H), 7.61-7.69 (m, 2H), 7.75-7.85 (m, 2H), 7.90 (s, 1H), 7.96 (s, 1H), 8.03 (s, 1H), 8.12-8.20 (m, 2H), 8.27 (s, 1H), 8.64 (s, 1H), 9.46 (s, 1H).

Example 22

N-(5-cyano-6-(2H-1,2,3-triazol-2-yl)pyridin-3-yl)-1-(thieno[3,2-c]pyridin-4-yl)-5-(trifluoromethyl)-1H-pyrazole-4-carboxamide, Cpd 90

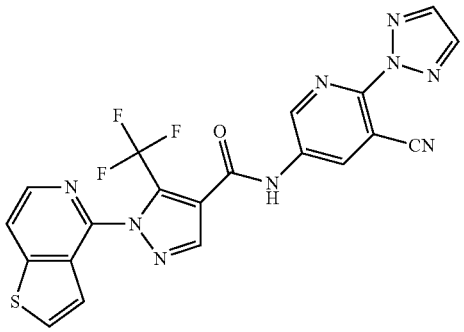 [SMILES: N#Cc1cc(NC(=O)c2cnn(-c3nccc4sccc34)c2C(F)(F)F)cnc1-n1nccn1]

A. 4-Hydrazinylthieno[3,2-c]pyridine, 22a

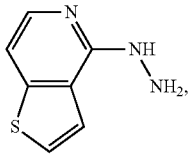

A mixture of 4-chlorothieno[3,2-c]pyridine (150 mg, 0.88 mmol) in hydrazine hydrate (4 mL) was stirred at 80° C. for 12 h. The mixture was extracted with dichloromethane (30 mL×2). The organic portion was concentrated under reduced pressure to afford a crude product (120 mg, 82%) as a yellow solid.

B. Ethyl 1-(thieno[3,2-c]pyridin-4-yl)-5-(trifluoromethyl)-1H-pyrazole-4-carboxylate, 22b

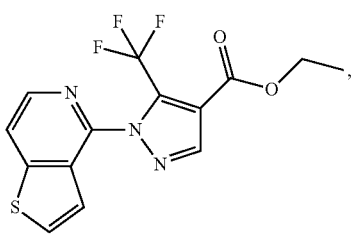

A solution of 4-hydrazinylthieno[3,2-c]pyridine, 22a (120 mg, 7.26 mmol) and ethyl 2-(ethoxymethylene)-4,4,4-trifluoro-3-oxobutanoate, 1f (227 mg, 0.944 mmol) in EtOH (50 mL) was stirred at 80° C. for 16 h. The resultant solution was cooled to room temperature and concentrated to dryness under reduced pressure to afford a crude product, which was purified by column chromatography over silica gel (petroleum ether/ethyl acetate=100:0 to 70:30) to afford compound 22b (120 mg, 48%) as a yellow solid. LCMS (ESI) m/z M+1: 341.9.

C. 1-(Thieno[3,2-c]pyridin-4-yl)-5-(trifluoromethyl)-1H-pyrazole-4-carboxylic acid, 22c

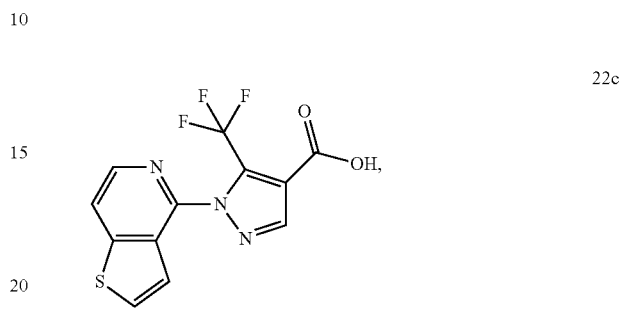

A solution of ethyl 1-(thieno[3,2-c]pyridin-4-yl)-5-(trifluoromethyl)-1H-pyrazole-4-carboxylate, 22b (120 mg, 0.352 mmol) in concentrated hydrochloric acid (3 mL) was stirred at 130° C. for 3 h. The solvent was concentrated under reduced pressure to afford a crude product (110 mg, 100%) as a yellow solid, which was used in the following reaction without further purification. LCMS (ESI) m/z M+1: 313.8.

D. N-(5-Cyano-6-(2H-1,2,3-triazol-2-yl)pyridin-3-yl)-1-(thieno[3,2-c]pyridin-4-yl)-5-(trifluoromethyl)-1H-pyrazole-4-carboxamide, Cpd 90

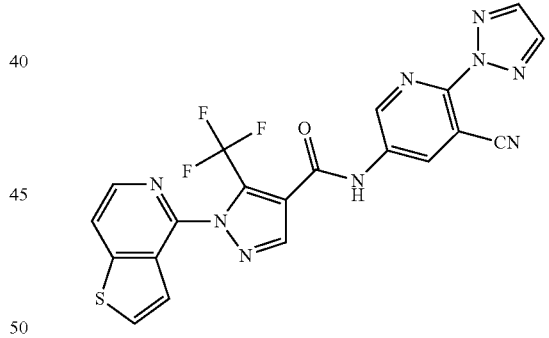

To a solution of 1-(thieno[3,2-c]pyridin-4-yl)-5-(trifluoromethyl)-1H-pyrazole-4-carboxylic acid, 22c (90 mg, 0.29 mmol), 5-amino-2-(2H-1,2,3-triazol-2-yl)nicotinonitrile, 7b (45.6 mg, 0.23 mmol) and pyridine (115.9 µL, 1.44 mmol) in dichloromethane (5 mL), was added POCl$_3$ (52.6 µL, 0.575 mmol) dropwise to the mixture. The reaction mixture was stirred at 20° C. for 1 h. Sat. aqueous NaHCO$_3$ (20 mL) was added and the mixture was extracted with dichloromethane (20 mL×2). The combined organic extracts were washed with brine, dried over Na$_2$SO$_4$, filtered, and the filtrates were concentrated under reduced pressure to afford a crude yellow oil. The crude oil was purified by column chromatography over silica gel (petroleum ether/ethyl acetate=10:1 to petroleum ether/ethyl acetate=0:1) to afford compound 90 (71.2 mg, 51%) as a white solid. LCMS (ESI) m/z M+1: 481.9. $^1$H NMR (400 MHz, DMSO-d$_6$) δ ppm 7.45 (d, J=5.51 Hz, 1H), 8.11 (d, J=5.51 Hz, 1H), 8.30 (s, 2H), 8.39 (d, J=5.51 Hz, 1H), 8.46 (d, J=5.51 Hz, 1H), 8.60 (s, 1H), 8.88 (d, J=2.43 Hz, 1H), 9.11 (d, J=2.43 Hz, 1H), 11.46 (s, 1H).

Example 23

N-(5-Chloro-6-(2H-1,2,3-triazol-2-yl)pyridin-3-yl)-1-(6-methylquinolin-5-yl)-5-(trifluoromethyl)-1H-pyrazole-4-carboxamide, Cpd 27

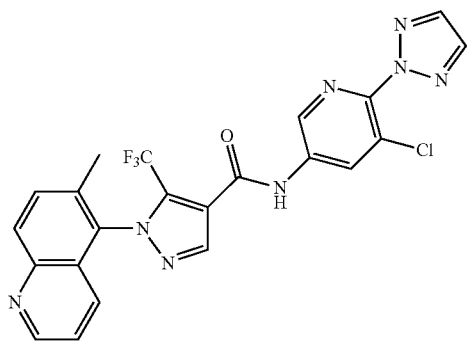 [SMILES: Cc1ccc2ncccc2c1-n1ncc(C(=O)Nc2cnc(-n3nccn3)c(Cl)c2)c1C(F)(F)F]

A. 5-Hydrazinyl-6-methylquinoline, 23a

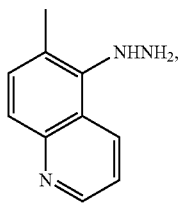

A solution of 6-methylquinolin-5-amine (800 mg, 5.06 mmol) in concentrated hydrochloric acid (5 mL) was stirred at 0° C. for 10 min. A solution of sodium nitrite (419 mg, 6.07 mmol) and water (0.5 mL) was added slowly, then stirred at 0° C. for 1 h. L-ascorbic acid (935 mg, 5.31 mmol) was then added to the reaction mixture over 10 min. The mixture was warmed to room temperature and stirred for 1 h before heating at 80° C. for 30 min. Water (4 mL) was added. The suspension was cooled to 0° C. and stirred for 2 h. The resulting mixture was basified to pH 10 with 4 M aq. NaOH, extracted with ethyl acetate (30 mL×3), and dried over anhydrous $Na_2SO_4$. The mixture was filtered and the filtrate concentrated to dryness under reduced pressure to afford a crude product, which was purified by FCC (petroleum ether: ethyl acetate=100:0 to 30:70) to afford compound 23a (150 mg, 17%). $^1$H NMR (400 MHz, DMSO-$d_6$) δ ppm 8.93-8.89 (m, 1H), 8.75-8.72 (m, 1H), 7.49 (d, J=7.6 Hz, 1H), 7.46 (d, J=6.8 Hz, 1H), 7.40-7.35 (m, 1H), 4.87-4.60 (m, 1H), 2.52-2.50 (m, 2H), 2.42 (s, 3H).

B. Ethyl 1-(6-methylquinolin-5-yl)-5-(trifluoromethyl)-1H-pyrazole-4-carboxylate, 23b

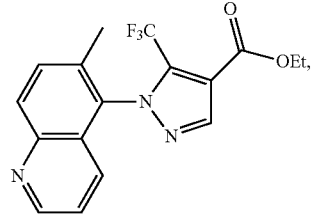

A solution consisting of ethyl 2-(ethoxymethylene)-4,4,4-trifluoro-3-oxobutanoate, 1f (130 mg, 0.541 mmol), 5-hydrazinyl-6-methylquinoline, 23a (113 mg, 0.541 mmol) and ethanol (5 mL) was refluxed at 80° C. for 16 h before cooling to room temperature. The mixture was concentrated to dryness under reduced pressure to afford the crude product, which was purified by FCC (petroleum ether: ethyl acetate=100:0 to 50:50) to give compound 23b (130 mg, 60%). $^1$H NMR (400 MHz, CDCl$_3$) δ ppm 8.91 (d, J=3.2 Hz, 1H), 8.31 (s, 1H), 8.20 (d, J=9.2 Hz, 1H), 7.66 (d, J=8.8 Hz 1H), 7.42-7.29 (m, 2H), 4.41 (q, J=6.8 Hz, 2H), 2.21 (s, 3H), 1.40 (t, J=7.2 Hz, 3H).

C. 1-(6-Methylquinolin-5-yl)-5-(trifluoromethyl)-1H-pyrazole-4-carboxylic acid, 23c A solution consisting of ethyl 1-(6-methylquinolin-5-yl)-5-(trifluoromethyl)-1H-pyrazole-4-carboxylate, 23b (100 mg, 0.286 mmol), NaOH (34.4 mg, 0.859 mmol) and water:EtOH (3 mL, 1:2) was stirred at room temperature for 16 h. The solution was concentrated under reduced pressure, neutralized to pH 7 with 4 N aq. HCl, and a solid, compound 23, was collected by filtration (90 mg, crude), which was used in the following reaction without further purification. LCMS (ESI): $R_T$=0.65 min, mass calcd. for $C_{15}H_{10}F_3N_3O_2$ 321.254, m/z found 322.0 [M+H]$^+$.

D. N-(5-Chloro-6-(2H-1,2,3-triazol-2-yl)pyridin-3-yl)-1-(6-methylquinolin-5-yl)-5-(trifluoromethyl)-1H-pyrazole-4-carboxamide, Cpd 27

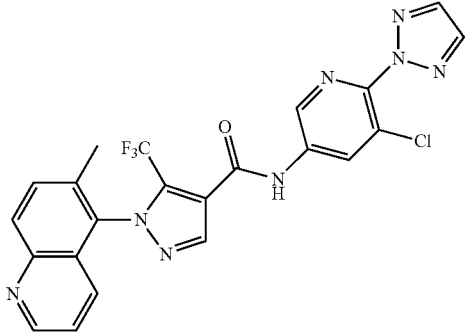 [SMILES: Cc1ccc2ncccc2c1-n1ncc(C(=O)Nc2cnc(-n3nccn3)c(Cl)c2)c1C(F)(F)F]

POCl$_3$ (45.8 mg, 0.299 mmol) was added dropwise to a solution consisting of 1-(6-methylquinolin-5-yl)-5-(trifluoromethyl)-1H-pyrazole-4-carboxylic acid, 23c (80.0 mg, 0.249 mmol), 5-chloro-6-(2H-1,2,3-triazol-2-yl)pyridin-3-amine, 1j (97.4 mg, 0.498 mmol) and pyridine (5 mL). The mixture was stirred at 0° C. for 1 h. The resultant mixture was poured into sat. aqueous NaHCO$_3$ (10 mL), extracted with ethyl acetate (10 mL×3), dried over anhydrous Na$_2$SO$_4$ and concentrated under reduced pressure to give a crude product, which was purified by preparative high performance liquid chromatography using Boston Green ODS 150×30 mm×5 μm (27% to 57% (v/v) ACN and water with 0.05% HCl) to afford compound 27. The product was suspended in water (10 mL), the mixture frozen using dry ice/acetone, and then lyophilized to dryness to give compound 27 (23.5 mg, 18%). LCMS (ESI): mass calcd. for C$_{22}$H$_{14}$ClF$_3$N$_8$O 498.848, m/z found 499.0 [M+H]$^+$. $^1$H NMR (400 MHz, DMSO-d$_6$) δ ppm 11.50 (s, 1H), 9.08 (dd, J=1.2, 4.0 Hz, 1H), 8.95 (d, J=2.0 Hz, 1H), 8.79-8.73 (m, 2H), 8.32 (d, J=8.8 Hz, 1H), 8.21 (s, 2H), 7.98 (d, J=8.8 Hz, 1H), 7.74 (dd, J=4.4, 8.4 Hz, 1H), 7.61 (d, J=8.4 Hz, 1H), 2.24 (s, 3H).

Example 24

N-(5-Chloro-6-methoxypyridin-3-yl)-1-(quinolin-5-yl)-5-(trifluoromethyl)-1H-pyrazole-4-carboxamide, Cpd 7

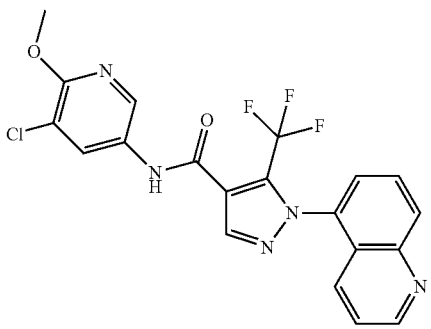 [SMILES: COc1ncc(NC(=O)c2cnn(-c3cccc4ncccc34)c2C(F)(F)F)cc1Cl]

A. 1-(Quinolin-5-yl)-5-(trifluoromethyl)-1H-pyrazole-4-carbonyl chloride, 24a

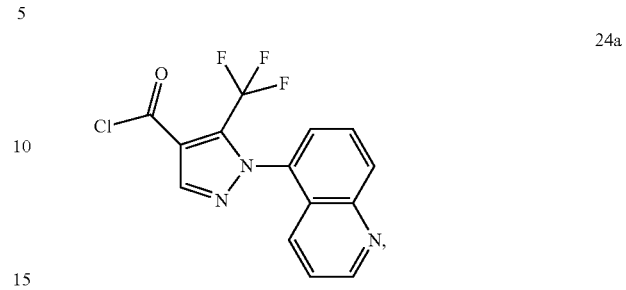

Oxalyl dichloride (0.0830 mL, 0.976 mmol) was added to solution consisting of 1-(quinolin-5-yl)-5-(trifluoromethyl)-1H-pyrazole-4-carboxylic acid, 3b (200 mg, 0.651 mmol), dichloromethane (15 mL), and DMF (catalytic amount). The resultant solution was stirred at room temperature for 1 h. The resultant solution was concentrated to dryness to afford compound 24a (200 mg, crude), which was used in the following reaction without further purification.

B. N-(5-Chloro-6-methoxypyridin-3-yl)-1-(quinolin-5-yl)-5-(trifluoromethyl)-1H-pyrazole-4-carboxamide, Cpd 7

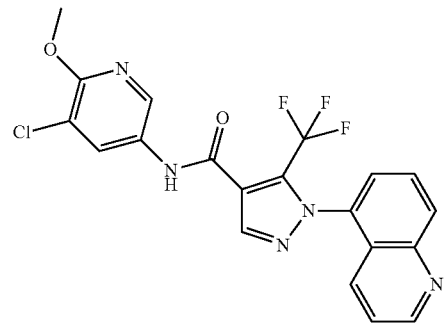 [SMILES: COc1ncc(NC(=O)c2cnn(-c3cccc4ncccc34)c2C(F)(F)F)cc1Cl]

A solution consisting of 1-(quinolin-5-yl)-5-(trifluoromethyl)-1H-pyrazole-4-carbonyl chloride, 24a (200 mg, 0.614 mmol), 5-chloro-6-methoxypyridin-3-amine (117 mg, 0.737 mmol), and pyridine (10 mL) was stirred at 90° C. for 1 h before cooling to room temperature. The resultant mixture was concentrated to dryness under reduced pressure to give the crude product, which was purified by reverse phase HPLC (38% to 68% (v/v) CH$_3$CN and water with 0.05% NH$_3$) to afford compound 7 (74.80 mg, 27%) as a brown solid. LCMS (ESI): mass calcd. for C$_{20}$H$_{13}$ClF$_3$N$_5$O$_2$ 447.07, m/z found 448.1 [M+H]$^+$. $^1$H NMR (400 MHz, CDCl$_3$) δ ppm 9.03 (dd, J=1.6, 4.4 Hz, 1H), 8.36 (d, J=8.4 Hz, 1H), 8.28-8.10 (m, 3H), 7.88-7.80 (m, 1H), 7.70 (s, 1H), 7.66-7.59 (m, 2H), 7.47 (dd, J=4.4, 8.4 Hz, 1H), 4.04 (s, 3H).

Example 25

1-(Quinolin-5-yl)-5-(trifluoromethyl)-N-(2-(trifluoromethyl)pyridin-4-yl)-1H-pyrazole-4-carboxamide, Cpd 6

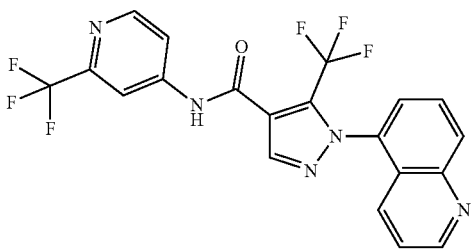 [SMILES: O=C(Nc1ccnc(C(F)(F)F)c1)c1cnn(-c2cccc3ncccc23)c1C(F)(F)F]

A solution consisting of 1-(quinolin-5-yl)-5-(trifluoromethyl)-1H-pyrazole-4-carbonyl chloride, 24a (200 mg, 0.614 mmol), 2-(trifluoromethyl)pyridin-4-amine (119 mg, 0.737 mmol), and pyridine (10 mL) was stirred at 90° C. for 1 h before cooling to room temperature. The resultant mixture was concentrated to dryness under reduced pressure to give the crude product, which was purified by reverse phase HPLC (43% to 63% (v/v) CH$_3$CN and water with 0.05% NH$_3$) to afford compound 6 (107.30 mg, 39%) as a white solid. LCMS (ESI): mass calcd. for C$_{20}$H$_{11}$F$_6$N$_5$O 451.09, m/z found 452.1 [M+H]$^+$. $^1$H NMR (400 MHz, CDCl$_3$) δ ppm 9.04 (dd, J=1.6, 4.4 Hz, 1H), 8.71 (d, J=5.6 Hz, 1H), 8.37 (d, J=8.4 Hz, 1H), 8.23 (s, 1H), 8.16 (s, 1H), 8.01 (d, J=2.0 Hz, 1H), 7.88-7.81 (m, 2H), 7.67-7.57 (m, 2H), 7.49 (dd, J=4.4, 8.4 Hz, 1H).

Example 26

N-(5-Chloro-6-(2H-1,2,3-triazol-2-yl)pyridin-3-yl)-1-(8-methylquinolin-5-yl)-5-(trifluoromethyl)-1H-pyrazole-4-carboxamide, Cpd 28

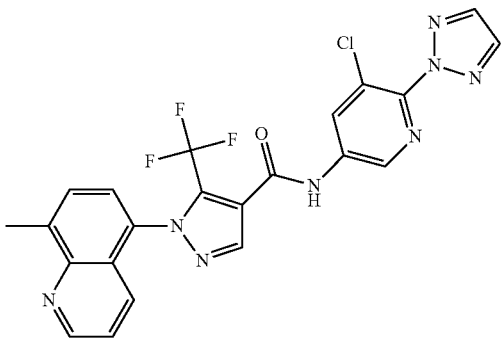 [SMILES: Cc1ccc(-n2ncc(C(=O)Nc3cnc(-n4nccn4)c(Cl)c3)c2C(F)(F)F)c2cccnc12]

A. 5-Hydrazinyl-8-methylquinoline, 26a

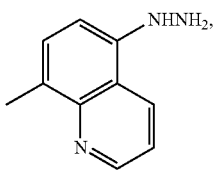

26a

A solution of sodium nitrite (65.4 mg, 0.948 mmol) and water (0.5 mL) was added dropwise to a solution consisting of 8-methylquinolin-5-amine (100 mg, 0.632 mmol) and concentrated hydrochloric acid (4 mL) at a temperature between −10° C. and 0° C. The mixture was stirred at a temperature between −10° C. and 0° C. for 1.5 h. A solution consisting of SnCl$_2$ (285 mg, 1.26 mmol) and concentrated hydrochloric acid (0.5 mL) was added dropwise at a temperature between −10° C. and 0° C., then the mixture was stirred at room temperature for 16 h before filtration. The collected solid was washed with MeOH (2 mL×2) to give compound 26a (90 mg, crude), which was used in the following reaction without further purification. LCMS (ESI): mass calcd. for C$_{10}$H$_{11}$N$_3$ 173.214, m/z found 174.2 [M+H]$^+$. $^1$H NMR (400 MHz, DMSO-d$_6$) δ ppm 10.72 (br. s., 2H), 9.82-9.31 (m, 1H), 9.14 (d, J=4.4 Hz, 1H), 9.05 (d, J=8.4 Hz, 1H), 7.98-7.85 (m, 1H), 7.80 (d, J=7.6 Hz, 1H), 7.17 (d, J=8.0 Hz, 1H), 2.71 (s, 3H).

B. Ethyl 1-(8-methylquinolin-5-yl)-5-(trifluoromethyl)-1H-pyrazole-4-carboxylate, 26b

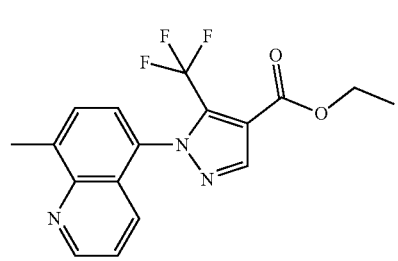

26b

A solution consisting of ethyl 2-(ethoxymethylene)-4,4,4-trifluoro-3-oxobutanoate, 1f (87.8 mg, 0.366 mmol), 5-hydrazinyl-8-methylquinoline, 26a (90.0 mg, 0.366 mmol) and ethanol (3 mL) was refluxed at 80° C. for 16 h before cooling to room temperature. The mixture was concentrated to dryness under reduced pressure to afford a crude product, which was purified by FCC (petroleum ether: ethyl acetate=100:0 to 70:30) to afford compound 26b (90 mg, 70%). $^1$H NMR (400 MHz, CDCl$_3$) δ ppm 9.06-8.98 (m, 1H), 8.24 (s, 1H), 7.66 (d, J=8.0 Hz, 1H), 7.58-7.43 (m, 3H), 4.41 (d, J=6.8 Hz, 2H), 2.90 (s, 3H), 1.41 (t, J=7.2 Hz, 3H).

C. 1-(8-Methylquinolin-5-yl)-5-(trifluoromethyl)-1H-pyrazole-4-carboxylic acid, 26c

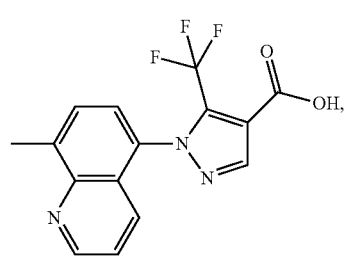

26c

A solution of ethyl 1-(8-methylquinolin-5-yl)-5-(trifluoromethyl)-1H-pyrazole-4-carboxylate, 26b (70 mg, 0.20 mmol), NaOH (24.0 mg, 0.601 mmol) and water: EtOH (3 mL, 1:2) was stirred at room temperature for 16 h. The reaction mixture was neutralized to pH 7 with 4 M aq. HCl, and then concentrated to dryness under reduced pressure to give the crude compound 26c (110 mg, crude), which was used in the following reaction without further purification. LCMS (ESI): mass calcd. for $C_{15}H_{10}F_3N_3O_2$ 321.254, m/z found 322.0 [M+H]$^+$.

D. N-(5-Chloro-6-(2H-1,2,3-triazol-2-yl)pyridin-3-yl)-1-(8-methylquinolin-5-yl)-5-(trifluoromethyl)-1H-pyrazole-4-carboxamide, Cpd 28

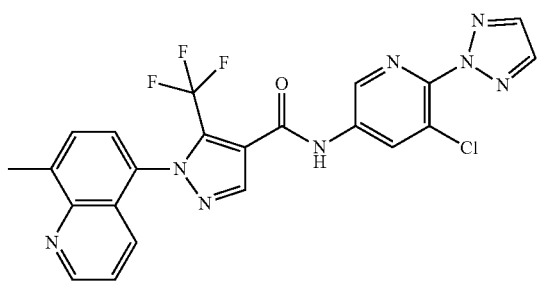 [SMILES: Cc1ccc(-n2ncc(C(=O)Nc3cnc(-n4nccn4)c(Cl)c3)c2C(F)(F)F)c2cccnc12]

POCl$_3$ (52.7 mg, 0.344 mmol) was added dropwise to a solution of ethyl 1-(8-methylquinolin-5-yl)-5-(trifluoromethyl)-1H-pyrazole-4-carboxylate, 26c (100 mg, 0.286 mmol), 5-chloro-6-(2H-1,2,3-triazol-2-yl)pyridin-3-amine, 1j (112 mg, 0.573 mmol) and pyridine (3 mL). The mixture was stirred at 0° C. for 1 h. The resultant mixture was poured into sat. aqueous NaHCO$_3$ (10 mL), extracted with ethyl acetate (10 mL×3), dried over anhydrous Na$_2$SO$_4$, filtered, and the filtrate concentrated under reduced pressure to give a crude product, which was purified by reverse phase HPLC (48% to 78% (v/v) ACN and water with 0.05% NH$_3$) to afford pure compound 28. The compound was suspended in water (10 mL), the mixture frozen using dry ice/acetone, and then lyophilized to dryness to give compound 28 (39.20 mg, 27%). LCMS (ESI): mass calcd. for $C_{22}H_{14}ClF_3N_8O$ 498.848, m/z found 498.9 [M+H]$^+$. $^1$H NMR (400 MHz, DMSO-d$_6$) δ ppm 9.08 (dd, J=1.6, 4.0 Hz, 1H), 8.86 (d, J=2.4 Hz, 1H), 8.68 (d, J=2.4 Hz, 1H), 8.57 (s, 1H), 8.19 (s, 2H), 7.85-7.79 (m, 2H), 7.68 (dd, J=4.4, 8.4 Hz, 1H), 7.57 (dd, J=1.6, 8.4 Hz, 1H), 2.85 (s, 3H).

Example 27

N-(5-Chloro-6-(2H-1,2,3-triazol-2-yl)pyridin-3-yl)-1-(3-methylquinolin-5-yl)-5-(trifluoromethyl)-1H-pyrazole-4-carboxamide, Cpd 65

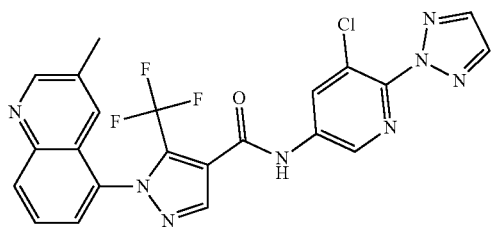 [SMILES: Cc1cnc2cccc(-n3ncc(C(=O)Nc4cnc(-n5nccn5)c(Cl)c4)c3C(F)(F)F)c2c1]

A. 3-Methyl-5-nitroquinoline (27a) and 3-methyl-8-nitroquinoline (27a-1)

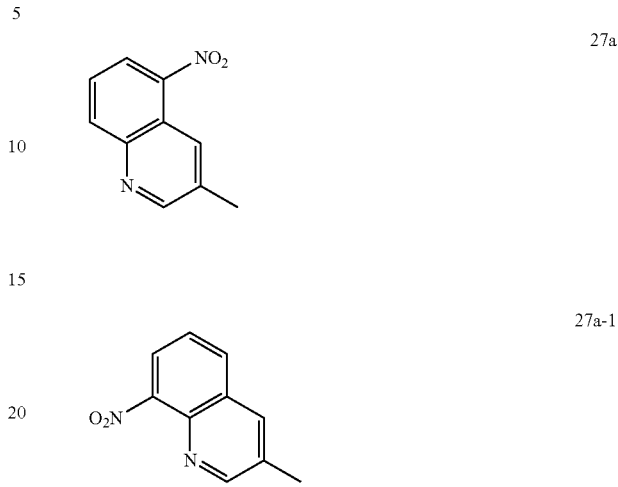

HNO$_3$ (4.72 mL, 105 mmol) was added dropwise to a mixture consisting of 3-methylquinoline (5.0 g, 35 mmol) and H$_2$SO$_4$ (5 mL) at 0° C., and the reaction mixture was stirred at room temperature for 1 h. The resultant mixture was neutralized to pH 7 with 1 M aq. NaOH, extracted with ethyl acetate (30 mL×3), and the extracts were concentrated under reduced pressure and purified by FCC (petroleum ether: ethyl acetate=100:0 to 50:50) to afford a mixture of compounds 27a and 27a-1 (4 g, 30%). LCMS (ESI): mass calcd. for $C_{10}H_8N_2O_2$ 188.18, m/z found 189.0 [M+H]$^+$.

B. 3-Methylquinolin-5-amine, 27b

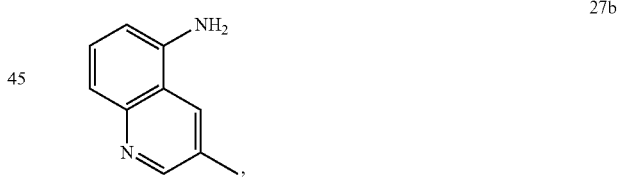

A mixture of 3-methyl-5-nitroquinoline (27a) and 3-methyl-8-nitroquinoline (27a-1) (3.50 g, 9.30 mmol), MeOH (30 mL) and dry Pd/C (350 mg, 5%) was added to a 500 mL hydrogenation bottle. The mixture was stirred under a H$_2$ (30 psi) atmosphere at room temperature for 16 h. The suspension was filtered though a pad of diatomaceous earth and the pad was washed with MeOH (100 mL). The filtrate was concentrated to dryness under reduced pressure to give crude compound 27b, which was purified by FCC (ethyl acetate:methanol=100:0 to 95:5) to afford compound 27b (300 mg, 20%). $^1$H NMR (400 MHz, DMSO-d$_6$) δ ppm 8.64 (d, J=1.6 Hz, 1H), 8.30 (s, 1H), 7.37-7.30 (m, 1H), 7.15 (d, J=8.0 Hz, 1H), 6.68 (d, J=7.2 Hz, 1H), 5.83 (s, 2H), 2.46 (s, 3H).

C. 5-Hydrazinyl-3-methylquinoline, 27c

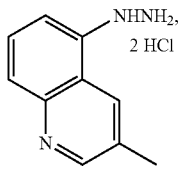

A solution of sodium nitrite (131 mg, 1.90 mmol) and water (1 mL) was added dropwise to a solution of 3-methylquinolin-5-amine, 27b (200 mg, 1.26 mmol) and concentrated hydrochloric acid (1 mL) at a temperature between −10° C. and 0° C. The mixture was stirred at a temperature between −10° C. and 0° C. for 1.5 h. A solution consisting of SnCl$_2$ (571 mg, 2.53 mmol) and concentrated hydrochloric acid (1 mL) was added dropwise at a temperature between −10° C. and 0° C., then the mixture was stirred at room temperature for 16 h. The suspension was filtered to give compound 27c (200 mg, crude), which was used in the next step without purification. LCMS (ESI): mass calcd. for C$_{10}$H$_{11}$N$_3$ 173.214, m/z found 174.0 [M+H]$^+$.

D. Ethyl 1-(3-methylquinolin-5-yl)-5-(trifluoromethyl)-1H-pyrazole-4-carboxylate, 27d

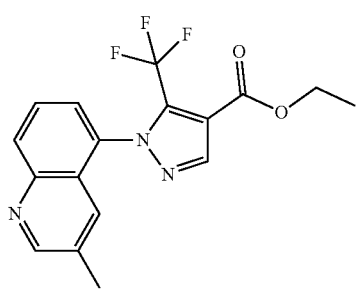

A solution consisting of ethyl 2-(ethoxymethylene)-4,4,4-trifluoro-3-oxobutanoate, 1f (195 mg, 0.813 mmol), 5-hydrazinyl-3-methylquinoline, 27c (200 mg, 0.813 mmol), triethylamine (164 mg, 1.63 mmol), and ethanol (2 mL) was stirred at 80° C. for 16 h before cooling to room temperature. The reaction was concentrated to dryness under reduced pressure to give crude product, which was purified by FCC (petroleum ether: ethyl acetate=100:0 to 60:40) to give compound 27d (100 mg, 35%). $^1$H NMR (400 MHz, CDCl$_3$) δ ppm 8.85 (d, J=2.0 Hz, 1H), 8.27 (d, J=8.0 Hz, 2H), 7.76-7.70 (m, 1H), 7.56 (d, J=7.6 Hz, 1H), 7.33-7.29 (m, 1H), 4.43 (q, J=7.2 Hz, 2H), 2.48 (s, 3H), 1.42 (t, J=7.2 Hz, 3H).

E. N-(5-Chloro-6-(2H-1,2,3-triazol-2-yl)pyridin-3-yl)-1-(3-methylquinolin-5-yl)-5-(trifluoromethyl)-1H-pyrazole-4-carboxamide, Cpd 65

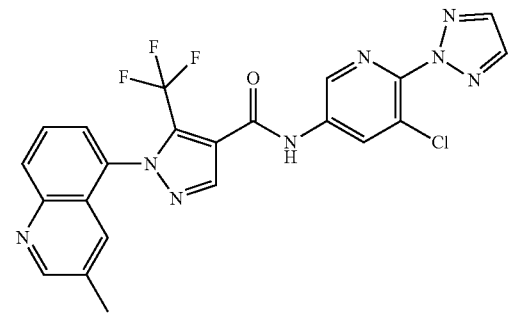 [SMILES: Cc1cnc2cccc(-n3ncc(C(=O)Nc4cnc(-n5nccn5)c(Cl)c4)c3C(F)(F)F)c2c1]

A solution consisting of 5-chloro-6-(2H-1,2,3-triazol-2-yl)pyridin-3-amine, 1j (44.8 mg, 0.229 mmol) and THF (0.5 mL) was added to potassium tert-butoxide in THF (0.687 mL, 0.687 mmol, 1 M) at 0° C., then a solution consisting of ethyl 1-(3-methylquinolin-5-yl)-5-(trifluoromethyl)-1H-pyrazole-4-carboxylate, 27d (60.0 mg, 0.229 mmol) and THF (0.5 mL) was added. The resultant mixture was stirred at room temperature for 16 h. The reaction mixture was concentrated under reduced pressure to give a crude product, which was purified by reverse phase HPLC (41% to 71% (v/v) ACN and water with 0.05% NH$_3$) to afford pure compound 65. The product was suspended in water (10 mL), the mixture frozen using dry ice/acetone, and then lyophilized to dryness to afford compound 65 (45.40 mg, 40%). LCMS (ESI): mass calcd. for C$_{22}$H$_{14}$ClF$_3$N$_8$O 498.848, m/z found 499.0 [M+H]$^+$. $^1$H NMR (400 MHz, DMSO-d$_6$) δ ppm 11.28 (br.s., 1H), 8.93 (d, J=2.0 Hz, 1H), 8.88 (d, J=2.4 Hz, 1H), 8.70 (d, J=2.4 Hz, 1H), 8.60 (s, 1H), 8.31-8.27 (m, 1H), 8.20 (s, 2H), 7.92-7.85 (m, 2H), 7.40-7.38 (m, 1H), 2.47 (s, 3H).

Example 28

N-(5-Chloro-6-(2H-1,2,3-triazol-2-yl)pyridin-3-yl)-1-(8-fluoroquinolin-5-yl)-5-(trifluoromethyl)-1H-pyrazole-4-carboxamide, Cpd 40

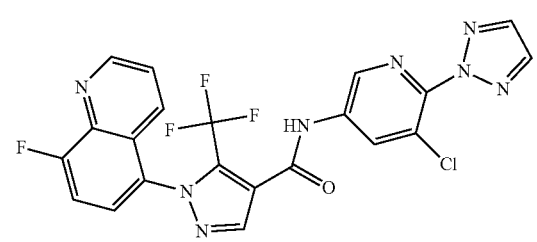 [SMILES: O=C(Nc1cnc(-n2nccn2)c(Cl)c1)c1cnn(-c2ccc(F)c3ncccc23)c1C(F)(F)F]

A. 8-Fluoro-5-hydrazinylquinoline, 28a

A solution of sodium nitrite (95.7 mg, 1.39 mmol) and water (0.5 mL) was added dropwise to a solution consisting of 8-fluoroquinolin-5-amine (150 mg, 0.925 mmol) and conc. hydrochloric acid (4 mL, 36%) at a temperature between −10° C. and 0° C. The mixture was stirred at a temperature between −10° C. and 0° C. for 1.5 h. A solution of SnCl$_2$ (417 mg, 1.85 mmol) and conc. hydrochloric acid (1 mL) was added dropwise at a temperature between −10° C. and 0° C. and the reaction was stirred at room temperature for 16 h. The mixture was filtered. The resultant solid was washed with MeOH (1 mL×2) and dried under reduced pressure to afford compound 28a (220 mg, crude) as a yellow solid, which was used in the next step without further purification. LCMS (ESI): mass calcd. for C$_9$H$_8$FN$_3$ 177.178, m/z found 178.1 [M+H]$^+$.

B. Ethyl 1-(8-fluoroquinolin-5-yl)-5-(trifluoromethyl)-1H-pyrazole-4-carboxylate, 28b

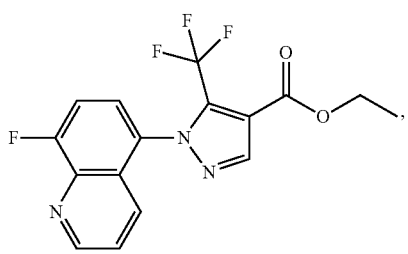

A solution consisting of ethyl 2-(ethoxymethylene)-4,4,4-trifluoro-3-oxobutanoate, 1f (207 mg, 0.864 mmol), 8-fluoro-5-hydrazinylquinoline HCl salt, 28a (360 mg, 0.864 mmol), triethylamine (175 mg, 1.73 mmol), and ethanol (5 mL) was refluxed at 80° C. for 16 h before cooling to room temperature. The reaction was concentrated to dryness under reduced pressure to afford a crude product, which was purified by FCC (petroleum ether: ethyl acetate=100:0 to 70:30) to give compound 28b (100 mg, 33%). $^1$H NMR (400 MHz, CDCl$_3$) δ ppm 9.06 (dd, J=1.6, 4.0 Hz, 1H), 8.25 (s, 1H), 7.61-7.48 (m, 4H), 4.41 (q, J=7.2 Hz, 2H), 1.41 (t, J=7.2 Hz, 3H).

C. 1-(8-Fluoroquinolin-5-yl)-5-(trifluoromethyl)-1H-pyrazole-4-carboxylic acid, 28c

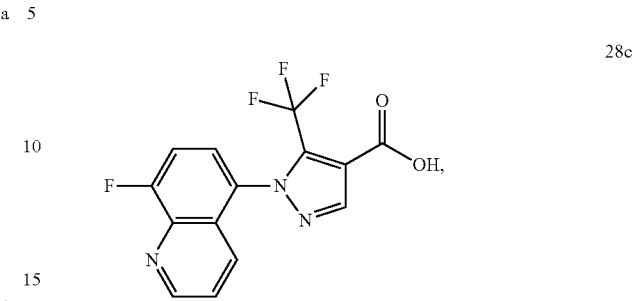

A solution of ethyl 1-(8-fluoroquinolin-5-yl)-5-(trifluoromethyl)-1H-pyrazole-4-carboxylate, 28b (100 mg, 0.283 mmol), NaOH (34.0 mg, 0.849 mmol) and water: EtOH (3 mL, 1:2) was stirred at room temperature for 16 h. The solution was neutralized to pH 7 with 4 M aq. HCl, and then concentrated to dryness under reduced pressure to give compound 28c (120 mg, crude), which was used in the following reaction without further purification. LCMS (ESI): mass calcd. for C$_{14}$H$_7$F$_4$N$_3$O$_2$ 325.218, m/z found 325.9 [M+H]$^+$.

D. N-(5-Chloro-6-(2H-1,2,3-triazol-2-yl)pyridin-3-yl)-1-(8-fluoroquinolin-5-yl)-5-(trifluoromethyl)-1H-pyrazole-4-carboxamide, Cpd 40

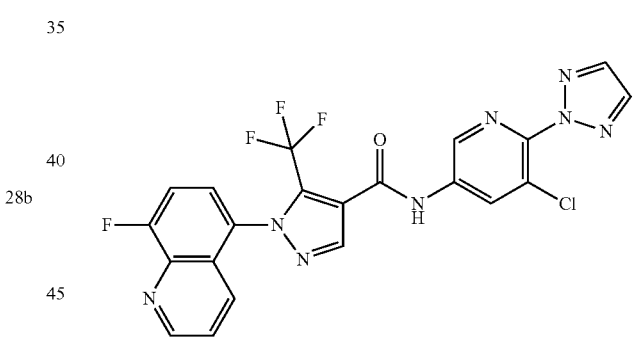

POCl$_3$ (56.6 mg, 0.369 mmol) was added dropwise to a solution of 1-(8-fluoroquinolin-5-yl)-5-(trifluoromethyl)-1H-pyrazole-4-carboxylic acid, 28c (100 mg, 0.307 mmol), 5-chloro-6-(2H-1,2,3-triazol-2-yl)pyridin-3-amine, 1j (120 mg, 0.615 mmol) and pyridine (5 mL) at 0° C. The mixture was stirred at 0° C. for 1 h. The reaction mixture was concentrated under reduced pressure to give a crude product, which was purified by reverse phase HPLC (38% to 68% (v/v) ACN and water with 0.05% NH$_3$) to afford pure compound 40. Compound was suspended in water (10 mL), the mixture frozen using dry ice/acetone, and then lyophilized to dryness to give compound 40 (20.10 mg, 13%). LCMS (ESI): mass calcd. for C$_{21}$H$_{11}$ClF$_4$N$_8$O 502.812, m/z found 502.9 [M+H]$^+$. $^1$H NMR (400 MHz, DMSO-d$_6$) δ ppm 11.28 (br.s., 1H), 9.13 (dd, J=1.6, 4.0 Hz, 1H), 8.87 (d, J=2.0 Hz, 1H), 8.69 (d, J=2.0 Hz, 1H), 8.60 (s, 1H), 8.20 (s, 2H), 8.00 (dd, J=4.4, 8.4 Hz, 1H), 7.87-7.78 (m, 2H), 7.67 (d, J=8.4 Hz, 1H).

Example 29

N-(5-Chloro-6-(2H-1,2,3-triazol-2-yl)pyridin-3-yl)-1-(3-fluoroquinolin-5-yl)-5-(trifluoromethyl)-1H-pyrazole-4-carboxamide, Cpd 25

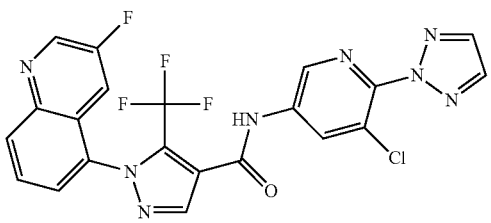 [SMILES: O=C(Nc1cnc(-n2nccn2)c(Cl)c1)c1cnn(-c2cccc3ncc(F)cc23)c1C(F)(F)F]

A. 3-Fluoro-5-hydrazinylquinoline, 29a

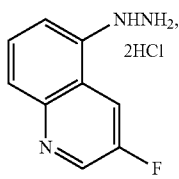

A solution of sodium nitrite (95.7 mg, 1.39 mmol) and water (0.5 mL) was added dropwise to a solution consisting of 3-fluoroquinolin-5-amine (150 mg, 0.925 mmol) and concentrated hydrochloric acid (4 mL, 36%) at −10° C.-0° C. The mixture was stirred at a temperature between −10° C. and 0° C. for 1.5 h. A solution of SnCl$_2$ (417 mg, 1.85 mmol) and concentrated hydrochloric acid (1 mL) was added dropwise at a temperature between −10° C. and 0° C. The mixture was stirred at room temperature for 16 h. The mixture was filtered. The resultant solid was washed with MeOH (1 mL×2) and dried under reduced pressure to afford compound 29a (220 mg, crude), which was used in the following reaction without further purification. LCMS (ESI): mass calcd. for C$_9$H$_8$FN$_3$ 177.178, m/z found 178.1 [M+H]$^+$.

B. Ethyl 1-(3-fluoroquinolin-5-yl)-5-(trifluoromethyl)-1H-pyrazole-4-carboxylate, 29b

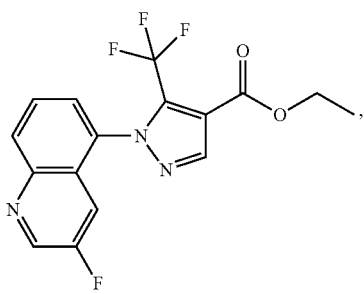

A solution consisting of ethyl 2-(ethoxymethylene)-4,4,4-trifluoro-3-oxobutanoate, 1f (211 mg, 0.880 mmol), 3-fluoro-5-hydrazinylquinoline, 29a (220 mg, 0.880 mmol), triethylamine (178 mg, 1.76 mmol), and ethanol (5 mL) was refluxed at 80° C. for 16 h before cooling to room temperature. The reaction mixture was concentrated to dryness under reduced pressure to afford crude compound 29b, which was purified by FCC (petroleum ether: ethyl acetate=100:0 to 70:30) to give compound 29b (160 mg, 51%). $^1$H NMR (400 MHz, CDCl$_3$) δ ppm 8.94-8.89 (m, 1H), 8.34 (d, J=8.4 Hz, 1H), 8.28 (s, 1H), 7.83-7.76 (m, 1H), 7.65 (d, J=7.2 Hz, 1H), 7.25-7.19 (m, 1H), 4.43 (q, J=7.2 Hz, 2H), 1.42 (t, J=7.2 Hz, 3H).

C. 1-(3-Fluoroquinolin-5-yl)-5-(trifluoromethyl)-1H-pyrazole-4-carboxylic acid, 29c

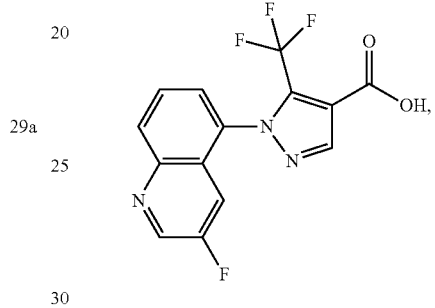

A solution consisting of ethyl 1-(3-fluoroquinolin-5-yl)-5-(trifluoromethyl)-1H-pyrazole-4-carboxylate, 29b (160 mg, 0.453 mmol), NaOH (54.3 mg, 1.54 mmol) and water: EtOH (3 mL, 1:2) was stirred at room temperature for 16 h. The solution was neutralized to pH 7 with 4 M aq. HCl, and the resultant solid was collected by filtration to afford compound 29c (150 mg, crude), which was used in the following reaction without further purification. LCMS (ESI): mass calcd. for C$_{14}$H$_7$F$_4$N$_3$O$_2$ 325.218, m/z found 325.9 [M+H]$^+$.

D. N-(5-Chloro-6-(2H-1,2,3-triazol-2-yl)pyridin-3-yl)-1-(3-fluoroquinolin-5-yl)-5-(trifluoromethyl)-1H-pyrazole-4-carboxamide, Cpd 25

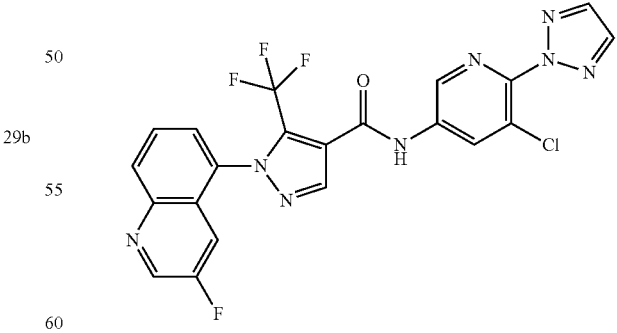

POCl$_3$ (5.7 mg, 0.037 mmol) was added dropwise to a solution of 1-(3-fluoroquinolin-5-yl)-5-(trifluoromethyl)-1H-pyrazole-4-carboxylic acid, 29c (160 mg, 0.492 mmol), 5-chloro-6-(2H-1,2,3-triazol-2-yl)pyridin-3-amine, 1j (192 mg, 0.984 mmol) and pyridine (5 mL). The mixture was stirred at 0° C. for 1 h. The resultant mixture was poured into sat. aqueous NaHCO$_3$ (10 mL), extracted with ethyl acetate (10 mL×3), dried over anhydrous Na$_2$SO$_4$, filtered, and the filtrate concentrated under reduced pressure to give the crude compound 25, which was purified by reverse phase HPLC (42% to 72% (v/v) ACN and H$_2$O with 0.05% NH$_3$) to afford pure compound 25. The product was suspended in water (10 mL), the mixture frozen using dry ice/acetone, and then lyophilized to dryness to give compound 25 (53.60 mg, 21%). LCMS (ESI): mass calcd. for C$_{21}$H$_{11}$ClF$_4$N$_8$O 502.812, m/z found 502.9 [M+H]$^+$. $^1$H NMR (400 MHz, DMSO-d$_6$) δ ppm 11.24 (br.s., 1H), 9.14 (d, J=2.8 Hz, 1H), 8.88 (d, J=2.4 Hz, 1H), 8.70 (d, J=2.0 Hz, 1H), 8.61 (s, 1H), 8.40 (d, J=7.6 Hz, 1H), 8.21 (s, 2H), 8.03-7.96 (m, 2H), 7.52-7.49 (m, 1H).

Example 30

N-(5-Chloro-6-(2H-1,2,3-triazol-2-yl)pyridin-3-yl)-1-(6-methylisoquinolin-4-yl)-5-(trifluoromethyl)-1H-pyrazole-4-carboxamide, Cpd 36

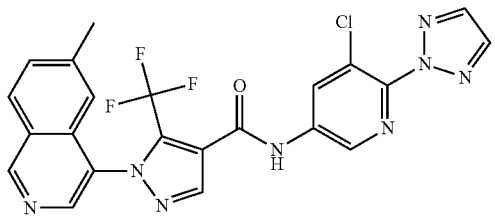 [SMILES: Cc1ccc2cncc(-n3ncc(C(=O)Nc4cnc(-n5nccn5)c(Cl)c4)c3C(F)(F)F)c2c1]

A. 4-(2-(Diphenylmethylene)hydrazinyl)-6-methyl-isoquinoline, 30a

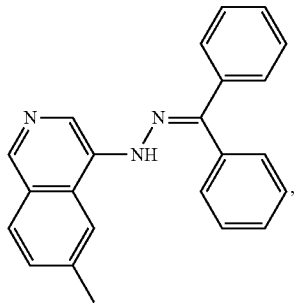

A mixture of 4-bromo-6-methylisoquinoline (500 mg, 2.25 mmol), benzophenone hydrazone (442 mg, 2.25 mmol), BINAP (140 mg, 0.225 mmol), palladium(II) acetate (50.5 mg, 0.225 mmol), sodium tert-butoxide (325 mg, 3.38 mmol), and toluene (3 mL) was heated to 100° C. and stirred for 20 h under a N$_2$ atmosphere before cooling to room temperature. The mixture was filtered and concentrated to give a black oil, which was purified by FCC (petroleum ether: ethyl acetate=30:70) to afford compound 30a (280 mg, 37%) as a yellow solid. LCMS (ESI): mass calcd. for C$_{23}$H$_{19}$N$_3$ 337.4, m/z found 338.0 [M+H]$^+$.

B. 4-Hydrazinyl-6-methylisoquinoline hydrochloride, 30b

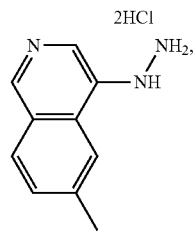

A mixture of 4-(2-(diphenylmethylene)hydrazinyl)-6-methylisoquinoline, 30a (260 mg, 0.771 mmol), conc. hydrochloride (10 mL, 12 M in water, 43 mmol), and EtOH (1 mL) was stirred for 20 h at room temperature. The solid was collected by filtration, washed with DCM (3 mL×2), and dried under reduced pressure to afford compound 30b (145 mg, 76%) as a yellow solid, which was used in the following reaction without further purification. LCMS (ESI): Mass calcd. for C$_{10}$H$_{11}$N$_3$ 173.2, m/z found 174.1 [M+H]$^+$.

C. Ethyl 1-(6-methylisoquinolin-4-yl)-5-(trifluoromethyl)-1H-pyrazole-4-carboxylate, 30c

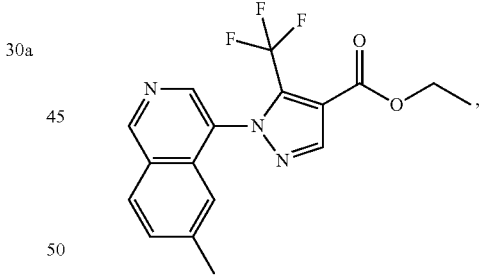

A mixture of 4-hydrazinyl-6-methylisoquinoline hydrochloride, 30b (145 mg, 0.589 mmol), ethyl 2-(ethoxymethylene)-4,4,4-trifluoro-3-oxobutanoate, 1f (200 mg, 0.707 mmol), triethylamine (0.246 mL, 1.77 mmol), and EtOH (5 mL) was heated to 90° C. and stirred for 20 h before cooling to room temperature. The mixture was concentrated under reduced pressure to afford a yellow oil, which was purified by FCC (ethyl acetate: petroleum ether=40: 60) to afford compound 30c (96 mg, 47%) as a yellow solid. LCMS (ESI): mass calcd. for C$_{17}$H$_{14}$F$_3$N$_3$O$_2$ 349.3, m/z found 350.1 [M+H]$^+$.

D. N-(5-Chloro-6-(2H-1,2,3-triazol-2-yl)pyridin-3-yl)-1-(6-methylisoquinolin-4-yl)-5-(trifluoromethyl)-1H-pyrazole-4-carboxamide, Cpd 36

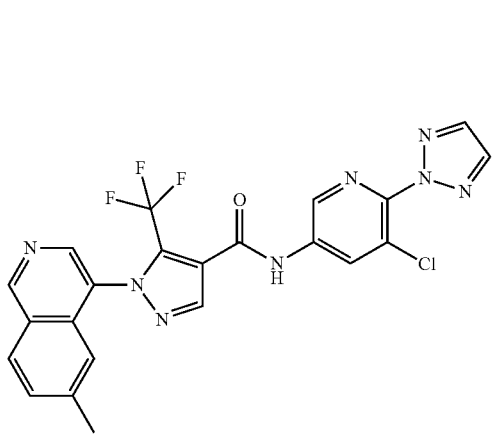 [SMILES: Cc1ccc2cncc(-n3ncc(C(=O)Nc4cnc(-n5nccn5)c(Cl)c4)c3C(F)(F)F)c2c1]

Ethyl 1-(6-methylisoquinolin-4-yl)-5-(trifluoromethyl)-1H-pyrazole-4-carboxylate, 30c (90.0 mg, 0.258 mmol) in THF (0.5 mL) and 5-chloro-6-(2H-1,2,3-triazol-2-yl)pyridin-3-amine, 1j (50.4 mg, 0.258 mmol) in THF (0.5 mL) were added into a suspension of potassium tert-butoxide (43.4 mg, 0.386 mmol) in THF (2 mL) at 0° C. The mixture was stirred at room temperature for 20 h before evaporating under reduced pressure to give a yellow solid, which was purified by reverse phase HPLC (CH$_3$CN in Basic water (0.05% NH$_3$.H$_2$O) from 45% to 75%, v/v). The resultant residue was re-suspended in water (50 mL) and the resulting mixture was lyophilized to dryness to remove the solvent residue completely. Compound 36 (40.40 mg, 31%) was obtained as an off-white solid. LCMS (ESI): mass calcd. for C$_{22}$H$_{14}$ClF$_3$N$_8$O 498.8, m/z found 498.9 [M+H]$^+$. $^1$H NMR (400 MHz, DMSO-d$_6$) δ ppm 11.28 (br s, 1H), 9.53 (s, 1H), 8.88 (d, J=2.0 Hz, 1H), 8.72 (s, 1H), 8.70 (d, J=2.4 Hz, 1H), 8.63 (s, 1H), 8.28 (d, J=8.4 Hz, 1H), 8.20 (s, 2H), 7.72 (dd, J=1.6, 8.8 Hz, 1H), 7.08 (s, 1H), 2.53-2.52 (m, 3H).

Example 31

N-(5-Chloro-6-(2H-1,2,3-triazol-2-yl)pyridin-3-yl)-1-(3-methylisoquinolin-1-yl)-5-(trifluoromethyl)-1H-pyrazole-4-carboxamide, Cpd 9

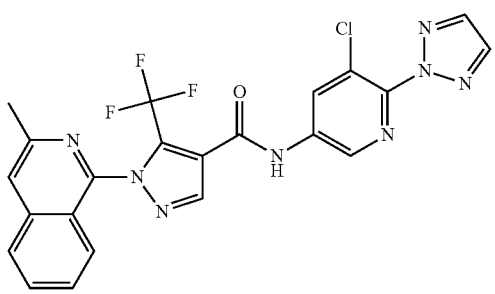 [SMILES: Cc1cc2ccccc2c(-n2ncc(C(=O)Nc3cnc(-n4nccn4)c(Cl)c3)c2C(F)(F)F)n1]

A. 3-Methylisoquinoline 2-oxide, 31a

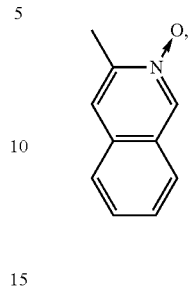

3-Chloroperoxybenzoic acid (2.53 g, 14.7 mmol) was added in portions into a mixture consisting of 3-methylisoquinoline (1.91 g, 13.3 mmol) and DCM (10 mL). The resultant mixture was stirred for 2 days at room temperature before diluting with DCM (100 mL), washing with aqueous NaHCO$_3$ (70 mL×2) and brine (70 mL), drying over anhydrous Na$_2$SO$_4$, filtering, and the filtrate concentrating under reduced pressure to afford compound 31a (1.4 g, 66%) as a yellow solid, which was used in the following reaction without further purification. LCMS (ESI): mass calcd. for C$_{10}$H$_9$NO 159.2, m/z found 160.0 [M+H]$^+$.

B. 1-Chloro-3-methylisoquinoline, 31b

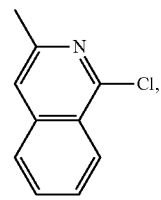

To a stirred solution of 3-methylisoquinoline 2-oxide, 31a (1.40 g, 8.80 mmol) in anhydrous CH$_2$Cl$_2$ (5 mL) at 0° C. was added phosphorus oxychloride (0.902 mL, 9.67 mmol) followed by dropwise addition of DMF (0.338 mL, 4.40 mmol) under an Argon atmosphere. The resulting reaction mixture was warmed to room temperature and stirred for 20 h. Saturated aqueous sodium carbonate solution was added to the reaction mixture slowly to adjust the pH to 7-8. The resulting mixture was separated and the aqueous phase was extracted with dichloromethane. The organic extracts were combined and washed with brine, dried over Na$_2$SO$_4$, filtered and the filtrate concentrated under reduced pressure to afford a crude compound 31b, which was purified by flash column chromatography (ethyl acetate: pretroleum ether=20: 80) to afford compound 31b (670 mg, 43%) as a yellow oil. LCMS (ESI): mass calcd. for C$_{10}$H$_8$ClN 177.6, m/z found 177.9 [M+H]$^+$.

C. 1-Hydrazinyl-3-methylisoquinoline, 31c

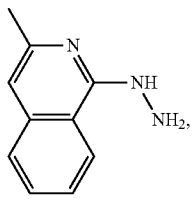

A mixture of 1-chloro-3-methylisoquinoline, 31b (670 mg, 3.77 mmol), hydrazine hydrate (4.44 g, 75.4 mmol), and EtOH (5 mL) was heated to 90° C. and stirred for 20 h before cooling to room temperature. The mixture was concentrated to give a yellow solid, which was dissolved into ethyl acetate (100 mL), washed with water (100 mL×2), dried over anhydrous $Na_2SO_4$, filtered, and the filtrate was concentrated under reduced pressure to afford compound 31c (715 mg, 98%) as a yellow solid. The crude product was used directly without further purification. LCMS (ESI): mass calcd. for $C_{10}H_{11}N_3$ 173.2, m/z found 174.0 $[M+H]^+$.

D. Ethyl 1-(3-methylisoquinolin-1-yl)-5-(trifluoromethyl)-1H-pyrazole-4-carboxylate, 31d

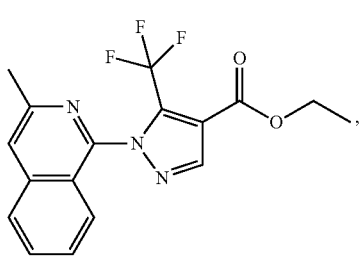

A mixture of 1-hydrazinyl-3-methylisoquinoline, 31c (710 mg, 4.10 mmol), ethyl 2-(ethoxymethylene)-4,4,4-trifluoro-3-oxobutanoate, 1f (1.27 g, 4.51 mmol), and EtOH (15 mL) was heated to 90° C. and stirred for 20 h before cooling to room temperature. The mixture was concentrated under reduced pressure to afford a yellow solid, which was treated with MeOH (5 mL) and stirred for 15 min. The solid was collected by filtration, washed with MeOH (3 mL×2), and dried under reduced pressure at room temperature to afford compound 31d (823.2 mg, 56%). LCMS (ESI): mass calcd. for $C_{17}H_{14}F_3N_3O_2$ 349.3, m/z found 350.0 $[M+H]^+$. $^1H$ NMR (400 MHz, $CDCl_3$) δ 8.27 (s, 1H), 7.87 (d, J=8.4 Hz, 1H), 7.77-7.66 (m, 2H), 7.59-7.48 (m, 2H), 4.42 (q, J=7.2 Hz, 2H), 2.73 (s, 3H), 1.42 (t, J=7.2 Hz, 3H).

E. 1-(3-Methylisoquinolin-1-yl)-5-(trifluoromethyl)-1H-pyrazole-4-carboxylic acid, 31e

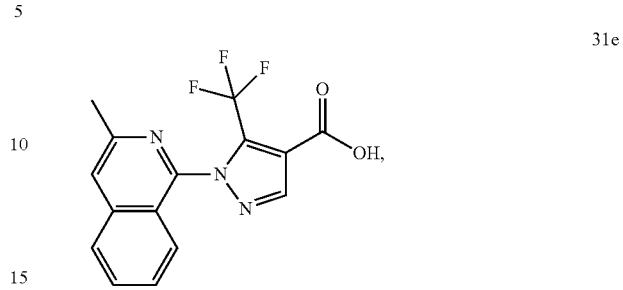

A mixture of ethyl 1-(3-methylisoquinolin-1-yl)-5-(trifluoromethyl)-1H-pyrazole-4-carboxylate, 31d (220 mg, 0.630 mmol), lithium hydroxide (45.2 mg, 1.89 mmol), MeOH (1 mL), THF (1 mL), and water (1 mL) was stirred for 20 h at room temperature. The pH of the mixture was adjusted to 2 with 6 N aq. HCl. The organic solvents were removed under reduced pressure. The residue was diluted with water (30 mL) and extracted with ethyl acetate (30 mL×2). The organic layers were combined and dried over anhydrous $Na_2SO_4$, filtered, and the filtrate concentrated under reduced pressure to afford compound 31e (140 mg, 69%) as a yellow solid. LCMS (ESI): mass calcd. for $C_{15}H_{10}F_3N_3O_2$ 321.2, m/z found 322.0 $[M+H]^+$.

F. N-(5-Chloro-6-(2H-1,2,3-triazol-2-yl)pyridin-3-yl)-1-(3-methylisoquinolin-1-yl)-5-(trifluoromethyl)-1H-pyrazole-4-carboxamide, Cpd 9

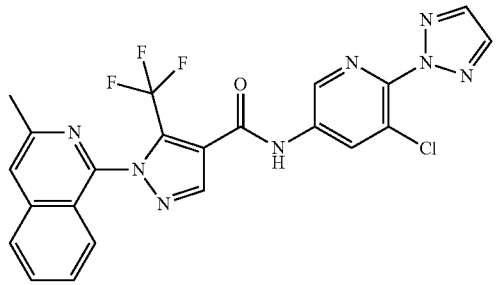 [SMILES: Cc1cc2ccccc2c(-n2ncc(C(=O)Nc3cnc(-n4nccn4)c(Cl)c3)c2C(F)(F)F)n1]

Phosphorus oxychloride (0.049 mL, 0.52 mmol) was added dropwise into a solution consisting of 1-(3-methylisoquinolin-1-yl)-5-(trifluoromethyl)-1H-pyrazole-4-carboxylic acid, 31e (140 mg, 0.436 mmol), 5-chloro-6-(2H-1,2,3-triazol-2-yl)pyridin-3-amine, 1j (93.8 mg, 0.479 mmol), and pyridine (2 mL). The mixture was stirred at 0° C. for 1 h before concentrating to dryness under reduced pressure to give crude product, which was purified by preparative HPLC using a Phenomenex Gemini C18 150×25 mm×5 μm column (50% to 80% (v/v) $CH_3CN$ and water with 0.05% $NH_3$) to afford pure compound 9. Compound was suspended in water (10 mL), the mixture frozen using dry ice/acetone, and then lyophilized to dryness to afford compound 9 (96.10 mg, 44%) as a white solid. LCMS (ESI): mass calcd. for $C_{22}H_{14}ClF_3N_8O$ 498.8, m/z found 498.9 $[M+H]^+$. $^1H$ NMR (400 MHz, DMSO-$d_6$) δ ppm 11.28 (br. s., 1H), 8.89 (s, 1H), 8.70 (s, 1H), 8.63 (s, 1H), 8.21 (s, 2H), 8.11 (d, J=8.4 Hz, 1H), 8.04 (s, 1H), 7.90 (m, 1H), 7.73 (m, 1H), 7.60 (d, J=8.4 Hz, 1H), 2.68 (s, 3H).

Example 32

N-(5-chloro-6-(2H-1,2,3-triazol-2-yl)pyridin-3-yl)-1-(1-methylisoquinolin-4-yl)-5-(trifluoromethyl)-1H-pyrazole-4-carboxamide, Cpd 66

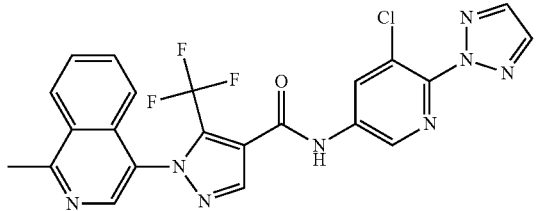 [SMILES: Cc1ncc(-n2ncc(C(=O)Nc3cnc(-n4nccn4)c(Cl)c3)c2C(F)(F)F)c2ccccc12]

A. 4-(2-(Diphenylmethylene)hydrazinyl)-1-methyl-isoquinoline, 32a

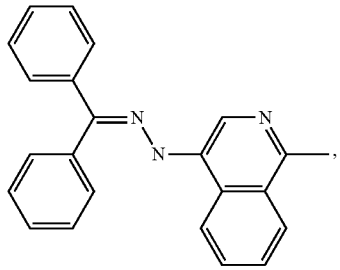

A mixture consisting of 4-bromo-1-methylisoquinoline (800 mg, 3.60 mmol), (diphenylmethylene)hydrazine (707 mg, 3.60 mmol), BINAP (224 mg, 0.360 mmol), palladium (II) acetate (80.9 mg, 0.360 mmol), t-BuONa (1.04 g, 10.8 mmol), and 1,4-dioxane (20 mL) was stirred at 100° C. for 16 h before cooling to room temperature. The suspension was filtered though a pad of diatomaceous earth and the pad was washed with ethyl acetate (30 mL). The filtrate was concentrated to dryness under reduced pressure to give a crude product, which was added into water (15 mL). The resultant mixture was extracted with ethyl acetate (20 mL×3). The combined organic extracts were dried over anhydrous Na$_2$SO$_4$, filtered, and the filtrate was concentrated to dryness under reduced pressure to afford crude compound 32a, which was purified by FCC (petroleum ether: ethyl acetate=4:1) to afford compound 32a (500 mg, 41%) as a brown oil. LCMS (ESI): mass calcd. for C$_{23}$H$_{19}$N$_3$ 337.16, m/z found 337.9 [M+H]$^+$. $^1$H NMR (400 MHz, CDCl$_3$) δ ppm 8.74 (s, 1H), 8.05 (m, 1H), 7.87 (s, 1H), 7.70-7.64 (m, 4H), 7.63-7.59 (m, 1H), 7.58-7.53 (m, 2H), 7.49-7.43 (m, 2H), 7.41-7.31 (m, 4H), 2.91 (s, 3H).

B. 4-Hydrazinyl-1-methylisoquinoline, 32b

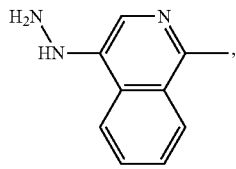

Conc. HCl (5 mL) was added to a solution consisting of 4-(2-(diphenylmethylene) hydrazinyl)-1-methylisoquinoline, 32a (500 mg, 1.48 mmol) and EtOH (2 mL). The resultant solution was stirred at room temperature for 16 h. The resultant mixture was added into dichloromethane (20 mL), filtered and the pad was washed with dichloromethane (10 mL). The organic solution was concentrated to dryness under reduced pressure to afford compound 32b (940 mg, crude), which was used in the following reaction without further purification. LCMS (ESI): mass calcd. for C$_{10}$H$_{11}$N$_3$ 173.10, m/z found 174.1 [M+H]$^+$.

C. Ethyl 1-(1-methylisoquinolin-4-yl)-5-(trifluoromethyl)-1H-pyrazole-4-carboxylate, 32c

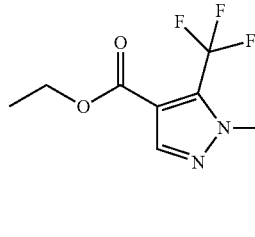

A solution consisting of ethyl 2-(ethoxymethylene)-4,4,4-trifluoro-3-oxobutanoate, 1f (984 mg, 4.10 mmol), 4-hydrazinyl-1-methylisoquinoline, 32b (840 mg, 3.41 mmol), triethylamine (0.950 mL, 6.83 mmol), and ethanol (20 mL) was stirred at 80° C. for 16 h before cooling to room temperature. The resultant solution was concentrated to dryness under reduced pressure to afford a crude product, which was added into water (10 mL). The resultant mixture was extracted with ethyl acetate (20 mL×3). The combined organic extracts were dried over anhydrous Na$_2$SO$_4$, filtered, and the filtrated concentrated to dryness under reduced pressure to afford compound 32c, which was purified by FCC (petroleum ether: ethyl acetate=4:1) to afford compound 32c (250 mg, 21%) as a brown solid. LCMS (ESI): mass calcd. for C$_{17}$H$_{14}$F$_3$N$_3$O$_2$ 349.10, m/z found 349.9 [M+H]$^+$. $^1$H NMR (400 MHz, CDCl$_3$) δ ppm 8.45 (s, 1H), 8.29-8.21 (m, 2H), 7.77-7.68 (m, 2H), 7.28-7.23 (m, 1H), 4.42 (q, J=7.2 Hz, 2H), 3.07 (s, 3H), 1.41 (t, J=7.2 Hz, 3H).

331

D. N-(5-Chloro-6-(2H-1,2,3-triazol-2-yl)pyridin-3-yl)-1-(1-methylisoquinolin-4-yl)-5-(trifluoromethyl)-1H-pyrazole-4-carboxamide, Cpd 66

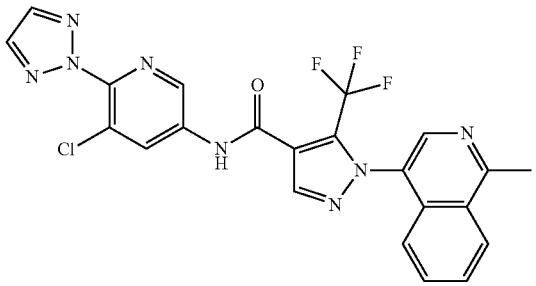 [SMILES: Cc1ncc(-n2ncc(C(=O)Nc3cnc(-n4nccn4)c(Cl)c3)c2C(F)(F)F)c2ccccc12]

A solution consisting of 5-chloro-6-(2H-1,2,3-triazol-2-yl)pyridin-3-amine, 1j (193 mg, 0.988 mmol) and THF (1 mL), and a solution consisting of ethyl 1-(1-methylisoquinolin-4-yl)-5-(trifluoromethyl)-1H-pyrazole-4-carboxylate, 32c (230 mg, 0.658 mmol) and THF (1 mL) were added to a solution consisting of potassium tert-butoxide (1.98 mL, 1.98 mmol, 1 M in THF) at 0° C. The resultant mixture was stirred at room temperature for 16 h. The resultant mixture was added water (5 mL) and extracted with ethyl acetate (15 mL×3). The combined organic extracts were dried over anhydrous Na$_2$SO$_4$, filtered, and the filtrate was concentrated to dryness under reduced pressure to afford a crude product, which was purified by preparative HPLC using a Kromasil 150×25 mm×10 μm column (35% to 65% (v/v) CH$_3$CN and water with 0.05% NH$_3$) to afford pure compound 66. The product was suspended in water (10 mL), the mixture frozen using dry ice/acetone, and then lyophilized to dryness to afford compound 66 (126.40 mg, 38%). LCMS (ESI): mass calcd. for C$_{22}$H$_{17}$ClN$_8$O 444.12, m/z found 449.0 [M+H]$^+$. $^1$H NMR (400 MHz, DMSO-d$_6$) δ ppm 11.29 (s, 1H), 8.86 (d, J=2.4 Hz, 1H), 8.68 (d, J=2.4 Hz, 1H), 8.62 (d, J=9.2 Hz, 2H), 8.42 (d, J=8.0 Hz, 1H), 8.20 (s, 2H), 7.94-7.83 (m, 2H), 7.23 (d, J=8.4 Hz, 1H), 3.04 (s, 3H).

Example 33

N-(5-chloro-6-methoxypyridin-3-yl)-1-(isoquinolin-4-yl)-5-(trifluoromethyl)-1H-pyrazole-4-carboxamide, Cpd 23

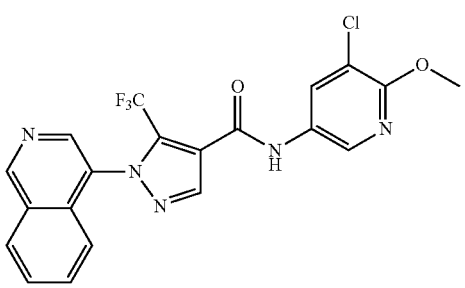 [SMILES: COc1ncc(NC(=O)c2cnn(-c3cncc4ccccc34)c2C(F)(F)F)cc1C#N]

332

A. Ethyl 1-(isoquinolin-4-yl)-5-(trifluoromethyl)-1H-pyrazole-4-carboxylate, 33a

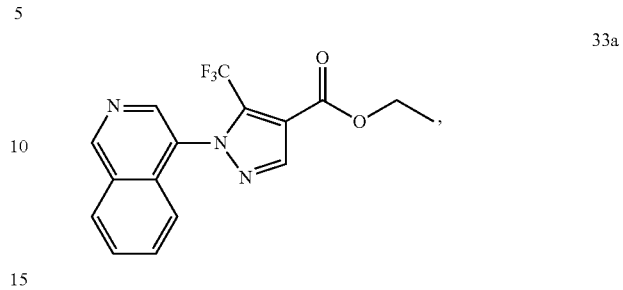

A 20 mL vial with stirbar was charged with 4-chloroisoquinoline (103.6 mg, 0.633 mmol), palladium(II)(pi-cinnamyl) chloride dimer (9.1 mg, 0.0176 mmol), n-[2-(di-1-adamantylphosphino)phenyl]morpholine (22 mg, 0.0475 mmol), sodium tert-butoxide (110 mg, 1.145 mmol), hydrazine hydrate (0.0614 mL, 1.032 g/mL, 1.266 mmol), and toluene (6.3 mL) under air at room temperature. The dark yellow mixture was quickly bubbled with Argon gas for 1 min, and the vial was then sealed and stirred at 100° C. under an Argon atmosphere overnight (14 h). The reaction was then cooled to room temperature and treated with ethyl 2-(ethoxymethylene)-4,4,4-trifluoro-3-oxobutanoate, 1f (0.123 mL, 1.235 g/mL, 0.633 mmol) and stirred at 100° C. under air (sealed). After 20 min at 100° C., the reaction was concentrated at 46° C. under reduced pressure to give a light green residue. This was taken up in THF (3 mL) and stirred at 60° C. for 5 min to maximize dissolution of compound 33a from the reaction mixture, and the reaction mixture was then cooled to room temperature. The amber solution in THF (assumed 0.2 M) was split into two (4 mL) vials and used in the next step immediately without further purification or characterization.

B. N-(5-chloro-6-methoxypyridin-3-yl)-1-(isoquinolin-4-yl)-5-(trifluoromethyl)-1H-pyrazole-4-carboxamide, Cpd 23

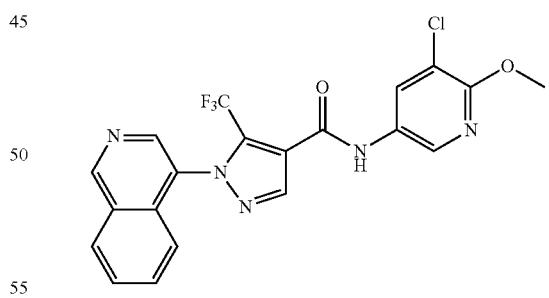

A solution of crude ethyl 1-(isoquinolin-4-yl)-5-(trifluoromethyl)-1H-pyrazole-4-carboxylate, 33a in THF, (Step A, assumed 106 mg, 0.316 mmol) was treated with 5-chloro-6-methoxypyridin-3-amine (52.7 mg, 0.332 mmol) and the mixture was stirred until it was homogeneous. The mixture was then treated with KOtBu (56 mg, 0.499 mmol) in one portion, and the resulting dark reddish reaction was stirred at room temperature under air (sealed) for 45 min. About 100 mg of thiol-functionalized silica gel (1.2 mmol/g, ~3 eq) was then added, and the reaction stirred at room temperature for another 45 min. The mixture was then filtered and concentrated to provide a dark residue (136 mg) that was dissolved in a co-solvent (0.14 mL DMSO/0.2 mL DCM), and purified by flash column chromatography (10 to 100% EtOAc in heptane over 24 CVs). Concentration from MeOH provided compound 23 as a white foam (11.6 mg, 8% overall from 3 steps). $^1$H NMR (400 MHz, CDCl$_3$) δ ppm 9.43 (s, 1H), 8.54 (s, 1H), 8.08-8.26 (m, 5H), 7.77 (quind, 2H), 7.34 (br d, J=7.58 Hz, 1H), 4.03 (s, 3H); MS m/e 448.0 (M+H).

Example 34

N-(5-cyano-6-methoxypyridin-3-yl)-1-(isoquinolin-4-yl)-5-(trifluoromethyl)-1H-pyrazole-4-carboxamide, Cpd 24

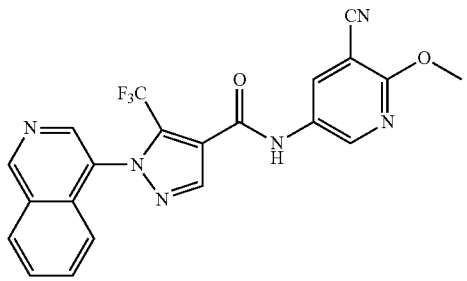

A solution of crude ethyl 1-(isoquinolin-4-yl)-5-(trifluoromethyl)-1H-pyrazole-4-carboxylate, 33a in THF, (assumed 106 mg, 0.316 mmol) was treated as described in Example 33, Step B, substituting 5-amino-2-methoxynicotinonitrile (47.4 mg, 0.318 mmol) for 5-chloro-6-methoxypyridin-3-amine, and the reaction was quenched with solid NH$_4$Cl rather than thiol-functionalized silica gel. Purification by flash column chromatography provided, following concentration from MeOH, compound 24 (18 mg, 13% overall in 3 steps) $^1$H NMR (400 MHz, CDCl$_3$) δ ppm 9.45 (s, 1H), 8.61 (s, 1H), 8.45 (s, 2H), 8.24 (s, 1H), 8.17 (d, J=7.58 Hz, 1H), 7.74-7.83 (m, 2H), 7.69 (s, 1H), 7.28-7.37 (m, 1H), 4.08 (s, 3H). MS m/e 439.2 (M+H).

Example 35

N-(5-cyano-6-(2H-1,2,3-triazol-2-yl)pyridin-3-yl)-1-(1,6-naphthyridin-5-yl)-5-(trifluoromethyl)-1H-pyrazole-4-carboxamide, Cpd 100

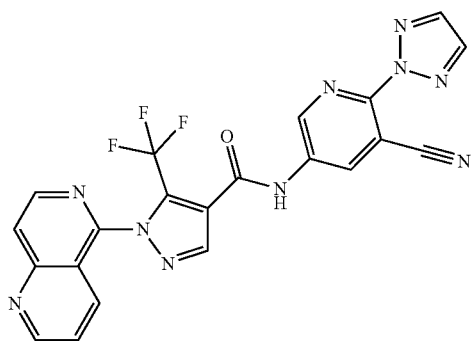 [SMILES: N#Cc1cc(NC(=O)c2cnn(-c3nccc4ncccc34)c2C(F)(F)F)cnc1-n1nccn1]

A. 5-Hydrazinyl-1,6-naphthyridine, 35a

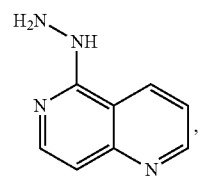

A solution of 5-chloro-1,6-naphthyridine (150 mg, 0.91 mmol) was added into hydrazine hydrate (3 mL), the mixture was heated to 80° C. and stirred for 16 h. The mixture afforded compound 35a as a solid, collected by filtration. (100 mg, 42%). LCMS (ESI) m/z M+1: 161.1.

B. Ethyl 1-(1,6-naphthyridin-5-yl)-5-(trifluoromethyl)-1H-pyrazole-4-carboxylate, 35b

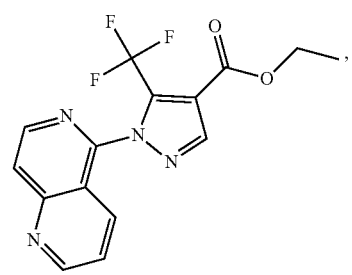

A solution consisting of 5-hydrazinyl-1,6-naphthyridine, 35a (100 mg, 0.38 mmol) and ethyl 2-(ethoxymethylene)-4,4,4-trifluoro-3-oxobutanoate, 1f (119.5 mg, 0.50 mmol) in ethanol (5 mL) was stirred at 80° C. for 4 h. The resultant solution was cooled to room temperature and concentrated to dryness under reduced pressure to afford crude compound 35b. The crude product was purified by column chromatography over silica gel (petroleum ether/ethyl acetate=100:0 to 70:30) to afford compound 35b as a yellow solid (100 mg, 85.5%). LCMS (ESI) m/z M+1: 337.1.

C. 1-(1,6-Naphthyridin-5-yl)-5-(trifluoromethyl)-1H-pyrazole-4-carboxylic acid, 35c

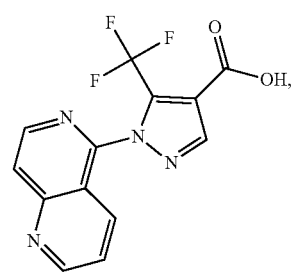

To a solution of ethyl 1-(1,6-naphthyridin-5-yl)-5-(trifluoromethyl)-1H-pyrazole-4-carboxylate, 35b (90 mg, 0.27 mmol) in water (1 mL) and ethanol (1 mL) was added NaOH

335

(12.85 mg, 0.32 mmol) at room temperature. The mixture was stirred for 3 h. 2N HCl (aq) was added to the mixture until the solution was adjusted to pH 2. The solvent was removed under reduced pressure to afford crude compound 35c as a white solid (82.5 mg, 100%). LCMS (ESI) m/z M+1: 308.8.

D. N-(5-cyano-6-(2H-1,2,3-triazol-2-yl)pyridin-3-yl)-1-(1,6-naphthyridin-5-yl)-5-(trifluoromethyl)-1H-pyrazole-4-carboxamide, Cpd 100

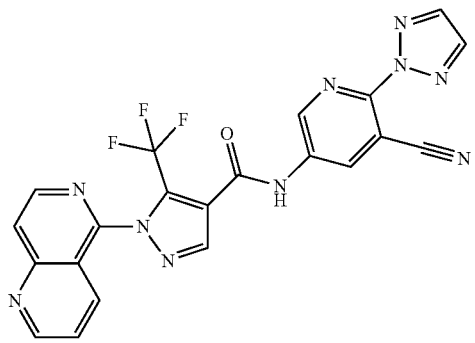 [SMILES: N#Cc1cc(NC(=O)c2cnn(-c3nccc4ncccc34)c2C(F)(F)F)cnc1-n1nccn1]

Phosphoryl trichloride (49.4 mg, 0.32 mmol) was added to a mixture of 1-(1,6-naphthyridin-5-yl)-5-(trifluoromethyl)-1H-pyrazole-4-carboxylic acid, 35c (82 mg, 0.27 mmol), 5-amino-2-(2H-1,2,3-triazol-2-yl)nicotinonitrile, 7b (59.4 mg, 0.32 mmol), and pyridine (107 μL, 1.33 mmol) in dichloromethane at room temperature. The reaction was stirred at room temperature for 2 h. Sat. aqueous NH$_4$Cl (aq) (10 mL) was added to the mixture. The mixture was extracted with dichloromethane (30 mL). The organic extracts were washed with water (5 mL), and brine (10 mL), dried over Na$_2$SO$_4$, filtered, and the filtrate concentrated under reduced pressure. The crude product was purified by column chromatography over silica gel (petroleum ether/ethyl acetate=100:0 to ethyl acetate/methanol=90:10). The solvent was removed under reduced pressure to afford compound 100 as a white solid (56.4 mg, 43%). LCMS (ESI) m/z M+1: 447.0. $^1$H NMR (400 MHz, CDCl$_3$) δ ppm 7.63 (dd, J=8.60, 4.19 Hz, 1H), 8.03 (s, 2H), 8.15 (s, 1H), 8.16-8.22 (m, 2H), 8.27 (s, 1H), 8.73 (d, J=5.73 Hz, 1H), 8.83 (d, J=2.65 Hz, 1H), 8.96 (d, J=2.65 Hz, 1H), 9.21 (dd, J=4.30, 1.65 Hz, 1H).

Example 36

N-(5-cyano-6-(2H-1,2,3-triazol-2-yl)pyridin-3-yl)-1-(furo[2,3-c]pyridin-7-yl)-5-(trifluoromethyl)-1H-pyrazole-4-carboxamide, Cpd 99

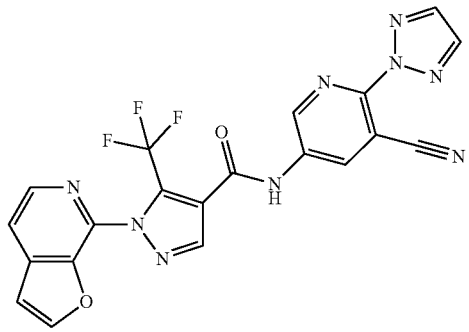 [SMILES: N#Cc1cc(NC(=O)c2cnn(-c3nccc4ccoc34)c2C(F)(F)F)cnc1-n1nccn1]

A. 7-Hydrazinylfuro[2,3-c]pyridine, 36a

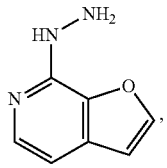

7-Chlorofuro[2,3-c]pyridine (300 mg, 1.95 mmol) was dissolved in ethanol (5 mL), hydrazine hydrate (345 mg, 5.86 mmol) was added, and the reaction mixture was stirred at 110° C. for 16 h. The reaction mixture was concentrated under reduced pressure to afford crude compound 36a as a yellow solid. Compound 36a was purified by flash column chromatography over silica gel (dichloromethane/MeOH from 100/0 to 80/20) to afford compound 36a as a yellow solid (250 mg, 83.9%). LCMS (ESI) m/z M+1: 150.1.

B. Ethyl 1-(furo[2,3-c]pyridin-7-yl)-5-(trifluoromethyl)-1H-pyrazole-4-carboxylate, 36b

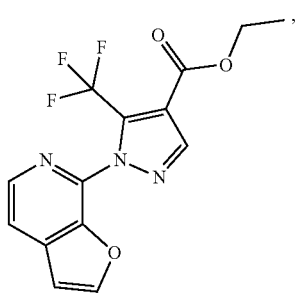

7-Hydrazinylfuro[2,3-c]pyridine, 36a (250 mg, 1.64 mmol) was dissolved in ethanol (10 mL), ethyl 2-(ethoxymethylene)-4,4,4-trifluoro-3-oxobutanoate, 1f (788 mg, 3.28 mmol) was added and the reaction mixture was stirred at 80° C. for 16 h. The reaction mixture was concentrated under reduced pressure to afford a crude yellow oil. The oil was purified by flash column chromatography over silica gel (petroleum ether/ethyl acetate from 100/0 to 80/20) to afford compound 36b as a yellow oil (360 mg, 68%). LCMS (ESI) m/z M+1: 325.9.

C. 1-(Furo[2,3-c]pyridin-7-yl)-5-(trifluoromethyl)-1H-pyrazole-4-carboxylic acid, 36c

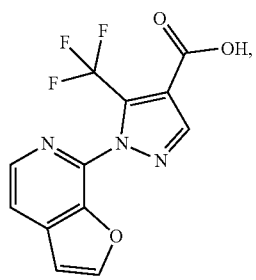

36c

Concentrated HCl (4.7 mL) was added to ethyl 1-(furo[2,3-c]pyridin-7-yl)-5-(trifluoromethyl)-1H-pyrazole-4-carboxylate, 36b (170 mg, 0.52 mmol) and the reaction mixture was stirred at 130° C. for 2 h. The reaction mixture was concentrated under reduced pressure to afford compound 36c as a yellow solid (160 mg, 98%), which was used in the following reaction without further purification. LCMS (ESI) m/z M+1: 297.9.

D. N-(5-Cyano-6-(2H-1,2,3-triazol-2-yl)pyridin-3-yl)-1-(furo[2,3-c]pyridin-7-yl)-5-(trifluoromethyl)-1H-pyrazole-4-carboxamide, Cpd 99

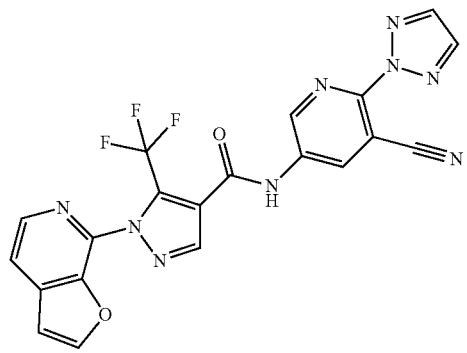 [SMILES: N#Cc1cc(NC(=O)c2cnn(-c3nccc4ccoc34)c2C(F)(F)F)cnc1-n1nccn1]

1-(Furo[2,3-c]pyridin-7-yl)-5-(trifluoromethyl)-1H-pyrazole-4-carboxylic acid, 36c (160 mg, 0.51 mmol), 5-amino-2-(2H-1,2,3-triazol-2-yl)nicotinonitrile, 7b (63.8 mg, 0.34 mmol), and pyridine (122 mg, 1.54 mmol) were dissolved in dichloromethane (3 mL), and phosphoryl trichloride (78.8 mg, 0.51 mmol) was added. The mixture was stirred at 25° C. for 16 h. Sat. aqueous NaHCO₃ (20 mL) was added and the mixture was extracted with dichloromethane (30 mL×2). The combined organic layers were dried over Na₂SO₄, filtered, and the filtrate was concentrated under reduced pressure to afford crude compound 99 as a yellow oil. The oil was purified by reverse phase HPLC (A: water (0.05% HCl), B: MeCN; then: AB (65%/35% to 40%/60%). The pure fractions were concentrated under reduced pressure and lyophilized to dryness to afford compound 99 as a yellow solid (65 mg, 41%). LCMS (ESI) m/z M+1: 465.9; $^1$H NMR (400 MHz, DMSO-d$_6$) δ ppm 11.41 (s, 1H), 9.06 (d, J=2.4 Hz, 1H), 8.83 (d, J=2.4 Hz, 1H), 8.53 (s, 1H), 8.48 (d, J=5.7 Hz, 1H), 8.32 (d, J=2.4 Hz, 1H), 8.29 (s, 2H), 7.95 (dd, J=0.9, 5.7 Hz, 1H), 7.13 (dd, J=0.9, 2.2 Hz, 1H).

Example 37

N-(5-cyano-6-(2H-1,2,3-triazol-2-yl)pyridin-3-yl)-1-(furo[3,2-c]pyridin-4-yl)-5-(trifluoromethyl)-1H-pyrazole-4-carboxamide, Cpd 94

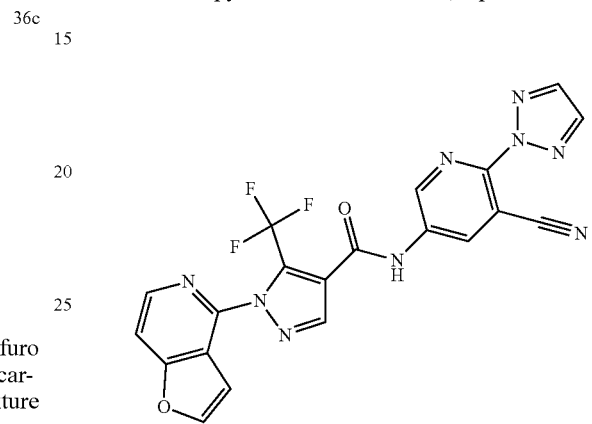

A. 4-Hydrazinylfuro[3,2-c]pyridine, 37a

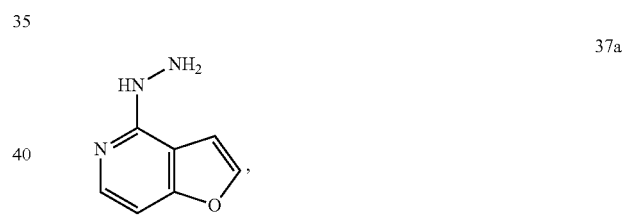

37a

A mixture of 4-chlorofuro[3,2-c]pyridine (200 mg, 1.30 mmol) in hydrazine (6.52 g, 130 mmol) was stirred at 80° C. for 12 h. The reaction mixture was extracted with dichloromethane (30 mL×2). The organic layer partitioned and concentrated to afford compound 37a as a yellow solid (0.15 g, 77%).

B. Ethyl 1-(furo[3,2-c]pyridin-4-yl)-5-(trifluoromethyl)-1H-pyrazole-4-carboxylate, 37b

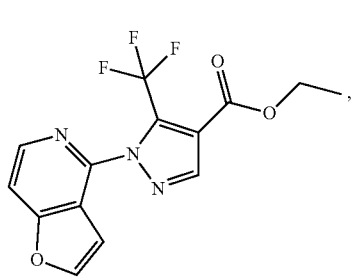

37b

A solution consisting of 4-hydrazinylfuro[3,2-c]pyridine, 37a (150 mg, 1.01 mmol) and ethyl 2-(ethoxymethylene)-4,4,4-trifluoro-3-oxobutanoate, 1f (314 mg, 1.31 mmol) in ethanol (5 mL) was stirred at 80° C. for 3 h. The resultant solution was cooled to room temperature and concentrated to dryness under reduced pressure to afford the crude product. The crude product was purified by column chromatography over silica gel (petroleum ether/ethyl acetate=100:0 to 70:30) to afford crude compound 37b as a yellow solid (170 mg, 51%). LCMS (ESI) m/z M+1: 325.9.

C. 1-(Furo[3,2-c]pyridin-4-yl)-5-(trifluoromethyl)-1H-pyrazole-4-carboxylic acid, 37c

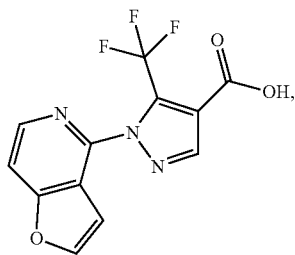

37c

A mixture of ethyl 1-(furo[3,2-c]pyridin-4-yl)-5-(trifluoromethyl)-1H-pyrazole-4-carboxylate, 37b (170 mg, 0.52 mmol) in concentrated HCl (4.4 mL) was stirred at 110° C. for 5 h. The solvent was removed under reduced pressure to afford compound 37c as a yellow solid (155 mg, 100%). LCMS (ESI) m/z M+1: 297.9.

D. N-(5-Cyano-6-(2H-1,2,3-triazol-2-yl)pyridin-3-yl)-1-(furo[3,2-c]pyridin-4-yl)-5-(trifluoromethyl)-1H-pyrazole-4-carboxamide, Cpd 94

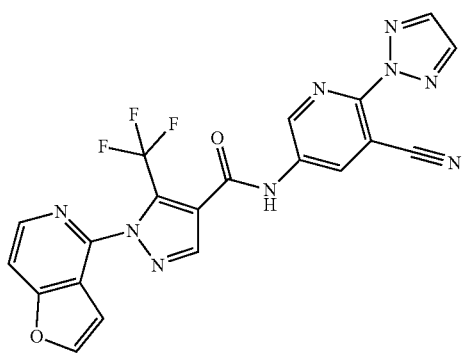

Phosphoryl trichloride (61.6 µL, 0.67 mmol) was added to the mixture of 1-(furo[3,2-c]pyridin-4-yl)-5-(trifluoromethyl)-1H-pyrazole-4-carboxylic acid, 37c (100 mg, 0.34 mmol), 5-amino-2-(2H-1,2,3-triazol-2-yl)nicotinonitrile, 7b (75.2 mg, 0.40 mmol), and pyridine (135 µL, 1.68 mmol) in dichloromethane at 0° C. The reaction was stirred at room temperature for 2 h. Sat. aqueous $NH_4Cl$ (aq) (10 mL) was added to the mixture. The mixture was extracted with dichloromethane (30 mL). The organic extracts were washed with water (5 mL), and brine (10 mL), dried over $Na_2SO_4$, filtered, and the filtrate concentrated under reduced pressure. The crude product was purified by reverse phase HPLC (A: water (0.05% HCl), B: MeCN; then: AB (65%/35% to 35%/65%). The pure fractions were concentrated under reduced pressure and lyophilized to dryness to afford compound 94 as a white solid (73.6 mg, 46%). LCMS (ESI) m/z M+1: 447.0; $^1$H NMR (400 MHz, DMSO-$d_6$) δ ppm 7.13 (d, J=1.32 Hz, 1H), 7.94-7.99 (m, 1H), 8.30 (s, 2H), 8.33 (d, J=2.21 Hz, 1H), 8.49 (d, J=5.73 Hz, 1H), 8.55 (s, 1H), 8.85 (d, J=2.43 Hz, 1H), 9.07 (d, J=2.43 Hz, 1H), 11.45 (s, 1H).

Example 38

1-(Cinnolin-4-yl)-N-(5-cyano-6-(2H-1,2,3-triazol-2-yl)pyridin-3-yl)-5-(trifluoromethyl)-1H-pyrazole-4-carboxamide, Cpd 93

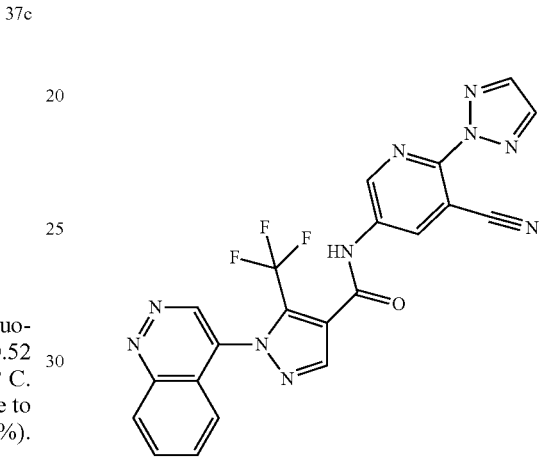

A. 4-Hydrazinylcinnoline, 38a

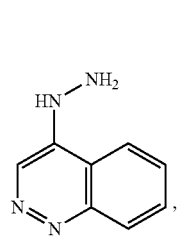

38a

A vial with stirbar was charged with 4-chlorocinnoline (212 mg, 1.288 mmol) and hydrazine (0.4 mL, 1.021 g/mL, 12.745 mmol), and the mixture was evacuated and flushed with argon (4×). Within 1-2 min at room temperature, the reaction mixture became a homogeneous amber solution and spontaneously warmed, becoming an orange paste. The reaction was then heated at 110° C. for 5 min. The reaction was allowed to cool to room temperature, water (8 mL) was added to the resulting paste, and the mixture was filtered. The filter cake was washed with water (4 mL×2) and dried under reduced pressure to afford compound 38a as a yellow powder (142.1 mg, 69%).

B. Ethyl 1-(cinnolin-4-yl)-5-(trifluoromethyl)-1H-pyrazole-4-carboxylate, 38b

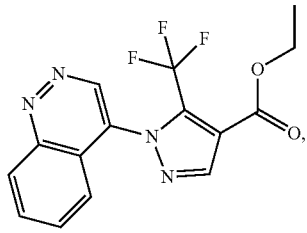

38b

A solution consisting of 4-hydrazinylcinnoline, 38a (100 mg, 0.51 mmol) and ethyl 2-(ethoxymethylene)-4,4,4-trifluoro-3-oxobutanoate, 1f (244 mg, 1.02 mmol) in ethanol (5 mL) was stirred at 80° C. for 3 h. The resultant solution was cooled to room temperature and concentrated to dryness under reduced pressure to afford crude compound 38b. The crude product was purified by column chromatography over silica gel (petroleum ether/ethyl acetate=100:0 to 70:30) to afford crude compound 38b as a yellow solid (90 mg, 53%). LCMS (ESI) m/z M+1:336.9. $^1$H NMR (400 MHz, CDCl$_3$) δ ppm 1.42 (t, J=7.17 Hz, 3H), 4.43 (q, J=7.28 Hz, 2H), 7.54 (d, J=8.60 Hz, 1H), 7.87 (t, J=7.61 Hz, 1H), 7.99 (td, J=7.72, 1.10 Hz, 1H), 8.33 (s, 1H), 8.74 (d, J=8.60 Hz, 1H), 9.33 (s, 1H).

C. 1-(Cinnolin-4-yl)-5-(trifluoromethyl)-1H-pyrazole-4-carboxylic acid, 38c

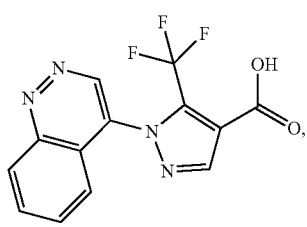

38c

A mixture of ethyl 1-(cinnolin-4-yl)-5-(trifluoromethyl)-1H-pyrazole-4-carboxylate, 38b (90 mg, 0.27 mmol) in concentrated HCl (2.23 mL) was stirred at 110° C. for 5 h. The solvent was removed under reduced pressure to give compound 38c as a yellow solid (82 mg, 100%). LCMS (ESI) m/z M+1:308.9.

D. 1-(Cinnolin-4-yl)-N-(5-cyano-6-(2H-1,2,3-triazol-2-yl)pyridin-3-yl)-5-(trifluoromethyl)-1H-pyrazole-4-carboxamide, Cpd 93

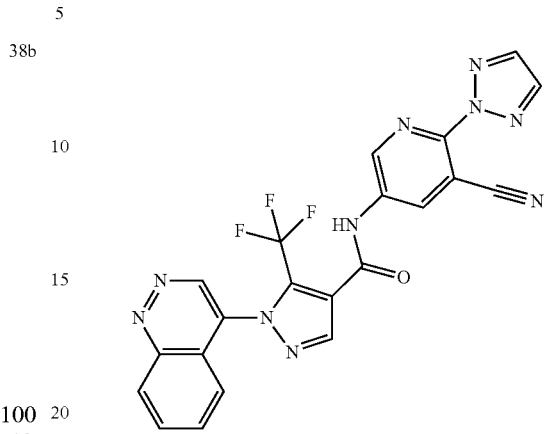

Phosphoryl trichloride (163.2 mg, 1.01 mmol) was added to a mixture of 1-(cinnolin-4-yl)-5-(trifluoromethyl)-1H-pyrazole-4-carboxylic acid, 38c (82 mg, 0.27 mmol), 5-amino-2-(2H-1,2,3-triazol-2-yl)nicotinonitrile, 7b (59.4 mg, 0.32 mmol), and pyridine (126 mg, 1.60 mmol) in dichloromethane at 0° C. The reaction was stirred at room temperature for 2 h. Sat. NH$_4$Cl (aq) (10 mL) was added to the mixture. The mixture was extracted with dichloromethane (30 mL×2). The organic extracts were washed with water (5 mL), and brine (10 mL), dried over Na$_2$SO$_4$, filtered, and the filtrated concentrated under reduced pressure. The crude product was purified by reverse phase HPLC (A: water (0.05% HCl), B: MeCN; then: AB (62%/38% to 32%/68%). The pure fractions were concentrated under reduced pressure and lyophilized to dryness to afford compound 93 as a pale yellow solid (20 mg, 16%). LCMS (ESI) m/z M+1: 477.0; $^1$H NMR (400 MHz, DMSO-d$_6$) δ ppm 7.58 (d, J=8.38 Hz, 1H), 8.01-8.10 (m, 1H), 8.15 (t, J=7.50 Hz, 1H), 8.29 (s, 2H), 8.71 (s, 1H), 8.74 (d, J=8.60 Hz, 1H), 8.87 (d, J=2.65 Hz, 1H), 9.09 (d, J=2.65 Hz, 1H), 9.77 (s, 1H), 11.37 (s, 1H).

Example 39

N-(5-cyano-6-(2H-1,2,3-triazol-2-yl)pyridin-3-yl)-1-(8-fluoroquinolin-4-yl)-5-(trifluoromethyl)-1H-pyrazole-4-carboxamide, Cpd 92

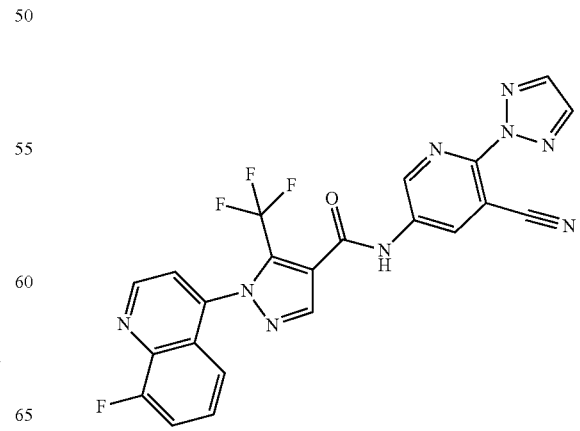

343

A. 8-Fluoro-4-hydrazinylquinoline, 39a

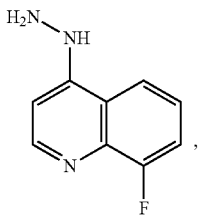

4-Chloro-8-fluoroquinoline (300 mg, 1.65 mmol) was dissolved in ethanol (5 mL), hydrazine hydrate (292 mg, 5.0 mmol) was added and the reaction was stirred at 80° C. for 16 h. The reaction mixture was concentrated under reduced pressure to afford crude compound 39a as a yellow solid. The solid was purified by flash column chromatography over silica gel (dichloromethane/MeOH from 100/0 to 80/20) to afford compound 39a as a yellow solid (350 mg, 82%). LCMS (ESI) m/z M+1: 178.1.

B. Ethyl 1-(8-fluoroquinolin-4-yl)-5-(trifluoromethyl)-1H-pyrazole-4-carboxylate, 39b

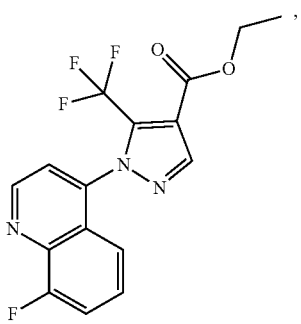

A solution consisting of 8-fluoro-4-hydrazinylquinoline, 39a (350 mg, 1.35 mmol) and ethyl 2-(ethoxymethylene)-4,4,4-trifluoro-3-oxobutanoate, 1f (648 mg, 2.70 mmol) in ethanol (10 mL) was stirred at 80° C. for 16 h. The resultant solution was cooled to room temperature and concentrated to dryness under reduced pressure to afford a crude product. The crude product was purified by column chromatography over silica gel (petroleum ether/ethyl acetate=100:0 to 80:20). The solvent was removed under reduced pressure to afford compound 39b as a yellow solid (780 mg, 61%).

344

C. 1-(8-Fluoroquinolin-4-yl)-5-(trifluoromethyl)-1H-pyrazole-4-carboxylic acid, 39c

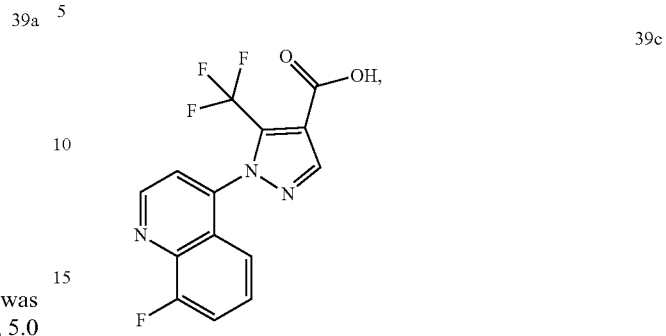

A mixture of ethyl 1-(8-fluoroquinolin-4-yl)-5-(trifluoromethyl)-1H-pyrazole-4-carboxylate, 39b (150 mg, 0.43 mmol) in concentrated HCl (10 mL) was stirred at 130° C. for 4 h. The solvent was concentrated under reduced pressure to afford compound 39c as a yellow solid (140 mg, 100%). LCMS (ESI) m/z M+1: 325.9.

D. N-(5-Cyano-6-(2H-1,2,3-triazol-2-yl)pyridin-3-yl)-1-(8-fluoroquinolin-4-yl)-5-(trifluoromethyl)-1H-pyrazole-4-carboxamide, Cpd 92

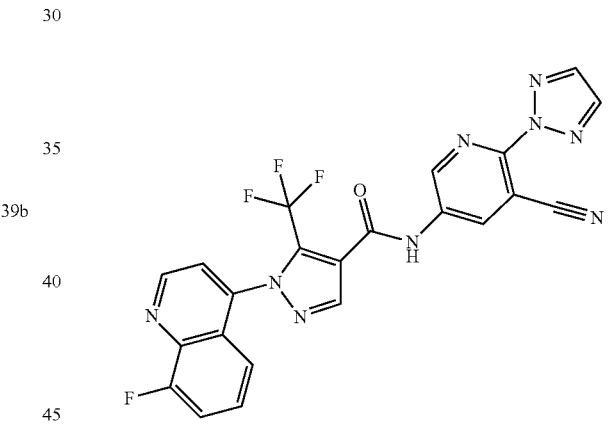

Phosphoryl trichloride (81.2 mg, 0.53 mmol) was added to a mixture of 1-(8-fluoroquinolin-4-yl)-5-(trifluoromethyl)-1H-pyrazole-4-carboxylic acid, 39c (150 mg, 0.46 mmol), 5-amino-2-(2H-1,2,3-triazol-2-yl)nicotinonitrile, 7b (65.7 mg, 0.35 mmol), and pyridine (126 mg, 1.60 mmol) in dichloromethane (3 mL) at 0° C. The reaction was stirred at room temperature for 2 h. Sat. NH$_4$Cl (aq) (10 mL) was added to the mixture. The mixture was extracted with dichloromethane (30 mL×2). The organic layer was washed with water (5 mL), and brine (10 mL), dried over Na$_2$SO$_4$, filtered, and the filtrate concentrated under reduced pressure. The resultant residue was purified by reverse phase HPLC (A: water (0.05% HCl), B: MeCN; then: A/B (57%/43% to 27%/73%). The pure fractions were concentrated under reduced pressure and lyophilized to dryness to afford compound 92 as a yellow solid (54 mg, 31%). LCMS (ESI) m/z M+1: 493.9; $^1$H NMR (400 MHz, DMSO-d$_6$) δ ppm 11.41 (s, 1H), 9.21 (d, J=4.4 Hz, 1H), 9.10 (d, J=2.2 Hz, 1H), 8.87 (d, J=2.4 Hz, 1H), 8.68 (s, 1H), 8.29 (s, 2H), 8.01 (d, J=4.4 Hz, 1H), 7.82-7.67 (m, 2H), 7.14 (d, J=8.4 Hz, 1H).

Example 40

N-(5-chloro-6-(oxazol-2-yl)pyridin-3-yl)-1-(quinolin-5-yl)-5-(trifluoromethyl)-1H-pyrazole-4-carboxamide, Cpd 91

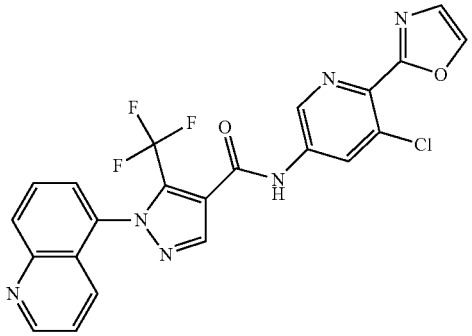 [SMILES: O=C(Nc1cnc(-c2ncco2)c(Cl)c1)c1cnn(-c2cccc3ncccc23)c1C(F)(F)F]

Phosphoryl trichloride (38.5 mg, 0.25 mmol) was added to a mixture of 1-(quinolin-5-yl)-5-(trifluoromethyl)-1H-pyrazole-4-carboxylic acid, 3b (51.4 mg, 0.17 mmol), 5-chloro-6-(oxazol-2-yl)pyridin-3-amine, 6b (60 mg, 0.25 mmol), and pyridine (60 mg, 0.75 mmol) in dichloromethane (3 mL) at 0° C. The reaction was stirred at room temperature for 16 h. Sat. NaHCO$_3$ (aq) (20 mL) was added to the mixture. The mixture was extracted with dichloromethane (20 mL×2). The organic layer was washed with water (5 mL), dried over Na$_2$SO$_4$, filtered, and the filtrate concentrated under reduced pressure. The resultant residue was purified by reverse phase HPLC (A: water (0.05% HCl), B: MeCN; then: A/B (64%/36% to 34%/66%). The pure fractions were concentrated under reduced pressure and lyophilized to dryness to afford compound 91 as a yellow solid (40 mg, 49%). LCMS (ESI) m/z M+1: 484.9; $^1$H NMR (400 MHz, DMSO-d$_6$) δ ppm 11.40 (s, 1H), 9.11 (dd, J=2.1, 3.6 Hz, 1H), 9.01 (d, J=1.5 Hz, 1H), 8.66 (s, 1H), 8.59 (d, J=2.2 Hz, 1H), 8.37 (d, J=8.4 Hz, 1H), 8.32 (s, 1H), 8.05-7.94 (m, 2H), 7.79-7.71 (m, 2H), 7.49 (s, 1H).

Example 41

N-(5-cyano-6-cyclopropoxypyridin-3-yl)-1-(quinolin-5-yl)-5-(trifluoromethyl)-1H-pyrazole-4-carboxamide, Cpd 88

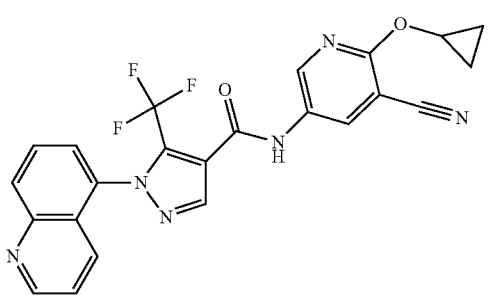 [SMILES: N#Cc1cc(NC(=O)c2cnn(-c3cccc4ncccc34)c2C(F)(F)F)cnc1OC1CC1]

A. 2-Cyclopropoxy-5-nitronicotinonitrile, 41a

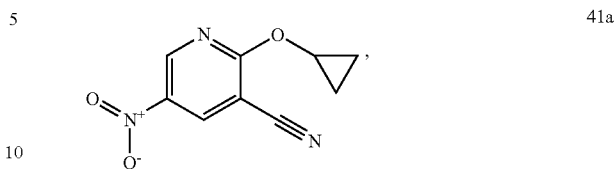

2-Chloro-5-nitronicotinonitrile (300 mg, 1.64 mmol) and cyclopropanol (380 mg, 6.54 mmol) were added to potassium carbonate (339 mg, 2.45 mmol), and the mixture was stirred at room temperature overnight. The mixture was concentrated to dryness and dissolved in ethyl acetate (5 mL). Water (10 mL) was added to the reaction mixture. The mixture was extracted with ethyl acetate (10 mL×3). The combined organic extracts were dried over Na$_2$SO$_4$, filtered, and the filtrate concentrated to dryness to give crude compound 41a. The crude product was purified by flash column chromatography over silica gel (petroleum ether/ethyl acetate from 100/0 to 60/40) to afford compound 41a as a yellow solid (310 mg, 92%). $^1$H NMR (400 MHz, DMSO-d$_6$) δ ppm 0.85-0.90 (m, 4H), 4.52-4.58 (m, 1H), 9.18 (d, J=2.76 Hz, 1H), 9.35 (d, J=2.76 Hz, 1H).

B. 5-Amino-2-cyclopropoxynicotinonitrile, 41b

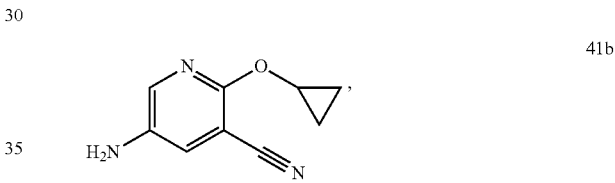

Fe (0) (422 mg, 7.56 mmol) and NH$_4$Cl (404 mg, 7.56 mmol) was added to a solution of 2-cyclopropoxy-5-nitronicotinonitrile, 41a (310 mg, 1.51 mmol) in THF (10 mL), methanol (10 mL) and water (10 mL). The reaction mixture was stirred at 65° C. for 2 h. The mixture was filtered. Sat. aqueous NaHCO$_3$ was added to adjust the pH of the reaction mixture to 7-8. The mixture was extracted with ethyl acetate (10 mL×3). The organic extracts were dried over MgSO$_4$, filtered, and the filtrate was concentrated under reduced pressure to afford compound 41b as a yellow solid (280 mg, 87%). LCMS (ESI) m/z M+1: 175.8.

C. N-(5-Cyano-6-cyclopropoxypyridin-3-yl)-1-(quinolin-5-yl)-5-(trifluoromethyl)-1H-pyrazole-4-carboxamide, Cpd 88

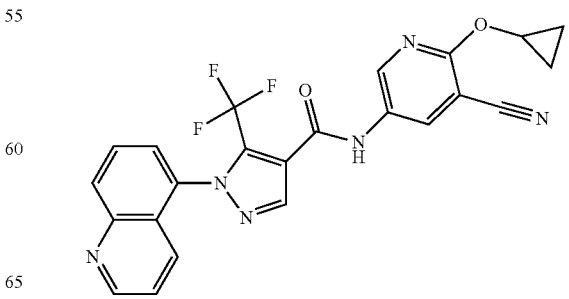

2-(7-Aza-1H-benzotriazole-1-yl)-1,1,3,3-tetramethyluronium hexafluorophosphate (186 mg, 0.49 mmol) was added to a solution of 1-(quinolin-5-yl)-5-(trifluoromethyl)-1H-pyrazole-4-carboxylic acid, 3b (100 mg, 0.325 mmol), 5-amino-2-cyclopropoxynicotinonitrile, 41b (97.1 mg, 0.46 mmol) and triethylamine (142 μL, 0.81 mmol) in DMF (2 mL). The reaction mixture was stirred at room temperature for 1 h. Water (5 mL) was added to the mixture. The aqueous portion was extracted with dichloromethane (5 mL×3). The separated organic layer was dried over MgSO$_4$, filtered, and the filtrate was concentrated under reduced pressure to afford a crude product. The crude product was purified by reverse phase HPLC (A: water (0.05% HCl), B: MeCN; then: AB (74%/26% to 44%/56%). The pure fractions were concentrated under reduced pressure and lyophilized to dryness to afford compound 88 as a white solid (90 mg, 43%). LCMS (ESI) m/z M+1: 465.0; $^1$H NMR (400 MHz, DMSO-d$_6$) δ ppm 0.75-0.80 (m, 2H), 0.81-0.87 (m, 2H), 4.39 (tt, J=6.12, 3.14 Hz, 1H), 7.63-7.73 (m, 2H), 7.91-7.95 (m, 1H), 7.96-8.02 (m, 1H), 8.34 (d, J=8.38 Hz, 1H), 8.52-8.58 (m, 2H), 8.75 (d, J=2.43 Hz, 1H), 9.08 (dd, J=4.08, 1.65 Hz, 1H), 11.01 (br s, 1H).

Example 42

N-(5-cyano-6-(2H-1,2,3-triazol-2-yl)pyridin-3-yl)-1-(phthalazin-1-yl)-5-(trifluoromethyl)-1H-pyrazole-4-carboxamide, Cpd 102

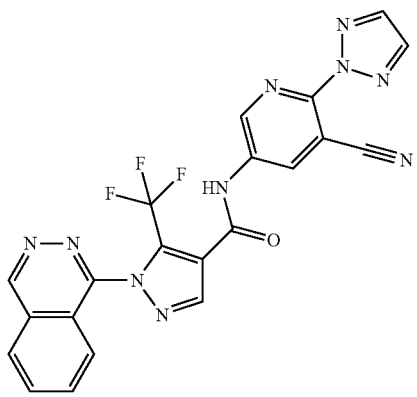 [SMILES: N#Cc1cc(NC(=O)c2cnn(-c3nncc4ccccc34)c2C(F)(F)F)cnc1-n1nccn1]

A. 1-Hydrazinylphthalazine, 42a

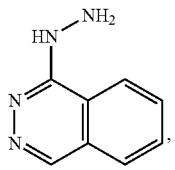

A mixture of 1-chlorophthalazine (350 mg, 2.13 mmol) in hydrazine (5.32 g, 106.3 mmol) was stirred at 80° C. for 4 h. The mixture was extracted with dichloromethane (50 mL×2). The organic layer was concentrated under reduced pressure to afford a crude product. The crude product was purified by column chromatography over silica gel (petroleum ether/ethyl acetate=100:0 to 0:100) to afford crude compound 42a as a yellow solid (0.25 g, 73.3%).

B. Ethyl 1-(phthalazin-1-yl)-5-(trifluoromethyl)-1H-pyrazole-4-carboxylate, 42b

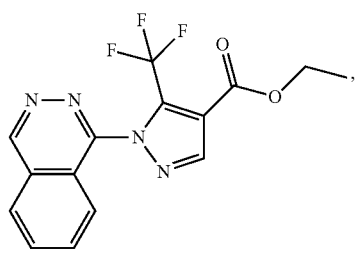

A solution consisting of 1-hydrazinylphthalazine, 42a (250 mg, 1.56 mmol) and ethyl 2-(ethoxymethylene)-4,4,4-trifluoro-3-oxobutanoate, 1f (750 mg, 3.12 mmol) in ethanol (5 mL) was stirred at 80° C. for 3 h. The resultant solution was cooled to room temperature and concentrated to dryness under reduced pressure to afford a crude product. The crude product was purified by column chromatography over silica gel (petroleum ether/ethyl acetate=100:0 to 70:30) to afford crude compound 42b as a yellow solid (160 mg, 27.4%). LCMS (ESI) m/z M+1: 336.9.

C. 1-(Phthalazin-1-yl)-5-(trifluoromethyl)-1H-pyrazole-4-carboxylic acid, 42c

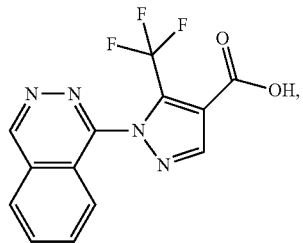

A mixture of ethyl 1-(phthalazin-1-yl)-5-(trifluoromethyl)-1H-pyrazole-4-carboxylate, 42b (160 mg, 0.43 mmol) in concentrated HCl (3.5 mL) was stirred at 110° C. for 5 h. The solvent was removed under reduced pressure to afford compound 42c as a yellow solid (140 mg, 100%). LCMS (ESI) m/z M+1: 308.9.

D. N-(5-cyano-6-(2H-1,2,3-triazol-2-yl)pyridin-3-yl)-1-(phthalazin-1-yl)-5-(trifluoromethyl)-1H-pyrazole-4-carboxamide, Cpd 102

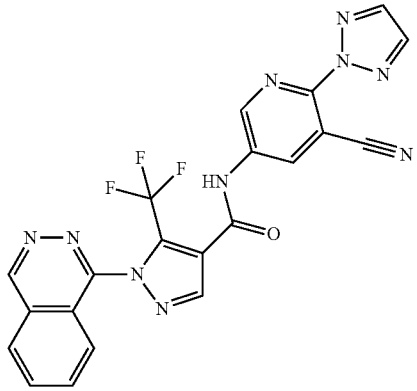 [SMILES: N#Cc1cc(NC(=O)c2cnn(-c3nncc4ccccc34)c2C(F)(F)F)cnc1-n1nccn1]

Phosphoryl trichloride (218.2 mg, 1.42 mmol) was added to the mixture of 1-(phthalazin-1-yl)-5-(trifluoromethyl)-1H-pyrazole-4-carboxylic acid, 42c (130 mg, 0.36 mmol), 5-amino-2-(2H-1,2,3-triazol-2-yl)nicotinonitrile, 7b (79.5 mg, 0.43 mmol), pyridine (170 mg, 2.14 mmol) in dichloromethane (10 mL) at 0° C. The reaction was stirred at room temperature for 2 h. Water (20 mL) was added to the mixture. The mixture was extracted with dichloromethane (20 mL×2). The organic portion was concentrated under reduced pressure to afford a crude product. The crude product was purified by reverse phase HPLC (A: water (0.05% HCl), B: MeCN; then: AB (65%/35% to 35%/65%). The pure fractions were concentrated under reduced pressure and lyophilized to dryness to afford compound 102 as a white solid (15 mg, 9%). LCMS (ESI) m/z M+1: 477.0; $^1$H NMR (400 MHz, DMSO-d$_6$) δ ppm 7.81 (d, J=8.38 Hz, 1H), 8.14-8.25 (m, 2H), 8.44 (d, J=7.72 Hz, 1H), 8.73 (s, 1H), 8.89 (d, J=2.43 Hz, 1H), 9.12 (d, J=2.43 Hz, 1H), 9.98 (s, 1H), 11.45 (s, 1H).

Example 43

Methyl 3-chloro-5-(3-chloro-5-(1-(isoquinolin-4-yl)-5-(trifluoromethyl)-1H-pyrazole-4-carboxamido)picolinamido)picolinate, Cpd 44

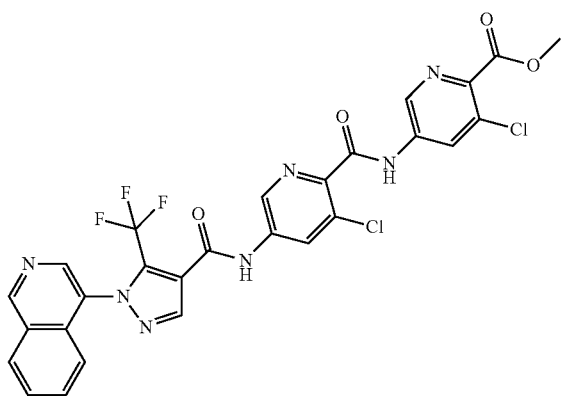 [SMILES: COC(=O)c1ncc(NC(=O)c2ncc(NC(=O)c3cnn(-c4cncc5ccccc45)c3C(F)(F)F)cc2Cl)cc1Cl]

A. Methyl 5-amino-3-chloropicolinate, 43a

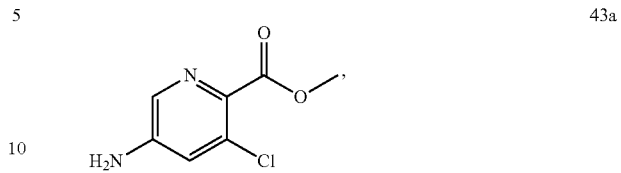

A mixture of 6-bromo-5-chloropyridin-3-amine (500 mg, 2.41 mmol), 1,1-bis(diphenylphosphino)ferrocene (134 mg, 0.24 mmol) and triethylamine (732 mg, 7.23 mmol) in MeOH (3 mL) and toluene (15 mL) was heated at 70° C. under a CO (35 psi) atmosphere with dichloro[1,1'-bis(diphenylphosphino)ferrocene]palladium(II) dichloromethane adduct (catalyst, 197 mg, 0.24 mmol), and the mixture was stirred overnight. After uptake of CO (1 equiv), the catalyst was removed by filtration and the filtrate was concentrated under reduced pressure to give a crude product. The crude product was purified by flash column chromatography over silica gel (petroleum ether/ethyl acetate from 100/0 to 50/50) to afford compound 43a as a red solid (300 mg, 67%). $^1$H NMR (400 MHz, CDCl$_3$) δ ppm 3.96 (s, 3H), 4.14-4.24 (m, 2H), 7.03 (d, J=2.26 Hz, 1H), 8.03 (d, J=2.51 Hz, 1H).

B. Methyl 3-chloro-5-(3-chloro-5-(1-(isoquinolin-4-yl)-5-(trifluoromethyl)-1H-pyrazole-4-carboxamido)picolinamido)picolinate, Cpd 44

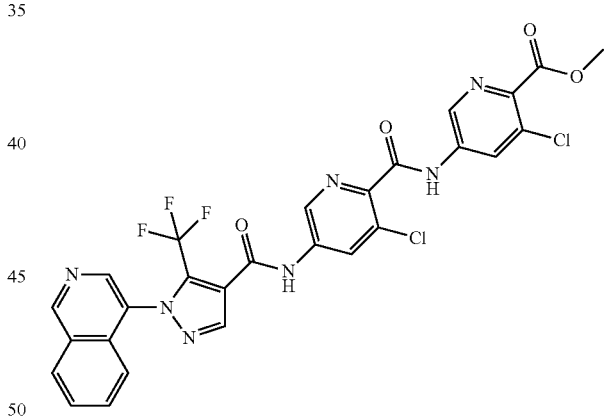

Phosphoryl trichloride (29.8 mg, 0.32 mmol) was added dropwise to a solution of 1-(isoquinolin-4-yl)-5-(trifluoromethyl)-1H-pyrazole-4-carboxylic acid, 4c (50 mg, 0.16 mmol), methyl 5-amino-3-chloropicolinate, 43a (38.8 mg, 0.21 mmol) and pyridine (64.7 mg, 0.80 mmol) in dichloromethane (2 mL). The reaction mixture was stirred at room temperature for 1 h. Water (5 mL) was added to the mixture. The aqueous portion was extracted with dichloromethane (5 mL×3). The separated organic extracts were dried over MgSO$_4$, filtered, and the filtrate concentrated under reduced pressure to afford a crude product. The crude product was purified by reverse phase HPLC (A: water (0.05% HCl), B: MeCN; then: AB (55%/45% to 25%/75%). The pure fractions were concentrated under reduced pressure and lyophilized to dryness to afford compound 44 as a white solid (22 mg, 21%). LCMS (ESI) m/z M+1: 629.8; $^1$H NMR (400

MHz, DMSO-d$_6$) δ ppm 3.90 (s, 3H), 7.30 (d, J=8.38 Hz, 1H), 7.84-8.00 (m, 2H), 8.39 (d, J=8.16 Hz, 1H), 8.58 (dd, J=10.69, 1.87 Hz, 2H), 8.68 (s, 1H), 8.81 (s, 1H), 9.01 (dd, J=10.03, 1.87 Hz, 2H), 9.64 (s, 1H), 11.36 (d, J=19.40 Hz, 2H).

Example 44

N-(5-Chloro-6-(2H-1,2,3-triazol-2-yl)pyridin-3-yl)-5-ethyl-1-(quinolin-5-yl)-1H-pyrazole-4-carboxamide, Cpd 17

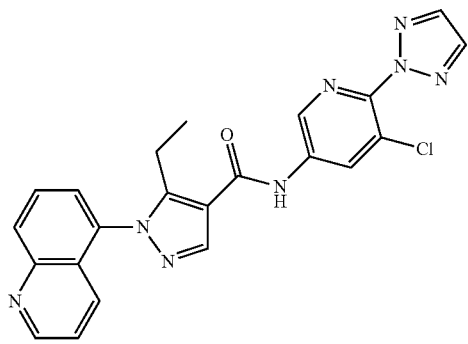 [SMILES: CCc1c(C(=O)Nc2cnc(-n3nccn3)c(Cl)c2)cnn1-c1cccc2ncccc12]

A. 3-(Ethoxymethylene)-1-methoxyhexane-2,4-dione, 44a

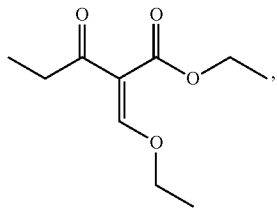

44a

A solution consisting of ethyl 3-oxopentanoate (1.0 g, 6.9 mmol), triethoxymethane (3.1 g, 21 mmol), and acetic anhydride (20 mL) was stirred at 135° C. for 16 h before cooling to room temperature. The resultant mixture was concentrated to dryness under reduced pressure to afford crude compound 44a (1.8 g, crude), which was used in the following reaction without further purification. $^1$H NMR (400 MHz, CDCl$_3$) δ ppm 7.69-7.54 (m, 1H), 4.33-4.15 (m, 4H), 2.70 (dd, J=7.6, 13.2 Hz, 2H), 1.41-1.26 (m, 6H), 1.13-1.05 (m, 3H).

B. 5-Hydrazinylquinoline, 44b

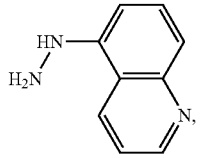

44b

A solution consisting of 5-aminoquinoline (1.0 g, 6.9 mmol) and concentrated hydrochloric acid (5 mL) was stirred at 0° C. (ice/water) for 10 min. A solution consisting of sodium nitrite (0.57 g, 8.3 mmol) and water (0.5 mL) was added to the cold reaction mixture over 10 min and stirred at 0° C. (ice/water) for 1 h. L-ascorbic acid (1.3 g, 7.3 mmol) was added to the reaction mixture over 10 min. The resultant mixture was warmed to room temperature and stirred for 50 min. The reaction mixture was then heated at 80° C. for 20 min and water (4 mL) was added. The suspension was again cooled to 0° C. (ice/water) and stirred for 2 h. A solid was collected by filtration and washed with methanol to afford compound 44b (870 mg, 79%). $^1$H NMR (400 MHz, DMSO-d$_6$) δ ppm 10.01 (br. s., 1H), 9.28-9.13 (m, 2H), 8.06-7.86 (m, 3H), 7.33-7.20 (m, 1H).

C. Ethyl 5-ethyl-1-(quinolin-5-yl)-1H-pyrazole-4-carboxylate, 44c

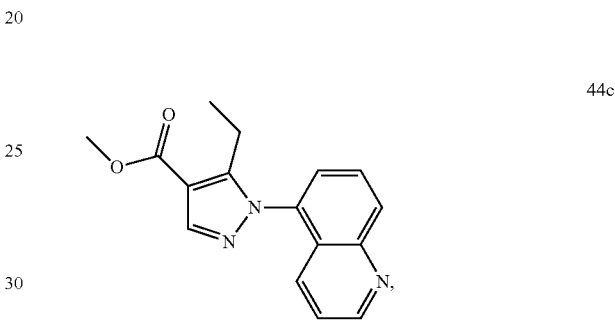

44c

A solution consisting of 3-(ethoxymethylene)-1-methoxyhexane-2,4-dione, 44a (755 mg, 3.77 mmol), 5-hydrazinylquinoline, 44b (500 mg, 3.14 mmol), and ethanol (15 mL) was stirred at 80° C. for 16 h before cooling to room temperature. The resultant solution was concentrated to dryness under reduced pressure to afford a crude product, which was purified by FCC (dichloromethane:methanol=10:1) to afford compound 44c (700 mg, 75%) as a brown solid. The solid was purified by reverse phase HPLC (95% water containing 0.038% TFA (solvent A) and 5% acetonitrile containing 0.02% TFA (solvent B), followed by a gradient up to 5% solvent A and 95% solvent B). $^1$H NMR (400 MHz, DMSO-d$_6$) δ ppm 9.17-9.11 (m, 1H), 8.40 (d, J=8.4 Hz, 1H), 8.17 (s, 1H), 8.06 (t, J=8.0 Hz, 1H), 7.93 (d, J=7.6 Hz, 1H), 7.83-7.78 (m, 1H), 7.77-7.71 (m, 1H), 4.30 (q, J=7.2 Hz, 2H), 2.78-2.68 (m, 2H), 1.33 (t, J=7.2 Hz, 3H), 0.92 (t, J=7.6 Hz, 3H).

D. 5-Ethyl-1-(quinolin-5-yl)-1H-pyrazole-4-carboxylic acid, 44d

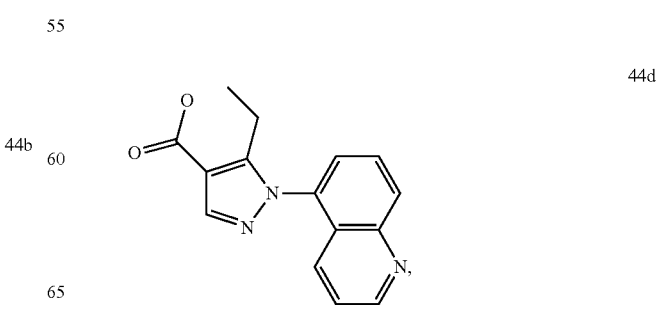

44d

A solution consisting of lithium hydroxide hydrate (298 mg, 7.11 mmol) and water (5 mL) was added to a solution consisting of ethyl 5-ethyl-1-(quinolin-5-yl)-1H-pyrazole-4-carboxylate, 44c (700 mg, 2.37 mmol) and ethanol (10 mL). The resultant solution was stirred at room temperature for 16 h. The resultant solution was concentrated to dryness under reduced pressure to afford a crude product, which was poured into water (3 mL) and acidified with 3N HCl to pH 5. A precipitate was removed by filtration, the filter cake was washed with water (3 mL), and then dried under reduced pressure to afford compound 44d (400 mg, 63%) as a brown solid. LCMS (ESI): $R_T$=0.54 min, mass calcd. for $C_{15}H_{13}N_3O_2$ 267.10, m/z found 268.0 [M+H]$^+$. Purification by reverse phase HPLC (95% water containing 0.038% TFA (solvent A) and 5% acetonitrile containing 0.02% TFA (solvent B), followed by a gradient up to 5% solvent A and 95% solvent B) afforded compound 44d. $^1$H NMR (400 MHz, DMSO-$d_6$) δ ppm 12.55 (br. s., 1H), 9.02 (d, J=2.4 Hz, 1H), 8.27 (d, J=8.8 Hz, 1H), 8.10 (s, 1H), 7.97-7.91 (m, 1H), 7.82 (d, J=7.2 Hz, 1H), 7.63-7.53 (m, 2H), 2.77-2.65 (m, 2H), 0.88 (t, J=7.6 Hz, 3H).

E. N-(5-Chloro-6-(2H-1,2,3-triazol-2-yl)pyridin-3-yl)-5-ethyl-1-(quinolin-5-yl)-1H-pyrazole-4-carboxamide, Cpd 17

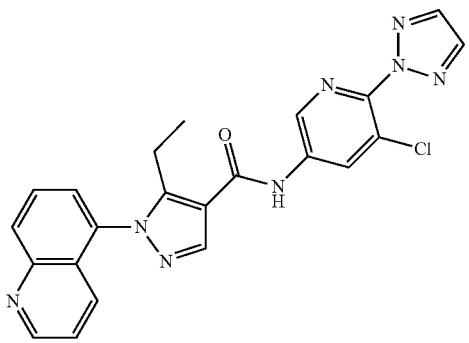 [SMILES: CCc1c(C(=O)Nc2cnc(-n3nccn3)c(Cl)c2)cnn1-c1cccc2ncccc12]

POCl$_3$ (172 mg, 1.12 mmol) was added dropwise to a solution consisting of 5-ethyl-1-(quinolin-5-yl)-1H-pyrazole-4-carboxylic acid, 44d (250 mg, 0.935 mmol), 5-chloro-6-(2H-1,2,3-triazol-2-yl)pyridin-3-amine, 1j (201 mg, 1.03 mmol), and pyridine (5 mL) at 0° C. The resultant mixture was stirred at 0° C. for 1 h. To the resultant mixture was added sat. aqueous NaHCO$_3$ (10 mL) and the mixture was extracted with ethyl acetate (15 mL×3). The organic extracts were dried over anhydrous Na$_2$SO$_4$, filtered, and the filtrate was concentrated to dryness under reduced pressure to give a crude product. The crude material was purified by reverse phase HPLC (40% to 50% (v/v) CH$_3$CN and water with 0.05% NH$_3$) to afford compound 17 (100 mg). Compound 17 was further purified by reverse phase HPLC (30% to 60% (v/v) CH$_3$CN and water with 10 mM NH$_4$HCO$_3$) to afford pure compound 17, which was suspended in water (10 mL), frozen using dry ice/acetone, and then lyophilized to dryness to afford compound 17 (56.50 mg, 13%). LCMS (ESI): $R_T$=4.51 min, mass calcd. for $C_{22}H_{17}ClN_8O$ 444.12, m/z found 445.0 [M+H]$^+$. $^1$H NMR (400 MHz, CDCl$_3$) δ ppm 9.02 (dd, J=1.6, 4.4 Hz, 1H), 8.78 (d, J=2.4 Hz, 1H), 8.54 (d, J=2.4 Hz, 1H), 8.34 (d, J=8.4 Hz, 1H), 8.20 (s, 1H), 8.15 (s, 1H), 7.96 (s, 2H), 7.89-7.83 (m, 1H), 7.65-7.57 (m, 2H), 7.46 (dd, J=4.4, 8.4 Hz, 1H), 2.88 (br.s., 2H), 1.07 (t, J=7.6 Hz, 3H).

Example 45

N-(5-Chloro-6-(2H-1,2,3-triazol-2-yl)pyridin-3-yl)-1-(1H-indazol-4-yl)-5-(trifluoromethyl)-1H-pyrazole-4-carboxamide, Cpd 68

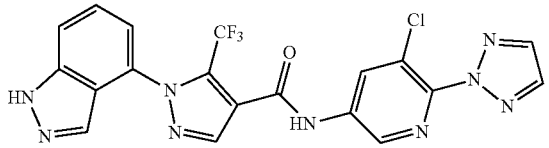 [SMILES: O=C(Nc1cnc(-n2nccn2)c(Cl)c1)c1cnn(-c2cccc3[nH]ncc23)c1C(F)(F)F]

A. 4-(2-(Diphenylmethylene)hydrazinyl)-1H-indazole, 45a

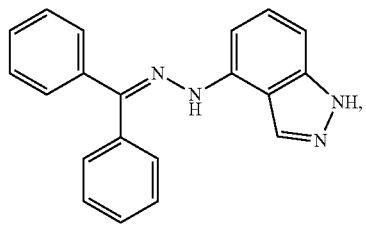

A mixture consisting of 4-bromo-1H-indazole (1.50 g, 0.760 mmol), (diphenylmethylene)hydrazine (1.49 g, 7.61 mmol), t-BuONa (2.19 g, 22.8 mmol), Pd$_2$(dba)$_3$ (697 mg, 0.760 mmol), Xantphos (440 mg, 0.760 mmol), and 1,4-dioxane (20 mL) was stirred at 110° C. for 24 h under a N$_2$ atmosphere. The mixture was cooled to room temperature, filtered and the filtrate was concentrated to dryness under reduced pressure to give a residue, which was purified by FCC (petroleum ether: ethyl acetate=1:2) to afford compound 45a (1 g, 42%). $^1$H NMR (400 MHz, CDCl$_3$) δ ppm 10.37 (br s, 1H), 8.52 (s, 1H), 7.95 (s, 1H), 7.67-7.56 (m, 5H), 7.42-7.33 (m, 5H), 7.25-7.21 (m, 1H), 6.96 (d, J=8.0 Hz, 1H), 6.54 (d, J=7.6 Hz, 1H).

B. 4-Hydrazinyl-1H-indazole, 45b

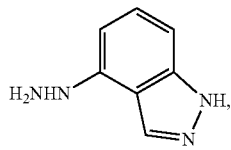

A mixture consisting of 4-(2-(diphenylmethylene)hydrazinyl)-1H-indazole, 45a (800 mg, 2.56 mmol), conc. HCl (10 mL), and ethanol (5 mL) was stirred at room temperature for 16 h. The ethanol was removed under reduced pressure and the aqueous phase was extracted with ethyl acetate (20 mL×2). The extracts were concentrated to dryness under reduced pressure to afford compound 45b (450 mg, 95%).

¹H NMR (400 MHz, DMSO-d₆) δ ppm 10.50 (br s, 3H), 8.17 (s, 1H), 7.28-7.20 (m, 1H), 7.09 (d, J=8.5 Hz, 1H), 6.55 (d, J=7.3 Hz, 1H).

C. Ethyl 1-(1H-indazol-4-yl)-5-(trifluoromethyl)-1H-pyrazole-4-carboxylate, 45c

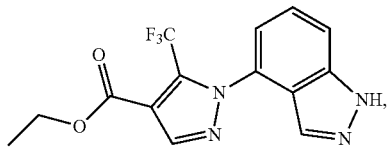

A mixture consisting of ethyl 2-(ethoxymethylene)-4,4,4-trifluoro-3-oxobutanoate, cpd 1f (39.0 mg, 0.160 mmol), 4-hydrazinyl-1H-indazole, 45b (30.0 mg, 0.160 mmol), triethylamine (18.0 mg, 0.180 mmol), and ethanol (3 mL) was stirred at 80° C. for 16 h. The mixture was cooled to room temperature and concentrated to dryness under reduced pressure to give a residue, which was purified by FCC (petroleum ether: ethyl acetate=2:1) to afford impure compound 45c (550 mg). The post-chromatographic product (550 mg) was further purified by preparative HPLC (32% to 62% (v/v) CH₃CN and water with 0.05% NH₃) to afford compound 45c, which was suspended in water (10 mL), the mixture frozen using dry ice/acetone, and then lyophilized to dryness to afford compound 45c (260 mg, 33%). ¹H NMR (400 MHz, CDCl₃) δ ppm 11.01 (br s, 1H), 8.24 (s, 1H), 7.96 (s, 1H), 7.65 (d, J=8.4 Hz, 1H), 7.50-7.46 (m, 1H), 7.23 (d, J=7.2 Hz, 1H), 4.42 (q, J=7.2 Hz, 2H), 1.41 (t, J=7.2 Hz, 3H).

D. N-(5-Chloro-6-(2H-1,2,3-triazol-2-yl)pyridin-3-yl)-1-(1H-indazol-4-yl)-5-(trifluoromethyl)-1H-pyrazole-4-carboxamide, Cpd 68

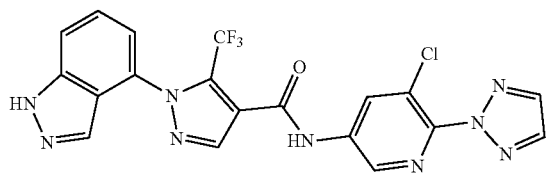 [SMILES: O=C(Nc1cnc(-n2nccn2)c(Cl)c1)c1cnn(-c2cccc3[nH]ncc23)c1C(F)(F)F]

A solution consisting of 5-chloro-6-(2H-1,2,3-triazol-2-yl)pyridin-3-amine, 1j (79.6 mg, 0.410 mmol) and THF (1 mL) was added dropwise to a solution of t-BuOK (1.02 mL, 1.02 mmol, 1 M in THF) at 0° C. Then a solution consisting of ethyl 1-(1H-indazol-4-yl)-5-(trifluoromethyl)-1H-pyrazole-4-carboxylate, 45c (20.0 mg, 0.0600 mmol), and THF (1 mL) was added dropwise. The mixture was warmed to room temperature and stirred for 16 h before quenching with water and extracting with ethyl acetate (50 mL×3). The combined extracts were dried over anhydrous Na₂SO₄, filtered, and the filtrate concentrated to dryness under reduced pressure to give a residue, which was purified by reverse phase HPLC (26% to 56% (v/v) CH₃CN and water with 0.05% NH₃) to afford pure compound 68. The product was suspended in water (10 mL), the mixture frozen using dry ice/acetone, and then lyophilized to dryness to afford compound 68 (70 mg, 44%). ¹H NMR (400 MHz, DMSO-d₆) δ ppm 13.63 (br s, 1H), 11.29 (br s, 1H), 8.86 (d, J=2.4 Hz, 1H), 8.68 (d, J=2.4 Hz, 1H), 8.54 (s, 1H), 8.20 (s, 2H), 7.88 (s, 1H), 7.82 (d, J=8.4 Hz, 1H), 7.60-7.51 (m, 1H), 7.32 (d, J=7.6 Hz, 1H).

Example 46

1-(Naphthalen-1-yl)-5-(trifluoromethyl)-N-(2-(trifluoromethyl)pyridin-4-yl)-1H-pyrazole-4-carboxamide, Cpd 3

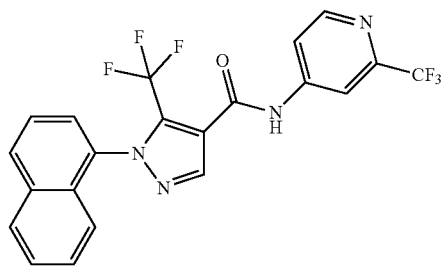 [SMILES: O=C(Nc1ccnc(C(F)(F)F)c1)c1cnn(-c2cccc3ccccc23)c1C(F)(F)F]

POCl₃ (90.1 mg, 0.588 mmol) was added dropwise to a solution consisting of 1-(naphthalen-1-yl)-5-(trifluoromethyl)-1H-pyrazole-4-carboxylic acid, 2b (150 mg, 0.490 mmol), 2-(trifluoromethyl)pyridin-4-amine (87.3 mg, 0.539 mmol) and pyridine (3 mL). The mixture was stirred at 0° C. for 1 h. The resulting mixture was concentrated to dryness under reduced pressure to give a crude product, which was purified by preparative high performance liquid chromatography using Kromasil 150×25 mm×10 μm (55% to 55% (v/v) ACN and water with 0.05% NH₃) to afford pure compound 3. The product was suspended in water (10 mL), the mixture frozen using dry ice/acetone, and then lyophilized to afford compound 3 (76.90 mg, 35%). ¹H NMR (400 MHz, DMSO-d₆) δ ppm 11.28 (br.s., 1H), 8.72 (d, J=6.0 Hz, 1H), 8.56 (s, 1H), 8.25 (d, J=6.4 Hz, 2H), 8.15 (d, J=7.6 Hz, 1H), 7.99 (d, J=4.8 Hz, 1H), 7.83-7.76 (m, 1H), 7.75-7.60 (m, 3H), 7.12 (d, J=8.0 Hz, 1H).

Example 47

1-(Naphthalen-1-yl)-5-(trifluoromethyl)-N-(5-(trifluoromethyl)pyridin-3-yl)-1H-pyrazole-4-carboxamide, Cpd 4

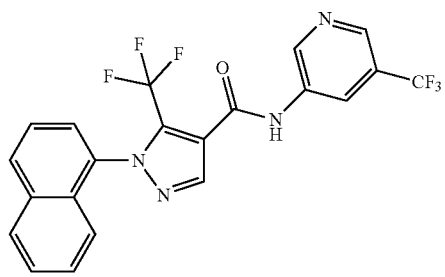 [SMILES: O=C(Nc1cncc(C(F)(F)F)c1)c1cnn(-c2cccc3ccccc23)c1C(F)(F)F]

POCl₃ (120 mg, 0.784 mmol) was added dropwise to a solution consisting of 1-(naphthalen-1-yl)-5-(trifluoromethyl)-1H-pyrazole-4-carboxylic acid, 2b (200 mg, 0.653 mmol), 5-(trifluoromethyl)pyridin-3-amine (116 mg, 0.718 mmol) and pyridine (3 mL). The mixture was stirred at 0° C.

for 1 h. The resultant mixture was concentrated to dryness under reduced pressure to give a crude product, which was purified by reverse phase HPLC (54% to 84% (v/v) ACN and water with 0.05% NH$_3$) to afford pure compound 4. The product was suspended in water (10 mL), the mixture frozen using dry ice/acetone, and then lyophilized to dryness to afford compound 4 (81.70 mg, 28%). LCMS (ESI): RT=4.32 min, mass calcd. for C$_{21}$H$_{12}$F$_6$N$_4$O 450.337, m/z found 451.1 [M+H]$^+$. $^1$H NMR (400 MHz, DMSO-d$_6$) δ ppm 11.15 (br.s., 1H), 9.14 (s, 1H), 8.77 (s, 1H), 8.62 (s, 1H), 8.55 (s, 1H), 8.25 (d, J=8.4 Hz, 1H), 8.15 (d, J=7.6 Hz, 1H), 7.83-7.77 (m, 1H), 7.75-7.61 (m, 3H), 7.12 (d, J=8.0 Hz, 1H).

Example 48

N-(5-Cyanopyridin-3-yl)-1-(naphthalen-1-yl)-5-(trifluoromethyl)-1H-pyrazole-4-carboxamide, Cpd 5

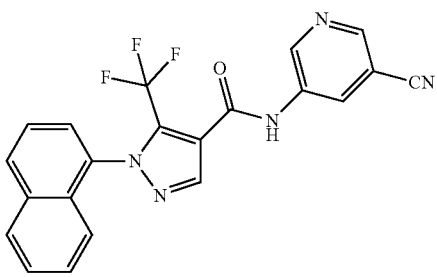 [SMILES: N#Cc1cncc(NC(=O)c2cnn(-c3cccc4ccccc34)c2C(F)(F)F)c1]

POCl$_3$ (22.9 mg, 0.149 mmol) was added dropwise to a solution consisting of 1-(naphthalen-1-yl)-5-(trifluoromethyl)-1H-pyrazole-4-carboxylic acid, 48b (200 mg, 0.653 mmol), 5-aminonicotinonitrile (85.6 mg, 0.718 mmol) and pyridine (5 mL). The mixture was stirred at 0° C. for 1 h. The resulting mixture was washed with water (20 mL), extracted with ethyl acetate (10 mL×3), dried over anhydrous Na$_2$SO$_4$, filtered, and the filtrate was concentrated under reduced pressure to give a crude product. The crude product was purified by reverse phase HPLC (46% to 76% (v/v) ACN and water with 0.05% NH$_3$) to afford pure compound 5 (74.90 mg, 28%). LCMS (ESI): R$_T$=5.12 min, mass calcd. for C$_{21}$H$_{12}$F$_3$N$_5$O 407.348, m/z found 408.1[M+H]$^+$. $^1$H NMR (400 MHz, DMSO-d$_6$) δ ppm 11.15 (s, 1H), 9.12 (d, J=2.4 Hz, 1H), 8.81 (d, J=2.0 Hz, 1H), 8.65 (t, J=2.0 Hz, 1H), 8.55 (s, 1H), 8.25 (d, J=8.4 Hz, 1H), 8.17-8.12 (m, 1H), 7.81-7.76 (m, 1H), 7.75-7.61 (m, 3H), 7.13 (d, J=8.4 Hz, 1H).

Example 49

N-(5-Chloro-6-(2H-1,2,3-triazol-2-yl)pyridin-3-yl)-5-(difluoromethyl)-1-(isoquinolin-1-yl)-1H-pyrazole-4-carboxamide, Cpd 56

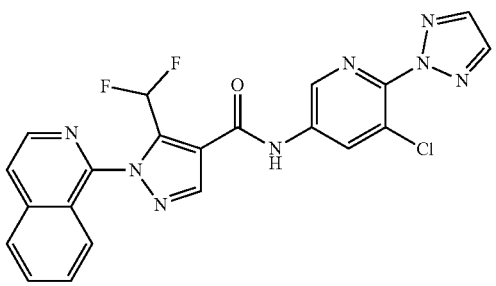 [SMILES: O=C(Nc1cnc(-n2nccn2)c(Cl)c1)c1cnn(-c2nccc3ccccc23)c1C(F)F]

A 4 mL vial with stirbar was charged with 1-hydrazinylisoquinoline, 10a (44.9 mg, 0.282 mmol), THF (0.56 mL, 0.5 M, 0.28 mmol), ethyl 2-(ethoxymethylene)-4,4-difluoro-3-oxobutanoate/THF (0.56 mL, 0.5 M, 0.28 mmol), and the resulting amber homogeneous solution was stirred at room temperature (capped) for 10 min, followed by stirring at 70° C. for 1 h. The reaction was then cooled to room temperature and treated with calcium sulfate (184 mg, 1.352 mmol) and stirred (capped) for 10 min. The reaction was then cooled to room temperature, treated with 5-chloro-6-(2H-1,2,3-triazol-2-yl)pyridin-3-amine, 1j (55.7 mg, 0.284 mmol) and 1.01 M KOtBu/THF (0.42 mL, 0.424 mmol), and the resulting dark reaction was stirred at room temperature for 3 h. The mixture was partitioned with 5 M NH$_4$Cl (1 mL) and ethyl acetate (1 mL). The organic layer was dried over Na$_2$SO$_4$, filtered, and the filtrate concentrated to provide a clear red/amber oil (119 mg). This oil was purified by flash column chromatography on a 12 g Silicycle HP column (50-100% EtOAc in heptane over 10 CVs, then isocratic) to provide impure compound 56 (43 mg) as a beige solid. This was crystallized from MeOH (1 mL) to provide, after washing the crystals with MeOH (2×0.5 mL), compound as an off-white powder (31.3 mg, 24%). $^1$H NMR (400 MHz, CDCl$_3$) δ ppm 8.72-8.75 (m, 1H), 8.55-8.57 (m, 1H), 8.51 (d, J=5.56 Hz, 1H), 8.39-8.44 (m, 1H), 8.34 (s, 1H), 7.97-8.02 (m, 2H), 7.96 (s, 2H), 7.88-7.91 (m, 1H), 7.80-7.87 (m, 1H), 7.67-7.73 (m, 1H), 7.40 (t, J=53.1 Hz, 1H); MS m/e 467.1 (M+H).

Example 50

N-(5-chloro-6-(2H-1,2,3-triazol-2-yl)pyridin-3-yl)-5-isopropyl-1-(quinolin-5-yl)-1H-pyrazole-4-carboxamide, Cpd 26

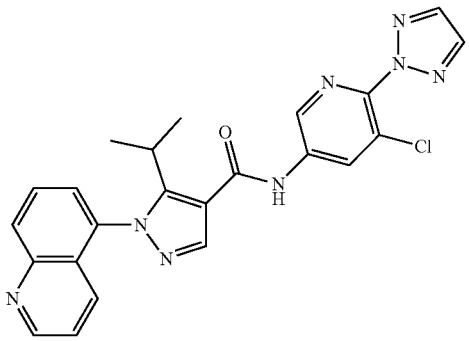 [SMILES: CC(C)c1c(C(=O)Nc2cnc(-n3nccn3)c(Cl)c2)cnn1-c1cccc2ncccc12]

A. Ethyl 2-(ethoxymethylene)-4-methyl-3-oxopentanoate, 50a

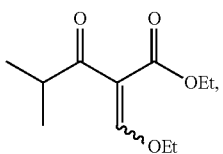

A solution consisting of ethyl 4-methyl-3-oxopentanoate (500 mg, 3.16 mmol), triethoxymethane (1.41 mg, 9.48 mmol) and Ac$_2$O (5 mL) was stirred at 130° C. for 16 h before cooling to room temperature and concentrating to dryness under reduced pressure to afford compound 50a (550 mg, crude), which was used in the following reaction without further purification.

B. Ethyl 5-isopropyl-1-(quinolin-5-yl)-1H-pyrazole-4-carboxylate, 50b

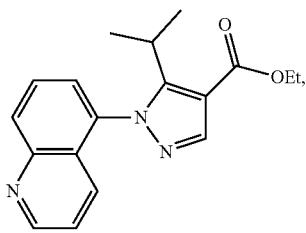

A solution consisting of ethyl 2-(ethoxymethylene)-4-methyl-3-oxopentanoate, 50a (550 mg, 2.57 mmol), 5-hydrazinylquinoline, 13a (408 mg, 2.57 mmol) and ethanol (5 mL) was stirred at 80° C. for 16 h before cooling to room temperature and concentrating to dryness under reduced pressure to give a crude product, which was purified by FCC (dichloromethane:methanol=100:0 to 90:10) to afford compound 50b (450 mg, 57%). LCMS (ESI): R$_T$=0.75 min, mass calcd. for C$_{18}$H$_{19}$N$_3$O$_2$ 309.362, m/z found 310.0 [M+H]$^+$. The compound was further purified by reverse phase HPLC (95% water containing 0.038% TFA (solvent A) and 5% acetonitrile containing 0.02% TFA (solvent B), followed by a gradient up to 5% solvent A and 95% solvent B).

C. 5-Isopropyl-1-(quinolin-5-yl)-1H-pyrazole-4-carboxylic acid, 50c

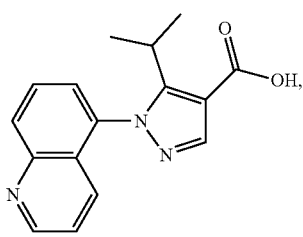

A solution consisting of ethyl 5-isopropyl-1-(quinolin-5-yl)-1H-pyrazole-4-carboxylate, 50b (450 mg, 1.46 mmol), LiOH (183 mg, 4.36 mmol) and water: EtOH (6 mL, 1:2) was stirred at room temperature for 16 h. The solution was neutralized to pH 7 with 4 M aq. HCl, and a solid was collected by filtration to afford compound 50c (280 mg, crude), which was used in the next step without purification. LCMS (ESI): R$_T$=0.62 min, mass calcd. for C$_{16}$H$_{15}$N$_3$O$_2$ 281.309, m/z found 282.0 [M+H]$^+$.

D. N-(5-chloro-6-(2H-1,2,3-triazol-2-yl)pyridin-3-yl)-5-isopropyl-1-(quinolin-5-yl)-1H-pyrazole-4-carboxamide, Cpd 26

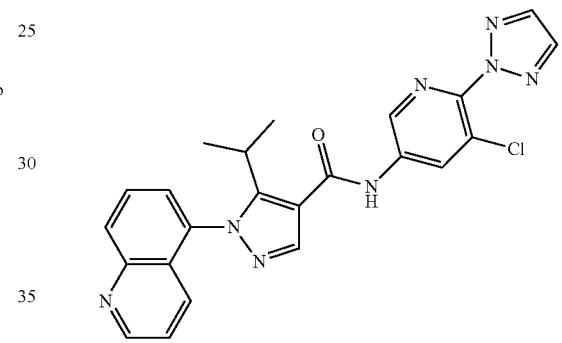

POCl$_3$ (183 mg, 1.19 mmol) was added dropwise to a solution consisting of 5-isopropyl-1-(quinolin-5-yl)-1H-pyrazole-4-carboxylic acid, 50c (280 mg, 0.995 mmol), 5-chloro-6-(2H-1,2,3-triazol-2-yl)pyridin-3-amine, 1j (389 mg, 1.99 mmol) and pyridine (5 mL). The mixture was stirred at 0° C. for 1 h. The resultant mixture was poured into sat. aqueous NaHCO$_3$ (10 mL), extracted with ethyl acetate (10 mL×3), dried over anhydrous Na$_2$SO$_4$, filtered, and the filtrate concentrated under reduced pressure to give a crude product, which was purified by reverse phase HPLC (40% to 70% (v/v) ACN and H$_2$O with 0.05% NH$_3$) to afford pure compound 26. Compound 26 was suspended in water (10 mL), the mixture frozen using dry ice/acetone, and then lyophilized to dryness to afford compound 26 (48.60 mg, 10%). LCMS (ESI): R$_T$=4.79 min, mass calcd. for C$_{23}$H$_{19}$ClN$_8$O 458.903, m/z found 459.0 [M+H]$^+$. $^1$H NMR (400 MHz, DMSO-d$_6$) δ ppm 10.70 (s, 1H), 9.04 (dd, J=1.6, 4.4 Hz, 1H), 8.91 (d, J=2.8 Hz, 1H), 8.72 (d, J=2.0 Hz, 1H), 8.48 (s, 1H), 8.30 (d, J=8.8 Hz, 1H), 8.18 (s, 2H), 7.99-7.95 (m, 1H), 7.83-7.82 (m, 1H), 7.64 (dd, J=4.4, 8.4 Hz, 1H), 7.51 (d, J=8.0 Hz, 1H), 3.10-3.00 (m, 1H), 1.28-1.13 (m, 6H).

Example 51

N-(5-Chloro-6-(2H-1,2,3-triazol-2-yl)pyridin-3-yl)-5-isobutyl-1-(quinolin-5-yl)-1H-pyrazole-4-carboxamide, Cpd 16

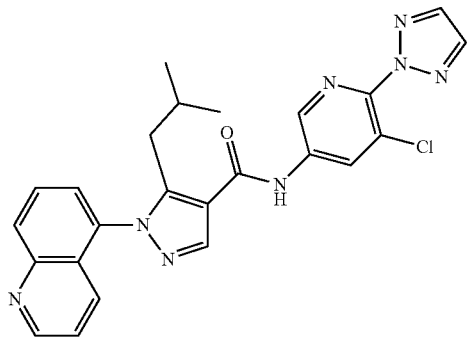 [SMILES: CC(C)Cc1c(C(=O)Nc2cnc(-n3nccn3)c(Cl)c2)cnn1-c1cccc2ncccc12]

A. Ethyl 2-(ethoxymethylene)-5-methyl-3-oxohexanoate, 51a

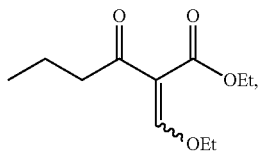

51a

A solution consisting of ethyl 5-methyl-3-oxohexanoate (500 mg, 2.90 mmol), triethoxymethane (1.29 mg, 8.71 mmol) and Ac$_2$O (5 mL) was stirred at 130° C. for 16 h. The reaction was cooled to room temperature and concentrated to dryness under reduced pressure to afford crude compound 51a (580 mg, 88%), which was used in the following step without purification.

B. Ethyl 5-isobutyl-1-(quinolin-5-yl)-1H-pyrazole-4-carboxylate, 51b

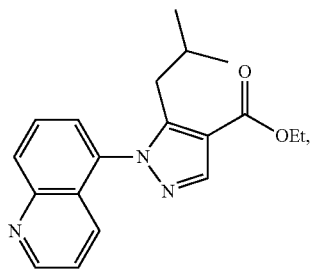

51b

A solution consisting of ethyl 2-(ethoxymethylene)-5-methyl-3-oxohexanoate, 51a (430 mg, 1.89 mmol), 5-hydrazinylquinoline, 13a (300 mg, 1.89 mmol) and ethanol (10 mL) was refluxed at 80° C. for 16 h before cooling to room temperature and concentrating to dryness under reduced pressure to afford crude compound 51b, which was purified by FCC (dichloromethane:methanol=100:0 to 95:5) to afford compound 51b (330 mg, 54%). $^1$H NMR (400 MHz, DMSO-d$_6$) δ ppm 9.22-9.15 (m, 1H), 8.49-8.41 (m, 1H), 8.20 (s, 1H), 8.14-8.06 (m, 1H), 7.97 (d, J=6.8 Hz, 2H), 7.85-7.77 (m, 1H), 4.29 (d, J=6.8 Hz, 2H), 2.74 (d, J=7.2 Hz, 2H), 1.61-1.48 (m, 1H), 1.31 (t, J=6.8 Hz, 3H), 0.70-0.50 (m, 6H).

C. 5-Isobutyl-1-(quinolin-5-yl)-1H-pyrazole-4-carboxylic acid, 51c

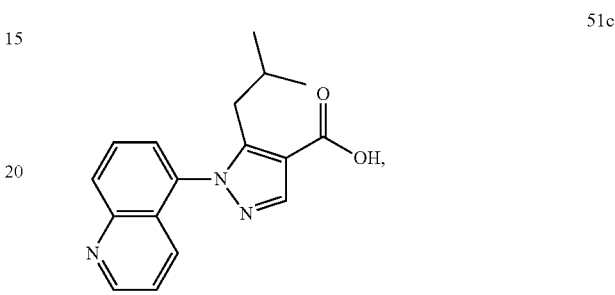

51c

A solution consisting of ethyl 5-isobutyl-1-(quinolin-5-yl)-1H-pyrazole-4-carboxylate, 51b (200 mg, 0.618 mmol), LiOH (77.9 mg, 1.86 mmol) and water: EtOH (6 mL, 1:2) was stirred at room temperature for 16 h. The reaction mixture was neutralized to pH 7 with 4 N aq. HCl, extracted with ethyl acetate (10 mL×3), dried over anhydrous Na$_2$SO$_4$, and filtered. The filtrate was concentrated to dryness under reduced pressure to give crude compound 51c (160 mg), which was used in the following reaction without further purification.

D. N-(5-Chloro-6-(2H-1,2,3-triazol-2-yl)pyridin-3-yl)-5-isobutyl-1-(quinolin-5-yl)-1H-pyrazole-4-carboxamide, Cpd 16

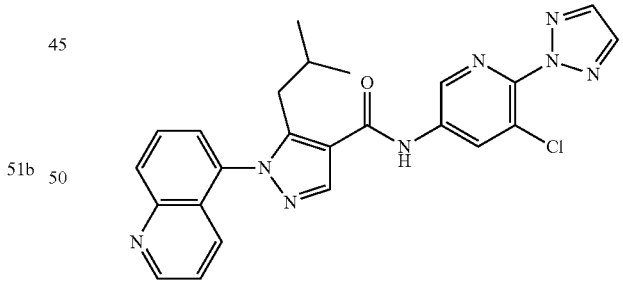

POCl$_3$ (74.8 mg, 0.488 mmol) was added dropwise to a solution consisting of 5-isobutyl-1-(quinolin-5-yl)-1H-pyrazole-4-carboxylic acid, 51c (140 mg, 0.474 mmol), 5-chloro-6-(2H-1,2,3-triazol-2-yl)pyridin-3-amine, 1j (87.4 mg, 0.447 mmol) and pyridine (5 mL). The mixture was stirred at 0° C. for 1 h. The resultant mixture was washed with water (20 mL), extracted with ethyl acetate (10 mL×3), dried over anhydrous Na$_2$SO$_4$, filtered, and the filtrate concentrated under reduced pressure to give a crude product, which was purified by reverse phase HPLC (40% to 70% (v/v) ACN and water with 0.05% NH$_3$) to afford pure compound 16. Compound 16 was suspended in water (10 mL), the mixture frozen using dry ice/acetone, and then lyophilized to dryness to give compound 16 (24.30 mg, 11%). LCMS (ESI): $R_T$=3.66 min, mass calcd. for $C_{24}H_{21}ClN_8O$ 472.93, m/z found 473.0 [M+H]+. 1H NMR (400 MHz, DMSO-$d_6$) δ ppm 10.63 (br.s., 1H), 9.05-9.02 (m, 1H), 8.91-8.89 (m, 1H), 8.72-8.71 (m, 1H), 8.55 (s, 1H), 8.30-8.26 (m, 1H), 8.19 (s, 2H), 7.99-7.93 (m, 1H), 7.85-7.81 (m, 1H), 7.69-7.61 (m, 2H), 2.85-2.78 (m, 2H), 1.66-1.57 (m, 1H), 0.62 (d, J=6.0 Hz, 6H).

Example 52

N-(5-Chloro-6-(2H-1,2,3-triazol-2-yl)pyridin-3-yl)-5-methyl-1-(quinolin-5-yl)-1H-pyrazole-4-carboxamide, Cpd 39

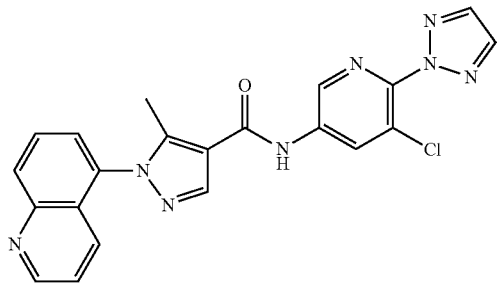 [SMILES: Cc1c(C(=O)Nc2cnc(-n3nccn3)c(Cl)c2)cnn1-c1cccc2ncccc12]

A. Ethyl 2-(ethoxymethylene)-3-oxobutanoate, 52a

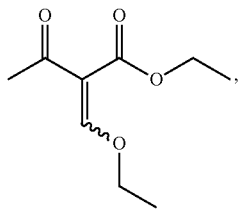

52a

A solution consisting of ethyl 3-oxobutanoate (10.0 g, 76.8 mmol), triethylorthoformate (38.3 g, 230 mmol), and acetic anhydride (100 mL) was stirred at 135° C. for 18 h. The mixture was concentrated to dryness under reduced pressure to give compound 52a (21 g, crude), which was used in the following reaction without further purification. 1H NMR (400 MHz, CDCl3) δ ppm 7.64, 7.61 (s, 1H), 4.30-4.18 (m, 4H), 2.32, 3.38 (s, 3H), 1.40-1.27 (m, 6H).

B. Ethyl 5-methyl-1-(quinolin-5-yl)-1H-pyrazole-4-carboxylate, 52b

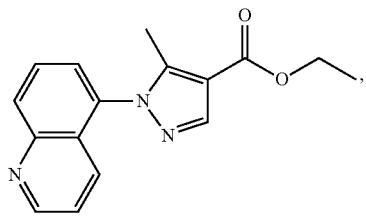

52b

A mixture consisting of ethyl 2-(ethoxymethylene)-3-oxobutanoate, 52a (1.50 g, 8.06 mmol), 5-hydrazinylquinoline, 13a (1.28 g, 8.06 mmol), triethylamine (0.89 g, 8.86 mmol), and ethanol (15 mL) was stirred at 80° C. for 16 h. The mixture was concentrated to dryness under reduced pressure to give a crude residue, which was purified by FCC (petroleum ether: ethyl acetate=2:1 to 1:2) to afford compound 52b (520 mg, 23%). 1H NMR (400 MHz, CDCl3) δ ppm 9.02-8.97 (m, 1H), 8.32-8.27 (m, 1H), 8.16 (s, 1H), 7.83 (dd, J=7.2, 8.4 Hz, 1H), 7.67 (d, J=8.4 Hz, 1H), 7.56 (dd, J=1.2, 7.2 Hz, 1H), 7.44 (dd, J=4.0, 8.4 Hz, 1H), 7.27 (s, 1H), 4.40-4.34 (m, 2H), 2.38 (s, 3H), 1.43-1.39 (m, 3H).

C. N-(5-Chloro-6-(2H-1,2,3-triazol-2-yl)298rim-ethy-3-yl)-5-methyl-1-(quinolin-5-yl)-1H-pyrazole-4-carboxamide, Cpd 39

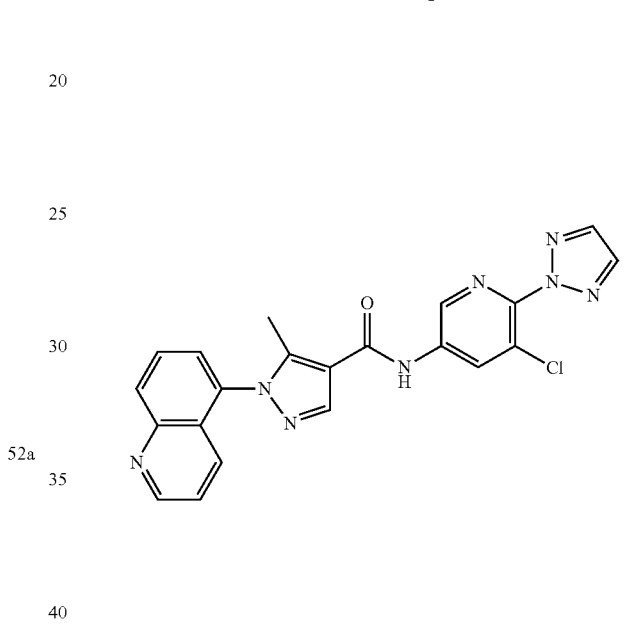

A solution consisting of 5-chloro-6-(2H-1,2,3-triazol-2-yl)pyridin-3-amine, 1j (194 mg, 0.990 mmol) and THF (2 mL) was added dropwise to a solution of t-BuOK (3.3 mL, 3.3 mmol, 1 M in THF) at 0° C. A solution consisting of ethyl 5-methyl-1-(quinolin-5-yl)-1H-pyrazole-4-carboxylate, 52b (186 mg, 0.660 mmol) and THF (2 mL) was added dropwise. The mixture was warmed to room temperature and stirred for 16 h before quenching with water and extracting with ethyl acetate (50 mL×3). The combined organic extracts were dried over anhydrous Na2SO4, filtered, and the filtrate concentrated to dryness under reduced pressure to give crude compound 39, which was purified by reverse phase chromatography (33% to 43% (v/v) CH3CN and water with 0.05% NH3) to afford pure compound 39. The product was suspended in water (10 mL), the mixture frozen using dry ice/acetone, and then lyophilized to dryness to afford compound 39 (61.3 mg, 22%). LCMS (ESI): $R_T$=4.16 min, mass calcd. for $C_{21}H_{15}ClN_8O$ 430.850, m/z found 431.0 (M+H)+. 1H NMR (400 MHz, CDCl3) δ ppm 9.02 (dd, J=1.6, 4.0 Hz, 1H), 8.77 (d, J=2.4 Hz, 1H), 8.56 (d, J=2.4 Hz, 1H), 8.33 (d, J=8.4 Hz, 1H), 8.15 (s, 1H), 7.99 (s, 1H), 7.95 (s, 2H), 7.89-7.83 (m, 1H), 7.67 (d, J=8.4 Hz, 1H), 7.60 (d, J=7.2 Hz, 1H), 7.47 (dd, J=4.4, 8.4 Hz, 1H), 2.47 (s, 3H).

Example 53

N-(5-Chloro-6-(2H-1,2,3-triazol-2-yl)pyridin-3-yl)-5-(1-methoxyethyl)-1-(quinolin-5-yl)-1H-pyrazole-4-carboxamide, Cpd 35

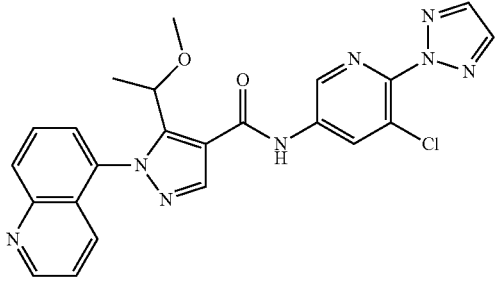 [SMILES: COC(C)c1c(C(=O)Nc2cnc(-n3nccn3)c(Cl)c2)cnn1-c1cccc2ncccc12]

A. Ethyl 4-methoxy-3-oxopentanoate, 53a

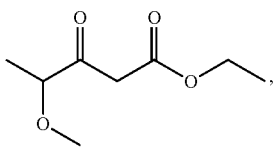

Bis(1H-imidazol-1-yl)methanone (8.57 g, 52.8 mmol) was added to a solution consisting of 2-methoxypropanoic acid (5.00 g, 48.0 mmol), and THF (100 mL) at 0° C. The reaction mixture was stirred at room temperature for 3 h. In a separate flask, isopropylmagnesium chloride (110 mL, 144 mmol, 1.3 M in THF) was added dropwise to a solution consisting of 3-ethoxy-3-oxopropanoic acid (9.52 g, 72.0 mmol), and THF (90 mL) at 0° C. The mixture was stirred at room temperature for 3 h. This solution was added dropwise to the acyl imidazole solution at 0° C. and the resulting mixture was stirred at room temperature for 1 h. The reaction mixture was quenched with aqueous citric acid (25 mL, 10 wt. %) and extracted with ethyl acetate (100 mL×3). The combined organic extracts were washed with sat. aqueous NaHCO₃, dried over anhydrous Na₂SO₄, filtered, and concentrated to dryness under reduced pressure to give a residue, which was purified by FCC (petroleum ether: ethyl acetate=10:1) to afford compound 53a (3.6 g, 43%). ¹H NMR (400 MHz, CDCl₃) δ ppm 4.21-4.19 (m, 2H), 3.86-3.79 (m, 1H), 3.39-3.38 (m, 3H), 3.36 (s, 2H), 1.29-1.26 (m, 6H).

B. Ethyl 2-(ethoxymethylene)-4-methoxy-3-oxopentanoate, 53b

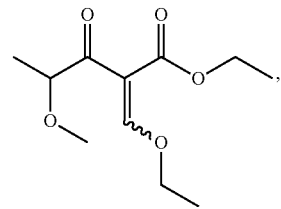

A solution consisting of ethyl 4-methoxy-3-oxopentanoate, 53a (3.60 g, 20.6 mmol), triethylorthoformate (9.19 g, 1.72 mmol), and acetic anhydride (30 mL) was stirred at 135° C. for 18 h. The mixture was cooled to room temperature and concentrated to dryness under reduced pressure to give compound 53b (5.4 g), which was used in the following reaction without further purification. ¹H NMR (400 MHz, CDCl₃) δ ppm 7.70 (s, 0.5H), 7.58 (s, 0.5H), 4.30-4.21 (m, 4H), 3.60 (q, J=7.2 Hz, 1H), 3.35, 3.32 (s, 3H), 1.38-1.29 (m, 9H).

C. Ethyl 5-(1-methoxyethyl)-1-(quinolin-5-yl)-1H-pyrazole-4-carboxylate, 53c

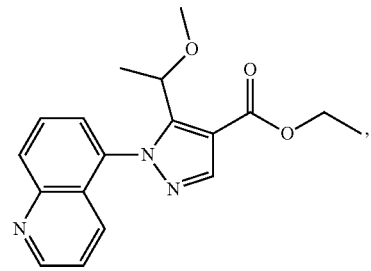

A mixture consisting of ethyl 2-(ethoxymethylene)-4-methoxy-3-oxopentanoate, 53b (600 mg, 2.61 mmol), 5-hydrazinylquinoline, 13a (414 mg, 2.61 mmol), triethylamine (290 mg, 2.87 mmol), and ethanol (12 mL) was stirred at 80° C. for 16 h. The mixture was cooled to room temperature and concentrated to dryness under reduced pressure to give a residue, which was purified by FCC (dichloromethane: methanol=10:1) to afford compound 53c (300 mg, 35%). ¹H NMR (400 MHz, CDCl₃) δ ppm 9.00-8.93 (m, 1H), 8.28 (d, J=8.4 Hz, 1H), 8.17 (s, 1H), 7.80 (dd, J=7.2, 8.4 Hz, 1H), 7.65 (br d, J=7.2 Hz, 1H), 7.62-7.56 (m, 1H), 7.41 (dd, J=4.0, 8.4 Hz, 1H), 5.29-5.14 (m, 1H), 4.44-4.32 (m, 2H), 3.33-2.91 (m, 3H), 1.42 (t, J=7.2 Hz, 3H), 1.36-1.27 (m, 3H).

D. 5-(1-Methoxyethyl)-1-(quinolin-5-yl)-1H-pyrazole-4-carboxylic acid, 53d

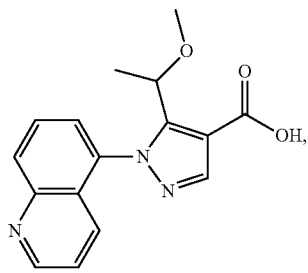

A mixture consisting of ethyl 5-(1-methoxyethyl)-1-(quinolin-5-yl)-1H-pyrazole-4-carboxylate, 53c (265 mg, 0.840 mmol), aq. NaOH (2.44 mL, 2.44 mmol, 1 M), and ethanol (3 mL) was stirred at room temperature for 16 h. The mixture was neutralized with 1 M HCl and extracted with ethyl acetate (50 mL×3). The combined organic extracts were dried over anhydrous $Na_2SO_4$, filtered, and the filtrate concentrated to dryness under reduced pressure to afford compound 53d (120 mg, 50%). $^1$H NMR (400 MHz, $CD_3OD$) δ ppm 8.97 (dd, J=1.6, 4.4 Hz, 1H), 8.28 (d, J=8.4 Hz, 1H), 8.19 (s, 1H), 7.93 (dd, J=7.2, 8.4 Hz, 1H), 7.80 (d, J=6.4 Hz, 1H), 7.71 (d, J=8.0 Hz, 1H), 7.60 (dd, J=4.4, 8.4 Hz, 1H), 5.36-5.24 (m, 1H), 3.32 (s, 3H), 1.37-1.29 (m, 3H).

E. N-(5-Chloro-6-(2H-1,2,3-triazol-2-yl)pyridin-3-yl)-5-(1-methoxyethyl)-1-(quinolin-5-yl)-1H-pyrazole-4-carboxamide, Cpd 35

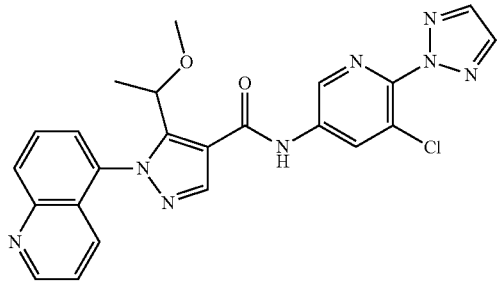 [SMILES: COC(C)c1c(C(=O)Nc2cnc(-n3nccn3)c(Cl)c2)cnn1-c1cccc2ncccc12]

$POCl_3$ (0.1 mL) was added to a mixture consisting of 5-(1-methoxyethyl)-1-(quinolin-5-yl)-1H-pyrazole-4-carboxylic acid, 53d (120 mg, 0.40 mmol), 5-chloro-6-(2H-1,2,3-triazol-2-yl)pyridin-3-amine, 1j (78.95 mg, 0.40 mmol), and pyridine (3 mL) at 0° C. The mixture was stirred at 0° C. for 1 h before quenching with aq. $NaHCO_3$. The mixture was extracted with ethyl acetate (50 mL×3), and the combined organic extracts were dried over $Na_2SO_4$, filtered, and the filtrate concentrated to dryness under reduced pressure to afford a residue, which was purified by reverse phase HPLC (16% to 46% (v/v) $CH_3CN$ and water with 0.05% $NH_4HCO_3$) to afford pure compound 35. Compound 35 was suspended in water (10 mL), the mixture frozen using dry ice/acetone, and then lyophilized to dryness to afford compound 35 (29.1 mg, 15%). LCMS (ESI): $R_T$=4.61 min, mass calcd. for $C_{23}H_{19}ClN_8O_2$ 474.902, m/z found 475.0 [M+H]$^+$. $^1$H NMR (400 MHz, $CDCl_3$) δ ppm 10.72 (s, 0.5H), 10.68 (s, 0.5H), 9.08-9.01 (m, 1H), 8.79-8.78 (m, 1H), 8.50 (dd, J=2.0, 7.6 Hz, 1H), 8.44 (s, 1H), 8.39 (s, 0.5H), 8.37 (s, 0.5H), 7.94 (s, 2H), 7.92-7.84 (m, 1H), 7.73 (d, J=8.4 Hz, 0.5H), 7.67 (d, J=7.2 Hz, 0.5H), 7.55-7.46 (m, 2H), 4.41 (q, J=6.4 Hz, 0.5H), 4.30 (q, J=6.4 Hz, 0.6H), 3.54 (s, 1.4H), 3.25 (s, 1.7H), 1.68 (d, J=6.8 Hz, 1.6H), 1.42 (d, J=6.8 Hz, 1.4H).

Example 54

N-(5-Chloro-6-(2H-1,2,3-triazol-2-yl)pyridin-3-yl)-1-(4-methylisoquinolin-8-yl)-5-(trifluoromethyl)-1H-pyrazole-4-carboxamide, Cpd 33

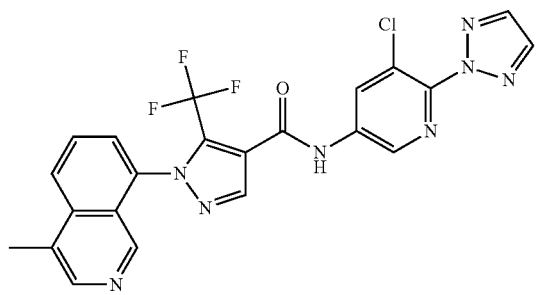 [SMILES: Cc1cncc2c(-n3ncc(C(=O)Nc4cnc(-n5nccn5)c(Cl)c4)c3C(F)(F)F)cccc12]

A. 8-(2-(Diphenylmethylene)hydrazinyl)-4-methylisoquinoline, 54a

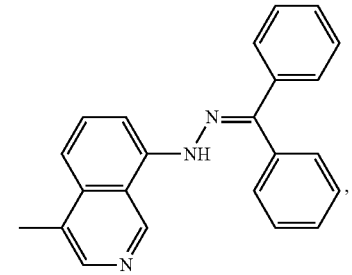

Palladium diacetate (30.3 mg, 0.135 mmol) and Binap (84.1 mg, 0.135 mmol) were added to a solution consisting of 8-bromo-4-methylisoquinoline (300 mg, 1.35 mmol), (diphenylmethylene)hydrazine (265 mg, 1.35 mmol), sodium tert-butoxide (389 mg, 4.05 mmol), and 1,4-dioxane (5 mL). The mixture was heated at 100° C. for 16 h before cooling to room temperature. The resultant mixture was filtered, and the filtrate concentrated under reduced pressure to give crude compound 54a, which was purified by FCC (petroleum ether: ethyl acetate=100:0 to 70:30) to afford compound 54a (250 mg, 55%). $^1$H NMR (400 MHz, DMSO-$d_6$) δ ppm 9.99 (s, 1H), 9.41 (s, 1H), 8.40 (s, 1H), 8.14-8.08 (m, 1H), 7.99 (d, J=8.0 Hz, 1H), 7.70-7.63 (m, 4H), 7.59-7.55 (m, 2H), 7.54-7.50 (m, 2H), 7.44-7.42 (m, 3H), 2.67 (s, 3H).

B. 8-Hydrazinyl-4-methylisoquinoline, 54b

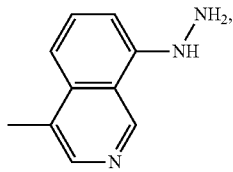

A solution consisting of 8-(2-(diphenylmethylene)hydrazinyl)-4-methylisoquinoline, 54a (250 mg, 0.741 mmol), conc. HCl (4 mL) and EtOH (2 mL) was stirred at room temperature for 16 h. The reaction mixture was concentrated under reduced pressure, diluted with water (10 mL), and washed with dichloromethane (20 mL). The mixture was concentrated under reduced pressure to give crude compound 54b (180 mg, crude), which was used in the following reaction without further purification.

C. Ethyl 1-(4-methylisoquinolin-8-yl)-5-(trifluoromethyl)-1H-pyrazole-4-carboxylate, 54c

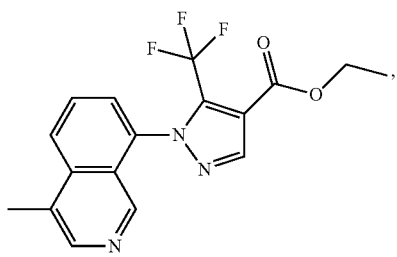

A solution consisting of ethyl 2-(ethoxymethylene)-4,4,4-trifluoro-3-oxobutanoate, 1f (150 mg, 0.650 mmol), 8-hydrazinyl-4-methylisoquinoline, 54b (160 mg, 0.650 mmol), triethylamine (132 mg, 1.30 mmol), and ethanol (5 mL) was stirred at 80° C. for 16 h before cooling to room temperature and concentrating to dryness under reduced pressure to afford crude compound 54c, which was purified by FCC (petroleum ether: ethyl acetate=100:0 to 70:30) to give compound 54c (110 mg, 48%). $^1$H NMR (400 MHz, CDCl$_3$) δ ppm 8.54 (s, 1H), 8.27 (s, 1H), 8.16 (d, J=8.4 Hz, 1H), 7.96 (t, J=7.6 Hz, 1H), 7.82 (dd, J=7.2, 8.4 Hz, 1H), 7.60 (d, J=7.2 Hz, 1H), 4.42 (q, J=7.2 Hz, 2H), 2.69 (s, 3H), 1.41 (t, J=7.2 Hz, 3H).

D. N-(5-Chloro-6-(2H-1,2,3-triazol-2-yl)pyridin-3-yl)-1-(4-methylisoquinolin-8-yl)-5-(trifluoromethyl)-1H-pyrazole-4-carboxamide, Cpd 33

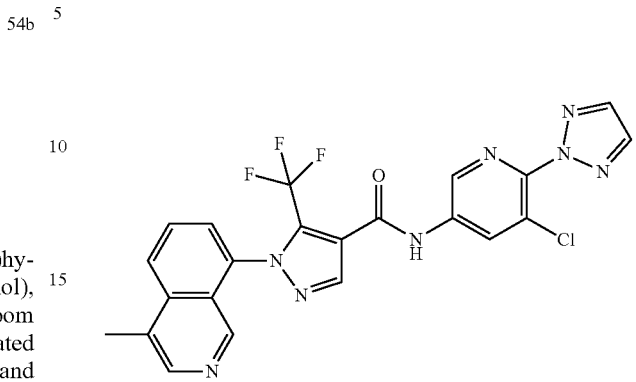

A solution consisting of 5-chloro-6-(2H-1,2,3-triazol-2-yl)pyridin-3-amine, 1j (56.0 mg, 0.286 mmol) and THF (1 mL) were added to potassium tert-butoxide (0.8 mL, 0.8 mmol, 1 M in THF) at 0° C., then a solution consisting of ethyl 1-(4-methylisoquinolin-8-yl)-5-(trifluoromethyl)-1H-pyrazole-4-carboxylate, 54c (100 mg, 0.286 mmol) and THF (1 mL) was added. The resultant mixture was stirred at room temperature for 16 h. The reaction mixture was concentrated under reduced pressure to give a crude product, which was purified by preparative high performance liquid chromatography using Phenomenex Gemini 150×25 mm×5 μm (45% to 75% (v/v) ACN and water with 0.05% NH$_3$) to afford pure compound 33. The product was suspended in water (10 mL), the mixture frozen using dry ice/acetone, and then lyophilized to dryness to afford compound 33 (31.50 mg, 22%). LCMS (ESI): R$_T$=4.46 min, mass calcd. for C$_{22}$H$_{14}$ClF$_3$N$_8$O 498.848, m/z found 499.0 [M+H]$^+$. $^1$H NMR (400 MHz, DMSO-d$_6$) δ ppm 8.84 (d, J=2.4 Hz, 1H), 8.69 (d, J=2.0 Hz, 1H), 8.58 (s, 1H), 8.55 (s, 1H), 8.45 (s, 1H), 8.37 (d, J=8.4 Hz, 1H), 8.19 (s, 2H), 8.06-7.96 (m, 2H), 2.71 (s, 3H).

Example 55

N-(8-Chloro-4-methyl-3-oxo-3,4-dihydro-2H-benzo[b][1,4]oxazin-6-yl)-1-(quinolin-5-yl)-5-(trifluoromethyl)-1H-pyrazole-4-carboxamide, Cpd 95

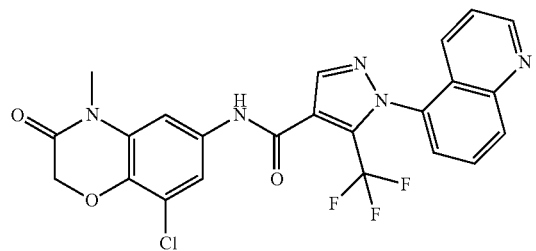 [SMILES: CN1C(=O)COc2c(Cl)cc(NC(=O)c3cnn(-c4cccc5ncccc45)c3C(F)(F)F)cc21]

A. 2-Chloro-N-(3-chloro-2-hydroxy-5-nitrophenyl)acetamide, 55a

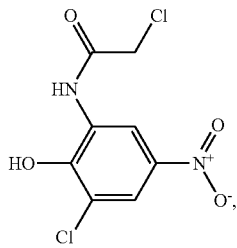

Chloroacetyl chloride (1.98 g, 17.5 mmol) was added to a solution of 2-amino-6-chloro-4-nitrophenol (3.0 g, 15.9 mmol), triethylamine (3.2 g, 31.8 mmol) in dichloromethane (30 mL). The mixture was stirred at rt for 3 h. Water (50 mL) and dichloromethane (50 mL) were added to the mixture. The organic layer was partitioned and washed with brine (50 mL), dried over MgSO$_4$, filtered, and the filtrate concentrated under reduced pressure to afford compound 55a as a yellow oil (4.0 g, 94.9%), which was used in the following reaction without further purification.

B. 8-Chloro-6-nitro-2H-benzo[b][1,4]oxazin-3(4H)-one, 55b

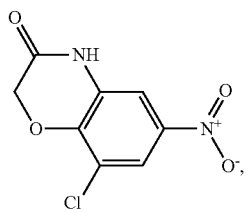

Sodium methoxide (896.8 mg, 16.6 mmol) was added to a solution of 2-chloro-N-(3-chloro-2-hydroxy-5-nitrophenyl)acetamide, 55a (4.0 g, 15.1 mmol) in methanol (40 mL). The mixture was stirred at 80° C. for 16 h. Water (150 mL) and dichloromethane (100 mL) were added to the mixture. The organic layer was partitioned, washed with brine (100 mL), dried over MgSO$_4$, filtered, and the filtrate concentrated under reduced pressure to afford compound 55b as a yellow oil. The crude product was purified by column chromatography over silica gel (petroleum ether/ethyl acetate=10:1 to petroleum ether/ethyl acetate=1:1) to afford compound 55b as a yellow solid (2.5 g, 73%). $^1$H NMR (400 MHz, METHANOL-d$_4$) δ ppm 4.84 (s, 2H), 7.72 (d, J=2.65 Hz, 1H), 7.98 (d, J=2.65 Hz, 1H).

C. 8-Chloro-4-methyl-6-nitro-2H-benzo[b][1,4]oxazin-3(4H)-one, 55c

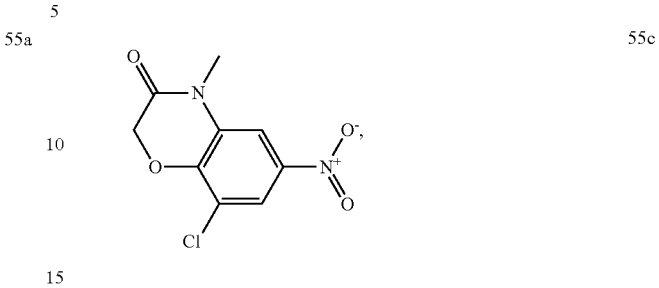

Iodomethane (931 mg, 6.56 mmol) was added to a mixture of 8-chloro-6-nitro-2H-benzo[b][1,4]oxazin-3(4H)-one, 55b (500 mg, 2.19 mmol) and potassium carbonate (1.51 g, 10.94 mmol) in DMF (5 mL). The mixture was stirred at 25° C. for 18 h. The solvent was concentrated under reduced pressure. A crude product was purified by column chromatography over silica gel (petroleum ether/ethyl acetate=10:1 to petroleum ether/ethyl acetate=1:1) to afford compound 55c as a white solid (0.3 g, 56.5%). $^1$H NMR (400 MHz, CDCl$_3$) δ ppm 3.44 (s, 3H), 4.85 (s, 2H), 7.78 (d, J=2.51 Hz, 1H), 8.04 (d, J=2.51 Hz, 1H).

D. 6-Amino-8-chloro-4-methyl-2H-benzo[b][1,4]oxazin-3(4H)-one, 55d

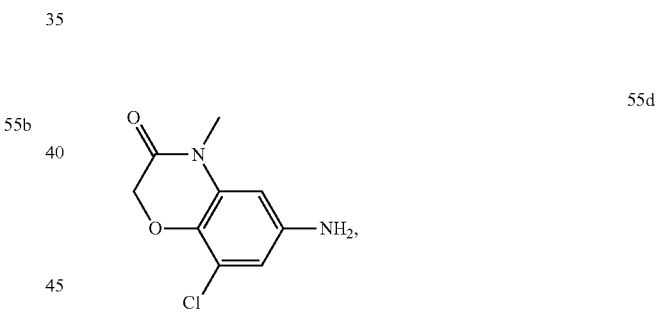

Zinc (804 mg, 12.37 mmol) was added to a solution of 8-chloro-4-methyl-6-nitro-2H-benzo[b][1,4]oxazin-3(4H)-one, 55c (300 mg, 1.24 mmol) in aqueous NH$_4$Cl (2 mL) and methanol (2 mL). The mixture was stirred at rt for 16 h. To the suspension was added aqueous NaHCO$_3$ to adjust the pH to 9-10, and the mixture was filtered though a pad of diatomaceous earth. The filter cake was washed with dichloromethane (30 mL×3). The combined filtrates were washed with brine (100 mL), dried over MgSO$_4$, filtered, and the filtrate concentrated under reduced pressure to afford compound 55d as a brown solid. The crude product was purified by column chromatography over silica gel (petroleum ether/ethyl acetate=2:1 to petroleum ether/ethyl acetate=0:1) to afford compound 55d as a yellow solid (200 mg, 76.1%). $^1$H NMR (400 MHz, CDCl$_3$) δ ppm 3.31 (s, 3H), 4.61 (s, 2H), 6.23 (d, J=2.43 Hz, 1H), 6.42 (d, J=2.43 Hz, 1H).

E. N-(8-Chloro-4-methyl-3-oxo-3,4-dihydro-2H-benzo[b][1,4]oxazin-6-yl)-1-(quinolin-5-yl)-5-(trifluoromethyl)-1H-pyrazole-4-carboxamide, Cpd 95

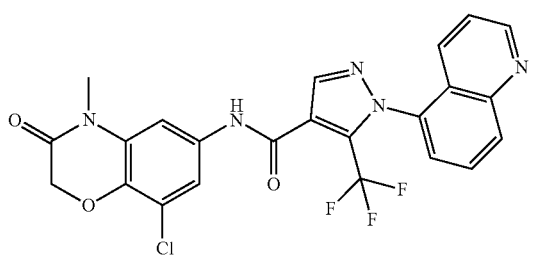 [SMILES: CN1C(=O)COc2c(Cl)cc(NC(=O)c3cnn(-c4cccc5ncccc45)c3C(F)(F)F)cc21]

1-(Quinolin-5-yl)-5-(trifluoromethyl)-1H-pyrazole-4-carboxylic acid, 3b (120 mg, 0.39 mmol), 6-amino-8-chloro-4-methyl-2H-benzo[b][1,4]oxazin-3(4H)-one, 55d (100 mg, 0.47 mmol), and HATU (223 mg, 0.59 mmol) were dissolved in DIPEA (253 mg, 1.96 mmol) and DMF (2 mL). The mixture was stirred at 25° C. for 3 h. Sat. aqueous NH$_4$Cl (20 mL) was added and the mixture was extracted with dichloromethane (20 mL×2). The combined organic layers were dried over Na$_2$SO$_4$, filtered, and the filtrates were concentrated under reduced pressure to afford compound 95 as a crude brown oil. The crude product was purified by reverse phase HPLC (A: water (0.05% HCl), B: MeCN; then: AB (70%/30% to 40%/60%). The pure fractions were concentrated under reduced pressure and lyophilized to dryness to afford compound 95 as a pale white solid (139 mg, 71%). LCMS (ESI): m/z 501.9 [M+H]$^+$. $^1$H NMR (400 MHz, DMSO-d$_6$) δ ppm 3.27 (s, 3H), 4.77 (s, 2H), 7.47 (s, 1H), 7.57-7.63 (m, 1H), 7.64-7.70 (m, 2H), 7.87-7.92 (m, 1H), 7.93-7.99 (m, 1H), 8.31 (d, J=8.60 Hz, 1H), 8.50 (s, 1H), 9.04 (d, J=2.65 Hz, 1H), 10.74 (s, 1H).

Example 56

N-(4-(2-Aminopyrimidin-4-yl)-3-chlorophenyl)-1-(isoquinolin-4-yl)-5-(trifluoromethyl)-1H-pyrazole-4-carboxamide, Cpd 58

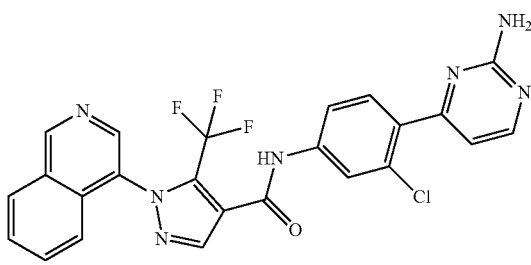 [SMILES: Nc1nccc(-c2ccc(NC(=O)c3cnn(-c4cncc5ccccc45)c3C(F)(F)F)cc2Cl)n1]

A. 4-(2-Chloro-4-nitrophenyl)pyrimidin-2-amine, 56a

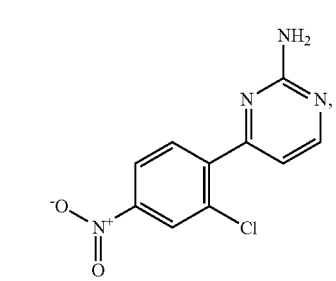

A mixture of 2-(2-chloro-4-nitrophenyl)-4,4,5,5-tetramethyl-1,3,2-dioxaborolane (250 mg, 0.882 mmol), 2-amino-4-chloropyrimidine (126 mg, 0.97 mmol) and cesium carbonate (862 mg, 2.65 mmol) in dioxane/water (4:1) was stirred at rt. Pd(PPh$_3$)$_2$Cl$_2$ was added under N$_2$ at rt. The reaction mixture was stirred at 80° C. overnight. The mixture was filtered though a pad of diatomaceous earth and the filter cake was washed with ethyl acetate (50 mL). The filtrate was washed with water (10 mL). The organic layer was separated and concentrated under reduced pressure. The resultant residue was purified by flash column chromatography over silica gel (petroleum ether/ethyl acetate from 100/0 to 0/100) to afford compound 56a as a yellow solid (155 mg, 70%). LCMS (ESI): m/z 250.9 [M+H]$^+$. $^1$H NMR (400 MHz, CDCl$_3$) δ ppm 5.17 (br s, 2H), 6.99 (d, J=5.07 Hz, 1H), 7.78 (d, J=8.38 Hz, 1H), 8.21 (dd, J=8.49, 2.09 Hz, 1H), 8.36 (d, J=2.20 Hz, 1H), 8.43 (d, J=5.07 Hz, 1H).

B. 4-(4-Amino-2-chlorophenyl)pyrimidin-2-amine, 56b

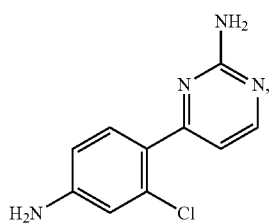

4-(2-Chloro-4-nitrophenyl)pyrimidin-2-amine, 56a (132 mg, 0.53 mmol), Fe(0) (294 mg, 5.27 mmol), and NH$_4$Cl (282, 5.27 mmol) were added to a mixture of THF (5 mL) and water (1 mL). The reaction mixture was stirred at 80° C. for 3 h. The reaction mixture was filtered though a pad of diatomaceous earth and the pad was washed with ethyl acetate (20 mL×3). The combined filtrates were concentrated to dryness to give crude compound 56b as a yellow solid. The crude compound was purified by flash column chromatography over silica gel (petroleum ether/ethyl acetate from 50/50 to 0/100) to afford compound 56b as a yellow solid (85 mg, 73%). $^1$H NMR (400 MHz, CDCl$_3$) δ ppm 3.76-3.88 (m, 2H), 4.98 (br s, 2H), 6.57 (dd, J=8.27, 2.32 Hz, 1H), 6.68 (d, J=2.21 Hz, 1H), 6.96 (d, J=5.07 Hz, 1H), 7.41 (d, J=8.38 Hz, 1H), 8.22 (d, J=5.29 Hz, 1H).

C. N-(4-(2-Aminopyrimidin-4-yl)-3-chlorophenyl)-1-(isoquinolin-4-yl)-5-(trifluoromethyl)-1H-pyrazole-4-carboxamide, Cpd 58

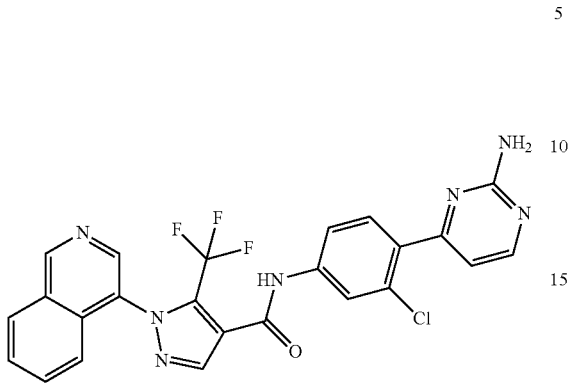

4-(4-Amino-2-chlorophenyl)pyrimidin-2-amine, 56b (80 mg, 0.36 mmol), 1-(isoquinolin-4-yl)-5-(trifluoromethyl)-1H-pyrazole-4-carboxylic acid, 4c (111 mg, 0.36 mmol), and HATU (207 mg, 0.54 mmol) were dissolved in triethylamine (234 mg, 1.81 mmol) and DMF (2 mL). The mixture was stirred at 25° C. for 3 h. Sat. aqueous $NH_4Cl$ (20 mL) was added and the mixture was extracted with dichloromethane (20 mL×2). The combined organic layers were dried over $Na_2SO_4$, filtered, and the filtrates were concentrated under reduced pressure to afford crude compound 58 as a yellow oil. The crude product was purified by reverse phase HPLC (A: water (0.05% HCl), B: MeCN; then: AB (82%/18% to 52%/48%). The pure fractions were concentrated under reduced pressure and lyophilized to dryness to afford compound 58 as a pale white solid (20.1 mg, 11%). LCMS (ESI): m/z 510.0 (M+H)+. 1H NMR (400 MHz, METHANOL-$d_4$) δ ppm 7.46 (d, J=6.61 Hz, 1H), 7.57 (d, J=8.60 Hz, 1H), 7.83-7.89 (m, 2H), 8.02-8.07 (m, 1H), 8.12-8.19 (m, 2H), 8.39 (d, J=6.62 Hz, 1H), 8.46 (s, 1H), 8.55 (d, J=8.38 Hz, 1H), 8.91 (s, 1H), 9.83 (s, 1H).

Example 57

N-(8-Chloro-3-oxo-3,4-dihydro-2H-benzo[b][1,4]oxazin-6-yl)-1-(isoquinolin-4-yl)-5-(trifluoromethyl)-1H-pyrazole-4-carboxamide, Cpd 87

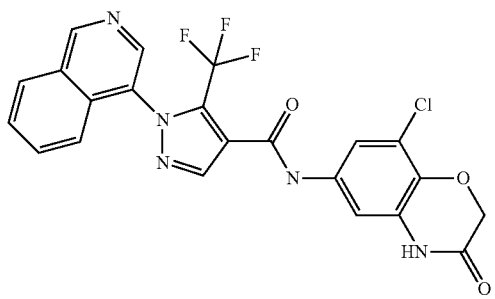 [SMILES: O=C1COc2c(Cl)cc(NC(=O)c3cnn(-c4cncc5ccccc45)c3C(F)(F)F)cc2N1]

A. 6-Amino-8-chloro-2H-benzo[b][1,4]oxazin-3(4H)-one, 57a

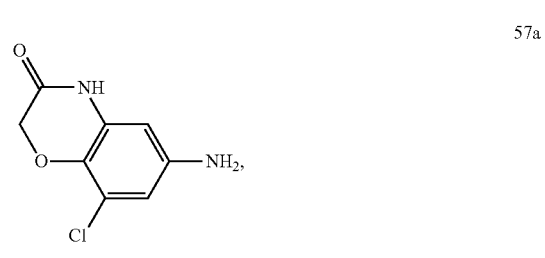 [SMILES: Nc1cc(Cl)c2c(c1)NC(=O)CO2]

Zinc (0) (426.5 mg, 6.56 mmol) was added to a solution of 8-chloro-6-nitro-2H-benzo[b][1,4]oxazin-3(4H)-one, 55b (150 mg, 0.66 mmol) in aqueous $NH_4Cl$ (2 mL) and MeOH (2 mL). The mixture was stirred at rt for 16 h. To the suspension was added aqueous $NaHCO_3$ to adjust the pH to 9-10, and the mixture was filtered though a pad of diatomaceous earth. The filter cake was washed with dichloromethane (30 mL×3). The combined filtrates were washed with brine (100 mL), dried over $MgSO_4$, filtered, and the filtrate concentrated under reduced pressure to afford compound 57a as a brown solid. The crude product was purified by column chromatography over silica gel (petroleum ether/ethyl acetate=2:1 to petroleum ether/ethyl acetate=0:1) to afford compound 57a as a yellow solid (90 mg, 69.1%). 1H NMR (400 MHz, $CDCl_3$) δ ppm 3.57 (br s, 2H), 4.61 (s, 2H), 6.05 (d, J=2.43 Hz, 1H), 6.39 (d, J=2.43 Hz, 1H), 7.90-8.05 (m, 1H).

B. N-(8-Chloro-3-oxo-3,4-dihydro-2H-benzo[b][1,4]oxazin-6-yl)-1-(isoquinolin-4-yl)-5-(trifluoromethyl)-1H-pyrazole-4-carboxamide, Cpd 87

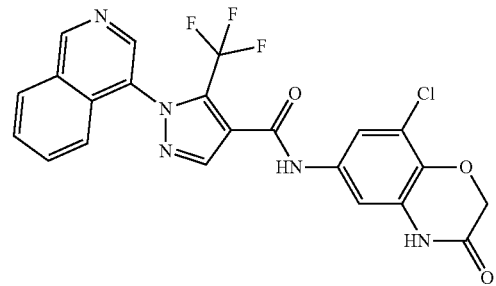 [SMILES: O=C1COc2c(Cl)cc(NC(=O)c3cnn(-c4cncc5ccccc45)c3C(F)(F)F)cc2N1]

1-(Isoquinolin-4-yl)-5-(trifluoromethyl)-1H-pyrazole-4-carboxylic acid, 4c (100 mg, 0.29 mmol), 6-amino-8-chloro-2H-benzo[b][1,4]oxazin-3(4H)-one, 57a (57.1 mg, 0.29 mmol), HATU (164.1 mg, 0.43 mmol) and DIEA (185.9 mg, 1.44 mmol) were dissolved in DMF (2 mL). The mixture was stirred at 25° C. for 3 h. Sat. aqueous $NH_4Cl$ (20 mL) was added and the mixture was extracted with dichloromethane (20 mL×2). The combined organic layers were dried over $Na_2SO_4$, filtered, and the filtrates were concentrated under reduced pressure to afford crude compound 87 as a yellow oil. The crude product was purified by reverse phase HPLC (A: water (0.05% HCl), B: MeCN; then: AB (95%/5% to 65%/35%). The pure fractions were concentrated under reduced pressure and lyophilized to dryness to afford compound 87 as a pale white solid (54 mg, 38%). LCMS (ESI): m/z 487.9 (M+H)+. 1H NMR (400 MHz, METHA- NOL-d$_4$) δ ppm 4.68 (s, 2H), 7.36 (d, J=2.21 Hz, 1H), 7.43 (d, J=2.43 Hz, 1H), 7.55 (d, J=8.38 Hz, 1H), 8.00-8.08 (m, 1H), 8.11-8.19 (m, 1H), 8.37 (s, 1H), 8.54 (d, J=8.16 Hz, 1H), 8.90 (s, 1H), 9.82 (s, 1H).

Example 58

N-(5-Chloro-6-(1,1-dioxidoisothiazolidin-2-yl)pyridin-3-yl)-1-(isoquinolin-4-yl)-5-(trifluoromethyl)-1H-pyrazole-4-carboxamide, Cpd 42

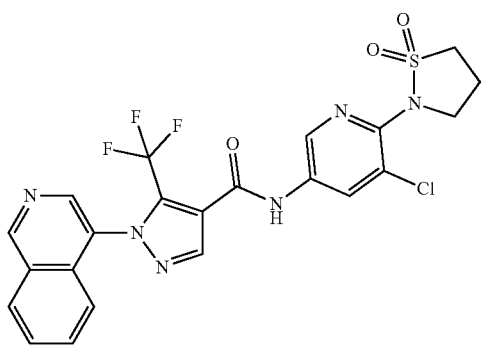 [SMILES: O=C(Nc1cnc(N2CCCS2(=O)=O)c(Cl)c1)c1cnn(-c2cncc3ccccc23)c1C(F)(F)F]

A. 2-(3-Chloro-5-nitropyridin-2-yl)isothiazolidine 1,1-dioxide, 58a

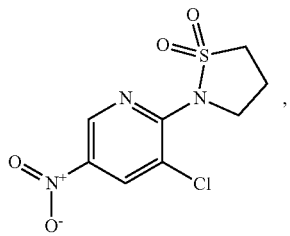

(1S,2S)—N1,N2-Dimethylcyclohexane-1,2-diamine (46.1 mg, 0.30 mmol) and copper iodide (56.3 mg, 0.30 mmol) were added to a mixture of 2,3-dichloro-5-nitropyridine (571 mg, 2.96 mmol), isothiazolidine 1,1-dioxide (430 mg, 3.55 mmol) and potassium carbonate (817.5 mg, 5.92 mmol) in dioxane (6 mL) under N2. The reaction mixture was stirred at 100° C. for 16 h. The mixture was filtered, and the filtrate was extracted with ethyl acetate. The organic extracts were dried over Na$_2$SO$_4$, filtered, and the filtrate concentrated under reduced pressure. The resultant crude product was purified by flash chromatography (petroleum ether/ethyl acetate=100:0 to petroleum ether/ethyl acetate=50:50) to afford compound 58a as a white solid (600 mg, 73%).

B. 2-(5-Amino-3-chloropyridin-2-yl)isothiazolidine 1,1-dioxide, 58b

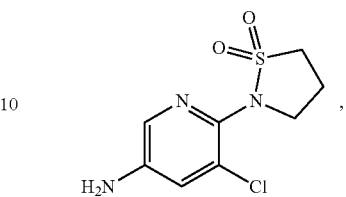

2-(3-Chloro-5-nitropyridin-2-yl)isothiazolidine 1,1-dioxide, 58a (600 mg, 2.12 mmol), Fe(0) (967 mg, 17.29 mmol), and NH$_4$Cl (925 mg, 17.29 mmol) were added to a mixture of THF (6 mL), MeOH (3 mL), and water (1.5 mL). The reaction mixture was stirred at 60° C. for 2 h. The reaction mixture was filtered though a pad of diatomaceous earth, and the pad was washed with ethyl acetate (20 mL×3). The combined filtrates were concentrated to dryness to give crude compound 58b as a yellow oil (530 mg, 99%).

C. N-(5-chloro-6-(1,1-dioxidoisothiazolidin-2-yl)pyridin-3-yl)-1-(isoquinolin-4-yl)-5-(trifluoromethyl)-1H-pyrazole-4-carboxamide, Cpd 42

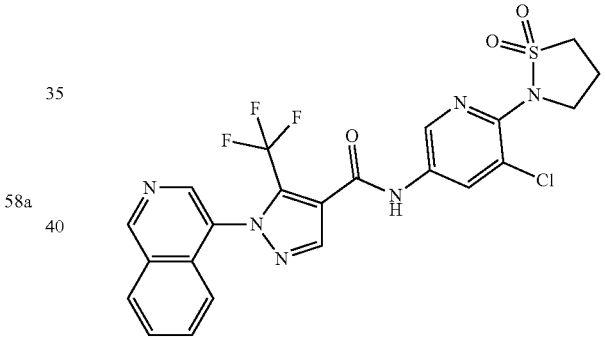

Phosphoryl trichloride (0.052 mL, 0.57 mmol) was added to a solution of 1-(isoquinolin-4-yl)-5-(trifluoromethyl)-1H-pyrazole-4-carboxylic acid, 4c (60 mg, 0.19 mmol), 2-(5-amino-3-chloropyridin-2-yl)isothiazolidine 1,1-dioxide, 58b (60.6 mg, 0.245 mmol), and pyridine (0.091 mL, 1.13 mmol) in dichloromethane at room temperature. The mixture was stirred for 2 h. The mixture was poured into water (10 mL), and the mixture was extracted with dichloromethane (20 mL×2). The separated organic layer was dried over Na$_2$SO$_4$, filtered, and the filtrate concentrated under reduced pressure to afford a crude product. The crude product was purified by reverse phase HPLC (0.05% ammonia hydroxide v/v); B: MeCN; then: AB (65%/35% to 35%/65%). The pure fractions were concentrated under reduced pressure and lyophilized to dryness to afford compound 42 as a white solid (35.6 mg, 35%). LCMS (ESI): m/z 536.9 [M+H]$^+$. $^1$H NMR (400 MHz, CDCl$_3$) δ ppm 2.53-2.60 (m, 2H), 3.19 (br t, J=7.50 Hz, 2H), 4.05 (br t, J=6.84 Hz, 2H), 7.29 (br d, J=7.94 Hz, 1H), 7.73 (dt, J=13.40, 6.64 Hz, 2H), 7.94 (br s, 1H), 8.09 (br d, J=8.16 Hz, 1H), 8.19 (s, 1H), 8.29 (br s, 1H), 8.44 (br s, 1H), 8.55 (s, 1H), 9.38 (s, 1H).

Example 59

N-(5-chloro-6-(2H-1,2,3-triazol-2-yl)pyridin-3-yl)-1-(isoquinolin-4-yl)-1H-pyrazole-4-carboxamide, Cpd 76

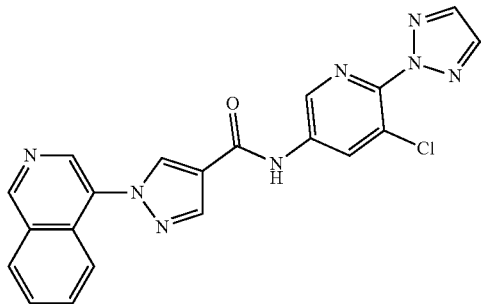 [SMILES: O=C(Nc1cnc(-n2nccn2)c(Cl)c1)c1cnn(-c2cncc3ccccc23)c1]

A. Ethyl 1-(isoquinolin-4-yl)-1H-pyrazole-4-carboxylate, 59a

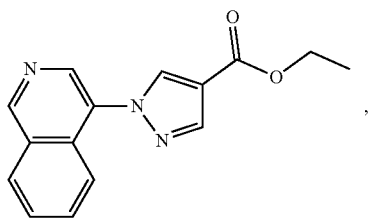

A solution consisting of ethyl 2-formyl-3-oxopropanoate (90.5 mg, 0.628 mmol), 4-hydrazinylisoquinoline, 4a (100 mg, 0.628 mmol) and 2-propanol (2 mL) was stirred at 80° C. overnight before cooling to room temperature and concentrating to dryness under reduced pressure to give the crude product, which was purified by FCC (petroleum ether: ethyl acetate=100:0 to 80:20) to give compound 59a (140 mg, 84%). LCMS (ESI): $R_T$=0.70 min, mass calcd. for $C_{15}H_{13}N_3O_2$ 267.283, m/z found 268.0 [M+H]$^+$.

B. N-(5-Chloro-6-(2H-1,2,3-triazol-2-yl)pyridin-3-yl)-1-(isoquinolin-4-yl)-1H-pyrazole-4-carboxamide, Cpd 76

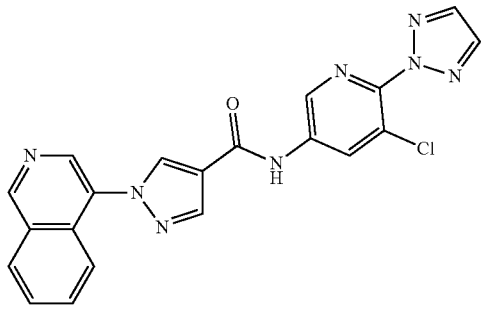 [SMILES: O=C(Nc1cnc(-n2nccn2)c(Cl)c1)c1cnn(-c2cncc3ccccc23)c1]

A solution consisting of 5-chloro-6-(2H-1,2,3-triazol-2-yl)pyridin-3-amine, 1j (87.8 mg, 0.449 mmol) and THF (1 mL) were added to 1 M potassium tert-butoxide in THF (1.35 mL, 1.35 mmol) at 0° C., then a solution consisting of ethyl 1-(isoquinolin-4-yl)-1H-pyrazole-4-carboxylate, 59a (120 mg, 0.449 mmol) and THF (1 mL) was added. The resultant mixture was stirred at room temperature for 16 h. The reaction mixture was concentrated under reduced pressure to give a crude product, which was purified by preparative reverse phase HPLC (30% to 60% (v/v) ACN and H$_2$O with 0.05% NH$_3$). The pure fractions were concentrated under reduced pressure and lyophilized to dryness to afford compound 76 (69.3 mg, 36%). LCMS (ESI): $R_T$=4.36 min, mass calcd. for $C_{20}H_{13}ClN_8O$ 416.823, m/z found 416.9 [M+H]$^+$. $^1$H NMR (400 MHz, DMSO-d$_6$) δ 10.74 (br.s., 1H), 9.52 (s, 1H), 9.01 (s, 1H), 8.88 (d, J=2.4 Hz, 1H), 8.76 (s, 1H), 8.70 (d, J=2.4 Hz, 1H), 8.54 (s, 1H), 8.35 (d, J=8.0 Hz, 1H), 8.19 (s, 2H), 7.98-7.92 (m, 2H), 7.89-7.84 (m, 1H).

Example 60

N-(5-chloro-6-(2H-1,2,3-triazol-2-yl)pyridin-3-yl)-5-methyl-1-(quinolin-4-yl)-1H-pyrazole-4-carboxamide, Cpd 64

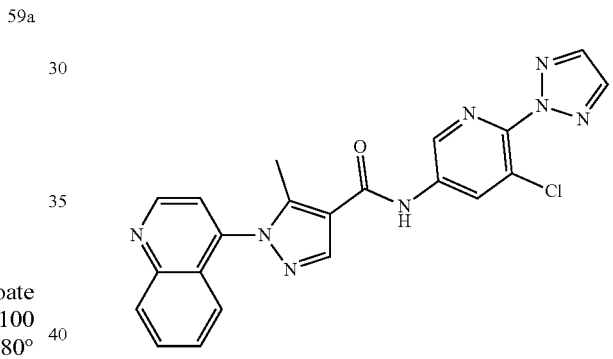

A. 7-Chloro-4-methoxyquinoline, 60a

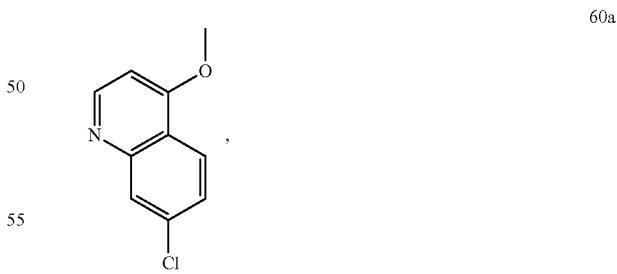

4,7-Dichloroquinoline (6.00 g, 30.3 mmol) was added portionwise to a solution consisting of sodium methoxide (1.80 g, 33.3 mmol) and methanol (60 mL) at room temperature. The mixture was stirred at 80° C. for 12 h before quenching with water and extracting with ethyl acetate (200 mL×3). The combined organic extracts were dried over anhydrous Na$_2$SO$_4$, filtered, and the filtrate concentrated to dryness under reduced pressure to give a residue, which was purified by FCC (petroleum ether: ethyl acetate=2:1 to 1:2)

to afford compound 60a (4.1 g, 70%). $^1$H NMR (400 MHz, CDCl$_3$) δ ppm 8.73 (d, J=5.2 Hz, 1H), 8.11 (d, J=8.8 Hz, 1H), 8.01 (d, J=2.0 Hz, 1H), 7.43 (dd, J=2.0, 8.8 Hz, 1H), 6.71 (d, J=5.2 Hz, 1H), 4.03 (s, 3H).

B. 4-Methoxyquinoline, 60b

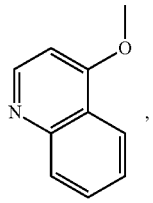
60b

A mixture consisting of 7-chloro-4-methoxyquinoline, 60a (4.10 g, 21.1 mmol), dry Pd/C (400 mg, 10 wt. %, 0.377 mmol), and methanol (100 mL) was stirred at room-temperature for 16 h under H$_2$ (15 psi). The mixture was filtered through a pad of diatomaceous earth and the pad was washed with methanol (50 mL). The filtrate was concentrated to dryness under reduced pressure to give a residue, which was dissolved in aqueous NaHCO$_3$ (80 mL) and extracted with ethyl acetate (100 mL×3). The combined organic extracts were dried over anhydrous Na$_2$SO$_4$, filtered, and the filtrate concentrated to dryness under reduced pressure to give a crude product, which was purified by FCC (petroleum ether: ethyl acetate=1:3) and further purified by reverse phase HPLC (10% to 40% (v/v) CH$_3$CN and H$_2$O with 0.05% NH$_3$). The pure fractions were concentrated under reduced pressure and lyophilized to dryness to afford compound 60b (1.1 g, 33%). $^1$H NMR (400 MHz, CDCl$_3$) δ 8.74 (d, J=5.2 Hz, 1H), 8.22-8.15 (m, 1H), 8.03 (d, J=8.4 Hz, 1H), 7.73-7.65 (m, 1H), 7.51-7.47 (m, 1H), 6.72 (d, J=5.2 Hz, 1H), 4.03 (s, 3H).

C. 4-Hydrazinylquinoline, 60c

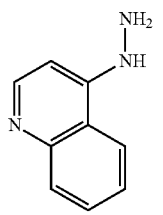
60c

A mixture consisting of 4-methoxyquinoline, 60b (1.00 g, 6.28 mmol), hydrazine hydrate (10 mL, 85 wt. %), and ethanol (5 mL) was refluxed for 16 h. Then the ethanol was removed under reduced pressure and the resultant aqueous mixture was filtered to afford compound 60c (713 mg, 71%), which was dried under reduced pressure. $^1$H NMR (400 MHz, DMSO-d$_6$) δ ppm 8.37 (d, J=5.2 Hz, 1H), 8.10 (d, J=8.4 Hz, 1H), 7.74 (d, J=8.4 Hz, 1H), 7.56 (t, J=7.6 Hz, 1H), 7.34 (t, J=7.6 Hz, 1H), 6.83 (d, J=5.2 Hz, 1H), 4.37 (br s, 1H).

D. Ethyl 5-methyl-1-(quinolin-4-yl)-1H-pyrazole-4-carboxylate, 60d

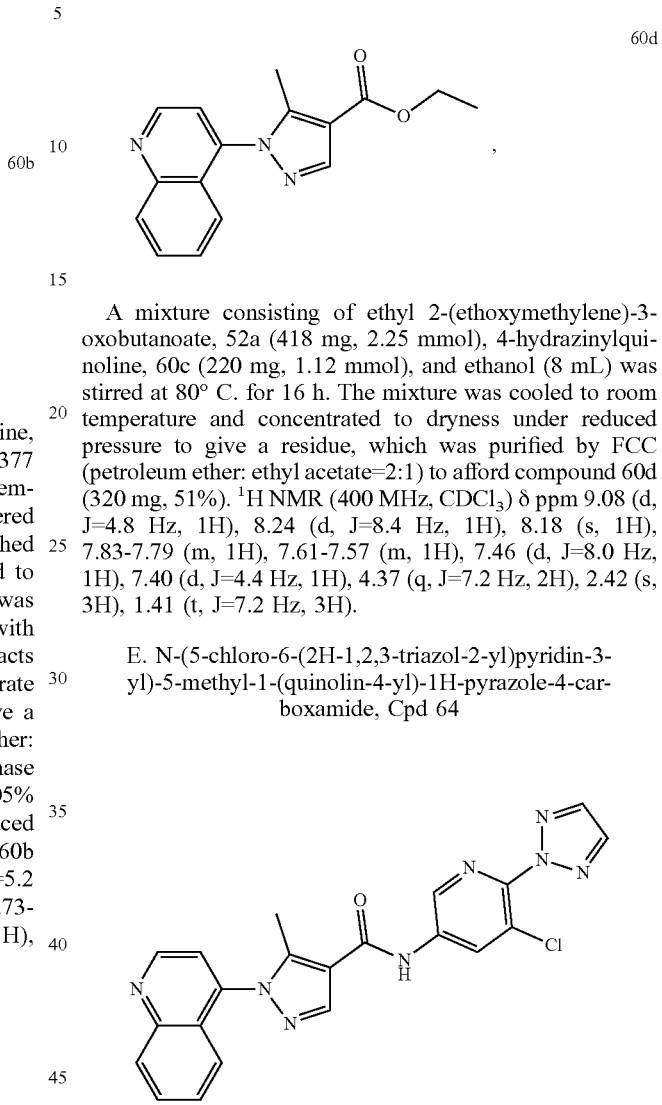

A mixture consisting of ethyl 2-(ethoxymethylene)-3-oxobutanoate, 52a (418 mg, 2.25 mmol), 4-hydrazinylquinoline, 60c (220 mg, 1.12 mmol), and ethanol (8 mL) was stirred at 80° C. for 16 h. The mixture was cooled to room temperature and concentrated to dryness under reduced pressure to give a residue, which was purified by FCC (petroleum ether: ethyl acetate=2:1) to afford compound 60d (320 mg, 51%). $^1$H NMR (400 MHz, CDCl$_3$) δ ppm 9.08 (d, J=4.8 Hz, 1H), 8.24 (d, J=8.4 Hz, 1H), 8.18 (s, 1H), 7.83-7.79 (m, 1H), 7.61-7.57 (m, 1H), 7.46 (d, J=8.0 Hz, 1H), 7.40 (d, J=4.4 Hz, 1H), 4.37 (q, J=7.2 Hz, 2H), 2.42 (s, 3H), 1.41 (t, J=7.2 Hz, 3H).

E. N-(5-chloro-6-(2H-1,2,3-triazol-2-yl)pyridin-3-yl)-5-methyl-1-(quinolin-4-yl)-1H-pyrazole-4-carboxamide, Cpd 64

A solution consisting of 5-chloro-6-(2H-1,2,3-triazol-2-yl)pyridin-3-amine, 1j (229 mg, 1.17 mmol) and THF (1 mL) was added dropwise to a solution of t-BuOK (3.2 mL, 3.2 mmol, 1 M in THF) at 0° C. Then a solution consisting of ethyl 5-methyl-1-(quinolin-4-yl)-1H-pyrazole-4-carboxylate, 60d (300 mg, 1.07 mmol) and THF (1 mL) was added dropwise. The resultant mixture was warmed to room temperature and stirred for 16 h before quenching with water and extracting with ethyl acetate (50 mL×3). The combined extracts were dried over anhydrous Na$_2$SO$_4$, filtered, and the filtrate concentrated to dryness under reduced pressure to give a residue, which was purified by preparative reverse phase HPLC (30% to 60% (v/v) CH$_3$CN and H$_2$O with 0.05% NH$_3$). The pure fractions were concentrated under reduced pressure and lyophilized to dryness to afford compound 64 (153 mg, 33%). LCMS (ESI): R$_T$=4.52 min, mass calcd. for C$_{21}$H$_{15}$ClN$_8$O 430.850, m/z found 431.0 [M+H]$^+$. $^1$H NMR (400 MHz, DMSO-d$_6$) δ 10.66 (s, 1H), 9.14 (d, J=4.4 Hz, 1H), 8.92 (d, J=2.4 Hz, 1H), 8.71 (d, J=2.4 Hz, 1H), 8.57 (s, 1H), 8.23 (d, J=8.4 Hz, 1H), 8.19 (s, 2H), 7.93-7.89 (m, 1H), 7.78 (d, J=4.4 Hz, 1H), 7.73-7.69 (m, 1H), 7.49 (d, J=8.0 Hz, 1H), 2.45 (s, 3H).

Example 61

N-(5-chloro-6-(2H-1,2,3-triazol-2-yl)pyridin-3-yl)-1-(quinolin-5-yl)-1H-pyrazole-4-carboxamide, Cpd 60

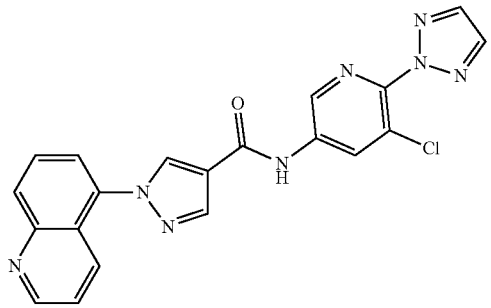 [SMILES: O=C(Nc1cnc(-n2nccn2)c(Cl)c1)c1cnn(-c2cccc3ncccc23)c1]

A. Ethyl 1-(quinolin-5-yl)-1H-pyrazole-4-carboxylate, 61a

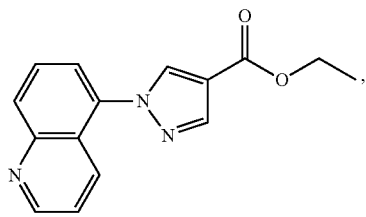

Copper(II) acetate (1.43 g, 7.88 mmol) was added to a mixture consisting of ethyl 1H-pyrazole-4-carboxylate (368 mg, 2.63 mmol), quinolin-5-ylboronic acid (500 mg, 2.89 mmol), molecular sieve (4 A, 30 mg), pyridine (624 mg, 7.88 mmol), pyridine 1-oxide (750 mg, 7.88 mmol), and DMF (10 mL). The reaction mixture was stirred under O2 (1 atm., balloon) at room temperature for 16 h. The suspension was filtered through a pad of diatomaceous earth and the pad was washed with ethyl acetate (100 mL). The filtrate was washed with water (100 mL×2), dried over anhydrous $Na_2SO_4$, filtered, and the filtrate concentrated to dryness under reduced pressure to afford a crude product, which was purified by FCC (petroleum ether: ethyl acetate=100:0 to 70:30) to give compound 61a (160 mg, 23%). $^1$H NMR (400 MHz, $CDCl_3$) δ 9.00 (d, J=4.0 Hz, 1H), 8.32-8.22 (m, 4H), 7.82-7.78 (m, 1H), 7.62 (d, J=7.2 Hz, 1H), 7.48 (dd, J=4.4, 8.4 Hz, 1H), 4.37 (q, J=7.2 Hz, 2H), 1.40 (t, J=7.2 Hz, 3H).

B. N-(5-Chloro-6-(2H-1,2,3-triazol-2-yl)pyridin-3-yl)-1-(quinolin-5-yl)-1H-pyrazole-4-carboxamide, Cpd 60

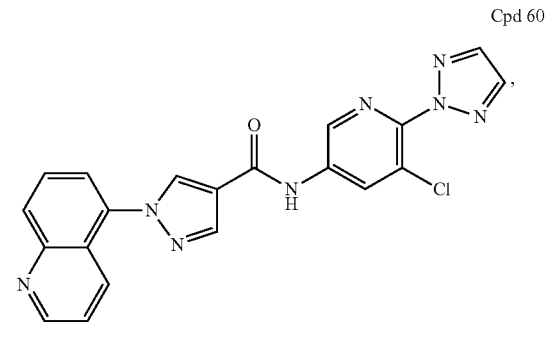 [SMILES: O=C(Nc1cnc(-n2nccn2)c(Cl)c1)c1cnn(-c2cccc3ncccc23)c1]

A solution consisting of 5-chloro-6-(2H-1,2,3-triazol-2-yl)pyridin-3-amine, 1j (102 mg, 0.524 mmol) and THF (1 mL) were added to 1 M potassium tert-butoxide in THF (1.57 mL, 1.57 mmol) at 0° C., then a solution consisting of ethyl 1-(quinolin-5-yl)-1H-pyrazole-4-carboxylate, 61a (140 mg, 0.524 mmol) and THF (1 mL) was added. The resultant mixture was stirred at room temperature for 16 h. The reaction mixture was concentrated under reduced pressure to give a crude product, which was purified by preparative reverse phase HPLC (30% to 60% (v/v) ACN and $H_2O$ with 0.05% $NH_3$). The pure fractions were concentrated under reduced pressure and lyophilized to dryness to afford compound 60 (104.50 mg, 49%). LCMS (ESI): $R_T$=4.01 min, mass calcd. for $C_{20}H_{13}ClN_8O$ 416.823, m/z found 417.0 $[M+H]^+$. $^1$H NMR (400 MHz, DMSO-$d_6$) δ 9.04 (dd, J=1.6, 4.0 Hz, 1H), 8.96 (s, 1H), 8.88 (d, J=2.4 Hz, 1H), 8.70 (d, J=2.4 Hz, 1H), 8.50 (s, 1H), 8.33-8.28 (m, 1H), 8.24 (d, J=8.4 Hz, 1H), 8.19 (s, 2H), 7.98-7.92 (m, 1H), 7.89-7.85 (m, 1H), 7.68 (dd, J=4.0, 8.4 Hz, 1H).

Example 61

N-(5-Chloro-6-(2H-1,2,3-triazol-2-yl)pyridin-3-yl)-1-(2-methylquinolin-5-yl)-5-(trifluoromethyl)-1H-pyrazole-4-carboxamide, Cpd 37

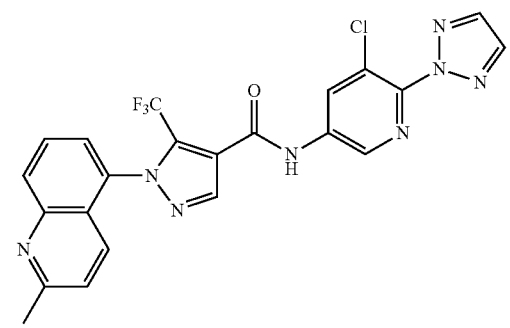 [SMILES: Cc1ccc2c(-n3ncc(C(=O)Nc4cnc(-n5nccn5)c(Cl)c4)c3C(F)(F)F)cccc2n1]

385

A. Ethyl 1-(2-methylquinolin-5-yl)-5-(trifluoromethyl)-1H-pyrazole-4-carboxylate, 61a

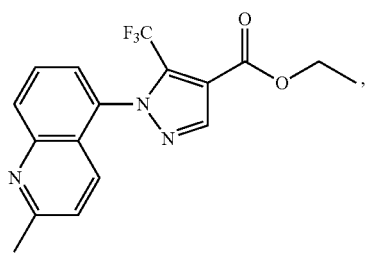

61a

A mixture of 5-chloro-2-methylquinoline (200 mg, 1.12 mmol), hydrazine hydrate (0.111 mL, 98%, 2.25 mmol), palladium(II)(pi-cinnamyl) chloride dimer (16 mg, 0.030 mmol), N-[2-(di-1-adamantylphosphino)phenyl]morpholine (42 mg, 0.090 mmol), sodium tert-butoxide (216 mg, 2.25 mmol), and toluene (11 mL, 0.1 M, 1.1 mmol) was bubbled with Argon for 1 min, sealed, and stirred at 100° C. for 2.5 h before cooling to room temperature and treating with ethyl 2-(ethoxymethylene)-4,4,4-trifluoro-3-oxobutanoate (270 mg, 1.13 mmol) in one portion under air. The reaction was then sealed under air and stirred at 100° C. for 40 min, then at 90° C. for another 20 h before cooling to room temperature. The mixture was filtered and concentrated under reduced pressure to give a yellow oil, which was purified by FCC (petroleum ether: ethyl acetate=40: 60) to afford compound 61a (210 mg, 16%). LCMS (ESI): $R_T$=0.75 min, mass calcd. for $C_{17}H_{14}F_3N_3O_2$ 349.3, m/z found 350.0 [M+H]$^+$.

B. N-(5-Chloro-6-(2H-1,2,3-triazol-2-yl)pyridin-3-yl)-1-(2-methylquinolin-5-yl)-5-(trifluoromethyl)-1H-pyrazole-4-carboxamide, Cpd 37

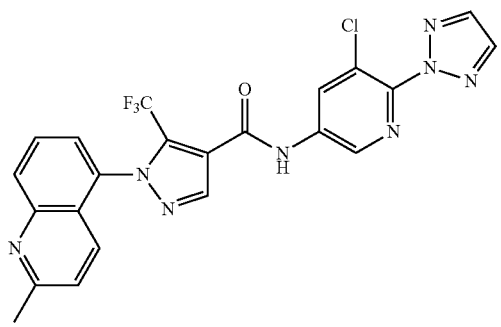 [SMILES: Cc1ccc2c(-n3ncc(C(=O)Nc4cnc(-n5nccn5)c(Cl)c4)c3C(F)(F)F)cccc2n1]

Ethyl 1-(2-methylquinolin-5-yl)-5-(trifluoromethyl)-1H-pyrazole-4-carboxylate, 61a (210 mg, 0.180 mmol) in THF (1 mL) and 5-chloro-6-(2H-1,2,3-triazol-2-yl)pyridin-3-amine, 1j (117 mg, 0.601 mmol) in THF (1 mL) were added into a suspension of potassium tert-butoxide (101 mg, 0.902 mmol) in THF (3 mL) at 0° C. The mixture was stirred at room temperature for 20 h before concentrating under reduced pressure to afford a yellow solid, which was purified by preparative reverse phase HPLC (42% to 72% (v/v) CH$_3$CN and H$_2$O with 0.05% NH$_3$) from 42% to 72%, v/v) and lyophilized to afford compound 37 (12.0 mg, 13%). LCMS (ESI): $R_T$=4.34 min, mass calcd. for $C_{22}H_{14}ClF_3N_8O$ 498.093, m/z found 499.0 [M+H]$^+$. $^1$H NMR (400 MHz,

386

DMSO-d$_6$) δ 11.30 (br s, 1H), 8.86 (d, J=2.4 Hz, 1H), 8.68 (d, J=2.0 Hz, 1H), 8.58 (s, 1H), 8.23 (d, J=8.8 Hz, 1H), 8.20 (s, 2H), 7.92 (dd, J=7.2, 8.4 Hz, 1H), 7.83 (d, J=7.2 Hz, 1H), 7.59-7.53 (m, 1H), 7.52-7.47 (m, 1H), 2.72 (s, 3H).

Example 62

N-(5-Chloro-6-(2H-1,2,3-triazol-2-yl)pyridin-3-yl)-1-(6-fluoroquinolin-7-yl)-5-(trifluoromethyl)-1H-pyrazole-4-carboxamide, Cpd 67

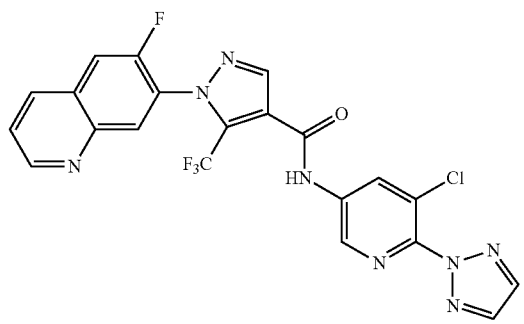 [SMILES: O=C(Nc1cnc(-n2nccn2)c(Cl)c1)c1cnn(-c2cc3ncccc3cc2F)c1C(F)(F)F]

A. 5-Bromo-6-fluoroquinoline, 62a and 7-Bromo-6-fluoroquinoline, 62a-1

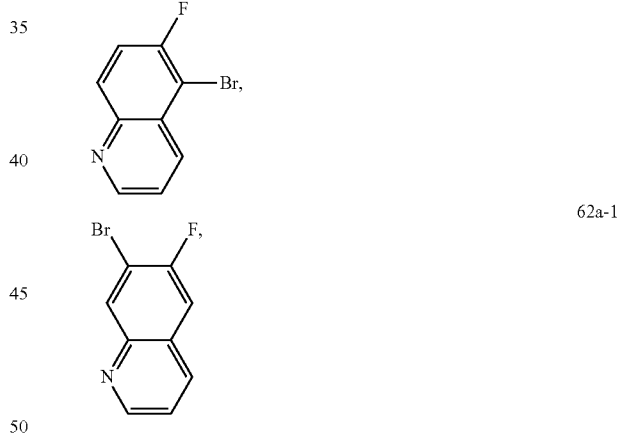

Water (11.38 mL) was added to a solution consisting of 3-bromo-4-fluoroaniline (10 g, 53 mmol), sodium 3-nitrobenzenesulfonate (21 g, 95 mmol), and propane-1,2,3-triol (14 g, 0.15 mol). The resultant mixture was carefully treated with concentrated H$_2$SO$_4$ (21.1 mL), and then heated to 150° C. with stirring for 2 h before cooling to room temperature. The resultant mixture was carefully neutralized with 5 N sodium hydroxide, filtered through a pad of diatomaceous earth, and the pad was washed with dichloromethane (50 mL). The resultant mixture was extracted with dichloromethane (100 mL×3) and the combined organic extracts were dried over Na$_2$SO$_4$, filtered, and the filtrate concentrated to give a crude product, which was purified by FCC (petroleum ether: ethyl acetate=3:1) to afford the compounds 62a and 62a-1 (9.5 g, 80%). LCMS (ESI): $R_T$=0.64, 0.68 min, mass calcd. for $C_9H_5BrFN$ 224.96, m/z found 227.6 [M+H]⁺. ¹H NMR (400 MHz, CDCl₃) δ 8.96-8.87 (m, 2H), 8.55 (d, J=8.8 Hz, 1H), 8.39 (d, J=6.8 Hz, 1H), 8.15-8.07 (m, 2H), 7.60-7.42 (m, 4H).

B. 5-(2-(Diphenylmethylene)hydrazinyl)-6-fluoroquinoline, 62b and 7-(2-(Diphenylmethylene)hydrazinyl)-6-fluoroquinoline, 62b-1

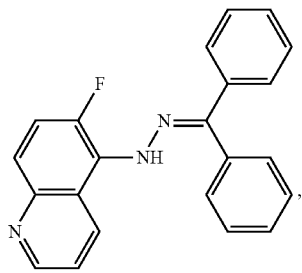

62b

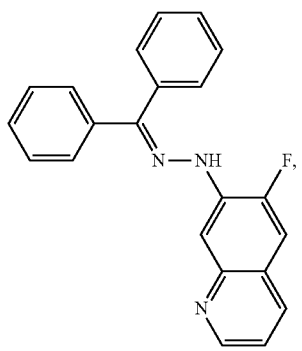

62b-1

A mixture of 5-bromo-6-fluoroquinoline, 62a and 7-bromo-6-fluoroquinoline, 62a-1 (10 g, 22 mmol), (diphenylmethylene)hydrazine (4.3 g, 22 mmol), 2,2'-bis(diphenylphosphino)-1,1'-binaphthyl (1.4 g, 2.2 mmol), palladium (II) acetate (0.50 g, 2.2 mmol), t-BuONa (6.4 g, 66 mmol), and 1,4-dioxane (150 mL) was stirred at 100° C. for 16 h. The suspension was filtered through a pad of diatomaceous earth and the pad was washed with ethyl acetate (30 mL). The filtrate was concentrated to dryness under reduced pressure to give a crude product, which was added into water (30 mL). The resultant mixture was extracted with ethyl acetate (50 mL×3). The combined organic extracts were dried over anhydrous Na₂SO₄, filtered, and the filtrate concentrated to dryness under reduced pressure to afford the crude product, which was purified by FCC (petroleum ether:ethyl acetate=3:1) to afford compounds 62b and 62b-1 (5 g, 33%). LCMS (ESI): R$_T$=0.68 min, mass calcd. for C₂₂H₁₆FN₃ 341.13, m/z found 341.9 [M+H]⁺.

C. 6-Fluoro-5-hydrazinylquinoline, 62c and 6-Fluoro-7-hydrazinylquinoline, 62c-1

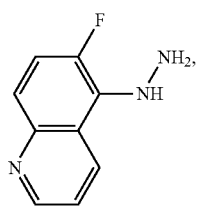

62c

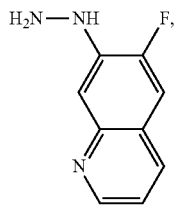

62c-1

Concentrated HCl (10 mL) was added to a solution consisting of 5-(2-(diphenylmethylene)hydrazinyl)-6-fluoroquinoline, 62b and 7-(2-(diphenylmethylene)hydrazinyl)-6-fluoroquinoline, 62b-1 (5.0 g, 7.3 mmol) and EtOH (3 mL). The resultant solution was stirred at room temperature for 16 h. The resultant mixture was treated with water (30 mL) and extracted with dichloromethane (30 mL×3). The aqueous phase was basified with 5 M NaOH to pH 12. The suspension was filtered and the collected solids were washed with water (20 mL) and dried under reduced pressure to afford compounds 62c and 62c-1 (1.2 g, 46%). LCMS (ESI): R$_T$=1.24 min, mass calcd. for C₉H₈FN₃ 177.07, m/z found 178.1 [M+H]⁺.

D. Ethyl 1-(6-fluoroquinolin-7-yl)-5-(trifluoromethyl)-1H-pyrazole-4-carboxylate, 62d

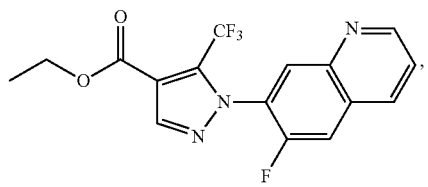

62d

A solution consisting of ethyl 2-(ethoxymethylene)-4,4,4-trifluoro-3-oxobutanoate, 1f (1.79 g, 7.45 mmol), 6-fluoro-5-hydrazinylquinoline and 6-fluoro-7-hydrazinylquinoline, 62c and 62c-1 (1.10 g, 6.21 mmol), and ethanol (20 mL) was stirred at 80° C. for 16 h before cooling to room temperature. The resultant solution was concentrated to dryness under reduced pressure to afford the crude product. This was purified by FCC (eluent: petroleum ether:ethyl acetate=3:1) to afford the title compound (1.3 g, 59%). LCMS (ESI): R$_T$=3.90 min, mass calcd. for C₁₆H₁₁F₄N₃O₂ 353.08, m/z found 353.9 [M+H]⁺. ¹H NMR (400 MHz, CDCl₃) δ 9.01 (d, J=4.0 Hz, 1H), 8.30-8.18 (m, 3H), 7.65 (d, J=9.7 Hz, 1H), 7.55 (dd, J=4.2, 8.4 Hz, 1H), 4.41 (q, J=7.2 Hz, 2H), 1.41 (t, J=7.2 Hz, 3H).

E. N-(5-Chloro-6-(2H-1,2,3-triazol-2-yl)pyridin-3-yl)-1-(6-fluoroquinolin-7-yl)-5-(trifluoromethyl)-1H-pyrazole-4-carboxamide, Cpd 67

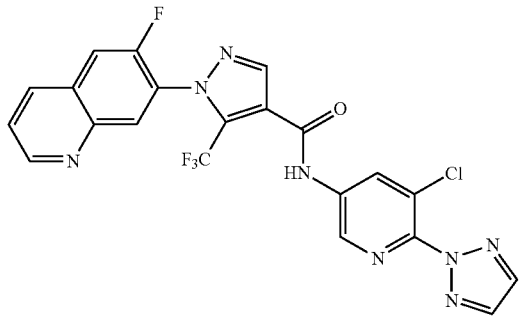 [SMILES: O=C(Nc1cnc(-n2nccn2)c(Cl)c1)c1cnn(-c2cc3ncccc3cc2F)c1C(F)(F)F]

A solution consisting of 5-chloro-6-(2H-1,2,3-triazol-2-yl)pyridin-3-amine, 1j (249 mg, 1.27 mmol) and THF (1 mL), and a solution consisting of ethyl 1-(6-fluoroquinolin-7-yl)-5-(trifluoromethyl)-1H-pyrazole-4-carboxylate, 62d (300 mg, 0.849 mmol) and THF (1 mL) were added to a solution consisting of potassium tert-butoxide (2.55 mL, 2.55 mmol, 1 M in THF) at 0° C. The resultant mixture was stirred at room temperature for 16 h. The resultant mixture was added water (5 mL) and extracted with ethyl acetate (15 mL×3). The combined organic extracts were dried over anhydrous Na$_2$SO$_4$, filtered, and the filtrate concentrated to dryness under reduced pressure to afford a crude product, which was purified by preparative reverse phase HPLC (35% to 55% (v/v) CH$_3$CN and H$_2$O with 10 mM NH$_4$HCO$_3$) and lyophilized to afford compound 67 (70.7 mg, 17%). LCMS (ESI): RT=5.05 min, mass calcd. for C$_{21}$H$_{11}$ClF$_4$N$_8$O 502.07, m/z found 502.9 [M+H]$^+$. $^1$H NMR (400 MHz, DMSO-d$_6$) δ 10.81 (br.s., 1H), 9.06 (d, J=4.0 Hz, 1H), 8.85 (d, J=2.4 Hz, 1H), 8.67 (d, J=2.4 Hz, 1H), 8.59 (s, 1H), 8.53 (d, J=8.4 Hz, 1H), 8.50 (d, J=7.2 Hz, 1H), 8.25-8.17 (m, 3H), 7.76 (dd, J=4.2, 8.4 Hz, 1H).

Example 63

N-(5-Chloro-6-(1-methyl-1H-pyrazol-3-yl)pyridin-3-yl)-1-(isoquinolin-8-yl)-5-(trifluoromethyl)-1H-pyrazole-4-carboxamide, Cpd 21

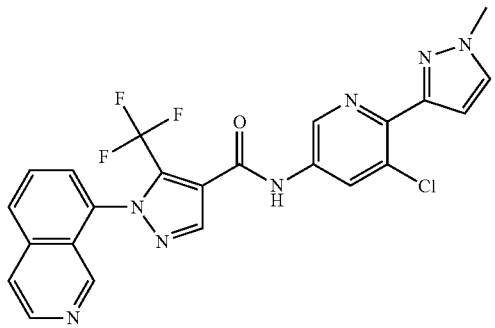 [SMILES: Cn1ccc(-c2ncc(NC(=O)c3cnn(-c4cccc5ccncc45)c3C(F)(F)F)cc2Cl)n1]

A. 8-Hydrazinylisoquinoline, 63a

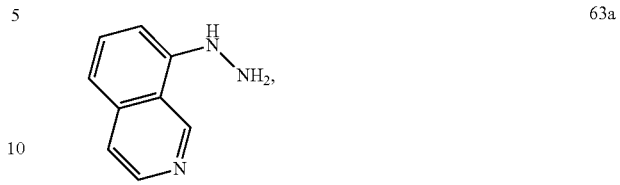

To a stirring solution of isoquinolin-8-amine (4.3 g, 29.8 mmol) in concentrated HCl (43 mL, 215 mmol) at 0° C. was added a solution of sodium nitrite (3.1 g, 44.7 mmol) in water (5 mL) below 0° C. The reaction mixture was stirred at 0° C. for 30 min and a solution of tin chloride (16.8 g, 74.6 mmol) in concentrated HCl (8 mL) was added dropwise. The mixture was stirred at room temperature for 2 h. The mixture was adjusted to pH 12-14 with 20% aqueous sodium hydroxide. The mixture was extracted with ethyl acetate. The organic layer was dried over Na$_2$SO$_4$, filtered, and the filtrate concentrated in under reduced pressure. The resulting crude product was purified by flash chromatography (petroleum ether/ethyl acetate=100:0 to ethyl acetate/methnol=90:10) to give compound 63a (2.83 g, 60%) as a brown solid.

B. Ethyl 1-(isoquinolin-8-yl)-5-(trifluoromethyl)-1H-pyrazole-4-carboxylate, 63b

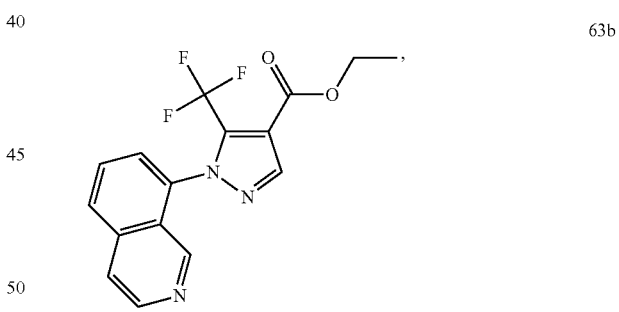

A solution consisting of 8-hydrazinylisoquinoline, 63a (2.83 g, 17.8 mmol) and ethyl 2-(ethoxymethylene)-4,4,4-trifluoro-3-oxobutanoate, 1f (5.12 g, 21.3 mmol) in ethanol (42 mL) was stirred at 80° C. for 16 h. The resultant solution was cooled to room temperature and concentrated to dryness under reduced pressure to afford a crude product, which was then purified by column chromatography over silica gel (petroleum ether/ethyl acetate=100:0 to 70:30) to afford compound 63b as a yellow solid (3.14 g, 53%). MS m/e 335.9 (M+H).

C. 1-(Isoquinolin-8-yl)-5-(trifluoromethyl)-1H-pyrazole-4-carboxylic acid, 63c

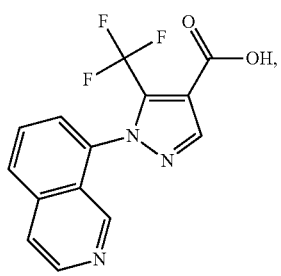

NaOH (375 mg, 9.4 mmol) was added to a solution of ethyl 1-(isoquinolin-8-yl)-5-(trifluoromethyl)-1H-pyrazole-4-carboxylate, 63b (3.14 g, 9.4 mmol) in methanol (5 mL) and water (15 mL) at room temperature. The mixture was stirred for 4 h. The solvent was concentrated under reduced pressure to afford compound 63c as a yellow solid (3.093 g 100%). $^1$H NMR (400 MHz, DMSO-$d_6$) δ ppm 9.12 (s, 1H), 8.77 (d, J=5.3 Hz, 1H), 8.53-8.37 (m, 3H), 8.23-8.16 (m, 1H), 8.11 (d, J=7.1 Hz, 1H).

D. N-(5-Chloro-6-(1-methyl-1H-pyrazol-3-yl)pyridin-3-yl)-1-(isoquinolin-8-yl)-5-(trifluoromethyl)-1H-pyrazole-4-carboxamide, Cpd 21

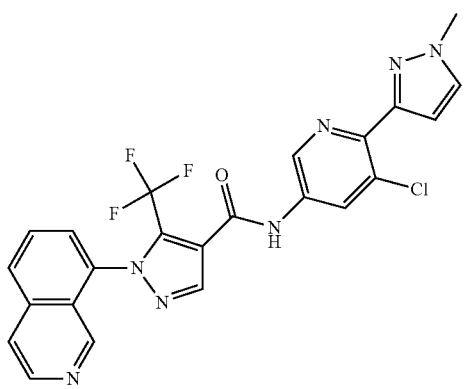 [SMILES: Cn1ccc(-c2ncc(NC(=O)c3cnn(-c4cccc5ccncc45)c3C(F)(F)F)cc2Cl)n1]

To a solution of 1-(isoquinolin-8-yl)-5-(trifluoromethyl)-1H-pyrazole-4-carboxylic acid, 63c (95 mg, 0.29 mmol), 5-chloro-6-(1-methyl-1H-pyrazol-3-yl)pyridin-3-amine, 8a (60 mg, 0.29 mmol) and pyridine (132.7 mg, 1.7 mmol) in dichloromethane (5 mL) was added POCl$_3$ (102.9 mg, 0.67 mmol) dropwise. The reaction mixture was stirred at 20° C. for 1 h. A solution of saturated aqueous NaHCO$_3$ (20 mL) was added and the mixture was extracted with dichloromethane (20 mL×2). The combined organic phases were washed with brine and dried over Na$_2$SO$_4$. The mixture was filtered, and the filtrates concentrated under reduced pressure to afford a crude product as a yellow oil. The crude product was purified by preparative HPLC to afford compound 21 as a white solid (55 mg, 38%). $^1$H NMR (400 MHz, DMSO-$d_6$) δ ppm 11.02 (s, 1H), 8.82 (d, J=2.2 Hz, 1H), 8.67 (d, J=5.7 Hz, 1H), 8.60 (s, 1H), 8.54 (s, 1H), 8.42 (d, J=2.3 Hz, 1H), 8.29 (d, J=7.4 Hz, 1H), 8.08-8.03 (m, 1H), 8.00-7.93 (m, 2H), 7.77 (d, J=2.2 Hz, 1H), 6.75 (d, J=2.2 Hz, 1H), 3.92 (s, 3H). MS m/e 498.1 (M+H).

Example 64

N-(2-Cyanopyridin-4-yl)-1-(naphthalen-1-yl)-5-(trifluoromethyl)-1H-pyrazole-4-carboxamide, Cpd 1

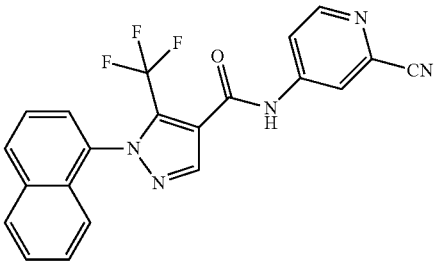 [SMILES: N#Cc1cc(NC(=O)c2cnn(-c3cccc4ccccc34)c2C(F)(F)F)ccn1]

POCl$_3$ (0.3 mL) was added dropwise to a solution consisting of 1-(naphthalen-1-yl)-5-(trifluoromethyl)-1H-pyrazole-4-carboxylic acid 2b (150 mg, 0.490 mmol), 4-aminopicolinonitrile (64.2 mg, 0.539 mmol) and pyridine (5 mL). The mixture was stirred at 0° C. for 1 h. The resulting mixture was concentrated under reduced pressure to give a crude product, which was purified by preparative HPLC (40% to 70% (v/v) ACN and H$_2$O with 0.05% NH$_3$) to afford compound 1. Compound 1 was concentrated to dryness under reduced pressure (101.30 mg, 51%). LCMS (ESI): R$_T$=5.45 min, mass calcd. for C$_{21}$H$_{12}$F$_3$N$_5$O 407.348, m/z found 408.0 [M+H]$^+$. $^1$H NMR (400 MHz, DMSO-$d_6$) δ ppm 11.31 (s, 1H), 8.71 (d, J=5.2 Hz, 1H), 8.56 (s, 1H), 8.30 (s, 1H), 8.26 (d, J=8.0 Hz, 1H), 8.15 (d, J=8.0 Hz, 1H), 8.00 (d, J=4.0 Hz, 1H), 7.83-7.77 (m, 1H), 7.76-7.62 (m, 3H), 7.14 (d, J=8.0 Hz, 1H).

Example 65

N-(5-Cyano-6-(2H-1,2,3-triazol-2-yl)pyridin-3-yl)-1-(imidazo[1,2-a]pyrazin-8-yl)-5-(trifluoromethyl)-1H-pyrazole-4-carboxamide, Cpd 103

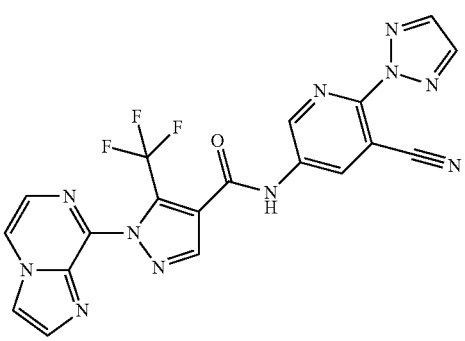 [SMILES: N#Cc1cc(NC(=O)c2cnn(-c3nccn4ccnc34)c2C(F)(F)F)cnc1-n1nccn1]

A. tert-Butyl 2-(imidazo[1,2-a]pyrazin-8-yl)hydrazine-1-carboxylate, 65a

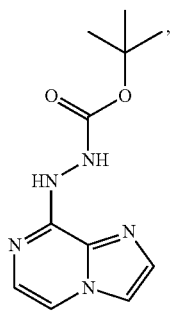

65a

8-Chloroimidazo[1,2-a]pyrazine (400 mg, 2.6 mmol) and tert-butyl hydrazinecarboxylate (516.4 g, 3.9 mmol) were dissolved in THF (8 mL), sodium hydride (312.5 mg, 7.8 mmol) was added, and the mixture stirred at 30° C. for 16 h. Saturated aqueous NH$_4$Cl (10 mL) was added and the mixture was extracted with EtOAc (10 mL×2). The combined organic layers were dried over Na$_2$SO$_4$, filtered, and the filtrates concentrated under reduced pressure to afford a crude product as a black oil. The crude product was purified by flash column chromatography over silica gel (petroleum ether/ethyl acetate from 100/0 to 30/70). The solvent was concentrated under reduced pressure to afford compound 65a as a yellow solid (220 mg, 28%). LCMS (ESI): m/z 250.1 [M+H]$^+$.

B. 8-Hydrazinylimidazo[1,2-a]pyrazine, 65b

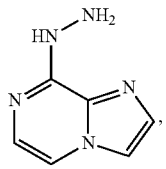

65b tert-Butyl 2-(imidazo[1,2-a]pyrazin-8-yl)hydrazine-1-carboxylate, 65a (220 mg, 0.72 mmol) was suspended in dichloromethane (5 mL) and HCl/dioxane (10 mL) was added. The reaction mixture was stirred at 30° C. for 1 h, then concentrated under reduced pressure to afford compound 65b as a yellow solid. The solid was used for the next step without further purification.

C. Ethyl 1-(imidazo[1,2-a]pyrazin-8-yl)-5-(trifluoromethyl)-1H-pyrazole-4-carboxylate, 65c

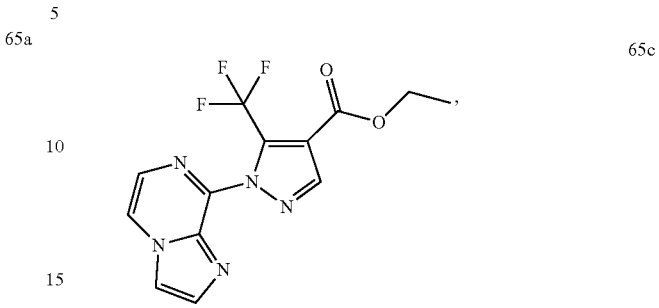

65c

8-Hydrazinylimidazo[1,2-a]pyrazine, 65b (160 mg, 1.1 mmol) and triethylamine (325.6 mg, 3.2 mmol) were dissolved in ethanol (3 mL), ethyl 2-(ethoxymethylene)-4,4,4-trifluoro-3-oxobutanoate, 1f (515.3 mg, 2.15 mmol) was added and the mixture stirred at 80° C. for 16 h. The reaction mixture was concentrated under reduced pressure to afford a crude brown solid. The solid was purified by flash column chromatography over silica gel (petroleum ether/ethyl acetate from 100/0 to 20/80). The solvent was concentrated under reduced pressure to afford compound 65c as a yellow oil (160 mg, 41%). LCMS (ESI): m/z 326.0 [M+H]$^+$.

D. 1-(Imidazo[1,2-a]pyrazin-8-yl)-5-(trifluoromethyl)-1H-pyrazole-4-carboxylic acid, 65d

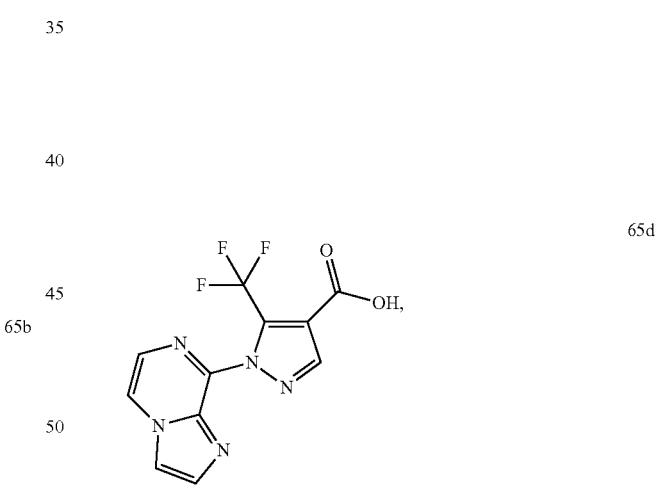

65d

Lithium hydroxide monohydrate (183.4 mg, 4.4 mmol) was added to ethyl 1-(imidazo[1,2-a]pyrazin-8-yl)-5-(trifluoromethyl)-1H-pyrazole-4-carboxylate, 65c (160 mg, 0.44 mmol) and the mixture stirred at 30° C. for 16 h. The reaction mixture was concentrated under reduced pressure to afford a crude yellow solid, which was used for the next step without further purification (160 mg).

E. N-(5-Cyano-6-(2H-1,2,3-triazol-2-yl)pyridin-3-yl)-1-(imidazo[1,2-a]pyrazin-8-yl)-5-(trifluoromethyl)-1H-pyrazole-4-carboxamide, Cpd 103

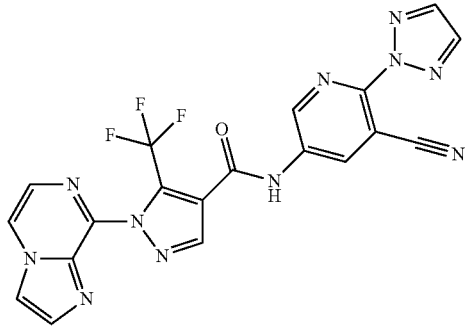 [SMILES: N#Cc1cc(NC(=O)c2cnn(-c3nccn4ccnc34)c2C(F)(F)F)cnc1-n1nccn1]

To a solution of 1-(imidazo[1,2-a]pyrazin-8-yl)-5-(trifluoromethyl)-1H-pyrazole-4-carboxylic acid, 65d (115 mg, 0.39 mmol), 5-amino-2-(2H-1,2,3-triazol-2-yl)nicotinonitrile, 7b (47.9 mg, 0.26 mmol) and pyridine (91.5 mg, 1.2 mmol) in dichloromethane (3 mL) was added POCl$_3$ (59.1 mg, 0.39 mmol) dropwise. The reaction mixture was stirred at 20° C. for 16 h. A solution of saturated aqueous NaHCO$_3$ (20 mL) was added and the mixture was extracted with dichloromethane (20 mL×2). The combined organic phases were washed with brine and dried over Na$_2$SO$_4$. The mixture was filtered, and the filtrates concentrated under reduced pressure to afford a crude product as a yellow oil. The crude product was purified by preparative HPLC to afford compound 103 as a white solid (5 mg, 4%). $^1$H NMR (400 MHz, METHANOL-d$_4$) δ ppm 9.04 (br s, 1H), 8.89 (d, J=2.6 Hz, 1H), 8.86 (d, J=4.6 Hz, 1H), 8.50-8.43 (m, 2H), 8.19 (d, J=4.6 Hz, 1H), 8.16 (s, 1H), 8.13 (s, 2H). LCMS (ESI): m/z 465.9 [M+H]$^+$.

Example 66

N-(5-Cyano-6-(2H-1,2,3-triazol-2-yl)pyridin-3-yl)-1-(quinoxalin-5-yl)-5-(trifluoromethyl)-1H-pyrazole-4-carboxamid, Cpd 105

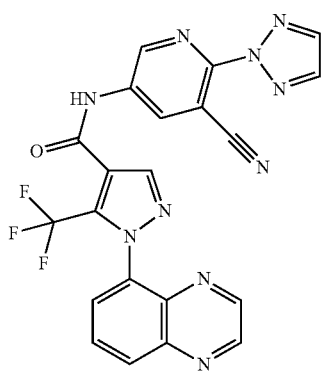 [SMILES: N#Cc1cc(NC(=O)c2cnn(-c3cccc4nccnc34)c2C(F)(F)F)cnc1-n1nccn1]

A. Di-tert-butyl 1-(quinoxalin-5-yl)hydrazine-1,2-dicarboxylate, 66a

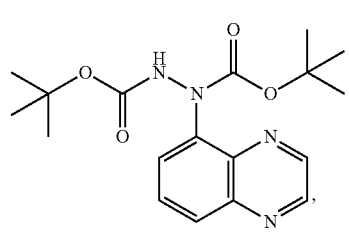

5-Bromoquinoxaline (300 mg, 1.44 mmol) and di-tert-butyl hydrazine-1,2-dicarboxylate (500 mg, 2.15 mmol) were dissolved in DMF (5 mL). CuI (27.5 mg, 0.14 mmol) and K$_3$PO$_4$ (609.3 mg, 2.87 mmol) were added and purged with N$_2$, cyclohexane-1,3-diamine (32.8 mg, 0.29 mmol) was added and the reaction mixture was stirred at 110° C. for 16 h. The reaction mixture was filtered through a pad of diatomaceous earth and the pad was washed with EtOAc (20 mL×3). The filtrate was concentrated under reduced pressure to afford a crude produce as a brown oil. The crude product was purified by column chromatography over silica gel (petroleum ether/ethyl acetate=100:0 to petroleum ether/ethyl acetate=50:50), and the solvents were removed under reduced pressure to afford compound 66a as a brown oil (0.3 g, 58%). LCMS (ESI): m/z 383.0 [M+H]$^+$.

B. 5-Hydrazinylquinoxaline, 66b

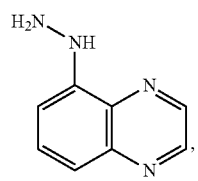

Di-tert-butyl 1-(quinoxalin-5-yl)hydrazine-1,2-dicarboxylate, 66a (300 mg, 0.48 mmol) in HCl in dioxane (10 mL) was mixed at 28° C. for 2 h. The solvent was concentrated under reduced pressure to afford compound 66b.

C. Ethyl 1-(quinoxalin-5-yl)-5-(trifluoromethyl)-1H-pyrazole-4-carboxylate, 66c

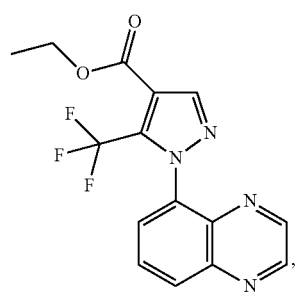

5-Hydrazinylquinoxaline, 66b (200 mg, 1.0 mmol) was dissolved in ethanol (5 mL), ethyl 2-(ethoxymethylene)-4,4,4-trifluoro-3-oxobutanoate, 1f (336.4 mg, 1.53 mmol) was added and the mixture stirred at 80° C. for 3 h. The reaction mixture was concentrated under reduced pressure to afford a crude product as a brown solid. The solid was purified by flash column chromatography over silica gel (petroleum ether/ethyl acetate from 100/0 to 50/50), and the solvent was concentrated under reduced pressure to afford compound 66c as a yellow oil (155 mg, 26%). LCMS (ESI): m/z 336.9 [M+H]+.

D. 1-(Quinoxalin-5-yl)-5-(trifluoromethyl)-1H-pyrazole-4-carboxylic acid, 66d

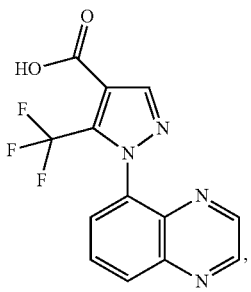

66d

Lithium hydroxide monohydrate (92 mg, 2.2 mmol) was added to ethyl 1-(quinoxalin-5-yl)-5-(trifluoromethyl)-1H-pyrazole-4-carboxylate, 66c (125 mg, 0.37 mmol) and stirred at 30° C. for 16 h. The reaction mixture was concentrated under reduced pressure to afford a crude product as a yellow solid. The crude product was used for the next step without further purification (95 mg).

E. N-(5-cyano-6-(2H-1,2,3-triazol-2-yl)pyridin-3-yl)-1-(quinoxalin-5-yl)-5-(trifluoromethyl)-1H-pyrazole-4-carboxamid, Cpd 105

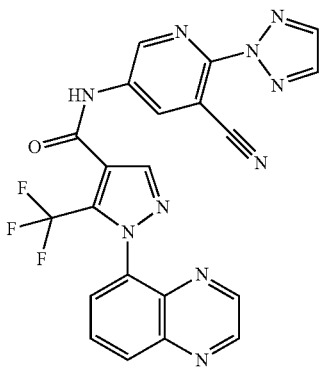 [SMILES: N#Cc1cc(NC(=O)c2cnn(-c3cccc4nccnc34)c2C(F)(F)F)cnc1-n1nccn1]

To a solution of 1-(quinoxalin-5-yl)-5-(trifluoromethyl)-1H-pyrazole-4-carboxylic acid, 66d (56.2 mg, 0.30 mmol), 5-amino-2-(2H-1,2,3-triazol-2-yl)nicotinonitrile, 7b (100 mg, 0.30 mmol) and pyridine (119 mg, 1.5 mmol) in dichloromethane (5 mL) was added POCl₃ (92.5 mg, 0.60 mmol) dropwise. The reaction mixture was stirred at 20° C. for 16 h. A solution of saturated aqueous NaHCO₃ (20 mL) was added and the mixture was extracted with dichloromethane (20 mL×2). The combined organic phases were washed with brine and dried over Na₂SO₄. The mixture was filtered, and the filtrates concentrated under reduced pressure to afford a crude product as a yellow oil. The crude product was purified by preparative HPLC to afford the compound 105 as a white solid (21 mg, 15%). ¹H NMR (400 MHz, DMSO-d₆) δ ppm 8.04-8.11 (m, 1H), 8.19-8.23 (m, 1H), 8.29 (s, 2H), 8.39 (d, J=8.38 Hz, 1H), 8.56 (s, 1H), 8.87 (d, J=2.43 Hz, 1H), 8.97 (d, J=1.54 Hz, 1H), 9.05-9.12 (m, 2H), 11.29 (s, 1H). LCMS (ESI): m/z 477.0 [M+H]+.

Example 67

N-(5-Chloro-6-(2H-1,2,3-triazol-2-yl)pyridin-3-yl)-1-(isoquinolin-4-yl)-1H-pyrazole-4-carboxamide, Cpd 76

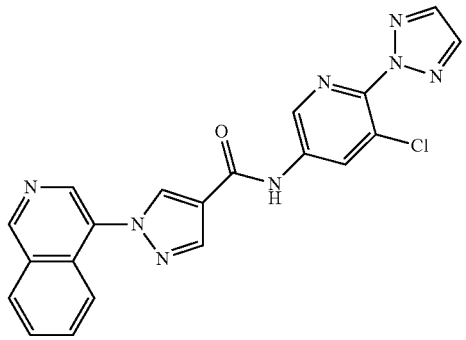 [SMILES: O=C(Nc1cnc(-n2nccn2)c(Cl)c1)c1cnn(-c2cncc3ccccc23)c1]

A solution consisting of 5-chloro-6-(2H-1,2,3-triazol-2-yl)pyridin-3-amine, 1j (87.8 mg, 0.449 mmol) and THF (1 mL) were added to 1 M potassium tert-butoxide in THF (1.35 mL, 1.35 mmol) at 0° C., then a solution consisting of ethyl 1-(isoquinolin-4-yl)-1H-pyrazole-4-carboxylate, 59a (120 mg, 0.449 mmol) and THF (1 mL) was added.

The resultant mixture was stirred at room temperature for 16 h. The reaction mixture was concentrated under reduced pressure to give a crude product, which was purified by preparative reverse phase HPLC (30% to 60% (v/v) ACN and H₂O with 0.05% NH₃) and lyophilized to give compound 76 (69.3 mg, 36%). LCMS (ESI): R$_T$=4.36 min, mass calcd. for C₂₀H₁₃ClN₈O 416.823, m/z found 416.9 [M+H]+. ¹H NMR (400 MHz, DMSO-d₆) δ ppm 10.74 (br.s., 1H), 9.52 (s, 1H), 9.01 (s, 1H), 8.88 (d, J=2.4 Hz, 1H), 8.76 (s, 1H), 8.70 (d, J=2.4 Hz, 1H), 8.54 (s, 1H), 8.35 (d, J=8.0 Hz, 1H), 8.19 (s, 2H), 7.98-7.92 (m, 2H), 7.89-7.84 (m, 1H)

Example 68

N-(5-Chloro-6-(2H-1,2,3-triazol-2-yl)pyridin-3-yl)-5-methyl-1-(quinolin-4-yl)-1H-pyrazole-4-carboxamide, Cpd 64

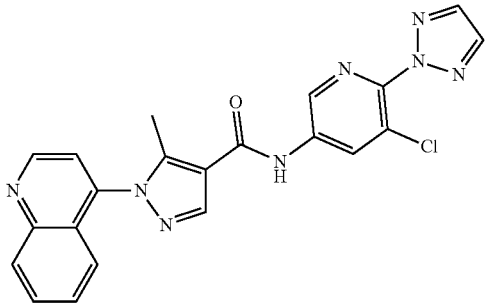 [SMILES: Cc1c(C(=O)Nc2cnc(-n3nccn3)c(Cl)c2)cnn1-c1ccnc2ccccc12]

A solution consisting of 5-chloro-6-(2H-1,2,3-triazol-2-yl)pyridin-3-amine, 1j (229 mg, 1.17 mmol) and THF (1 mL) was added dropwise to a solution of t-BuOK (3.2 mL, 3.2 mmol, 1 M in THF) at 0° C. Then a solution consisting of ethyl 5-methyl-1-(quinolin-4-yl)-1H-pyrazole-4-carboxylate, 60d (300 mg, 1.07 mmol) and THF (1 mL) was added dropwise. The resultant mixture was warmed to room temperature and stirred for 16 h before quenching with water and extracting with ethyl acetate (50 mL×3). The combined extracts were dried over anhydrous $Na_2SO_4$, filtered, and the filtrate concentrated to dryness under reduced pressure to give a residue, which was purified by preparative reverse phase HPLC (30% to 60% (v/v) $CH_3CN$ and $H_2O$ with 0.05% $NH_3$) and lyophilized to afford compound 64 (153 mg, 33%). LCMS (ESI): $R_T$=4.52 min, mass calcd. for $C_{21}H_{15}ClN_8O$ 430.850, m/z found 431.0 [M+H]$^+$. $^1$H NMR (400 MHz, DMSO-d$_6$) δ ppm 10.66 (s, 1H), 9.14 (d, J=4.4 Hz, 1H), 8.92 (d, J=2.4 Hz, 1H), 8.71 (d, J=2.4 Hz, 1H), 8.57 (s, 1H), 8.23 (d, J=8.4 Hz, 1H), 8.19 (s, 2H), 7.93-7.89 (m, 1H), 7.78 (d, J=4.4 Hz, 1H), 7.73-7.69 (m, 1H), 7.49 (d, J=8.0 Hz, 1H), 2.45 (s, 3H).

Example 69

N-(5-Chloro-6-(2H-1,2,3-triazol-2-yl)pyridin-3-yl)-1-(quinolin-5-yl)-1H-pyrazole-4-carboxamide, Cpd 60

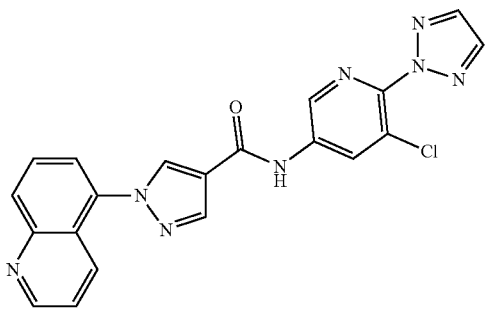 [SMILES: O=C(Nc1cnc(-n2nccn2)c(Cl)c1)c1cnn(-c2cccc3ncccc23)c1]

A solution consisting of 5-chloro-6-(2H-1,2,3-triazol-2-yl)pyridin-3-amine, 1j (102 mg, 0.524 mmol) and THF (1 mL) were added to 1 M potassium tert-butoxide in THF (1.57 mL, 1.57 mmol) at 0° C., then a solution consisting of ethyl 1-(quinolin-5-yl)-1H-pyrazole-4-carboxylate, 61a (140 mg, 0.524 mmol) and THF (1 mL) was added. The resultant mixture was stirred at room temperature for 16 h. The reaction mixture was concentrated under reduced pressure to give a crude product, which was purified by preparative reverse phase HPLC (30% to 60% (v/v) ACN and $H_2O$ with 0.05% $NH_3$) to afford compound 60 (104.50 mg, 49%). LCMS (ESI): $R_T$=4.01 min, mass calcd. for $C_{20}H_{13}ClN_8O$ 416.823, m/z found 417.0 [M+H]$^+$. $^1$H NMR (400 MHz, DMSO-d$_6$) δ 9.04 (dd, J=1.6, 4.0 Hz, 1H), 8.96 (s, 1H), 8.88 (d, J=2.4 Hz, 1H), 8.70 (d, J=2.4 Hz, 1H), 8.50 (s, 1H), 8.33-8.28 (m, 1H), 8.24 (d, J=8.4 Hz, 1H), 8.19 (s, 2H), 7.98-7.92 (m, 1H), 7.89-7.85 (m, 1H), 7.68 (dd, J=4.0, 8.4 Hz, 1H).

Example 70

Methyl 2-(3-chloro-5-(1-(quinolin-5-yl)-5-(trifluoromethyl)-1H-pyrazole-4-carboxamido)pyridin-2-yl)-2H-1,2,3-triazole-4-carboxylate, Cpd 108

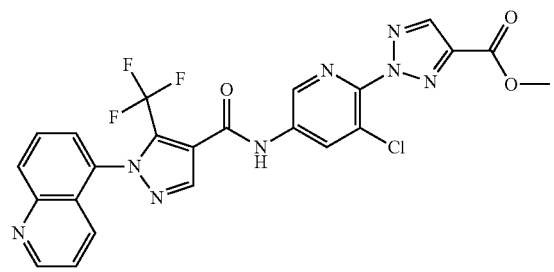 [SMILES: COC(=O)c1cnn(-c2ncc(NC(=O)c3cnn(-c4cccc5ncccc45)c3C(F)(F)F)cc2Cl)n1]

A. Mixture of methyl 1-(3-chloro-5-nitropyridin-2-yl)-1H-1,2,3-triazole-5-carboxylate compound with methyl 2-(3-chloro-5-nitropyridin-2-yl)-2H-1,2,3-triazole-4-carboxylate, 70a

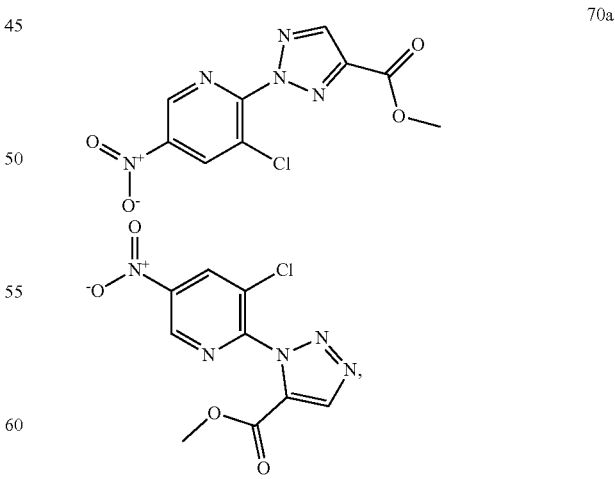

Potassium carbonate (7249.14 mg, 52.45 mmol) was added to a solution of 2,3-dichloro-5-nitropyridine (7249.14 mg, 17.48 mmol) and methyl 1h-1,2,3-triazole-4-carboxylate (2000 mg, 15.76 mmol) in MeCN (20 mL). The mixture was reacted at 60° C. for 12 h. The reaction mixture was filtered, the filtrate was concentrated under reduced pressure to give the crude product as yellow oil, which was purified by FFS (petroleum ether/ethyl acetate=100:0 to petroleum ether/ethyl acetate=40:60). The pure fractions were collected and the solvent was concentrated under reduced pressure to give the product as yellow solid.

B. Methyl 2-(5-amino-3-chloropyridin-2-yl)-2H-1,2,3-triazole-4-carboxylate, 108b

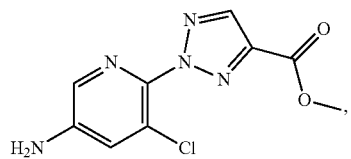

108b

Mixture of methyl 1-(3-chloro-5-nitropyridin-2-yl)-1H-1,2,3-triazole-5-carboxylate and methyl 2-(3-chloro-5-nitropyridin-2-yl)-2H-1,2,3-triazole-4-carboxylate (2500 mg, 4.41 mmol) was added to a solution of Fe (1230 mg, 22.04 mmol) and NH₄Cl (1178 mg, 22.04 mmol) in THF (10 mL)/water (5 mL). The reaction mixture was filtered through a pad of diatomaceous earth and the pad was washed with EtOAc (50 mL×2). The combined filtrates were concentrated to dryness to give crude as yellow solid, which was purified by FFS (petroleum ether/ethyl acetate=50:50 to petroleum ether/ethyl acetate=0:100). The desired fractions were collected and the solvent was concentrated under reduced pressure. $^1$H NMR (400 MHz, CHLOROFORM-d) δ ppm 3.98 (s, 3H), 4.17 (br s, 2H), 7.17 (d, J=2.43 Hz, 1H), 7.91 (d, J=2.65 Hz, 1H), 8.30 (s, 1H).

C. Methyl 2-(3-chloro-5-(1-(quinolin-5-yl)-5-(trifluoromethyl)-1H-pyrazole-4-carboxamido)pyridin-2-yl)-2H-1,2,3-triazole-4-carboxylate, Cpd 108

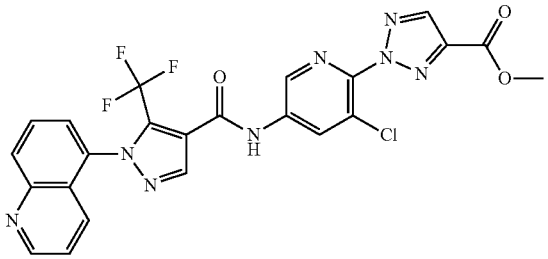 [SMILES: COC(=O)c1cnn(-c2ncc(NC(=O)c3cnn(-c4cccc5ncccc45)c3C(F)(F)F)cc2Cl)n1]

1-(Quinolin-5-yl)-5-(trifluoromethyl)-1H-pyrazole-4-carboxylic acid (240.87 mg, 0.77 mmol), methyl 2-(5-amino-3-chloropyridin-2-yl)-2H-1,2,3-triazole-4-carboxylate (200 mg, 0.79 mmol), POCl₃ (142.24 mg, 0.93 mmol) were dissolved in DCM (8 mL), and pyridine (183.44 mg, 2.32 mmol) was added. The mixture was stirred at 25° C. for 1 h, sat. NaHCO₃ (30 mL) was added and extracted with CH₂Cl₂ (30 mL×2). The combined organic layers were dried over Na₂SO₄, filtered and the filtrates were concentrated under reduced pressure to afford a brown oil, which was purified by FFS (petroleum ether/ethyl acetate=50:50 to petroleum ether/ethyl acetate=0:100). The desired fractions were collected and the solvent was concentrated under reduced pressure to give the product as yellow solid. $^1$H NMR (400 MHz, DMSO-d₆) δ ppm 3.90 (s, 3H), 7.58-7.62 (m, 1H), 7.64-7.69 (m, 1H), 7.90-7.99 (m, 2H), 8.32 (d, J=8.38 Hz, 1H), 8.59 (s, 1H), 8.69 (s, 1H), 8.71 (d, J=2.21 Hz, 1H), 8.87 (d, J=2.43 Hz, 1H), 9.05 (dd, J=3.97, 1.54 Hz, 1H), 11.32 (s, 1H). LCMS (ESI) m/z M+1: 543.2.

Example 109

2-(3-chloro-5-(1-(quinolin-5-yl)-5-(trifluoromethyl)-1H-pyrazole-4-carboxamido)pyridin-2-yl)-2H-1,2,3-triazole-4-carboxylic acid, Cpd 109

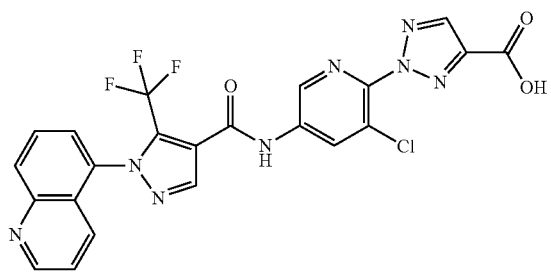 [SMILES: O=C(O)c1cnn(-c2ncc(NC(=O)c3cnn(-c4cccc5ncccc45)c3C(F)(F)F)cc2Cl)n1]

NaOH (63.528 mg, 1.588 mmol) was added to a solution of methyl 2-(3-chloro-5-(1-(quinolin-5-yl)-5-(trifluoromethyl)-1H-pyrazole-4-carboxamido)pyridin-2-yl)-2H-1,2,3-triazole-4-carboxylate, cpd 108 (445 mg, 0.794 mmol) in EtOH/H₂O=1:1 (5 mL) was reacted at 18° C. for 2 h. The solvent was concentrated under reduced pressure, 1M HCl solution was add to the mixture to adjust the pH to ~5 and solid formed. The solid was collected to afford the product. $^1$H NMR (400 MHz, DMSO-d₆) δ ppm 7.58-7.62 (m, 1H), 7.64-7.69 (m, 1H), 7.90-7.99 (m, 2H), 8.32 (d, J=7.94 Hz, 1H), 8.58 (d, J=11.47 Hz, 2H), 8.70 (d, J=2.21 Hz, 1H), 8.87 (d, J=2.21 Hz, 1H), 9.05 (dd, J=3.97, 1.54 Hz, 1H), 11.34 (s, 1H). LCMS (ESI) m/z M+1: 542.9.

Example 110

1-(1-amino-8-fluoroisoquinolin-4-yl)-N-(5-chloro-6-(2H-1,2,3-triazol-2-yl)pyridin-3-yl)-5-(trifluoromethyl)-1H-pyrazole-4-carboxamide, Cpd 110

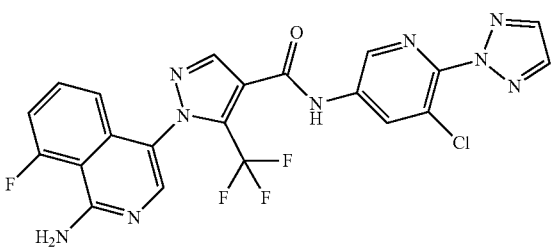 [SMILES: Nc1ncc(-n2ncc(C(=O)Nc3cnc(-n4nccn4)c(Cl)c3)c2C(F)(F)F)c2cccc(F)c12]

A. 8-Fluoro-4-hydrazinylisoquinoline, 110a

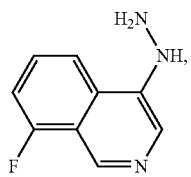

110a

A mixture of palladium (II) (pi-cinnamyl) (103.14 mg, 0.20 mmol) chloride dimer and N-[2-(di-1-adamantylphosphino) phenyl] morpholine (184.6 mg, 0.40 mmol) in dioxane (20 mL) was evacuated with argon (4×). The resulting clear yellow solution was stirred at room temp under argon for 10 min. 4-Bromo-8-fluoroisoquinoline (900 mg, 3.98 mmol) and tBuONa (765.27 mg, 7.96 mmol) were added to the mixture and purged with argon (4×). The resulting yellow reaction was stirred at room temperature for 5 min and then treated with hydrazine (398.63 mg, 7.96 mmol) via syringe and purged with argon (4×). Then the mixture was stirred at 55° C. under argon for 2 h. The reaction mixture was filtered. The filtrate was concentrated under reduced pressure to give the crude product as a brown solid.

B. Ethyl 1-(8-fluoroisoquinolin-4-yl)-5-(trifluoromethyl)-1H-pyrazole-4-carboxylate, 110b

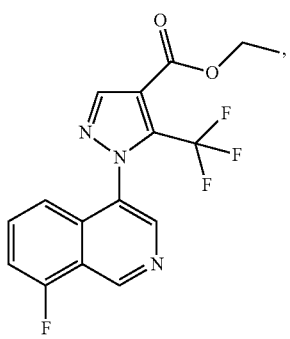

110b

8-Fluoro-4-hydrazinylisoquinoline (700 mg, 3.95 mmol) was added to a solution of ethyl ethyl 2-(ethoxymethylene)-4,4,4-trifluoro-3-oxobutanoate (1423.34 mg, 5.93 mmol) in EtOH (15 mL) was reacted at 80° C. for 1 h. The mixture was concentrated under reduced pressure, then was purified by FFS (petroleum ether/ethyl acetate=100:0 to petroleum ether/ethyl acetate=80:20). The desired fractions were collected and the solvent was concentrated under reduced pressure to give the product as brown oil. LCMS (ESI) m/z M+1: 353.9.

C. 4-(4-(Ethoxycarbonyl)-5-(trifluoromethyl)-1H-pyrazol-1-yl)-8-fluoroisoquinoline 2-oxide, 110c

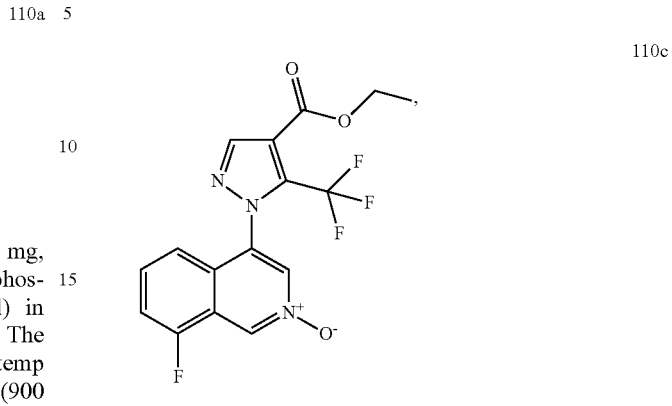

110c m-CPBA (700 mg, 3.95 mmol) was added to a solution of ethyl 1-(8-fluoroisoquinolin-4-yl)-5-(trifluoromethyl)-1H-pyrazole-4-carboxylate (800 mg, 2.25 mmol) in DCM (10 mL) was reacted at 30° C. for 2 h. The mixture was added to 40 mL sat.Na$_2$CO$_3$ solution, extracted with 50 mL CH$_2$Cl$_2$, the organic layer was concentrated under reduced pressure and purified by FFS (petroleum ether/ethyl acetate=100:0 to petroleum ether/ethyl acetate=50:50). The desired fractions were collected and the solvent was concentrated under reduced pressure to give the product as a yellow oil. LCMS (ESI) m/z M+1: 370.0.

D. Ethyl 1-(1-chloro-8-fluoroisoquinolin-4-yl)-5-(trifluoromethyl)-1H-pyrazole-4-carboxylate, 110d

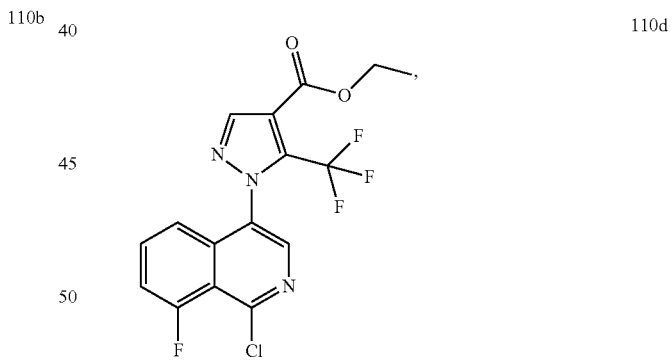

110d

POCl$_3$ (5 mL) was added to a solution of 4-(4-(ethoxycarbonyl)-5-(trifluoromethyl)-1H-pyrazol-1-yl)-8-fluoroisoquinoline 2-oxide, (720 mg, 1.95 mmol) in CHCl$_3$ (15 mL) was reacted at 70° C. for 2 h. The mixture was added to 30 mL sat.Na$_2$CO$_3$ solution, extracted with 30 mL CH$_2$Cl$_2$, the organic layer was concentrated under reduced pressure, then purified by FFS (petroleum ether/ethyl acetate=100:0 to petroleum ether/ethyl acetate=85:15). The desired fractions were collected and the solvent was concentrated under reduced pressure to give the product as colorless oil. LCMS (ESI) m/z M+1: 388.0.

E. 1-(1-Chloro-8-fluoroisoquinolin-4-yl)-5-(trifluoromethyl)-1H-pyrazole-4-carboxylic acid, 110e

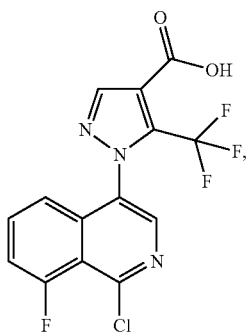

110e

LiOH (70.415 mg, 2.940 mmol) was added to a solution of ethyl 1-(thieno[2,3-c]pyridin-7-yl)-5-(trifluoromethyl)-1H-pyrazole-4-carboxylate (240 mg, 0.59 mmol) in THF/H$_2$O=1:1 (10 mL) was reacted at 23° C. for 2 h. The solvent was concentrated under reduced pressure, 1M HCl solution was add to the mixture to adjust the pH to ~5 and EtOAc (30 mL×3) was added to the mixture. The combined organic layers were dried over Na$_2$SO$_4$, filtered and the filtrates were concentrated under reduced pressure to afford the product as a brown oil. LCMS (ESI) m/z M+1: 359.9.

F. N-(5-Chloro-6-(2H-1,2,3-triazol-2-yl)pyridin-3-yl)-1-(1-chloro-8-fluoroisoquinolin-4-yl)-5-(trifluoromethyl)-1H-pyrazole-4-carboxamide, 110f

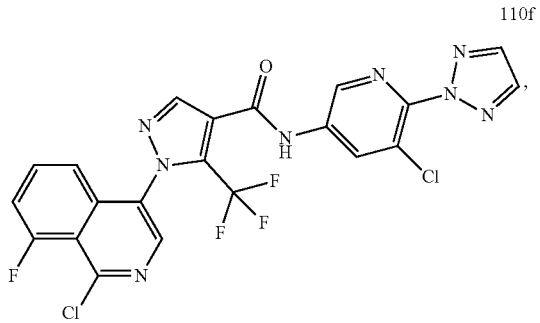 [SMILES: O=C(Nc1cnc(-n2nccn2)c(Cl)c1)c1cnn(-c2cnc(Cl)c3c(F)cccc23)c1C(F)(F)F]

110f 1-(1-Chloro-8-fluoroisoquinolin-4-yl)-5-(trifluoromethyl)-1H-pyrazole-4-carboxylic acid (210 mg, 0.22 mmol), 5-chloro-6-(2H-1,2,3-triazol-2-yl)pyridin-3-amine (107.93 mg, 0.55 mmol), POCl$_3$ (96.69 mg, 0.63 mmol) were dissolved in DCM (5 mL), and pyridine (124.7 mg, 1.58 mmol) was added. The mixture was stirred at 25° C. for 1 h, sat.NaHCO$_3$ (10 mL) was added and extracted with CH$_2$Cl$_2$ (15 mL×2). The combined organic layers were dried over Na$_2$SO$_4$, filtered and the filtrates were concentrated under reduced pressure to afford the product as a brown oil. LCMS (ESI) m/z M+1: 536.9.

G. 1-(1-amino-8-fluoroisoquinolin-4-yl)-N-(5-chloro-6-(2H-1,2,3-triazol-2-yl)pyridin-3-yl)-5-(trifluoromethyl)-1H-pyrazole-4-carboxamide, Cpd 110

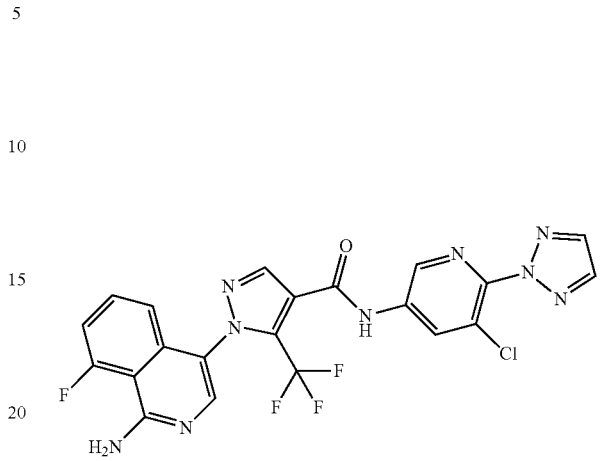

N-(5-Chloro-6-(2H-1,2,3-triazol-2-yl)pyridin-3-yl)-1-(1-chloro-8-fluoroisoquinolin-4-yl)-5-(trifluoromethyl)-1H-pyrazole-4-carboxamide (200 mg, 0.18 mmol) in NH$_3$.H$_2$O (12 mL) was reacted at 80° C. for 16 h. The solvent was concentrated under reduced pressure the give the crude compound, which was purified by preparative HPLC (77% to 57% (v/v) CH$_3$CN and H$_2$O with 0.05% HCl) and lyophilized to dryness to afford the title compound (29 mg, 31.5%). LCMS (ESI) m/z M+1: 518.0. $^1$H NMR (400 MHz, DMSO-d$_6$) δ ppm 6.77 (d, J=8.53 Hz, 1H), 7.56 (dd, J=12.92, 7.91 Hz, 1H), 7.81-7.91 (m, 1H), 8.20 (s, 2H), 8.22 (s, 1H), 8.61 (s, 1H), 8.70 (d, J=2.01 Hz, 1H), 8.89 (d, J=2.01 Hz, 1H), 11.36 (s, 1H).

Example 111

1-(1-amino-8-fluoroisoquinolin-4-yl)-N-(5-cyano-6-(2H-1,2,3-triazol-2-yl)pyridin-3-yl)-5-(trifluoromethyl)-1H-pyrazole-4-carboxamide, Cpd 111

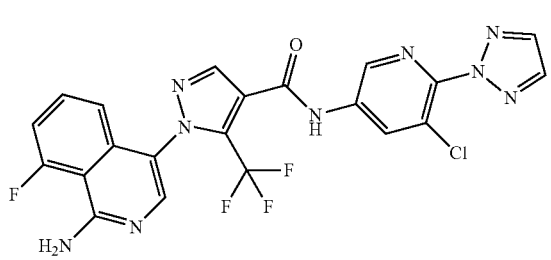 [SMILES: Nc1ncc(-n2ncc(C(=O)Nc3cnc(-n4nccn4)c(Cl)c3)c2C(F)(F)F)c2cccc(F)c12]

A. 1-(1-chloro-8-fluoroisoquinolin-4-yl)-N-(5-cyano-6-(2H-1,2,3-triazol-2-yl)pyridin-3-yl)-5-(trifluoromethyl)-1H-pyrazole-4-carboxamide, 111a

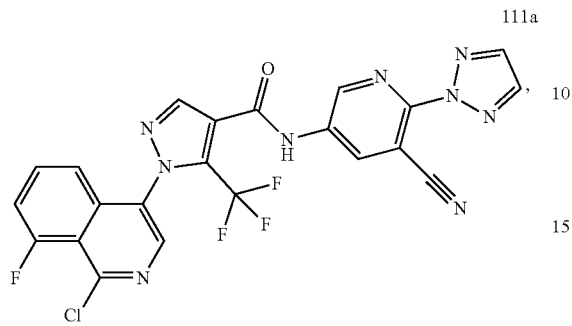

111a 1-(1-chloro-8-fluoroisoquinolin-4-yl)-5-(trifluoromethyl)-1H-pyrazole-4-carboxylic acid, cpd 110e (230 mg, 0.588 mmol), 5-amino-2-(2H-1,2,3-triazol-2-yl)nicotinonitrile (109.474 mg, 0.588 mmol), POCl₃ (108.195 mg, 0.706 mmol) were dissolved in DCM (5 mL), and pyridine (139.537 mg, 1.764 mmol) was added. The mixture was stirred at 25° C. for 1 h, sat. NaHCO₃ (10 mL) was added and extracted with CH₂Cl₂ (15 mL×2). The combined organic layers were dried over Na₂SO₄, filtered and the filtrates were concentrated under reduced pressure to afford crude as brown oil which was purified by FFS (petroleum ether/ethyl acetate=10:1 to ethyl acetate). The desired fractions were collected and the solvent was concentrated under reduced pressure to give the product as colorless oil. LCMS (ESI) m/z M+1: 528.1

B. 1-(1-amino-8-fluoroisoquinolin-4-yl)-N-(5-cyano-6-(2H-1,2,3-triazol-2-yl)pyridin-3-yl)-5-(trifluoromethyl)-1H-pyrazole-4-carboxamide, Cpd 111

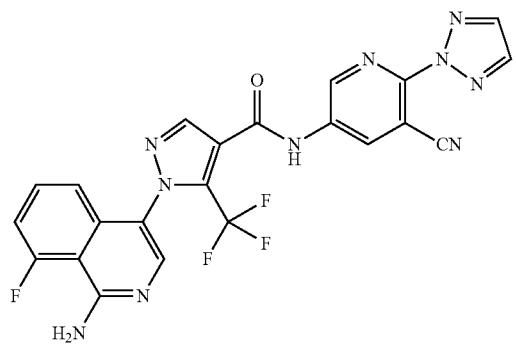 [SMILES: N#Cc1cc(NC(=O)c2cnn(-c3cnc(N)c4c(F)cccc34)c2C(F)(F)F)cnc1-n1nccn1]

1-(1-Chloro-8-fluoroisoquinolin-4-yl)-N-(5-cyano-6-(2H-1,2,3-triazol-2-yl)pyridin-3-yl)-5-(trifluoromethyl)-1H-pyrazole-4-carboxamide (140 mg, 0.262 mmol) in NH₃.H₂O (10 mL) was stirred at 60° C. for 2 h. The solvent was concentrated under reduced pressure the give the crude compound, which was purified by preparative HPLC (83% to 53% (v/v) CH₃CN and H₂O with 0.05% HCl) and lyophilized to dryness to afford the title compound (50.0 mg, 37.6%). ¹H NMR (400 MHz, DMSO-d₆) δ ppm 6.79 (d, J=8.28 Hz, 1H), 7.60 (dd, J=12.92, 7.91 Hz, 1H), 7.90 (td, J=8.16, 5.27 Hz, 1H), 8.27 (s, 1H), 8.32 (s, 2H), 8.64 (s, 1H), 8.91 (d, J=2.51 Hz, 1H), 9.15 (d, J=2.26 Hz, 1H). LCMS (ESI) m/z M+1: 508.9. 11.51 (s, 1H).

Example 112

N-(5-chloro-2-methyl-6-(2H-1,2,3-triazol-2-yl)pyridin-3-yl)-1-(1-oxo-1,2-dihydroisoquinolin-5-yl)-5-(trifluoromethyl)-1H-pyrazole-4-carboxamide, Cpd 112

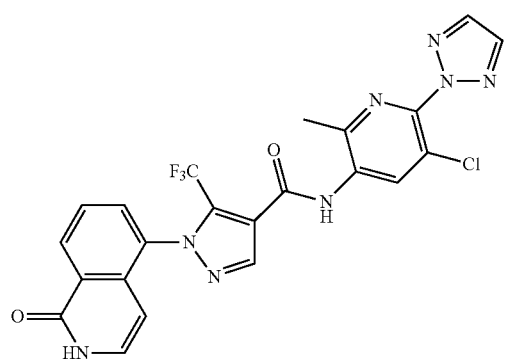 [SMILES: Cc1nc(-n2nccn2)c(Cl)cc1NC(=O)c1cnn(-c2cccc3c(=O)[nH]ccc23)c1C(F)(F)F]

A. 5-hydrazinylisoquinoline, 112a

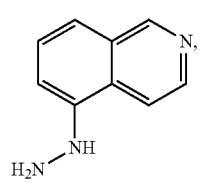

112a

To a stirring solution of isoquinolin-5-amine (30 g, 208.1 mmol) in concentrated HCl (300 mL) at 0° C. was added a solution of sodium nitrite (21.5 g, 312.1 mmol) in H₂O (85 mL) below 0° C. The reaction mixture was stirred at 0° C. for 30 min and a solution of tin(II) chloride dehydrate (117.4 g, 520.2 mmol) dissolved in concentrated HCl (55 mL) was added dropwise. The mixture was stirred at room temperature for 3 h. The mixture was adjusted to pH 12-14 with 20% aqueous sodium hydroxide. The mixture was extracted with ethyl acetate. The organic layer was dried (Na₂SO₄), filtered, and concentrated under reduced pressure to afford the title product as a yellow solid (27 g, 81.5% yield).

B. Ethyl 1-(isoquinolin-5-yl)-5-(trifluoromethyl)-1H-pyrazole-4-carboxylate, 112b

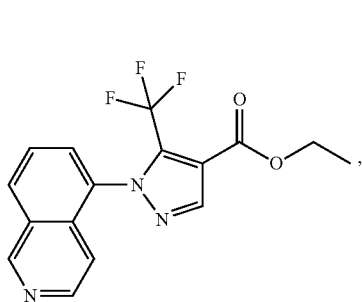

112b

A solution consisting of 5-hydrazinylisoquinoline (27 g, 169.6 mmol) and ethyl 2-(ethoxymethylene)-4,4,4-trifluoro-3-oxobutanoate (40.7 g, 169.6 mmol) in EtOH (300 mL) was stirred at 60° C. for 3 h. The resultant solution was cooled to room temperature and concentrated to dryness under reduced pressure to afford the crude product. The crude product was purified by column chromatography over silica gel (petroleum ether/ethyl acetate=100:0 to 70:30). The solvent was concentrated to get the title product as yellow solid (22 g, 38.7% yield). LCMS (ESI) m/z M+1: 336.0.

C. 5-(4-(ethoxycarbonyl)-5-(trifluoromethyl)-1H-pyrazol-1-yl)isoquinoline 2-oxide, 112c

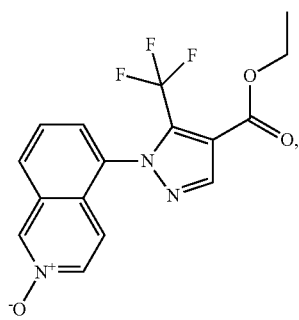

112c

To a cooled (0° C.) solution of ethyl 1-(isoquinolin-5-yl)-5-(trifluoromethyl)-1H-pyrazole-4-carboxylate (3 g, 8.95 mmol) in DCM (40 mL) was added mCPBA (4.63 g, 26.8 mmol) over 10 min. The mixture was warmed to rt and allowed to stir overnight. The solution was washed twice with a half-saturated aqueous solution of sodium bisulfite (100 mL) to destroy excess oxidant. The mixture was then twice washed with half-saturated aqueous potassium carbonate (100 mL), and brine (100 mL). The extracts were dried over magnesium sulfate, filtered and concentrated to afford a crude oil that was purified by flash column chromatography over silica gel (eluent: petroleum ether/ethyl acetate from 100/0 to 20/80). The desired fractions were collected and the solvent was concentrated to dryness under reduced pressure to give title product as yellow solid (2 g, 63.6% yield). LCMS (ESI) m/z M+1: 351.9.

D. Ethyl 1-(1-chloroisoquinolin-5-yl)-5-(trifluoromethyl)-1H-pyrazole-4-carboxylate, 112d

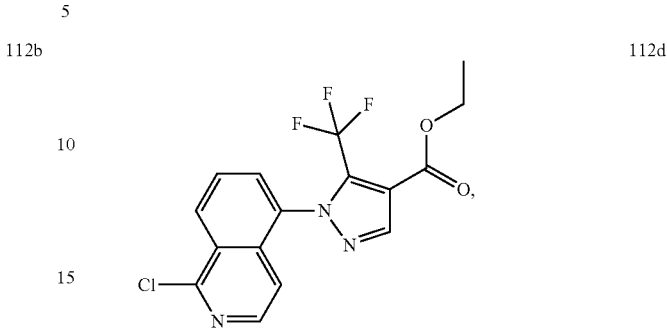

112d

A solution consisting of POCl₃ (16.6 g, 108.2 mmol) and 5-(4-(ethoxycarbonyl)-5-(trifluoromethyl)-1H-pyrazol-1-yl)isoquinoline 2-oxide (19 g, 54.1 mmol) in CHCl₃ (40 mL) was stirred at 60° C. for 3 h. The resulting solution was cooled to room temperature and concentrated to dryness under reduced pressure to afford the crude product. The crude product was purified by column chromatography over silica gel (petroleum ether/ethyl acetate=100:0 to 70:30). The solvent was concentrated to get the title product as a yellow solid (12 g, 60.0% yield). LCMS (ESI) m/z M+1: 369.9

E. 1-(1-Oxo-1,2-dihydroisoquinolin-5-yl)-5-(trifluoromethyl)-1H-pyrazole-4-carboxylic acid, 112e

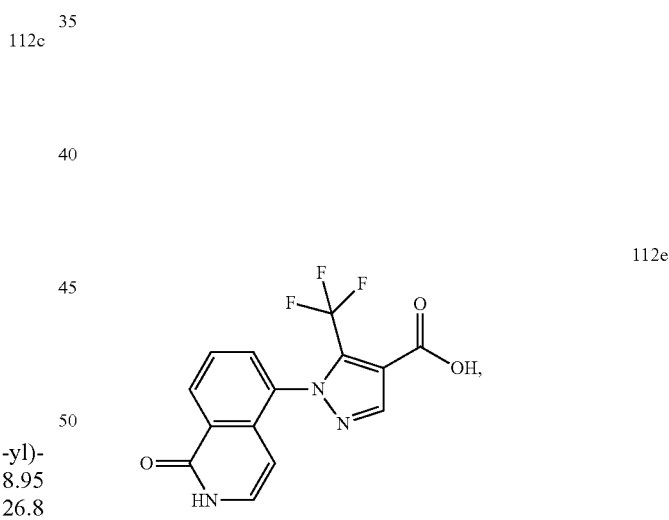

112e

A mixture of ethyl 1-(1-chloroisoquinolin-5-yl)-5-(trifluoromethyl)-1H-pyrazole-4-carboxylate (12 g, 32.546 mmol) in concentrated HCl (20 mL) was stirred at 120° C. for 3 h. The solvent concentrated under reduced pressure to give the product as a yellow solid (11 g, 83% yield). LCMS (ESI) m/z M+H: 324.1.

F. N-(5-chloro-2-methyl-6-(2H-1,2,3-triazol-2-yl)pyridin-3-yl)-1-(1-oxo-1,2-dihydroisoquinolin-5-yl)-5-(trifluoromethyl)-1H-pyrazole-4-carboxamide, Cpd 112

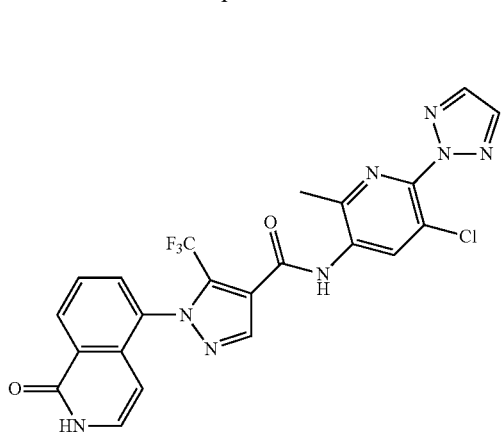

POCl₃ (5.26 g, 30.3 mmol) was added to a solution of 1-(1-oxo-1,2-dihydroisoquinolin-5-yl)-5-(trifluoromethyl)-1H-pyrazole-4-carboxylic acid (7.0 g, 17.2 mmol), 5-chloro-2-methyl-6-(2H-1,2,3-triazol-2-yl)pyridin-3-amine (3.96 g, 18.9 mmol) in pyridine (20 mL). The mixture was stirred at rt for 3h, 50 mL sat. NaHCO₃ (500 mL) added to the mixture, extracted with CH₂Cl₂ (500 mL×2). The organic layer was washed with brine (200 mL), dried over MgSO₄ and concentrated under reduced pressure to afford the crude product, which was purified by preparative HPLC (5% to 60% (v/v) CH₃CN and H₂O with 0.05% HCl) and concentrated to dryness to afford the title compound (5.7 g, 64.4% yield) as a white solid. LCMS (ESI) m/z M+1: 515.2. ¹H NMR (400 MHz, DMSO-d₆) δ ppm 2.54 (s, 3H), 5.67 (d, J=7.50 Hz, 1H), 7.28 (dd, J=7.17, 5.84 Hz, 1H), 7.66 (t, J=7.83 Hz, 1H), 7.93 (dd, J=7.61, 0.99 Hz, 1H), 8.14-8.20 (m, 2H), 8.43 (t, J=3.97 Hz, 2H), 8.51 (s, 1H), 10.59 (s, 1H), 11.61 (br d, J=5.29 Hz, 1H).

Example 113

N-(5-cyano-6-(2H-1,2,3-triazol-2-yl)pyridin-3-yl)-1-(1-oxo-1,2-dihydroisoquinolin-5-yl)-5-(trifluoromethyl)-1H-pyrazole-4-carboxamide, Cpd 113

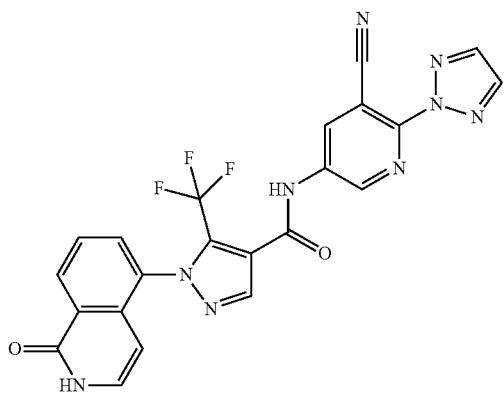 [SMILES: N#Cc1cc(NC(=O)c2cnn(-c3cccc4c(=O)[nH]ccc34)c2C(F)(F)F)cnc1-n1nccn1]

A. 5-bromo-1-methoxyisoquinoline, 113a

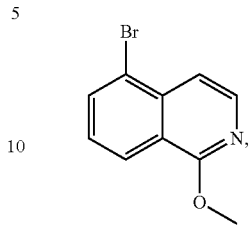

Iodomethane (9.50 g, 66.95 mmol) was added to a solution of 5-bromoisoquinolin-1(2H)-one (5 g, 22.32 mmol), Ag₂CO₃ (18.46 g, 66.95 mmol) in CH₃CN (100 mL). The mixture was stirred at 40° C. for 16 h. The mixture was filtered and washed with ethyl acetate (100 mL×3). The filtrate was collected and concentrated under reduced pressure, and the crude product was purified by column chromatography over silica gel (petroleum ether/ethyl acetate from 100:1 to 10:1). The desired fractions were collected and the solvent was concentrated under reduced pressure to afford 113a (2 g, 37.6% yield) as a white oil.

B. 5-hydrazinyl-1-methoxyisoquinoline, 113b

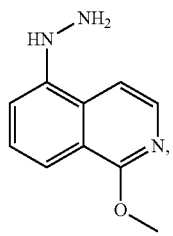

The mixture of {Pd(cinnamyl)Cl}₂ (217.607 mg, 0.420 mmol) and Mor-DalPhos (389.476 mg, 0.840 mmol) in dioxane (60 mL) was purged with argon (4×). The resulting clear yellow solution was stirred at room temp under argon for 10 min. cpd 113a (2 g, 8.401 mmol) and t-BuONa (1612.896 mg, 16.801 mmol) was added to the mixture and the mixture was purged with argon (4×). The resulting yellow reaction was stirred at room temp for 5 min and was then treated with hydrazine hydrate (858.230 mg, 16.801 mmol) via syringe. The reaction was purged with argon (4×). Then the mixture was stirred at 50° C. under argon for 4 h. The mixture was filtered and washed with ethyl acetate (50 mL×3). The filtrate was collected and concentrated to afford crude cpd 113b (1.6 g) as a yellow solid which was used directly for the next step.

C. Ethyl 1-(1-methoxyisoquinolin-5-yl)-5-(trifluoromethyl)-1H-pyrazole-4-carboxylate, 113c

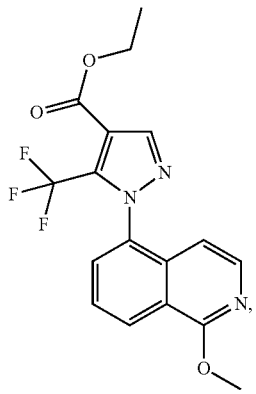

A solution of 5-hydrazinyl-1-methoxyisoquinoline, cpd 113b (1.6 g, 8.46 mmol), ethyl 2-(ethoxymethylene)-4,4,4-trifluoro-3-oxobutanoate (3.05 g, 12.68 mmol), triethylamine (2.562 g, 25.368 mmol) in EtOH (50 mL) was stirred at 80° C. for 12 h. The mixture was concentrated under reduced pressure, the crude product was purified by column chromatography over silica gel (petroleum ether/ethyl acetate from 100:0 to 10:1). The desired fractions were collected and the solvent was concentrated under reduced pressure to afford cpd 113c (2.2 g, 71.2% yield) as a yellow solid. LCMS (ESI) m/z M+1: 365.9.

D. 1-(1-hydroxyisoquinolin-5-yl)-5-(trifluoromethyl)-1H-pyrazole-4-carboxylic acid, 113d

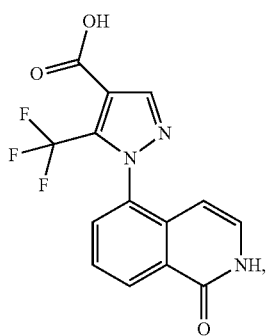

Ethyl 1-(1-methoxyisoquinolin-5-yl)-5-(trifluoromethyl)-1H-pyrazole-4-carboxylate, cpd 113c g, 2.74 mmol) was added to HCl (10 mL). The mixture was stirred at 130° C. for 3h and concentrated under reduced pressure to afford cpd 113d (530 mg, 55.5% yield) as brown solid which used directly for the next step. LCMS (ESI) m/z M+H: 323.9.

E. N-(5-cyano-6-(2H-1,2,3-triazol-2-yl)pyridin-3-yl)-1-(1-oxo-1,2-dihydroisoquinolin-5-yl)-5-(trifluoromethyl)-1H-pyrazole-4-carboxamide, Cpd 113

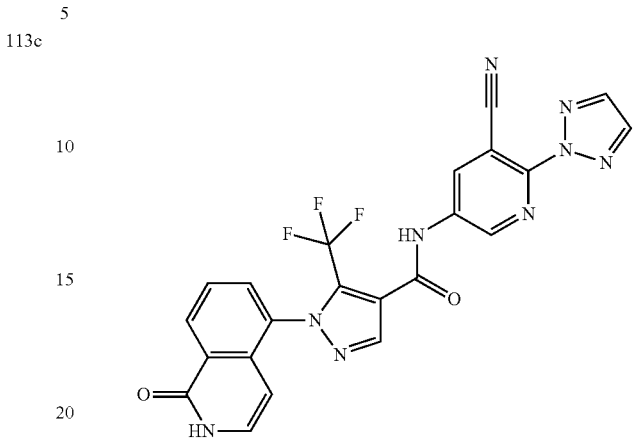

1-(1-Oxo-1,2-dihydroisoquinolin-5-yl)-5-(trifluoromethyl)-1H-pyrazole-4-carboxylic acid, cpd 113d (170 mg, 0.37 mmol), 5-amino-2-(2H-1,2,3-triazol-2-yl)nicotinonitrile, (69.15 mg, 0.37 mmol), pyridine (0.15 mL, 1.86 mmol) were dissolved in $CH_2Cl_2$ (10 mL), and phosphorus oxychloride (0.14 mL, 1.49 mmol) was added. The mixture was stirred at 25° C. for 2 h. Sat.NaHCO$_3$ (20 mL) was added and extracted with $CH_2Cl_2$ (30 mL×2). The combined organic extracts were dried over anhydrous $Na_2SO_4$, filtered, and concentrated to dryness under reduced pressure to afford the crude product, which was purified by preparative HPLC (35% to 65% (v/v) $CH_3CN$ and $H_2O$ with 0.05% HCl) and lyophilized to dryness to afford the title compound (46 mg, 24.6%). LCMS (ESI) m/z M+1: 491.9. $^1$H NMR (400 MHz, DMSO-d$_6$) δ ppm 11.62 (1H, br d, J=5.51 Hz), 11.30 (1H, s), 9.06 (1H, d, J=2.65 Hz), 8.85 (1H, d, J=2.43 Hz), 8.53 (1H, s), 8.42 (1H, d, J=7.94 Hz), 8.29 (2H, s), 7.89-7.98 (1H, m), 7.66 (1H, t, J=7.94 Hz), 7.28 (1H, dd, J=7.28, 6.17 Hz), 5.64 (1H, d, J=7.28 Hz).

Example 114

1-(benzo[d]thiazol-7-yl)-N-(5-cyano-6-(2H-1,2,3-triazol-2-yl)pyridin-3-yl)-5-(trifluoromethyl)-1H-pyrazole-4-carboxamide, Cpd 114

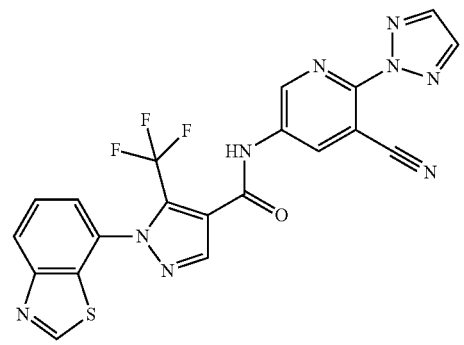 [SMILES: N#Cc1cc(NC(=O)c2cnn(-c3cccc4ncsc34)c2C(F)(F)F)cnc1-n1nccn1]

A. 7-hyrazinylbenzo[d]thiazole, 114a

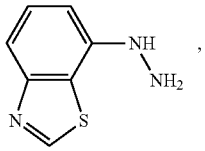

7-bromobenzo[d]thiazole (300 mg, 1.40 mmol), palladium(ii)(pi-cinnamyl) chloride dimer (36.3 mg, 0.07 mmol), N-[2-(di-1-adamantylphosphino)phenyl]morpholine (64.97 mg, 0.14 mmol) and sodium tert-butoxide (269.35 mg, 2.80 mmol) was dissolved in dioxane (20 mL) under $N_2$ atmosphere. Hydrazine hydrate (140.30 mg, 2.80 mmol) was added and stirred at 50° C. for 2 h. The combined mixture was filtered and the solid was washed by 10 mL ethyl acetate. The solvent was concentrated under reduced pressure to afford the title compound (200 mg, 86.4%) as brown solid.

B. ethyl 1-(benzo[d]thiazol-7-yl)-5-(trifluoromethyl)-1H-pyrazole-4-carboxylate, 114b

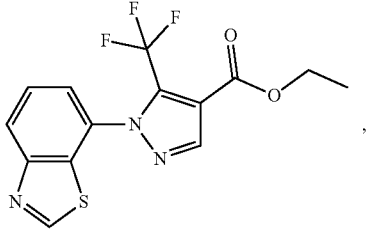

7-hydrazinylbenzo[d]thiazole (200 mg, 1.21 mmol) was dissolved in ethanol (5 mL), ethyl 2-(ethoxymethylene)-4,4,4-trifluoro-3-oxobutanoate (436.11 mg, 1.82 mmol) was added. The reaction mixture was stirred at 80° C. for 3 h. The reaction mixture was concentrated under reduced pressure to afford the crude product as yellow solid, which was purified by FCC (eluent: petroleum ether/ethyl acetate from 100/0 to 70/30) to afford the title compound (195 mg, 43.6%) as white solid. LCMS (ESI) m/z M+1: 342.0.

C. 1-(benzo[d]thiazol-7-yl)-5-(trifluoromethyl)-1H-pyrazole-4-carboxylic acid, 114c

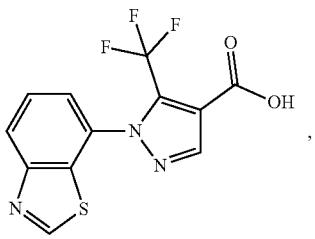

Ethyl 1-(benzo[d]thiazol-7-yl)-5-(trifluoromethyl)-1H-pyrazole-4-carboxylate (195 mg, 0.53 mmol) was dissolved in THF (10 mL) and water (10 mL) sodium hydroxide (31.64 mg, 0.79 mmol) was added. The reaction mixture was stirred at 25° C. for 4 h. The reaction mixture was adjusted to pH=5 using HCl (2 N), extracted with EtOAc (30 mL×2). The combined organic layers were dried over $Na_2SO_4$, filtered and the filtrates were concentrated under reduced pressure to afford crude the title compound (140 mg, 81.8%) as brown solid. LCMS (ESI) m/z M+1: 313.9.

D. 1-(benzo[d]thiazol-7-yl)-N-(5-cyano-6-(2H-1,2,3-triazol-2-yl)pyridin-3-yl)-5-(trifluoromethyl)-1H-pyrazole-4-carboxamide, Cpd 114

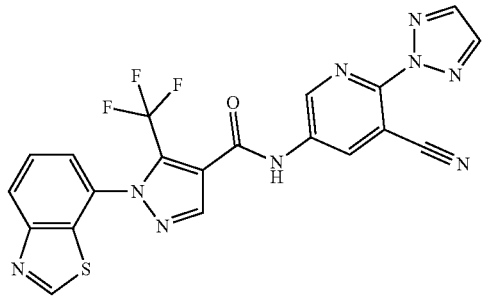 [SMILES: N#Cc1cc(NC(=O)c2cnn(-c3cccc4ncsc34)c2C(F)(F)F)cnc1-n1nccn1]

1-(benzo[d]thiazol-7-yl)-5-(trifluoromethyl)-1H-pyrazole-4-carboxylic acid (140 mg, 0.37 mmol), 5-amino-2-(2H-1,2,3-triazol-2-yl)nicotinonitrile (81.71 mg, 0.44 mmol), pyridine (173.59 mg, 2.20 mmol) were dissolved in $CH_2Cl_2$ (10 mL), and phosphorus oxychloride (224.33 mg, 1.46 mmol) was added. The mixture was stirred at 25° C. for 4 h. Sat.NaHCO$_3$ (40 mL) was added and extracted with $CH_2Cl_2$ (40 mL×2). The combined organic layers were dried over $Na_2SO_4$, filtered and the filtrates were concentrated under reduced pressure to afford the crude product as brown oil, which was purified by preparative HPLC (25% to 55% (v/v) $CH_3CN$ and $H_2O$ with 0.05% HCl) and lyophilized to dryness to afford the title compound (49.0 mg, 27.8%). LCMS (ESI) m/z M+1: 481.9. $^1$H NMR (400 MHz, DMSO-$d_6$) δ=11.52 (s, 1H), 9.00 (d, J=2.6 Hz, 1H), 8.78 (d, J=2.6 Hz, 1H), 8.63 (s, 1H), 8.60 (s, 1H), 8.37 (dd, J=1.4, 2.5 Hz, 1H), 8.27 (s, 2H), 7.28 (dd, J=1.3, 4.6 Hz, 1H), 7.20 (dd, J=2.6, 4.4 Hz, 1H).

Example 115

N-(5-chloro-6-(4-(hydroxymethyl)-2H-1,2,3-triazol-2-yl)pyridin-3-yl)-1-(1-oxo-1,2-dihydroisoquinolin-5-yl)-5-(trifluoromethyl)-1H-pyrazole-4-carboxamide, Cpd 115

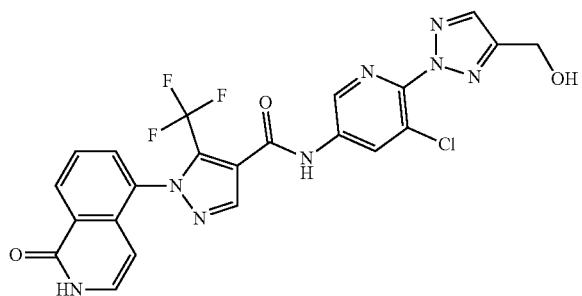 [SMILES: O=C(Nc1cnc(-n2ncc(CO)n2)c(Cl)c1)c1cnn(-c2cccc3c(=O)[nH]ccc23)c1C(F)(F)F]

A. 5-hydrazinyl-1-methoxyisoquinoline, 115a

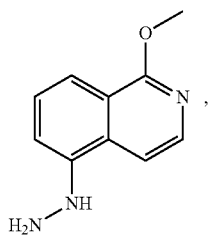

The mixture of {Pd(cinnamyl)Cl}$_2$ (457 mg, 0.88 mmol) and Mor-DalPhos (818 mg, 1.76 mmol) in dioxane (50 mL) was evacuated with argon (4×). The resulting clear yellow solution was stirred at room temp under argon for 10 min. 5-Bromo-1-methoxyisoquinoline (4.2 g, 17.6 mmol) and sodium tert-butoxide (3.39 g, 35.3 mmol) was added to the mixture and the mixture was evacuated with argon (4×). The resulting yellow reaction was stirred at room temp for 5 min and was then treated with hydrazine (1.77 g, 35.3 mmol) via syringe. Then the mixture was stirred at 50° C. under argon for 2 h. The precipitate was filtered, washed with ethyl acetate (200 mL) and the dried under reduced pressure to afford the product (3.4 g).

B. ethyl 1-(1-methoxyisoquinolin-5-yl)-5-(trifluoromethyl)-1H-pyrazole-4-carboxylate, 115b

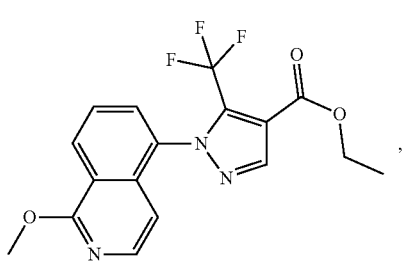

A solution consisting of ethyl 2-(ethoxymethylene)-4,4,4-trifluoro-3-oxobutanoate, 1f (8.89 g, 37.0 mmol), 5-hydrazinyl-1-methoxyisoquinoline (3.4 g, 18.5 mmol), and ethanol (200 mL) was stirred at 80° C. for 3 h before cooling to room temperature. The resulting solution was concentrated to dryness under reduced pressure, and then purified by column chromatography over silica gel (petroleum ether/ethyl acetate=100:0 to 70:30) to afford product as white solid (5.4 g, 80%).

C. 1-(1-methoxyisoquinolin-5-yl)-5-(trifluoromethyl)-1H-pyrazole-4-carboxylic acid, 115c

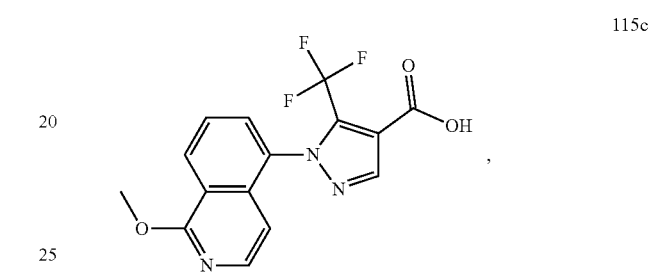

Sodium hydroxide (1.15 g, 28.7 mmol) was added to a solution of ethyl 1-(1-methoxyisoquinolin-5-yl)-5-(trifluoromethyl)-1H-pyrazole-4-carboxylate (3.0 g, 8.2 mmol) in THF/H$_2$O (2:1, 15 mL), and the mixture was heated at 23° C. for 2 h. The solvent was concentrated under reduced pressure, 1M HCl solution was added to the mixture to adjust the pH to ~5, and the mixture extracted with EtOAc (30 mL×3). The combined organic layers were dried over Na$_2$SO$_4$, filtered and the filtrates were concentrated under reduced pressure to afford the product as a yellow solid (2.5 g, 90.3% yield). LC-MS: (ES, m/z): [M+1]$^+$ 338.0.

D. methyl 2-(3-chloro-5-(1-(1-methoxyisoquinolin-5-yl)-5-(trifluoromethyl)-1H-pyrazole-4-carboxamido)pyridin-2-yl)-2H-1,2,3-triazole-4-carboxylatee, 115d

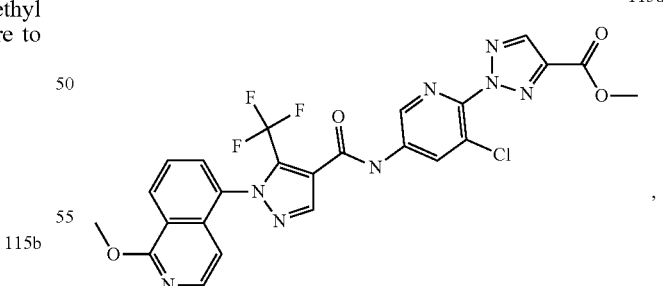

1-(1-methoxyisoquinolin-5-yl)-5-(trifluoromethyl)-1H-pyrazole-4-carboxylic acid (1000 mg, 2.97 mmol), methyl 2-(5-amino-3-chloropyridin-2-yl)-2H-1,2,3-triazole-4-carboxylate (827.30 mg, 3.26 mmol), POCl$_3$ (545.58 mg, 3.56 mmol) were dissolved in DCM (6 mL), and pyridine (703.63 mg, 8.90 mmol) was added. The mixture was stirred at 25° C. for 1 h, sat.NaHCO$_3$ (10 mL) was added and extracted with CH$_2$Cl$_2$ (15 mL×2). The combined organic layers were dried over Na₂SO₄, filtered and the filtrates were concentrated under reduced pressure to afford a crude product as a brown oil, which was purified by FFS (petroleum ether/ethyl acetate=50:50 to petroleum ether/ethyl acetate=0:100). The desired fractions were collected and the solvent was concentrated under reduced pressure to give the product as a yellow oil. LCMS (ESI) m/z M+1: 573.1.

E. N-(5-chloro-6-(4-(hydroxymethyl)-2H-1,2,3-triazol-2-yl)pyridin-3-yl)-1-(1-methoxyisoquinolin-5-yl)-5-(trifluoromethyl)-1H-pyrazole-4-carboxamide, 115e

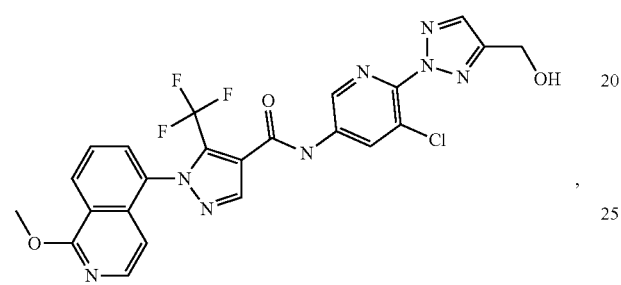

115e

Methyl 2-(3-chloro-5-(1-(1-methoxyisoquinolin-5-yl)-5-(trifluoromethyl)-1H-pyrazole-4-carboxamido)pyridin-2-yl)-2H-1,2,3-triazole-4-carboxylatee (250 mg, 0.38 mmol) was dissolved in THF (5 mL) at 0° C., LiAlH₄ (49.85 mg, 1.31 mmol) was added slowly. The reaction mixture was stirred at room temperature for 2 h. Water (80 uL) was added to the mixture at 0° C. and the mixture was stirred for 10 min. NaOH (80 uL, 15% in water) was added to the mixture at 0° C. and the mixture was stirred for 10 min. Water (240 uL) was added to the mixture at 0° C. and the mixture was stirred for 10 min. MgSO₄ was added to the mixture and the mixture was filtered. The filtrate was concentrated to give the crude product as a brown oil (200 mg, 86.8%). LCMS (ESI) m/z M+1: 545.0.

C. N-(5-chloro-6-(4-(hydroxymethyl)-2H-1,2,3-triazol-2-yl)pyridin-3-yl)-1-(1-oxo-1,2-dihydroisoquinolin-5-yl)-5-(trifluoromethyl)-1H-pyrazole-4-carboxamide, Cpd 115

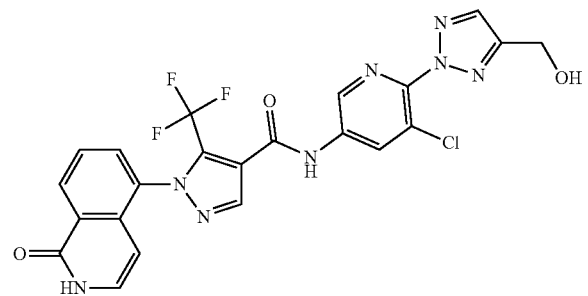 [SMILES: O=C(Nc1cnc(-n2ncc(CO)n2)c(Cl)c1)c1cnn(-c2cccc3c(=O)[nH]ccc23)c1C(F)(F)F]

N-(5-Chloro-6-(4-(hydroxymethyl)-2H-1,2,3-triazol-2-yl)pyridin-3-yl)-1-(1-methoxyisoquinolin-5-yl)-5-(trifluoromethyl)-1H-pyrazole-4-carboxamide (200 mg, 0.33 mmol), and con.HCl (4 mL) was added i-PrOH (8 mL), stirred at 60° C. for 2 h. The mixture was concentrated under reduced pressure to afford crude product as a brown oil, which was purified by preparative HPLC (75% to 45% (v/v) CH₃CN and H₂O with 0.05% HCl) and lyophilized to dryness to afford the title compound (108 mg, 62.4%). LCMS (ESI) m/z M+1: 530.9. ¹H NMR (400 MHz, DMSO-d₆) δ ppm 4.63 (s, 2H), 5.63 (d, J=7.06 Hz, 1H), 7.28 (dd, J=7.39, 5.84 Hz, 1H), 7.65 (t, J=7.83 Hz, 1H), 7.94 (d, J=7.50 Hz, 1H), 8.05 (s, 1H), 8.42 (d, J=7.94 Hz, 1H), 8.52 (s, 1H), 8.63 (d, J=2.20 Hz, 1H), 8.81 (d, J=2.21 Hz, 1H), 11.22 (s, 1H), 11.62 (br d, J=5.95 Hz, 1H).

Example 116

N-(5-chloro-6-(2H-1,2,3-triazol-2-yl)pyridin-3-yl)-1-(1-hydroxyisoquinolin-5-yl)-5-(trifluoromethyl)-1H-pyrazole-4-carboxamide, Cpd 116

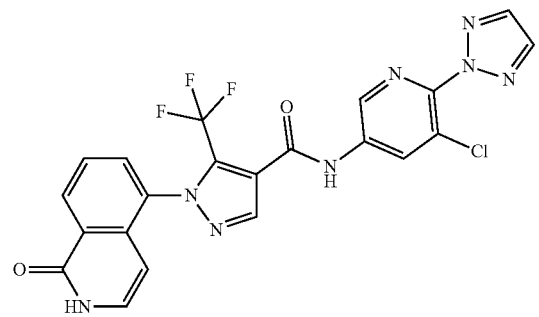 [SMILES: O=C(Nc1cnc(-n2nccn2)c(Cl)c1)c1cnn(-c2cccc3c(=O)[nH]ccc23)c1C(F)(F)F]

A. N-(5-chloro-6-(2H-1,2,3-triazol-2-yl)pyridin-3-yl)-1-(1-methoxyisoquinolin-5-yl)-5-(trifluoromethyl)-1H-pyrazole-4-carboxamide, 116a

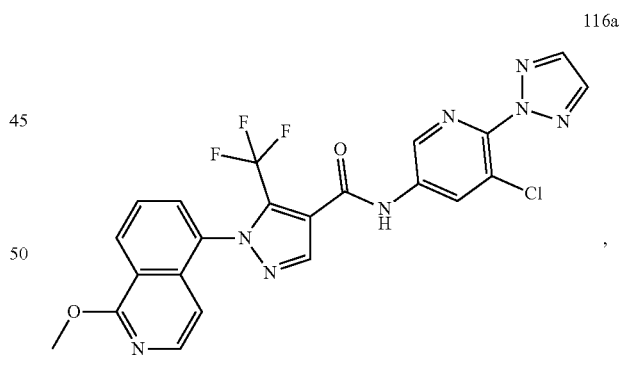

116a 1-(1-Methoxyisoquinolin-5-yl)-5-(trifluoromethyl)-1H-pyrazole-4-carboxylic acid (200 mg, 0.587 mmol), 5-chloro-6-(2H-1,2,3-triazol-2-yl)pyridin-3-amine (117.16 mg, 0.60 mmol), POCl₃ (108.05 mg, 0.71 mmol) were dissolved in DCM (8 mL), and pyridine (139.35 mg, 1.76 mmol) was added. The mixture was stirred at 25° C. for 1 h, sat. NaHCO₃ (20 mL) was added and extracted with CH₂Cl₂ (30 mL×2). The combined organic layers were dried over Na₂SO₄, filtered and the filtrates were concentrated under reduced pressure to afford crude product as a brown oil, which was purified by preparative HPLC (50% to 20% (v/v) CH₃CN and H₂O with 0.05% HCl) and lyophilized to dryness to afford the title compound (142 mg, 46.7%). LCMS (ESI) m/z M+1: 514.9. ¹H NMR (400 MHz, DMSO-d₆) δ ppm 4.10 (s, 3H), 6.56 (d, J=6.17 Hz, 1H), 7.78-7.85 (m, 1H), 8.06 (d, J=6.39 Hz, 1H), 8.10 (d, J=5.95 Hz, 1H), 8.18 (s, 2H), 8.45 (d, J=8.16 Hz, 1H), 8.56 (s, 1H), 8.66 (d, J=2.21 Hz, 1H), 8.83 (d, J=2.21 Hz, 1H), 11.25 (s, 1H).

B. N-(5-chloro-6-(2H-1,2,3-triazol-2-yl)pyridin-3-yl)-1-(1-hydroxyisoquinolin-5-yl)-5-(trifluoromethyl)-1H-pyrazole-4-carboxamide, Cpd 116

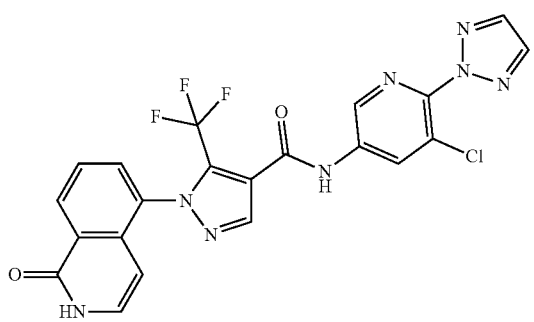 [SMILES: O=C(Nc1cnc(-n2nccn2)c(Cl)c1)c1cnn(-c2cccc3c(=O)[nH]ccc23)c1C(F)(F)F]

N-(5-chloro-6-(2H-1,2,3-triazol-2-yl)pyridin-3-yl)-1-(1-methoxyisoquinolin-5-yl)-5-(trifluoromethyl)-1H-pyrazole-4-carboxamide (70 mg, 0.14 mmol), and con.HCl (4 mL) was added i-PrOH (8 mL), stirred at 60° C. for 2 hrs. The mixture was concentrated under reduced pressure to afford crude as yellow oil, which was purified by preparative HPLC (84% to 54% (v/v) CH₃CN and H₂O with 0.05% HCl) and lyophilized to dryness to afford the title compound (47 mg, 69.4%). LCMS (ESI) m/z M+1: 500.9. ¹H NMR (400 MHz, DMSO-d₆) δ ppm 5.63 (d, J=7.50 Hz, 1H), 7.27 (dd, J=7.17, 6.06 Hz, 1H), 7.65 (t, J=7.83 Hz, 1H), 7.93 (d, J=7.06 Hz, 1H), 8.16 (s, 2H), 8.41 (d, J=7.94 Hz, 1H), 8.53 (s, 1H), 8.64 (d, J=2.21 Hz, 1H), 8.82 (d, J=2.20 Hz, 1H), 11.25 (s, 1H), 11.62 (br d, J=5.73 Hz, 1H).

Example 117

N-(5-chloro-6-(2H-1,2,3-triazol-2-yl)pyridin-3-yl)-1-(8-fluoroisoquinolin-4-yl)-5-(trifluoromethyl)-1H-pyrazole-4-carboxamide, Cpd 117

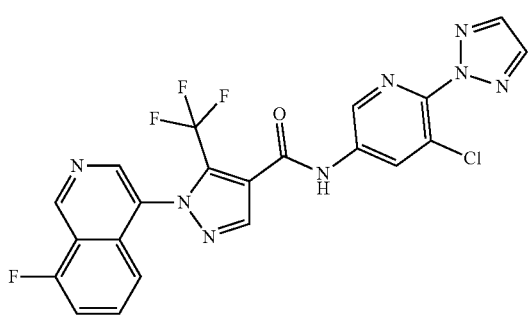 [SMILES: O=C(Nc1cnc(-n2nccn2)c(Cl)c1)c1cnn(-c2cncc3c(F)cccc23)c1C(F)(F)F]

A. 4-bromo-8-fluoroisoquinoline, 117a

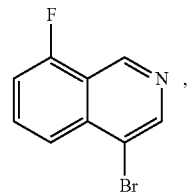

To a solution of 8-fluoroisoquinoline (0.5 g, 3.40 mmol) in CCl₄ (15 mL) was added 1-bromopyrrolidine-2,5-dione (604.78 mg, 3.40 mmol) and (E)-3,3'-(diazene-1,2-diyl)bis(2-methylpropanenitrile) (55.8 mg, 0.34 mmol). The mixture was stirred at 80° C. for 3 h. The solvent was concentrated under reduced pressure to give crude product, which was purified by FCC(petroleum ether/ethyl acetate=1:0 to petroleum ether/ethyl acetate=1:1) to afford the title compound (0.21 g, 27.1%) as a yellow oil. LCMS (ESI) m/z M+1: 225.9. ¹H NMR (400 MHz, CHLOROFORM-d) δ ppm 9.44 (1H, s), 8.78 (1H, s), 7.93 (1H, br d, J=8.38 Hz), 7.74 (1H, td, J=7.94, 5.51 Hz), 7.27-7.36 (1H, m).

B. 8-fluoro-4-hydrazinylisoquinoline, 117b

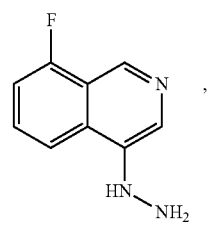

Palladium(11)(pi-cinnamyl) chloride dimer (23.81 mg, 0.046 mmol) and 4-(2-(di((3S,5S,7S)-adamantan-1-yl)phosphino)phenyl)morpholine (42.62 mg, 0.092 mmol) was added to dioxane (8 mL), immediately evacuated with N₂. The resulting solution was stirred at room temp under N₂ for 10 min. Then was charged with sodium 2-methylpropan-2-olate (176.69 mg, 1.84 mmol) and 4-bromo-8-fluoroisoquinoline (210 mg, 0.92 mmol), sealed, and evacuated with N₂. The resulting mixture was stirred at room temp for 5 min and was then treated with hydrazine hydrate (92.04 mg, 1.84 mmol) via syringe. The mixture was stirred at 50° C. under N₂ for 1.5 hrs, filtered. The filtrate was concentrated under reduced pressure to give the crude product as a yellow solid (260 mg). The mixture was directly used for next step.

C. Ethyl 1-(8-fluoroisoquinolin-4-yl)-5-(trifluoromethyl)-1H-pyrazole-4-carboxylate, 117c

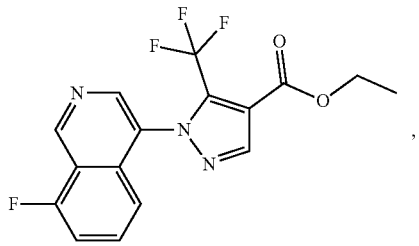

A solution consisting of ethyl 2-(ethoxymethylene)-4,4,4-trifluoro-3-oxobutanoate (1.762 g, 7.34 mmol), 8-fluoro-4-hydrazinylisoquinoline (260 mg, 1.47 mmol) and ethanol (10 mL) was stirred at 80° C. for 2 h. The resultant solution was concentrated to dryness under reduced pressure to afford the crude product, which was purified by FCC (petroleum ether: ethyl acetate=100/0 to 70/30) to afford the title compound (0.22 g, 42.4%) as a yellow solid. LCMS (ESI) m/z M+1: 354.0.

D. 1-(8-fluoroisoquinolin-4-yl)-5-(trifluoromethyl)-1H-pyrazole-4-carboxylic acid, 117d

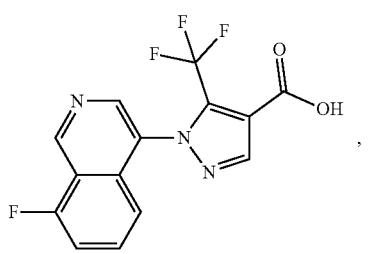

Sodium hydroxide (37.36 mg, 0.93 mmol) was added to a solution of ethyl 1-(8-fluoroisoquinolin-4-yl)-5-(trifluoromethyl)-1H-pyrazole-4-carboxylate (220 mg, 0.62 mmol) in THF/H$_2$O=3:1(12 mL). The mixture was stirred at room temperature for 3 h. The solvent was concentrated under reduced pressure and 20 mL H$_2$O was added to the mixture. The mixture was acidified using 1M hydrochloric to pH=5 and extracted with ethyl acetate (20 mL×3). The combined organic layers were washed with brine, dried over anhydrous MgSO$_4$ and filtered. The filtrates were concentrated under reduced pressure to afford product as a yellow solid (160 mg, 79.0%).

E. N-(5-chloro-6-(2H-1,2,3-triazol-2-yl)pyridin-3-yl)-1-(8-fluoroisoquinolin-4-yl)-5-(trifluoromethyl)-1H-pyrazole-4-carboxamide, Cpd 117

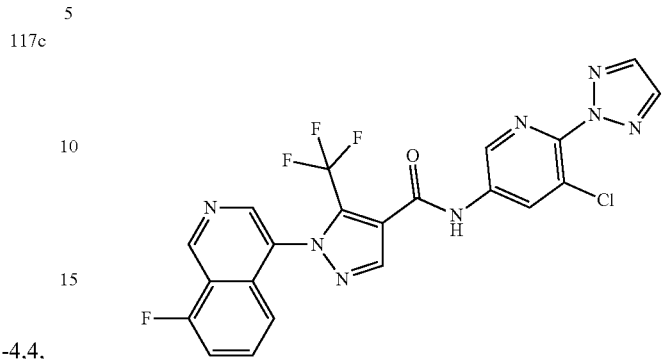

1-(8-Fluoroisoquinolin-4-yl)-5-(trifluoromethyl)-1H-pyrazole-4-carboxylic acid (80 mg, 0.25 mmol), 5-chloro-6-(2H-1,2,3-triazol-2-yl)pyridin-3-amine (48.12 mg, 0.25 mmol), pyridine (0.10 mL, 1.23 mmol) were dissolved in CH$_2$Cl$_2$ (10 mL), and phosphorus oxychloride (0.090 mL, 0.98 mmol) was added. The mixture was stirred at 25° C. for 2 h, Sat.NaHCO$_3$ (20 mL) was added and extracted with CH$_2$Cl$_2$ (30 mL×2). The combined organic extracts were dried over anhydrous Na$_2$SO$_4$, filtered, and concentrated to dryness under reduced pressure to afford the crude product, which was purified by preparative HPLC (43% to 73% (v/v) CH$_3$CN and H$_2$O with 0.05% HCl) and lyophilized to dryness to afford the title compound (35 mg, 28.2%). LCMS (ESI) m/z M+1: 502.9. $^1$H NMR (400 MHz, DMSO-d$_6$) δ ppm 11.33 (1H, s), 9.73 (1H, s), 8.93 (1H, s), 8.85 (1H, d, J=1.98 Hz), 8.67 (1H, d, J=2.21 Hz), 8.65 (1H, s), 8.17 (2H, s), 7.90-7.98 (1H, m), 7.69 (1H, dd, J=10.36, 8.38 Hz), 7.12 (1H, d, J=8.60 Hz).

Example 118

N-(5-cyano-6-(2H-1,2,3-triazol-2-yl)pyridin-3-yl)-1-(8-fluoroisoquinolin-4-yl)-5-(trifluoromethyl)-1H-pyrazole-4-carboxamide, Cpd 118

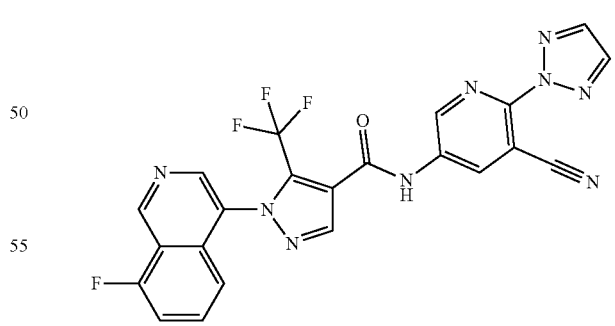

1-(8-Fluoroisoquinolin-4-yl)-5-(trifluoromethyl)-1H-pyrazole-4-carboxylic acid (80 mg, 0.25 mmol), 5-amino-2-(2H-1,2,3-triazol-2-yl)nicotinonitrile, (45.8 mg, 0.25 mmol), pyridine (0.10 mL, 1.23 mmol) were dissolved in CH$_2$Cl$_2$ (10 mL), and phosphorus oxychloride (0.090 mL, 0.98 mmol) was added. The mixture was stirred at 25° C. for 2 h, Sat.NaHCO$_3$ (20 mL) was added and extracted with CH$_2$Cl$_2$ (30 mL×2). The combined organic extracts were dried over anhydrous Na$_2$SO$_4$, filtered, and concentrated to dryness under reduced pressure to afford the crude product, which was purified by preparative HPLC (43% to 63% (v/v) CH$_3$CN and H$_2$O with 0.05% HCl) and lyophilized to dryness to afford the title compound (36 mg, 29.1%). LCMS (ESI) m/z M+1: 493.9. $^1$H NMR (400 MHz, DMSO-d$_6$) δ ppm 11.40 (1H, s), 9.73 (1H, s), 9.09 (1H, d, J=2.43 Hz), 8.93 (1H, s), 8.87 (1H, d, J=2.43 Hz), 8.65 (1H, s) 8.29 (2H, s), 7.89-7.99 (1H, m), 7.64-7.72 (1H, m), 7.12 (1H, d, J=8.38 Hz).

Example 119

1-(benzo[d][1,2,3]thiadiazol-7-yl)-N-(5-cyano-6-(2H-1,2,3-triazol-2-yl)pyridin-3-yl)-5-(trifluoromethyl)-1H-pyrazole-4-carboxamide, Cpd 119

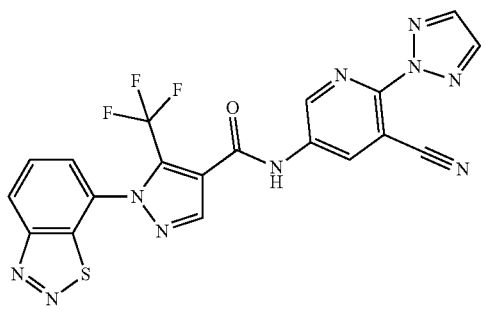 [SMILES: N#Cc1cc(NC(=O)c2cnn(-c3cccc4nnsc34)c2C(F)(F)F)cnc1-n1nccn1]

A. 7-hydrazinylbenzo[d][1,2,3]thiadiazole, 119a

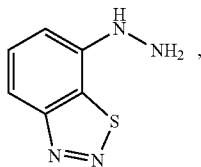

To a stirring solution of benzo[d][1,2,3]thiadiazol-7-amine (2 g, 13.23 mmol) in HCl (6 N, 50 mL) at −10° C. was added a solution of sodium nitrite (1.37 g, 19.85 mmol) in H$_2$O (20 mL) below −20° C. The reaction mixture was stirred at rt for 0.5 hr. Then cooled to −20° C., tin(ii) chloride dihydrate (5.97 g, 26.45 mmol) was added portions to the mixture and stirred for 1 h. The reaction mixture was basified with 3 M NaOH and the aqueous extracted with EtOAc (200 mL×3). The combined organic layers were dried over Na$_2$SO$_4$, filtered and the filtrates were concentrated under reduced pressure to afford crude (2.5 g) as brown solid, which was used for the next step without further purification. LCMS (ESI) m/z M+1: 167.1.

B. Ethyl 1-(benzo[d][1,2,3]thiadiazol-7-yl)-5-(trifluoromethyl)-1H-pyrazole-4-carboxylate, 119b

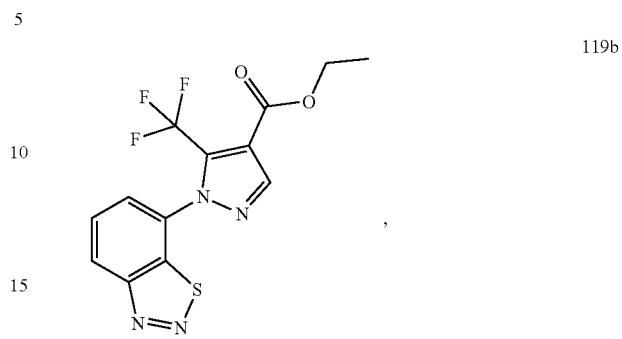

7-Hydrazinylbenzo[d][1,2,3]thiadiazole (2.5 g, 5.71 mmol) was dissolved in ethanol (30 mL), ethyl 2-(ethoxymethylene)-4,4,4-trifluoro-3-oxobutanoate (3.28 g, 13.64 mmol) was added and stirred at 70° C. for 2 h before cooling to room-temperature. The combined mixture was concentrated under reduced pressure to afford crude product as yellow oil, which was purified by FCC (eluent: petroleum ether/ethyl acetate from 100/0 to 85/15) to afford the title compound (1.2 g, 61.4%) as a yellow solid. LCMS (ESI) m/z M+1: 342.9.

C. 1-(benzo[d][1,2,3]thiadiazol-7-yl)-5-(trifluoromethyl)-1H-pyrazole-4-carboxylic acid, 119c

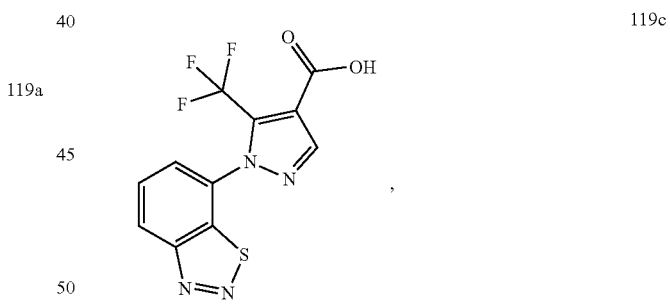

Ethyl 1-(benzo[d][1,2,3]thiadiazol-7-yl)-5-(trifluoromethyl)-1H-pyrazole-4-carboxylate (1.2 g, 3.51 mmol) was dissolved in THF (8 mL) and water (8 mL). Lithium hydroxide (251.87 mg, 10.52 mmol) was added. The reaction mixture was stirred at 30° C. for 16 h. The reaction mixture was adjust to pH=5 using HCl (2 N), extracted with CH$_2$Cl$_2$/MeOH (10/1, 60 mL×5). The combined organic layers were dried over Na$_2$SO$_4$, filtered and the filtrates were concentrated under reduced pressure to afford crude title compound (900 mg, 81.0%) as a yellow solid. LCMS (ESI) m/z M+1: 315.1.

D. 1-(benzo[d][1,2,3]thiadiazol-7-yl)-N-(5-cyano-6-(2H-1,2,3-triazol-2-yl)pyridin-3-yl)-5-(trifluoromethyl)-1H-pyrazole-4-carboxamide, Cpd 119

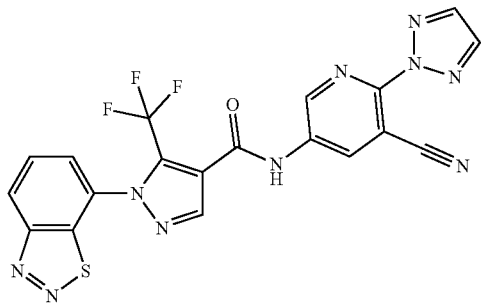 [SMILES: N#Cc1cc(NC(=O)c2cnn(-c3cccc4nnsc34)c2C(F)(F)F)cnc1-n1nccn1]

1-(Benzo[d][1,2,3]thiadiazol-7-yl)-5-(trifluoromethyl)-1H-pyrazole-4-carboxylic acid (300 mg, 0.95 mmol), 5-amino-2-(2H-1,2,3-triazol-2-yl)nicotinonitrile, (229.0 mg, 1.23 mmol), pyridine (449.05 mg, 5.68 mmol) were dissolved in $CH_2Cl_2$ (30 mL), and phosphorus oxychloride (435.23, 2.84 mmol) was added. The mixture was stirred at 25° C. for 2 h. Sat.NaHCO$_3$ (20 mL) was added and extracted with $CH_2Cl_2$ (50 mL×2). The combined organic layers were dried over $Na_2SO_4$, filtered and the filtrates were concentrated under reduced pressure to afford the crude product as yellow oil, which was purified by preparative HPLC (45% to 75% (v/v) $CH_3CN$ and $H_2O$ with 0.05% HCl) and lyophilized to dryness to afford the title compound (200 mg, 43.1%). LCMS (ESI) m/z M+1: 483.0. $^1$H NMR (400 MHz, DMSO-d$_6$) δ=11.47 (s, 1H), 9.08 (d, J=2.4 Hz, 1H), 8.99 (d, J=8.4 Hz, 1H), 8.85 (d, J=2.2 Hz, 1H), 8.63 (s, 1H), 8.31 (s, 2H), 8.15-8.10 (m, 1H), 8.06-7.99 (m, 1H).

Example 120

1-(benzo[d][1,2,3]thiadiazol-7-yl)-N-(5-chloro-6-(2H-1,2,3-triazol-2-yl)pyridin-3-yl)-5-(trifluoromethyl)-1H-pyrazole-4-carboxamide, Cpd 120

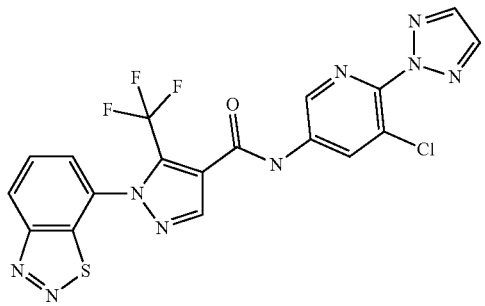 [SMILES: O=C(Nc1cnc(-n2nccn2)c(Cl)c1)c1cnn(-c2cccc3nnsc23)c1C(F)(F)F]

1-(Benzo[d][1,2,3]thiadiazol-7-yl)-5-(trifluoromethyl)-1H-pyrazole-4-carboxylic acid (100 mg, 0.28 mmol), 5-chloro-6-(2H-1,2,3-triazol-2-yl)pyridin-3-amine, (53.95 mg, 0.28 mmol), pyridine (130.9 mg, 1.66 mmol) were dissolved in $CH_2Cl_2$ (10 mL), and phosphorus oxychloride (126.87, 0.83 mmol) was added. The mixture was stirred at 25° C. for 2 h. Sat.NaHCO$_3$ (20 mL) was added and extracted with $CH_2Cl_2$ (50 mL×2). The combined organic layers were dried over $Na_2SO_4$, filtered and the filtrates were concentrated under reduced pressure to afford the crude product as yellow oil, which was purified by preparative HPLC (45% to 75% (v/v) $CH_3CN$ and $H_2O$ with 0.05% HCl) and lyophilized to dryness to afford the title compound (18 mg, 13.2%). LCMS (ESI) m/z M+1: 492.0. $^1$H NMR (400 MHz, DMSO-d$_6$) δ=11.43 (s, 1H), 8.99 (d, J=8.2 Hz, 1H), 8.84 (d, J=2.2 Hz, 1H), 8.66 (d, J=2.2 Hz, 1H), 8.64 (s, 1H), 8.20 (s, 2H), 8.15-8.10 (m, 1H), 8.06-8.00 (m, 1H).

Example 121

1-(benzo[d][1,2,3]thiadiazol-7-yl)-N-(5-chloro-2-methyl-6-(2H-1,2,3-triazol-2-yl)pyridin-3-yl)-5-(trifluoromethyl)-1H-pyrazole-4-carboxamide, Cpd 121

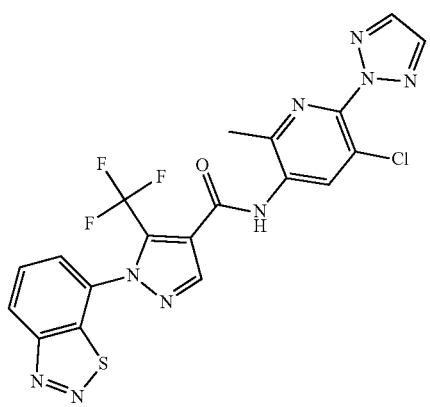 [SMILES: Cc1nc(-n2nccn2)c(Cl)cc1NC(=O)c1cnn(-c2cccc3nnsc23)c1C(F)(F)F]

1-(Benzo[d][1,2,3]thiadiazol-7-yl)-5-(trifluoromethyl)-1H-pyrazole-4-carboxylic acid (149.93 mg, 0.47 mmol), 5-chloro-2-methyl-6-(2H-1,2,3-triazol-2-yl)pyridin-3-amine, (109.09 mg, 0.52 mmol), pyridine (224.52 mg, 2.84 mmol) were dissolved in $CH_2Cl_2$ (10 mL), and phosphorus oxychloride (217.62 mg, 1.42 mmol) was added. The mixture was stirred at 25° C. for 2 h. Sat.NaHCO$_3$ (20 mL) was added and extracted with $CH_2Cl_2$ (50 mL×2). The combined organic layers were dried over $Na_2SO_4$, filtered and the filtrates were concentrated under reduced pressure to afford the crude product as a yellow oil, which was purified by preparative HPLC (45% to 75% (v/v) $CH_3CN$ and $H_2O$ with 0.05% HCl) and lyophilized to dryness to afford the title compound (102 mg, 42.4%). LCMS (ESI) m/z M+1: 505.9. $^1$H NMR (400 MHz, DMSO-d$_6$) δ=10.73 (s, 1H), 8.98 (d, J=8.2 Hz, 1H), 8.63 (s, 1H), 8.47 (s, 1H), 8.19 (s, 2H), 8.13-8.09 (m, 1H), 8.06-8.01 (m, 1H), 2.56 (s, 3H).

Example 122

N-(5-cyano-6-(2H-1,2,3-triazol-2-yl)pyridin-3-yl)-1-(5-fluoronaphthalen-1-yl)-5-(trifluoromethyl)-1H-pyrazole-4-carboxamide, Cpd 122

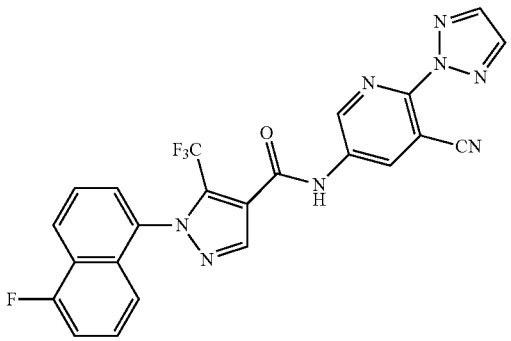 [SMILES: N#Cc1cc(NC(=O)c2cnn(-c3cccc4c(F)cccc34)c2C(F)(F)F)cnc1-n1nccn1]

A. (5-fluoronaphthalen-1-yl)hydrazine, 122a

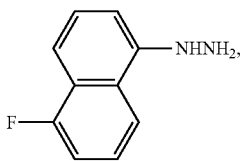

A mixture of {Pd(cinnamyl)Cl}$_2$ (11.51 mg, 0.022 mmol) and Mor-DalPhos (20.60 mg, 0.044 mmol) in dioxane (2 mL) was evacuated with argon (4×). The resulting clear yellow solution was stirred at room temp under argon for 10 min. 1-Bromo-5-fluoronaphthalene (100 mg, 0.44 mmol) and t-BuONa (85.31 mg, 0.89 mmol) was added to the mixture and the mixture was evacuated with argon (4×). The resulting yellow mixture was stirred at room temp for 5 min and was then treated with hydrazine hydrate (45.40 mg, 0.889 mmol) via syringe. The reaction mixture was evacuated with argon (4×). Then the mixture was stirred at 50° C. under argon for 4 hrs. The mixture was filtered and washed with ethyl acetate (5 mL×3). The filtrate was collected and concentrated to afford crude product (100 mg, >100% yield) as a brown solid which was used directly for the next step.

B. Ethyl 1-(5-fluoronaphthalen-1-yl)-5-(trifluoromethyl)-1H-pyrazole-4-carboxylate, 122b

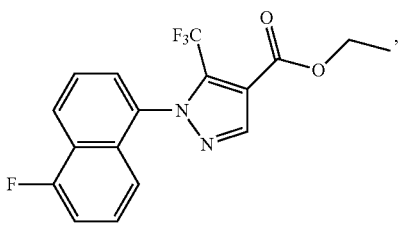

A solution of (5-fluoronaphthalen-1-yl)hydrazine, 122a (100 mg, 0.57 mmol), ethyl 2-(ethoxymethylene)-4,4,4-trifluoro-3-oxobutanoate (204.48 mg, 0.85 mmol), triethylamine (171.97 mg, 1.70 mmol) in EtOH (10 mL) was stirred at 80° C. for 12 h. The mixture was concentrated under reduced pressure and the crude product was purified by column chromatography over silica gel (petroleum ether/ethyl acetate from 20:1 to 1:1). The desired fractions were collected and the solvent was concentrated under reduced pressure to afford 122b (100 mg, 46.7% yield) as a yellow solid. LCMS (ESI) m/z M+1: 352.9.

C. 1-(5-fluoronaphthalen-1-yl)-5-(trifluoromethyl)-1H-pyrazole-4-carboxylic acid, 122c

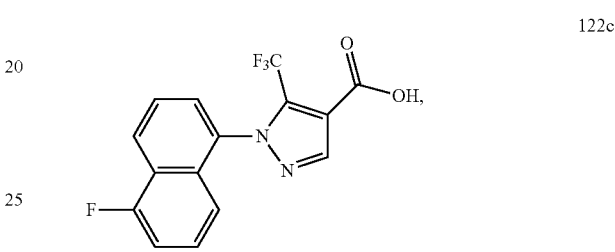

A solution of ethyl 1-(5-fluoronaphthalen-1-yl)-5-(trifluoromethyl)-1H-pyrazole-4-carboxylate, 122b (100 mg, 0.27 mmol), LiOH (22.23 mg, 0.53 mmol) in MeOH (10 mL), THF (10 mL) and water (10 mL) was stirred at rt for 3h. To the mixture was added 5% KHSO$_4$ to adjust the pH to 3-4. Water (100 mL) and ethyl acetate (100 mL) were added to the mixture. The organic layer was washed with brine (50 mL), dried over MgSO$_4$, filtered, and the filtrate concentrated under reduced pressure to afford 122c (90 mg, 94.1% yield) as a yellow solid used for the next step directly. LCMS (ESI) m/z M+H: 324.8

D. N-(5-cyano-6-(2H-1,2,3-triazol-2-yl)pyridin-3-yl)-1-(5-fluoronaphthalen-1-yl)-5-(trifluoromethyl)-1H-pyrazole-4-carboxamide, Cpd 122

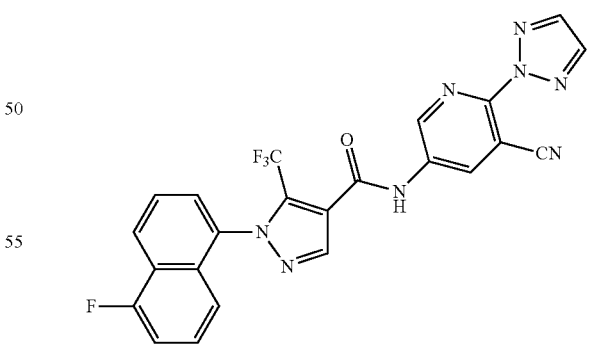

POCl$_3$ (76.46 mg, 0.50 mmol) was added to a solution of 1-(5-fluoronaphthalen-1-yl)-5-(trifluoromethyl)-1H-pyrazole-4-carboxylic acid, 122c (90 mg, 0.25 mmol), 5-amino-2-(2H-1,2,3-triazol-2-yl)nicotinonitrile (46.42 mg, 0.25 mmol), pyridine (49.30 mg 0.62 mmol) in CH$_2$Cl$_2$ (10 mL). The mixture was stirred at rt for 2 h, 50 mL water and 50 mL CH$_2$Cl$_2$ were added to the mixture. The organic layer was washed with brine (50 mL), dried over MgSO₄, filtered, and the filtrate concentrated under reduced pressure to afford the crude product, which was purified by preparative HPLC (47% to 77% (v/v) CH₃CN and H₂O with 0.05% HCl) and lyophilized to dryness to afford the title compound (33.5 mg 26.5% yield) as a white solid. LCMS (ESI) m/z M+1: 492.9. $^1$H NMR (400 MHz, DMSO-d₆) δ ppm 9.08 (d, J=2.43 Hz, 1H), 8.86 (d, J=2.43 Hz, 1H), 8.58 (s, 1H), 8.32 (d, J=8.38 Hz, 1H), 8.28 (s, 2H), 7.90 (d, J=7.28 Hz, 1H), 7.74-7.83 (m, 1H), 7.60 (td, J=8.10, 5.62 Hz, 1H), 7.49 (dd, J=10.47, 7.61 Hz, 1H), 6.93 (d, J=8.38 Hz, 1H).

Example 123

N-(5-chloro-2-methyl-6-(2H-1,2,3-triazol-2-yl)pyridin-3-yl)-1-(8-fluoroisoquinolin-4-yl)-5-(trifluoromethyl)-1H-pyrazole-4-carboxamide, Cpd 123

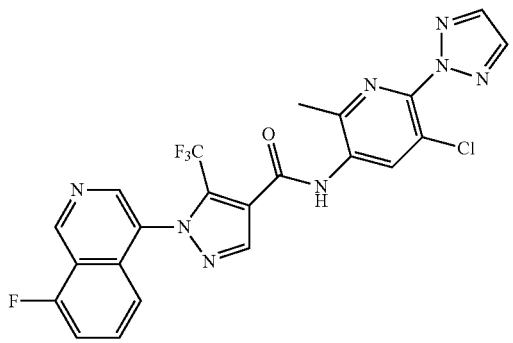 [SMILES: Cc1nc(-n2nccn2)c(Cl)cc1NC(=O)c1cnn(-c2cncc3c(F)cccc23)c1C(F)(F)F]

A. 8-fluoro-4-hydrazinylisoquinoline, 123a

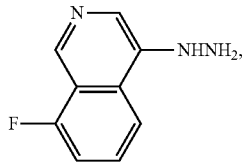

A mixture of {Pd(cinnamyl)Cl}₂ (68.76 mg, 0.13 mmol) and Mor-DalPhos (123.06 mg, 0.27 mmol) in dioxane (10 mL) was evacuated with argon (4×). The resulting clear yellow solution was stirred at room temp under argon for 10 min. 4-bromo-8-fluoroisoquinoline (600 mg, 2.65 mmol) and t-BuONa (509.63 mg, 5.31 mmol) was added to the mixture and the mixture was evacuated with argon (4×). The resulting yellow reaction was stirred at room temp for 5 min and was then treated with hydrazine hydrate (271.18 mg, 5.31 mmol) via syringe. The reaction mixture was evacuated with argon (4×). Then the mixture was stirred at 50° C. under argon for 2 h. The mixture was filtered and washed with ethyl acetate (50 mL×3), the filtrate was collected and concentrated to afford crude 123a (510 mg, >100% yield) as a brown solid, used directly for the next step.

B. Ethyl 1-(8-fluoroisoquinolin-4-yl)-5-(trifluoromethyl)-1H-pyrazole-4-carboxylate, 123b

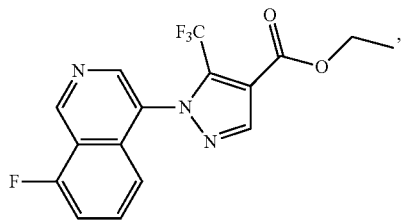

A solution of 8-fluoro-4-hydrazinylisoquinoline, 123a (510 mg, 2.88 mmol), ethyl 2-(ethoxymethylene)-4,4,4-trifluoro-3-oxobutanoate (1037.0 mg, 4.32 mmol), triethylamine (872.17 mg, 8.64 mmol) in EtOH (20 mL) was stirred at 80° C. for 12 h. The mixture was concentrated under reduced pressure, the crude product was purified by column chromatography over silica gel (petroleum ether/ethyl acetate from 20:1 to 5:1). The desired fractions were collected and the solvent was concentrated under reduced pressure to afford 123b (510 mg, 40.7% yield) as a yellow solid. LCMS (ESI) m/z M+1: 353.9.

C. 1-(8-fluoroisoquinolin-4-yl)-5-(trifluoromethyl)-1H-pyrazole-4-carboxylic acid, 123c

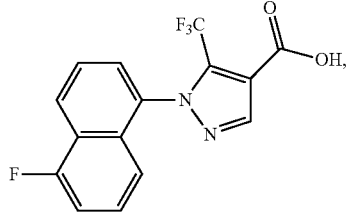

A solution of ethyl 1-(8-fluoroisoquinolin-4-yl)-5-(trifluoromethyl)-1H-pyrazole-4-carboxylate, 123b (510 mg, 1.17 mmol), LiOH (98.21 mg, 2.34 mmol) in THF (20 mL) and water (20 mL) was stirred at rt for 2 h. The mixture was added 5% KHSO₄ to adjust pH 3-4. Water (100 mL) and ethyl acetate (100 mL) were added to the mixture. The organic layer was washed with brine (50 mL), dried over MgSO₄ and concentrated under reduced pressure to afford 123c (420 mg) as a yellow solid used directly for the next step. LCMS (ESI) m/z M+H: 325.9.

D. N-(5-chloro-2-methyl-6-(2H-1,2,3-triazol-2-yl)pyridin-3-yl)-1-(8-fluoroisoquinolin-4-yl)-5-(trifluoromethyl)-1H-pyrazole-4-carboxamide, Cpd 123

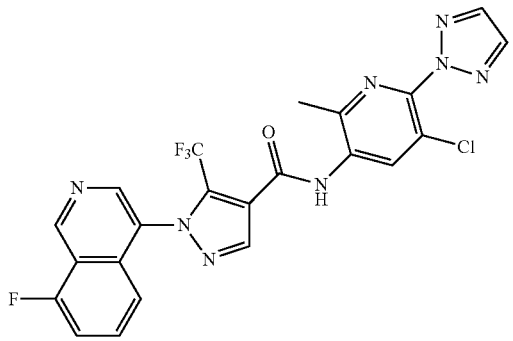 [SMILES: Cc1nc(-n2nccn2)c(Cl)cc1NC(=O)c1cnn(-c2cncc3c(F)cccc23)c1C(F)(F)F]

POCl₃ (198.02 mg, 1.29 mmol) was added to a solution of 1-(8-fluoroisoquinolin-4-yl)-5-(trifluoromethyl)-1H-pyrazole-4-carboxylic acid, 123c (210 mg, 0.65 mmol), 5-chloro-2-methyl-6-(2H-1,2,3-triazol-2-yl)pyridin-3-amine (162.44 mg, 0.78 mmol), pyridine (127.69 mg 1.61 mmol) in CH₂Cl₂ (10 mL). The mixture was stirred at rt for 3h, 50 mL H₂O and 50 mL CH₂Cl₂ were added to the mixture. The organic layer was washed with brine (50 mL), dried over MgSO₄, filtered, and the filtrate concentrated under reduced pressure to afford the crude product, which was purified by preparative HPLC (37% to 67% (v/v) CH₃CN and H₂O with 0.05% HCl) and lyophilized to dryness to afford the title compound (86.0 mg 25.8% yield) as a white solid. LCMS (ESI) m/z M+1: 516.9. ¹H NMR (400 MHz, DMSO-d₆) δ ppm 10.66 (s, 1H), 9.72 (s, 1H), 8.91 (s, 1H), 8.62 (s, 1H), 8.42 (s, 1H), 8.16 (s, 2H), 7.94 (td, J=8.10, 5.62 Hz, 1H), 7.68 (dd, J=10.36, 7.94 Hz, 1H), 7.13 (d, J=8.38 Hz, 1H), 2.54 (s, 3H).

Example 124

N-(5-cyano-2-methyl-6-(2H-1,2,3-triazol-2-yl)pyridin-3-yl)-1-(8-fluoroisoquinolin-4-yl)-5-(trifluoromethyl)-1H-pyrazole-4-carboxamide, Cpd 124

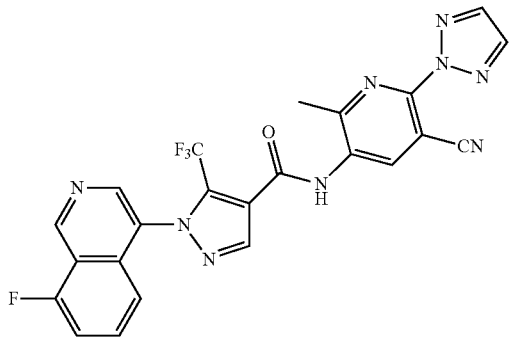

POCl₃ (94.27 mg, 0.62 mmol) was added to a solution of 1-(8-fluoroisoquinolin-4-yl)-5-(trifluoromethyl)-1H-pyrazole-4-carboxylic acid (100 mg, 0.31 mmol), 5-amino-6-methyl-2-(2H-1,2,3-triazol-2-yl)nicotinonitrile (73.87 mg, 0.37 mmol), pyridine (60.81 mg 0.77 mmol) in CH₂Cl₂ (10 mL). The mixture was stirred at rt for 3h, 50 mL H₂O and 50 mL CH₂Cl₂ were added to the mixture. The organic layer was washed with brine (50 mL), dried over MgSO₄ and concentrated under reduced pressure to afford the crude product, which was purified by preparative HPLC (30% to 60% (v/v) CH₃CN and H₂O with 0.05% HCl) and lyophilized to dryness to afford the title compound (37.6 mg 24.1% yield) as a white solid. LCMS (ESI) m/z M+1: 507.9. ¹H NMR (400 MHz, DMSO-d₆) δ ppm 10.71 (s, 1H), 9.72 (s, 1H), 8.91 (s, 1H), 8.64 (d, J=15.88 Hz, 2H), 8.29 (s, 2H), 7.90-7.98 (m, 1H), 7.64-7.72 (m, 1H), 7.13 (d, J=8.60 Hz, 1H), 2.64 (s, 3H).

Example 125

N-(5-chloro-6-(4-methyl-2H-1,2,3-triazol-2-yl)pyridin-3-yl)-1-(quinolin-5-yl)-5-(trifluoromethyl)-1H-pyrazole-4-carboxamide, 125

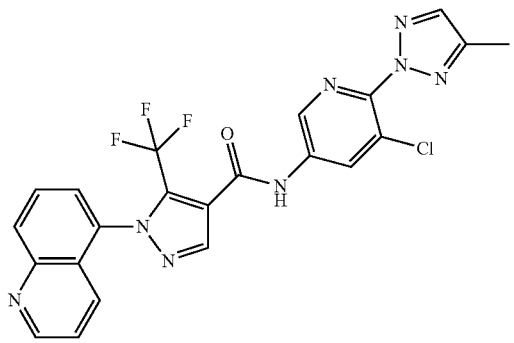 [SMILES: Cc1cnn(-c2ncc(NC(=O)c3cnn(-c4cccc5ncccc45)c3C(F)(F)F)cc2Cl)n1]

A. mixture of 3-chloro-2-(4-methyl-2H-1,2,3-triazol-2-yl)-5-nitropyridine and 3-chloro-2-(4-methyl-1H-1,2,3-triazol-1-yl)-5-nitropyridine, 125a

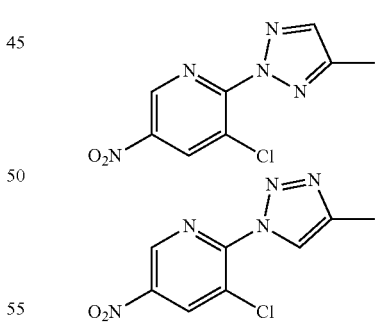

A solution of 4-methyl-1H-1,2,3-triazole (500 mg, 6.02 mmol), 2,3-dichloro-5-nitropyridine (1277.42 mg, 6.62 mmol), K₂CO₃ (2491.22 mg, 18.05 mmol) in CH₃CN (5 mL) was stirred at rt for 12 h. The mixture was concentrated under reduced pressure, the crude product was purified by column chromatography over silica gel (petroleum ether/ethyl acetate from 20:1 to 1:1). The desired fractions were collected and the solvent was concentrated under reduced pressure to afford 125a (1.1 g, 76.3%) as a yellow solid. LCMS (ESI) m/z M+1: 239.7.

B. mixture of 5-chloro-6-(4-methyl-2H-1,2,3-triazol-2-yl)pyridin-3-amine and 5-chloro-6-(4-methyl-1H-1,2,3-triazol-1-yl)pyridin-3-amine, 125b

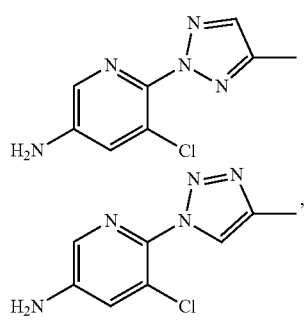

125b

Zn (1491.96 mg, 22.95 mmol) was added to a solution of mixture of 3-chloro-2-(4-methyl-2H-1,2,3-triazol-2-yl)-5-nitropyridine and 3-chloro-2-(4-methyl-1H-1,2,3-triazol-1-yl)-5-nitropyridine, 125a (1.1 g, 2.30 mmol) in aqNH$_4$Cl (30 mL) and H$_2$O (30 mL). The mixture was stirred at rt for 16 h. To the suspension was added aq NaHCO$_3$ to adjust to pH 9-10, and the mixture was filtered through a pad of diatomaceous earth. The filter cake was washed with CH$_2$Cl$_2$ (100 mL×3). The combined filtrates were washed with brine (200 mL), dried over MgSO$_4$ and concentrated under reduced pressure to afford mixture of 5-chloro-6-(4-methyl-2H-1,2,3-triazol-2-yl)pyridin-3-amine and 5-chloro-6-(4-methyl-1H-1,2,3-triazol-1-yl)pyridin-3-amine, 125b (1 g) as a brown solid, used directly for the next step. LCMS (ESI) m/z M+H: 209.7

C. N-(5-chloro-6-(4-methyl-2H-1,2,3-triazol-2-yl)pyridin-3-yl)-1-(quinolin-5-yl)-5-(trifluoromethyl)-1H-pyrazole-4-carboxamide, Cpd 125

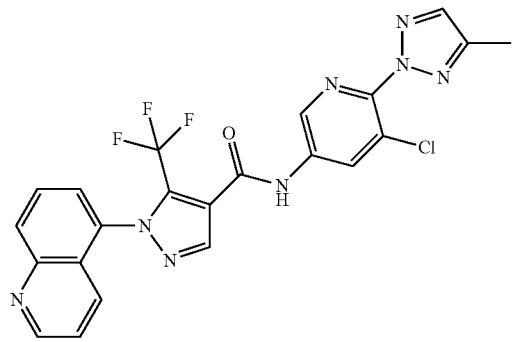 [SMILES: Cc1cnn(-c2ncc(NC(=O)c3cnn(-c4cccc5ncccc45)c3C(F)(F)F)cc2Cl)n1]

POCl$_3$ (182.86 mg, 1.19 mmol) was added to a solution of 125b (300 mg, 0.72 mmol), 1-(quinolin-5-yl)-5-(trifluoromethyl)-1H-pyrazole-4-carboxylic acid (183.19 mg, 0.60 mmol), pyridine (117.91 mg 1.49 mmol) in CH$_2$Cl$_2$ (10 mL). The mixture was stirred at rt for 2h, 50 mL H$_2$O and 50 mL CH$_2$Cl$_2$ were added to the mixture. The organic layer was washed with brine (50 mL), dried over MgSO$_4$ and concentrated under reduced pressure to afford the crude product, which was purified by preparative HPLC (35% to 65% (v/v) CH$_3$CN and H$_2$O with 0.05% HCl) and lyophilized to dryness to afford the title compound (208 mg 69.8% yield) as a white solid. LCMS (ESI) m/z M+1: 499.0. $^1$H NMR (400 MHz, DMSO-d$_6$) δ ppm 11.45 (s, 1H), 9.06 (t, J=2.54 Hz, 1H), 8.89 (s, 1H), 8.60-8.75 (m, 2H), 8.33 (d, J=8.38 Hz, 1H), 7.88-8.03 (m, 3H), 7.68 (d, J=2.65 Hz, 2H), 2.34 (s, 3H).

Example 126

N-(5-cyano-6-(2H-1,2,3-triazol-2-yl)pyridin-3-yl)-1-(thieno[2,3-b]pyridin-4-yl)-5-(trifluoromethyl)-1H-pyrazole-4-carboxamide, Cpd 126

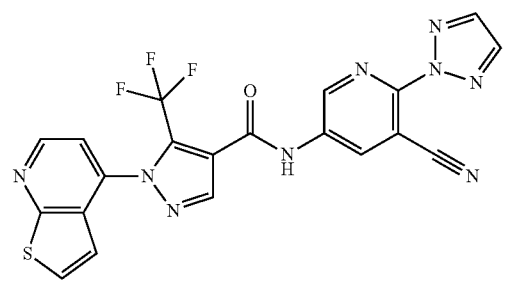 [SMILES: N#Cc1cc(NC(=O)c2cnn(-c3ccnc4sccc34)c2C(F)(F)F)cnc1-n1nccn1]

A. 4-hydrazinylthieno[2,3-b]pyridine, 126a

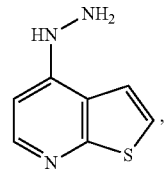

126a

A solution of 4-chlorothieno[2,3-b]pyridine (600 mg, 3.54 mmol) in hydrazine (5 mL, 98%) was stirred at 100° C. overnight. The solid was filtered and washed by 2 mL water. The solid was collected and dried to afford 126a (550 mg, 88.2% yield) as a white solid. LCMS (ESI) m/z M+1: 165.9.

B. ethyl 1-(thieno[2,3-b]pyridin-4-yl)-5-(trifluoromethyl)-1H-pyrazole-4-carboxylate, 126b

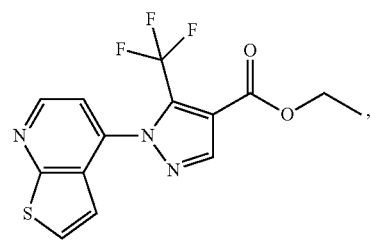

126b

A solution of 4-hydrazinylthieno[2,3-b]pyridine (300 mg, 1.70 mmol), ethyl 2-(ethoxymethylene)-4,4,4-trifluoro-3-oxobutanoate (613.23 mg, 2.55 mmol), in EtOH (5 mL) was stirred at 80° C. for 3 h. The mixture was concentrated under reduced pressure, the crude product was purified by column chromatography over silica gel (petroleum ether/ethyl acetate from 100/0 to 20/80). The desired fractions were collected and the solvent was concentrated under reduced pressure to afford 126b (500 mg, 86.1% yield) as a yellow solid.

C. 1-(thieno[2,3-b]pyridin-4-yl)-5-(trifluoromethyl)-1H-pyrazole-4-carboxylic acid, 126c

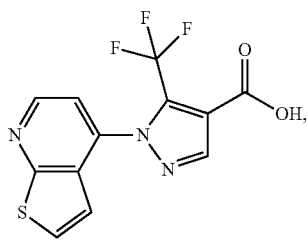

126c

A solution of ethyl 1-(thieno[2,3-b]pyridin-4-yl)-5-(trifluoromethyl)-1H-pyrazole-4-carboxylate, 126b (150 mg, 0.44 mmol), LiOH (18.44 mg, 0.44 mmol) in EtOH/H$_2$O (2/1, 2 mL) was stirred at room temperature overnight. 1N HCl solution was added to neutralize the reaction solution. The mixture was extracted with ethyl acetate (5 mL×3). The separated organic layer was dried (Na$_2$SO$_4$), filtered, and the filtrate was concentrated to afford 126c (137 mg, crude product) as a yellow solid. LCMS (ESI) m/z M+1: 313.9.

D. N-(5-cyano-6-(2H-1,2,3-triazol-2-yl)pyridin-3-yl)-1-(thieno[2,3-b]pyridin-4-yl)-5-(trifluoromethyl)-1H-pyrazole-4-carboxamide, Cpd 126

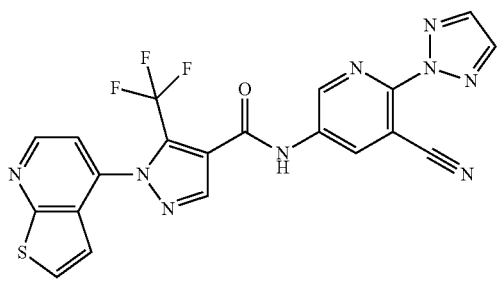 [SMILES: N#Cc1cc(NC(=O)c2cnn(-c3ccnc4sccc34)c2C(F)(F)F)cnc1-n1nccn1]

Phosphorus oxychloride (41.66 uL, 0.45 mmol) was added to a solution of 1-(thieno[2,3-b]pyridin-4-yl)-5-(trifluoromethyl)-1H-pyrazole-4-carboxylic acid, 126c (70 mg, 0.22 mmol), 5-amino-2-(2H-1,2,3-triazol-2-yl)nicotinonitrile (62.40 mg, 0.34 mmol), pyridine (180.73 uL, 2.24 mmol) in CH$_2$Cl$_2$ (2 mL). The mixture was stirred at room temperature for 2 h, 5 mL H$_2$O was added to the mixture. Sat. NaHCO$_3$ was added to adjust the pH of reaction mixture to 7-8. The mixture was extracted with CH$_2$Cl$_2$ (5 mL×3). The combined organic extracts were dried over anhydrous Mg$_2$SO$_4$, filtered, and concentrated to dryness under reduced pressure to afford the crude product, which was purified by preparative HPLC (42% to 72% (v/v) CH$_3$CN and H$_2$O with 0.05% HCl) and lyophilized to dryness to afford the title compound (50 mg, 46.4%). LCMS (ESI) m/z M+1: 481.9. $^1$H NMR (400 MHz, DMSO-d$_6$) δ ppm 7.17 (d, J=6.17 Hz, 1H), 7.73 (d, J=5.07 Hz, 1H), 8.13 (d, J=6.17 Hz, 1H), 8.31 (s, 2H), 8.62 (s, 1H), 8.84 (d, J=4.85 Hz, 1H), 8.87 (d, J=2.43 Hz, 1H), 9.08 (d, J=2.43 Hz, 1H), 11.36 (s, 1H).

Example 127

N-(5-chloro-6-(oxazol-2-yl)pyridin-3-yl)-1-(1-oxo-1,2-dihydroisoquinolin-5-yl)-5-(trifluoromethyl)-1H-pyrazole-4-carboxamide, Cpd 127

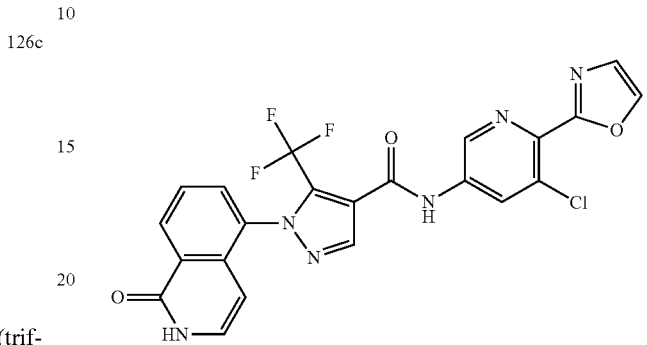

A. 5-bromo-3-chloropicolinoyl chloride, 127a

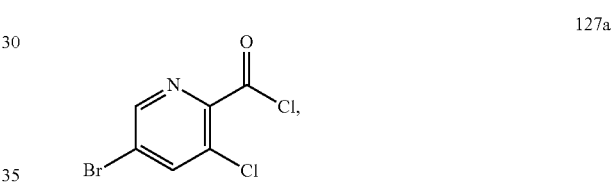

5-bromo-3-chloropicolinic acid (15 g, 63.44 mmol) was suspended in CH$_2$Cl$_2$ (250 mL) and stirred at 0° C. oxalyl chloride (15 mL, 176.09 mmol) was added dropwise then DMF (drops) added. The reaction mixture was stirred at 0° C. for 1 h and stirred at 20° C. for 1 h. The yellow solution was concentrated under reduced pressure to afford the compound (17 g) as a yellow solid.

B. 5-bromo-3-chloro-N-(2,2-dimethoxyethyl)picolinamide, 127b

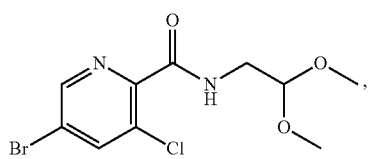

5-Bromo-3-chloropicolinoyl chloride (17 g, 66.69 mmol) was dissolved in CH$_2$Cl$_2$ (250 mL) and added dropwise to the mixture of 2,2-dimethoxyethanamine (14.02 g, 133.39 mmol) and TEA (13.50 g, 133.39 mmol) at 0° C. The mixture was stirred at 0° C. for 1.5 h. H$_2$O (300 mL) was added and extracted with CH$_2$Cl$_2$ (300 mL×3). The combined organic layers were dried over Na$_2$SO$_4$, filtered and the filtrates were concentrated under reduced pressure to afford crude as a brown oil, which was purified by flash column chromatography over silica gel (eluent: CH$_2$Cl$_2$/ ethyl acetate from 100/0 to 80/20). The desired fractions were collected and the solvent was concentrated under reduced pressure to afford the title compound (16 g, 74.1%) as a yellow solid.

C. 5-bromo-3-chloro-N-(2-oxoethyl)picolinamide, 127c

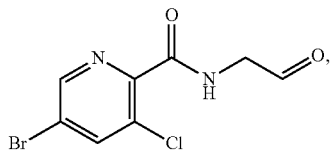

127c

To a solution of 5-bromo-3-chloro-N-(2,2-dimethoxyethyl)picolinamide (16 g, 49.45 mmol) in MeCN (160 mL) was added 2 N HCl (160 mL). The reaction mixture was stirred at rt for 16 h. The reaction mixture was adjust to pH 7.5 using sat. NaHCO$_3$, extracted with EtOAc (200 mL×3). The combined organic layers were dried over Na$_2$SO$_4$, filtered and the filtrates were concentrated under reduced pressure to afford crude (12 g, 87.5%) as a yellow solid. LCMS (ESI) m/z M+1: 278.8.

D. 2-(5-bromo-3-chloropyridin-2-yl)oxazole, 127d

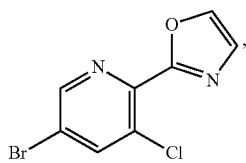

127d

5-Bromo-3-chloro-N-(2-oxoethyl)picolinamide (12 g, 43.24 mmol) was dissolved in dioxane (200 mL) and phosphorus oxychloride (19.89 g, 129.73 mmol) added. The reaction mixture was stirred at 80° C. for 6 h. The reaction mixture was poured into water (800 mL), stirred at rt for 0.5 h, then extracted with EtOAc (400 mL×3). The combined organic layers were dried over Na$_2$SO$_4$, filtered, and the filtrates were concentrated under reduced pressure to afford a black oil. The black oil was purified by flash column chromatography over silica gel (eluent: petroleum ether/ethyl acetate from 100/0 to 70/30) to afford the title compound (1.5 g, 13.3%) as a yellow solid. LCMS (ESI) m/z M+1: 258.9.

E. tert-butyl (5-chloro-6-(oxazol-2-yl)pyridin-3-yl)carbamate, 127e

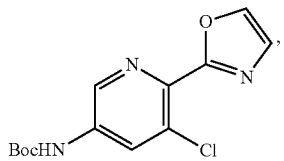

127e 2-(5-Bromo-3-chloropyridin-2-yl)oxazole (1.5 g, 5.78 mmol) and tert-butyl carbamate (1.35 g, 11.56 mmol) were dissolved in dioxane (30 mL), Pd$_2$(dba)$_3$ (264.67 mg, 0.29 mmol), Xantphos (333.48 mg, 0.58 mmol) and cesium carbonate (3.77 g, 11.56 mmol) were added and purged with N$_2$ for 1 min. The reaction mixture was stirred at 90° C. for 16 h. The combined mixture was filtered through a pad of diatomaceous earth and the pad was washed with EtOAc (50 mL×3). The filtrates were concentrated under reduced pressure to afford a crude product as a yellow oil, which was purified by flash column chromatography over silica gel (petroleum ether/ethyl acetate from 100/0 to 40/60). The desired fraction was collected and the solvent was concentrated under reduced pressure to afford the title compound (970 mg, 61.4%) as a yellow solid. LCMS (ESI) m/z M+1: 296.1.

F. 5-chloro-6-(oxazol-2-yl)pyridin-3-amine, 127f

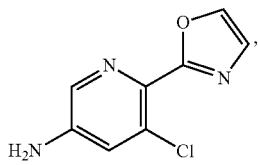

127f

Tert-Butyl (5-chloro-6-(oxazol-2-yl)pyridin-3-yl)carbamate (970 mg, 3.28 mmol) was dissolved in CH$_2$Cl$_2$ (5 mL) and HCl/dioxane (5.4 mL, 21.6 mmol) was added. The reaction mixture was stirred at 30° C. for 4 h. The reaction mixture was concentrated under reduced pressure to afford crude as a yellow oil, and adjust to pH 8 using sat.Na$_2$CO$_3$, extracted with CH$_2$Cl$_2$ (50 mL×2). The combined organic layers were dried over Na$_2$SO$_4$, filtered and the filtrates were concentrated under reduced pressure to afford the product (650 mg, 95.4%) as a yellow oil. LCMS (ESI) m/z M+1: 196.1.

G. N-(5-chloro-6-(oxazol-2-yl)pyridin-3-yl)-1-(1-oxo-1,2-dihydroisoquinolin-5-yl)-5-(trifluoromethyl)-1H-pyrazole-4-carboxamide Cpd 127

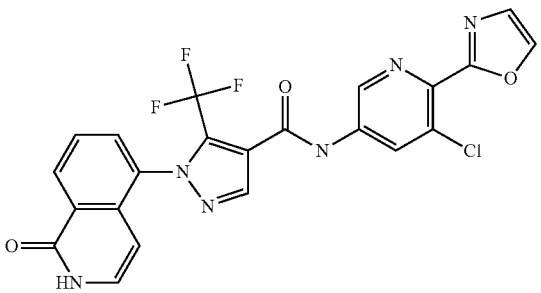

1-(1-Oxo-1,2-dihydroisoquinolin-5-yl)-5-(trifluoromethyl)-1H-pyrazole-4-carboxylic acid (876.66 mg, 2.25 mmol), 5-chloro-6-(oxazol-2-yl)pyridin-3-amine (400 mg, 2.05 mmol) and pyridine (970.52 mg, 12.27 mmol) were dissolved in CH$_2$Cl$_2$ (40 mL), and phosphorus oxychloride (940.66 mg, 6.14 mmol) was added. The mixture was stirred at 25° C. for 3 h, sat. NaHCO$_3$ (20 mL) was added and extracted with CH₂Cl₂ (50 mL×3). The combined organic layers were dried over Na₂SO₄, filtered and the filtrates were concentrated under reduced pressure to afford the crude product as a yellow oil, which was purified by preparative HPLC (34% to 54% (v/v) CH₃CN and H₂O with 0.05% HCl) and lyophilized to dryness to afford the title compound (240 mg, 23.2%). LCMS (ESI) m/z M+1: 500.9. ¹H NMR (400 MHz, DMSO-d₆) δ=11.64 (br d, J=5.3 Hz, 1H), 11.29 (s, 1H), 8.97 (s, 1H), 8.63-8.53 (m, 2H), 8.44 (d, J=8.2 Hz, 1H), 8.34 (s, 1H), 7.95 (d, J=7.7 Hz, 1H), 7.67 (t, J=7.9 Hz, 1H), 7.51 (s, 1H), 7.30 (t, J=6.6 Hz, 1H), 5.66 (d, J=7.3 Hz, 1H).

Example 128

N-(5-cyano-6-(2H-1,2,3-triazol-2-yl)pyridin-3-yl)-1-(thieno[3,2-b]pyridin-7-yl)-5-(trifluoromethyl)-1H-pyrazole-4-carboxamide, Cpd 128

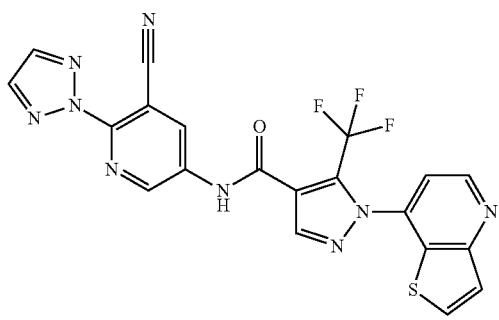 [SMILES: N#Cc1cc(NC(=O)c2cnn(-c3ccnc4ccsc34)c2C(F)(F)F)cnc1-n1nccn1]

A. 7-hydrazinylthieno[3,2-b]pyridine, 128a

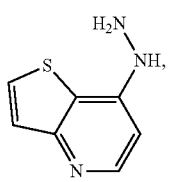

7-chlorothieno[3,2-b]pyridine (180 mg, 1.06 mmol) in NH₂NH₂.H₂O (7 mL) was reacted at 26° C. for 16 h. The mixture was extracted with 20×3 mL CH₂Cl₂, the solvent was concentrated under reduced pressure the give the desired compound.

B. ethyl 1-(thieno[3,2-b]pyridin-7-yl)-5-(trifluoromethyl)-1H-pyrazole-4-carboxylate, 128b

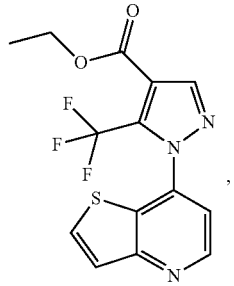

7-Hydrazinylthieno[3,2-b]pyridine (90 mg, 0.55 mmol) was added to a solution of ethyl 2-(ethoxymethylene)-4,4,4-trifluoro-3-oxobutanoate (196.25 mg, 0.82 mmol) in EtOH (5 mL) was reacted at 80° C. for 3 h. The mixture was concentrated under reduced pressure, then was purified by FFS (petroleum ether/ethyl acetate=100:0 to petroleum ether/ethyl acetate=60:40). The desired fractions were collected and the solvent was concentrated under reduced pressure to give the product as brown oil. LCMS (ESI) m/z M+1: 342.2.

C. 1-(thieno[3,2-b]pyridin-7-yl)-5-(trifluoromethyl)-1H-pyrazole-4-carboxylic acid, 128c

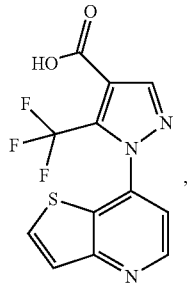

NaOH (25.23 mg, 0.63 mmol) was added to a solution of ethyl 1-(thieno[3,2-b]pyridin-7-yl)-5-(trifluoromethyl)-1H-pyrazole-4-carboxylate (75 mg, 0.21 mmol) in EtOH/H20=1:1 (3 mL) was reacted at 28° C. for 2 h. The solvent was concentrated under reduced pressure the give the desired compound. LCMS (ESI) m/z M+1: 314.2

443

D. N-(5-cyano-6-(2H-1,2,3-triazol-2-yl)pyridin-3-yl)-1-(thieno[3,2-b]pyridin-7-yl)-5-(trifluoromethyl)-1H-pyrazole-4-carboxamide, Cpd 128

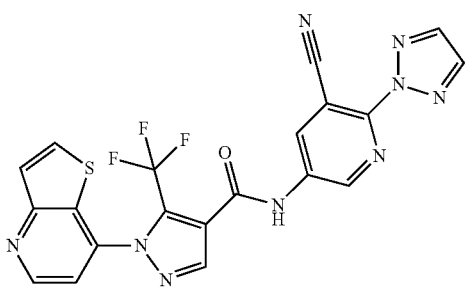 [SMILES: N#Cc1cc(NC(=O)c2cnn(-c3ccnc4ccsc34)c2C(F)(F)F)cnc1-n1nccn1]

1-(Thieno[3,2-b]pyridin-7-yl)-5-(trifluoromethyl)-1H-pyrazole-4-carboxylic acid (65 mg, 0.19 mmol), 5-amino-2-(2H-1,2,3-triazol-2-yl)nicotinonitrile (42.76 mg, 0.23 mmol), POCl$_3$ (35.21 mg, 0.23 mmol) were dissolved in DCM (2 mL), and pyridine (45.41 mg, 0.57 mmol) was added. The mixture was stirred at 25° C. for 2 h, sat.NH$_4$Cl (20 mL) was added and extracted with CH$_2$Cl$_2$ (20 mL×2). The combined organic layers were dried over Na$_2$SO$_4$, filtered and the filtrates were concentrated under reduced pressure to afford crude as a yellow oil, which was purified by preparative HPLC (73% to 43% (v/v) CH$_3$CN and H$_2$O with 0.05% HCl) and lyophilized to dryness to afford the title compound (46 mg, 49.7%). LCMS (ESI) m/z M+1: 481.9. $^1$H NMR (400 MHz, DMSO-d$_6$) δ ppm 7.67 (br d, J=4.63 Hz, 1H), 7.75 (d, J=5.51 Hz, 1H), 8.21-8.38 (m, 1H), 8.23-8.37 (m, 2H), 8.74 (s, 1H), 8.87-8.96 (m, 2H), 9.14 (d, J=2.21 Hz, 1H), 11.66 (s, 1H).

Example 129

N-(3-chloro-4-(2H-1,2,3-triazol-2-yl)phenyl)-1-(1-oxo-1,2-dihydroisoquinolin-5-yl)-5-(trifluoromethyl)-1H-pyrazole-4-carboxamide, Cpd 129

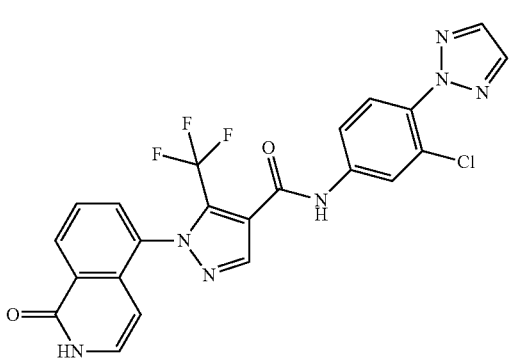 [SMILES: O=C(Nc1ccc(-n2nccn2)c(Cl)c1)c1cnn(-c2cccc3c(=O)[nH]ccc23)c1C(F)(F)F]

444

A. 2-(2-chloro-4-nitrophenyl)-2H-1,2,3-triazole, 129a

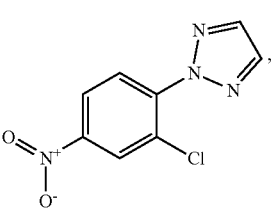

2-Chloro-1-fluoro-4-nitrobenzene (3 g, 17.09 mmol), 1H-1,2,3-triazole (1.30 g, 18.80 mmol) and potassium carbonate (3.54 g, 25.63 mmol) were added to DMF (50 mL) and stirred at 55° C. for 3 hr. The reaction mixture was concentrated under reduced pressure to afford crude as a yellow solid. Sat.NH$_4$Cl (100 mL) was added and extracted with EtOAc (100 mL×3). The combined organic layers were dried over Na$_2$SO$_4$, filtered and the filtrates were concentrated under reduced pressure to afford crude as a yellow solid, which was purified by FCC (eluent: petroleum ether/ethyl acetate from 100/0 to 60/40) to afford the title compound (1.9 g, 49.5%) as a yellow solid. $^1$H NMR (400 MHz, CHLOROFORM-d) δ=8.49 (d, J=2.5 Hz, 1H), 8.28 (dd, J=2.5, 8.8 Hz, 1H), 7.97 (s, 2H), 7.93 (d, J=8.8 Hz, 1H), 7.95-7.91 (m, 1H).

B. 3-Chloro-4-(2H-1,2,3-triazol-2-yl)aniline, 129b

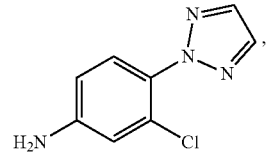

2-(2-Chloro-4-nitrophenyl)-2H-1,2,3-triazole (1.9 g, 8.46 mmol) was dissolved in THF (20 mL), Fe (2.83 g, 50.76 mmol), NH$_4$Cl (2.72 g, 50.76 mmol) and H$_2$O (20 mL) were added. The reaction mixture was stirred at 80° C. for 3 hr. The reaction mixture was filtered through a pad of Diatomaceous earth and the pad was washed with EtOAc (30 mL×3). The filtrates were concentrated to dryness to give crude as a yellow solid, which was purified by FCC (eluent: petroleum ether/ethyl acetate from 100/0 to 70/30). The desired fractions were collected and the solvent was concentrated under reduced pressure to afford (1.5 g, 89.5%) as a yellow solid. LCMS (ESI) m/z M+1: 194.8.

C. N-(3-chloro-4-(2H-1,2,3-triazol-2-yl)phenyl)-1-(1-oxo-1,2-dihydroisoquinolin-5-yl)-5-(trifluoromethyl)-1H-pyrazole-4-carboxamide, 129

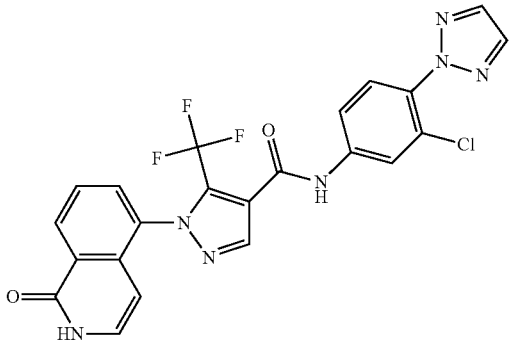

1-(1-oxo-1,2-dihydroisoquinolin-5-yl)-5-(trifluoromethyl)-1H-pyrazole-4-carboxylic acid (300 mg, 0.77 mmol), 3-chloro-4-(2H-1,2,3-triazol-2-yl)aniline (182.95 mg, 0.92 mmol) and pyridine (608.89 mg, 7.70 mmol) were dissolved in $CH_2Cl_2$ (15 mL), and phosphorus oxychloride (354.09 mg, 2.31 mmol) was added. The mixture was stirred at 25° C. for 3 h, sat.$NaHCO_3$ (20 mL) was added and extracted with $CH_2Cl_2$ (50 mL×3). The combined organic layers were dried over $Na_2SO_4$, filtered and the filtrates were concentrated under reduced pressure to afford the crude product as a yellow oil, which was purified by preparative HPLC (40% to 40% (v/v) $CH_3CN$ and $H_2O$ with 0.05% HCl) and lyophilized to dryness to afford the title compound (135 mg, 34.8%). LCMS (ESI) m/z M+1: 499.9. $^1$H NMR (400 MHz, DMSO-$d_6$) δ=11.64 (br d, J=5.5 Hz, 1H), 11.02 (s, 1H), 8.52 (s, 1H), 8.44 (d, J=8.2 Hz, 1H), 8.17 (d, J=2.0 Hz, 1H), 8.15 (s, 2H), 7.94 (d, J=7.5 Hz, 1H), 7.86 (dd, J=2.1, 8.7 Hz, 1H), 7.71 (d, J=8.8 Hz, 1H), 7.67 (t, J=7.8 Hz, 1H), 7.30 (t, J=6.6 Hz, 1H), 5.67 (d, J=7.1 Hz, 1H).

Example 130

N-(5-cyano-6-(2H-1,2,3-triazol-2-yl)pyridin-3-yl)-1-(2-D-quinolin-5-yl)-5-(trifluoromethyl)-1H-pyrazole-4-carboxamide, Cpd 130

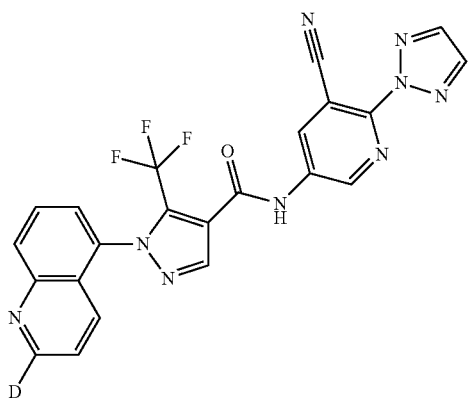 [SMILES: [2H]c1ccc2c(-n3ncc(C(=O)Nc4cnc(-n5nccn5)c(C#N)c4)c3C(F)(F)F)cccc2n1]

A. 2-D-quinoline, 130a

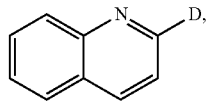

A solution of quinoline-2-carboxylic acid (1.5 g, 8.66 mmol), silver(I) carbonate (238.85 mg, 0.87 mmol) and deuteroxide (9 mL) in DMSO (45 m L) was stirred at 140° C. for 16 h. The reaction mixture was filtered, the filtrate was concentrated under reduced pressure to give the crude product as colorless oil, which was purified by FCC (petroleum ether: ethyl acetate=100:0 to petroleum ether/ethyl acetate=0:100) to afford the title compound (0.88 g, 78.049%) as a colorless oil.

B. 5-bromo-2D-quinoline, 130b

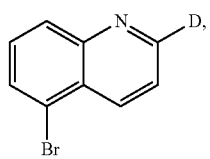

1-Bromopyrrolidine-2,5-dione (1.203 g, 6.76 mmol) was added to a solution of 2-D-quinoline (0.88 g, 6.76 mmol) in conc.$H_2SO_4$ (15 mL). The reaction mixture was poured onto 75 mL crushed ice, pH was adjusted to 9.0 using coned aq $NH_3$, the alkaline slurry was then extracted with ethyl acetate (3×30 mL). The combined organic fractions were washed with 1.0 M NaOH then water, dried ($MgSO_4$), filtered, concentrated to give crude product, which was purified by FCC (petroleum ether: ethyl acetate=100:0 to 0:100) to afford relatively high purity product, which was purified by preparative HPLC (10% to 40% (v/v) $CH_3CN$ and $H_2O$ with 0.05% ammonia hydroxide) and lyophilized to dryness to afford the title compound (390 mg, 27.6%). $^1$H NMR (400 MHz, DMSO-$d_6$) δ ppm 8.70 (1H, d, J=8.78 Hz), 8.18 (1H, d, J=8.53 Hz), 8.09 (1H, d, J=7.53 Hz), 7.77-7.87 (2H, m).

C. 2-D-5-hydrazinylquinoline, 130c

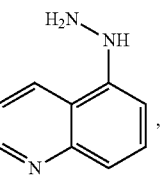

Palladium(11)(pi-cinnamyl) chloride dimer (24.78 mg, 0.048 mmol) and 4-(2-(di((3S,5S,7S)-adamantan-1-yl)phosphino)phenyl)morpholine (44.35 mg, 0.096 mmol) was added to dioxane (10 mL), immediately purged with $N_2$. The resulting solution was stirred at room temp under $N_2$ for 10 min, and then charged with sodium 2-methylpropan-2-olate (183.88 mg, 1.91 mmol) and 5-bromo-2-D-quinoline (200 mg, 0.96 mmol). The reaction vessel was sealed, and purged with N₂. The resulting reaction was stirred at room temp for 5 min and was then treated with hydrazine hydrate (95.78 mg, 1.91 mmol) via syringe. The reaction was stirred at 50° C. under N₂ for 1.5 h. The mixture was filtered, the filtrate was concentrated under reduced pressure to give the crude product as a yellow solid (140 mg, 91.4%) which directly used for the next step without further purification.

D. ethyl 1-(2-D-quinolin-5-yl)-5-(trifluoromethyl)-1H-pyrazole-4-carboxylate, 130d

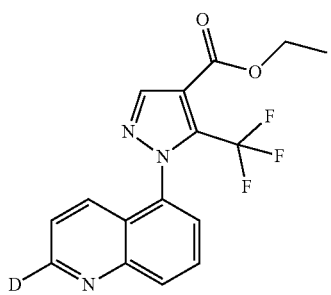

130d

A solution consisting of ethyl 2-(ethoxymethylene)-4,4,4-trifluoro-3-oxobutanoate, (1.05 g, 4.37 mmol), 2-D-5-hydrazinylquinoline (140 mg, 0.87 mmol), and ethanol (10 mL) was stirred at 80° C. for 2 h. The resultant solution was concentrated to dryness under reduced pressure to afford the crude product, which was purified by FCC (petroleum ether: ethyl acetate=100/0 to 50/50) to afford the title compound (0.26 g, 87.7%) as a yellow solid. LCMS (ESI) m/z M+1: 336.9.

E. 1-(2-Dquinolin-5-yl)-5-(trifluoromethyl)-1H-pyrazole-4-carboxylic acid, 130e

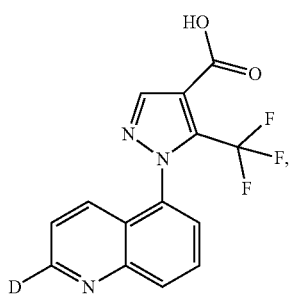

130e

Sodium hydroxide (45.96 mg, 1.15 mmol) was added to a solution of ethyl 1-(2-D-quinolin-5-yl)-5-(trifluoromethyl)-1H-pyrazole-4-carboxylate (260 mg, 0.77 mmol) in THF/H₂O 3:1 (12 mL). The mixture was reacted at room temperature for 16 h, the solvent was concentrated under reduced pressure and 20 mL H₂O was added to the mixture. The mixture was acidified by 1M hydrochloric to pH 5 and extracted with ethyl acetate (20 mL×3). The combined organic layers were washed with brine, dried over anhydrous MgSO₄, and filtered. The filtrates were concentrated under reduced pressure to afford the product as a white solid (200 mg, 84.695%).

F. N-(5-cyano-6-(2H-1,2,3-triazol-2-yl)pyridin-3-yl)-1-(2-D-quinolin-5-yl)-5-(trifluoromethyl)-1H-pyrazole-4-carboxamide, Cpd 130

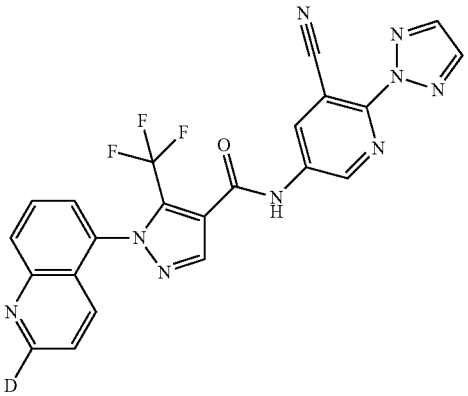 [SMILES: [2H]c1ccc2c(-n3ncc(C(=O)Nc4cnc(-n5nccn5)c(C#N)c4)c3C(F)(F)F)cccc2n1]

1-(2-D-quinolin-5-yl)-5-(trifluoromethyl)-1H-pyrazole-4-carboxylic acid (100 mg, 0.32 mmol), 5-amino-2-(2H-1,2,3-triazol-2-yl)nicotinonitrile, (60.40 mg, 0.32 mmol), pyridine (0.13 mL, 1.62 mmol) were dissolved in CH₂Cl₂ (10 mL), and phosphorus oxychloride (0.12 mL, 1.30 mmol) was added. The mixture was stirred at 25° C. for 2 h, sat.NaHCO₃ (20 mL) was added and the mixture extracted with CH₂Cl₂ (30 mL×2). The combined organic extracts were dried over anhydrous Na₂SO₄, filtered, and the filtrate concentrated to dryness under reduced pressure to afford the crude product, which was purified by preparative HPLC (21% to 51% (v/v) CH₃CN and H₂O with 0.05% HCl) and lyophilized to dryness to afford the title compound (45 mg, 28.8%). LCMS (ESI) m/z M+1: 477.0. ¹H NMR (400 MHz, METHANOL-d₄) δ ppm 12.20 (1H, s), 9.93 (1H, d, J=2.51 Hz), 9.71 (1H, d, J=2.51 Hz), 9.43 (1H, s), 9.12-9.18 (3H, m), 8.73-8.84 (2H, m), 8.42-8.53 (2H, m).

Example 131

N-(5-chloro-6-(2H-1,2,3-triazol-2-yl)pyridin-3-yl)-1-(2-Dquinolin-5-yl)-5-(trifluoromethyl)-1H-pyrazole-4-carboxamide, Cpd 131

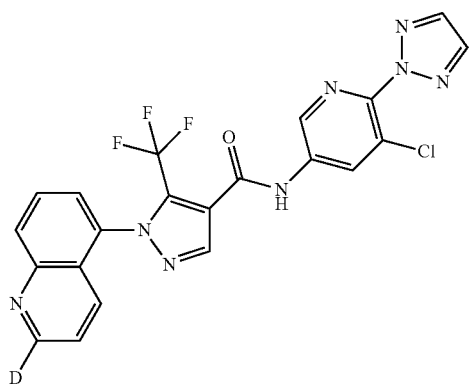 [SMILES: [2H]c1ccc2c(-n3ncc(C(=O)Nc4cnc(-n5nccn5)c(Cl)c4)c3C(F)(F)F)cccc2n1]

1-(2-D-quinolin-5-yl)-5-(trifluoromethyl)-1H-pyrazole-4-carboxylic acid (240.00 mg, 0.78 mmol), 5-chloro-6-(2H-1,2,3-triazol-2-yl)pyridin-3-amine, (152.31 mg, 0.78 mmol), pyridine (0.31 mL, 3.89 mmol) were dissolved in CH$_2$Cl$_2$ (10 mL), and phosphorus oxychloride (0.285 mL, 3.12 mmol) was added. The mixture was stirred at 25° C. for 2 h, sat. NaHCO$_3$ (20 mL) was added and extracted with CH$_2$Cl$_2$ (30 mL×2). The combined organic extracts were dried over anhydrous Na$_2$SO$_4$, filtered, and concentrated to dryness under reduced pressure to afford the crude product, which was purified by preparative HPLC (25% to 55% (v/v) CH$_3$CN and H$_2$O with 0.05% HCl) and lyophilized to dryness to afford the title compound (183 mg, 48.4%). LCMS (ESI) m/z M+1: 485.9. $^1$H NMR (400 MHz, DMSO-d$_6$) δ ppm 11.40 (1H, s), 8.91 (1H, d, J=2.01 Hz), 8.72 (1H, d, J=2.01 Hz), 8.66 (1H, s), 8.36 (1H, d, J=8.28 Hz), 8.21 (2H, s), 7.93-8.05 (2H, m), 7.64-7.74 (2H, m).

Example 132

1-(4-aminonaphthalen-1-yl)-N-(5-cyano-6-(2H-1,2,3-triazol-2-yl)pyridin-3-yl)-5-(trifluoromethyl)-1H-pyrazole-4-carboxamide, Cpd 132

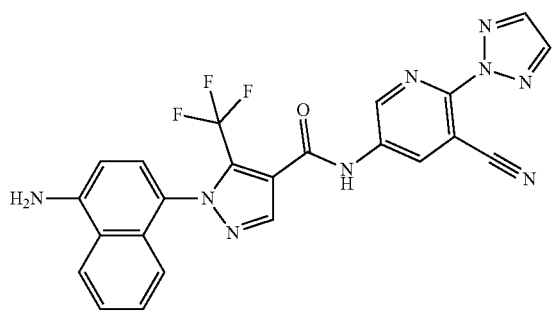 [SMILES: N#Cc1cc(NC(=O)c2cnn(-c3ccc(N)c4ccccc34)c2C(F)(F)F)cnc1-n1nccn1]

A. (4-nitronaphthalen-1-yl)hydrazine, 132a

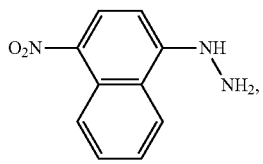

132a

A solution of 1-fluoro-4-nitronaphthalene (670 mg, 3.51 mmol) in iPrOH (20 mL) was added N2H$_4$.H$_2$O (460 mg, 9.19 mmol) and heated to 60° C. for 2 hrs. After cooled to RT, the solid was collected, washed with H$_2$O (5 mL) and EtOH (5 mL), and then dried under vacuo to give product as a yellowish solid (500 mg, 70.2%).

B. ethyl 1-(4-nitronaphthalen-1-yl)-5-(trifluoromethyl)-1H-pyrazole-4-carboxylate, 132b

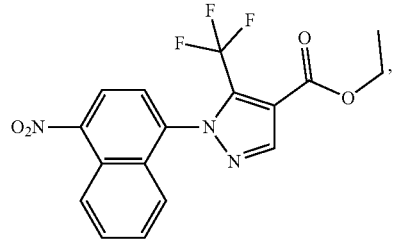

132b

A solution consisting of ethyl 2-(ethoxymethylene)-4,4,4-trifluoro-3-oxobutanoate (827.39 mg, 3.445 mmol), (4-nitronaphthalen-1-yl)hydrazine (500 mg, 2.461 mmol) and ethanol (30 mL) was stirred at 25° C. for 2 h. The resultant solution was concentrated to dryness under reduced pressure to afford the crude product, which was purified by FCC (petroleum ether: ethyl acetate=100/0 to 0/100) to afford the title compound (0.8 g, 85.7%) as a yellow oil. LCMS (ESI) m/z M+1: 380.0.

C. 1-(4-nitronaphthalen-1-yl)-5-(trifluoromethyl)-1H-pyrazole-4-carboxylic acid, 132c

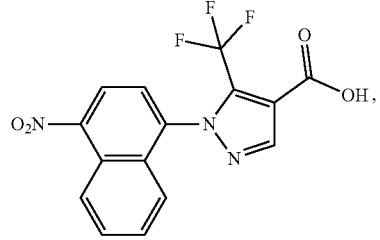

132c

Sodium hydroxide (126.54 mg, 3.16 mmol) was added to a solution of ethyl 1-(4-nitronaphthalen-1-yl)-5-(trifluoromethyl)-1H-pyrazole-4-carboxylate (800 mg, 2.11 mmol) in THF/H$_2$O 1:1 (20 mL). The mixture was stirred at room temperature for 16 h, the solvent was concentrated under reduced pressure and 20 mL H$_2$O was added to the mixture. The mixture was acidified using 1M hydrochloric to pH 5 and extracted with ethyl acetate (20 mL×3). The combined organic layers were washed with brine, dried over anhydrous MgSO$_4$, filtered, the filtrates were concentrated under reduced pressure to afford product as a yellow solid (630 mg, 85.0%). LCMS (ESI) m/z M+1: 352.0.

D. N-(5-cyano-6-(2H-1,2,3-triazol-2-yl)pyridin-3-yl)-1-(4-nitronaphthalen-1-yl)-5-(trifluoromethyl)-1H-pyrazole-4-carboxamide, Cpd 132d

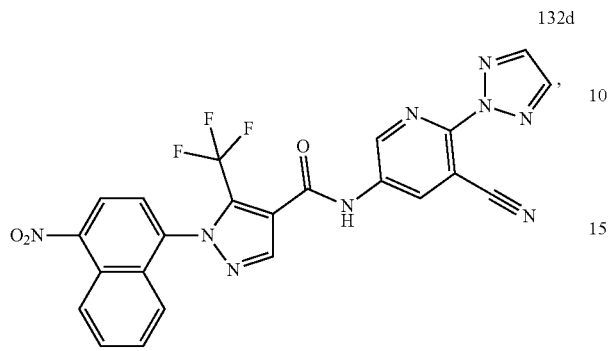

1-(4-Nitronaphthalen-1-yl)-5-(trifluoromethyl)-1H-pyrazole-4-carboxylic acid (400 mg, 1.14 mmol), 5-amino-2-(2H-1,2,3-triazol-2-yl)nicotinonitrile, (212.02 mg, 1.14 mmol), pyridine (0.46 mL, 5.69 mmol) were dissolved in $CH_2Cl_2$ (20 mL), and phosphorus oxychloride (0.42 mL, 4.56 mmol) was added. The mixture was stirred at 25° C. for 2 h, sat. $NaHCO_3$ (20 mL) was added and extracted with $CH_2Cl_2$ (30 mL×2). The combined organic extracts were dried over anhydrous $Na_2SO_4$, filtered, and the filtrate concentrated to dryness under reduced pressure to afford the crude product, which was purified by FCC (petroleum ether: ethyl acetate=100/0 to 0/100) to afford the title compound (0.41 g, 61.7%) as a yellow solid. LCMS (ESI) m/z M+1: 520.1.

E. 1-(4-Aminonaphthalen-1-yl)-N-(5-cyano-6-(2H-1,2,3-triazol-2-yl)pyridin-3-yl)-5-(trifluoromethyl)-1H-pyrazole-4-carboxamide, Cpd 132

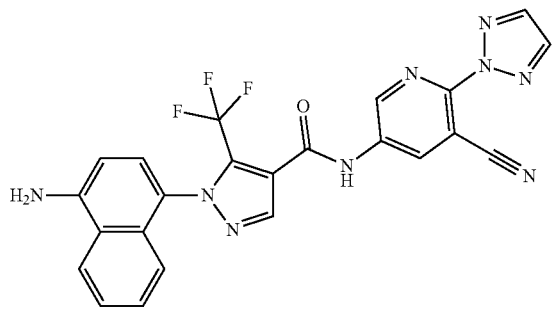 [SMILES: N#Cc1cc(NC(=O)c2cnn(-c3ccc(N)c4ccccc34)c2C(F)(F)F)cnc1-n1nccn1]

Fe (196.27 mg, 3.52 mmol) and $NH_4Cl$ (188.0 mg, 3.52 mmol) were added to the mixture of N-(5-cyano-6-(2H-1,2,3-triazol-2-yl)pyridin-3-yl)-1-(4-nitronaphthalen-1-yl)-5-(trifluoromethyl)-1H-pyrazole-4-carboxamide (410 mg, 0.70 mmol) in THF (20 mL), $H_2O$ (10 mL), MeOH (10 mL). The reaction was stirred at 70° C. for 2 h, filtered through a pad of diatomaceous earth, and the pad was washed with EtOAc (20 mL×2). The combined filtrates were concentrated to dryness to give a crude brown solid, which was purified by preparative HPLC (35% to 65% (v/v) $CH_3CN$ and $H_2O$ with 0.05% ammonia hydroxide) and lyophilized to dryness to afford the title compound (220 mg, 63.4%).

LCMS (ESI) m/z M+1: 490.0. $^1$H NMR (400 MHz, DMSO-$d_6$) δ ppm 11.39 (1H, s), 9.10 (1H, d, J=2.20 Hz), 8.88 (1H, d, J=2.43 Hz), 8.49 (1H, s) 8.30 (2H, s), 8.15-8.24 (1H, m), 7.44-7.53 (2H, m), 7.40 (1H, d, J=7.94 Hz), 6.86-6.93 (1H, m), 6.78 (1H, d, J=8.16 Hz).

Example 133

N-(3-cyano-4-(2H-1,2,3-triazol-2-yl)phenyl)-1-(quinolin-5-yl)-5-(trifluoromethyl)-1H-pyrazole-4-carboxamide, Cpd 133

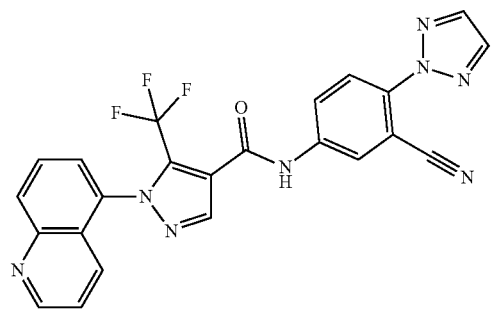 [SMILES: N#Cc1cc(NC(=O)c2cnn(-c3cccc4ncccc34)c2C(F)(F)F)ccc1-n1nccn1]

A. 5-nitro-2-(2H-1,2,3-triazol-2-yl)benzonitrile, 133a

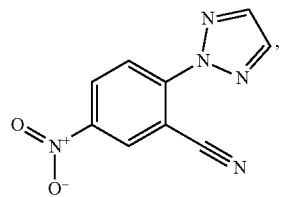

2-Fluoro-5-nitrobenzonitrile (500 mg, 3.01 mmol), 1H-1,2,3-triazole (228.68 mg, 3.31 mmol) and potassium carbonate (832.02 mg, 6.02 mmol) were added to MeCN (10 mL) and stirred at 25° C. for 16 h. The reaction mixture was filtered and the residue was washed with EtOAc (30 mL×2). The combined organic layers were concentrated under reduced pressure to afford a crude yellow solid, which was purified by FCC (petroleum ether/ethyl acetate from 100:0 to 70:30) to afford the title compound (600 mg, 92.6%) as a white solid. $^1$H NMR (400 MHz, CHLOROFORM-d) δ=8.72 (d, J=2.6 Hz, 1H), 8.55 (dd, J=2.4, 9.0 Hz, 1H), 8.42 (d, J=9.3 Hz, 1H), 8.03 (s, 2H).

B. 5-amino-2-(2H-1,2,3-triazol-2-yl)benzonitrile, 133b

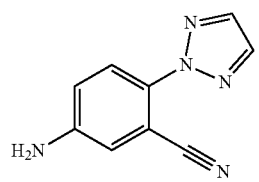

5-Nitro-2-(2H-1,2,3-triazol-2-yl)benzonitrile (600 mg, 2.79 mmol) was dissolved in THF (10 mL), Fe (1.25 g, 22.31 mmol), NH₄Cl (1.19 g, 22.31 mmol) and H₂O (10 mL) were added. The reaction mixture was stirred at 80° C. for 4 h, filtered through a pad of diatomaceous earth and the pad was washed with EtOAc (20 mL×3). The filtrates were concentrated to dryness to give crude product as a yellow solid, which was purified by FCC (eluent: petroleum ether/ethyl acetate from 100/0 to 50/50). The desired fractions were collected and the solvent was concentrated under reduced pressure to afford the title compound (440 mg, 82.1%) as a yellow oil. LCMS (ESI) m/z M+1: 186.1. ¹H NMR (400 MHz, DMSO-d₆) δ=8.08 (s, 2H), 7.57 (d, J=8.8 Hz, 1H), 6.99 (d, J=2.6 Hz, 1H), 6.94 (dd, J=2.6, 8.8 Hz, 1H), 5.98 (s, 2H).

C. N-(3-cyano-4-(2H-1,2,3-triazol-2-yl)phenyl)-1-(quinolin-5-yl)-5-(trifluoromethyl)-1H-pyrazole-4-carboxamide, Cpd 133

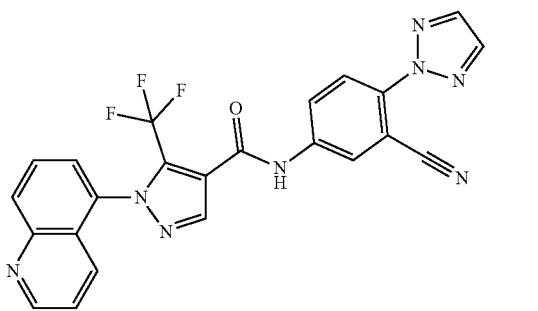 [SMILES: N#Cc1cc(NC(=O)c2cnn(-c3cccc4ncccc34)c2C(F)(F)F)ccc1-n1nccn1]

5-Amino-2-(2H-1,2,3-triazol-2-yl)benzonitrile (110.98 mg, 0.58 mmol), 1-(quinolin-5-yl)-5-(trifluoromethyl)-1H-pyrazole-4-carboxylic acid (120 mg, 0.39 mmol) and pyridine (45.7 mg, 0.58 mmol) were dissolved in CH₂Cl₂ (10 mL), and phosphorus oxychloride (88.58 mg, 0.58 mmol) was added. The mixture was stirred at 25° C. for 16 h, sat.NaHCO₃ (20 mL) was added and extracted with CH₂Cl₂ (50 mL×2). The combined organic layers were dried over Na₂SO₄, filtered and the filtrates were concentrated under reduced pressure to afford the crude product as a yellow solid, which was purified by preparative HPLC (35% to 65% (v/v) CH₃CN and H₂O with 0.05% HCl) and lyophilized to dryness to afford the title compound (87 mg, 47.8%). LCMS (ESI) m/z M+1: 474.9. ¹H NMR (400 MHz, DMSO-d₆) δ ppm 11.22 (s, 1H), 9.11 (dd, J=1.9, 3.9 Hz, 1H), 8.62 (s, 1H), 8.44 (d, J=2.2 Hz, 1H), 8.37 (d, J=8.2 Hz, 1H), 8.28 (s, 2H), 8.26-8.21 (m, 1H), 8.17-8.11 (m, 1H), 8.05-7.98 (m, 1H), 7.98-7.94 (m, 1H), 7.76-7.68 (m, 2H).

Example 134

N-(6-(4-amino-2H-1,2,3-triazol-2-yl)-5-chloropyridin-3-yl)-1-(1-oxo-1,2-dihydroisoquinolin-5-yl)-5-(trifluoromethyl)-1H-pyrazole-4-carboxamide, Cpd 134

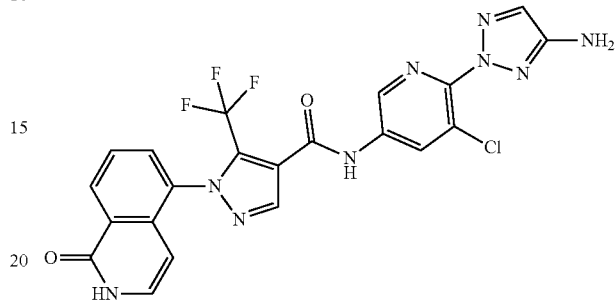

A. 2-(3-chloro-5-(1-(1-methoxyisoquinolin-5-yl)-5-(trifluoromethyl)-1H-pyrazole-4-carboxamido)pyridin-2-yl)-2H-1,2,3-triazole-4-carboxylic acid, 134a

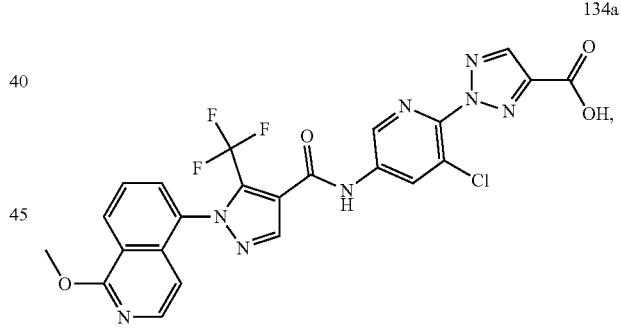

NaOH (72.62 mg, 1.82 mmol) was added to a solution of methyl 2-(3-chloro-5-(1-(1-methoxyisoquinolin-5-yl)-5-(trifluoromethyl)-1H-pyrazole-4-carboxamido)pyridin-2-yl)-2H-1,2,3-triazole-4-carboxylate (600 mg, 0.91 mmol) in THF/H₂O 1:1 (10 mL) was reacted at 23° C. for 2 h. The solvent was concentrated under reduced pressure, 1M HCl solution was add to the mixture to adjust to pH 5 and a solid formed. The solid was collected to afford the product. LCMS (ESI) m/z M+1: 530.9.

B. tert-butyl(2-(3-chloro-5-(1-(1-methoxyisoquinolin-5-yl)-5-(trifluoromethyl)-1H-pyrazole-4-carboxamido)pyridin-2-yl)-2H-1,2,3-triazol-4-yl)carbamate, 134b

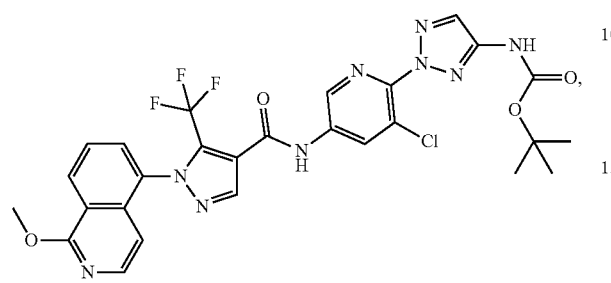

To a solution of 2-(3-chloro-5-(1-(1-methoxyisoquinolin-5-yl)-5-(trifluoromethyl)-1H-pyrazole-4-carboxamido)pyridin-2-yl)-2H-1,2,3-triazole-4-carboxylic acid (500 mg, 0.82 mmol) in t-BuOH (10 mL), DPPA (271.3 mg, 0.99 mmol) and TEA (249.4 ul, 2.47 mmol) were added under $N_2$ atmosphere. The mixture was stirred at 80° C. overnight, sat. $NaHCO_3$ (20 mL) was added and extracted with EtOAc (30 mL×2). The combined organic layers were dried over $Na_2SO_4$, filtered and the filtrates were concentrated under reduced pressure to afford crude as a brown oil. The crude product was purified by column chromatography over silica gel (petroleum ether/ethyl acetate=2:1 to petroleum ether/ethyl acetate=1:2). The desired fractions were collected and the solvent was concentrated under reduced pressure to give the product as a yellow solid. LCMS (ESI) m/z M+1: 630.0.

C. N-(6-(4-amino-2H-1,2,3-triazol-2-yl)-5-chloropyridin-3-yl)-1-(1-oxo-1,2-dihydroisoquinolin-5-yl)-5-(trifluoromethyl)-1H-pyrazole-4-carboxamide, Cpd 134

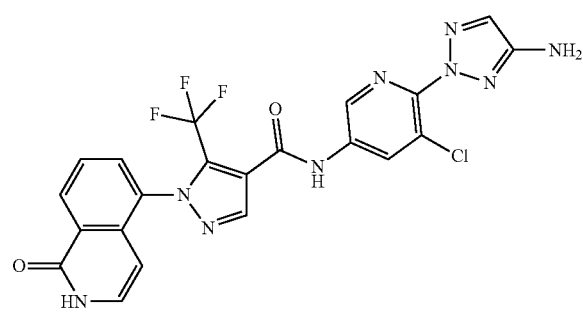 [SMILES: Nc1cnn(-c2ncc(NC(=O)c3cnn(-c4cccc5c(=O)[nH]ccc45)c3C(F)(F)F)cc2Cl)n1]

tert-Butyl (2-(3-chloro-5-(1-(1-methoxyisoquinolin-5-yl)-5-(trifluoromethyl)-1H-pyrazole-4-carboxamido)pyridin-2-yl)-2H-1,2,3-triazol-4-yl)carbamate (180 mg, 0.27 mmol), and conc. HCl (2 mL) was added i-PrOH (4 mL), stirred at 60° C. for 2 h. The mixture was concentrated under reduced pressure to afford crude product as a brown oil, which was purified by preparative HPLC (72% to 42% (v/v) $CH_3CN$ and $H_2O$ with 0.05% ammonia hydroxide) and lyophilized to dryness to afford the title compound (64 mg, 44.3%). LCMS (ESI) m/z M+1: 515.9. $^1$H NMR (400 MHz, DMSO-$d_6$) δ ppm 5.47 (s, 2H), 5.64 (d, J=7.28 Hz, 1H), 7.27 (d, J=7.28 Hz, 1H), 7.31 (s, 1H), 7.65 (t, J=7.94 Hz, 1H), 7.92 (d, J=7.50 Hz, 1H), 8.42 (d, J=7.94 Hz, 1H), 8.54 (s, 1H), 8.56 (d, J=2.43 Hz, 1H), 8.77 (d, J=2.21 Hz, 1H).

Example 135

N-(3-cyano-4-(2H-1,2,3-triazol-2-yl)phenyl)-1-(quinolin-5-yl)-5-(trifluoromethyl)-1H-pyrazole-4-carboxamide, Cpd 135

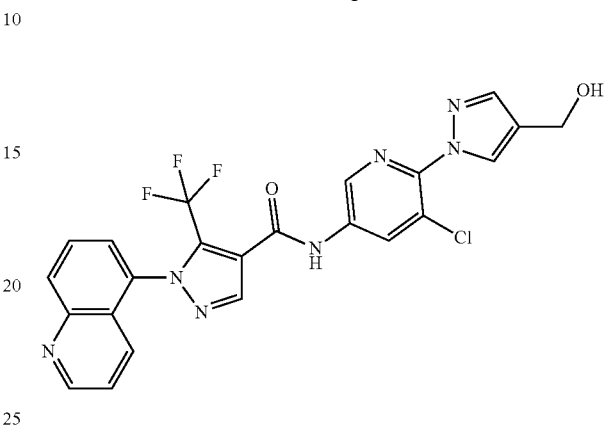

A. ethyl 1-(3-chloro-5-nitropyridin-2-yl)-1H-pyrazole-4-carboxylate, 135a

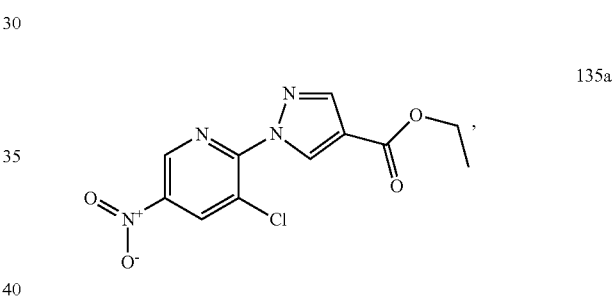

2,3-Dichloro-5-nitropyridine (500 mg, 2.59 mmol), ethyl 1H-pyrazole-4-carboxylate (435.7 mg, 3.11 mmol) and cesium carbonate (1.01 g, 3.11 mmol) were added to MeCN (10 mL) and stirred at 80° C. for 16 h. The reaction mixture was filtered and the residue was washed with EtOAc (20 mL×3). The combined organic layers were concentrated under reduced pressure to afford crude product as a yellow solid, which was purified by FCC (petroleum ether/ethyl acetate from 100:0 to 70:30) to afford the title compound (650 mg, 84.6%) as a yellow solid.

B. ethyl 1-(5-amino-3-chloropyridin-2-yl)-1H-pyrazole-4-carboxylate, 135b

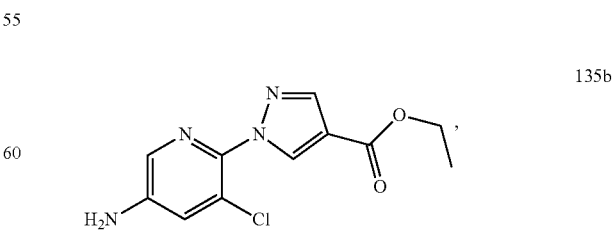

Ethyl 1-(3-chloro-5-nitropyridin-2-yl)-1H-pyrazole-4-carboxylate (650 mg, 2.19 mmol) was dissolved in THF (10 mL), Fe (856.5 mg, 15.34 mmol), $NH_4Cl$ (820.4 mg, 15.34 mmol) and H₂O (10 mL) were added. The reaction mixture was stirred at 80° C. for 2 h. The reaction mixture was filtered through a pad of diatomaceous earth and the pad was washed with EtOAc (20 mL×3). The filtrates were concentrated to dryness to give crude as a yellow solid, which was purified by FCC (eluent: petroleum ether/ethyl acetate from 100/0 to 70/30). The desired fractions were collected and the solvent was concentrated under reduced pressure to afford the title compound (440 mg, 64.5%) as a yellow oil. LCMS (ESI) m/z M+1: 267.1.

C. Ethyl 1-(3-chloro-5-(1-(quinolin-5-yl)-5-(trifluoromethyl)-1H-pyrazole-4-carboxamido)pyridin-2-yl)-1H-pyrazole-4-carboxylate, 135c

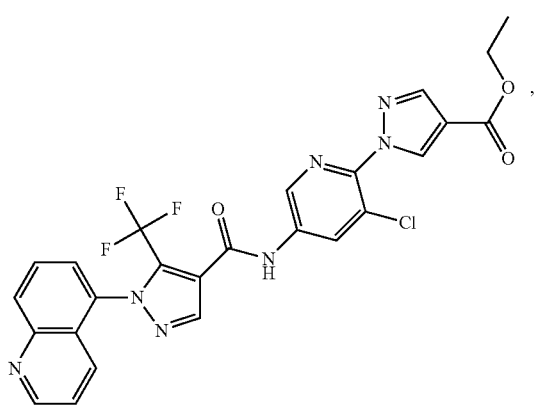

135c

Ethyl 1-(5-amino-3-chloropyridin-2-yl)-1H-pyrazole-4-carboxylate (293.93 mg, 0.94 mmol), 1-(quinolin-5-yl)-5-(trifluoromethyl)-1H-pyrazole-4-carboxylic acid (220 mg, 0.71 mmol) and pyridine (83.77 mg, 1.06 mmol) were dissolved in CH₂Cl₂ (20 mL), and phosphorus oxychloride (162.39, 1.06 mmol) was added. The mixture was stirred at 30° C. for 16 h. Sat. NaHCO₃ (40 mL) was added and extracted with CH₂Cl₂ (40 mL×2). The combined organic layers were dried over Na₂SO₄, filtered and the filtrates were concentrated under reduced pressure to afford the crude product as a yellow solid, which was purified by FCC (eluent: petroleum ether/ethyl acetate from 100/0 to 0/100). The desired fractions were collected and the solvent was concentrated under reduced pressure to afford (120 mg, 22.9%) as a yellow solid. LCMS (ESI) m/z M+1: 556.2.

D. N-(5-chloro-6-(4-(hydroxymethyl)-1H-pyrazol-1-yl)pyridin-3-yl)-1-(quinolin-5-yl)-5-(trifluoromethyl)-1H-pyrazole-4-carboxamide, 135

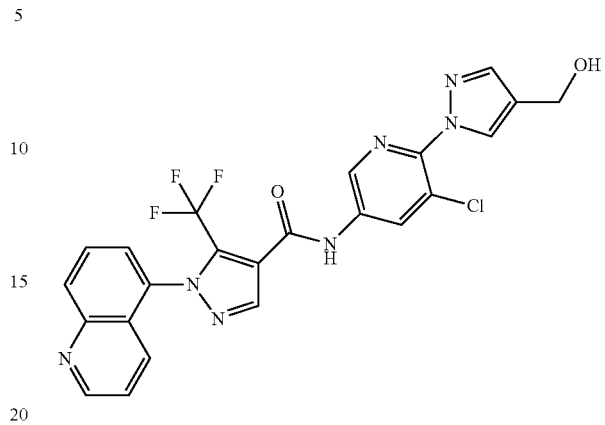

Ethyl 1-(3-chloro-5-(1-(quinolin-5-yl)-5-(trifluoromethyl)-1H-pyrazole-4-carboxamido)pyridin-2-yl)-1H-pyrazole-4-carboxylate (120 mg, 0.20 mmol) was dissolved in THF (20 mL) and stirred at 0° C., aluminum(III) lithium hydride (68.24 mg, 1.80 mmol) was added in portions. The reaction mixture was stirred at 30° C. for 1 h. H₂O (20 mL) was added and extracted with EtOAc (40 mL×2). The combined organic layer was dried over Na₂SO₄, filtered and the filtrate was concentrated under reduced pressure to afford the crude product, which was purified by preparative HPLC (22% to 52% (v/v) CH₃CN and H₂O with 0.05% HCl) and lyophilized to dryness to afford the title compound (35 mg, 33.6%). LCMS (ESI) m/z M+1: 513.9. ¹H NMR (400 MHz, DMSO-d₆) ☐ ppm 11.56 (br s, 1H), 9.08 (br s, 1H), 8.91 (br s, 1H), 8.73 (br s, 1H), 8.63 (br s, 1H), 8.35 (br d, J=7.9 Hz, 1H), 8.09 (br s, 1H), 7.96 (br dd, J=6.9, 18.2 Hz, 2H), 7.81-7.62 (m, 3H), 4.43 (br s, 2H).

Example 136

N-(5-chloro-6-(4-(hydroxymethyl)-2H-1,2,3-triazol-2-yl)pyridin-3-yl)-1-(quinolin-5-yl)-5-(trifluoromethyl)-1H-pyrazole-4-carboxamide, Cpd 136

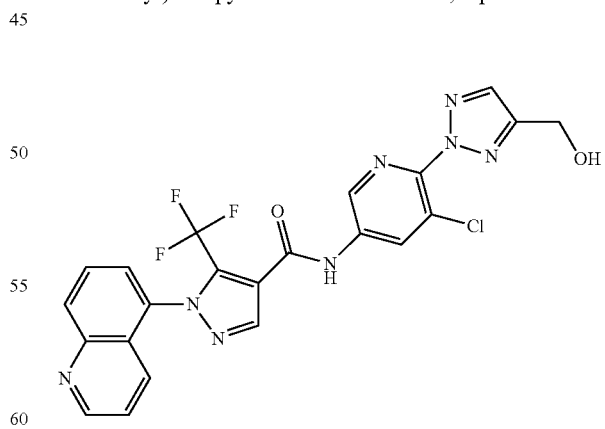

Methyl 2-(3-chloro-5-(1-(quinolin-5-yl)-5-(trifluoromethyl)-1H-pyrazole-4-carboxamido)pyridin-2-yl)-2H-1,2,3-triazole-4-carboxylate (86 mg, 0.079 mmol) was dissolved in THF (5 mL) at 0° C., LiAlH₄ (84 mg, 2.21 mmol) was added in portions. The reaction mixture was stirred at 40° C. for 18 h, then H₂O (10 mL) was added and the mixture extracted with EtOAc (20 mL×2). The combined organic layers were dried over Na$_2$SO$_4$, filtered and the filtrate was concentrated under reduced pressure to afford the crude product as a yellow oil, which was purified by preparative HPLC (76% to 46% (v/v) CH$_3$CN and H$_2$O with 0.05% HCl) and lyophilized to dryness to afford the title compound (17.3 mg, 5.0%). LCMS (ESI) m/z M+1: 514.9. $^1$H NMR (400 MHz, DMSO-d$_6$) δ ppm 4.63 (s, 2H), 7.69-7.83 (m, 2H), 7.94-8.09 (m, 3H), 8.37 (d, J=8.38 Hz, 1H), 8.63-8.73 (m, 2H), 8.91 (d, J=2.21 Hz, 1H), 9.11 (dd, J=3.97, 1.54 Hz, 1H), 11.51 (s, 1H).

Example 137

N-(5-chloro-6-(4-((dimethylamino)methyl)-2H-1,2,3-triazol-2-yl)pyridin-3-yl)-1-(quinolin-5-yl)-5-(trifluoromethyl)-1H-pyrazole-4-carboxamide, Cpd 137

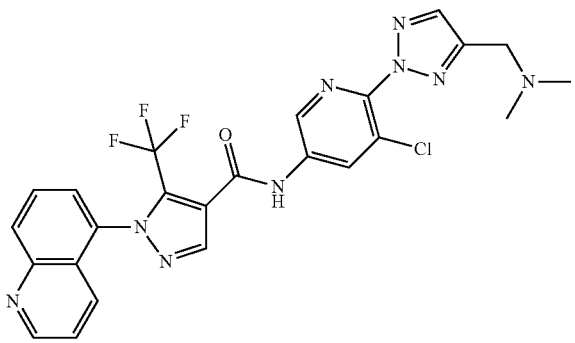 [SMILES: CN(C)Cc1cnn(-c2ncc(NC(=O)c3cnn(-c4cccc5ncccc45)c3C(F)(F)F)cc2Cl)n1]

A. (2-(3-chloro-5-(1-(quinolin-5-yl)-5-(trifluoromethyl)-1H-pyrazole-4-carboxamido)pyridin-2-yl)-2H-1,2,3-triazol-4-yl)methyl methanesulfonate, 137a

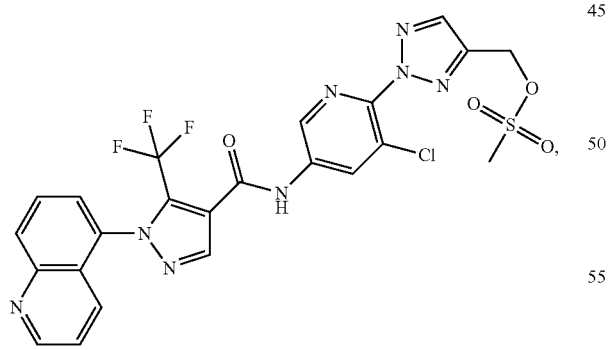

N-(5-chloro-6-(4-(hydroxymethyl)-2H-1,2,3-triazol-2-yl)pyridin-3-yl)-1-(quinolin-5-yl)-5-(trifluoromethyl)-1H-pyrazole-4-carboxamide (420 mg, 0.79 mmol) in CH$_2$Cl$_2$ (8 mL) was cooled to 0° C. Triethylamine (239.84 mg, 2.37 mmol) was added, then methanesulfonyl chloride (135.75 mg, 1.19 mmol) was added dropwise and stirred at 0° C. for 1 h. The mixture concentrated, dried, and used directly for the next step.

B. N-(5-chloro-6-(4-((dimethylamino)methyl)-2H-1,2,3-triazol-2-yl)pyridin-3-yl)-1-(quinolin-5-yl)-5-(trifluoromethyl)-1H-pyrazole-4-carboxamide, Cpd 137

(2-(3-Chloro-5-(1-(quinolin-5-yl)-5-(trifluoromethyl)-1H-pyrazole-4-carboxamido)pyridin-2-yl)-2H-1,2,3-triazol-4-yl)methyl methanesulfonate (250 mg, 0.40 mmol) was added Me$_2$NH in THF (1M) (20 mL). The mixture was concentrated under reduced pressure to afford a crude product as a yellow oil, which was purified by preparative HPLC (84% to 54% (v/v) CH$_3$CN and H$_2$O with 0.05% HCl) and lyophilized to dryness to afford the title compound (201 mg, 92.7%). LCMS (ESI) m/z M+1: 514.9. $^1$H NMR (400 MHz, METHANOL-d$_4$) δ ppm 2.99 (s, 6H), 4.64 (s, 2H), 8.17-8.26 (m, 3H), 8.33-8.41 (m, 1H), 8.48-8.60 (m, 2H), 8.62-8.74 (m, 1H), 8.77 (d, J=2.20 Hz, 1H), 8.88 (br s, 1H), 9.29-9.48 (m, 1H).

Example 138

N-(5-cyano-6-(2H-1,2,3-triazol-2-yl)pyridin-3-yl)-1-(quinolin-4-yl)-5-(trifluoromethyl)-1H-pyrazole-4-carboxamide, Cpd 138

461

A. ethyl 1-(quinolin-4-yl)-5-(trifluoromethyl)-1H-pyrazole-4-carboxylate, 138a

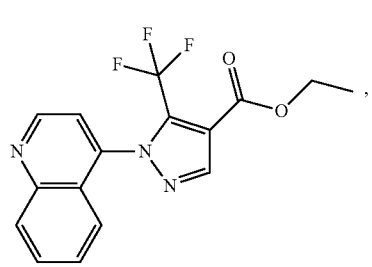

A solution of 4-hydrazinylquinoline, 60c (300 mg, 1.89 mmol), ethyl 2-(ethoxymethylene)-4,4,4-trifluoro-3-oxobutanoate (543.15 mg, 2.26 mmol), in EtOH (5 mL) was stirred at 80° C. for 2 h. The mixture was concentrated under reduced pressure. The crude product was purified by column chromatography over silica gel (petroleum ether/ethyl acetate from 100/0 to 50/50). The desired fractions were collected and the solvent was concentrated under reduced pressure to afford ethyl 1-(quinolin-4-yl)-5-(trifluoromethyl)-1H-pyrazole-4-carboxylate (130 mg, 20.6% yield) as a yellow solid. LCMS (ESI) m/z M+1: 335.9.

B. 1-(quinolin-4-yl)-5-(trifluoromethyl)-1H-pyrazole-4-carboxylic acid, 138b

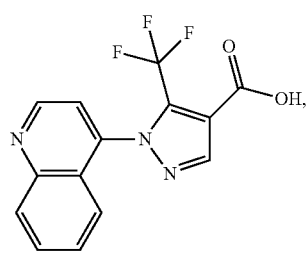

A solution of ethyl 1-(quinolin-4-yl)-5-(trifluoromethyl)-1H-pyrazole-4-carboxylate, 138a (130 mg, 0.61 mmol), LiOH (16.27 mg, 0.39 mmol) in EtOH/H$_2$O (2/1, 2 mL) was stirred at room temperature for 2 h, 1N HCl solution was added to neutralize the reaction solution. The mixture was extracted with ethyl acetate (5 mL×3). The separated organic layer was dried (Na$_2$SO$_4$), filtered, and the solvent was concentrated to afford 1-(quinolin-4-yl)-5-(trifluoromethyl)-1H-pyrazole-4-carboxylic acid, 138b (119 mg) as a yellow solid. LCMS (ESI) m/z M+1: 308.0.

462

C. N-(5-cyano-6-(2H-1,2,3-triazol-2-yl)pyridin-3-yl)-1-(quinolin-4-yl)-5-(trifluoromethyl)-1H-pyrazole-4-carboxamide, Cpd 138

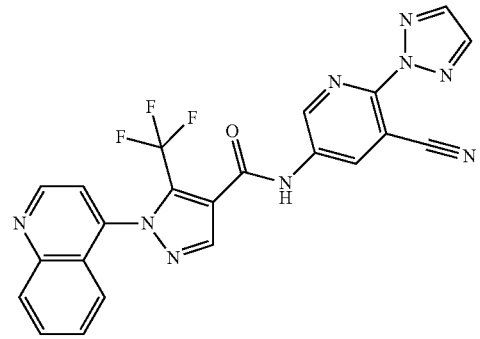 [SMILES: N#Cc1cc(NC(=O)c2cnn(-c3ccnc4ccccc34)c2C(F)(F)F)cnc1-n1nccn1]

Phosphorus oxychloride (39.44 uL, 0.42 mmol) was added to a solution of 1-(quinolin-4-yl)-5-(trifluoromethyl)-1H-pyrazole-4-carboxylic acid, 138b (67.35 mg, 0.21 mmol), 5-amino-2-(2H-1,2,3-triazol-2-yl)nicotinonitrile (59.08 mg, 0.32 mmol), pyridine (171.12 uL, 2.12 mmol) in CH$_2$Cl$_2$ (2 mL). The mixture was stirred at room temperature for 2 h, 5 mL H$_2$O was added to the mixture and sat. NaHCO$_3$ was added to adjust the pH of reaction mixture to 7-8. The mixture was extracted with CH$_2$Cl$_2$ (5 mL×3). The combined organic extracts were dried over anhydrous Mg$_2$SO$_4$, filtered, and the filtrate concentrated to dryness under reduced pressure to afford the crude product, which was purified by preparative HPLC (40% to 70% (v/v) CH$_3$CN and H$_2$O with 0.05% HCl) and lyophilized to dryness to afford the title compound (57 mg, 56.4%). LCMS (ESI) m/z M+1: 475.9. $^1$H NMR (400 MHz, DMSO-d$_6$) δ ppm 7.33 (d, J=8.16 Hz, 1H), 7.77 (t, J=7.61 Hz, 1H), 7.91-7.98 (m, 2H), 8.26 (d, J=8.60 Hz, 1H), 8.32 (s, 2H), 8.71 (s, 1H), 8.91 (d, J=2.43 Hz, 1H), 9.13 (d, J=2.43 Hz, 1H), 9.19 (d, J=4.41 Hz, 1H), 11.47 (s, 1H).

Example 139

N-(5-bromo-6-(2H-1,2,3-triazol-2-yl)pyridin-3-yl)-1-(quinolin-5-yl)-5-(trifluoromethyl)-1H-pyrazole-4-carboxamide, Cpd 139

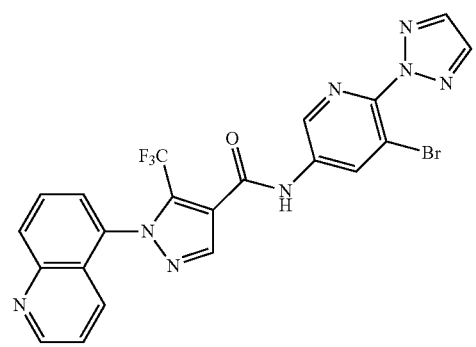 [SMILES: O=C(Nc1cnc(-n2nccn2)c(Br)c1)c1cnn(-c2cccc3ncccc23)c1C(F)(F)F]

A. 3-bromo-5-nitro-2-(2H-1,2,3-triazol-2-yl)pyridine, 139a

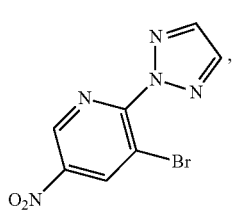

A solution of 3-bromo-2-chloro-5-nitropyridine (1 g, 4.21 mmol), 1H-1,2,3-triazole (582 mg, 8.42 mmol), K$_2$CO$_3$ (1.74 g, 12.64 mmol) in CH$_3$CN (30 mL) was stirred at 50° C. for 12 h. The mixture was concentrated under reduced pressure, the crude product was purified by column chromatography over silica gel (petroleum ether/ethyl acetate from 20:1 to 1:1). The desired fractions were collected and the solvent was concentrated under reduced pressure to afford 3-bromo-5-nitro-2-(2H-1,2,3-triazol-2-yl)pyridine, 139a (520 mg, 45.7%) as a yellow solid. LCMS (ESI) m/z M+1: 272.1.

B. 5-bromo-6-(2H-1,2,3-triazol-2-yl)pyridin-3-amine, 139b

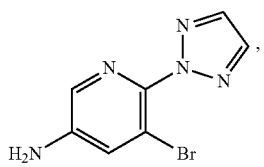

Fe (323.50 mg, 5.78 mmol) was added to a solution of 3-bromo-5-nitro-2-(2H-1,2,3-triazol-2-yl)pyridine, 139a (520 mg, 1.93 mmol) and NH$_4$Cl (515.10 mg, 9.63 mmol) in MeOH (20 mL), THF (20 mL) and H$_2$O (10 mL). The mixture was stirred at 80° C. for 1 h, and then aq. NaHCO$_3$ was added to the suspension to adjust the mixture to pH 9-10. The resulting mixture was filtered through a pad of diatomaceous earth and the filter cake was washed with CH$_2$Cl$_2$ (100 mL×3). The combined filtrates were washed with brine (200 mL), dried over MgSO$_4$ and concentrated under reduced pressure to afford 1b (310 mg, 67.1%) as a brown solid, which was used directly in the next step. LCMS (ESI) m/z M+H: 242.1

C. N-(5-bromo-6-(2H-1,2,3-triazol-2-yl)pyridin-3-yl)-1-(quinolin-5-yl)-5-(trifluoromethyl)-1H-pyrazole-4-carboxamide, Cpd 139

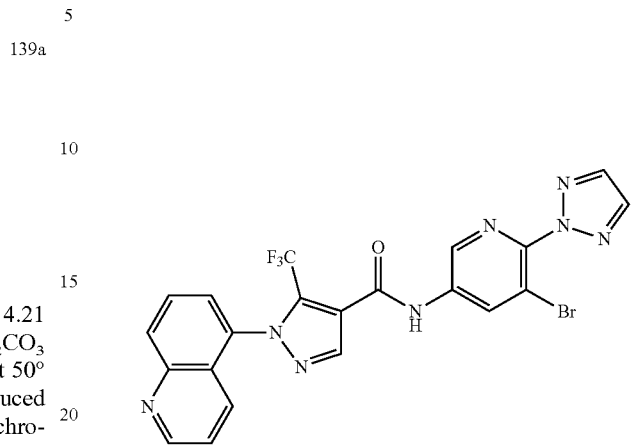

POCl$_3$ (232.263 mg, 1.515 mmol) was added to a solution of 5-bromo-6-(2H-1,2,3-triazol-2-yl)pyridin-3-amine, 5-bromo-6-(2H-1,2,3-triazol-2-yl)pyridin-3-amine, 139b (200 mg, 0.83 mmol), 1-(quinolin-5-yl)-5-(trifluoromethyl)-1H-pyrazole-4-carboxylic acid (232.69 mg, 0.76 mmol), pyridine (149.77 mg 1.89 mmol) in CH$_2$Cl$_2$ (10 mL). The mixture was stirred at rt for 2 h, then 50 mL H$_2$O and 50 mL CH$_2$Cl$_2$ were added to the mixture. The organic layer was washed with brine (50 mL), dried over MgSO$_4$ filtered, and the filtrate concentrated under reduced pressure to afford the crude product, which was purified by preparative HPLC (35% to 65% (v/v) CH$_3$CN and H$_2$O with 0.05% HCl). The desired fractions were lyophilized to dryness to afford the title compound (86.8 mg 20.8% yield) as a white solid. LCMS (ESI) m/z M+1: 528.9. $^1$H NMR (400 MHz, DMSO-d$_6$) δ ppm 11.45 (s, 1H), 9.01-9.12 (m, 1H), 8.89-8.99 (m, 1H), 8.78-8.86 (m, 1H), 8.64-8.72 (m, 1H), 8.29-8.38 (m, 1H), 8.15 (s, 2H), 7.90-8.02 (m, 2H), 7.69 (d, J=3.09 Hz, 2H).

Example 140

N-(5-cyano-6-(2H-1,2,3-triazol-2-yl)pyridin-3-yl)-1-(pyrrolo[2,1-f][1,2,4]triazin-4-yl)-5-(trifluoromethyl)-1H-pyrazole-4-carboxamide, Cpd 140

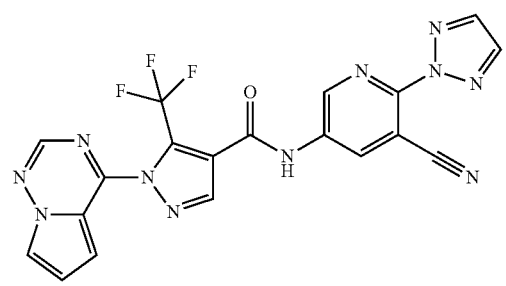 [SMILES: N#Cc1cc(NC(=O)c2cnn(-c3ncnn4cccc34)c2C(F)(F)F)cnc1-n1nccn1]

A. 4-hydrazinylpyrrolo[2,1-f][1,2,4]triazine, 140a

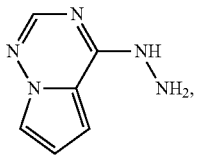

4-Chloropyrrolo[2,1-f][1,2,4]triazine (200 mg, 1.302 mmol) was dissolved in hydrazine hydrate (8 mL). The reaction mixture was stirred at 40° C. for 2 h. The solvent was removed to afford product as a white solid (200 mg, 100%), which was used directly for the next step.

B. ethyl 1-(pyrrolo[2,1-f][1,2,4]triazin-4-yl)-5-(trifluoromethyl)-1H-pyrazole-4-carboxylate, 140b

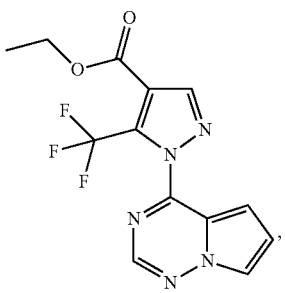

4-Hydrazinylpyrrolo[2,1-f][1,2,4]triazine (200 mg, 1.34 mmol) was dissolved in ethanol (10 mL), ethyl 2-(ethoxymethylene)-4,4,4-trifluoro-3-oxobutanoate (483.08 mg, 2.01 mmol) was added. The reaction mixture was stirred at 80° C. for 2 h, concentrated under reduced pressure to afford the crude product as a white solid, which was purified by FCC (eluent: petroleum ether/ethyl acetate from 100/0 to 60/40) to afford the title compound (200 mg, 43.4%) as a white solid. LCMS (ESI) m/z M+1: 326.0.

C. 1-(pyrrolo[2,1-f][1,2,4]triazin-4-yl)-5-(trifluoromethyl)-1H-pyrazole-4-carboxylic acid, 140c

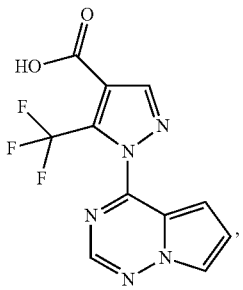

Ethyl 1-(pyrrolo[2,1-f][1,2,4]triazin-4-yl)-5-(trifluoromethyl)-1H-pyrazole-4-carboxylate (200 mg, 0.58 mmol) was dissolved in THF (10 mL) and water (10 mL). Sodium hydroxide (46.51 mg, 1.16 mmol) was added. The reaction mixture was stirred at 25° C. for 12 h, adjusted to pH 5 using HCl (2 N), and extracted with EtOAc (30 mL×2). The combined organic layers were dried over $Na_2SO_4$, filtered, and the filtrates were concentrated under reduced pressure to afford crude the title compound (130 mg, 73.6%) as a yellow solid. LCMS (ESI) m/z M+1: 298.0.

D. N-(5-cyano-6-(2H-1,2,3-triazol-2-yl)pyridin-3-yl)-1-(pyrrolo[2,1-f][1,2,4]triazin-4-yl)-5-(trifluoromethyl)-1H-pyrazole-4-carboxamide, Cpd 140

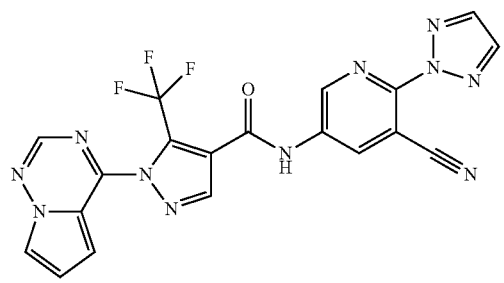 [SMILES: N#Cc1cc(NC(=O)c2cnn(-c3ncnn4cccc34)c2C(F)(F)F)cnc1-n1nccn1]

1-(Pyrrolo[2,1-f][1,2,4]triazin-4-yl)-5-(trifluoromethyl)-1H-pyrazole-4-carboxylic acid (130 mg, 0.43 mmol), 5-amino-2-(2H-1,2,3-triazol-2-yl)nicotinonitrile (95.57 mg, 0.51 mmol), pyridine (203.04 mg, 2.57 mmol) were dissolved in $CH_2Cl_2$ (10 mL), and phosphorus oxychloride (262.38, 1.71 mmol) was added. The mixture was stirred at 25° C. for 4 h, sat.$NaHCO_3$ (30 mL) was added and extracted with $CH_2Cl_2$ (30 mL×2). The combined organic layers were dried over $Na_2SO_4$, filtered, and the filtrates were concentrated under reduced pressure to afford the crude product as a yellow oil, which was purified by preparative HPLC (35% to 65% (v/v) $CH_3CN$ and $H_2O$ with 0.05% HCl) and lyophilized to dryness to afford the title compound (87.1 mg, 43.5%). LCMS (ESI) m/z M+1: 465.9. $^1$H NMR (400 MHz, DMSO-$d_6$) δ=11.52 (s, 1H), 9.00 (d, J=2.6 Hz, 1H), 8.78 (d, J=2.6 Hz, 1H), 8.63 (s, 1H), 8.60 (s, 1H), 8.37 (dd, J=1.4, 2.5 Hz, 1H), 8.27 (s, 2H), 7.28 (dd, J=1.3, 4.6 Hz, 1H), 7.20 (dd, J=2.6, 4.4 Hz, 1H).

Example 141

N-(5-chloro-6-(2H-1,2,3-triazol-2-yl)pyridin-3-yl)-1-(pyrazolo[1,5-a]pyrazin-4-yl)-5-(trifluoromethyl)-1H-pyrazole-4-carboxamide, Cpd 141

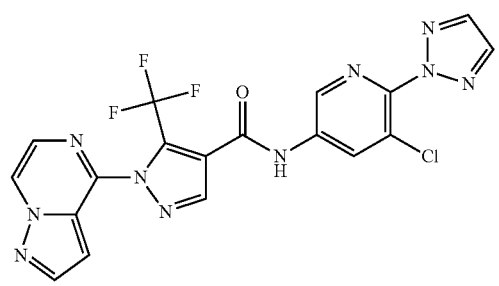 [SMILES: O=C(Nc1cnc(-n2nccn2)c(Cl)c1)c1cnn(-c2nccn3nccc23)c1C(F)(F)F]

A. 4-hydrazinylpyrazolo[1,5-a]pyrazine, 141a

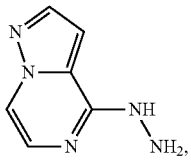

141a

4-Chloropyrazolo[1,5-a]pyrazine (300 mg, 1.95 mmol) was dissolved in hydrazine hydrate (10 mL). The reaction mixture was stirred at 25° C. for 2 h. The solvent was removed to afford product as a white solid (300 mg, 100%), which was used directly for the next step.

B. ethyl 1-(pyrazolo[1,5-a]pyrazin-4-yl)-5-(trifluoromethyl)-1H-pyrazole-4-carboxylate, 141b

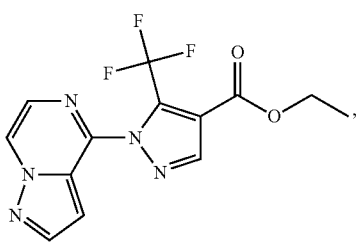

141b

4-Hydrazinylpyrazolo[1,5-a]pyrazine (300 mg, 2.01 mmol) was dissolved in ethanol (10 mL), ethyl 2-(ethoxymethylene)-4,4,4-trifluoro-3-oxobutanoate (966.16 mg, 4.02 mmol) was added. The reaction mixture was stirred at 80° C. for 2 h, then concentrated under reduced pressure to afford a crude product as a yellow solid, which was purified by FCC (eluent: petroleum ether/ethyl acetate from 100/0 to 60/40) to afford the title compound (500 mg, 61.2%) as a yellow solid. LCMS (ESI) m/z M+1: 326.0.

C. 1-(pyrazolo[1,5-a]pyrazin-4-yl)-5-(trifluoromethyl)-1H-pyrazole-4-carboxylic acid, 141c

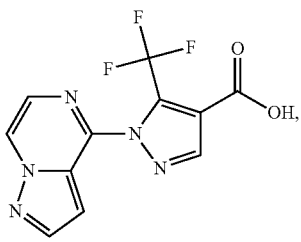

141c

Ethyl 1-(pyrazolo[1,5-a]pyrazin-4-yl)-5-(trifluoromethyl)-1H-pyrazole-4-carboxylate (500 mg, 1.23 mmol) was dissolved in THF (10 mL) and water (10 mL). Sodium hydroxide (98.4 mg, 2.46 mmol) was added. The reaction mixture was stirred at 25° C. for 12 h, then adjusted to pH 5 using HCl (2 N). The mixture was extracted with EtOAc (50 mL×2). The combined organic layers were dried over Na$_2$SO$_4$, filtered, and the filtrates were concentrated under reduced pressure to afford the crude the title compound (400 mg, 89.2%) as a yellow solid. LCMS (ESI) m/z M+1: 298.2.

D. N-(5-chloro-6-(2H-1,2,3-triazol-2-yl)pyridin-3-yl)-1-(pyrazolo[1,5-a]pyrazin-4-yl)-5-(trifluoromethyl)-1H-pyrazole-4-carboxamide, Cpd 141

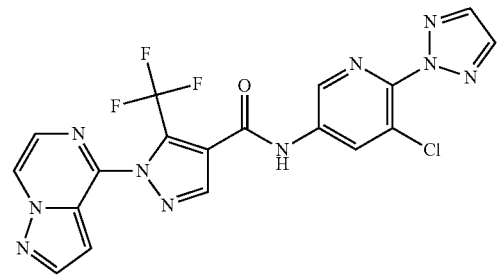 [SMILES: O=C(Nc1cnc(-n2nccn2)c(Cl)c1)c1cnn(-c2nccn3nccc23)c1C(F)(F)F]

1-(Pyrazolo[1,5-a]pyrazin-4-yl)-5-(trifluoromethyl)-1H-pyrazole-4-carboxylic acid (250 mg, 0.69 mmol), 5-chloro-6-(2H-1,2,3-triazol-2-yl)pyridin-3-amine (161.0 mg, 0.82 mmol), pyridine (325.52 mg, 4.12 mmol) were dissolved in CH$_2$Cl$_2$ (10 mL), and phosphorus oxychloride (420.67, 2.74 mmol) was added. The mixture was stirred at 25° C. for 4 h, then sat. NaHCO$_3$ (50 mL) was added and the mixture extracted with CH$_2$Cl$_2$ (30 mL×2). The combined organic layers were dried over Na$_2$SO$_4$, filtered and the filtrates were concentrated under reduced pressure to afford the crude product as a yellow oil, which was purified by preparative HPLC (45% to 75% (v/v) CH$_3$CN and H$_2$O with 0.05% HCl) and lyophilized to dryness to afford the title compound (22.4 mg, 6.6%). LCMS (ESI) m/z M+1: 474.9. $^1$H NMR (400 MHz, DMSO-d$_6$) δ ppm 11.42 (s, 1H), 9.05 (dd, J=4.85, 0.88 Hz, 1H), 8.81 (d, J=2.21 Hz, 1H), 8.63 (d, J=2.43 Hz, 1H), 8.60 (s, 1H), 8.37 (d, J=2.43 Hz, 1H), 8.17 (s, 2H), 7.96 (d, J=4.63 Hz, 1H), 7.11 (dd, J=2.32, 0.77 Hz, 1H).

Example 142

N-(5-cyano-6-(2H-1,2,3-triazol-2-yl)pyridin-3-yl)-1-(thieno[2,3-d]pyrimidin-4-yl)-5-(trifluoromethyl)-1H-pyrazole-4-carboxamide, Cpd 142

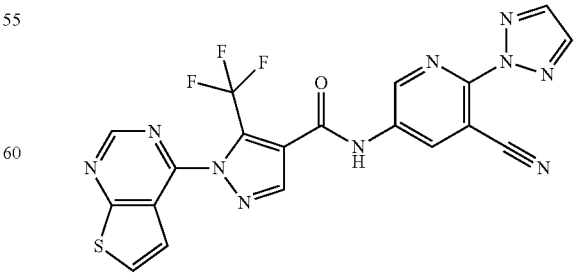

A. 4-hydrazinylthieno[2,3-d]pyrimidine, 142a

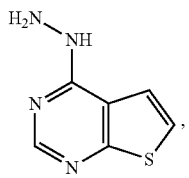

142a

A solution of 4-chlorothieno[2,3-d]pyrimidine (450 mg, 2.64 mmol) in hydrazine (5 mL, 98%) was stirred at 80° C. for 2 h. The solid was filtered and washed by 2 mL water. The solid was collected and dried to afford 4-hydrazinylthieno[2,3-d]pyrimidine, 142a (400 mg, 91.3% yield) as a white solid. LCMS (ESI) m/z M+1: 166.9.

B. ethyl 1-(thieno[2,3-d]pyrimidin-4-yl)-5-(trifluoromethyl)-1H-pyrazole-4-carboxylate, 142b

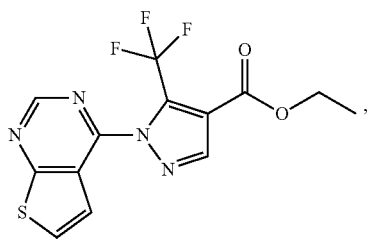

142b

A solution of 4-hydrazinylthieno[2,3-d]pyrimidine, 142a (400 mg, 2.41 mmol), ethyl 2-(ethoxymethylene)-4,4,4-trifluoro-3-oxobutanoate (1040 mg, 4.33 mmol), in EtOH (5 mL) was stirred at 80° C. for 1 h. The mixture was concentrated under reduced pressure, the crude product was purified by column chromatography over silica gel (petroleum ether/ethyl acetate from 100/0 to 70/30). The desired fractions were collected and the solvent was concentrated under reduced pressure to afford ethyl 1-(thieno[2,3-d]pyrimidin-4-yl)-5-(trifluoromethyl)-1H-pyrazole-4-carboxylate, 142b (700 mg, 85.0% yield) as a yellow solid. LCMS (ESI) m/z M+1: 343.1.

C. 1-(thieno[2,3-d]pyrimidin-4-yl)-5-(trifluoromethyl)-1H-pyrazole-4-carboxylic acid, 142c

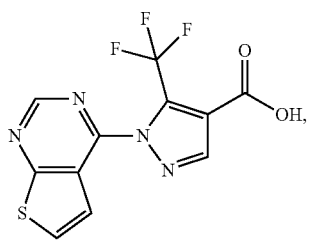

142c

A solution of ethyl 1-(thieno[2,3-d]pyrimidin-4-yl)-5-(trifluoromethyl)-1H-pyrazole-4-carboxylate, 142b (120 mg, 0.35 mmol), LiOH.H$_2$O (22.07 mg, 0.53 mmol) in EtOH/H$_2$O (2/1, 3 mL) was stirred at room temperature overnight. 1N HCl solution was added to neutralize the reaction solution. The mixture was extracted with ethyl acetate (10 mL×3). The separated organic layer was dried (Na$_2$SO$_4$), filtered, and the filtrate was concentrated to afford 142c (90 mg, 81.7% yield) as a yellow solid. LCMS (ESI) m/z M+1: 314.9.

D. N-(5-cyano-6-(2H-1,2,3-triazol-2-yl)pyridin-3-yl)-1-(thieno[2,3-d]pyrimidin-4-yl)-5-(trifluoromethyl)-1H-pyrazole-4-carboxamide, Cpd 142

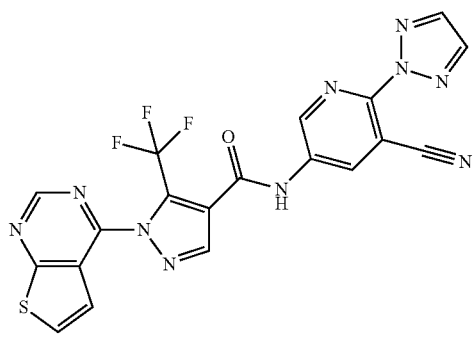 [SMILES: N#Cc1cc(NC(=O)c2cnn(-c3ncnc4sccc34)c2C(F)(F)F)cnc1-n1nccn1]

Phosphorus oxychloride (53.39 uL, 0.57 mmol) was added to a solution of 1-(thieno[2,3-d]pyrimidin-4-yl)-5-(trifluoromethyl)-1H-pyrazole-4-carboxylic acid, 142c (90 mg, 0.29 mmol), 5-amino-2-(2H-1,2,3-triazol-2-yl)nicotinonitrile (58.65 mg, 0.32 mmol), pyridine (231.64 uL, 2.86 mmol) in CH$_2$Cl$_2$ (2 mL). The mixture was stirred at room temperature for 1 h, 5 mL H$_2$O was added to the mixture and sat. NaHCO$_3$ was added to adjust the pH of reaction mixture to 7-8. The mixture was extracted with CH$_2$Cl$_2$ (5 mL×3), the combined organic extracts were dried over anhydrous Mg$_2$SO$_4$, filtered, and the filtrate concentrated to dryness under reduced pressure to afford the crude product, which was purified by preparative HPLC (36% to 66% (v/v) CH$_3$CN and H$_2$O with 0.05% HCl) and lyophilized to dryness to afford the title compound (40 mg, 27.9%). LCMS (ESI) m/z M+1: 482.9. $^1$H NMR (400 MHz, DMSO-d$_6$) δ ppm 7.78 (d, J=6.17 Hz, 1H), 8.24 (d, J=6.17 Hz, 1H), 8.32 (s, 2H), 8.65 (s, 1H), 8.85 (d, J=2.21 Hz, 1H), 9.07 (d, J=2.21 Hz, 1H), 9.21 (s, 1H), 11.52 (s, 1H).

Example 143

N-(5-cyano-6-(2H-1,2,3-triazol-2-yl)pyridin-3-yl)-1-(thieno[2,3-c]pyridin-7-yl)-5-(trifluoromethyl)-1H-pyrazole-4-carboxamide, Cpd 143

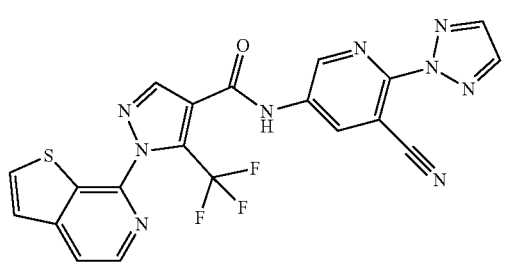 [SMILES: N#Cc1cc(NC(=O)c2cnn(-c3nccc4ccsc34)c2C(F)(F)F)cnc1-n1nccn1]

A. 7-hydrazinylthieno[2,3-c]pyridine, 143a

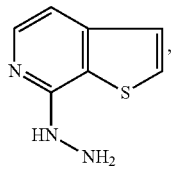
143a

7-Chlorothieno[2,3-c]pyridine (300 mg, 1.06 mmol) in NH₂NH₂.H₂O (5 mL) was stirred at 26° C. for 16 h. The mixture was extracted with CH₂Cl₂ (20×3 mL). The solvent was concentrated under reduced pressure the give the desired compound, used directly for the next step without further purification.

B. ethyl 1-(thieno[2,3-c]pyridin-7-yl)-5-(trifluoromethyl)-1H-pyrazole-4-carboxylate, 143b

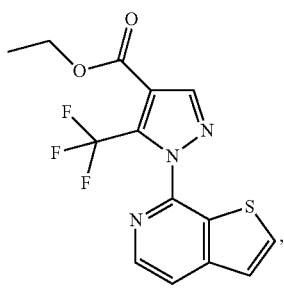
143b

7-Hydrazinylthieno[2,3-c]pyridine (200 mg, 1.21 mmol) was added to a solution of ethyl 2-(ethoxymethylene)-4,4,4-trifluoro-3-oxobutanoate (436.11 mg, 1.82 mmol) in EtOH (5 mL) and was reacted at 80° C. for 3 h. The mixture was concentrated under reduced pressure, then was purified by FFS (petroleum ether/ethyl acetate=100:0 to petroleum ether/ethyl acetate 60:40). The desired fractions were collected and the solvent was concentrated under reduced pressure to give the product as a brown oil. LCMS (ESI) m/z M+1: 341.9.

C. 1-(thieno[2,3-c]pyridin-7-yl)-5-(trifluoromethyl)-1H-pyrazole-4-carboxylic acid, 143c

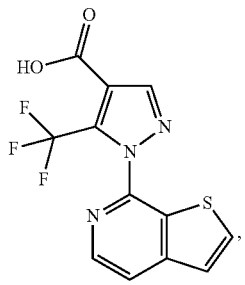
143c

NaOH (20.56 mg, 0.51 mmol) was added to a solution of ethyl 1-(thieno[2,3-c]pyridin-7-yl)-5-(trifluoromethyl)-1H-pyrazole-4-carboxylate (120 mg, 0.34 mmol) in EtOH/H₂O=1:1 (5 mL) was reacted at 28° C. for 2 h. The solvent was concentrated under reduced pressure the give the desired compound. LCMS (ESI) m/z M+1: 313.9.

D. N-(5-cyano-6-(2H-1,2,3-triazol-2-yl)pyridin-3-yl)-1-(thieno[2,3-c]pyridin-7-yl)-5-(trifluoromethyl)-1H-pyrazole-4-carboxamide, Cpd 143

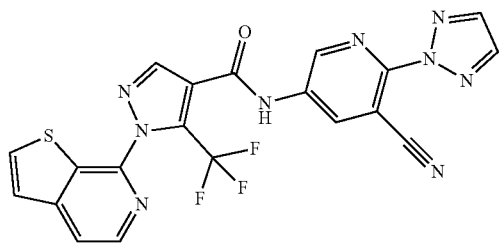 [SMILES: N#Cc1cc(NC(=O)c2cnn(-c3nccc4ccsc34)c2C(F)(F)F)cnc1-n1nccn1]

1-(Thieno[2,3-c]pyridin-7-yl)-5-(trifluoromethyl)-1H-pyrazole-4-carboxylic acid (70 mg, 0.22 mmol), 5-amino-2-(2H-1,2,3-triazol-2-yl)nicotinonitrile (50 mg, 0.27 mmol), POCl₃ (41.18 mg, 0.27 mmol) were dissolved in DCM (2 mL), and pyridine (53.11 mg, 0.67 mmol) was added. The mixture was stirred at 25° C. for 2 h, then sat.NH₄Cl (20 mL) was added and the mixture extracted with CH₂Cl₂ (20 mL×2). The combined organic layers were dried over Na₂SO₄, filtered and the filtrates were concentrated under reduced pressure to afford crude as a yellow oil, which was purified by preparative HPLC (54% to 27% (v/v) CH₃CN and H₂O with 0.05% HCl) and lyophilized to dryness to afford the title compound (46 mg, 49.7%). LCMS (ESI) m/z M+1: 482.1. ¹H NMR (400 MHz, DMSO-d₆) δ ppm 7.73 (d, J=5.29 Hz, 1H), 8.09 (d, J=5.29 Hz, 1H), 8.25-8.35 (m, 3H), 8.49 (d, J=5.29 Hz, 1H), 8.57 (s, 1H), 8.83 (d, J=2.43 Hz, 1H), 9.05 (d, J=2.43 Hz, 1H), 11.50 (s, 1H).

Example 144

2-(3-chloro-5-(1-(quinolin-5-yl)-5-(trifluoromethyl)-1H-pyrazole-4-carboxamido)pyridin-2-yl)-2H-1,2,3-triazole-4-carboxamide, Cpd 144

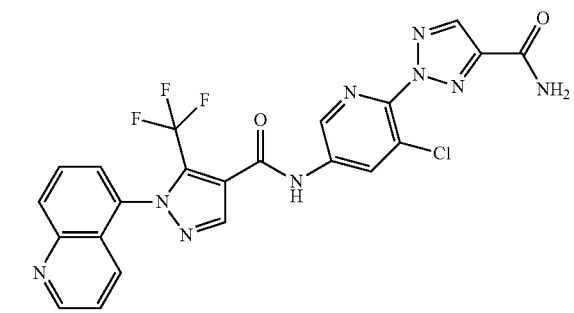 [SMILES: NC(=O)c1cnn(-c2ncc(NC(=O)c3cnn(-c4cccc5ncccc45)c3C(F)(F)F)cc2Cl)n1]

2-(3-Chloro-5-(1-(quinolin-5-yl)-5-(trifluoromethyl)-1H-pyrazole-4-carboxamido)pyridin-2-yl)-2H-1,2,3-triazole-4-carboxylic acid (80 mg, 0.15 mmol), NH₄Cl (23.23 mg, 0.43 mmol), HATU (82.56 mg, 0.22 mmol) were dissolved in DMF (4 mL), and DIEA (93.54 mg, 0.72 mmol) was added.

The mixture was stirred at 25° C. for 2 h, sat.NH₄Cl (20 mL) was added and extracted with CH₂Cl₂ (20 mL×2). The combined organic layers were dried over Na₂SO₄, filtered and the filtrates were concentrated under reduced pressure to afford a crude product as a yellow oil, which was purified by preparative HPLC (66% to 36% (v/v) CH₃CN and H₂O with 0.05% HCl) and lyophilized to dryness to afford the title compound (44 mg, 47.5%). LCMS (ESI) m/z M+1: 529.2. ¹H NMR (400 MHz, DMSO-d₆) δ ppm 7.74-7.87 (m, 3H), 8.00-8.10 (m, 2H), 8.15 (br s, 1H), 8.42 (d, J=8.53 Hz, 1H), 8.51 (s, 1H), 8.73-8.81 (m, 2H), 9.01 (d, J=2.26 Hz, 1H), 9.16 (dd, J=4.27, 1.51 Hz, 1H), 11.64 (s, 1H).

Example 145

N-(5-cyano-6-(2H-1,2,3-triazol-2-yl)pyridin-3-yl)-1-(1,7-naphthyridin-5-yl)-5-(trifluoromethyl)-1H-pyrazole-4-carboxamide, Cpd 145

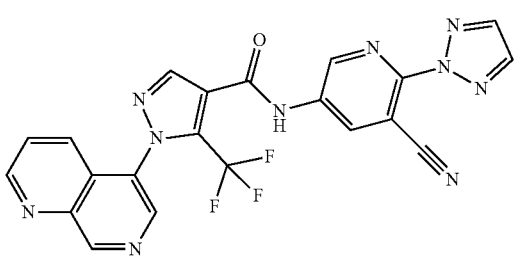 [SMILES: N#Cc1cc(NC(=O)c2cnn(-c3cncc4ncccc34)c2C(F)(F)F)cnc1-n1nccn1]

A. 5-bromo-8-hydrazinyl-1,7-naphthyridine, 145a

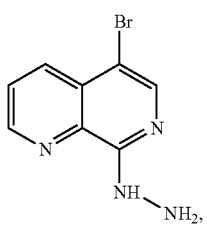

5-Bromo-8-chloro-1,7-naphthyridine (800 mg, 3.29 mmol) was dissolved in hydrazine hydrate (5 mL). The reaction mixture was stirred at 50° C. for 2 h. The solvent was removed to afford the desired product as a yellow oil (785 mg, 100%), which was used directly for the next step.

B. 5-bromo-1,7-naphthyridine, 145b

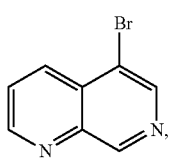

5-Bromo-8-hydrazinyl-1,7-naphthyridine (785 mg, 3.29 mmol) was dissolved in water (10 mL) and acetic acid (30 mL). Copper(II) sulfate (524.48 mg, 3.29 mmol) was added and stirred at 70° C. for 3 h. The solvent was removed, 30% NH₃.H₂O (50 mL) was added and the mixture was extracted with CH₂Cl₂ (50 mL×2). The combined organic layers were dried over Na₂SO₄, filtered and the filtrates were concentrated under reduced pressure to afford the crude product as a yellow solid, which was purified by FCC (eluent: petroleum ether/ethyl acetate from 100/0 to 85/15) to afford the title compound (420 mg, 59.9%) as a yellow solid. LCMS (ESI) m/z M+1: 208.8.

C. 5-hydrazinyl-1,7-naphthyridine, 145c

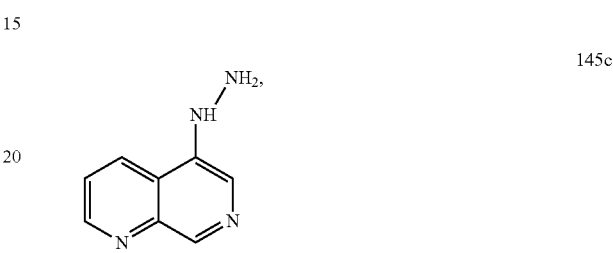

5-Bromo-1,7-naphthyridine (340 mg, 1.63 mmol), palladium(ii)(pi-cinnamyl) chloride dimer (42.13 mg, 0.081 mmol), N-[2-(di-1-adamantylphosphino)phenyl] morpholine (75.41 mg, 0.16 mmol) and sodium tert-butoxide (624.56 mg, 6.51 mmol) was dissolved in dioxane (10 mL) under N2 atmosphere. Hydrazine hydrate (162.84 mg, 3.25 mmol) was added and stirred at 60° C. for 3 h. The mixture was filtered and the solid was washed with 10 mL CH₂Cl₂. The solvent was partioned between H₂O (10 mL) and CH₂Cl₂ (50×2 mL). The combined organic layers were dried over Na₂SO₄, filtered and the filtrates were concentrated under reduced pressure to afford the title compound (260 mg, 99.8%) as brown solid. LCMS (ESI) m/z M+1: 161.1.

D. ethyl 1-(1,7-naphthyridin-5-yl)-5-(trifluoromethyl)-1H-pyrazole-4-carboxylate, 145d

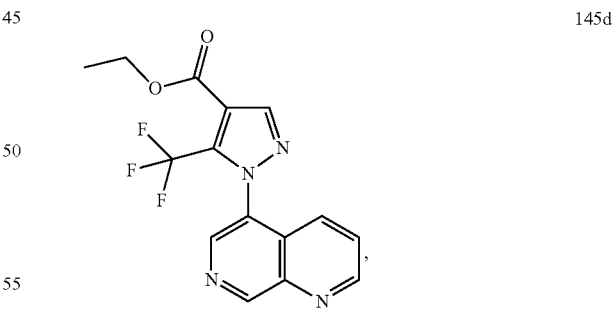

5-Hydrazinyl-1,7-naphthyridine (260 mg, 1.62 mmol) was dissolved in ethanol (10 mL), and ethyl 2-(ethoxymethylene)-4,4,4-trifluoro-3-oxobutanoate (467.8 mg, 1.95 mmol) was added. The reaction mixture was stirred at 80° C. for 12 h. The reaction mixture was concentrated under reduced pressure to afford the crude product as a yellow solid, which was purified by FCC (eluent: petroleum ether/ ethyl acetate from 100/0 to 50/50) to afford the title compound (100 mg, 17.3%) as a yellow solid. LCMS (ESI) M+1: 337.0.

E. 1-(1,7-naphthyridin-5-yl)-5-(trifluoromethyl)-1H-pyrazole-4-carboxylic acid, 145e

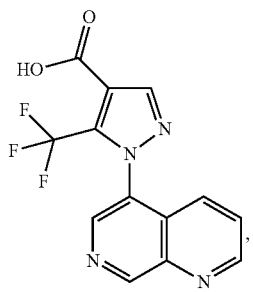

145e

Ethyl-(1,7-naphthyridin-5-yl)-5-(trifluoromethyl)-1H-pyrazole-4-carboxylate (100 mg, 0.27 mmol) was dissolved in THF (10 mL) and water (10 mL). Lithium hydroxide (64.1 mg, 2.68 mmol) was added. The reaction mixture was stirred at 25° C. for 12 h. The reaction mixture was adjusted to pH 5 using HCl (2 N), extracted with EtOAc (30 mL×2). The combined organic layers were dried over Na$_2$SO$_4$, filtered and the filtrates were concentrated under reduced pressure to afford crude the title compound (75 mg, 90.9%) as a yellow solid. LCMS (ESI) m/z M+1: 309.0.

F. N-(5-cyano-6-(2H-1,2,3-triazol-2-yl)pyridin-3-yl)-1-(1,7-naphthyridin-5-yl)-5-(trifluoromethyl)-1H-pyrazole-4-carboxamide, Cpd 145

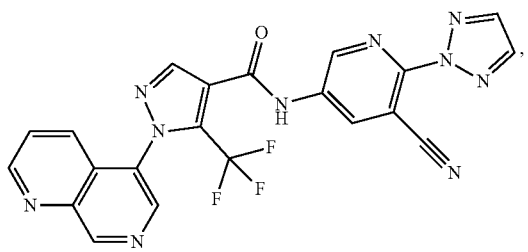 [SMILES: N#Cc1cc(NC(=O)c2cnn(-c3cncc4ncccc34)c2C(F)(F)F)cnc1-n1nccn1]

1-(1,7-Naphthyridin-5-yl)-5-(trifluoromethyl)-1H-pyrazole-4-carboxylic acid (75 mg, 0.24 mmol), 5-amino-2-(2H-1,2,3-triazol-2-yl)nicotinonitrile (54.36 mg, 0.29 mmol), pyridine (115.49 mg, 1.46 mmol) were dissolved in CH$_2$Cl$_2$ (10 mL), and phosphorus oxychloride (149.25 mg, 0.97 mmol) was added. The mixture was stirred at 25° C. for 4 h, sat. NaHCO$_3$ (30 mL) was added and the mixture was extracted with CH$_2$Cl$_2$ (30 mL×2). The combined organic layers were dried over Na$_2$SO$_4$, filtered and the filtrates were concentrated under reduced pressure to afford the crude product as a yellow oil, which was purified by preparative HPLC (22% to 52% (v/v) CH$_3$CN and H$_2$O with 0.05% HCl) and lyophilized to dryness to afford the title compound (35 mg, 30.2%). LCMS (ESI) m/z M+1: 477.0. $^1$H NMR (400 MHz, DMSO-d$_6$) δ ppm 11.50 (s, 1H), 9.69 (s, 1H), 9.22 (dd, J=1.5, 4.2 Hz, 1H), 9.14 (d, J=2.4 Hz, 1H), 8.95 (s, 1H), 8.90 (d, J=2.4 Hz, 1H), 8.71 (s, 1H), 8.30 (s, 2H), 7.94 (dd, J=4.2, 8.6 Hz, 1H), 7.87-7.82 (m, 1H).

Example 146

N-(6-(2H-1,2,3-triazol-2-yl)-5-(trifluoromethyl)pyridin-3-yl)-1-(quinolin-5-yl)-5-(trifluoromethyl)-1H-pyrazole-4-carboxamide, Cpd 146

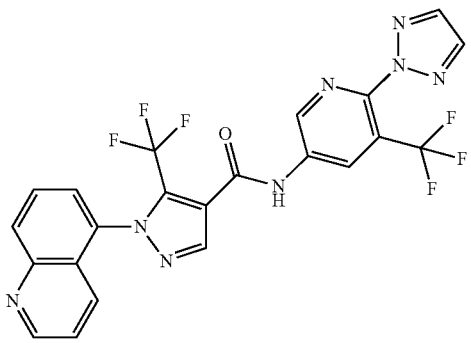 [SMILES: O=C(Nc1cnc(-n2nccn2)c(C(F)(F)F)c1)c1cnn(-c2cccc3ncccc23)c1C(F)(F)F]

A. 5-nitro-2-(2H-1,2,3-triazol-2-yl)-3-(trifluoromethyl)pyridine, 146a

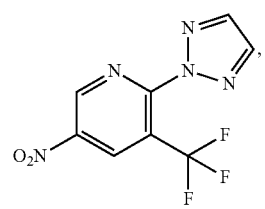

146a

To a solution of 3-chloro-4-fluoronitrobenzene (1.2 g, 6.84 mmol) and 2H-1,2,3-triazole (0.567 g, 8.20 mmol) in anhydrous DMA (5 mL) was added K$_2$CO$_3$ (1.89 g, 13.67 mmol). The reaction mixture was stirred at room temperature for 2 h. The mixture was filtered and washed with ethyl acetate (10 mL×3). The filtrate was concentrated to dryness to give a crude product. The crude product was purified by a flash column chromatography over silica gel (eluent: petroleum ether/ethyl acetate from 100/0 to 0/100). The desired fractions were collected and the solvent was concentrated under reduced pressure to afford 2-chloro-5-nitro-3-(trifluoromethyl)pyridine, 146a (600 mg, 65.6% yield) as a yellow solid. $^1$H NMR (400 MHz, DMSO-d$_6$) δ ppm 8.37 (s, 2H), 9.16 (d, J=2.20 Hz, 1H), 9.68 (d, J=2.21 Hz, 1H).

B. 6-(2H-1,2,3-triazol-2-yl)-5-(trifluoromethyl)pyridin-3-amine, 146b

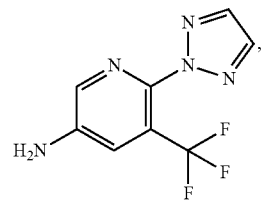

146b

To a solution of 5-nitro-2-(2H-1,2,3-triazol-2-yl)-3-(trifluoromethyl)pyridine (550 mg, 1.78 mmol) in MeOH/THF/H₂O (5 mL/10 mL/5 mL) was added iron (593 mg, 10.61 mmol) and ammonium chloride (568 mg, 10.61 mmol). The reaction mixture was stirred at 70° C. for 2 h, sat. NaHCO₃ was added to the mixture to adjust the pH to 7-9. The reaction was filtered and the organic solvent was concentrated. The mixture was extracted with CH₂Cl₂ (10 mL×3). The separated organic layer was dried (MgSO₄), filtered, and the solvent was concentrated to give a crude product as solid. The crude product was purified by a flash column chromatography over silica gel (eluent: petroleum ether/ethyl acetate from 100/0 to 0/100). The desired fractions were collected and the solvent was concentrated under reduced pressure to afford ethyl 6-(2H-1,2,3-triazol-2-yl)-5-(trifluoromethyl)pyridin-3-amine, 146b (400 mg, 82.2% yield) as a white solid. LCMS (ESI) m/z M+1: 230.0; ¹H NMR (400 MHz, DMSO-d₆) δ ppm 6.38 (s, 2H), 7.43 (d, J=2.43 Hz, 1H), 8.04 (s, 2H), 8.08 (d, J=2.43 Hz, 1H).

C. N-(5-cyano-6-(2H-1,2,3-triazol-2-yl)pyridin-3-yl)-1-(4-fluoro-2-methoxyphenyl)-5-(trifluoromethyl)-1H-pyrazole-4-carboxamide, Cpd 146

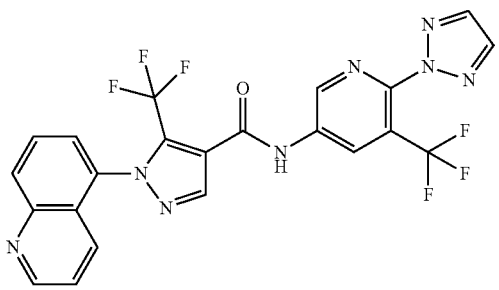 [SMILES: O=C(Nc1cnc(-n2nccn2)c(C(F)(F)F)c1)c1cnn(-c2cccc3ncccc23)c1C(F)(F)F]

Phosphorus oxychloride (75.85 uL, 0.39 mmol) was added to a solution of 1-(quinolin-5-yl)-5-(trifluoromethyl)-1H-pyrazole-4-carboxylic acid, 3b (100 mg, 0.33 mmol), 6-(2H-1,2,3-triazol-2-yl)-5-(trifluoromethyl)pyridin-3-amine (89.51 mg, 0.39 mmol), pyridine (263.26 uL, 3.26 mmol) in CH₂Cl₂ (2 mL). The mixture was stirred at room temperature for 2 h, 5 mL H₂O was added to the mixture and sat. NaHCO₃ was added to adjust the pH of the reaction mixture to 7-8. The mixture was extracted with CH₂Cl₂ (5 mL×3), the combined organic extracts were dried over anhydrous MgSO₄, filtered, and concentrated to dryness under reduced pressure to afford the crude product, which was purified by preparative HPLC (42% to 72% (v/v) CH₃CN and H₂O with 0.05% HCl) and lyophilized to dryness to afford the title compound (120 mg, 70.9%). LCMS (ESI) m/z M+1: 518.9. ¹H NMR (400 MHz, DMSO-d₆) δ ppm 7.62-7.66 (m, 1H), 7.68-7.72 (m, 1H), 7.94-8.02 (m, 2H), 8.22 (s, 2H), 8.35 (d, J=7.94 Hz, 1H), 8.63 (s, 1H), 8.91 (d, J=1.98 Hz, 1H), 9.08 (d, J=2.65 Hz, 1H), 9.19 (s, 1H), 11.45 (s, 1H).

Example 147

N-(5-chloro-6-(2H-1,2,3-triazol-2-yl)pyridin-3-yl)-1-(pyrrolo[1,2-a]pyrazin-1-yl)-5-(trifluoromethyl)-1H-pyrazole-4-carboxamide, Cpd 147

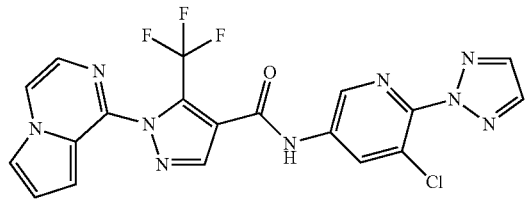 [SMILES: O=C(Nc1cnc(-n2nccn2)c(Cl)c1)c1cnn(-c2nccn3cccc23)c1C(F)(F)F]

A. N'-(pyrrolo[1,2-a]pyrazin-1-yl)pivalohydrazide, 147a

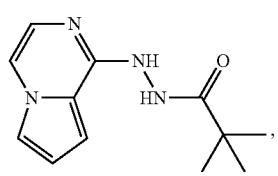

The mixture of 1-chloropyrrolo[1,2-a]pyrazine (200 mg, 1.31 mmol) and pivalohy-drazide (346.47 mg, 2.62 mmol) in MeCN (20 mL) was stirred at 80° C. for 24 h. The solvent was removed to give the crude product, the crude product was purified by FCC (petroleum ether/ethyl acetate=100:0 to 70:30). The solvent was concentrated to get the crude product (200 mg, 61.5%).

B. 1-hydrazinylpyrrolo[1,2-a]pyrazine, 147b

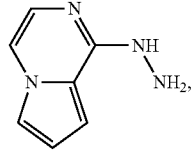

The mixture of N'-(pyrrolo[1,2-a]pyrazin-1-yl)pivalohydrazide (0.18 g, 0.73 mmol) and HCl in dioxane (1 mL) in CH₂Cl₂ (10 mL) was stirred at room temperature for 1 h. The solvent was removed to give the product as a white solid (133.85 mg, 100%).

C. ethyl 1-(pyrrolo[1,2-a]pyrazin-1-yl)-5-(trifluoromethyl)-1H-pyrazole-4-carboxylate, 147c

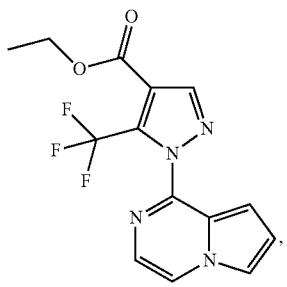

147c

A solution consisting of ethyl 2-(ethoxymethylene)-4,4,4-trifluoro-3-oxobutanoate (348.25 mg, 1.45 mmol), 1-hydrazinylpyrrolo[1,2-a]pyrazine (133.85 mg, 0.73 mmol), DIEA (0.468 g, 3.63 mmol) and ethanol (20 mL) was stirred at 80° C. for 1 h. The resultant solution was concentrated to dryness under reduced pressure to afford the crude product, which was purified by FCC (petroleum ether: ethyl acetate=100/0 to 70/30) to afford the title compound (0.15 g, 58.7%) as a yellow oil. LCMS (ESI) m/z M+1: 325.0.

D. 1-(pyrrolo[1,2-a]pyrazin-1-yl)-5-(trifluoromethyl)-1H-pyrazole-4-carboxylic acid, 147d

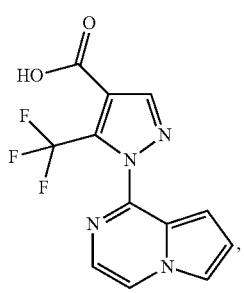

147d

Sodium hydroxide (34.05 mg, 0.85 mmol) was added to a solution of ethyl 1-(pyrrolo[1,2-a]pyrazin-1-yl)-5-(trifluoromethyl)-1H-pyrazole-4-carboxylate (160 mg, 0.43 mmol) in THF/H$_2$O=1:1(10 mL). The mixture was reacted at room temperature for 2 h, the solvent was concentrated under reduced pressure and 20 mL H$_2$O was added to the mixture. The mixture was acidified using 1M hydrochloric to pH 5 and extracted with ethyl acetate (20 mL×3). The combined organic layers were washed with brine, dried over anhydrous MgSO$_4$, and filtered. The filtrates were concentrated under reduced pressure to afford the product as a yellow solid (100 mg, 79.3%).

E. N-(5-chloro-6-(2H-1,2,3-triazol-2-yl)pyridin-3-yl)-1-(pyrrolo[1,2-a]pyrazin-1-yl)-5-(trifluoromethyl)-1H-pyrazole-4-carboxamide, Cpd 147

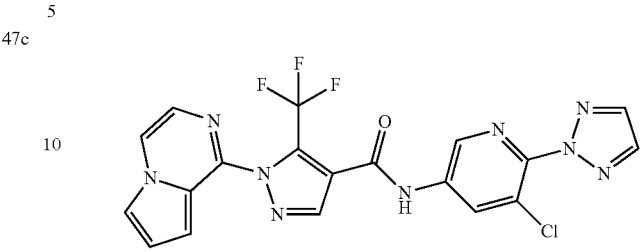

1-(Pyrrolo[1,2-a]pyrazin-1-yl)-5-(trifluoromethyl)-1H-pyrazole-4-carboxylic acid (100 mg, 0.34 mmol), 5-chloro-6-(2H-1,2,3-triazol-2-yl)pyridin-3-amine, (66.04 mg, 0.34 mmol), pyridine (0.14 mL, 1.69 mmol) were dissolved in CH$_2$Cl$_2$ (5 mL), and phosphorus oxychloride (0.12 mL, 1.35 mmol) was added. The mixture was stirred at 25° C. for 2 h. Sat. NaHCO$_3$ (20 mL) was added and the mixture extracted with CH$_2$Cl$_2$ (30 mL×2). The combined organic extracts were dried over anhydrous Na$_2$SO$_4$, filtered, and the filtrate concentrated to dryness under reduced pressure to afford the crude product, which was purified by preparative HPLC (38% to 68% (v/v) CH$_3$CN and H$_2$O with 0.05% HCl) and lyophilized to dryness to afford the title compound (66 mg, 40.6%). LCMS (ESI) m/z M+1: 473.9; $^1$H NMR (400 MHz, METHANOL-d$_4$) δ ppm 8.78 (1H, s), 8.70 (1H, d, J=2.20 Hz), 8.34 (1H, s), 8.32 (1H, d, J=4.85 Hz), 8.03 (2H, s), 7.88 (1H, s), 7.47 (1H, d, J=4.85 Hz), 6.99-7.07 (1H, m), 6.87 (1H, d, J=4.19 Hz).

Example 148

N-(5-cyano-6-(2H-1,2,3-triazol-2-yl)pyridin-3-yl)-1-(pyrrolo[1,2-a]pyrazin-1-yl)-5-(trifluoromethyl)-1H-pyrazole-4-carboxamide, Cpd 148

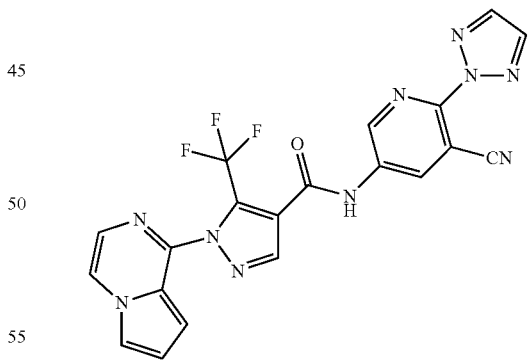

1-(Pyrrolo[1,2-a]pyrazin-1-yl)-5-(trifluoromethyl)-1H-pyrazole-4-carboxylic acid (180 mg, 0.18 mmol, 30% pure), 5-amino-2-(2H-1,2,3-triazol-2-yl)nicotinonitrile (33.94 mg, 0.18 mmol), pyridine (43.26 mg, 0.55 mmol) were dissolved in CH$_2$Cl$_2$ (3 mL), and phosphorus oxychloride (41.93 mg, 0.27 mmol) was added. The mixture was stirred at 25° C. for 16 h, sat. NaHCO$_3$ (20 mL) was added and extracted with CH$_2$Cl$_2$ (30 mL×2). The combined organic layers were dried over Na$_2$SO$_4$, filtered and the filtrates were concentrated under reduced pressure to afford the crude product as a yellow oil, which was purified by preparative HPLC (43% to 63% (v/v) CH$_3$CN and H$_2$O with 0.05% HCl) and lyophilized to dryness to afford the title compound (11 mg, 12.9%). LCMS (ESI) m/z M+1: 454.9.0; $^1$H NMR (400 MHz, METHANOL-d$_4$) δ ppm 9.07 (br s, 1H), 8.90 (s, 1H), 8.31-8.39 (m, 2H), 8.15 (br s, 2H), 7.89 (d, J=1.32 Hz, 1H), 7.48 (d, J=4.63 Hz, 1H), 7.04 (dd, J=4.19, 2.65 Hz, 1H), 6.87 (d, J=4.19 Hz, 1H).

Example 149

N-(5-cyano-6-(2-methyl-2H-tetrazol-5-yl)pyridin-3-yl)-1-(quinolin-5-yl)-5-(trifluoromethyl)-1H-pyrazole-4-carboxamide, Cpd 149

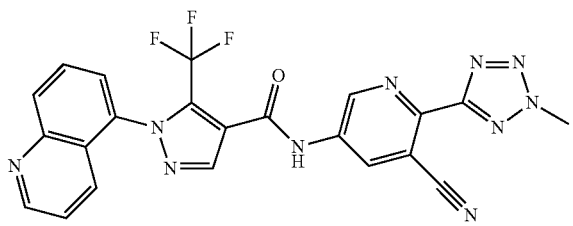 [SMILES: Cn1nnc(-c2ncc(NC(=O)c3cnn(-c4cccc5ncccc45)c3C(F)(F)F)cc2C#N)n1]

A. 1-(quinolin-5-yl)-5-(trifluoromethyl)-1H-pyrazole-4-carboxamide, 149a

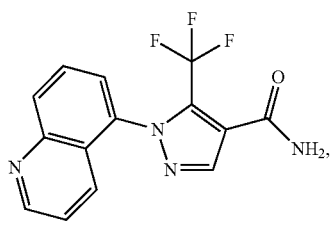

HATU (2.79 g, 7.32 mmol) was added to a solution of 1-(quinolin-5-yl)-5-(trifluoromethyl)-1H-pyrazole-4-carboxylic acid, 3b (1.5 g, 4.88 mmol), NH$_3$/dioxane (19.53 mL, 9.77 mmol), DIEA (1.26 g, 9.77 mmol) in CH$_2$Cl$_2$. The mixture was stirred at rt for 16 h, 50 mL H$_2$O and 50 mL ethyl acetate were added to the mixture. The organic layer was washed with brine (50 mL), dried over MgSO$_4$ and the filtrate concentrated under reduced pressure. The residue was purified by FCC (petroleum ether/ethyl acetate=100:5 to 100:50) to afford the title compound (1 g, 63.8%) as a yellow solid.

B. 5-bromo-3-methyl-2-(2H-tetrazol-5-yl)pyridine, 149b

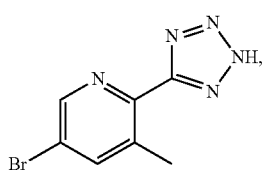

To a stirring solution of 5-bromo-3-methylpicolinonitrile (3.43 g, 17.39 mmol) in DMF (30 mL) was added zinc(II) chloride (2.37 g, 17.39 mmol) and sodium azide (1.47 g, 22.61 mmol). The reaction mixture was stirred at 95° C. for 16 h. The solution was used directly for the next step.

C. 5-bromo-3-methyl-2-(2-methyl-2H-tetrazol-5-yl)pyridine, 149c

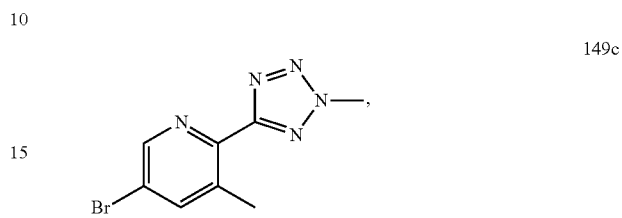

To a stirring solution of 5-bromo-3-methyl-2-(2H-tetrazol-5-yl)pyridine (2 g, 8.33 mmol) in DMF (30 mL) was added potassium carbonate (5.76 g, 41.66 mmol) and iodomethane (5.20 g, 36.66 mmol). The reaction mixture was stirred at 25° C. for 2 h and filtered. The filtrate was concentrated to dryness under reduced pressure to afford the crude product, which was purified by FCC (petroleum ether: ethyl acetate=100:0 to 60:40) to afford the title compound (480 mg, 23.1%) as a white solid.

D. 5-bromo-3-(bromomethyl)-2-(2-methyl-2H-tetrazol-5-yl)pyridine, 149d

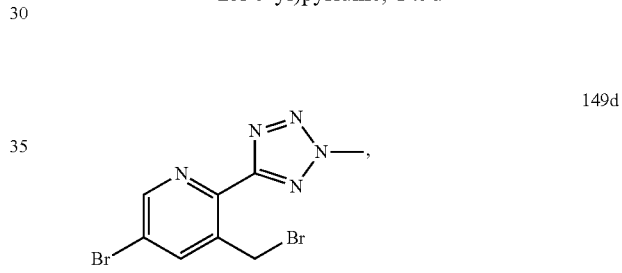

Benzoic peroxyanhydride (28.60 mg, 0.12 mmol) was added to a solution of 5-bromo-3-methyl-2-(2-methyl-2H-tetrazol-5-yl)pyridine (0.3 g, 1.18 mmol) and 1,3-dibromo-5,5-dimethylimidazolidine-2,4-dione (185.67 mg, 0.65 mmol) in acetonitrile (10 mL). The mixture was stirred at 80° C. under N$_2$ for 4 h. The solvent was concentrated under reduced pressure and extracted with acetate (30 mL×2). The combined organic layers were concentrated under reduced pressure to give crude product. The crude product was purified by FCC (petroleum ether: ethyl acetate=100:0 to 70:30) to afford the title compound (326 mg, 24.5%) as a white solid. LCMS (ESI) m/z M+1: 333.8.

E. 5-bromo-2-(2-methyl-2H-tetrazol-5-yl)nicotinonitrile, 149e

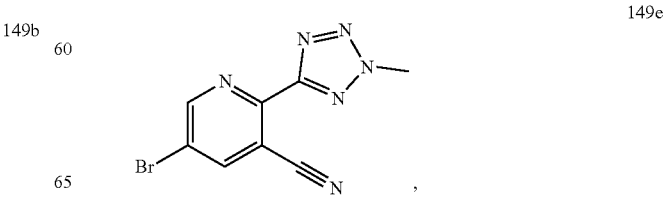

Diiodine (333.84 mg, 1.32 mmol) was added to a solution of 5-bromo-3-(bromomethyl)-2-(2-methyl-2H-tetrazol-5-yl)pyridine (296.00 mg, 0.26 mmol) in ammonia hydrate (5 mL). The mixture was stirred at 60° C. for 16 h. The solvent was concentrated under reduced pressure and extracted with acetate (30 mL×2). The combined organic layers were concentrated under reduced pressure to give crude product. The crude product was purified by FCC (petroleum ether:ethyl acetate=100:0 to 70:30) to afford the title compound (160 mg) as a white solid. LCMS (ESI) m/z M+1: 267.0.

F. N-(5-cyano-6-(2-methyl-2H-tetrazol-5-yl)pyridin-3-yl)-1-(quinolin-5-yl)-5-(trifluoromethyl)-1H-pyrazole-4-carboxamide, Cpd 149

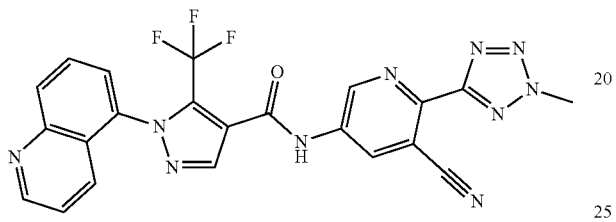

To a mixture of 5-bromo-2-(2-methyl-2H-tetrazol-5-yl)nicotinonitrile (160.0 mg, 0.31 mmol), 1-(quinolin-5-yl)-5-(trifluoromethyl)-1H-pyrazole-4-carboxamide (188.76 mg, 0.62 mmol), and sodium 2-methylpropan-2-olate (118.47 mg, 1.23 mmol) were dissolved in dioxane (10 mL) was added tris(dibenzylideneactone)dipalladium(0) (56.44 mg, 0.062 mmol) and (9,9-dimethyl-9H-xanthene-4,5-diyl)bis(diphenylphosphine) (35.67 mg, 0.062 mmol). The mixture was stirred at 100° C. for 12 h. The reaction mixture was filtered, the filtrate was concentrated under reduced pressure to give the crude product as a yellow oil, which was purified by preparative HPLC (26% to 46% (v/v) CH$_3$CN and H$_2$O with 0.05% HCl) and lyophilized to dryness to afford the title compound (28 mg, 17.7%). LCMS (ESI) m/z M+1: 490.9; $^1$H NMR (400 MHz, DMSO-d$_6$) δ ppm 11.46 (1H, s), 9.27 (1H, d, J=2.43 Hz), 9.04 (1H, d, J=2.43 Hz), 8.84 (1H, d, J=2.43 Hz), 8.63 (1H, s), 8.32 (1H, d, J=8.38 Hz), 7.93-7.99 (1H, m), 7.89-7.93 (1H, m), 7.64-7.69 (1H, m), 7.58-7.63 (1H, m), 4.50 (3H, s).

Example 150 and Example 151

N-(5-cyano-6-(2H-1,2,3-triazol-2-yl)pyridin-3-yl)-1-(furo[3,2-b]pyridin-7-yl)-5-(trifluoromethyl)-1H-pyrazole-4-carboxamide, Cpd 150

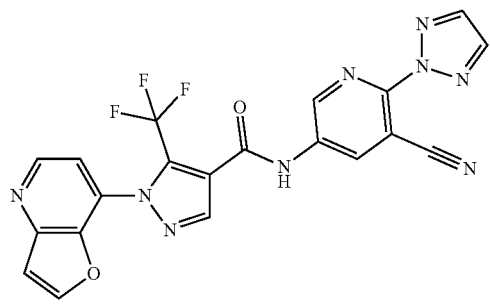 [SMILES: N#Cc1cc(NC(=O)c2cnn(-c3ccnc4ccoc34)c2C(F)(F)F)cnc1-n1nccn1]

N-(5-cyano-6-(2H-1,2,3-triazol-2-yl)pyridin-3-yl)-1-(2-methylfuro[3,2-b]pyridin-7-yl)-5-(trifluoromethyl)-1H-pyrazole-4-carboxamide, Cpd 151

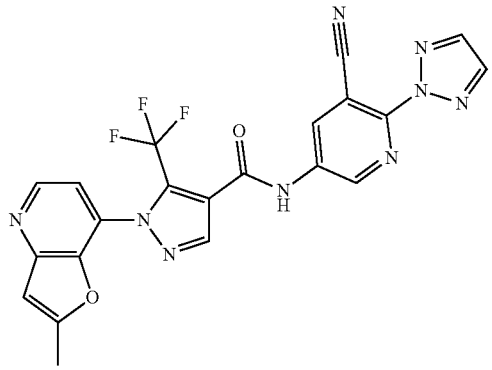 [SMILES: Cc1cc2nccc(-n3ncc(C(=O)Nc4cnc(-n5nccn5)c(C#N)c4)c3C(F)(F)F)c2o1]

A. mixture of 7-chloro-2-methylfuro[3,2-b]pyridine with 7-chlorofuro[3,2-b]pyridine, 150a

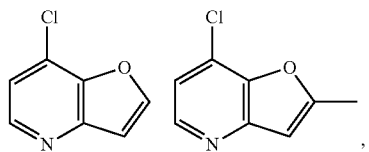

A mixture of 7-chloro-2-iodofuro[3,2-b]pyridine (180 mg, 0.66 mmol), dicyclohexyl(2',6'-diisopropoxy-[1,1'-biphenyl]-2-yl)phosphine (30 mg, 0.064 mmol), methylboronic acid (50 mg, 0.84 mmol), and K$_3$PO$_4$ (628 mg, 1.93 mmol) in dioxane (6 mL) and H$_2$O (1.5 mL) was added diacetoxypalladium (7.23 mg, 0.032 mmol) under N$_2$ and heated to 100° C. for 10 h. The mixture was extracted with EtOAc (10 mL×3). The combined organic layers were dried over MgSO$_4$, filtered and the filtrates were concentrated under reduced pressure to afford the crude product. The residue was further purified by column chromatography (eluent: petrol ether/EtOAc=100:0 to 50:50). The desired fraction was collected and the solvent was removed to give the desired product as a brown oil. (80 mg, 35% yield).

B. mixture of 7-hydrazinyl-2-methylfuro[3,2-b]pyridine and 7-hydrazinylfuro[3,2-b]pyridine, Cpd 150b

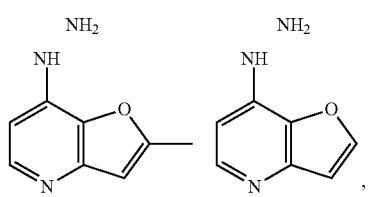

A mixture of 7-chloro-2-methylfuro[3,2-b]pyridine and 7-chlorofuro[3,2-b]pyridine (80 mg, 0.23 mmol) and hydrazine hydrate (95 mg, 1.9 mmol) was heated to 50° C. overnight. The solvent was removed under reduced pressure and directly used for the next step.

C. Mixture of ethyl 1-(2-methylfuro[3,2-b]pyridin-7-yl)-5-(trifluoromethyl)-1H-pyrazole-4-carboxylate and ethyl 1-(furo[3,2-b]pyridin-7-yl)-5-(trifluoromethyl)-1H-pyrazole-4-carboxylate, 150c 150c

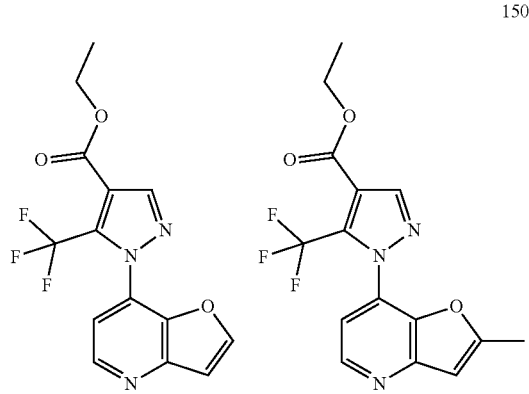

A mixture of 7-hydrazinyl-2-methylfuro[3,2-b]pyridine and 7-hydrazinylfuro[3,2-b]pyridine (65 mg, 0.21 mmol) was dissolved in ethanol (20 mL), and ethyl 2-(ethoxymethylene)-4,4,4-trifluoro-3-oxobutanoate (111.96 mg, 0.50 mmol) was added. The reaction mixture was stirred at 25° C. for 2 h. The reaction mixture was concentrated under reduced pressure to afford the crude product as a brown oil, which was purified by FCC (eluent: petroleum ether/ethyl acetate from 100/0 to 50/50) to afford the title compound (50 mg, 35% yield) as a brown oil.

D. Mixture of 1-(2-methylfuro[3,2-b]pyridin-7-yl)-5-(trifluoromethyl)-1H-pyrazole-4-carboxylic acid and 1-(furo[3,2-b]pyridin-7-yl)-5-(trifluoromethyl)-1H-pyrazole-4-carboxylic acid, 150d 150d

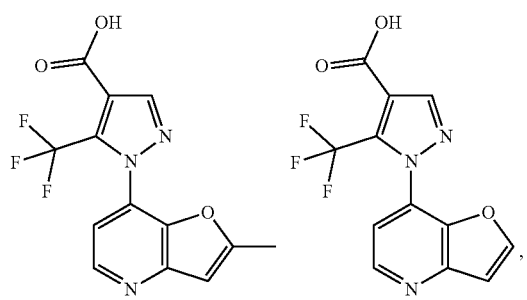

A mixture of ethyl 1-(2-methylfuro[3,2-b]pyridin-7-yl)-5-(trifluoromethyl)-1H-pyrazole-4-carboxylate and ethyl 1-(furo[3,2-b]pyridin-7-yl)-5-(trifluoromethyl)-1H-pyrazole-4-carboxylate (50 mg, 0.075 mmol) was dissolved in THF (5 mL) and water (1 mL). Lithium hydroxide (62.95 mg, 1.5 mmol) was added. The reaction mixture was stirred at 25° C. for 1 h. THF was removed, and the resultant residue was washed with ether (5 mL). To the aqueous layer was added 3M HCl to adjust the mixture to pH 1, and the aqueous phase was extracted with EtOAc (5 mL×3). The organic layers were dried over MgSO$_4$, filtered and the filtrates concentrated to afford the product as a brown oil (50 mg).

E. N-(5-cyano-6-(2H-1,2,3-triazol-2-yl)pyridin-3-yl)-1-(furo[3,2-b]pyridin-7-yl)-5-(trifluoromethyl)-1H-pyrazole-4-carboxamide, Cpd 150

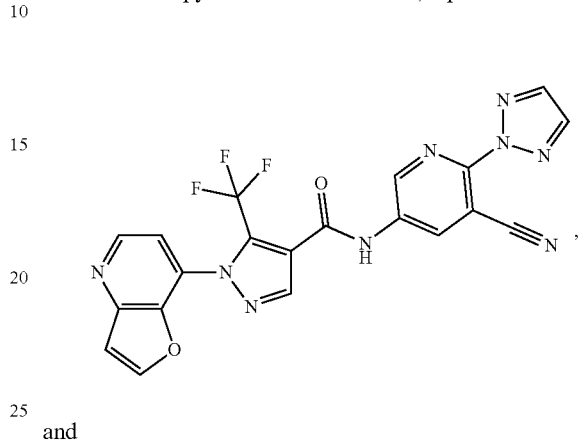

and

N-(5-cyano-6-(2H-1,2,3-triazol-2-yl)pyridin-3-yl)-1-(2-methylfuro[3,2-b]pyridin-7-yl)-5-(trifluoromethyl)-1H-pyrazole-4-carboxamide, 151

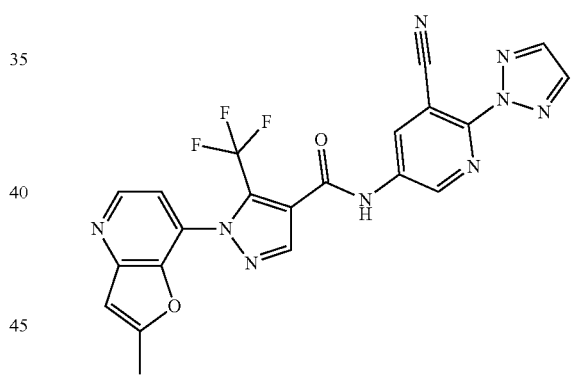

A mixture of 1-(2-methylfuro[3,2-b]pyridin-7-yl)-5-(trifluoromethyl)-1H-pyrazole-4-carboxylic acid and 1-(furo[3,2-b]pyridin-7-yl)-5-(trifluoromethyl)-1H-pyrazole-4-carboxylic acid (50 mg, 0.082 mmol), 5-amino-2-(2H-1,2,3-triazol-2-yl)nicotinonitrile (15.3 mg, 0.082 mmol), and pyridine (19.5 mg, 0.25 mmol) were dissolved in CH$_2$Cl$_2$ (3 mL), and phosphorus oxychloride (18.9 mg, 0.12 mmol) was added. The mixture was stirred at 25° C. for 16 h. Sat. NaHCO$_3$ (20 mL) was added and the mixture was extracted with CH$_2$Cl$_2$ (30 mL×2). The combined organic layers were dried over Na$_2$SO$_4$, filtered and the filtrates were concentrated under reduced pressure to afford the crude product as a yellow oil, which was purified by preparative HPLC (22% to 52% (v/v) CH$_3$CN and H$_2$O with 0.05% HCl) and lyophilized to dryness to afford the title N-(5-cyano-6-(2H-1,2,3-triazol-2-yl)pyridin-3-yl)-1-(furo[3,2-b]pyridin-7-yl)-5-(trifluoromethyl)-1H-pyrazole-4-carboxamide, Cpd 150 (5 mg, 13%). LCMS (ESI) m/z M+1: 465.9. 1H NMR (400 MHz, METHANOL-d$_4$) δ ppm 9.07 (br s, 1H) 8.89 (d, J=2.43 Hz, 1H) 8.79 (d, J=5.51 Hz, 1H) 8.47 (s, 1H) 8.34 (d, J=2.43 Hz, 1H) 8.14 (s, 2H) 7.71 (d, J=5.29 Hz, 1H) 7.28 (d, J=2.43 Hz, 1H); and N-(5-cyano-6-(2H-1,2,3-triazol-2-yl)pyridin-3-yl)-1-(2-methylfuro[3,2-b]pyridin-7-yl)-5-(trifluoromethyl)-1H-pyrazole-4-carboxamide, Cpd 151 (4 mg, 10%). $^1$H NMR (400 MHz, METHANOL-$d_4$) δ ppm 9.06 (s, 1H), 8.90 (d, J=2.65 Hz, 1H), 8.71 (d, J=5.73 Hz, 1H), 8.48 (s, 1H), 8.14 (s, 2H), 7.68 (d, J=5.73 Hz, 1H), 6.98 (d, J=1.10 Hz, 1H), 2.61 (d, J=0.88 Hz, 3H). LC-MS: (ES, m/z): [M+1]$^+$ 480.0.

Example 152

N-(5-cyano-6-(2H-1,2,3-triazol-2-yl)pyridin-3-yl)-1-(4-fluoro-2-methoxyphenyl)-5-(trifluoromethyl)-1H-pyrazole-4-carboxamide, Cpd 152

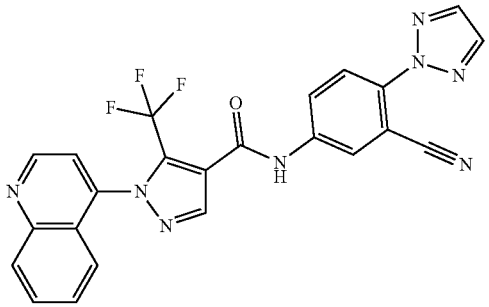 [SMILES: N#Cc1cc(NC(=O)c2cnn(-c3ccnc4ccccc34)c2C(F)(F)F)ccc1-n1nccn1]

Phosphorus oxychloride (48.54 uL, 0.52 mmol) was added to a solution of 1-(quinolin-4-yl)-5-(trifluoromethyl)-1H-pyrazole-4-carboxylic acid, (80 mg, 0.26 mmol), 5-amino-2-(2H-1,2,3-triazol-2-yl)benzonitrile (53.04 mg, 0.29 mmol), pyridine (210.61 uL, 2.60 mmol) in CH$_2$Cl$_2$ (2 mL). The mixture was stirred at room temperature for 1 h, then 5 mL H$_2$O was added to the mixture. Sat. NaHCO$_3$ was added to adjust the pH of reaction mixture to 7-8. The mixture was extracted with CH$_2$Cl$_2$ (5 mL×3). The combined organic extracts were dried over anhydrous Mg$_2$SO$_4$, filtered, and the filtrate concentrated to dryness under reduced pressure to afford the crude product, which was purified by preparative HPLC (35% to 65% (v/v) CH$_3$CN and H$_2$O with 0.05% HCl) and lyophilized to dryness to afford the title compound (45 mg, 36.2%). LCMS (ESI) m/z M+1: 475.0. $^1$H NMR (400 MHz, DMSO-$d_6$) δ ppm 7.34 (d, J=8.16 Hz, 1H), 7.76 (t, J=7.28 Hz, 1H), 7.90 (d, J=4.41 Hz, 1H), 7.92-7.98 (m, 1H), 8.11-8.16 (m, 1H), 8.22 (d, J=2.21 Hz, 1H), 8.24 (s, 1H), 8.26-8.28 (m, 2H), 8.43 (d, J=2.20 Hz, 1H), 8.67 (s, 1H), 9.18 (d, J=4.63 Hz, 1H), 11.22 (s, 1H).

Example 153

1-(benzo[d]thiazol-7-yl)-N-(5-chloro-6-(2H-1,2,3-triazol-2-yl)pyridin-3-yl)-5-(trifluoromethyl)-1H-pyrazole-4-carboxamide, Cpd 153

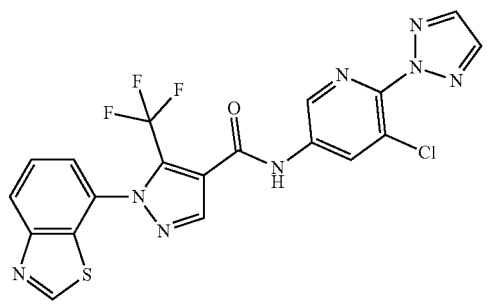 [SMILES: O=C(Nc1cnc(-n2nccn2)c(Cl)c1)c1cnn(-c2cccc3ncsc23)c1C(F)(F)F]

A. 7-hydrazinylbenzo[d]thiazole, 153a

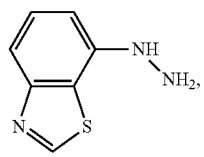

153a

A mixture of palladium(II)(pi-cinnamyl) chloride dimer (24.2 mg, 0.047 mmol) and N-[2-(di-1-adamantylphosphino)phenyl]morpholine (43.31 mg, 0.093 mmol) in dioxane (2.5 mL) was purged with argon (4×). The resulting clear yellow solution was stirred at room temperature under argon for 10 min. 7-Bromobenzo[d]thiazole (200 mg, 0.93 mmol) and t-BuONa (179.56 mg, 1.87 mmol) were added to the mixture and purged with argon (4×). The resulting yellow reaction was stirred at room temperature for 5 min and then treated with hydrazine (93.53 mg, 1.87 mmol) via syringe and purged with argon (4×). Then the mixture was stirred at 50° C. under argon for 2 h. The mixture was filtered and washed with ethyl acetate (20 mL). The filtrate was concentrated under reduced pressure to afford 7-hydrazinylbenzo[d]thiazole (150 mg, crude product) as a black solid.

B. ethyl 1-(benzo[d]thiazol-7-yl)-5-(trifluoromethyl)-1H-pyrazole-4-carboxylate, 153b

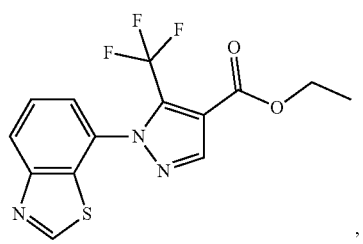

153b

A solution of 7-hydrazinylbenzo[d]thiazole, 153a (150 mg, 0.91 mmol), ethyl 2-(ethoxymethylene)-4,4,4-trifluoro- 3-oxobutanoate (327 mg, 1.36 mmol) in EtOH (20 mL) was stirred at 80° C. for 3 h. The mixture was concentrated under reduced pressure. The crude product was purified by column chromatography over silica gel (petroleum ether/ethyl acetate from 100/0 to 70/30). The desired fractions were collected and the solvent was concentrated under reduced pressure to afford the title product (130 mg, 42.0% yield) as a yellow solid.

C. 1-(benzo[d]thiazol-7-yl)-5-(trifluoromethyl)-1H-pyrazole-4-carboxylic acid, 153c

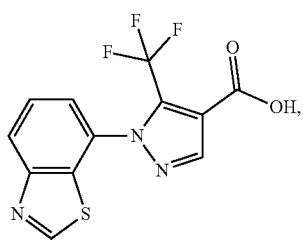

153c

A solution of ethyl 1-(benzo[d]thiazol-7-yl)-5-(trifluoromethyl)-1H-pyrazole-4-carboxylate, 153b (130 mg, 0.38 mmol), LiOH.H$_2$O (23.98 mg, 0.57 mmol) in EtOH/H$_2$O (2/1, 2 mL) was stirred at room temperature overnight. 1N HCl solution was added to neutralize the reaction solution. The mixture was extracted with ethyl acetate (10 mL×3). The separated organic layer was dried (MgSO$_4$), filtered, and the filtrate was concentrated to afford the title product (100 mg, 83.8% yield) as a white solid.

D. 1-(benzo[d]thiazol-7-yl)-N-(5-chloro-6-(2H-1,2,3-triazol-2-yl)pyridin-3-yl)-5-(trifluoromethyl)-1H-pyrazole-4-carboxamide, Cpd 153

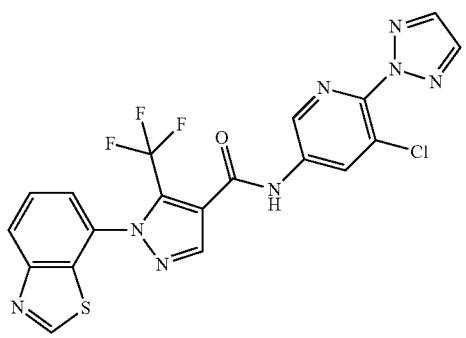 [SMILES: O=C(Nc1cnc(-n2nccn2)c(Cl)c1)c1cnn(-c2cccc3ncsc23)c1C(F)(F)F]

Phosphorus oxychloride (39.71 uL, 0.43 mmol) was added to a solution of 1-(benzo[d]thiazol-7-yl)-5-(trifluoromethyl)-1H-pyrazole-4-carboxylic acid, 153c (66.73 mg, 0.21 mmol), 5-chloro-6-(2H-1,2,3-triazol-2-yl)pyridin-3-amine (50 mg, 0.26 mmol), pyridine (172.28 uL, 2.13 mmol) in CH$_2$Cl$_2$ (2 mL). The mixture was stirred at room temperature for 1 h and 5 mL H$_2$O was added to the mixture. Sat. NaHCO$_3$ was added to adjust the pH of the reaction mixture to 7-8. The mixture was extracted with CH$_2$Cl$_2$ (5 mL×3). The combined organic extracts were dried over anhydrous Mg$_2$SO$_4$, filtered, and the filtrate concentrated to dryness under reduced pressure to afford the crude product, which was purified by preparative HPLC (35% to 65% (v/v) CH$_3$CN and H$_2$O with 0.05% HCl) and lyophilized to dryness to afford the title compound (180 mg, 60.6%). LCMS (ESI) m/z M+1: 490.9. $^1$H NMR (400 MHz, METHANOL-d$_4$) δ ppm 7.69 (d, J=7.72 Hz, 1H), 7.76-7.81 (m, 1H), 8.06 (s, 2H), 8.32 (d, J=8.16 Hz, 1H), 8.38 (s, 1H), 8.72 (d, J=1.76 Hz, 1H), 8.80 (s, 1H), 9.36 (s, 1H).

Example 154

N-(6-(4-amino-2H-1,2,3-triazol-2-yl)-5-chloropyridin-3-yl)-1-(quinolin-5-yl)-5-(trifluoromethyl)-1H-pyrazole-4-carboxamide, Cpd 154

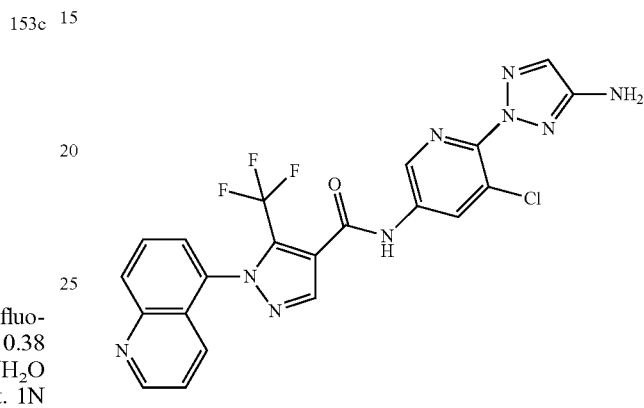

To a solution of 2-(3-chloro-5-(1-(quinolin-5-yl)-5-(trifluoromethyl)-1H-pyrazole-4-carboxamido)pyridin-2-yl)-2H-1,2,3-triazole-4-carboxylic acid, Cpd 109 (160 mg, 0.29 mmol) in DMF (5 mL), DPPA (95.92 mg, 0.35 mmol) and TEA (118.83 ul, 0.87 mmol) were added under N$_2$ atmosphere. The mixture was stirred at 80° C. overnight. The mixture was concentrated to give a crude product, which was purified by preparative HPLC (40% to 70% (v/v) CH$_3$CN and H$_2$O with 0.05% HCl) and lyophilized to dryness to afford the title compound (45 mg, 30.8%). LCMS (ESI) m/z M+1: 499.9. $^1$H NMR (400 MHz, DMSO-d$_6$) δ ppm 5.51 (s, 2H), 7.33 (s, 1H), 7.59-7.64 (m, 1H), 7.66-7.71 (m, 1H), 7.91-8.01 (m, 2H), 8.33 (d, J=8.60 Hz, 1H), 8.58-8.62 (m, 2H), 8.79 (d, J=2.21 Hz, 1H), 9.06 (d, J=2.43 Hz, 1H), 11.23 (br s, 1H).

Example 155

1-(1-aminoisoquinolin-4-yl)-N-(5-chloro-6-(2H-1,2,3-triazol-2-yl)pyridin-3-yl)-5-(trifluoromethyl)-1H-pyrazole-4-carboxamide, Cpd 155

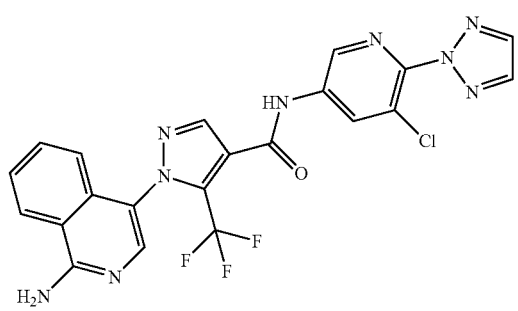 [SMILES: Nc1ncc(-n2ncc(C(=O)Nc3cnc(-n4nccn4)c(Cl)c3)c2C(F)(F)F)c2ccccc12]

491

A. ethyl 1-(2-chloro-4-fluorophenyl)-5-(trifluoromethyl)-1H-pyrazole-4-carboxylate, 155a

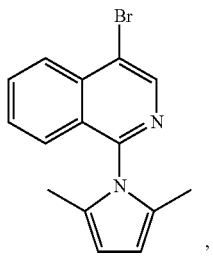

155a

A solution of 4-bromoisoquinolin-1-amine (5.5 g, 24.656 mmol), hexane-2,5-dione (3.377 g, 29.59 mmol) and p-TSA (93.8 mg, 0.49 mmol) in toluene (50 mL) was heated to reflux for 36 h. The mixture was concentrated under reduced pressure. The crude product was purified by column chromatography over silica gel (petroleum ether/ethyl acetate from 100/0 to 0/100). The desired fractions were collected and the solvent was concentrated under reduced pressure to afford the title product (3.3 g, 42.7% yield) as a white solid. LCMS (ESI) m/z M+1: 302.9.

B. 1-(2,5-dimethyl-1H-pyrrol-1-yl)-4-hydrazinylisoquinoline, 155b

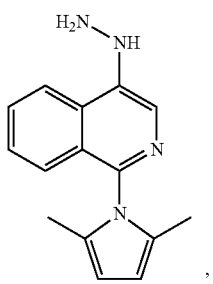

155b

A mixture of ethyl 1-(2-chloro-4-fluorophenyl)-5-(trifluoromethyl)-1H-pyrazole-4-carboxylate, 155a (2.6 g, 8.63 mmol), hydrazine (864.30 mg, 17.27 mmol), palladium(II)(pi-cinnamyl) chloride dimer (134.17 mg, 0.26 mmol) and N-[2-(di-1-adamantylphosphino)phenyl]morpholine (240.14 mg, 0.52 mmol) and t-BuONa (2486.21 mg, 25.90 mmol) in dioxane (50 mL) with N₂ atmosphere was stirred at 60° C. for 10 h. After filtering through diatomaceous earth, the mixture was partitioned between H₂O (50 mL) and CH₂Cl₂ (100×3 mL). The organic layer was separated, dried over MgSO₄, filtered and the filtrate concentrated to give the title product as a brown oil. LCMS (ESI) m/z M+1: 253.

492

C. ethyl 1-(1-(2,5-dimethyl-1H-pyrrol-1-yl)isoquinolin-4-yl)-5-(trifluoromethyl)-1H-pyrazole-4-carboxylate, 155c

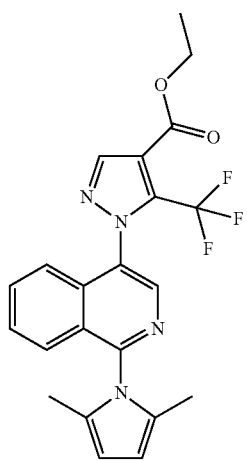

155c

A solution of 1-(2,5-dimethyl-1H-pyrrol-1-yl)-4-hydrazinylisoquinoline, 155b (3.3 g, 8.63 mmol), ethyl 2-(ethoxymethylene)-4,4,4-trifluoro-3-oxobutanoate (2.90 g, 12.09 mmol) in EtOH (50 mL) was stirred at room temperature for 2 h. The mixture was concentrated under reduced pressure, the crude product was purified by column chromatography over silica gel (petroleum ether/ethyl acetate from 100/0 to 50/50). The desired fractions were collected and the solvent was concentrated under reduced pressure to afford the product (3.5 g, 94.6% yield) as a yellow solid. LCMS (ESI) m/z M+1: 429.

D. ethyl 1-(1-(2,5-dimethyl-1H-pyrrol-1-yl)isoquinolin-4-yl)-5-(trifluoromethyl)-1H-pyrazole-4-carboxylate, 155d

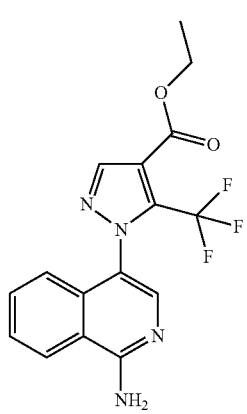

155d

A solution of ethyl 1-(1-(2,5-dimethyl-1H-pyrrol-1-yl)isoquinolin-4-yl)-5-(trifluoromethyl)-1H-pyrazole-4-carboxylate, 4c (3.4 g, 7.94 mmol) and hydroxylamine hydrochloride (13.24 g, 190.47 mmol) in EtOH (120 mL) was heated to reflux for 2 days. The solvent was removed and the residue was made basic by the addition of sat. NaHCO$_3$ solution (100 mL). The mixture was extracted with EtOAc (100 mL×3). The combined organic layers were collected, dried over MgSO$_4$, filtered and the filtrate concentrated to give a crude product. The crude product was purified by column chromatography over silica gel (petroleum ether/ethyl acetate from 100/0 to 0/100). The desired fractions were collected and the solvent was concentrated under reduced pressure to afford the title product (1.6 g, 57.6% yield) as a brown solid. LCMS (ESI) m/z M+1: 350.9.

E. mixture of ethyl 1-(1-((tert-butoxycarbonyl)amino)isoquinolin-4-yl)-5-(trifluoromethyl)-1H-pyrazole-4-carboxylate and ethyl 1-(1-((di-tert-butoxycarbonyl)amino)isoquinolin-4-yl)-5-(trifluoromethyl)-1H-pyrazole-4-carboxylate, 155e F. Mixture of 1-(1-((tert-butoxycarbonyl)amino)isoquinolin-4-yl)-5-(trifluoromethyl)-1H-pyrazole-4-carboxylic acid; 1-(1-((di-tert-butoxycarbonyl)amino)isoquinolin-4-yl)-5-(trifluoromethyl)-1H-pyrazole-4-carboxylic acid, 155f

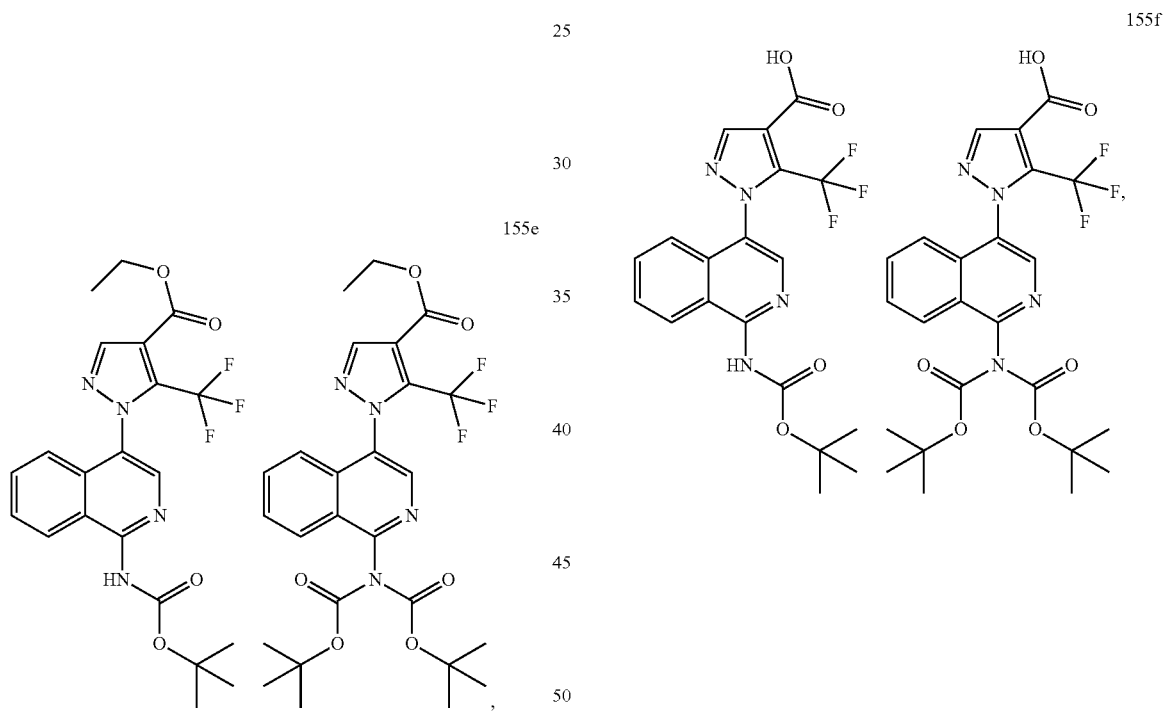

A solution of ethyl 1-(1-(2,5-dimethyl-1H-pyrrol-1-yl)isoquinolin-4-yl)-5-(trifluoromethyl)-1H-pyrazole-4-carboxylate, 155d (600 mg, 1.71 mmol) and Boc$_2$O (1121.47 mg, 5.14 mmol), DMAP (10.46 mg, 0.086 mmol) and TEA (715.22 ul, 5.14 mmol) in THF (5 mL) was stirred at room temperature overnight. The mixture was concentrated to give a crude product. The crude product was purified by column chromatography over silica gel (petroleum ether/ethyl acetate from 100/0 to 50/50). The desired fractions were collected and the solvent was concentrated under reduced pressure to afford the title product (650 mg, 68.9% yield) as a yellow solid.

A solution of mixture of ethyl 1-(1-((tert-butoxycarbonyl)amino)isoquinolin-4-yl)-5-(trifluoromethyl)-1H-pyrazole-4-carboxylate and ethyl 1-(1-((di-tert-butoxycarbonyl)amino)isoquinolin-4-yl)-5-(trifluoromethyl)-1H-pyrazole-4-carboxylate, 4e (420 mg, 0.42 mmol), LiOH (35.22 mg, 0.84 mmol) in THF/H$_2$O (2/1, 0.75 mL) was stirred at room temperature for 2 h. 1N HCl solution was added to neutralize the reaction solution. The mixture was extracted with ethyl acetate (10 mL×3). The separated organic layer was dried (Na$_2$SO$_4$), filtered, and the filtrate was concentrated to afford the title product (400 mg, crude product) as a white solid.

495

G. Mixture of tert-butyl (4-(4-((5-chloro-6-(2H-1,2,3-triazol-2-yl)pyridin-3-yl)carbamoyl)-5-(trifluoromethyl)-1H-pyrazol-1-yl)isoquinolin-1-yl)carbamate and di-tert-butyl (4-(4-((5-chloro-6-(2H-1,2,3-triazol-2-yl)pyridin-3-yl)carbamoyl)-5-(trifluoromethyl)-1H-pyrazol-1-yl)isoquinolin-1-yl)carbamate, 155g

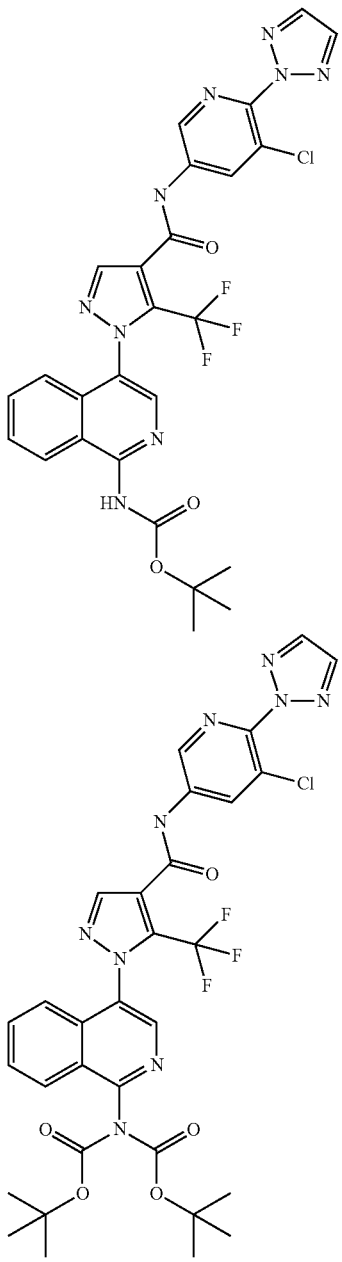

155g

Phosphorus oxychloride (63.18 uL, 0.68 mmol) was added to a solution of mixture of 1-(1-((tert-butoxycarbonyl)amino)isoquinolin-4-yl)-5-(trifluoromethyl)-1H-pyrazole-4-carboxylic acid; 1-(1-((di-tert-butoxycarbonyl)amino)isoquinolin-4-yl)-5-(trifluoromethyl)-1H-pyrazole-4-carboxylic acid, 155f (150 mg, 0.15 mmol), 5-chloro-6-(2H-1,2,3-triazol-2-yl)pyridin-3-amine (86.18 mg, 0.44 mmol),

496 pyridine (274.09 uL, 3.39 mmol) in $CH_2Cl_2$ (4 mL). The mixture was stirred at room temperature for 1 h. 5 mL water was added to the mixture. Sat. $NaHCO_3$ was added to adjust the pH of reaction mixture to 7-8. The mixture was extracted with $CH_2Cl_2$ (5 mL×3). The combined organic extracts were dried over anhydrous $Mg_2SO_4$, filtered, and the filtrate concentrated to dryness under reduced pressure to afford the crude product. LCMS (ESI) m/z M+1: 544.2.

H. 1-(1-aminoisoquinolin-4-yl)-N-(5-chloro-6-(2H-1,2,3-triazol-2-yl)pyridin-3-yl)-5-(trifluoromethyl)-1H-pyrazole-4-carboxamide, Cpd 155

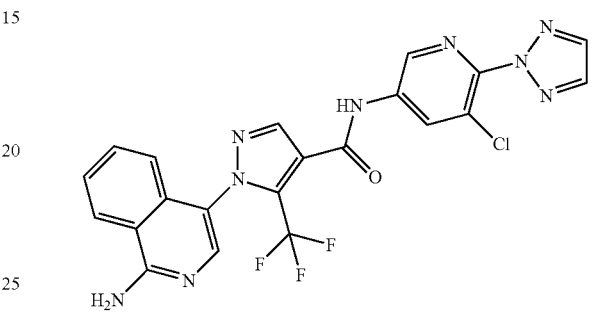

A mixture of mixture of tert-butyl (4-(4-((5-chloro-6-(2H-1,2,3-triazol-2-yl)pyridin-3-yl)carbamoyl)-5-(trifluoromethyl)-1H-pyrazol-1-yl)isoquinolin-1-yl)carbamate and di-tert-butyl (4-(4-((5-chloro-6-(2H-1,2,3-triazol-2-yl)pyridin-3-yl)carbamoyl)-5-(trifluoromethyl)-1H-pyrazol-1-yl)isoquinolin-1-yl)carbamate, 155g (180 mg, 012 mmol) and HCl in dioxane (4N, 1.3 mL) in $CH_2Cl_2$ (2.6 mL) was stirred at room temperature for 2 h. Water (5 mL) was added to the mixture. Sat. $NaHCO_3$ was added to adjust the pH of reaction mixture to 7-8. The mixture was extracted with $CH_2Cl_2$ (5 mL×3). The combined organic extracts were dried over anhydrous $Mg_2SO_4$, filtered, and the filtrate concentrated to dryness under reduced pressure to afford the crude product, which was purified by preparative HPLC (14% to 44% (v/v) $CH_3CN$ and $H_2O$ with 0.05% HCl) and lyophilized to dryness to afford the title compound (100 mg, 70.2%). LCMS (ESI) m/z M+1: 499.9. $^1H$ NMR (400 MHz, DMSO-$d_6$) δ ppm 7.04 (d, J=8.16 Hz, 1H), 7.87 (t, J=7.50 Hz, 1H), 7.97-8.03 (m, 1H), 8.16 (s, 2H), 8.33 (s, 1H), 8.64-8.75 (m, 3H), 8.90 (d, J=2.20 Hz, 1H), 9.57 (br s, 2H), 11.48 (s, 1H).

Example 156

1-(1-aminoisoquinolin-4-yl)-N-(5-cyano-6-(2H-1,2,3-triazol-2-yl)pyridin-3-yl)-5-(trifluoromethyl)-1H-pyrazole-4-carboxamide, Cpd 156

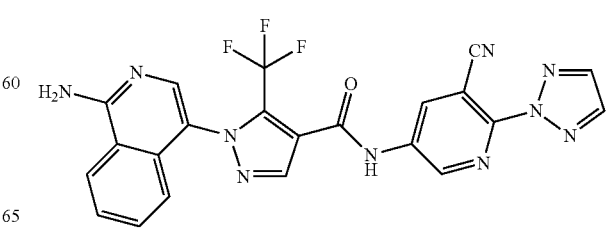

A. Mixture of tert-butyl (4-(4-((5-cyano-6-(2H-1,2,3-triazol-2-yl)pyridin-3-yl)carbamoyl)-5-(trifluoromethyl)-1H-pyrazol-1-yl)isoquinolin-1-yl)carbamate and di-tert-butyl (4-(4-((5-cyano-6-(2H-1,2,3-triazol-2-yl)pyridin-3-yl)carbamoyl)-5-(trifluoromethyl)-1H-pyrazol-1-yl)isoquinolin-1-yl)carbamate, 156a

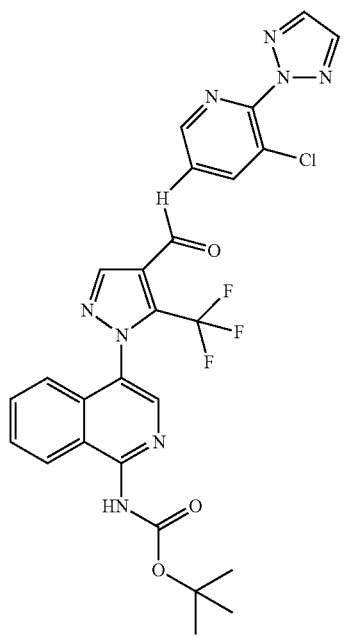

155g

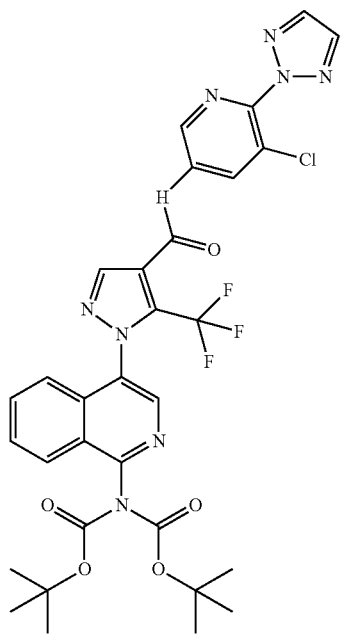

Phosphorus oxychloride (97.104 uL, 1.042 mmol) was added to a solution of mixture of 1-(1-((tert-butoxycarbonyl)amino)isoquinolin-4-yl)-5-(trifluoromethyl)-1H-pyrazole-4-carboxylic acid and 1-(1-(((di-tert-butoxycarbonyl)amino)isoquinolin-4-yl)-5-(trifluoromethyl)-1H-pyrazole-4-carboxylic acid, 155f (220 mg, 0.22 mmol), 5-amino-2-(2H-1,2,3-triazol-2-yl)nicotinonitrile (145.46 mg, 0.71 mmol), pyridine (421.29 uL, 5.21 mmol) in CH$_2$Cl$_2$ (2 mL). The mixture was stirred at room temperature for 1 h. Water (5 mL) was added to the mixture. Sat. NaHCO$_3$ was added to adjust the pH of the reaction mixture to 7-8. The mixture was extracted with CH$_2$Cl$_2$ (5 mL×3). The combined organic extracts were dried over anhydrous Mg$_2$SO$_4$, filtered, and the filtrate concentrated to dryness under reduced pressure to afford the crude product (300 mg). LCMS (ESI) m/z M+1: 535.1.

B. 1-(1-aminoisoquinolin-4-yl)-N-(5-cyano-6-(2H-1,2,3-triazol-2-yl)pyridin-3-yl)-5-(trifluoromethyl)-1H-pyrazole-4-carboxamide, Cpd 156

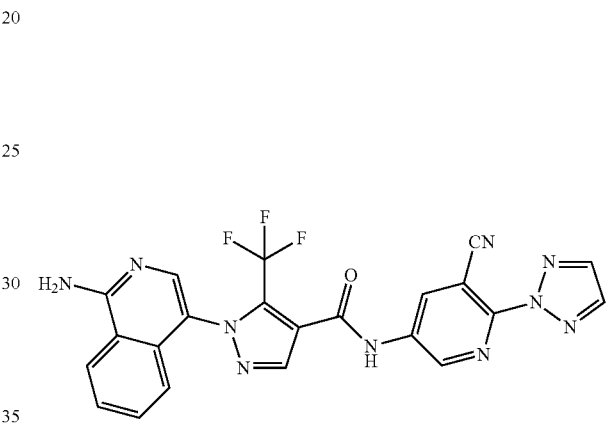

A mixture of tert-butyl (4-(4-((5-cyano-6-(2H-1,2,3-triazol-2-yl)pyridin-3-yl)carbamoyl)-5-(trifluoromethyl)-1H-pyrazol-1-yl)isoquinolin-1-yl)carbamate and di-tert-butyl (4-(4-((5-cyano-6-(2H-1,2,3-triazol-2-yl)pyridin-3-yl)carbamoyl)-5-(trifluoromethyl)-1H-pyrazol-1-yl)isoquinolin-1-yl)carbamate, 156a (300 mg, 0.20 mmol) and HCl in dioxane (4N, 1.3 mL) in CH$_2$Cl$_2$ (2.6 mL) was stirred at room temperature for 2 h. Water (5 mL) was added to the mixture. Sat. NaHCO$_3$ was added to adjust the pH of the reaction mixture to 7-8. The mixture was extracted with CH$_2$Cl$_2$ (5 mL×3). The combined organic extracts were dried over anhydrous Mg$_2$SO$_4$, filtered, and the filtrate concentrated to dryness under reduced pressure to afford the crude product, which was purified by preparative HPLC (25% to 55% (v/v) CH$_3$CN and H$_2$O with 0.05% HCl) and lyophilized to dryness to afford the title compound (115 mg, 49.3%). LCMS (ESI) m/z M+1: 491.1; $^1$H NMR (400 MHz, ACETONITRILE-d$_3$) δ ppm 9.06 (br s, 1H), 8.83 (d, J=1.76 Hz, 1H), 8.47 (d, J=8.38 Hz, 1H), 8.38 (s, 1H), 8.11 (br s, 2H), 7.98-8.05 (m, 2H), 7.86-7.95 (m, 1H), 7.69 (s, 1H), 7.21 (d, J=8.38 Hz, 1H).

Example 157

N-(5-chloro-6-(1-methyl-1H-pyrazol-3-yl)pyridin-3-yl)-1-(1-oxo-1,2-dihydroisoquinolin-5-yl)-5-(trifluoromethyl)-1H-pyrazole-4-carboxamide, Cpd 157

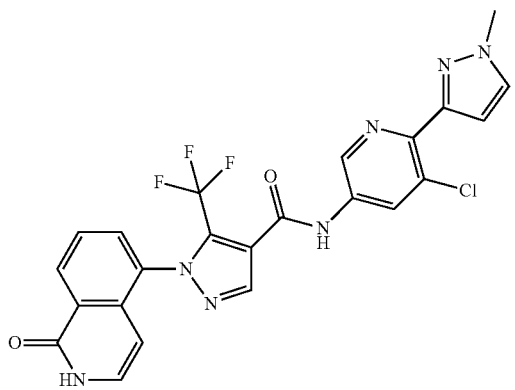 [SMILES: Cn1ccc(-c2ncc(NC(=O)c3cnn(-c4cccc5c(=O)[nH]ccc45)c3C(F)(F)F)cc2Cl)n1]

A. 5-chloro-6-(1-methyl-1H-pyrazol-3-yl)pyridin-3-amine, 157a

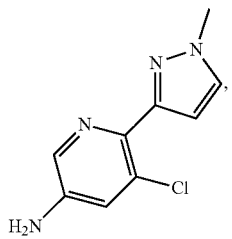

Pd$_2$(dba)$_3$ (176.56 mg, 0.19 mmol) and Xphos (183.83 mg, 0.39 mmol) were added to a solution of 6-bromo-5-chloropyridin-3-amine (800 mg, 3.86 mmol), 1-methyl-3-(4,4,5,5-tetramethyl-1,3,2-dioxaborolan-2-yl)-1H-pyrazole (1203.52 mg, 5.78 mmol) and K$_3$PO$_4$ (2.456 g, 11.57 mmol) in dioxane/H$_2$O (6/1, 20 mL) under an N$_2$ atmosphere. The mixture was stirred at 100° C. overnight. The reaction solution was filtered and the filtrate was concentrated to give a crude product. The crude product was purified by column chromatography over silica gel (petroleum ether/ethyl acetate from 100/0 to 0/100). The desired fractions were collected and the solvent was concentrated under reduced pressure to afford 157a (530 mg, 59.0% yield) as a yellow solid. LCMS (ESI) m/z M+1: 209.1.

B. N-(5-chloro-6-(1-methyl-1H-pyrazol-3-yl)pyridin-3-yl)-1-(1-oxo-1,2-dihydroisoquinolin-5-yl)-5-(trifluoromethyl)-1H-pyrazole-4-carboxamide, Cpd 157

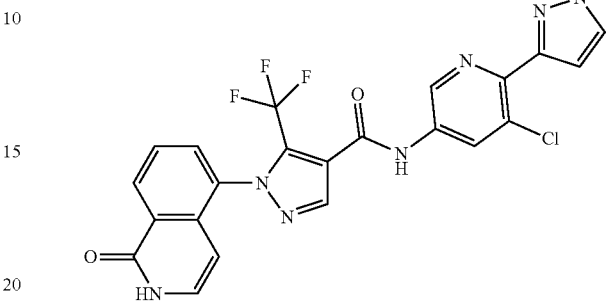

Phosphorus oxychloride (115.35 uL, 1.24 mmol) was added to a solution of 1-(1-oxo-1,2-dihydroisoquinolin-5-yl)-5-(trifluoromethyl)-1H-pyrazole-4-carboxylic acid (400 mg, 1.24 mmol), 5-chloro-6-(1-methyl-1H-pyrazol-3-yl)pyridin-3-amine (344.28 mg, 1.49 mmol), pyridine (1000.9 uL, 12.38 mmol) in CH$_2$Cl$_2$ (10 mL). The mixture was stirred at room temperature for 1 h. Water (5 mL) was added to the mixture and sat. NaHCO$_3$ was added to adjust the pH of the reaction mixture to 7-8. The mixture was extracted with CH$_2$Cl$_2$ (5 mL×3). The combined organic extracts were dried over anhydrous Mg$_2$SO$_4$, filtered, and concentrated to dryness under reduced pressure to afford the crude product, which was purified by preparative HPLC (29% to 59% (v/v) CH$_3$CN and H$_2$O with 0.05% HCl) and lyophilized to dryness to afford the title compound (190 mg, 29.0%). LCMS (ESI) m/z M+1: 513.9. $^1$H NMR (400 MHz, DMSO-d$_6$) δ ppm 3.94 (s, 3H), 5.67 (d, J=7.28 Hz, 1H), 6.78 (d, J=2.21 Hz, 1H), 7.30 (t, J=6.50 Hz, 1H), 7.68 (t, J=7.83 Hz, 1H), 7.80 (d, J=2.20 Hz, 1H), 7.95 (d, J=7.28 Hz, 1H), 8.42-8.48 (m, 2H), 8.56 (s, 1H), 8.88 (d, J=1.98 Hz, 1H), 11.13 (s, 1H), 11.64 (br d, J=5.51 Hz, 1H).

Example 158

1-(1-oxo-1,2-dihydroisoquinolin-5-yl)-5-(trifluoromethyl)-N-(2-(trifluoromethyl)pyridin-4-yl)-1H-pyrazole-4-carboxamide, Cpd 158

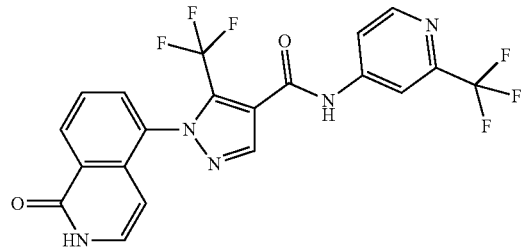 [SMILES: O=C(Nc1ccnc(C(F)(F)F)c1)c1cnn(-c2cccc3c(=O)[nH]ccc23)c1C(F)(F)F]

Phosphorus oxychloride (6.64 g, 43.3 mmol) was added to a solution of 1-(1-oxo-1,2-dihydroisoquinolin-5-yl)-5-(trifluoromethyl)-1H-pyrazole-4-carboxylic acid (7.60 g, 21.7 mmol), 2-(trifluoromethyl)pyridin-4-amine (3.51 g, 21.7 mmol) in pyridine (50 mL). The mixture was stirred at room temperature for 2 h, sat. NaHCO₃ (500 mL) was added. The mixture was extracted with CH₂Cl₂ (500 mL×3). The combined organic extracts were dried over anhydrous Na₂SO₄, filtered, and the filtrate concentrated to dryness under reduced pressure to afford the crude product, which was purified by preparative HPLC (5% to 60% (v/v) CH₃CN and H₂O with 0.05% HCl). The desired fraction was collected and adjusted to pH 7-8 with aqueous NaHCO₃ (10%). The organic solvent was concentrated under reduced pressure and a white solid was formed. The solid was collected and washed with water (3×300 mL) and dried to afford the title compound (5.90 g, 58.1%). LCMS (ESI) m/z M+1: 467.9; ¹H NMR (400 MHz, DMSO-d₆) δ ppm 5.66 (d, J=7.28 Hz, 1H), 7.25-7.32 (m, 1H), 7.67 (t, J=7.83 Hz, 1H), 7.94 (d, J=7.28 Hz, 1H), 7.99 (dd, J=5.62, 1.65 Hz, 1H), 8.26 (d, J=1.76 Hz, 1H), 8.44 (d, J=8.16 Hz, 1H), 8.56 (s, 1H), 8.70 (d, J=5.51 Hz, 1H), 11.35 (s, 1H), 11.64 (br d, J=5.29 Hz, 1H).

Example 159

1-(2-amino-[1,2,4]triazolo[1,5-a]pyridin-5-yl)-N-(5-cyano-6-(2H-1,2,3-triazol-2-yl)pyridin-3-yl)-5-(trifluoromethyl)-1H-pyrazole-4-carboxamide, Cpd 159

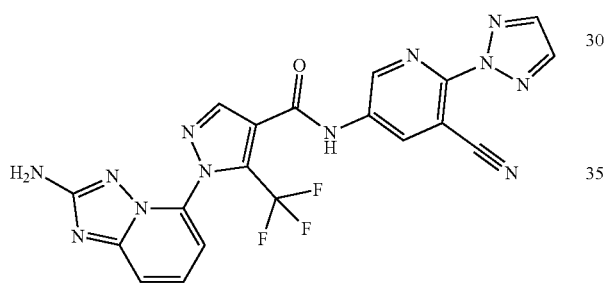

A. 5-bromo-2-(2,5-dimethyl-1H-pyrrol-1-yl)-[1,2,4]triazolo[1,5-a]pyridine, 159a

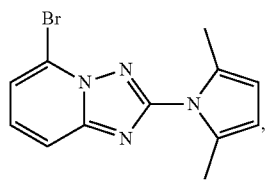

159a

Hexane-2,5-dione (428.6 mg, 3.76 mmol) was added to a solution of 5-bromo-[1,2,4]triazolo[1,5-a]pyridin-2-amine (400 mg, 1.88 mmol) and acetic acid (215 μL) in toluene (5 mL). The mixture was stirred at 155° C. for 12 h. The mixture was concentrated to give a crude product. The crude product was purified by flash column chromatography over silica gel (eluent: petroleum ether/ethyl acetate from 100/0 to 40/60). The eluant was collected and the solvent was concentrated under reduced pressure to give 5-bromo-2-(2,5-dimethyl-1H-pyrrol-1-[1,2,4]triazolo[1,5-a]pyridine as a yellow solid (500 mg, 91%). LC-MS: (ES, m/z): [M+1]⁺ 292.9

B. 2-(2,5-dimethyl-1H-pyrrol-1-yl)-5-hydrazinyl-[1,2,4]triazolo[1,5-a]pyridine, 159b

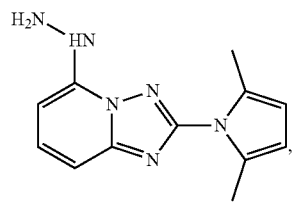

159b

5-Bromo-2-(2,5-dimethyl-1H-pyrrol-1-yl)-[1,2,4]triazolo[1,5-a]pyridine (500 mg, 1.72 mmol) in hydrazine monohydrate (1 mL) was stirred at 80° C. overnight. The solid was filtered and washed with water (2 mL×3). The solid was collected and dried to afford 2-(2,5-dimethyl-1H-pyrrol-1-yl)-5-hydrazinyl-[1,2,4]triazolo[1,5-a]pyridine as a white solid (416 mg, crude product).

C. ethyl 1-(2-(2,5-dimethyl-1H-pyrrol-1-yl)-[1,2,4]triazolo[1,5-a]pyridin-5-yl)-5-(trifluoromethyl)-1H-pyrazole-4-carboxylate, 159c

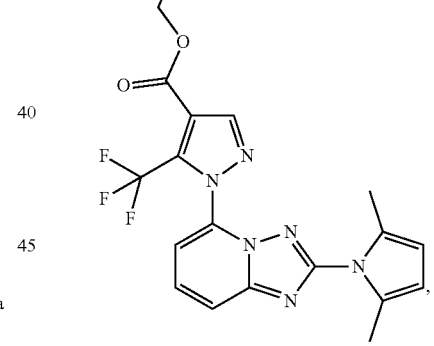

159c

Ethyl (Z)-2-(ethoxymethylene)-4,4,4-trifluoro-3-oxobutanoate, 1f (824.8 mg, 3.43 mmol) was added to a solution of 2-(2,5-dimethyl-1H-pyrrol-1-yl)-5-hydrazinyl-[1,2,4]triazolo[1,5-a]pyridine (416 mg, 1.72 mmol) in ethanol (5 mL). The mixture was stirred at 80° C. overnight. The mixture was concentrated to give a crude product. The crude product was purified by flash column chromatography over silica gel (eluent: petroleum ether/ethyl acetate from 100/0 to 0/100). The eluant was collected and the solvent was concentrated under reduced pressure to give ethyl 1-(2-(2,5-dimethyl-1H-pyrrol-1-yl)-[1,2,4]triazolo[1,5-a]pyridin-5-yl)-5-(trifluoromethyl)-1H-pyrazole-4-carboxylate as a yellow solid (650 mg, 90%). LC-MS: (ES, m/z): [M+1]⁺ 419.1.

D. 1-(2-(2,5-dimethyl-1H-pyrrol-1-yl)-[1,2,4]triazolo[1,5-a]pyridin-5-yl)-5-(trifluoromethyl)-1H-pyrazole-4-carboxylic acid, 159d

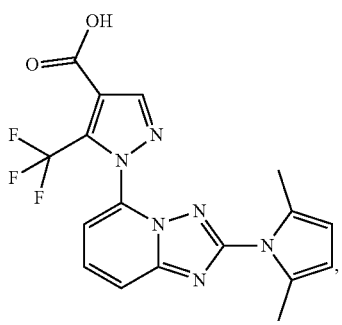

159d

Lithium hydroxide monohydrate (49.7 mg, 1.2 mmol) was added to ethyl 1-(2-(2,5-dimethyl-1H-pyrrol-1-[1,2,4]triazolo[1,5-a]pyridin-5-yl)-5-(trifluoromethyl)-1H-pyrazole-4-carboxylate (330 mg, 0.79 mmol) in ethanol/water (2:1, 3 mL) and the mixture was stirred at rt for 2 h. The mixture was concentrated to give a crude product. The crude product was dissolved in 2 mL water and 1M HCl was added to adjust the pH to 6-7. The mixture was extracted with ethyl acetate (10 mL×3). The combined organic layers were dried over $Na_2SO_4$, filtered and the filtrates were concentrated to give 1-(2-(2,5-dimethyl-1H-pyrrol-1-yl)-[1,2,4]triazolo[1,5-a]pyridin-5-yl)-5-(trifluoromethyl)-1H-pyrazole-4-carboxylic acid as a white solid (307 mg, crude product).

E. N-(5-cyano-6-(2H-1,2,3-triazol-2-yl)pyridin-3-yl)-1-(2-(2,5-dimethyl-1H-pyrrol-1-yl)-[1,2,4]triazolo[1,5-a]pyridin-5-yl)-5-(trifluoromethyl)-1H-pyrazole-4-carboxamide, 159e

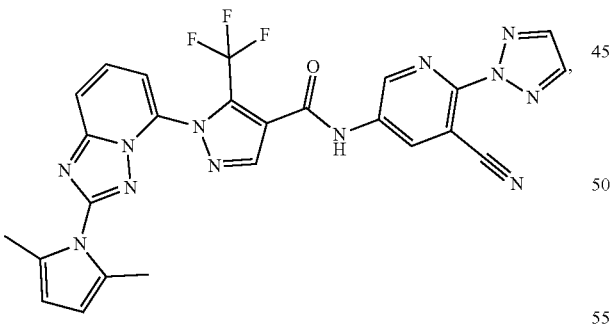

159e

To a solution of 1-(2-(2,5-dimethyl-1H-pyrrol-1-yl)-[1,2,4]triazolo[1,5-a]pyridin-5-yl)-5-(trifluoromethyl)-1H-pyrazole-4-carboxylic acid (300 mg, 0.77 mmol), 5-amino-2-(2H-1,2,3-triazol-2-yl)nicotinonitrile, 7b (172 mg, 0.922 mmol) and pyridine (622 µL, 7.69 mmol) in dichloromethane (2 mL) was added $POCl_3$ (143.3 µL, 1.54 mmol) dropwise. The reaction mixture was stirred at 20° C. for 1 h. Water (5 mL) was added to the mixture, saturated aqueous $NaHCO_3$ (20 mL) was added and the pH was adjusted to 7-8. The mixture was extracted with dichloromethane (5 mL×3). The combined organic extracts were washed with brine, dried over $MgSO_4$, filtered, and the filtrates concentrated under reduced pressure to afford the crude product. The crude product was purified by column chromatography over silica gel (eluent: petroleum ether/ethyl acetate from 100/0 to 0/100) to afford N-(5-cyano-6-(2H-1,2,3-triazol-2-yl)pyridin-3-yl)-1-(2-(2,5-dimethyl-1H-pyrrol-1-yl)-[1,2,4]triazolo[1,5-a]pyridin-5-yl)-5-(trifluoromethyl)-1H-pyrazole-4-carboxamide (260 mg, 60%) as a yellow solid. $^1$H NMR (400 MHz, DMSO-$d_6$) δ ppm 2.16 (s, 6H), 5.86 (s, 2H), 7.94 (d, J=6.61 Hz, 1H), 8.03 (t, J=8.27 Hz, 1H), 8.25 (d, J=9.04 Hz, 1H), 8.31 (s, 2H), 8.74 (s, 1H), 8.89 (d, J=2.43 Hz, 1H), 9.08 (d, J=2.43 Hz, 1H). LC-MS: (ES, m/z): [M+1]$^+$ 558.9.

F. 1-(2-amino-[1,2,4]triazolo[1,5-a]pyridin-5-yl)-N-(5-cyano-6-(2H-1,2,3-triazol-2-yl)pyridin-3-yl)-5-(trifluoromethyl)-1H-pyrazole-4-carboxamide, Cpd 159

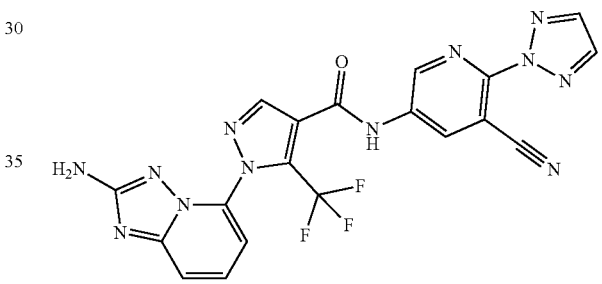

A solution of N-(5-cyano-6-(2H-1,2,3-triazol-2-yl)pyridin-3-yl)-1-(2-(2,5-dimethyl-1H-pyrrol-1-[1,2,4]triazolo[1,5-a]pyri fluoromethyl)-1H-pyrazole-4-carboxamide (200 mg, 0.357 mmol) in TFA (2 mL) and dioxane/water (4:1, 4 mL) was stirred at 70° C. for 5 h. Sat. $NaHCO_3$ was added to the mixture to adjust the pH to 7-8. The aqueous phase was extracted with ethyl acetate (5 mL×3). The separated organic layer was dried ($MgSO_4$), filtered, and the filtrate concentrated to give a crude product. The crude product was purified by preparative high-performance liquid chromatography (25% to 55% (v/v) $CH_3CN$ and $H_2O$ with 10 mM $NH_4CO_3$) to give 1-(2-amino-[1,2,4]triazolo[1,5-a]pyridin-5-yl)-N-(5-cyano-6-(2H-1,2,3-triazol-2-yl)pyridin-3-yl)-5-(trifluoromethyl)-1H-pyrazole-4-carboxamide (12 mg, 7% yield). $^1$H NMR (400 MHz, DMSO-$d_6$) δ ppm 7.46 (dd, J=5.95, 2.20 Hz, 1H), 7.65-7.74 (m, 2H), 8.31 (s, 2H), 8.77 (s, 1H), 8.93 (d, J=2.20 Hz, 1H), 9.17 (d, J=2.43 Hz, 1H), 11.55 (s, 1H). LC-MS: (ES, m/z): [M+1]$^+$ 558.9.

Example 160

N-(5-chloro-6-(2H-1,2,3-triazol-2-yl)pyridin-3-yl)-3-fluoro-1-(quinolin-5-yl)-5-(trifluoromethyl)-1H-pyrazole-4-carboxamide, Cpd 160

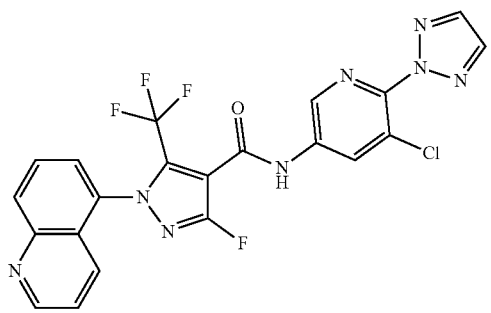 [SMILES: O=C(Nc1cnc(-n2nccn2)c(Cl)c1)c1c(F)nn(-c2cccc3ncccc23)c1C(F)(F)F]

A. ethyl 3-fluoro-1-(quinolin-5-yl)-5-(trifluoromethyl)-1H-pyrazole-4-carboxylate, 160a

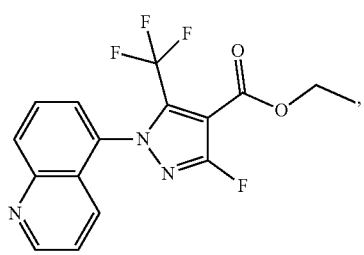

Ethyl 1-(quinolin-5-yl)-5-(trifluoromethyl)-1H-pyrazole-4-carboxylate, 13b (1 g, 2.98 mmol) was dissolved in acetonitrile (8 mL) and silver (II) fluoride (2.18 g, 14.9 mmol) was added. The reaction mixture was kept in a dark place with stirring at 60° C. for 16 h. The reaction was filtered though diatomaceous earth and washed with CH₃CN (200 mL), the filtrates were concentrated under reduced pressure to afford a crude product which was purified by preparative high-performance liquid chromatography. The pure fractions were collected and the solvent was concentrated under reduced pressure, lyophilized to dryness to give ethyl 3-fluoro-1-(quinolin-5-yl)-5-(trifluoromethyl)-1H-pyrazole-4-carboxylate as a yellow solid (30 mg). LC-MS: (ES, m/z): [M+1]⁺ 354.0.

B. 3-fluoro-1-(quinolin-5-yl)-5-(trifluoromethyl)-1H-pyrazole-4-carboxylic acid, 160b

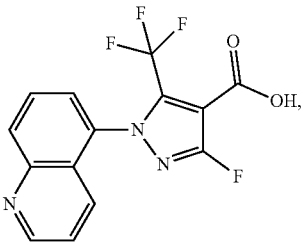

Ethyl 3-fluoro-1-(quinolin-5-yl)-5-(trifluoromethyl)-1H-pyrazole-4-carboxylate (30 mg, 0.035 mmol) was dissolved in THF (2 mL) and water (2 mL) and lithium hydroxide (8.41 mg, 0.35 mmol) were added. The reaction mixture was stirred at 30° C. for 16 h. The reaction mixture was concentrated under reduced pressure to afford 3-fluoro-1-(quinolin-5-yl)-5-(trifluoromethyl)-1H-pyrazole-4-carboxylic acid as a white solid (30 mg, 73.5%). LC-MS: (ES, m/z): [M+1]⁺ 325.9.

C. N-(5-chloro-6-(2H-1,2,3-triazol-2-yl)pyridin-3-yl)-3-fluoro-1-(quinolin-5-yl)-5-(trifluoromethyl)-1H-pyrazole-4-carboxamide, Cpd 160

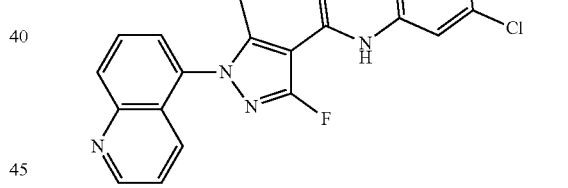

To a solution of 3-fluoro-1-(quinolin-5-yl)-5-(trifluoromethyl)-1H-pyrazole-4-carboxylic acid (30 mg, 30% pure by HPLC, 0.026 mmol), 5-chloro-6-(2H-1,2,3-triazol-2-yl)pyridin-3-amine, 1j (7.6 mg, 0.038 mmol), and pyridine (133.8 mg, 1.69 mmol) in dichloromethane (10 mL) was added POCl₃ (86.5 mg, 0.56 mmol) dropwise. The mixture was stirred at 25° C. for 3 h. Sat. NaHCO₃ (20 mL) was added and extracted with CH₂Cl₂ (30 mL×2). The combined organic layers were dried over Na₂SO₄, filtered and the filtrates were concentrated under reduced pressure to afford crude product as a yellow oil. The crude product was then purified by preparative HPLC (37% to 57% (v/v) CH₃CN and H₂O with 0.05% HCl) to afford N-(5-chloro-6-(2H-1,2,3-triazol-2-yl)pyridin-3-yl)-3-fluoro-1-(quinolin-5-yl)-5-(trifluoromethyl)-1H-pyrazole-4-carboxamide (2.5 mg, 18.7%). ¹H NMR (400 MHz, ACETONITRILE-d₃) δ ppm 9.75 (br s, 1H), 9.06 (d, J=2.8 Hz, 1H), 8.82 (d, J=2.3 Hz, 1H), 8.63 (d, J=2.3 Hz, 1H), 8.37 (d, J=8.5 Hz, 1H), 8.02 (s, 2H), 7.96-7.91 (m, 1H), 7.90-7.84 (m, 2H), 7.63 (dd, J=4.1, 8.7 Hz, 1H). LC-MS: (ES, m/z): [M+1]⁺ 502.9.

Example 161

N-(2,5-dimethyl-6-(2H-1,2,3-triazol-2-yl)pyridin-3-yl)-1-(1-oxo-1,2-dihydroisoquinolin-5-yl)-5-(trifluoromethyl)-1H-pyrazole-4-carboxamide, Cpd 161

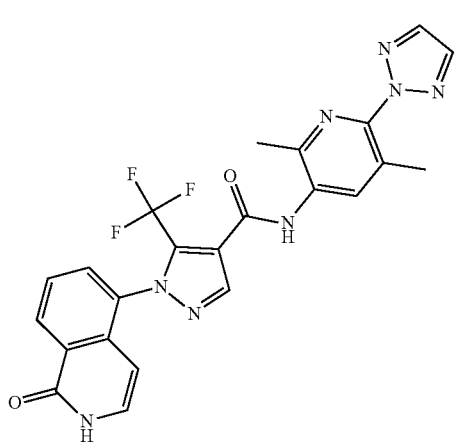 [SMILES: Cc1cc(NC(=O)c2cnn(-c3cccc4c(=O)[nH]ccc34)c2C(F)(F)F)c(C)nc1-n1nccn1]

A. 3-bromo-6-methyl-5-nitro-2-(2H-1,2,3-triazol-2-yl)pyridine, 161a

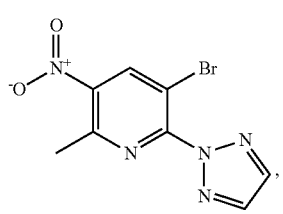

3-Bromo-2-chloro-6-methyl-5-nitropyridine (4.0 g, 15.9 mmol) and 1H-1,2,3-triazole (1.43 g, 20.7 mmol) were dissolved in acetonitrile (30 mL) and potassium carbonate (3.30 g, 23.9 mmol) was added. The reaction mixture was stirred at 60° C. for 2 h. Sat. NH$_4$Cl (100 mL) was added and the reaction mixture extracted with EtOAc (200 mL×3). The combined organic layers were dried over Na$_2$SO$_4$, filtered and the filtrates were concentrated under reduced pressure to afford the crude product as a purple oil. The oil was purified by flash column chromatography over silica gel (eluent: petroleum ether/ethyl acetate from 100/0 to 85/15). The desired fractions were collected and the solvent was concentrated under reduced pressure to afford product as purple solid (2.5 g, 55.3%, yield).

B. 2,5-dimethyl-3-nitro-6-(2H-1,2,3-triazol-2-yl)pyridine, 161b

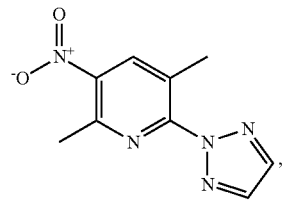

3-Bromo-6-methyl-5-nitro-2-(2H-1,2,3-triazol-2-yl)pyridine (1.0 g, 3.52 mmol) and methylboronic acid (316.1 mg, 5.28 mmol) were dissolved in dioxane (20 mL), palladium diacetate (79.0 mg, 0.35 mmol), Xantphos (407.4 mg, 0.70 mmol) and potassium carbonate (973 mg, 7.04 mmol) were added and the reaction mixture purged with N$_2$ for 1 min. The reaction mixture was stirred at 100° C. for 16 h, then filtered, and the residue was washed with EtOAc (50 mL×3). The combined filtrates were concentrated under reduced pressure to afford crude product as a brown oil. The crude product was purified by flash column chromatography over silica gel (eluent: petroleum ether/ethyl acetate from 100/0 to 40/60). The desired fractions were collected and the solvent was concentrated under reduced pressure to afford the product as a yellow solid (700 mg, 90.7%).

C. 2,5-dimethyl-6-(2H-1,2,3-triazol-2-yl)pyridin-3-amine, 161c

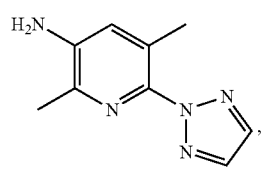

2,5-Dimethyl-3-nitro-6-(2H-1,2,3-triazol-2-yl)pyridine (200 mg. 3.19 mmol), iron (1.07 g, 19.2 mmol), NH$_4$Cl (1.03 g, 19.2 mmol) were added to the mixture of THF (20 mL) and water (20 mL). The reaction mixture was stirred at 80° C. for 3 h. The reaction mixture was filtered though a pad of diatomaceous earth and the pad was washed with EtOAc (50 mL×3). The combined filtrates were concentrated to dryness to give the crude product as a yellow oil. The crude product was purified by flash column chromatography over silica gel (eluent: petroleum ether/ethyl acetate from 100/0 to 40/60). The desired fractions were collected and the solvent was concentrated under reduced pressure to afford product as a yellow oil (360 mg, 59.6%). $^1$H NMR (400 MHz, CHLOROFORM-d) δ ppm 7.82 (s, 2H), 6.91 (s, 1H), 3.78 (br s, 2H), 2.42 (s, 3H), 2.20 (s, 3H).

D. N-(2,5-dimethyl-6-(2H-1,2,3-triazol-2-yl)pyridin-3-yl)-1-(1-oxo-1,2-dihydroisoquinolin-5-yl)-5-(trifluoromethyl)-1H-pyrazole-4-carboxamide, Cpd 161

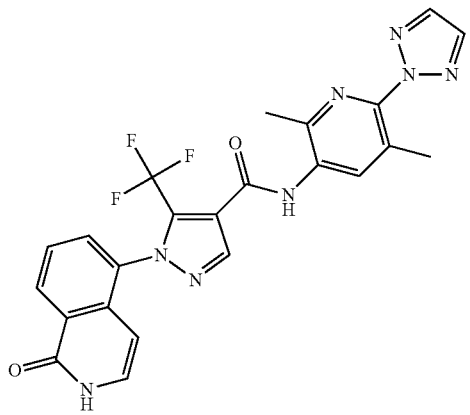 [SMILES: Cc1cc(NC(=O)c2cnn(-c3cccc4c(=O)[nH]ccc34)c2C(F)(F)F)c(C)nc1-n1nccn1]

To a solution of 1-(1-oxo-1,2-dihydroisoquinolin-5-yl)-5-(trifluoromethyl)-1H-pyrazole-4-carboxylic acid (213.2 mg, 0.66 mmol), 2,5-dimethyl-6-(2H-1,2,3-triazol-2-yl)pyridin-3-amine (150 mg, 0.79 mmol) and pyridine (522.5 mg, 6.61 mmol) in $CH_2Cl_2$ (15 mL) was added $POCl_3$ (304 mg, 1.98 mmol) dropwise. The mixture was stirred at 25° C. for 4 h and at 40° C. for 3 h. 30 mL sat.$NaHCO_3$ was added and extracted with $CH_2Cl_2$ (30 mL×3). The combined organic layers were dried over $Na_2SO_4$, filtered and the filtrates were concentrated under reduced pressure to afford crude product as a yellow oil. The crude product was then purified by preparative HPLC (33% to 63% (v/v) $CH_3CN$ and $H_2O$ with 0.05% HCl) to afford product (190 mg, 57.4%). $^1$H NMR (400 MHz, DMSO-$d_6$) δ ppm 11.60 (br d, J=5.7 Hz, 1H), 10.44 (s, 1H), 8.50 (s, 1H), 8.42 (d, J=7.9 Hz, 1H), 8.11 (s, 2H), 8.02 (s, 1H), 7.95-7.89 (m, 1H), 7.65 (t, J=7.9 Hz, 1H), 7.28 (dd, J=6.1, 7.2 Hz, 1H), 5.67 (d, J=7.3 Hz, 1H), 2.47 (br s, 3H), 2.19 (s, 3H). LC-MS: (ES, m/z): $[M+1]^+$ 495.0.

Example 162 and Example 163

N-(6-(2H-[1,2,3]triazolo[4,5-c]pyridin-2-yl)-5-chloropyridin-3-yl)-1-(quinolin-5-yl)-5-(trifluoromethyl)-1H-pyrazole-4-carboxamide, Cpd 162

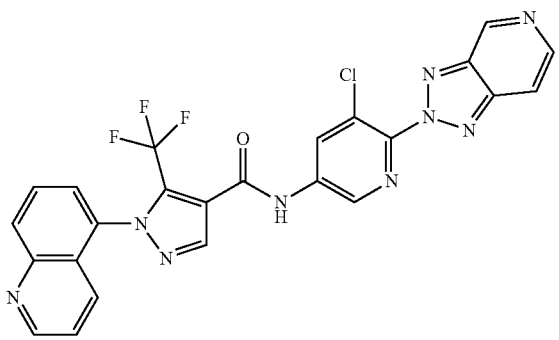 [SMILES: O=C(Nc1cnc(-n2nc3ccncc3n2)c(Cl)c1)c1cnn(-c2cccc3ncccc23)c1C(F)(F)F]

and

N-(6-(1H-[1,2,3]triazolo[4,5-c]pyridin-1-yl)-5-chloropyridin-3-yl)-1-(quinolin-5-yl)-5-(trifluoromethyl)-1H-pyrazole-4-carboxamide, Cpd 163

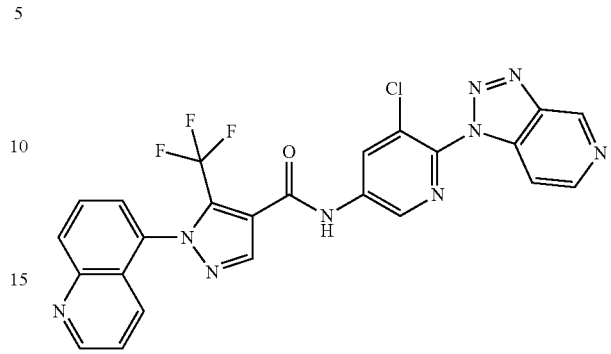

A. Mixture of 2-(3-chloro-5-nitropyridin-2-yl)-2H-[1,2,3]triazolo[4,5-c]pyridine and 1-(3-chloro-5-nitropyridin-2-yl)-1H-[1,2,3]triazolo[4,5-c]pyridine, 162a

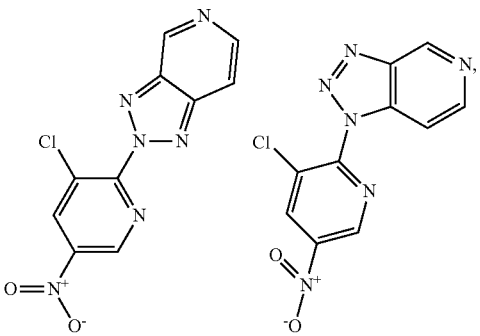

162a

3H-[1,2,3]triazolo[4,5-c]pyridine (0.62 g, 5.18 mmol) was added to a mixture of 2,3-dichloro-5-nitropyridine (1 g, 5.18 mmol) and potassium carbonate (3.58 g, 25.9 mmol) in acetonitrile (20 mL). The mixture was stirred at rt for 3 h. The reaction mixture was filtered. The filtrate was concentrated under reduced pressure to give the crude product as a yellow solid. The crude product was purified by column chromatography over silica gel (petroleum ether/ethyl acetate=1:0 to petroleum ether/ethyl acetate=0:1). The pure fractions were collected and the solvent was concentrated under reduced pressure to give the product as a yellow solid (580 mg, 40%).

511

B. mixture of 6-(2H-[1,2,3]triazolo[4,5-c]pyridin-2-yl)-5-chloropyridin-3-amine and 6-(1H-[1,2,3]triazolo[4,5-c]pyridin-1-yl)-5-chloropyridin-3-amine, 162b

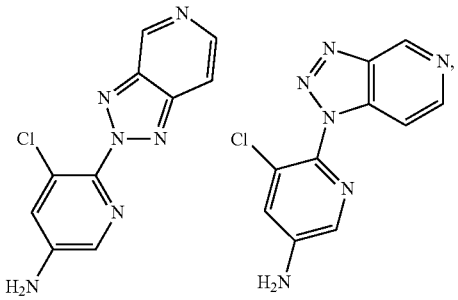

Iron (0.535 g, 9.58 mmol) and ammonium chloride (0.512 g, 9.58 mmol) were added to the mixture of 2-(3-chloro-5-nitropyridin-2-yl)-2H-[1,2,3]triazolo[4,5-c]pyridine and 1-(3-chloro-5-nitropyridin-2-yl)-1H-[1,2,3]triazolo[4,5-c]pyridine (530 mg, 0.958 mmol) in THF (20 mL), water (10 mL) and methanol (10 mL). The reaction was stirred at 80° C. for 2 h. The reaction mixture was filtered though a pad of diatomaceous earth and the pad was washed with EtOAc (20 mL×2). The combined filtrates were concentrated to dryness to give a crude product as a brown solid. The crude product was purified by flash column chromatography over silica gel (eluent: petroleum ether/ethyl acetate from 100/0 to 0/100). The desired fractions were collected and the solvent was concentrated under reduced pressure to afford product as a brown oil (330 mg, 69.8%).

N-(6-(2H-[1,2,3]triazolo[4,5-c]pyridin-2-yl)-5-chloropyridin-3-yl)-1-(quinolin-5-yl)-5-(trifluoromethyl)-1H-pyrazole-4-carboxamide, Cpd 162

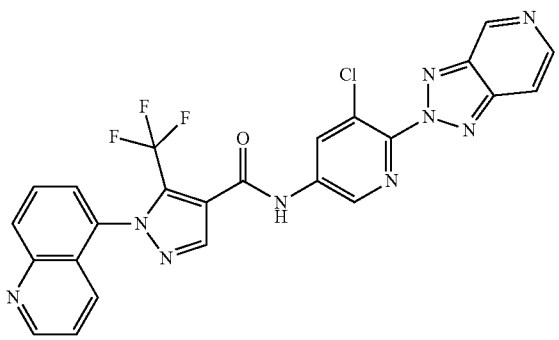 [SMILES: O=C(Nc1cnc(-n2nc3ccncc3n2)c(Cl)c1)c1cnn(-c2cccc3ncccc23)c1C(F)(F)F]

and

512

N-(6-(1H-[1,2,3]triazolo[4,5-c]pyridin-1-yl)-5-chloropyridin-3-yl)-1-(quinolin-5-yl)-5-(trifluoromethyl)-1H-pyrazole-4-carboxamide, Cpd 163

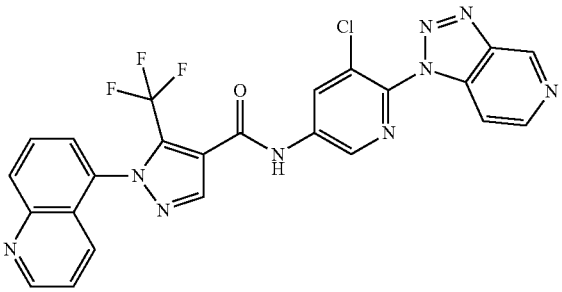 [SMILES: O=C(Nc1cnc(-n2nnc3cnccc32)c(Cl)c1)c1cnn(-c2cccc3ncccc23)c1C(F)(F)F]

POCl$_3$ (0.49 mL, 5.36 mmol) was added to a mixture of 6-(2H-[1,2,3]triazolo[4,5-c]pyridin-2-yl)-5-chloropyridin-3-amine and 6-(1H-[1,2,3]triazolo[4,5-c]pyridin-1-yl)-5-chloropyridin-3-amine (330 mg, 1.34 mmol), 1-(quinolin-5-yl)-5-(trifluoromethyl)-1H-pyrazole-4-carboxylic acid, 3b (493.9 mg, 1.61 mmol), and pyridine (0.54 mL, 6.70 mmol) in dichloromethane (5 mL). The reaction mixture was stirred at 20° C. for 2 h. Sat. NaHCO$_3$ solution (20 mL) was added to the mixture. The mixture was extracted with ethyl acetate (30 mL×2). The organic layers were concentrated under reduced pressure to afford a crude product, which was purified by reverse phase HPLC (27% to 57% (v/v) CH$_3$CN and H$_2$O with 0.05% HCl) to afford N-(6-(2H-[1,2,3]triazolo[4,5-c]pyridin-2-yl)-5-chloropyridin-3-yl)-1-(quinolin-5-yl)-5-(trifluoromethyl)-1H-pyrazole-4-carboxamide, Cpd 162 (340 mg, 47.3%). $^1$H NMR (400 MHz, DMSO-d$_6$) δ ppm 11.73 (1H, s), 9.87 (1H, s), 9.06-9.12 (2H, m), 8.87 (1H, d, J=2.20 Hz), 8.77 (1H, d, J=5.95 Hz), 8.75 (1H, s), 8.36 (1H, d, J=8.60 Hz), 8.07 (1H, d, J=5.51 Hz), 7.98-8.03 (1H, m), 7.94-7.98 (1H, m), 7.69-7.76 (2H, m). LC-MS: (ES, m/z): [M+1]$^+$ 535.9; and N-(6-(1H-[1,2,3]triazolo[4,5-c]pyridin-1-yl)-5-chloropyridin-3-yl)-1-(quinolin-5-yl)-5-(trifluoromethyl)-1H-pyrazole-4-carboxamide, Cpd 163 (70 mg, 9.4%). $^1$H NMR (400 MHz, DMSO-d$_6$) δ ppm 11.77 (1H, s), 9.53 (1H, d, J=0.88 Hz), 9.08-9.18 (2H, m), 8.88 (1H, d, J=2.21 Hz), 8.78 (1H, s), 8.70 (1H, d, J=5.95 Hz), 8.37-8.44 (2H, m), 7.98-8.09 (2H, m), 7.83-7.89 (1H, m), 7.75-7.82 (1H, m). LC-MS: (ES, m/z): [M+1]$^+$ 535.9

Example 164 and Example 165

N-(6-(2H-[1,2,3]triazolo[4,5-b]pyridin-2-yl)-5-chloropyridin-3-yl)-1-(quinolin-5-yl)-5-(trifluoromethyl)-1H-pyrazole-4-carboxamide, Cpd 164 and

N-(6-(3H-[1,2,3]triazolo[4,5-b]pyridin-3-yl)-5-chloropyridin-3-yl)-1-(quinolin-5-yl)-5-(trifluoromethyl)-1H-pyrazole-4-carboxamide, Cpd 165

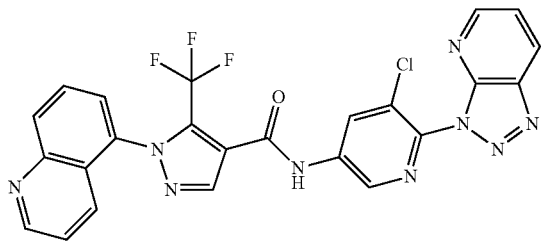 [SMILES: O=C(Nc1cnc(-n2nnc3cccnc32)c(Cl)c1)c1cnn(-c2cccc3ncccc23)c1C(F)(F)F]

A. Mixture of 2-(3-chloro-5-nitropyridin-2-yl)-2H-[1,2,3]triazolo[4,5-b]pyridine and 3-(3-chloro-5-nitropyridin-2-yl)-3H-[1,2,3]triazolo[4,5-b]pyridine, 164a

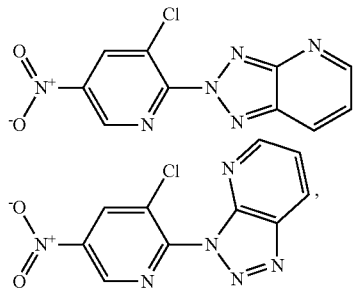

164a

1H-[1,2,3]triazolo[4,5-c]pyridine (3.5 g, 18.14 mmol) was added to a mixture of 2,3-dichloro-5-nitropyridine (2.18 g, 18.14 mmol) and potassium carbonate (7.5 g, 54.41 mmol) in acetonitrile (50 mL). The mixture was stirred at rt for 12 h. The reaction mixture was filtered. The filtrate was concentrated under reduced pressure to give the crude product as a yellow solid. The crude product was purified by column chromatography over silica gel (petroleum ether/ethyl acetate=100:0 to petroleum ether/ethyl acetate=70:30). The pure fractions were collected and the solvent was concentrated under reduced pressure to give the product as a yellow solid (4.2 g, 83.7%).

B. mixture of 6-(2H-[1,2,3]triazolo[4,5-b]pyridin-2-yl)-5-chloropyridin-3-amine and 6-(3H-[1,2,3]triazolo[4,5-b]pyridin-3-yl)-5-chloropyridin-3-amine, 164b

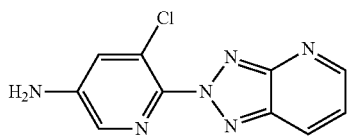

164b

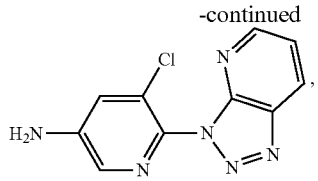

Iron (2.02 g, 36.1 mmol) and ammonium chloride (1.93 g, 36.1 mmol) were added to a mixture of 2-(3-chloro-5-nitropyridin-2-yl)-2H-[1,2,3]triazolo[4,5-b]pyridine and 3-(3-chloro-5-nitropyridin-2-yl)-3H-[1,2,3]triazolo[4,5-b]pyridine (4.0 g, 7.23 mmol) in THF (40 mL), water (10 mL) and methanol (20 mL). The reaction was stirred at 80° C. for 2 h. The reaction mixture was filtered though a pad of diatomaceous earth and the pad was washed with EtOAc (20 mL×3). The combined filtrates were concentrated to dryness to give crude product as a brown solid. The crude product was purified by flash column chromatography over silica gel (eluent: petroleum ether/ethyl acetate from 10:1 to 1:1). The desired fractions were collected and the solvent was concentrated under reduced pressure to afford the product as a brown oil (3.2 g, 86.1%).

C. N-(6-(2H-[1,2,3]triazolo[4,5-b]pyridin-2-yl)-5-chloropyridin-3-yl)-1-(quinolin-5-yl)-5-(trifluoromethyl)-1H-pyrazole-4-carboxamide, Cpd 164

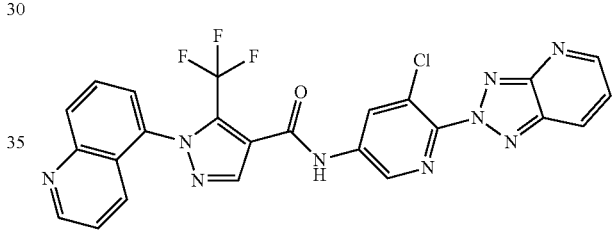

and

N-(6-(3H-[1,2,3]triazolo[4,5-b]pyridin-3-yl)-5-chloropyridin-3-yl)-1-(quinolin-5-yl)-5-(trifluoromethyl)-1H-pyrazole-4-carboxamide, Cpd 165

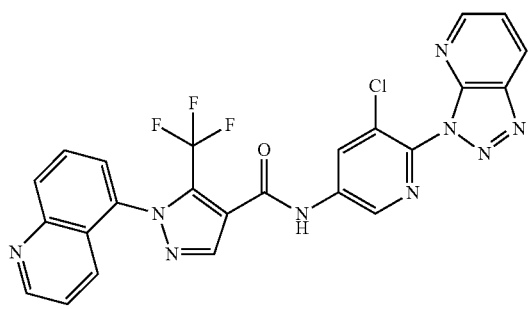 [SMILES: O=C(Nc1cnc(-n2nnc3cccnc32)c(Cl)c1)c1cnn(-c2cccc3ncccc23)c1C(F)(F)F]

POCl$_3$ (239 mg, 1.56 mmol) was added to a mixture of 6-(2H-[1,2,3]triazolo[4,5-b]pyridin-2-yl)-5-chloropyridin-3-amine and 6-(3H-[1,2,3]triazolo[4,5-b]pyridin-3-yl)-5-chloropyridin-3-amine (200 mg, 0.39 mmol), 1-(quinolin-5-yl)-5-(trifluoromethyl)-1H-pyrazole-4-carboxylic acid, 3b (143.5 mg, 0.47 mmol), and pyridine (185 mg, 2.34 mmol) in dichloromethane (8 mL). The reaction mixture was stirred at 20° C. for 4 h. Sat. NaHCO₃ solution (10 mL) was added to the mixture. The mixture was extracted with dichloromethane (20 mL×3). The organic layers were concentrated under reduced pressure to afford a crude product, which was purified by reverse phase HPLC (35% to 65% (v/v) CH₃CN and H₂O with 0.05% HCl) to afford N-(6-(2H-[1,2,3]triazolo[4,5-b]pyridin-2-yl)-5-chloropyridin-3-yl)-1-(quinolin-5-yl)-5-(trifluoromethyl)-1H-pyrazole-4-carboxamide, Cpd 164 (35.7, 16.9%). ¹H NMR (400 MHz, DMSO-d₆) δ ppm 11.44 (s, 1H), 9.06 (br s, 1H), 8.98 (s, 1H), 8.84 (br d, J=3.7 Hz, 1H), 8.78 (s, 1H), 8.63 (s, 1H), 8.35 (br dd, J=8.2, 16.5 Hz, 2H), 8.01-7.88 (m, 2H), 7.76-7.59 (m, 3H). LC-MS: (ES, m/z): [M+1]⁺ 535.9; and N-(6-(3H-[1,2,3]triazolo[4,5-b]pyridin-3-yl)-5-chloropyridin-3-yl)-1-(quinolin-5-yl)-5-(trifluoromethyl)-1H-pyrazole-4-carboxamide, Cpd 165 (21 mg, 9.6%). ¹H NMR (400 MHz, DMSO-d₆) δ ppm 11.51 (s, 1H), 9.08 (dd, J=2.2, 3.5 Hz, 1H), 9.02 (d, J=2.2 Hz, 1H), 8.84-8.75 (m, 3H), 8.68 (s, 1H), 8.35 (d, J=8.2 Hz, 1H), 8.02-7.94 (m, 2H), 7.73-7.68 (m, 2H), 7.64 (dd, J=4.6, 8.4 Hz, 1H). LC-MS: (ES, m/z): [M+1]⁺ 535.9.

Example 166

N-(3-chloro-4-(5-oxo-4,5-dihydro-1H-1,2,4-triazol-3-yl)phenyl)-1-(quinolin-5-yl)-5-(trifluoromethyl)-1H-pyrazole-4-carboxamide, Cpd 166

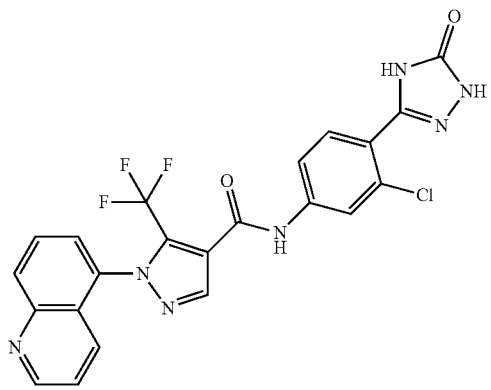 [SMILES: O=C(Nc1ccc(-c2n[nH]c(=O)[nH]2)c(Cl)c1)c1cnn(-c2cccc3ncccc23)c1C(F)(F)F]

A. 2-(4-bromo-2-chlorobenzylidene)hydrazine-1-carboxamide, 166a

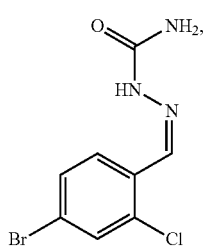

166a

A solution of 4-bromo-2-chlorobenzaldehyde (5.0 g, 22.78 mmol), sodium acetate (3.74 g, 45.57 mmol), hydrazinecarboxamide (1.71 g, 22.78 mmol) in methanol (50 mL) and water (50 mL) was stirred at 50° C. for 5 h. The mixture was cooled to temperature and filtered. The solid was washed with ethyl acetate (10 mL×3). The solid was dried to give the product as a white solid (3 g, 47.6%). ¹H NMR (400 MHz, DMSO-d₆) δ ppm 6.63 (br s, 2H), 7.54 (dd, J=8.60, 1.76 Hz, 1H), 7.75 (d, J=1.98 Hz, 1H), 8.12-8.19 (m, 2H), 10.55 (s, 1H). LC-MS: (ES, m/z): [M+1]⁺ 277.9.

B. 5-(4-bromo-2-chlorophenyl)-2,4-dihydro-3H-1,2,4-triazol-3-one, 166b

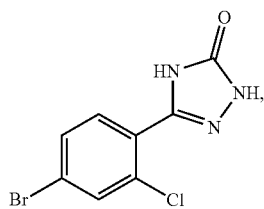

166b

Bromine (931.5 µL, 18.1 mmol) was added dropwise to a solution of 2-(4-bromo-2-chlorobenzylidene)hydrazine-1-carboxamide (2.0 g, 7.23 mmol) in acetic acid (15 mL). The mixture was stirred at 80° C. for 3 h. The mixture was cooled to room temperature, TMEB (60 mL) was added to the mixture and stirred for 10 min. The mixture was filtered and the solid was dried to give the product as a white solid (1 g, 50%). LC-MS: (ES, m/z): [M+1]⁺ 275.9

C. 5-(4-bromo-2-chlorophenyl)-2,4-bis((2-(trimethylsilyl)ethoxy)methyl)-2,4-dihydro-3H-1,2,4-triazol-3-one, 166c

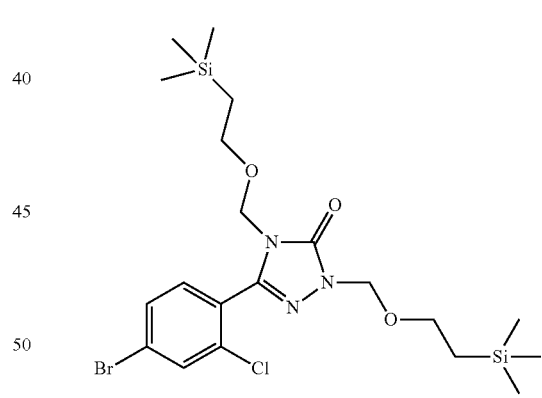

166c

Sodium hydride (437.1 mg, 10.93 mmol) was added in portion to solution of 5-(4-bromo-2-chlorophenyl)-2,4-dihydro-3H-1,2,4-triazol-3-one (1.0 g, 3.64 mmol) in DMF (10 mL) at 0° C. After stirring at 0° C. for 1 h, (2-(chloromethoxy)ethyl)trimethylsilane (2.579 mL, 14.57 mmol) was added dropwise to the mixture. The reaction was stirred at room temperature overnight. Water (20 mL) was added to the reaction and the aqueous phase was extracted with ethyl acetate (30 mL×3). The separated organic layer was dried (MgSO₄), filtered, and the filtrate was concentrated to give a crude product. The crude product was purified by flash column chromatography over silica gel (eluent: petroleum ether/ethyl acetate from 100/0 to 50/50). The eluent was collected and the solvent was concentrated under reduced pressure to give the product as a colorless oil (400 mg, 21% yield). $^1$H NMR (400 MHz, CHLOROFORM-d) δ ppm −0.05−−0.02 (m, 9H), −0.01-0.01 (m, 9H), 0.80-0.87 (m, 2H), 0.94-1.00 (m, 2H), 3.52-3.59 (m, 2H), 3.68-3.74 (m, 2H), 4.95 (s, 2H), 5.25 (s, 2H), 7.40 (d, J=8.16 Hz, 1H), 7.54 (dd, J=8.27, 1.87 Hz, 1H), 7.70 (d, J=1.76 Hz, 1H). LC-MS: (ES, m/z): [M+1]$^+$ 536.2

D. 1-(quinolin-5-yl)-5-(trifluoromethyl)-1H-pyrazole-4-carboxamide, 166d

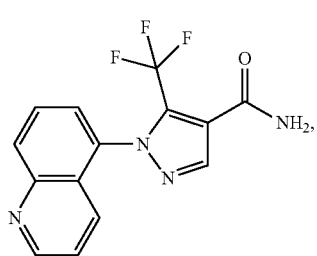

166d

HBTU (1.65 g, 4.35 mmol) was added to the mixture of 1-(quinolin-5-yl)-5-(trifluoromethyl)-1H-pyrazole-4-carboxylic acid, 3b (0.89 g, 2.90 mmol), ammonium chloride (775 mg, 14.5 mmol), DIEA (2.46 mL, 14.5 mmol) in DMF (15 mL). The reaction mixture was stirred at room temperature for 4 h. Water (20 mL) was added to the reaction solution. The aqueous layer was extracted with ethyl acetate (30 mL×3). The organic layer was concentrated to give a crude product. The crude product was purified by chromatography (eluent:petroleum ether/ethyl acetate from 100/0 to 0/100). The pure fractions were collected and the solvent was concentrated under reduced pressure to give the product as a yellow solid (600 mg, 65% yield). LC-MS: (ES, m/z): [M+1]$^+$ 307.0.

E. N-(3-chloro-4-(5-oxo-1,4-bis((2-(trimethylsilyl)ethoxy)methyl)-4,5-dihydro-1H-1,2,4-triazol-3-yl)phenyl)-1-(quinolin-5-yl)-5-(trifluoromethyl)-1H-pyrazole-4-carboxamide, 166e

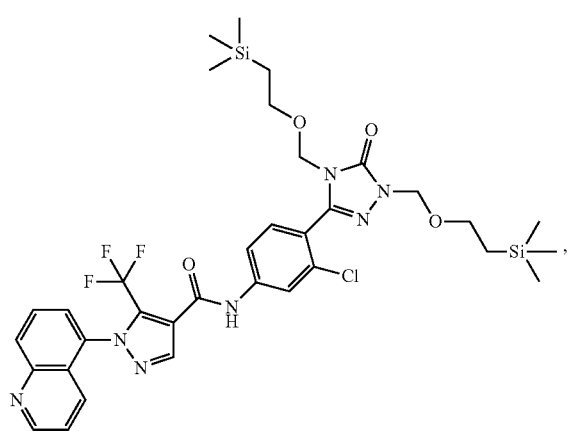

166e

Pd (OAc)$_2$ (15.95 mg, 0.071 mmol) and Xantphos (41.1 mg, 0.071 mmol) were added to a solution of 5-(4-bromo-2-chlorophenyl)-2,4-bis((2-(trimethylsilyl)ethoxy)methyl)-2,4-dihydro-3H-1,2,4-triazol-3-one (380 mg, 0.71 mmol), 1-(quinolin-5-yl)-5-(trifluoromethyl)-1H-pyrazole-4-carboxamide (293 mg, 0.92 mmol) and cesium carbonate (810 mg, 2.49 mmol) in dioxane (5 mL) under N$_2$ atmosphere. The mixture was stirred at 100° C. overnight. The mixture was filtered and the filtrate concentrated to give a crude product, which was purified by flash column chromatography over silica gel (eluent: petroleum ether/ethyl acetate from 100/0 to 0/100). The eluent was collected and the solvent was concentrated under reduced pressure to give the product as a yellow solid (480 mg, 76% yield). LC-MS: (ES, m/z): [M+1]$^+$ 760.1.

F. N-(3-chloro-4-(1-(hydroxymethyl)-5-oxo-4,5-dihydro-1H-1,2,4-triazol-3-yl)phenyl)-1-(quinolin-5-yl)-5-(trifluoromethyl)-1H-pyrazole-4-carboxamide, 166f

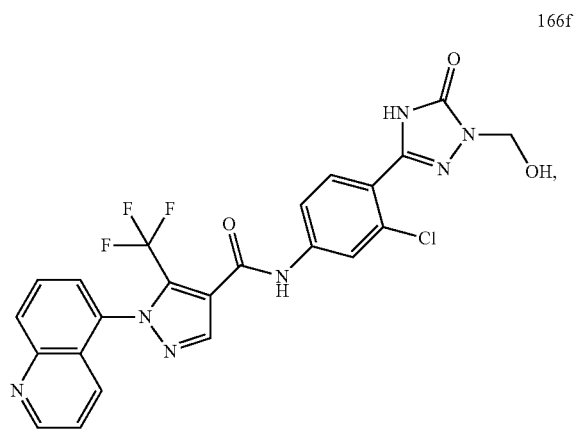 [SMILES: O=C(Nc1ccc(-c2nn(CO)c(=O)[nH]2)c(Cl)c1)c1cnn(-c2cccc3ncccc23)c1C(F)(F)F]

166f

N-(3-Chloro-4-(5-oxo-1,4-bis((2-(trimethylsilyl)ethoxy)methyl)-4,5-dihydro-1H-1,2,4-triazol-3-yl)phenyl)-1-(quinolin-5-yl)-5-(trifluoromethyl)-1H-pyrazole-4-carboxamide (400 mg, 0.45 mmol) in TFA/DCM (1:2, 1.5 mL) was stirred at room temperature for 3 h. The mixture was concentrated to give a crude product which was used directly for the next step. LC-MS: (ES, m/z): [M+1]$^+$ 531.0

G. N-(3-chloro-4-(5-oxo-4,5-dihydro-1H-1,2,4-triazol-3-yl)phenyl)-1-(quinolin-5-yl)-5-(trifluoromethyl)-1H-pyrazole-4-carboxamide, Cpd 166

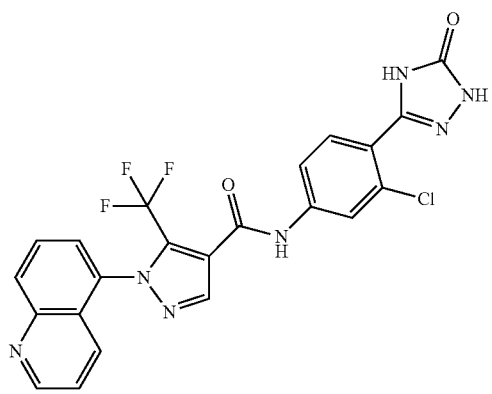 [SMILES: O=C(Nc1ccc(-c2n[nH]c(=O)[nH]2)c(Cl)c1)c1cnn(-c2cccc3ncccc23)c1C(F)(F)F]

N-(3-Chloro-4-(1-(hydroxymethyl)-5-oxo-4,5-dihydro-1H-1,2,4-triazol-3-yl)phenyl)-1-(quinolin-5-yl)-5-(trifluoromethyl)-1H-pyrazole-4-carboxamide (386 mg, 0.525 mmol) and TEA (1061 mg, 10.49 mmol) in methanol (5 mL) was stirred at 50° C. for 3 h. The mixture was concentrated to give a crude product. The crude product was purified by preparative high-performance liquid chromatography (20% to 50% (v/v) CH₃CN and H₂O with 0.05% HCl) to give the product as a white solid (120 mg, 45.5% yield). ¹H NMR (400 MHz, DMSO-$d_6$) δ ppm 7.58-7.71 (m, 3H), 7.77 (dd, J=8.60, 1.98 Hz, 1H), 7.88-7.93 (m, 1H), 7.94-8.00 (m, 1H), 8.06 (d, J=1.98 Hz, 1H), 8.33 (d, J=8.38 Hz, 1H), 8.54 (s, 1H), 9.06 (dd, J=4.08, 1.65 Hz, 1H), 10.93 (br s, 1H), 11.77 (br s, 2H). LC-MS: (ES, m/z): [M+1]⁺ 489.9

Example 167

1-(1-oxo-1,2-dihydroisoquinolin-5-yl)-5-(trifluoromethyl)-N-(5-(trifluoromethyl)pyridin-3-yl)-1H-pyrazole-4-carboxamide, Cpd 167

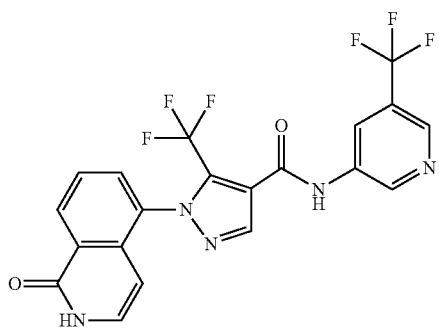 [SMILES: O=C(Nc1cncc(C(F)(F)F)c1)c1cnn(-c2cccc3c(=O)[nH]ccc23)c1C(F)(F)F]

To a solution of 1-(1-oxo-1,2-dihydroisoquinolin-5-yl)-5-(trifluoromethyl)-1H-pyrazole-4-carboxylic acid (345.9 mg, 0.888 mmol) and 5-(trifluoromethyl)pyridin-3-amine (120 mg, 0.74 mmol) in pyridine (3 mL) was added POCl₃ (227 mg, 1.48 mmol) dropwise. The mixture was stirred at 25° C. for 4 h and at 40° C. for 3 h. Sat. NaHCO₃ was added to adjust the pH to 7-8 and the mixture was extracted with ethyl acetate (30 mL×2). The combined organic layers were dried over MgSO₄, filtered and the filtrates were concentrated under reduced pressure to afford crude product as a yellow oil. The crude product was then purified by preparative HPLC (37% to 57% (v/v) CH₃CN and H₂O with 0.05% HCl) to afford 1-(1-oxo-1,2-dihydroisoquinolin-5-yl)-5-(trifluoromethyl)-N-(5-(trifluoromethyl)pyridin-3-yl)-1H-pyrazole-4-carboxamide (130 mg, 37%). ¹H NMR (400 MHz, DMSO-$d_6$) δ ppm 5.67 (d, J=7.28 Hz, 1H), 7.26-7.31 (m, 1H), 7.68 (t, J=7.94 Hz, 1H), 7.94 (d, J=7.50 Hz, 1H), 8.44 (d, J=7.94 Hz, 1H), 8.53 (s, 1H), 8.60 (s, 1H), 8.75 (s, 1H), 9.12 (s, 1H), 11.18 (s, 1H), 11.64 (br d, J=4.63 Hz, 1H). LC-MS: (ES, m/z): [M+1]⁺ 467.9

Example 168

N-(5-chloro-6-(5-(hydroxymethyl)-1H-1,2,3-triazol-1-yl)pyridin-3-yl)-1-(1-oxo-1,2-dihydroisoquinolin-5-yl)-5-(trifluoromethyl)-1H-pyrazole-4-carboxamide, Cpd 168

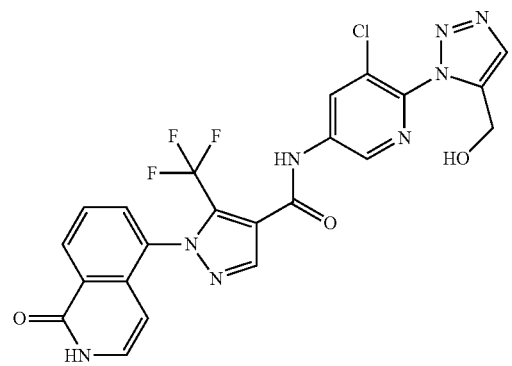 [SMILES: O=C(Nc1cnc(-n2nncc2CO)c(Cl)c1)c1cnn(-c2cccc3c(=O)[nH]ccc23)c1C(F)(F)F]

A. mixture of methyl 2-(3-chloro-5-nitropyridin-2-yl)-2H-1,2,3-triazole-4-carboxylate and methyl 1-(3-chloro-5-nitropyridin-2-yl)-1H-1,2,3-triazole-5-carboxylate, 168a

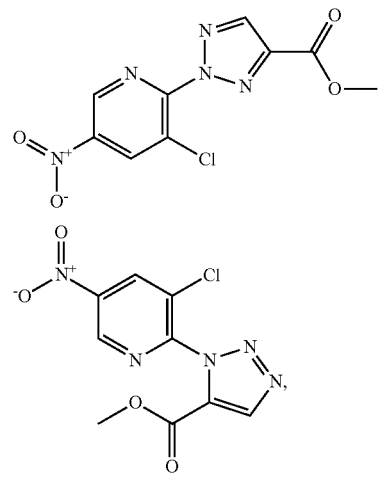

168a

Potassium carbonate (10.0 g, 72.5 mmol) was added to a solution of 2,3-dichloro-5-nitropyridine (7.0 g, 36.3 mmol) and methyl 1H-1,2,3-triazole-4-carboxylate (4.61 g, 36.3 mmol) in MeCN (30 mL). The mixture was reacted at 60° C. for 16 h. The reaction mixture was filtered. The filtrate was concentrated under reduced pressure to give the crude product as a yellow oil. The crude product was purified by column chromatography over silica gel (petroleum ether/ethyl acetate=100:0 to petroleum ether/ethyl acetate=40:60). The pure fractions were collected and the solvent was concentrated under reduced pressure to give the product as a yellow solid (8.8 g, 42.8 yield).

B. methyl 2-(5-amino-3-chloropyridin-2-yl)-2H-1,2,3-triazole-4-carboxylate, 168b

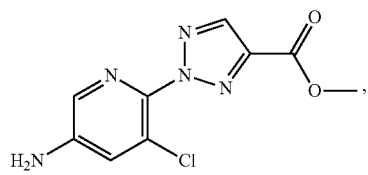

and methyl 1-(5-amino-3-chloropyridin-2-yl)-1H-1,2,3-triazole-5-carboxylate, 168c

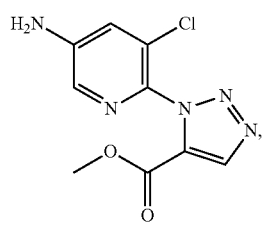

A mixture of methyl 2-(3-chloro-5-nitropyridin-2-yl)-2H-1,2,3-triazole-4-carboxylate and methyl 1-(3-chloro-5-nitropyridin-2-yl)-1H-1,2,3-triazole-5-carboxylate (8.8 g, 15.5 mmol) was added to a mixture of iron (8.66 g, 155.1 mmol), NH₄Cl (8.30 g, 155.1 mmol) in THF (30 mL) and water (15 mL). The reaction was stirred at 60° C. for 2 h. The reaction mixture was filtered, the filtrate was concentrated under reduced pressure to give the crude product as a brown oil, the crude product was purified by column chromatography over silica gel (petroleum ether/ethyl acetate=2:1 to ethyl acetate). The desired fractions were collected and the solvent was concentrated under reduced pressure to give methyl 2-(5-amino-3-chloropyridin-2-yl)-2H-1,2,3-triazole-4-carboxylate as a yellow solid, 168c (1.80 g, 45.7%). ¹H NMR (400 MHz, CHLOROFORM-d) δ ppm 3.98 (s, 3H), 4.21 (s, 2H), 7.16 (d, J=2.51 Hz, 1H), 7.90 (d, J=2.51 Hz, 1H), 8.26-8.33 (m, 1H). LC-MS: (ES, m/z): [M+1]⁺ 254.0; and methyl 1-(5-amino-3-chloropyridin-2-yl)-1H-1,2,3-triazole-5-carboxylate as a yellow oil, 168d (1.10 g, 28.0%), ¹H NMR (400 MHz, CHLOROFORM-d) δ ppm 3.99 (s, 3H), 4.33 (br s, 2H), 7.20 (d, J=2.51 Hz, 1H), 7.91 (d, J=2.76 Hz, 1H), 8.48 (s, 1H), 8.46-8.53 (m, 1H). LC-MS: (ES, m/z): [M+1]⁺ 254.0

D. methyl 1-(3-chloro-5-(1-(1-methoxyisoquinolin-5-yl)-5-(trifluoromethyl)-1H-pyrazole-4-carboxamido)pyridin-2-yl)-1H-1,2,3-triazole-5-carboxylate, 168e

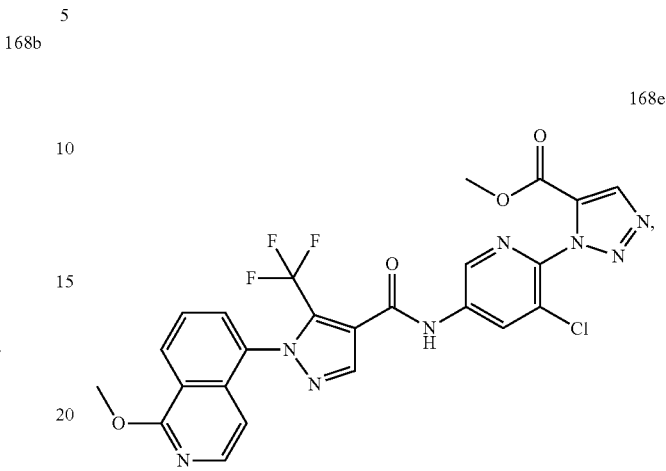

To a solution of 1-(1-methoxyisoquinolin-5-yl)-5-(trifluoromethyl)-1H-pyrazole-4-carboxylic acid (1.10 g, 3.26 mmol), methyl 1-(5-amino-3-chloropyridin-2-yl)-1H-1,2,3-triazole-5-carboxylate (910 mg, 3.59 mmol) and pyridine (774 mg, 9.79 mmol) in CH₂Cl₂ (20 mL) was added POCl₃ (600 mg, 3.91 mmol) dropwise. The mixture was stirred at 25° C. for 2 h, and 20 mL sat. NaHCO₃ was added. The reaction mixture was extracted with CH₂Cl₂ (30 mL×2). The combined organic layers were dried over Na₂SO₄, filtered and the filtrates were concentrated under reduced pressure to afford crude product as a yellow oil. The crude product was then purified by column chromatography over silica gel (petroleum ether/ethyl acetate=1:1 to ethyl acetate) to afford the product (1.10 g, 52.1%). LC-MS: (ES, m/z): [M+1]⁺ 573.1.

E. N-(5-chloro-6-(5-(hydroxymethyl)-1H-1,2,3-triazol-1-yl)pyridin-3-yl)-1-(1-methoxyisoquinolin-5-yl)-5-(trifluoromethyl)-1H-pyrazole-4-carboxamide, 168f

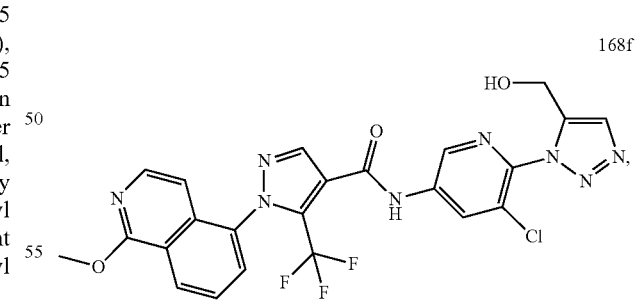

LiAlH₄ (61.6 mg, 1.62 mmol) was added to a solution of methyl 1-(3-chloro-5-(1-(1-methoxyisoquinolin-5-yl)-5-(trifluoromethyl)-1H-pyrazole-4-carboxamido)pyridin-2-yl)-1H-1,2,3-triazole-5-carboxylate (300 mg, 0.46 mmol) in THF (10 mL) at 0° C. slowly, the mixture was stirred for 2 h at room temperature. Water (61 uL) was added to the mixture at 0° C. and the mixture was stirred for 10 min. NaOH (61 uL, 15% in water) was added to the mixture at 0° C. and the mixture was stirred for 10 min. Additional water

523

(183 uL) was added to the mixture at 0° C. and the mixture was stirred for 10 min. MgSO₄ was added to the mixture and the mixture was filtered. The filtrate was concentrated to give the crude product as a brown oil (180 mg, 61.2% yield). LC-MS: (ES, m/z): [M+1]⁺ 545.1

F. N-(5-chloro-6-(5-(hydroxymethyl)-1H-1,2,3-triazol-1-yl)pyridin-3-yl)-1-(1-oxo-1,2-dihydroisoquinolin-5-yl)-5-(trifluoromethyl)-1H-pyrazole-4-carboxamide, Cpd 168

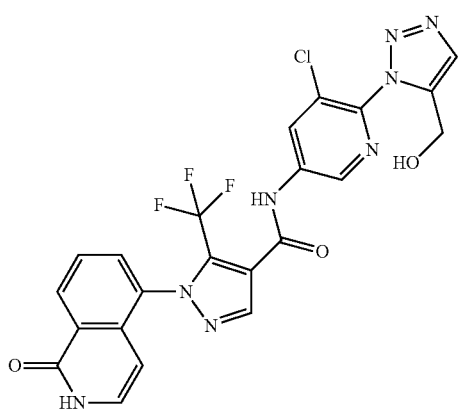 [SMILES: O=C(Nc1cnc(-n2nncc2CO)c(Cl)c1)c1cnn(-c2cccc3c(=O)[nH]ccc23)c1C(F)(F)F]

N-(5-Chloro-6-(5-(hydroxymethyl)-1H-1,2,3-triazol-1-yl)pyridin-3-yl)-1-(1-methoxyisoquinolin-5-yl)-5-(trifluoromethyl)-1H-pyrazole-4-carboxamide (180 mg, 0.28 mmol) in isopropanol (4 mL) was added to concentrated HCl (2 mL) and the reaction was stirred at 60° C. for 2 h. The mixture was concentrated under reduced pressure to afford the crude product as a yellow oil. The crude product was purified by preparative high-performance liquid chromatography (12% to 42% (v/v) CH₃CN and H₂O with 0.05% HCl), the pure fractions were collected and the organic solvent was concentrated under reduced pressure and lyophilized to dryness to give the product as a white solid (36 mg, 23.9% yield). ¹H NMR (400 MHz, DMSO-d₆) δ ppm 4.65 (s, 2H), 5.67 (d, J=7.28 Hz, 1H), 7.31 (t, J=6.53 Hz, 1H), 7.68 (t, J=7.78 Hz, 1H), 7.96 (d, J=7.28 Hz, 1H), 8.42-8.50 (m, 2H), 8.54-8.73 (m, 2H), 8.90 (br s, 1H), 11.27-11.47 (m, 1H), 11.65 (br d, J=5.02 Hz, 1H). LC-MS: (ES, m/z): [M+1]⁺ 530.9.

524

Example 169

N-(5-chloro-2-methyl-6-(1-methyl-1H-pyrazol-3-yl)pyridin-3-yl)-1-(1-oxo-1,2-dihydroisoquinolin-5-yl)-5-(trifluoromethyl)-1H-pyrazole-4-carboxamide, Cpd 169

A. 5,6-dichloro-2-methylpyridin-3-amine, 169a

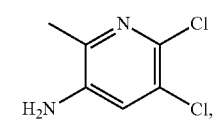

Iron (0.811 g, 14.5 mmol) and ammonium chloride (0.775 g, 14.5 mmol) were added to a mixture of 2,3-dichloro-6-methyl-5-nitropyridine (0.60 g, 2.90 mmol) in methanol (20 mL), THF (40 mL) and water (10 mL). The mixture was stirred at 60° C. for 2 h. Ethyl acetate (100 mL) was added to the mixture. The precipitate was collected by filtration. The residue was washed by (100×3 mL) ethyl acetate. The filtrate was collected and concentrated under reduced pressure. 10% NaHCO₃ (100 mL) was added to the mixture and the mixture was extracted with ethyl acetate (100 mL×2). The organic layers were dried (Na₂SO₄), filtered, and the filtrate removed to afford the product as a yellow solid. The crude product was purified by column chromatography over silica gel (petroleum ether/ethyl acetate=10:1 to petroleum ether/ethyl acetate=0:1). The desired fractions were collected and the solvent was concentrated under reduced pressure to give the product as a yellow solid (0.45 g, 88% yield).

B. 5-chloro-2-methyl-6-(1-methyl-1H-pyrazol-3-yl)pyridin-3-amine, 169b

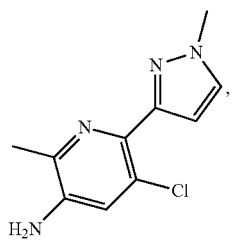

[1,1'-Bis(diphenylphosphino)ferrocene]dichloropalladium(II), complexed with dichloromethane (113 mg, 0.14 mmol) was added to a solution of 5,6-dichloro-2-methylpyridin-3-amine (350 mg, 1.98 mmol), 1-methyl-3-(4,4,5,5-tetramethyl-1,3,2-dioxaborolan-2-yl)-1H-pyrazole (535 mg, 2.57 mmol) and potassium acetate (582 mg, 5.93 mmol) in dioxane/water (3:1, 10 mL) under $N_2$ atmosphere at 100° C. overnight. The mixture was filtered and the filtrate was concentrated to give a crude product. The crude product was purified by flash column chromatography over silica gel (eluent: petroleum ether/ethyl acetate from 100/0 to 0/100). The eluent was collected and the solvent was concentrated under reduced pressure to give the product as a yellow solid (315 mg, 72% yield). LC-MS: (ES, m/z): $[M+1]^+$ 222.9.

C. N-(5-chloro-2-methyl-6-(1-methyl-1H-pyrazol-3-yl)pyridin-3-yl)-1-(1-oxo-1,2-dihydroisoquinolin-5-yl)-5-(trifluoromethyl)-1H-pyrazole-4-carboxamide, Cpd 169

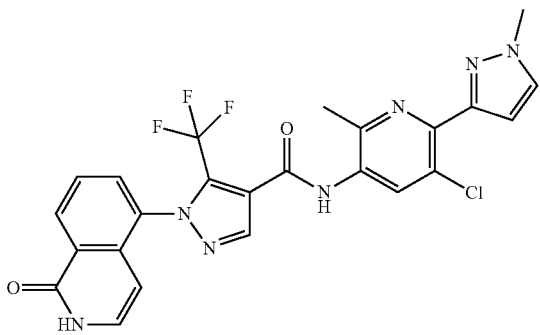 [SMILES: Cc1nc(-c2ccn(C)n2)c(Cl)cc1NC(=O)c1cnn(-c2cccc3c(=O)[nH]ccc23)c1C(F)(F)F]

To a solution of 1-(1-oxo-1,2-dihydroisoquinolin-5-yl)-5-(trifluoromethyl)-1H-pyrazole-4-carboxylic acid (175 mg, 0.45 mmol) and 5-chloro-2-methyl-6-(1-methyl-1H-pyrazol-3-yl)pyridin-3-amine (110 mg, 0.49 mmol) and pyridine (363 μL, 4.49 mmol) in dichloromethane (5 mL) was added $POCl_3$ (68.9 mg, 0.45 mmol) dropwise. The mixture was stirred at 25° C. for 2 h. Water (5 mL) was added, sat. $NaHCO_3$ was added to adjust the pH to 7-8 and the reaction mixture was extracted with dichloromethane (5 mL×2). The combined organic layers were dried over $MgSO_4$, filtered and the filtrates were concentrated under reduced pressure to afford crude product. The crude product was then purified by preparative HPLC (30% to 60% (v/v) $CH_3CN$ and $H_2O$ with 0.05% HCl) to afford product as a white solid (105 mg, 44%). $^1H$ NMR (400 MHz, DMSO-$d_6$) δ ppm 2.52 (br s, 3H), 3.93 (s, 3H), 5.69 (br d, J=7.50 Hz, 1H), 6.75 (d, J=2.21 Hz, 1H), 7.29 (br s, 1H), 7.67 (t, J=7.83 Hz, 1H), 7.79 (d, J=2.21 Hz, 1H), 7.93 (d, J=7.50 Hz, 1H), 8.09 (s, 1H), 8.44 (d, J=8.38 Hz, 1H), 8.49 (s, 1H), 10.40 (s, 1H), 11.62 (br s, 1H). LC-MS: (ES, m/z): $[M+1]^+$ 527.9

Example 170

N-(5-chloro-2-methyl-6-(1H-pyrazol-1-yl)pyridin-3-yl)-1-(1-oxo-1,2-dihydroisoquinolin-5-yl)-5-(trifluoromethyl)-1H-pyrazole-4-carboxamide, Cpd 170

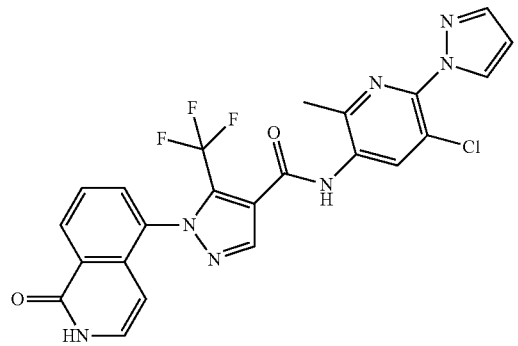 [SMILES: Cc1nc(-n2cccn2)c(Cl)cc1NC(=O)c1cnn(-c2cccc3c(=O)[nH]ccc23)c1C(F)(F)F]

A. 3-chloro-6-methyl-5-nitro-2-(1H-pyrazol-1-yl)pyridine, 170a

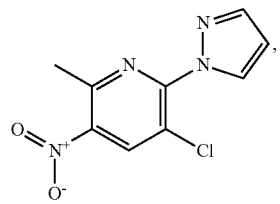

A solution of 2,3-dichloro-6-methyl-5-nitropyridine (1.2 g, 5.80 mmol), 1H-pyrazole (987 mg, 14.5 mmol) and potassium carbonate (2.40 g, 17.4 mmol) in MeCN (20 mL) was stirred at rt overnight and at 40° C. for another 8 h. The mixture was filtered and the solid was washed with ethyl acetate (20 mL×3). The filtrate was concentrated to give a crude product. The crude product was purified by flash column chromatography over silica gel (eluent: petroleum ether/ethyl acetate from 100/0 to 50/50). The eluent was collected and the solvent was concentrated under reduced pressure to give the product as a yellow solid (650 mg, 47% yield). $^1H$ NMR (400 MHz, DMSO-$d_6$) δ ppm 2.77 (s, 3H), 6.64 (t, J=1.76 Hz, 1H), 7.92 (s, 1H), 8.49 (d, J=2.65 Hz, 1H), 8.84 (s, 1H).

B. 5-chloro-2-methyl-6-(1H-pyrazol-1-yl)pyridin-3-amine, 170b

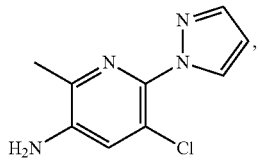

Iron (0.761 g, 13.6 mmol) and ammonium chloride (0.718 g, 13.6 mmol) were added to a mixture of 3-chloro-6-methyl-5-nitro-2-(1H-pyrazol-1-yl)pyridine (0.650 g, 2.72 mmol) in methanol (5 mL), THF (10 mL) and water (5 mL). The mixture was stirred at 70° C. for 2 h. 10 mL Sat. NaHCO$_3$ solution was added to the mixture, the mixture was filtered, and the filtrate was extracted with ethyl acetate (15 mL×3). The organic layer was dried (Na$_2$SO$_4$) and the solvent removed to afford the product as a yellow solid (500 mg, 88%).

C. N-(5-chloro-2-methyl-6-(1H-pyrazol-1-yl)pyridin-3-yl)-1-(1-oxo-1,2-dihydroisoquinolin-5-yl)-5-(trifluoromethyl)-1H-pyrazole-4-carboxamide, Cpd 170

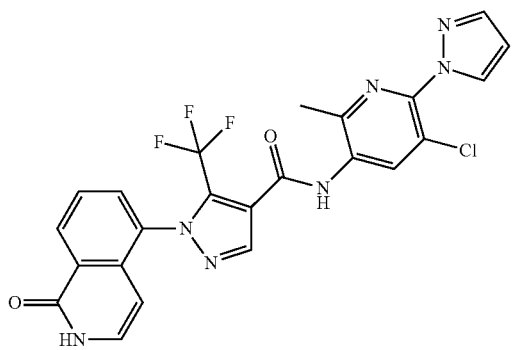 [SMILES: Cc1nc(-n2cccn2)c(Cl)cc1NC(=O)c1cnn(-c2cccc3c(=O)[nH]ccc23)c1C(F)(F)F]

To a solution of 1-(1-oxo-1,2-dihydroisoquinolin-5-yl)-5-(trifluoromethyl)-1H-pyrazole-4-carboxylic acid (146 mg, 0.70 mmol) and 5-chloro-2-methyl-6-(1H-pyrazol-1-yl)pyridin-3-amine (200 mg, 0.58 mmol) in pyridine (5 mL) was added POCl$_3$ (108 µL, 1.16 mmol) dropwise. The mixture was stirred at 25° C. for 2 h. Water (5 mL) was added, sat. NaHCO$_3$ was added to adjust the pH to 7-8 and the reaction mixture was extracted with ethyl acetate (20 mL×3). The combined organic layers were dried over MgSO$_4$, filtered and the filtrates were concentrated under reduced pressure to afford crude product. The crude product was then purified by preparative HPLC (32% to 62% (v/v) CH$_3$CN and H$_2$O with 0.05% HCl) to afford the product as a white solid (160 mg, 53%). $^1$H NMR (400 MHz, DMSO-d$_6$) δ ppm 2.53 (br s, 3H), 5.68 (d, J=7.72 Hz, 1H), 6.52-6.58 (m, 1H), 7.27-7.33 (m, 1H), 7.68 (t, J=7.94 Hz, 1H), 7.81 (d, J=1.32 Hz, 1H), 7.94 (d, J=7.72 Hz, 1H), 8.27 (d, J=2.21 Hz, 1H), 8.30 (s, 1H), 8.44 (d, J=7.94 Hz, 1H), 8.52 (s, 1H), 10.54 (s, 1H), 11.63 (br d, J=5.95 Hz, 1H). LC-MS: (ES, m/z): [M+1]$^+$ 514.2

Example 171

N-(5-chloro-2-methyl-4-(2H-1,2,3-triazol-2-yl)phenyl)-1-(1-oxo-1,2-dihydroisoquinolin-5-yl)-5-(trifluoromethyl)-1H-pyrazole-4-carboxamide, Cpd 171

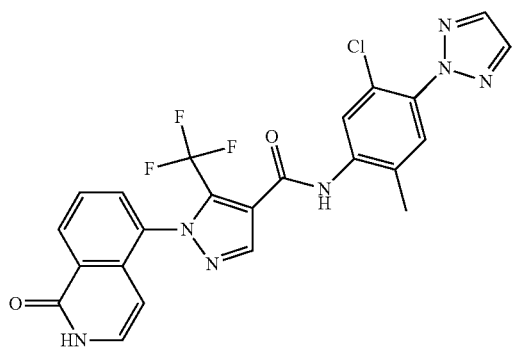 [SMILES: Cc1cc(-n2nccn2)c(Cl)cc1NC(=O)c1cnn(-c2cccc3c(=O)[nH]ccc23)c1C(F)(F)F]

A. 2-(2-chloro-5-methyl-4-nitrophenyl)-2H-1,2,3-triazole, 171a

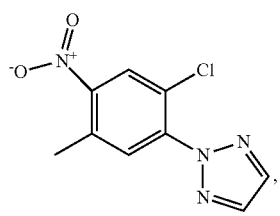

The mixture of 1,2-dichloro-4-methyl-5-nitrobenzene (1.0 g, 4.85 mmol), 2H-1,2,3-triazole (0.32 mL, 5.83 mmol), potassium carbonate (2.01 g, 14.56 mmol) and potassium fluoride (226 mg, 3.88 mmol) in acetonitrile (10 mL) was stirred at 80° C. overnight. The solid was collected by filtration and then was washed with 50 mL ethyl acetate. The solvent was concentrated to give the crude product as a yellow solid. The crude product was purified by column chromatography over silica gel (petroleum ether/ethyl acetate=100:0 to 50:50). The solvent was concentrated to afford the product as a white solid (180 mg, 15.5% yield). $^1$H NMR (400 MHz, CHLOROFORM-d) δ ppm 7.69 (s, 1H), 7.64 (d, J=1.00 Hz, 1H), 7.40 (d, J=1.25 Hz, 1H), 7.21 (s, 1H) 2.11 (s, 3H).

B. 5-chloro-2-methyl-4-(2H-1,2,3-triazol-2-yl)aniline, 171b

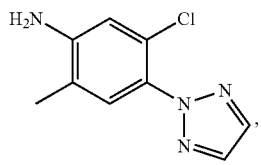

Iron (0.772 g, 13.8 mmol) and ammonium chloride (0.74 g, 13.8 mmol) were added to a mixture of 2-(2-chloro-5-methyl-4-nitrophenyl)-2H-1,2,3-triazole (660 mg, 2.77 mmol) in methanol (4 mL), THF (6 mL) and water (3 mL). The mixture was stirred at 60° C. for 2 h. Ethyl acetate (50 mL) was added to the mixture. The precipitate was collected by filtration, and the residue was washed with ethyl acetate (50×3 mL). The filtrate was collected and concentrated under reduced pressure. The crude product was purified by column chromatography over silica gel (petroleum ether/ethyl acetate=10:1 to petroleum ether/ethyl acetate=1:1). The pure fractions were collected and the solvent was concentrated under reduced pressure to give the product as a white solid (0.50 g, 95% yield). $^1$H NMR (400 MHz, DMSO-$d_6$) δ ppm 7.97 (s, 2H), 7.13 (s, 1H), 6.77 (s, 1H), 5.58 (s, 2H), 3.33 (s, 2H), 2.48 (br s, 2H), 2.05 (s, 3H).

C. N-(5-chloro-2-methyl-4-(2H-1,2,3-triazol-2-yl)phenyl)-1-(1-oxo-1,2-dihydroisoquinolin-5-yl)-5-(trifluoromethyl)-1H-pyrazole-4-carboxamide, Cpd 171

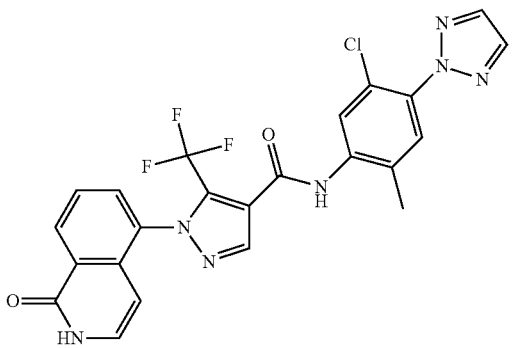 [SMILES: Cc1cc(-n2nccn2)c(Cl)cc1NC(=O)c1cnn(-c2cccc3c(=O)[nH]ccc23)c1C(F)(F)F]

To a solution of 1-(1-oxo-1,2-dihydroisoquinolin-5-yl)-5-(trifluoromethyl)-1H-pyrazole-4-carboxylic acid (150 mg, 0.46 mmol) and 5-chloro-2-methyl-4-(2H-1,2,3-triazol-2-yl)aniline (96.8 mg, 0.46 mmol) and pyridine (220 mg, 2.78 mmol) in dichloromethane (10 mL) was added POCl$_3$ (285 mg, 1.86 mmol) dropwise. The mixture was stirred at room temperature for 4 h. Sat. NaHCO$_3$ was added to adjust the pH to 9-10, and the reaction mixture was extracted with dichloromethane (30 mL×3). The combined organic layers were dried over MgSO$_4$, filtered and the filtrates were concentrated under reduced pressure to afford crude product as a yellow oil. The crude product was then purified by preparative HPLC (35% to 65% (v/v) CH$_3$CN and H$_2$O with 0.05% HCl) to afford product as a white solid (131 mg, 54.7%). $^1$H NMR (400 MHz, DMSO-$d_6$) δ ppm 11.60 (br d, J=5.51 Hz, 1H), 10.35 (s, 1H), 8.36-8.53 (m, 2H), 8.13 (s, 2H), 7.81-7.95 (m, 2H), 7.59-7.68 (m, 2H), 7.26 (dd, J=7.17, 6.06 Hz, 1H), 5.66 (br d, J=7.50 Hz, 1H), 2.27-2.37 (m, 3H). LC-MS: (ES, m/z): [M+1]$^+$ 514.2

Example 172

N-(5-chloro-2-fluoro-4-(2H-1,2,3-triazol-2-yl)phenyl)-1-(1-oxo-1,2-dihydroisoquinolin-5-yl)-5-(trifluoromethyl)-1H-pyrazole-4-carboxamide, Cpd 172

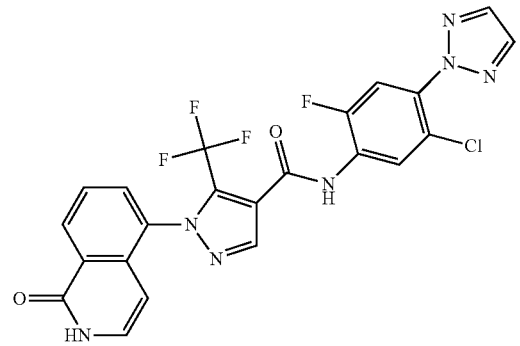 [SMILES: O=C(Nc1cc(Cl)c(-n2nccn2)cc1F)c1cnn(-c2cccc3c(=O)[nH]ccc23)c1C(F)(F)F]

A. 2-(2-chloro-5-fluoro-4-nitrophenyl)-2H-1,2,3-triazole, 172a

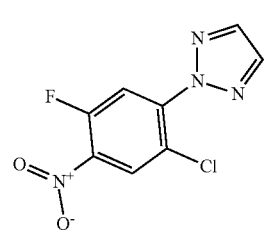

172a

A mixture of 1-chloro-2,4-difluoro-5-nitrobenzene (3.0 g, 15.5 mmol), 2H-1,2,3-triazole (1.61 mL, 23.3 mmol), and potassium carbonate (6.42 g, 46.5 mmol) in acetonitrile (50 mL) was stirred at 30° C. for 2 h. The solid was collected by filtration and washed with 100 mL ethyl acetate and 100 mL dichloromethane. The solvent was concentrated to give the crude product as a yellow solid. The crude product was purified by column chromatography over silica gel (petroleum ether/ethyl acetate=10:1 to 1:2). The solvent was concentrated to afford the product as a yellow solid (0.6 g, 16%). $^1$H NMR (400 MHz, CHLOROFORM-d) δ ppm 7.79 (br d, J=10.80 Hz, 1H), 7.95 (s, 2H), 8.32 (br d, J=7.06 Hz, 1H).

B. 5-chloro-2-fluoro-4-(2H-1,2,3-triazol-2-yl)aniline, 172b

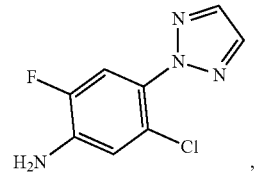

172b

531

Iron (0.692 g, 12.4 mmol) and ammonium chloride (0.661 g, 12.4 mmol) were added to a mixture of 2-(2-chloro-5-fluoro-4-nitrophenyl)-2H-1,2,3-triazole (600 mg, 2.47 mmol) in methanol (20 mL), THF (40 mL) and water (10 mL). The mixture was stirred at 60° C. for 2 h. Ethyl acetate (50 mL) was added to the mixture. The precipitate was collected by filtration. The residue was washed with (50×3 mL) ethyl acetate. The filtrate was collected and concentrated under reduced pressure. The crude product was purified by column chromatography over silica gel (petroleum ether/ethyl acetate=10:1 to petroleum ether/ethyl acetate=0:1). The pure fractions were collected and the solvent was concentrated under reduced pressure to afford the product as a white solid (0.50 g, 81%). 1H NMR (400 MHz, DMSO-$d_6$) δ ppm 5.93 (s, 2H), 6.93 (d, J=8.60 Hz, 1H), 7.36 (d, J=11.25 Hz, 1H), 7.99-8.04 (m, 2H). LC-MS: (ES, m/z): [M+1]$^+$ 212.9

C. N-(5-chloro-2-fluoro-4-(2H-1,2,3-triazol-2-yl)phenyl)-1-(1-oxo-1,2-dihydroisoquinolin-5-yl)-5-(trifluoromethyl)-1H-pyrazole-4-carboxamide, Cpd 172

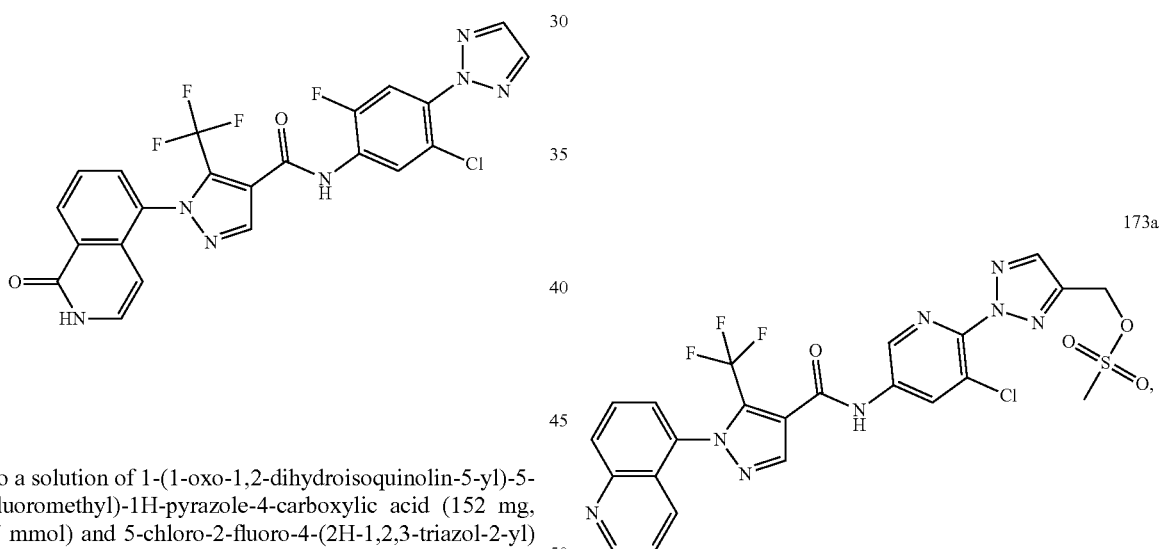

To a solution of 1-(1-oxo-1,2-dihydroisoquinolin-5-yl)-5-(trifluoromethyl)-1H-pyrazole-4-carboxylic acid (152 mg, 0.47 mmol) and 5-chloro-2-fluoro-4-(2H-1,2,3-triazol-2-yl)aniline (100 mg, 0.47 mmol) and pyridine (149 mg, 1.888 mmol) in dichloromethane (10 mL) was added POCl$_3$ (144 mg, 0.94 mmol) dropwise. The mixture was stirred at room temperature for 4 h. Sat. NaHCO$_3$ was added to adjust the pH to 9-10 and the reaction mixture was extracted with dichloromethane (30 mL×3). The combined organic layers were dried over MgSO$_4$, filtered and the filtrates were concentrated under reduced pressure to afford crude product as a yellow oil. The crude product was then purified by preparative HPLC (32% to 62% (v/v) CH$_3$CN and H$_2$O with 0.05% HCl) to afford product as a yellow solid (135 mg, 55.4%). $^1$H NMR (400 MHz, DMSO-$d_6$) δ ppm 5.67 (d, J=7.28 Hz, 1H), 7.27 (dd, J=7.28, 5.95 Hz, 1H), 7.65 (t, J=7.83 Hz, 1H), 7.86 (d, J=10.58 Hz, 1H), 7.90-7.94 (m, 1H), 8.18 (s, 2H), 8.24 (d, J=7.50 Hz, 1H), 8.42 (d, J=8.16 Hz, 1H), 8.45 (s, 1H), 10.81 (s, 1H), 11.60 (br d, J=5.07 Hz, 1H). LC-MS: (ES, m/z): [M+1]$^+$ 518.0

532

Example 173

N-(5-chloro-6-(4-(methoxymethyl)-2H-1,2,3-triazol-2-yl)pyridin-3-yl)-1-(quinolin-5-yl)-5-(trifluoromethyl)-1H-pyrazole-4-carboxamide, Cpd 173

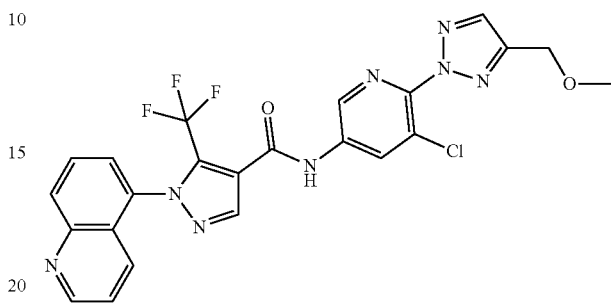

A. (2-(3-chloro-5-(1-(quinolin-5-yl)-5-(trifluoromethyl)-1H-pyrazole-4-carboxamido)pyridin-2-yl)-2H-1,2,3-triazol-4-yl)methyl methanesulfonate, 173a 173a A solution of N-(5-chloro-6-(4-(hydroxymethyl)-2H-1,2,3-triazol-2-yl)pyridin-3-yl)-1-(quinolin-5-yl)-5-(trifluoromethyl)-1H-pyrazole-4-carboxamide, Cpd 136 (420 mg, 0.79 mmol) in DCM (8 mL) was cooled to 0° C., TEA (240 mg, 2.37 mmol) was added and then methanesulfonyl chloride (136 mg, 1.19 mmol) was added dropwise. The solution was stirred at 0° C. for 1 h. The mixture was concentrated, dried, and used directly for the next step.

B. N-(5-chloro-6-(4-(methoxymethyl)-2H-1,2,3-triazol-2-yl)pyridin-3-yl)-1-(quinolin-5-yl)-5-(trifluoromethyl)-1H-pyrazole-4-carboxamide, Cpd 173

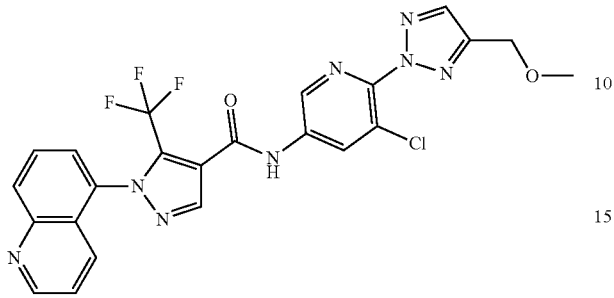

A solution of (2-(3-chloro-5-(1-(quinolin-5-yl)-5-(trifluoromethyl)-1H-pyrazole-4-carboxamido)pyridin-2-yl)-2H-1,2,3-triazol-4-yl)methyl methanesulfonate (150 mg, 95% pure, 0.24 mmol) in methanol (20 mL) was stirred at 50° C. for 2 h. The mixture was concentrated under reduced pressure to afford crude product as a yellow oil which was purified by preparative high-performance liquid chromatography (31% to 61% (v/v) CH₃CN and H₂O with 0.05% HCl). The pure fractions were collected and the solvent was concentrated under reduced pressure, lyophilized to dryness to give product as a white solid (25 mg, 19.3% yield). $^1$H NMR (400 MHz, METHANOL-$d_4$) δ ppm 3.44 (d, J=0.66 Hz, 3H), 4.67 (s, 2H), 7.61-7.66 (m, 1H), 7.75 (d, J=8.60 Hz, 1H), 7.83 (d, J=7.50 Hz, 1H), 7.94-7.99 (m, 1H), 8.01 (s, 1H), 8.33 (d, J=8.60 Hz, 1H), 8.39 (s, 1H), 8.72 (dd, J=2.21, 1.32 Hz, 1H), 8.79 (d, J=2.21 Hz, 1H), 9.00 (d, J=3.97 Hz, 1H). LC-MS: (ES, m/z): [M+1]⁺ 528.9

Example 174

N-(4-(4-(aminomethyl)-1H-pyrazol-1-yl)-3-chlorophenyl)-1-(quinolin-5-yl)-5-(trifluoromethyl)-1H-pyrazole-4-carboxamide, Cpd 174

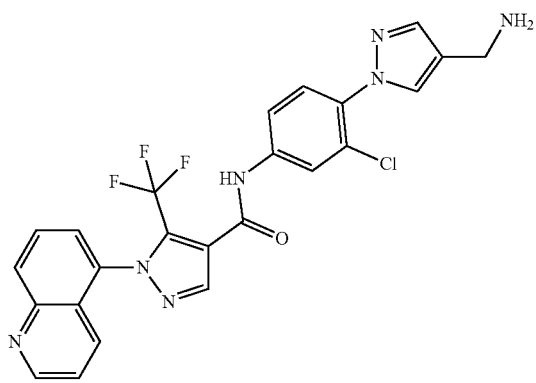 [SMILES: NCc1cnn(-c2ccc(NC(=O)c3cnn(-c4cccc5ncccc45)c3C(F)(F)F)cc2Cl)c1]

A. tert-butyl ((1-(2-chloro-4-nitrophenyl)-1H-pyrazol-4-yl)methyl)carbamate, 174a

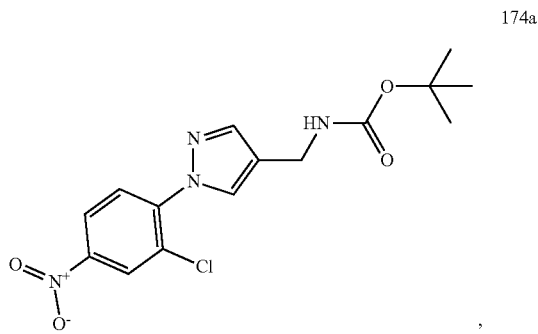 [SMILES: CC(C)(C)OC(=O)NCc1cnn(-c2ccc([N+](=O)[O-])cc2Cl)c1]

Potassium carbonate (350 mg, 2.54 mmol) was added a solution of 2-chloro-1-fluoro-4-nitrobenzene (245 mg, 1.39 mmol), tert-butyl ((1H-pyrazol-4-yl)methyl)carbamate (250 mg, 1.27 mmol) in MeCN (5 mL), the mixture was stirred at 80° C. for 12 h. The reaction mixture was filtered, and the filtrate was concentrated under reduced pressure to give the crude product as a yellow solid, which was then purified by column chromatography over silica gel (petroleum ether/ethyl acetate=10:1 to petroleum ether/ethyl acetate=1:1). The pure fractions were collected and the solvent was concentrated under reduced pressure to give the product as a yellow solid (440 mg, 98.4% yield). LC-MS: (ES, m/z): [M+1]⁺ 353.0

B. tert-butyl ((1-(4-amino-2-chlorophenyl)-1H-pyrazol-4-yl)methyl)carbamate, 174b

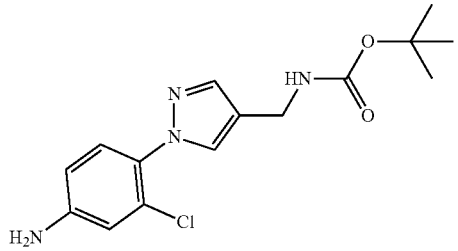

Iron (348.3 mg, 6.24 mmol) and NH₄Cl (333.6 mg, 6.24 mmol) were added to the mixture of tert-butyl ((1-(2-chloro-4-nitrophenyl)-1H-pyrazol-4-yl)methyl)carbamate (440 mg, 1.25 mmol) in THF (20 mL), H₂O (5 mL), MeOH (5 mL), the reaction mixture was stirred at 60° C. for 2 h. The reaction mixture was filtered though a pad of diatomaceous earth and the pad was washed with EtOAc (20 mL×2), the combined filtrates were concentrated to dryness to give a crude product as a brown solid which was purified by flash column chromatography over silica gel (eluent: petroleum ether/ethyl acetate from 100/0 to 20/80). The desired fractions were collected and the solvent was concentrated under reduced pressure to afford product as a brown solid (388 mg, 96.4%). LC-MS: (ES, m/z): [M+1]⁺ 323.0

C. tert-butyl ((1-(2-chloro-4-(1-(quinolin-5-yl)-5-(trifluoromethyl)-1H-pyrazole-4-carboxamido)phenyl)-1H-pyrazol-4-yl)methyl)carbamate, 174c

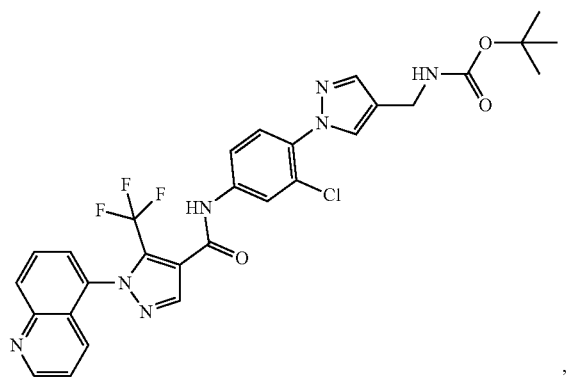

174c tert-Butyl ((1-(4-amino-2-chlorophenyl)-1H-pyrazol-4-yl)methyl)carbamate (140 mg, 0.43 mmol), 1-(Quinolin-5-yl)-5-(trifluoromethyl)-1H-pyrazole-4-carboxylic acid, 3b (133.3 mg, 0.43 mmol), DIEA (280.3 mg, 2.17 mmol) were dissolved in DMF (4 mL), and HATU (247.4 mg, 0.65 mmol) was added, the mixture was stirred at 25° C. for 3 h. Sat. NaHCO$_3$ (20 mL) was added and the reaction mixture was extracted with CH$_2$Cl$_2$ (20 mL×2), the combined organic layers were dried over anhydrous Na$_2$SO$_4$, and filtered. The solvent was concentrated under reduced pressure to afford product as a brown solid (200 mg, 36.8% yield). LC-MS: (ES, m/z): [M+1]$^+$ 612.2

D. N-(4-(4-(aminomethyl)-1H-pyrazol-1-yl)-3-chlorophenyl)-1-(quinolin-5-yl)-5-(trifluoromethyl)-1H-pyrazole-4-carboxamide, Cpd 174

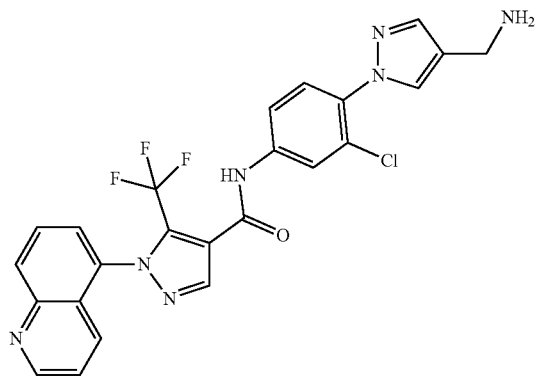 [SMILES: NCc1cnn(-c2ccc(NC(=O)c3cnn(-c4cccc5ncccc45)c3C(F)(F)F)cc2Cl)c1]

HCl/dioxane (10 mL) was added to tert-butyl ((1-(2-chloro-4-(1-(quinolin-5-yl)-5-(trifluoromethyl)-1H-pyrazole-4-carboxamido)phenyl)-1H-pyrazol-4-yl)methyl)carbamate (88 mg, 0.14 mmol), the mixture was stirred at rt 10 min. The solvent was concentrated under reduced pressure. The residue purified by preparative high-performance liquid chromatography (15% to 45% (v/v) CH$_3$CN and H$_2$O with 0.05% HCl). The pure fractions were collected and the organic solvent was concentrated under reduced pressure and lyophilized to dryness to give the product as a pale white solid (55 mg 73.9% yield). $^1$H NMR (400 MHz, METHANOL-d$_4$) δ ppm 9.37 (1H, d, J=3.76 Hz), 8.55 (1H, s), 8.52 (1H, s), 8.45 (1H, s), 8.33 (1H, t, J=8.16 Hz), 8.20 (1H, s), 8.18-8.20 (1H, m), 8.17 (1H, s), 8.11-8.16 (1H, m), 7.89 (1H, s), 7.83 (1H, dd, J=8.78, 2.26 Hz), 7.60 (1H, d, J=8.78 Hz), 4.18 (2H, s). LC-MS: (ES, m/z): [M+1]$^+$ 513.0

Example 175

N-(3-chloro-4-(4-(hydroxymethyl)-1H-pyrazol-1-yl)phenyl)-1-(quinolin-5-yl)-5-(trifluoromethyl)-1H-pyrazole-4-carboxamide, Cpd 175

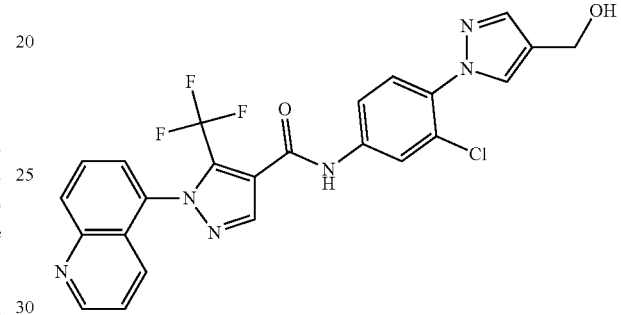

A. ethyl 1-(2-chloro-4-nitrophenyl)-1H-pyrazole-4-carboxylate, 175a

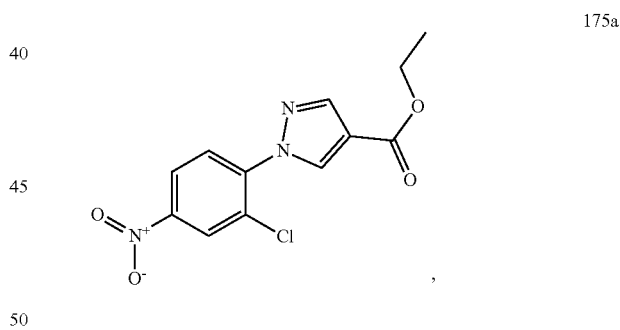

175a

2-Chloro-1-fluoro-4-nitrobenzene (334 mg, 1.90 mmol) was dissolved in MeCN (10 mL), ethyl 1H-pyrazole-4-carboxylate (222.2 mg, 1.59 mmol) and cesium carbonate (568 mg, 1.74 mmol) were added and stirred at 80° C. for 16 h. The reaction mixture was filtered and the residue was washed with EtOAc (20 mL×3), the combined organic layers were concentrated under reduced pressure to afford the product as a yellow solid. The crude product was purified by flash column chromatography over silica gel (eluent: petroleum ether/ethyl acetate from 100/0 to 70/30). The desired fractions were collected and the solvent was concentrated under reduced pressure to afford product as a white solid (400 mg, 85.3% yield). $^1$H NMR (400 MHz, DMSO-d$_6$) δ ppm 8.90 (s, 1H), 8.58 (d, J=2.5 Hz, 1H), 8.36 (dd, J=2.5, 8.8 Hz, 1H), 8.26 (s, 1H), 7.97 (d, J=8.8 Hz, 1H), 4.29 (q, J=7.1 Hz, 2H), 1.30 (t, J=7.2 Hz, 3H).

B. ethyl 1-(4-amino-2-chlorophenyl)-1H-pyrazole-4-carboxylate, 175b

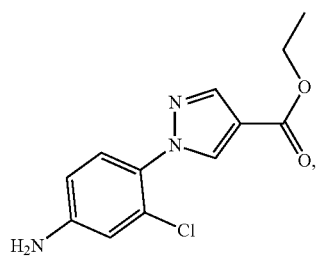

Ethyl 1-(2-chloro-4-nitrophenyl)-1H-pyrazole-4-carboxylate (400 mg, 1.25 mmol) was dissolved in THF (10 mL), iron (453 mg, 8.12 mmol), NH$_4$Cl (434 mg, 2.12 mmol) and H$_2$O (10 mL) were added, the reaction mixture was stirred at 80° C. for 4 h. The reaction mixture was filtered though a pad of diatomaceous earth and the pad was washed with EtOAc (20 mL×3). The filtrates were concentrated under reduced pressure to afford crude product as a yellow oil which was purified by flash column chromatography over silica gel (petroleum ether/ethyl acetate from 100/0 to 70/30). The desired fraction was collected and the solvent was concentrated under reduced pressure to afford product as a yellow solid (280 mg, 74.2% yield). LC-MS: (ES, m/z): [M+1]$^+$ 266.1

C. ethyl 1-(2-chloro-4-(1-(quinolin-5-yl)-5-(trifluoromethyl)-1H-pyrazole-4-carboxamido)phenyl)-1H-pyrazole-4-carboxylate, 175c

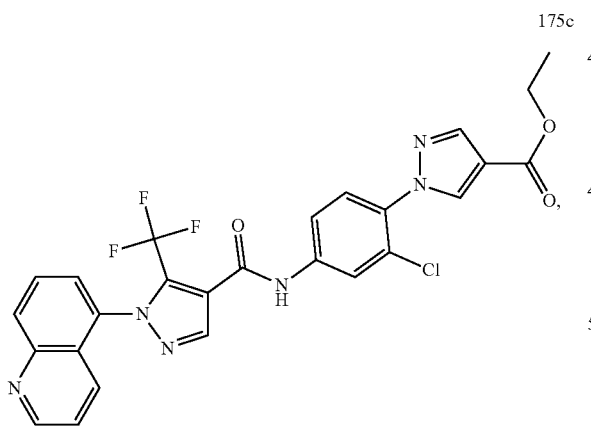

Ethyl 1-(4-amino-2-chlorophenyl)-1H-pyrazole-4-carboxylate (130 mg, 0.49 mmol), 1-(quinolin-5-yl)-5-(trifluoromethyl)-1H-pyrazole-4-carboxylic acid, 3b (100 mg, 0.33 mmol) and pyridine (38.6 mg, 0.49 mmol) were added to DCM (10 mL), and POCl$_3$ (74.9 mg, 0.49 mmol) was added dropwise. The reaction mixture was stirred at 30° C. for 16 h. Sat. NaHCO$_3$ (20 mL) was added and the reaction mixture extracted with CH$_2$Cl$_2$ (20 mL×2). The combined organic layers were dried over Na$_2$SO$_4$, filtered and the filtrates were concentrated under reduced pressure to afford crude product as a yellow oil which was purified by flash column chromatography over silica gel (eluent: petroleum ether/ethyl acetate from 100/0 to 40/60). The desired fractions were collected and the solvent was concentrated under reduced pressure to afford product as a yellow solid (170 mg, 84.4% yield).

D. N-(3-chloro-4-(4-(hydroxymethyl)-1H-pyrazol-1-yl)phenyl)-1-(quinolin-5-yl)-5-(trifluoromethyl)-1H-pyrazole-4-carboxamide, Cpd 175

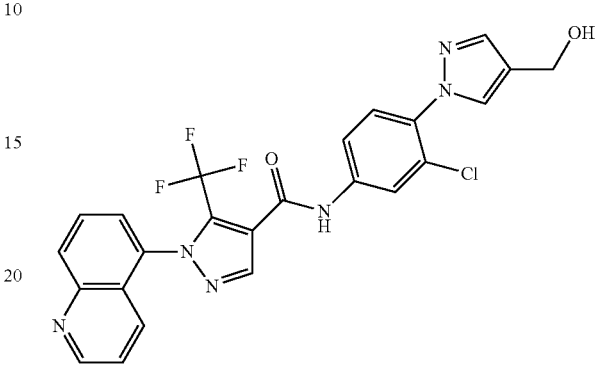

Ethyl 1-(2-chloro-4-(1-(quinolin-5-yl)-5-(trifluoromethyl)-1H-pyrazole-4-carboxamido)phenyl)-1H-pyrazole-4-carboxylate (170 mg, 90% pure, 0.28 mmol) was dissolved in THF (10 mL) and stirred at 0° C., LiAlH$_4$ (83.4 mg, 2.2 mmol) was added slowly. The reaction mixture was stirred at 40° C. for 40 h. Water (10 mL) was added and the reaction mixture was extracted with EtOAc (10 mL×2). The combined organic layers were dried over Na$_2$SO$_4$, filtered and the filtrate was concentrated under reduced pressure to afford the crude product as a yellow oil which was purified by preparative high-performance liquid chromatography (25% to 55% (v/v) CH$_3$CN and H$_2$O with 0.05% HCl). The pure fractions were collected and the solvent was concentrated under reduced pressure, lyophilized to dryness to give product as a white solid (34 mg, 24.1% yield). $^1$H NMR (400 MHz, DMSO-d$_6$) δ ppm 11.12 (br s, 1H), 9.16 (br s, 1H), 8.63 (br s, 1H), 8.41 (br d, J=7.0 Hz, 1H), 8.16 (br s, 1H), 8.11-7.93 (m, 3H), 7.82 (br s, 3H), 7.69 (br s, 1H), 7.60 (br s, 1H), 4.46 (br s, 2H). LC-MS: (ES, m/z): [M+1]$^+$ 512.9

Example 176

N-(5-cyano-2-methyl-6-(2H-1,2,3-triazol-2-yl)pyridin-3-yl)-1-(1-oxo-1,2-dihydroisoquinolin-5-yl)-5-(trifluoromethyl)-1H-pyrazole-4-carboxamide, Cpd 176

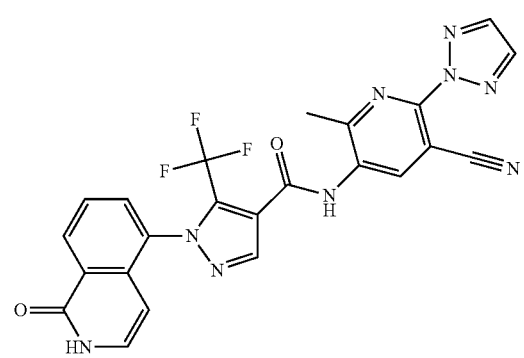 [SMILES: Cc1nc(-n2nccn2)c(C#N)cc1NC(=O)c1cnn(-c2cccc3c(=O)[nH]ccc23)c1C(F)(F)F]

A. 5-bromo-2-hydroxy-6-methylnicotinonitrile, 176a

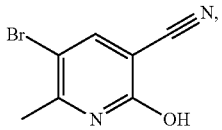

176a

1-Bromopyrrolidine-2,5-dione (26.54 g, 149.1 mmol) was added dropwise to a solution of 2-hydroxy-6-methylnicotinonitrile (10 g, 74.6 mmol) in DMF (120 mL). The mixture was stirred at 70° C. for 2 h. Sat. NaHCO$_3$ solution (100 mL) was added to the mixture. The mixture was extracted with ethyl acetate (300 mL×3). The separated organic layers were dried (MgSO$_4$), filtered, and the filtrate was concentrated to afford the product as a black solid (14 g, 79% yield). LC-MS: (ES, m/z): [M+1]$^+$ 212.8

B. 5-bromo-2-chloro-6-methylnicotinonitrile, 176b

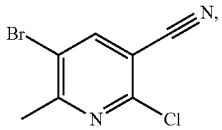

176b

5-Bromo-2-hydroxy-6-methylnicotinonitrile (14 g, 58.65 mmol) in phosphoryl trichloride (101.4 g, 661.2 mmol) was stirred at 80° C. overnight. The phosphoryl trichloride was concentrated. Sat. NaHCO$_3$ solution (1000 mL) was added dropwise to the residue to adjust the pH to 7-8. The aqueous phase was extracted with ethyl acetate (500 mL×3). The organic phase was dried (MgSO$_4$), filtered, and the filtrate was concentrated to afford the product as a black solid (9 g, 66% yield).

C. 5-bromo-6-methyl-2-(2H-1,2,3-triazol-2-yl)nicotinonitrile, 176c

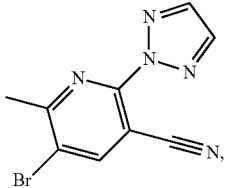

176c

A solution of 5-bromo-2-chloro-6-methylnicotinonitrile (8.5 g, 36.7 mmol), 2H-1,2,3-triazole (5.07 g, 73.4 mmol) and potassium carbonate (15.2 g, 110.2 mmol) in acetonitrile (150 mL) was stirred at 40° C. overnight. The mixture was filtered and washed with ethyl acetate (200 mL×3). The filtrate was concentrated to afford a crude product. The crude product was purified by flash column chromatography over silica gel (eluent: petroleum ether/ethyl acetate from 100/0 to 30/70). The eluent was collected and the solvent was concentrated under reduced pressure to give the product as a yellow solid (7 g, 72% yield). $^1$H NMR (400 MHz, DMSO-d$_6$) δ ppm 2.71 (s, 3H), 8.31 (s, 2H), 8.90 (s, 1H). LC-MS: (ES, m/z): [M+1]$^+$ 264.0

D. 5-amino-6-methyl-2-(2H-1,2,3-triazol-2-yl)nicotinonitrile, 176d

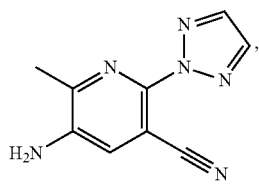

176d

Palladium diacetate (170 mg, 0.76 mmol) and (9,9-dimethyl-9H-xanthene-4,5-diyl)bis(diphenylphosphane) (438 mg, 0.76 mmol) were added to a solution of 5-bromo-6-methyl-2-(2H-1,2,3-triazol-2-yl)nicotinonitrile (2.0 g, 7.57 mmol), tert-butyl carbamate (1331 mg, 11.36 mmol) and cesium carbonate (7.40 g, 22.7 mmol) in dioxane under N$_2$ bubbling. The reaction was stirred at 120° C. overnight. The mixture was filtered and the filtrate was concentrated to give a crude product. The crude product was purified by flash column chromatography over silica gel (eluent: petroleum ether/ethyl acetate from 100/0 to 0/100). The eluent was collected and the solvent was concentrated under reduced pressure to give 5-amino-6-methyl-2-(2H-1,2,3-triazol-2-yl)nicotinonitrile as a yellow solid (300 mg, 18%), LC-MS: (ES, m/z): [M+1]$^+$ 200.8 and tert-butyl (5-cyano-2-methyl-6-(2H-1,2,3-triazol-2-yl)pyridin-3-yl)carbamate as a yellow solid (600 mg, 26%).

E. N-(5-cyano-2-methyl-6-(2H-1,2,3-triazol-2-yl)pyridin-3-yl)-1-(1-oxo-1,2-dihydroisoquinolin-5-yl)-5-(trifluoromethyl)-1H-pyrazole-4-carboxamide, Cpd 176

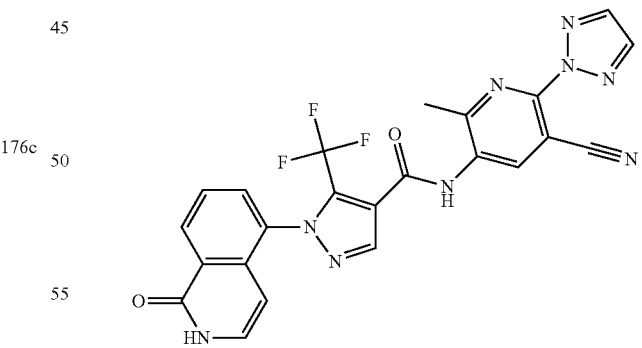

To a solution of 1-(1-oxo-1,2-dihydroisoquinolin-5-yl)-5-(trifluoromethyl)-1H-pyrazole-4-carboxylic acid (132 mg, 0.41 mmol) and 5-amino-6-methyl-2-(2H-1,2,3-triazol-2-yl)nicotinonitrile (90 mg, 0.45 mmol) and pyridine (129 mg, 1.64 mmol) in dichloromethane (20 mL) was added POCl$_3$ (125 mg, 0.82 mmol) dropwise. The mixture was stirred at room temperature for 2 h. Sat. NaHCO$_3$ solution (20 mL) was added to the mixture and the mixture was extracted with dichloromethane (20 mL×3). The combined organic layers were dried over Na₂SO₄, filtered and the filtrates were concentrated under reduced pressure to afford crude product as a yellow oil. The crude product was then purified by preparative HPLC (28% to 58% (v/v) CH₃CN and H₂O with 0.05% HCl) to afford the product as a yellow solid (65 mg, 31%). ¹H NMR (400 MHz, DMSO-d₆) δ ppm 2.64 (s, 3H), 5.66 (d, J=7.50 Hz, 1H), 7.24-7.31 (m, 1H), 7.66 (t, J=7.83 Hz, 1H), 7.93 (d, J=7.72 Hz, 1H), 8.29 (s, 2H) 8.42 (d, J=7.94 Hz, 1H), 8.51 (s, 1H), 8.66 (s, 1H), 10.64 (br s, 1H), 11.61 (br d, J=5.07 Hz, 1H). LC-MS: (ES, m/z): [M+1]⁺ 505.9

Example 177

N-(5-cyano-6-(4-(hydroxymethyl)-2H-1,2,3-triazol-2-yl)pyridin-3-yl)-1-(quinolin-5-yl)-5-(trifluoromethyl)-1H-pyrazole-4-carboxamide, Cpd 177

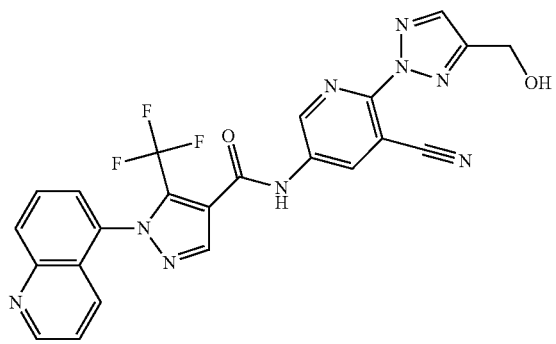 [SMILES: N#Cc1cc(NC(=O)c2cnn(-c3cccc4ncccc34)c2C(F)(F)F)cnc1-n1ncc(CO)n1]

A. methyl 2-(3-cyano-5-nitropyridin-2-yl)-2H-1,2,3-triazole-4-carboxylate, 177a

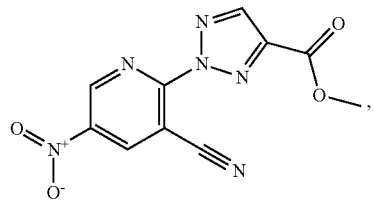

177a

Potassium carbonate (376.5 mg, 2.72 mmol) was added to a solution of 2-chloro-5-nitronicotinonitrile (500 mg, 2.72 mmol) and methyl 1H-1,2,3-triazole-4-carboxylate (415.5 mg, 3.27 mmol) in MeCN (10 mL). The mixture was reacted at rt for 3 h, filtered and the resultant residue was washed with EtOAc (50 mL×3). The filtrates were concentrated under reduced pressure. EtOAc (10 mL) was added, the mixture stirred at rt for 0.5 h, filtered, and the resultant solid was collected and dried under reduced pressure to afford the product as a yellow solid (550 mg, 73.6% yield).

B. methyl 2-(5-amino-3-cyanopyridin-2-yl)-2H-1,2,3-triazole-4-carboxylate, 177b

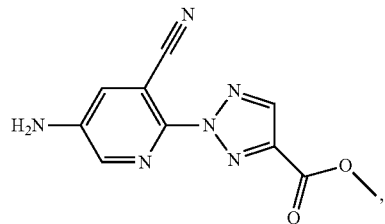

177b

Methyl 2-(3-cyano-5-nitropyridin-2-yl)-2H-1,2,3-triazole-4-carboxylate (550 mg, 2.0 mmol) was dissolved in THF (20 mL) and methanol (10 mL), iron (1.12 g, 20.0 mmol), NH₄Cl (1.07 g, 20.0 mmol) and H₂O (5 mL) were added, and the reaction mixture was stirred at 60° C. for 2 h. The mixture was filtered through a pad of diatomaceous earth and the pad was washed with EtOAc (20 mL×3). The combined filtrates were concentrated under reduced pressure to afford crude product which was purified by flash column chromatography over silica gel (petroleum ether/ethyl acetate from 10:1 to 1:1). The desired fraction was collected and the solvent was concentrated under reduced pressure to afford the product as a yellow solid (180 mg, 31.2% yield). ¹H NMR (400 MHz, DMSO-d₆) δ ppm 8.70-8.54 (m, 1H), 8.10 (d, J=2.9 Hz, 1H), 7.48 (d, J=2.6 Hz, 1H), 6.42 (s, 2H), 3.89 (s, 3H). LC-MS: (ES, m/z): [M+1]⁺ 245.1

C. methyl 2-(3-cyano-5-(1-(quinolin-5-yl)-5-(trifluoromethyl)-1H-pyrazole-4-carboxamido)pyridin-2-yl)-2H-1,2,3-triazole-4-carboxylate, 177c

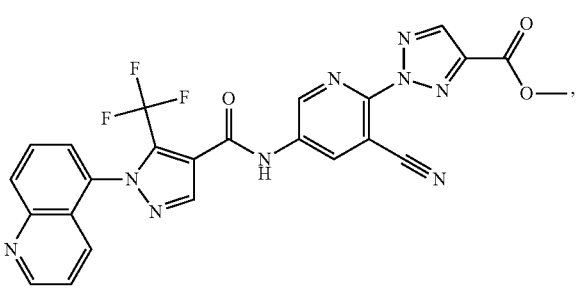

177c

Methyl 2-(3-cyano-5-nitropyridin-2-yl)-2H-1,2,3-triazole-4-carboxylate (155 mg, 0.63 mmol), 1-(quinolin-5-yl)-5-(trifluoromethyl)-1H-pyrazole-4-carboxylic acid, 3b (230 mg, 0.75 mmol) and pyridine (297 mg, 3.76 mmol) were added to DCM (10 mL), POCl₃ (384 mg, 2.509 mmol) was added dropwise. The reaction mixture was stirred at rt for 4 h. Sat. NaHCO₃ was added to adjust the pH to 9-10, water (30 mL) was added, and the mixture was extracted with CH₂Cl₂ (30 mL×3). The combined organic layers were dried over Na₂SO₄, filtered and the filtrates were concentrated under reduced pressure to afford product as a yellow solid (450 mg, 98.7% yield). LC-MS: (ES, m/z): [M+1]⁺ 533.9

D. N-(5-cyano-6-(4-(hydroxymethyl)-2H-1,2,3-triazol-2-yl)pyridin-3-yl)-1-(quinolin-5-yl)-5-(trifluoromethyl)-1H-pyrazole-4-carboxamide, Cpd 177

A. 1-(3-chloro-5-(1-(1-methoxyisoquinolin-5-yl)-5-(trifluoromethyl)-1H-pyrazole-4-carboxamido)pyridin-2-yl)-1H-1,2,3-triazole-5-carboxylic acid, 178a

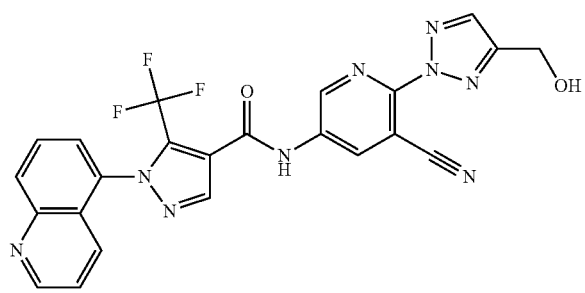 [SMILES: N#Cc1cc(NC(=O)c2cnn(-c3cccc4ncccc34)c2C(F)(F)F)cnc1-n1ncc(CO)n1]

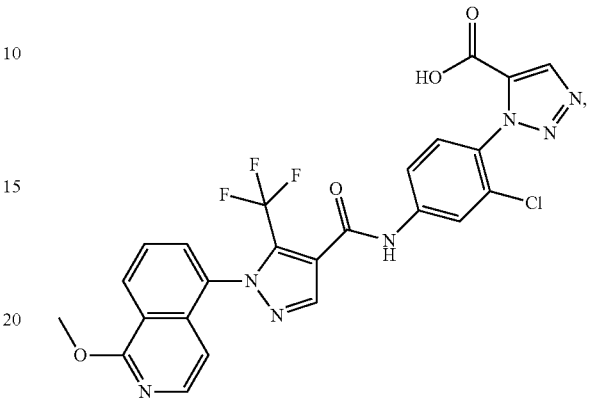

178a

Methyl 2-(3-cyano-5-(1-(quinolin-5-yl)-5-(trifluoromethyl)-1H-pyrazole-4-carboxamido)pyridin-2-yl)-2H-1,2,3-triazole-4-carboxylate (400 mg, 730% pure, 0.55 mmol) was dissolved in THF (10 mL) and the reaction was stirred at 0° C., then LiAlH$_4$ (167 mg, 4.4 mmol) was added slowly. The reaction mixture was stirred at 40° C. for 10 h. Water (10 mL) was added and the mixture extracted with EtOAc (10 mL×2). The combined organic layers were dried over Na$_2$SO$_4$, filtered and the filtrate was concentrated under reduced pressure to afford the crude product as a yellow oil which was purified by preparative high-performance liquid chromatography. The pure fractions were collected and the solvent was concentrated under reduced pressure, lyophilized to dryness to give product as a light yellow solid (20 mg, 6.9% yield). $^1$H NMR (400 MHz, METHANOL-d$_4$) δ ppm 9.27 (d, J=3.7 Hz, 1H), 9.07 (br s, 1H), 8.89 (d, J=2.4 Hz, 1H), 8.51-8.43 (m, 2H), 8.39 (d, J=8.4 Hz, 1H), 8.24 (t, J=8.2 Hz, 1H), 8.13-8.07 (m, 2H), 8.03 (dd, J=5.1, 8.6 Hz, 1H), 4.82 (s, 2H). LC-MS: (ES, m/z): [M+1]$^+$ 506.1

Lithium hydroxide (139 mg, 5.8 mmol) was added to a solution of methyl 1-(3-chloro-5-(1-(1-methoxyisoquinolin-5-yl)-5-(trifluoromethyl)-1H-pyrazole-4-carboxamido)pyridin-2-yl)-1H-1,2,3-triazole-5-carboxylate (750 mg, 1.16 mmol) in THF/H$_2$O (2:1, 6 mL), the mixture was reacted at 25° C. for 2 h. The solvent was concentrated under reduced pressure, 1M HCl solution was added to the mixture to adjust the pH to ~5, and a solid formed. The solid was collected by filtration and dried to afford the product (600 mg, 88.7% yield). LC-MS: (ES, m/z): [M+1]$^+$ 559.0

B. tert-butyl (1-(3-chloro-5-(1-(1-methoxyisoquinolin-5-yl)-5-(trifluoromethyl)-1H-pyrazole-4-carboxamido)pyridin-2-yl)-1H-1,2,3-triazol-5-yl)carbamate, 178b Example 178

N-(6-(5-amino-1H-1,2,3-triazol-1-yl)-5-chloropyridin-3-yl)-1-(1-oxo-1,2-dihydroisoquinolin-5-yl)-5-(trifluoromethyl)-1H-pyrazole-4-carboxamide, Cpd 178

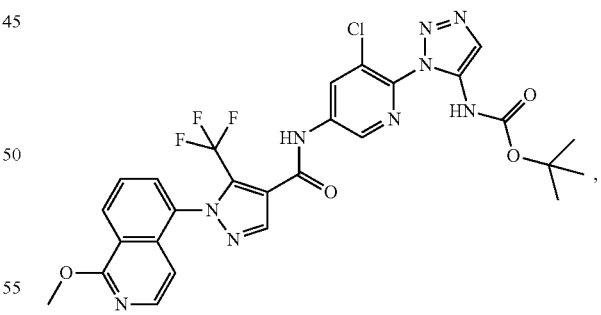

178b

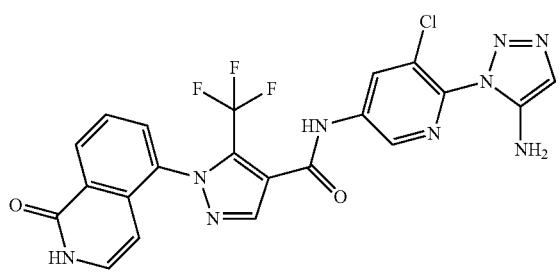 [SMILES: Nc1cnnn1-c1ncc(NC(=O)c2cnn(-c3cccc4c(=O)[nH]ccc34)c2C(F)(F)F)cc1Cl]

To a solution of 1-(3-chloro-5-(1-(1-methoxyisoquinolin-5-yl)-5-(trifluoromethyl)-1H-pyrazole-4-carboxamido)pyridin-2-yl)-1H-1,2,3-triazole-5-carboxylic acid (550 mg, 0.94 mmol) in tert-butanol (10 mL) under N$_2$ was added DPPA (311 mg, 1.13 mmol) and TEA (286 mg, 2.83 mmol). The reaction mixture was stirred at 80° C. overnight, sat. NaHCO$_3$ (20 mL) was added, and the mixture was extracted with EtOAc (30 mL×2). The combined organic layers were dried over Na$_2$SO$_4$, filtered and the filtrates were concentrated under reduced pressure to afford the crude product as a brown oil. The crude product was purified by column chromatography over silica gel (petroleum ether/ethyl acetate=2:1 to ethyl acetate). The desired fractions were collected and the solvent was concentrated under reduced pressure to give the product as a yellow solid (180 mg, 27.9% yield). LC-MS: (ES, m/z): [M+1]⁺ 630.2

C. N-(6-(5-amino-1H-1,2,3-triazol-1-yl)-5-chloro-pyridin-3-yl)-1-(1-oxo-1,2-dihydroisoquinolin-5-yl)-5-(trifluoromethyl)-1H-pyrazole-4-carboxamide, Cpd 178

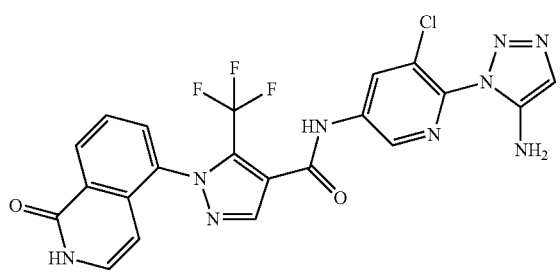 [SMILES: Nc1cnnn1-c1ncc(NC(=O)c2cnn(-c3cccc4c(=O)[nH]ccc34)c2C(F)(F)F)cc1Cl]

tert-Butyl (1-(3-chloro-5-(1-(1-methoxyisoquinolin-5-yl)-5-(trifluoromethyl)-1H-pyrazole-4-carboxamido)pyridin-2-yl)-1H-1,2,3-triazol-5-yl)carbamate (180 mg, 0.26 mmol) and concentrated HCl (2 mL) was added isopropanol (4 mL) and stirred at 60° C. for 2 h. The mixture was concentrated under reduced pressure to afford a crude product as a yellow oil, which was purified by preparative high-performance liquid chromatography. The pure fractions were collected and the organic solvent was concentrated under reduced pressure, lyophilized to dryness to give the product as a white solid (31.2 mg, 22.7% yield). ¹H NMR (400 MHz, DMSO-d₆) δ ppm 5.63 (d, J=7.28 Hz, 1H), 7.26 (t, J=6.73 Hz, 1H), 7.64 (t, J=7.72 Hz, 1H), 7.83 (s, 1H), 7.92 (d, J=7.94 Hz, 1H), 8.41 (d, J=8.16 Hz, 1H), 8.56 (s, 1H), 8.63 (d, J=1.76 Hz, 1H), 8.84 (d, J=1.76 Hz, 1H), 11.30 (s, 1H), 11.61 (br d, J=5.29 Hz, 1H). LC-MS: (ES, m/z): [M+1]⁺ 515.9

Example 179

N-(5-chloro-6-(4-cyano-2H-1,2,3-triazol-2-yl)pyridin-3-yl)-1-(quinolin-5-yl)-5-(trifluoromethyl)-1H-pyrazole-4-carboxamide, Cpd 179

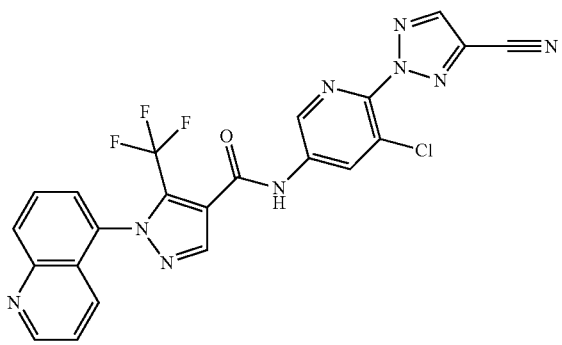 [SMILES: N#Cc1cnn(-c2ncc(NC(=O)c3cnn(-c4cccc5ncccc45)c3C(F)(F)F)cc2Cl)n1]

POCl₃ (348.6 mg, 2.27 mmol) was added to a solution of 2-(3-chloro-5-(1-(quinolin-5-yl)-5-(trifluoromethyl)-1H-pyrazole-4-carboxamido)pyridin-2-yl)-2H-1,2,3-triazole-4-carboxamide (120 mg, 0.23 mmol) in CH₃C₁ (1 mL). The mixture was reacted at 80° C. for 1 h, 10% NaHCO₃ (10 mL) was added, and the mixture extracted with CH₂Cl₂ (15 mL×2). The combined organic layers were dried over Na₂SO₄, filtered and the filtrates were concentrated under reduced pressure to afford the crude product as a yellow oil. The crude product was purified by preparative high-performance liquid chromatography. The pure fractions were collected and the solvent was concentrated under reduced pressure, lyophilized to dryness to give product as a white solid (82 mg, 69.7% yield). ¹H NMR (400 MHz, DMSO-d₆) δ ppm 7.72 (br s, 2H), 7.93-8.08 (m, 2H), 8.37 (br d, J=8.03 Hz, 1H), 8.69 (br s, 1H), 8.79 (br d, J=2.01 Hz, 1H), 8.93-9.04 (m, 2H), 9.10 (br s, 1H), 11.53 (br s, 1H). LC-MS: (ES, m/z): [M+1]⁺ 515.9

Example 180

1-(1-aminoisoquinolin-4-yl)-N-(5-chloro-2-methyl-6-(2H-1,2,3-triazol-2-yl)pyridin-3-yl)-5-(trifluoromethyl)-1H-pyrazole-4-carboxamide, Cpd 180

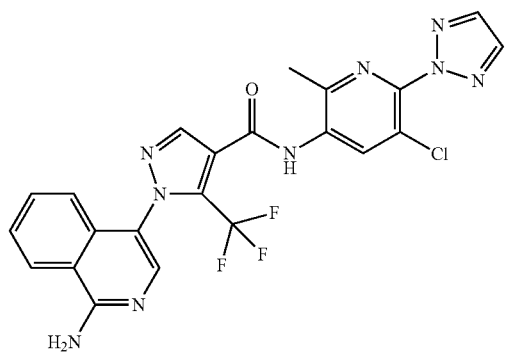 [SMILES: Cc1nc(-n2nccn2)c(Cl)cc1NC(=O)c1cnn(-c2cnc(N)c3ccccc23)c1C(F)(F)F]

A. 4-hydrazinylisoquinoline, 180a

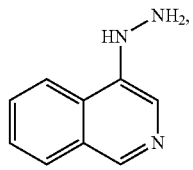

To a stirring solution of isoquinolin-4-amine (15 g, 104.04 mmol) in HCl (150 mL, 5 mol/L) at 0° C. was added a solution of sodium nitrite (10.77 g, 156.06 mmol) in water (15 mL) at below 0° C. The reaction mixture was stirred at 0° C. for 30 min and a solution of SnCl₂.2H₂O (58.69 g, 260.10 mmol) dissolved in HCl (27 mL, 12 mol/L) was added dropwise. The mixture was stirred at room temperature for 12 h. The mixture was adjusted to pH 12-14 with 20% aqueous sodium hydroxide. The mixture was extracted with CH₂Cl₂ (1000 mL×3). The organic layer was dried (Na₂SO₄), filtered, and the filtrate concentrated under reduced pressure to afford crude 180a (15.8 g, 95.4% yield) as a brown solid, used directly for the next step.

B. ethyl 1-(isoquinolin-4-yl)-5-(trifluoromethyl)-1H-pyrazole-4-carboxylate, 180b

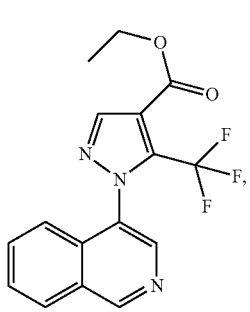

180b

A solution of 4-hydrazinylisoquinoline, 180a (15.8 g, 99.25 mmol), ethyl 2-(ethoxymethylene)-4,4,4-trifluoro-3-oxobutanoate (35.758 g, 148.88 mmol), triethylamine (30.074 g, 297.76 mmol) in EtOH (200 mL) was stirred at 80° C. for 12 h. The mixture was concentrated under reduced pressure. The crude product was purified by column chromatography over silica gel (petroleum ether/ethyl acetate from 100:1 to 20:1). The desired fractions were collected and the solvent was concentrated under reduced pressure to afford 180b (16 g, 41.8% yield) as a yellow solid. LCMS (ESI) m/z M+1: 336.0.

C. 4-(4-(ethoxycarbonyl)-5-(trifluoromethyl)-1H-pyrazol-1-yl)isoquinoline 2-oxide, 180c

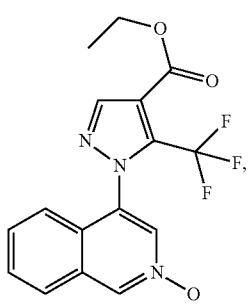

180c

A solution of ethyl 1-(isoquinolin-4-yl)-5-(trifluoromethyl)-1H-pyrazole-4-carboxylate, 180b (16 g, 41.44 mmol), 3-chlorobenzoperoxoic acid (26.817 g, 124.32 mmol) in CH$_2$Cl$_2$ (300 mL) was stirred at rt for 16 h. The reaction mixture was quenched with sat. NaHCO$_3$ (1000 mL) and the mixture was extracted with ethyl acetate (500 mL×3). The organic layers were combined, dried over Na$_2$SO$_4$, filtered and the filtrate concentrated under reduced pressure to afford 180c (11 g, 74.4% yield) as a yellow solid. LCMS (ESI) m/z M+1: 352.0.

D. ethyl 1-(1-chloroisoquinolin-4-yl)-5-(trifluoromethyl)-1H-pyrazole-4-carboxylate, 180d

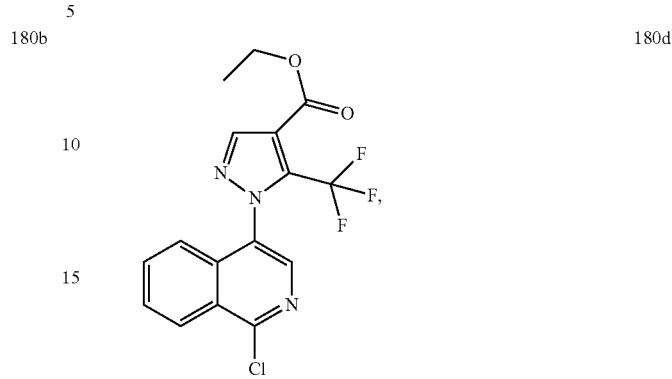

180d 4-(4-(ethoxycarbonyl)-5-(trifluoromethyl)-1H-pyrazol-1-yl)isoquinoline 2-oxide, 180c (11 g, 30.81 mmol) was added to a solution of POCl$_3$ (20 mL, 214.57 mmol) in CHCl$_3$ (40 mL). The mixture was stirred at 80° C. for 18 h. The mixture was diluted with water (1000 mL) and extracted with ethyl acetate (300 mL×3). The combined organic layers were dried (MgSO$_4$), filtered, and concentrated. The crude product was purified by column chromatography over silica gel (petroleum ether/ethyl acetate from 20:1 to 5:1). The desired fractions were collected and the solvent was concentrated under reduced pressure to afford 180d (10 g, 70.6% yield) as a white solid. LCMS (ESI) m/z M+1: 370.0. $^1$H NMR (400 MHz, CHLOROFORM-d) δ ppm 8.44-8.53 (m, 1H), 8.37 (s, 1H), 8.29 (s, 1H), 7.79-7.87 (m, 2H), 7.27-7.32 (m, 1H), 4.42 (q, J=7.20 Hz, 2H), 1.42 (t, J=7.17 Hz, 3H)

E. 1-(1-chloroisoquinolin-4-yl)-5-(trifluoromethyl)-1H-pyrazole-4-carboxylic acid, 180e

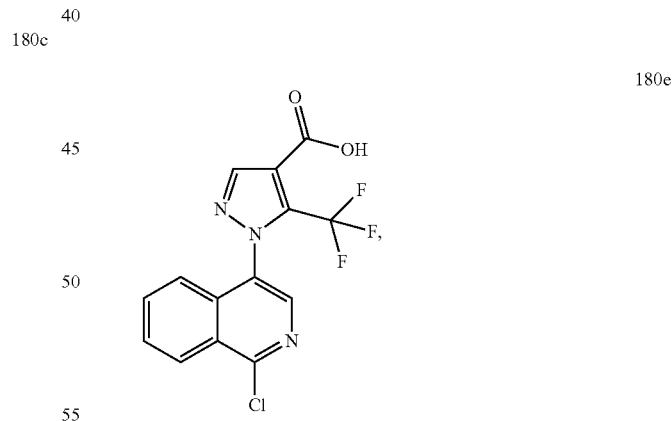

180e

LiOH (1.825 g, 43.49 mmol) was added to a solution of ethyl 1-(1-chloroisoquinolin-4-yl)-5-(trifluoromethyl)-1H-pyrazole-4-carboxylate, 180d (10 g, 21.75 mmol), THF (100 mL) in water (100 mL). The mixture was stirred at rt for 1 h. The mixture was added 5% KHSO$_4$ to adjust pH 3-4. Water (1000 mL) and ethyl acetate (1000 mL) were added to the mixture. The organic layer was washed with brine (500 mL), dried over MgSO$_4$ and concentrated under reduced pressure to afford 180e (9.7 g, >100% yield) as a white solid which was used directly for the next step. LCMS (ESI) m/z M+1: 341.9.

F. N-(5-chloro-2-methyl-6-(2H-1,2,3-triazol-2-yl)pyridin-3-yl)-1-(1-chloroisoquinolin-4-yl)-5-(trifluoromethyl)-1H-pyrazole-4-carboxamide, 180f

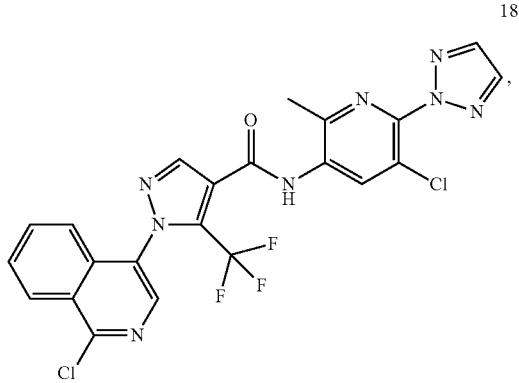

180f

POCl$_3$ (302.082 mg, 1.97 mmol) was added to a solution of 1-(1-chloroisoquinolin-4-yl)-5-(trifluoromethyl)-1H-pyrazole-4-carboxylic acid, 180e (350 mg, 0.99 mmol), 5-chloro-2-methyl-6-(2H-1,2,3-triazol-2-yl)pyridin-3-amine (206.504 mg, 0.99 mmol), pyridine (194.795 mg, 2.46 mmol) in CH$_2$Cl$_2$ (10 mL). The mixture was stirred at rt for 2 h. Water (50 mL) and CH$_2$Cl$_2$ (50 mL) were added to the mixture. The organic layer was washed with brine (50 mL), dried over MgSO$_4$, filtered, and the filtrate concentrated under reduced pressure. The crude product was purified by column chromatography over silica gel (petroleum ether/ethyl acetate from 20:1 to 0:100). The desired fractions were collected and the solvent was concentrated under reduced pressure to afford 180f (310 mg, 58.2% yield) as a white solid. LCMS (ESI) m/z M+1: 532.9.

G. 1-(1-aminoisoquinolin-4-yl)-N-(5-chloro-2-methyl-6-(2H-1,2,3-triazol-2-yl)pyridin-3-yl)-5-(trifluoromethyl)-1H-pyrazole-4-carboxamide, Cpd 180

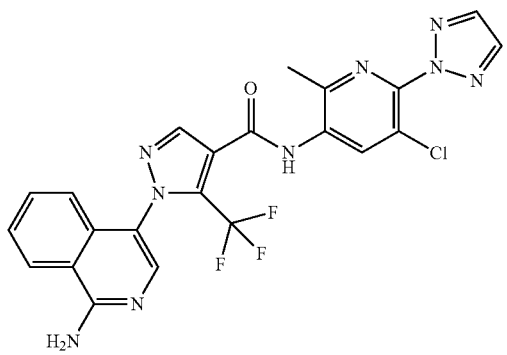 [SMILES: Cc1nc(-n2nccn2)c(Cl)cc1NC(=O)c1cnn(-c2cnc(N)c3ccccc23)c1C(F)(F)F]

A solution of N-(5-chloro-2-methyl-6-(2H-1,2,3-triazol-2-yl)pyridin-3-yl)-1-(1-chloroisoquinolin-4-yl)-5-(trifluoromethyl)-1H-pyrazole-4-carboxamide, 180f (290 mg, 0.54 mmol), NH$_3$.H$_2$O (3 mL) in dioxane (3 mL) was stirred at 120° C. for 5 h. The mixture was concentrated under reduced pressure to afford the crude product, which was purified by preparative HPLC (20% to 50% (v/v) CH$_3$CN and H$_2$O with 0.05% HCl). The pure fractions were collected and the solvent was concentrated under reduced pressure. The aqueous layer was lyophilized to dryness to afford the title compound (100.5 mg, 34.1% yield) as a yellow solid. LCMS (ESI) m/z M+1: 513.9; $^1$H NMR (400 MHz, DMSO-d$_6$) δ ppm 10.71 (s, 1H), 9.01-9.45 (m, 2H), 8.66 (d, J=8.60 Hz, 1H), 8.57 (s, 1H), 8.39 (s, 1H), 8.25 (s, 1H), 8.16 (s, 2H), 7.92-8.00 (m, 1H), 7.82 (t, J=7.61 Hz, 1H), 7.04 (d, J=8.16 Hz, 1H), 2.53 (s, 3H).

Example 181

N-(6-(5-amino-1-methyl-1H-pyrazol-3-yl)-5-cyanopyridin-3-yl)-1-(quinolin-5-yl)-5-(trifluoromethyl)-1H-pyrazole-4-carboxamide, Cpd 181

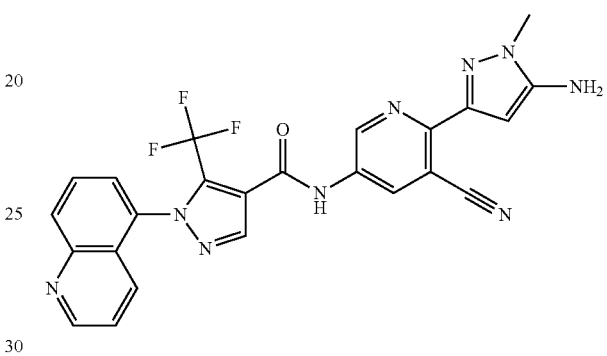

To a solution of 3-(3-cyano-5-(1-(quinolin-5-yl)-5-(trifluoromethyl)-1H-pyrazole-4-carboxamido)pyridin-2-yl)-1-methyl-1H-pyrazole-5-carboxylic acid (165 mg, 0.31 mmol) in DMF (10 mL) under N$_2$ was added DPPA (92.2 mg, 0.34 mmol) and TEA (92.5 mg, 0.91 mmol). The reaction mixture was stirred at 80° C. for 16 h and concentrated. The residue was purified by preparative high-performance liquid chromatography. The pure fractions were collected, the organic solvent was concentrated under reduced pressure and lyophilized to dryness to give the product as a yellow solid (35 mg, 22.1% yield). $^1$H NMR (400 MHz, DMSO-d$_6$) δ ppm 11.14 (1H, s), 9.00-9.07 (2H, m), 8.54-8.61 (2H, m), 8.32 (1H, d, J=8.82 Hz), 7.87-7.99 (2H, m), 7.64-7.70 (1H, m), 7.57-7.63 (1H, m), 5.93 (1H, s), 3.62 (3H, s). LC-MS: (ES, m/z): [M+1]$^+$ 504.0

Example 182

N-(5-chloro-6-(4-(hydroxymethyl)-1H-pyrazol-1-yl)pyridin-3-yl)-1-(1-oxo-1,2-dihydroisoquinolin-5-yl)-5-(trifluoromethyl)-1H-pyrazole-4-carboxamide, Cpd 182

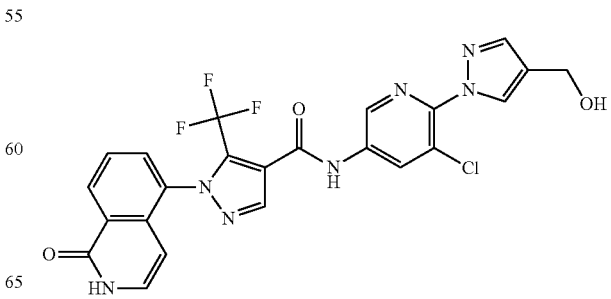

A. ethyl 1-(3-chloro-5-(1-(1-oxo-1,2-dihydroisoquinolin-5-yl)-5-(trifluoromethyl)-1H-pyrazole-4-carboxamido)pyridin-2-yl)-1H-pyrazole-4-carboxylate, 182a

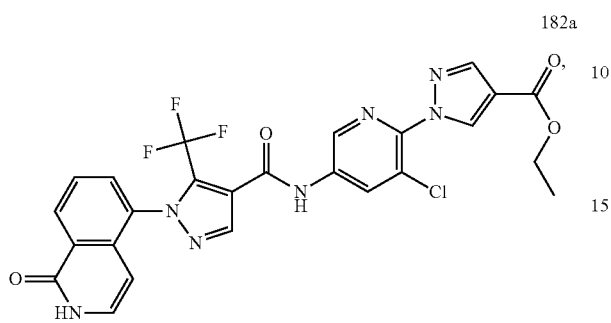

182a

To a solution of 1-(1-oxo-1,2-dihydroisoquinolin-5-yl)-5-(trifluoromethyl)-1H-pyrazole-4-carboxylic acid (556 mg, 1.92 mmol) and ethyl 1-(5-amino-3-chloropyridin-2-yl)-1H-pyrazole-4-carboxylate (559 mg, 2.06 mmol) and pyridine (816 mg, 10.3 mmol) in dichloromethane (30 mL) was added POCl₃ (791 mg, 5.16 mmol) dropwise. The mixture was stirred at room temperature for 3 h. The reaction mixture was concentrated under reduced pressure to afford the crude product as a yellow oil which was purified by preparative high-performance liquid chromatography to afford the product as a yellow solid (470 mg, 47.8%). LC-MS: (ES, m/z): [M+1]⁺ 572.0

D. N-(5-chloro-6-(4-(hydroxymethyl)-1H-pyrazol-1-yl)pyridin-3-yl)-1-(1-oxo-1,2-dihydroisoquinolin-5-yl)-5-(trifluoromethyl)-1H-pyrazole-4-carboxamide, Cpd 182

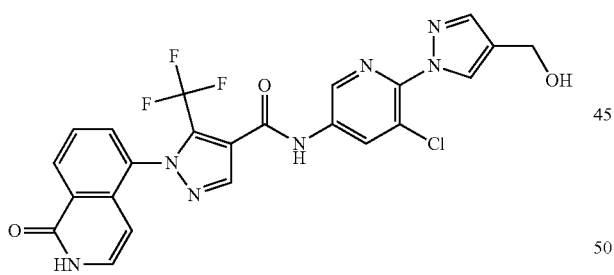

Ethyl 1-(3-chloro-5-(1-(1-oxo-1,2-dihydroisoquinolin-5-yl)-5-(trifluoromethyl)-1H-pyrazole-4-carboxamido)pyridin-2-yl)-1H-pyrazole-4-carboxylate (470 mg, 0.82 mmol) was dissolved in THF (25 mL) and cooled to 0° C. LiAlH₄ (156 mg, 4.11 mmol) was added and the reaction mixture was stirred at 0° C. for 2 h. The reaction mixture was cooled to 0° C., quenched by addition of 0.15 mL of H₂O, followed by 0.15 mL of 15% aqueous NaOH and 0.45 mL of H₂O. CH₂Cl₂/MeOH (10/1, 100 mL) and Na₂SO₄ was added, stirred at room temperature for 0.5 h, and the mixture was filtered through diatomaceous earth. The resultant residue was washed with CH₂Cl₂/MeOH (10/1, 100 mL×2). The filtrate was concentrated to dryness to give crude product which was purified by preparative high-performance liquid chromatography. The pure fractions were collected, concentrated under reduced pressure and lyophilized to dryness to afford the product (150 mg, 34.4% yield). ¹H NMR (400 MHz, METHANOL-d₄) δ ppm 8.75 (br s, 1H), 8.62 (d, J=2.4 Hz, 1H), 8.56 (dd, J=0.8, 8.0 Hz, 1H), 8.34 (s, 1H), 8.15 (s, 1H), 7.88-7.83 (m, 1H), 7.81 (s, 1H), 7.74-7.65 (m, 1H), 7.26-7.22 (m, 1H), 5.95-5.90 (m, 1H), 4.62 (s, 2H). LC-MS: (ES, m/z): [M+1]⁺ 529.9

Example 183

N-(6-(5-amino-1-methyl-1H-pyrazol-3-yl)-5-chloropyridin-3-yl)-1-(1-oxo-1,2-dihydroisoquinolin-5-yl)-5-(trifluoromethyl)-1H-pyrazole-4-carboxamide, Cpd 183

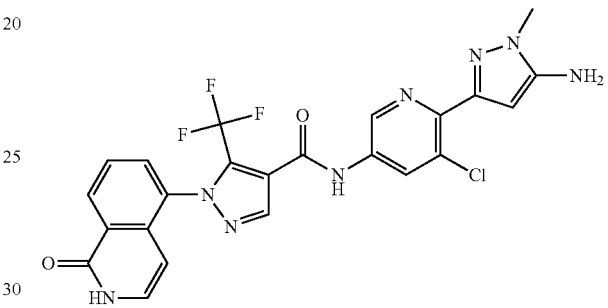

A. methyl 3-hydroxy-1-methyl-1H-pyrazole-5-carboxylate, 183a

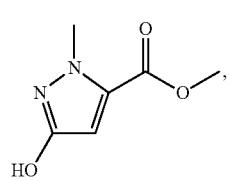

183a

TEA (44.2 mL, 316.7 mmol) was added to a solution of methylhydrazine sulfate (20.3 g, 140.7 mmol) in H₂O (100 mL) and MeOH (200 mL) at room temperature, and the mixture was stirred for 0.5 h at rt. Dimethyl but-2-ynedioate (20 g, 140.7 mmol) was added to the mixture, the mixture was stirred for 18 h at 70° C., followed by stirring at rt for 36 h. The reaction mixture was filtered, and the filtrate concentrated under reduced pressure to give the product as a white solid (3.65 g, 16.6% yield).

B. methyl 1-methyl-3-(((trifluoromethyl)sulfonyl)oxy)-1H-pyrazole-5-carboxylate, 183b

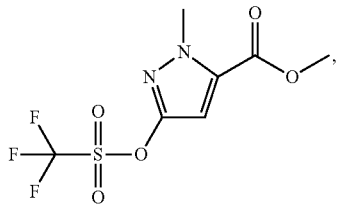

Methyl 3-hydroxy-1-methyl-1H-pyrazole-5-carboxylate (3.65 g, 23.4 mmol) was dissolved in $CH_2Cl_2$ (70 mL) and the reaction was cooled to −5° C. TEA (6.52 mL, 46.8 mmol) and trifluoromethanesulfonic anhydride (7.87 mL, 46.8 mmol) were added to the mixture, and the mixture was stirred at rt for 1 h. The mixture was then poured into 60 mL $H_2O$, the organic layer was separated, and the aqueous layer was extracted with $CH_2Cl_2$ (2×100 mL). The combined extracts were washed with water. The combined organic layers were dried ($MgSO_4$), filtered, and the filtrate concentrated to a brown oil. The brown oil was purified by column chromatography over silica gel (petroleum ether/ethyl acetate=10: 1 to petroleum ether/ethyl acetate=1:1). The desired fractions were collected and the solvent was concentrated under reduced pressure to give the product as a yellow oil (6 g, 86.1% yield). LC-MS: (ES, m/z): $[M+1]^+$ 288.9

C. methyl 1-methyl-3-(4,4,5,5-tetramethyl-1,3,2-dioxaborolan-2-yl)-1H-pyrazole-5-carboxylate, 183

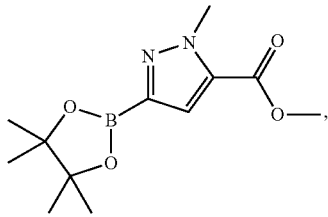

Methyl 1-methyl-3-(((trifluoromethyl)sulfonyl)oxy)-1H-pyrazole-5-carboxylate (3.0 g, 10.07 mmol), bis(pinacolate) diboro (2.81 g, 11.08 mmol), and potassium acetate (2.97 g, 30.21 mmol) were added to dioxane (20 mL), [1,1'-Bis(diphenylphosphino) ferrocene]dichloropalladium(II) (1:1) (412 mg, 0.50 mmol), dppf (279 mg, 0.50 mmol) were added to the mixture under $N_2$, and the reaction mixture was stirred at 100° C. for 16 h under $N_2$. The reaction mixture was filtered, and the filtrates were concentrated under reduced pressure to afford a black oil which was purified by flash column chromatography over silica gel (petroleum ether/ethyl acetate from 100/0 to 60/40). The desired fractions were collected and the solvent was concentrated under reduced pressure to afford the product as a white solid (2.5 g, 93.3% yield).

D. methyl 3-(5-amino-3-chloropyridin-2-yl)-1-methyl-1H-pyrazole-5-carboxylate, 183d

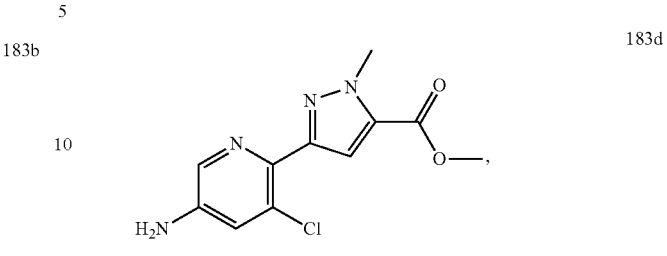

Methyl 1-methyl-3-(4,4,5,5-tetramethyl-1,3,2-dioxaborolan-2-yl)-1H-pyrazole-5-carboxylate (1.0 g, 3.76 mmol), 5,6-dichloropyridin-3-amine (0.61 g, 3.76 mmol) and potassium carbonate (1.56 g, 11.3 mmol) were added to dioxane/water (9:1, 20 mL) and the reaction was purged with $N_2$. [1,1'-bis(diphenylphosphino)ferrocene] dichloropalladium (II) (1:1) (0.31 g, 0.38 mmol) was added and the reaction stirred at 100° C. for 12 h. The reaction mixture was filtered, the filtrates were concentrated under reduced pressure to afford a black oil which was purified by flash column chromatography over silica gel (petroleum ether/ethyl acetate from 100/0 to 0/100). The desired fractions were collected and the solvent was concentrated under reduced pressure to afford the product as a black solid (560 mg, 46.5% yield). LC-MS: (ES, m/z): $[M+1]^+$ 267.0

E. methyl 3-(3-chloro-5-(1-(1-methoxyisoquinolin-5-yl)-5-(trifluoromethyl)-1H-pyrazole-4-carboxamido)pyridin-2-yl)-1-methyl-1H-pyrazole-5-carboxylate, 183e

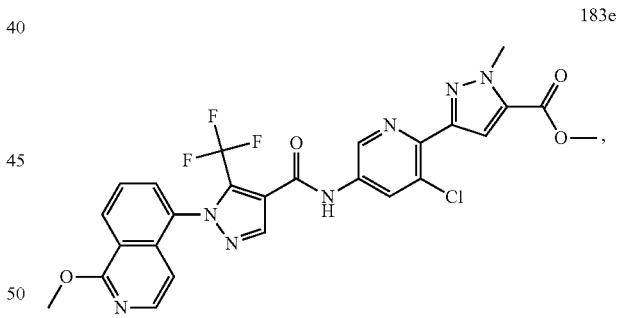

To a solution of 1-(1-methoxyisoquinolin-5-yl)-5-(trifluoromethyl)-1H-pyrazole-4-carboxylic acid (315.4 mg, 0.94 mmol), methyl 3-(5-amino-3-chloropyridin-2-yl)-1-methyl-1H-pyrazole-5-carboxylate (300 mg, 0.94 mmol) and pyridine (0.38 mL, 4.68 mmol) in $CH_2Cl_2$ (10 mL) was added $POCl_3$ (0.34 mL, 3.74 mmol) dropwise. The mixture was stirred at 25° C. for 2 h, 20 mL sat. $NaHCO_3$ was added and the mixture was extracted with $CH_2Cl_2$ (30 mL×2). The combined organic layers were dried over $Na_2SO_4$, filtered and the filtrates were concentrated under reduced pressure to afford crude product as a brown oil. The crude product was then purified by column chromatography over silica gel (petroleum ether/ethyl acetate=1:0 to ethyl acetate) to afford product as a brown oil (340 mg, 48.1%). LC-MS: (ES, m/z): $[M+1]^+$ 586.1

F. 3-(3-chloro-5-(1-(1-methoxyisoquinolin-5-yl)-5-(trifluoromethyl)-1H-pyrazole-4-carboxamido)pyridin-2-yl)-1-methyl-1H-pyrazole-5-carboxylic acid, 183f

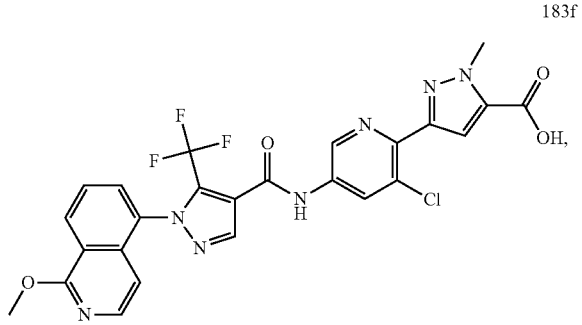 [SMILES: COc1nccc2c(-n3ncc(C(=O)Nc4cnc(-c5cc(C(=O)O)n(C)n5)c(Cl)c4)c3C(F)(F)F)cccc12]

183f

Sodium hydroxide (27.0 mg, 0.67 mmol) was added to a solution of methyl 3-(3-chloro-5-(1-(1-methoxyisoquinolin-5-yl)-5-(trifluoromethyl)-1H-pyrazole-4-carboxamido)pyridin-2-yl)-1-methyl-1H-pyrazole-5-carboxylate (340 mg, 0.45 mmol) in THF/H₂O (3:1, 8 mL), the mixture was stirred at room temperature for 3 h. The solvent was concentrated under reduced pressure and water (10 mL) was added to the mixture. The mixture was adjusted to pH 5 using 1M HCl, and extracted with ethyl acetate (20 mL×3). The combined organic layers were washed with brine, dried over anhydrous MgSO₄, filtered, the filtrates were concentrated under reduced pressure to afford product as a brown oil (250 mg, 78.4% yield). LC-MS: (ES, m/z): [M+1]⁺ 572.0

G. tert-butyl (3-(3-chloro-5-(1-(1-methoxyisoquinolin-5-yl)-5-(trifluoromethyl)-1H-pyrazole-4-carboxamido)pyridin-2-yl)-1-methyl-1H-pyrazol-5-yl)carbamate, 183g

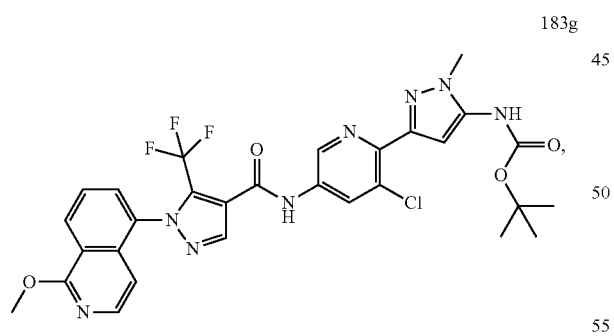

183g

To a solution of 3-(3-chloro-5-(1-(1-methoxyisoquinolin-5-yl)-5-(trifluoromethyl)-1H-pyrazole-4-carboxamido)pyridin-2-yl)-1-methyl-1H-pyrazole-5-carboxylic acid (200 mg, 0.28 mmol) in tert-butanol (8 mL) under N2 was added DPPA (85.4 mg, 0.31 mmol) and TEA (85.6 mg, 0.85 mmol), then the reaction mixture was stirred at 80° C. for 5 h. The solvent was removed under reduced pressure to give the crude product as a brown oil. The crude product was purified by column chromatography over silica gel (petroleum ether/ethyl acetate=1:0 to ethyl acetate). The desired fractions were collected and the solvent was concentrated under reduced pressure to give the product as a brown oil (150 mg, 78.2% yield). LC-MS: (ES, m/z): [M+1]⁺ 643.1

H. N-(6-(5-amino-1-methyl-1H-pyrazol-3-yl)-5-chloropyridin-3-yl)-1-(1-oxo-1,2-dihydroisoquinolin-5-yl)-5-(trifluoromethyl)-1H-pyrazole-4-carboxamide, Cpd 183

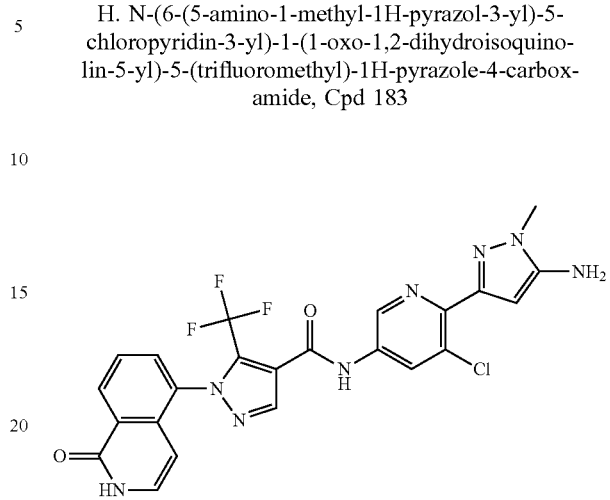

Concentrated HCl (2 mL) was added to a solution of tert-butyl (3-(3-chloro-5-(1-(1-methoxyisoquinolin-5-yl)-5-(trifluoromethyl)-1H-pyrazole-4-carboxamido)pyridin-2-yl)-1-methyl-1H-pyrazol-5-yl)carbamate (120 mg, 0.18 mmol) in isopropanol (4 mL), then the mixture was stirred at rt for 1 h. The solvent was concentrated under reduced pressure to give the crude product as a yellow solid which was purified by preparative high-performance liquid chromatography. The pure fractions were collected and the organic solvent was concentrated under reduced pressure, the solid lyophilized to afford the product as pale yellow solid (72 mg, 73.3% yield). ¹H NMR (400 MHz, DMSO-d₆) δ ppm 11.61 (1H, br d, J=5.73 Hz), 11.16 (1H, s), 8.86-8.92 (1H, m), 8.53 (1H, s), 8.44 (1H, s), 8.41 (1H, d, J=8.16 Hz), 7.91 (1H, d, J=7.72 Hz), 7.64 (1H, t, J=7.72 Hz), 7.23-7.29 (1H, m), 6.18 (1H, s), 5.62 (1H, d, J=7.28 Hz), 3.67 (3H, s). LC-MS: (ES, m/z): [M+1]⁺ 528.9

Example 184

N-(5-chloro-6-(2H-1,2,3-triazol-2-yl)pyridin-3-yl)-1-(8-fluoro-1-oxo-1,2-dihydroisoquinolin-4-yl)-5-(trifluoromethyl)-1H-pyrazole-4-carboxamide, Cpd 184

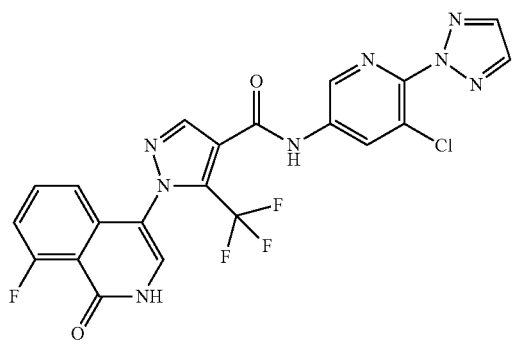 [SMILES: O=C(Nc1cnc(-n2nccn2)c(Cl)c1)c1cnn(-c2c[nH]c(=O)c3c(F)cccc23)c1C(F)(F)F]

A. 8-fluoro-4-hydrazinylisoquinoline, 184a

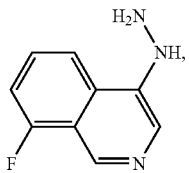

{Pd(cinnamyl)Cl}$_2$ (34.4 mg, 0.066 mmol) and Mor-DalPhos (61.5 mg, 0.13 mmol) in dioxane (5 mL) was stirred at rt for 10 min under N$_2$, sodium tert-butoxide (255 mg, 2.65 mmol) and 4-bromo-8-fluoroisoquinoline (300 mg, 1.33 mmol) was added to the mixture at rt with stirring for 5 min under N$_2$, and the mixture was treated with hydrazine monohydrate (133 mg, 2.65 mmol) at 50° C. for 2 h under N$_2$. The reaction mixture was filtered, the filtrate was concentrated under reduced pressure to give the crude product as a brown solid (240 mg), used directly for the next step.

B. ethyl 1-(8-fluoroisoquinolin-4-yl)-5-(trifluoromethyl)-1H-pyrazole-4-carboxylate, 184b

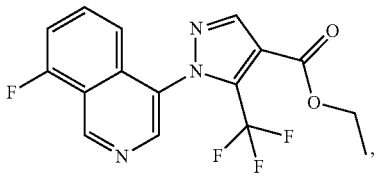

A solution consisting of ethyl 2-(ethoxymethylene)-4,4,4-trifluoro-3-oxobutanoate, 1f (1.63 g, 6.77 mmol), 8-fluoro-4-hydrazinylisoquinoline (800 mg, 4.52 mmol), and ethanol (20 mL) was stirred at 80° C. for 1 h before cooling to room temperature. The resulting solution was concentrated to dryness under reduced pressure, and then purified by column chromatography over silica gel (petroleum ether/ethyl acetate=100:0 to 80:20) to afford the product as a brown oil (820 mg, 47.6%). LC-MS: (ES, m/z): [M+1]$^+$ 353.9

C. 4-(4-(ethoxycarbonyl)-5-(trifluoromethyl)-1H-pyrazol-1-yl)-8-fluoroisoquinoline 2-oxide, 184c

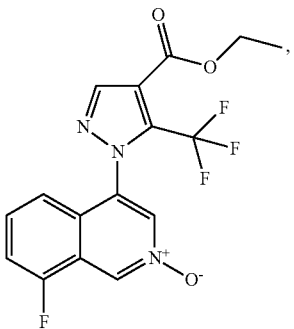

m-CPBA (791.6 mg, 4.59 mmol) was added to a solution of ethyl 1-(8-fluoroisoquinolin-4-yl)-5-(trifluoromethyl)-1H-pyrazole-4-carboxylate (700 mg, 92.6% pure, 1.84 mmol) in DCM (5 mL). The mixture was reacted at 30° C. for 2 h, 40 mL sat. Na$_2$CO$_3$ solution was added to the mixture, and the mixture was extracted with 50 mL CH$_2$Cl$_2$. The organic layer was concentrated under reduced pressure. The crude product was purified by column chromatography over silica gel (petroleum ether/ethyl acetate=100:0 to petroleum ether/ethyl acetate=60:40). The desired fractions were collected and the solvent was concentrated under reduced pressure to give the product as a yellow oil (675 mg, 99.6% yield). LC-MS: (ES, m/z): [M+1]$^+$ 369.9

D. ethyl 1-(1-chloro-8-fluoroisoquinolin-4-yl)-5-(trifluoromethyl)-1H-pyrazole-4-carboxylate, 184d

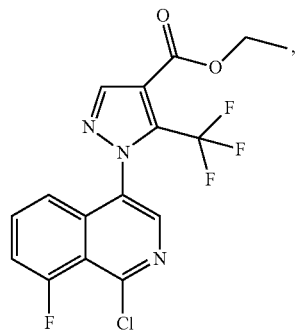

POCl$_3$ (5 mL) was added to a solution of 4-(4-(ethoxycarbonyl)-5-(trifluoromethyl)-1H-pyrazol-1-yl)-8-fluoroisoquinoline 2-oxide (650 mg, 1.76 mmol) in chloroform (15 mL). The mixture was reacted at 70° C. for 2 h. Sat. Na$_2$CO$_3$ solution (30 mL) was added to the mixture, and the mixture was extracted with 30 mL CH$_2$Cl$_2$. The organic layer was concentrated under reduced pressure, the crude product was purified by column chromatography over silica gel (petroleum ether/ethyl acetate=100:0 to petroleum ether/ethyl acetate=85:15). The desired fractions were collected and the solvent was concentrated under reduced pressure to give the product as a colorless oil (400 mg, 58.6% yield).

E. 1-(1-ethoxy-8-fluoroisoquinolin-4-yl)-5-(trifluoromethyl)-1H-pyrazole-4-carboxylic acid, 184e

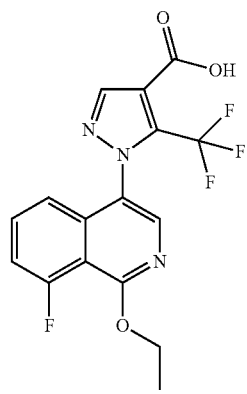 [SMILES: CCOc1ncc(-n2ncc(C(=O)O)c2C(F)(F)F)c2cccc(F)c12]

Lithium hydroxide (124 mg, 5.16 mmol) was added to a solution of ethyl 1-(1-chloro-8-fluoroisoquinolin-4-yl)-5-(trifluoromethyl)-1H-pyrazole-4-carboxylate (400 mg, 1.03 mmol) in ethanol/water (1:1, 10 mL). The mixture was reacted at 23° C. for 2 h and the solvent was concentrated under reduced pressure. 1M HCl solution was added to the mixture to adjust the pH to ~5 and the mixture was extracted with EtOAc (30 mL×3). The combined organic layers were dried over Na$_2$SO$_4$, filtered and the filtrates were concentrated under reduced pressure to afford crude product as a brown oil (335 mg, 44.5% yield). LC-MS: (ES, m/z): [M+1]$^+$ 370.0

F. N-(5-chloro-6-(2H-1,2,3-triazol-2-yl)pyridin-3-yl)-1-(1-ethoxy-8-fluoroisoquinolin-4-yl)-5-(trifluoromethyl)-1H-pyrazole-4-carboxamide, 184f

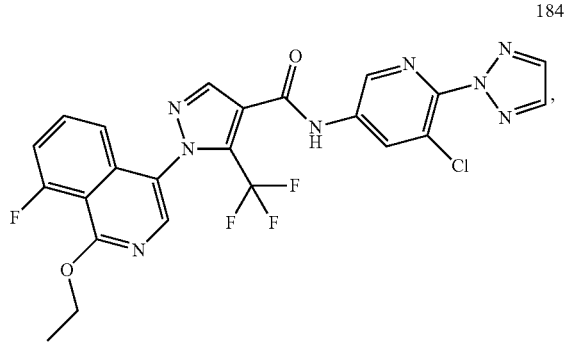 [SMILES: CCOc1ncc(-n2ncc(C(=O)Nc3cnc(-n4nccn4)c(Cl)c3)c2C(F)(F)F)c2cccc(F)c12]

184f

To a solution of 1-(1-ethoxy-8-fluoroisoquinolin-4-yl)-5-(trifluoromethyl)-1H-pyrazole-4-carboxylic acid (280 mg, 50.6% purity, 0.38 mmol), 5-chloro-6-(2H-1,2,3-triazol-2-yl)pyridin-3-amine, 1j (75.1 mg, 0.38 mmol) and pyridine (91 mg, 1.15 mmol) in CH$_2$Cl$_2$ (5 mL) was added POCl$_3$ (70.6 mg, 0.46 mmol) dropwise. The mixture was stirred at 25° C. for 2 h, 10 mL sat. NaHCO$_3$ was added and the mixture aextracted with CH$_2$Cl$_2$ (15 mL×2). The combined organic layers were dried over Na$_2$SO$_4$, filtered and the filtrates were concentrated under reduced pressure to afford the crude product as a brown oil (258 mg, 68.8%). LC-MS: (ES, m/z): [M+1]$^+$ 547.0

G. N-(5-chloro-6-(2H-1,2,3-triazol-2-yl)pyridin-3-yl)-1-(8-fluoro-1-oxo-1,2-dihydroisoquinolin-4-yl)-5-(trifluoromethyl)-1H-pyrazole-4-carboxamide, Cpd 184

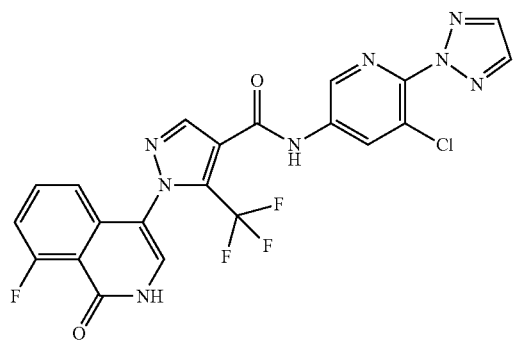 [SMILES: O=C(Nc1cnc(-n2nccn2)c(Cl)c1)c1cnn(-c2c[nH]c(=O)c3c(F)cccc23)c1C(F)(F)F]

Concentrated HCl (2 mL) was added to a solution of N-(5-chloro-6-(2H-1,2,3-triazol-2-yl)pyridin-3-yl)-1-(1-ethoxy-8-fluoroisoquinolin-4-yl)-5-(trifluoromethyl)-1H-pyrazole-4-carboxamide (75 mg, 0.14 mmol) in isopropanol (4 mL), and the mixture was reacted at 60° C. for 2 h. The solvent was concentrated under reduced pressure to afford the crude compound, which was purified by preparative high-performance liquid chromatography to afford the product as a white solid (15 mg, 21% yield). $^1$H NMR (400 MHz, DMSO-d$_6$) δ ppm 6.48 (d, J=8.16 Hz, 1H), 7.33 (dd, J=11.69, 8.16 Hz, 1H), 7.73 (td, J=8.16, 4.85 Hz, 1H), 7.88 (d, J=6.39 Hz, 1H), 8.16 (s, 2H), 8.50 (s, 1H), 8.64 (d, J=2.20 Hz, 1H), 8.82 (d, J=2.21 Hz, 1H), 11.22 (s, 1H), 11.83 (d, J=6.62 Hz, 1H). LC-MS: (ES, m/z): [M+1]$^+$ 518.9

Example 185

N-(5-bromo-2-methyl-6-(2H-1,2,3-triazol-2-yl)pyridin-3-yl)-1-(1-oxo-1,2-dihydroisoquinolin-5-yl)-5-(trifluoromethyl)-1H-pyrazole-4-carboxamide, Cpd 185

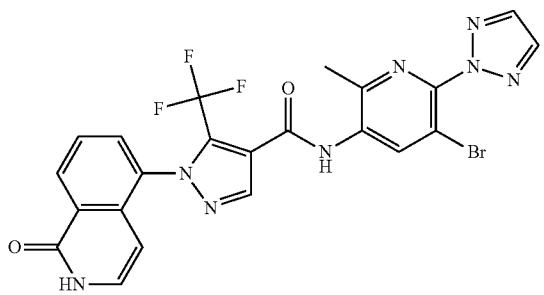 [SMILES: Cc1nc(-n2nccn2)c(Br)cc1NC(=O)c1cnn(-c2cccc3c(=O)[nH]ccc23)c1C(F)(F)F]

A. 3-bromo-6-methyl-5-nitropyridin-2-ol, 185a

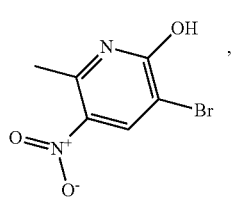

185a

To an ice-bath cooled suspension of 6-methyl-5-nitropyridin-2-ol (10 g, 64.9 mmol) in DMF (100 mL) was added N-bromosuccinimide (13.9 g, 77.9 mmol) portion-wise under N$_2$. The reaction mixture was stirred at 67° C. overnight, cooled to 0° C., and 500 mL water was added to the mixture. The resultant solid was collected by filtration to afford the product as a yellow solid (9.2 g, 60.9% yield).

B. 3-bromo-2-chloro-6-methyl-5-nitropyridine, 185b

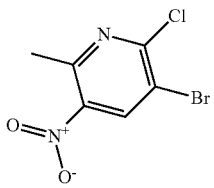

3-Bromo-6-methyl-5-nitropyridin-2-ol (9.2 g, 36.7 mmol) in POCl$_3$ (56.2 g, 366.7 mmol) was stirred at 80° C. overnight. The mixture was slowly poured into water (800 mL) and a solid was formed. The solid was collected and dried to afford the desired product (7.5 g, 81.4% yield).

C. 3-bromo-6-methyl-5-nitro-2-(2H-1,2,3-triazol-2-yl)pyridine, 185c

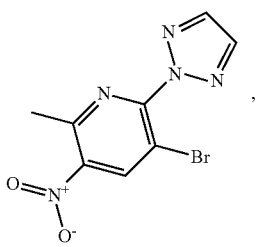

A solution of 3-bromo-2-chloro-6-methyl-5-nitropyridine (7.5 g, 29.83 mmol), 2H-1,2,3-triazole (3.09 g, 44.74 mmol) and potassium carbonate (12.37 g, 89.48 mmol) in acetonitrile (40 mL) was stirred at 40° C. overnight. The mixture was filtered and washed with ethyl acetate (30 mL×3). The filtrate was concentrated to afford a crude product. The crude product was purified by flash column chromatography over silica gel (eluent: petroleum ether/ethyl acetate from 100/0 to 20/80). The eluent was collected and the solvent was concentrated under reduced pressure to give the product as a yellow solid (5 g, 59% yield). $^1$H NMR (400 MHz, DMSO-d$_6$) δ ppm 2.76 (s, 3H), 8.28 (s, 2H), 9.05 (s, 1H).

D. 5-bromo-2-methyl-6-(2H-1,2,3-triazol-2-yl)pyridin-3-amine, 185d

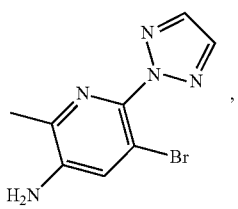

3-Bromo-6-methyl-5-nitro-2-(2H-1,2,3-triazol-2-yl)pyridine (4.0 g, 14.1 mmol) was added to the mixture of iron (7.86 g, 140.8 mmol), NH$_4$Cl (7.53 g, 140.8 mmol) in THF (20 mL) and water (7 mL). The reaction mixture was stirred at 60° C. for 2 h and filtered. The filtrate was concentrated under reduced pressure to give the crude product as a brown oil which was purified by column chromatography over silica gel (petroleum ether/ethyl acetate=30:70 to 80:20). The desired fractions were collected and the solvent was concentrated under reduced pressure to give the product as a yellow solid (2.3 g, 64.3% yield). LC-MS: (ES, m/z): [M+1]$^+$ 256.0

E. N-(5-bromo-2-methyl-6-(2H-1,2,3-triazol-2-yl)pyridin-3-yl)-1-(1-oxo-1,2-dihydroisoquinolin-5-yl)-5-(trifluoromethyl)-1H-pyrazole-4-carboxamide, Cpd 185

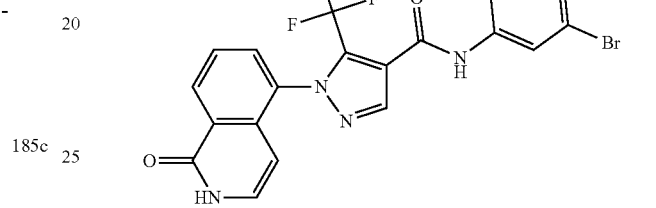

To a solution of 1-(1-oxo-1,2-dihydroisoquinolin-5-yl)-5-(trifluoromethyl)-1H-pyrazole-4-carboxylic acid (190 mg, 0.58 mmol) and 5-bromo-2-methyl-6-(2H-1,2,3-triazol-2-yl)pyridin-3-amine (147 mg, 0.58 mmol) and pyridine (137 mg, 1.74 mmol) in dichloromethane (10 mL) was added POCl$_3$ (106 mg, 0.69 mmol) dropwise. Sat. NaHCO$_3$ (10 mL) was added and the mixture extracted with CH$_2$Cl$_2$ (15 mL×2). The combined organic layers were dried over Na$_2$SO$_4$, filtered, and the filtrates were concentrated under reduced pressure to afford the crude product as a brown oil. The brown oil was purified by preparative high-performance liquid chromatography (35% to 65% (v/v) CH$_3$CN and H$_2$O with 0.05% HCl) and lyophilized to dryness to afford the product as a white solid (125.5 mg, 38.3%). $^1$H NMR (400 MHz, DMSO-d$_6$) δ ppm 2.51 (s, 3H), 5.65 (d, J=7.06 Hz, 1H), 7.27 (dd, J=7.28, 5.95 Hz, 1H), 7.65 (t, J=7.94 Hz, 1H), 7.92 (d, J=7.72 Hz, 1H), 8.16 (s, 1H), 8.15 (s, 1H), 8.41 (d, J=7.72 Hz, 1H), 8.51 (d, J=5.73 Hz, 2H), 10.59 (s, 1H), 11.62 (br d, J=5.51 Hz, 1H). LC-MS: (ES, m/z): [M+1]$^+$ 561.1

Example 186

N-(5-Chloro-6-(2H-1,2,3-triazol-2-yl)pyridin-3-yl)-5-cyano-1-(quinolin-5-yl)-1H-pyrazole-4-carboxamide, Cpd 186

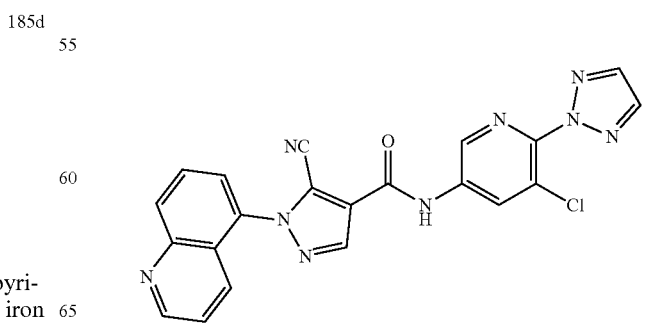

A. Ethyl 1-(quinolin-5-yl)-1H-pyrazole-4-carboxylate, 186a

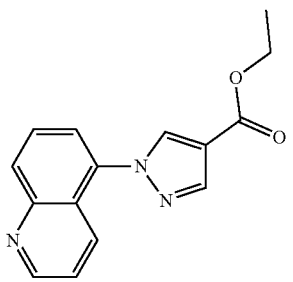

186a

In a 100 mL round-bottom flask was combined ethyl 4-pyrazolecarboxylate (500 mg, 3.6 mmol), 5-bromoquinoline (816 mg, 3.9 mmol), RockPhos G3 catalyst (150 mg, 0.18 mmol), $K_3PO_4$ (1.52 g, 7.1 mmol), and 1,4-dioxane (20 mL). The flask was fitted with a reflux condenser and pumped and backfilled with $N_2$ several times. The reaction was heated at reflux for 5 h, cooled, and concentrated. The reaction mixture was partitioned between water and $CH_2Cl_2$. The aqueous layer was extracted once with $CH_2Cl_2$. The combined organic layers were washed once with 1 M NaOH. The organic layers were dried ($Na_2SO_4$), filtered, and the filtrate concentrated to afford the crude product, which was purified by flash chromatography (40 g silica gel cartridge, gradient 30-70% EtOAc/hex). Yield=375 mg (35%). MS (ESI): m/z 268 [M+H]$^+$. $^1$H NMR (400 MHz, CDCl$_3$) δ ppm 9.00 (dd, J=4.2, 1.6 Hz, 1H), 8.3 (s, 1H), 8.28-8.24 (m, 1H), 8.24 (s, 1H), 7.80 (dd, J=8.6, 7.5 Hz, 1H), 7.62 (dd, J=7.5, 1.0 Hz, 1H), 7.48 (dd, J=8.7, 4.2 Hz, 1H), 4.38 (q, J=7.2 Hz, 2H), 1.40 (t, J=7.2 Hz, 3H).

B. Ethyl 5-cyano-1-(quinolin-5-yl)-1H-pyrazole-4-carboxylate, 186b

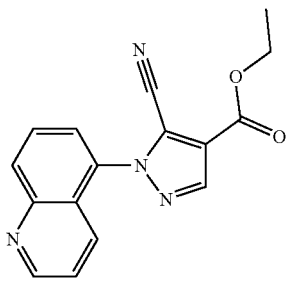

186b

To a 4 mL vial were added ethyl 1-(quinolin-5-yl)-1H-pyrazole-4-carboxylate (100 mg, 0.37 mmol) and THF (1 mL). TMPMgCl.LiCl (0.56 mL of a 1 M solution in THF/toluene, 0.56 mmol) was added, and the reaction was allowed to stir for 1 h at rt. Solid p-toluenesulfonyl cyanide (102 mg, 0.56 mmol) was added in one portion. The reaction was allowed to stir overnight and then was poured into saturated aqueous NH$_4$Cl solution. The mixture was diluted with water and extracted twice with EtOAc. MeOH was added to dissolve the precipitate, and the homogeneous organic layer was dried (Na$_2$SO$_4$), filtered, and the filtrate concentrated to afford the crude product. The crude product was dissolved in warm CH$_2$Cl$_2$, then filtered. The filrate and concentrated and further purified by flash chromatography (12 g silica gel cartridge, gradient 5-60% EtOAc/hex). Yield=69 mg (63%). MS (ESI): m/z 293 [M+H]$^+$. $^1$H NMR (400 MHz, CDCl$_3$) δ ppm 9.05 (dd, J=4.2, 1.7 Hz, 1H), 8.37 (ddd, J=8.6, 1.0, 1.0 Hz, 1H), 8.33 (s, 1H), 7.92-7.87 (m, 1H), 7.88 (dd, J=8.6, 7.5 Hz, 1H), 7.73 (dd, J=7.4, 1.1 Hz, 1H), 7.51 (dd, J=8.6, 4.2 Hz, 1H), 4.46 (q, J=7.1 Hz, 2H), 1.45 (t, J=7.1 Hz, 3H).

C. 5-Cyano-1-(quinolin-5-yl)-1H-pyrazole-4-carboxylic acid, 186c

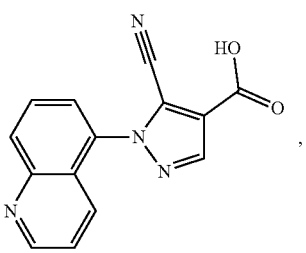

186c

To a 15 mL round bottom flask were added ethyl 5-cyano-1-(quinolin-5-yl)-1H-pyrazole-4-carboxylate (56 mg, 0.19 mmol), LiOH.H$_2$O (24 mg, 0.58 mmol), THF (2 mL), and water (2 mL). The reaction was allowed to stir for 30 min at rt. THF was removed under reduced pressure, and the remaining aqueous layer was acidified to precipitate the acid. The solid product was allowed to dry. Yield=34 mg (67%). MS (ESI): m/z 265 [M+H]$^+$. $^1$H NMR (400 MHz, DMSO-d$_6$) δ ppm 13.75 (bs, 1H), 9.06 (ddd, J=3.7, 1.7, 1.7 Hz, 1H), 8.49 (d, J=1.6 Hz, 1H), 8.41 (bd, J=8.4 Hz, 1H), 8.07 (ddd, J=7.4, 1.5, 1.5 Hz, 1H), 8.03-7.94 (m, 2H), 7.66 (ddd, J=8.6, 4.1, 1.6 Hz, 1H).

D. N-(5-Chloro-6-(2H-1,2,3-triazol-2-yl)pyridin-3-yl)-5-cyano-1-(quinolin-5-yl)-1H-pyrazole-4-carboxamide, Cpd 186

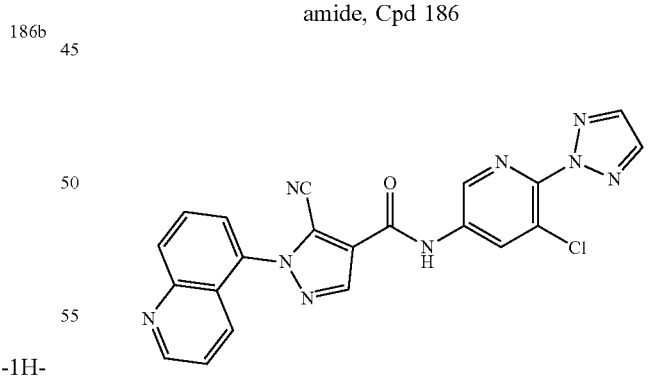

To a 10 mL round bottom flask were added 5-cyano-1-(quinolin-5-yl)-1H-pyrazole-4-carboxylic acid (33 mg, 0.12 mmol), 5-chloro-6-(2H-1,2,3-triazol-2-yl)pyridin-3-amine (29 mg, 0.15 mmol), pyridine (60 µL, 0.75 mmol), and CH$_2$Cl$_2$ (3 mL). POCl$_3$ (46 µL, 0.5 mmol) was added, and the reaction was allowed to stir overnight. The reaction was concentrated, redissolved in DMSO (2.5 mL), and treated with 1 drop of saturated NaHCO$_3$ solution to neutralize the acid. The mixture was purified by reversed-phase preparative HPLC (C$_{18}$ silica column, 50×250 mm, gradient 10%-100% ACN/H$_2$O with 0.05% TFA, 80 mL/min). Yield=21 mg (38%). MS (ESI): m/z 442 [M+H]$^+$. $^1$H NMR (400 MHz, DMSO-d$_6$) δ ppm 11.14 (s, 1H), 9.09 (dd, J=4.1, 1.6 Hz, 1H), 8.91 (d, J=2.3 Hz, 1H), 8.81 (s, 1H), 8.72 (d, J=2.3 Hz, 1H), 8.36 (ddd, J=8.4, 1.0, 1.0 Hz, 1H), 8.20 (s, 2H), 8.10 (dd, J=7.4, 1.3 Hz, 1H), 8.03 (dd, J=8.4, 7.5 Hz, 1H), 8.02-7.97 (m, 1H), 7.70 (dd, J=8.6, 4.2 Hz, 1H).

Example 187

5-Chloro-N-(5-chloro-6-(2H-1,2,3-triazol-2-yl)pyridin-3-yl)-1-(quinolin-5-yl)-1H-pyrazole-4-carboxamide, Cpd 187

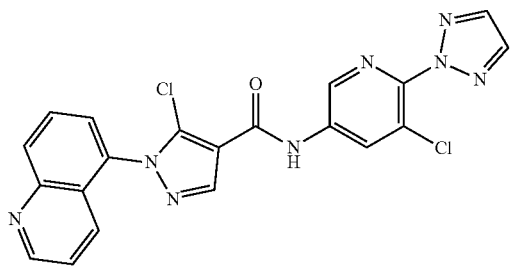 [SMILES: O=C(Nc1cnc(-n2nccn2)c(Cl)c1)c1cnn(-c2cccc3ncccc23)c1Cl]

A. Ethyl 5-chloro-1-(quinolin-5-yl)-1H-pyrazole-4-carboxylate, 187a

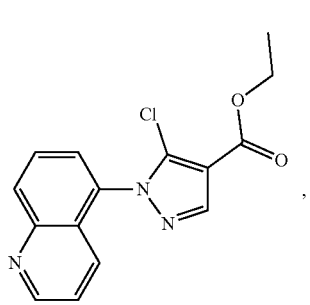

187a

This compound was made using the procedure of 186b using ethyl 1-(quinolin-5-yl)-1H-pyrazole-4-carboxylate (100 mg, 0.37 mmol), TMPMgCl.LiCl (0.49 mL of a 1 M solution in THF/toluene, 0.49 mmol), and hexachloroethane (133 mg, 0.56 mmol). Purification was accomplished by flash chromatography (12 g silica gel cartridge, gradient 5-40% EtOAc/hex). Yield=78 mg (69%). MS (ESI): m/z 302 [M+H]$^+$. $^1$H NMR (400 MHz, CDCl$_3$) δ ppm 9.01 (dd, J=4.2, 1.7 Hz, 1H), 8.33 (ddd, J=8.6, 1.0, 1.0 Hz, 1H), 8.25 (s, 1H), 7.85 (dd, J=8.6, 7.4 Hz, 1H), 7.73 (ddd, J=8.6, 1.7, 0.9 Hz, 1H), 7.63 (dd, J=7.4, 1.1 Hz, 1H), 7.46 (dd, J=8.6, 4.2 Hz, 1H), 4.40 (q, J=7.1 Hz, 2H), 1.42 (t, J=7.2 Hz, 3H).

B. 5-Chloro-1-(quinolin-5-yl)-1H-pyrazole-4-carboxylic acid, 187b

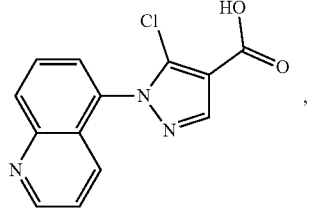

187b

This compound was made using the procedure of 186c using ethyl 5-chloro-1-(quinolin-5-yl)-1H-pyrazole-4-carboxylate (72 mg, 0.24 mmol), LiOH.H$_2$O (30 mg, 0.72 mmol), THF (2 mL), and water (2 mL). Yield=48 mg (74%). MS (ESI): m/z 274 [M+H]$^+$. $^1$H NMR (400 MHz, DMSO-d$_6$) δ ppm 13.08 (bs, 1H), 9.04 (dd, J=4.2, 1.7 Hz, 1H), 8.32 (s, 1H), 8.30 (ddd, J=8.4, 1.1, 1.1 Hz, 1H), 7.97 (dd, J=8.5, 7.4 Hz, 1H), 7.88 (dd, J=7.3, 1.2 Hz, 1H), 7.75-7.70 (m, 1H), 7.63 (dd, J=8.6, 4.2 Hz, 1H).

C. 5-Chloro-N-(5-chloro-6-(2H-1,2,3-triazol-2-yl)pyridin-3-yl)-1-(quinolin-5-yl)-1H-pyrazole-4-carboxamide, Cpd 187

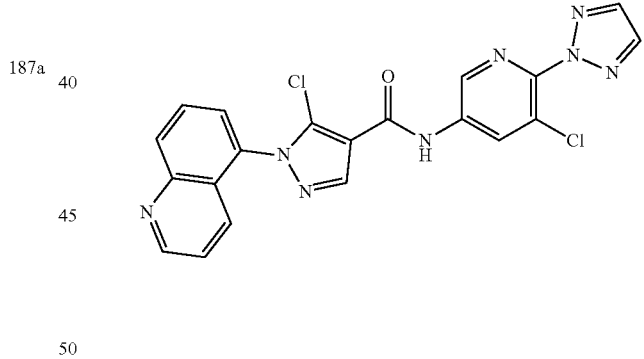

The title compound was made using the procedure of 186d using 5-chloro-1-(quinolin-5-yl)-1H-pyrazole-4-carboxylic acid (41 mg, 0.15 mmol), 5-chloro-6-(2H-1,2,3-triazol-2-yl)pyridin-3-amine (35 mg, 0.18 mmol), pyridine (72 μL, 0.90 mmol), CH$_2$Cl$_2$ (3 mL), and POCl$_3$ (56 μL, 0.60 mmol). The mixture was purified by reversed-phase preparative HPLC (C18 silica column, 50×250 mm, gradient 10%-100% ACN/H$_2$O with 0.05% TFA, 80 mL/min). Yield=36 mg (53%). MS (ESI): m/z 451 [M+H]$^+$. $^1$H NMR (400 MHz, DMSO-d$_6$) δ ppm 10.82 (s, 1H), 9.06 (dd, J=4.2, 1.7 Hz, 1H), 8.90 (d, J=2.3 Hz, 1H), 8.69 (d, J=2.2 Hz, 1H), 8.66 (s, 1H), 8.33 (ddd, J=8.5, 1.1, 1.1 Hz, 1H), 8.19 (s, 2H), 8.00 (dd, J=8.5, 7.4 Hz, 1H), 7.91 (dd, J=7.4, 1.2 Hz, 1H), 7.78-7.73 (m, 1H), 7.67 (dd, J=8.6, 4.2 Hz, 1H).

Example 188

5-Bromo-N-(5-chloro-6-(2H-1,2,3-triazol-2-yl)pyridin-3-yl)-1-(quinolin-5-yl)-1H-pyrazole-4-carboxamide, Cpd 188

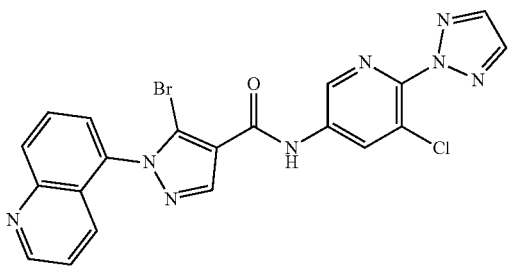 [SMILES: O=C(Nc1cnc(-n2nccn2)c(Cl)c1)c1cnn(-c2cccc3ncccc23)c1Br]

A. Ethyl 5-bromo-1-(quinolin-5-yl)-1H-pyrazole-4-carboxylate, 188a

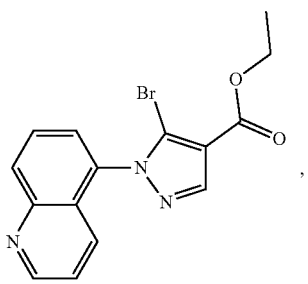

188a

This compound was made using the procedure of 186b using ethyl 1-(quinolin-5-yl)-1H-pyrazole-4-carboxylate (100 mg, 0.37 mmol), TMPMgCl.LiCl (0.49 mL of a 1 M solution in THF/toluene, 0.49 mmol), and 1,2-dibromotetrachloroethane (183 mg, 0.56 mmol). Purification was accomplished by flash chromatography (12 g silica gel cartridge, gradient 5-40% EtOAc/hex). Yield=69 mg (53%). MS (ESI): m/z 346, 348 [M+H]$^+$. $^1$H NMR (400 MHz, CDCl$_3$) δ ppm 9.01 (dd, J=4.2, 1.7 Hz, 1H), 8.33 (ddd, J=8.6, 1.0, 1.0 Hz, 1H), 8.27 (s, 1H), 7.85 (dd, J=8.6, 7.4 Hz, 1H), 7.66 (ddd, J=8.5, 1.7, 0.9 Hz, 1H), 7.63 (dd, J=7.4, 1.1 Hz, 1H), 7.46 (dd, J=8.6, 4.2 Hz, 1H), 4.41 (q, J=7.1 Hz, 2H), 1.42 (t, J=7.2 Hz, 3H).

B. 5-Bromo-1-(quinolin-5-yl)-1H-pyrazole-4-carboxylic acid, 188b

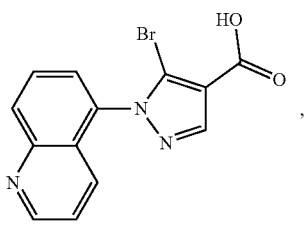

188b

This compound was made using the procedure of 186c using ethyl 5-bromo-1-(quinolin-5-yl)-1H-pyrazole-4-carboxylate (64 mg, 0.18 mmol), LiOH.H$_2$O (23 mg, 0.56 mmol), THF (2 mL), and water (2 mL). Yield=46 mg (78%). MS (ESI): m/z 318, 320 [M+H]$^+$. $^1$H NMR (400 MHz, DMSO-d$_6$) δ ppm 13.00 (bs, 1H), 9.04 (t, J=2.9 Hz, 1H), 8.31 (s, 1H), 8.30 (dd, J=8.4, 1.1 Hz, 1H), 7.97 (dd, J=8.5, 7.4 Hz, 1H), 7.85 (dd, J=7.4, 1.2 Hz, 1H), 7.62 (d, J=2.9 Hz, 2H).

C. 5-Bromo-N-(5-chloro-6-(2H-1,2,3-triazol-2-yl)pyridin-3-yl)-1-(quinolin-5-yl)-1H-pyrazole-4-carboxamide, Cpd 188

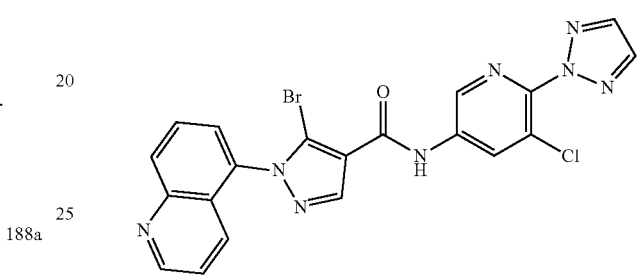

The title compound was made using the procedure of 186d using 5-bromo-1-(quinolin-5-yl)-1H-pyrazole-4-carboxylic acid (43 mg, 0.14 mmol), 5-chloro-6-(2H-1,2,3-triazol-2-yl)pyridin-3-amine (32 mg, 0.16 mmol), pyridine (65 μL, 0.81 mmol), CH$_2$Cl$_2$ (3 mL), and POCl$_3$ (50 μL, 0.54 mmol). The mixture was purified by reversed-phase preparative HPLC (C$_{18}$ silica column, 50×250 mm, gradient 10%-100% ACN/H$_2$O with 0.05% TFA, 80 mL/min). Yield=40 mg (60%). MS (ESI): m/z 495, 497 [M+H]$^+$. $^1$H NMR (400 MHz, DMSO-d$_6$) δ ppm 10.81 (s, 1H), 9.06 (t, J=2.9 Hz, 1H), 8.90 (d, J=2.3 Hz, 1H), 8.69 (d, J=2.3 Hz, 1H), 8.65 (s, 1H), 8.32 (dd, J=8.6, 1.1 Hz, 1H), 8.19 (s, 2H), 8.00 (dd, J=8.6, 7.4 Hz, 1H), 7.88 (dd, J=8.6, 1.2 Hz, 1H), 7.66 (d, J=3.0 Hz, 2H).

Example 189

N-(5-cyano-6-(2H-1,2,3-triazol-2-yl)pyridin-3-yl)-1-(imidazo[1,2-a]pyridin-3-yl)-5-(trifluoromethyl)-1H-pyrazole-4-carboxamide, Cpd 189

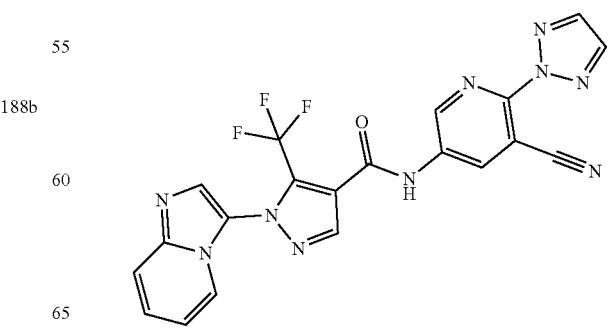

A. di-tert-butyl 1-(imidazo[1,2-a]pyridin-3-yl)hydrazine-1,2-dicarboxylate, 189a

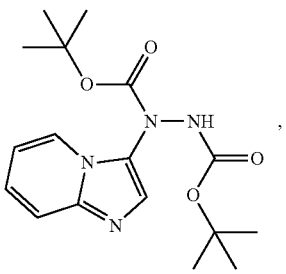

A mixture of imidazo[1,2-a]pyridine (2.0 g, 16.9 mmol) and di-tert-butyl diazene-1,2-dicarboxylate in CH$_3$CN (50 mL) was heated to reflux for 2 days. The solvent was removed and the residue was purified by column chromatography over silica gel (eulent: petrol ether/EtOAc=100:0 to 0:100). The desired fraction was collected and the solvent was removed to afford the product as a yellow solid (700 mg, 11.2%). LC-MS: (ES, m/z): [M+1]$^+$ 349.0

B. 3-hydrazinylimidazo[1,2-a]pyridine, 189b

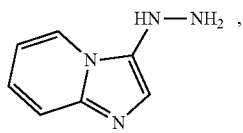

Di-tert-butyl 1-(imidazo[1,2-a]pyridin-3-yl)hydrazine-1,2-dicarboxylate in 4M HCl in MeOH (30 mL) was stirred at rt for 1 h. The solvent was removed to afford a white solid that was used directly for the next step.

C. ethyl 1-(imidazo[1,2-a]pyridin-3-yl)-5-(trifluoromethyl)-1H-pyrazole-4-carboxylate, 189c

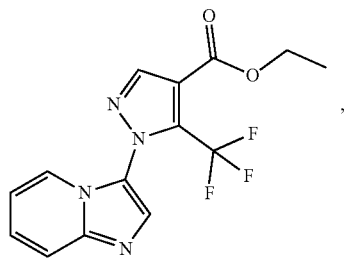

A solution consisting of ethyl 2-(ethoxymethylene)-4,4,4-trifluoro-3-oxobutanoate, 1f (722 mg, 3.0 mmol), 3-hydrazinylimidazo[1,2-a]pyridine (370 mg, 2.0 mmol), and ethanol (20 mL) was stirred at rt for 2 h. The resulting solution was concentrated to dryness under reduced pressure, partioned between EtOAc (30 mL) and aq. NaHCO$_3$ (20 mL). The organic layer was separated, washed with water (10 mL), dried over MgSO$_4$, filtered and the filtrate concentrated to afford the crude product. The crude product was purified by column chromatography over silica gel (petroleum ether/ethyl acetate=100:0 to 100:0) to afford the product as gray solid (120 mg, 18.3%). LC-MS: (ES, m/z): [M+1]$^+$ 324.9.

D. 1-(imidazo[1,2-a]pyridin-3-yl)-5-(trifluoromethyl)-1H-pyrazole-4-carboxylic acid, 189d

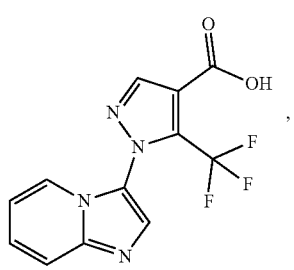

Sodium hydroxide (44 mg, 1.1 mmol) was added to a solution of ethyl 1-(imidazo[1,2-a]pyridin-3-yl)-5-(trifluoromethyl)-1H-pyrazole-4-carboxylate (120 mg, 0.37 mmol) in EtOH/H$_2$O (1:1, 2 mL). The mixture was reacted at 28° C. for 2 h. 10% HCl solution was add to the mixture to adjust the pH to ~5. The mixture was extracted with ethyl acetate, dried over MgSO$_4$, filtered, and the filtrate concentrated under reduced pressure the give the desired compound (100 mg, 90.5% yield). LC-MS: (ES, m/z): [M+1]$^+$ 297.0.

E. N-(5-cyano-6-(2H-1,2,3-triazol-2-yl)pyridin-3-yl)-1-(imidazo[1,2-a]pyridin-3-yl)-5-(trifluoromethyl)-1H-pyrazole-4-carboxamide, Cpd 189

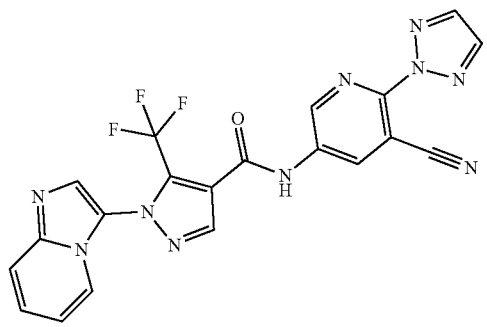 [SMILES: N#Cc1cc(NC(=O)c2cnn(-c3cnc4ccccn34)c2C(F)(F)F)cnc1-n1nccn1]

1-(Imidazo[1,2-a]pyridin-3-yl)-5-(trifluoromethyl)-1H-pyrazole-4-carboxylic acid (67.5 mg, 0.22 mmol), 5-amino-2-(2H-1,2,3-triazol-2-yl)nicotinonitrile (50 mg, 0.27 mmol), pyridine (53.1 mg, 0.67 mmol) were dissolved in CH$_2$Cl$_2$ (2 mL), and phosphorus oxychloride (41.2 mg, 0.27 mmol) was added. The mixture was stirred at 25° C. for 3 h, sat.NaHCO$_3$ (20 mL) was added and the mixture extracted with CH$_2$Cl$_2$ (20 mL×2). The combined organic layers were dried over Na$_2$SO$_4$, filtered and the filtrates were concentrated under reduced pressure to afford the crude product as a yellow oil, which was purified by preparative HPLC (20% to 50% (v/v) CH$_3$CN and H$_2$O with 0.05% HCl) and lyophilized to dryness to afford the title compound (40 mg, 37.6%). $^1$H NMR (400 MHz, DMSO-d$_6$) δ ppm 7.22-7.33 (m, 1H), 7.68 (br t, J=7.28 Hz, 1H), 7.84-7.95 (m, 1H), 8.18-8.40 (m, 4H), 8.76 (s, 1H), 8.90 (s, 1H), 9.14 (br s, 1H), 11.63 (s, 1H). LC-MS: (ES, m/z): [M+1]⁺ 464.9.

Example 190

N-(5-ethynyl-2-methyl-6-(2H-1,2,3-triazol-2-yl)pyridin-3-yl)-1-(1-oxo-1,2-dihydroisoquinolin-5-yl)-5-(trifluoromethyl)-1H-pyrazole-4-carboxamide, Cpd 190

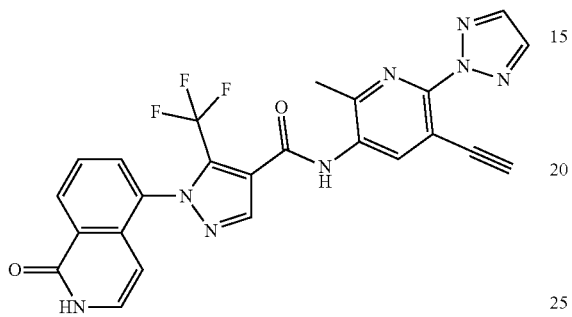

A. 5-ethynyl-2-methyl-6-(2H-1,2,3-triazol-2-yl)pyridin-3-amine, 190a

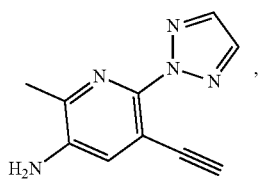

190a

Pd(PPh₃)₄ (109 mg, 0.095 mmol) was added to a solution of 5-bromo-2-methyl-6-(2H-1,2,3-triazol-2-yl)pyridin-3-amine (200 mg, 0.79 mmol), trimethyl((4,4,5,5-tetramethyl-1,3,2-dioxaborolan-2-yl)ethynyl)silane (338 mg, 1.73 mmol), K₃PO₄ (109 mg, 0.095 mmol) in THF (8 mL) at 90° C. under N2 bubbling for 12 h. The reaction mixture was filtered though a pad of diatomaceous earth and the pad was washed with EtOAc (10 mL×2). The filtrate was concentrated under reduced pressure to afford crude product which was purified by column chromatography over silica gel (petroleum ether/ethyl acetate=100:0 to petroleum ether/ethyl acetate=40:60). The desired fractions were collected and the solvent was concentrated under reduced pressure to afford the product as a brown oil (20 mg, 12.8% yield). LC-MS: (ES, m/z): [M+1]⁺ 200.2.

B. N-(5-ethynyl-2-methyl-6-(2H-1,2,3-triazol-2-yl)pyridin-3-yl)-1-(1-oxo-1,2-dihydroisoquinolin-5-yl)-5-(trifluoromethyl)-1H-pyrazole-4-carboxamide, Cpd 190

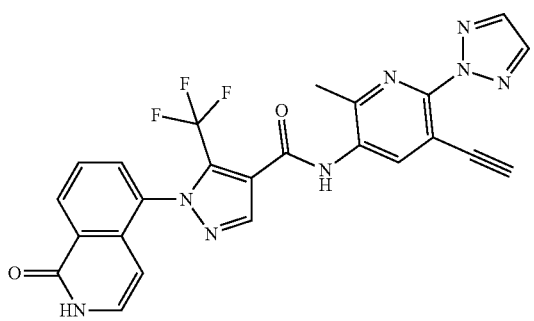 [SMILES: C#Cc1cc(NC(=O)c2cnn(-c3cccc4c(=O)[nH]ccc34)c2C(F)(F)F)c(C)nc1-n1nccn1]

To a solution of 1-(1-oxo-1,2-dihydroisoquinolin-5-yl)-5-(trifluoromethyl)-1H-pyrazole-4-carboxylic acid (24.3 mg, 0.075 mmol) and 5-ethynyl-2-methyl-6-(2H-1,2,3-triazol-2-yl)pyridin-3-amine (15 mg, 0.075 mmol) and pyridine (17.9 mg, 0.23 mmol) in dichloromethane (2 mL) was added POCl₃ (13.9 mg, 0.090 mmol) dropwise. Sat. NaHCO₃ (5 mL) was added and the mixture extracted with CH₂Cl₂ (10 mL×2). The combined organic layers were dried over Na₂SO₄, filtered and the filtrates were concentrated under reduced pressure to afford the crude product as a brown oil which was purified by preparative high-performance liquid chromatography (26% to 56% (v/v) CH₃CN and H₂O with 0.05% HCl) and lyophilized to dryness to afford the product as a white solid (14.8 mg, 38.5%). ¹H NMR (400 MHz, DMSO-d₆) δ ppm 2.56 (s, 3H), 4.43 (s, 1H), 5.67 (br d, J=6.84 Hz, 1H), 7.28 (br s, 1H), 7.66 (br t, J=7.83 Hz, 1H), 7.92 (br d, J=7.06 Hz, 1H), 8.14 (s, 2H), 8.30 (s, 1H), 8.42 (br d, J=7.94 Hz, 1H), 8.51 (s, 1H), 10.55 (s, 1H), 11.61 (br d, J=4.41 Hz, 1H). LC-MS: (ES, m/z): [M+1]⁺ 505.0

Example 191

N-(5-chloro-2-methyl-6-(2H-1,2,3-triazol-2-yl)pyridin-3-yl)-1-(isoquinolin-4-yl)-5-(trifluoromethyl)-1H-pyrazole-4-carboxamide, Cpd 191

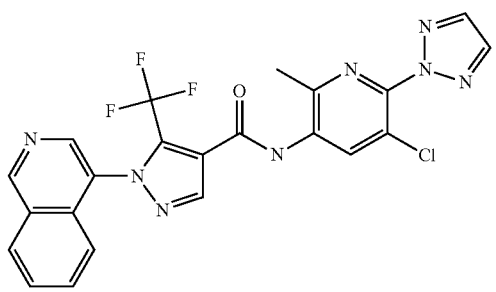 [SMILES: Cc1nc(-n2nccn2)c(Cl)cc1NC(=O)c1cnn(-c2cncc3ccccc23)c1C(F)(F)F]

573

A. 1-(isoquinolin-4-yl)-5-(trifluoromethyl)-1H-pyrazole-4-carboxylic acid, 191a

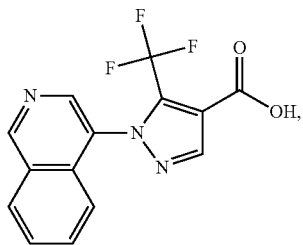

191a

A mixture of ethyl 1-(isoquinolin-4-yl)-5-(trifluoromethyl)-1H-pyrazole-4-carboxylate (750 mg, 2.24 mmol) in conc. HCl (12 M, 25 mL) was stirred at 130° C. for 2 h. The solvent was removed under reduced pressure to give the crude product as a yellow solid (700 mg, 95.5%), which was used directly for the next step. LCMS (ESI) m/z M+1: 307.8.

B. N-(5-chloro-2-methyl-6-(2H-1,2,3-triazol-2-yl)pyridin-3-yl)-1-(isoquinolin-4-yl)-5-(trifluoromethyl)-1H-pyrazole-4-carboxamide, Cpd 191

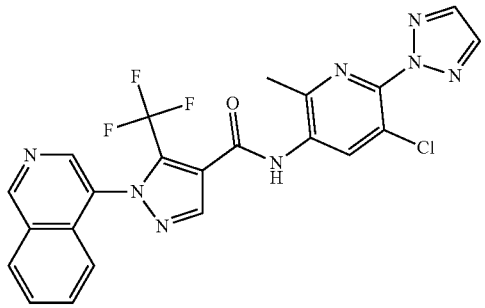 [SMILES: Cc1nc(-n2nccn2)c(Cl)cc1NC(=O)c1cnn(-c2cncc3ccccc23)c1C(F)(F)F]

POCl$_3$ (112.3 mg, 0.732 mmol) was added to a mixture of 1-(isoquinolin-4-yl)-5-(trifluoromethyl)-1H-pyrazole-4-carboxylic acid (120 mg, 0.37 mmol), 5-chloro-2-methyl-6-(2H-1,2,3-triazol-2-yl)pyridin-3-amine (76.77 mg, 0.37 mmol), pyridine (144.83 mg, 1.83 mmol) in CH$_2$Cl$_2$ (5 mL) at rt. The reaction mixture was stirred at room temperature for 1 h. The reaction mixture was quenched with 10 mL sat. K$_2$CO$_3$ aq, and the mixture extracted with CH$_2$Cl$_2$ (20 mL×3). The organic layer was separated and concentrated under reduced pressure. It was purified by preparative high-performance liquid chromatography (40% to 70% (v/v) CH$_3$CN and H$_2$O with 0.05% HCl). The pure fractions were collected and the organic solvent was concentrated under reduced pressure. The aqueous layer was lyophilized to dryness to give the desired product as a pale yellow solid (55 mg, purity: 99.145%, yield: 29.85%). LCMS (ESI) m/z M+1: 498.9. $^1$H NMR (400 MHz, CHLOROFORM-d) δ ppm 2.59 (s, 3H), 7.31 (d, J=8.60 Hz, 1H), 7.61 (s, 1H), 7.68-7.79 (m, 2H), 7.88 (s, 2H), 8.11 (d, J=7.72 Hz, 1H), 8.24 (s, 1H), 8.58 (s, 1H), 8.90 (s, 1H), 9.39 (s, 1H).

574

Example 192

N-(5-chloro-6-(1,3,4-oxadiazol-2-yl)pyridin-3-yl)-1-(quinolin-5-yl)-5-(trifluoromethyl)-1H-pyrazole-4-carboxamide, Cpd 192

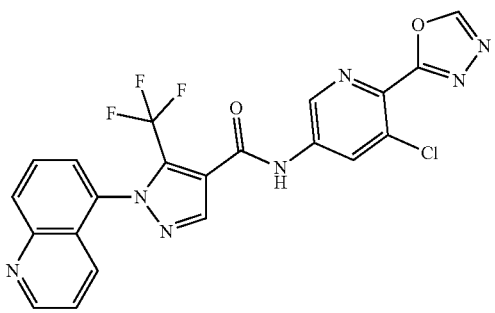 [SMILES: O=C(Nc1cnc(-c2nnco2)c(Cl)c1)c1cnn(-c2cccc3ncccc23)c1C(F)(F)F]

A. N-(5-chloro-6-(hydrazinecarbonyl)pyridin-3-yl)-1-(quinolin-5-yl)-5-(trifluoromethyl)-1H-pyrazole-4-carboxamide, 192a

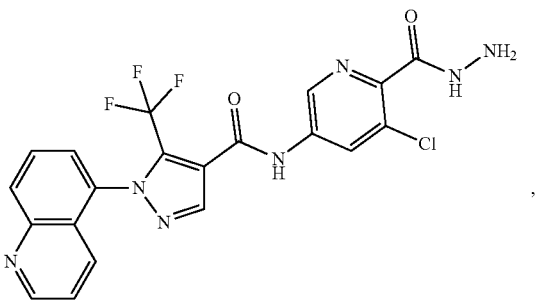

192a

Methyl 3-chloro-5-(1-(quinolin-5-yl)-5-(trifluoromethyl)-1H-pyrazole-4-carboxamido)picolinate (120 mg, 0.25 mmol) and hydrazine monohydride (25.3 mg, 0.50 mmol) in ethanol (1 mL) was stirred at 80° C. overnight. The mixture was concentrated to give a crude product (120 mg) which was used directly for the next step.

B. N-(5-chloro-6-(1,3,4-oxadiazol-2-yl)pyridin-3-yl)-1-(quinolin-5-yl)-5-(trifluoromethyl)-1H-pyrazole-4-carboxamide, Cpd 192

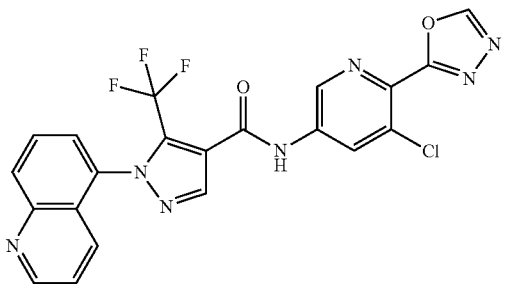 [SMILES: O=C(Nc1cnc(-c2nnco2)c(Cl)c1)c1cnn(-c2cccc3ncccc23)c1C(F)(F)F]

A mixture of N-(5-chloro-6-(hydrazinecarbonyl)pyridin-3-yl)-1-(quinolin-5-yl)-5-(trifluoromethyl)-1H-pyrazole-4-carboxamide (100 mg, 0.21 mmol), triethoxymethane (105 µL, 0.63 mmol) and acetic acid (6.3 µL, 0.11 mmol) in toluene (2 mL) was stirred at 100° C. for 4 h. The mixture was concentrated to give a crude product. The crude product was purified by preparative high-performance liquid chromatography (30% to 60% (v/v) CH$_3$CN and H$_2$O with 0.05% ammonia hydroxide). The pure fractions were collected and the solvent was concentrated under reduced pressure to give the product as a white solid (45 mg, 43% yield). $^1$H NMR (400 MHz, DMSO-d$_6$) δ ppm 7.57-7.62 (m, 1H), 7.64-7.69 (m, 1H), 7.89-7.99 (m, 2H), 8.32 (d, J=8.38 Hz, 1H), 8.57 (s, 1H), 8.62 (d, J=1.98 Hz, 1H), 8.99 (d, J=1.98 Hz, 1H), 9.04 (dd, J=4.08, 1.65 Hz, 1H), 9.45 (s, 1H). LCMS (ESI) m/z M+1: 485.9

Example 193

N-(5-chloro-6-(2H-1,2,3-triazol-2-yl)pyridin-3-yl)-1-(imidazo[1,2-a]pyridin-5-yl)-5-(trifluoromethyl)-1H-pyrazole-4-carboxamide, Cpd 193

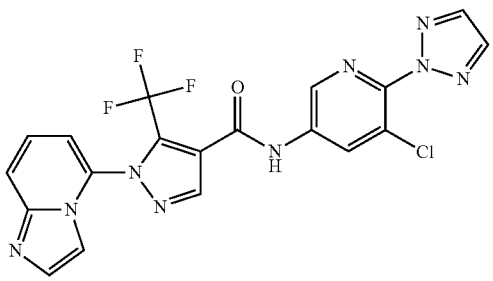 [SMILES: O=C(Nc1cnc(-n2nccn2)c(Cl)c1)c1cnn(-c2cccc3nccn23)c1C(F)(F)F]

A. ethyl 1-(6-bromopyridin-2-yl)-5-(trifluoromethyl)-1H-pyrazole-4-carboxylate, 193a

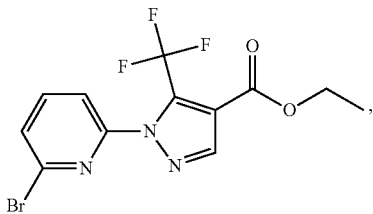

A solution of 2-bromo-6-hydrazinopyridine (3.0 g, 16.0 mmol) and ethyl 2-(ethoxymethylene)-4,4,4-trifluoro-3-oxobutanoate (5.75 g, 23.9 mmo) in EtOH (150 mL) was stirred at 80° C. overnight then cooled to rt. The solvent was removed under reduced pressure to afford a yellow oil. The yellow oil was purified by flash column chromatography over silica gel (eluent: petroleum ether/EtOAc 100/0 to petroleum ether/EtOAc 80/20). The desired fractions were collected and the solvent was concentrated to dryness under reduced pressure to afford the desired product as a yellow solid (5.7 g, yield: 98.1%).

B. ethyl 1-(6-(((tert-butoxycarbonyl)amino)pyridin-2-yl)-5-(trifluoromethyl)-1H-pyrazole-4-carboxylate, 193b

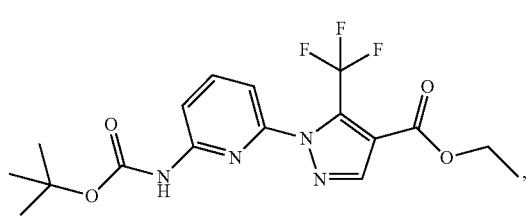

Pd(OAc)$_2$ (93.3 mg, 0.415 mmol) and Xantphos (238 mg, 0.412 mmol) in dioxane (75 mL) were stirred at rt for 10 min under nitrogen. Ethyl 1-(6-bromopyridin-2-yl)-5-(trifluoromethyl)-1H-pyrazole-4-carboxylate (3.0 g, 8.24 mmol), Cs$_2$CO$_3$ (8.05 g, 24.7 mmol) and tert-butyl carbamate (1.16 g, 9.89 mmol) are then added at room temperature. The reaction mixture is then allowed to heat at 90° C. overnight and then cooled to rt. The reaction mixture was filtered though a pad of diatomaceous earth. The filtrate was concentrated under reduced pressure. It was purified by flash column chromatography over silica gel (eluent: petroleum ether/EtOAc 100/0 to petroleum ether/EtOAc 80/20). The desired fractions were collected and the solvent was concentrated to dryness under reduced pressure to give the desired product as a white solid (3.09 g, yield: 93.7%).

C. 1-(6-(((tert-butoxycarbonyl)amino)pyridin-2-yl)-5-(trifluoromethyl)-1H-pyrazole-4-carboxylic acid, 193c

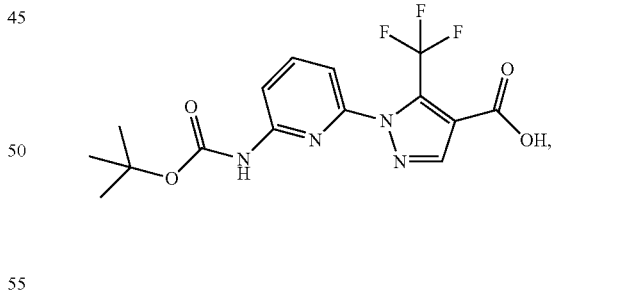

A mixture of ethyl 1-(6-(((tert-butoxycarbonyl)amino) pyridin-2-yl)-5-(trifluoromethyl)-1H-pyrazole-4-carboxylate and LiOH.H$_2$O (628 mg, 15.0 mmol) in THF/MeOH/H$_2$O (1:1:1, 60 mL) was stirred at rt for 2 h. The organic solvent was removed under reduced pressure. 2N HCl was added to adjust the mixture to pH 4-5, then it was extracted with EtOAc (50 mL×3). The organic layer was separated, dried over Na$_2$SO$_4$, filtered and the filtrate concentrated under reduced pressure to give the crude product as a white solid (1.8 g, yield: 96.8%).

D. tert-butyl (6-(4-((5-chloro-6-(2H-1,2,3-triazol-2-yl)pyridin-3-yl)carbamoyl)-5-(trifluoromethyl)-1H-pyrazol-1-yl)pyridin-2-yl)carbamate, 193d

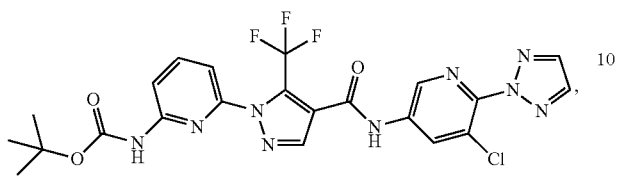

193d

POCl$_3$ (824 mg, 5.37 mmol) was added to a mixture of 1-(6-((tert-butoxycarbonyl)amino)pyridin-2-yl)-5-(trifluoromethyl)-1H-pyrazole-4-carboxylic acid (1 g, 2.69 mmol), 5-chloro-6-(2H-1,2,3-triazol-2-yl)pyridin-3-amine (525 mg, 2.69 mmol), pyridine (1.06 g, 13.4 mmol) in CH$_2$Cl$_2$ (30 mL) at rt. The reaction mixture was stirred at room temperature for 1 h. The reaction mixture was slowly quenched with 30 mL sat. K$_2$CO$_3$ aq, and extracted with CH$_2$Cl$_2$ (50 mL×3). The organic layer was separated and concentrated under reduced pressure. The resultant residue was purified by flash column chromatography over silica gel (eluent: petroleum ether/EtOAc 100/0 to petroleum ether/EtOAc 0/100). The desired fractions were collected and the solvent was concentrated to dryness under reduced pressure to give the desired product as a brown solid (850 mg, purity: 98.4%, yield: 70.8%). LCMS (ESI) m/z M+1: 450.0 (M-100).

E. 1-(6-aminopyridin-2-yl)-N-(5-chloro-6-(2H-1,2,3-triazol-2-yl)pyridin-3-yl)-5-(trifluoromethyl)-1H-pyrazole-4-carboxamide, 193e

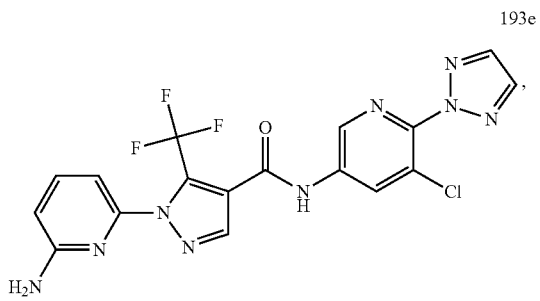 [SMILES: Nc1cccc(-n2ncc(C(=O)Nc3cnc(-n4nccn4)c(Cl)c3)c2C(F)(F)F)n1]

193e

A solution of tert-butyl (6-(4-((5-chloro-6-(2H-1,2,3-triazol-2-yl)pyridin-3-yl)carbamoyl)-5-(trifluoromethyl)-1H-pyrazol-1-yl)pyridin-2-yl)carbamate (1.76 g, 3.20 mmol) in HCl/MeOH (4M, 50 mL) was stirred at rt for 2 h. The solvent was removed under reduced pressure to afford the crude product as a red solid. The red solid was purified by preparative high-performance liquid chromatography (15% to 55% (v/v) CH$_3$CN and H$_2$O with 0.1% TFA). The pure fractions were collected and the organic solvent was concentrated under reduced pressure. Sat. K$_2$CO$_3$ aq was added to adjust pH ~12, then it was extracted with EtOAc (50 mL×2). The organic layer was separated, dried over Na$_2$SO$_4$, filtered and concentrated under reduced pressure to give the desired product as a yellow solid (1.4 g, purity: 97.2%, yield: 94.6%). LCMS (ESI) m/z M+1: 449.9. $^1$H NMR (400 MHz, CHLOROFORM-d) δ ppm 4.57 (br s, 2H), 6.54 (d, J=8.16 Hz, 1H), 6.90 (d, J=7.72 Hz, 1H), 7.57 (t, J=8.05 Hz, 1H), 7.81 (s, 1H), 7.87 (s, 2H), 7.977 (s, 1H), 8.42 (d, J=2.21 Hz, 1H), 8.68 (d, J=2.43 Hz, 1H).

F. N-(5-chloro-6-(2H-1,2,3-triazol-2-yl)pyridin-3-yl)-1-(imidazo[1,2-a]pyridin-5-yl)-5-(trifluoromethyl)-1H-pyrazole-4-carboxamide, Cpd 193

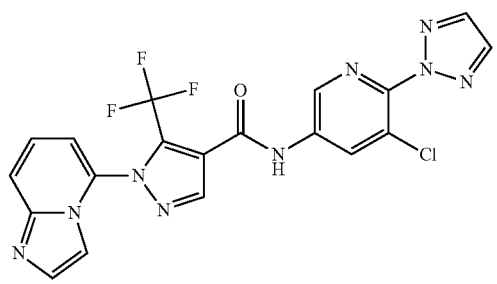 [SMILES: O=C(Nc1cnc(-n2nccn2)c(Cl)c1)c1cnn(-c2cccc3nccn23)c1C(F)(F)F]

1-(6-Aminopyridin-2-yl)-N-(5-chloro-6-(2H-1,2,3-triazol-2-yl)pyridin-3-yl)-5-(trifluoromethyl)-1H-pyrazole-4-carboxamide (1.48 g, 2.70 mmol, 97.2% purity) is taken up in i-PrOH (40 mL) under N$_2$. Bromoacetaldehyde diethyl acetal (1.07 g, 5.41 mmol) is added to the suspension followed by HBr aq. (48%, 2.5 mL). The reaction mixture was stirred at 90° C. overnight and cooled to rt. The solvent was removed under reduced pressure and then purified by preparative high-performance liquid chromatography (30% to 60% (v/v) CH$_3$CN and H$_2$O with 0.05% ammonia hydroxide). The pure fractions were collected and the organic solvent was concentrated under reduced pressure. The pure fractions were collected and the organic solvent was concentrated under reduced pressure. The aqueous layer was lyophilized to dryness to give the desired product as off-white solid (290 mg, purity: 96.7%, yield: 21.9%). LCMS (ESI) m/z M+1: 473.9. $^1$H NMR (400 MHz, CHLOROFORM-d) δ ppm 7.01 (d, J=7.06 Hz, 1H), 7.08 (s, 1H), 7.37 (dd, J=9.04, 7.28 Hz, 1H), 7.63 (d, J=1.10 Hz, 1H), 7.81 (d, J=9.04 Hz, 1H), 7.96 (s, 2H), 8.30 (s, 1H), 8.67 (d, J=2.21 Hz, 1H), 8.83 (d, J=2.43 Hz, 1H), 9.48 (s, 1H).

Example 194

N-(5-chloro-2-methyl-6-(2H-1,2,3-triazol-2-yl)pyridin-3-yl)-1-(imidazo[1,2-a]pyridin-5-yl)-5-(trifluoromethyl)-1H-pyrazole-4-carboxamide, Cpd 194

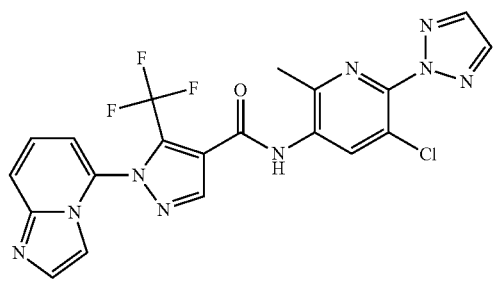 [SMILES: Cc1nc(-n2nccn2)c(Cl)cc1NC(=O)c1cnn(-c2cccc3nccn23)c1C(F)(F)F]

A. 5-hydrazinylimidazo[1,2-a]pyridine, 194a

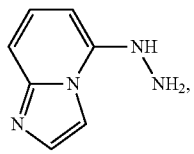

194a

The mixture of {Pd(cinnamyl)Cl}₂ (131 mg, 0.254 mmol) and Mor-DalPhos (235 mg, 0.508 mmol) in dioxane (100 mL) was evacuated with argon (4×). The resulting clear yellow solution was stirred at room temp under argon for 10 min. 5-Bromoimidazo[1,2-a]pyridine (1 g, 5.08 mmol) and t-BuONa (975 mg, 10.2 mmol) were added to the mixture and the mixture was evacuated with argon (4×). The resulting yellow reaction was stirred at room temp for 5 min and was then treated with NH₂NH₂.H₂O (98%, 504 μL, 10.2 mmol) via syringe. The reaction was evacuated with argon (4×). Then the mixture was stirred at 50° C. under argon for 2 h. The mixture was filtered though a pad of diatomaceous earth and washed with ethyl acetate/MeOH (v/v 20/1, 100 mL). The filtrate was collected and concentrated to give crude product as a brown solid (750 mg, crude). It was used directly in the next step.

B. ethyl 1-(imidazo[1,2-a]pyridin-5-yl)-5-(trifluoromethyl)-1H-pyrazole-4-carboxylate, 194b

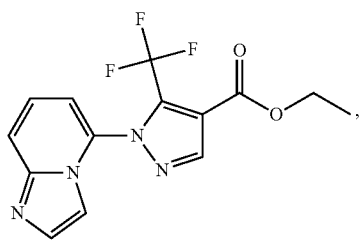

194b

A solution of 5-hydrazinylimidazo[1,2-a]pyridine (750 mg crude, 5.06 mmol) and ethyl 2-(ethoxymethylene)-4,4,4-trifluoro-3-oxobutanoate (1.82 g, 7.59 mmol) in EtOH (50 mL) was stirred at 80° C. for 1 h then cooled to rt. The solvent was removed under reduced pressure to give a black oil. It was purified by flash column chromatography over silica gel (eluent: petroleum ether/EtOAc 100/0 to petroleum ether/EtOAc 20/80). The desired fractions were collected and the solvent was concentrated to dryness under reduced pressure to give the desired product as a brown solid (850 mg, purity: 98.0%, yield: 50.7%). LCMS (ESI) m/z M+1: 325.1.

C. 1-(imidazo[1,2-a]pyridin-5-yl)-5-(trifluoromethyl)-1H-pyrazole-4-carboxylic acid, 194c

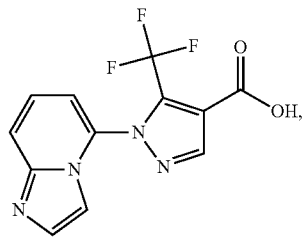

194c

The mixture of ethyl 1-(imidazo[1,2-a]pyridin-5-yl)-5-(trifluoromethyl)-1H-pyrazole-4-carboxylate (1.2 g, 3.70 mmol) in conc. HCl (12M, 25 mL) was stirred at 130° C. for 2 h. The solvent was concentrated under reduced pressure to give the crude product as a dark yellow solid (1.1 g, purity: 96.5%, yield: 96.8%). LCMS (ESI) m/z M+1: 296.9.

D. 5-chloro-2-methyl-3-nitropyridine 1-oxide, 194d

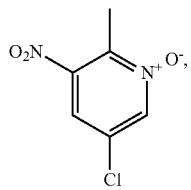

194d

A mixture of 5-chloro-2-methyl-3-nitropyridine (3.0 g, 17.4 mmol) and mCPBA (85%, 7.06 g, 34.8 mmol) in CH₂Cl₂ (60 mL) was stirred at rt for 72 h. The reaction mixture was quenched with 60 mL sat. Na₂SO₃ aq. Sat. K₂CO₃ aq was added to adjust the mixture pH to 9~10 and the mixture was extracted with CH₂Cl₂ (100 mL×3). The organic layer was separated, dried over Na₂SO₄, filtered and the filtrate concentrated to afford a yellow solid. The solid was purified by flash column chromatography over silica gel (eluent: petroleum ether/EtOAc 100/0 to petroleum ether/EtOAc 0/100). The desired fractions were collected and the solvent was concentrated to dryness under reduced pressure to afford the desired product as a yellow solid (2.4 g, yield: 73.2%). ¹H NMR (400 MHz, CHLOROFORM-d) δ ppm 2.65 (s, 3H), 7.71 (d, J=1.54 Hz, 1H), 8.46 (d, J=1.54 Hz, 1H).

E. 2,3-dichloro-6-methyl-5-nitropyridine, 194e

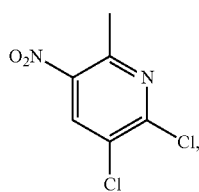

194e

POCl₃ (24.9 mL, 267 mmol) was added to a mixture of 5-chloro-2-methyl-3-nitropyridine 1-oxide (2.4 g, 12.7 mmol) in CHCl₃ (80 mL). The reaction mixture was stirred at reflux for 6 h. The reaction mixture was cooled to rt, then slowly added to 200 mL sat. K₂CO₃ aq, and extracted with CH₂Cl₂ (200 mL×3). The organic layer was separated, dried over Na₂SO₄, filtered and the filtrate concentrated to afford a brown solid. The solid was purified by flash column chromatography over silica gel (eluent: petroleum ether/ EtOAc 100/0 to petroleum ether/EtOAc 80/20). The desired fractions were collected and the solvent was concentrated to dryness under reduced pressure to afford the desired product as a yellow solid (1.1 g, yield: 41.8%). ¹H NMR (400 MHz, CHLOROFORM-d) δ ppm 2.86 (s, 3H), 8.43 (s, 1H).

F. 3-chloro-6-methyl-5-nitro-2-(2H-1,2,3-triazol-2-yl)pyridine, 194f

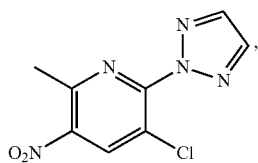

1H-1,2,3-triazole (550 mg, 7.97 mmol) was added to a solution of 2,3-dichloro-6-methyl-5-nitropyridine (1.1 g, 5.31 mol) and K₂CO₃ (2.20 g, 15.9 mmol) in CH₃CN (60 mL). The mixture was stirred at 40° C. for 2 h. The reaction mixture was filtered though a pad of diatomaceous earth and the pad was washed with EtOAc (50 mL×3). The filtrate was concentrated under reduced pressure to give the crude product as a black solid (1.2 g, yield: 94.2%).

G. 5-chloro-2-methyl-6-(2H-1,2,3-triazol-2-yl)pyridin-3-amine, 194g

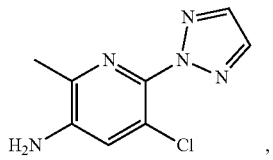

A mixture of 3-chloro-6-methyl-5-nitro-2-(2H-1,2,3-triazol-2-yl)pyridine (crude 1.2 g), iron powder (1.40 g, 25.0 mmol) and NH₄Cl (1.34 g, 25.0 mmol) in MeOH/THF/H₂O (1:1:1, 60 mL) was stirred at 70° C. for 2 h. The reaction mixture was filtered though a pad of diatomaceous earth and the pad washed with EtOAc (50 mL×2). The filtrate was washed with 50 mL sat. K₂CO₃ aq. and separated. The organic layer was dried over Na₂SO₄, filtered and the filtrate concentrated to afford a brown solid. The solid was purified by flash column chromatography over silica gel (eluent: petroleum ether/EtOAc 100/0 to petroleum ether/EtOAc 0/100). The desired fractions were collected and the solvent was concentrated to dryness under reduced pressure to afford the desired product as a yellow solid. ¹H NMR (400 MHz, CHLOROFORM-d) δ ppm 2.44 (s, 3H), 3.97 (br s, 2H), 7.13 (s, 1H), 7.88 (s, 2H).

H. N-(5-chloro-2-methyl-6-(2H-1,2,3-triazol-2-yl)pyridin-3-yl)-1-(imidazo[1,2-a]pyridin-5-yl)-5-(trifluoromethyl)-1H-pyrazole-4-carboxamide, Cpd 194

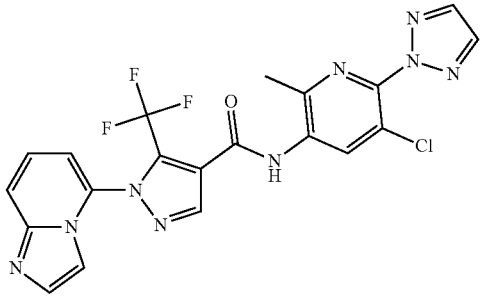 [SMILES: Cc1nc(-n2nccn2)c(Cl)cc1NC(=O)c1cnn(-c2cccc3nccn23)c1C(F)(F)F]

POCl₃ (0.364 mL, 3.91 mmol) was added to a mixture of 1-(imidazo[1,2-a]pyridin-5-yl)-5-(trifluoromethyl)-1H-pyrazole-4-carboxylic acid (600 mg, 1.96 mmol, 96.5% purity), 5-chloro-2-methyl-6-(2H-1,2,3-triazol-2-yl)pyridin-3-amine (410 mg, 1.96 mmol), pyridine (0.786 mL, 9.77 mmol) in CH₂Cl₂ (20 mL) at rt. The reaction mixture was stirred at room temperature for 1 h. The reaction mixture was quenched with 30 mL sat. K₂CO₃ aq, and the mixture extracted with CH₂Cl₂ (50 mL×3). The organic layer was separated and concentrated under reduced pressure. It was purified by preparative high-performance liquid chromatography (30% to 60% (v/v) CH₃CN and H₂O with 0.05% ammonia hydroxide). The pure fractions were collected and the organic solvent was concentrated under reduced pressure. The aqueous layer was lyophilized to dryness to give the desired product as a pale yellow solid (435 mg, purity: 100%, yield: 45.6%). LCMS (ESI) m/z M+1: 487.9. ¹H NMR (400 MHz, DMSO-d₆) δ ppm 2.54 (s, 3H), 7.35-7.44 (m, 2H), 7.48 (dd, J=9.04, 7.28 Hz, 1H), 7.72 (d, J=1.10 Hz, 1H), 7.90 (d, J=9.04 Hz, 1H), 8.17 (s, 2H), 8.43 (s, 1H), 8.68 (s, 1H).

Example 195

N-(5-chloro-2-ethyl-6-(2H-1,2,3-triazol-2-yl)pyridin-3-yl)-1-(imidazo[1,2-a]pyridin-5-yl)-5-(trifluoromethyl)-1H-pyrazole-4-carboxamide, Cpd 195

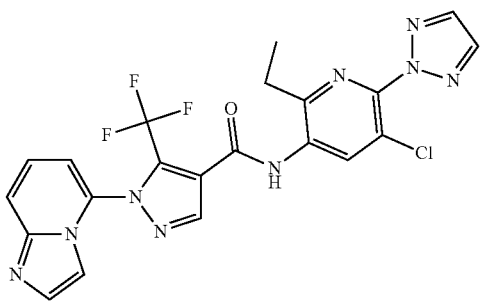 [SMILES: CCc1nc(-n2nccn2)c(Cl)cc1NC(=O)c1cnn(-c2cccc3nccn23)c1C(F)(F)F]

583

A. 2-bromo-5-chloro-6-(2H-1,2,3-triazol-2-yl)pyridin-3-amine, 195a

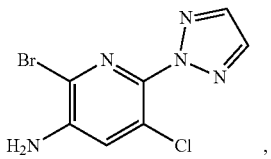

195a

NBS (2.73 g, 15.3 mmol) was added to a mixture of 5-chloro-6-(2H-1,2,3-triazol-2-yl)pyridin-3-amine (3 g, 15.3 mmol) in CH₃CN (300 mL) at 0° C., then the mixture was stirred at rt for 1 h. The reaction mixture was quenched with 100 mL sat. NaHCO₃ aq, and then extracted with EtOAc (100 mL×3). The organic layer was combined, washed with 50 mL of sat NaCl aq., dried over Na₂SO₄, filtered and the filtrate concentrated under reduced pressure to give a brown sticky residue. It was concentrated and purified by flash column chromatography over silica gel (eluent: petroleum ether/EtOAc 100/0 to petroleum ether/EtOAc 50/50). The desired fractions were collected and the solvent was concentrated to dryness under reduced pressure to give the product as a yellow solid (4.00 g, yield: 95.0%).

B. 5-chloro-2-ethyl-6-(2H-1,2,3-triazol-2-yl)pyridin-3-amine, 195b

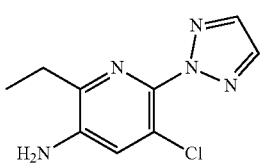

195b

To a solution of 2-bromo-5-chloro-6-(2H-1,2,3-triazol-2-yl)pyridin-3-amine (100 mg, 0.364 mmol) in dioxane (3 mL) was added ZnEt₂/toluene (1 M, 0.546 mL, 0.546 mmol) and Pd(dppf)Cl₂ (40.0 mg, 0.055 mmol) under N₂. The reaction mixture was stirred at 90° C. for 1.5 h. The reaction mixture was quenched with 10 mL sat. NaHCO₃ aq, then the mixture was filtered though a pad of diatomaceous earth and washed with 20 mL EtOAc. The filtrate was extracted with EtOAc (20 mL×2). The organic layer was separated, dried over Na₂SO₄, filtered and the filtrate concentrated to give a brown residue. It was purified by flash column chromatography over silica gel (eluent: petroleum ether/ethyl acetate from 100/0 to 50/50). The desired fractions were collected and the solvent was concentrated to dryness under reduced pressure to give product as a yellow solid (70 mg, yield: 86%). ¹H NMR (400 MHz, CHLOROFORM-d) δ ppm 1.29 (t, J=7.61 Hz, 3H), 2.71 (q, J=7.50 Hz, 2H), 3.96 (br s, 2H), 7.10 (s, 1H), 7.87 (s, 2H).

584

C. N-(5-chloro-2-ethyl-6-(2H-1,2,3-triazol-2-yl)pyridin-3-yl)-1-(imidazo[1,2-a]pyridin-5-yl)-5-(trifluoromethyl)-1H-pyrazole-4-carboxamide, Cpd 195

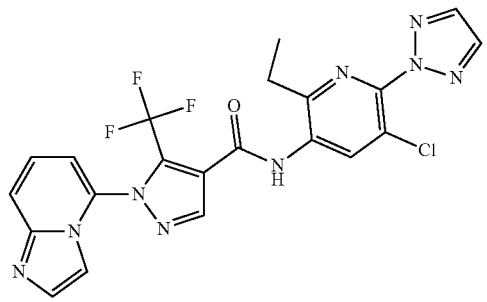 [SMILES: CCc1nc(-n2nccn2)c(Cl)cc1NC(=O)c1cnn(-c2cccc3nccn23)c1C(F)(F)F]

POCl₃ (0.58 mL, 0.626 mmol) was added to a mixture of 1-(imidazo[1,2-a]pyridin-5-yl)-5-(trifluoromethyl)-1H-pyrazole-4-carboxylic acid (96.1 mg, 0.313 mmol, 96.5% purity), 5-chloro-2-ethyl-6-(2H-1,2,3-triazol-2-yl)pyridin-3-amine (70 mg, 0.313 mmol), pyridine (124 mg, 1.57 mmol) in CH₂Cl₂ (5 mL) at rt. The reaction mixture was stirred at room temperature for 1 h. The reaction mixture was quenched with 20 mL sat. K₂CO₃ aq, and extracted with CH₂Cl₂ (20 mL×3). The organic layer was separated and concentrated under reduced pressure. It was purified by preparative high-performance liquid chromatography (35% to 65% (v/v) CH₃CN and H₂O with 0.05% ammonia hydroxide). The pure fractions were collected and the organic solvent was concentrated under reduced pressure. The aqueous layer was lyophilized to dryness to give the desired product as an off-white solid (95 mg, purity: 99%, yield: 60%). LCMS (ESI) m/z M+1: 501.9. ¹H NMR (400 MHz, DMSO-d₆) δ ppm 1.16-1.23 (m, 3H), 2.81-2.93 (m, 2H), 7.38 (s, 2H), 7.48 (t, J=8.20 Hz, 1H), 7.72 (s, 1H), 7.89 (d, J=8.20 Hz, 1H), 8.17 (s, 2H), 8.40 (s, 1H), 8.65 (s, 1H), 9.83 (s, 1H).

Example 196

N-(2,5-diethyl-6-(2H-1,2,3-triazol-2-yl)pyridin-3-yl)-1-(imidazo[1,2-a]pyridin-5-yl)-5-(trifluoromethyl)-1H-pyrazole-4-carboxamide, Cpd 196

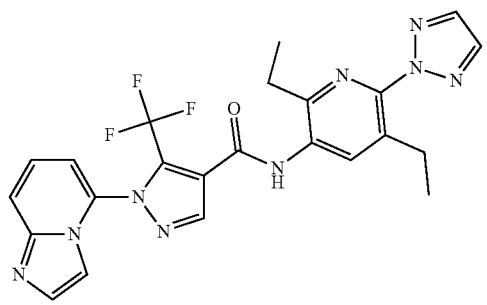 [SMILES: CCc1cc(NC(=O)c2cnn(-c3cccc4nccn34)c2C(F)(F)F)c(CC)nc1-n1nccn1]

A. 2,5-diethyl-6-(2H-1,2,3-triazol-2-yl)pyridin-3-amine, 196a

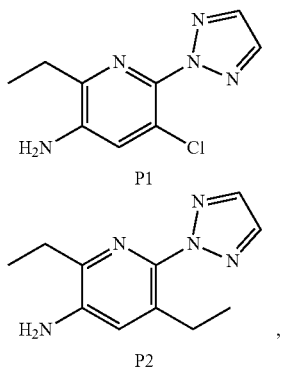

To a solution of 2-bromo-5-chloro-6-(2H-1,2,3-triazol-2-yl)pyridin-3-amine (200 mg, 0.729 mmol) in dioxane (6 mL) was added ZnEt$_2$/toluene (1 M, 2.55 mL, 2.55 mmol) and Pd(dppf)Cl$_2$ (80.0 mg, 0.109 mmol) under N$_2$. The reaction mixture was stirred at 110° C. overnight. LCMS showed 45.4% P2 formed in the reaction mixture, but only trace P1 formed. The reaction was quenched by 10 mL sat. aq. NH$_4$Cl, filtered though a pad of diatomaceous earth and washed with 30 mL EtOAc. The filtrate was washed with 20 mL sat. NaHCO$_3$ aq., then the organic layer was separated, dried over Na$_2$SO$_4$, filtered and the filtrate concentrated to give a brown sticky residue. The residue was purified by flash column chromatography over silica gel (eluent: petroleum ether/ethyl acetate from 100/0 to 0/100). The desired fractions were collected and the solvent was concentrated to dryness under reduced pressure to give the product as a yellow sticky residue (crude 125 mg). $^1$H NMR reflected ~10% 5-chloro-2-ethyl-6-(2H-1,2,3-triazol-2-yl)pyridin-3-amine. $^1$H NMR (400 MHz, CHLOROFORM-d) δ ppm 1.04 (t, J=7.61 Hz, 3H), 1.26-1.31 (m, 3H), 2.48 (q, J=7.64 Hz, 2H), 2.68-2.77 (m, 2H), 3.81 (br s, 2H), 6.93 (s, 1H), 7.82 (s, 2H).

B. N-(2,5-diethyl-6-(2H-1,2,3-triazol-2-yl)pyridin-3-yl)-1-(imidazo[1,2-a]pyridin-5-yl)-5-(trifluoromethyl)-1H-pyrazole-4-carboxamide, Cpd 196

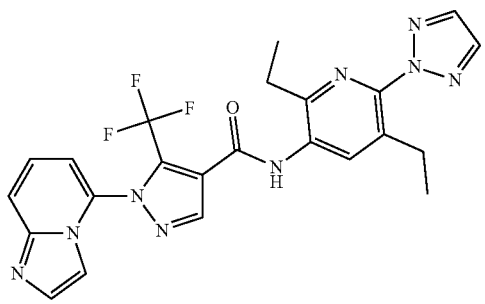 [SMILES: CCc1cc(NC(=O)c2cnn(-c3cccc4nccn34)c2C(F)(F)F)c(CC)nc1-n1nccn1]

POCl$_3$ (0.103 mL, 1.11 mmol) was added to a mixture of 1-(imidazo[1,2-a]pyridin-5-yl)-5-(trifluoromethyl)-1H-pyrazole-4-carboxylic acid (170 mg, 0.552 mmol), 2,5-diethyl-6-(2H-1,2,3-triazol-2-yl)pyridin-3-amine (crude 120 mg), pyridine (218 mg, 2.76 mmol) in CH$_2$Cl$_2$ (5 mL) at rt. The reaction mixture was stirred at rt for 1 h. The reaction mixture was quenched with 20 mL sat. K$_2$CO$_3$ aq, and extracted with CH$_2$Cl$_2$ (20 mL×3). The organic layer was separated and concentrated under reduced pressure. It was purified by preparative high-performance liquid chromatography (35% to 65% (v/v) CH$_3$CN and H$_2$O with 0.05% ammonia hydroxide). The pure fractions were collected and the organic solvent was concentrated under reduced pressure. The aqueous layer was lyophilized to dryness to give the desired product as a pale yellow solid which was further purified by SFC (Column: Chiralcel OJ 250×30 5u; Condition: 0.1% NH$_3$H$_2$O MEOH, Flow Rate (mL/min) 65). The pure fractions were collected and the organic solvent was concentrated under reduced pressure, then lyophilized to dryness to give the desired product as a white solid (105 mg, purity: 100%, yield: 38.8%). LCMS (ESI) m/z M+1: 496.0. $^1$H NMR (400 MHz, DMSO-d$_6$) δ ppm 0.99 (t, J=7.61 Hz, 3H), 1.19 (t, J=7.50 Hz, 3H), 2.50-2.55 (m, 2H), 2.83 (q, J=7.50 Hz, 2H), 7.40 (d, J=7.28 Hz, 2H), 7.44-7.53 (m, 1H), 7.72 (d, J=1.10 Hz, 1H), 7.90 (dd, J=9.04, 0.88 Hz, 1H), 8.00 (s, 1H), 8.12 (s, 2H), 8.66 (s, 1H), 10.52 (s, 1H).

Example 197

N-(5-chloro-6-(2H-1,2,3-triazol-2-yl)pyridin-3-yl)-1-(pyrazolo[1,5-a]pyridin-4-yl)-5-(trifluoromethyl)-1H-pyrazole-4-carboxamide, Cpd 197

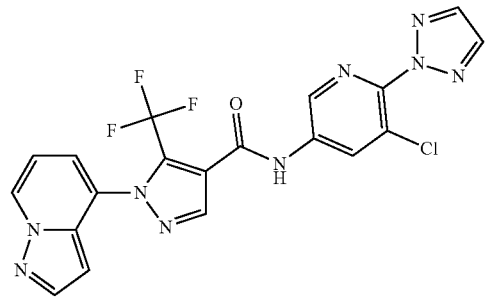 [SMILES: O=C(Nc1cnc(-n2nccn2)c(Cl)c1)c1cnn(-c2cccn3nccc23)c1C(F)(F)F]

A. 4-hydrazinylpyrazolo[1,5-a]pyridine, 197a

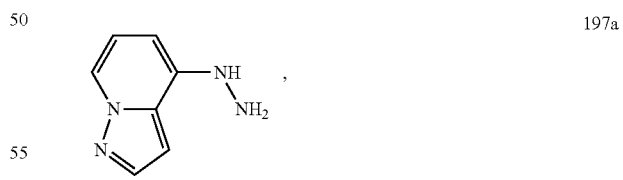

A mixture of {Pd(cinnamyl)Cl}$_2$ (131 mg, 0.254 mmol) and Mor-DalPhos (235 mg, 0.508 mmol) in dioxane (100 mL) was evacuated with argon (4×). The resulting clear yellow solution was stirred at rt under argon for 10 min. 4-Bromopyrazolo[1,5-a]pyridine (1.00 g, 5.08 mmol) and t-BuONa (975 mg, 10.2 mmol) were added to the mixture and the mixture was evacuated with argon (4×). The resulting yellow reaction was stirred at rt for 5 min and was then treated with NH$_2$NH$_2$.H$_2$O (98%, 0.502 mL, 10.2 mmol) via syringe. The reaction was evacuated with argon (4×). Then the mixture was stirred at 50° C. under argon for 3 h. The mixture was filtered though a pad of diatomaceous earth and washed with ethyl acetate (200 mL). The filtrate was collected and concentrated to give a crude product as a dark yellow solid (750 mg). It was used directly for the next step.

B. ethyl 1-(pyrazolo[1,5-a]pyridin-4-yl)-5-(trifluoromethyl)-1H-pyrazole-4-carboxylate, 197b

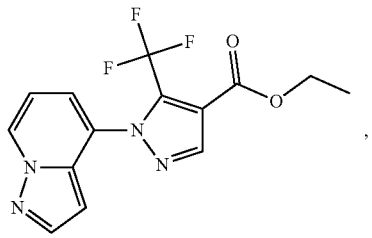

197b

A solution of 4-hydrazinylpyrazolo[1,5-a]pyridine (750 mg crude) and ethyl 2-(ethoxymethylene)-4,4,4-trifluoro-3-oxobutanoate (1.84 g, 7.59 mmol) in EtOH (100 mL) was stirred at 80° C. for 1 h then cooled to rt. The solvent was removed under reduced pressure to give the crude product as a brown solid. The solid was purified by flash column chromatography over silica gel (eluent: petroleum ether/ethyl acetate from 100/0 to 50/50). The desired fractions were collected and the solvent was concentrated to dryness under reduced pressure to give product as a yellow solid (1.11 g, 67.4% yield in two steps). LCMS (ESI) m/z M+1: 324.9.

C. 1-(pyrazolo[1,5-a]pyridin-4-yl)-5-(trifluoromethyl)-1H-pyrazole-4-carboxylic acid, 197c

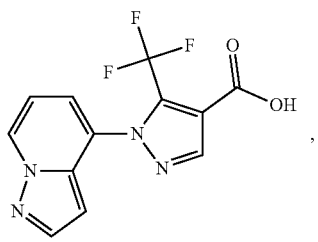

197c

A mixture of ethyl 1-(pyrazolo[1,5-a]pyridin-4-yl)-5-(trifluoromethyl)-1H-pyrazole-4-carboxylate (650 mg, 1.96 mmol) in conc. HCl (12 M, 50 mL) was stirred at 130° C. for 1 h. The solvent was removed under reduced pressure to give the crude as a pale yellow solid (600 mg, purity: 98.8%, quantitative yield). LCMS (ESI) m/z M+1: 296.9.

D. N-(5-chloro-6-(2H-1,2,3-triazol-2-yl)pyridin-3-yl)-1-(pyrazolo[1,5-a]pyridin-4-yl)-5-(trifluoromethyl)-1H-pyrazole-4-carboxamide, Cpd 197

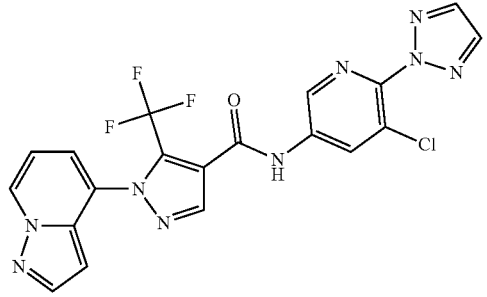 [SMILES: O=C(Nc1cnc(-n2nccn2)c(Cl)c1)c1cnn(-c2cccn3nccc23)c1C(F)(F)F]

POCl₃ (0.0755 mL, 0.81 mmol) was added to a mixture of 1-(pyrazolo[1,5-a]pyridin-4-yl)-5-(trifluoromethyl)-1H-pyrazole-4-carboxylic acid (120 mg, 0.405 mmol), 5-chloro-6-(2H-1,2,3-triazol-2-yl)pyridin-3-amine (79.2 mg, 0.405 mmol), pyridine (160 mg, 2.03 mmol) in CH₂Cl₂ (5 mL) at rt. The reaction mixture was stirred rt for 1 h. The reaction mixture was quenched with 20 mL sat. K₂CO₃ aq, and extracted with CH₂Cl₂ (20 mL×3). The organic layer was separated and concentrated under reduced pressure. It was purified by preparative high-performance liquid chromatography (40% to 70% (v/v) CH₃CN and H₂O with 0.05% ammonia hydroxide). The pure fractions were collected and the organic solvent was concentrated under reduced pressure. The aqueous layer was lyophilized to dryness to give the desired product as a yellow solid (80 mg, purity: 97%, yield: 40%). LCMS (ESI) m/z M+1: 473.9. ¹H NMR (400 MHz, DMSO-d₆) δ ppm 6.34 (dd, J=2.43, 0.88 Hz, 1H), 7.08 (t, J=7.28 Hz, 1H), 7.58 (d, J=7.28 Hz, 1H), 8.13 (d, J=2.43 Hz, 1H), 8.17 (s, 2H), 8.55 (s, 1H), 8.64 (d, J=2.43 Hz, 1H), 8.83 (d, J=2.21 Hz, 1H), 8.96 (d, J=7.06 Hz, 1H).

Example 198

N-(5-chloro-6-(2H-1,2,3-triazol-2-yl)pyridin-3-yl)-1-(pyrazolo[1,5-a]pyridin-4-yl)-5-(trifluoromethyl)-1H-pyrazole-4-carboxamide, Cpd 198

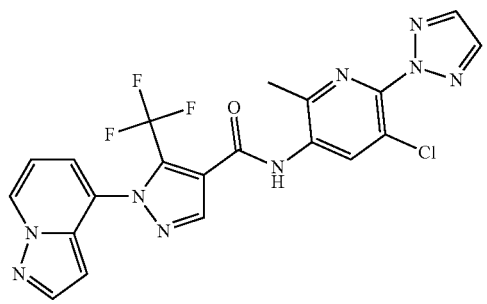 [SMILES: Cc1nc(-n2nccn2)c(Cl)cc1NC(=O)c1cnn(-c2cccn3nccc23)c1C(F)(F)F]

POCl₃ (0.076 mL, 0.81 mmol) was added dropwise to a solution of 1-(pyrazolo[1,5-a]pyridin-4-yl)-5-(trifluoromethyl)-1H-pyrazole-4-carboxylic acid (120 mg, 0.405 mmol), 5-chloro-2-methyl-6-(2H-1,2,3-triazol-2-yl)pyridin-3-amine (0.085 g, 0.405 mmol) and pyridine (0.164 mL, 2.03 mmol) in CH₂Cl₂ (5 mL). The reaction mixture was stirred at room temperature for 2 h. Water (5 mL) was added to the mixture. The aqueous was extracted with $CH_2Cl_2$ (10 mL×3). The separated organic layer was dried ($Na_2SO_4$), filtered, and the solvent was concentrated to give a crude product. The crude product was purified by preparative high-performance liquid chromatography (35% to 65% (v/v) $CH_3CN$ and $H_2O$ with 0.05% ammonia hydroxide). The pure fractions were collected and the organic solvent was concentrated under reduced pressure. The aqueous layer was lyophilized to dryness to give the desired product as a white solid (89.2 mg, purity: 98.4%, yield: 44.4%). LCMS (ESI) m/z M+1: 487.9. $^1$H NMR (400 MHz, DMSO-$d_6$) δ ppm 2.53 (s, 3H) 6.36 (dd, J=2.43, 0.88 Hz, 1H) 7.08 (t, J=7.17 Hz, 1H) 7.54-7.58 (m, 1H) 8.13 (d, J=2.43 Hz, 1H) 8.17 (s, 2H) 8.43 (s, 1H) 8.52 (s, 1H) 8.96 (d, J=7.06 Hz, 1H).

Example 199

N-(5-chloro-6-(2H-1,2,3-triazol-2-yl)pyridin-3-yl)-1-(2-methylimidazo[1,2-a]pyridin-5-yl)-5-(trifluoromethyl)-1H-pyrazole-4-carboxamide, Cpd 199

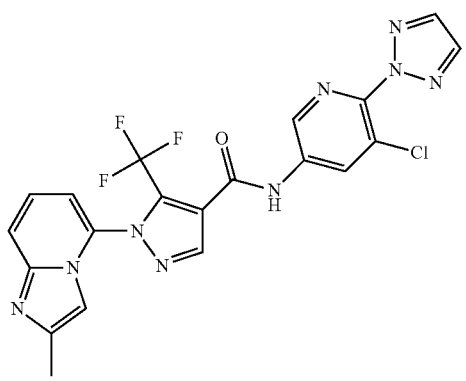 [SMILES: Cc1cn2c(-n3ncc(C(=O)Nc4cnc(-n5nccn5)c(Cl)c4)c3C(F)(F)F)cccc2n1]

A. 5-hydrazinyl-2-methylimidazo[1,2-a]pyridine, 199a

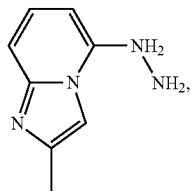

A mixture of {Pd(cinnamyl)Cl}$_2$ (49.1 mg, 0.095 mmol) and Mor-DalPhos (87.9 mg, 0.19 mmol) in dioxane (40 mL) was evacuated with argon (4×). The resulting clear yellow solution was stirred at rt under argon for 10 min. 5-Bromo-2-methylimidazo[1,2-a]pyridine (400 mg, 1.9 mmol) and t-BuONa (364.3 mg, 3.79 mmol) were added to the mixture and the mixture was evacuated with argon (4×). The resulting yellow reaction was stirred at rt for 5 min and was then treated with $NH_2NH_2 \cdot H_2O$ (0.188 mL, 3.79 mmol) via syringe. The reaction was evacuated with argon (4×). Then the mixture was stirred at 50° C. under argon for 2 h. The mixture was filtered though a pad of diatomaceous earth and washed with ethyl acetate (50 mL). The filtrate was collected and concentrated to give the crude product as a yellow residue (250 mg crude), which was used directly for the next step.

B. ethyl 1-(2-methylimidazo[1,2-a]pyridin-5-yl)-5-(trifluoromethyl)-1H-pyrazole-4-carboxylate, 199b

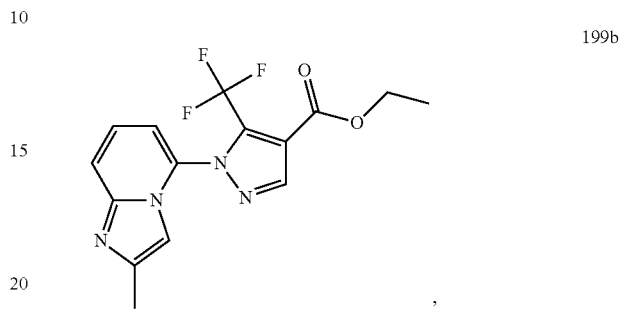

A solution of 5-hydrazinyl-2-methylimidazo[1,2-a]pyridine (250 mg crude, 1.54 mmol) and ethyl 2-(ethoxymethylene)-4,4,4-trifluoro-3-oxobutanoate (555.3 mg, 2.31 mmol) in EtOH (30 mL) was stirred at 80° C. for 1 h then cooled to rt. The solvent was removed under reduced pressure to give the crude product as dark brown residue. The residue was purified by flash column chromatography over silica gel (eluent: petroleum ether/EtOAc 100/0 to petroleum ether/EtOAc 0/100). The desired fractions were collected and the solvent was concentrated to dryness under reduced pressure to give the product as a black oil, which was further purified by preparative high-performance liquid chromatography (40% to 70% (v/v) $CH_3CN$ and $H_2O$ with 0.05% ammonia hydroxide). The pure fractions were collected and the organic solvent was concentrated under reduced pressure. The aqueous layer was lyophilized to dryness to give the desired product as a yellow solid (100 mg, yield: 19.2%).

C. 1-(2-methylimidazo[1,2-a]pyridin-5-yl)-5-(trifluoromethyl)-1H-pyrazole-4-carboxylic acid, 199c

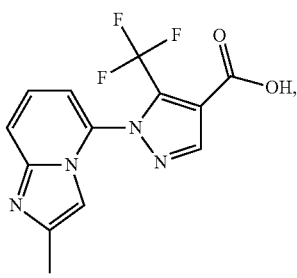

A mixture of ethyl 1-(2-methylimidazo[1,2-a]pyridin-5-yl)-5-(trifluoromethyl)-1H-pyrazole-4-carboxylate (100 mg, 0.30 mmol) in conc. HCl (12 M, 5 mL) was stirred at 130° C. for 1 h. The solvent was removed under reduced pressure to give the crude product as pale yellow solid (100 mg crude, purity: 100%), which was used directly for the next step. LCMS (ESI) m/z M+1: 310.9.

D. N-(5-chloro-6-(2H-1,2,3-triazol-2-yl)pyridin-3-yl)-1-(2-methylimidazo[1,2-a]pyridin-5-yl)-5-(trifluoromethyl)-1H-pyrazole-4-carboxamide, Cpd 199

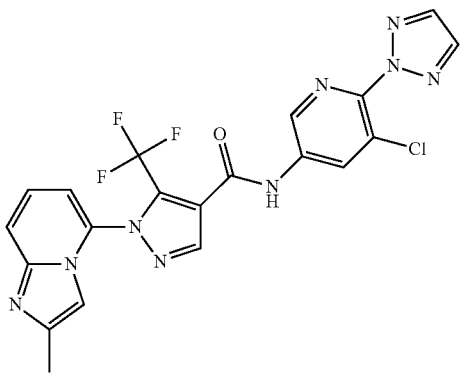 [SMILES: Cc1cn2c(-n3ncc(C(=O)Nc4cnc(-n5nccn5)c(Cl)c4)c3C(F)(F)F)cccc2n1]

POCl$_3$ (98.9 mg, 0.65 mmol) was added to a mixture of 1-(2-methylimidazo[1,2-a]pyridin-5-yl)-5-(trifluoromethyl)-1H-pyrazole-4-carboxylic acid (100 mg, 0.32 mmol, 100% purity), 5-chloro-6-(2H-1,2,3-triazol-2-yl)pyridin-3-amine (63.05 mg, 0.32 mol), pyridine (127.49 mg, 1.61 mmol) in CH$_2$Cl$_2$ (3 mL) at rt. The reaction mixture was stirred at room temperature for 1 h. The reaction mixture was quenched with 20 mL sat. K$_2$CO$_3$ aq, and extracted with CH$_2$Cl$_2$ (20 mL×3). The organic layer was separated and concentrated under reduced pressure. The resulting residue was purified by preparative high-performance liquid chromatography (40% to 70% (v/v) CH$_3$CN and H$_2$O with 0.05% ammonia hydroxide). The pure fractions were collected and the organic solvent was concentrated under reduced pressure. The aqueous layer was lyophilized to dryness to give the desired product as a pale yellow solid (65 mg, purity: 99.7%, yield: 41.2%). LCMS (ESI) m/z M+1: 488.1. $^1$H NMR (400 MHz, DMSO-d$_6$) δ ppm 2.32 (s, 3H), 7.10 (s, 1H), 7.33 (dd, J=7.17, 0.99 Hz, 1H), 7.39-7.44 (m, 1H), 7.74-7.78 (m, 1H), 8.17 (s, 2H), 8.65 (d, J=2.21 Hz, 1H), 8.68 (s, 1H), 8.83 (d, J=2.43 Hz, 1H), 11.27 (br s, 1H).

Example 200

N-(5-cyano-6-(2H-1,2,3-triazol-2-yl)pyridin-3-yl)-1-(imidazo[1,2-a]pyridin-5-yl)-5-(trifluoromethyl)-1H-pyrazole-4-carboxamide, Cpd 200

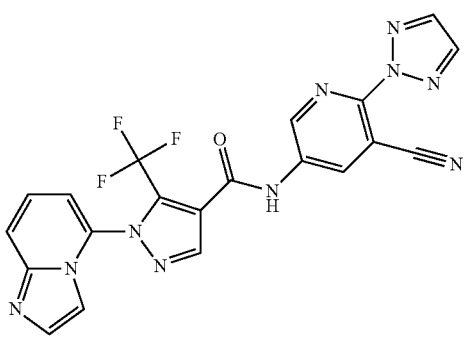 [SMILES: N#Cc1cc(NC(=O)c2cnn(-c3cccc4nccn34)c2C(F)(F)F)cnc1-n1nccn1]

POCl$_3$ (82.83 mg, 0.54 mmol) was added to a mixture of 1-(imidazo[1,2-a]pyridin-5-yl)-5-(trifluoromethyl)-1H-pyrazole-4-carboxylic acid (80 mg, 0.27 mmol), 5-amino-2-(2H-1,2,3-triazol-2-yl)nicotinonitrile (50.28 mg, 0.27 mmol) and pyridine (106.82 mg, 1.35 mmol) in CH$_2$Cl$_2$ (2 mL). The reaction mixture was stirred at 20° C. for 1 h. Sat. NaHCO$_3$ solution (20 mL) was added to the mixture. The mixture was extracted with 30 mL ethyl acetate. The combined organic layers were dried over Na$_2$SO$_4$ and filtered. The filtrates were concentrated under reduced pressure to afford crude product as a brown oil. The crude product was purified by preparative high-performance liquid chromatography (26% to 56% (v/v) CH$_3$CN and H$_2$O with 0.05% ammonia hydroxide). The pure fractions were collected and the solvent was concentrated under reduced pressure. The aqueous layer was concentrated to dryness to give product as a light yellow solid (45.6 mg, purity: 99.9%, yield: 36.3%). LCMS (ESI) m/z M+1: 465.0. $^1$H NMR (400 MHz, DMSO-d$_6$) δ ppm 7.38-7.52 (m, 3H), 7.71 (d, J=1.1 Hz, 1H), 7.90 (d, J=9.0 Hz, 1H), 8.30 (s, 2H), 8.75 (s, 1H), 8.89 (d, J=2.4 Hz, 1H), 9.11 (d, J=2.4 Hz, 1H), 11.27 (br s, 1H).

Example 201

N-(5-chloro-6-(2H-1,2,3-triazol-2-yl)pyridin-3-yl)-1-(3-chloroimidazo[1,2-a]pyridin-5-yl)-5-(trifluoromethyl)-1H-pyrazole-4-carboxamide, Cpd 201

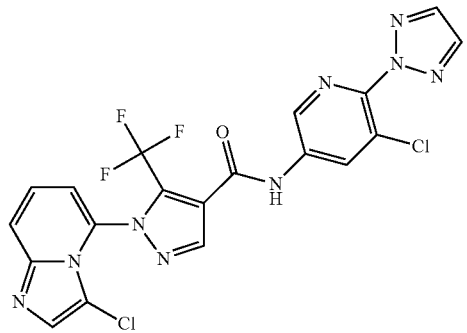 [SMILES: O=C(Nc1cnc(-n2nccn2)c(Cl)c1)c1cnn(-c2cccc3ncc(Cl)n23)c1C(F)(F)F]

To a stirred solution of N-(5-chloro-6-(2H-1,2,3-triazol-2-yl)pyridin-3-yl)-1-(imidazo[1,2-a]pyridin-5-yl)-5-(trifluoromethyl)-1H-pyrazole-4-carboxamide (70 mg, 0.15 mmol) in MeCN (2 mL) was added NCS (39.46 mg, 0.30 mmol). The mixture was stirred at 60° C. for 4 h. The mixture was purified by preparative high-performance liquid chromatography (40% to 70% (v/v) CH$_3$CN and H$_2$O with 0.05% ammonia hydroxide). The pure fractions were collected and the solvent was concentrated under reduced pressure. The aqueous layer was lyophilized to dryness to give the product as a light yellow solid (65.6 mg, purity: 98.5%, yield: 86.0%). The structure is first assigned as such, NMR could not distinguish the position of the Cl at 2 or 3 position of the imidazopyridine. LCMS (ESI) m/z M+1: 507.9. $^1$H NMR (400 MHz, DMSO-d$_6$) δ ppm 6.10 (br s, 1H), 7.51-7.63 (m, 2H), 7.85 (s, 1H), 8.00 (dd, J=1.3, 8.8 Hz, 1H), 8.19 (s, 2H), 8.62 (s, 1H), 8.69 (d, J=2.3 Hz, 1H), 8.81 (d, J=2.3 Hz, 1H).

Example 202

N-(5-chloro-6-(2H-1,2,3-triazol-2-yl)pyridin-3-yl)-1-(8-fluoroimidazo[1,2-a]pyridin-5-yl)-5-(trifluoromethyl)-1H-pyrazole-4-carboxamide, Cpd 202

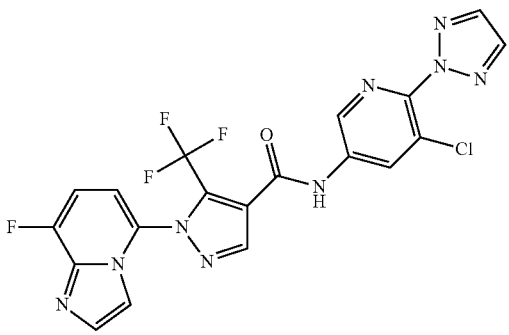 [SMILES: O=C(Nc1cnc(-n2nccn2)c(Cl)c1)c1cnn(-c2ccc(F)c3nccn23)c1C(F)(F)F]

A. 3,6-difluoro-2-hydrazinylpyridine, 202a

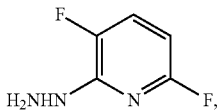

To an ice-cold solution of 2,3,6-trifluoropyridine (4 g, 30.06 mmol) in EtOH (50 mL) was added hydrazine hydrate (3.071 g, 60.12 mmol). The reaction mixture was warmed up to r.t. and then heated at reflux for 2 h. After it was cooled to r.t., the reaction mixture was diluted with water (50 mL) and extracted with CH$_2$Cl$_2$ (2×100 mL). The combined organic layers were dried over anhydrous Na$_2$SO$_4$, filtered, and the filtrate concentrated under reduced pressure. The residue was re-crystallized from EtOH to obtain the product as a light yellow solid (3 g, yield: 68.8%).

B. 2-bromo-3,6-difluoropyridine, 202b

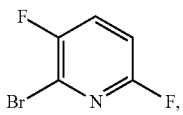

Br$_2$ (2.13 mL, 41.35 mmol) was added dropwise to a stirred solution of 3,6-difluoro-2-hydrazinylpyridine (3 g, 20.67 mmol) in CHCl$_3$ (45 mL) at room temperature. The mixture was stirred at 60° C. for 1 h. The mixture was cooled at 0° C. and a saturated solution of NaHCO$_3$ (200 mL) was added dropwise. CH$_2$Cl$_2$ (200 mL) was added, the organic layer was separated, dried (Na$_2$SO$_4$), filtered and the solvents concentrated under reduced pressure. The residue was purified by flash column chromatography over silica gel (petroleum ether:EtOAc=1:0~9:1) to yield the product as a yellow oil (1.7 g, yield: 42.4%). $^1$H NMR (400 MHz, DMSO-d$_6$) δ ppm 6.92 (td, J=3.1, 8.7 Hz, 1H), 7.55 (td, J=6.2, 8.6 Hz, 1H).

C. 2-bromo-3-fluoro-6-hydrazinylpyridine, 202c

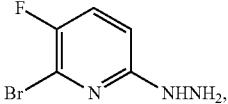

2-Bromo-3,6-difluoropyridine (2.7 g, 13.92 mmol) was dissolved in MeCN (50 mL) and hydrazine hydrate (1.422 g, 27.84 mmol) was added. The reaction mixture was stirred at 80° C. for 16 h. The reaction mixture was concentrated under reduced pressure to afford crude as a yellow solid (2.868 g, yield:100%).

D. ethyl 1-(6-bromo-5-fluoropyridin-2-yl)-5-(trifluoromethyl)-1H-pyrazole-4-carboxylate, 202d

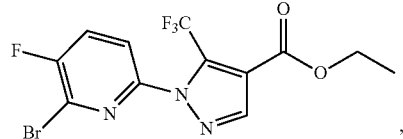

2-Bromo-3-fluoro-6-hydrazinylpyridine (2.8 g, 13.59 mmol) was dissolved in EtOH (60 mL), ethyl 2-(ethoxymethylene)-4,4,4-trifluoro-3-oxobutanoate (6.529 g, 27.18 mmol) was added and stirred at 60° C. for 2 h. The mixture was concentrated under reduced pressure to afford crude product. The crude product was purified by flash column chromatography over silica gel (eluent: petroleum ether/ethyl acetate from 100/0 to 80/20). The desired fractions were collected and the solvent was concentrated under reduced pressure to afford compound as a yellow solid (2 g, yield: 38.5%). $^1$H NMR (400 MHz, DMSO-d$_6$) δ ppm 1.38-1.41 (m, 3H), 4.37-4.41 (m, 2H), 7.63-7.67 (m, 2H), 8.11 (s, 1H).

E. ethyl 1-(6-((tert-butoxycarbonyl)amino)-5-fluoropyridin-2-yl)-5-(trifluoromethyl)-1H-pyrazole-4-carboxylate, 202e

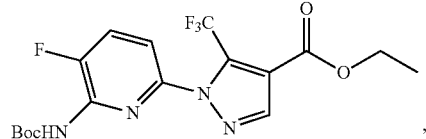

Pd(OAc)$_2$ (58.755 mg, 0.26 mmol) and Xantphos (151.428 mg, 0.26 mmol) in dioxane (50 mL) were stirred at rt for 10 min under nitrogen. Ethyl 1-(6-bromo-5-fluoropyridin-2-yl)-5-(trifluoromethyl)-1H-pyrazole-4-carboxylate (2 g, 5.23 mmol), Cs$_2$CO$_3$ (5.116 g, 15.70 mmol) and tert-butyl carbamate (0.736 g, 6.28 mmol) were then added at room temperature. The reaction mixture was then allowed to heat at 90° C. overnight and before cooling to rt. The reaction mixture was filtered though a pad of diatomaceous earth. The filtrate was concentrated under reduced pressure, then purified by flash column chromatography over silica gel (eluent: petroleum ether/EtOAc 100/0 to petroleum ether/EtOAc 80/20). The desired fractions were collected and the solvent was concentrated to dryness under reduced pressure to give the desired product as a yellow solid (1800 mg, yield: 82.2%).

F. 1-(6-(((tert-butoxycarbonyl)amino)-5-fluoropyridin-2-yl)-5-(trifluoromethyl)-1H-pyrazole-4-carboxylic acid, 202f

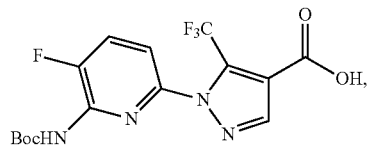

202f

To a mixture of ethyl 1-(6-(((tert-butoxycarbonyl)amino)-5-fluoropyridin-2-yl)-5-(trifluoromethyl)-1H-pyrazole-4-carboxylate (1800 mg, 4.30 mmol) in MeOH (15 mmL) and $H_2O$ (15 mL) was added $LiOH.H_2O$ (361.11 mg, 8.61 mmol) at 0° C. The mixture was stirred at 0° C. for 1 h. The mixture was concentrated to dryness. To the residue was added water/EtOAc (100 mL/100 mL). HCl (1 M in water) was used to adjust the pH of the mixture to pH=5. The organic layer was concentrated to dryness to give the product (1500 mg, yield: 89.3%) as a yellow solid.

G. tert-butyl (6-(4-((5-chloro-6-(2H-1,2,3-triazol-2-yl)pyridin-3-yl)carbamoyl)-5-(trifluoromethyl)-1H-pyrazol-1-yl)-3-fluoropyridin-2-yl)carbamate, 202g

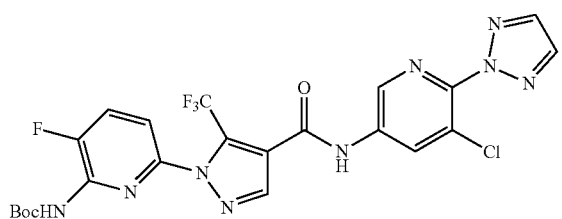

202g $POCl_3$ (1178.60 mg, 7.69 mmol) was added to a mixture of 1-(6-(((tert-butoxycarbonyl)amino)-5-fluoropyridin-2-yl)-5-(trifluoromethyl)-1H-pyrazole-4-carboxylic acid (1500 mg, 3.84 mmol), 5-chloro-6-(2H-1,2,3-triazol-2-yl)pyridin-3-amine (751.78 mg, 3.84 mmol) and pyridine (1520.0 mg, 19.22 mmol) in $CH_2Cl_2$ (30 mL). The reaction mixture was stirred at 20° C. for 1 h. $Sat.K_2CO_3$ solution (100 mL) was added to the mixture. The mixture was extracted with 100 mL ethyl acetate. The combined organic layers were dried over $Na_2SO_4$, then filtered. The filtrates were concentrated under reduced pressure to afford a crude product as a brown oil. The crude material was purified by flash column chromatography over silica gel column (petroleum ether:ethyl acetate=1:1~0:1). The desired fraction was collected and the solvent was concentrated under reduced pressure to afford the product as a yellow solid (2000 mg, yield: 91.6%).

H. 1-(6-amino-5-fluoropyridin-2-yl)-N-(5-chloro-6-(2H-1,2,3-triazol-2-yl)pyridin-3-yl)-5-(trifluoromethyl)-1H-pyrazole-4-carboxamide, 202h

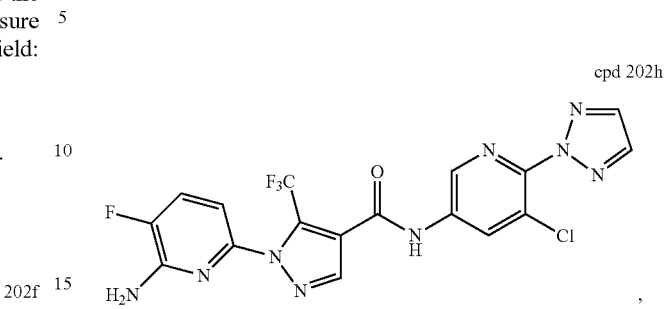

cpd 202h

Tert-butyl (6-(4-((5-chloro-6-(2H-1,2,3-triazol-2-yl)pyridin-3-yl)carbamoyl)-5-(trifluoromethyl)-1H-pyrazol-1-yl)-3-fluoropyridin-2-yl)carbamate (2000 mg, 3.522 mmol) and HCl/MeOH (60 mL, 4M) were stirred at 30° C. for 1 h. The mixture was concentrated to dryness. To the residue was added saturated aqueous $K_2CO_3$ (100 mL). The mixture was extracted with EtOAc (100 mL×3). The combined organic layers were dried over $Na_2SO_4$, filtered and the filtrate was concentrated to dryness to give a crude orange gum. The crude product was purified by preparative high-performance liquid chromatography (20% to 505% (v/v) $CH_3CN$ and $H_2O$). The pure fractions were collected and the solvent was concentrated under reduced pressure. The residue was extracted with EtOAc (100 mL×3). The combined organic layers were concentrated to dryness to give product as a light yellow solid (800 mg, yield: 48.6%). LCMS (ESI) m/z M+1: 467.9. $^1H$ NMR (400 MHz, DMSO-$d_6$) δ ppm 4.83 (br s, 2H), 6.95 (dd, J=2.6, 8.2 Hz, 1H), 7.37-7.45 (m, 1H), 7.95 (s, 2H), 8.04 (s, 1H), 8.49 (d, J=2.4 Hz, 1H), 8.75 (d, J=2.2 Hz, 1H).

I. N-(5-chloro-6-(2H-1,2,3-triazol-2-yl)pyridin-3-yl)-1-(8-fluoroimidazo[1,2-a]pyridin-5-yl)-5-(trifluoromethyl)-1H-pyrazole-4-carboxamide, Cpd 202

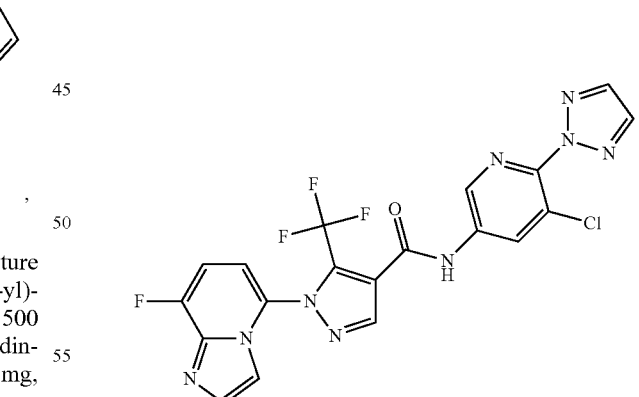

1-(6-amino-5-fluoropyridin-2-yl)-N-(5-chloro-6-(2H-1,2,3-triazol-2-yl)pyridin-3-yl)-5-(trifluoromethyl)-1H-pyrazole-4-carboxamide (800 mg, 1.71 mmol) was dissolved in i-PrOH (20 mL) under $N_2$. 2-Bromo-1,1-diethoxyethane (674.08 mg, 3.42 mmol) was added to the suspension followed by HBr (2 mL, 48% in water). The resulting mixture was then refluxed for 12 h and cooled down to room temperature. The solvent was removed under reduced pressure. The residue was purified by preparative high-performance liquid chromatography (30% to 60% (v/v) CH$_3$CN and H$_2$O with 0.05% ammonia hydroxide). The pure fractions were collected and the solvent was concentrated under reduced pressure. The residue was lyophilized to dryness to give the product as a light yellow solid (422.2 mg, purity: 100%, yield: 50.2%). LCMS (ESI) m/z M+1: 491.9. $^1$H NMR (400 MHz, DMSO-d$_6$) δ ppm 7.40-7.47 (m, 1H), 7.47-7.51 (m, 1H), 7.53 (dd, J=1.2, 3.2 Hz, 1H), 7.76 (d, J=1.1 Hz, 1H), 8.17 (s, 2H), 8.65 (d, J=2.2 Hz, 1H), 8.69 (s, 1H), 8.83 (d, J=2.2 Hz, 1H), 11.42-11.07 (m, 1H).

Example 203

N-(5-chloro-2-methyl-6-(2H-1,2,3-triazol-2-yl)pyridin-3-yl)-1-(8-fluoroimidazo[1,2-a]pyridin-5-yl)-5-(trifluoromethyl)-1H-pyrazole-4-carboxamide, Cpd 203

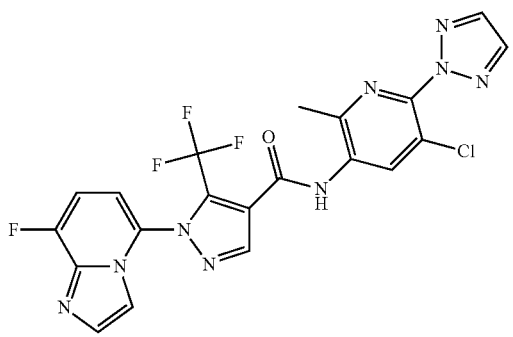 [SMILES: Cc1nc(-n2nccn2)c(Cl)cc1NC(=O)c1cnn(-c2ccc(F)c3nccn23)c1C(F)(F)F]

A. tert-butyl (6-(4-((5-chloro-2-methyl-6-(2H-1,2,3-triazol-2-yl)pyridin-3-yl)carbamoyl)-5-(trifluoromethyl)-1H-pyrazol-1-yl)-3-fluoropyridin-2-yl)carbamate, 203a

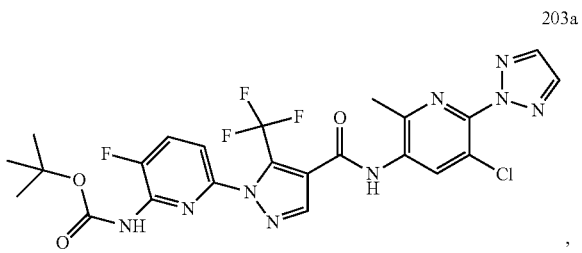 [SMILES: Cc1nc(-n2nccn2)c(Cl)cc1NC(=O)c1cnn(-c2ccc(F)c(NC(=O)OC(C)(C)C)n2)c1C(F)(F)F]

POCl$_3$ (1.571 g, 10.25 mmol) was added to a mixture of 1-(6-(((tert-butoxycarbonyl)amino)-5-fluoropyridin-2-yl)-5-(trifluoromethyl)-1H-pyrazole-4-carboxylic acid (2 g, 5.12 mmol), 5-chloro-2-methyl-6-(2H-1,2,3-triazol-2-yl)pyridin-3-amine (1.074 g, 5.12 mmol) and pyridine (2.027 g, 25.62 mmol) in CH$_2$Cl$_2$ (50 mL). The reaction mixture was stirred at 20° C. for 1 h. Sat.K$_2$CO$_3$ (120 mL) solution was added to the mixture. The mixture was extracted with 100 mL ethyl acetate. The combined organic layers were dried over Na$_2$SO$_4$ and filtered. The filtrates were concentrated under reduced pressure to afford crude as a brown oil. The crude was purified by flash column chromatography over silica gel (petroleum ether: ethyl acetate=1:1~0:1). The desired fraction was collected and the solvent was concentrated under reduced pressure to afford product as a yellow solid (1.4 g, purity: 58.3%, yield: 27.4%). LCMS (ESI) m/z M+Na$^+$: 604.0 (M+23).

B. 1-(6-amino-5-fluoropyridin-2-yl)-N-(5-chloro-2-methyl-6-(2H-1,2,3-triazol-2-yl)pyridin-3-yl)-5-(trifluoromethyl)-1H-pyrazole-4-carboxamide, 203b

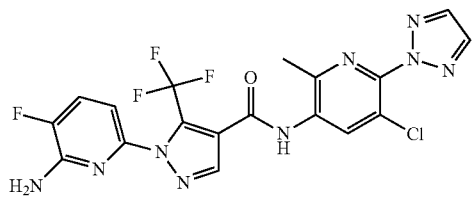

Tert-butyl (6-(4-((5-chloro-2-methyl-6-(2H-1,2,3-triazol-2-yl)pyridin-3-yl)carbamoyl)-5-(trifluoromethyl)-1H-pyrazol-1-yl)-3-fluoropyridin-2-yl)carbamate (1.4 g, 1.40 mmol) and HCl/MeOH (50 mL, 4 M) were stirred at 30° C. for 1 h. The mixture was concentrated to dryness. To the residue was added saturated aqueous K$_2$CO$_3$ (100 mL). The mixture was extrated with EtOAc (100 mL×3). The combined organic layers were dried over Na$_2$SO$_4$, filtered and the filtrate was concentrated to dryness to give the product (1.1 g, crude) as an orange gum.

C. N-(5-chloro-2-methyl-6-(2H-1,2,3-triazol-2-yl)pyridin-3-yl)-1-(8-fluoroimidazo[1,2-a]pyridin-5-yl)-5-(trifluoromethyl)-1H-pyrazole-4-carboxamide, cpd 203

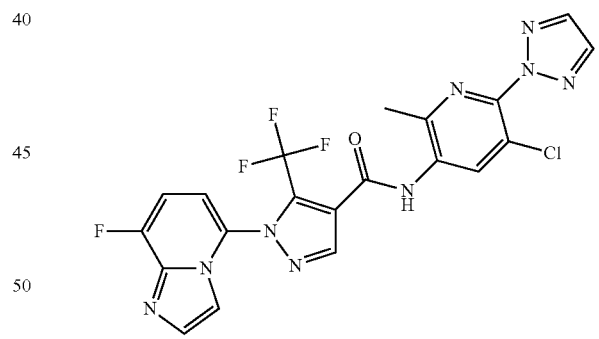

1-(6-Amino-5-fluoropyridin-2-yl)-N-(5-chloro-2-methyl-6-(2H-1,2,3-triazol-2-yl)pyridin-3-yl)-5-(trifluoromethyl)-1H-pyrazole-4-carboxamide (1.1 g, 2.28 mmol) was taken up in i-PrOH (20 mL) under N$_2$. 2-Bromo-1,1-diethoxyethane (899.85 mg, 4.57 mmol) was added to the suspension followed by HBr (2 mL, 48% in water). The resulting mixture was then refluxed for 12 h and cooled to room temperature. The solvent was removed under reduced pressure. The residue was purified by preparative high-performance liquid chromatography (30% to 60% (v/v) CH$_3$CN and H$_2$O with 0.05% ammonia hydroxide). The pure fractions were collected and the solvent was concentrated under reduced pressure. The residue was lyophilized to dryness to give the product as a light yellow solid. (302 mg, purity:

99.2%, yield: 26.0%). LCMS (ESI) m/z M+1: 505.9. $^1$H NMR (400 MHz, DMSO-$d_6$) δ ppm 2.53 (s, 3H), 7.40-7.49 (m, 2H), 7.52 (d, J=2.0 Hz, 1H), 7.77 (d, J=1.1 Hz, 1H), 8.17 (s, 2H), 8.42 (s, 1H), 8.67 (s, 1H), 9.73-10.40 (m, 1H).

Example 204

N-(5-cyano-6-(2H-1,2,3-triazol-2-yl)pyridin-3-yl)-1-(8-fluoroimidazo[1,2-a]pyridin-5-yl)-5-(trifluoromethyl)-1H-pyrazole-4-carboxamide, Cpd 204

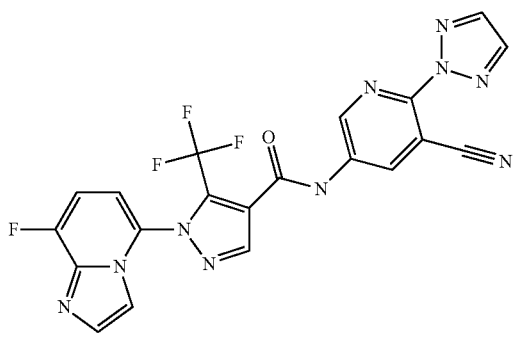 [SMILES: N#Cc1cc(NC(=O)c2cnn(-c3ccc(F)c4nccn34)c2C(F)(F)F)cnc1-n1nccn1]

A. ethyl 1-(6-amino-5-fluoropyridin-2-yl)-5-(trifluoromethyl)-1H-pyrazole-4-carboxylate, 204a

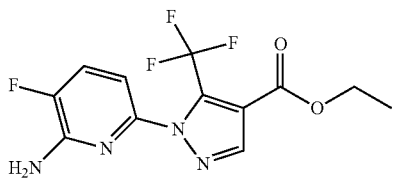

Ethyl 1-(6-((tert-butoxycarbonyl)amino)-fluoropyridin-2-yl)-5-(trifluoromethyl)-1H-pyrazole-4-carboxylate (0.9 g, 2.15 mmol) and HCl/MeOH (18 mL, 4 M) were stirred at 30° C. for 1 h. The mixture was concentrated to dryness. To the residue was added saturated aqueous $K_2CO_3$ (50 mL). The mixture was extracted with EtOAc (50 mL×3). The combined organic layers were dried over $Na_2SO_4$, filtered and the filtrate was concentrated to dryness to give the product as an orange gum (650 mg, yield: 94.9%).

B. ethyl 1-(8-fluoroimidazo[1,2-a]pyridin-5-yl)-5-(trifluoromethyl)-1H-pyrazole-4-carboxylate, 204b

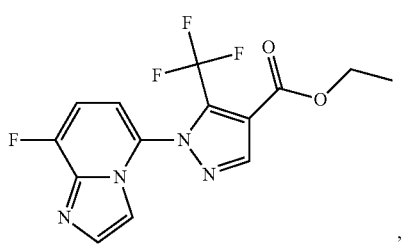

Ethyl 1-(6-amino-5-fluoropyridin-2-yl)-5-(trifluoromethyl)-1H-pyrazole-4-carboxylate (650 mg, 2.043 mmol) was dissolved in EtOH (20 mL) under $N_2$. 2-Bromo-1,1-diethoxyethane (805.057 mg, 4.085 mmol) was added to the suspension followed by HBr (2 mL, 48% in water). The resulting mixture was then refluxed for 12 h and cooled to room temperature. The solvent was removed under reduced pressure. The residue was purified by flash column chromatography over silica gel (petroleum ether: ethyl acetate=10:1~1:1). The pure fractions were collected and the solvent was concentrated under reduced pressure to afford the product as a light yellow solid (320 mg, yield: 45.8%). $^1$H NMR (400 MHz, CHLOROFORM-d) δ ppm 1.40 (t, J=7.2 Hz, 3H), 4.42 (q, J=7.1 Hz, 2H), 6.91 (dd, J=4.0, 7.9 Hz, 1H), 7.04 (dd, J=8.0, 9.4 Hz, 1H), 7.12 (s, 1H), 7.70 (s, 1H), 8.30 (s, 1H).

C. 1-(8-fluoroimidazo[1,2-a]pyridin-5-yl)-5-(trifluoromethyl)-1H-pyrazole-4-carboxylic acid, 204c

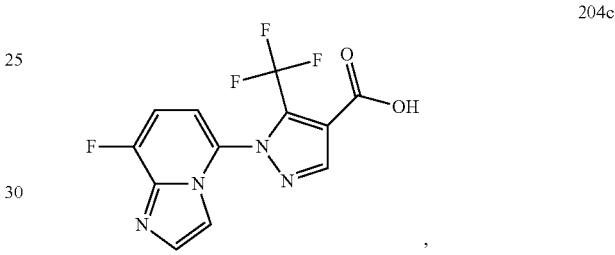

The mixture of ethyl 1-(8-fluoroimidazo[1,2-a]pyridin-5-yl)-5-(trifluoromethyl)-1H-pyrazole-4-carboxylate (320 mg, 0.935 mmol) in concentrated HCl (6.064 mL) was stirred at 130° C. for 2 h. The solvent was concentrated under reduced pressure to afford the product as a yellow solid (300 mg, crude).

D. N-(5-cyano-6-(2H-1,2,3-triazol-2-yl)pyridin-3-yl)-1-(8-fluoroimidazo[1,2-a]pyridin-5-yl)-5-(trifluoromethyl)-1H-pyrazole-4-carboxamide, Cpd 204

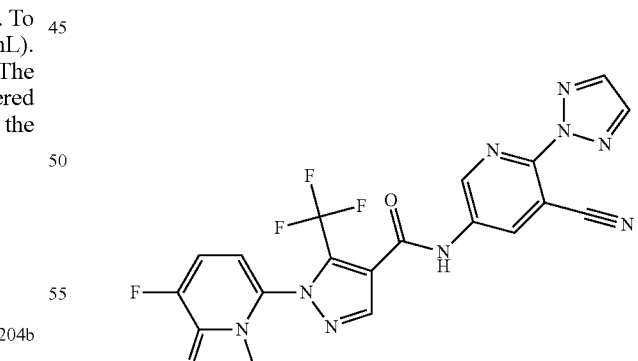

POCl$_3$ (292.81 mg, 1.91 mmol) was added to a mixture of 1-(8-fluoroimidazo[1,2-a]pyridin-5-yl)-5-(trifluoromethyl)-1H-pyrazole-4-carboxylic acid (300 mg, 0.96 mmol), 5-amino-2-(2H-1,2,3-triazol-2-yl)nicotinonitrile (177.76 mg. 0.96 mmol) and pyridine (377.63 mg, 4.77 mmol) in CH$_2$Cl$_2$ (10 mL). The reaction mixture was stirred at 20° C. for 1 h. Sat.NaHCO$_3$ solution (20 mL) was added to the mixture. The mixture was extracted with 30 mL ethyl acetate. The combined organic layers were dried over Na₂SO₄, filtered, and the filtrates concentrated under reduced pressure to afford crude product as a brown oil. The crude product was purified by preparative high-performance liquid chromatography (30% to 60% (v/v) CH₃CN and H₂O with 0.05% ammonia hydroxide). The pure fractions were collected and the solvent was concentrated under reduced pressure. The residue was lyophilized to dryness to give the product as a light yellow solid. (182 mg, purity: 99.2%, yield: 39.2%). LCMS (ESI) m/z M+1: 482.9. ¹H NMR (400 MHz, DMSO-d₆) δ ppm 7.38-7.51 (m, 2H), 7.53 (dd, J=1.1, 3.1 Hz, 1H), 7.76 (d, J=1.1 Hz, 1H), 8.29 (s, 2H), 8.68 (s, 1H), 8.85 (d, J=2.6 Hz, 1H), 9.06 (d, J=2.4 Hz, 1H), 11.32 (br s, 1H).

Example 205

N-(5-chloro-6-(2H-1,2,3-triazol-2-yl)pyridin-3-yl)-1-(6-fluoroimidazo[1,2-a]pyridin-5-yl)-5-(trifluoromethyl)-1H-pyrazole-4-carboxamide, Cpd 205

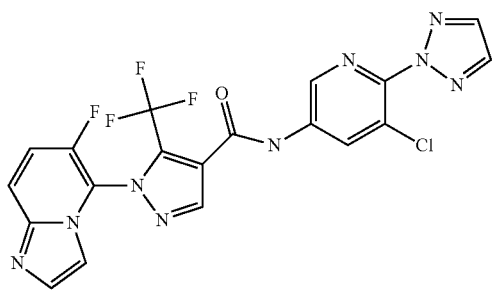 [SMILES: O=C(Nc1cnc(-n2nccn2)c(Cl)c1)c1cnn(-c2c(F)ccc3nccn23)c1C(F)(F)F]

A. tert-butyl (6-bromo-5-fluoropyridin-2-yl)carbamate, 205a

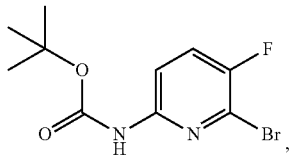

6-Bromo-5-fluoropicolinic acid (2000 mg, 9.09 mmol) was dissolved in t-BuOH (60 mL). Then DPPA (2576.9 mg, 9.36 mmol) and DIEA (1292.5 mg, 10.00 mmol) were added. The reaction mixture was stirred at 100° C. for 12 h under N2. The solvent was concentrated. The residue was purified by flash column chromatography over silica gel (gradient eluent: EtOAc/petrol ether from 1/20 to 1/5). The product fractions were collected and the solvent was concentrated to give the desired product as a colorless gum (1.6 g, yield: 60.5%). ¹H NMR (400 MHz, DMSO-d₆) δ ppm 1.50 (s, 9H), 7.21 (br s, 1H), 7.39 (dd, J=6.9, 8.9 Hz, 1H), 7.88 (dd, J=3.1, 8.8 Hz, 1H).

B. tert-butyl (5-fluoro-6-hydrazinylpyridin-2-yl)carbamate, 205b

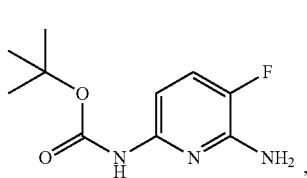

The mixture of {Pd(cinnamyl)Cl}₂ (26.69 mg, 0.052 mmol) and Mor-DalPhos (47.78 mg, 0.10 mmol) in dioxane (20 mL) was evacuated with argon (4×). The resulting clear yellow solution was stirred at rt under argon for 10 min. Tert-butyl (6-bromo-5-fluoropyridin-2-yl)carbamate (300 mg, 1.03 mmol) and t-BuONa (198.07 mg, 2.06 mmol) was added to the mixture and the mixture evacuated with argon (4×). The resulting yellow reaction was then treated with NH₂NH₂·H₂O (105.28 mg, 98%, 2.06 mmol) via syringe. The reaction was evacuated with argon (4×). Then the mixture was stirred at 50° C. under argon for 2 h. The mixture was filtered and the filter cake was washed with CH₂Cl₂/MeOH (20/1, 20 mL). The filtrate was collected and concentrated to give the crude product which was used directly for the next step (249.6 mg, yield: 100%).

C. ethyl 1-(6-((tert-butoxycarbonyl)amino)-3-fluoropyridin-2-yl)-5-(trifluoromethyl)-1H-pyrazole-4-carboxylate, 205c

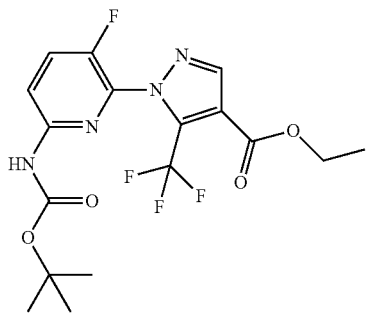

Tert-butyl (5-fluoro-6-hydrazinylpyridin-2-yl)carbamate (249 mg, 1.03 mmol) was dissolved in EtOH (10 mL), ethyl 2-(ethoxymethylene)-4,4,4-trifluoro-3-oxobutanoate (493.74 mg, 2.06 mmol) was added and stirred at 80° C. for 12 h. The mixture was concentrated under reduced pressure to afford crude product. The crude product was purified by flash column chromatography over silica gel (eluent: petroleum ether/ethyl acetate from 100/0 to 80/20). The desired fractions were collected and the solvent was concentrated under reduced pressure to afford product as a yellow solid (150 mg, yield: 34.9%). LCMS (ESI) m/z M+1: 362.9 (M-55). ¹H NMR (400 MHz, DMSO-d₆) δ ppm 1.38 (t, J=7.2 Hz, 3H), 1.52 (s, 9H), 4.38 (q, J=7.1 Hz, 2H), 7.22 (s, 1H), 7.60-7.68 (m, 1H), 8.15-8.21 (m, 2H).

D. ethyl 1-(6-amino-3-fluoropyridin-2-yl)-5-(trifluoromethyl)-1H-pyrazole-4-carboxylate, 205d

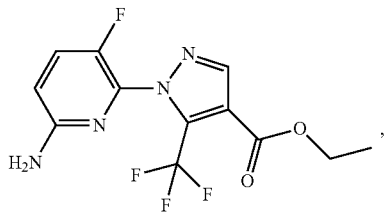

205d

Ethyl 1-(6-((tert-butoxycarbonyl)amino)-3-fluoropyridin-2-yl)-5-(trifluoromethyl)-1H-pyrazole-4-carboxylate (0.150 g, 0.36 mmol) and HCl/MeOH (3 mL, 4 M) were stirred at 30° C. for 1 h. The mixture was concentrated to dryness. The residue was used directly for the next step (120 mg, yield: 94.4%).

E. ethyl 1-(6-fluoroimidazo[1,2-a]pyridin-5-yl)-5-(trifluoromethyl)-1H-pyrazole-4-carboxylate, 205e

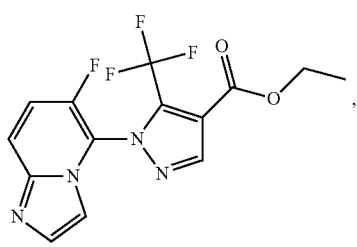

205e

Ethyl 1-(6-amino-3-fluoropyridin-2-yl)-5-(trifluoromethyl)-1H-pyrazole-4-carboxylate (120 mg, 0.34 mmol) was dissolved in EtOH (2 mL) under $N_2$. 2-Bromo-1,1-diethoxyethane (133.35 mg, 0.68 mmol) was added to the suspension followed by HBr (0.2 mL, 48% in water). The resulting mixture was then heated to 80° C. for 12 h and cooled to room temperature. The solvent was removed under reduced pressure. The residue was purified by flash column chromatography over silica gel (petroleum ether:ethyl acetate=10:1~1:1). The pure fractions were collected and the solvent was concentrated under reduced pressure to afford the product as a light yellow solid (130 mg, purity: 86.4%, yield: 97.0%). LCMS (ESI) m/z M+1: 342.9.

F. 1-(6-fluoroimidazo[1,2-a]pyridin-5-yl)-5-(trifluoromethyl)-1H-pyrazole-4-carboxylic acid, 205f

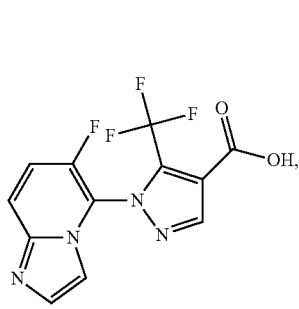

205f

The mixture of ethyl 1-(6-fluoroimidazo[1,2-a]pyridin-5-yl)-5-(trifluoromethyl)-1H-pyrazole-4-carboxylate (130 mg, 0.33 mmol) in concentrated HCl (2.13 mL) was stirred at 130° C. for 2 h. The solvent was concentrated under reduced pressure to give the product as a yellow solid (120 mg, crude).

G. N-(5-chloro-6-(2H-1,2,3-triazol-2-yl)pyridin-3-yl)-1-(6-fluoroimidazo[1,2-a]pyridin-5-yl)-5-(trifluoromethyl)-1H-pyrazole-4-carboxamide, Cpd 205

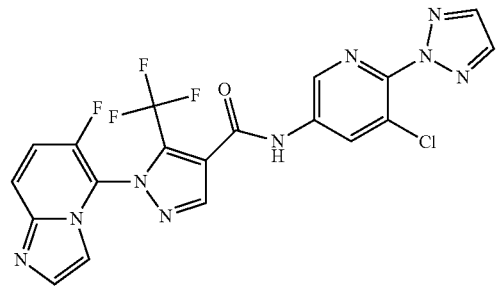 [SMILES: O=C(Nc1cnc(-n2nccn2)c(Cl)c1)c1cnn(-c2c(F)ccc3nccn23)c1C(F)(F)F]

POCl$_3$ (117.12 mg, 0.76 mmol) was added to a mixture of 1-(6-fluoroimidazo[1,2-a]pyridin-5-yl)-5-(trifluoromethyl)-1H-pyrazole-4-carboxylic acid (120 mg, 0.38 mmol), 5-chloro-6-(2H-1,2,3-triazol-2-yl)pyridin-3-amine (74.71 mg, 0.38 mmol) and pyridine (151.05 mg, 1.91 mmol) in CH$_2$Cl$_2$ (3 mL). The reaction mixture was stirred at 20° C. for 1 h. Sat.K$_2$CO$_3$ solution (100 mL) was added to the mixture. The mixture was extracted with 100 mL ethyl acetate. The combined organic layers were dried over Na$_2$SO$_4$, then filtered. The filtrates were concentrated under reduced pressure to afford crude product as a brown oil. The crude product was purified by preparative high-performance liquid chromatography (35% to 65% (v/v) CH$_3$CN and H$_2$O with 0.05% ammonia hydroxide). The pure fractions were collected and the solvent was concentrated under reduced pressure. The residue was lyophilized to dryness to afford the product as a light yellow solid (86.9 mg, purity: 100%, yield: 46.3%). LCMS (ESI) m/z M+1: 491.9. $^1$H NMR (400 MHz, DMSO-d$_6$) δ ppm 7.61 (s, 1H), 7.68 (dd, J=8.8, 9.7 Hz, 1H), 7.80 (d, J=1.3 Hz, 1H), 8.05 (dd, J=4.6, 10.1 Hz, 1H), 8.17 (s, 2H), 8.65 (d, J=2.4 Hz, 1H), 8.79 (s, 1H), 8.82 (d, J=2.2 Hz, 1H), 11.30 (br s, 1H).

Example 206

1-(2-methylimidazo[1,2-a]pyridin-5-yl)-5-(trifluoromethyl)-N-(2-(trifluoromethyl)pyridin-4-yl)-1H-pyrazole-4-carboxamide, Cpd 206

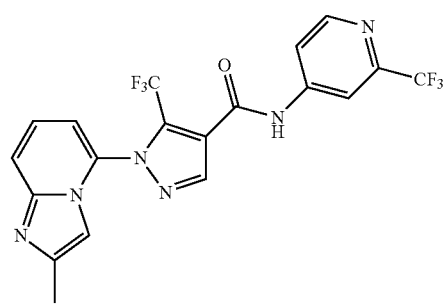 [SMILES: Cc1cn2c(-n3ncc(C(=O)Nc4ccnc(C(F)(F)F)c4)c3C(F)(F)F)cccc2n1]

POCl₃ (98.85 mg, 0.65 mmol) was added to a mixture of 1-(2-methylimidazo[1,2-a]pyridin-5-yl)-5-(trifluoromethyl)-1H-pyrazole-4-carboxylic acid (100 mg, 0.32 mmol), 2-(trifluoromethyl)pyridin-4-amine (52.26 mg, 0.32 mmol), pyridine (127.49 mg, 1.61 mmol) in CH₂Cl₂ (3 mL) at rt. The reaction mixture was stirred at room temperature for 1 h. The reaction mixture was quenched with 20 mL sat. K₂CO₃ aq, and extracted with CH₂Cl₂ (20 mL×3). The organic layer was separated and concentrated under reduced pressure. It was purified by preparative high-performance liquid chromatography (35% to 65% (v/v) CH₃CN and H₂O with 0.05% ammonia hydroxide). The pure fractions were collected and the organic solvent was concentrated under reduced pressure. The aqueous layer was lyophilized to dryness to give the desired product as a white solid. (80 mg, purity: 99.5%, yield: 54.3%). LCMS (ESI) m/z M+1: 454.9. ¹H NMR (400 MHz, DMSO-d₆) δ ppm 2.32 (s, 3H), 7.08 (s, 1H), 7.32 (d, J=7.06 Hz, 1H), 7.41 (dd, J=9.04, 7.28 Hz, 1H), 7.75 (d, J=9.04 Hz, 1H), 7.94 (dd, J=5.73, 1.76 Hz, 1H), 8.21 (d, J=1.76 Hz, 1H), 8.65 (s, 1H), 8.69 (d, J=5.29 Hz, 1H), 11.29 (s, 1H).

Example 207

1-(7-methylpyrazolo[1,5-a]pyridin-4-yl)-5-(trifluoromethyl)-N-(2-(trifluoromethyl)pyridin-4-yl)-1H-pyrazole-4-carboxamide, Cpd 207

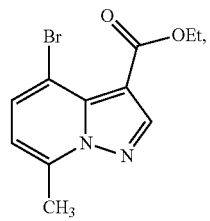

A. 1-amino-5-bromo-2-methylpyridin-1-ium 2,4-dinitrophenolate, 207a

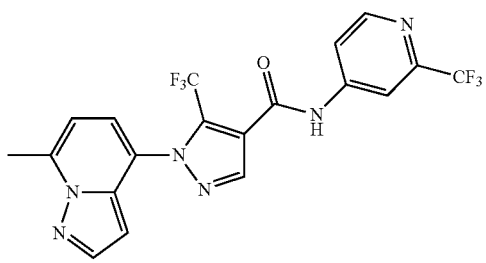 [SMILES: Cc1ccc(-n2ncc(C(=O)Nc3ccnc(C(F)(F)F)c3)c2C(F)(F)F)c2ccnn12]

5-Bromo-2-methylpyridine (5 g, 29.07 mmol) was dissolved in CH₂Cl₂ (30 mL) and O-(2,4-dinitrophenyl)hydroxylamine (6.366 g 31.97 mmol) was added to the mixture. The reaction mixture was stirred at 30° C. for 16 h. The reaction mixture was concentrated under reduced pressure to afford crude product as black solid (11 g), which was used directly for the next step.

B. ethyl 4-bromo-7-methylpyrazolo[1,5-a]pyridine-3-carboxylate, 207b

207b

1-Amino-5-bromo-2-methylpyridin-1-ium 2,4-dinitrophenolate (3.989 g, 10.75 mmol) was dissolved in DMF (20 mL), and then ethyl propiolate (1.054 g, 10.75 mmol) and K₂CO₃ (2.971 g, 21.50 mmol) were added. The reaction mixture was stirred at rt for 16 h. The reaction mixture was concentrated under reduced pressure to afford the crude product as a black solid. The crude product was purified by flash column chromatography over silica gel (eluent: petroleum ether/ethyl acetate from 100/0 to 85/15). The desired fractions were collected and the solvent was concentrated under reduced pressure to afford product as a yellow oil (0.9 g, purity: 85.2%%, yield: 25.2%). LCMS (ESI) m/z M+1: 285.0

C. 4-bromo-7-methylpyrazolo[1,5-a]pyridine, 207c

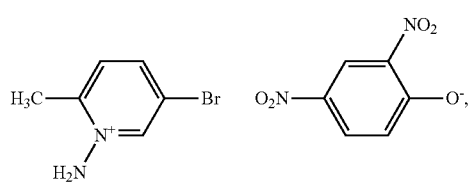

Ethyl 4-bromo-7-methylpyrazolo[1,5-a]pyridine-3-carboxylate (800 mg, 2.53 mmol, 85.2% purity) and HBr (48%, 5 mL) was stirred at 100° C. for 16 h. The reaction mixture was adjusted to pH 6 using 5 N NaOH, and extracted with EtOAc (30 mL×3). The combined organic layers were concentrated under reduced pressure to afford crude product as a yellow oil. The oil was purified by flash column chromatography over silica gel (eluent: petroleum ether/ ethyl acetate from 100/0 to 90/10). The desired fractions were collected and the solvent was concentrated under reduced pressure to afford product as a yellow solid (500 mg, 93.6% yield).

D. 4-(2-(diphenylmethylene)hydrazinyl)-7-methylpyrazolo[1,5-a]pyridine, 207d

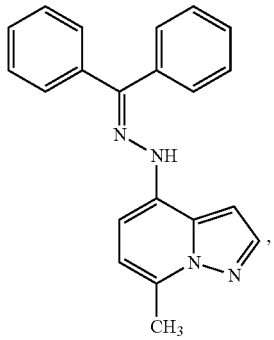

Pd(OAc)$_2$ (46.80 mg, 0.21 mmol) and BINAP (259.62 mg, 0.42 mmol) were suspended in dioxane (15 mL) and bubbled with N$_2$ for 3 min. 4-Bromo-7-methylpyrazolo[1,5-a]pyridine (440 mg, 2.09 mmol), (diphenylmethylene)hydrazine (818.25 mg, 4.17 mmol) and Cs$_2$CO$_3$ (1.358 g, 4.17 mmol) were added and purged with N$_2$ for 1 min. The reaction mixture was stirred at 120° C. for 16 h. The reaction mixture was filtered and the residue was washed with EtOAc (50 mL×5). The filtrates were concentrated under reduced pressure to afford crude product as a brown oil. The oil was purified by flash column chromatography over silica gel (eluent: petroleum ether/ethyl acetate from 100/0 to 70/30). The desired fractions were collected and the solvent was concentrated under reduced pressure to afford product as a yellow solid (600 mg, purity: 75.7%, yield: 66.7%). LCMS (ESI) m/z M+1: 327.0

E. 4-hydrazinyl-7-methylpyrazolo[1,5-a]pyridine, 207e

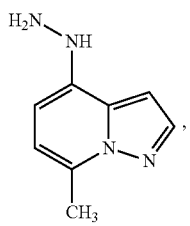

4-(2-(Diphenylmethylene)hydrazinyl)-7-methylpyrazolo[1,5-a]pyridine (550 mg, 1.28 mmol, 75.7% purity) was dissolved in dioxane (5 mL) and conc. HCl (12 M, 0.5 mL) was added. The reaction was stirred at rt for 16 h. The reaction mixture was concentrated under reduced pressure to afford a crude product as a black solid (350 mg). The crude product was used for the next step without further purification.

F. ethyl 1-(7-methylpyrazolo[1,5-a]pyridin-4-yl)-5-(trifluoromethyl)-1H-pyrazole-4-carboxylate, 207f

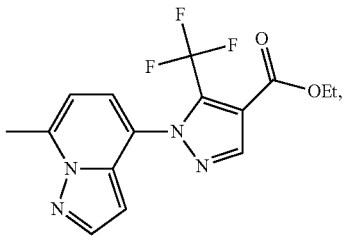

4-Hydrazinyl-7-methylpyrazolo[1,5-a]pyridine (350 mg, 1.76 mmol, HCl salt) was dissolved in EtOH (10 mL), ethyl 2-(ethoxymethylene)-4,4,4-trifluoro-3-oxobutanoate (423.16 mg, 1.76 mmol) and Et$_3$N (356.57 mg, 3.52 mmol) were added and stirred at 70° C. for 2 h. The reaction mixture was concentrated under reduced pressure to afford the crude product as a black oil. The crude product was purified by flash column chromatography over silica gel (petroleum ether/ethyl acetate from 100/0 to 85/15). The desired fraction was collected and the solvent was concentrated under reduced pressure to afford product as a yellow oil (400 mg, purity: 98.8%, yield: 66.3%). LCMS (ESI) m/z M+1: 339.2

G. 1-(7-methylpyrazolo[1,5-a]pyridin-4-yl)-5-(trifluoromethyl)-1H-pyrazole-4-carboxylic acid, 207g

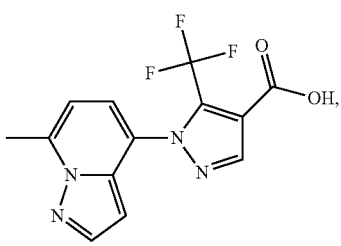

Ethyl 1-(7-methylpyrazolo[1,5-a]pyridin-4-yl)-5-(trifluoromethyl)-1H-pyrazole-4-carboxylate (400 mg, 1.18 mmol) was dissolved in THF/H$_2$O=1/1 (10 mL) and LiOH (56.64 mg, 2.37 mmol) added. The reaction mixture was stirred at rt for 16 h. The reaction mixture was adjusted to pH 5 using 2 N HCl and extracted with EtOAc (30 mL×3). The combined organic layers were dried over Na$_2$SO$_4$, filtered and the filtrates were concentrated under reduced pressure to afford the crude product as a yellow solid (350 mg, purity: 97.2%, yield: 92.7%). LCMS (ESI) m/z M+1: 311.0

H. 1-(7-methylpyrazolo[1,5-a]pyridin-4-yl)-5-(trifluoromethyl)-1H-pyrazole-4-carboxylic acid, Cpd 207

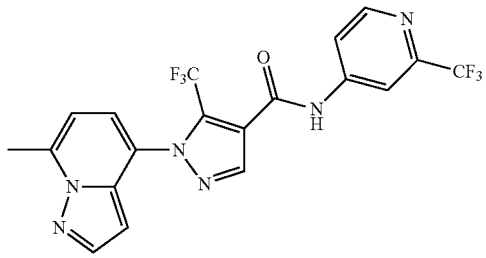 [SMILES: Cc1ccc(-n2ncc(C(=O)Nc3ccnc(C(F)(F)F)c3)c2C(F)(F)F)c2ccnn12]

POCl$_3$ (0.07 mL, 0.75 mmol) was added dropwise to a solution of 1-(7-methylpyrazolo[1,5-a]pyridin-4-yl)-5-(trifluoromethyl)-1H-pyrazole-4-carboxylic acid (120 mg, 0.38 mmol, 97.2% purity), 2-(trifluoromethyl)pyridin-4-amine (60.9 mg, 0.38 mmol) and pyridine (0.15 mL, 1.88 mmol) in CH$_2$Cl$_2$ (6 mL). The reaction mixture was stirred at room temperature for 1.5 h. Water (5 mL) was added to the mixture. The aqueous was extracted with CH$_2$Cl$_2$ (15 mL×3). The separated organic layer was dried (Na$_2$SO$_4$), filtered, and the solvent was concentrated to give a crude product. The crude product was purified by preparative high-performance liquid chromatography (35% to 68% (v/v) CH$_3$CN and H$_2$O with 0.05% ammonia hydroxide). The pure fractions were collected and the organic solvent was concentrated under reduced pressure. The aqueous layer was lyophilized to dryness to give product as a white solid product (61.8 mg, purity: 98.1%, yield: 35.5%). LCMS (ESI) m/z M+1: 454.9. $^1$H NMR (400 MHz, DMSO-d$_6$) δ ppm 2.78 (s, 3H) 6.36 (d, J=2.43 Hz, 1H) 7.02 (d, J=7.94 Hz, 1H) 7.53 (d, J=7.50 Hz, 1H) 7.95 (dd, J=5.40, 1.65 Hz, 1H) 8.15 (d, J=2.21 Hz, 1H) 8.21 (d, J=1.54 Hz, 1H) 8.51 (s, 1H) 8.69 (d, J=5.51 Hz, 1H) 11.24 (br s, 1H).

Example 208

1-(imidazo[1,2-a]pyridin-5-yl)-5-(trifluoromethyl)-N-(2-(trifluoromethyl)pyridin-4-yl)-1H-pyrazole-4-carboxamide, Cpd 208

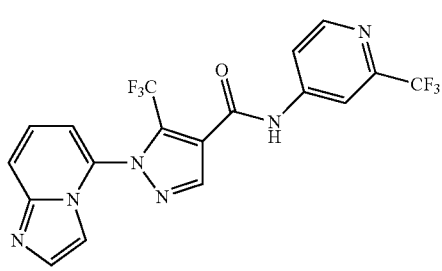 [SMILES: O=C(Nc1ccnc(C(F)(F)F)c1)c1cnn(-c2cccc3nccn23)c1C(F)(F)F]

POCl$_3$ (149.87 mg, 0.98 mmol) was added to a mixture of 1-(imidazo[1,2-a]pyridin-5-yl)-5-(trifluoromethyl)-1H-pyrazole-4-carboxylic acid (150 mg, 0.49 mmol, 96.5% purity), 2-(trifluoromethyl)pyridin-4-amine (79.22 mg, 0.49 mmol) and pyridine (193.28 mg, 2.44 mmol) in CH$_2$Cl$_2$ (3 mL). The reaction mixture was stirred at 20° C. for 1 h. Sat.K$_2$CO$_3$ solution (5 mL) was added to the mixture. The mixture was extracted with 5 mL ethyl acetate. The combined organic layers were dried over Na$_2$SO$_4$, then filtered. The filtrates were concentrated under reduced pressure to afford a crude product as a brown oil. The crude oil was purified by preparative high-performance liquid chromatography (30% to 55% (v/v) CH$_3$CN and H$_2$O with 0.05% ammonia hydroxide). The pure fractions were collected and the solvent was concentrated under reduced pressure. The residue was lyophilized to dryness to give product as a light yellow solid (60.2 mg, purity: 99.3%, yield: 27.8%). LCMS (ESI) m/z M+1: 440.9. $^1$H NMR (400 MHz, DMSO-d$_6$) δ ppm 7.36 (d, J=0.7 Hz, 1H), 7.39-7.43 (m, 1H), 7.45-7.51 (m, 1H), 7.71 (d, J=1.3 Hz, 1H), 7.90 (d, J=8.8 Hz, 1H), 7.96 (dd, J=1.9, 5.4 Hz, 1H), 8.22 (d, J=1.5 Hz, 1H), 8.67 (s, 1H), 8.70 (d, J=5.5 Hz, 1H), 11.28 (br s, 1H).

Example 209

1-(8-fluoroimidazo[1,2-a]pyridin-5-yl)-5-(trifluoromethyl)-N-(2-(trifluoromethyl)pyridin-4-yl)-1H-pyrazole-4-carboxamide, Cpd 209

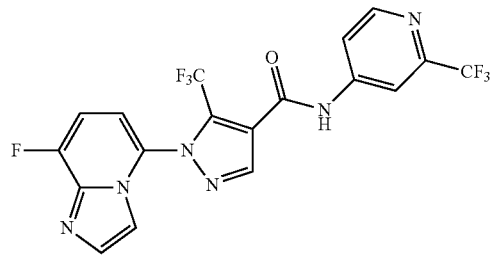 [SMILES: O=C(Nc1ccnc(C(F)(F)F)c1)c1cnn(-c2ccc(F)c3nccn23)c1C(F)(F)F]

POCl$_3$ (117.12 mg, 0.76 mmol) was added dropwise to a solution of 1-(8-fluoroimidazo[1,2-a]pyridin-5-yl)-5-(trifluoromethyl)-1H-pyrazole-4-carboxylic acid (120 mg, 0.38 mmol), 2-(trifluoromethyl)pyridin-4-amine (61.92 mg, 0.38 mmol) and pyridine (151.05 mg, 1.91 mmol) in CH$_2$Cl$_2$ (5 mL). The reaction mixture was stirred at room temperature for 2 h. Water (2.5 mL) was added to the mixture. The pH was adjusted to about 7 by progressively adding NaHCO$_3$ (aq). The aqueous phase was extracted with CH$_2$Cl$_2$ (5 mL×3). The separated organic layer was dried (Na$_2$SO$_4$), filtered, and the solvent was concentrated to give a crude product which was purified by preparative high-performance liquid chromatography (35% to 65% (v/v) CH$_3$CN and H$_2$O with 0.05% ammonia hydroxide). The pure fractions were collected and the organic solvent was concentrated under reduced pressure. The aqueous layer was lyophilized to dryness to afford the product as a white solid (110 mg, purity: 99.0%, yield: 62.2%). LCMS (ESI) m/z M+1: 458.9. $^1$H NMR (400 MHz, DMSO-d$_6$) δ ppm 7.41-7.46 (m, 1H), 7.46-7.49 (m, 1H), 7.51 (d, J=3.1 Hz, 1H), 7.76 (s, 1H), 7.96 (dd, J=1.9, 5.4 Hz, 1H), 8.22 (d, J=2.0 Hz, 1H), 8.68 (s, 1H), 8.71 (d, J=5.5 Hz, 1H), 11.25 (br s, 1H).

Example 210

1-(7-(3-hydroxyazetidin-1-yl)thieno[2,3-c]pyridin-4-yl)-5-(trifluoromethyl)-N-(2-(trifluoromethyl)pyridin-4-yl)-1H-pyrazole-4-carboxamide, Cpd 210

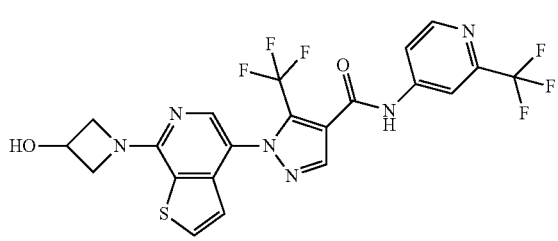 [SMILES: O=C(Nc1ccnc(C(F)(F)F)c1)c1cnn(-c2cnc(N3CC(O)C3)c3sccc23)c1C(F)(F)F]

A. 4-(5-(trifluoromethyl)-4-((2-(trifluoromethyl)pyridin-4-yl)carbamoyl)-1H-pyrazol-1-yl)thieno[2,3-c]pyridine 6-oxide, 210a

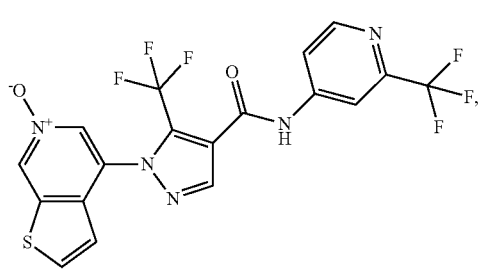

m-CPBA (0.566 g, 3.28 mmol) was added to a solution of 1-(thieno[2,3-c]pyridin-4-yl)-5-(trifluoromethyl)-N-(2-(trifluoromethyl)pyridin-4-yl)-1H-pyrazole-4-carboxamide (0.5 g, 1.09 mmol) in CH$_2$Cl$_2$ (10 mL). The mixture was stirred at 50° C. for 4 h. The solution was washed with saturated aqueous solution of Na$_2$SO$_3$ (30 mL), saturated aqueous NaHCO$_3$ (30 mL), and brine (50 The extracts were dried over anhydrous Na$_2$SO$_4$, filtered and the filtrate concentrated to afford a crude oil. The oil was purified by flash column chromatography over silica gel (eluent: petroleum ether/ethyl acetate from 100/0 to 0/100). The desired fractions were collected and the solvent was concentrated to dryness under reduced pressure to afford the product as a white solid (0.35 g, 66.7%).

B. 1-(7-chlorothieno[2,3-c]pyridin-4-yl)-5-(trifluoromethyl)-N-(2-(trifluoromethyl)pyridin-4-yl)-1H-pyrazole-4-carboxamide, 210b 4-(5-(Trifluoromethyl)-4-((2-(trifluoromethyl)pyridin-4-yl)carbamoyl)-1H-pyrazol-1-yl)thieno[2,3-c]pyridine 6-oxide (180 mg, 0.38 mmol) was added to the mixture of POCl$_3$ (0.34 mL, 3.75 mmol) in CHCl$_3$ (10 mL). The mixture was stirred at 60° C. for 2 h. The mixture was cooled to rt and was added to a stirring aqueous solution (50 mL). Then the mixture was made basic using NaHCO$_3$, followed by extraction with CH$_2$Cl$_2$ (50 mL×2). The combined organic layers were washed with brine, dried over anhydrous Na$_2$SO$_4$, then filtered. The filtrates were concentrated under reduced pressure to afford a crude product as a brown oil. The brown oil was purified by flash column chromatography over silica gel (petroleum ether/ethyl acetate=1:0 to petroleum ether/ethyl acetate=1:1). The desired fractions were collected and the solvent was concentrated under reduced pressure to give the product as a colorless oil (0.15 g, 81.3%).

C. 1-(7-(3-hydroxyazetidin-1-yl)thieno[2,3-c]pyridin-4-yl)-5-(trifluoromethyl)-N-(2-(trifluoromethyl)pyridin-4-yl)-1H-pyrazole-4-carboxamide, Cpd 210

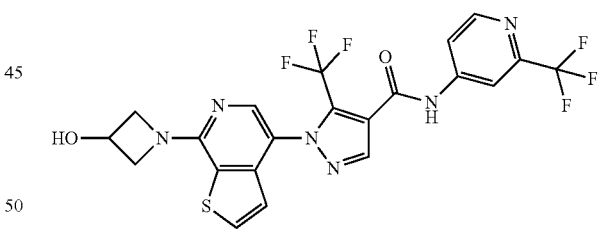

Na$_2$CO$_3$ (53.88 mg, 0.51 mmol) was added to a solution of 1-(7-chlorothieno[2,3-c]pyridin-4-yl)-5-(trifluoromethyl)-N-(2-(trifluoromethyl)pyridin-4-yl)-1H-pyrazole-4-carboxamide (100 mg, 0.20 mmol) and azetidin-3-ol hydrochloride (33.42 mg, 0.31 mmol) in DMA (4 mL). The mixture was stirred at 80° C. for 16 h. Water (20 mL) was added to the mixture, and extracted with ethyl acetate (30 mL×2). The combined organic layers were washed with brine, dried over anhydrous Na$_2$SO$_4$, and filtered. The filtrates were concentrated under reduced pressure to afford a crude product as a yellow solid, which was purified by preparative HPLC (26% to 56% (v/v) CH$_3$CN and H$_2$O with 0.05% ammonia hydroxide). The pure fractions were collected and the organic solvent was concentrated under reduced pressure and lyophilized to dryness to give the

Example 211

N-(5-chloro-6-(2H-1,2,3-triazol-2-yl)pyridin-3-yl)-1-(3-methylimidazo[1,2-a]pyridin-5-yl)-5-(trifluoromethyl)-1H-pyrazole-4-carboxamide, Cpd 211

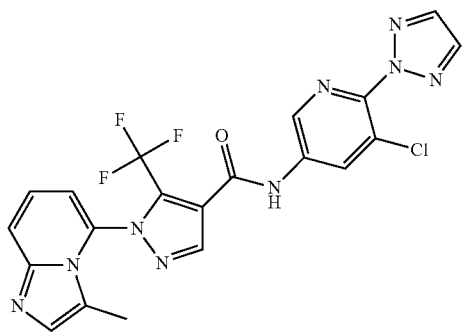 [SMILES: Cc1cnc2cccc(-n3ncc(C(=O)Nc4cnc(-n5nccn5)c(Cl)c4)c3C(F)(F)F)n12]

The title prepared according to Example 205 by substituting the appropriate reagents, starting materials, and purification methods, and adjusting reaction temperatures, times and other variables or parameters. ¹H NMR (400 MHz, DMSO-d₆) δ ppm 11.346 (br s, 1H), 8.833 (d, J=2.21 Hz, 1H), 8.614-8.684 (m, 2H), 8.171 (s, 2H), 7.808-7.888 (m, 1H), 7.487 (s, 1H), 7.328-7.392 (m, 2H), 1.787 (s, 3H). LCMS (ESI): m/z 487.9 [M+H]⁺

Following the procedures described in Examples 3 or 4, above, and selecting and substituting the appropriate reagents, starting materials, and purification methods, and adjusting reaction temperatures, times and other variables or parameters, as needed or desirable, as would be readily recognized by those skilled in the art, the following compounds were prepared.

Example 70

N-(5-cyano-6-ethoxypyridin-3-yl)-1-(quinolin-5-yl)-5-(trifluoromethyl)-1H-pyrazole-4-carboxamide, Cpd 81

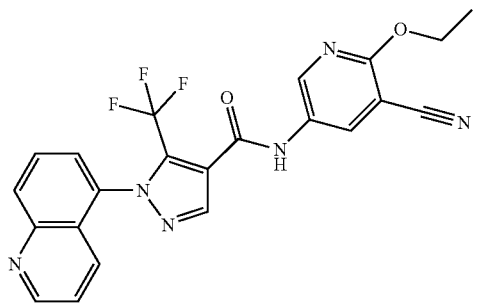 [SMILES: CCOc1ncc(NC(=O)c2cnn(-c3cccc4ncccc34)c2C(F)(F)F)cc1C#N]

¹H NMR (400 MHz, CHLOROFORM-d) δ ppm 1.46 (t, J=7.06 Hz, 2H), 4.50 (q, J=7.06 Hz, 2H), 7.48 (dd, J=8.49, 4.30 Hz, 1H), 7.59-7.66 (m, 2H), 7.70 (br s, 1H), 7.82-7.87 (m, 1H), 8.20 (s, 1H), 8.34-8.38 (m, 1H), 8.43 (br s, 2H), 9.03 (br d, J=2.65 Hz, 1H). LCMS (ESI): m/z 487.9 [M+H]⁺

Example 71

N-(5-cyano-6-methoxypyridin-3-yl)-1-(quinolin-5-yl)-5-(trifluoromethyl)-1H-pyrazole-4-carboxamide, Cpd 85

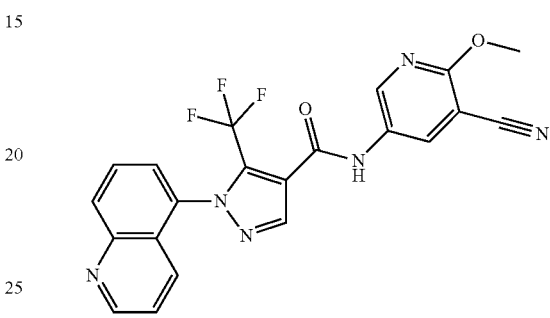

¹H NMR (400 MHz, DMSO-d₆) δ ppm 3.99 (s, 3H), 7.55-7.61 (m, 1H), 7.62-7.68 (m, 1H), 7.85-7.91 (m, 1H), 7.92-7.98 (m, 1H), 8.31 (d, J=8.38 Hz, 1H), 8.46-8.56 (m, 2H), 8.69 (d, J=2.65 Hz, 1H), 9.03 (dd, J=4.08, 1.65 Hz, 1H), 10.93 (br s, 1H). LCMS (ESI): m/z 439.0 [M+H]⁺

Example 72

N-(6-cyano-5-(trifluoromethyl)pyridin-3-yl)-1-(isoquinolin-4-yl)-5-(trifluoromethyl)-1H-pyrazole-4-carboxamide, Cpd 49

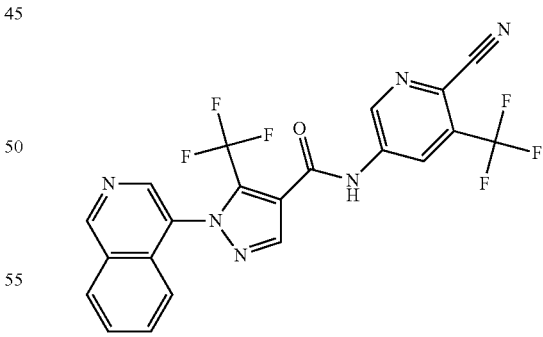

¹H NMR (400 MHz, DMSO-d₆) δ ppm 7.26 (d, J=8.38 Hz, 1H), 7.83-7.88 (m, 1H), 7.90-7.96 (m, 1H), 8.37 (d, J=7.94 Hz, 1H), 8.63 (s, 1H), 8.78 (s, 1H), 8.80 (d, J=1.98 Hz, 1H), 9.25 (d, J=1.98 Hz, 1H), 9.60 (s, 1H), 11.58 (br s, 1H). LCMS (ESI): m/z 476.9 [M+H]⁺

Example 73

N-(3-chloro-4-(3-methyl-1H-1,2,4-triazol-1-yl)phenyl)-1-(isoquinolin-4-yl)-5-(trifluoromethyl)-1H-pyrazole-4-carboxamide, Cpd 55

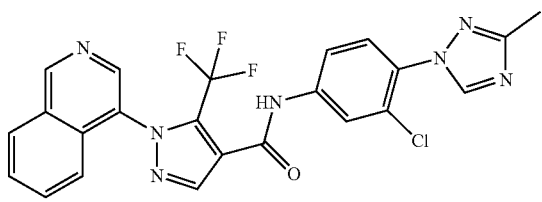 [SMILES: Cc1ncn(-c2ccc(NC(=O)c3cnn(-c4cncc5ccccc45)c3C(F)(F)F)cc2Cl)n1]

$^1$H NMR (400 MHz, METHANOL-$d_4$) δ ppm 2.41 (s, 3H), 7.44 (d, J=8.38 Hz, 1H), 7.60 (d, J=8.60 Hz, 1H), 7.84-8.01 (m, 3H), 8.17-8.26 (m, 2H), 8.36-8.43 (m, 2H), 8.72 (br s, 1H), 9.49-9.66 (m, 1H), 9.60 (br s, 1H). LCMS (ESI): m/z 498.0 [M+H]$^+$

Example 74

N-(5-chloro-6-(1-methyl-1H-imidazol-2-yl)pyridin-3-yl)-1-(isoquinolin-4-yl)-5-(trifluoromethyl)-1H-pyrazole-4-carboxamide, Cpd 98

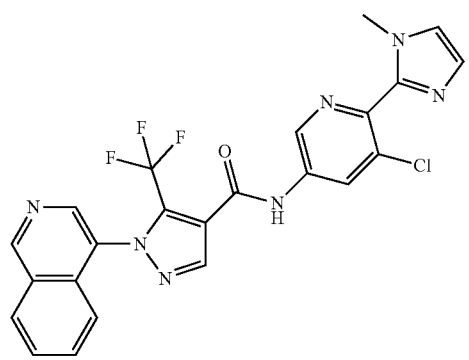 [SMILES: Cn1ccnc1-c1ncc(NC(=O)c2cnn(-c3cncc4ccccc34)c2C(F)(F)F)cc1Cl]

$^1$H NMR (400 MHz, METHANOL-$d_4$) δ ppm 3.70 (s, 3H), 7.12 (s, 1H), 7.27 (s, 1H), 7.39 (d, J=8.16 Hz, 1H), 7.84-7.89 (m, 1H), 7.90-7.95 (m, 1H), 8.34 (d, J=8.16 Hz, 1H), 8.42 (s, 1H), 8.60 (d, J=1.98 Hz, 1H), 8.65 (s, 1H), 8.91 (d, J=1.98 Hz, 1H), 9.52 (s, 1H). LCMS (ESI): m/z 497.9 [M+H]$^+$

Example 75

N-(8-chloro-4-methyl-3-oxo-3,4-dihydro-2H-benzo[b][1,4]oxazin-6-yl)-1-(isoquinolin-4-yl)-5-(trifluoromethyl)-1H-pyrazole-4-carboxamide, Cpd 97

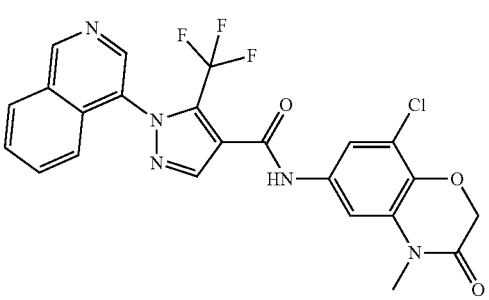 [SMILES: CN1C(=O)COc2c(Cl)cc(NC(=O)c3cnn(-c4cncc5ccccc45)c3C(F)(F)F)cc21]

$^1$H NMR (400 MHz, DMSO-$d_6$) δ ppm 3.28 (s, 3H), 4.77 (s, 2H), 7.26 (d, J=8.38 Hz, 1H), 7.45 (br s, 1H), 7.64 (s, 1H), 7.81-7.89 (m, 1H), 7.89-7.98 (m, 1H), 8.37 (d, J=8.38 Hz, 1H), 8.52 (s, 1H), 8.76 (s, 1H), 9.60 (s, 1H), 10.71 (br s, 1H). LCMS (ESI): m/z 501.9 [M+H]$^+$

Example 76

N-(6-(4-aminobutoxy)-5-cyanopyridin-3-yl)-1-(isoquinolin-4-yl)-5-(trifluoromethyl)-1H-pyrazole-4-carboxamide, Cpd 84

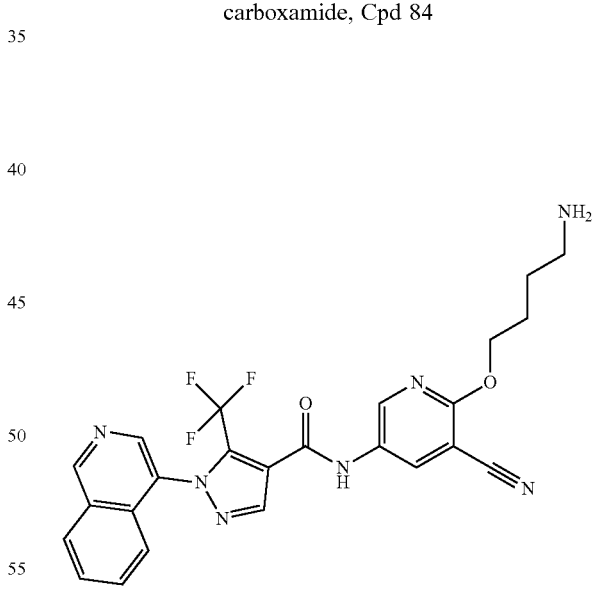

$^1$H NMR (400 MHz, DMSO-$d_6$) δ ppm 11.31 (s, 1H), 9.62 (s, 1H), 8.81 (d, J=2.4 Hz, 1H), 8.78 (s, 1H), 8.73 (s, 1H), 8.61 (d, J=2.4 Hz, 1H), 8.38 (br d, J=8.2 Hz, 1H), 8.09-7.89 (m, 4H), 7.89-7.82 (m, 1H), 7.28 (br d, J=8.2 Hz, 1H), 4.41 (br t, J=6.1 Hz, 2H), 2.84 (br d, J=6.0 Hz, 2H), 1.87-1.63 (m, 4H). LCMS (ESI): m/z 496.1 [M+H]$^+$

Example 77

N-(5-fluoro-6-(2H-1,2,3-triazol-2-yl)pyridin-3-yl)-1-(isoquinolin-4-yl)-5-(trifluoromethyl)-1H-pyrazole-4-carboxamide, Cpd 61

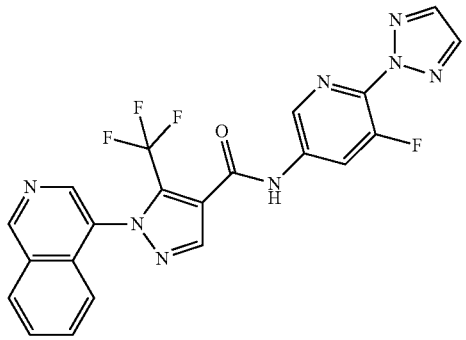 [SMILES: O=C(Nc1cnc(-n2nccn2)c(F)c1)c1cnn(-c2cncc3ccccc23)c1C(F)(F)F]

$^1$H NMR (400 MHz, DMSO-d$_6$) δ ppm 7.28 (br d, J=8.38 Hz, 1H), 7.84-7.96 (m, 3H), 8.03 (d, J=3.09 Hz, 1H), 8.37 (br d, J=7.94 Hz, 1H), 8.54-8.73 (m, 2H), 8.78 (s, 1H), 8.96 (s, 1H), 9.61 (s, 1H), 11.41 (br s, 1H). LCMS (ESI): m/z 500.9 [M+H]$^+$

Example 78

Methyl 6-chloro-4-(1-(isoquinolin-4-yl)-5-(trifluoromethyl)-1H-pyrazole-4-carboxamido)picolinate, Cpd 74

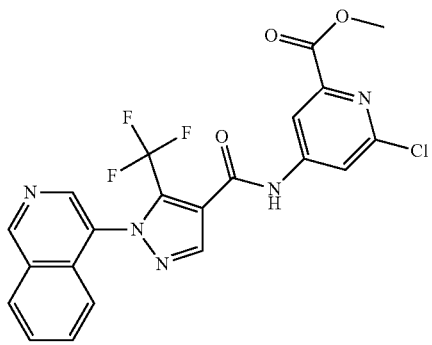 [SMILES: COC(=O)c1cc(NC(=O)c2cnn(-c3cncc4ccccc34)c2C(F)(F)F)cc(Cl)n1]

$^1$H NMR (400 MHz, DMSO-d$_6$) δ ppm 3.89 (s, 3H), 7.26 (d, J=8.38 Hz, 1H), 7.80-7.88 (m, 1H), 7.89-7.97 (m, 1H), 8.11 (s, 1H), 8.30-8.40 (m, 2H), 8.61 (s, 1H), 8.77 (s, 1H), 9.59 (s, 1H), 11.33 (br s, 1H). LCMS (ESI): m/z 475.9 [M+H]$^+$

Example 79

N-(5-chloro-6-((1-methylpiperidin-4-yl)oxy)pyridin-3-yl)-1-(isoquinolin-4-yl)-5-(trifluoromethyl)-1H-pyrazole-4-carboxamide, Cpd 45

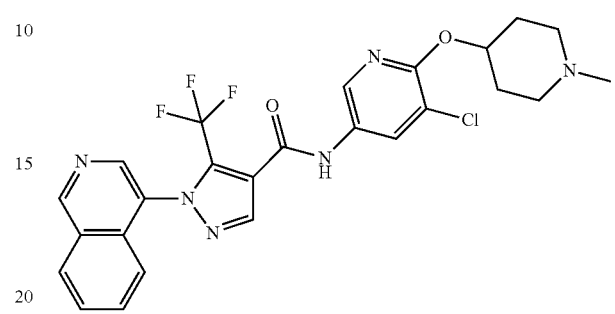

$^1$H NMR (400 MHz, DMSO-d$_6$) δ ppm 1.70-1.81 (m, 2H), 1.98 (br s, 2H), 2.26 (s, 3H), 2.33 (br s, 2H), 2.48-2.52 (m, 34H), 2.67 (br s, 2H), 5.08 (br d, J=4.41 Hz, 1H), 7.27 (d, J=8.38 Hz, 1H), 7.82-7.90 (m, 1H), 7.90-7.98 (m, 1H), 8.29 (d, J=2.21 Hz, 1H), 8.35-8.42 (m, 2H), 8.55 (s, 1H), 8.76 (s, 1H), 9.61 (s, 1H), 10.80 (s, 1H). LCMS (ESI): m/z 531.0 [M+H]$^+$

Example 80

N-(4-aminobutyl)-3-chloro-5-(1-(isoquinolin-4-yl)-5-(trifluoromethyl)-1H-pyrazole-4-carboxamido)picolinamide, Cpd 72

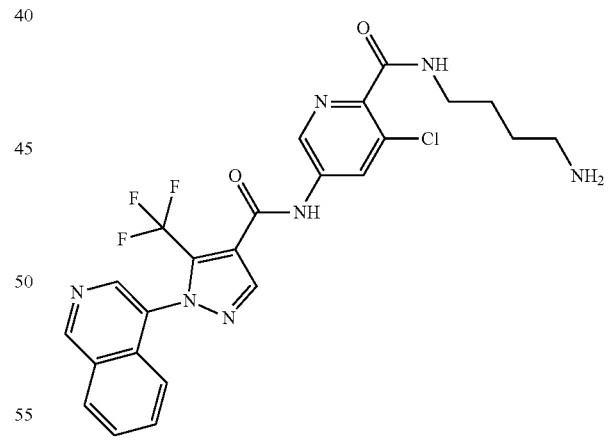

$^1$H NMR (400 MHz, DMSO-d$_6$) δ ppm 1.57 (br s, 4H), 2.73-2.85 (m, 2H), 3.19-3.33 (m, 2H), 7.30 (d, J=8.16 Hz, 1H), 7.84-7.90 (m, 1H), 7.95 (br t, J=7.06 Hz, 3H), 8.39 (d, J=8.16 Hz, 1H), 8.50 (d, J=1.98 Hz, 1H), 8.68 (br t, J=5.84 Hz, 1H), 8.79 (d, J=7.94 Hz, 1H), 8.95-9.02 (m, 1H), 8.97 (d, J=1.98 Hz, 1H), 9.64 (s, 1H), 11.53 (s, 1H). LCMS (ESI): m/z 532.0 [M+H]$^+$

Example 81

N-(2-cyanopyridin-4-yl)-1-(isoquinolin-4-yl)-5-(trifluoromethyl)-1H-pyrazole-4-carboxamide, Cpd 77

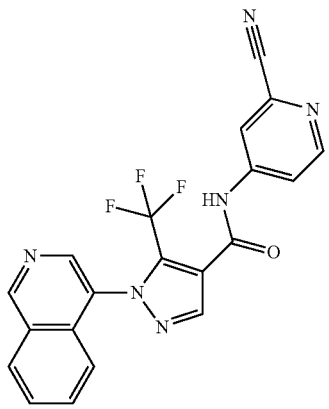 [SMILES: N#Cc1cc(NC(=O)c2cnn(-c3cncc4ccccc34)c2C(F)(F)F)ccn1]

$^1$H NMR (400 MHz, DMSO-d$_6$) δ ppm 11.30 (br s, 1H), 9.62 (s, 1H), 8.79 (s, 1H), 8.70 (br d, J=5.5 Hz, 1H), 8.61 (s, 1H), 8.39 (br d, J=8.3 Hz, 1H), 8.28 (s, 1H), 8.02-7.91 (m, 2H), 7.91-7.84 (m, 1H), 7.29 (br d, J=8.5 Hz, 1H). LCMS (ESI): m/z 531.0 [M+H]$^+$

Example 82

N-(5-chloro-6-(1H-imidazol-1-yl)pyridin-3-yl)-1-(isoquinolin-4-yl)-5-(trifluoromethyl)-1H-pyrazole-4-carboxamide, Cpd 70

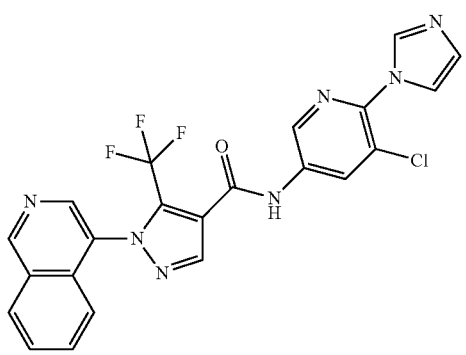 [SMILES: O=C(Nc1cnc(-n2ccnc2)c(Cl)c1)c1cnn(-c2cncc3ccccc23)c1C(F)(F)F]

$^1$H NMR (400 MHz, CHLOROFORM-d) δ ppm 7.20 (s, 1H), 7.34 (d, J=7.94 Hz, 1H), 7.63 (s, 1H), 7.74-7.84 (m, 2H), 8.14-8.21 (m, 2H), 8.30 (s, 1H), 8.55 (d, J=2.21 Hz, 1H), 8.61 (s, 1H), 8.75 (d, J=2.21 Hz, 1H), 9.08 (s, 1H), 9.46 (s, 1H). LCMS (ESI): m/z 483.9 [M+H]$^+$

Example 83

N-(5-chloro-6-(4-methylpiperazine-1-carbonyl)pyridin-3-yl)-1-(isoquinolin-4-yl)-5-(trifluoromethyl)-1H-pyrazole-4-carboxamide, Cpd 48

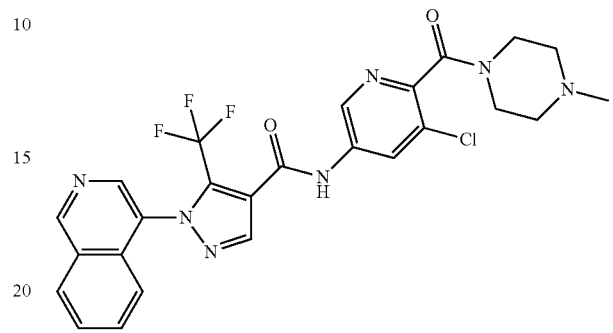

$^1$H NMR (400 MHz, METHANOL-d$_4$) δ ppm 2.99 (s, 3H), 3.15-3.29 (m, 2H), 3.32-3.44 (m, 2H), 3.47-3.64 (m, 2H), 3.66-3.79 (m, 2H), 7.65 (br d, J=8.60 Hz, 1H), 8.14 (br t, J=7.61 Hz, 1H), 8.23-8.32 (m, 1H), 8.52 (s, 1H), 8.56 (d, J=1.76 Hz, 1H), 8.67 (br d, J=8.16 Hz, 1H), 8.90 (s, 1H), 9.05 (br s, 1H), 9.99 (br s, 1H). LCMS (ESI): m/z 543.9 [M+H]$^+$

Example 84

N-(5-cyanopyridin-3-yl)-1-(isoquinolin-4-yl)-5-(trifluoromethyl)-1H-pyrazole-4-carboxamide, Cpd 82

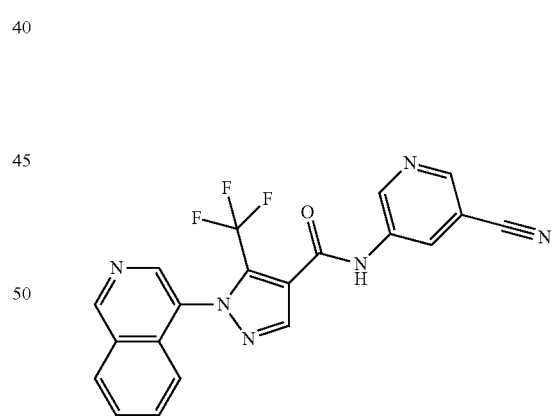

$^1$H NMR (400 MHz, DMSO-d$_6$) δ ppm 11.44 (br s, 1H), 9.66 (br s, 1H), 9.18 (br s, 1H), 8.80 (br d, J=16.3 Hz, 2H), 8.70 (br d, J=17.0 Hz, 2H), 8.40 (br d, J=7.7 Hz, 1H), 8.02-7.79 (m, 2H), 7.30 (br d, J=7.9 Hz, 1H). LCMS (ESI): m/z 409.1 [M+H]$^+$

Example 85

1-(isoquinolin-4-yl)-N-(2-methyl-6-(trifluoromethyl) pyridin-4-yl)-5-(trifluoromethyl)-1H-pyrazole-4-carboxamide, Cpd 73

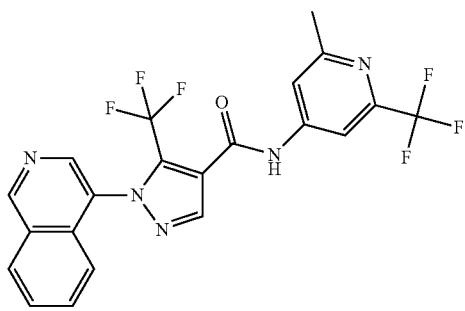 [SMILES: Cc1cc(NC(=O)c2cnn(-c3cncc4ccccc34)c2C(F)(F)F)cc(C(F)(F)F)n1]

$^1$H NMR (400 MHz, METHANOL-$d_4$) δ ppm 2.60 (s, 3H), 7.38 (d, J=8.16 Hz, 1H), 7.81-7.96 (m, 3H), 8.04 (d, J=1.54 Hz, 1H), 8.33 (d, J=7.94 Hz, 1H), 8.40 (s, 1H), 8.63 (s, 1H), 9.51 (s, 1H). LCMS (ESI): m/z 531.0 [M+H]$^+$

Example 86

N-(5-cyano-6-((1-methylpiperidin-4-yl)oxy)pyridin-3-yl)-1-(isoquinolin-4-yl)-5-(trifluoromethyl)-1H-pyrazole-4-carboxamide, Cpd 80

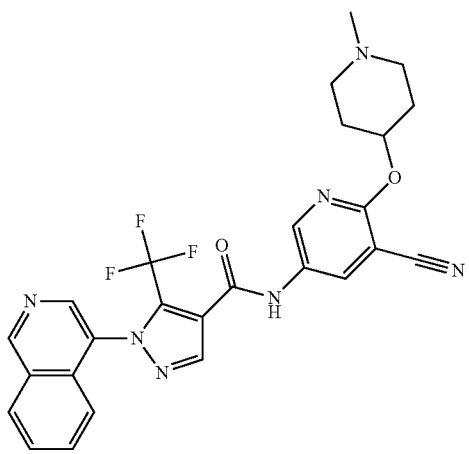 [SMILES: CN1CCC(Oc2ncc(NC(=O)c3cnn(-c4cncc5ccccc45)c3C(F)(F)F)cc2C#N)CC1]

$^1$H NMR (400 MHz, DMSO-$d_6$) δ ppm 1.26 (br s, 1H), 10.82 (br s, 1H), 9.62 (br s, 1H), 8.89-8.51 (m, 4H), 8.38 (br s, 1H), 8.04-7.73 (m, 2H), 7.28 (br s, 1H), 5.45-5.09 (m, 1H), 3.50-3.31 (m, 2H), 3.21-2.97 (m, 2H), 2.75 (br d, J=12.3 Hz, 3H), 2.35-2.11 (m, 3H), 2.01 (br s, 1H). LCMS (ESI): m/z 522.0 [M+H]$^+$

Example 87

N-(5-cyano-6-(4-methylpiperazine-1-carbonyl)pyridin-3-yl)-1-(isoquinolin-4-yl)-5-(trifluoromethyl)-1H-pyrazole-4-carboxamide, Cpd 96

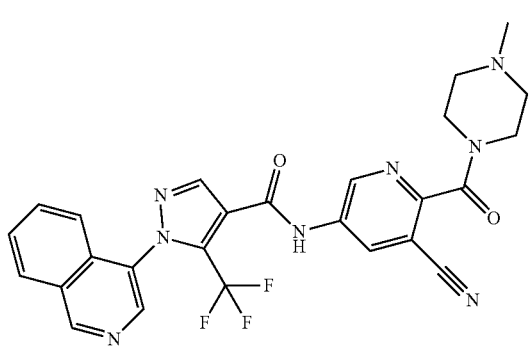 [SMILES: CN1CCN(C(=O)c2ncc(NC(=O)c3cnn(-c4cncc5ccccc45)c3C(F)(F)F)cc2C#N)CC1]

$^1$H NMR (400 MHz, METHANOL-$d_4$) δ ppm 2.99 (s, 3H), 3.18-3.28 (m, 1H), 3.31-3.35 (m, 1H), 3.35-3.79 (m, 5H), 4.18 (br s, 1H), 7.40 (d, J=8.16 Hz, 1H), 7.83-7.97 (m, 2H), 8.35 (d, J=8.16 Hz, 1H), 8.46 (s, 1H), 8.64-8.74 (m, 1H), 8.78 (d, J=2.21 Hz, 1H), 9.14 (d, J=2.21 Hz, 1H), 9.58 (br s, 1H). LCMS (ESI): m/z 535.0 [M+H]$^+$

Example 88

N-(6-cyano-5-fluoropyridin-3-yl)-1-(isoquinolin-4-yl)-5-(trifluoromethyl)-1H-pyrazole-4-carboxamide, Cpd 41

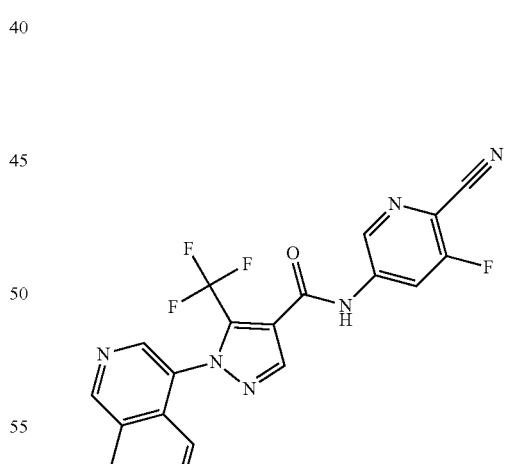

$^1$H NMR (400 MHz, METHANOL-$d_4$) δ ppm 7.56-7.64 (m, 1H), 8.03-8.13 (m, 1H), 8.16-8.25 (m, 1H), 8.50-8.57 (m, 2H), 8.57-8.63 (m, 1H), 8.75-8.82 (m, 1H), 8.94-8.98 (m, 1H), 9.89 (s, 1H). LCMS (ESI): m/z 427.0 [M+H]$^+$

Example 89

N-(6-(2H-1,2,3-triazol-2-yl)pyridin-3-yl)-1-(isoquinolin-4-yl)-5-(trifluoromethyl)-1H-pyrazole-4-carboxamide, Cpd 71

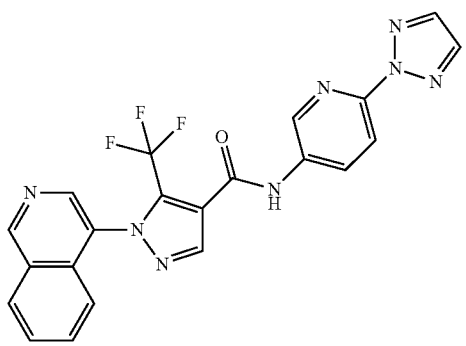 [SMILES: O=C(Nc1ccc(-n2nccn2)nc1)c1cnn(-c2cncc3ccccc23)c1C(F)(F)F]

$^1$H NMR (400 MHz, CHLOROFORM-d) δ ppm 7.34 (d, J=8.16 Hz, 1H), 7.74-7.84 (m, 2H), 7.92 (s, 2H), 8.10-8.19 (m, 3H), 8.27 (s, 1H), 8.57-8.62 (m, 2H), 8.64 (d, J=2.65 Hz, 1H), 9.45 (s, 1H). LCMS (ESI): m/z 451.0 [M+H]$^+$

Example 90

N-(6-(4-(4-aminobutyl)piperazine-1-carbonyl)-5-cyanopyridin-3-yl)-1-(isoquinolin-4-yl)-5-(trifluoromethyl)-1H-pyrazole-4-carboxamide, Cpd 101

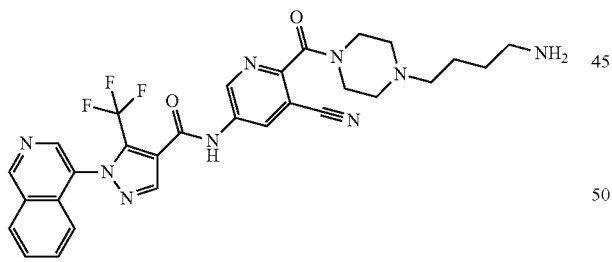

$^1$H NMR (400 MHz, METHANOL-d$_4$) δ ppm 1.72 (br s, 4H), 2.64-2.87 (m, 4H), 2.98 (br s, 2H), 3.49-3.70 (m, 1H), 3.58 (br s, 1H), 3.76-4.09 (m, 1H), 3.92 (br s, 1H), 4.66 (br s, 2H), 7.39 (d, J=8.16 Hz, 1H), 7.83-7.96 (m, 2H), 8.34 (d, J=8.16 Hz, 1H), 8.45 (s, 1H), 8.64 (s, 1H), 8.78 (d, J=2.20 Hz, 1H), 9.12 (d, J=1.76 Hz, 1H), 9.52 (s, 1H). LCMS (ESI): m/z 592.0 [M+H]$^+$

Example 91

N-(5-chloro-6-(1H-imidazol-2-yl)pyridin-3-yl)-1-(isoquinolin-4-yl)-5-(trifluoromethyl)-1H-pyrazole-4-carboxamide, Cpd 104

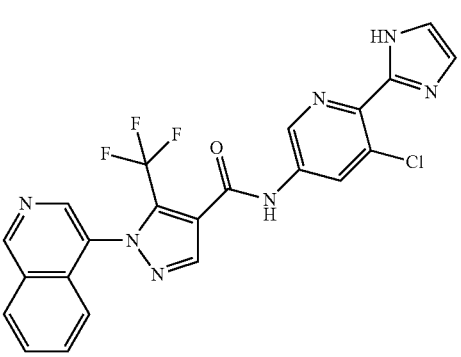 [SMILES: O=C(Nc1cnc(-c2ncc[nH]2)c(Cl)c1)c1cnn(-c2cncc3ccccc23)c1C(F)(F)F]

$^1$H NMR (400 MHz, DMSO-d$_6$) δ ppm 7.07-7.33 (m, 2H) 7.75-7.96 (m, 3H), 8.37 (br d, J=7.94 Hz, 2H), 8.71 (br d, J=1.76 Hz, 2H), 8.79 (d, J=11.47 Hz, 1H), 9.20 (br d, J=1.76 Hz, 1H), 9.61 (s, 1H), 11.77 (s, 1H). LCMS (ESI): m/z 477.0 [M+H]$^+$

Example 92

Methyl 4-(1-(isoquinolin-4-yl)-5-(trifluoromethyl)-1H-pyrazole-4-carboxamido)picolin, Cpd 75

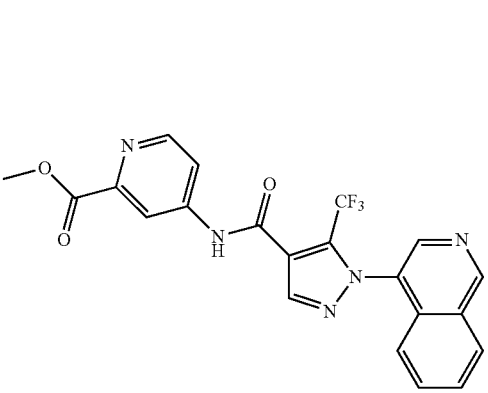 [SMILES: COC(=O)c1cc(NC(=O)c2cnn(-c3cncc4ccccc34)c2C(F)(F)F)ccn1]

$^1$H NMR (400 MHz, METHANOL-d$_4$) δ ppm 4.15 (s, 3H) 7.64 (d, J=8.38 Hz, 1H) 8.08-8.16 (m, 1H) 8.22-8.29 (m, 1H) 8.58-8.69 (m, 3H) 8.80 (d, J=6.61 Hz, 1H) 8.90-8.97 (m, 1H) 9.03 (br s, 1H) 9.96 (br s, 1H). LCMS (ESI): m/z 442.0 [M+H]$^+$

Example 106

N-(5-chloro-6-(difluoromethoxy)pyridin-3-yl)-1-(isoquinolin-4-yl)-5-(trifluoromethyl)-1H-pyrazole-4-carboxamide, Cpd 106

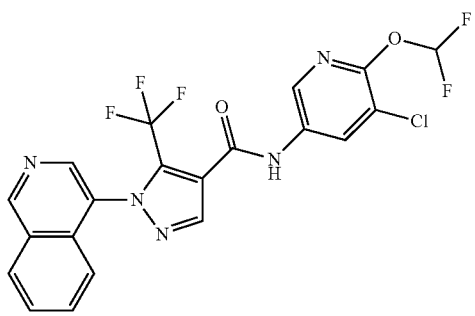 [SMILES: O=C(Nc1cnc(OC(F)F)c(Cl)c1)c1cnn(-c2cncc3ccccc23)c1C(F)(F)F]

¹H NMR (400 MHz, CHLOROFORM-d) δ ppm 7.32 (br d, J=7.94 Hz, 1H), 7.60 (s, 1H), 7.71-7.90 (m, 4H), 8.14-8.19 (m, 2H), 8.21 (s, 1H), 8.59 (s, 1H), 9.44 (s, 1H). LCMS (ESI): m/z 483.8 [M+H]⁺

Example 107

N-(5-chloro-6-(2-oxopyrrolidin-1-yl)pyridin-3-yl)-1-(isoquinolin-4-yl)-5-(trifluoromethyl)-1H-pyrazole-4-carboxamide, Cpd 107

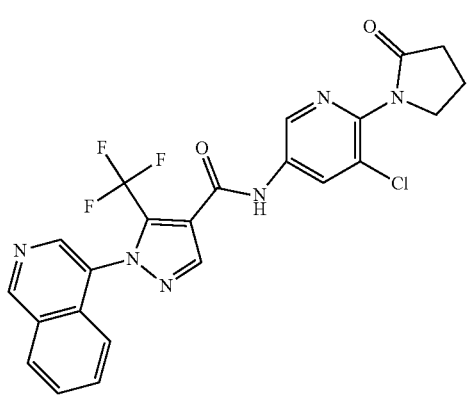 [SMILES: O=C(Nc1cnc(N2CCCC2=O)c(Cl)c1)c1cnn(-c2cncc3ccccc23)c1C(F)(F)F]

¹H NMR (400 MHz, DMSO-d₆) δ ppm 2.09-2.21 (m, 2H), 2.46 (br s, 2H), 3.81 (s, 2H), 7.27 (d, J=8.38 Hz, 1H), 7.81-7.89 (m, 1H), 7.90-7.97 (m, 1H), 8.31-8.40 (m, 1H), 8.41-8.47 (m, 1H), 8.56-8.61 (m, 1H), 8.70-8.82 (m, 2H), 9.56-9.66 (m, 1H), 11.06-11.12 (m, 1H). LCMS (ESI): m/z 501.0 [M+H]⁺

Example 212

N-(2-methyl-1-oxo-1,2,3,4-tetrahydroisoquinolin-7-yl)-1-(quinolin-5-yl)-5-(trifluoromethyl)-1H-pyrazole-4-carboxamide, Cpd 212

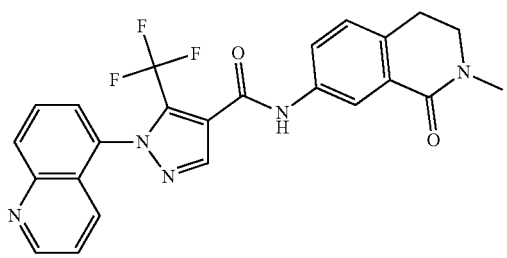 [SMILES: CN1CCc2ccc(NC(=O)c3cnn(-c4cccc5ncccc45)c3C(F)(F)F)cc2C1=O]

¹H NMR (400 MHz, DMSO-d₆) δ ppm 2.96 (br t, J=6.62 Hz, 2H), 3.04 (s, 3H) 3.53-3.56 (m, 2H), 7.30 (d, J=8.16 Hz, 1H), 7.75 (d, J=3.09 Hz, 2H), 7.89 (dd, J=8.16, 1.98 Hz, 1H), 7.94-7.98 (m, 1H), 7.99-8.05 (m, 1H), 8.23 (d, J=1.98 Hz, 1H), 8.37 (d, J=8.38 Hz, 1H), 8.54 (s, 1H), 9.12 (t, J=2.87 Hz, 1H), 10.71 (s, 1H). LC-MS: (ES, m/z): [M+1]⁺ 466.0

Example 213

N-(3-(methylsulfonyl)-4-(1H-1,2,3-triazol-1-yl)phenyl)-1-(quinolin-5-yl)-5-(trifluoromethyl)-1H-pyrazole-4-carboxamide, Cpd 213

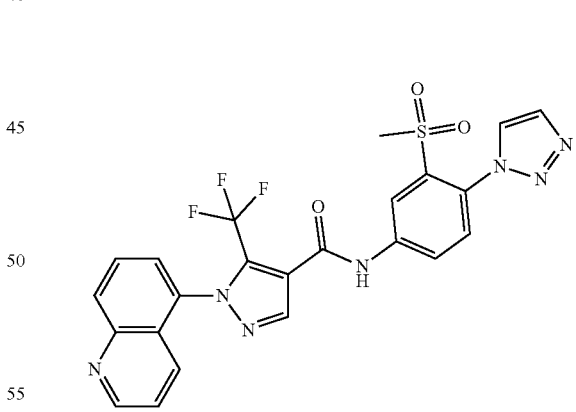

¹H NMR (400 MHz, METHANOL-d₄) δ ppm 3.24 (s, 3H), 7.69 (d, J=8.60 Hz, 1H), 7.95 (s, 1H), 8.15-8.23 (m, 2H), 8.32-8.38 (m, 3H), 8.48 (s, 1H), 8.53 (d, J=8.82 Hz, 1H), 8.61 (d, J=8.82 Hz, 1H), 8.66 (d, J=2.21 Hz, 1H), 9.38 (d, J=4.41 Hz, 1H). LC-MS: (ES, m/z): [M+1]⁺ 528.2

Example 214

N-(4-methyl-3-oxo-3,4-dihydro-2H-benzo[b][1,4]oxazin-6-yl)-1-(quinolin-5-yl)-5-(trifluoromethyl)-1H-pyrazole-4-carboxamide, Cpd 214

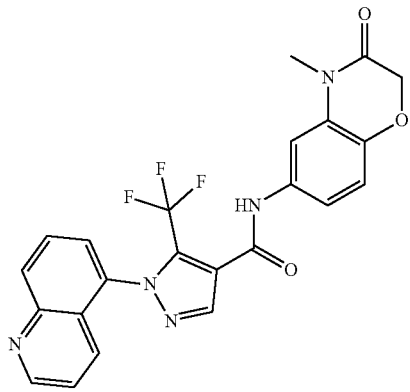 [SMILES: CN1C(=O)COc2ccc(NC(=O)c3cnn(-c4cccc5ncccc45)c3C(F)(F)F)cc21]

¹H NMR (400 MHz, DMSO-d₆) δ ppm 10.66 (1H, s), 9.06-9.18 (1H, m), 8.51 (1H, s), 8.38 (1H, d, J=8.38 Hz), 8.00-8.07 (1H, m), 7.91-7.99 (1H, m), 7.73-7.81 (2H, m), 7.60 (1H, d, J=2.21 Hz), 7.37 (1H, dd, J=8.60, 2.21 Hz), 7.00 (1H, d, J=8.60 Hz), 4.63 (2H, s) 3.26 (3H, s). LC-MS: (ES, m/z): [M+1]⁺ 468.0

Example 215

N-(3-(methylsulfonyl)-4-(2H-1,2,3-triazol-2-yl)phenyl)-1-(quinolin-5-yl)-5-(trifluoromethyl)-1H-pyrazole-4-carboxamide, Cpd 215

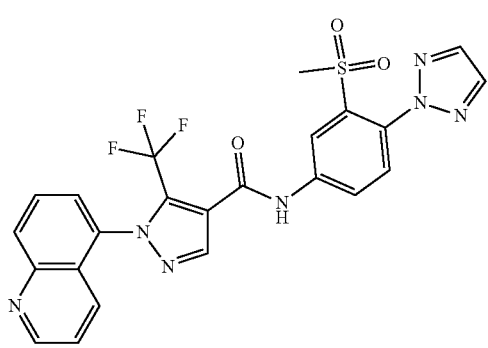 [SMILES: CS(=O)(=O)c1cc(NC(=O)c2cnn(-c3cccc4ncccc34)c2C(F)(F)F)ccc1-n1nccn1]

¹H NMR (400 MHz, METHANOL-d₄) δ ppm 3.53 (s, 3H), 7.77 (d, J=8.60 Hz, 1H), 8.00 (s, 2H), 8.10 (dd, J=8.60, 5.07 Hz, 1H), 8.16 (d, J=7.50 Hz, 1H), 8.27-8.34 (m, 2H), 8.44-8.53 (m, 3H), 8.64 (d, J=1.98 Hz, 1H), 9.33 (d, J=3.97 Hz, 1H). LC-MS: (ES, m/z): [M+1]⁺ 528.1

Example 216

N-(2-methyl-1-oxo-1,2-dihydroisoquinolin-7-yl)-1-(quinolin-5-yl)-5-(trifluoromethyl)-1H-pyrazole-4-carboxamide, Cpd 216

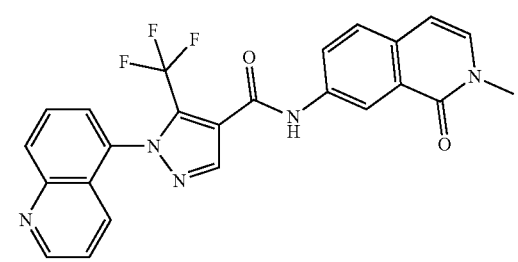 [SMILES: Cn1ccc2ccc(NC(=O)c3cnn(-c4cccc5ncccc45)c3C(F)(F)F)cc2c1=O]

¹H NMR (400 MHz, DMSO-d₆) δ ppm 3.51 (s, 3H), 3.99 (br s, 18H), 6.59 (d, J=7.06 Hz, 1H), 7.41 (d, J=7.28 Hz, 1H), 7.64-7.74 (m, 3H), 7.90-8.03 (m, 2H), 8.07 (br d, J=7.72 Hz, 1H), 8.34 (br d, J=8.38 Hz, 1H), 8.56 (s, 1H), 8.63 (s, 1H), 9.08 (br s, 1H), 10.86 (s, 1H). LC-MS: (ES, m/z): [M+1]⁺ 464.0

Example 217

N-(3-oxo-3,4-dihydro-2H-benzo[b][1,4]oxazin-6-yl)-1-(quinolin-5-yl)-5-(trifluoromethyl)-1H-pyrazole-4-carboxamide, Cpd 217

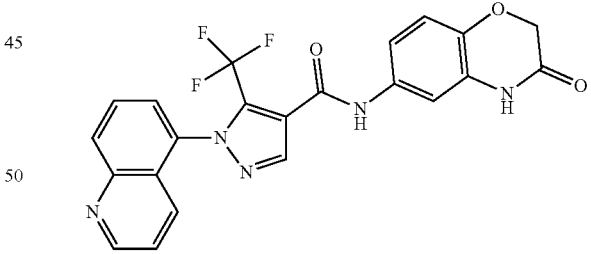

¹H NMR (400 MHz, DMSO-d₆) δ ppm 10.78 (s, 1H), 10.56 (s, 1H), 9.08-9.01 (m, 1H), 8.47 (s, 1H), 8.31 (d, J=8.4 Hz, 1H), 7.99-7.93 (m, 1H), 7.90-7.86 (m, 1H), 7.69-7.64 (m, 1H), 7.63-7.59 (m, 1H), 7.51 (d, J=2.2 Hz, 1H), 7.19 (dd, J=2.2, 8.8 Hz, 1H), 6.94 (d, J=8.6 Hz, 1H), 4.53 (s, 2H). LC-MS: (ES, m/z): [M+1]⁺ 453.9

Example 218

N-(5-methyl-6-(3-methyl-2-oxo-2,3-dihydro-1H-imidazol-1-yl)pyridin-3-yl)-1-(quinolin-5-yl)-5-(trifluoromethyl)-1H-pyrazole-4-carboxamide, Cpd 218

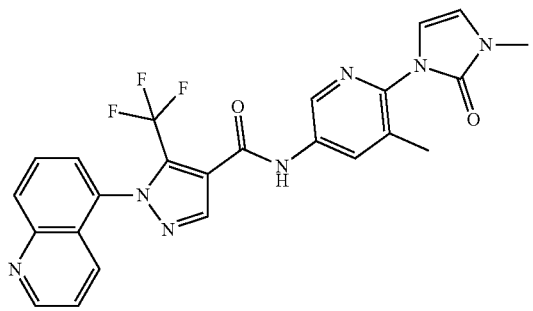 [SMILES: Cc1cc(NC(=O)c2cnn(-c3cccc4ncccc34)c2C(F)(F)F)cnc1-n1ccn(C)c1=O]

$^1$H NMR (400 MHz, METHANOL-d$_4$) δ ppm 2.34 (s, 3H), 3.36 (s, 3H), 6.69 (d, J=3.01 Hz, 1H), 6.74 (d, J=2.76 Hz, 1H), 7.66 (dd, J=8.53, 4.27 Hz, 1H), 7.78 (d, J=8.03 Hz, 1H), 7.85 (d, J=7.28 Hz, 1H), 7.96-8.02 (m, 1H), 8.29 (d, J=2.01 Hz, 1H), 8.32-8.39 (m, 2H), 8.72 (d, J=2.51 Hz, 1H), 9.03 (dd, J=4.27, 1.51 Hz, 1H). LC-MS: (ES, m/z): [M+1]$^+$ 494.0

Example 219

N-(5-cyano-6-(2H-1,2,3-triazol-2-yl)pyridin-3-yl)-1-(2-methylbenzo[d]oxazol-4-yl)-5-(trifluoromethyl)-1H-pyrazole-4-carboxamide, cpd 219

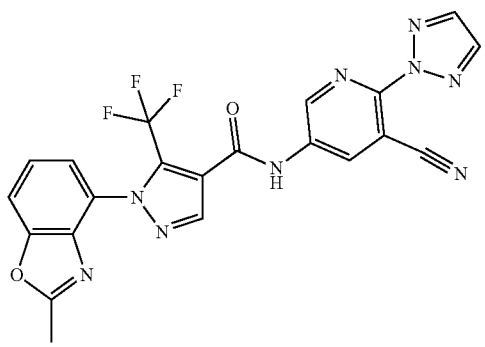 [SMILES: Cc1nc2c(-n3ncc(C(=O)Nc4cnc(-n5nccn5)c(C#N)c4)c3C(F)(F)F)cccc2o1]

$^1$H NMR (400 MHz, DMSO-d$_6$) δ ppm 9.12 (d, J=2.3 Hz, 1H), 8.89 (d, J=2.5 Hz, 1H), 8.54 (s, 1H), 8.32 (s, 2H), 8.01-7.93 (m, 1H), 7.64-7.53 (m, 2H), 2.65 (s, 3H). LC-MS: (ES, m/z): [M+1]$^+$ 479.9

Example 220

1-(2-chloroquinolin-4-yl)-N-(5-cyano-6-(2H-1,2,3-triazol-2-yl)pyridin-3-yl)-5-(trifluoromethyl)-1H-pyrazole-4-carboxamide, Cpd 220

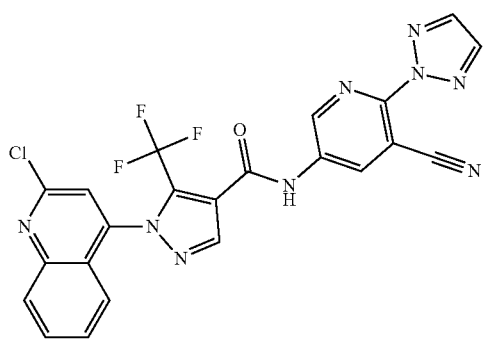 [SMILES: N#Cc1cc(NC(=O)c2cnn(-c3cc(Cl)nc4ccccc34)c2C(F)(F)F)cnc1-n1nccn1]

$^1$H NMR (400 MHz, DMSO-d$_6$) δ ppm 11.54 (s, 1H), 9.08 (d, J=2.43 Hz, 1H), 8.85 (d, J=2.43 Hz, 1H), 8.55 (s, 1H), 8.25-8.36 (m, 4H), 8.05-8.13 (m, 1H), 8.01 (t, J=7.17 Hz, 1H), 7.87-7.93 (m, 1H). LC-MS: (ES, m/z): [M+1]$^+$ 509.9

Example 221

N-(5-chloro-6-(2H-1,2,3-triazol-2-yl)pyridin-3-yl)-1-(2-chloroquinolin-5-yl)-5-(trifluoromethyl)-1H-pyrazole-4-carboxamide, Cpd 221

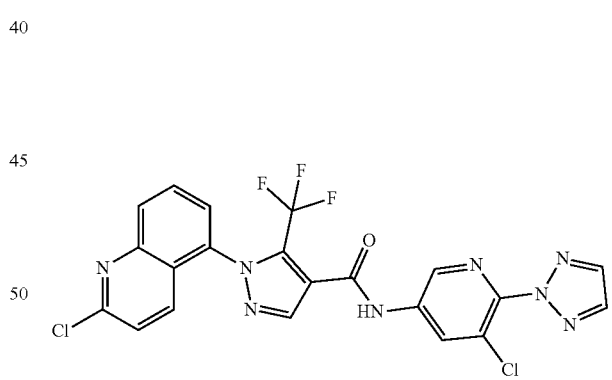

$^1$H NMR (400 MHz, METHANOL-d$_4$) δ ppm 7.60-7.64 (m, 1H), 7.73 (d, J=8.60 Hz, 1H), 7.83 (d, J=7.28 Hz, 1H), 7.96-8.01 (m, 1H), 8.04 (s, 2H), 8.23 (d, J=8.60 Hz, 1H), 8.40 (s, 1H), 8.72 (d, J=2.20 Hz, 1H), 8.79 (d, J=2.21 Hz, 1H). LC-MS: (ES, m/z): [M+1]$^+$ 518.9

Example 222

N-(5-chloro-6-(2H-1,2,3-triazol-2-yl)pyridin-3-yl)-1-(1H-pyrazolo[3,4-d]pyrimidin-4-yl)-5-(trifluoromethyl)-1H-pyrazole-4-carboxamide, Cpd 222

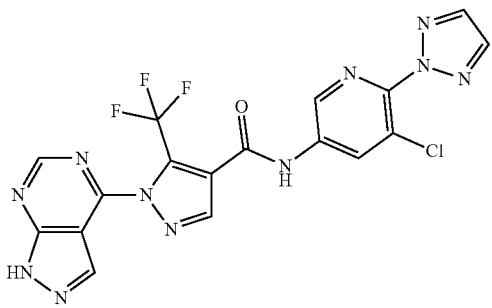 [SMILES: O=C(Nc1cnc(-n2nccn2)c(Cl)c1)c1cnn(-c2ncnc3[nH]ncc23)c1C(F)(F)F]

$^1$H NMR (400 MHz, DMSO-d$_6$) δ ppm 8.98 (s, 1H), 8.78 (d, J=2.20 Hz, 1H), 8.63 (s, 1H), 8.60 (d, J=2.21 Hz, 1H), 8.53 (s, 1H), 8.16 (s, 2H). LC-MS: (ES, m/z): [M+1]$^+$ 475.9

Example 223

N-(5-cyano-6-(2H-1,2,3-triazol-2-yl)pyridin-3-yl)-1-(1,6-naphthyridin-4-yl)-5-(trifluoromethyl)-1H-pyrazole-4-carboxamide, Cpd 223

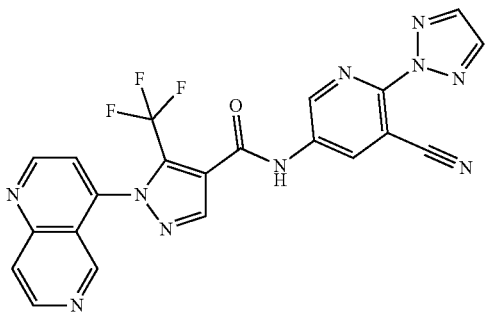 [SMILES: N#Cc1cc(NC(=O)c2cnn(-c3ccnc4ccncc34)c2C(F)(F)F)cnc1-n1nccn1]

$^1$H NMR (400 MHz, DMSO-d$_6$) δ ppm 11.48 (s, 1H), 9.39-9.43 (m, 1H), 9.10-9.15 (m, 1H), 8.89-8.95 (m, 3H), 8.71-8.76 (m, 1H), 8.31 (s, 2H), 8.14-8.20 (m, 1H), 8.03-8.10 (m, 1H). LC-MS: (ES, m/z): [M+1]$^+$ 476.9

Example 224

N-(5-cyano-6-(4-methylpiperazin-1-yl)pyridin-3-yl)-1-(quinolin-5-yl)-5-(trifluoromethyl)-1H-pyrazole-4-carboxamide, Cpd 224

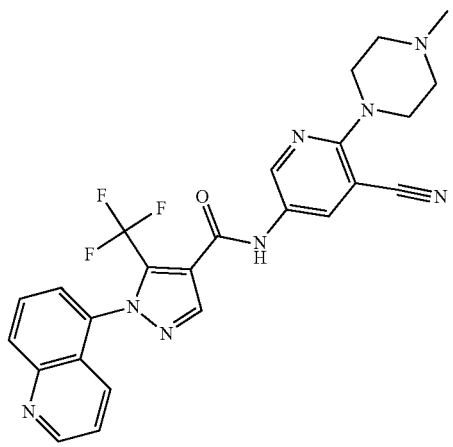 [SMILES: CN1CCN(c2ncc(NC(=O)c3cnn(-c4cccc5ncccc45)c3C(F)(F)F)cc2C#N)CC1]

$^1$H NMR (400 MHz, DMSO-d$_6$) δ ppm 11.08-11.18 (m, 1H), 10.83-10.99 (m, 1H), 9.05 (br s, 1H), 8.73-8.82 (m, 1H), 8.56-8.64 (m, 1H), 8.44-8.55 (m, 1H), 8.27-8.38 (m, 1H), 7.94-8.02 (m, 1H), 7.88-7.93 (m, 1H), 7.59-7.71 (m, 2H), 4.07-4.21 (m, 2H), 3.52-3.64 (m, 4H), 3.16 (br d, J=9.92 Hz, 2H), 2.75-2.87 (m, 3H). LC-MS: (ES, m/z): [M+1]$^+$ 507.0

Example 225

N-(1-methyl-1H-pyrazolo[3,4-b]pyridin-5-yl)-1-(quinolin-5-yl)-5-(trifluoromethyl)-1H-pyrazole-4-carboxamide, Cpd 225

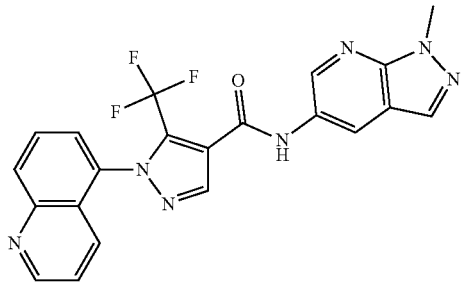 [SMILES: Cn1ncc2cc(NC(=O)c3cnn(-c4cccc5ncccc45)c3C(F)(F)F)cnc21]

$^1$H NMR (400 MHz, DMSO-d$_6$) δ ppm 11.09 (s, 1H), 9.21 (d, J=4.0 Hz, 1H), 8.81 (d, J=2.0 Hz, 1H), 8.71-8.62 (m, 2H), 8.47 (d, J=8.6 Hz, 1H), 8.14 (s, 1H), 8.11 (t, J=8.0 Hz, 1H), 8.06-8.02 (m, 1H), 7.99 (br d, J=8.4 Hz, 1H), 7.87 (dd, J=4.5, 8.5 Hz, 1H), 4.04 (s, 3H). LC-MS: (ES, m/z): [M+1]$^+$ 438.0

Example 226

N-(5-chloro-6-(2H-1,2,3-triazol-2-yl)pyridin-3-yl)-1-(2-methyl-1-oxo-1,2-dihydroisoquinolin-5-yl)-5-(trifluoromethyl)-1H-pyrazole-4-carboxamide, Cpd 226

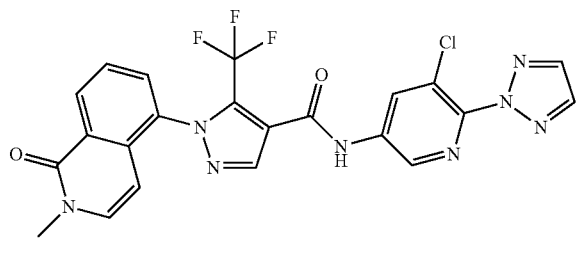 [SMILES: Cn1ccc2c(-n3ncc(C(=O)Nc4cnc(-n5nccn5)c(Cl)c4)c3C(F)(F)F)cccc2c1=O]

$^1$H NMR (400 MHz, DMSO-d$_6$) δ ppm 11.24 (1H, s), 8.82 (1H, d, J=2.21 Hz), 8.64 (1H, d, J=2.20 Hz), 8.53 (1H, s), 8.45 (1H, d, J=8.16 Hz), 8.16 (2H, s), 7.93 (1H, d, J=7.06 Hz), 7.66 (1H, t, J=7.94 Hz), 7.56 (1H, d, J=7.50 Hz), 5.71 (1H, d, J=7.72 Hz), 3.50 (3H, s). LC-MS: (ES, m/z): [M+1]$^+$ 514.9

Example 227

N-(5-chloro-6-(5-cyano-1H-1,2,3-triazol-1-yl)pyridin-3-yl)-1-(quinolin-5-yl)-5-(trifluoromethyl)-1H-pyrazole-4-carboxamide, Cpd 227

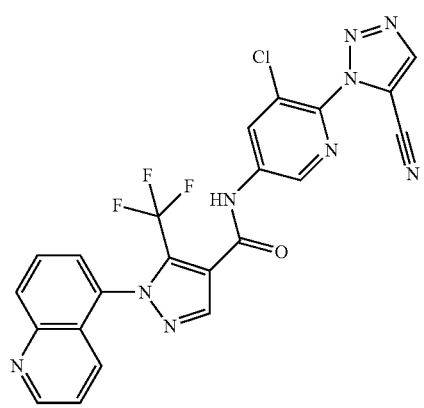 [SMILES: N#Cc1cnnn1-c1ncc(NC(=O)c2cnn(-c3cccc4ncccc34)c2C(F)(F)F)cc1Cl]

$^1$H NMR (400 MHz, METHANOL-d$_4$) δ ppm 7.97 (dd, J=8.60, 5.07 Hz, 1H), 8.06 (d, J=7.50 Hz, 1H), 8.18-8.23 (m, 1H), 8.28 (d, J=8.60 Hz, 1H), 8.42-8.47 (m, 2H), 8.77 (d, J=2.21 Hz, 1H), 8.85 (d, J=2.20 Hz, 1H), 9.21 (s, 1H), 9.23 (dd, J=4.85, 1.32 Hz, 1H). LC-MS: (ES, m/z): [M+1]$^+$ 509.9

Example 228

2-(2-chloro-4-(1-(quinolin-5-yl)-5-(trifluoromethyl)-1H-pyrazole-4-carboxamido)phenyl)-2H-1,2,3-triazole-4-carboxylic acid, Cpd 228

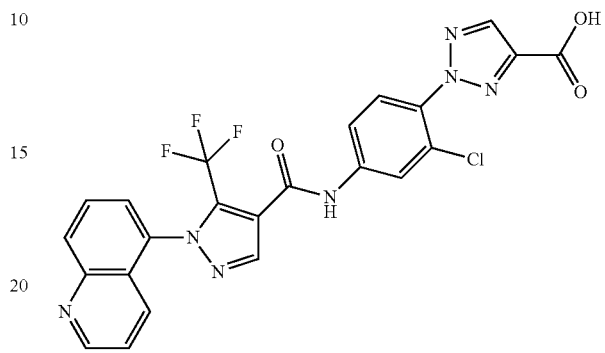

$^1$H NMR (400 MHz, DMSO-d$_6$) δ ppm 11.27 (s, 1H), 9.12 (s, 1H), 9.03 (br d, J=2.21 Hz, 1H), 8.63 (s, 1H), 8.30 (br d, J=8.38 Hz, 1H), 8.25 (s, 1H), 7.86-7.97 (m, 3H), 7.74 (d, J=8.60 Hz, 1H), 7.58-7.68 (m, 2H). LC-MS: (ES, m/z): [M+1]$^+$ 527.8

Example 229

N-(1H-pyrazolo[3,4-b]pyridin-5-yl)-1-(quinolin-5-yl)-5-(trifluoromethyl)-1H-pyrazole-4-carboxamide, Cpd 229

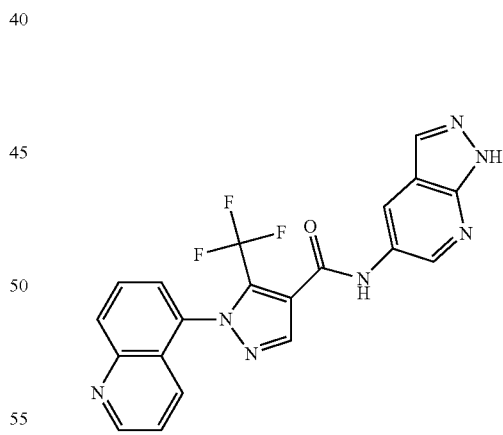

$^1$H NMR (400 MHz, DMSO-d$_6$) δ ppm 10.99 (s, 1H), 9.13 (br d, J=2.9 Hz, 1H), 8.76 (d, J=1.8 Hz, 1H), 8.66 (s, 1H), 8.62 (s, 1H), 8.39 (d, J=8.6 Hz, 1H), 8.16 (s, 1H), 8.07-8.00 (m, 1H), 7.99-7.94 (m, 1H), 7.85-7.70 (m, 2H). LC-MS: (ES, m/z): [M+1]$^+$ 424.0

Example 230

N-(5-cyano-6-(2H-1,2,3-triazol-2-yl)pyridin-3-yl)-1-(imidazo[1,2-a]pyridin-8-yl)-5-(trifluoromethyl)-1H-pyrazole-4-carboxamide, Cpd 230

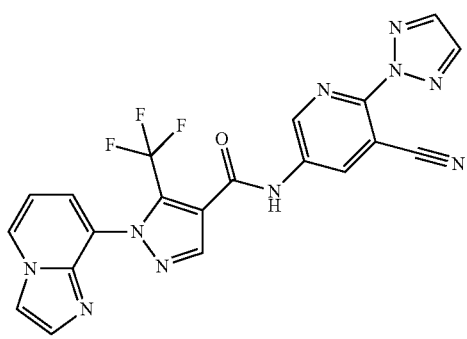 [SMILES: N#Cc1cc(NC(=O)c2cnn(-c3cccn4ccnc34)c2C(F)(F)F)cnc1-n1nccn1]

$^1$H NMR (400 MHz, DMSO-d$_6$) δ ppm 7.35 (br t, J=7.06 Hz, 1H), 7.90-7.95 (m, 2H), 8.32 (s, 2H), 8.34 (s, 1H), 8.70 (s, 1H), 8.94 (d, J=2.43 Hz, 1H), 8.97 (d, J=6.84 Hz, 1H), 9.18 (d, J=1.98 Hz, 1H), 11.49 (s, 1H). LC-MS: (ES, m/z): [M+1]$^+$ 465.0

Example 231

1-(benzo[d][1,2,3]thiadiazol-4-yl)-N-(5-chloro-6-(2H-1,2,3-triazol-2-yl)pyridin-3-yl)-5-(trifluoromethyl)-1H-pyrazole-4-carboxamide, Cpd 231

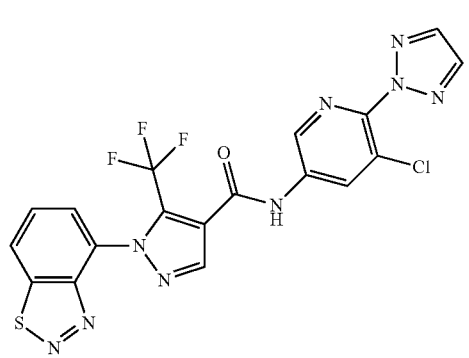 [SMILES: O=C(Nc1cnc(-n2nccn2)c(Cl)c1)c1cnn(-c2cccc3snnc23)c1C(F)(F)F]

$^1$H NMR (400 MHz, DMSO-d$_6$) δ ppm 11.32 (s, 1H), 8.85 (s, 1H), 8.73-8.64 (m, 2H), 8.61 (s, 1H), 8.17 (s, 2H), 8.11-7.95 (m, 2H). LC-MS: (ES, m/z): [M+1]$^+$ 491.9

Example 232

N-(5-cyano-6-(2H-1,2,3-triazol-2-yl)pyridin-3-yl)-1-(2-methylthieno[3,2-b]pyridin-7-yl)-5-(trifluoromethyl)-1H-pyrazole-4-carboxamide, Cpd 232

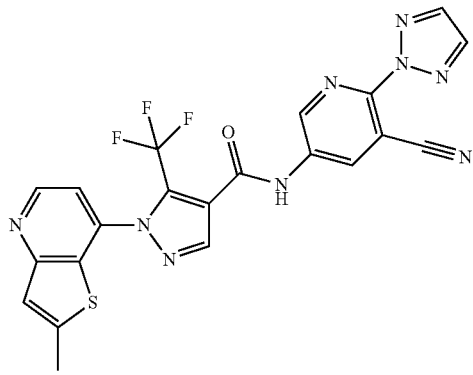 [SMILES: Cc1cc2nccc(-n3ncc(C(=O)Nc4cnc(-n5nccn5)c(C#N)c4)c3C(F)(F)F)c2s1]

$^1$H NMR (400 MHz, DMSO-d$_6$) δ ppm 2.66 (s, 3H), 7.49 (s, 1H), 7.59 (d, J=4.85 Hz, 1H), 8.31 (s, 2H), 8.67 (s, 1H), 8.84 (d, J=5.07 Hz, 1H), 8.88 (d, J=2.21 Hz, 1H), 9.11 (d, J=2.20 Hz, 1H), 11.54 (s, 1H). LC-MS: (ES, m/z): [M+1]$^+$ 495.9

Example 233

N-(5-chloro-6-(2H-1,2,3-triazol-2-yl)pyridin-3-yl)-1-(imidazo[1,5-a]pyridin-5-yl)-5-(trifluoromethyl)-1H-pyrazole-4-carboxamide, Cpd 233

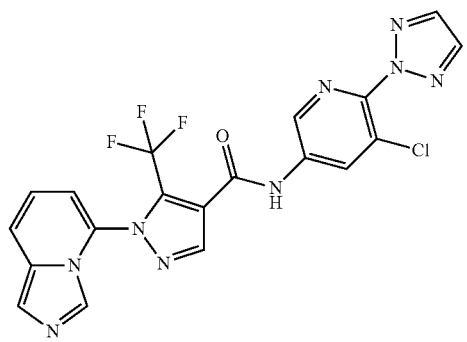 [SMILES: O=C(Nc1cnc(-n2nccn2)c(Cl)c1)c1cnn(-c2cccc3cncn23)c1C(F)(F)F]

$^1$H NMR (400 MHz, DMSO-d$_6$) δ ppm 7.19 (dd, J=9.15, 6.95 Hz, 1H), 7.42 (d, J=6.84 Hz, 1H), 7.96-8.04 (m, 2H), 8.20 (s, 2H), 8.57 (s, 1H), 8.73 (d, J=1.98 Hz, 1H), 8.84 (s, 1H), 8.95 (d, J=2.21 Hz, 1H), 11.60 (s, 1H). LC-MS: (ES, m/z): [M+1]$^+$ 473.9

Example 234

1-(3-chloro-5-(1-(quinolin-5-yl)-5-(trifluoromethyl)-1H-pyrazole-4-carboxamido)pyridin-2-yl)-1H-1,2,3-triazole-4-carboxylic acid, Cpd 234

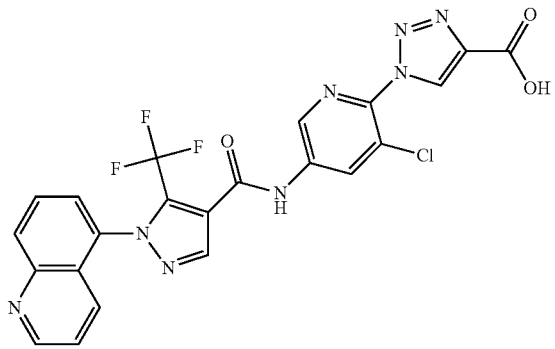 [SMILES: O=C(O)c1cn(-c2ncc(NC(=O)c3cnn(-c4cccc5ncccc45)c3C(F)(F)F)cc2Cl)nn1]

$^1$H NMR (400 MHz, METHANOL-d$_4$) δ ppm 8.09 (dd, J=8.53, 5.02 Hz, 1H), 8.15 (d, J=7.28 Hz, 1H), 8.29 (t, J=8.16 Hz, 1H), 8.44-8.53 (m, 3H), 8.78 (d, J=2.26 Hz, 1H), 8.88 (d, J=2.26 Hz, 1H), 8.99 (s, 1H), 9.32 (br d, J=5.02 Hz, 1H). LC-MS: (ES, m/z): [M+1]$^+$ 528.8

Example 235

N-(5-methoxy-6-(1H-1,2,3-triazol-1-yl)pyridin-3-yl)-1-(quinolin-5-yl)-5-(trifluoromethyl)-1H-pyrazole-4-carboxamide, Cpd 235

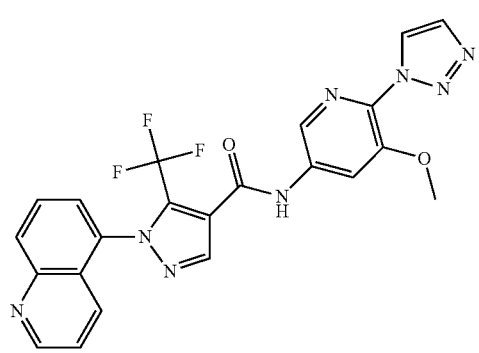 [SMILES: COc1cc(NC(=O)c2cnn(-c3cccc4ncccc34)c2C(F)(F)F)cnc1-n1ccnn1]

$^1$H NMR (400 MHz, DMSO-d$_6$) δ ppm 11.22 (s, 1H), 9.02-9.11 (m, 1H), 8.60-8.66 (m, 1H), 8.53-8.57 (m, 1H), 8.48-8.52 (m, 1H), 8.32-8.37 (m, 1H), 8.25-8.29 (m, 1H), 7.90-8.02 (m, 3H), 7.62-7.73 (m, 2H), 3.85-3.92 (m, 3H). LC-MS: (ES, m/z): [M+1]$^+$ 480.9

Example 236

N-(4-aminobutyl)-3-cyano-5-(1-(isoquinolin-4-yl)-5-(trifluoromethyl)-1H-pyrazole-4-carboxamido)picolinamide, Cpd 236

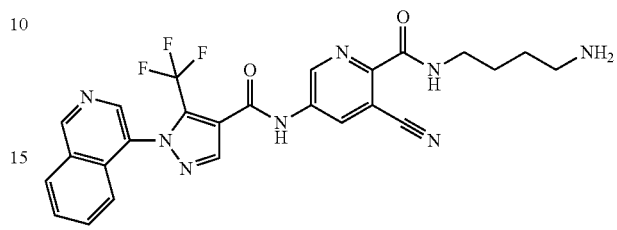

$^1$H NMR (400 MHz, METHANOL-d$_4$) δ ppm 1.65-1.87 (m, 3H), 1.69-1.82 (m, 1H), 3.00 (br s, 2H), 3.42-3.57 (m, 1H), 3.48 (br s, 1H), 7.57 (d, J=8.38 Hz, 1H), 8.06 (t, J=7.39 Hz, 1H), 8.13-8.21 (m, 1H), 8.47-8.53 (m, 1H), 8.57 (d, J=8.38 Hz, 1H), 8.74 (d, J=2.43 Hz, 1H), 8.93 (s, 1H), 9.20 (d, J=2.43 Hz, 1H), 9.85 (s, 1H). LC-MS: (ES, m/z): [M+1]$^+$ 523.0

Example 237

2-cyano-4-(1-(quinolin-5-yl)-5-(trifluoromethyl)-1H-pyrazole-4-carboxamido)benzoic acid, Cpd 237

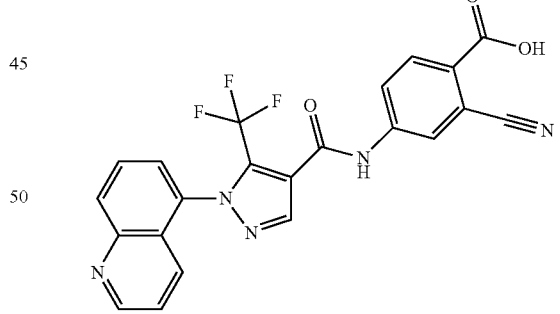

$^1$H NMR (400 MHz, DMSO-d$_6$) δ ppm 7.55-7.60 (m, 1H), 7.62-7.67 (m, 1H), 7.86-7.90 (m, 1H), 7.91-7.97 (m, 1H), 7.99-8.04 (m, 1H), 8.06-8.11 (m, 1H), 8.23 (s, 1H), 8.30 (d, J=8.38 Hz, 1H), 8.53 (s, 1H), 9.03 (dd, J=4.08, 1.65 Hz, 1H), 11.08 (s, 1H). LC-MS: (ES, m/z): [M+1]$^+$ 451.9

Example 238

N-(4-(4-(aminomethyl)-1H-pyrazol-1-yl)-3-methylphenyl)-1-(quinolin-5-yl)-5-(trifluoromethyl)-1H-pyrazole-4-carboxamide, Cpd 238

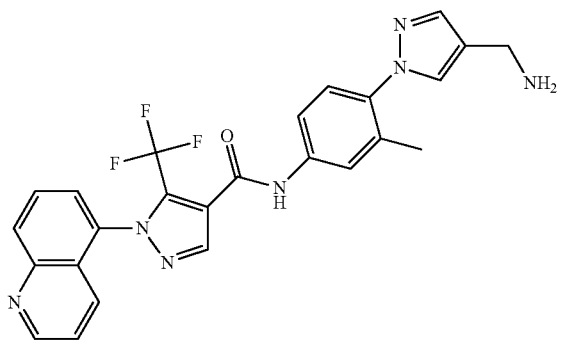 [SMILES: Cc1cc(NC(=O)c2cnn(-c3cccc4ncccc34)c2C(F)(F)F)ccc1-n1cc(CN)cn1]

$^1$H NMR (400 MHz, DMSO-d$_6$) δ ppm 2.23 (s, 3H), 3.99 (br d, J=5.51 Hz, 2H), 7.33 (d, J=8.60 Hz, 1H), 7.76 (br d, J=8.60 Hz, 1H), 7.78-7.87 (m, 4H), 7.98-8.02 (m, 1H), 8.04-8.09 (m, 1H), 8.12 (s, 1H), 8.36 (br s, 2H), 8.43 (d, J=8.60 Hz, 1H), 8.60 (s, 1H), 9.16 (d, J=2.65 Hz, 1H), 10.89 (s, 1H). LC-MS: (ES, m/z): [M+1]$^+$ 492.0

Example 239

N-(5-cyano-6-(2H-1,2,3-triazol-2-yl)pyridin-3-yl)-1-(1-methyl-1H-indazol-4-yl)-5-(trifluoromethyl)-1H-pyrazole-4-carboxamide, Cpd 239

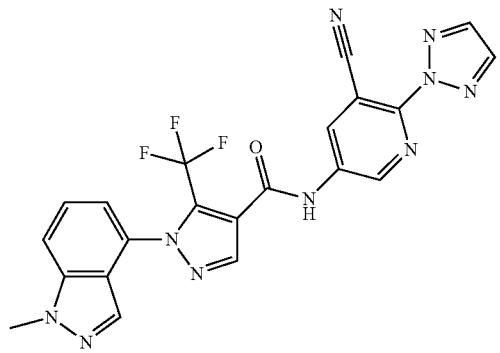 [SMILES: Cn1ncc2c(-n3ncc(C(=O)Nc4cnc(-n5nccn5)c(C#N)c4)c3C(F)(F)F)cccc21]

$^1$H NMR (400 MHz, DMSO-d$_6$) δ ppm 4.14 (s, 3H), 7.33 (d, J=7.28 Hz, 1H), 7.58 (t, J=7.83 Hz, 1H), 7.84 (s, 1H), 7.93 (d, J=8.60 Hz, 1H), 8.30 (s, 2H), 8.53 (s, 1H), 8.86 (d, J=2.21 Hz, 1H), 9.08 (d, J=2.43 Hz, 1H), 11.36 (s, 1H). LC-MS: (ES, m/z): [M+1]$^+$ 479.0

Example 240

5-fluorocarbonyl-N-(5-methyl-6-(1-methyl-1H-tetrazol-5-yl)pyridin-3-yl)-1-(quinolin-5-yl)-1H-pyrazole-4-carboxamide, Cpd 240

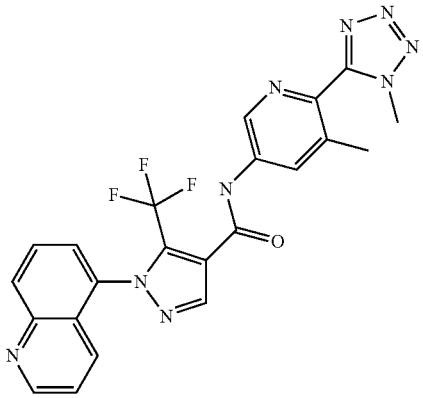 [SMILES: Cc1cc(NC(=O)c2cnn(-c3cccc4ncccc34)c2C(F)(F)F)cnc1-c1nnnn1C]

$^1$H NMR (400 MHz, DMSO-d$_6$) δ ppm 11.37 (1H, s), 9.00-9.08 (2H, m), 8.68 (1H, s), 8.37 (1H, s), 8.31 (1H, d, J=8.38 Hz), 7.92-8.00 (1H, m), 7.85-7.92 (1H, m), 7.60-7.70 (2H, m), 4.19 (3H, s), 2.52 (3H, s). LC-MS: (ES, m/z): [M+1]$^+$ 480.0

Example 241

N-(5-cyano-6-(2H-1,2,3-triazol-2-yl)pyridin-3-yl)-1-(1-methyl-1H-pyrazolo[3,4-b]pyridin-4-yl)-5-(trifluoromethyl)-1H-pyrazole-4-carboxamide, Cpd 241

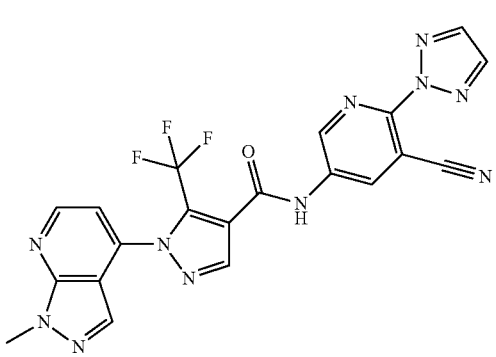 [SMILES: Cn1ncc2c(-n3ncc(C(=O)Nc4cnc(-n5nccn5)c(C#N)c4)c3C(F)(F)F)ccnc21]

$^1$H NMR (400 MHz, DMSO-d$_6$) δ ppm 4.17 (s, 3H), 7.49 (d, J=5.07 Hz, 1H), 8.12 (s, 1H), 8.32 (s, 2H), 8.65 (s, 1H), 8.83 (d, J=4.85 Hz, 1H), 8.87 (d, J=1.98 Hz, 1H), 9.10 (d, J=2.21 Hz, 1H), 11.44 (s, 1H). LC-MS: (ES, m/z): [M+1]$^+$ 479.9

Example 242

N-(5-chloro-6-(2H-1,2,3-triazol-2-yl)pyridin-3-yl)-1-(imidazo[1,2-b]pyridazin-6-yl)-5-(trifluoromethyl)-1H-pyrazole-4-carboxamide, Cpd 242

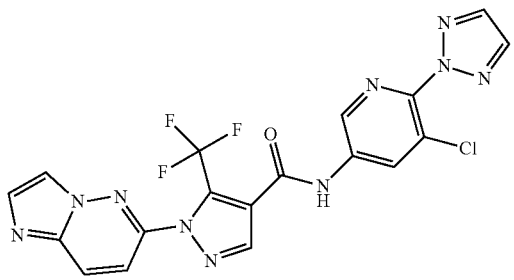 [SMILES: O=C(Nc1cnc(-n2nccn2)c(Cl)c1)c1cnn(-c2ccc3nccn3n2)c1C(F)(F)F]

$^{1}$H NMR (400 MHz, DMSO-d$_{6}$) δ ppm 7.85 (d, J=9.70 Hz, 1H), 8.12 (s, 1H), 8.19 (s, 2H), 8.54-8.60 (m, 2H), 8.63-8.72 (m, 2H), 8.89 (d, J=2.21 Hz, 1H), 11.55 (s, 1H). LC-MS: (ES, m/z): [M+1]$^{+}$ 474.9

Example 243

N-(5-chloro-6-(2H-1,2,3-triazol-2-yl)pyridin-3-yl)-1-(1-methoxyisoquinolin-5-yl)-5-(trifluoromethyl)-1H-pyrazole-4-carboxamide, Cpd 243

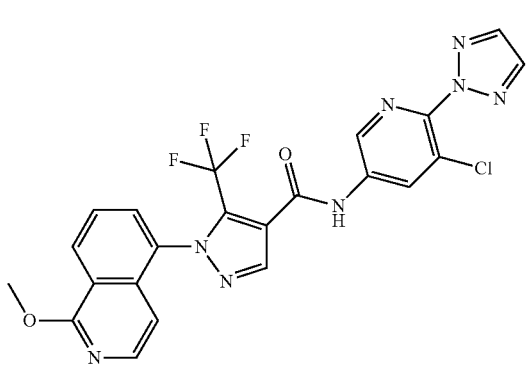 [SMILES: COc1nccc2c(-n3ncc(C(=O)Nc4cnc(-n5nccn5)c(Cl)c4)c3C(F)(F)F)cccc12]

$^{1}$H NMR (400 MHz, DMSO-d$_{6}$) δ ppm 4.10 (s, 3H), 6.56 (d, J=6.17 Hz, 1H), 7.78-7.85 (m, 1H), 8.06 (d, J=6.39 Hz, 1H), 8.10 (d, J=5.95 Hz, 1H), 8.18 (s, 2H), 8.45 (d, J=8.16 Hz, 1H), 8.56 (s, 1H), 8.66 (d, J=2.21 Hz, 1H), 8.83 (d, J=2.21 Hz, 1H), 11.25 (s, 1H). LC-MS: (ES, m/z): [M+1]$^{+}$ 514.9

Example 244

2-(2-chloro-4-(1-(quinolin-5-yl)-5-(trifluoromethyl)-1H-pyrazole-4-carboxamido)phenyl)-2H-1,2,3-triazole-4-carboxamide, Cpd 244

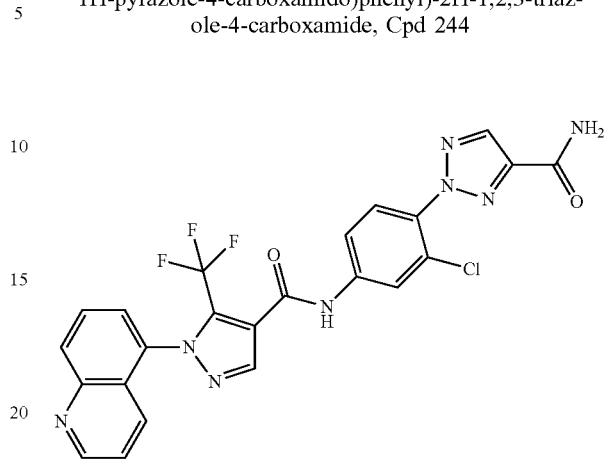

$^{1}$H NMR (400 MHz, DMSO-d$_{6}$) δ ppm 11.14 (s, 1H), 9.00-9.08 (m, 1H), 8.95 (s, 1H), 8.58 (s, 1H), 8.31 (d, J=8.38 Hz, 1H), 8.21 (d, J=1.98 Hz, 1H), 8.04 (s, 1H), 7.93-7.99 (m, 1H), 7.85-7.92 (m, 2H), 7.74 (d, J=8.60 Hz, 1H), 7.59-7.69 (m, 2H), 7.59-7.69 (m, 1H). LC-MS: (ES, m/z): [M+1]$^{+}$ 526.9

Example 245

N-(5-cyano-6-(2H-1,2,3-triazol-2-yl)pyridin-3-yl)-1-(2-methylbenzo[d]thiazol-4-yl)-5-(trifluoromethyl)-1H-pyrazole-4-carboxamide, Cpd 245

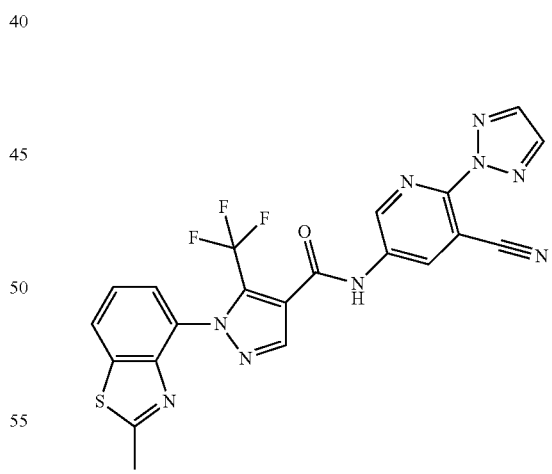

$^{1}$H NMR (400 MHz, DMSO-d$_{6}$) δ ppm 11.35 (s, 1H), 9.10 (d, J=2.2 Hz, 1H), 8.88 (d, J=2.2 Hz, 1H), 8.52 (s, 1H), 8.32 (br s, 1H), 8.30 (s, 2H), 7.70 (d, J=7.3 Hz, 1H), 7.63-7.51 (m, 1H), 2.77 (s, 3H). LC-MS: (ES, m/z): [M+1]$^{+}$ 496.0

Example 246

1-(3-chloro-5-(1-(quinolin-5-yl)-5-(trifluoromethyl)-1H-pyrazole-4-carboxamido)pyridin-2-yl)-1H-1,2,3-triazole-4-carboxamide, Cpd 246

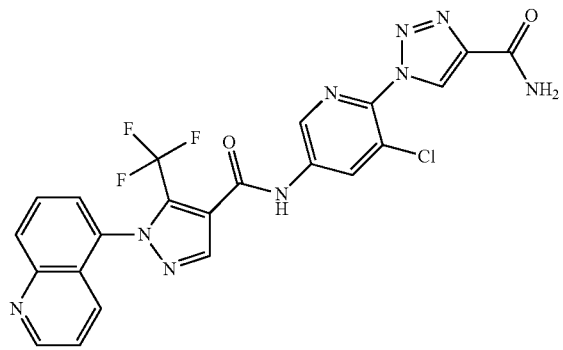 [SMILES: NC(=O)c1cn(-c2ncc(NC(=O)c3cnn(-c4cccc5ncccc45)c3C(F)(F)F)cc2Cl)nn1]

$^1$H NMR (400 MHz, METHANOL-$d_4$) δ ppm 7.65 (dd, J=8.49, 4.30 Hz, 1H), 7.76 (d, J=8.82 Hz, 1H), 7.84 (d, J=7.28 Hz, 1H), 7.95-8.01 (m, 1H), 8.34 (d, J=8.60 Hz, 1H), 8.41 (s, 1H), 8.77 (d, J=2.43 Hz, 1H), 8.84-8.87 (m, 1H), 9.01 (dd, J=4.19, 1.54 Hz, 1H). LC-MS: (ES, m/z): [M+1]$^+$ 527.9

Example 247

N-(5-cyano-6-(2H-1,2,3-triazol-2-yl)pyridin-3-yl)-1-(2-methylbenzo[d]thiazol-7-yl)-5-(trifluoromethyl)-1H-pyrazole-4-carboxamide, Cpd 247

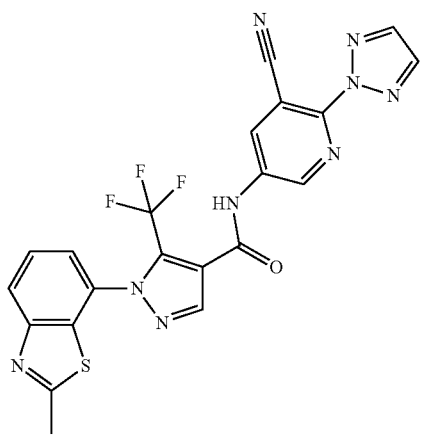 [SMILES: Cc1nc2cccc(-n3ncc(C(=O)Nc4cnc(-n5nccn5)c(C#N)c4)c3C(F)(F)F)c2s1]

NMR (400 MHz, DMSO-$d_6$) δ ppm 2.81 (s, 3H), 7.59-7.73 (m, 2H), 8.14 (d, J=7.72 Hz, 1H), 8.29 (s, 2H), 8.53 (s, 1H), 8.83 (d, J=2.43 Hz, 1H), 9.06 (br s, 1H), 11.37 (s, 1H). LC-MS: (ES, m/z): [M+1]$^+$ 495.9

Example 248

N-(6-(5-(aminomethyl)-1H-1,2,3-triazol-1-yl)-5-chloropyridin-3-yl)-1-(quinolin-5-yl)-5-(trifluoromethyl)-1H-pyrazole-4-carboxamide, Cpd 248

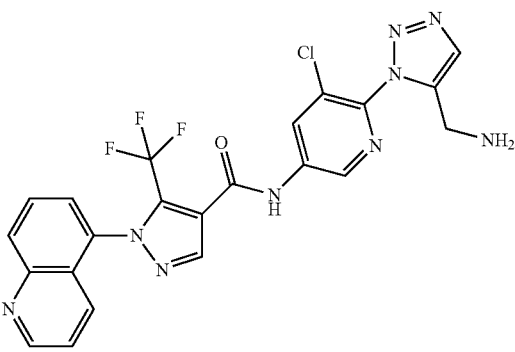 [SMILES: NCc1cnnn1-c1ncc(NC(=O)c2cnn(-c3cccc4ncccc34)c2C(F)(F)F)cc1Cl]

$^1$H NMR (400 MHz, METHANOL-$d_4$) δ ppm 4.05 (s, 2H), 4.60 (br s, 2H), 7.61-7.68 (m, 1H), 7.75 (d, J=7.72 Hz, 1H), 7.83 (d, J=7.28 Hz, 1H), 7.94-8.01 (m, 1H), 8.31-8.35 (m, 2H), 8.39 (s, 1H), 8.73 (d, J=2.43 Hz, 1H), 8.83 (d, J=2.21 Hz, 1H), 9.00 (d, J=4.41 Hz, 1H). LC-MS: (ES, m/z): [M+1]$^+$ 513.9

Example 249 methyl 1-(3-chloro-5-(1-(quinolin-5-yl)-5-(trifluoromethyl)-1H-pyrazole-4-carboxamido)pyridin-2-yl)-1H-1,2,3-triazole-4-carboxylate, Cpd 249

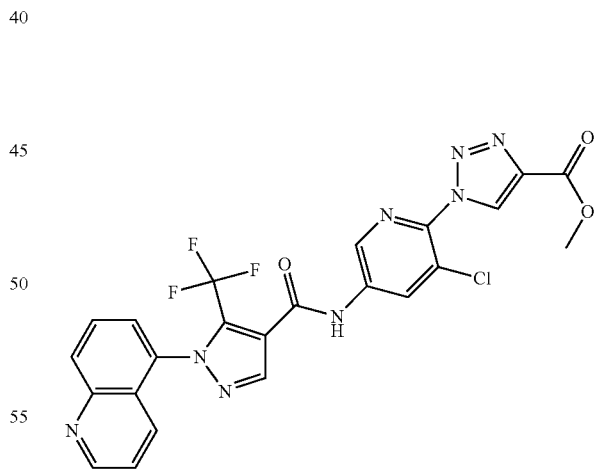

$^1$H NMR (400 MHz, CHLOROFORM-d) δ ppm 4.03 (s, 3H), 7.48-7.53 (m, 1H), 7.61-7.68 (m, 2H), 7.87 (t, J=7.94 Hz, 1H), 8.05 (s, 1H), 8.28 (s, 1H), 8.38 (d, J=9.26 Hz, 1H), 8.61 (s, 1H), 8.67 (s, 1H), 8.80 (s, 1H), 9.05 (d, J=3.97 Hz, 1H). LC-MS: (ES, m/z): [M+1]$^+$ 542.9

Example 250

N-(5-cyano-6-(2H-1,2,3-triazol-2-yl)pyridin-3-yl)-1-(imidazo[1,2-a]pyrimidin-5-yl)-5-(trifluoromethyl)-1H-pyrazole-4-carboxamide, Cpd 250

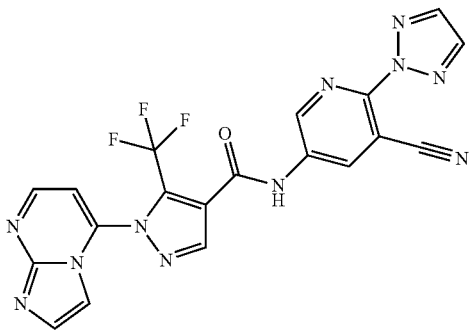 [SMILES: N#Cc1cc(NC(=O)c2cnn(-c3ccnc4nccn34)c2C(F)(F)F)cnc1-n1nccn1]

$^1$H NMR (400 MHz, METHANOL-d$_4$) δ ppm 9.28 (d, J=4.63 Hz, 1H), 9.02-9.21 (m, 1H), 8.89-8.93 (m, 1H), 8.65-8.71 (m, 1H), 8.32-8.39 (m, 1H), 8.11-8.25 (m, 3H), 7.96-8.03 (m, 1H). LC-MS: (ES, m/z): [M+1]$^+$ 465.9

Example 251

N-(5-methoxy-6-(2H-1,2,3-triazol-2-yl)pyridin-3-yl)-1-(quinolin-5-yl)-5-(trifluoromethyl)-1H-pyrazole-4-carboxamide, Cpd 251

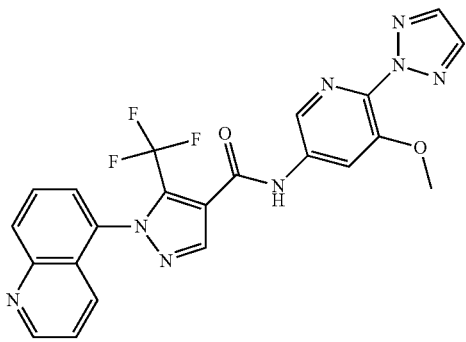 [SMILES: COc1cc(NC(=O)c2cnn(-c3cccc4ncccc34)c2C(F)(F)F)cnc1-n1nccn1]

$^1$H NMR (400 MHz, DMSO-d$_6$) δ ppm 11.25 (s, 1H), 9.05-9.12 (m, 1H), 8.63-8.68 (m, 1H), 8.50-8.57 (m, 1H), 8.31-8.38 (m, 1H), 8.21-8.30 (m, 1H), 8.03-8.10 (m, 1H), 7.92-8.02 (m, 2H), 7.65-7.75 (m, 1H), 3.80-3.87 (m, 1H). LC-MS: (ES, m/z): [M+1]$^+$ 481.0

Example 252

1-(benzo[d]thiazol-4-yl)-N-(5-chloro-2-methyl-6-(2H-1,2,3-triazol-2-yl)pyridin-3-yl)-5-(trifluoromethyl)-1H-pyrazole-4-carboxamide, Cpd 252

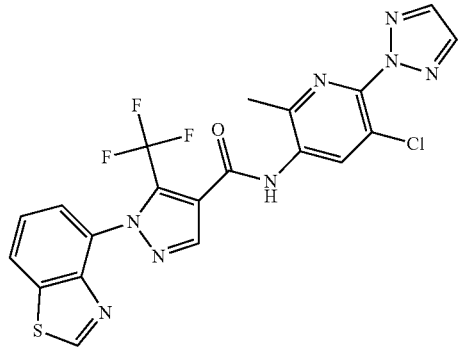 [SMILES: Cc1nc(-n2nccn2)c(Cl)cc1NC(=O)c1cnn(-c2cccc3scnc23)c1C(F)(F)F]

$^1$H NMR (400 MHz, DMSO-d$_6$) δ ppm 10.64 (1H, s), 9.49 (1H, s), 8.53 (1H, s), 8.48 (1H, dd, J=8.28, 1.00 Hz), 8.45 (1H, s), 8.20 (2H, s), 7.79-7.83 (1H, m), 7.69-7.75 (1H, m), 2.57 (3H, s). LC-MS: (ES, m/z): [M+1]$^+$ 504.9

Example 253

N-(5-chloro-6-(5-(methoxymethyl)-1H-1,2,3-triazol-1-yl)pyridin-3-yl)-1-(quinolin-5-yl)-5-(trifluoromethyl)-1H-pyrazole-4-carboxamide, Cpd 253

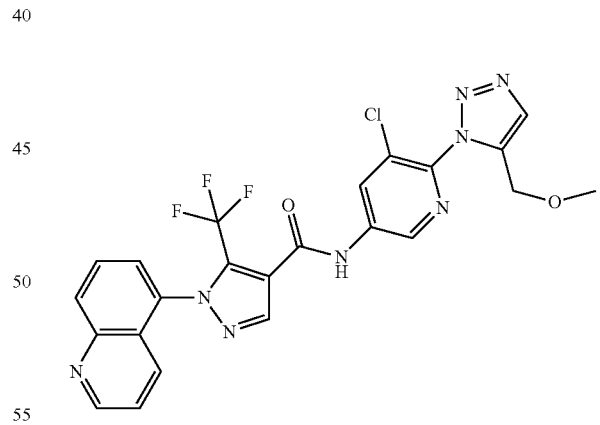

$^1$H NMR (400 MHz, METHANOL-d$_4$) δ ppm 3.44 (s, 3H), 4.66 (s, 2H), 7.64 (dd, J=8.60, 4.19 Hz, 1H), 7.75 (d, J=8.38 Hz, 1H), 7.83 (d, J=7.28 Hz, 1H), 7.97 (dd, J=8.60, 7.28 Hz, 1H), 8.33 (d, J=8.60 Hz, 1H), 8.40 (s, 1H), 8.44 (s, 1H), 8.74 (d, J=2.43 Hz, 1H), 8.83 (d, J=2.21 Hz, 1H), 9.00 (dd, J=4.30, 1.65 Hz, 1H). LC-MS: (ES, m/z): [M+1]$^+$ 529.0

Example 254

N-(5-cyano-6-(2H-1,2,3-triazol-2-yl)pyridin-3-yl)-1-(2-methyl-[1,2,4]triazolo[1,5-a]pyridin-5-yl)-5-(trifluoromethyl)-1H-pyrazole-4-carboxamide, Cpd 254

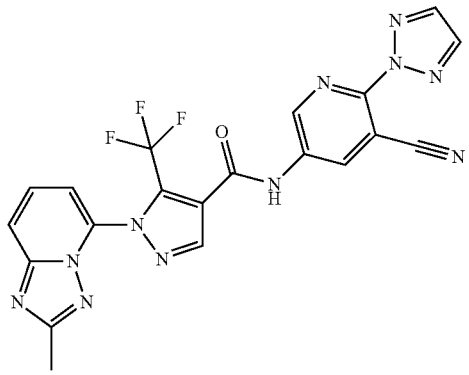 [SMILES: Cc1nc2cccc(-n3ncc(C(=O)Nc4cnc(-n5nccn5)c(C#N)c4)c3C(F)(F)F)n2n1]

$^1$H NMR (400 MHz, DMSO-d$_6$) δ ppm 11.39 (s, 1H), 9.08 (d, J=2.4 Hz, 1H), 8.86 (d, J=2.4 Hz, 1H), 8.67 (s, 1H), 8.30 (s, 2H), 8.04 (d, J=9.0 Hz, 1H), 7.86 (dd, J=7.4, 8.9 Hz, 1H), 7.72 (d, J=6.4 Hz, 1H), 3.34 (s, 131H), 2.44 (s, 3H). LC-MS: (ES, m/z): [M+1]$^+$ 480.0

Example 255

3-(3-cyano-5-(1-(quinolin-5-yl)-5-(trifluoromethyl)-1H-pyrazole-4-carboxamido)pyridin-2-yl)-1-methyl-1H-pyrazole-5-carboxylic acid, Cpd 255

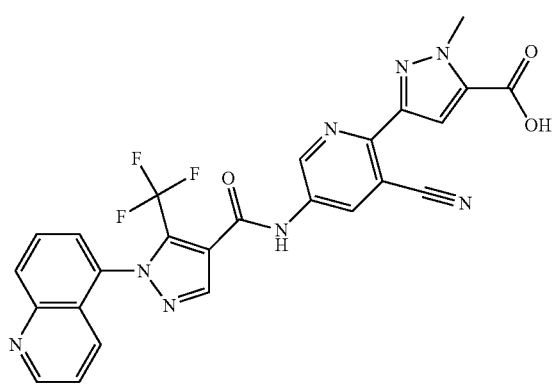 [SMILES: Cn1nc(-c2ncc(NC(=O)c3cnn(-c4cccc5ncccc45)c3C(F)(F)F)cc2C#N)cc1C(=O)O]

$^1$H NMR (400 MHz, METHANOL-d$_4$) δ ppm 9.08 (1H, d, J=2.20 Hz), 9.00 (1H, br d, J=3.75 Hz), 8.71 (1H, d, J=1.98 Hz), 8.38 (1H, s), 8.33 (1H, d, J=8.38 Hz), 7.96 (1H, t, J=8.05 Hz), 7.83 (1H, d, J=7.72 Hz), 7.71-7.78 (1H, m), 7.64 (1H, dd, J=8.38, 4.19 Hz), 7.51 (1H, s) 4.27 (3H, s). LC-MS: (ES, m/z): [M+1]$^+$ 533.0

Example 256 methyl 2-(2-chloro-4-(1-(quinolin-5-yl)-5-(trifluoromethyl)-1H-pyrazole-4-carboxamido)phenyl)-2H-1,2,3-triazole-4-carboxylate, Cpd 256

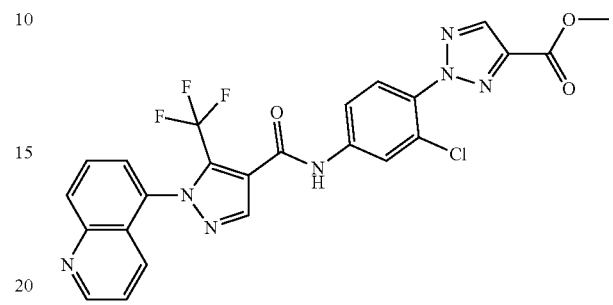

$^1$H NMR (400 MHz, DMSO-d$_6$) δ ppm 11.11 (s, 1H), 9.27 (s, 1H), 9.04 (dd, J=4.08, 1.65 Hz, 1H), 8.57 (s, 1H), 8.31 (d, J=8.60 Hz, 1H), 8.21 (d, J=2.21 Hz, 1H), 7.93-7.98 (m, 1H), 7.84-7.92 (m, 2H), 7.76 (d, J=8.60 Hz, 1H), 7.64-7.68 (m, 1H), 7.58-7.63 (m, 1H), 3.86 (s, 3H). LC-MS: (ES, m/z): [M+1]$^+$ 541.9

Example 257

N-(5-cyano-6-(2-methyl-2H-1,2,3-triazol-4-yl)pyridin-3-yl)-1-(quinolin-5-yl)-5-(trifluoromethyl)-1H-pyrazole-4-carboxamide, Cpd 257

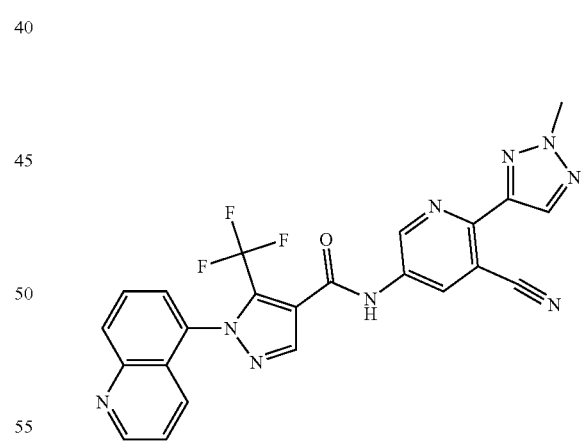

$^1$H NMR (400 MHz, DMSO-d$_6$) δ ppm 11.29-11.48 (1H, m), 9.20 (1H, d, J=2.51 Hz), 9.01-9.09 (1H, in), 8.78 (1H, d, J=2.26 Hz), 8.65 (1H, s), 8.27-8.37 (2H, m), 7.96-8.03 (1H, m), 7.89-7.95 (1H, m), 7.66-7.73 (1H, m), 7.59-7.65 (1H, m), 4.29 (3H, s). LC-MS: (ES, m/z): [M+1]$^+$ 489.9

Example 258 methyl 3-chloro-5-(1-(quinolin-5-yl)-5-(trifluoromethyl)-1H-pyrazole-4-carboxamido)picolinate, Cpd 258

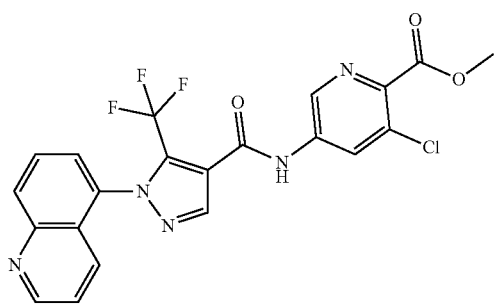 [SMILES: COC(=O)c1ncc(NC(=O)c2cnn(-c3cccc4ncccc34)c2C(F)(F)F)cc1Cl]

$^1$H NMR (400 MHz, DMSO-d$_6$) δ ppm 3.88 (s, 3H), 7.57-7.60 (m, 1H), 7.63-7.67 (m, 1H), 7.89-7.98 (m, 2H), 8.31 (d, J=8.60 Hz, 1H), 8.50 (d, J=1.98 Hz, 1H), 8.55 (s, 1H), 8.85 (d, J=2.21 Hz, 1H), 9.04 (dd, J=4.19, 1.76 Hz, 1H), 11.19 (s, 1H). LC-MS: (ES, m/z): [M+1]$^+$ 475.9

Example 259

N-(5-cyano-6-(2H-1,2,3-triazol-2-yl)pyridin-3-yl)-1-(1-methyl-1H-pyrazolo[3,4-c]pyridin-7-yl)-5-(trifluoromethyl)-1H-pyrazole-4-carboxamide, Cpd 259

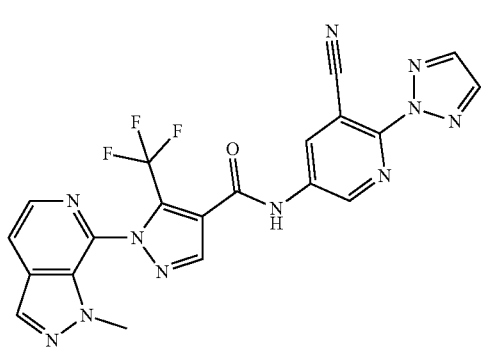 [SMILES: Cn1ncc2ccnc(-n3ncc(C(=O)Nc4cnc(-n5nccn5)c(C#N)c4)c3C(F)(F)F)c21]

$^1$H NMR (400 MHz, DMSO-d$_6$) δ ppm 3.68 (s, 3H), 8.11 (d, J=5.51 Hz, 1H), 8.24-8.32 (m, 3H) 8.46 (s, 1H), 8.64 (s, 1H), 8.86 (d, J=2.65 Hz, 1H), 9.08 (d, J=2.65 Hz, 1H), 11.39 (s, 1H). LC-MS: (ES, m/z): [M+1]$^+$ 479.9

Example 260

N-(5-cyano-6-(2H-1,2,3-triazol-2-yl)pyridin-3-yl)-1-(1-methyl-1H-indazol-7-yl)-5-(trifluoromethyl)-1H-pyrazole-4-carboxamide, Cpd 260

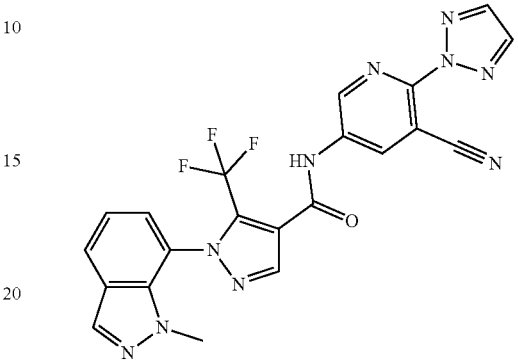

$^1$H NMR (400 MHz, DMSO-d$_6$) δ ppm 11.41 (br s, 1H), 9.08 (d, J=2.4 Hz, 1H), 8.87 (d, J=2.4 Hz, 1H), 8.57 (s, 1H), 8.36-8.20 (m, 3H), 8.06 (d, J=8.2 Hz, 1H), 7.62 (d, J=7.3 Hz, 1H), 7.30 (t, J=7.8 Hz, 1H), 3.43 (s, 3H). LC-MS: (ES, m/z): [M+1]$^+$ 479.0

Example 261

N-(5-chloro-6-(2H-1,2,3-triazol-2-yl)pyridin-3-yl)-1-(5-fluoroquinolin-8-yl)-5-(trifluoromethyl)-1H-pyrazole-4-carboxamide, Cpd 261

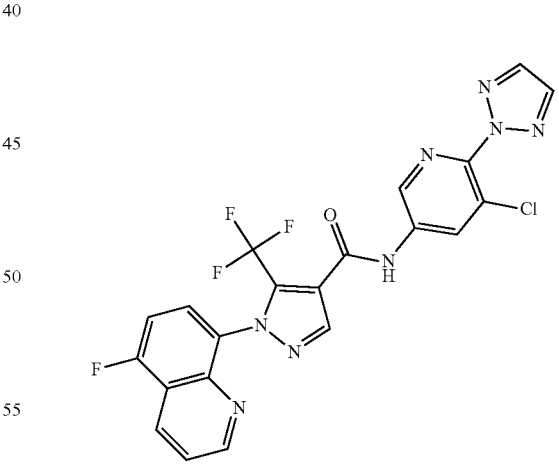

$^1$H NMR (400 MHz, METHANOL-d$_4$) δ ppm 8.92 (dd, J=4.30, 1.65 Hz, 1H), 8.80 (d, J=2.21 Hz, 1H), 8.71 (d, J=2.20 Hz, 1H), 8.64 (dd, J=8.60, 1.54 Hz, 1H), 8.36 (s, 1H) 8.02 (s, 2H), 7.98 (dd, J=8.38, 5.29 Hz, 1H), 7.67-7.74 (m, 1H), 7.47-7.57 (m, 1H). LC-MS: (ES, m/z): [M+1]$^+$ 502.9

Example 262

N-(5-cyano-6-(2H-1,2,3-triazol-2-yl)pyridin-3-yl)-1-(1H-pyrazolo[4,3-b]pyridin-7-yl)-5-(trifluoromethyl)-1H-pyrazole-4-carboxamide, Cpd 262

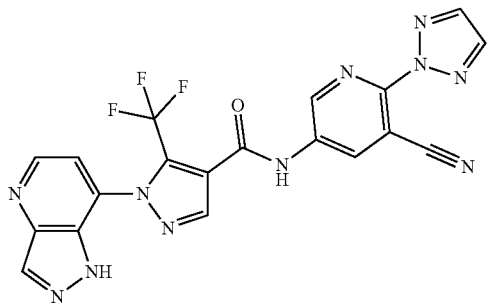 [SMILES: N#Cc1cc(NC(=O)c2cnn(-c3ccnc4cn[nH]c34)c2C(F)(F)F)cnc1-n1nccn1]

$^1$H NMR (400 MHz, DMSO-d$_6$) δ ppm 11.40 (1H, s), 9.12 (1H, d, J=2.65 Hz), 8.88 (1H, d, J=2.43 Hz), 8.69-8.77 (1H, m), 8.66 (1H, s), 8.56 (1H, s), 8.30 (2H, s), 7.62 (1H, d, J=4.63 Hz). LC-MS: (ES, m/z): [M+1]$^+$ 466.0

Example 263

N-(5-cyano-6-(2H-1,2,3-triazol-2-yl)pyridin-3-yl)-1-(4-fluoroisoquinolin-1-yl)-5-(trifluoromethyl)-1H-pyrazole-4-carboxamide, Cpd 263

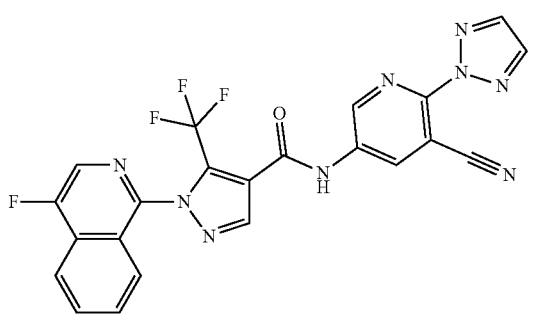 [SMILES: N#Cc1cc(NC(=O)c2cnn(-c3ncc(F)c4ccccc34)c2C(F)(F)F)cnc1-n1nccn1]

$^1$H NMR (400 MHz, DMSO-d$_6$) δ ppm 7.68 (br d, J=8.16 Hz, 1H), 7.93 (t, J=7.50 Hz, 1H), 8.09 (t, J=7.39 Hz, 1H), 8.26-8.34 (m, 3H), 8.64 (s, 2H), 8.88 (d, J=2.65 Hz, 1H), 9.09 (d, J=2.43 Hz, 1H). LC-MS: (ES, m/z): [M+1]$^+$ 493.9

Example 264

N-(5-chloro-6-(2H-1,2,3-triazol-2-yl)pyridin-3-yl)-1-(1-fluoroisoquinolin-4-yl)-5-(trifluoromethyl)-1H-pyrazole-4-carboxamide, Cpd 264

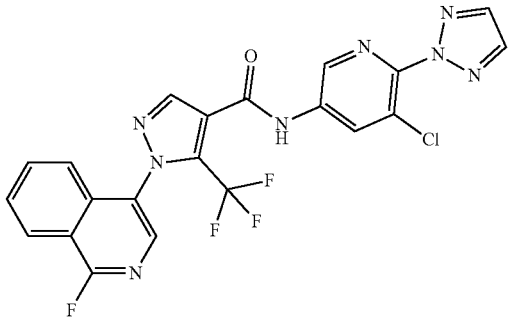 [SMILES: O=C(Nc1cnc(-n2nccn2)c(Cl)c1)c1cnn(-c2cnc(F)c3ccccc23)c1C(F)(F)F]

$^1$H NMR (400 MHz, DMSO-d$_6$) δ ppm 11.33 (br s, 1H), 8.85 (d, J=2.43 Hz, 1H), 8.60-8.70 (m, 2H), 8.50 (s, 1H), 8.34 (d, J=8.16 Hz, 1H), 8.16 (s, 2H), 8.04 (td, J=7.72, 1.10 Hz, 1H), 7.89-7.98 (m, 1H), 7.30 (d, J=8.38 Hz, 1H). LC-MS: (ES, m/z): [M+1]$^+$ 568.9

Example 265

N-(5-cyano-6-(2H-1,2,3-triazol-2-yl)pyridin-3-yl)-1-(1-methyl-1H-pyrazolo[3,4-b]pyridin-3-yl)-5-(trifluoromethyl)-1H-pyrazole-4-carboxamide, Cpd 265

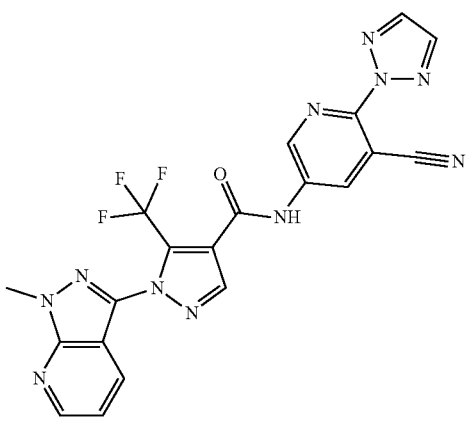 [SMILES: Cn1nc(-n2ncc(C(=O)Nc3cnc(-n4nccn4)c(C#N)c3)c2C(F)(F)F)c2cccnc21]

$^1$H NMR (400 MHz, DMSO-d$_6$) δ ppm 4.16 (s, 3H), 7.43 (dd, J=8.16, 4.41 Hz, 1H), 8.24 (dd, J=8.16, 1.32 Hz, 1H), 8.30 (s, 2H), 8.59 (s, 1H), 8.75 (dd, J=4.30, 1.21 Hz, 1H), 8.85 (d, J=2.43 Hz, 1H), 9.08 (d, J=2.43 Hz, 1H), 11.47 (s, 1H). LC-MS: (ES, m/z): [M+1]$^+$ 480.0

Example 266

N-(5-cyano-6-(2H-1,2,3-triazol-2-yl)pyridin-3-yl)-1-(1-methyl-1H-indazol-3-yl)-5-(trifluoromethyl)-1H-pyrazole-4-carboxamide, Cpd 266

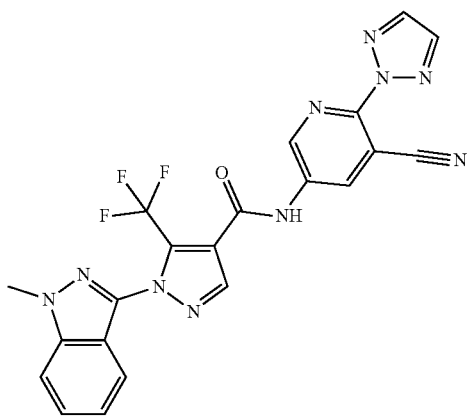 [SMILES: Cn1nc(-n2ncc(C(=O)Nc3cnc(-n4nccn4)c(C#N)c3)c2C(F)(F)F)c2ccccc21]

$^1$H NMR (400 MHz, DMSO-d$_6$) δ ppm 4.14 (s, 3H), 7.29-7.34 (m, 1H), 7.54-7.59 (m, 1H), 7.63 (d, J=8.16 Hz, 1H), 7.82 (d, J=8.60 Hz, 1H), 8.30 (s, 2H), 8.55 (s, 1H), 8.85 (d, J=2.65 Hz, 1H), 9.08 (d, J=2.65 Hz, 1H), 11.41 (s, 1H). LC-MS: (ES, m/z): [M+1]$^+$ 479.0

Example 267 methyl 3-(3-cyano-5-(1-(quinolin-5-yl)-5-(trifluoromethyl)-1H-pyrazole-4-carboxamido)pyridin-2-yl)-1-methyl-1H-pyrazole-5-carboxylate, Cpd 267

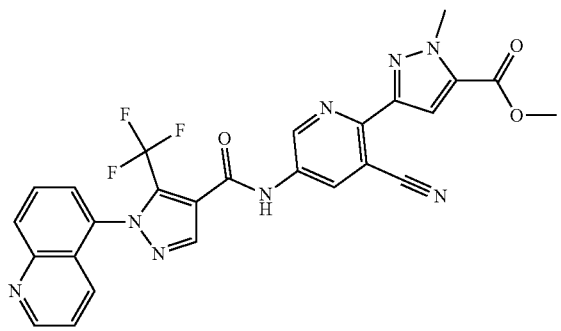 [SMILES: COC(=O)c1cc(-c2ncc(NC(=O)c3cnn(-c4cccc5ncccc45)c3C(F)(F)F)cc2C#N)nn1C]

$^1$H NMR (400 MHz, METHANOL-d$_4$) δ ppm 9.30 (1H, dd, J=5.18, 1.43 Hz), 9.10 (1H, d, J=2.43 Hz), 8.72 (1H, d, J=2.65 Hz), 8.48 (1H, d, J=8.82 Hz), 8.45 (1H, s), 8.43 (1H, d, J=8.60 Hz), 8.27 (1H, t, J=8.05 Hz), 8.13 (1H, d, J=7.06 Hz), 8.06 (1H, dd, J=8.60, 5.07 Hz), 7.53 (1H, s), 4.28 (3H, s), 3.94 (3H, s). LC-MS: (ES, m/z): [M+1]$^+$ 546.9

Example 268

N-(5-cyano-6-(1-methyl-1H-pyrazol-3-yl)pyridin-3-yl)-1-(8-fluoroquinolin-5-yl)-5-(trifluoromethyl)-1H-pyrazole-4-carboxamide, Cpd 268

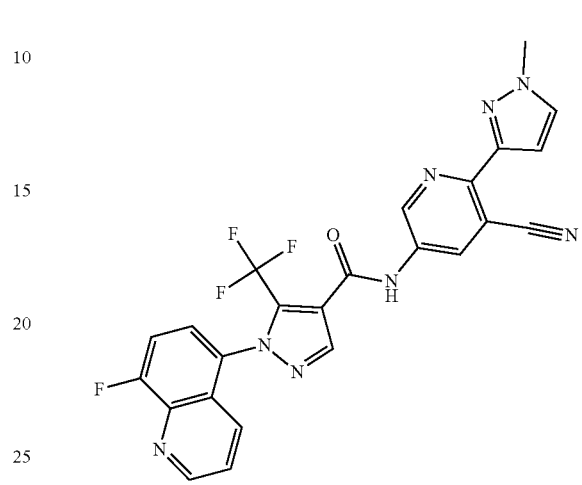

$^1$H NMR (400 MHz, DMSO-d$_6$) δ ppm 11.37 (br s, 1H), 9.13 (br d, J=13.6 Hz, 2H), 8.67 (br d, J=18.3 Hz, 2H), 8.08-7.55 (m, 5H), 6.86 (br s, 1H), 3.96 (br s, 3H). LC-MS: (ES, m/z): [M+1]$^+$ 507.0

Example 269

N-(5-cyano-6-(2H-1,2,3-triazol-2-yl)pyridin-3-yl)-1-(1,5-naphthyridin-4-yl)-5-(trifluoromethyl)-1H-pyrazole-4-carboxamide, Cpd 269

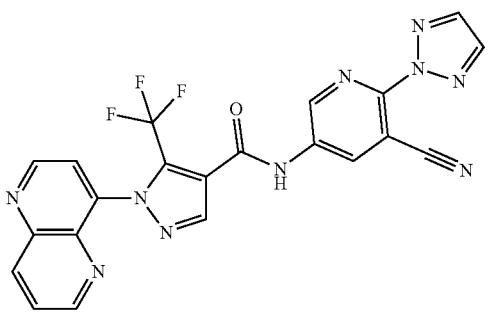 [SMILES: N#Cc1cc(NC(=O)c2cnn(-c3ccnc4cccnc34)c2C(F)(F)F)cnc1-n1nccn1]

$^1$H NMR (400 MHz, CHLOROFORM-d) δ ppm 7.81 (dd, J=8.71, 4.08 Hz, 1H), 7.85 (d, J=4.63 Hz, 1H), 8.04 (s, 2H), 8.29 (s, 2H), 8.59 (d, J=8.82 Hz, 1H), 8.84 (d, J=2.43 Hz, 1H), 8.98 (d, J=2.65 Hz, 1H), 9.00 (d, J=2.87 Hz, 1H), 9.23 (d, J=4.19 Hz, 1H). LC-MS: (ES, m/z): [M+1]$^+$ 476.9

Example 270

N-(5-chloro-6-(5-((dimethylamino)methyl)-1H-1,2,3-triazol-1-yl)pyridin-3-yl)-1-(quinolin-5-yl)-5-(trifluoromethyl)-1H-pyrazole-4-carboxamide, Cpd 270

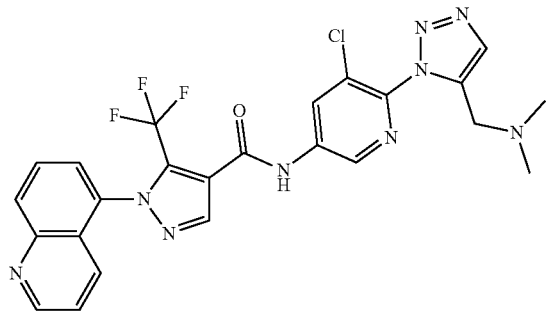 [SMILES: CN(C)Cc1cnnn1-c1ncc(NC(=O)c2cnn(-c3cccc4ncccc34)c2C(F)(F)F)cc1Cl]

$^1$H NMR (400 MHz, METHANOL-d$_4$) δ ppm 2.97 (s, 6H) 4.61 (s, 2H), 8.08 (dd, J=8.71, 5.18 Hz, 1H), 8.13 (d, J=7.50 Hz, 1H), 8.27 (t, J=8.05 Hz, 1H), 8.45-8.53 (m, 3H), 8.74 (s, 1H), 8.77 (d, J=2.21 Hz, 1H), 8.91 (d, J=2.21 Hz, 1H), 9.28-9.32 (m, 1H). LC-MS: (ES, m/z): [M+1]$^+$ 541.9

Example 271

N-(5-cyano-6-(2H-1,2,3-triazol-2-yl)pyridin-3-yl)-1-(2-methylbenzo[d]oxazol-7-yl)-5-(trifluoromethyl)-1H-pyrazole-4-carboxamide, Cpd 271

$^1$H NMR (400 MHz, DMSO-d$_6$) δ ppm 2.64 (s, 3H), 7.52-7.59 (m, 1H), 7.61-7.67 (m, 1H), 7.95 (d, J=7.72 Hz, 1H), 8.32 (s, 2H), 8.57 (s, 1H), 8.88 (d, J=2.43 Hz, 1H), 9.09 (d, J=2.21 Hz, 1H), 11.41 (br s, 1H). LC-MS: (ES, m/z): [M+1]$^+$ 479.9

Example 272

N-(6-(4-(aminomethyl)-2H-1,2,3-triazol-2-yl)-5-chloropyridin-3-yl)-1-(quinolin-5-yl)-5-(trifluoromethyl)-1H-pyrazole-4-carboxamide, Cpd 272

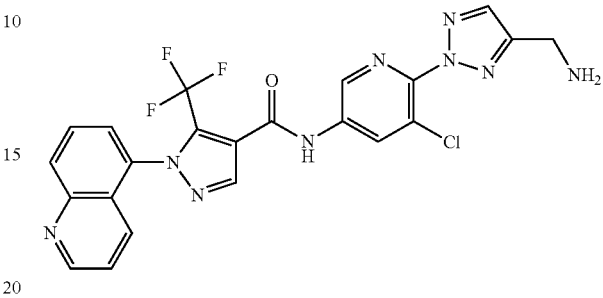

$^1$H NMR (400 MHz, DMSO-d$_6$) δ ppm 4.09 (s, 2H), 7.58-7.61 (m, 1H), 7.63-7.67 (m, 1H), 7.88-7.98 (m, 2H), 8.14 (s, 1H), 8.30 (d, J=8.38 Hz, 1H), 8.66 (s, 1H), 8.70 (d, J=1.98 Hz, 1H), 8.91 (d, J=2.20 Hz, 1H), 9.01-9.06 (m, 1H). LC-MS: (ES, m/z): [M+1]$^+$ 514.0

Example 273

N-(5-chloro-6-(1-methyl-1H-pyrazol-3-yl)pyridin-3-yl)-1-(8-fluoroquinolin-5-yl)-5-(trifluoromethyl)-1H-pyrazole-4-carboxamide, Cpd 273

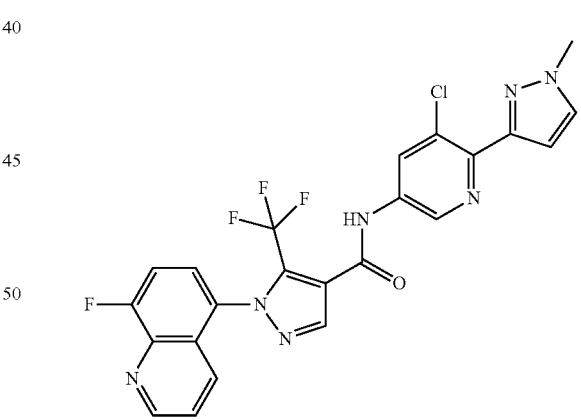

$^1$H NMR (400 MHz, DMSO-d$_6$) δ ppm 3.92 (s, 3H), 6.77 (d, J=2.21 Hz, 1H), 7.65 (d, J=8.60 Hz, 1H), 7.73-7.86 (m, 3H), 7.96 (dd, J=8.38, 4.41 Hz, 1H), 8.49 (d, J=1.98 Hz, 1H), 8.64 (s, 1H), 8.92 (d, J=2.20 Hz, 1H), 9.09 (dd, J=4.19, 1.54 Hz, 1H), 11.25 (s, 1H). LC-MS: (ES, m/z): [M+1]$^+$ 516.2

Example 274

1-([1,2,4]triazolo[1,5-a]pyridin-5-yl)-N-(5-cyano-6-(2H-1,2,3-triazol-2-yl)pyridin-3-yl)-5-(trifluoromethyl)-1H-pyrazole-4-carboxamide, Cpd 274

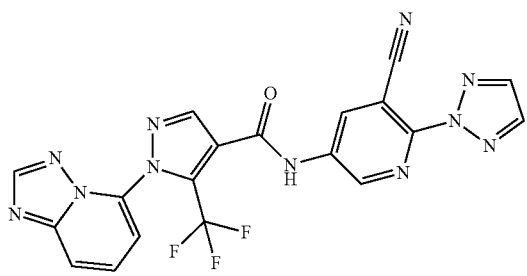 [SMILES: N#Cc1cc(NC(=O)c2cnn(-c3cccc4ncnn34)c2C(F)(F)F)cnc1-n1nccn1]

$^1$H NMR (400 MHz, DMSO-d$_6$) δ ppm 7.85 (d, J=6.62 Hz, 1H), 7.94 (dd, J=8.93, 7.39 Hz, 1H), 8.20 (dd, J=8.93, 0.99 Hz, 1H), 8.31 (s, 2H), 8.61 (s, 1H), 8.69 (s, 1H), 8.86 (d, J=2.43 Hz, 1H), 9.07 (d, J=2.43 Hz, 1H), 11.38 (s, 1H). LC-MS: (ES, m/z): [M+1]$^+$ 465.9

Example 275

N-(5-cyano-6-(2H-1,2,3-triazol-2-yl)pyridin-3-yl)-1-(imidazo[1,2-a]pyrazin-5-yl)-3-(trifluoromethyl)-1H-pyrazole-4-carboxamide, Cpd 275

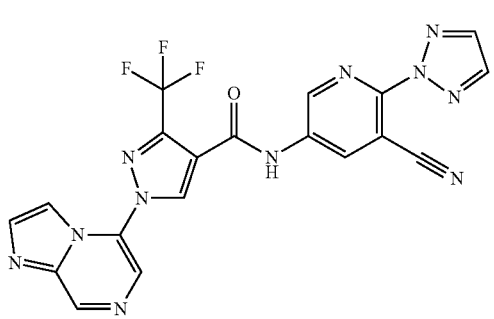 [SMILES: N#Cc1cc(NC(=O)c2cn(-c3cncc4nccn34)nc2C(F)(F)F)cnc1-n1nccn1]

$^1$H NMR (400 MHz, METHANOL-d$_4$) δ ppm 9.40 (s, 1H), 9.07 (br s, 1H), 8.91 (d, J=2.43 Hz, 1H), 8.59 (s, 1H), 8.47 (s, 1H), 8.15 (br s, 3H), 7.90 (s, 1H). LC-MS: (ES, m/z): [M+1]$^+$ 466.0

Example 276

N-(5-cyano-6-(2H-1,2,3-triazol-2-yl)pyridin-3-yl)-1-(1,7-naphthyridin-4-yl)-5-(trifluoromethyl)-1H-pyrazole-4-carboxamide, Cpd 276

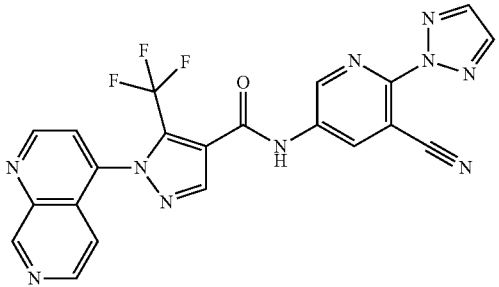 [SMILES: N#Cc1cc(NC(=O)c2cnn(-c3ccnc4cnccc34)c2C(F)(F)F)cnc1-n1nccn1]

$^1$H NMR (400 MHz, DMSO-d$_6$) δ ppm 7.38 (d, J=5.73 Hz, 1H), 8.21 (d, J=4.41 Hz, 1H), 8.31 (s, 2H), 8.74 (s, 1H), 8.78 (br d, J=5.73 Hz, 1H), 8.91 (d, J=2.43 Hz, 1H), 9.14 (d, J=2.43 Hz, 1H), 9.36 (d, J=4.41 Hz, 1H), 9.66 (s, 1H), 11.48 (s, 1H). LC-MS: (ES, m/z): [M+1]$^+$ 476.9

Example 277

N-(5-chloro-6-(2H-1,2,3-triazol-2-yl)pyridin-3-yl)-1-(2-fluoroquinolin-5-yl)-5-(trifluoromethyl)-1H-pyrazole-4-carboxamide, Cpd 277

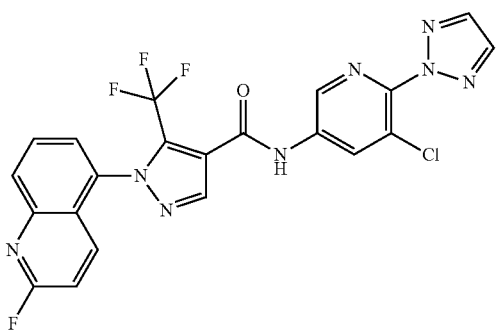 [SMILES: O=C(Nc1cnc(-n2nccn2)c(Cl)c1)c1cnn(-c2cccc3nc(F)ccc23)c1C(F)(F)F]

$^1$H NMR (400 MHz, CHLOROFORM-d) δ ppm 7.18 (dd, J=9.03, 2.76 Hz, 1H), 7.63 (d, J=7.53 Hz, 1H), 7.73 (t, J=8.28 Hz, 1H), 7.87 (t, J=8.03 Hz, 1H), 7.96 (s, 2H), 8.16 (s, 1H), 8.19 (s, 1H), 8.24 (s, 1H), 8.54 (d, J=2.26 Hz, 1H), 8.78 (d, J=2.26 Hz, 1H). LC-MS: (ES, m/z): [M+1]$^+$ 502.9

Example 278

1-(2-aminobenzo[d]thiazol-7-yl)-N-(5-chloro-6-(2H-1,2,3-triazol-2-yl)pyridin-3-yl)-5-(trifluoromethyl)-1H-pyrazole-4-carboxamide, Cpd 278

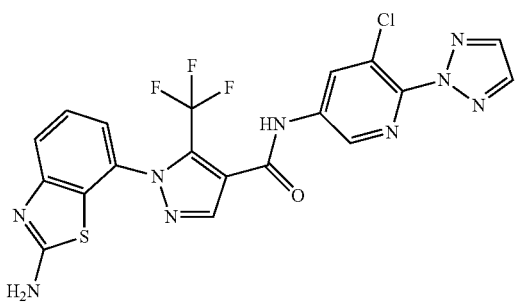 [SMILES: Nc1nc2cccc(-n3ncc(C(=O)Nc4cnc(-n5nccn5)c(Cl)c4)c3C(F)(F)F)c2s1]

$^1$H NMR (400 MHz, DMSO-d$_6$) δ ppm 7.18 (d, J=7.72 Hz, 1H), 7.42 (t, J=7.94 Hz, 1H), 7.54 (d, J=7.50 Hz, 1H), 7.68 (s, 2H), 8.16 (s, 2H), 8.48 (s, 1H), 8.63 (d, J=2.43 Hz, 1H), 8.84 (d, J=2.20 Hz, 1H). LC-MS: (ES, m/z): [M+1]$^+$ 505.9

Example 279

N-(5-chloro-6-(2H-1,2,3-triazol-2-yl)pyridin-3-yl)-1-(isothiazolo[5,4-b]pyridin-3-yl)-5-(trifluoromethyl)-1H-pyrazole-4-carboxamide, Cpd 279

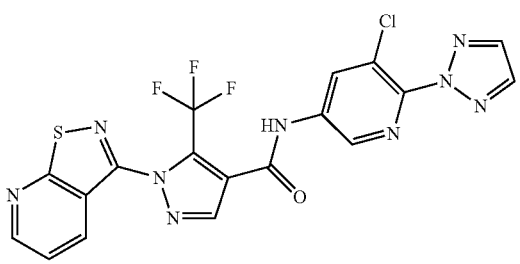 [SMILES: O=C(Nc1cnc(-n2nccn2)c(Cl)c1)c1cnn(-c2nsc3ncccc23)c1C(F)(F)F]

$^1$H NMR (400 MHz, DMSO-d$_6$) δ ppm 7.79 (dd, J=8.16, 4.39 Hz, 1H), 8.20 (s, 2H), 8.61-8.74 (m, 3H), 8.87 (s, 1H), 9.05 (br d, J=3.26 Hz, 1H), 11.52 (s, 1H). LC-MS: (ES, m/z): [M+1]$^+$ 491.8

Example 280

N-(5-cyano-6-(1H-pyrrol-1-yl)pyridin-3-yl)-1-(quinolin-5-yl)-5-(trifluoromethyl)-1H-pyrazole-4-carboxamide, Cpd 280

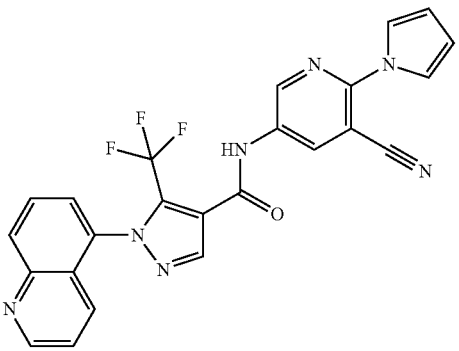 [SMILES: N#Cc1cc(NC(=O)c2cnn(-c3cccc4ncccc34)c2C(F)(F)F)cnc1-n1cccc1]

$^1$H NMR (400 MHz, DMSO-d$_6$) δ ppm 11.37 (1H, s), 9.08 (1H, br s), 9.03 (1H, br s), 8.78 (1H, br s), 8.64 (1H, s), 8.34 (1H, br d, J=7.94 Hz), 7.96-8.02 (1H, m), 7.90-7.96 (1H, m), 7.69 (2H, br s), 7.55 (2H, br s), 6.37 (2H, br s). LC-MS: (ES, m/z): [M+1]$^+$ 474.0

Example 281

N-(5-cyano-6-(2H-1,2,3-triazol-2-yl)pyridin-3-yl)-1-(1-methoxyisoquinolin-5-yl)-5-(trifluoromethyl)-1H-pyrazole-4-carboxamide, Cpd 281

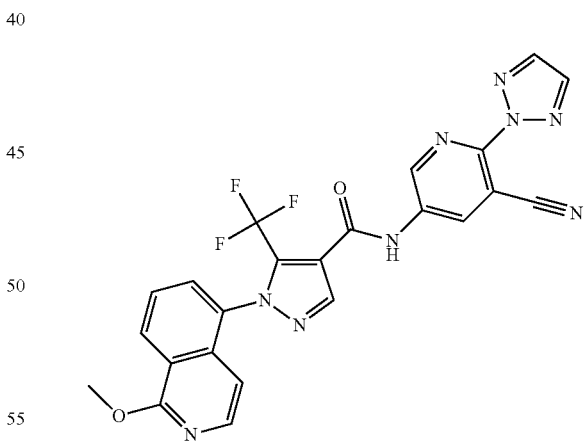

$^1$H NMR (400 MHz, DMSO-d$_6$) δ ppm 4.12 (s, 3H), 6.58 (d, J=6.17 Hz, 1H), 7.83 (t, J=7.94 Hz, 1H), 8.06-8.14 (m, 2H), 8.32 (s, 2H), 8.47 (d, J=8.38 Hz, 1H), 8.59 (s, 1H), 8.89 (d, J=2.43 Hz, 1H), 9.09 (d, J=2.65 Hz, 1H), 11.34 (br s, 1H). LC-MS: (ES, m/z): [M+1]$^+$ 505.9

Example 282

1-(2-aminobenzo[d]thiazol-7-yl)-N-(5-cyano-6-(2H-1,2,3-triazol-2-yl)pyridin-3-yl)-5-(trifluoromethyl)-1H-pyrazole-4-carboxamide, Cpd 282

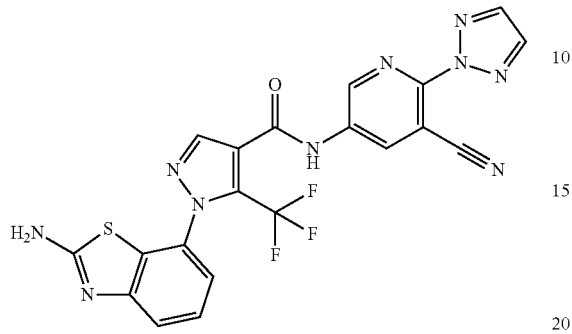

$^1$H NMR (400 MHz, DMSO-$d_6$) δ ppm 7.25 (d, J=7.72 Hz, 1H), 7.45 (t, J=7.94 Hz, 1H), 7.52-7.57 (m, 1H), 8.30 (s, 2H), 8.55 (s, 1H), 8.86 (d, J=2.21 Hz, 1H), 9.09 (d, J=2.43 Hz, 1H), 11.49 (s, 1H). LC-MS: (ES, m/z): [M+1]$^+$ 497.2

Example 283

N-(6-(1H-1,2,3-triazol-1-yl)-5-(trifluoromethyl)pyridin-3-yl)-1-(quinolin-5-yl)-5-(trifluoromethyl)-1H-pyrazole-4-carboxamide, Cpd 283

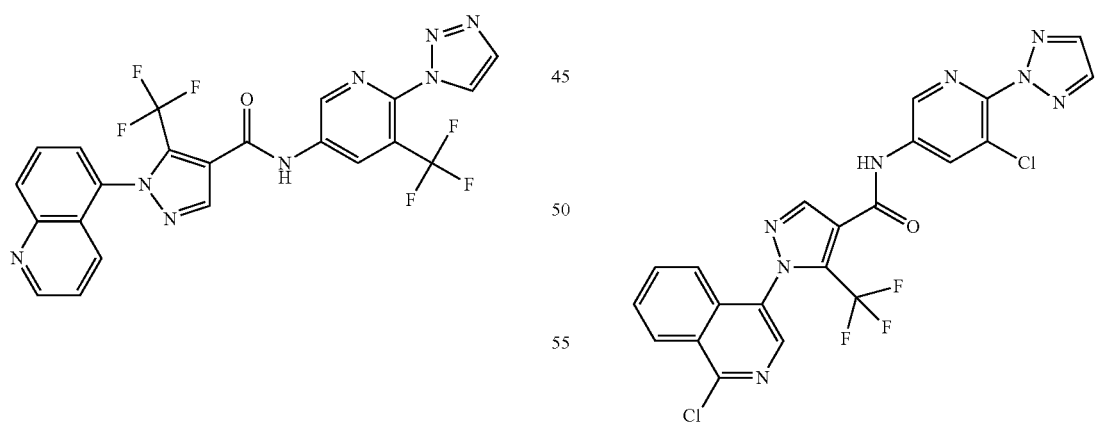

$^1$H NMR (400 MHz, DMSO-$d_6$) δ ppm 7.69-7.75 (m, 2H), 7.95-8.04 (m, 3H), 8.36 (d, J=8.16 Hz, 1H), 8.69 (d, J=3.31 Hz, 2H), 8.95 (d, J=1.98 Hz, 1H), 9.10 (dd, J=3.53, 1.98 Hz, 1H), 9.25 (d, J=2.21 Hz, 1H), 11.59 (s, 1H). LC-MS: (ES, m/z): [M+1]$^+$ 518.9

Example 284

1-(benzo[d]isoxazol-3-yl)-N-(5-chloro-6-(2H-1,2,3-triazol-2-yl)pyridin-3-yl)-5-(trifluoromethyl)-1H-pyrazole-4-carboxamide, Cpd 284

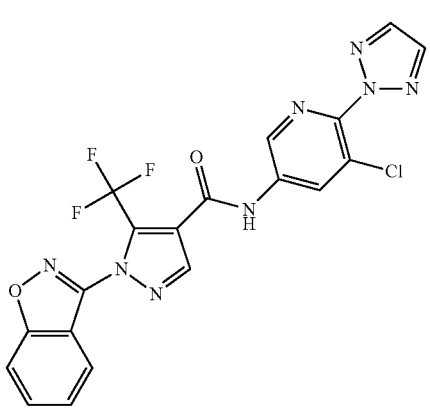 [SMILES: O=C(Nc1cnc(-n2nccn2)c(Cl)c1)c1cnn(-c2noc3ccccc23)c1C(F)(F)F]

$^1$H NMR (400 MHz, DMSO-$d_6$) δ ppm 11.49 (1H, s), 8.83 (1H, d, J=2.01 Hz), 8.74 (1H, s), 8.66 (1H, d, J=2.01 Hz), 8.20 (2H, s), 7.98-8.05 (2H, m), 7.89 (1H, t, J=7.91 Hz), 7.63 (1H, t, J=7.53 Hz). LC-MS: (ES, m/z): [M+1]$^+$ 474.9

Example 285

N-(5-chloro-6-(2H-1,2,3-triazol-2-yl)pyridin-3-yl)-1-(1-chloroisoquinolin-4-yl)-5-(trifluoromethyl)-1H-pyrazole-4-carboxamide, Cpd 285

$^1$H NMR (400 MHz, DMSO-$d_6$) δ ppm 7.34 (d, J=8.38 Hz, 1H), 7.96-8.07 (m, 2H), 8.18 (s, 2H), 8.47 (d, J=8.16 Hz, 1H), 8.70-8.75 (m, 2H), 8.77 (s, 1H), 8.94 (d, J=2.21 Hz, 1H), 11.57 (s, 1H). LC-MS: (ES, m/z): [M+1]$^+$ 518.8

Example 286

N-(5-cyano-6-(2H-1,2,3-triazol-2-yl)pyridin-3-yl)-1-(1H-indazol-7-yl)-5-(trifluoromethyl)-1H-pyrazole-4-carboxamide, Cpd 286

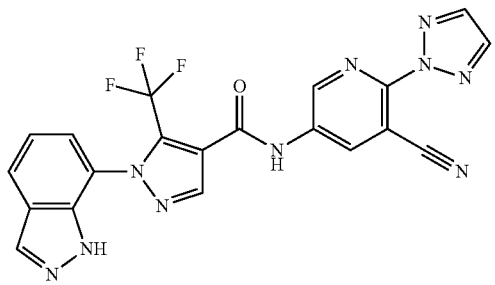 [SMILES: N#Cc1cc(NC(=O)c2cnn(-c3cccc4cn[nH]c34)c2C(F)(F)F)cnc1-n1nccn1]

$^{1}$H NMR (400 MHz, DMSO-d$_{6}$) δ ppm 11.30 (1H, s), 9.11 (1H, d, J=2.21 Hz), 8.88 (1H, d, J=2.43 Hz), 8.55 (1H, s), 8.23-8.35 (3H, m), 8.02 (1H, d, J=8.16 Hz), 7.50 (1H, d, J=7.28 Hz), 7.27 (1H, t, J=7.72 Hz). LC-MS: (ES, m/z): [M+1]$^{+}$ 464.9

Example 287

N-(5-bromo-6-(1H-1,2,3-triazol-1-yl)pyridin-3-yl)-1-(quinolin-5-yl)-5-(trifluoromethyl)-1H-pyrazole-4-carboxamide, Cpd 287

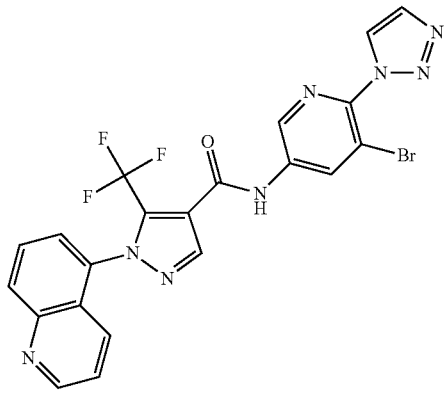 [SMILES: O=C(Nc1cnc(-n2ccnn2)c(Br)c1)c1cnn(-c2cccc3ncccc23)c1C(F)(F)F]

$^{1}$H NMR (400 MHz, DMSO-d$_{6}$) δ ppm 11.49 (s, 1H), 9.07 (br s, 1H), 8.93-9.00 (m, 1H), 8.81-8.89 (m, 1H), 8.65-8.73 (m, 1H), 8.55-8.63 (m, 1H), 8.30-8.37 (m, 1H), 7.97 (br d, J=0.88 Hz, 3H), 7.63-7.75 (m, 2H). LC-MS: (ES, m/z): [M+1]$^{+}$ 528.8

Example 288

N-(5-chloro-6-(oxazol-2-yl)pyridin-3-yl)-1-(8-fluoroquinolin-5-yl)-5-(trifluoromethyl)-1H-pyrazole-4-carboxamide, Cpd 288

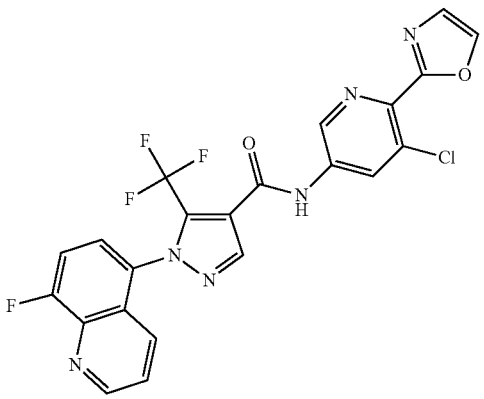 [SMILES: O=C(Nc1cnc(-c2ncco2)c(Cl)c1)c1cnn(-c2ccc(F)c3ncccc23)c1C(F)(F)F]

$^{1}$H NMR (400 MHz, DMSO-d$_{6}$) δ ppm 11.36 (s, 1H), 9.10 (dd, J=1.4, 4.1 Hz, 1H), 9.00 (d, J=2.2 Hz, 1H), 8.64 (s, 1H), 8.58 (d, J=2.0 Hz, 1H), 8.33 (d, J=0.7 Hz, 1H), 7.97 (dd, J=4.2, 8.4 Hz, 1H), 7.82 (dd, J=8.3, 10.3 Hz, 1H), 7.77 (dd, J=4.2, 8.6 Hz, 1H), 7.65 (d, J=8.6 Hz, 1H), 7.49 (d, J=0.7 Hz, 1H). LC-MS: (ES, m/z): [M+1]$^{+}$ 502.9

Example 289

N-(5-cyano-6-(2H-1,2,3-triazol-2-yl)pyridin-3-yl)-1-(1-fluoroisoquinolin-4-yl)-5-(trifluoromethyl)-1H-pyrazole-4-carboxamide, Cpd 289

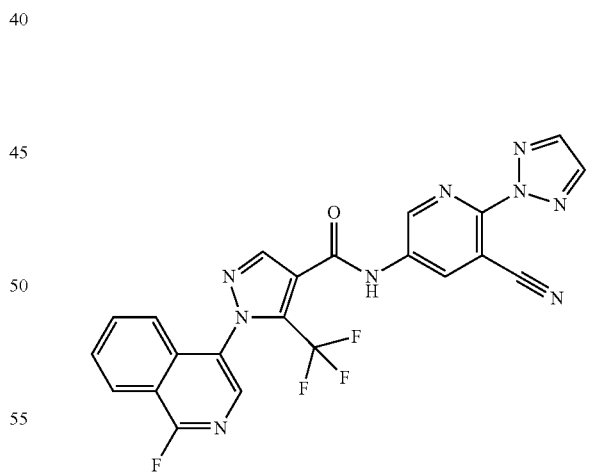

$^{1}$H NMR (400 MHz, DMSO-d$_{6}$) δ ppm 11.35 (br s, 1H), 9.07 (d, J=2.65 Hz, 1H), 8.86 (d, J=2.65 Hz, 1H), 8.62 (s, 1H), 8.50 (s, 1H), 8.34 (d, J=8.38 Hz, 1H), 8.29 (s, 2H), 8.00-8.07 (m, 1H), 7.90-7.97 (m, 1H), 7.29 (d, J=8.16 Hz, 1H). LC-MS: (ES, m/z): [M+1]$^{+}$ 493.9

Example 290

1-(benzo[d]isothiazol-3-yl)-N-(5-chloro-6-(2H-1,2,3-triazol-2-yl)pyridin-3-yl)-5-(trifluoromethyl)-1H-pyrazole-4-carboxamide, Cpd 290

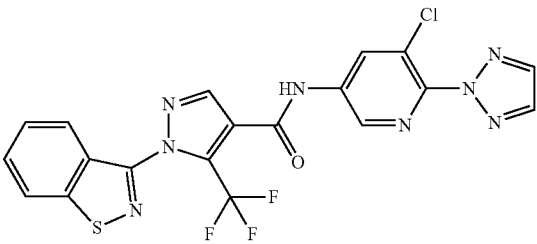 [SMILES: O=C(Nc1cnc(-n2nccn2)c(Cl)c1)c1cnn(-c2nsc3ccccc23)c1C(F)(F)F]

$^1$H NMR (400 MHz, DMSO-d$_6$) δ ppm 7.60-7.67 (m, 1H), 7.76 (t, J=7.61 Hz, 1H), 8.04 (d, J=8.16 Hz, 1H), 8.16 (s, 2H), 8.39 (d, J=8.38 Hz, 1H), 8.60-8.66 (m, 2H), 8.83 (d, J=2.21 Hz, 1H), 11.42 (s, 1H). LC-MS: (ES, m/z): [M+1]$^+$ 491.0

Example 291

N-(5-cyano-6-(2H-1,2,3-triazol-2-yl)pyridin-3-yl)-1-(2-fluoroquinolin-5-yl)-5-(trifluoromethyl)-1H-pyrazole-4-carboxamide, Cpd 291

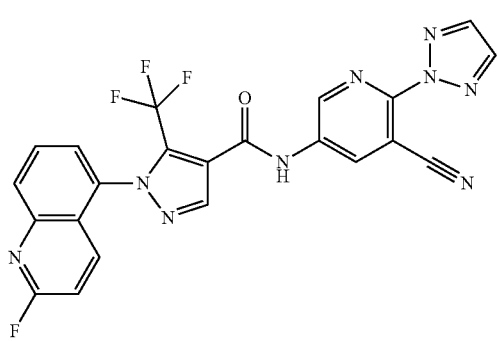 [SMILES: N#Cc1cc(NC(=O)c2cnn(-c3cccc4nc(F)ccc34)c2C(F)(F)F)cnc1-n1nccn1]

$^1$H NMR (400 MHz, CHLOROFORM-d) δ ppm 8.94 (d, J=2.43 Hz, 1H), 8.78 (d, J=2.43 Hz, 1H), 8.20 (s, 1H), 8.14 (d, J=8.60 Hz, 1H), 8.09 (s, 1H), 7.97 (s, 2H), 7.81 (t, J=8.05 Hz, 1H), 7.67 (t, J=8.27 Hz, 1H), 7.56 (d, J=7.06 Hz, 1H), 7.12 (dd, J=9.15, 2.54 Hz, 1H). LC-MS: (ES, m/z): [M+1]$^+$ 494.0

Example 292

N-(5-cyano-6-(2H-1,2,3-triazol-2-yl)pyridin-3-yl)-1-(furo[2,3-d]pyrimidin-4-yl)-5-(trifluoromethyl)-1H-pyrazole-4-carboxamide, Cpd 292

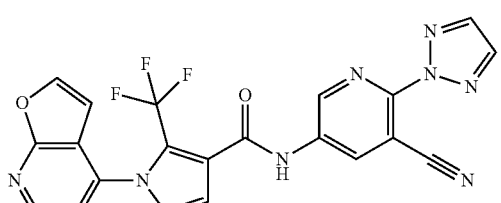

$^1$H NMR (400 MHz, DMSO-d$_6$) δ ppm=11.51 (s, 1H), 9.00 (s, 2H), 8.78 (d, J=2.2 Hz, 1H), 8.58 (s, 1H), 8.39 (d, J=2.2 Hz, 1H), 8.27 (s, 2H), 7.32 (d, J=2.0 Hz, 1H). LC-MS: (ES, m/z): [M+1]$^+$ 466.9

Example 293

1-(benzo[d][1,2,3]thiadiazol-7-yl)-N-(5-chloro-6-(1-methyl-1H-pyrazol-3-yl)pyridin-3-yl)-5-(trifluoromethyl)-1H-pyrazole-4-carboxamide, Cpd 293

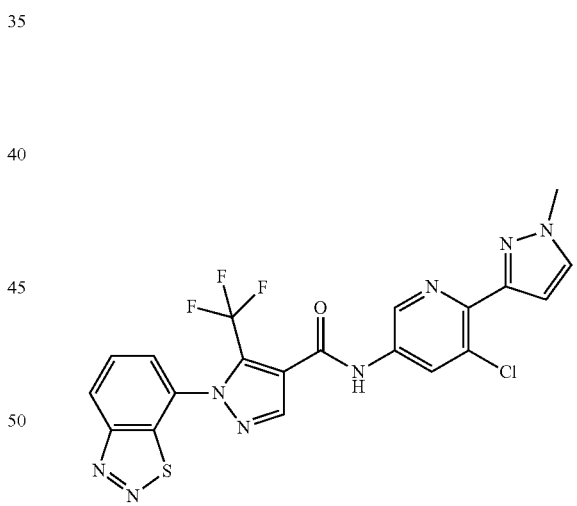

$^1$H NMR (400 MHz, DMSO-d$_6$) δ ppm 11.18 (s, 1H), 8.98 (dd, J=0.9, 8.2 Hz, 1H), 8.84 (d, J=2.2 Hz, 1H), 8.62 (s, 1H), 8.42 (d, J=2.2 Hz, 1H), 8.13-8.08 (m, 1H), 8.06-8.00 (m, 1H), 7.79 (d, J=2.2 Hz, 1H), 6.76 (d, J=2.2 Hz, 1H), 3.93 (s, 3H). LC-MS: (ES, m/z): [M+1]$^+$ 505.1

Example 294

N-(5-cyano-6-(2H-1,2,3-triazol-2-yl)pyridin-3-yl)-1-(thiazolo[5,4-d]pyrimidin-7-yl)-5-(trifluoromethyl)-1H-pyrazole-4-carboxamide, Cpd 294

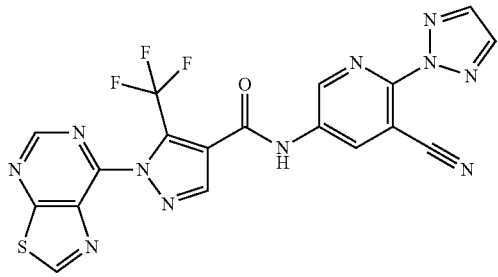 [SMILES: N#Cc1cc(NC(=O)c2cnn(-c3ncnc4scnc34)c2C(F)(F)F)cnc1-n1nccn1]

$^1$H NMR (400 MHz, DMSO-d$_6$) δ ppm 11.42 (br s, 1H), 9.79 (s, 1H), 9.38 (s, 1H), 9.05 (d, J=2.6 Hz, 1H), 8.84 (d, J=2.4 Hz, 1H), 8.64 (s, 1H), 8.30 (s, 2H). LC-MS: (ES, m/z): [M+1]$^+$ 483.9

Example 295

N-(5-cyano-6-(2H-1,2,3-triazol-2-yl)pyridin-3-yl)-1-(2-methylimidazo[1,2-a]pyridin-3-yl)-5-(trifluoromethyl)-1H-pyrazole-4-carboxamide, Cpd 295

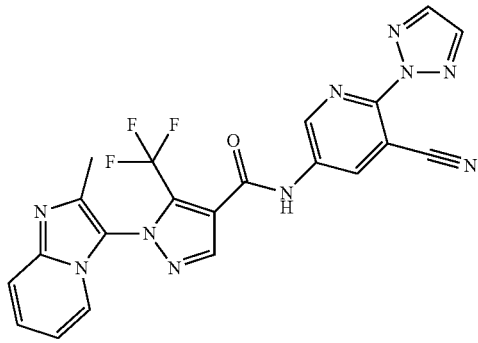 [SMILES: Cc1nc2ccccn2c1-n1ncc(C(=O)Nc2cnc(-n3nccn3)c(C#N)c2)c1C(F)(F)F]

$^1$H NMR (400 MHz, DMSO-d$_6$) δ ppm 11.51 (s, 1H), 9.09 (d, J=2.2 Hz, 1H), 8.87 (d, J=2.4 Hz, 1H), 8.71 (s, 1H), 8.29 (s, 2H), 8.12 (br d, J=6.6 Hz, 1H), 7.79 (br d, J=9.3 Hz, 1H), 7.65 (br t, J=7.6 Hz, 1H), 7.34-7.12 (m, 3H), 2.28 (s, 3H). LC-MS: (ES, m/z): [M+1]$^+$ 478.9

Example 296

N-(5-cyano-6-(2H-1,2,3-triazol-2-yl)pyridin-3-yl)-1-(quinazolin-4-yl)-5-(trifluoromethyl)-1H-pyrazole-4-carboxamide, Cpd 296

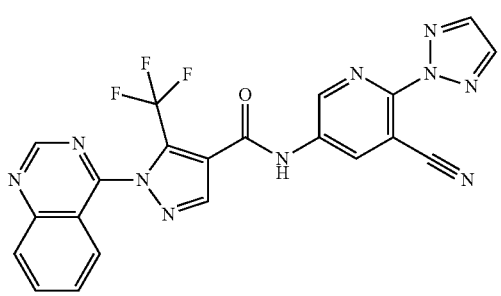 [SMILES: N#Cc1cc(NC(=O)c2cnn(-c3ncnc4ccccc34)c2C(F)(F)F)cnc1-n1nccn1]

$^1$H NMR (400 MHz, DMSO-d$_6$) δ ppm 11.20-11.63 (m, 1H), 9.43 (s, 1H), 9.05-9.10 (m, 1H), 8.83-8.88 (m, 1H), 8.66-8.71 (m, 1H), 8.17-8.33 (m, 4H), 8.01-8.08 (m, 1H), 7.89-7.96 (m, 1H). LC-MS: (ES, m/z): [M+1]$^+$ 476.9

Example 297

1-(benzo[d]thiazol-4-yl)-N-(5-cyano-2-methyl-6-(2H-1,2,3-triazol-2-yl)pyridin-3-yl)-5-(trifluoromethyl)-1H-pyrazole-4-carboxamide, Cpd 297

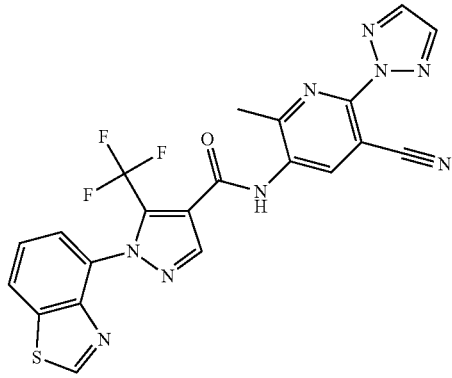 [SMILES: Cc1nc(-n2nccn2)c(C#N)cc1NC(=O)c1cnn(-c2cccc3scnc23)c1C(F)(F)F]

$^1$H NMR (400 MHz, DMSO-d$_6$) δ ppm 10.64 (1H, s), 9.45 (1H, s), 8.65 (1H, s), 8.49 (1H, s), 8.44 (1H, dd, J=7.94, 1.10 Hz), 8.28 (2H, s), 7.75-7.82 (1H, m), 7.64-7.73 (1H, m), 2.62-2.66 (3H, m). LC-MS: (ES, m/z): [M+1]$^+$ 496.1

Example 298

1-(benzo[d]thiazol-4-yl)-N-(5-cyano-2-methyl-4-(2H-1,2,3-triazol-2-yl)phenyl)-5-(trifluoromethyl)-1H-pyrazole-4-carboxamide, Cpd 298

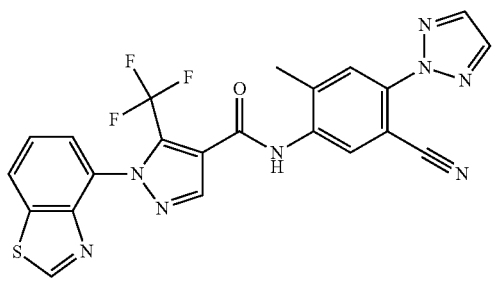 [SMILES: Cc1cc(-n2nccn2)c(C#N)cc1NC(=O)c1cnn(-c2cccc3scnc23)c1C(F)(F)F]

$^1$H NMR (400 MHz, CHLOROFORM-d) δ ppm 9.08 (1H, s), 8.66 (1H, s), 8.22 (1H, s), 8.18 (1H, dd, J=7.50, 1.76 Hz), 7.97 (1H, s), 7.92 (2H, s), 7.73 (1H, s), 7.58-7.69 (2H, m), 2.47 (3H, s). LC-MS: (ES, m/z): [M+1]$^+$ 495.1

Example 299

N-(6-(4-amino-2H-1,2,3-triazol-2-yl)-5-chloropyridin-3-yl)-1-(benzo[d]thiazol-4-yl)-5-(trifluoromethyl)-1H-pyrazole-4-carboxamide, Cpd 299

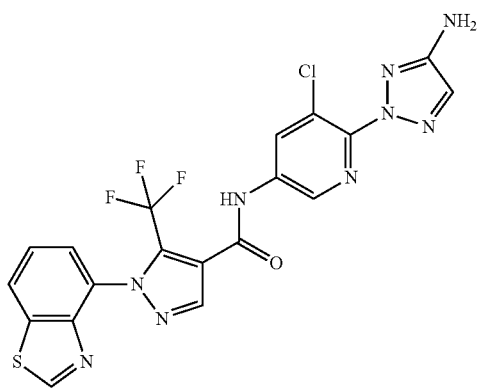 [SMILES: Nc1cnn(-c2ncc(NC(=O)c3cnn(-c4cccc5scnc45)c3C(F)(F)F)cc2Cl)n1]

$^1$H NMR (400 MHz, DMSO-d$_6$) δ ppm 11.15 (1H, s) 9.45 (1H, s), 8.78 (1H, d, J=2.21 Hz), 8.57 (1H, d, J=2.21 Hz), 8.52 (1H, s), 8.44 (1H, dd, J=8.16, 1.10 Hz), 7.76-7.81 (1H, m), 7.64-7.72 (1H, m), 7.31 (1H, s). LC-MS: (ES, m/z): [M+1]$^+$ 506.1

Example 300

1-(benzo[d]thiazol-4-yl)-N-(2,5-dimethyl-6-(2H-1,2,3-triazol-2-yl)pyridin-3-yl)-5-(trifluoromethyl)-1H-pyrazole-4-carboxamide, Cpd 300

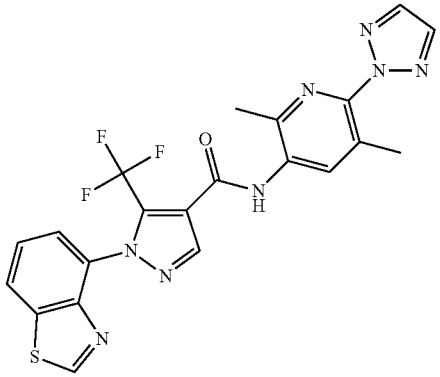 [SMILES: Cc1cc(NC(=O)c2cnn(-c3cccc4scnc34)c2C(F)(F)F)c(C)nc1-n1nccn1]

$^1$H NMR (400 MHz, CHLOROFORM-d) δ ppm 9.08 (1H, s), 8.60 (1H, br s), 8.23 (1H, br s), 8.18 (1H, dd, J=7.50, 1.54 Hz), 7.88 (2H, s), 7.73 (1H, br s), 7.59-7.68 (2H, m), 2.62 (3H, br s), 2.43 (3H, s). LC-MS: (ES, m/z): [M+1]$^+$ 485.0

Example 301

1-(benzo[d][1,2,3]thiadiazol-7-yl)-N-(5-chloro-2-fluoro-4-(2H-1,2,3-triazol-2-yl)phenyl)-5-(trifluoromethyl)-1H-pyrazole-4-carboxamide, Cpd 301

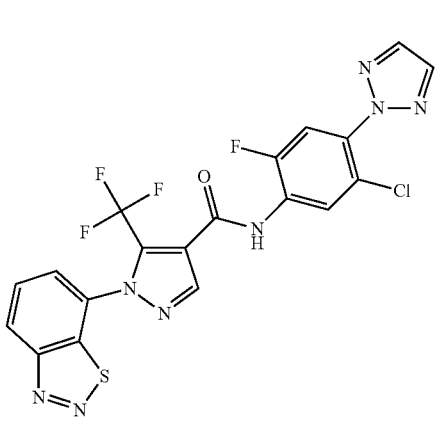 [SMILES: O=C(Nc1cc(Cl)c(-n2nccn2)cc1F)c1cnn(-c2cccc3nnsc23)c1C(F)(F)F]

$^1$H NMR (400 MHz, DMSO-d$_6$) δ ppm 10.98 (s, 1H), 8.97 (d, J=8.2 Hz, 1H), 8.57 (s, 1H), 8.28 (d, J=7.3 Hz, 1H), 8.20 (s, 2H), 8.12-8.07 (m, 1H), 8.06-7.99 (m, 1H), 7.88 (d, J=10.4 Hz, 1H). LC-MS: (ES, m/z): [M+1]$^+$ 508.8

Example 302

N-(5-chloro-2-fluoro-4-(2H-1,2,3-triazol-2-yl)phenyl)-1-(8-fluoroisoquinolin-4-yl)-5-(trifluoromethyl)-1H-pyrazole-4-carboxamide, Cpd 302

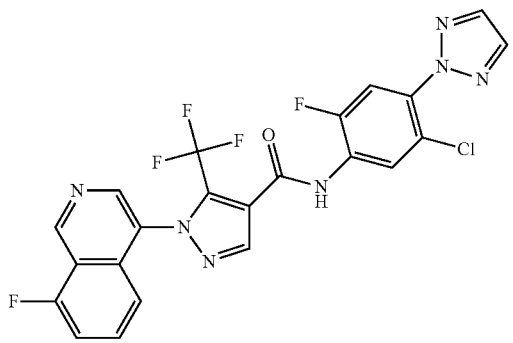 [SMILES: O=C(Nc1cc(Cl)c(-n2nccn2)cc1F)c1cnn(-c2cncc3c(F)cccc23)c1C(F)(F)F]

$^1$H NMR (400 MHz, DMSO-d$_6$) δ ppm 10.87 (s, 1H), 9.72 (s, 1H), 8.90 (s, 1H), 8.56 (s, 1H), 8.24 (d, J=7.28 Hz, 1H), 8.17 (s, 2H), 7.93 (td, J=8.16, 5.51 Hz, 1H), 7.86 (d, J=10.36 Hz, 1H), 7.68 (dd, J=10.36, 7.72 Hz, 1H), 7.14 (d, J=8.60 Hz, 1H). LC-MS: (ES, m/z): [M+1]$^+$ 519.9

Example 303

1-(benzo[d][1,2,3]thiadiazol-7-yl)-N-(5-chloro-2-methyl-6-(1H-pyrazol-1-yl)pyridin-3-yl)-5-(trifluoromethyl)-1H-pyrazole-4-carboxamide, Cpd 303

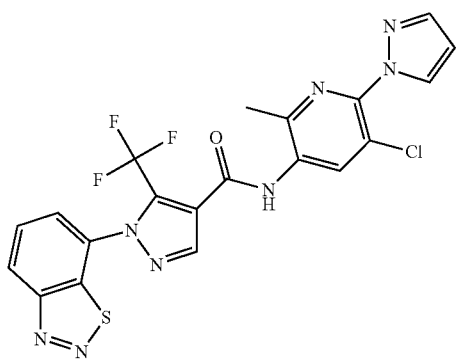 [SMILES: Cc1nc(-n2cccn2)c(Cl)cc1NC(=O)c1cnn(-c2cccc3nnsc23)c1C(F)(F)F]

$^1$H NMR (400 MHz, DMSO-d$_6$) δ ppm 10.65 (s, 1H), 8.98 (d, J=8.4 Hz, 1H), 8.61 (s, 1H), 8.32 (s, 1H), 8.26 (d, J=2.2 Hz, 1H), 8.13-8.07 (m, 1H), 8.06-7.99 (m, 1H), 7.81 (s, 1H), 6.55 (s, 1H), 2.53 (s, 3H). LC-MS: (ES, m/z): [M+1]$^+$ 504.9

Example 304

N-(5-chloro-6-(4-methyl-2H-1,2,3-triazol-2-yl)pyridin-3-yl)-1-(quinolin-5-yl)-5-(trifluoromethyl)-1H-pyrazole-4-carboxamide, Cpd 304

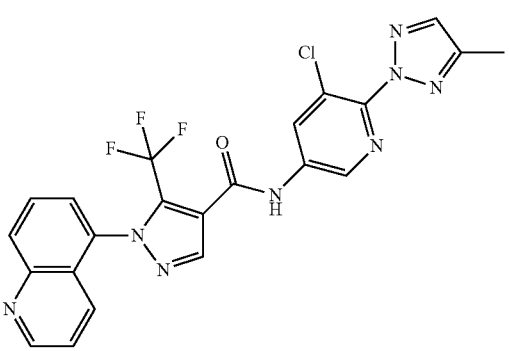 [SMILES: Cc1cnn(-c2ncc(NC(=O)c3cnn(-c4cccc5ncccc45)c3C(F)(F)F)cc2Cl)n1]

$^1$H NMR (400 MHz, DMSO-d$_6$) δ ppm 11.45 (s, 1H), 9.06 (t, J=2.54 Hz, 1H), 8.89 (s, 1H), 8.60-8.75 (m, 2H), 8.33 (d, J=8.38 Hz, 1H), 7.88-8.03 (m, 3H), 7.68 (d, J=2.65 Hz, 2H), 2.34 (s, 3H). LC-MS: (ES, m/z): [M+1]$^+$ 499.0

Example 305

N-(5-methyl-6-(2-methyl-2H-tetrazol-5-yl)pyridin-3-yl)-1-(quinolin-5-yl)-5-(trifluoromethyl)-1H-pyrazole-4-carboxamide, Cpd 305

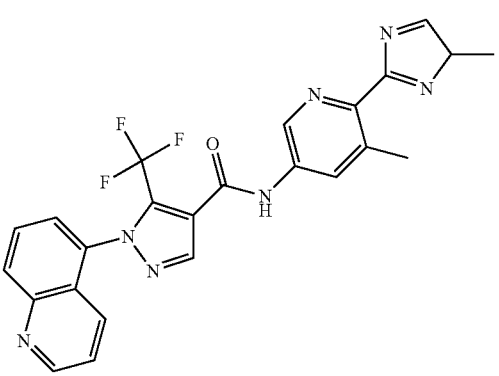 [SMILES: Cc1cc(NC(=O)c2cnn(-c3cccc4ncccc34)c2C(F)(F)F)cnc1C1=NC(C)C=N1]

$^1$H NMR (400 MHz, DMSO-d$_6$) δ ppm 11.16 (1H, s), 9.03-9.10 (1H, m), 8.92 (1H, s), 8.62 (1H, s), 8.33 (1H, d, J=8.38 Hz), 8.29 (1H, d, J=1.76 Hz), 7.95-8.03 (1H, m), 7.88-7.94 (1H, m), 7.64-7.72 (2H, m), 4.44 (3H, s), 2.55 (3H, s). LC-MS: (ES, m/z): [M+1]$^+$ 480.0

Example 306

1-(benzo[d]thiazol-4-yl)-N-(5-chloro-6-(2H-1,2,3-triazol-2-yl)pyridin-3-yl)-5-(trifluoromethyl)-1H-pyrazole-4-carboxamide, Cpd 306

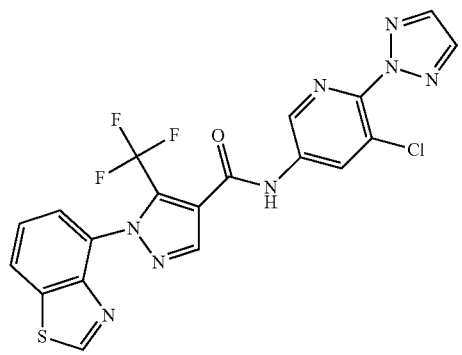 [SMILES: O=C(Nc1cnc(-n2nccn2)c(Cl)c1)c1cnn(-c2cccc3scnc23)c1C(F)(F)F]

$^1$H NMR (400 MHz, DMSO-d$_6$) δ ppm 11.26 (1H, s), 9.48 (1H, s), 8.88 (1H, d, J=2.43 Hz), 8.68 (1H, d, J=2.21 Hz), 8.54 (1H, s), 8.47 (1H, dd, J=8.05, 0.99 Hz), 8.19 (2H, s), 7.82 (1H, dd, J=7.61, 0.99 Hz), 7.68-7.75 (1H, m). LC-MS: (ES, m/z): [M+1]$^+$ 490.9

Example 307

N-(5-chloro-6-(2H-tetrazol-5-yl)pyridin-3-yl)-1-(quinolin-5-yl)-5-(trifluoromethyl)-1H-pyrazole-4-carboxamide, Cpd 307

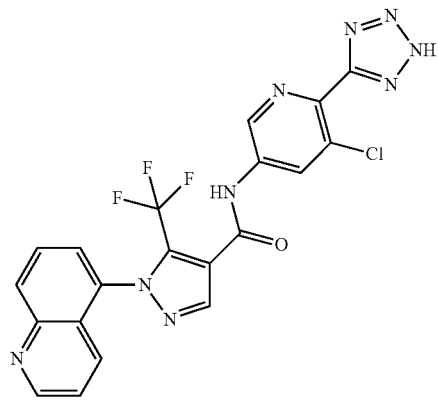 [SMILES: O=C(Nc1cnc(-c2nn[nH]n2)c(Cl)c1)c1cnn(-c2cccc3ncccc23)c1C(F)(F)F]

$^1$H NMR (400 MHz, DMSO-d$_6$) δ ppm 11.35 (1H, s), 9.05 (2H, br s), 8.61 (2H, s), 8.32 (1H, br d, J=8.16 Hz), 7.87-8.02 (2H, m), 7.60-7.73 (2H, m). LC-MS: (ES, m/z): [M+1]$^+$ 485.9

Example 308

N-(5-cyano-6-(2H-1,2,3-triazol-2-yl)pyridin-3-yl)-1-(8-fluoroquinolin-5-yl)-5-(trifluoromethyl)-1H-pyrazole-4-carboxamide, Cpd 308

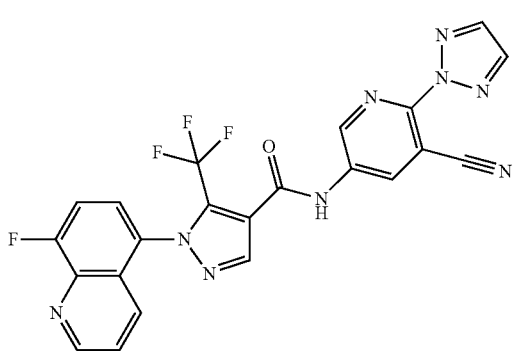 [SMILES: N#Cc1cc(NC(=O)c2cnn(-c3ccc(F)c4ncccc34)c2C(F)(F)F)cnc1-n1nccn1]

$^1$H NMR (400 MHz, DMSO-d$_6$) δ ppm 11.36 (s, 1H), 9.13-9.05 (m, 2H), 8.87 (d, J=2.6 Hz, 1H), 8.59 (s, 1H), 8.29 (s, 2H), 7.97 (dd, J=4.3, 8.5 Hz, 1H), 7.82 (dd, J=8.4, 10.4 Hz, 1H), 7.77 (dd, J=4.2, 8.6 Hz, 1H), 7.64 (d, J=8.6 Hz, 1H). LC-MS: (ES, m/z): [M+1]$^+$ 493.9

Example 309

N-(5-chloro-6-(2H-1,2,3-triazol-4-yl)pyridin-3-yl)-1-(quinolin-5-yl)-5-(trifluoromethyl)-1H-pyrazole-4-carboxamide, Cpd 309

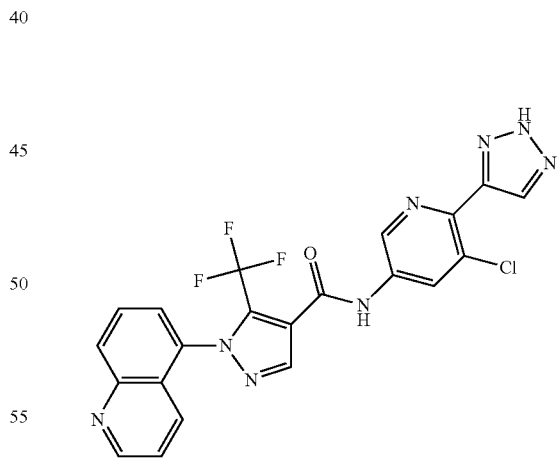

$^1$H NMR (400 MHz, DMSO-d$_6$) δ ppm 11.46 (s, 1H), 9.09-9.16 (m, 1H), 9.02 (d, J=2.20 Hz, 1H), 8.72 (s, 1H), 8.57 (d, J=1.98 Hz, 1H), 8.33-8.43 (m, 2H), 7.93-8.06 (m, 2H), 7.72-7.84 (m, 2H). LC-MS: (ES, m/z): [M+1]$^+$ 484.9

Example 310

N-(5-cyano-6-(2H-1,2,3-triazol-2-yl)pyridin-3-yl)-1-(3-methylthieno[3,2-b]pyridin-7-yl)-5-(trifluoromethyl)-1H-pyrazole-4-carboxamide, Cpd 310

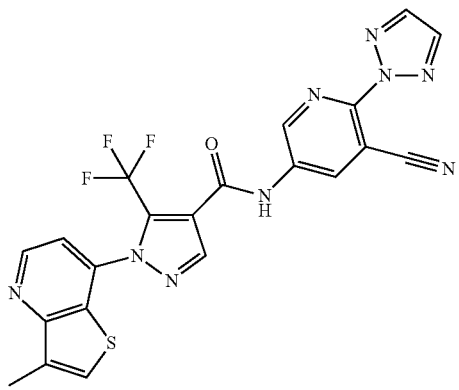 [SMILES: Cc1csc2c(-n3ncc(C(=O)Nc4cnc(-n5nccn5)c(C#N)c4)c3C(F)(F)F)ccnc12]

$^1$H NMR (400 MHz, DMSO-d$_6$) δ ppm 3.46-3.47 (m, 3H), 7.70 (d, J=4.85 Hz, 1H), 7.97 (d, J=0.88 Hz, 1H), 8.32 (s, 2H), 8.68 (s, 1H), 8.88 (d, J=2.65 Hz, 1H), 8.94 (d, J=4.85 Hz, 1H), 9.10 (d, J=2.43 Hz, 1H), 11.54 (s, 1H). LC-MS: (ES, m/z): [M+1]$^+$ 495.9

Example 311

1-(benzo[d]oxazol-4-yl)-N-(5-cyano-6-(2H-1,2,3-triazol-2-yl)pyridin-3-yl)-5-(trifluoromethyl)-1H-pyrazole-4-carboxamide, Cpd 311

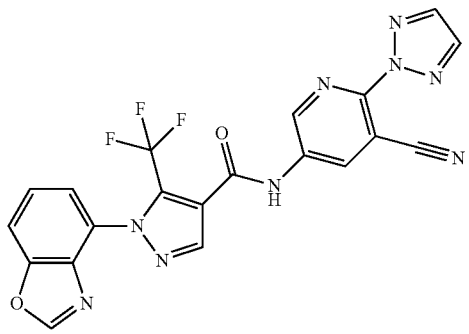 [SMILES: N#Cc1cc(NC(=O)c2cnn(-c3cccc4ocnc34)c2C(F)(F)F)cnc1-n1nccn1]

$^1$H NMR (400 MHz, DMSO-d$_6$) δ ppm 11.84-11.15 (m, 1H), 11.50 (br s, 1H), 9.15 (br s, 1H), 8.92 (s, 2H), 8.62 (s, 1H), 8.31 (s, 2H), 8.10 (br d, J=3.8 Hz, 1H), 7.69 (br s, 2H). LC-MS: (ES, m/z): [M+1]$^+$ 465.9

Example 312

N-(5-cyano-6-(2H-1,2,3-triazol-2-yl)pyridin-3-yl)-1-(4-fluoronaphthal-1-yl)-5-(trifluoromethyl)-1H-pyrazole-4-carboxamide, Cpd 312

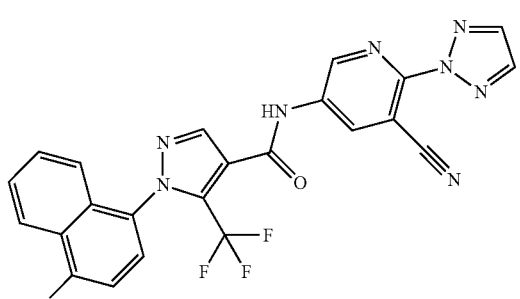

$^1$H NMR (400 MHz, DMSO-d$_6$) δ ppm 11.59 (1H, s), 9.20 (1H, d, J=2.01 Hz), 8.95 (1H, d, J=2.01 Hz), 8.70 (1H, s), 8.33 (2H, s), 8.24 (1H, br d, J=8.28 Hz), 7.88 (1H, dd, J=8.16, 4.64 Hz), 7.72-7.83 (2H, m), 7.58 (1H, br t, J=9.16 Hz), 7.17 (1H, br d, J=8.03 Hz). LC-MS: (ES, m/z): [M+1]$^+$ 492.9

Example 313 methyl 2-cyano-4-(1-(quinolin-5-yl)-5-(trifluoromethyl)-1H-pyrazole-4-carboxamido)benzoate, Cpd 313

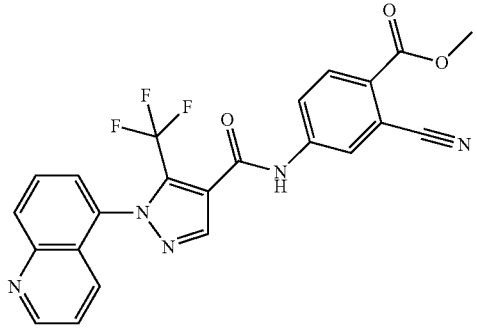 [SMILES: COC(=O)c1ccc(NC(=O)c2cnn(-c3cccc4ncccc34)c2C(F)(F)F)cc1C#N]

$^1$H NMR (400 MHz, DMSO-d$_6$) δ ppm 3.91 (s, 3H), 7.62-7.72 (m, 2H), 7.90-8.02 (m, 2H), 8.15-8.21 (m, 2H), 8.32-8.39 (m, 2H), 8.60 (s, 1H), 9.07 (dd, J=3.97, 1.76 Hz, 1H), 11.29 (s, 1H). LC-MS: (ES, m/z): [M+1]$^+$ 451.9

Example 314

1-(benzo[d][1,2,3]thiadiazol-7-yl)-N-(5-cyano-2-methyl-6-(2H-1,2,3-triazol-2-yl)pyridin-3-yl)-5-(trifluoromethyl)-1H-pyrazole-4-carboxamide, Cpd 314

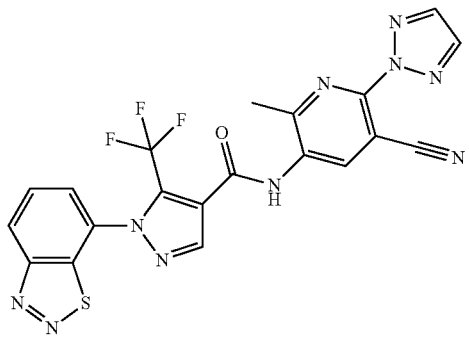 [SMILES: Cc1nc(-n2nccn2)c(C#N)cc1NC(=O)c1cnn(-c2cccc3nnsc23)c1C(F)(F)F]

$^1$H NMR (400 MHz, DMSO-d$_6$) δ ppm 10.78 (s, 1H), 8.99 (d, J=8.4 Hz, 1H), 8.70 (s, 1H), 8.63 (s, 1H), 8.32 (s, 2H), 8.15-8.08 (m, 1H), 8.07-8.01 (m, 1H), 2.67 (s, 3H). LC-MS: (ES, m/z): [M+1]$^+$ 496.9

Example 315

N-(5-cyano-6-(2H-1,2,3-triazol-2-yl)pyridin-3-yl)-1-(thieno[3,2-d]pyrimidin-4-yl)-5-(trifluoromethyl)-1H-pyrazole-4-carboxamide, Cpd 315

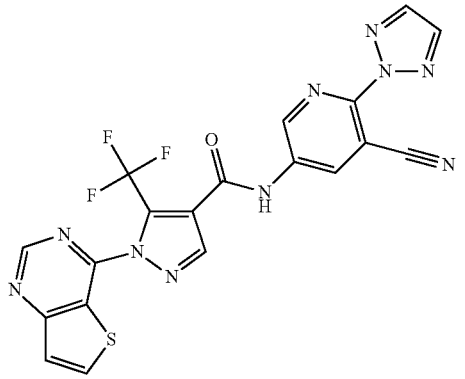 [SMILES: N#Cc1cc(NC(=O)c2cnn(-c3ncnc4ccsc34)c2C(F)(F)F)cnc1-n1nccn1]

$^1$H NMR (400 MHz, DMSO-d$_6$) δ ppm 7.80 (d, J=5.73 Hz, 1H), 8.32 (s, 2H), 8.62-8.74 (m, 2H), 8.83 (d, J=2.43 Hz, 1H), 9.05 (d, J=2.21 Hz, 1H), 9.22 (s, 1H), 11.59 (br s, 1H). LC-MS: (ES, m/z): [M+1]$^+$ 482.9

Example 316

1-(benzo[d]thiazol-4-yl)-N-(5-cyano-6-(2H-1,2,3-triazol-2-yl)pyridin-3-yl)-5-(trifluoromethyl)-1H-pyrazole-4-carboxamide, Cpd 316

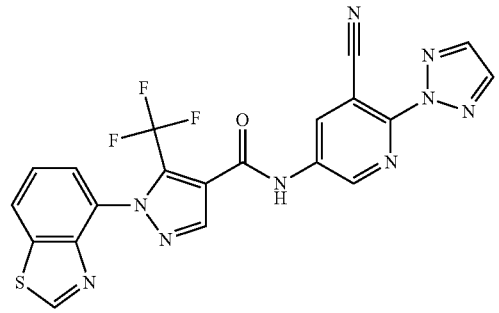 [SMILES: N#Cc1cc(NC(=O)c2cnn(-c3cccc4scnc34)c2C(F)(F)F)cnc1-n1nccn1]

$^1$H NMR (400 MHz, DMSO-d$_6$) δ ppm 11.27 (s, 1H), 9.46 (s, 1H), 9.07 (d, J=2.4 Hz, 1H), 8.86 (d, J=2.6 Hz, 1H), 8.53-8.42 (m, 2H), 8.30 (s, 2H), 7.80 (d, J=6.6 Hz, 1H), 7.74-7.64 (m, 1H). LC-MS: (ES, m/z): [M+1]$^+$ 481.9

Example 317

N-(5-chloro-2-methyl-4-(2H-1,2,3-triazol-2-yl)phenyl)-1-(8-fluoroisoquinolin-4-yl)-5-(trifluoromethyl)-1H-pyrazole-4-carboxamide, Cpd 317

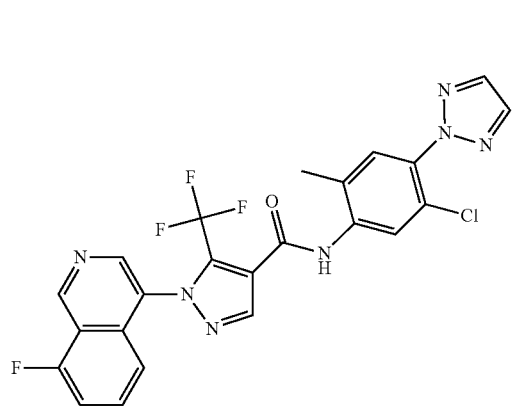 [SMILES: Cc1cc(-n2nccn2)c(Cl)cc1NC(=O)c1cnn(-c2cncc3c(F)cccc23)c1C(F)(F)F]

$^1$H NMR (400 MHz, DMSO-d$_6$) δ ppm 10.44 (s, 1H), 9.76 (s, 1H), 8.94 (s, 1H), 8.62 (s, 1H), 8.15-8.20 (m, 2H), 7.97 (td, J=8.21, 5.40 Hz, 1H), 7.89 (s, 1H), 7.67-7.76 (m, 2H), 7.17 (d, J=8.38 Hz, 1H), 2.38 (s, 3H). LC-MS: (ES, m/z): [M+1]$^+$ 516.0

Example 318

N-(5-chloro-2-methyl-6-(2H-1,2,3-triazol-2-yl)pyridin-3-yl)-1-(7-methylpyrazolo[1,5-a]pyridin-4-yl)-5-(trifluoromethyl)-1H-pyrazole-4-carboxamide, Cpd 318

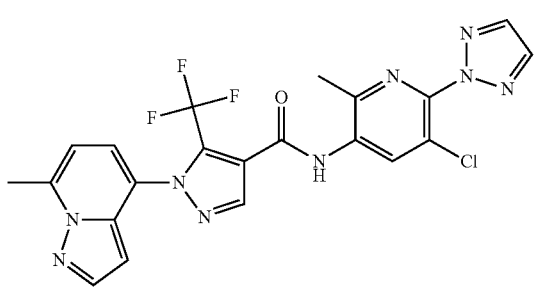 [SMILES: Cc1nc(-n2nccn2)c(Cl)cc1NC(=O)c1cnn(-c2ccc(C)n3nccc23)c1C(F)(F)F]

$^1$H NMR (400 MHz, DMSO-d$_6$) δ ppm 10.65 (s, 1H), 8.54 (s, 1H), 8.44 (s, 1H), 8.19 (s, 2H), 8.17 (d, J=2.2 Hz, 1H), 7.54 (d, J=7.3 Hz, 1H), 7.04 (d, J=7.7 Hz, 1H), 6.41 (d, J=2.2 Hz, 1H), 2.80 (s, 3H), 2.56 (s, 3H). LC-MS: (ES, m/z): [M+1]$^+$ 502.2

Example 319

1-(pyrazolo[1,5-a]pyridin-4-yl)-5-(trifluoromethyl)-N-(2-(trifluoromethyl)pyridin-4-yl)-1H-pyrazole-4-carboxamide, Cpd 319

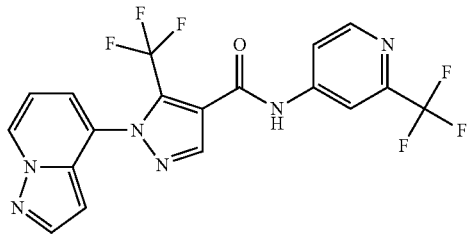 [SMILES: O=C(Nc1ccnc(C(F)(F)F)c1)c1cnn(-c2cccn3nccc23)c1C(F)(F)F]

$^1$H NMR (400 MHz, DMSO-d$_6$) δ ppm 6.32 (dd, J=2.21, 0.66 Hz, 1H), 7.07 (t, J=7.17 Hz, 1H), 7.56 (d, J=7.28 Hz, 1H), 7.94 (dd, J=5.51, 1.98 Hz, 1H), 8.11 (d, J=2.43 Hz, 1H), 8.21 (d, J=1.76 Hz, 1H), 8.53 (s, 1H), 8.67 (d, J=5.73 Hz, 1H), 8.94 (d, J=7.06 Hz, 1H), 11.28 (s, 1H). LC-MS: (ES, m/z): [M+1]$^+$ 440.9

Example 320

1-(8-fluoroisoquinolin-4-yl)-5-(trifluoromethyl)-N-(2-(trifluoromethyl)pyridin-4-yl)-1H-pyrazole-4-carboxamide, Cpd 320

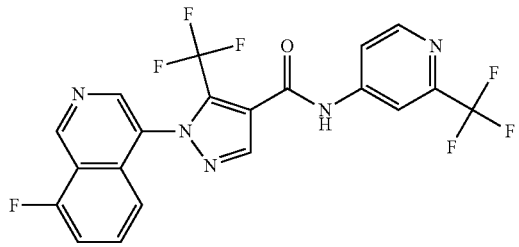 [SMILES: O=C(Nc1ccnc(C(F)(F)F)c1)c1cnn(-c2cncc3c(F)cccc23)c1C(F)(F)F]

$^1$H NMR (400 MHz, DMSO-d$_6$) δ ppm 7.12 (d, J=8.38 Hz, 1H), 7.69 (dd, J=10.36, 7.94 Hz, 1H), 7.94 (td, J=8.21, 5.40 Hz, 1H), 8.01 (br s, 1H), 8.27 (br s, 1H), 8.64-8.72 (m, 2H), 8.92 (s, 1H), 9.73 (s, 1H), 11.43 (br s, 1H). LC-MS: (ES, m/z): [M+1]$^+$ 469.9

Example 321

N-(5-chloro-2-methyl-6-(2H-1,2,3-triazol-2-yl)pyridin-3-yl)-1-(thieno[2,3-c]pyridin-4-yl)-5-(trifluoromethyl)-1H-pyrazole-4-carboxamide, Cpd 321

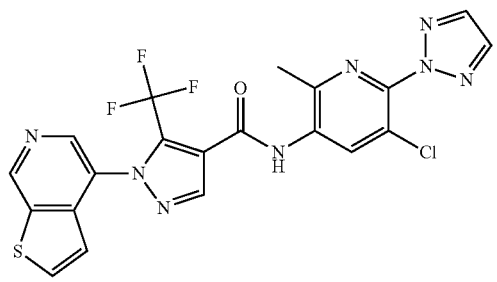 [SMILES: Cc1nc(-n2nccn2)c(Cl)cc1NC(=O)c1cnn(-c2cncc3sccc23)c1C(F)(F)F]

$^1$H NMR (400 MHz, DMSO-d$_6$) δ ppm 10.61 (1H, s), 9.52 (1H, s), 8.65 (1H, s), 8.57 (1H, s), 8.43 (1H, s), 8.34 (1H, d, J=5.51 Hz), 8.16-8.18 (2H, m), 7.14-7.21 (1H, m), 2.55 (3H, s). LC-MS: (ES, m/z): [M+1]$^+$ 505.1

Example 425

N-(5-cyano-6-(2H-1,2,3-triazol-2-yl)pyridin-3-yl)-1-(pyrazolo[1,5-a]pyrazin-4-yl)-5-(trifluoromethyl)-1H-pyrazole-4-carboxamide, Cpd 425

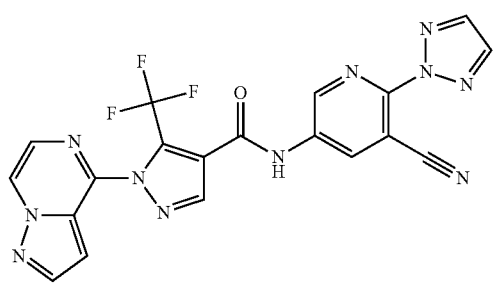 [SMILES: N#Cc1cc(NC(=O)c2cnn(-c3nccn4nccc34)c2C(F)(F)F)cnc1-n1nccn1]

¹H NMR (400 MHz, DMSO-d₆) δ ppm 11.54 (s, 1H), 9.02-9.09 (m, 2H), 8.84 (d, J=2.43 Hz, 1H), 8.62 (s, 1H), 8.37 (d, J=2.43 Hz, 1H), 8.30 (s, 2H), 7.96 (d, J=4.63 Hz, 1H), 7.11 (dd, J=2.32, 0.99 Hz, 1H). LC-MS: (ES, m/z): [M+1]⁺ 465.9

Example 449

N-(5-chloro-6-(2H-1,2,3-triazol-2-yl)pyridin-3-yl)-1-(isoquinolin-5-yl)-5-(trifluoromethyl)-1H-pyrazole-4-carboxamide, Cpd 449

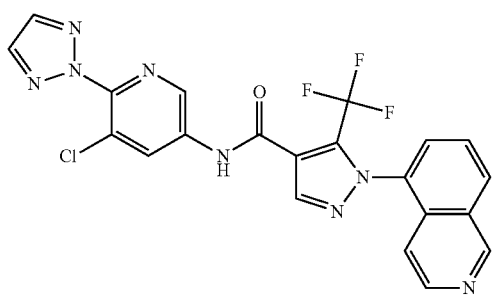 [SMILES: O=C(Nc1cnc(-n2nccn2)c(Cl)c1)c1cnn(-c2cccc3cnccc23)c1C(F)(F)F]

LCMS (ESI): mass calcd. for C₂₁H₁₂ClF₃N₈O 484.1 m/z found 485.3 [M+H]⁺. ¹H NMR (400 MHz, DMSO-d₆) δ ppm 7.09 (d, J=6.1 Hz, 1H) 7.89-7.95 (m, 1H) 8.12 (d, J=6.9 Hz, 1H) 8.20 (s, 2H) 8.48 (d, J=8.5 Hz, 1H) 8.61 (s, 1H) 8.64 (d, J=5.7 Hz, 1H) 8.69 (d, J=2.0 Hz, 1H) 8.88 (d, J=2.0 Hz, 1H) 9.56 (s, 1H) 11.28 (br s, 1H)

Example 450

N-(5-chloro-6-(2H-1,2,3-triazol-2-yl)pyridin-3-yl)-1-(quinolin-4-yl)-5-(trifluoromethyl)-1H-pyrazole-4-carboxamide, Cpd 450

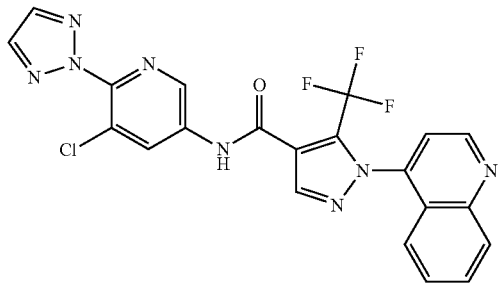 [SMILES: O=C(Nc1cnc(-n2nccn2)c(Cl)c1)c1cnn(-c2ccnc3ccccc23)c1C(F)(F)F]

LCMS (ESI): mass calcd. for C₂₁H₁₂ClF₃N₈O 484.1 m/z found 485.3 [M+H]⁺. ¹H NMR (400 MHz, DMSO-d₆) δ ppm 7.34 (d, J=8.1 Hz, 1H) 7.77 (td, J=7.6, 1.0 Hz, 1H) 7.91 (d, J=4.5 Hz, 1H) 7.95 (ddd, J=8.4, 7.0, 1.6 Hz, 1H) 8.20 (s, 2H) 8.26 (d, J=8.5 Hz, 1H) 8.66 (s, 1H) 8.69 (d, J=2.0 Hz, 1H) 8.87 (d, J=2.4 Hz, 1H) 9.19 (d, J=4.5 Hz, 1H) 11.24-11.35 (m, 1H)

Following the procedure described in Example 59, and selecting and substituting the appropriate reagents, starting materials, and purification methods, and adjusting reaction temperatures, times and other variables or parameters, as needed or desirable, as would be readily recognized by those skilled in the art, the following compounds were prepared.

Example 93

N-(3-chloro-4-methoxyphenyl)-1-(isoquinolin-8-yl)-5-(trifluoromethyl)-1H-pyrazole-4-carboxamide, Cpd 10

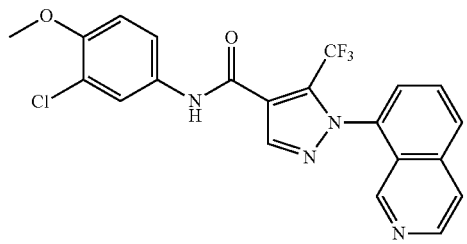 [SMILES: COc1ccc(NC(=O)c2cnn(-c3cccc4ccncc34)c2C(F)(F)F)cc1Cl]

¹H NMR (400 MHz, DMSO-d₆) δ ppm 3.92 (s, 3H) 6.94 (d, J=8.61 Hz, 1H) 7.51 (d, J=8.22 Hz, 1H) 7.65 (d, J=7.43 Hz, 1H) 7.69-7.85 (m, 4H) 8.06 (d, J=8.22 Hz, 1H) 8.18 (s, 1H) 8.66 (d, J=5.87 Hz, 1H) 8.74 (s, 1H). LCMS (ESI): m/z 446.9 [M+H]⁺

Example 94

N-(3-chloro-4-(1H-pyrazol-1-yl)phenyl)-1-(isoquinolin-8-yl)-5-(trifluoromethyl)-1H-pyrazole-4-carboxamide, Cpd 12

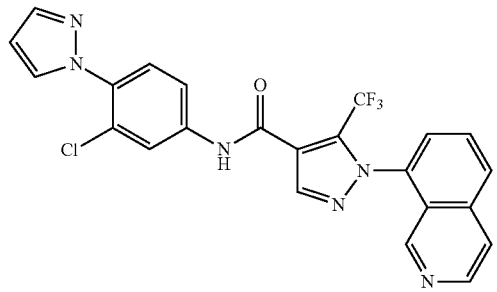 [SMILES: O=C(Nc1ccc(-n2cccn2)c(Cl)c1)c1cnn(-c2cccc3ccncc23)c1C(F)(F)F]

¹H NMR (400 MHz, DMSO-d₆) δ ppm 11.10 (s, 1H), 8.92 (s, 1H), 8.74 (d, J=6.1 Hz, 1H), 8.63 (s, 1H), 8.42 (d, J=8.4 Hz, 1H), 8.34 (d, J=6.1 Hz, 1H), 8.17-8.11 (m, 2H), 8.11-8.05 (m, 2H), 7.83 (dd, J=2.2, 8.7 Hz, 1H), 7.73 (d, J=1.4 Hz, 1H), 7.59 (d, J=8.8 Hz, 1H), 7.62-7.57 (m, 1H), 6.56-6.46 (m, 1H). LCMS (ESI): m/z 482.9 [M+H]⁺

Example 95

N-(6-cyano-5-(trifluoromethyl)pyridin-3-yl)-1-(isoquinolin-8-yl)-5-(trifluoromethyl)-1H-pyrazole-4-carboxamide, Cpd 13

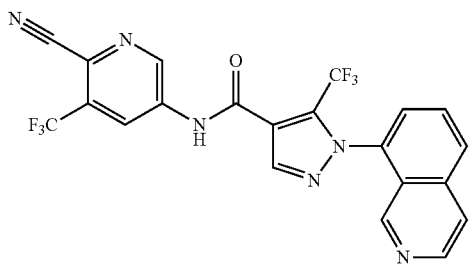 [SMILES: N#Cc1ncc(NC(=O)c2cnn(-c3cccc4ccncc34)c2C(F)(F)F)cc1C(F)(F)F]

$^1$H NMR (400 MHz, DMSO-d$_6$) δ ppm 7.97 (br. s., 2H) 8.07 (d, J=4.70 Hz, 1H) 8.29 (br. s., 1H) 8.61 (br. s., 2H) 8.67 (d, J=5.09 Hz, 1H) 8.81 (br. s., 1H) 9.26 (br. s., 1H) 11.61 (br. s., 1H). LCMS (ESI): m/z 477.0 [M+H]$^+$

Example 96

N-(4-(2-aminopyrimidin-4-yl)-3-chlorophenyl)-1-(isoquinolin-8-yl)-5-(trifluoromethyl)-1H-pyrazole, Cpd 14

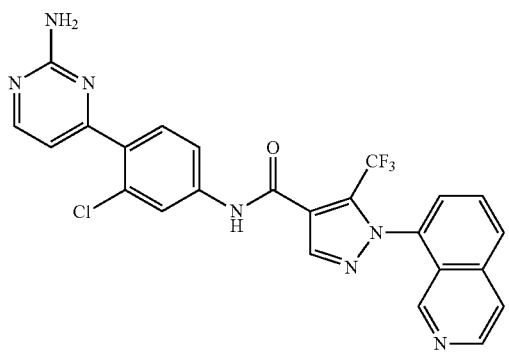 [SMILES: Nc1nccc(-c2ccc(NC(=O)c3cnn(-c4cccc5ccncc45)c3C(F)(F)F)cc2Cl)n1]

$^1$H NMR (400 MHz, DMSO-d$_6$) ☐ ppm 11.27 (s, 1H), 8.91 (s, 1H), 8.74 (d, J=6.1 Hz, 1H), 8.67 (s, 1H), 8.49 (d, J=6.3 Hz, 1H), 8.42 (d, J=8.4 Hz, 1H), 8.33 (d, J=6.1 Hz, 1H), 8.17-8.10 (m, 2H), 8.09-8.04 (m, 1H), 7.92 (dd, J=2.0, 8.6 Hz, 1H), 7.74 (d, J=8.6 Hz, 1H), 7.24 (d, J=6.3 Hz, 1H), 4.46 (br s, 15H), 5.16-3.77 (m, 1H), 3.91 (br s, 1H), 5.16-3.77 (m, 1H). LCMS (ESI): m/z 509.9 [M+H]$^+$

Example 97

N-(5-chloro-6-(1H-pyrazol-1-yl)pyridin-3-yl)-1-(isoquinolin-8-yl)-5-(trifluoromethyl)-1H-pyrazole-4-carboxamide, Cpd 15

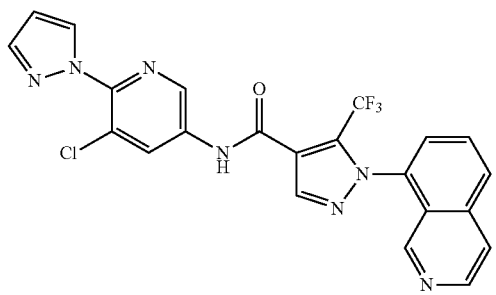 [SMILES: O=C(Nc1cnc(-n2cccn2)c(Cl)c1)c1cnn(-c2cccc3ccncc23)c1C(F)(F)F]

$^1$H NMR (400 MHz, DMSO-d$_6$) δ ppm 6.54 (br. s., 1H) 7.78 (s, 1H) 8.09-8.29 (m, 3H) 8.40-8.53 (m, 2H) 8.61-8.70 (m, 1H) 8.65 (br. s., 1H) 8.77 (br. s., 2H) 8.91 (br. s., 1H) 9.00-9.14 (m, 1H) 9.06 (br. s., 1H) 11.54 (br. s., 1H). LCMS (ESI): m/z 483.9 [M+H]$^+$

Example 98

N-(5-chloro-6-(1,1-dioxidoisothiazolidin-2-yl)pyridin-3-yl)-1-(isoquinolin-8-yl)-5-(trifluoromethyl)-1H-pyrazole-4-carboxamide, Cpd 20

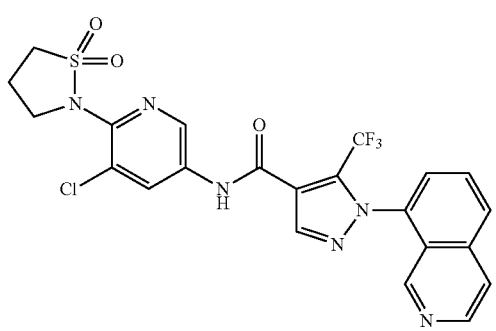 [SMILES: O=C(Nc1cnc(N2CCCS2(=O)=O)c(Cl)c1)c1cnn(-c2cccc3ccncc23)c1C(F)(F)F]

$^1$H NMR (400 MHz, CHLOROFORM-d) δ ppm 8.78 (s, 1H), 8.66 (d, J=5.3 Hz, 1H), 8.55 (d, J=2.2 Hz, 1H), 8.53 (br. s., 1H), 8.36 (d, J=2.2 Hz, 1H), 8.25 (s, 1H), 8.07 (d, J=8.4 Hz, 1H), 7.86-7.82 (m, 1H), 7.82-7.79 (m, 1H), 7.67 (d, J=7.1 Hz, 1H), 4.11 (t, J=7.1 Hz, 2H), 3.28 (t, J=7.5 Hz, 2H), 2.67-2.61 (m, 2H). LCMS (ESI): m/z 536.9 [M+H]$^+$

Example 99

N-(5-chloro-6-(3-methyl-1H-1,2,4-triazol-1-yl)pyridin-3-yl)-1-(isoquinolin-8-yl)-5-(trifluoromethyl)-1H-pyrazole-4-carboxamide, Cpd 30

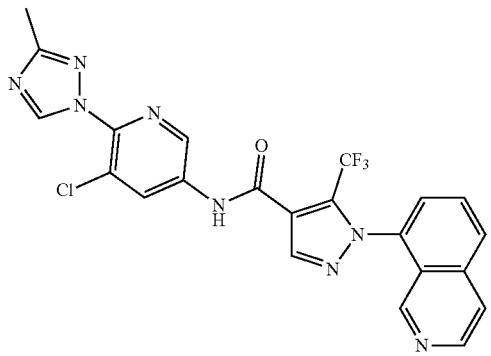 [SMILES: Cc1ncn(-c2ncc(NC(=O)c3cnn(-c4cccc5ccncc45)c3C(F)(F)F)cc2Cl)n1]

$^1$H NMR (400 MHz, METHANOL-d$_4$) δ ppm 2.46-2.49 (m, 1H) 2.48 (s, 2H) 7.87 (d, J=7.28 Hz, 1H) 7.98 (dd, J=8.27, 7.39 Hz, 1H) 8.04 (dd, J=5.95, 0.88 Hz, 1H) 8.26 (d, J=8.60 Hz, 1H) 8.41 (s, 1H) 8.62 (d, J=5.73 Hz, 1H) 8.66 (s, 1H) 8.70 (d, J=2.43 Hz, 1H) 8.80 (d, J=2.43 Hz, 1H) 8.87 (s, 1H). LCMS (ESI): m/z 498.9 [M+H]$^+$

Example 100

N-(3-chloro-4-(5-methyl-1H-1,2,4-triazol-1-yl)phenyl)-1-(isoquinolin-8-yl)-5-(trifluoromethyl)-1H-pyrazole-4-carboxamide, Cpd 31

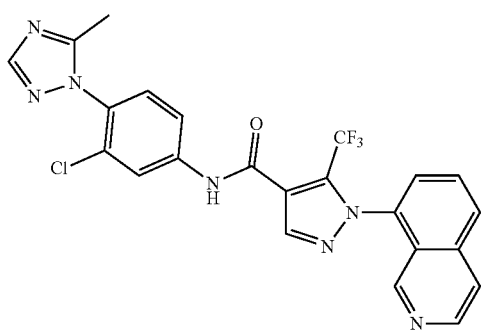 [SMILES: Cc1ncnn1-c1ccc(NC(=O)c2cnn(-c3cccc4ccncc34)c2C(F)(F)F)cc1Cl]

$^1$H NMR (400 MHz, METHANOL-d$_4$) δ ppm 2.44 (s, 3H) 7.87 (d, J=7.28 Hz, 1H) 7.95-8.02 (m, 1H) 8.04 (d, J=5.95 Hz, 1H) 8.09 (s, 1H) 8.27 (d, J=8.38 Hz, 1H) 8.43 (s, 1H) 8.63 (d, J=5.73 Hz, 1H) 8.66 (s, 1H) 8.75 (d, J=2.43 Hz, 1H) 8.85 (d, J=2.43 Hz, 1H). LCMS (ESI): m/z 498.9 [M+H]$^+$

Example 101

N-(5-cyano-6-(2H-1,2,3-triazol-2-yl)pyridin-3-yl)-1-(isoquinolin-8-yl)-5-(trifluoromethyl)-1H-pyrazole-4-carboxamide, Cpd 19

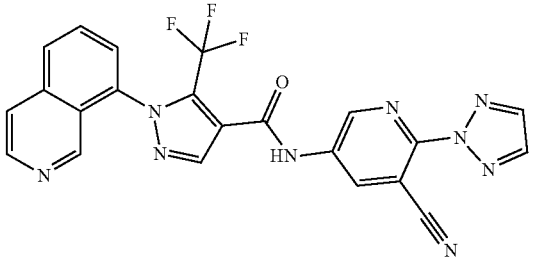 [SMILES: N#Cc1cc(NC(=O)c2cnn(-c3cccc4ccncc34)c2C(F)(F)F)cnc1-n1nccn1]

$^1$H NMR (400 MHz, METHANOL-d$_4$) δ ppm 8.14 (s, 2H), 8.20 (d, J=7.50 Hz, 1H), 8.36 (t, J=7.94 Hz, 1H), 8.52 (s, 1H), 8.56 (d, J=8.38 Hz, 1H), 8.64 (d, J=6.17 Hz, 1H), 8.77 (d, J=6.17 Hz, 1H), 8.92 (d, J=2.65 Hz, 1H), 9.10 (br. s., 1H), 9.28 (s, 1H). LCMS (ESI): m/z 476.0 [M+H]$^+$

Example 102

N-(5-chloro-6-(oxazol-2-yl)pyridin-3-yl)-1-(isoquinolin-8-yl)-5-(trifluoromethyl)-1H-pyrazole-4-carboxamide, Cpd 22

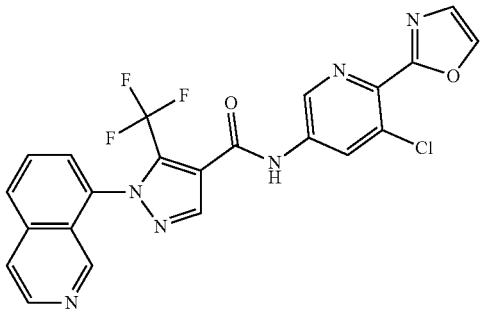 [SMILES: O=C(Nc1cnc(-c2ncco2)c(Cl)c1)c1cnn(-c2cccc3ccncc23)c1C(F)(F)F]

$^1$H NMR (400 MHz, DMSO-d$_6$) δ ppm 8.93 (d, J=2.2 Hz, 1H), 8.67 (d, J=5.9 Hz, 1H), 8.60 (s, 1H), 8.58-8.53 (m, 2H), 8.33 (d, J=0.8 Hz, 1H), 8.29 (dd, J=1.7, 7.3 Hz, 1H), 8.08-8.04 (m, 1H), 8.00-7.94 (m, 2H), 7.50 (s, 1H). LCMS (ESI): m/z 531.0 [M+H]$^+$

Example 103

N-(3-chloro-4-(2H-1,2,3-triazol-2-yl)phenyl)-1-(isoquinolin-8-yl)-5-(trifluoromethyl)-1H-pyrazole-4-carboxamide, Cpd 11

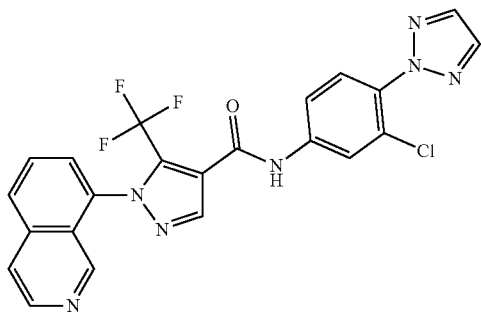 [SMILES: O=C(Nc1ccc(-n2nccn2)c(Cl)c1)c1cnn(-c2cccc3ccncc23)c1C(F)(F)F]

$^1$H NMR (400 MHz, CHLOROFORM-d) δ ppm 7.61-7.69 (m, 3H), 7.79-7.86 (m, 2H), 7.91 (s, 2H), 8.02-8.11 (m, 3H), 8.24 (s, 1H), 8.69 (d, J=5.67 Hz, 1H), 8.75 (s, 1H). LCMS (ESI): m/z 531.0 [M+H]$^+$

Example 104

N-(3-chloro-4-(1H-1,2,3-triazol-1-yl)phenyl)-1-(isoquinolin-8-yl)-5-(trifluoromethyl)-1H-pyrazole-4-carboxamide, Cpd 18

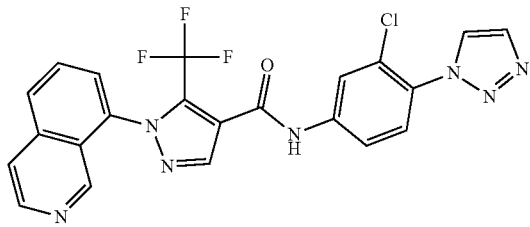 [SMILES: O=C(Nc1ccc(-n2ccnn2)c(Cl)c1)c1cnn(-c2cccc3ccncc23)c1C(F)(F)F]

$^1$H NMR (400 MHz, CHLOROFORM-d) δ ppm 7.63-7.70 (m, 3H), 7.80-7.87 (m, 2H), 7.90 (s, 1H), 8.01-8.11 (m, 3H), 8.15 (s, 1H), 8.26 (s, 1H), 8.70 (d, J=5.67 Hz, 1H), 8.76 (s, 1H). LCMS (ESI): m/z 483.9 [M+H]$^+$

Example 105

N-(3-chloro-4-(3-methyl-1H-1,2,4-triazol-1-yl)phenyl)-1-(isoquinolin-8-yl)-5-(trifluoromethyl)-1H-pyrazole-4-carboxamide, Cpd 29

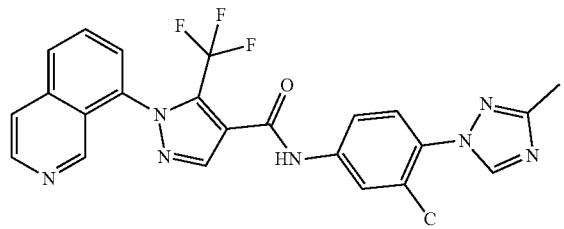 [SMILES: Cc1ncn(-c2ccc(NC(=O)c3cnn(-c4cccc5ccncc45)c3C(F)(F)F)cc2C)n1]

$^1$H NMR (400 MHz, METHANOL-d$_4$) δ ppm 2.58 (s, 3H), 7.70 (d, J=8.61 Hz, 1H), 7.91 (dd, J=8.61, 2.15 Hz, 1H), 8.21-8.28 (m, 2H), 8.40 (t, J=7.92 Hz, 1H), 8.48 (s, 1H), 8.60 (d, J=8.41 Hz, 1H), 8.70-8.75 (m, 1H), 8.76-8.82 (m, 1H), 9.40 (s, 1H), 9.56 (s, 1H). LCMS (ESI): m/z 497.9 [M+H]$^+$ Following the procedure described in Example 180, above, selecting and substituting the appropriate reagents, starting materials, and purification methods, and adjusting reaction temperatures, times and other variables or parameters, as needed or desirable, as would be readily recognized by those skilled in the art, the following compounds were prepared:

Example 322

N-(5-chloro-6-(2H-1,2,3-triazol-2-yl)pyridin-3-yl)-1-(1-(dimethylamino)isoquinolin-4-yl)-5-(trifluoromethyl)-1H-pyrazole-4-carboxamide, Cpd 322

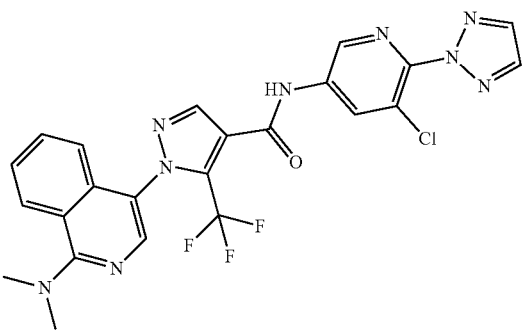 [SMILES: CN(C)c1ncc(-n2ncc(C(=O)Nc3cnc(-n4nccn4)c(Cl)c3)c2C(F)(F)F)c2ccccc12]

$^1$H NMR (400 MHz, DMSO-d$_6$) δ ppm 11.43 (s, 1H), 8.89 (d, J=2.21 Hz, 1H), 8.69 (d, J=2.21 Hz, 1H), 8.61 (s, 1H), 8.33 (d, J=8.60 Hz, 1H), 8.21 (s, 1H), 8.16 (s, 2H), 7.76-7.83 (m, 1H), 7.63-7.72 (m, 1H), 7.00 (d, J=7.94 Hz, 1H), 3.29 (s, 6H). LC-MS: (ES, m/z): [M+1]$^+$ 527.9

Example 323

N-(5-chloro-6-(2H-1,2,3-triazol-2-yl)pyridin-3-yl)-1-(1-(methylamino)isoquinolin-4-yl)-5-(trifluoromethyl)-1H-pyrazole-4-carboxamide, Cpd 323

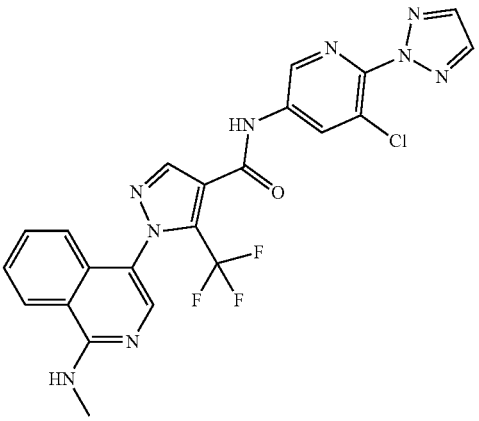 [SMILES: CNc1ncc(-n2ncc(C(=O)Nc3cnc(-n4nccn4)c(Cl)c3)c2C(F)(F)F)c2ccccc12]

¹H NMR (400 MHz, DMSO-d₆) δ ppm 11.54 (s, 1H), 8.95 (d, J=2.21 Hz, 1H), 8.74 (d, J=2.21 Hz, 1H), 8.70 (s, 2H), 8.26 (s, 1H), 8.20 (s, 2H), 7.89-7.96 (m, 1H), 7.78-7.86 (m, 1H), 7.03 (d, J=8.16 Hz, 1H), 3.18 (br d, J=2.65 Hz, 3H). LC-MS: (ES, m/z): [M+1]⁺ 513.9

Example 324

N-(5-chloro-6-(2H-1,2,3-triazol-2-yl)pyridin-3-yl)-1-(8-fluoro-1-(methylamino)isoquinolin-4-yl)-5-(trifluoromethyl)-1H-pyrazole-4-carboxamide, Cpd 324

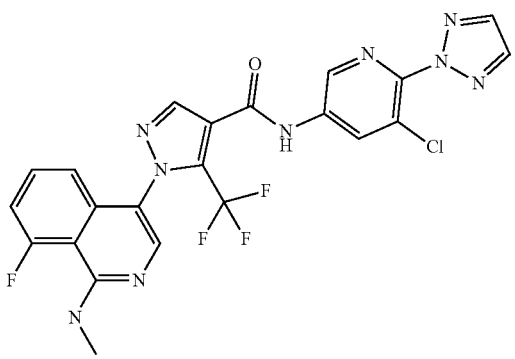 [SMILES: CNc1ncc(-n2ncc(C(=O)Nc3cnc(-n4nccn4)c(Cl)c3)c2C(F)(F)F)c2cccc(F)c12]

¹H NMR (400 MHz, METHANOL-d₄) δ ppm 3.33 (d, J=1.76 Hz, 3H), 6.98 (br d, J=8.82 Hz, 1H), 7.61-7.70 (m, 1H), 7.93-8.01 (m, 1H), 8.04 (s, 2H), 8.14 (d, J=1.54 Hz, 1H), 8.43 (s, 1H), 8.71 (d, J=2.20 Hz, 1H), 8.80 (br s, 1H). LC-MS: (ES, m/z): [M+1]⁺ 532.0

Example 325

N-(5-cyano-6-(2H-1,2,3-triazol-2-yl)pyridin-3-yl)-1-(8-fluoro-1-(methylamino)isoquinolin-4-yl)-5-(trifluoromethyl)-1H-pyrazole-4-carboxamide, Cpd 325

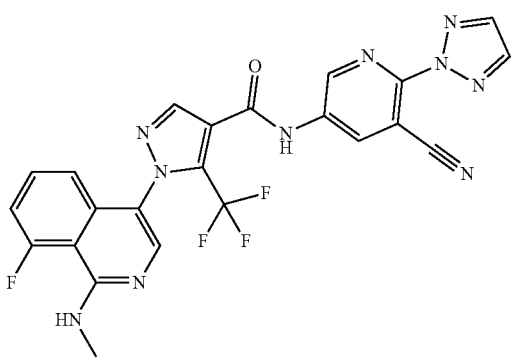 [SMILES: CNc1ncc(-n2ncc(C(=O)Nc3cnc(-n4nccn4)c(C#N)c3)c2C(F)(F)F)c2cccc(F)c12]

¹H NMR (400 MHz, DMSO-d₆) δ ppm 3.13 (s, 3H), 6.76 (d, J=8.16 Hz, 1H), 7.56 (dd, J=13.34, 8.05 Hz, 1H), 7.83 (td, J=8.16, 5.29 Hz, 1H), 8.23 (s, 1H), 8.28 (s, 2H), 8.54 (br d, J=10.80 Hz, 1H), 8.65 (s, 1H), 8.91 (d, J=2.43 Hz, 1H), 9.16 (d, J=2.43 Hz, 1H), 11.57 (s, 1H). LC-MS: (ES, m/z): [M+1]⁺ 522.9

Example 326

1-(8-aminoquinolin-5-yl)-N-(5-cyano-6-(2H-1,2,3-triazol-2-yl)pyridin-3-yl)-5-(trifluoromethyl)-1H-pyrazole-4-carboxamide, Cpd 326

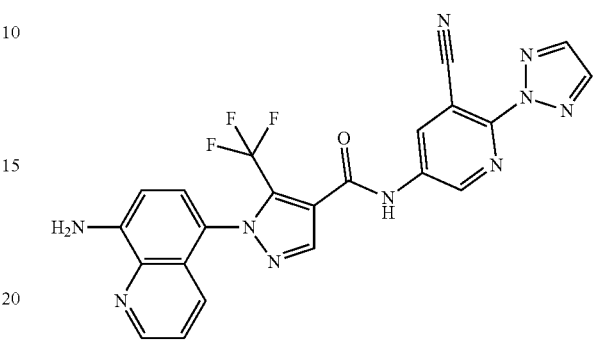

¹H NMR (400 MHz, METHANOL-d₄) δ ppm 9.07 (d, J=2.4 Hz, 1H), 8.90 (d, J=2.6 Hz, 1H), 8.83-8.76 (m, 1H), 8.31 (s, 1H), 8.13 (s, 2H), 7.51-7.48 (m, 2H), 7.45 (d, J=8.2 Hz, 1H), 6.96 (d, J=8.2 Hz, 1H). LC-MS: (ES, m/z): [M+1]⁺ 491.0

Example 327

1-(1-aminoisoquinolin-4-yl)-N-(5-chloro-2-fluoro-4-(2H-1,2,3-triazol-2-yl)phenyl)-5-(trifluoromethyl)-1H-pyrazole-4-carboxamide, Cpd 327

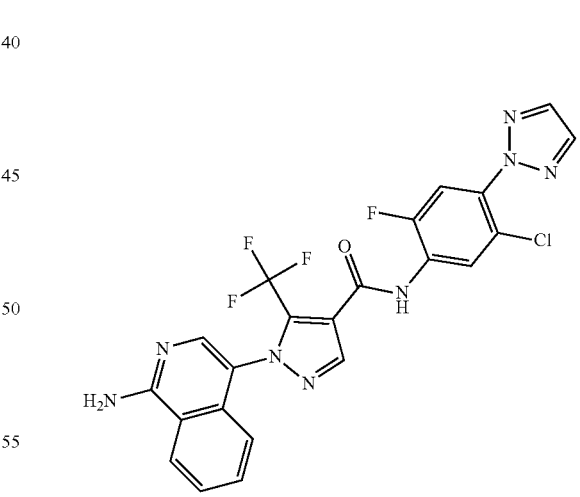

¹H NMR (400 MHz, DMSO-d₆) δ ppm 10.92 (s, 1H), 9.45 (br s, 2H), 8.73 (d, J=8.16 Hz, 1H), 8.56 (s, 1H), 8.32 (s, 1H), 8.27 (d, J=7.28 Hz, 1H), 8.21 (s, 2H), 7.99-8.06 (m, 1H), 7.85-7.93 (m, 2H), 7.09 (d, J=8.16 Hz, 1H). LC-MS: (ES, m/z): [M+1]⁺ 517.0

Example 328

1-(1-aminoisoquinolin-5-yl)-N-(5-cyano-6-(2H-1,2,3-triazol-2-yl)pyridin-3-yl)-5-(trifluoromethyl)-1H-pyrazole-4-carboxamide, Cpd 328

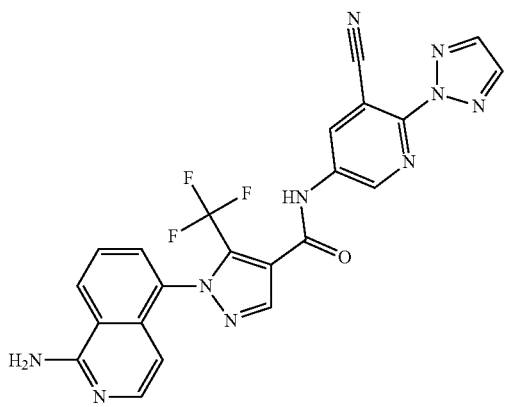 [SMILES: N#Cc1cc(NC(=O)c2cnn(-c3cccc4c(N)nccc34)c2C(F)(F)F)cnc1-n1nccn1]

¹H NMR (400 MHz, METHANOL-d₄) δ ppm 9.07 (s, 1H), 8.91 (s, 1H), 8.67 (d, J=8.60 Hz, 1H), 8.42 (s, 1H), 8.07-8.17 (m, 3H), 7.93 (t, J=8.16 Hz, 1H), 7.68 (br d, J=7.28 Hz, 1H), 6.45 (d, J=6.84 Hz, 1H). LC-MS: (ES, m/z): [M+1]⁺ 491.0

Example 329

1-(2-aminoquinolin-4-yl)-N-(5-cyano-6-(2H-1,2,3-triazol-2-yl)pyridin-3-yl)-5-(trifluoromethyl)-1H-pyrazole-4-carboxamide, Cpd 329

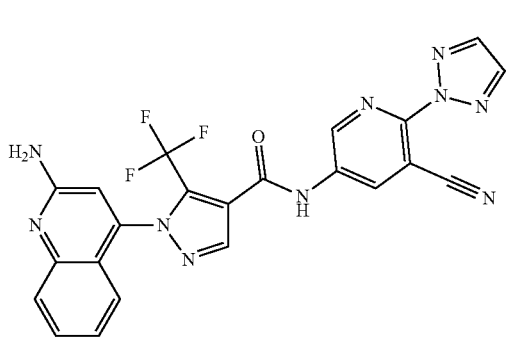 [SMILES: N#Cc1cc(NC(=O)c2cnn(-c3cc(N)nc4ccccc34)c2C(F)(F)F)cnc1-n1nccn1]

¹H NMR (400 MHz, METHANOL-d₄) δ ppm 9.07 (br s, 1H), 8.90 (s, 1H), 8.46 (s, 1H), 8.37 (d, J=8.38 Hz, 1H), 8.15 (br s, 2H), 7.96-8.02 (m, 1H), 7.90 (d, J=8.38 Hz, 1H), 7.74 (t, J=7.83 Hz, 1H), 6.99 (s, 1H). LC-MS: (ES, m/z): [M+1]⁺ 490.9

Example 330

1-(1-aminoisoquinolin-5-yl)-N-(5-chloro-6-(2H-1,2,3-triazol-2-yl)pyridin-3-yl)-5-(trifluoromethyl)-1H-pyrazole-4-carboxamide, Cpd 330

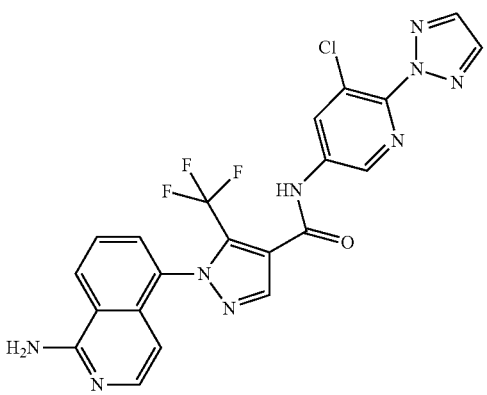 [SMILES: Nc1nccc2c(-n3ncc(C(=O)Nc4cnc(-n5nccn5)c(Cl)c4)c3C(F)(F)F)cccc12]

¹H NMR (400 MHz, METHANOL-d₄) δ ppm 6.25 (d, J=6.17 Hz, 1H), 7.65-7.70 (m, 1H), 7.79 (d, J=6.17 Hz, 1H), 7.83 (d, J=7.50 Hz, 1H), 8.04 (s, 2H), 8.37 (s, 1H), 8.42 (d, J=8.38 Hz, 1H), 8.73 (d, J=2.20 Hz, 1H), 8.81 (d, J=2.21 Hz, 1H). LC-MS: (ES, m/z): [M+1]⁺ 499.9

Example 331

1-(2-aminoquinolin-5-yl)-N-(5-chloro-6-(2H-1,2,3-triazol-2-yl)pyridin-3-yl)-5-(trifluoromethyl)-1H-pyrazole-4-carboxamide, Cpd 331

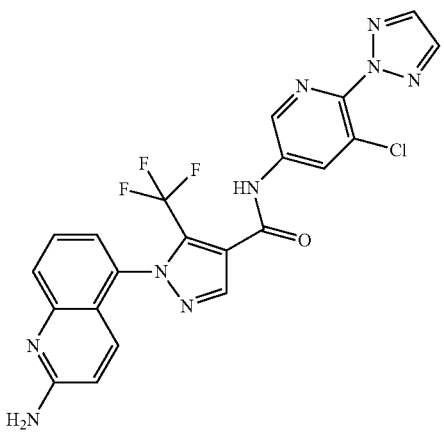 [SMILES: Nc1ccc2c(-n3ncc(C(=O)Nc4cnc(-n5nccn5)c(Cl)c4)c3C(F)(F)F)cccc2n1]

¹H NMR (400 MHz, DMSO-d₆) δ ppm 7.16 (d, J=9.70 Hz, 1H), 7.60 (d, J=9.48 Hz, 1H), 7.69 (d, J=7.06 Hz, 1H), 7.89-7.98 (m, 2H), 8.17 (s, 2H), 8.67 (s, 1H), 8.70 (d, J=2.20 Hz, 1H), 8.92 (d, J=2.20 Hz, 1H), 11.46 (s, 1H). LC-MS: (ES, m/z): [M+1]⁺ 499.9

Example 332

1-(2-aminoquinolin-5-yl)-N-(5-cyano-6-(2H-1,2,3-triazol-2-yl)pyridin-3-yl)-5-(trifluoromethyl)-1H-pyrazole-4-carboxamide, Cpd 332

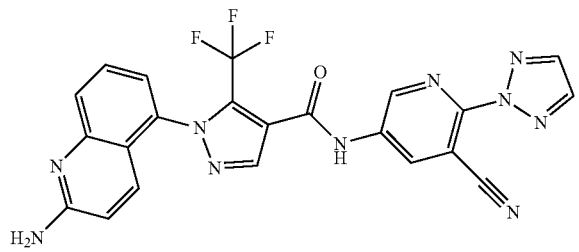 [SMILES: N#Cc1cc(NC(=O)c2cnn(-c3cccc4nc(N)ccc34)c2C(F)(F)F)cnc1-n1nccn1]

¹H NMR (400 MHz, DMSO-d₆) δ ppm 7.14-7.21 (m, 1H), 7.62 (d, J=9.70 Hz, 1H), 7.67-7.74 (m, 1H), 7.90-7.99 (m, 2H), 8.30 (s, 2H), 8.71 (s, 1H), 8.93 (d, J=2.43 Hz, 1H), 9.18 (d, J=2.21 Hz, 1H), 11.61 (br s, 1H). LC-MS: (ES, m/z): [M+1]⁺ 490.9

Example 333

1-(1-aminoisoquinolin-4-yl)-N-(5-chloro-2-methyl-6-(1-methyl-1H-pyrazol-3-yl)pyridin-3-yl)-5-(trifluoromethyl)-1H-pyrazole-4-carboxamide, Cpd 333

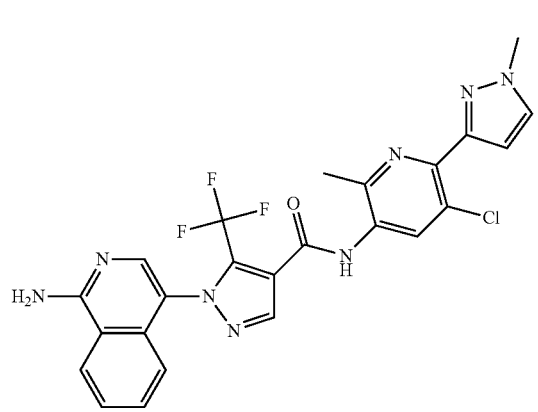 [SMILES: Cc1nc(-c2ccn(C)n2)c(Cl)cc1NC(=O)c1cnn(-c2cnc(N)c3ccccc23)c1C(F)(F)F]

¹H NMR (400 MHz, DMSO-d₆) δ ppm 10.48 (s, 1H), 9.54 (br s, 1H), 8.72 (d, J=8.38 Hz, 1H), 8.56 (s, 1H), 8.30 (s, 1H), 8.05 (s, 1H), 8.01 (t, J=7.94 Hz, 1H), 7.87 (t, J=7.72 Hz, 1H), 7.76 (s, 1H), 7.05 (br d, J=8.16 Hz, 1H), 6.73 (s, 1H), 3.90 (s, 3H), 2.49 (br s, 3H). LC-MS: (ES, m/z): [M+1]⁺ 526.9

Example 334

1-(1-aminoisoquinolin-4-yl)-N-(2,5-dimethyl-6-(2H-1,2,3-triazol-2-yl)pyridin-3-yl)-5-(trifluoromethyl)-1H-pyrazole-4-carboxamide, Cpd 334

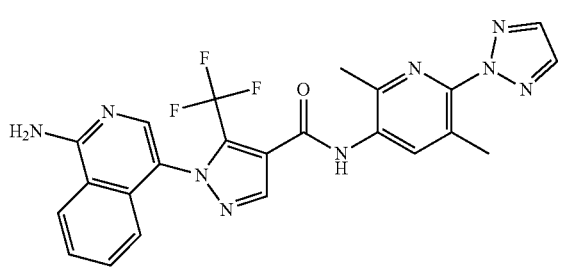 [SMILES: Cc1cc(NC(=O)c2cnn(-c3cnc(N)c4ccccc34)c2C(F)(F)F)c(C)nc1-n1nccn1]

¹H NMR (400 MHz, DMSO-d₆) δ ppm 10.59 (s, 1H), 9.69 (br s, 2H), 8.78 (d, J=8.2 Hz, 1H), 8.62 (s, 1H), 8.35 (s, 1H), 8.13 (s, 2H), 8.08-8.02 (m, 2H), 7.91 (t, J=7.7 Hz, 1H), 7.10 (d, J=8.4 Hz, 1H), 2.50 (br s, 2H), 2.50-2.49 (m, 1H), 2.23 (s, 3H). LC-MS: (ES, m/z): [M+1]⁺ 494.0

Example 335

1-(1-aminoisoquinolin-4-yl)-N-(5-chloro-2-methyl-4-(2H-1,2,3-triazol-2-yl)phenyl)-5-(trifluoromethyl)-1H-pyrazole-4-carboxamide, Cpd 335

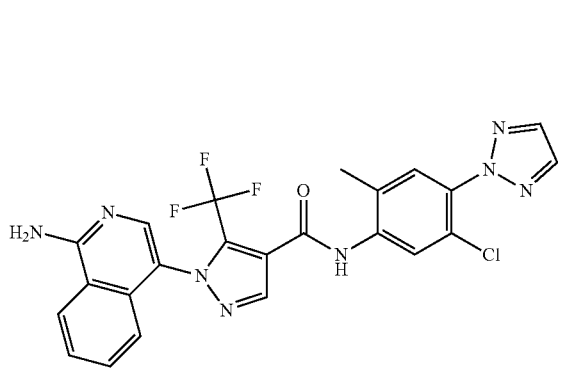 [SMILES: Cc1cc(-n2nccn2)c(Cl)cc1NC(=O)c1cnn(-c2cnc(N)c3ccccc23)c1C(F)(F)F]

¹H NMR (400 MHz, DMSO-d₆) δ ppm 10.48 (s, 1H), 8.98 (br s, 2H), 8.65 (d, J=8.38 Hz, 1H), 8.56 (s, 1H), 8.22 (s, 1H), 8.15 (s, 2H), 7.90-7.96 (m, 1H), 7.86 (s, 1H), 7.80 (t, J=7.39 Hz, 1H), 7.66 (s, 1H), 7.04 (br d, J=8.16 Hz, 1H), 2.36 (s, 3H). LC-MS: (ES, m/z): [M+1]⁺ 512.9

Example 336

1-(1-aminoisoquinolin-4-yl)-N-(5-chloro-2-methyl-6-(1H-pyrazol-1-yl)pyridin-3-yl)-5-(trifluoromethyl)-1H-pyrazole-4-carboxamide, Cpd 336

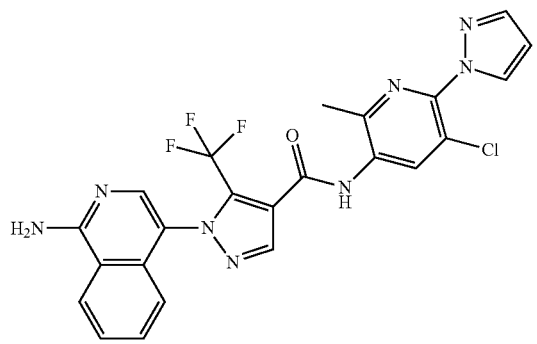 [SMILES: Cc1nc(-n2cccn2)c(Cl)cc1NC(=O)c1cnn(-c2cnc(N)c3ccccc23)c1C(F)(F)F]

$^1$H NMR (400 MHz, DMSO-d$_6$) δ ppm 2.53 (s, 3H), 6.55 (dd, J=2.43, 1.76 Hz, 1H), 6.94 (d, J=8.38 Hz, 1H), 7.50 (s, 2H), 7.57-7.63 (m, 1H), 7.69-7.75 (m, 1H), 7.80 (d, J=1.10 Hz, 1H), 7.97 (s, 1H), 8.26 (d, J=1.98 Hz, 1H), 8.29-8.37 (m, 2H), 8.46 (s, 1H) 10.53 (br s, 1H). LC-MS: (ES, m/z): [M+1]$^+$ 513.1

Example 337

1-(1-aminoisoquinolin-4-yl)-N-(5-cyano-2-methyl-4-(2H-1,2,3-triazol-2-yl)phenyl)-5-(trifluoromethyl)-1H-pyrazole-4-carboxamide, Cpd 337

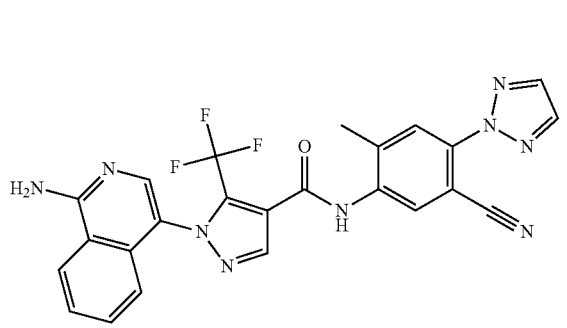 [SMILES: Cc1cc(-n2nccn2)c(C#N)cc1NC(=O)c1cnn(-c2cnc(N)c3ccccc23)c1C(F)(F)F]

$^1$H NMR (400 MHz, DMSO-d$_6$) δ ppm 10.50 (s, 1H), 9.09-9.43 (m, 2H), 8.67 (d, J=8.16 Hz, 1H), 8.56 (s, 1H), 8.22-8.30 (m, 1H), 8.27 (s, 2H), 8.14 (s, 1H), 8.05 (s, 1H), 7.95-8.01 (m, 1H), 7.84 (t, J=7.61 Hz, 1H), 7.05 (br d, J=8.38 Hz, 1H), 2.47 (br s, 3H). LC-MS: (ES, m/z): [M+1]$^+$ 504.1

Example 338

1-(1-aminoisoquinolin-4-yl)-N-(5-cyano-2-methyl-6-(2H-1,2,3-triazol-2-yl)pyridin-3-yl)-5-(trifluoromethyl)-1H-pyrazole-4-carboxamide, Cpd 338

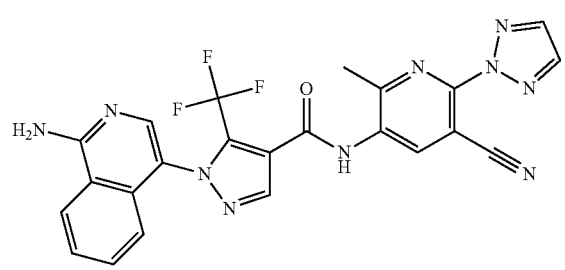 [SMILES: Cc1nc(-n2nccn2)c(C#N)cc1NC(=O)c1cnn(-c2cnc(N)c3ccccc23)c1C(F)(F)F]

$^1$H NMR. (400 MHz, DMSO-d$_6$) δ ppm 10.89 (s, 1H) 9.32 (br s, 2H), 8.70-8.75 (m, 1H), 8.66 (d, J=8.60 Hz, 2H), 8.32 (s, 2H), 8.30 (s, 1H), 7.96-8.02 (m, 1H), 7.85 (t, J=7.61 Hz, 1H), 7.07 (d, J=8.16 Hz, 1H), 2.68 (s, 3H). LC-MS: (ES, m/z): [M+1]$^+$ 505.1

Example 339

1-(1-aminoisoquinolin-4-yl)-5-(trifluoromethyl)-N-(2-(trifluoromethyl)pyridin-4-yl)-1H-pyrazole-4-carboxamide, Cpd 339

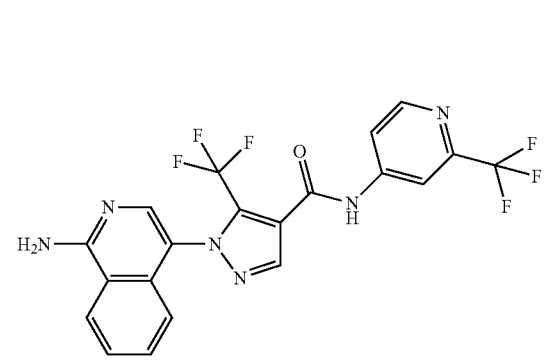 [SMILES: Nc1ncc(-n2ncc(C(=O)Nc3ccnc(C(F)(F)F)c3)c2C(F)(F)F)c2ccccc12]

$^1$H NMR (400 MHz, DMSO-d$_6$) δ ppm 7.05 (d, J=7.94 Hz, 1H), 7.84-7.91 (m, 1H), 7.97-8.03 (m, 2H), 8.28 (d, J=1.76 Hz, 1H), 8.31 (s, 1H), 8.63 (s, 1H), 8.66-8.74 (m, 2H), 9.37 (br s, 2H), 11.42 (s, 1H). LC-MS: (ES, m/z): [M+1]$^+$ 467.1

Example 377

1-(1-aminoisoquinolin-4-yl)-N-(6-methyl-5-(trifluoromethyl)pyridin-3-yl)-5-(trifluoromethyl)-1H-pyrazole-4-carboxamide, Cpd 377

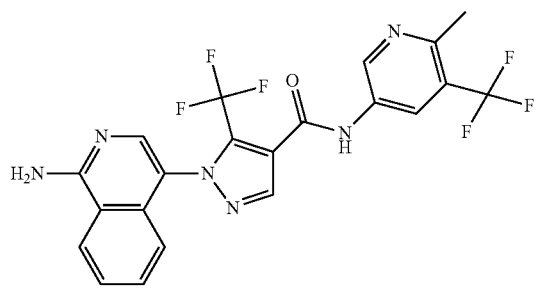 [SMILES: Cc1ncc(NC(=O)c2cnn(-c3cnc(N)c4ccccc34)c2C(F)(F)F)cc1C(F)(F)F]

$^1$H NMR (400 MHz, DMSO-$d_6$) δ ppm 11.31 (s, 1H), 9.23-10.37 (m, 2H), 9.07 (d, J=1.98 Hz, 1H), 8.77 (d, J=8.38 Hz, 1H), 8.66 (s, 1H), 8.58 (d, J=2.21 Hz, 1H), 8.35 (s, 1H), 7.97-8.05 (m, 1H), 7.83-7.91 (m, 1H), 7.02 (d, J=7.94 Hz, 1H), 2.60 (d, J=1.54 Hz, 3H). LC-MS: (ES, m/z): [M+1]$^+$ 480.9

Example 340

1-(1-aminoisoquinolin-4-yl)-N-(2-cyanopyridin-4-yl)-5-(trifluoromethyl)-1H-pyrazole-4-carboxamide, Cpd 340

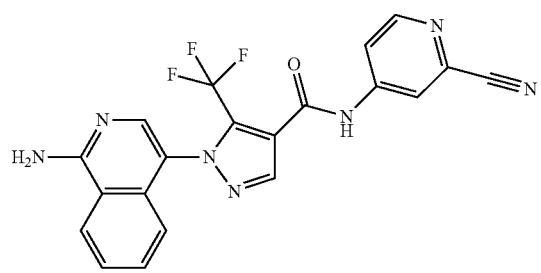 [SMILES: N#Cc1cc(NC(=O)c2cnn(-c3cnc(N)c4ccccc34)c2C(F)(F)F)ccn1]

$^1$H NMR (400 MHz, DMSO-$d_6$) δ ppm 7.06 (d, J=8.16 Hz, 1H), 7.86-7.92 (m, 1H), 7.99-8.08 (m, 2H), 8.35 (d, J=3.53 Hz, 2H), 8.66-8.72 (m, 2H), 8.76 (br d, J=8.60 Hz, 1H), 9.64 (br s, 2H), 11.59 (s, 1H). LC-MS: (ES, m/z): [M+1]$^+$ 424.0

Example 341

1-(1-aminoisoquinolin-4-yl)-N-(5-chloro-2-methyl-6-(4-methyl-2H-1,2,3-triazol-2-yl)pyridin-3-yl)-5-(trifluoromethyl)-1H-pyrazole-4-carboxamide, Cpd 341

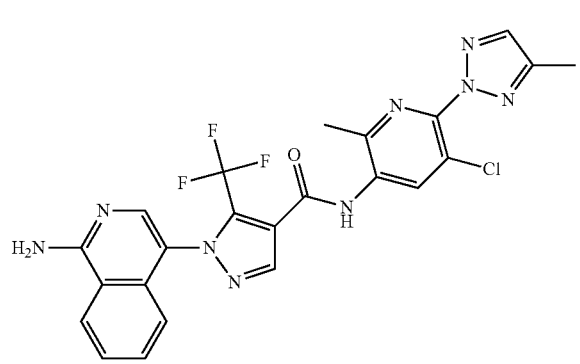 [SMILES: Cc1cnn(-c2nc(C)c(NC(=O)c3cnn(-c4cnc(N)c5ccccc45)c3C(F)(F)F)cc2Cl)n1]

$^1$H NMR (400 MHz, DMSO-$d_6$) δ ppm 2.36 (s, 3H), 2.53 (s, 3H), 6.97 (br d, J=8.16 Hz, 1H), 7.56-7.73 (m, 1H), 7.81 (br s, 1H), 7.93 (s, 1H), 8.08 (br s, 1H), 8.00-8.10 (m, 1H), 8.11-8.26 (m, 1H), 8.38 (s, 1H), 8.46 (br s, 1H), 8.51 (s, 1H), 10.63 (s, 1H). LC-MS: (ES, m/z): [M+1]$^+$ 527.9

Example 342

1-(1-aminoisoquinolin-4-yl)-5-(trifluoromethyl)-N-(5-(trifluoromethyl)pyridin-3-yl)-1H-pyrazole-4-carboxamide, Cpd 342

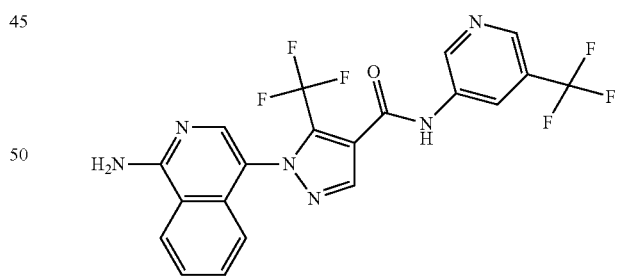

$^1$H NMR (400 MHz, DMSO-$d_6$) δ ppm 6.92 (d, J=8.16 Hz, 1H), 7.51 (s, 2H), 7.56-7.65 (m, 1H), 7.67-7.78 (m, 1H), 7.98 (s, 1H), 8.41 (br s, 1H), 8.48 (s, 1H), 8.61 (s, 1H), 8.76 (s, 1H), 9.13 (s, 1H), 11.14 (br s, 1H). LC-MS: (ES, m/z): [M+1]$^+$ 466.9

Example 343

1-(1-aminoisoquinolin-4-yl)-N-(5-bromo-2-methyl-6-(2H-1,2,3-triazol-2-yl)pyridin-3-yl)-5-(trifluoromethyl)-1H-pyrazole-4-carboxamide, Cpd 343

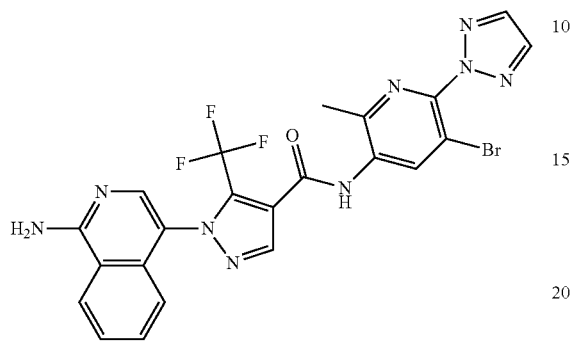

$^{1}$H NMR (400 MHz, DMSO-d$_6$) δ ppm 10.71 (s, 1H), 9.36 (br s, 2H), 8.68 (d, J=8.38 Hz, 1H), 8.58 (s, 1H), 8.50 (s, 1H), 8.28 (s, 1H), 8.11-8.18 (m, 2H), 7.94-8.02 (m, 1H), 7.84 (t, J=7.72 Hz, 1H), 7.04 (d, J=8.38 Hz, 1H), 2.51 (s, 3H). LC-MS: (ES, m/z): [M+1]$^+$ 557.9

Following the procedures described in Example 112 or 113, above, selecting and substituting the appropriate reagents, starting materials, and purification methods, and adjusting reaction temperatures, times and other variables or parameters, as needed or desirable, as would be readily recognized by those skilled in the art, the following compounds were prepared:

Example 344

N-(5-chloro-6-(2H-1,2,3-triazol-2-yl)pyridin-3-yl)-1-(2-oxo-1,2-dihydroquinolin-5-yl)-5-(trifluoromethyl)-1H-pyrazole-4-carboxamide, Cpd 344

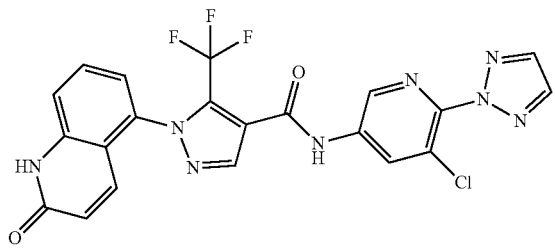 [SMILES: O=C(Nc1cnc(-n2nccn2)c(Cl)c1)c1cnn(-c2cccc3[nH]c(=O)ccc23)c1C(F)(F)F]

$^{1}$H NMR (400 MHz, DMSO-d$_6$) δ ppm 6.61 (d, J=9.70 Hz, 1H), 7.08 (d, J=9.70 Hz, 1H), 7.38 (d, J=7.72 Hz, 1H), 7.55 (d, J=8.16 Hz, 1H), 7.64-7.73 (m, 1H), 8.17 (s, 2H), 8.53 (s, 1H), 8.65 (s, 1H), 8.83 (s, 1H), 11.26 (s, 1H), 12.18 (br s, 1H). LC-MS: (ES, m/z): [M+1]$^+$ 501.1

Example 345

N-(5-chloro-6-methoxypyridin-3-yl)-1-(1-oxo-1,2-dihydroisoquinolin-5-yl)-5-(trifluoromethyl)-1H-pyrazole-4-carboxamide, Cpd 345

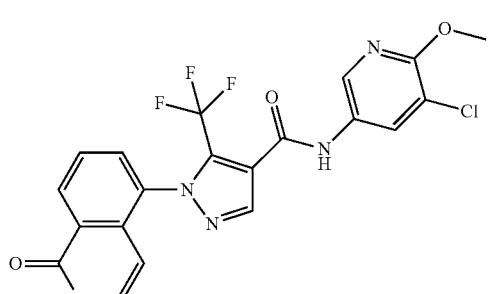

$^{1}$H NMR (400 MHz, DMSO-d$_6$) δ ppm 3.94 (s, 3H), 5.65 (d, J=7.28 Hz, 1H), 7.25-7.32 (m, 1H), 7.67 (t, J=7.83 Hz, 1H), 7.90-7.96 (m, 1H), 8.27 (d, J=2.43 Hz, 1H), 8.38-8.47 (m, 3H), 10.74 (s, 1H), 11.62 (br s, 1H). LC-MS: (ES, m/z): [M+1]$^+$ 463.9

Example 346

N-(5-cyanopyridin-3-yl)-1-(1-oxo-1,2-dihydroisoquinolin-5-yl)-5-(trifluoromethyl)-1H-pyrazole-4-carboxamide, Cpd 346

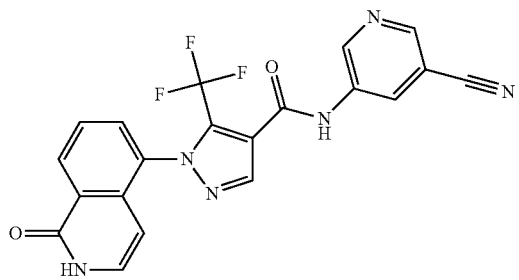 [SMILES: N#Cc1cncc(NC(=O)c2cnn(-c3cccc4c(=O)[nH]ccc34)c2C(F)(F)F)c1]

$^{1}$H NMR (400 MHz, DMSO-d$_6$) δ ppm 11.64 (br d, J=5.1 Hz, 1H), 11.31 (s, 1H), 9.14 (d, J=2.4 Hz, 1H), 8.79 (d, J=1.5 Hz, 1H), 8.68-8.63 (m, 1H), 8.60 (s, 1H), 8.43 (d, J=7.9 Hz, 1H), 7.94 (d, J=7.3 Hz, 1H), 7.67 (t, J=7.8 Hz, 1H), 7.32-7.25 (m, 1H), 5.66 (d, J=7.3 Hz, 1H). LC-MS: (ES, m/z): [M+1]$^+$ 425.1

Example 347

N-(2-methylpyridin-4-yl)-1-(1-oxo-1,2-dihydroiso-quinolin-5-yl)-5-(trifluoromethyl)-1H-pyrazole-4-carboxamide, Cpd 347

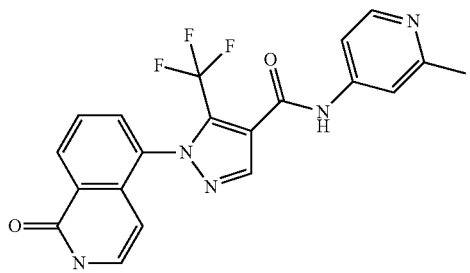 [SMILES: Cc1cc(NC(=O)c2cnn(-c3cccc4c(=O)[nH]ccc34)c2C(F)(F)F)ccn1]

$^{1}$H NMR (400 MHz, DMSO-d$_{6}$) δ ppm 2.69 (s, 3H), 5.66 (d, J=7.50 Hz, 1H), 7.25-7.31 (m, 1H), 7.67 (t, J=7.94 Hz, 1H), 7.94 (d, J=7.50 Hz, 1H), 8.09 (dd, J=6.73, 2.09 Hz, 1H), 8.21 (d, J=1.76 Hz, 1H), 8.43 (d, J=7.94 Hz, 1H), 8.63 (d, J=6.84 Hz, 1H), 8.71 (s, 1H), 11.65 (br d, J=5.51 Hz, 1H), 11.98 (s, 1H). LC-MS: (ES, m/z): [M+1]$^{+}$ 414.3

Example 348

N-(6-methyl-5-(trifluoromethyl)pyridin-3-yl)-1-(1-oxo-1,2-dihydroisoquinolin-5-yl)-5-(trifluorom-ethyl)-1H-pyrazole-4-carboxamide, Cpd 348

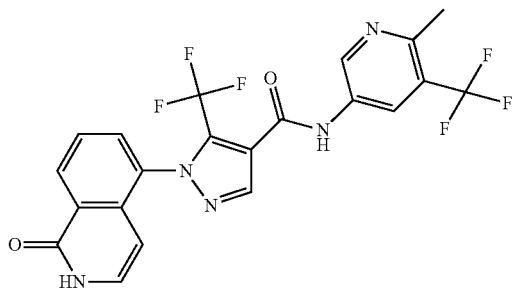 [SMILES: Cc1ncc(NC(=O)c2cnn(-c3cccc4c(=O)[nH]ccc34)c2C(F)(F)F)cc1C(F)(F)F]

$^{1}$H NMR (400 MHz, DMSO-d$_{6}$) δ ppm 11.61 (br d, J=5.51 Hz, 1H), 11.05 (s, 1H), 8.99 (d, J=1.98 Hz, 1H), 8.50 (s, 2H), 8.40 (d, J=7.94 Hz, 1H), 7.91 (dd, J=7.61, 0.99 Hz, 1H), 7.64 (t, J=7.83 Hz, 1H), 7.26 (dd, J=7.28, 5.95 Hz, 1H), 5.62 (d, J=7.28 Hz, 1H), 2.59 (d, J=1.54 Hz, 3H). LC-MS: (ES, m/z): [M+1]$^{+}$ 481.9

Example 349

1-(1-oxo-1,2-dihydroisoquinolin-5-yl)-N-(pyridin-4-yl)-5-(trifluoromethyl)-1H-pyrazole-4-carboxamide, Cpd 349

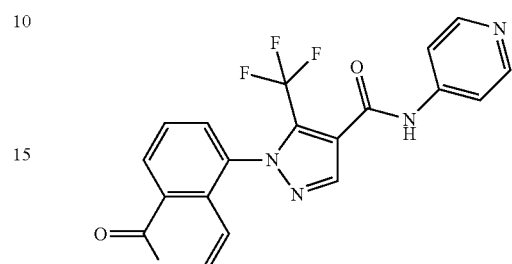

$^{1}$H NMR (400 MHz, DMSO-d$_{6}$) δ ppm 5.66 (d, J=7.28 Hz, 1H), 7.29 (br d, J=6.84 Hz, 1H), 7.63-7.75 (m, 3H), 7.93 (d, J=6.84 Hz, 1H), 8.44 (d, J=7.94 Hz, 1H), 8.47-8.54 (m, 3H), 10.93 (br s, 1H), 11.64 (br s, 1H). LC-MS: (ES, m/z): [M+1]$^{+}$ 399.9

Example 350

N-(2-cyclopropylpyridin-4-yl)-1-(1-oxo-1,2-dihy-droisoquinolin-5-yl)-5-(trifluoromethyl)-1H-pyra-zole-4-carboxamide, Cpd 350

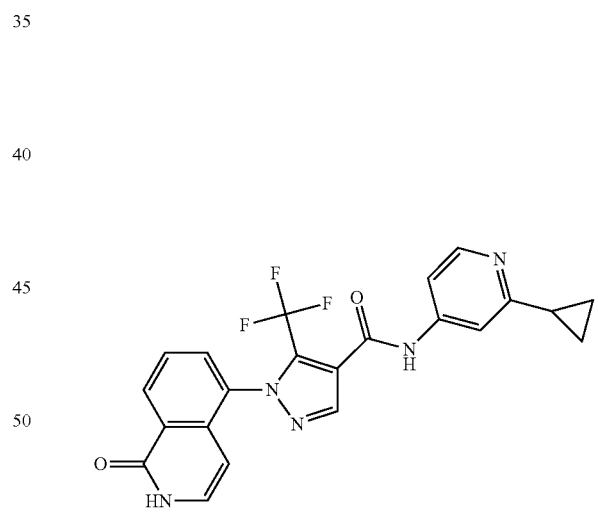

$^{1}$H NMR (400 MHz, DMSO-d$_{6}$) δ ppm 1.04-1.16 (m, 2H), 1.27-1.37 (m, 2H), 2.38 (br s, 1H), 5.63 (d, J=7.28 Hz, 1H), 7.27 (dd, J=7.28, 6.17 Hz, 1H), 7.65 (t, J=7.94 Hz, 1H), 7.87-7.97 (m, 2H), 8.03 (br s, 1H), 8.42 (d, J=7.94 Hz, 1H), 8.53 (d, J=6.61 Hz, 1H), 8.67 (br s, 1H), 11.63 (br d, J=5.51 Hz, 1H), 11.83 (br s, 1H). LC-MS: (ES, m/z): [M+1]$^{+}$ 440.2

Example 351

3-chloro-N,N-dimethyl-5-(1-(1-oxo-1,2-dihydroiso-quinolin-5-yl)-5-(trifluoromethyl)-1H-pyrazole-4-carboxamido)picolinamide, Cpd 351

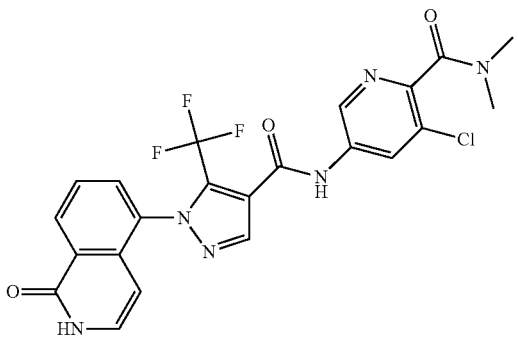 [SMILES: CN(C)C(=O)c1ncc(NC(=O)c2cnn(-c3cccc4c(=O)[nH]ccc34)c2C(F)(F)F)cc1Cl]

¹H NMR (400 MHz, DMSO-d₆) δ ppm 11.64 (br d, J=5.3 Hz, 1H), 11.13 (s, 1H), 8.82 (d, J=1.8 Hz, 1H), 8.52 (s, 1H), 8.43 (dd, J=2.8, 4.8 Hz, 2H), 7.94 (d, J=7.5 Hz, 1H), 7.67 (t, J=7.9 Hz, 1H), 7.29 (t, J=6.5 Hz, 1H), 5.65 (d, J=7.3 Hz, 1H), 3.02 (s, 3H), 2.78 (s, 3H). LC-MS: (ES, m/z): [M+1]⁺ 505.1

Example 352

3-chloro-N-methyl-5-(1-(1-oxo-1,2-dihydroisoqui-nolin-5-yl)-5-(trifluoromethyl)-1H-pyrazole-4-car-boxamido)picolinamide, Cpd 352

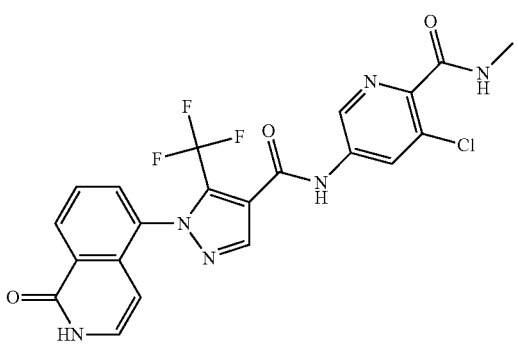

¹H NMR (400 MHz, DMSO-d₆) δ ppm 11.64 (br d, J=5.7 Hz, 1H), 11.24 (s, 1H), 8.86 (d, J=2.0 Hz, 1H), 8.61-8.52 (m, 2H), 8.47-8.38 (m, 2H), 7.94 (d, J=6.6 Hz, 1H), 7.67 (t, J=7.8 Hz, 1H), 7.35-7.23 (m, 1H), 5.66 (d, J=7.3 Hz, 1H), 2.78 (d, J=4.9 Hz, 3H). LC-MS: (ES, m/z): [M+1]⁺ 490.9

Example 428

N-(5-cyano-6-methoxypyridin-3-yl)-1-(1-oxo-1,2-dihydroisoquinolin-5-yl)-5-(trifluoromethyl)-1H-pyrazole-4-carboxamide, Cpd 428

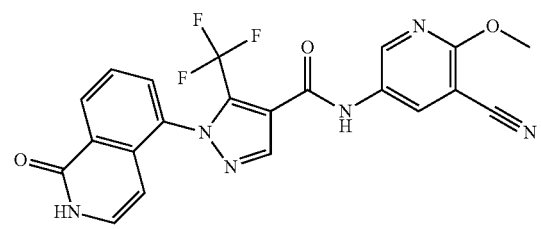 [SMILES: COc1ncc(NC(=O)c2cnn(-c3cccc4c(=O)[nH]ccc34)c2C(F)(F)F)cc1C#N]

¹H NMR (400 MHz, DMSO-d₆) δ ppm 11.58 (br s, 1H), 10.85 (br s, 1H), 8.65 (d, J=1.98 Hz, 1H), 8.49 (d, J=1.98 Hz, 1H), 8.44 (s, 1H), 8.40 (d, J=8.16 Hz, 1H), 7.90 (d, J=7.72 Hz, 1H), 7.63 (t, J=7.83 Hz, 1H), 7.25 (d, J=7.50 Hz, 1H), 5.61 (d, J=7.28 Hz, 1H), 3.97 (s, 3H). LC-MS: (ES, m/z): [M+1]⁺ 455.0

Example 446

N-(5-cyano-2-methyl-4-(2H-1,2,3-triazol-2-yl)phe-nyl)-1-(1-oxo-1,2-dihydroisoquinolin-5-yl)-5-(trif-luoromethyl)-1H-pyrazole-4-carboxamide, Cpd 446

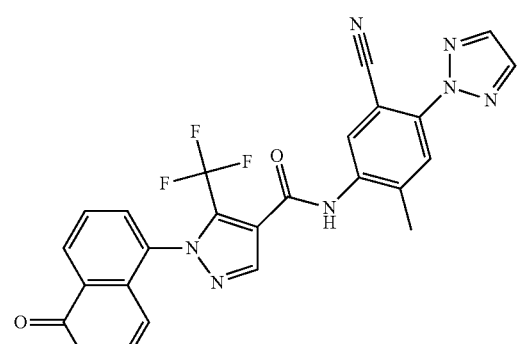

¹H NMR (400 MHz, DMSO-d₆) δ ppm 2.48 (s, 3H), 5.69 (d, J=7.06 Hz, 1H), 7.30 (dd, J=7.28, 6.17 Hz, 1H), 7.68 (t, J=7.83 Hz, 1H), 7.94 (d, J=7.72 Hz, 1H), 8.07 (s, 1H), 8.17 (s, 1H), 8.29 (s, 2H), 8.45 (d, J=7.72 Hz, 1H), 8.51 (s, 1H), 10.44 (s, 1H), 11.63 (br d, J=6.17 Hz, 1H). LC-MS: (ES, m/z): [M+1]⁺ 504.9

Example 353

N-(5-chloropyridin-3-yl)-1-(1-oxo-1,2-dihydroiso-quinolin-5-yl)-5-(trifluoromethyl)-1H-pyrazole-4-carboxamide, Cpd 353

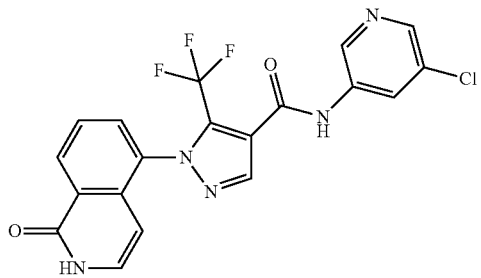 [SMILES: O=C(Nc1cncc(Cl)c1)c1cnn(-c2cccc3c(=O)[nH]ccc23)c1C(F)(F)F]

¹H NMR (400 MHz, DMSO-d₆) δ ppm 5.63 (d, J=7.50 Hz, 1H), 7.27 (br d, J=7.50 Hz, 1H), 7.65 (t, J=7.83 Hz, 1H), 7.89-7.94 (m, 1H), 8.34 (t, J=2.21 Hz, 1H), 8.38-8.43 (m, 2H), 8.47 (s, 1H), 8.77 (d, J=2.21 Hz, 1H), 10.96 (br s, 1H), 11.61 (br s, 1H). LC-MS: (ES, m/z): [M+1]⁺ 433.9

Example 354

N-(6-cyano-5-(trifluoromethyl)pyridin-3-yl)-1-(1-oxo-1,2-dihydroisoquinolin-5-yl)-5-(trifluoromethyl)-1H-pyrazole-4-carboxamide, Cpd 354

¹H NMR (400 MHz, DMSO-d₆) δ ppm 11.61 (br d, J=5.51 Hz, 1H), 11.57 (s, 1H), 9.24 (d, J=1.76 Hz, 1H), 8.78 (d, J=1.98 Hz, 1H), 8.56 (s, 1H), 8.41 (d, J=7.94 Hz, 1H), 7.92 (d, J=6.84 Hz, 1H), 7.64 (t, J=7.83 Hz, 1H), 7.26 (t, J=6.50 Hz, 1H), 5.61 (d, J=7.28 Hz, 1H). LC-MS: (ES, m/z): [M+1]⁺ 492.9

Example 355 methyl 3-chloro-5-(1-(1-oxo-1,2-dihydroisoquinolin-5-yl)-5-(trifluoromethyl)-1H-pyrazole-4-carboxamido)picolinate, Cpd 355

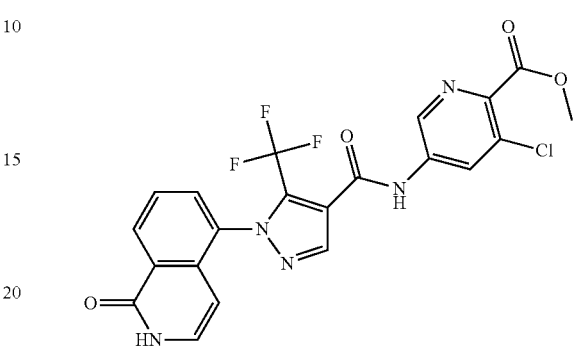

¹H NMR (400 MHz, DMSO-d₆) δ ppm 11.64 (br d, J=5.3 Hz, 1H), 11.27 (s, 1H), 8.88 (d, J=2.0 Hz, 1H), 8.56 (s, 1H), 8.52 (d, J=2.0 Hz, 1H), 8.44 (d, J=8.0 Hz, 1H), 7.95 (d, J=7.3 Hz, 1H), 7.67 (t, J=7.9 Hz, 1H), 7.29 (t, J=6.5 Hz, 1H), 5.65 (d, J=7.3 Hz, 1H), 3.90 (s, 3H). LC-MS: (ES, m/z): [M+1]⁺ 491.9

Example 356

N-(2-cyanopyridin-4-yl)-1-(1-oxo-1,2-dihydroiso-quinolin-5-yl)-5-(trifluoromethyl)-1H-pyrazole-4-carboxamide, Cpd 356

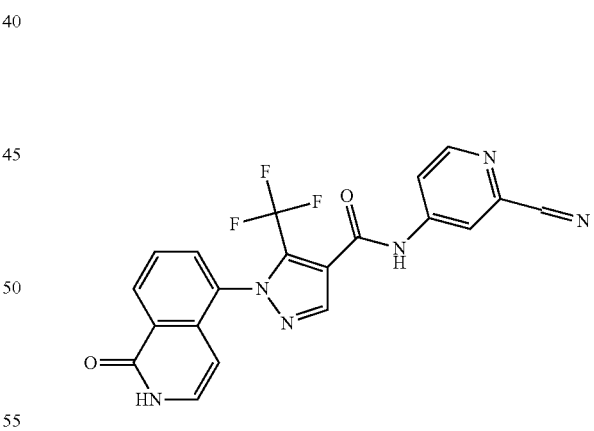

¹H NMR (400 MHz, DMSO-d₆) δ ppm 11.65 (br d, J=4.8 Hz, 1H), 11.44 (s, 1H), 8.67 (d, J=5.5 Hz, 1H), 8.59 (s, 1H), 8.44 (d, J=7.8 Hz, 1H), 8.31 (d, J=1.8 Hz, 1H), 8.01 (dd, J=2.0, 5.5 Hz, 1H), 7.94 (d, J=7.5 Hz, 1H), 7.67 (t, J=7.9 Hz, 1H), 7.29 (br t, J=6.4 Hz, 1H), 5.66 (d, J=7.3 Hz, 1H). LC-MS: (ES, m/z): [M+1]⁺ 425.1

Example 357

N-(2-(2-methoxyethoxy)-5-(trifluoromethyl)pyridin-3-yl)-1-(1-oxo-1,2-dihydroisoquinolin-5-yl)-5-(trifluoromethyl)-1H-pyrazole-4-carboxamide, Cpd 357

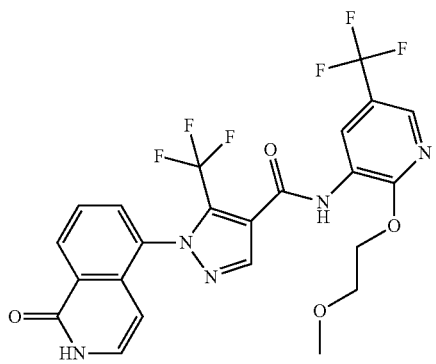 [SMILES: COCCOc1ncc(C(F)(F)F)cc1NC(=O)c1cnn(-c2cccc3c(=O)[nH]ccc23)c1C(F)(F)F]

¹H NMR (400 MHz, DMSO-d₆) δ ppm 11.64 (br d, J=5.5 Hz, 1H), 10.26 (s, 1H), 8.58 (s, 1H), 8.46-8.39 (m, 3H), 7.93 (d, J=7.5 Hz, 1H), 7.67 (t, J=7.9 Hz, 1H), 7.29 (t, J=6.5 Hz, 1H), 5.72 (br d, J=7.3 Hz, 1H), 4.63-4.55 (m, 2H), 3.79-3.70 (m, 2H), 3.30 (s, 3H). LC-MS: (ES, m/z): [M+1]⁺ 541.9

Example 358

N-(5-chloro-2-methyl-6-(2H-1,2,3-triazol-2-yl)pyridin-3-yl)-1-(2-oxo-1,2-dihydroquinolin-4-yl)-5-(trifluoromethyl)-1H-pyrazole-4-carboxamide, Cpd 358

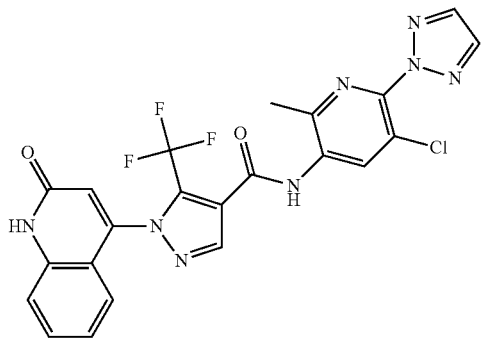 [SMILES: Cc1nc(-n2nccn2)c(Cl)cc1NC(=O)c1cnn(-c2cc(=O)[nH]c3ccccc23)c1C(F)(F)F]

¹H NMR (400 MHz, DMSO-d₆) δ ppm 12.37 (1H, br s), 10.65 (1H, s), 8.59 (1H, s), 8.40 (1H, s), 8.16 (2H, s), 7.57-7.69 (1H, m), 7.45 (1H, d, J=8.16 Hz), 7.21 (1H, t, J=7.72 Hz), 6.92 (1H, s), 6.85 (1H, d, J=7.94 Hz), 2.53 (3H, s). LC-MS: (ES, m/z): [M+1]⁺ 514.9

Example 359

N-(5-chloro-2-methyl-6-(4-methyl-2H-1,2,3-triazol-2-yl)pyridin-3-yl)-1-(1-oxo-1,2-dihydroisoquinolin-5-yl)-5-(trifluoromethyl)-1H-pyrazole-4-carboxamide, Cpd 359

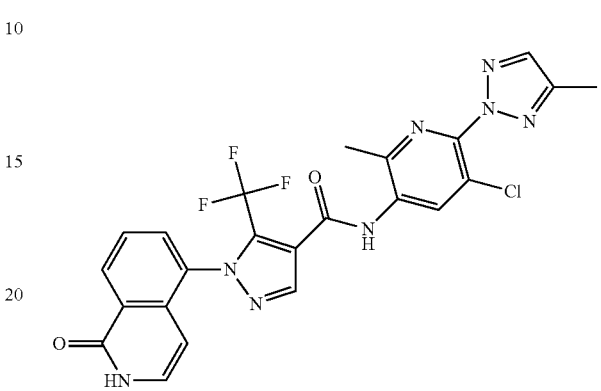

¹H NMR (400 MHz, DMSO-d₆) δ ppm 2.35 (s, 3H), 2.51 (s, 3H), 5.65 (d, J=7.50 Hz, 1H), 7.27 (t, J=6.62 Hz, 1H), 7.65 (t, J=7.94 Hz, 1H), 7.86-7.96 (m, 2H), 8.34-8.45 (m, 2H), 8.51 (s, 1H), 10.58 (s, 1H), 11.61 (br d, J=4.85 Hz, 1H). LC-MS: (ES, m/z): [M+1]⁺ 528.9

Example 360

N-(2-methoxypyridin-4-yl)-1-(1-oxo-1,2-dihydroisoquinolin-5-yl)-5-(trifluoromethyl)-1H-pyrazole-4-carboxamide, Cpd 360

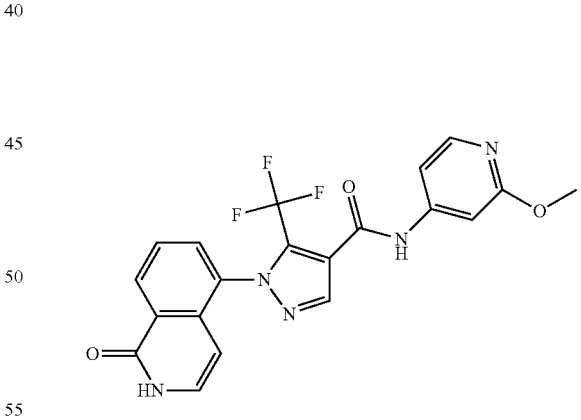

¹H NMR (400 MHz, DMSO-d₆) δ ppm 3.89 (s, 3H), 5.63 (d, J=7.28 Hz, 1H), 7.21-7.30 (m, 1H), 7.36-7.44 (m, 2H), 7.63 (t, J=7.83 Hz, 1H), 7.90 (d, J=7.50 Hz, 1H), 8.13 (d, J=5.95 Hz, 1H), 8.40 (d, J=7.94 Hz, 1H), 8.55 (s, 1H), 11.22 (br s, 1H), 11.62 (br d, J=5.29 Hz, 1H). LC-MS: (ES, m/z): [M+1]⁺ 429.9

Example 361

N-(2-morpholinopyridin-4-yl)-1-(1-oxo-1,2-dihydroisoquinolin-5-yl)-5-(trifluoromethyl)-1H-pyrazole-4-carboxamide, Cpd 361

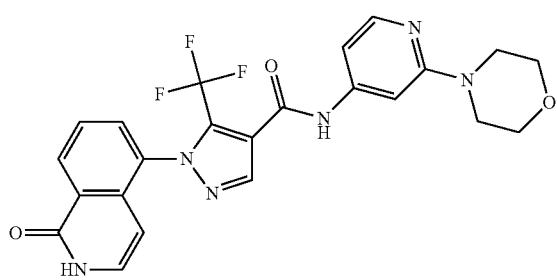 [SMILES: O=C(Nc1ccnc(N2CCOCC2)c1)c1cnn(-c2cccc3c(=O)[nH]ccc23)c1C(F)(F)F]

$^1$H NMR (400 MHz, DMSO-d$_6$) δ ppm 3.59-3.67 (m, 4H), 3.75-3.83 (m, 4H), 5.67 (d, J=7.28 Hz, 1H), 7.30 (dd, J=7.28, 5.95 Hz, 1H), 7.42 (dd, J=6.95, 1.65 Hz, 1H), 7.68 (t, J=7.94 Hz, 1H), 7.86 (d, J=1.54 Hz, 1H), 7.95 (dd, J=7.50, 1.10 Hz, 1H), 8.07 (d, J=6.84 Hz, 1H), 8.45 (d, J=7.94 Hz, 1H), 8.73 (s, 1H), 11.63-11.74 (m, 2H). LC-MS: (ES, m/z): [M+1]$^+$ 485.0

Example 362

N-(5-chloro-2-methyl-6-(4-methyl-1H-1,2,3-triazol-1-yl)pyridin-3-yl)-1-(1-oxo-1,2-dihydroisoquinolin-5-yl)-5-(trifluoromethyl)-1H-pyrazole-4-carboxamide, Cpd 362

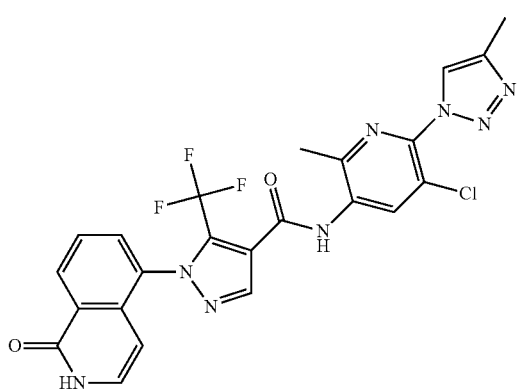 [SMILES: Cc1cn(-c2nc(C)c(NC(=O)c3cnn(-c4cccc5c(=O)[nH]ccc45)c3C(F)(F)F)cc2Cl)nn1]

$^1$H NMR (400 MHz, DMSO-d$_6$) δ ppm 2.26 (s, 3H), 2.59 (s, 3H), 5.70 (d, J=7.53 Hz, 1H), 7.31 (t, J=6.65 Hz, 1H), 7.69 (t, J=7.78 Hz, 1H), 7.76 (s, 1H), 7.95 (d, J=7.78 Hz, 1H), 8.45 (d, J=8.78 Hz, 1H), 8.53 (d, J=11.80 Hz, 2H), 10.64 (s, 1H), 11.65 (br d, J=5.27 Hz, 1H). LC-MS: (ES, m/z): [M+1]$^+$ 528.9

Example 363

N-(5-(2H-1,2,3-triazol-2-yl)pyridin-3-yl)-1-(1-oxo-1,2-dihydroisoquinolin-5-yl)-5-(trifluoromethyl)-1H-pyrazole-4-carboxamide, Cpd 363

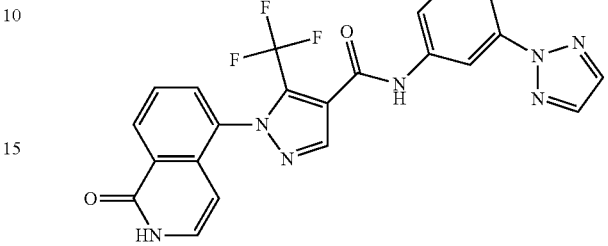

$^1$H NMR (400 MHz, DMSO-d$_6$) δ ppm 5.68 (d, J=7.28 Hz, 1H), 7.31 (dd, J=7.28, 5.95 Hz, 1H), 7.68 (t, J=7.83 Hz, 1H), 7.96 (d, J=7.50 Hz, 1H), 8.25 (s, 2H), 8.45 (d, J=7.94 Hz, 1H), 8.57 (s, 1H), 8.94 (d, J=2.21 Hz, 1H), 8.99 (t, J=2.09 Hz, 1H), 9.04 (d, J=2.20 Hz, 1H), 11.15 (s, 1H), 11.65 (br d, J=5.51 Hz, 1H). LC-MS: (ES, m/z): [M+1]$^+$ 466.9

Example 364

1-(thieno[2,3-c]pyridin-4-yl)-5-(trifluoromethyl)-N-(2-(trifluoromethyl)pyridin-4-yl)-1H-pyrazole-4-carboxamide, Cpd 364

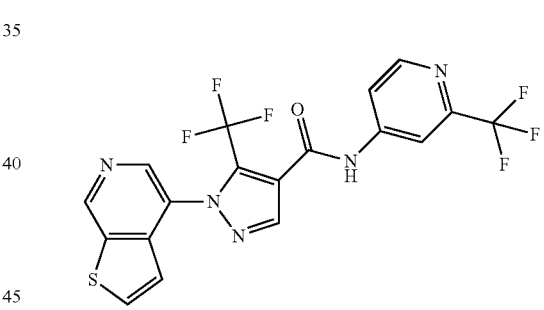

A. Methyl 4-bromothieno[2,3-c]pyridine-2-carboxylate, 364a

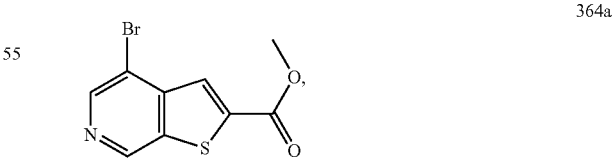

To the solution of 3,5-dibromoisonicotinaldehyde (15 g, 56.63 mmol) in THF (80 mL) was added methyl 2-mercaptoacetate (6.4 g, 60.3 mmol) at 0° C. The mixture was stirred at 0° C. for 1 h. Then the mixture was warmed to 25° C. and stirred for another 1 h and Cs$_2$CO$_3$ (18.45 g, 56.63 mmol) was added to the mixture. Then the mixture was stirred at rt for 16 h. The reaction mixture was filtered. The filtrate was concentrated under reduced pressure to give the crude product as a yellow solid. The crude product was purified by FCC (petroleum ether/ethyl acetate=100:0 to 80:20). The solvents were concentrated to get the crude products as a pale yellow solid (15 g, 97.3%).

B. 4-bromothieno[2,3-c]pyridine-2-carboxylic acid, 364b

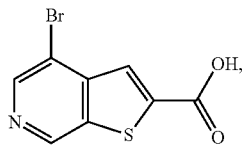

Lithium hydroxide (2.640 g, 110.246 mmol) was added to a solution of methyl 4-bromothieno[2,3-c]pyridine-2-carboxylate (15 g, 55.123 mmol) in THF/H₂O=1:1 (20 mL). The mixture was reacted at room temperature for 4 h. The solvent was concentrated under reduced pressure and 30 mL H₂O was added to the mixture. The mixture was acidized by 1M hydrochloric to pH=5 and the solid was filtered, washed with H₂O (30 mL×2). The solid was dried under reduced pressure to afford product as a white solid (12 g, 84.3%).

C. 4-bromothieno[2,3-c]pyridine, 364c

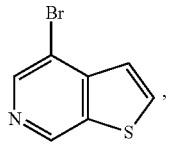

4-Bromothieno[2,3-c]pyridine-2-carboxylic acid (11.9 g, 46.11 mmol) was added to oxydibenzene (120 mL). The mixture was stirred at 230° C. for 8 h. The mixture was purified by FCC (petroleum ether/ethyl acetate=100:0 to 0:100). The solvents were concentrated to afford the crude product as a pale gray solid (8 g, 81.0%).

D. 4-hydrazinylthieno[2,3-c]pyridine, 364d

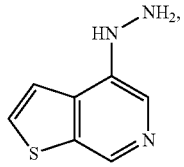

Palladium(11)(pi-cinnamyl) chloride dimer (363.0 mg, 0.70 mmol) and 4-(2-(di((3S,5S,7S)-adamantan-1-yl)phosphino)phenyl)morpholine (649.7 mg, 1.40 mmol) was added to dioxane (15 mL), and the reaction was immediately evacuated with N₂. The resulting solution was stirred at rt under N₂ for 10 min. The reaction vessel was then charged with sodium 2-methylpropan-2-olate (2.69 g, 28.03 mmol) and 4-bromothieno[2,3-c]pyridine (3 g, 14.01 mmol). The vessel was sealed and evacuated with N₂. The resulting reaction was stirred at rt for 5 min, then treated with hydrazine hydrate (701.5 mg, 4.01 mmol) via syringe. The reaction was stirred at 50° C. under N₂ for 1.5 h. The mixture was filtered, and the filtrate concentrated under reduced pressure to afford the crude product as a brown oil (8 g).

E. ethyl 1-(thieno[2,3-c]pyridin-4-yl)-5-(trifluoromethyl)-1H-pyrazole-4-carboxylate, 364e

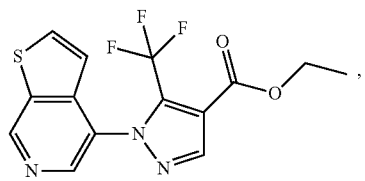

A solution consisting of ethyl 2-(ethoxymethylene)-4,4,4-trifluoro-3-oxobutanoate, ethyl 2-(ethoxymethylene)-4,4,4-trifluoro-3-oxobutanoate (5.815 g, 24.21 mmol), 4-hydrazinylthieno[2,3-c]pyridine (8 g, 48.421 mmol) and ethanol (20 mL) was stirred at 80° C. for 2 h. The resultant solution was concentrated to dryness under reduced pressure to afford the crude product, which was purified by FCC (petroleum ether: ethyl acetate=100/0 to 70/30) to afford the title compound (6 g, 35.2%) as a yellow solid. LCMS (ESI) m/z M+1: 342.2.

F. 1-(thieno[2,3-c]pyridin-4-yl)-5-(trifluoromethyl)-1H-pyrazole-4-carboxylic acid, 364f

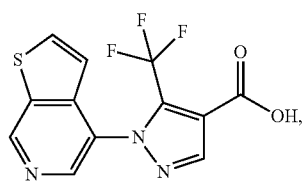

Lithium hydroxide (679.7 mg, 28.38 mmol) was added to a solution of ethyl 1-(thieno[2,3-c]pyridin-4-yl)-5-(trifluoromethyl)-1H-pyrazole-4-carboxylate (5 g, 14.19 mmol) in THF/H₂O=1:1 (20 mL). The mixture was stirred at room temperature for 4 h. The solvent was concentrated under reduced pressure and 30 mL H₂O was added to the mixture. The solution was adjusted to pH 5 by the addition of 1M hydrochloric acid, and extracted with ethyl acetate (40 mL×3). The combined organic layers were washed with brine, dried over anhydrous MgSO₄, filtered, and the filtrates concentrated under reduced pressure to afford the product as a white solid. (4.6 g, 97.1%).

G. 1-(thieno[2,3-c]pyridin-4-yl)-5-(trifluoromethyl)-N-(2-(trifluoromethyl)pyridin-4-yl)-1H-pyrazole-4-carboxamide, Cpd 364

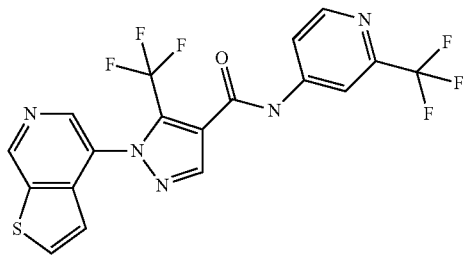 [SMILES: O=C(Nc1ccnc(C(F)(F)F)c1)c1cnn(-c2cncc3sccc23)c1C(F)(F)F]

1-(1-oxo-1,2-dihydroisoquinolin-5-yl)-5-(trifluoromethyl)-1H-pyrazole-4-carboxylic acid (2.25 g, 6.74 mmol), 2-(trifluoromethyl)pyridin-4-amine (1.092 g, 6.74 mmol), pyridine (2.72 mL, 33.70 mmol) were dissolved in $CH_2Cl_2$ (10 mL), and phosphorus oxychloride (2.47 mL, 26.96 mmol) was added. The mixture was stirred at 25° C. for 2 h. Sat.$NaHCO_3$ (30 mL) was added and the reaction mixture extracted with $CH_2Cl_2$ (40 mL×2). The combined organic extracts were dried over anhydrous $Na_2SO_4$, filtered, and the filtrate concentrated to dryness under reduced pressure to afford the crude product, which was purified by preparative HPLC (35% to 60% (v/v) $CH_3CN$ and $H_2O$ with 0.05% TFA). The pure fractions were collected and the mixture was adjusted to pH>7 by the addition of aq.$NaHCO_3$. The organic solvent was concentrated under reduced pressure until a white solid precipitated from solution. The white solid was collected and dried under reduced pressure to afford the product (1.6 g, 51.9%). LCMS (ESI) m/z M+1: 457.9. $^1$H NMR (400 MHz, DMSO-$d_6$) δ ppm 7.15 (1H, d, J=5.73 Hz), 7.96 (1H, dd, J=5.40, 1.87 Hz), 8.22 (1H, d, J=1.76 Hz), 8.34 (1H, d, J=5.51 Hz), 8.56 (1H, s), 8.65 (1H, s), 8.69 (1H, d, J=5.73 Hz), 9.52 (1H, s), 11.26 (1H, br s).

Example 447

N-(5-chloro-6-(2H-1,2,3-triazol-2-yl)pyridin-3-yl)-1-(thieno[2,3-c]pyridin-4-yl)-5-(trifluoromethyl)-1H-pyrazole-4-carboxamide, Cpd 447

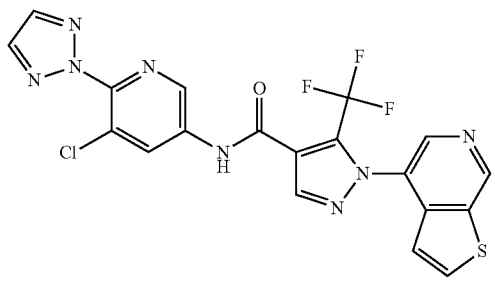 [SMILES: O=C(Nc1cnc(-n2nccn2)c(Cl)c1)c1cnn(-c2cncc3sccc23)c1C(F)(F)F]

Following the procedure described in Example 364, above, selecting and substituting the appropriate reagents, starting materials, and purification methods, and adjusting reaction temperatures, times and other variables or parameters, as needed or desirable, as would be readily recognized by those skilled in the art, Compound 447 was prepared.

LCMS (ESI): mass calcd. for $C_{19}H_{10}ClF_3N_8OS$ 490.1 m/z found 491.2 [M+H]$^+$. $^1$H NMR (400 MHz, DMSO-$d_6$) δ ppm 7.18 (d, J=5.3 Hz, 1H) 8.16 (s, 2H) 8.35 (d, J=5.7 Hz, 1H) 8.51 (s, 1H) 8.66 (s, 1H) 8.69 (d, J=2.4 Hz, 1H) 8.71-8.75 (m, 1H) 9.52 (s, 1H)

Example 365 and Example 366

N-(5-chloro-6-(2H-1,2,3-triazol-2-yl)pyridin-3-yl)-1-(1-(tetrahydrofuran-2-yl)isoquinolin-4-yl)-5-(trifluoromethyl)-1H-pyrazole-4-carboxamide, Cpd 365

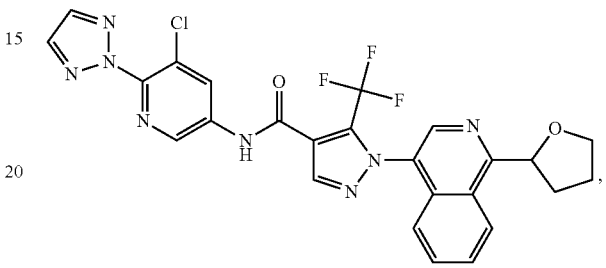

and 1-(1,5-bis(tetrahydrofuran-2-yl)isoquinolin-4-yl)-N-(5-chloro-6-(2H-1,2,3-triazol-2-yl)pyridin-3-yl)-5-(trifluoromethyl)-1H-pyrazole-4-carboxamide, Cpd 366

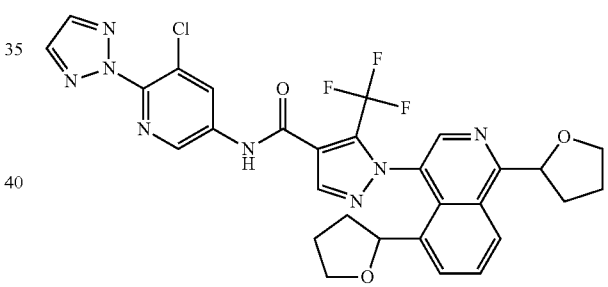

A mixture of THF (1800 mg, 25 mmol), $CH_3CN$ (2.5 mL), $H_2O$ (2.5 mL), N-(5-chloro-6-(2H-1,2,3-triazol-2-yl)pyridin-3-yl)-1-(isoquinolin-4-yl)-5-(trifluoromethyl)-1H-pyrazole-4-carboxamide (242.5 mg, 0.5 mmol), TFA (0.038 mL, 0.5 mmol) and ammonium persulfate (228 mg, 1 mmol) was weighted in a 10 mL vial. (IR[DF(CF$_3$)PPY]2(DTBPY))PF$_6$ (11.2 mg, 0.01 mmol) was successively added. The reaction mixture was degassed for 15 min and the vessel sealed. The reaction was stirred under blue LED irradiation at rt for 1 h. The reaction mixture was poured into water and extracted with DCM. The organic layer was dried over MgSO$_4$, filtered and the filtrate was concentrated to dryness. The residue was purified via Prep HPLC (Stationary phase: RP XBridge Prep C18 OBD-5 μm, 30×250 mm, Mobile phase: 0.25% NH$_4$HCO$_3$ solution in water, CH$_3$CN) to afford Cpd 365 (44 mg, 16%) and compound 366 (46 mg, 15%).

Cpd 365.

LCMS (ESI): mass calcd. for $C_{25}H_{18}ClF_3N_8O_2$ 554.1, m/z found 555.1 [M+H]$^+$. $^1$H NMR (400 MHz, CHLOROFORM-d) δ ppm 2.08-2.25 (m, 2H), 2.49 (br s, 2H), 4.01-4.12 (m, 1H), 4.12-4.26 (m, 1H), 5.79 (t, J=7.1 Hz, 1H), 7.21-7.26 (m, 1 H), 7.65-7.77 (m, 2H), 7.93 (s, 2H), 8.23 (s, 1H), 8.44 (br s, 1H), 8.53 (s, 1H), 8.62 (d, J=2.4 Hz, 1H), 8.75 (d, J=2.4 Hz, 1H), 9.22 (s, 1H).
Cpd 366.
LCMS (ESI): mass calcd. for $C_{29}H_{24}ClF_3N_8O_3$ 624.2, m/z found 625.2 [M+H]$^+$. $^1$H NMR (400 MHz, CHLOROFORM-d) δ ppm 1.74-1.84 (m, 1H), 1.91-2.07 (m, 2H), 2.07-2.25 (m, 2H), 2.34-2.44 (m, 1H), 2.44-2.62 (m, 2H), 3.92-4.00 (m, 1H), 4.02-4.11 (m, 2H), 4.19 (br s, 1H), 5.01 (q, J=6.5 Hz, 1H), 5.77 (br t, J=6.9 Hz, 1H), 7.21 (d, J=6.9 Hz, 1H), 7.64 (t, J=8.0 Hz, 1H), 7.94 (s, 2H), 8.22 (s, 1H), 8.43 (br s, 1H), 8.52 (s, 1H), 8.54 (d, J=2.4 Hz, 1H), 8.75 (d, J=2.0 Hz, 1H), 8.81 (br s, 1H).

Following the procedure described in Example 365, above, selecting and substituting the appropriate reagents, starting materials, and purification methods, and adjusting reaction temperatures, times and other variables or parameters, as needed or desirable, as would be readily recognized by those skilled in the art, the following compounds were prepared.

Example 367

1-(1-(1,4-dioxan-2-yl)isoquinolin-4-yl)-N-(5-chloro-6-(2H-1,2,3-triazol-2-yl)pyridin-3-yl)-5-(trifluoromethyl)-1H-pyrazole-4-carboxamide, Cpd 367

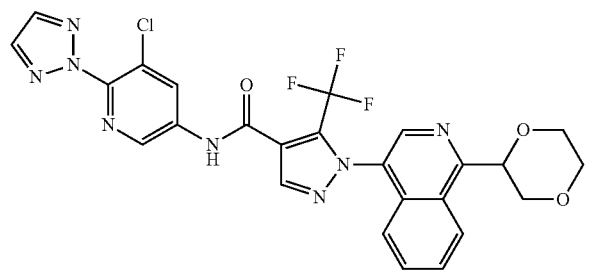 [SMILES: O=C(Nc1cnc(-n2nccn2)c(Cl)c1)c1cnn(-c2cnc(C3COCCO3)c3ccccc23)c1C(F)(F)F]

LCMS (ESI): mass calcd. for $C_{25}H_{18}ClF_3N_8O_3$ 570.1, m/z found 571.1[M+H]$^+$. $^1$H NMR (400 MHz, DMSO-d$_6$) δ ppm 3.70 (td, J=11.6, 2.8 Hz, 1H), 3.85 (dd, J=11.8, 2.0 Hz, 1H), 3.92 (dd, J=11.6, 2.2 Hz, 1H), 4.09 (td, J=11.5, 2.6 Hz, 1H), 4.21 (d, J=6.1 Hz, 2H), 5.44-5.52 (m, 1H) 7.27 (d, J=8.5 Hz, 1H), 7.84-7.91 (m, 1H), 7.92-7.99 (m, 1H), 8.19 (s, 2H), 8.60-8.67 (m, 2H), 8.69 (d, J=2.0 Hz, 1H), 8.76 (s, 1H), 8.86 (d, J=2.0 Hz, 1H), 11.29 (br s, 1H).

Example 368

N-(5-chloro-6-(2H-1,2,3-triazol-2-yl)pyridin-3-yl)-1-(1-(1-ethoxyethyl)isoquinolin-4-yl)-5-(trifluoromethyl)-1H-pyrazole-4-carboxamide, Cpd 368

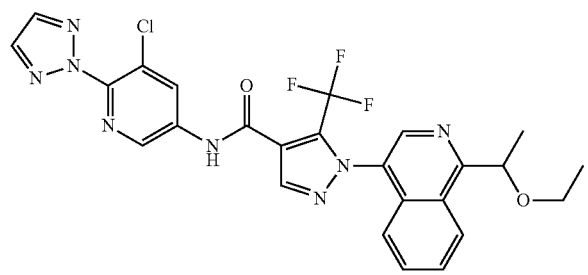 [SMILES: CCOC(C)c1ncc(-n2ncc(C(=O)Nc3cnc(-n4nccn4)c(Cl)c3)c2C(F)(F)F)c2ccccc12]

LCMS (ESI): mass calcd. for $C_{25}H_{20}ClF_3N_8O_2$ 556.1 m/z found 557.2 [M+H]$^+$. $^1$H NMR (400 MHz, DMSO-d$_6$) δ ppm 1.12 (t, J=6.9 Hz, 3H), 1.66 (d, J=6.5 Hz, 3H), 3.36-3.47 (m, 1H), 3.48-3.67 (m, 1H), 5.34 (q, J=6.5 Hz, 1H), 7.27 (d, J=8.5 Hz, 1H), 7.82-7.89 (m, 1H), 7.90-7.98 (m, 1H), 8.19 (s, 2H), 8.63 (s, 1H), 8.70 (d, J=2.4 Hz, 1H), 8.74 (s, 1H), 8.80 (d, J=8.5 Hz, 1H), 8.86 (d, J=2.0 Hz, 1H), 11.36 (br s, 1H).

Example 369

N-(5-chloro-6-(2H-1,2,3-triazol-2-yl)pyridin-3-yl)-1-(1-(5-oxopyrrolidin-2-yl)isoquinolin-4-yl)-5-(trifluoromethyl)-1H-pyrazole-4-carboxamide, Cpd 369

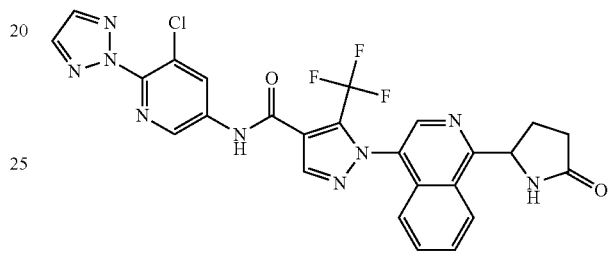

LCMS (ESI): mass calcd. for $C_{25}H_{17}ClF_3N_9O_2$ 567.1 m/z found 568.1 [M+H]$^+$. $^1$H NMR (400 MHz, DMSO-d$_6$) δ ppm 2.09 (br d, J=13.8 Hz, 1H), 2.32 (br s, 2H), 2.65-2.86 (m, 1H), 5.82 (dd, J=8.3, 3.9 Hz, 1H), 7.28 (d, J=8.1 Hz, 1H), 7.89 (td, J=7.6, 1.0 Hz, 1H), 7.86-7.92 (m, 1H), 7.93-7.99 (m, 1H), 7.93-8.00 (m, 1H), 8.08 (s, 1H), 8.19 (s, 2H), 8.56 (d, J=8.5 Hz, 1H), 8.64 (s, 1H), 8.69 (d, J=2.4 Hz, 1H), 8.78 (s, 1H), 8.88 (d, J=2.4 Hz, 1H), 11.32 (br s, 1H).

Example 370

N-(5-chloro-6-(2H-1,2,3-triazol-2-yl)pyridin-3-yl)-1-(1-(4-oxotetrahydrofuran-2-yl)isoquinolin-4-yl)-5-(trifluoromethyl)-1H-pyrazole-4-carboxamide, Cpd 370

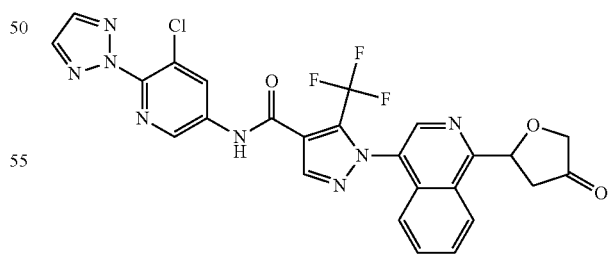

LCMS (ESI): mass calcd. for $C_{25}H_{16}ClF_3N_8O_3$ 568.1 m/z found 569.1[M+H]$^+$. $^1$H NMR (400 MHz, DMSO-d$_6$) δ ppm 2.96-3.08 (m, 1H), 4.17 (s, 1H), 4.07 (br s, 1H), 4.13 (s, 1H), 6.50 (s, 1H), 7.30 (d, J=8.1 Hz, 1H), 7.90-7.95 (m, 1H), 7.98 (dd, 1.2 Hz, 1H), 8.19 (s, 2H), 8.64 (s, 1H), 8.68 (d, J=2.0 Hz, 1H), 8.70 (s, 1H), 8.80 (s, 1H), 8.87 (d, J=2.0 Hz, 1H), 11.29 (s, 1H).

Example 371

N-(5-chloro-6-(2H-1,2,3-triazol-2-yl)pyridin-3-yl)-1-(1-(1-hydroxyethyl)isoquinolin-4-yl)-5-(trifluoromethyl)-1H-pyrazole-4-carboxamide, Cpd 371

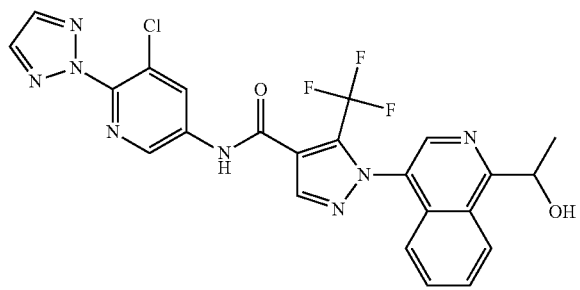 [SMILES: CC(O)c1ncc(-n2ncc(C(=O)Nc3cnc(-n4nccn4)c(Cl)c3)c2C(F)(F)F)c2ccccc12]

LCMS (ESI): mass calcd. for $C_{23}H_{16}ClF_3N_8O_2$ 528.1 m/z found 529.2 [M+H]$^+$. $^1$H NMR (400 MHz, DMSO-d$_6$) δ ppm 1.64 (d, J=6.5 Hz, 3H), 5.61 (br s, 1H), 5.66-5.74 (m, 1H), 5.69 (br d, J=11.0 Hz, 1H), 7.24 (d, J=8.1 Hz, 1H), 7.81-7.87 (m, 1H), 7.89-7.94 (m, 1H), 8.19 (s, 2H), 8.61 (s, 1H), 8.68 (d, J=2.0 Hz, 1H), 8.72 (s, 1H), 8.77 (br s, 1H), 8.86 (d, J=2.0 Hz, 1H), 11.30 (br s, 1H).

Example 372

N-(5-chloro-6-(2H-1,2,3-triazol-2-yl)pyridin-3-yl)-1-(2-(tetrahydrofuran-2-yl)quinolin-5-yl)-5-(trifluoromethyl)-1H-pyrazole-4-carboxamide, Cpd 372

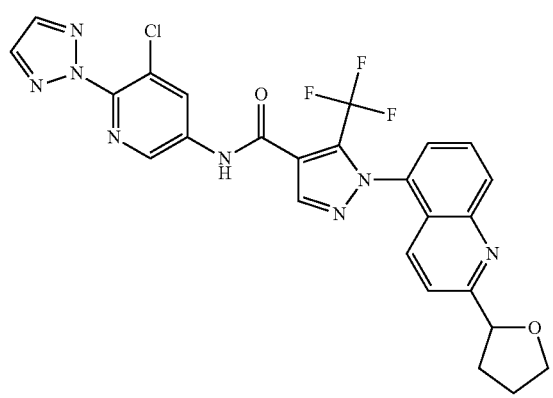 [SMILES: O=C(Nc1cnc(-n2nccn2)c(Cl)c1)c1cnn(-c2cccc3nc(C4CCCO4)ccc23)c1C(F)(F)F]

LCMS (ESI): mass calcd. for $C_{25}H_{18}ClF_3N_8O_2$ 554.1 m/z found 555.2[M+H]$^+$. $^1$H NMR (400 MHz, DMSO-d$_6$) δ ppm 1.92-2.14 (m, 2H), 2.41-2.49 (m, 1H), 3.60 (spt, J=6.1 Hz, 1H), 3.87-3.99 (m, 1H), 3.99-4.15 (m, 1H), 5.06-5.19 (m, 1H), 7.63 (d, J=9.0 Hz, 1H), 7.72-7.78 (m, 1H), 7.85-7.90 (m, 1H), 7.92-7.99 (m, 1H), 8.19 (s, 2H), 8.27 (d, J=8.1 Hz, 1H), 8.59 (s, 1H), 8.68 (d, J=2.4 Hz, 1H), 8.86 (d, J=2.4 Hz, 1H), 11.27 (br s, 1H).

Example 373

N-(5-chloro-6-(2H-1,2,3-triazol-2-yl)pyridin-3-yl)-1-(1-((N-methylformamido)methyl)isoquinolin-4-yl)-5-(trifluoromethyl)-1H-pyrazole-4-carboxamide, Cpd 373

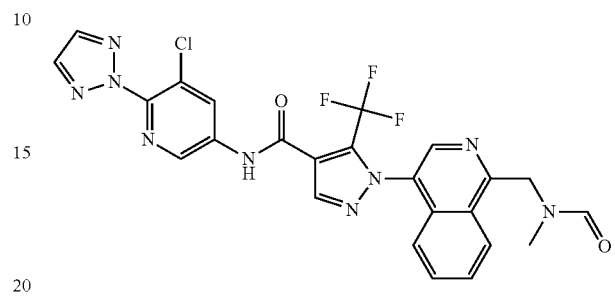

LCMS (ESI): mass calcd. for $C_{24}H_{17}ClF_3N_9O$ 555.1 m/z found 556.1 [M+H]$^+$. $^1$H NMR (400 MHz, DMSO-d$_6$) δ ppm 2.75-3.10 (m, 3H), 5.24 (br d, J=3.7 Hz, 1H), 5.37 (s, 1H), 7.29 (dd, J=8.3, 3.1 Hz, 1H), 7.85-8.01 (m, 2H), 8.19 (s, 2H), 8.24-8.36 (m, 1H), 8.52 (dd, J=8.3, 3.5 Hz, 1H), 8.62 (s, 1H), 8.68 (d, J=2.0 Hz, 1H), 8.76 (d, J=12.6 Hz, 1H), 8.86 (d, J=2.4 Hz, 1H), 11.29 (br s, 1H).

Example 374

N-(5-chloro-6-(2H-1,2,3-triazol-2-yl)pyridin-3-yl)-1-(2-(1-hydroxyethyl)quinolin-4-yl)-5-(trifluoromethyl)-1H-pyrazole-4-carboxamide, Cpd 374

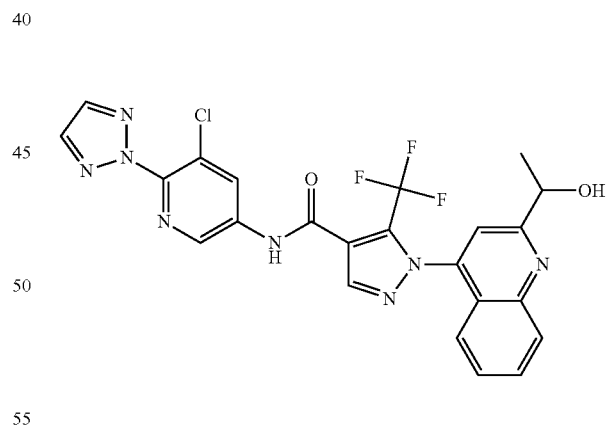

LCMS (ESI): mass calcd. for $C_{23}H_{16}ClF_3N_8O_2$ 528.1 m/z found 529.1 [M+H]$^+$. $^1$H NMR (400 MHz, DMSO-d$_6$) δ ppm 1.51 (d, J=6.5 Hz, 3H), 5.02 (dd, 4.5 Hz, 1H), 5.79 (d, J=4.5 Hz, 1H), 7.32 (d, J=8.5 Hz, 1H), 7.71 (ddd, J=8.2, 7.0, 1.0 Hz, 1H), 7.89-7.95 (m, 2H), 8.16-8.21 (m, 3H), 8.65 (s, 1H), 8.69 (d, J=2.0 Hz, 1H), 8.87 (d, J=2.0 Hz, 1H), 11.28 (br s, 1H).

Example 375

1-(2-acetylquinolin-4-yl)-N-(5-chloro-6-(2H-1,2,3-triazol-2-yl)pyridin-3-yl)-5-(trifluoromethyl)-1H-pyrazole-4-carboxamide, Cpd 375

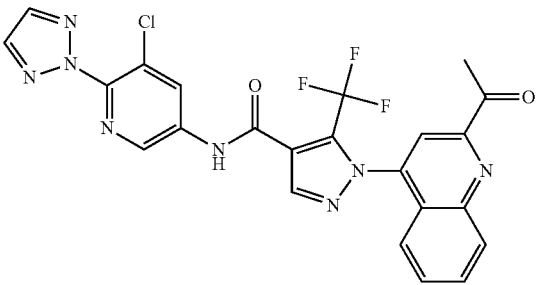 [SMILES: CC(=O)c1cc(-n2ncc(C(=O)Nc3cnc(-n4nccn4)c(Cl)c3)c2C(F)(F)F)c2ccccc2n1]

LCMS (ESI): mass calcd. for $C_{23}H_{14}ClF_3N_8O_2$ 526.1 m/z found 527.2[M+H]$^+$. $^1$H NMR (400 MHz, DMSO-d$_6$) δ ppm 2.86 (s, 3H), 7.43 (d, J=8.1 Hz, 1H), 7.91 (td, 1.0 Hz, 1H), 8.04-8.09 (m, 1H), 8.20 (s, 2H), 8.29 (s, 1H), 8.41 (d, J=8.5 Hz, 1H), 8.67-8.70 (m, 2H), 8.87 (d, J=2.4 Hz, 1H), 11.27 (s, 1H).

Example 376

N-(5-chloro-6-(2H-1,2,3-triazol-2-yl)pyridin-3-yl)-1-(7-(1-hydroxy ethyl)thieno[2,3-c]pyridin-4-yl)-5-(trifluoromethyl)-1H-pyrazole-4-carboxamide, Cpd 376

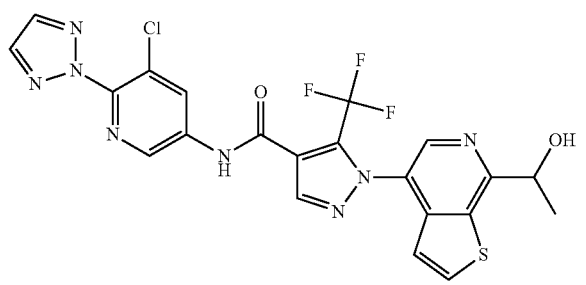 [SMILES: CC(O)c1ncc(-n2ncc(C(=O)Nc3cnc(-n4nccn4)c(Cl)c3)c2C(F)(F)F)c2ccsc12]

LCMS (ESI): mass calcd. for $C_{21}H_{14}ClF_3N_8O_2S$ 534.1, m/z found 535.1 [M+H]$^+$. $^1$H NMR (400 MHz, DMSO-d$_6$) δ ppm 1.55 (d, J=6.5 Hz, 3H), 5.17 (qd, 4.5 Hz, 1H), 6.21 (d, J=4.1 Hz, 1H), 7.09 (d, J=5.7 Hz, 1H), 8.19 (s, 2H), 8.28 (d, J=5.3 Hz, 1H), 8.54-8.59 (m, 2H), 8.67 (d, J=2.0 Hz, 1H), 8.85 (d, J=2.0 Hz, 1H), 11.26 (br s, 1H).

Example 378

1-(1-acetylisoquinolin-5-yl)-N-(5-chloro-6-(2H-1,2,3-triazol-2-yl)pyridin-3-yl)-5-(trifluoromethyl)-1H-pyrazole-4-carboxamide, Cpd 378

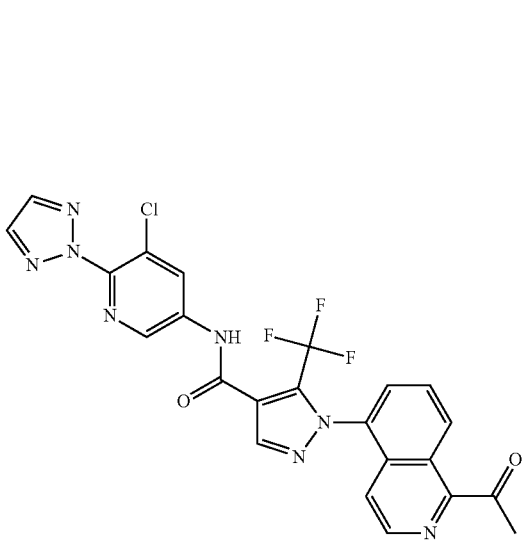 [SMILES: CC(=O)c1nccc2c(-n3ncc(C(=O)Nc4cnc(-n5nccn5)c(Cl)c4)c3C(F)(F)F)cccc12]

LCMS (ESI): mass calcd. for $C_{23}H_{14}ClF_3N_8O_2$ 526.1, m/z found 527.2 [M+H]$^+$. $^1$H NMR (400 MHz, DMSO-d$_6$) δ ppm 2.83 (s, 3H), 7.28 (d, J=5.9 Hz, 1H), 7.99 (dd, J=8.9, 7.3 Hz, 1H), 8.18 (d, J=6.9 Hz, 1H), 8.19 (s, 2H), 8.64 (s, 1H), 8.69 (d, J=2.4 Hz, 1H), 8.74 (d, J=6.1 Hz, 1H), 8.88 (d, J=2.1 Hz, 1H), 9.03 (dt, J=8.8, 1.1 Hz, 1H), 11.24 (br s, 1H).

Example 379

1-(1-(azetidin-2-yl)isoquinolin-4-yl)-N-(5-chloro-6-(2H-1,2,3-triazol-2-yl)pyridin-3-yl)-5-(trifluoromethyl)-1H-pyrazole-4-carboxamide, Cpd 379

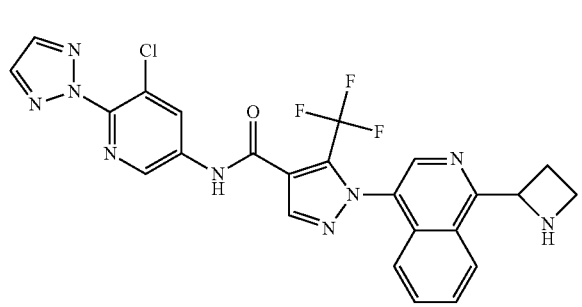 [SMILES: O=C(Nc1cnc(-n2nccn2)c(Cl)c1)c1cnn(-c2cnc(C3CCN3)c3ccccc23)c1C(F)(F)F]

721

A. tert-butyl 2-(4-(4-((5-chloro-6-(2H-1,2,3-triazol-2-yl)pyridin-3-yl)carbamoyl)-5-(trifluoromethyl)-1H-pyrazol-1-yl)isoquinolin-1-yl)azetidine-1-carboxylate, Cpd 379a

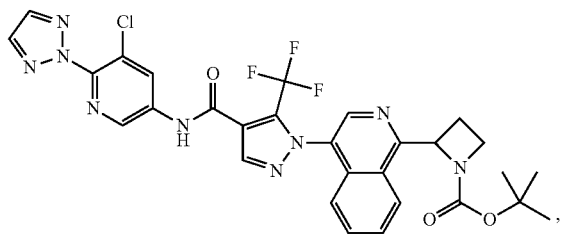

379a

A mixture of tert-butyl azetidine-1-carboxylate (236 mg, 1.5 mmol), CH$_3$CN (2.5 mL), H$_2$O (2.5 mL), N-(5-chloro-6-(2H-1,2,3-triazol-2-yl)pyridin-3-yl)-1-(isoquinolin-4-yl)-5-(trifluoromethyl)-1H-pyrazole-4-carboxamide (242.5 mg, 0.5 mmol), TFA (0.038 mL, 0.5 mmol) and ammonium persulfate (228 mg, 1 mmol) was weighted in a 10 mL vial. (IR[DF(CF$_3$)PPY]2(DTBPY))PF$_6$ (11.2 mg, 0.01 mmol) was successively added. The reaction mixture was degassed for 15 min and the vessel sealed. The reaction was stirred under blue LED irradiation at rt for 1 h. The reaction mixture was poured into water and extracted with DCM. The organic layer was dried over MgSO$_4$, filtered and the filtrate was concentrated to dryness. The residue was purified via Prep HPLC (Stationary phase: RP XBridge Prep C18 OBD-10 μm, 50×150 mm, Mobile phase: 0.25% NH$_4$HCO$_3$ solution in water, CH$_3$CN) yielding cpd 379a (240 mg, 75%). LCMS (ESI): mass calcd. for C$_{29}$H$_{25}$ClF$_3$N$_9$O$_3$ 639.2, m/z found 640.2 [M+H]$^+$.

B. 1-(1-(azetidin-2-yl)isoquinolin-4-yl)-N-(5-chloro-6-(2H-1,2,3-triazol-2-yl)pyridin-3-yl)-5-(trifluoromethyl)-1H-pyrazole-4-carboxamide, Cpd 379

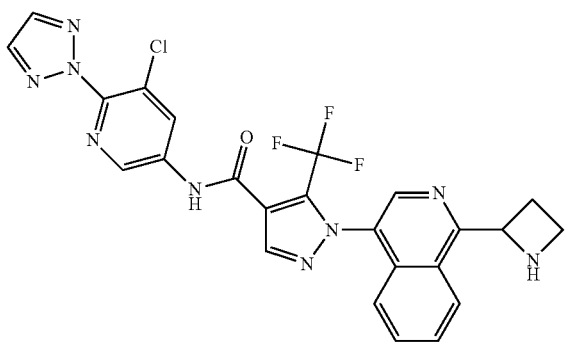 [SMILES: O=C(Nc1cnc(-n2nccn2)c(Cl)c1)c1cnn(-c2cnc(C3CCN3)c3ccccc23)c1C(F)(F)F]

A mixture of tert-butyl 2-(4-(4-((5-chloro-6-(2H-1,2,3-triazol-2-yl)pyridin-3-yl)carbamoyl)-5-(trifluoromethyl)-1H-pyrazol-1-yl)isoquinolin-1-yl)azetidine-1-carboxylate (240 mg, 0.375 mmol), TFA (2 mL) and DCM (6 mL) was stirred at room temperature for 3 h. The reaction mixture was concentrated to dryness. The residue was dissolved in water and made basic with K$_2$CO$_3$. The aqueous layer was extracted with DCM, and the organic layer was dried over MgSO$_4$, filtered, and the filtrate and concentrated. The residue was dissolved into diisopropylether, a solid collected by filtrationfiltered off and dried, to afford the product (74 mg, 35.5%). LCMS (ESI): mass calcd. for C$_{24}$H$_{17}$ClF$_3$N$_9$O 539.1, m/z found 540.2 [M+H]$^+$. $^1$H NMR (400 MHz, DMSO-d$_6$) δ ppm 2.55-2.79 (m, 1H), 2.89-3.05 (m, 1H), 3.54-3.62 (m, 1H), 3.67-3.79 (m, 1H), 5.81 (br t, J=7.7 Hz, 1H), 7.30 (br d, J=8.1 Hz, 1H), 7.81-7.90 (m, 1H), 7.91-7.99 (m, 1H), 8.20 (s, 2H), 8.29 (br d, J=8.5 Hz, 1H), 8.63 (s, 1H), 8.69 (d, J=2.0 Hz, 1H), 8.81 (s, 1H), 8.87 (d, J=2.4 Hz, 1H), 11.28 (br s, 1H).

Following the procedure described in Example 379, above, selecting and substituting the appropriate reagents, starting materials, and purification methods, and adjusting reaction temperatures, times and other variables or parameters, as needed or desirable, as would be readily recognized by those skilled in the art, the following compounds were prepared:

Example 380

N-(5-chloro-6-(2H-1,2,3-triazol-2-yl)pyridin-3-yl)-1-(1-(pyrrolidin-2-yl)isoquinolin-4-yl)-5-(trifluoromethyl)-1H-pyrazole-4-carboxamide, Cpd 380

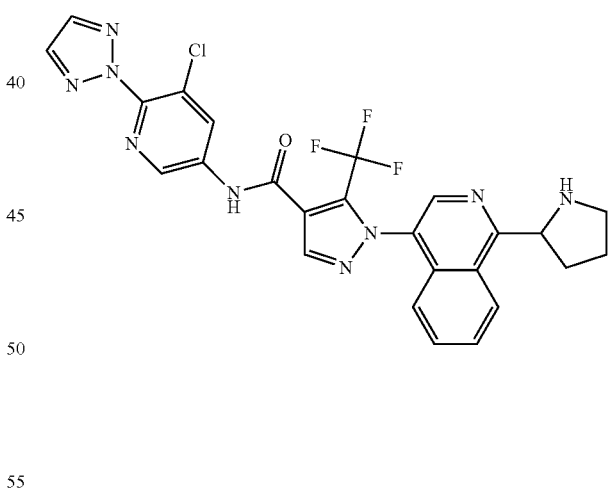

LCMS (ESI): mass calcd. for C$_{25}$H$_{19}$ClF$_3$N$_9$O 553.1, m/z found 554.2[M+H]$^+$. $^1$H NMR (400 MHz, DMSO-d$_6$) δ ppm 1.81-2.01 (m, 3H), 2.44-2.50 (m, 1H), 2.98-3.07 (m, 1H), 3.26-3.28 (m, 1H), 5.23 (br s, 1H), 7.28 (d, J=8.5 Hz, 1H), 7.83-7.92 (m, 1H), 7.92-8.01 (m, 1H), 8.19 (s, 2H), 8.59 (br d, J=7.7 Hz, 1H), 8.63 (s, 1H), 8.68 (d, J=2.4 Hz, 1H), 8.74 (s, 1H), 8.87 (d, J=2.4 Hz, 1H), 11.27 (br s, 1H).

Example 381

1-(2-(azetidin-2-yl)quinolin-5-yl)-N-(5-chloro-6-(2H-1,2,3-triazol-2-yl)pyridin-3-yl)-5-(trifluoromethyl)-1H-pyrazole-4-carboxamide, Cpd 381

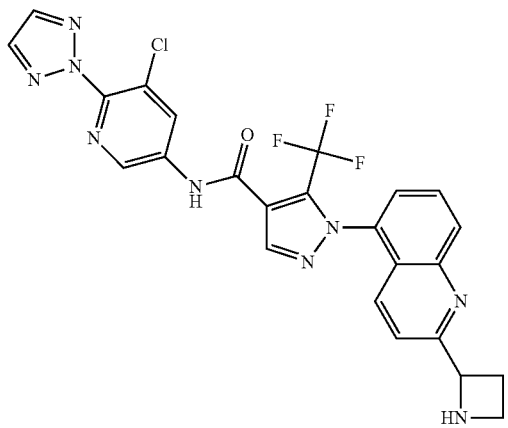 [SMILES: O=C(Nc1cnc(-n2nccn2)c(Cl)c1)c1cnn(-c2cccc3nc(C4CCN4)ccc23)c1C(F)(F)F]

LCMS (ESI): mass calcd. for $C_{24}H_{17}ClF_3N_9O$ 539.1 m/z found 540.2[M+H]$^+$. $^1$H NMR (400 MHz, DMSO-d$_6$) δ ppm 2.31-2.47 (m, 1H), 2.64-2.81 (m, 1H), 3.54-3.66 (m, 1H), 3.73 (q, J=8.0 Hz, 1H), 5.15 (t, J=7.9 Hz, 1H), 7.65 (d, J=9.0 Hz, 1H), 7.82-8.03 (m, 3H), 8.18-8.22 (m, 2H), 8.27 (d, J=8.5 Hz, 1H), 8.61 (s, 1H), 8.70 (d, J=2.4 Hz, 1H), 8.88 (d, J=2.0 Hz, 1H).

Example 382

1-(2-(azetidin-2-yl)quinolin-4-yl)-N-(5-chloro-6-(2H-1,2,3-triazol-2-yl)pyridin-3-yl)-5-(trifluoromethyl)-1H-pyrazole-4-carboxamide, Cpd 382

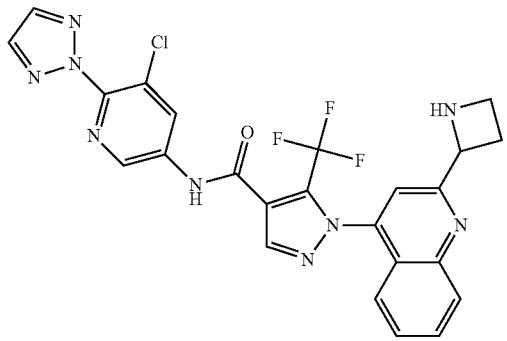 [SMILES: O=C(Nc1cnc(-n2nccn2)c(Cl)c1)c1cnn(-c2cc(C3CCN3)nc3ccccc23)c1C(F)(F)F]

LCMS (ESI): mass calcd. for $C_{24}H_{17}ClF_3N_9O$ 539.1, m/z found 540.2 [M+H]$^+$. $^1$H NMR (400 MHz, DMSO-d$_6$) δ ppm 2.32-2.45 (m, 1H), 2.72 (ddt, J=14.9, 8.2, 4.1, 4.1 Hz, 1H), 3.35-3.38 (m, 1H), 3.69-3.82 (m, 1H), 5.21 (t, J=8.1 Hz, 1H), 7.32 (d, J=7.7 Hz, 1H), 7.70 (ddd, J=8.2, 7.0, 1.0 Hz, 1H), 7.91 (ddd, J=8.4, 7.0, 1.2 Hz, 1H), 8.07 (s, 1H), 8.15-8.20 (m, 3H), 8.67 (s, 1H), 8.69 (d, J=2.0 Hz, 1H), 8.88 (d, J=2.4 Hz, 1H), 11.29 (br s, 1H).

Example 383 tert-butyl 2-(5-(4-((5-chloro-6-(2H-1,2,3-triazol-2-yl)pyridin-3-yl)carbamoyl)-5-(trifluoromethyl)-1H-pyrazol-1-yl)isoquinolin-1-yl)azetidine-1-carboxylate, Cpd 383

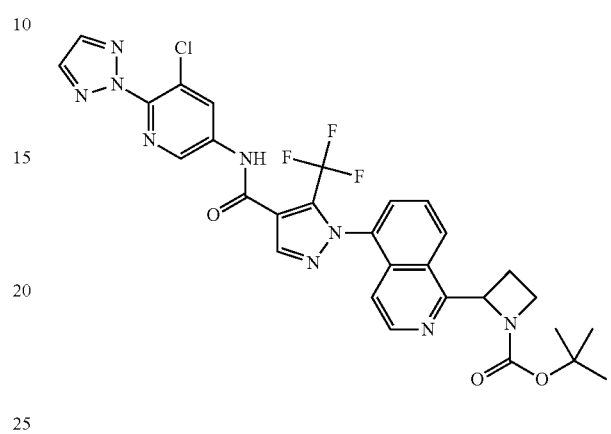

LCMS (ESI): mass calcd. For $C_{29}H_{25}ClF_3N_9O_3$ 639.2 m/z found 640.2[M+H]$^+$.

Example 384

1-(1-(azetidin-2-yl)isoquinolin-5-yl)-N-(5-chloro-6-(2H-1,2,3-triazol-2-yl)pyridin-3-yl)-5-(trifluoromethyl)-1H-pyrazole-4-carboxamide, Cpd 384

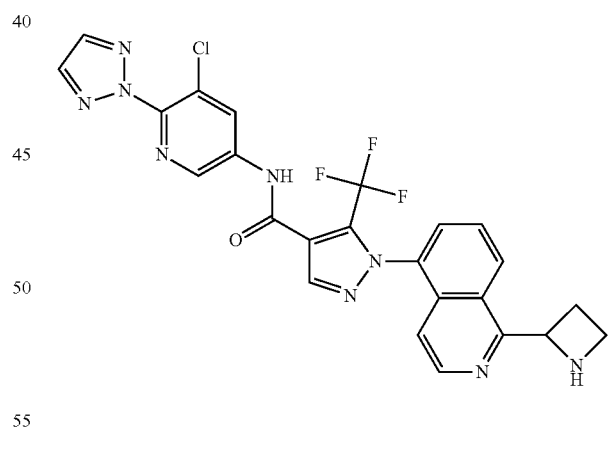

LCMS (ESI): mass calcd. for $C_{24}H_{17}ClF_3N_9O$ 539.1, m/z found 540.1 [M+H]$^+$. $^1$H NMR (400 MHz, DMSO-d$_6$) δ ppm 2.67 (br s, 1H), 3.03-3.15 (m, 1H), 3.80 (td, 5.9 Hz, 1H), 3.99-4.16 (m, 1H), 6.22 (br t, J=7.9 Hz, 1H), 7.10 (d, J=6.1 Hz, 1H), 7.92-8.00 (m, 1H), 8.17 (s, 1H), 8.20 (s, 2H), 8.38 (d, J=8.5 Hz, 1H), 8.63 (s, 1H), 8.67 (d, J=6.1 Hz, 1H), 8.69 (d, J=2.0 Hz, 1H), 8.88 (d, J=2.4 Hz, 1H), 11.29 (br s, 1H).

Example 385

N-(5-chloro-6-(2H-1,2,3-triazol-2-yl)pyridin-3-yl)-1-(1-(hydroxymethyl)isoquinolin-4-yl)-5-(trifluoromethyl)-1H-pyrazole-4-carboxamide, Cpd 385

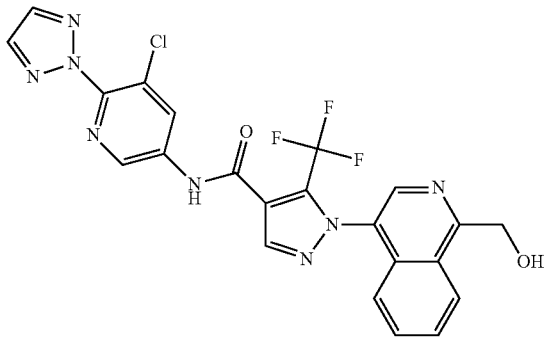 [SMILES: O=C(Nc1cnc(-n2nccn2)c(Cl)c1)c1cnn(-c2cnc(CO)c3ccccc23)c1C(F)(F)F]

N-(5-chloro-6-(2H-1,2,3-triazol-2-yl)pyridin-3-yl)-1-(isoquinolin-4-yl)-5-(trifluoromethyl)-1H-pyrazole-4-carboxamide (242.5 mg, 0.5 mmol), TFA (0.038 mL, 0.5 mmol) and BPO (302 mg, 1 mmol) were weighted in MeOH (2.5 mL) in a 10 mL vial. (IR[DF(CF$_3$)PPY]2(DTBPY))PF$_6$ (11.2 mg, 0.01 mmol) was successively added. The reaction mixture was degassed for 15 min and the vessel sealed. The reaction was stirred under blue LED irradiation at rt for 1 h. The reaction mixture was poured into water and extracted with DCM. The organic layer was dried over MgSO$_4$, filtered and the filtrate was concentrated to dryness. The residue was purified via Prep HPLC (Stationary phase: RP) (Bridge Prep C18 OBD-10 μm, 50×150 mm, Mobile phase: 0.25% NH$_4$HCO$_3$ solution in water, CH$_3$CN) to afford cpd 385 (12 mg, 4.7%). LCMS (ESI): mass calcd. for C$_{22}$H$_{14}$ClF$_3$N$_8$O$_2$ 514.1, m/z found 515.1 [M+H]$^+$. $^1$H NMR (400 MHz, DMSO-d$_6$) δ ppm 5.17 (d, J=5.7 Hz, 2H), 5.60-5.70 (m, 1H), 7.26 (d, J=8.1 Hz, 1H), 7.82-7.89 (m, 1H), 7.90-7.97 (m, 1H), 8.19 (s, 2H), 8.58 (d, J=8.1 Hz, 1H), 8.63 (s, 1H), 8.69 (d, J=2.0 Hz, 1H), 8.71 (s, 1H), 8.87 (d, J=2.0 Hz, 1H), 11.28 (br s, 1H).

Example 386

4-(4-((5-chloro-6-(2H-1,2,3-triazol-2-yl)pyridin-3-yl)carbamoyl)-5-(trifluoromethyl)-1H-pyrazol-1-yl)quinoline-2-carboxamide, Cpd 386

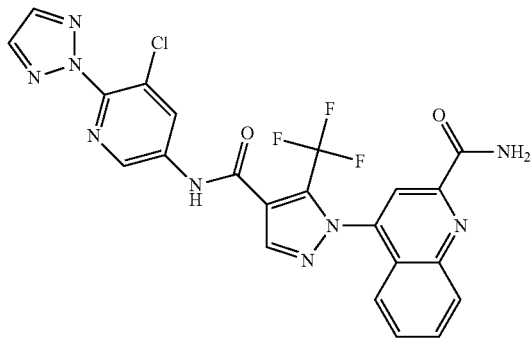 [SMILES: NC(=O)c1cc(-n2ncc(C(=O)Nc3cnc(-n4nccn4)c(Cl)c3)c2C(F)(F)F)c2ccccc2n1]

N-(5-chloro-6-(2H-1,2,3-triazol-2-yl)pyridin-3-yl)-1-(quinolin-4-yl)-5-(trifluoromethyl)-1H-pyrazole-4-carboxamide (485 mg, 1 mmol), iron (II) sulfate heptahydrate (139 mg, 0.5 mmol), formamide (450.5 mg, 10 mmol) and H$_2$SO$_4$ (147 mg, 1.5 mmol) were stirred in CH$_3$CN (5 mL) and water (5 mL) at 50° C. Hydrogen peroxide (0.486 mL, 0.35 g/mL, 5 mmol) was added slowly. The reaction mixture was stirred at 50° C. for 2 h. The reaction mixture was poured into water, the pH of the mixture was made basic with K$_2$CO$_3$, and the reaction mixture extracted with DCM/MeOH (90/10). The organic layer was concentrated. The resultant residue was purified by Prep HPLC (Stationary phase: RP XBridge Prep C18 OBD-10 μm, 50×150 mm, Mobile phase: 0.5% NH$_4$Ac solution in water+10% CH$_3$CN, CH$_3$CN) to afford cpd 386 (65 mg, 12.3%). LCMS (ESI): mass calcd. for C$_{22}$H$_{13}$ClF$_3$N$_9$O$_2$ 527.1, m/z found 528.1 [M+H]$^+$. $^1$H NMR (400 MHz, DMSO-d$_6$) δ ppm 7.42 (d, J=8.1 Hz, 1H), 7.87 (ddd, J=8.4, 7.0, 1.2 Hz, 1H), 7.99-8.08 (m, 2H), 8.19 (s, 2H), 8.33 (d, J=8.5 Hz, 1H), 8.35 (s, 1H), 8.48 (d, J=1.6 Hz, 1H), 8.67-8.70 (m, 2H), 8.87 (d, J=2.0 Hz, 1H), 11.27 (br s, 1H).

Following the procedure described in Example 386, above, selecting and substituting the appropriate reagents, starting materials, and purification methods, and adjusting reaction temperatures, times and other variables or parameters, as needed or desirable, as would be readily recognized by those skilled in the art, the following compounds were prepared:

Example 387

4-(4-((5-chloro-6-(2H-1,2,3-triazol-2-yl)pyridin-3-yl)carbamoyl)-5-(trifluoromethyl)-1H-pyrazol-1-yl)isoquinoline-1-carboxamide, cpd 387

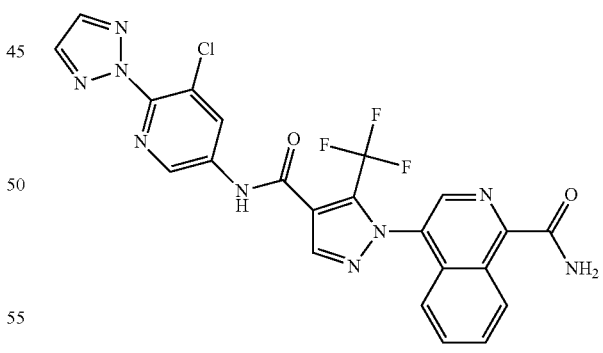

LCMS (ESI): mass calcd. for C$_{22}$H$_{13}$ClF$_3$N$_9$O$_2$ 527.1, m/z found 528.1[M+H]$^+$. $^1$H NMR (400 MHz, DMSO-d$_6$) δ ppm 7.32 (d, J=8.1 Hz, 1H), 7.87-7.93 (m, 1H), 7.95-8.01 (m, 1H), 8.02 (br s, 1H), 8.20 (s, 2H), 8.43 (br s, 1H), 8.66 (s, 1H), 8.69 (d, J=2.4 Hz, 1H), 8.85 (s, 1H), 8.87 (d, J=2.0 Hz, 1H), 8.90 (d, J=8.5 Hz, 1H), 11.29 (s, 1H).

Example 388

5-(4-((5-chloro-6-(2H-1,2,3-triazol-2-yl)pyridin-3-yl)carbamoyl)-5-(trifluoromethyl)-1H-pyrazol-1-yl)quinoline-2-carboxamide, Cpd 388

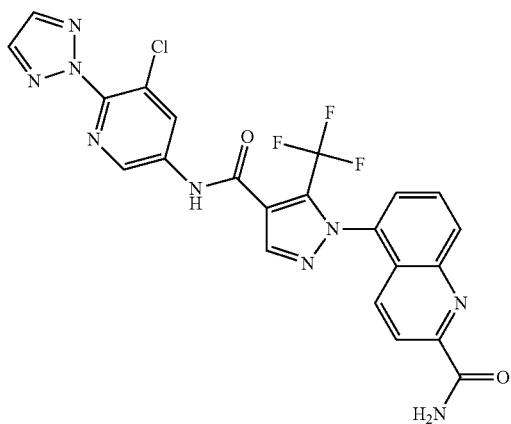 [SMILES: NC(=O)c1ccc2c(-n3ncc(C(=O)Nc4cnc(-n5nccn5)c(Cl)c4)c3C(F)(F)F)cccc2n1]

LCMS (ESI): mass calcd. for $C_{22}H_{13}ClF_3N_9O_2$ 527.1 m/z found 528.1 [M+H]$^+$. $^1$H NMR (400 MHz, DMSO-d$_6$) δ ppm 7.82 (d, J=8.5 Hz, 1H), 7.90 (d, J=2.0 Hz, 1H), 8.02-8.05 (m, 1H), 8.06-8.11 (m, 1H), 8.20 (s, 2H), 8.28 (d, J=8.5 Hz, 1H), 8.37-8.45 (m, 2H), 8.62 (s, 1H), 8.69 (d, J=2.0 Hz, 1H), 8.87 (d, J=2.0 Hz, 1H), 11.27 (br s, 1H).

Example 389

5-(4-((5-chloro-6-(2H-1,2,3-triazol-2-yl)pyridin-3-yl)carbamoyl)-5-(trifluoromethyl)-1H-pyrazol-1-yl)isoquinoline-1-carboxamide, Cpd 389

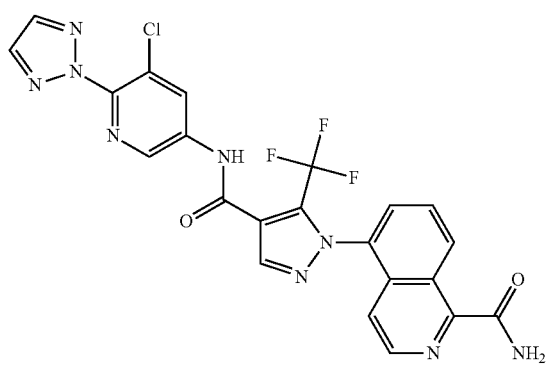 [SMILES: NC(=O)c1nccc2c(-n3ncc(C(=O)Nc4cnc(-n5nccn5)c(Cl)c4)c3C(F)(F)F)cccc12]

LCMS (ESI): mass calcd. for $C_{22}H_{13}ClF_3N_9O_2$ 527.1, m/z found 528.1 [M+H]$^+$. $^1$H NMR (400 MHz, DMSO-d$_6$) δ ppm 7.16-7.21 (m, 1H), 7.95 (dd, J=8.7, 7.5 Hz, 2H), 8.16 (d, J=6.5 Hz, 1H), 8.19 (s, 2H), 8.36 (s, 1H), 8.62 (s, 1H), 8.64 (d, J=6.1 Hz, 1H), 8.69 (d, J=2.0 Hz, 1H), 8.86 (d, J=2.4 Hz, 1H), 9.12-9.18 (m, 1H), 11.27 (br s, 1H).

Example 390

4-(4-((5-chloro-6-(2H-1,2,3-triazol-2-yl)pyridin-3-yl)carbamoyl)-5-(trifluoromethyl)-1H-pyrazol-1-yl)-N-methylisoquinoline-1-carboxamide, Cpd 390

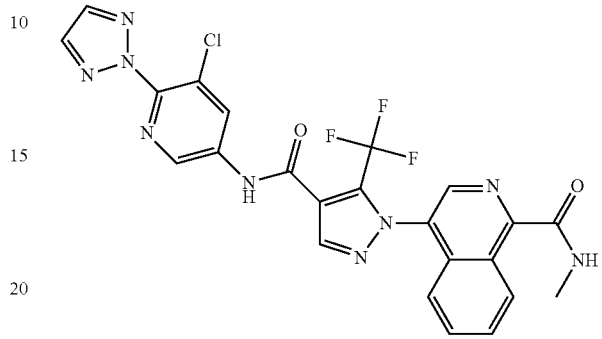

LCMS (ESI): mass calcd. for $C_{23}H_{15}ClF_3N_9O_2$ 541.1 m/z found 542.1 [M+H]$^+$. $^1$H NMR (400 MHz, DMSO-d$_6$) δ ppm 2.93 (d, J=4.9 Hz, 3H), 7.32 (d, J=8.5 Hz, 1H), 7.90 (ddd, J=8.4, 7.0, 1.2 Hz, 1H), 7.98 (ddd, J=8.2, 7.0, 1.4 Hz, 1H), 8.20 (s, 2H), 8.66 (s, 1H), 8.69 (d, J=2.4 Hz, 1H), 8.86 (s, 1H), 8.87 (d, J=2.0 Hz, 1H), 8.95 (dd, J=8.3, 1.0 Hz, 1H), 9.01 (q, J=4.5 Hz, 1H), 11.29 (s, 1H).

Example 391

4-(4-((5-chloro-6-(2H-1,2,3-triazol-2-yl)pyridin-3-yl)carbamoyl)-5-(trifluoromethyl)-1H-pyrazol-1-yl)thieno[2,3-c]pyridine-7-carboxamide, Cpd 391

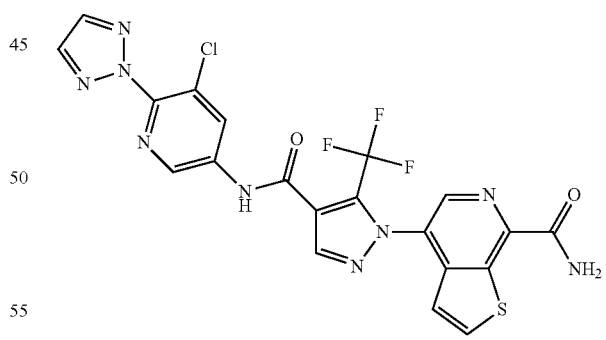

LCMS (ESI): mass calcd. for $C_{20}H_{11}ClF_3N_9O_2S$ 533, m/z found 534.1 [M+H]$^+$. $^1$H NMR (600 MHz, DMSO-d$_6$) δ ppm 7.21 (d, J=5.6 Hz, 1H), 8.14 (br s, 1H), 8.20 (s, 2H), 8.43 (d, J=5.6 Hz, 1H), 8.60 (br s, 1H), 8.64 (s, 1H), 8.68 (d, J=2.3 Hz, 1H), 8.81 (s, 1H), 8.86 (d, J=2.3 Hz, 1H), 11.28 (br s, 1H).

Example 392

4-(4-((5-chloro-6-(2H-1,2,3-triazol-2-yl)pyridin-3-yl)carbamoyl)-5-(trifluoromethyl)-1H-pyrazol-1-yl)-N-methylthieno[2,3-c]pyridine-7-carboxamide, Cpd 392

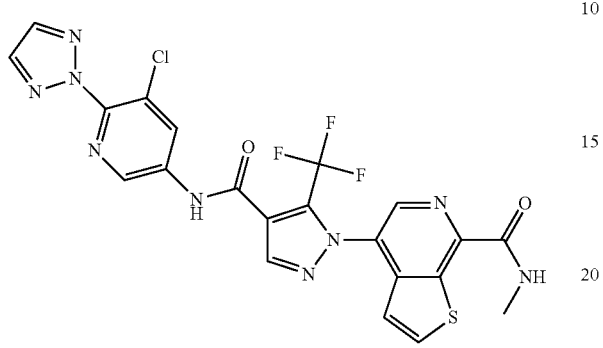

LCMS (ESI): mass calcd. for $C_{21}H_{13}ClF_3N_9O_2S$ 547.1 m/z found 548[M+H]$^+$. $^1$H NMR (400 MHz, DMSO-d$_6$) δ ppm 2.93 (d, J=4.8 Hz, 3H), 7.21 (d, J=5.7 Hz, 1H), 8.19 (s, 2H), 8.44 (d, J=5.5 Hz, 1H), 8.64 (s, 1H), 8.68 (d, J=2.2 Hz, 1H), 8.81 (s, 1H), 8.86 (d, J=2.2 Hz, 1H), 9.24 (q, J=4.5 Hz, 1H), 11.28 (br s, 1H).

Example 393

4-(4-((5-chloro-2-methyl-6-(2H-1,2,3-triazol-2-yl)pyridin-3-yl)carbamoyl)-5-(trifluoromethyl)-1H-pyrazol-1-yl)thieno[2,3-c]pyridine-7-carboxamide, Cpd 393

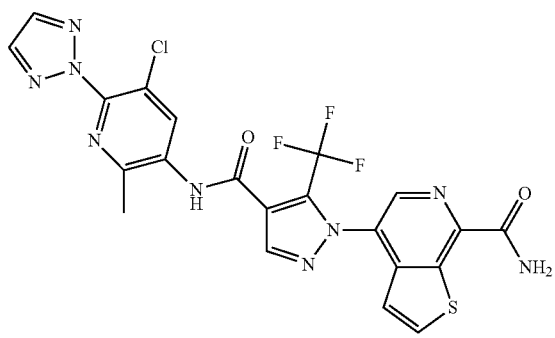

LCMS (ESI): mass calcd. for $C_{21}H_{13}ClF_3N_9O_2S$ 547.1 m/z found 548[M+H]$^+$. $^1$H NMR (400 MHz, DMSO-d$_6$) δ ppm 2.58 (s, 3H), 7.24 (d, J=5.7 Hz, 1H), 8.13 (br s, 1H), 8.19 (s, 2H), 8.40-8.48 (m, 2H), 8.58 (s, 1H), 8.67 (s, 1H), 8.80 (s, 1H).

Example 394

N-(5-chloro-6-(2H-1,2,3-triazol-2-yl)pyridin-3-yl)-1-(1-(difluoromethyl)isoquinolin-4-yl)-5-(trifluoromethyl)-1H-pyrazole-4-carboxamide, Cpd 394

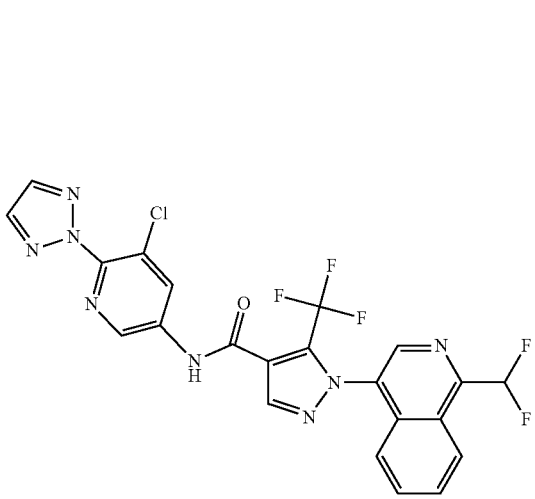 [SMILES: O=C(Nc1cnc(-n2nccn2)c(Cl)c1)c1cnn(-c2cnc(C(F)F)c3ccccc23)c1C(F)(F)F]

A mixture of N-(5-chloro-6-(2H-1,2,3-triazol-2-yl)pyridin-3-yl)-1-(isoquinolin-4-yl)-5-(trifluoromethyl)-1H-pyrazole-4-carboxamide (242 mg, 0.5 mmol), zinc difluoromethanesulfinate (400 mg, 1.35 mmol), water (1 mL), and DCM (2.5 mL) were stirred at rt. TFA (0.038 mL, 0.5 mmol) was added. Tert-butyl hydroperoxide (322 mg, 2.5 mmol) was added slowly. The reaction mixture was stirred for 16 h. Additional zinc difluoromethanesulfinate (400 mg, 1.35 mmol) and tert-butyl hydroperoxide (322 mg, 2.5 mmol) were added. The reaction mixture was stirred for 3 h. The reaction mixture was poured into water, the mixture was made basic by the addition of Na$_2$CO$_3$, and the mixture was extracted with DCM (20 mL×2). The organic layer was dried over MgSO$_4$, filtered, and the filtrate concentrated. The residue was purified via Prep HPLC (Stationary phase: RP XBridge Prep C18 OBD-10 μm, 30×150 mm, Mobile phase: 0.25% NH$_4$HCO$_3$ solution in water, MeOH). The pure fractions were concentrated and the residue was stirred in diisopropylether, the solid collected by filtration and then dried to afford cpd 394 (39 mg, 14.6%). LCMS (ESI): mass calcd. for $C_{22}H_{12}ClF_5N_8O$ 534.1, m/z found 535.1 [M+H]$^+$. $^1$H NMR (400 MHz, DMSO-d$_6$) δ ppm 7.42 (d, J=8.1 Hz, 1H), 7.62 (t, J=53.3 Hz, 1H), 7.95-8.01 (m, 1H), 8.01-8.07 (m, 1H), 8.16 (s, 2H), 8.58 (br d, J=8.1 Hz, 1H), 8.64 (s, 1H), 8.75 (d, J=2.0 Hz, 1H), 8.77 (d, J=2.0 Hz, 1H) 8.92 (s, 1H).

Following the procedure described in Example 394, above, selecting and substituting the appropriate reagents, starting materials, and purification methods, and adjusting

Example 395

N-(5-chloro-6-(2H-1,2,3-triazol-2-yl)pyridin-3-yl)-1-(2-(difluoromethyl)quinolin-5-yl)-5-(trifluoromethyl)-1H-pyrazole-4-carboxamide, Cpd 395

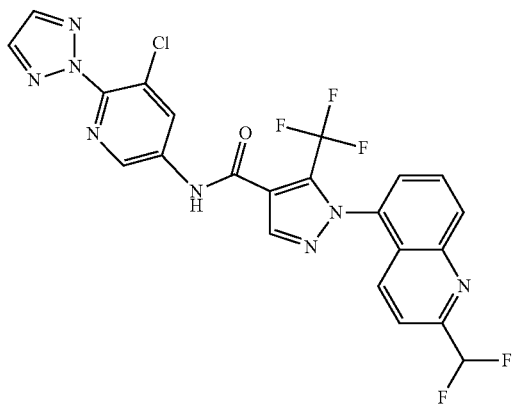 [SMILES: O=C(Nc1cnc(-n2nccn2)c(Cl)c1)c1cnn(-c2cccc3nc(C(F)F)ccc23)c1C(F)(F)F]

LCMS (ESI): mass calcd. for $C_{22}H_{12}ClF_5N_8O$ 534.1 m/z found 535.1 [M+H]$^+$. $^1$H NMR (600 MHz, DMSO-d$_6$) δ ppm 7.21 (t, J=54.7 Hz, 1H), 7.89 (d, J=8.8 Hz, 1H), 7.98 (d, J=8.9 Hz, 1H), 8.06-8.09 (m, 1H), 8.09-8.13 (m, 1H), 8.20 (s, 2H), 8.45 (d, J=8.1 Hz, 1H), 8.64 (s, 1H), 8.69 (d, J=2.3 Hz, 1H), 8.88 (d, J=2.3 Hz, 1H), 11.31 (s, 1H).

Example 396

N-(5-chloro-6-(2H-1,2,3-triazol-2-yl)pyridin-3-yl)-1-(4-(difluoromethyl)quinolin-5-yl)-5-(trifluoromethyl)-1H-pyrazole-4-carboxamide, Cpd 396

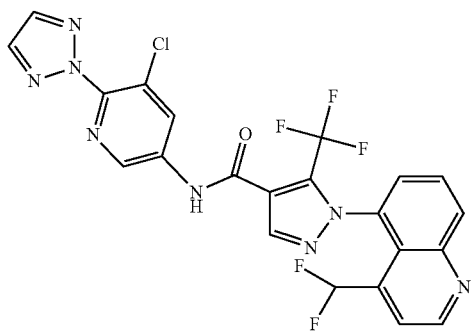 [SMILES: O=C(Nc1cnc(-n2nccn2)c(Cl)c1)c1cnn(-c2cccc3nccc(C(F)F)c23)c1C(F)(F)F]

LCMS (ESI): mass calcd. for $C_{22}H_{12}ClF_5N_8O$ 534.1 m/z found 535.1 [M+H]$^+$. $^1$H NMR (400 MHz, DMSO-d$_6$) δ ppm 5.96-6.33 (m, 1H), 7.91-7.96 (m, 1H), 8.01 (dd, J=4.3, 2.6 Hz, 1H), 8.03-8.10 (m, 1H), 8.20 (s, 2H), 8.50 (dd, J=8.1, 1.2 Hz, 1H), 8.66 (s, 1H), 8.69 (d, J=2.4 Hz, 1H), 8.88 (d, J=2.0 Hz, 1H), 9.24 (d, J=4.5 Hz, 1H), 11.25 (br s, 1H).

Example 397

N-(5-chloro-6-(2H-1,2,3-triazol-2-yl)pyridin-3-yl)-1-(8-(difluoromethyl)quinolin-5-yl)-5-(trifluoromethyl)-1H-pyrazole-4-carboxamide, Cpd 397

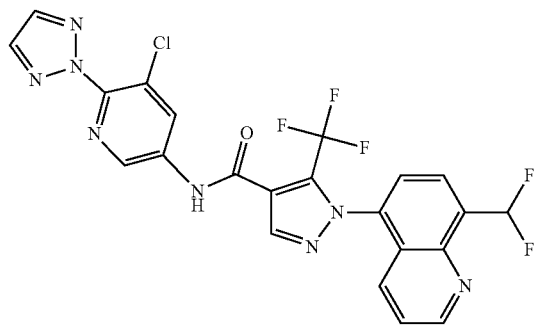 [SMILES: O=C(Nc1cnc(-n2nccn2)c(Cl)c1)c1cnn(-c2ccc(C(F)F)c3ncccc23)c1C(F)(F)F]

LCMS (ESI): mass calcd. for $C_{22}H_{12}ClF_5N_8O$ 534.1 m/z found 535.1 [M+H]$^+$. $^1$H NMR (400 MHz, DMSO-d$_6$) δ ppm 7.73-7.77 (m, 1H), 7.79-8.12 (m, 3H), 8.20 (s, 2H), 8.26 (d, J=7.7 Hz, 1H), 8.64 (s, 1H), 8.69 (d, J=2.4 Hz, 1H), 8.87 (d, J=2.4 Hz, 1H), 9.17 (dd, J=4.3, 1.8 Hz, 1H), 11.27 (br s, 1H).

Example 398

N-(5-chloro-6-(2H-1,2,3-triazol-2-yl)pyridin-3-yl)-1-(7-(difluoromethyl)thieno[2,3-c]pyridin-4-yl)-5-(trifluoromethyl)-1H-pyrazole-4-carboxamide, Cpd 398

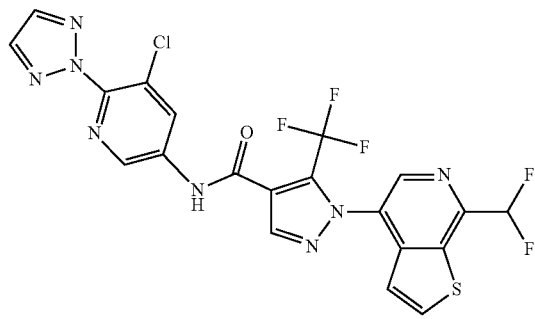 [SMILES: O=C(Nc1cnc(-n2nccn2)c(Cl)c1)c1cnn(-c2cnc(C(F)F)c3sccc23)c1C(F)(F)F]

LCMS (ESI): mass calcd. for $C_{20}H_{10}ClF_5N_8OS$ 540 m/z found 541 [M+H]$^+$. $^1$H NMR (400 MHz, DMSO-d$_6$) δ ppm 7.26-7.57 (m, 1H), 7.32 (d, J=5.3 Hz, 1H), 8.20 (s, 2H), 8.50 (d, J=5.7 Hz, 1H), 8.65 (s, 1H), 8.68 (d, J=2.4 Hz, 1H), 8.85-8.88 (m, 2H), 11.27 (s, 1H).

Example 399

N-(5-chloro-6-(2H-1,2,3-triazol-2-yl)pyridin-3-yl)-1-(2-(difluoromethyl)thieno[2,3-c]pyridin-4-yl)-5-(trifluoromethyl)-1H-pyrazole-4-carboxamide, Cpd 399

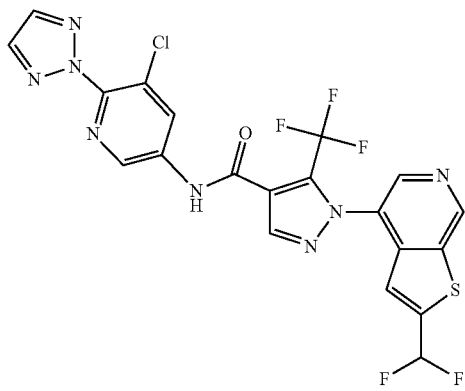 [SMILES: O=C(Nc1cnc(-n2nccn2)c(Cl)c1)c1cnn(-c2cncc3sc(C(F)F)cc23)c1C(F)(F)F]

LCMS (ESI): mass calcd. for $C_{20}H_{10}ClF_5N_8OS$ 540 m/z found 541.1 [M+H]$^+$. $^1$H NMR (400 MHz, DMSO-d$_6$) δ ppm 7.39-7.69 (m, 2H), 8.19 (s, 2H), 8.63 (s, 1H), 8.68 (d, J=2.4 Hz, 1H), 8.82 (s, 1H), 8.86 (d, J=2.4 Hz, 1H), 9.61-9.75 (m, 1H), 11.26 (br s, 1H).

Example 400

N-(5-chloro-6-(2H-1,2,3-triazol-2-yl)pyridin-3-yl)-1-(1-(difluoromethyl)isoquinolin-5-yl)-5-(trifluoromethyl)-1H-pyrazole-4-carboxamide, Cpd 400

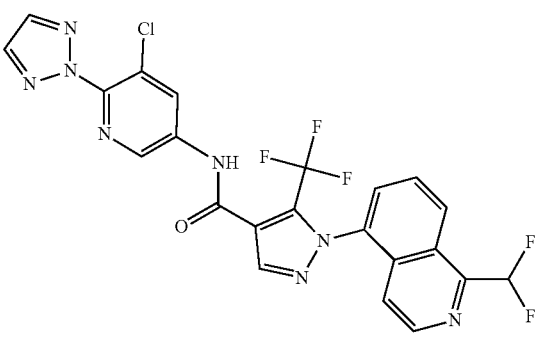 [SMILES: O=C(Nc1cnc(-n2nccn2)c(Cl)c1)c1cnn(-c2cccc3c(C(F)F)nccc23)c1C(F)(F)F]

LCMS (ESI): mass calcd. for $C_{22}H_{12}ClF_5N_8O$ 534.1, m/z found 535.1 [M+H]$^+$. $^1$H NMR (400 MHz, DMSO-d$_6$) δ ppm 7.28 (d, J=5.7 Hz, 1H), 7.55 (t, J=53.5 Hz, 1H), 8.04 (dd, J=8.5, 7.7 Hz, 1H), 8.19 (s, 2H), 8.25 (d, J=7.3 Hz, 1H), 8.63 (s, 1H), 8.66-8.74 (m, 3H), 8.87 (d, J=2.0 Hz, 1H), 11.28 (br s, 1H).

Example 401

N-(5-chloro-6-(2H-1,2,3-triazol-2-yl)pyridin-3-yl)-1-(2-(difluoromethyl)quinolin-4-yl)-5-(trifluoromethyl)-1H-pyrazole-4-carboxamide, Cpd 401

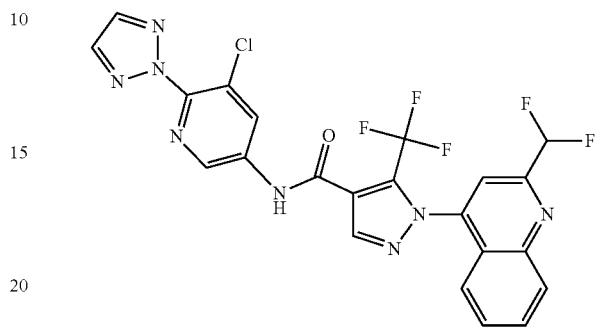

LCMS (ESI): mass calcd. for $C_{22}H_{12}ClF_5N_8O$ 534.1 m/z found 535.1 [M+H]$^+$. $^1$H NMR (400 MHz, DMSO-d$_6$) δ ppm 7.14-7.46 (m, 2H), 7.89 (t, J=7.5 Hz, 1H), 8.06 (t, J=7.7 Hz, 1H), 8.20 (s, 2H), 8.26 (s, 1H), 8.35 (d, J=8.5 Hz, 1H), 8.68-8.73 (m, 2H), 8.86-8.91 (m, 1H), 11.27 (s, 1H).

Example 402

N-(5-chloro-6-(2H-1,2,3-triazol-2-yl)pyridin-3-yl)-1-(1-(1,1-difluoroethyl)isoquinolin-4-yl)-5-(trifluoromethyl)-1H-pyrazole-4-carboxamide, Cpd 402

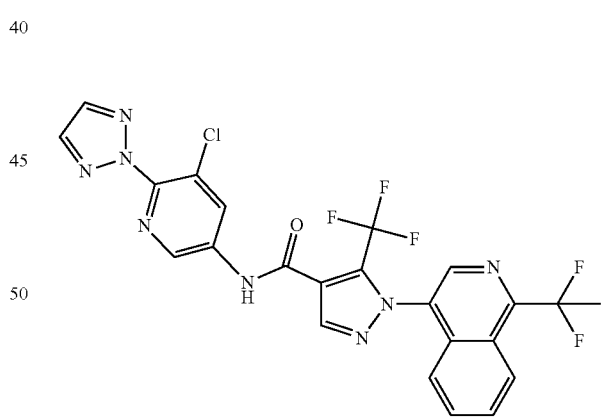

LCMS (ESI): mass calcd. for $C_{23}H_{14}ClF_5N_8O$ 548.1 m/z found 549.1 [M+H]$^+$. $^1$H NMR (400 MHz, DMSO-d$_6$) δ ppm 2.31 (t, J=19.9 Hz, 3H), 7.38 (d, J=7.7 Hz, 1H), 7.95-8.01 (m, 1H), 8.01-8.08 (m, 1H), 8.17-8.27 (m, 2H), 8.64 (s, 1H), 8.63-8.67 (m, 1H), 8.66 (br s, 1H), 8.68 (s, 1H), 8.69 (d, J=2.0 Hz, 1H), 8.87 (d, J=2.4 Hz, 1H), 8.93 (s, 1H), 11.30 (s, 1H).

Example 403

1-(1-(azetidin-3-yl)isoquinolin-4-yl)-N-(5-chloro-6-(2H-1,2,3-triazol-2-yl)pyridin-3-yl)-5-(trifluoromethyl)-1H-pyrazole-4-carboxamide, Cpd 403

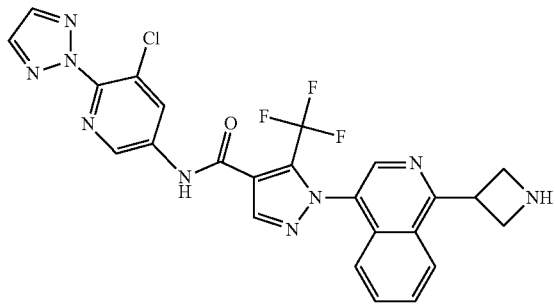 [SMILES: O=C(Nc1cnc(-n2nccn2)c(Cl)c1)c1cnn(-c2cnc(C3CNC3)c3ccccc23)c1C(F)(F)F]

A. tert-butyl 3-(4-(4-((5-chloro-6-(2H-1,2,3-triazol-2-yl)pyridin-3-yl)carbamoyl)-5-(trifluoromethyl)-1H-pyrazol-1-yl)isoquinolin-1-yl)azetidine-1-carboxylate, 403a

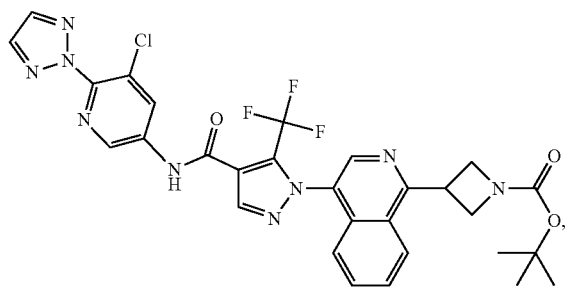

A mixture of 1-tert-butoxycarbonylazetidin-3-yl)-trifluoro-boranuide (289 mg, 1.1 mmol), N-(5-chloro-6-(2H-1,2,3-triazol-2-yl)pyridin-3-yl)-1-(isoquinolin-4-yl)-5-(trifluoromethyl)-1H-pyrazole-4-carboxamide (242 mg, 0.5 mmol), silver nitrate (34 mg, 0.2 mmol), ammonium persulfate (1141 mg, 5 mmol) and TFA (0.0383 mL, 0.5 mmol) was stirred in dioxane (5 mL) and water (5 mL) in a sealed tube. The reaction was stirred at rt for 4 h. The reaction mixture was poured into a 1:1 mixture sat aq. NaHCO₃/5% aq Na₂S₂O₃ and the aqueous layer was extracted with DCM (3×). The combined organic layers were dried over MgSO₄, filtered, and the filtrate concentrated. The residue was purified via Prep HPLC (Stationary phase: RP XBridge Prep C18 OBD-10×150 mm, Mobile phase: 0.25% NH₄HCO₃ solution in water, MeOH) to afford cpd 403a (16 mg, 5%). LCMS (ESI): mass calcd. for $C_{29}H_{25}ClF_3N_9O_3$ 639.2, m/z found 640.2 [M+H]⁺.

B. 1-(1-(azetidin-3-yl)isoquinolin-4-yl)-N-(5-chloro-6-(2H-1,2,3-triazol-2-yl)pyridin-3-yl)-5-(trifluoromethyl)-1H-pyrazole-4-carboxamide, Cpd 403

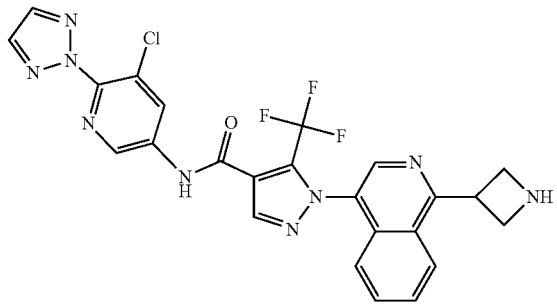 [SMILES: O=C(Nc1cnc(-n2nccn2)c(Cl)c1)c1cnn(-c2cnc(C3CNC3)c3ccccc23)c1C(F)(F)F]

A mixture of tert-butyl 3-(4-(4-((5-chloro-6-(2H-1,2,3-triazol-2-yl)pyridin-3-yl)carbamoyl)-5-(trifluoromethyl)-1H-pyrazol-1-yl)isoquinolin-1-yl)azetidine-1-carboxylate (16 mg, 0.025 mmol) and TFA (0.134 mL, 1.75 mmol) in DCM (0.5 mL) was stirred for 3 h. The reaction mixture was concentrated to dryness. The reaction mixture was poured into water and made basic by the addition of Na₂CO₃, then extracted with DCM (2×). The organic layer was dried over MgSO₄, filtered, and the filtrate concentrated. The residue was purified via Prep HPLC (Stationary phase: RP XBridge Prep C18 OBD-10 µm, 30×150 mm, Mobile phase: 0.25% NH₄HCO₃ solution in water, CH₃CN) to afford cpd 403 (7 mg, 52%). LCMS (ESI): mass calcd. for $C_{24}H_{17}ClF_3N_9O$ 539.2, m/z found 540.2 [M+H]⁺. ¹H NMR (400 MHz, CHLOROFORM-d) δ ppm 4.11 (br t, J=8.1 Hz, 2H), 4.32 (br s, 2H), 4.90 (quin, J=8.0 Hz, 1H), 7.30 (d, J=7.3 Hz, 1H), 7.67-7.79 (m, 2H), 7.96 (s, 2H), 8.04 (d, J=7.7 Hz, 1H), 8.26 (s, 1H), 8.55 (d, J=2.4 Hz, 1H), 8.61 (s, 1H), 8.78 (d, J=2.4 Hz, 1H).

Example 404

N-(5-chloro-6-(2H-1,2,3-triazol-2-yl)pyridin-3-yl)-1-(1-(methoxymethyl)isoquinolin-4-yl)-5-(trifluoromethyl)-1H-pyrazole-4-carboxamide, Cpd 404

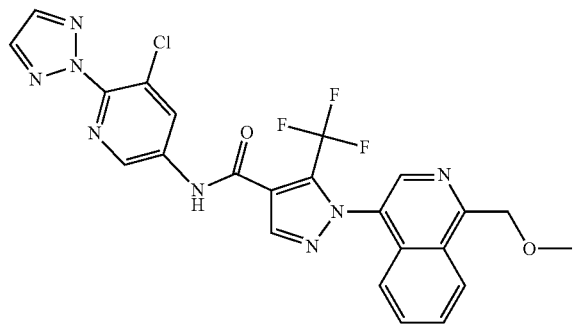 [SMILES: COCc1ncc(-n2ncc(C(=O)Nc3cnc(-n4nccn4)c(Cl)c3)c2C(F)(F)F)c2ccccc12]

A mixture of methoxyacetic acid (135 mg, 1.5 mmol), N-(5-chloro-6-(2H-1,2,3-triazol-2-yl)pyridin-3-yl)-1-(isoquinolin-4-yl)-5-(trifluoromethyl)-1H-pyrazole-4-carboxamide (242 mg, 0.5 mmol), silver nitrate (17 mg, 0.1 mmol), ammonium persulfate (342 mg, 1.5 mmol) and TFA (0.0383 mL, 0.5 mmol) was stirred in DMSO (5 mL) and water (5 mL) in a sealed tube. The reaction was stirred at rt for 16 h. Additional methoxyacetic acid (135 mg, 1.5 mmol), silver nitrate (17 mg, 0.1 mmol), and ammonium persulfate (342 mg, 1.5 mmol) were added. The reaction was stirred for 16 h. The reaction mixture was poured into water, made basic with $Na_2CO_3$ and extracted with DCM (2x). The combined organic layers were dried over $MgSO_4$, filtered, and the filtrate concentrated. The residue was purified via Prep HPLC (Stationary phase: RP)(Bridge Prep C18 OBD-10 μm, 30×150 mm, Mobile phase: 0.25% $NH_4HCO_3$ solution in water, $CH_3CN$). The pure fractions were collected, concentrated and the residue was stirred in disiopropylether, the solid collected by filtration and then dried to afford cpd 404 (21 mg, 8%). LCMS (ESI): mass calcd. for $C_{23}H_{16}ClF_3N_8O_2$ 528.1, m/z found 529.1 [M+H]$^+$. $^1$H NMR (400 MHz, DMSO-d$_6$) δ ppm 3.42 (s, 3H), 5.10 (br s, 2H), 7.28 (d, J=8.5 Hz, 1H), 7.82-7.91 (m, 1H), 7.91-7.99 (m, 1H), 8.19 (s, 2H), 8.52 (d, J=8.5 Hz, 1H), 8.64 (s, 1H), 8.69 (d, J=2.4 Hz, 1H), 8.74 (s, 1H), 8.87 (d, J=2.0 Hz, 1H), 11.28 (br s, 1H).

Example 405

4-(4-((5-chloro-6-(2H-1,2,3-triazol-2-yl)pyridin-3-yl)carbamoyl)-5-(trifluoromethyl)-1H-pyrazol-1-yl) quinoline 1-oxide, Cpd 405

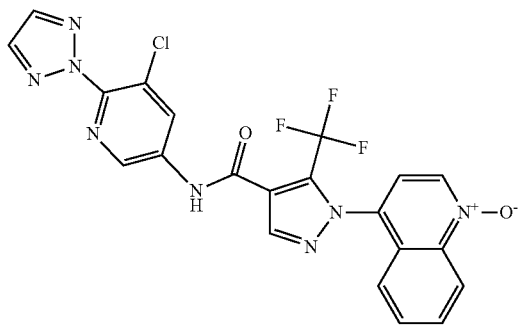 [SMILES: O=C(Nc1cnc(-n2nccn2)c(Cl)c1)c1cnn(-c2cc[n+]([O-])c3ccccc23)c1C(F)(F)F]

A solution of N-(5-chloro-6-(2H-1,2,3-triazol-2-yl)pyridin-3-yl)-1-(quinolin-4-yl)-5-(trifluoromethyl)-1H-pyrazole-4-carboxamide (2425 mg, 5 mmol) in DCM (150 mL) was stirred at rt. m-CPBA (1295 mg, 7.5 mmol) was added portion-wise. Stirring was continued for 16 h. Additional m-CPBA (1295 mg, 7.5 mmol) was added portion-wise. Stirring was continued for 4 h. Additional m-CPBA (1295 mg, 7.5 mmol) was added portion-wise. Stirring was continued for 16 h. The reaction mixture was poured into 100 mL water and was treated with sodium sulfite (4726 mg, 37.7 mmol) and stirred for 15 min before the addition of $NaHCO_3$ (3150 mg, 37.5 mmol). Stirring was continued for 5 min. DCM/MeOH (100 mL, 90/10) was added and stirring was continued for 10 min. The precipitate was collected by filtration. The aqueous layer was extracted with DCM/MeOH (100 mL, 90/10, 3x). The combined organic layers were concentrated. The resultant residue was boiled in $CH_3CN$, cooled, and the resulting precipitate was collected by filtration, then dried to afford crude cpd 405 (6.3 g, 251%) which was used as such in the next step. LCMS (ESI): mass calcd. for $C_{21}H_{12}ClF_3N_8O_2$ 500.1, m/z found 501.1[M+H]$^+$.

Following the procedure described in Example 405, above, selecting and substituting the appropriate reagents, starting materials, and purification methods, and adjusting reaction temperatures, times and other variables or parameters, as needed or desirable, as would be readily recognized by those skilled in the art, the following compounds were prepared:

Example 406

4-(4-((5-chloro-6-(2H-1,2,3-triazol-2-yl)pyridin-3-yl)carbamoyl)-5-(trifluoromethyl)-1H-pyrazol-1-yl) isoquinoline 2-oxide, Cpd 406

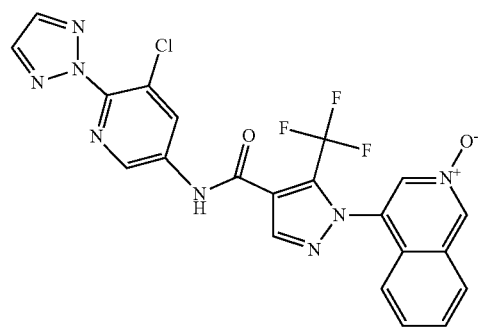 [SMILES: O=C(Nc1cnc(-n2nccn2)c(Cl)c1)c1cnn(-c2c[n+]([O-])cc3ccccc23)c1C(F)(F)F]

LCMS (ESI): mass calcd. For $C_{21}H_{12}ClF_3N_8O_2$ 500.1 m/z found 501.1 [M+H]$^+$.

Example 407

5-(4-((5-chloro-6-(2H-1,2,3-triazol-2-yl)pyridin-3-yl)carbamoyl)-5-(trifluoromethyl)-1H-pyrazol-1-yl) isoquinoline 2-oxide, Cpd 407

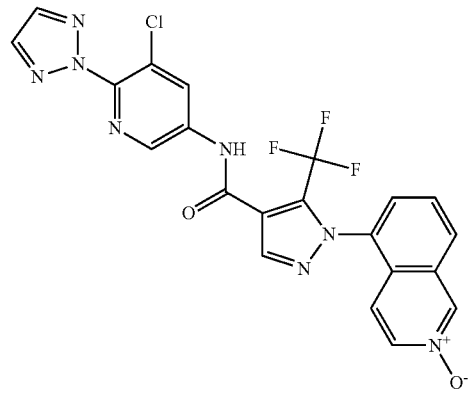 [SMILES: O=C(Nc1cnc(-n2nccn2)c(Cl)c1)c1cnn(-c2cccc3c[n+]([O-])ccc23)c1C(F)(F)F]

LCMS (ESI): mass calcd. For $C_{21}H_{12}ClF_3N_8O_2$ 500.1 m/z found 501.1 [M+H]$^+$.

Example 408

5-(4-((5-chloro-6-(2H-1,2,3-triazol-2-yl)pyridin-3-yl)carbamoyl)-5-(trifluoromethyl)-1H-pyrazol-1-yl)quinoline 1-oxide, Cpd 408

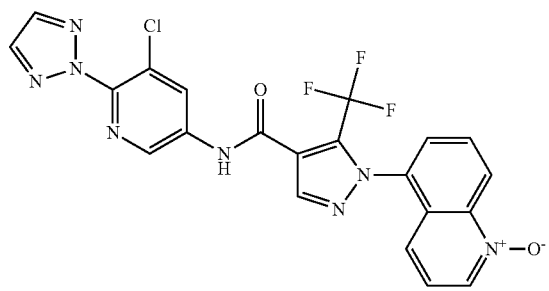 [SMILES: O=C(Nc1cnc(-n2nccn2)c(Cl)c1)c1cnn(-c2cccc3c2ccc[n+]3[O-])c1C(F)(F)F]

LCMS (ESI): mass calcd. For $C_{21}H_{12}ClF_3N_8O_2$ 500.1 m/z found 501.1 [M+H]$^+$.

Example 409

4-(4-((5-chloro-6-(2H-1,2,3-triazol-2-yl)pyridin-3-yl)carbamoyl)-5-(trifluoromethyl)-1H-pyrazol-1-yl)thieno[2,3-c]pyridine 6-oxide, Cpd 409

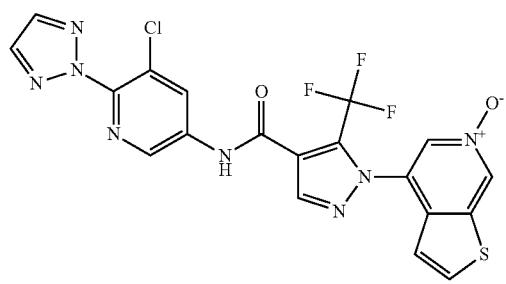 [SMILES: O=C(Nc1cnc(-n2nccn2)c(Cl)c1)c1cnn(-c2c[n+]([O-])cc3sccc23)c1C(F)(F)F]

LCMS (ESI): mass calcd. for $C_{19}H_{10}ClF_3N_8O_2S$ 506 m/z found 507[M+H]$^+$. $^1$H NMR (400 MHz, DMSO-d$_6$) δ ppm 7.05 (d, J=5.7 Hz, 1H), 8.18 (d, J=5.0 Hz, 1H), 8.19 (s, 2H), 8.62 (s, 1H), 8.67 (d, J=2.4 Hz, 1H), 8.77 (d, J=1.6 Hz, 1H), 8.86 (d, J=2.0 Hz, 1H), 9.36 (s, 1H), 11.23 (s, 1H).

Example 410

4-(4-((5-chloro-2-methyl-6-(2H-1,2,3-triazol-2-yl)pyridin-3-yl)carbamoyl)-5-(trifluoromethyl)-1H-pyrazol-1-yl)thieno[2,3-c]pyridine 6-oxide, Cpd 410

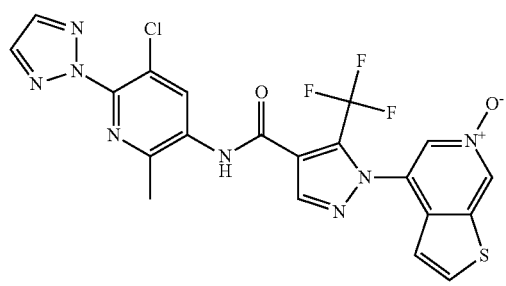 [SMILES: Cc1nc(-n2nccn2)c(Cl)cc1NC(=O)c1cnn(-c2c[n+]([O-])cc3sccc23)c1C(F)(F)F]

LCMS (ESI): mass calcd. for $C_{20}H_{12}ClF_3N_8O_2S$ 520 m/z found 521.1 [M+H]$^+$.

Example 411

N-(5-chloro-6-(2H-1,2,3-triazol-2-yl)pyridin-3-yl)-1-(1-cyanoisoquinolin-5-yl)-5-(trifluoromethyl)-1H-pyrazole-4-carboxamide, Cpd 411

A mixture of 5-(4-((5-chloro-6-(2H-1,2,3-triazol-2-yl)pyridin-3-yl)carbamoyl)-5-(trifluoromethyl)-1H-pyrazol-1-yl)isoquinoline 2-oxide (501 mg, 1 mmol), trimethylsilyl cyanide (119 mg, 1.2 mmol) and DBU (305 mg, 2 mmol in THF (3 mL) was stirred at 50° C. for 1 h. The reaction mixture was poured into water and extracted with ethyl acetate. The organic layer was dried over MgSO$_4$, filtered, and the filtrate concentrated. The residue was purified via Prep HPLC (Stationary phase: RP XBridge Prep C18 OBD-10 μm, 50×150 mm, Mobile phase: 0.25% NH$_4$HCO$_3$ solution in water, CH$_3$CN) to afford cpd 411 (330 mg, 65%). LCMS (ESI): mass calcd. for $C_{22}H_{11}ClF_3N_9O$ 509.1, m/z found 510.1[M+H]$^+$. $^1$H NMR (400 MHz, DMSO-d$_6$) δ ppm 7.50 (dd, J=5.7, 0.8 Hz, 1H), 8.15 (dd, J=8.5, 7.7 Hz, 1H), 8.19 (s, 2H), 8.32 (d, J=6.9 Hz, 1H), 8.57 (dt, J=8.4, 0.9 Hz, 1H), 8.64 (s, 1H), 8.68 (d, J=2.0 Hz, 1H), 8.81-8.84 (m, 1H), 8.87 (d, J=2.4 Hz, 1H), 11.26 (br s, 1H).

Following the procedure described in Example 411, above, selecting and substituting the appropriate reagents, starting materials, and purification methods, and adjusting

Example 412

N-(5-chloro-6-(2H-1,2,3-triazol-2-yl)pyridin-3-yl)-1-(2-cyanoquinolin-4-yl)-5-(trifluoromethyl)-1H-pyrazole-4-carboxamide, Cpd 412

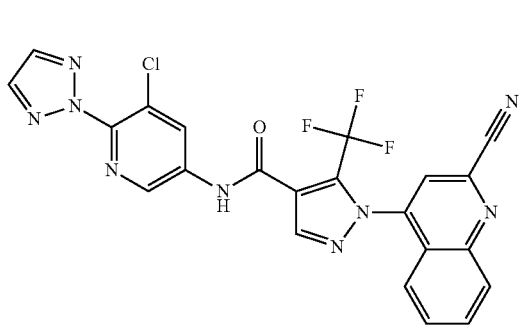 [SMILES: N#Cc1cc(-n2ncc(C(=O)Nc3cnc(-n4nccn4)c(Cl)c3)c2C(F)(F)F)c2ccccc2n1]

LCMS (ESI): mass calcd. for $C_{22}H_{11}ClF_3N_9O$ 509.1 m/z found 510.1 [M+H]$^+$. $^1$H NMR (400 MHz, DMSO-d$_6$) δ ppm 7.44 (d, J=8.5 Hz, 1H), 7.97 (ddd, J=8.3, 7.1, 0.8 Hz, 1H), 8.12 (ddd, J=8.4, 7.2, 1.4 Hz, 1H), 8.20 (s, 2H), 8.39 (d, J=8.5 Hz, 1H), 8.63 (s, 1H), 8.69 (d, J=2.4 Hz, 1H), 8.72 (s, 1H), 8.87 (d, J=2.4 Hz, 1H), 11.29 (br s, 1H).

Example 413

N-(5-chloro-6-(2H-1,2,3-triazol-2-yl)pyridin-3-yl)-1-(2-cyanoquinolin-5-yl)-5-(trifluoromethyl)-1H-pyrazole-4-carboxamide, Cpd 413

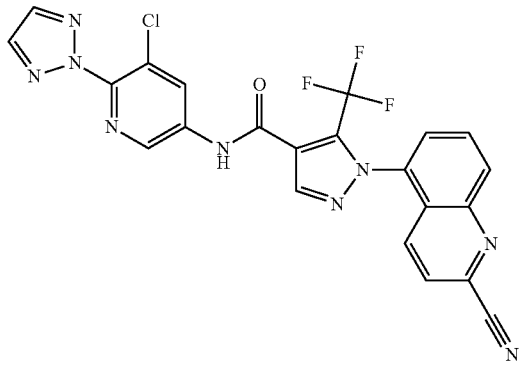 [SMILES: N#Cc1ccc2c(-n3ncc(C(=O)Nc4cnc(-n5nccn5)c(Cl)c4)c3C(F)(F)F)cccc2n1]

LCMS (ESI): mass calcd. for $C_{22}H_{11}ClF_3N_9O$ 509.1 m/z found 510.1 [M+H]$^+$. $^1$H NMR (400 MHz, DMSO-d$_6$) δ ppm 7.89-7.97 (m, 1H), 8.14-8.19 (m, 3H), 8.20 (s, 2H), 8.44-8.51 (m, 1H), 8.63 (s, 1H), 8.69 (d, J=2.4 Hz, 1H), 8.87 (d, J=2.0 Hz, 1H), 11.20 (br s, 1H).

Example 414

N-(5-chloro-6-(2H-1,2,3-triazol-2-yl)pyridin-3-yl)-1-(1-cyanoisoquinolin-4-yl)-5-(trifluoromethyl)-1H-pyrazole-4-carboxamide, Cpd 414

LCMS (ESI): mass calcd. for $C_{22}H_{11}ClF_3N_9O$ 509.1 m/z found 510.1 [M+H]$^+$. $^1$H NMR (400 MHz, DMSO-d$_6$) δ ppm 7.47-7.55 (m, 1H), 8.08-8.17 (m, 2H), 8.20 (s, 2H), 8.44-8.53 (m, 1H), 8.68-8.74 (m, 2H), 8.87 (d, J=2.4 Hz, 1H), 9.09 (s, 1H), 11.29 (br s, 1H).

Example 415

N-(5-chloro-6-(2H-1,2,3-triazol-2-yl)pyridin-3-yl)-1-(7-cyanothieno[2,3-c]pyridin-4-yl)-5-(trifluoromethyl)-1H-pyrazole-4-carboxamide, Cpd 415

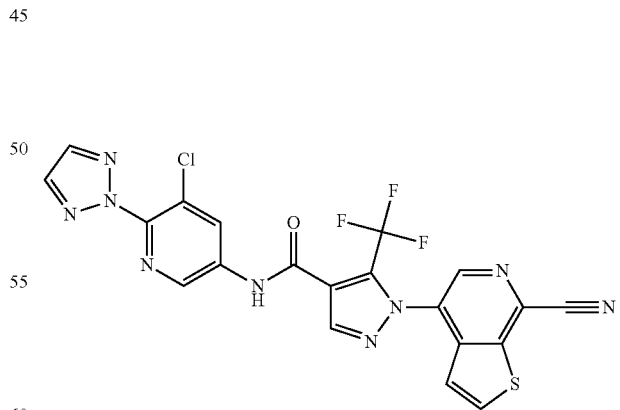

LCMS (ESI): mass calcd. For $C_{20}H_9ClF_3N_9OS$ 515, m/z found 516[M+H]$^+$.

Example 416

N-(5-chloro-2-methyl-6-(2H-1,2,3-triazol-2-yl)pyridin-3-yl)-1-(7-cyanothieno[2,3-c]pyridin-4-yl)-5-(trifluoromethyl)-1H-pyrazole-4-carboxamide, Cpd 416

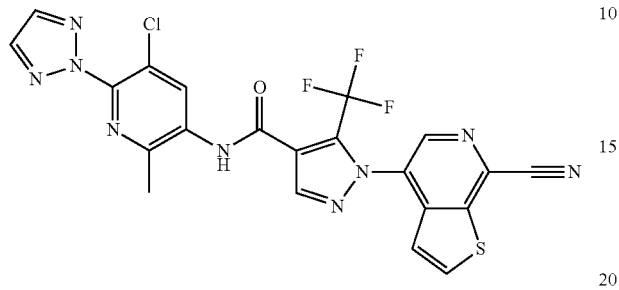

LCMS (ESI): mass calcd. for $C_{21}H_{11}ClF_3N_9OS$ 529 m/z found 530[M+H]+. 1H NMR (400 MHz, DMSO-$d_6$) δ ppm 2.57 (s, 3H), 7.43 (d, J=5.3 Hz, 1H), 8.19 (s, 2H), 8.44 (s, 1H), 8.58 (d, J=5.3 Hz, 1H), 8.67 (s, 1H), 8.95 (s, 1H).

Example 417, Example 418, and Example 419

N-(5-chloro-6-(2H-1,2,3-triazol-2-yl)pyridin-3-yl)-1-(2-methoxyquinolin-4-yl)-5-(trifluoromethyl)-1H-pyrazole-4-carboxamide, Cpd 417

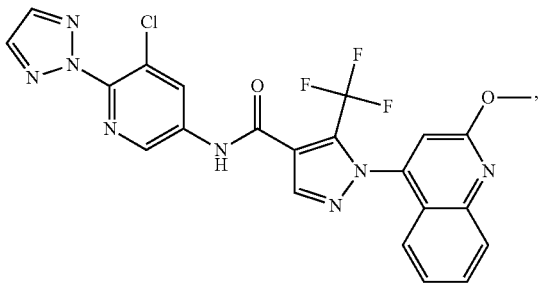 [SMILES: COc1cc(-n2ncc(C(=O)Nc3cnc(-n4nccn4)c(Cl)c3)c2C(F)(F)F)c2ccccc2n1]

N-(5-chloro-6-(2H-1,2,3-triazol-2-yl)pyridin-3-yl)-1-(2-oxo-1,2-dihydroquinolin-4-yl)-5-(trifluoromethyl)-1H-pyrazole-4-carboxamide, Cpd 418

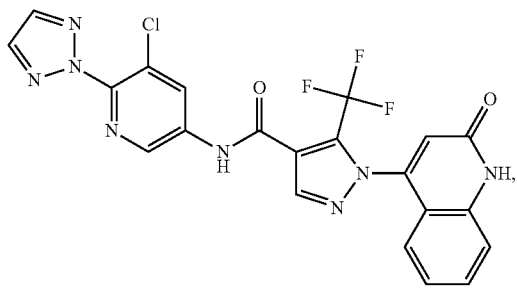 [SMILES: O=C(Nc1cnc(-n2nccn2)c(Cl)c1)c1cnn(-c2cc(=O)[nH]c3ccccc23)c1C(F)(F)F]

and

N-(5-chloro-6-(2H-1,2,3-triazol-2-yl)pyridin-3-yl)-1-(1-methyl-2-oxo-1,2-dihydroquinolin-4-yl)-5-(trifluoromethyl)-1H-pyrazole-4-carboxamide, Cpd 419

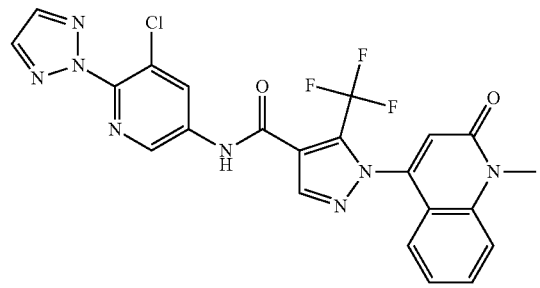 [SMILES: Cn1c(=O)cc(-n2ncc(C(=O)Nc3cnc(-n4nccn4)c(Cl)c3)c2C(F)(F)F)c2ccccc21]

A mixture of 4-(4-((5-chloro-6-(2H-1,2,3-triazol-2-yl)pyridin-3-yl)carbamoyl)-5-(trifluoromethyl)-1H-pyrazol-1-yl)quinoline 1-oxide (501 mg, 1 mmol), tosylanhydride (980 mg, 3 mmol), $Na_2CO_3$ (318 mg, 3 mmol) in MeOH (10 mL) was stirred at rt for 16 h. DMF (10 mL) was added. Additional tosylanhydride (980 mg, 3 mmol) and $Na_2CO_3$ (318 mg, 3 mmol) were added and stirring was continued for 16 h. The reaction mixture was poured into water and extracted with ethyl acetate (2×). The organic layer was washed with water, dried over $MgSO_4$, and the filtrate concentrated. The residue was purified via Prep HPLC (Stationary phase: RP XBridge Prep C18 OBD-10 μm, 50×150 mm, Mobile phase: 0.25% $NH_4HCO_3$ solution in water, $CH_3CN$) to afford cpd 418 (73 mg, 15%), cpd 419 (48 mg, 9%), and cpd 417 (80 mg, 16%).

Cpd 418.

LCMS (ESI): mass calcd. for $C_{21}H_{12}ClF_3N_8O_2$ 500.1, m/z found 501.1[M+H]+. 1H NMR (400 MHz, DMSO-$d_6$) δ ppm 6.85 (d, J=8.1 Hz, 1H), 6.97 (s, 1H), 7.24 (t, J=7.5 Hz, 1H), 7.49 (d, J=8.1 Hz, 1H), 7.65 (t, J=7.7 Hz, 1H), 8.19 (s, 2H), 8.64 (s, 1H), 8.68 (d, J=2.3 Hz, 1H), 8.87 (d, J=2.3 Hz, 1H), 10.93 (br s, 1H);

Cpd 419.

LCMS (ESI): mass calcd. for $C_{22}H_{14}ClF_3N_8O_2$ 514.1, m/z found 515.2[M+H]+. 1H NMR (600 MHz, DMSO-$d_6$) δ ppm 3.74 (s, 3H), 6.89 (dd, J=8.1, 1.3 Hz, 1H), 7.14 (s, 1H), 7.34 (ddd, J=8.0, 7.0, 1.2 Hz, 1H), 7.73-7.76 (m, 1H), 7.77-7.81 (m, 1H), 8.19 (s, 2H), 8.63 (s, 1H), 8.67 (d, J=2.3 Hz, 1H), 8.85 (d, J=2.1 Hz, 1H), 11.24 (br s, 1H);

Cpd 417.

LCMS (ESI): mass calcd. for $C_{22}H_{14}ClF_3N_8O_2$ 514.1, m/z found 515.2[M+H]+. 1H NMR (600 MHz, DMSO-$d_6$) δ ppm 4.09 (s, 3H), 7.15 (dd, J=8.4, 1.0 Hz, 1H), 7.52-7.56 (m, 2H), 7.83 (ddd, J=8.4, 7.0, 1.4 Hz, 1H), 7.98 (d, J=8.1 Hz, 1H), 8.20 (s, 2H), 8.65 (s, 1H), 8.68 (d, J=2.3 Hz, 1H), 8.86 (d, J=2.3 Hz, 1H), 11.01 (br s, 1H).

Following the procedure described in Example 417, above, selecting and substituting the appropriate reagents, starting materials, and purification methods, and adjusting reaction temperatures, times and other variables or param

Example 420

N-(5-chloro-6-(2H-1,2,3-triazol-2-yl)pyridin-3-yl)-1-(2-methoxyquinolin-5-yl)-5-(trifluoromethyl)-1H-pyrazole-4-carboxamide, Cpd 420

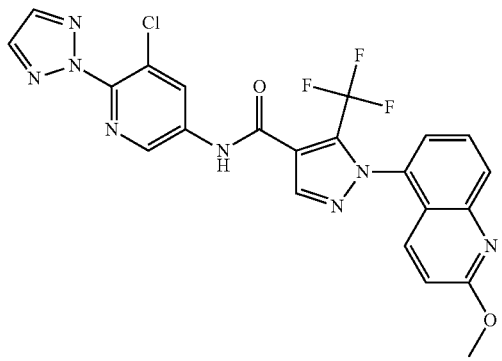 [SMILES: COc1ccc2c(-n3ncc(C(=O)Nc4cnc(-n5nccn5)c(Cl)c4)c3C(F)(F)F)cccc2n1]

LCMS (ESI): mass calcd. for $C_{22}H_{14}ClF_3N_8O_2$ 514.1 m/z found 515.1[M+H]$^+$. $^1$H NMR (400 MHz, DMSO-d$_6$) δ ppm 4.05 (s, 3H), 7.17 (d, J=9.4 Hz, 1H), 7.47 (d, J=9.4 Hz, 1H), 7.70 (d, J=7.3 Hz, 1H), 7.83-7.92 (m, 1H), 8.08 (d, J=8.5 Hz, 1H), 8.19 (s, 2H), 8.57 (s, 1H), 8.68 (d, J=2.0 Hz, 1H), 8.86 (d, J=2.4 Hz, 1H), 11.25 (br s, 1H).

Example 421

N-(5-chloro-6-(2H-1,2,3-triazol-2-yl)pyridin-3-yl)-1-(1-methoxyisoquinolin-4-yl)-5-(trifluoromethyl)-1H-pyrazole-4-carboxamide, Cpd 421

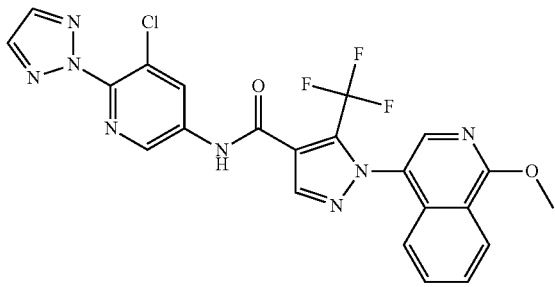 [SMILES: COc1ncc(-n2ncc(C(=O)Nc3cnc(-n4nccn4)c(Cl)c3)c2C(F)(F)F)c2ccccc12]

LCMS (ESI): mass calcd. for $C_{22}H_{14}ClF_3N_8O_2$ 514.1 m/z found 515.1 [M+H]$^+$. $^1$H NMR (400 MHz, CHLOROFORM-d) δ ppm 4.22 (d, J=1.2 Hz, 3H), 7.13 (d, J=8.1 Hz, 1H), 7.62-7.68 (m, 1H), 7.69-7.76 (m, 1H), 7.95 (d, J=1.2 Hz, 2H), 8.11 (s, 2H), 8.22 (s, 1H), 8.35 (d, J=8.5 Hz, 1H), 8.49-8.55 (m, 1H), 8.73-8.79 (m, 1H).

Example 422

N-(5-chloro-6-(2H-1,2,3-triazol-2-yl)pyridin-3-yl)-1-(1-ethoxyisoquinolin-4-yl)-5-(trifluoromethyl)-1H-pyrazole-4-carboxamide, Cpd 422

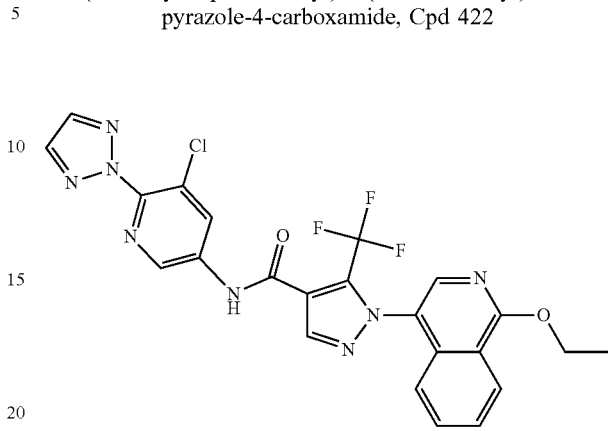

LCMS (ESI): mass calcd. for $C_{23}H_{16}ClF_3N_8O_2$ 528.1 m/z found 529.1 [M+H]$^+$. $^1$H NMR (400 MHz, CHLOROFORM-d) δ ppm 1.56 (t, J=7.1 Hz, 3H), 4.67 (q, J=6.9 Hz, 2H), 7.12 (d, J=8.1 Hz, 1H), 7.60-7.68 (m, 1H), 7.68-7.75 (m, 1H), 7.96 (s, 2H), 8.09 (s, 1H), 8.23 (s, 1H), 8.31 (br s, 1H), 8.38 (d, J=8.1 Hz, 1H), 8.54 (d, J=2.0 Hz, 1H), 8.78 (s, 1H).

Example 448

N-(5-chloro-6-(2H-1,2,3-triazol-2-yl)pyridin-3-yl)-1-(1-hydroxyisoquinolin-4-yl)-5-(trifluoromethyl)-1H-pyrazole-4-carboxamide, Cpd 448

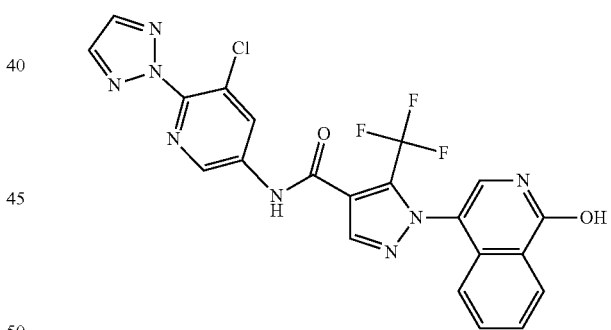

N-(5-chloro-6-(2H-1,2,3-triazol-2-yl)pyridin-3-yl)-1-(1-chloroisoquinolin-4-yl)-5-(trifluoromethyl)-1H-pyrazole-4-carboxamide (1000 mg, 1.9 mmol), iPrOH (30 mL) and HCl 37% in water (15 mL) were stirred at 60° C. for 4 h. The reaction mixture was concentrated to dryness and the residue was dissolved in 50 mL DCM. The solution was poured into 50 mL of water. The mixture was made basic with Na$_2$CO$_3$ and stirred for 15 min. The layers were separated and the aqueous layer was extracted with DCM. The organic layer was dried over MgSO$_4$, filtered, and the filtrate concentrated. The residue was purified by flash column chromatography over silica gel (eluent: DCM/MEOH ratio 5/95) to afford cpd 448 (600 mg, 62%). LCMS (ESI): mass calcd. For $C_{21}H_{12}ClF_3N_8O_2$ 500.1, m/z found 501.1[M+H]$^+$. $^1$H NMR (400 MHz, DMSO-d$_6$) δ ppm 6.78 (d, J=8.1 Hz, 1H), 7.58-7.65 (m, 1H), 7.74-7.82 (m, 1H), 7.86 (s, 1H), 8.18 (s, 2H), 8.29 (dd, J=8.1, 0.8 Hz, 1H), 8.51 (s, 1H), 8.67 (d, J=2.0 Hz, 1H), 8.84 (d, J=2.0 Hz, 1H), 11.53 (br s, 1H).

Example 423

N-(5-chloro-6-(2H-1,2,3-triazol-2-yl)pyridin-3-yl)-1-(2-methyl-1-oxo-1,2-dihydroisoquinolin-4-yl)-5-(trifluoromethyl)-1H-pyrazole-4-carboxamide, Cpd 423

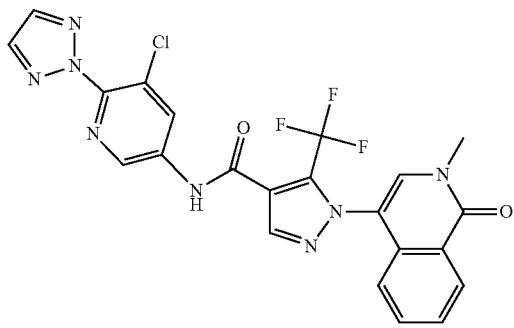 [SMILES: Cn1cc(-n2ncc(C(=O)Nc3cnc(-n4nccn4)c(Cl)c3)c2C(F)(F)F)c2ccccc2c1=O]

N-(5-chloro-6-(2H-1,2,3-triazol-2-yl)pyridin-3-yl)-1-(1-hydroxyisoquinolin-4-yl)-5-(trifluoromethyl)-1H-pyrazole-4-carboxamide (190 mg, 0.307 mmol, purity 81%)) $Cs_2CO_3$ (100 mg, 0.307 mmol) and iodomethane (43.6 mg, 0.307 mmol) in DMA (2 mL) were stirred at rt for 4 h. The reaction mixture was poured into 20 mL of water. The mixture was extracted 3× with ethyl acetate and the organic layer was washed with 20 mL water, dried over $MgSO_4$, filtered, and the filtrate concentrated. The residue was purified via Prep HPLC (Stationary phase: RP XBridge Prep C18 OBD-10 μm, 50×150 mm, Mobile phase: 0.25% $NH_4HCO_3$ solution in water, $CH_3CN$). The pure fractions were collected and concentrated. The residue was dissolved in water and extracted with ethyl acetate. The organic layer was dried over $MgSO_4$, filtered, and the filtrate concentrated. The residue was stirred in diisopropylether, the solid collected by filtration and then filtered off and dried to afford cpd 423 (155 mg, 98%). LCMS (ESI): mass calcd. For $C_{22}H_{14}ClF_3N_8O_2$ 514.1, m/z found 515.1[M+H]$^+$. $^1$H NMR (400 MHz, DMSO-d$_6$) δ ppm 3.60 (s, 3H), 6.82 (d, J=8.1 Hz, 1H), 7.65 (t, J=7.6 Hz, 1H), 7.79 (t, J=7.1 Hz, 1H), 8.19 (s, 2H), 8.23 (s, 1H), 8.34 (d, J=7.7 Hz, 1H), 8.55 (s, 1H), 8.67 (d, J=2.0 Hz, 1H), 8.86 (d, J=2.4 Hz, 1H), 11.26 (br s, 1H).

Example 424

N-(5-chloro-6-(2H-1,2,3-triazol-2-yl)pyridin-3-yl)-1-(7-chlorothieno[2,3-c]pyridin-4-yl)-5-(trifluoromethyl)-1H-pyrazole-4-carboxamide, Cpd 424

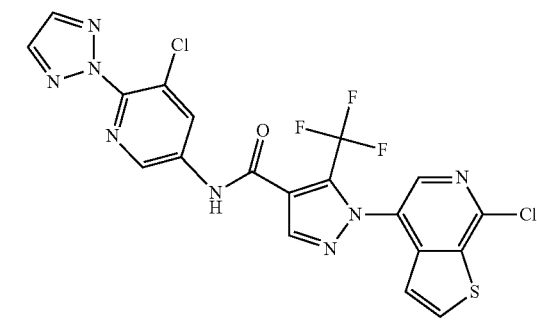 [SMILES: O=C(Nc1cnc(-n2nccn2)c(Cl)c1)c1cnn(-c2cnc(Cl)c3sccc23)c1C(F)(F)F]

A mixture of 4-(4-((5-chloro-6-(2H-1,2,3-triazol-2-yl)pyridin-3-yl)carbamoyl)-5-(trifluoromethyl)-1H-pyrazol-1-yl)thieno[2,3-c]pyridine 6-oxide (2900 mg, 5.72 mmol) and $POCl_3$ (100 mL) was stirred at 60° C. for 16 h. The reaction mixture was concentrated to dryness and dissolved in 150 mL DCM. The solution was added dropwise to 150 mL of water. The mixture was made basic with $Na_2CO_3$ and then stirred for 15 min. The layers were separated and the aqueous layer was extracted with DCM. The organic layer was dried and concentrated. The residue was purified by flash column chromatography over silica gel (DCM/MEOH ratio from 2/98 to 95/5) to afford a crude compound (2.55 mg, 85%). A portion of the crude compound (150 mg) was purified via Prep SFC (Stationary phase: Chiralpak Daicel IC 20×250 mm, Mobile phase: $CO_2$, EtOH+0.4 iPrNH$_2$) to afford cpd 424 (104 mg). LCMS (ESI): mass calcd. for $C_{19}H_9Cl_2F_3N_8OS$ 524 m/z found 525[M+H]$^+$. $^1$H NMR (400 MHz, DMSO-d$_6$) δ ppm 7.29 (d, J=5.3 Hz, 1H), 8.18 (s, 2H), 8.45 (d, J=5.3 Hz, 1H), 8.61 (s, 1H), 8.64 (s, 1H), 8.67 (d, J=2.4 Hz, 1H), 8.85 (d, J=2.0 Hz, 1H), 11.27 (br s, 1H).

Following the procedure described in Example 424, above, selecting and substituting the appropriate reagents, starting materials, and purification methods, and adjusting reaction temperatures, times and other variables or parameters, as needed or desirable, as would be readily recognized by those skilled in the art, the following compounds were prepared:

Example 426

N-(5-chloro-2-methyl-6-(2H-1,2,3-triazol-2-yl)pyridin-3-yl)-1-(7-chlorothieno[2,3-c]pyridin-4-yl)-5-(trifluoromethyl)-1H-pyrazole-4-carboxamide, Cpd 426

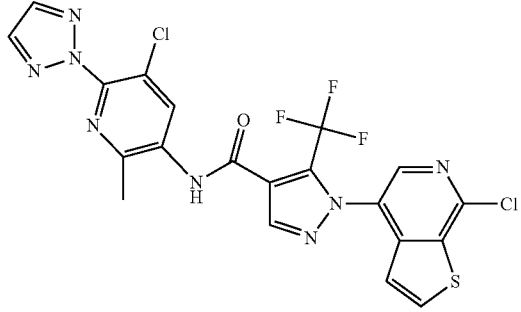 [SMILES: Cc1nc(-n2nccn2)c(Cl)cc1NC(=O)c1cnn(-c2cnc(Cl)c3sccc23)c1C(F)(F)F]

LCMS (ESI): mass calcd. for $C_{20}H_{11}Cl_2F_3N_8OS$ 538 m/z found 539 [M+H]$^+$. $^1$H NMR (400 MHz, DMSO-d$_6$) δ ppm 2.57 (s, 3H), 7.31 (d, J=5.3 Hz, 1H), 8.19 (s, 2H), 8.43-8.49 (m, 2H), 8.61 (s, 1H), 8.63 (s, 1H), 10.63 (br s, 1H).

Example 427

(R)—N-(5-chloro-6-(2H-1,2,3-triazol-2-yl)pyridin-3-yl)-1-(1-(3-hydroxypyrrolidin-1-yl)isoquinolin-4-yl)-5-(trifluoromethyl)-1H-pyrazole-4-carboxamide, Cpd 427

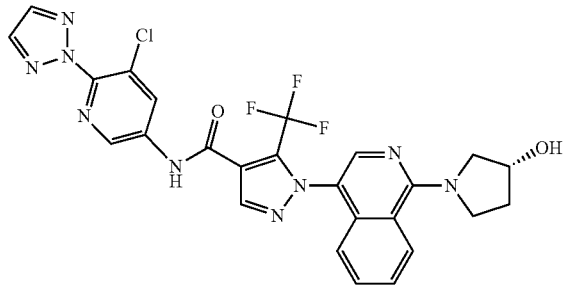 [SMILES: O=C(Nc1cnc(-n2nccn2)c(Cl)c1)c1cnn(-c2cnc(N3CC[C@@H](O)C3)c3ccccc23)c1C(F)(F)F]

N-(5-chloro-6-(2H-1,2,3-triazol-2-yl)pyridin-3-yl)-1-(1-chloroisoquinolin-4-yl)-5-(trifluoromethyl)-1H-pyrazole-4-carboxamide (250 mg, 0.48 mmol), (R)-3-hydroxypyrrolidine (87 mg, 0.96 mmol) and Cs$_2$CO$_3$ (314 mg, 0.96 mmol) in DMSO (2 mL) were stirred at 80° C. for 4 h. The reaction mixture was poured into water and extracted with ethyl acetate. The organic layer was washed with water, dried over MgSO$_4$, filtered, and the filtrate concentrated. The residue was purified via Prep HPLC (Stationary phase: RP XBridge Prep C18 OBD-10 μm, 50×150 mm, Mobile phase: 0.25% NH$_4$HCO$_3$ solution in water, CH$_3$CN) to afford cpd 427 (90 mg, 33%). LCMS (ESI): mass calcd. for $C_{25}H_{19}ClF_3N_9O_2$ 569.1 m/z found 570.2[M+H]$^+$. $^1$H NMR (400 MHz, DMSO-d$_6$) δ ppm 1.91-2.00 (m, 1H), 2.00-2.11 (m, 1H), 3.68 (br d, J=11.4 Hz, 1H), 3.85 (ddd, J=10.8, 7.9, 2.8 Hz, 1H), 4.10 (br d, J=10.2 Hz, 2H), 4.39-4.48 (m, 1H), 5.04 (d, J=3.3 Hz, 1H), 6.92 (d, J=8.5 Hz, 1H), 7.58 (t, J=7.7 Hz, 1H), 7.71 (t, J=7.6 Hz, 1H), 8.10 (s, 1H), 8.19 (s, 2H), 8.43 (d, J=8.5 Hz, 1H), 8.50 (br s, 1H), 8.67 (d, J=2.4 Hz, 1H), 8.85 (d, J=2.0 Hz, 1H), 11.25 (br s, 1H).

Following the procedure described in Example 427, above, selecting and substituting the appropriate reagents, starting materials, and purification methods, and adjusting reaction temperatures, times and other variables or parameters, as needed or desirable, as would be readily recognized by those skilled in the art, the following compounds were prepared:

Example 429

N-(5-chloro-6-(2H-1,2,3-triazol-2-yl)pyridin-3-yl)-1-(1-(methylthio)isoquinolin-4-yl)-5-(trifluoromethyl)-1H-pyrazole-4-carboxamide, Cpd 429

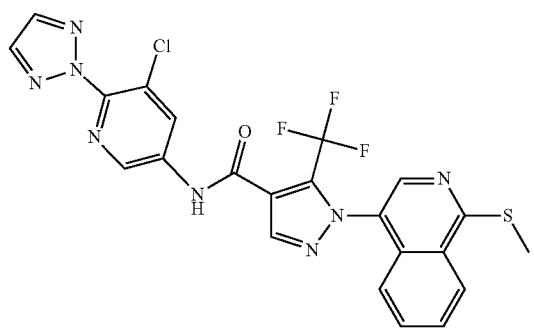 [SMILES: CSc1ncc(-n2ncc(C(=O)Nc3cnc(-n4nccn4)c(Cl)c3)c2C(F)(F)F)c2ccccc12]

LCMS (ESI): mass calcd. for $C_{22}H_{14}ClF_3N_8OS$ 530.1 m/z found 531.1 [M+H]$^+$. $^1$H NMR (400 MHz, DMSO-d$_6$) δ ppm 2.76 (s, 3H), 7.21 (d, J=8.1 Hz, 1H), 7.82-7.88 (m, 1H), 7.91-7.97 (m, 1H), 8.19 (s, 2H), 8.34 (d, J=8.5 Hz, 1H), 8.60 (s, 1H), 8.65 (s, 1H), 8.68 (d, J=2.0 Hz, 1H), 8.85 (d, J=2.4 Hz, 1H), 11.27 (br s, 1H).

Example 430

N-(5-chloro-6-(2H-1,2,3-triazol-2-yl)pyridin-3-yl)-1-(7-(3-hydroxyazetidin-1-yl)thieno[2,3-c]pyridin-4-yl)-5-(trifluoromethyl)-1H-pyrazole-4-carboxamide, Cpd 430

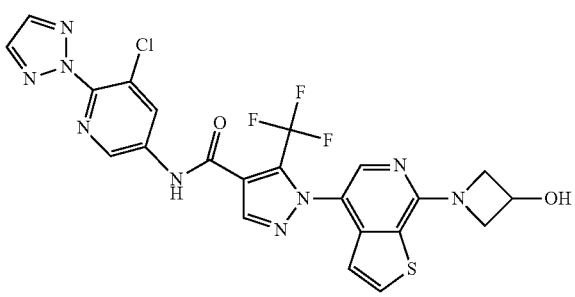 [SMILES: O=C(Nc1cnc(-n2nccn2)c(Cl)c1)c1cnn(-c2cnc(N3CC(O)C3)c3sccc23)c1C(F)(F)F]

LCMS (ESI): mass calcd. for $C_{22}H_{15}ClF_3N_9O_2S$ 561.1 m/z found 562[M+H]$^+$. $^1$H NMR (400 MHz, DMSO-d$_6$) δ ppm 4.12 (dd, J=9.3, 4.4 Hz, 2H), 4.55-4.62 (m, 2H), 4.67 (br d, J=6.2 Hz, 1H), 5.82 (br s, 1H), 6.94 (d, J=5.5 Hz, 1H), 8.07 (s, 1H), 8.14 (d, J=5.3 Hz, 1H), 8.18 (s, 2H), 8.48 (s, 1H), 8.66 (d, J=2.0 Hz, 1H), 8.84 (d, J=2.0 Hz, 1H), 11.14 (br s, 1H).

Example 431

(S)—N-(5-chloro-6-(2H-1,2,3-triazol-2-yl)pyridin-3-yl)-1-(7-(3-hydroxypyrrolidin-1-yl)thieno[2,3-c]pyridin-4-yl)-5-(trifluoromethyl)-1H-pyrazole-4-carboxamide, Cpd 431

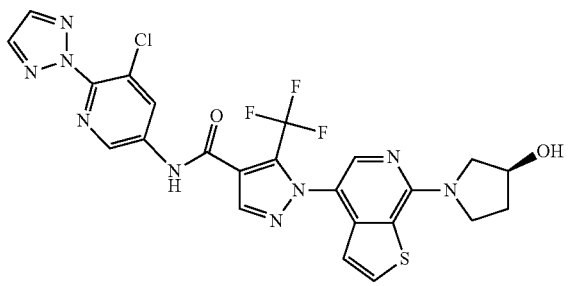 [SMILES: O=C(Nc1cnc(-n2nccn2)c(Cl)c1)c1cnn(-c2cnc(N3CC[C@H](O)C3)c3sccc23)c1C(F)(F)F]

LCMS (ESI): mass calcd. For $C_{23}H_{17}ClF_3N_9O_2S$ 575 m/z found 576 [M+H]$^+$. $^1$H NMR (400 MHz, DMSO-d$_6$) δ ppm 1.93-2.03 (m, 1H) 2.04-2.18 (m, 1H), 3.82 (br d, J=11.0 Hz, 1H), 3.90-4.06 (m, 3H), 4.46 (br s, 1H), 5.10 (d, J=3.7 Hz, 1H), 6.87 (d, J=5.3 Hz, 1H), 8.02 (s, 1H), 8.11 (d, J=5.3 Hz, 1H), 8.19 (s, 2H), 8.47 (s, 1H), 8.66 (d, J=2.4 Hz, 1H), 8.84 (d, J=2.0 Hz, 1H), 11.23 (br s, 1H).

Example 432

(R)—N-(5-chloro-6-(2H-1,2,3-triazol-2-yl)pyridin-3-yl)-1-(7-(3-hydroxypyrrolidin-1-yl)thieno[2,3-c]pyridin-4-yl)-5-(trifluoromethyl)-1H-pyrazole-4-carboxamide, Cpd 432

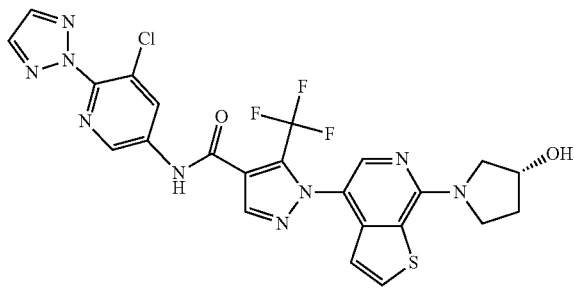 [SMILES: O=C(Nc1cnc(-n2nccn2)c(Cl)c1)c1cnn(-c2cnc(N3CC[C@@H](O)C3)c3sccc23)c1C(F)(F)F]

LCMS (ESI): mass calcd. for $C_{23}H_{17}ClF_3N_9O_2S$ 575.1 m/z found 576.1[M+H]$^+$. $^1$H NMR (400 MHz, DMSO-d$_6$) δ ppm 1.93-2.03 (m, 1H), 2.04-2.21 (m, 1H), 2.10 (m, J=13.0, 8.7, 8.7, 4.3 Hz, 1H), 3.82 (br d, J=11.0 Hz, 1H), 3.90-4.07 (m, 3H), 4.46 (br s, 1H), 5.10 (br d, J=2.8 Hz, 1H), 6.87 (d, J=5.3 Hz, 1H), 8.02 (s, 1H), 8.11 (d, J=5.3 Hz, 1H), 8.19 (s, 2H), 8.48 (s, 1H), 8.66 (d, J=2.0 Hz, 1H), 8.85 (d, J=2.4 Hz, 1H), 11.21 (br s, 1H).

Example 433

N-(5-chloro-2-methyl-6-(2H-1,2,3-triazol-2-yl)pyridin-3-yl)-1-(7-(3-hydroxyazetidin-1-yl)thieno[2,3-c]pyridin-4-yl)-5-(trifluoromethyl)-1H-pyrazole-4-carboxamide, Cpd 433

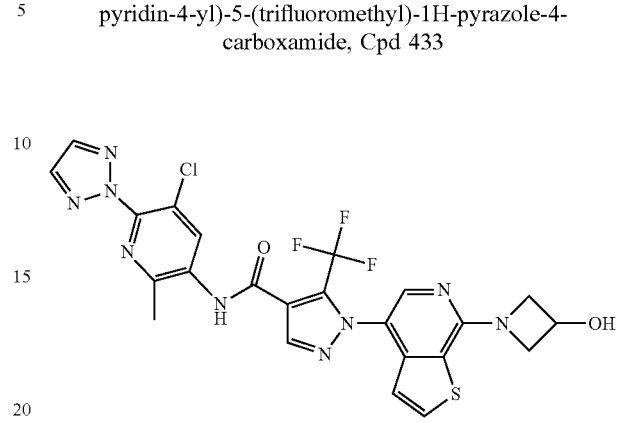

LCMS (ESI): mass calcd. For $C_{23}H_{17}ClF_3N_9O_2S$ 575.1 m/z found 576.1 [M+H]$^+$. $^1$H NMR (400 MHz, DMSO-d$_6$) δ ppm 2.57 (s, 3H), 3.33 (dd, J=10.4, 9.2 Hz, 1H), 4.13 (br dd, 4.5 Hz, 2H), 4.58 (br t, J=7.5 Hz, 2H), 4.65-4.73 (m, 1H), 6.97 (d, J=5.3 Hz, 1H), 8.07 (s, 1H), 8.14 (d, J=5.3 Hz, 1H), 8.19 (s, 2H), 8.43 (s, 1H), 8.53 (s, 1H).

Example 434

N-(5-chloro-6-(2H-1,2,3-triazol-2-yl)pyridin-3-yl)-1-(7-methylthieno[2,3-c]pyridin-4-yl)-5-(trifluoromethyl)-1H-pyrazole-4-carboxamide, Cpd 434

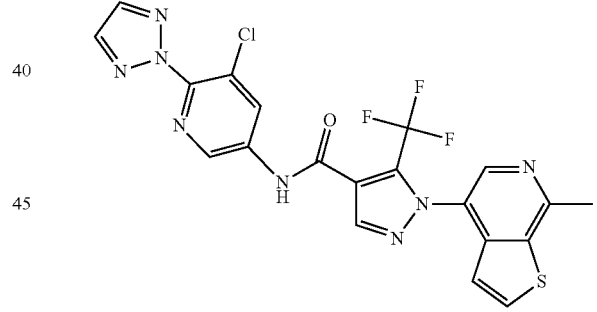

N-(5-chloro-6-(2H-1,2,3-triazol-2-yl)pyridin-3-yl)-1-(7-chlorothieno[2,3-c]pyridin-4-yl)-5-(trifluoromethyl)-1H-pyrazole-4-carboxamide (131 mg, 0.25 mmol), methylboronic acid (60 mg, 1 mmol) and K$_3$PO$_4$ (212 mg, 1 mmol) were suspended in dioxane (20 mL) and water (3 mL). PdCl$_2$(dppf).CH$_2$Cl$_2$ (20.5 mg, 0.025 mmol) was added and nitrogen gas was bubbled through the reaction mixture for 15 min, then heated at 100° C. overnight. The reaction mixture was poured into 20 mL of water, extracted with ethyl acetate (3×) and the organic layer was washed with 10 mL of water. The organic layer was then dried over MgSO$_4$, filtered, and the filtrate concentrated. The residue was purified via Prep HPLC (Stationary phase: RP XBridge Prep C18 OBD-10 μm, 30×150 mm, Mobile phase: 0.25% NH$_4$HCO$_3$ solution in water, CH$_3$CN) to afford cpd 434 (15 mg, 12%). LCMS (ESI): mass calcd. For $C_{20}H_{12}ClF_3N_8OS$ 504.1 m/z found 505.1 [M+H]$^+$.

Following the procedure described in Example 434, above, selecting and substituting the appropriate reagents, starting materials, and purification methods, and adjusting reaction temperatures, times and other variables or parameters, as needed or desirable, as would be readily recognized by those skilled in the art, the following compounds were prepared:

Example 435

N-(5-chloro-6-(2H-1,2,3-triazol-2-yl)pyridin-3-yl)-1-(7-cyclopropylthieno[2,3-c]pyridin-4-yl)-5-(trifluoromethyl)-1H-pyrazole-4-carboxamide, Cpd 435

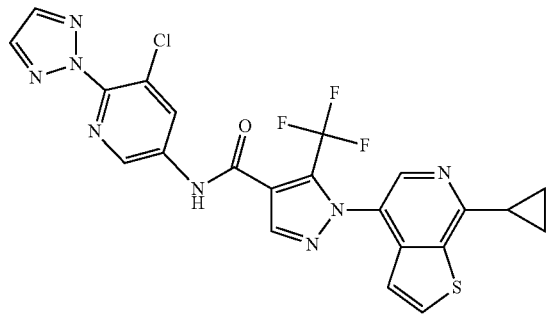 [SMILES: O=C(Nc1cnc(-n2nccn2)c(Cl)c1)c1cnn(-c2cnc(C3CC3)c3sccc23)c1C(F)(F)F]

LCMS (ESI): mass calcd. For $C_{22}H_{14}ClF_3N_8OS$ 530.1 m/z found 531 [M+H]$^+$.

The following compounds were prepared via separation of enantiomers using Prep SFC (Stationary phase: Chiralpak Diacel AD 20×250 mm, Mobile phase: CO$_2$, EtOH with 0.1% triethylamine). The pure fractions were collected, concentrated and the residues were stirred in diisopropylether, the solid collected by filtration, and then dried to give pure enantiomers (the steric centers are arbitrarily assigned).

Example 436

(*R)—N-(5-chloro-6-(2H-1,2,3-triazol-2-yl)pyridin-3-yl)-1-(1-(tetrahydrofuran-2-yl)isoquinolin-4-yl)-5-(trifluoromethyl)-1H-pyrazole-4-carboxamide, Cpd 436

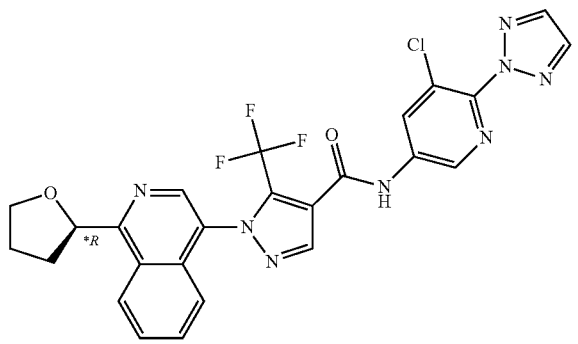 [SMILES: O=C(Nc1cnc(-n2nccn2)c(Cl)c1)c1cnn(-c2cnc([C@H]3CCCO3)c3ccccc23)c1C(F)(F)F]

LCMS (ESI): mass calcd. for $C_{25}H_{18}ClF_3N_8O_2$ 554.1, m/z found 555.2 [M+H]$^+$. $^1$H NMR (400 MHz, DMSO-d$_6$) δ ppm 2.01-2.18 (m, 2H), 2.31-2.43 (m, 1H), 2.56-2.71 (m, 1H), 3.60 (spt, J=6.0 Hz, 1H), 3.89-4.05 (m, 2H), 5.82 (t, J=6.9 Hz, 1H), 7.26 (d, J=8.1 Hz, 1H), 7.83-7.89 (m, 1H), 7.90-7.97 (m, 1H), 8.19 (s, 2H), 8.61-8.66 (m, 2H), 8.69 (d, J=2.0 Hz, 1H), 8.74 (s, 1H), 8.87 (d, J=2.4 Hz, 1H).

Example 437

(*S)—N-(5-chloro-6-(2H-1,2,3-triazol-2-yl)pyridin-3-yl)-1-(1-(tetrahydrofuran-2-yl)isoquinolin-4-yl)-5-(trifluoromethyl)-1H-pyrazole-4-carboxamide, Cpd 437

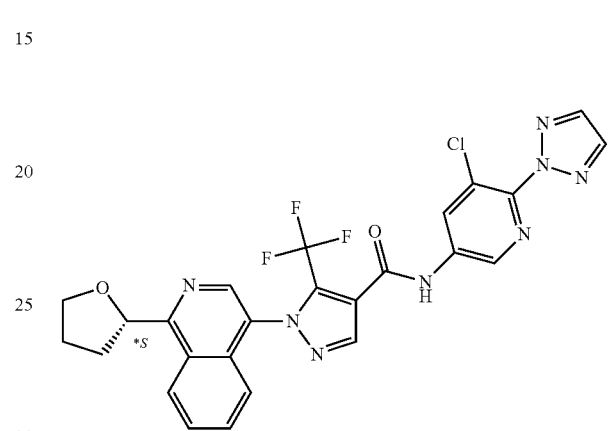

LCMS (ESI): mass calcd. for $C_{25}H_{18}ClF_3N_8O_2$ 554.1, m/z found 555.2 [M+H]$^+$. $^1$H NMR (400 MHz, DMSO-d$_6$) δ ppm 2.01-2.20 (m, 2H), 2.31-2.42 (m, 1H), 2.54-2.72 (m, 1H), 3.55-3.68 (m, 1H), 3.89-4.08 (m, 2H), 5.82 (t, J=6.9 Hz, 1H), 7.26 (d, J=8.1 Hz, 1H), 7.83-7.89 (m, 1H), 7.90-7.98 (m, 1H), 8.19 (s, 2H), 8.61-8.66 (m, 2H), 8.69 (d, J=2.4 Hz, 1H), 8.74 (s, 1H), 8.87 (d, J=2.4 Hz, 1H).

Example 438

(*R)—N-(5-chloro-6-(2H-1,2,3-triazol-2-yl)pyridin-3-yl)-1-(1-(4-oxotetrahydrofuran-2-yl)isoquinolin-4-yl)-5-(trifluoromethyl)-1H-pyrazole-4-carboxamide, Cpd 438

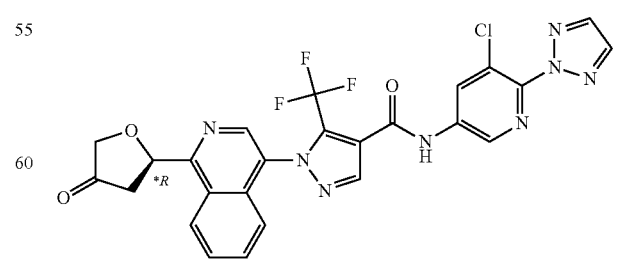

LCMS (ESI): mass calcd. for $C_{25}H_{16}ClF_3N_8O_3$ 568.1 m/z found 569 [M+H]$^+$.

Example 439

(*S)—N-(5-chloro-6-(2H-1,2,3-triazol-2-yl)pyridin-3-yl)-1-(1-(4-oxotetrahydrofuran-2-yl)isoquinolin-4-yl)-5-(trifluoromethyl)-1H-pyrazole-4-carboxamide, Cpd 439

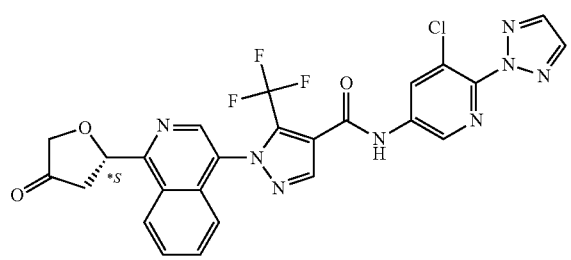 [SMILES: O=C1CO[C@H](c2ncc(-n3ncc(C(=O)Nc4cnc(-n5nccn5)c(Cl)c4)c3C(F)(F)F)c3ccccc23)C1]

LCMS (ESI): mass calcd. for $C_{25}H_{16}ClF_3N_8O_3$ 568.1 m/z found 569 [M+H]$^+$.

Example 440

(*R)—N-(5-chloro-6-(2H-1,2,3-triazol-2-yl)pyridin-3-yl)-1-(2-(tetrahydrofuran-2-yl)quinolin-5-yl)-5-(trifluoromethyl)-1H-pyrazole-4-carboxamide, Cpd 440

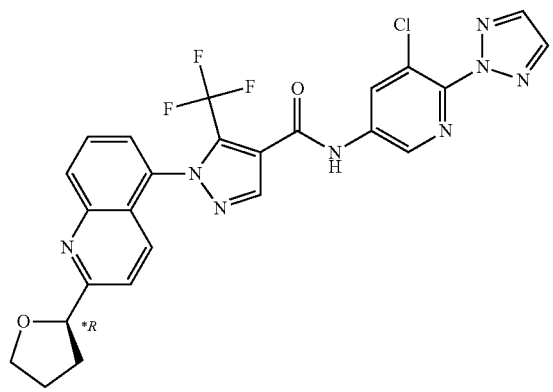 [SMILES: O=C(Nc1cnc(-n2nccn2)c(Cl)c1)c1cnn(-c2cccc3nc([C@H]4CCCO4)ccc23)c1C(F)(F)F]

LCMS (ESI): mass calcd. for $C_{25}H_{18}ClF_3N_8O_2$ 554.1 m/z found 555.1[M+H]$^+$.

Example 441

(*S)—N-(5-chloro-6-(2H-1,2,3-triazol-2-yl)pyridin-3-yl)-1-(2-(tetrahydrofuran-2-yl)quinolin-5-yl)-5-(trifluoromethyl)-1H-pyrazole-4-carboxamide, Cpd 441

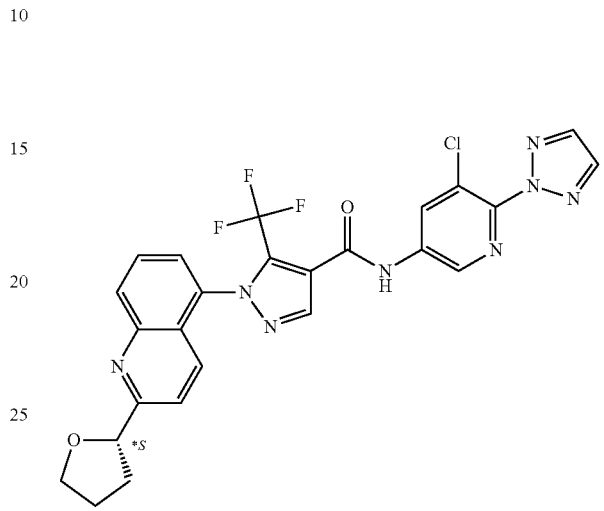

LCMS (ESI): mass calcd. for $C_{25}H_{18}ClF_3N_8O_2$ 554.1 m/z found 555.2[M+H]$^+$.

Example 442

(*R)—N-(5-chloro-6-(2H-1,2,3-triazol-2-yl)pyridin-3-yl)-1-(1-(1-hydroxyethyl)isoquinolin-4-yl)-5-(trifluoromethyl)-1H-pyrazole-4-carboxamide, Cpd 442

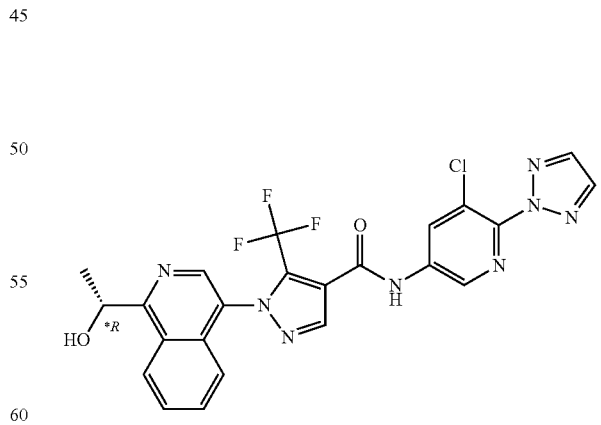

LCMS (ESI): mass calcd. for $C_{23}H_{16}ClF_3N_8O_2$ 528.1 m/z found 529.2 [M+H]$^+$.

Example 443

(*S)—N-(5-chloro-6-(2H-1,2,3-triazol-2-yl)pyridin-3-yl)-1-(1-(1-hydroxyethyl)isoquinolin-4-yl)-5-(trifluoromethyl)-1H-pyrazole-4-carboxamide, Cpd 443

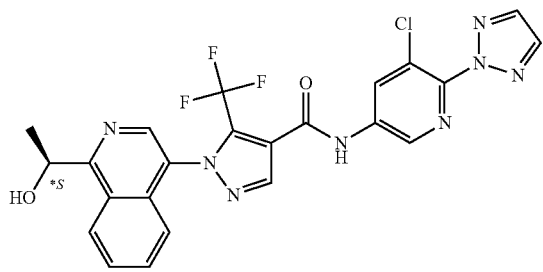 [SMILES: C[C@H](O)c1ncc(-n2ncc(C(=O)Nc3cnc(-n4nccn4)c(Cl)c3)c2C(F)(F)F)c2ccccc12]

LCMS (ESI): mass calcd. for $C_{23}H_{16}ClF_3N_8O_2$ 528.1 m/z found 529.1 [M+H]$^+$.

Example 444

(*R)—N-(5-chloro-6-(2H-1,2,3-triazol-2-yl)pyridin-3-yl)-1-(1-(1-hydroxyethyl)isoquinolin-5-yl)-5-(trifluoromethyl)-1H-pyrazole-4-carboxamide, Cpd 444

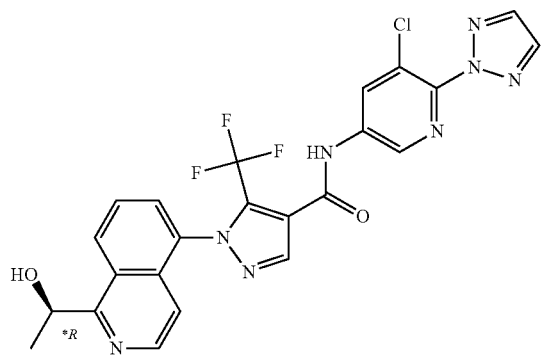 [SMILES: C[C@@H](O)c1nccc2c(-n3ncc(C(=O)Nc4cnc(-n5nccn5)c(Cl)c4)c3C(F)(F)F)cccc12]

LCMS (ESI): mass calcd. for $C_{23}H_{16}ClF_{31}N_8O_2$ 528.1 m/z found 529[M+H]$^+$. $^1$H NMR (400 MHz, DMSO-d$_6$) δ ppm 1.62 (d, J=6.5 Hz, 3H), 5.52-5.74 (m, 2H), 6.93 (d, J=6.1 Hz, 1H), 7.88 (m, J=8.5, 7.7 Hz, 1H), 8.09 (d, J=6.9 Hz, 1H), 8.20 (s, 2H), 8.53 (d, J=6.1 Hz, 1H), 8.61 (s, 1H), 8.69 (d, J=2.4 Hz, 1H), 8.88 (d, J=2.0 Hz, 1H), 11.18-11.52 (m, 1H), 11.29 (s, 1H).

Example 445

(*S)—N-(5-chloro-6-(2H-1,2,3-triazol-2-yl)pyridin-3-yl)-1-(1-(1-hydroxyethyl)isoquinolin-5-yl)-5-(trifluoromethyl)-1H-pyrazole-4-carboxamide, Cpd 445

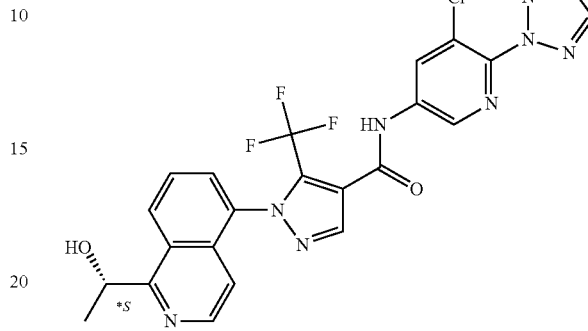

LCMS (ESI): mass calcd. for $C_{23}H_{16}ClF_3N_8O_2$ 528.1 m/z found 529[M+H]$^+$. $^1$H NMR (400 MHz, DMSO-d$_6$) δ ppm 1.62 (d, J=6.5 Hz, 3H), 5.52-5.74 (m, 2H), 6.93 (d, J=6.1 Hz, 1H), 7.88 (m, J=8.5, 7.7 Hz, 1H), 8.09 (d, J=6.9 Hz, 1H), 8.20 (s, 2H), 8.53 (d, J=6.1 Hz, 1H), 8.61 (s, 1H), 8.69 (d, J=2.4 Hz, 1H), 8.88 (d, J=2.0 Hz, 1H), 11.18-11.52 (m, 1H), 11.29 (s, 1H).

Biological Examples

In vitro assays include assays that determine cell morphology, protein expression, and/or the cytotoxicity, enzyme inhibitory activity, and/or the subsequent functional consequences of treatment of cells with compounds of the invention. Alternate or additional in vitro assays may be used to quantitate the ability of the inhibitor to bind to protein or nucleic acid molecules within the cell.

Inhibitor binding may be measured by radiolabelling the inhibitor prior to binding, isolating the inhibitor/target molecule complex and determining the amount of radiolabel bound. Alternatively or additionally, inhibitor binding may be determined by running a competition experiment where new inhibitors are incubated with purified proteins or nucleic acids bound to known radioligands. Detailed conditions of exemplary systems for assaying a compound of Formula (I) of the present invention as MALT1 inhibitors are set forth in the Biological Examples below.

Such assays are exemplary and not intended to limit the scope of the invention. The skilled practitioner can appreciate that modifications can be made to conventional assays to develop equivalent or other assays that can be employed to comparably assess activity or otherwise characterize compounds and/or compositions as described herein.

In Vitro Assays

Biological Example 1

MALT1 Biochemical Protease Assay

MALT1 protease activity was assessed in an in vitro assay using a tetrapeptide as substrate and full-length MALT1 protein (Strep-MALT1(1-824)-His) purified from baculovirus-infected insect cells. The tetrapeptide LRSR is coupled to AMC (7-amino-4-methylcoumarin) and provides a quenched, fluorescent substrate for the MALT1 protease (SM Biochemicals). Cleavage of AMC from the Arginine residue results in an increase in coumarin fluorescence measured at 460 nm (excitation 355 nm). The final assay buffer consisted of 10 nM FL MALT1 protein, 200 μM Ac-LRSR-AMC, 50 mM Tris pH 7.5, 0.6 M Citrate, 1 mM DTT, 1 mM EDTA, 0.05% BSA and 1.5% DMSO. Test compounds were spotted at 50 nL in 100% DMSO per well of a black 384-Proxiplate (Perkin Elmer). Test compound concentrations ranged from 30 μM to 0.5 nM using 11 dilution steps (1:3). Background signal was measured from control wells containing assay buffer without enzyme which functions as low control (LC). High control (HC) values were generated using the reaction with enzyme but no compound treatment. Compounds were pre-incubated with MALT1 enzyme for 50 minutes at RT. Substrate was added subsequently and fluorescence was measured in Labsystems fluoroskan at excitation 355 nm and emission 460 nm to determine time 0. The reaction was subsequently incubated for 4 h at RT and fluorescence was measured. For $IC_{50}$ calculations, timepoint 0 was subtracted from the 4 h timepoint to correct for any potential autofluorescence of the compounds. The enzyme reaction was linear during the 4 h incubation period. Characterization of the substrate Ac-LRSR-AMC determined the Michaelis constant KM at 200 μM.

$IC_{50}$ values were calculated using the following formula (Z prime should be >0.5):

LC=Median of the low control values
=Low control: Reaction without cells
HC=Median of the High control values
=High Control: Reaction with cells without compound % Effect=100−[(sample−LC)/(HC−LC)×100]

% Control=(sample/HC)×100%

Controlmin=(sample−LC)/(HC−LC)×100

A best-fit curve was fitted by a minimum sum of squares method to the plot of % Controlmin vs. compound concentration. From this an $IC_{50}$ value (inhibitory concentration causing 50% inhibition) can be obtained. An estimate of the slope of the plot in terms of the Hill coefficient was also obtained.

$IC_{50}$ Calculation:

$$DATA_i = LB + \frac{UB - LB}{1 + \exp(\text{HILL} * (LCONC_i - IC50))} + \varepsilon_i$$

With
UB=upper bound
LB=lower bound
Used in "Lexis Dose Response Curve Fitting" Version 1.0. Resultant data are shown in Table 2.

TABLE 2

| Cpd No. | MALT1_Biochemical activity (Ac-LRSR-amc) IC50 (μM) |
| --- | --- |
| 1 | 0.389 |
| 2 | 0.012 |
| 3 | 0.191 |
| 4 | 0.200 |
| 5 | 0.214 |

TABLE 2-continued

| Cpd No. | MALT1_Biochemical activity (Ac-LRSR-amc) IC50 (μM) |
| --- | --- |
| 6 | 0.091 |
| 7 | 0.041 |
| 8 | 0.013 |
| 9 | 0.065 |
| 11 | 0.977 |
| 12 | 4.073 |
| 13 | 6.026 |
| 14 | 4.571 |
| 15 | 4.169 |
| 16 | 0.724 |
| 17 | 0.141 |
| 18 | 2.291 |
| 19 | 0.229 |
| 20 | 9.550 |
| 21 | 1.445 |
| 22 | 0.661 |
| 23 | 0.089 |
| 24 | 0.074 |
| 25 | 0.072 |
| 26 | 0.631 |
| 27 | 0.035 |
| 28 | 0.068 |
| 29 | 2.455 |
| 30 | 5.012 |
| 31 | 8.913 |
| 32 | 0.019 |
| 33 | 1.096 |
| 34 | 0.009 |
| 35 | 0.813 |
| 36 | 0.063 |
| 37 | 1.445 |
| 38 | 0.020 |
| 39 | 0.759 |
| 40 | 0.048 |
| 41 | 0.891 |
| 42 | 0.162 |
| 43 | 0.060 |
| 44 | 0.083 |
| 45 | 0.398 |
| 46 | 0.056 |
| 47 | 0.011 |
| 48 | 0.631 |
| 49 | 0.155 |
| 50 | 0.020 |
| 51 | 0.045 |
| 52 | 0.035 |
| 53 | 0.100 |
| 54 | 0.275 |
| 55 | 0.182 |
| 56 | 0.257 |
| 57 | 0.043 |
| 58 | 0.141 |
| 59 | 0.031 |
| 60 | 11.482 |
| 61 | 0.102 |
| 62 | 0.059 |
| 63 | 0.295 |
| 64 | 1.148 |
| 65 | 0.060 |
| 66 | 0.069 |
| 67 | 2.042 |
| 68 | 0.151 |
| 69 | 0.060 |
| 70 | 0.479 |
| 71 | 1.585 |
| 72 | 0.407 |
| 73 | 0.724 |
| 74 | 0.372 |
| 75 | 27.542 |
| 76 | 8.318 |
| 77 | 0.417 |
| 78 | 0.055 |
| 79 | 0.098 |
| 80 | 0.724 |
| 81 | 0.123 |
| 82 | 0.676 |

TABLE 2-continued

| Cpd No. | MALT1_Biochemical activity (Ac-LRSR-amc) IC50 (μM) |
|---|---|
| 83 | 0.034 |
| 84 | 0.214 |
| 85 | 0.132 |
| 86 | 0.071 |
| 87 | 0.141 |
| 88 | 0.107 |
| 89 | 0.041 |
| 90 | 0.021 |
| 91 | 0.015 |
| 92 | 0.019 |
| 93 | 0.060 |
| 94 | 0.019 |
| 95 | 0.117 |
| 96 | 0.759 |
| 97 | 0.209 |
| 98 | 0.200 |
| 99 | 0.011 |
| 100 | 0.037 |
| 101 | 2.692 |
| 102 | 0.042 |
| 103 | 1.514 |
| 104 | 0.204 |
| 105 | 0.058 |
| 106 | 0.447 |
| 107 | 1.288 |
| 108 | 0.023 |
| 109 | 0.010 |
| 110 | 0.019 |
| 111 | 0.010 |
| 112 | 0.017 |
| 113 | 0.011 |
| 114 | 0.011 |
| 115 | 0.012 |
| 116 | 0.015 |
| 117 | 0.013 |
| 118 | 0.015 |
| 119 | 0.013 |
| 120 | 0.030 |
| 121 | 0.022 |
| 122 | 0.013 |
| 123 | 0.013 |
| 124 | 0.020 |
| 125 | 0.013 |
| 126 | 0.015 |
| 127 | 0.015 |
| 128 | 0.016 |
| 129 | 0.016 |
| 130 | 0.017 |
| 131 | 0.017 |
| 132 | 0.019 |
| 133 | 0.019 |
| 134 | 0.020 |
| 135 | 0.021 |
| 136 | 0.021 |
| 137 | 0.023 |
| 138 | 0.023 |
| 139 | 0.023 |
| 140 | 0.024 |
| 141 | 0.025 |
| 142 | 0.026 |
| 143 | 0.026 |
| 144 | 0.028 |
| 145 | 0.028 |
| 146 | 0.032 |
| 147 | 0.030 |
| 148 | 0.032 |
| 149 | 0.029 |
| 150 | 0.008 |
| 151 | 0.214 |
| 152 | 0.018 |
| 153 | 0.012 |
| 154 | 0.019 |
| 155 | 0.019 |
| 156 | 0.022 |
| 157 | 0.023 |
| 158 | 0.074 |
| 159 | 0.105 |
| 160 | 0.389 |
| 161 | 0.282 |
| 162 | 0.363 |
| 163 | 0.224 |
| 164 | 0.282 |
| 165 | 0.245 |
| 166 | 0.229 |
| 167 | 0.110 |
| 168 | 0.107 |
| 169 | 0.072 |
| 170 | 0.135 |
| 171 | 0.071 |
| 172 | 0.069 |
| 173 | 0.059 |
| 174 | 0.059 |
| 175 | 0.047 |
| 176 | 0.045 |
| 177 | 0.044 |
| 178 | 0.042 |
| 179 | 0.042 |
| 180 | 0.026 |
| 181 | 0.038 |
| 182 | 0.035 |
| 183 | 0.035 |
| 184 | 0.032 |
| 185 | 0.018 |
| 186 | 0.380 |
| 187 | 0.178 |
| 188 | 0.115 |
| 189 | 0.078 |
| 190 | 0.170 |
| 191 | 0.036 |
| 192 | 0.025 |
| 193 | 0.041 |
| 194 | 0.076 |
| 195 | 0.324 |
| 196 | 3.162 |
| 197 | 0.015 |
| 198 | 0.026 |
| 199 | 0.110 |
| 200 | 0.040 |
| 201 | 0.028 |
| 202 | 0.051 |
| 203 | 0.162 |
| 204 | 0.035 |
| 205 | 0.195 |
| 206 | 1.738 |
| 207 | 0.331 |
| 208 | 0.316 |
| 209 | 0.224 |
| 210 | 0.072 |
| 211 | 0.035 |
| 212 | 10.965 |
| 213 | 10.000 |
| 214 | 6.026 |
| 215 | 5.754 |
| 216 | 5.370 |
| 217 | 4.898 |
| 218 | 3.467 |
| 219 | 2.692 |
| 220 | 2.138 |
| 221 | 2.042 |
| 222 | 1.698 |
| 223 | 1.698 |
| 224 | 1.660 |
| 225 | 1.230 |
| 226 | 1.202 |
| 227 | 1.148 |
| 228 | 1.122 |
| 229 | 1.122 |
| 230 | 1.072 |
| 231 | 0.891 |
| 232 | 0.891 |
| 233 | 0.871 |
| 234 | 0.851 |

TABLE 2-continued

| Cpd No. | MALT1_Biochemical activity (Ac-LRSR-amc) IC50 (μM) |
|---|---|
| 235 | 0.776 |
| 236 | 0.724 |
| 237 | 0.676 |
| 238 | 0.676 |
| 239 | 0.661 |
| 240 | 0.631 |
| 241 | 0.562 |
| 242 | 0.437 |
| 243 | 0.417 |
| 244 | 0.398 |
| 245 | 0.389 |
| 246 | 0.380 |
| 247 | 0.347 |
| 248 | 0.331 |
| 249 | 0.331 |
| 250 | 0.316 |
| 251 | 0.302 |
| 252 | 0.282 |
| 253 | 0.282 |
| 254 | 0.282 |
| 255 | 0.275 |
| 256 | 0.240 |
| 257 | 0.234 |
| 258 | 0.229 |
| 259 | 0.219 |
| 260 | 0.204 |
| 261 | 0.195 |
| 262 | 0.191 |
| 263 | 0.191 |
| 264 | 0.166 |
| 265 | 0.166 |
| 266 | 0.158 |
| 267 | 0.155 |
| 268 | 0.155 |
| 269 | 0.155 |
| 270 | 0.145 |
| 271 | 0.145 |
| 272 | 0.145 |
| 273 | 0.145 |
| 274 | 0.141 |
| 275 | 0.138 |
| 276 | 0.138 |
| 277 | 0.132 |
| 278 | 0.129 |
| 279 | 0.126 |
| 280 | 0.126 |
| 281 | 0.123 |
| 282 | 0.123 |
| 283 | 0.123 |
| 284 | 0.120 |
| 285 | 0.112 |
| 286 | 0.110 |
| 287 | 0.095 |
| 288 | 0.095 |
| 289 | 0.091 |
| 290 | 0.081 |
| 291 | 0.081 |
| 292 | 0.079 |
| 293 | 0.076 |
| 294 | 0.076 |
| 295 | 0.074 |
| 296 | 0.072 |
| 297 | 0.251 |
| 298 | 1.349 |
| 299 | 0.105 |
| 300 | 4.169 |
| 301 | 0.141 |
| 302 | 0.054 |
| 303 | 0.282 |
| 304 | 0.062 |
| 305 | 0.062 |
| 306 | 0.058 |
| 307 | 0.058 |
| 308 | 0.058 |
| 309 | 0.055 |
| 310 | 0.052 |
| 311 | 0.050 |
| 312 | 0.049 |
| 313 | 0.043 |
| 314 | 0.039 |
| 315 | 0.033 |
| 316 | 0.037 |
| 317 | 0.065 |
| 318 | 0.083 |
| 319 | 0.107 |
| 320 | 0.069 |
| 321 | 0.021 |
| 322 | 0.214 |
| 323 | 0.174 |
| 324 | 0.117 |
| 325 | 0.055 |
| 326 | 0.045 |
| 327 | 0.079 |
| 328 | 2.570 |
| 329 | 0.661 |
| 330 | 0.646 |
| 331 | 0.501 |
| 332 | 0.417 |
| 333 | 0.245 |
| 334 | 0.417 |
| 335 | 0.174 |
| 336 | 0.214 |
| 337 | 0.141 |
| 338 | 0.058 |
| 339 | 0.117 |
| 340 | 0.209 |
| 341 | 0.025 |
| 342 | 0.115 |
| 343 | 0.020 |
| 344 | 1.230 |
| 345 | 0.093 |
| 346 | 0.275 |
| 347 | 0.933 |
| 348 | 0.195 |
| 349 | 13.490 |
| 350 | 1.259 |
| 351 | 0.068 |
| 352 | 0.044 |
| 353 | 0.115 |
| 354 | 0.052 |
| 355 | 0.010 |
| 356 | 0.123 |
| 357 | 0.977 |
| 358 | 0.019 |
| 359 | 0.028 |
| 360 | 2.692 |
| 361 | 12.303 |
| 362 | 0.138 |
| 363 | 26.303 |
| 364 | 0.098 |
| 365 | 0.060 |
| 366 | 8.913 |
| 367 | 0.110 |
| 368 | 0.331 |
| 369 | 0.155 |
| 370 | 0.107 |
| 371 | 0.069 |
| 372 | 1.995 |
| 373 | 0.138 |
| 374 | 0.087 |
| 375 | 0.355 |
| 376 | 0.024 |
| 377 | 0.457 |
| 378 | 0.447 |
| 379 | 0.501 |
| 380 | 0.447 |
| 381 | 4.898 |
| 382 | 0.331 |
| 383 | 10.000 |
| 384 | 5.888 |
| 385 | 0.054 |
| 386 | 0.107 |

TABLE 2-continued

| Cpd No. | MALT1_Biochemical activity (Ac-LRSR-amc) IC50 (µM) |
|---|---|
| 387 | 0.030 |
| 388 | 1.995 |
| 389 | 0.186 |
| 390 | 0.102 |
| 391 | 0.007 |
| 392 | 0.026 |
| 393 | 0.012 |
| 394 | 0.095 |
| 395 | 3.467 |
| 396 | 0.447 |
| 397 | 0.214 |
| 398 | 0.060 |
| 399 | 0.316 |
| 400 | 0.209 |
| 401 | 0.056 |
| 402 | 0.178 |
| 403 | 0.871 |
| 404 | 0.091 |
| 405 | 0.044 |
| 406 | 0.076 |
| 407 | 0.021 |
| 408 | 0.112 |
| 409 | 2.291 |
| 410 | 0.071 |
| 411 | 0.033 |
| 412 | 0.022 |
| 413 | 0.288 |
| 414 | 0.019 |
| 415 | 0.054 |
| 416 | 2.570 |
| 417 | 0.174 |
| 418 | 0.550 |
| 419 | 0.015 |
| 420 | 0.010 |
| 421 | 0.020 |
| 422 | 0.011 |
| 423 | 0.054 |
| 424 | 0.072 |
| 425 | 0.389 |
| 426 | 0.013 |
| 427 | 0.009 |
| 428 | 0.011 |
| 429 | 0.030 |
| 430 | 0.013 |
| 431 | 0.017 |
| 432 | 0.098 |
| 433 | 0.170 |
| 434 | 0.214 |
| 435 | 0.170 |
| 436 | 1.318 |
| 437 | 1.778 |
| 438 | 0.071 |
| 439 | 0.178 |
| 440 | 1.585 |
| 441 | 0.977 |
| 442 | 0.062 |
| 443 | 0.013 |
| 444 | 0.058 |
| 445 | 0.079 |
| 446 | 0.032 |
| 447 | 0.447 |
| 448 | 1.288 |
| 449 | 0.023 |
| 450 | 0.010 |

Biological Example 2

PMA Induced IL2 Production In Jurkat Cells

Jurkat cells were maintained in complete RPMI 1640 media containing 10% fetal bovine serum, 10 mM HEPES, 100 units/mL of penicillin and 100 µg/mL of streptomycin. Prior to the assay, compounds were made 2- to 4-fold serial dilutions in DMSO. A volume of 10 µL of DMSO-diluted compound in each well were further diluted into 240 µL RPMI1640 complete media. Jurkat cells were harvested by centrifuge at 1200 RPM for 5 min, washed one time with RPMI 1640 media, and suspended in fresh complete RPMI 1640 media at concentration of $1.25 \times 10^6$ cell/mL. A volume of 160 uL of Jurkat cells ($2 \times 10^5$ cells) were seeded in each well of 96 well plate-bottom plates. A volume of 20 uL of diluted compound in RMPI 1640 complete media were added to each well and incubated with Jurkat cells for 30 min at 37° C. in a 5% $CO_2$ incubator. A volume 20 µL of diluted PMA/Ionomycin (81 nM/1.3 uM respectively, ebioscience, catalog number 00-4970-93) in RMPI 1640 complete media were added to each well. After incubation at 37° C. in 5% $CO_2$ incubator for 20 h, supernatants were harvested. IL-2 concentration was assessed by ELISA (IL2 Duoset, R&D Systems, catalog number DY202). Colorimetric intensity at 450 nm was read by Spectramax plate reader and analyzed with Softmax Pro software. Cell viability was assessed by Cell Titer Glo kit (Promega, catalog number G7571) using Victor Luminescence reader (Victor 3V 4202938 by Perkin Elmer).

Resultant data are shown in Table 3.

Biological Example 3

Human IL6/IL10 Mesoscale Assay $NF_KB$ signaling regulates the secretion of multiple cytokines, including IL6 and IL10. Secretion of the cytokines IL6 and IL10 by TMD8 or OCI-LY3 ABC-DLBCL cells was measured using a mesoscale assay. Inhibition of $NF_KB$ signaling by MALT1 or BTK inhibitors results in a decrease of IL6/10 secretion.

TMD8 or OCI-LY3 cells were propagated in RPMI-1640 (Sigma Aldrich) supplemented with 10% fetal bovine serum (HyClone), 1 mM sodium pyruvate (Invitrogen), 2 mM L-glutamine (Sigma Aldrich) and 1% PenStrep (Sigma Aldrich). Cell passage number should not exceed 30. Cells should be kept between 0.5-2.5 million cells per mL during culturing and cells should be supplemented every 2-3 days with fresh 50 µM beta-mercaptoenthanol. No beta-mercaptoethanol was used during the mesoscale assay.

For the Mesoscale assay, 100,000 TMD8 or OCI-LY3 cells were seeded per well into black-colored 96-well plates with clear bottom (Corning #3904) and test compounds were added in 9 dilution steps (1:2) ranging from 15 µM to 58.6 nM (final DMSO concentration 0.3%). DMSO control wells were used to determine the maximum signal (High Control (HC)). Treatment with the BTK inhibitor RN486 in a dose range from 30 nM to 131 pM (9 dilutions of 1:2) served as a positive control for $NF_KB$ pathway inhibition and was used to determine the maximum inhibition (Low Control (LC)). Compounds and cells were incubated for 24 h at 37° C. and 5% $CO_2$ (assay volume is 150 µL). After 24 h of incubation 50 µL of the supernatant was transferred to a MSD plate (V-Plex Proinflammation Panel 1 (human) kit, Mesoscale (MSD)) and incubated for 2 h with vigorous shaking (600 rpm) at room temperature. Following incubation, plates were washed 3× with PBS+0.05% Tween-20 and 25 µL detection antibody solution (IL6 & IL10 antibodies in diluent 3 (MSD)) was added per well followed by 2 h of incubation with vigorous shaking (600 rpm) at room temperature. After 3× washes with PBS+0.05% Tween-20, plates were incubated with 150 µL 2× Read Buffer T and read on SECTOR imager. Resultant data are shown in Table 3.

TABLE 3

| Cpd No. | Human IL6 Mesoscale assay (TMD-8) IC50 (µM) | Human IL10 Mesoscale assay (TMD-8) IC50 (µM) | Human IL6 Mesoscale assay (OCI-LY3) IC50 (µM) | Human IL10 Mesoscale assay (OCI-LY3) IC50 (µM) | IL-2 prod h Jurkat PMA IC50 (µM) |
|---|---|---|---|---|---|
| 1 | | | | | 0.31 |
| 2 | 0.052 | 0.028 | | | 0.059 |
| 3 | 0.219 | 0.138 | | | 0.16 |
| 4 | 0.339 | 0.214 | | | 0.36 |
| 5 | 0.282 | | | | 0.14 |
| 6 | 0.112 | | | | 0.023 |
| 7 | 0.166 | | | | 0.13 |
| 8 | 0.032 | | | | 0.0052 |
| 9 | 0.195 | | | | 0.039 |
| 11 | ~13.5 | | | | 0.68 |
| 16 | 1.479 | | | | |
| 17 | 0.794 | | | | 0.17 |
| 19 | 1.950 | | | | 0.41 |
| 21 | >15 | | | | |
| 22 | >15 | | | | 1.86 |
| 23 | 0.107 | | | | 0.81 |
| 24 | 0.093 | 0.129 | | | 0.74 |
| 25 | 0.174 | | | | 0.21 |
| 26 | 0.575 | | | | 0.79 |
| 27 | 0.105 | | | | |
| 28 | 0.141 | | | | 0.2 |
| 32 | 0.017 | 0.014 | | | 0.002 |
| 33 | 7.413 | 1.047 | | | |
| 34 | ~0.011 | 0.007 | | | 0.016 |
| 35 | 6.026 | 2.884 | | | 3.24 |
| 36 | 0.135 | 0.141 | | | 0.27 |
| 38 | 0.046 | 0.014 | | | 0.021 |
| 39 | 1.950 | 0.955 | | | 1.97 |
| 40 | 0.030 | 0.035 | | | 0.095 |
| 41 | ~2.09 | 0.851 | | | 0.30 |
| 42 | 0.117 | ~0.11 | | | 0.011 |
| 43 | 0.102 | 0.081 | | | 0.054 |
| 45 | 0.355 | 0.204 | | | 0.073 |
| 46 | ~0.046 | 0.032 | | | 0.022 |
| 47 | ~0.048 | ~0.01 | | | 0.009 |
| 48 | ~0.83 | ~2.14 | | | 0.45 |
| 49 | ~0.083 | 0.076 | | | 0.018 |
| 50 | 0.107 | 0.047 | | | 0.031 |
| 51 | 0.062 | 0.126 | | | 0.096 |
| 52 | 0.079 | 0.091 | | | 0.13 |
| 53 | 0.200 | 0.240 | | | 0.38 |
| 54 | 0.110 | 0.269 | | | 0.37 |
| 55 | ~0.093 | 0.195 | | | 0.13 |
| 56 | 0.490 | 0.275 | | | |
| 57 | 0.081 | 0.085 | | | |
| 58 | 0.331 | 0.288 | | | |
| 59 | 0.068 | 0.074 | | | |
| 61 | 0.263 | 0.224 | | | |
| 62 | 0.112 | 0.085 | | | |
| 63 | 2.042 | 1.445 | | | |
| 65 | 0.282 | 0.120 | | | |
| 66 | 0.331 | 0.132 | | | |
| 68 | 0.417 | 0.257 | | | |
| 69 | 0.058 | 0.063 | | | |
| 70 | 1.096 | 0.891 | | | |
| 72 | 0.851 | 1.380 | | | |
| 73 | 0.417 | 0.339 | | | |
| 74 | 1.380 | 1.380 | | | |
| 78 | 0.081 | 0.112 | | | |
| 79 | ~0.34 | 0.251 | | | |
| 81 | 0.135 | 0.138 | | | |
| 82 | 0.240 | 0.295 | | | |
| 83 | 0.032 | 0.043 | | | |
| 84 | 0.148 | 0.355 | | | |
| 85 | 0.095 | 0.120 | | | |
| 86 | 0.037 | 0.148 | | | |
| 87 | 0.251 | 0.324 | | | |
| 88 | 0.331 | 0.209 | | | |
| 89 | 0.074 | 0.095 | | | |
| 90 | 0.098 | 0.135 | | | |
| 91 | 0.151 | 0.155 | | | |
| 92 | 0.102 | 0.132 | | | |
| 93 | 0.447 | 0.501 | | | |
| 94 | 0.089 | 0.105 | | | |
| 95 | 0.646 | 0.302 | | | |
| 96 | 1.047 | 0.676 | | | |
| 97 | 0.575 | 0.257 | | | |
| 98 | 0.468 | 0.417 | | | |
| 99 | 0.068 | 0.047 | | | |
| 100 | 0.251 | 0.155 | | | |
| 102 | 0.110 | 0.186 | | | |
| 103 | >15 | >15 | | | |
| 104 | >15 | >15 | | | |
| 105 | 0.851 | 0.813 | | | |
| 106 | 1.259 | 0.617 | | | |
| 107 | 3.467 | 1.175 | | | |
| 108 | >0.302 | >0.302 | | | |
| 109 | | | 0.028 | 0.031 | |
| 110 | | | 0.025 | 0.024 | |
| 111 | | | 0.107 | 0.089 | |
| 112 | | | 0.115 | 0.098 | |
| 113 | | | 0.170 | 0.079 | |
| 114 | | | 0.034 | 0.029 | |
| 115 | 0.054 | 0.046 | 0.013 | 0.010 | |
| 116 | 0.013 | 0.025 | 0.018 | 0.018 | |
| 117 | | | 0.012 | 0.012 | |
| 118 | | | 0.017 | 0.012 | |
| 119 | | | 0.072 | 0.040 | |
| 120 | 0.102 | 0.085 | | | |
| 121 | | | 0.058 | 0.050 | |
| 122 | | | 0.052 | 0.056 | |
| 123 | 0.389 | 0.182 | | | |
| 124 | 0.021 | 0.015 | | | |
| 125 | | | 0.046 | 0.024 | |
| 126 | 0.021 | 0.043 | | | |
| 127 | | | 0.029 | 0.026 | |
| 128 | 0.095 | 0.105 | 0.027 | 0.036 | |
| 129 | 0.120 | 0.123 | 0.018 | 0.014 | |
| 130 | 0.214 | 0.166 | | | |
| 131 | 0.056 | 0.021 | | | |
| 132 | | | 0.141 | 0.095 | |
| 133 | 0.126 | 0.054 | | | |
| 134 | 0.058 | 0.046 | | | |
| 135 | | | 0.098 | 0.083 | |
| 136 | 0.045 | 0.031 | | | |
| 137 | 0.170 | 0.200 | 0.026 | 0.017 | |
| 138 | 0.245 | 0.126 | | | |
| 139 | | | 0.050 | 0.036 | |
| 140 | 0.072 | 0.028 | | | |
| 141 | 0.051 | 0.039 | | | |
| 142 | 0.107 | 0.017 | | | |
| 143 | 0.098 | 0.056 | | | |
| 144 | 0.052 | 0.049 | | | |
| 145 | 0.126 | 0.047 | | | |
| 146 | 0.331 | 0.132 | | | |
| 147 | 0.200 | 0.085 | | | |
| 148 | 0.105 | 0.112 | | | |
| 149 | 0.912 | 2.630 | | | |
| 150 | 0.457 | 0.178 | | | |
| 151 | 0.224 | 0.200 | | | |
| 152 | 0.110 | 0.100 | 0.034 | 0.040 | |
| 153 | 0.141 | 0.162 | 0.054 | 0.081 | |
| 154 | | | 0.098 | 0.095 | |
| 155 | | | 0.093 | 0.068 | |
| 156 | 2.512 | 2.344 | | | |
| 157 | | | 1.778 | 0.912 | |
| 158 | >1.514 | 0.380 | | | |
| 159 | >15.136 | 0.955 | | | |
| 160 | 0.095 | 0.093 | | | |
| 161 | >15.136 | >15.136 | | | |
| 162 | | | 0.437 | 0.309 | |
| 163 | | | 0.095 | 0.071 | |
| 164 | | | 1.660 | | |
| 165 | | | 0.447 | 0.339 | |
| 166 | | | 0.457 | 0.479 | |
| 167 | | | 0.191 | 0.174 | |

TABLE 3-continued

| Cpd No. | Human IL6 Mesoscale assay (TMD-8) IC50 (μM) | Human IL10 Mesoscale assay (TMD-8) IC50 (μM) | Human IL6 Mesoscale assay (OCI-LY3) IC50 (μM) | Human IL10 Mesoscale assay (OCI-LY3) IC50 (μM) | IL-2 prod h Jurkat PMA IC50 (μM) |
|---|---|---|---|---|---|
| 168 | | | 0.123 | 0.044 | |
| 169 | | | 0.166 | 0.182 | |
| 170 | 0.339 | 0.112 | | | |
| 171 | 0.091 | 0.060 | | | |
| 172 | | | 0.204 | 0.158 | |
| 173 | 0.550 | 0.240 | | | |
| 174 | | | 0.251 | 0.112 | |
| 175 | >3.02 | 0.204 | | | |
| 176 | | | 0.117 | 0.095 | |
| 177 | 0.933 | 0.363 | | | |
| 178 | | | 0.589 | 0.427 | |
| 179 | | | 0.288 | 0.174 | |
| 180 | | | 0.079 | 0.081 | |
| 181 | | | 0.141 | 0.110 | |
| 182 | 7.586 | 2.512 | | | |
| 183 | 6.607 | 2.138 | | | |
| 184 | 4.266 | 1.000 | | | |
| 185 | 0.186 | 0.162 | | | |
| 186 | | | 1.122 | 0.891 | |
| 187 | | | 0.162 | 0.112 | |
| 188 | 0.046 | 0.050 | | | |
| 189 | 0.107 | 0.063 | 0.039 | 0.027 | |
| 190 | | | 0.186 | 0.093 | |
| 191 | | | 0.022 | 0.013 | |
| 192 | | | 0.046 | 0.042 | |
| 193 | | | 0.117 | 0.079 | |
| 194 | 0.078 | 0.098 | 0.100 | 0.068 | |
| 195 | | | 0.107 | 0.071 | |
| 196 | | | 0.083 | 0.041 | |
| 197 | | | 0.123 | 0.085 | |
| 198 | | | 0.115 | 0.091 | |
| 199 | | | 0.295 | | |
| 200 | | | 0.380 | 0.282 | |
| 201 | | | 0.117 | 0.120 | |
| 202 | 5.012 | 2.951 | | | |
| 203 | 5.623 | 2.692 | | | |
| 204 | 0.525 | 1.148 | | | |
| 205 | >15.136 | 1.905 | | | |
| 206 | 6.166 | 3.890 | | | |
| 207 | | | 0.525 | 0.513 | |
| 208 | >15.136 | 8.710 | | | |
| 209 | 1.479 | 1.122 | | | |
| 210 | | | 0.417 | 0.380 | |
| 211 | 1.660 | 2.291 | | | |
| 212 | 1.023 | 0.513 | | | |
| 213 | >15.136 | >15.136 | | | |
| 214 | 2.042 | 2.239 | | | |
| 215 | 12.303 | 2.089 | | | |
| 216 | 0.912 | 0.339 | | | |
| 217 | 0.537 | 0.269 | | | |
| 218 | 0.174 | 0.087 | | | |
| 219 | | | 0.102 | 0.126 | |
| 220 | 0.851 | 0.468 | | | |
| 221 | 0.331 | 0.331 | | | |
| 222 | 3.311 | 0.575 | | | |
| 223 | 0.759 | 1.175 | | | |
| 224 | 0.575 | 0.832 | | | |
| 225 | 0.407 | 0.794 | | | |
| 226 | 0.257 | 0.093 | | | |
| 227 | 6.457 | 0.550 | | | |
| 228 | 0.692 | 0.813 | | | |
| 229 | 0.912 | 0.331 | | | |
| 230 | 1.413 | 0.759 | | | |
| 231 | 0.724 | 0.851 | | | |
| 232 | | | 0.145 | 0.182 | |
| 233 | | | 0.331 | 0.240 | |
| 234 | 0.263 | 0.141 | | | |
| 235 | 0.708 | 1.122 | | | |
| 236 | 1.380 | 0.427 | 0.380 | 0.309 | |
| 237 | 0.275 | 0.182 | | | |
| 238 | 0.032 | 0.050 | 0.044 | 0.035 | |
| 239 | 0.324 | 0.562 | | | |
| 240 | 0.398 | 0.135 | | | |
| 241 | 0.049 | 0.069 | 0.051 | 0.037 | |
| 242 | | | 0.065 | 0.054 | |
| 243 | 0.363 | 0.339 | 0.120 | 0.129 | |
| 244 | 0.741 | 0.245 | 0.174 | 0.155 | |
| 245 | 0.708 | 0.141 | | | |
| 246 | | | 0.135 | 0.063 | |
| 247 | >1.5136 | 1.778 | | | |
| 248 | 1.514 | 0.468 | | | |
| 249 | 0.148 | 0.148 | | | |
| 250 | | | 0.269 | 0.407 | |
| 251 | | | 2.188 | 2.239 | |
| 252 | | | 0.158 | 0.123 | |
| 253 | | | >15.136 | 12.589 | |
| 254 | | | 0.081 | 0.079 | |
| 255 | | | 0.059 | 0.041 | |
| 256 | | | 0.257 | 0.240 | |
| 257 | >3.2 | 0.646 | | | |
| 258 | 0.589 | 0.316 | | | |
| 259 | | | 0.145 | 0.151 | |
| 260 | >3.02 | >3.02 | >3.02 | >3.02 | |
| 261 | 0.794 | 0.479 | | | |
| 262 | | | 0.182 | 0.129 | |
| 263 | >0.302 | >0.302 | | | |
| 264 | 0.123 | 0.036 | | | |
| 265 | >1.5136 | 0.120 | | | |
| 266 | | | 0.186 | 0.178 | |
| 267 | 0.035 | 0.056 | | | |
| 268 | 0.158 | 0.229 | 0.095 | 0.063 | |
| 269 | | | 0.083 | 0.085 | |
| 270 | | | 0.170 | 0.098 | |
| 271 | | | 0.112 | 0.095 | |
| 272 | | | 0.126 | 0.087 | |
| 273 | | | 0.085 | 0.066 | |
| 274 | | | 2.754 | 3.162 | |
| 275 | | | 0.240 | 0.234 | |
| 276 | | | 0.186 | 0.117 | |
| 277 | 0.170 | 0.095 | 0.089 | 0.087 | |
| 278 | | | 0.141 | 0.219 | |
| 279 | 3.715 | 2.754 | | | |
| 280 | 5.495 | 2.399 | | | |
| 281 | 2.570 | 3.020 | | | |
| 282 | | | 0.741 | 0.417 | |
| 283 | | | 0.851 | 0.550 | |
| 284 | | | 0.589 | 0.724 | |
| 285 | | | 0.229 | 0.204 | |
| 286 | | | 0.200 | 0.200 | |
| 287 | | | 0.229 | 0.234 | |
| 288 | | | 0.251 | 0.091 | |
| 289 | | | 0.132 | 0.123 | |
| 290 | | | 0.186 | 0.110 | |
| 291 | | | 0.110 | 0.100 | |
| 292 | | | 0.151 | 0.115 | |
| 293 | | | 0.447 | 0.251 | |
| 294 | | | 1.585 | 0.871 | |
| 295 | | | 1.259 | 0.724 | |
| 296 | | | 0.182 | 0.069 | |
| 297 | | | 0.135 | 0.115 | |
| 298 | | | 0.050 | 0.025 | |
| 299 | | | 0.537 | 0.309 | |
| 300 | | | 0.525 | 0.339 | |
| 301 | | | 0.501 | 0.417 | |
| 302 | | | 0.102 | 0.059 | |
| 303 | 0.234 | 0.174 | 0.251 | 0.275 | |
| 304 | 3.311 | 3.236 | | | |
| 305 | >15.136 | 7.943 | | | |
| 306 | >3.02 | >3.02 | >3.02 | 2.630 | |
| 307 | | | 0.447 | 0.427 | |
| 308 | | | 0.219 | 0.166 | |
| 309 | | | 0.151 | 0.117 | |
| 310 | | | 0.646 | 0.490 | |
| 311 | | | 0.034 | 0.037 | |
| 312 | 8.318 | 2.455 | | | |
| 313 | 7.244 | 4.169 | | | |

TABLE 3-continued

| Cpd No. | Human IL6 Mesoscale assay (TMD-8) IC50 (μM) | Human IL10 Mesoscale assay (TMD-8) IC50 (μM) | Human IL6 Mesoscale assay (OCI-LY3) IC50 (μM) | Human IL10 Mesoscale assay (OCI-LY3) IC50 (μM) | IL-2 prod h Jurkat PMA IC50 (μM) |
|---|---|---|---|---|---|
| 314 | | | 1.023 | 0.692 | |
| 315 | 0.447 | 0.339 | 0.095 | 0.132 | |
| 316 | | | 0.251 | 0.182 | |
| 317 | | | 0.072 | 0.066 | |
| 318 | | | 0.162 | 0.138 | |
| 319 | | | 0.020 | 0.018 | |
| 320 | | | 0.182 | 0.093 | |
| 321 | | | 0.066 | 0.049 | |
| 322 | 0.562 | 0.708 | 0.148 | 0.135 | |
| 323 | | | 0.195 | 0.141 | |
| 324 | | | 0.040 | 0.016 | |
| 325 | | | 0.646 | 0.794 | |
| 326 | | | 0.105 | 0.089 | |
| 327 | | | 0.129 | 0.100 | |
| 328 | | | 0.741 | 0.589 | |
| 329 | 1.660 | 1.445 | | | |
| 330 | | | 0.021 | 0.025 | |
| 331 | | | 0.309 | 0.339 | |
| 332 | | | 0.048 | 0.044 | |
| 333 | | | 0.155 | 0.123 | |
| 334 | | | 0.186 | 0.251 | |
| 335 | | | 0.132 | 0.060 | |
| 336 | | | 0.209 | 0.117 | |
| 337 | | | 0.209 | 0.182 | |
| 338 | | | 0.045 | 0.031 | |
| 339 | | | 0.107 | 0.087 | |
| 340 | | | 0.295 | 0.229 | |
| 341 | | | 0.479 | 0.389 | |
| 342 | | | 0.162 | 0.132 | |
| 343 | | | 0.069 | 0.037 | |
| 344 | | | 0.052 | 0.052 | |
| 345 | | | 0.079 | 0.058 | |
| 346 | | | 0.457 | 0.224 | |
| 347 | | | 0.043 | 0.031 | |
| 348 | | | 0.100 | 0.068 | |
| 349 | | | 0.079 | 0.060 | |
| 350 | | | 0.204 | 0.182 | |
| 351 | | | 0.078 | 0.046 | |
| 352 | | | 0.129 | 0.087 | |
| 353 | | | 0.692 | 0.537 | |
| 354 | | | 0.457 | 0.437 | |
| 355 | | | 0.912 | 0.407 | |
| 356 | | | 0.295 | 0.209 | |
| 357 | | | 0.015 | 0.015 | |
| 358 | | | 0.123 | 0.126 | |
| 359 | | | 0.098 | 0.091 | |
| 360 | | | 0.020 | 0.020 | |
| 361 | 1.259 | 0.617 | | | |
| 362 | 3.467 | 1.175 | | | |
| 363 | >0.302 | >0.302 | | | |
| 364 | | | 0.028 | 0.031 | |
| 365 | | | 0.025 | 0.024 | |
| 366 | | | 0.107 | 0.089 | |
| 367 | | | 0.115 | 0.098 | |
| 368 | | | 0.170 | 0.079 | |
| 369 | | | 0.034 | 0.029 | |
| 370 | 0.054 | 0.046 | 0.013 | 0.010 | |
| 371 | 0.013 | 0.025 | 0.018 | 0.018 | |
| 372 | | | 0.012 | 0.012 | |
| 373 | | | 0.017 | 0.012 | |
| 374 | | | 0.072 | 0.040 | |
| 375 | 0.102 | 0.085 | | | |
| 376 | | | 0.058 | 0.050 | |
| 377 | | | 0.052 | 0.056 | |
| 378 | 0.389 | 0.182 | | | |
| 379 | 0.021 | 0.015 | | | |
| 380 | | | 0.046 | 0.024 | |
| 381 | 0.021 | 0.043 | | | |
| 382 | | | 0.029 | 0.026 | |
| 383 | 0.095 | 0.105 | 0.027 | 0.036 | |
| 384 | 0.120 | 0.123 | 0.018 | 0.014 | |
| 385 | 0.214 | 0.166 | | | |
| 386 | 0.056 | 0.021 | | | |
| 387 | | | 0.141 | 0.095 | |
| 388 | 0.126 | 0.054 | | | |
| 389 | 0.058 | 0.046 | | | |
| 390 | | | 0.098 | 0.083 | |
| 391 | 0.045 | 0.031 | | | |
| 392 | 0.170 | 0.200 | 0.026 | 0.017 | |
| 393 | 0.245 | 0.126 | | | |
| 394 | | | 0.050 | 0.036 | |
| 395 | 0.072 | 0.028 | | | |
| 396 | 0.051 | 0.039 | | | |
| 397 | 0.107 | 0.017 | | | |
| 398 | 0.098 | 0.056 | | | |
| 399 | 0.052 | 0.049 | | | |
| 400 | 0.126 | 0.047 | | | |
| 401 | 0.331 | 0.132 | | | |
| 402 | 0.200 | 0.085 | | | |
| 403 | 0.105 | 0.112 | | | |
| 404 | 0.912 | 2.630 | | | |
| 405 | 0.457 | 0.178 | | | |
| 406 | 0.224 | 0.200 | | | |
| 407 | 0.110 | 0.100 | 0.034 | 0.040 | |
| 408 | 0.141 | 0.162 | 0.054 | 0.081 | |
| 409 | | | 0.098 | 0.095 | |
| 410 | | | 0.093 | 0.068 | |
| 411 | 2.512 | 2.344 | | | |
| 412 | | | 1.778 | 0.912 | |
| 413 | >1.514 | 0.380 | | | |
| 414 | >15.136 | 0.955 | | | |
| 415 | 0.095 | 0.093 | | | |
| 416 | >15.136 | >15.136 | | | |
| 417 | | | 0.437 | 0.309 | |
| 418 | | | 0.095 | 0.071 | |
| 419 | | | 1.660 | | |
| 420 | | | 0.447 | 0.339 | |
| 421 | | | 0.457 | 0.479 | |
| 422 | | | 0.191 | 0.174 | |
| 423 | | | 0.123 | 0.044 | |
| 424 | | | 0.166 | 0.182 | |
| 425 | 0.339 | 0.112 | | | |
| 426 | 0.091 | 0.060 | | | |
| 427 | | | 0.204 | 0.158 | |
| 428 | 0.550 | 0.240 | | | |
| 429 | | | 0.251 | 0.112 | |
| 430 | >3.02 | 0.204 | | | |
| 431 | | | 0.117 | 0.095 | |
| 432 | 0.933 | 0.363 | | | |
| 433 | | | 0.589 | 0.427 | |
| 434 | | | 0.288 | 0.174 | |
| 435 | | | 0.079 | 0.081 | |
| 436 | | | 0.141 | 0.110 | |
| 437 | 7.586 | 2.512 | | | |
| 438 | 6.607 | 2.138 | | | |
| 439 | 4.266 | 1.000 | | | |
| 440 | 0.186 | 0.162 | | | |
| 441 | | | 1.122 | 0.891 | |
| 442 | | | 0.162 | 0.112 | |
| 443 | 0.046 | 0.050 | | | |
| 444 | 0.107 | 0.063 | 0.039 | 0.027 | |
| 445 | | | 0.186 | 0.093 | |
| 446 | | | 0.022 | 0.013 | |
| 447 | | | 0.046 | 0.042 | |
| 448 | | | 0.117 | 0.079 | |
| 449 | 0.078 | 0.098 | 0.100 | 0.068 | |
| 450 | | | 0.107 | 0.071 | |

Biological Example 4

Proliferation Assays

To assess anti-proliferative effects, MALT1 inhibitor test compounds were tested in 4-day proliferation assays using three different DLBCL cell lines. Two ABC-DLBCL cell lines with activating mutations in the classical $NF_KB$ pathway were evaluated (OCI-Ly3 (CARD11, MYD88 & A20 mutations), TMD8 (CD79B & MYD88 mutations), which are generally sensitive to $NF_KB$ pathway inhibition. A GCB-DLBCL cell line (OCI-Ly7), which has not been shown to have active $NF_KB$ signaling, served as a negative control to exclude compounds with general cytotoxic effects.

OCI-Ly3 cells were propagated in RPMI-1640 (Sigma Aldrich) supplemented with 10% fetal bovine serum (HyClone), 2 mM L-glutamine (Sigma Aldrich) and 1% Pen-Strep (Sigma Aldrich). TMD8 cells were propagated in RPMI-1640 (Sigma Aldrich) supplemented with 10% fetal bovine serum (HyClone), 1 mM sodium pyruvate (Invitrogen), 2 mM L-glutamine (Sigma Aldrich) and 1% PenStrep (Sigma Aldrich). Cells should be kept between 0.5-2.5 million cells per mL during culturing and cells should be supplemented every 2-3 days with fresh 50 μM beta-mercaptoethanol. No beta-mercaptoethanol is used during the proliferation assay. OCI-Ly7 cells were propagated in IMDM (ThermoFisher) supplemented with 10% fetal bovine serum (HyClone), 2 mM L-glutamine (Sigma Aldrich) and 50 μg/mL Gentamycin. Cell passage numbers should not exceed 30 (for OCI-Ly3 cells with passage number lower than 10 were used).

To assess anti-proliferative effects, 400 nL of test compounds were spotted per well of 96-well plates (Costar, catalogue number 3904). 10,000 TMD8, 10,000 OCI-Ly3 or 2,000 OCI-Ly7 cells were seeded in 100 μL media per well and incubated for 4 days at 37° C. and 5% $CO_2$. Cell plating numbers were chosen based on growth curves to ensure linear cell growth. After 4 days of incubation 50 μL Cell-TiterGLO reagent (Promega) were added to each well and luminescence was measured on the Envision after 10 min of incubation at room temperature.

$IC_{50}$ values were calculated using the following formula (Z prime should be >0.5):

LC=median of the low control values

=Low control: Reaction without cells

HC=Median of the High control values

=High control: Reaction with cells without compound

% Effect=100−(sample−LC)/(HC−LC)×100%

Control=(sample/HC)×100%

Controlmin=(sample−LC)/(HC−LC)×100

A best-fit curve was fitted by a minimum sum of squares method to the plot of % Control vs compound concentration. From this an IC50 value (inhibitory concentration causing 50% cytotoxicity) can be obtained. An estimate of the slope of the plot in terms of the Hill coefficient was also obtained.

$IC_{50}$ Calculation:

$$DATA_i = LB + \frac{UB - LB}{1 + \exp(\text{HILL} * (LCONC_i - IC50))} + \varepsilon_i$$

With
UB=upper bound
LB=lower bound

Resultant data are shown in Table 4.

TABLE 4

| Cpd No. | Anti-proliferation: OCI-LY-3 IC50 (μM) | Anti-proliferation: TMD-8 IC50 (μM) |
|---|---|---|
| 2 | 0.42 | 13.80 |
| 3 | ~2.88 | 9.55 |
| 4 | ~0.50 | ~15.85 |
| 5 | ~0.78 | >20 |
| 6 | 0.62 | 9.33 |
| 7 | 0.43 | ~14.13 |
| 8 | 0.11 | ~7.59 |
| 9 | ~2.40 | 10.72 |
| 11 | ~9.55 | 12.59 |
| 16 | 0.58 | 10.72 |
| 17 | ~4.37 | 9.33 |
| 19 | 1.10 | >20 |
| 21 | ~12.88 | >20 |
| 22 | ~0.31 | 16.98 |
| 23 | 3.39 | 8.32 |
| 24 | ~1.95 | ~10 |
| 25 | 3.31 | ~14.13 |
| 26 | 4.79 | 8.71 |
| 27 | 1.95 | 13.80 |
| 28 | 1.51 | 6.61 |
| 32 | 0.11 | 4.90 |
| 33 | >20 | >20 |
| 34 | ~0.22 | ~12.02 |
| 35 | 10.72 | 10.96 |
| 36 | 1.91 | 7.94 |
| 38 | 1.15 | 3.80 |
| 39 | ~1.12 | 14.45 |
| 40 | 0.15 | 6.17 |
| 41 | 1.58 | >20 |
| 42 | 0.56 | 6.17 |
| 43 | ~0.26 | 4.68 |
| 45 | 0.34 | ~9.33 |
| 46 | 0.63 | 9.33 |
| 47 | ~0.19 | 8.13 |
| 48 | 0.30 | 16.22 |
| 49 | 0.41 | 5.01 |
| 50 | 0.09 | 7.08 |
| 51 | 0.20 | ~6.61 |
| 52 | 0.21 | 5.01 |
| 53 | 1.07 | ~13.49 |
| 54 | 0.46 | 8.71 |
| 55 | 0.54 | 5.25 |
| 56 | 0.54 | >20 |
| 57 | 0.22 | ~8.91 |
| 58 | 0.50 | 4.47 |
| 59 | 0.14 | 6.76 |
| 61 | 1.26 | ~14.12 |
| 62 | 0.23 | 10.00 |
| 63 | ~1.15 | >7.94 |
| 65 | 0.26 | 10.23 |
| 66 | 0.81 | ~8.71 |
| 68 | 0.37 | ~19.05 |
| 69 | 0.43 | ~16.22 |
| 70 | ~1.35 | ~13.81 |
| 72 | 1.66 | >20 |
| 73 | 1.95 | ~11.48 |
| 74 | 2.45 | >20 |
| 78 | ~0.49 | 7.59 |
| 79 | ~2.34 | 8.32 |
| 81 | ~1.35 | 11.48 |
| 82 | ~1.58 | 6.31 |
| 83 | 0.51 | ~8.32 |
| 84 | 1.7 | >20 |
| 85 | 1.66 | >20 |
| 86 | 0.78 | ~11.22 |
| 87 | 1.7 | ~13.80 |
| 88 | 1.35 | ~12.02 |
| 89 | 0.74 | >20 |
| 90 | 0.52 | ~3.89 |

TABLE 4-continued

| Cpd No. | Anti-proliferation: OCI-LY-3 IC50 (µM) | Anti-proliferation: TMD-8 IC50 (µM) |
|---|---|---|
| 95 | 3.8 | ~7.94 |
| 96 | 7.08 | ~15.49 |
| 97 | 3.47 | ~5.89 |
| 98 | 5.75 | ~10.96 |
| 99 | 0.65 | ~3.24 |
| 100 | 1.95 | ~5.25 |
| 108 | 1.122 | 1.660 |
| 109 | >19.953 | >19.953 |
| 110 | 0.220 | 1.445 |
| 111 | 0.284 | 3.311 |
| 112 | 0.966 | 6.310 |
| 113 | 0.912 | 13.804 |
| 114 | 0.193 | 2.692 |
| 115 | 1.212 | 19.953 |
| 116 | 0.344 | 6.918 |
| 117 | 0.211 | 1.585 |
| 118 | 0.158 | 0.832 |
| 119 | 0.193 | 0.355 |
| 120 | 0.325 | 1.950 |
| 121 | 0.692 | 1.905 |
| 122 | 0.132 | 0.162 |
| 123 | 0.395 | 0.501 |
| 124 | 0.593 | 0.977 |
| 125 | 0.285 | 1.023 |
| 126 | 0.135 | 0.794 |
| 127 | 0.432 | 11.220 |
| 128 | 0.188 | |
| 129 | 0.179 | 2.455 |
| 130 | 0.417 | 3.467 |
| 131 | 0.265 | 2.630 |
| 132 | 0.571 | 7.762 |
| 133 | 0.273 | 3.311 |
| 134 | 1.015 | 19.953 |
| 135 | 1.308 | 3.090 |
| 136 | 0.414 | 2.291 |
| 137 | 0.819 | 2.399 |
| 138 | 0.447 | 2.512 |
| 139 | 0.275 | 1.413 |
| 140 | 1.166 | 5.370 |
| 141 | 0.505 | 6.026 |
| 142 | 0.380 | 0.832 |
| 143 | 0.423 | 9.550 |
| 144 | 0.482 | 2.570 |
| 145 | 0.626 | 4.571 |
| 146 | 0.337 | 1.023 |
| 147 | 0.966 | 11.482 |
| 148 | 0.692 | 3.802 |
| 149 | 0.759 | 4.365 |
| 150 | 0.282 | >7.943 |
| 152 | 0.411 | 3.802 |
| 153 | 0.265 | 3.802 |
| 154 | 0.395 | 2.239 |
| 155 | 0.302 | 1.380 |
| 156 | 0.776 | 5.248 |
| 157 | 1.269 | 7.079 |
| 158 | 0.567 | 4.571 |
| 167 | 1.023 | 4.571 |
| 169 | 1.751 | 8.913 |
| 172 | 0.504 | 4.786 |
| 173 | 1.728 | 2.692 |
| 174 | 0.804 | 1.698 |
| 175 | 1.084 | 1.230 |
| 176 | 1.594 | >19.953 |
| 177 | 1.711 | 6.607 |
| 178 | 2.802 | >19.953 |
| 179 | 0.763 | 1.950 |
| 181 | 1.496 | >7.943 |
| 182 | 3.144 | 5.248 |
| 183 | 3.569 | >19.953 |
| 184 | 0.585 | 6.026 |
| 191 | 0.866 | 0.912 |
| 192 | 0.593 | 4.571 |
| 193 | 0.521 | 3.631 |
| 197 | 0.295 | 7.413 |
| 198 | 0.641 | 3.020 |
| 200 | 1.388 | 7.413 |
| 201 | 0.782 | 3.631 |
| 202 | 1.357 | 2.344 |
| 204 | 1.718 | 5.888 |
| 221 | 0.912 | 2.570 |
| 302 | 0.692 | 0.955 |
| 306 | 0.540 | 1.514 |
| 308 | 0.617 | 4.571 |
| 310 | 1.269 | |
| 311 | 2.317 | 3.548 |
| 312 | 0.516 | 0.501 |
| 313 | 0.939 | 7.943 |
| 314 | 0.631 | 1.862 |
| 315 | 1.084 | 6.761 |
| 316 | 1.454 | 3.090 |
| 326 | 0.881 | 3.236 |
| 338 | 1.148 | 1.445 |
| 376 | 1.072 | 1.445 |
| 385 | 0.837 | 1.514 |
| 387 | 0.692 | 2.188 |
| 391 | 0.505 | 0.676 |
| 405 | 0.513 | 4.365 |
| 411 | 0.486 | 0.871 |
| 418 | 0.464 | 3.631 |
| 419 | 1.116 | 5.754 |
| 425 | 0.905 | 10.965 |
| 446 | 1.065 | >19.953 |
| 447 | 0.313 | 2.188 |
| 448 | 0.550 | 5.623 |
| 450 | 0.295 | 2.818 |

Biological Example 5

Tumor Efficacy Studies

The OCI-Ly3 (DSMZ, catalog number ACC 761) human diffuse large B-cell lymphoma tumor cells may be maintained in vitro in RPMI medium supplemented with heat inactivated fetal bovine serum (10% v/v) and 2 mM L-Glutamine 200 mM at 37° C. in an atmosphere of 5% $CO_2$ in air. The cells may be routinely subcultured once weekly. The cells growing in an exponential growth phase may be harvested and counted, and cell suspension diluted 1:1 in Matrigel™ (Corning Matrigel™ Matrix Basement Membrane Growth Factor Reduced) for tumor cell inoculation.

Male NSG (NOD.Cg-Prkdcsc$^{scid}$ Il2rg$^{tm1Wjl}$/SzJ) mice may be subcutaneously inoculated with OCI-Ly3 cells ($10 \times 10^6$ cells in 1:1 medium:Matrige™ in a volume of 200 µL) in the inguinal region of each animal. The day of tumor cell inoculation may be denoted as day 0. Tumor measurements may be monitored twice weekly beginning seven days post-implantation, until the mean tumor volume is 169±42 mm$^3$, at which point mice may be randomized by tumor volume into treatment groups. Compound or vehicle may be orally administered according to body weight (5 mL/kg) once or twice daily until study termination. Tumor measurements and body weights may be recorded twice weekly.

The endpoints of the studies are tumor growth inhibition, maximal tumor burden (individual tumor size equaling 10% of body weight), and body weight loss greater than 20% treatment initiation body weight. Percent body weight change may be calculated using the formula: Body weight change=[(C−I)/I]×100 where C is the current body weight and I is the body weight at the initiation of treatment. Tumor size may be measured twice weekly in two dimensions using a caliper and the volume may be expressed in mm³ using the formula: V=0.5a×b² where and b are the long and short diameters of the tumor, respectively. Complete tumor regression (CR) is defined as tumors that are reduced to below the limit of palpation (20 mm³). Partial tumor regression (PR) is defined as tumors that are reduced by at least half from initial tumor volume. A minimum duration of CR or PR in thee or more successive tumor measurements is required for a CR or PR to be considered durable.

Summary statistics, including mean and the standard error of the mean (SEM), are provided for the tumor volume of difference in tumor volume among each group at each time-point are shown in corresponding study tables. Statistical analysis of difference in tumor volume among the groups may be evaluated using a two-way ANOVA repeated measures test, followed by Tukey post-test, using GraphPad Prism version 6.

While the foregoing specification teaches the principles of the present invention, with examples provided for the purpose of illustration, it will be understood that the practice of the invention encompasses all of the usual variations, adaptations and/or modifications as come within the scope of the following claims and their equivalents.

We claim:
1. A compound of Formula (I)

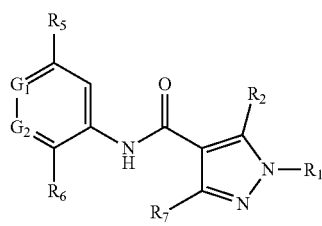

Formula (I)

wherein
$R_1$ is 1-oxo-1,2-dihydroisoquinolin-5-yl or 1-hydroxyisoquinolin-5-yl;
$R_2$ is selected from the group consisting of $C_{1-4}$alkyl, 1-methoxy-ethyl, difluoromethyl, fluoro, chloro, bromo, cyano, and trifluoromethyl;
$G_1$ is N or $C(R_4)$;
$G_2$ is N or $C(R_3)$; such that only one of $G_1$ and $G_2$ are N in any instance;
$R_3$ is independently selected from the group consisting of trifluoromethyl, cyano, $C_{1-4}$alkyl, fluoro, chloro, bromo, methylcarbonyl, methylthio, methylsulfinyl, and methanesulfonyl; or, when $G_1$ is N, $R_3$ is further selected from $C_{1-4}$alkoxycarbonyl;
$R_4$ is selected from the group consisting of
(i) hydrogen, when $G_2$ is N;
(ii) $C_{1-4}$alkoxy;
(iii) cyano;
(iv) cyclopropyloxy;
(v) (4-aminobutyl)aminocarbonyl;
(vi) (4-amino)butoxy;
(vii) methoxycarbonyl;
(viii) (E)-(4-aminobut-1-en-1-yl-aminocarbonyl; and
(ix) difluoromethoxy;
$R_5$ is independently selected from the group consisting of hydrogen, chloro, fluoro, bromo, methoxy, methylsulfonyl, cyano, $C_{1-4}$alkyl, ethynyl, trifluoromethyl, hydroxyethyl, methylcarbonyl, methylsulfinyl methylthio, and 1,1-difluoroethyl;

$R_6$ is hydrogen, $C_{1-4}$alkyl, fluoro, 2-methoxy-ethoxy, chloro, cyano, or trifluoromethyl; and
$R_7$ is hydrogen or fluoro;

or an enantiomer, diastereomer, or pharmaceutically acceptable salt form thereof.

2. The compound according to claim 1 wherein $R_2$ is independently selected from the group consisting of methyl, isopropyl, cyano, bromo, chloro, and trifluoromethyl.

3. The compound according to claim 2 wherein $R_2$ is independently selected from the group consisting of methyl, isopropyl, cyano, and trifluoromethyl.

4. The compound according to claim 3 wherein $R_2$ is trifluoromethyl.

5. The compound according to claim 1 wherein $R_3$ is independently selected from the group consisting of trifluoromethyl, cyano, methylcarbonyl, methylthio, methylsulfinyl, methanesulfonyl, and chloro; or, when $G_1$ is N, $R_3$ is further selected from $C_{1-4}$alkoxycarbonyl.

6. The compound according to claim 1 wherein $R_3$ is independently selected from the group consisting of trifluoromethyl, cyano, and chloro.

7. The compound according to claim 1 wherein $G_2$ is N or $C(R_3)$, and wherein $R_3$ is chloro.

8. The compound according to claim 7 wherein $G_2$ is N.

9. The compound according to claim 1 wherein $R_4$ is selected from the group consisting of
(i) hydrogen, when $G_2$ is N;
(ii) $C_{1-4}$alkoxy;
(iii) cyano;
(iv) cyclopropyloxy;
(v) (4-aminobutyl)aminocarbonyl;
(vi) (4-amino)butoxy; and
vii) methoxycarbonyl.

10. The compound according to claim 9 wherein $R_4$ is selected from the group consisting of
(i) hydrogen, when $G_2$ is N;
(ii) $C_{1-4}$alkoxy;
(iii) cyano;
(iv) cyclopropyloxy;
(v) (4-amino)butoxy; and
(vi) methoxycarbonyl.

11. The compound according to claim 1 wherein $R_4$ is selected from the group consisting of
(i) methoxy; and
(ii) methoxycarbonyl.

12. The compound according to claim 1 wherein $R_5$ is hydrogen, chloro, fluoro, bromo, cyano, methyl, ethyl, or trifluoromethyl.

13. The compound according to claim 12 wherein $R_5$ is hydrogen, chloro, bromo, cyano, or trifluoromethyl.

14. The compound according to claim 12 wherein $R_5$ is hydrogen, chioro, fluoro, or cyano.

15. The compound according to claim 14 wherein $R_5$ is hydrogen, chloro, or cyano.

16. The compound according to claim 1 wherein $R_6$ is hydrogen or methyl.

17. The compound according to claim 1 wherein $R_7$ is hydrogen.

18. A compound of Formula (I)

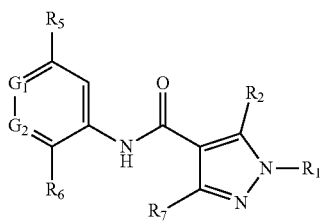

Formula (I)

wherein
- R₁ is 1-oxo-1,2-dihydroisoquinolin-5-yl or 1-hydroxyisoquinolin-5-yl;
- R₂ is independently selected from the group consisting of methyl, isopropyl, cyano, bromo, chloro, and trifluoromethyl;
- G₁ is N or C(R₄);
- G₂ is N or C(R₃); such that only one of G₁ and G₂ is N in any instance;
- R₃ is independently selected from the group consisting of trifluoromethyl, cyano, methylcarbonyl, methylthio, methylsulfinyl, methanesulfonyl, and chloro; or, when G₁ is N, R₃ is further selected from $C_{1-4}$alkoxycarbonyl;
- R₄ is independently selected from the group consisting of
  (i) hydrogen, when G₂ is N;
  (ii) $C_{1-4}$alkoxy;
  (iii) cyano;
  (iv) cyclopropyloxy;
  (v) carboxy;
  (vi) (4-aminobutyl)aminocarbonyl;
  (vii) (4-amino)butoxy; and
  (viii) methoxycarbonyl;
- R₅ is hydrogen, chloro, fluoro, bromo, cyano, methyl, ethyl, or trifluoromethyl;
- R₆ is hydrogen or methyl; and
- R₇ is hydrogen;

or an enantiomer, diastereomer, or pharmaceutically acceptable salt form thereof.

19. A compound of Formula (I)

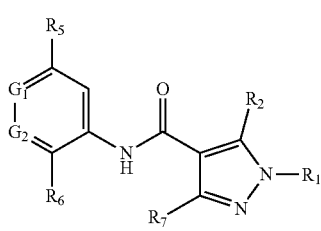

Formula (I)

wherein
- R₁ is 1-oxo-1,2-dihydroisoquinolin-5-yl or 1-hydroxyisoquinolin-5-yl;
- R₂ is selected from the group consisting of methyl, isopropyl, cyano, and trifluoromethyl;
- G₁ is N or C(R₄);
- G₂ is N or C(R₃); such that only one of G₁ and G₂ is N in any instance;
- R₃ is independently selected from the group consisting of trifluoromethyl, cyano, and chloro;
- R₄ is independently selected from the group consisting of
  (i) hydrogen, when G₂ is N;
  (ii) $C_{1-4}$alkoxy;
  (iii) cyano;
  (iv) cyclopropyloxy;
  (v) (4-amino)butoxy; and
  (vi) methoxycarbonyl;
- R₅ is hydrogen, chloro, bromo, or cyano;
- R₆ is hydrogen or methyl; and
- R₇ is hydrogen;

or an enantiomer, diastereomer, or pharmaceutically acceptable salt form thereof.

20. A compound of Formula (I)®

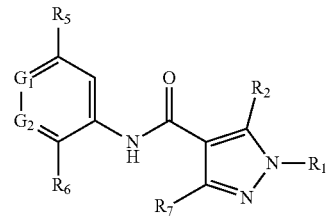

Formula (I)

wherein
- R₁ is 1-oxo-1,2-dihydroisoquinolin-5-yl or 1-hydroxyisoquinolin-5-yl;
- R₂ is selected from the group consisting of methyl, isopropyl, cyano, and trifluoromethyl;
- G₁ is N or C(R₄);
- G₂ is N or C(R₃); such that only one of G₁ and G₂ is N in any instance;
- R₃ is independently selected from the group consisting of trifluoromethyl, cyano, and chloro;
- R₄ is selected from the group consisting of
  (i) methoxy; and
  (ii) methoxycarbonyl;
- R₅ is hydrogen, chloro, or cyano;
- R₆ is hydrogen or methyl; and
- R₇ is hydrogen;

or an enantiomer, diastereomer, or pharmaceutically acceptable salt form thereof.

21. A compound of Formula (I)

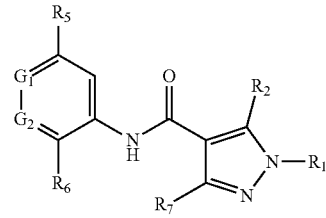

Formula (I)

selected from the group consisting of:

| Compound No. and Structure | Compound Name: |
|---|---|
| 158 | 1-(1-oxo-1,2-dihydroisoquinolin-5-yl)-5-(trifluoromethyl)-N-(2-(trifluoromethyl)pyridin-4-yl)-1H-pyrazole-4-carboxamide; |
| 167 | 1-(1-oxo-1,2-dihydroisoquinolin-5-yl)-5-(trifluoromethyl)-N-(5-(trifluoromethyl)pyridin-3-yl)-1H-pyrazole-4-carboxamide; |
| 345 | N-(5-chloro-6-methoxypyridin-3-yl)-1-(1-oxo-1,2-dihydroisoquinolin-5-yl)-5-(trifluoromethyl)-1H-pyrazole-4-carboxamide; |
| 346 | N-(5-cyanopyridin-3-yl)-1-(1-oxo-1,2-dihydroisoquinolin-5-yl)-5-(trifluoromethyl)-1H-pyrazole-4-carboxamide; |
| 347 | N-(2-methylpyridin-4-yl)-1-(1-oxo-1,2-dihydroisoquinolin-5-yl)-5-(trifluoromethyl)-1H-pyrazole-4-carboxamide; |
| 353 | N-(5-chloropyridin-3-yl)-1-(1-oxo-1,2-dihydroisoquinolin-5-yl)-5-(trifluoromethyl)-1H-pyrazole-4-carboxamide; |

-continued

| Compound No. and Structure | Compound Name: |
|---|---|
| 354 | N-(6-cyano-5-(trifluoromethyl)pyridin-3-yl)-1-(1-oxo-1,2-dihydroisoquinolin-5-yl)-5-(trifluoromethyl)-1H-pyrazole-4-carboxamide; |
| 355 | methyl 3-chloro-5-(1-(1-oxo-1,2-dihydroisoquinolin-5-yl)-5-(trifluoromethyl)-1H-pyrazole-4-carboxamido)picolinate; |
| 356 | N-(2-cyanopyridin-4-yl)-1-(1-oxo-1,2-dihydroisoquinolin-5-yl)-5-(trifluoromethyl)-1H-pyrazole-4-carboxamide; |
| 357 | N-(2-(2-methoxyethox-y)-5-(trifluoromethyl)pyridin-3-yl)-1-(1-oxo-1,2-dihydroisoquinolin-5-yl)-5-(trifluoromethyl)-1H-pyrazole-4-carboxamide; and |
| 428 | N-(5-cyano-6-methoxypyridin-3-yl)-1-(1-oxo-1,2-dihydroisoquinolin-5-yl)-5-(trifluoromethyl)-1H-pyrazole-4-carboxamide; | or an enantiomer, diastereomer, or pharmaceutically acceptable salt form thereof.

22. A pharmaceutical composition comprising a compound of claim 1, 2-11, 12-20 or 21 and at least one of a pharmaceutically acceptable carrier, a pharmaceutically acceptable excipient, and a pharmaceutically acceptable diluent.

23. The pharmaceutical composition of claim 22, wherein the composition is a solid oral dosage form.

24. The pharmaceutical composition of claim 22, wherein the composition is a syrup, an elixir or a suspension.

25. A compound of Formula (I)

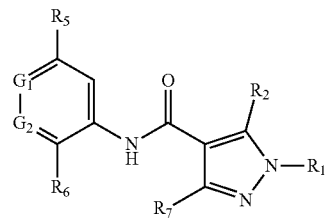

Formula (I)

selected from the group consisting of:

| Compound No. and Structure | Compound Name: |
|---|---|
| 158 | 1-(1-oxo-1,2-dihydroisoquinolin-5-yl)-5-(trifluoromethyl)-N-(2-(trifluoromethyl)pyridin-4-yl)-1H-pyrazole-4-carboxamide; |
| 355 | methyl 3-chloro-5-(1-(1-oxo-1,2-dihydroisoquinolin-5-yl)-5-(trifluoromethyl)-1H-pyrazole-4-carboxamido)picolinate; and |
| 428 | N-(5-cyano-6-methoxypyridin-3-yl)-1-(1-oxo-1,2-dihydroisoquinolin-5-yl)-5-(trifluoromethyl)-1H-pyrazole-4-carboxamide; | or an enantiomer, diastereomer, or pharmaceutically acceptable salt form thereof.

26. A compound that is

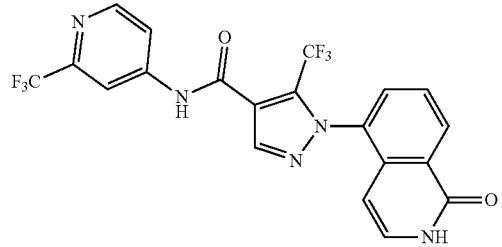 [SMILES: O=C(Nc1ccnc(C(F)(F)F)c1)c1cnn(-c2cccc3c(=O)[nH]ccc23)c1C(F)(F)F]

or an enantiomer, diastereomer, or pharmaceutically acceptable salt form thereof.

27. A crystalline form of

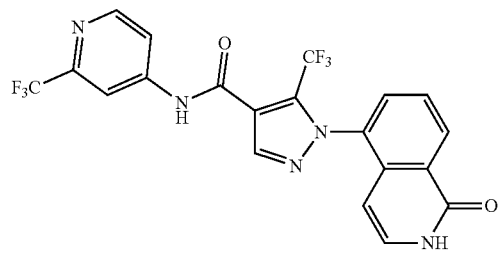 [SMILES: O=C(Nc1ccnc(C(F)(F)F)c1)c1cnn(-c2cccc3c(=O)[nH]ccc23)c1C(F)(F)F]

wherein the crystalline form is a hydrate, producing an X-ray powder diffraction pattern comprising peaks at 8.4, 12.7, 13.3 and 16.7 degrees two theta 0.2 degrees two theta.

28. A pharmaceutical composition comprising a compound of claim 25, 26 or 27 and at least one of a pharmaceutically acceptable carrier, a pharmaceutically acceptable excipient, and a pharmaceutically acceptable diluent.

29. The pharmaceutical composition of claim 28, wherein the composition is a solid oral dosage form.

30. The pharmaceutical composition of claim 28, wherein the composition is a syrup, an elixir or a suspension.

31. A pharmaceutical composition comprising a compound of claim 27 and at least one of a pharmaceutically acceptable carrier, a pharmaceutically acceptable excipient, and a pharmaceutically acceptable diluent.

32. The pharmaceutical composition of claim 31, wherein the composition is a solid oral dosage form.

33. The pharmaceutical composition of claim 31, wherein the composition is a syrup, an elixir or a suspension.

34. A compound selected from the group consisting of:

| Compound No. and Structure | | Compound Name: |
|---|---|---|
| 348 | (structure) | N-(6-methyl-5-(trifluoromethyl)pyridin-3-yl)-1-(1-oxo-1,2-dihydroisoquinolin-5-yl)-5-(trifluoromethyl)-1H-pyrazole-4-carboxamide; |
| 349 | (structure) | 1-(1-oxo-1,2-dihydroisoquinolin-5-yl)-N-(pyridin-4-yl)-5-(trifluoromethyl)-1H-pyrazole-4-carboxamide; |
| 350 | (structure) | N-(2-cyclopropylpyridin-4-yl)-1-(1-oxo-1,2-dihydroisoquinolin-5-yl)-5-(trifluoromethyl)-1H-pyrazole-4-carboxamide; |

-continued

| Compound No. and Structure | Compound Name: |
|---|---|
| 351 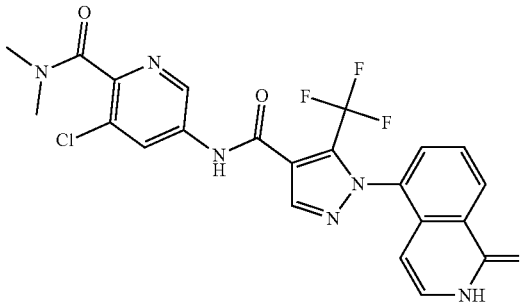 | 3-chloro-N,N-dimethyl-5-(1-(1-oxo-1,2-dihydroisoquinolin-5-yl)-5-(trifluoromethyl)-1H-pyrazole-4-carboxamido)picolinamide; |
| 352 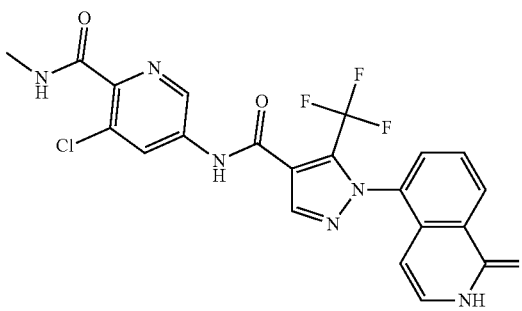 | 3-chloro-N-methyl-5-(1-(1-oxo-1,2-dihydroisoquinolin-5-yl)-5-(trifluoromethyl)-1H-pyrazole-4-carboxamido)picolinamide; and |
| 360 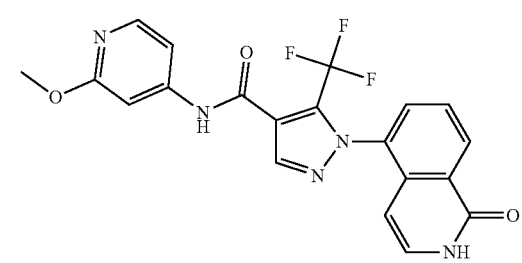 [SMILES: COc1cc(NC(=O)c2cnn(-c3cccc4c(=O)[nH]ccc34)c2C(F)(F)F)ccn1] | N-(2-methoxypyridin-4-yl)-1-(1-oxo-1,2-dihydroisoquinolin-5-yl)-5-(trifluoromethyl)-1H-pyrazole-4-carboxamide; | or an enantiomer, diastereomer, or pharmaceutically acceptable salt form thereof.

35. A pharmaceutical composition comprising a compound of claim 34 and at least one of a pharmaceutically acceptable carrier, a pharmaceutically acceptable excipient, and a pharmaceutically acceptable diluent.

36. The pharmaceutical composition of claim 35, wherein the composition is a solid oral dosage form.

37. The pharmaceutical composition of claim 35, wherein the composition is a syrup, an elixir or a suspension.

* * * * *